(12) United States Patent
Nakano et al.

(10) Patent No.: US 10,777,752 B2
(45) Date of Patent: Sep. 15, 2020

(54) ORGANIC ELECTROLUMINESCENCE DEVICE AND ELECTRONIC APPARATUS PROVIDED WITH THE SAME

(71) Applicant: IDEMITSU KOSAN CO., LTD., Tokyo (JP)

(72) Inventors: Yuki Nakano, Sodegaura (JP); Taro Yamaki, Sodegaura (JP); Satomi Tasaki, Sodegaura (JP); Tomoki Kato, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/557,725

(22) Filed: Aug. 30, 2019

(65) Prior Publication Data

US 2020/0111973 A1 Apr. 9, 2020

(30) Foreign Application Priority Data

Oct. 9, 2018 (JP) .................................. 2018-191297
May 30, 2019 (JP) .................................. 2019-101674

(51) Int. Cl.
*H01L 51/50* (2006.01)
*H01L 51/00* (2006.01)
(Continued)

(52) U.S. Cl.
CPC ........ *H01L 51/0073* (2013.01); *C07D 307/77* (2013.01); *C09K 11/025* (2013.01);
(Continued)

(58) Field of Classification Search
None
See application file for complete search history.

(56) References Cited

U.S. PATENT DOCUMENTS

| 2016/0351817 A1 | 12/2016 | Kim et al. |
| 2017/0125686 A1 | 5/2017 | Heil et al. |

(Continued)

FOREIGN PATENT DOCUMENTS

| JP | 2015-153911 A | 8/2015 |
| JP | 2017-514807 A | 6/2017 |

(Continued)

OTHER PUBLICATIONS

International Search Report dated Dec. 24, 2019 for corresponding Application No. PCT/JP2019/039918.

*Primary Examiner* — Gregory D Clark
(74) *Attorney, Agent, or Firm* — Foley & Lardner LLP

(57) ABSTRACT

An organic electroluminescence device including a cathode, an anode, and an emitting layer disposed between the cathode and the anode, wherein the emitting layer includes a compound represented by the following formula (1) and one or more compounds selected from the group consisting of compounds represented by formulas (11), (21), (31), (41), (51), (61), (71) and (81). In the formula (1), at least one of $R_1$ to $R_8$ is a deuterium atom, and $Ar_2$ is a monovalent group represented by following formula (2), (3) or (4).

(Continued)

-continued (2)

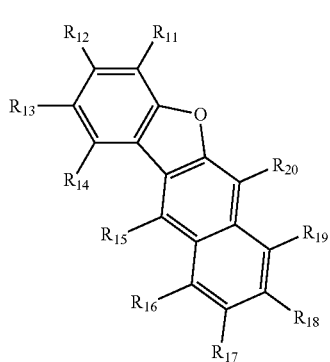

(3)

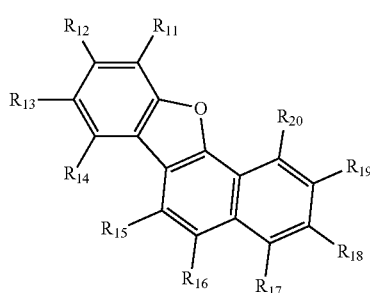

(4)

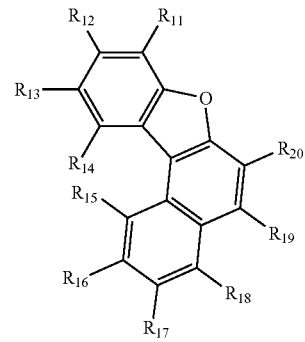

30 Claims, 1 Drawing Sheet

(51) Int. Cl.
    *C07D 307/77*     (2006.01)
    *C09K 11/02*     (2006.01)

(52) U.S. Cl.
    CPC ...... *H01L 51/0061* (2013.01); *H01L 51/0072* (2013.01); *H01L 51/5016* (2013.01); *H01L 51/5056* (2013.01); *H01L 51/5072* (2013.01)

(56) References Cited

U.S. PATENT DOCUMENTS

| | | |
|---|---|---|
| 2017/0133600 A1 | 5/2017 | Pyo et al. |
| 2017/0200899 A1 | 7/2017 | Kim et al. |
| 2017/0324045 A1 | 11/2017 | Takahashi et al. |
| 2018/0013071 A1 | 1/2018 | Cha et al. |
| 2018/0094000 A1 | 4/2018 | Hatakeyama et al. |
| 2018/0198076 A1 | 7/2018 | Takahashi et al. |
| 2018/0301629 A1 | 10/2018 | Hatakeyama et al. |
| 2019/0027694 A1 | 1/2019 | Hatakeyama et al. |
| 2019/0097142 A1 | 3/2019 | Takahashi et al. |
| 2019/0181350 A1 | 6/2019 | Hatakeyama et al. |
| 2019/0207112 A1 | 7/2019 | Hatakeyama et al. |
| 2019/0305227 A1 | 10/2019 | Yoon et al. |
| 2019/0341556 A1* | 11/2019 | Takahashi ........... H01L 51/0061 428/690 |
| 2019/0372023 A1 | 12/2019 | Hatakeyama et al. |
| 2019/0393420 A1 | 12/2019 | Takeda et al. |

FOREIGN PATENT DOCUMENTS

| | | | |
|---|---|---|---|
| JP | 2018-157209 A | 10/2018 | |
| KR | 20160102881 A | 8/2016 | |
| KR | 20160141361 | 12/2016 | |
| KR | 20190056338 A | 5/2019 | |
| KR | 20190122041 A | 10/2019 | |
| WO | WO 2010/099534 | * 9/2010 | ............. C09K 11/06 |
| WO | WO-2016/152544 A1 | 9/2016 | |
| WO | WO-2017/188111 A1 | 11/2017 | |
| WO | WO-2018/151065 A1 | 8/2018 | |
| WO | WO-2019/220283 A | 11/2019 | |
| WO | WO-2020/022751 | 1/2020 | |

* cited by examiner

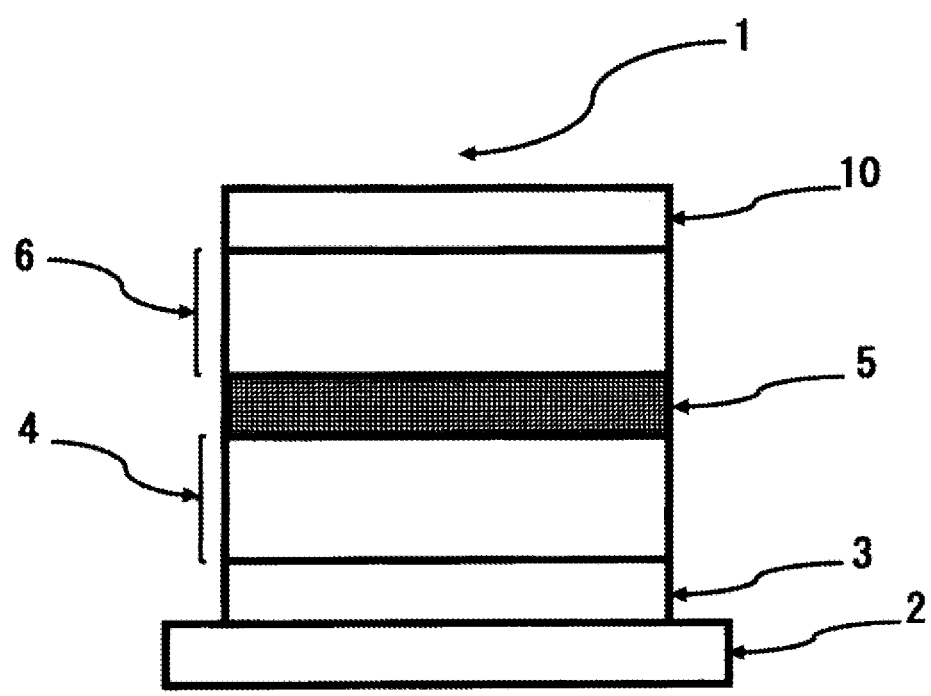

ORGANIC ELECTROLUMINESCENCE DEVICE AND ELECTRONIC APPARATUS PROVIDED WITH THE SAME

TECHNICAL FIELD

The invention relates to an organic electroluminescence device and an electronic apparatus provided with the organic electroluminescence device.

BACKGROUND ART

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

Although materials for an organic EL device are being improved gradually to increase the performances of the organic EL device (for example, Patent Documents 1 to 3), high performances are further offered. In particular, improvement in lifetime of an organic EL device is an important task relating to a lifetime of commercial products provided with the organic EL device, and thus a material enabling to realize a long-lifetime organic EL device is required.

RELATED ART DOCUMENTS

Patent Documents

Patent Document 1: WO2016/152544
Patent Document 2: WO2017/188111
Patent Document 3: Publication of US Patent Application No. 2017/324045

SUMMARY OF THE INVENTION

An object of the invention is to provide an organic EL device having a long lifetime, and to provide an electronic apparatus provided with the organic EL device.

As a result of extensive studies, the inventors have found that an organic EL device having a long lifetime can be obtained by using compounds having a specific structure in an emitting layer of the organic EL device in combination, and they have achieved the invention.

According to the invention, the following organic EL device and electric apparatus can be provided.

1. An organic electroluminescence device comprising:
   a cathode,
   an anode, and
   an emitting layer disposed between the cathode and the anode, wherein
   the emitting layer comprises a compound represented by the following formula (1) and one or more compounds selected from the group consisting of compounds represented by formulas (11), (21), (31), (41), (51), (61), (71) and (81):

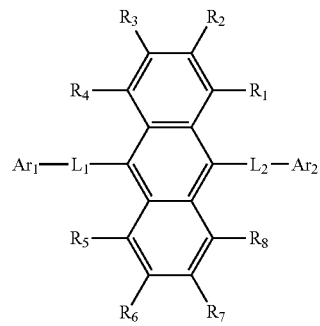

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms; $Ar_1$ is
a substituted or unsubstituted aryl group having 6 to 50 ring carbon atoms, or
a substituted or unsubstituted monovalent heterocyclic group having 5 to 50 ring atoms;
$Ar_2$ is a monovalent group represented by the following formula (2), (3) or (4);

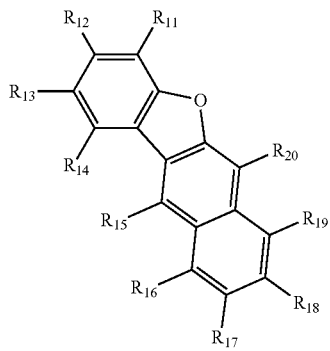

(2)

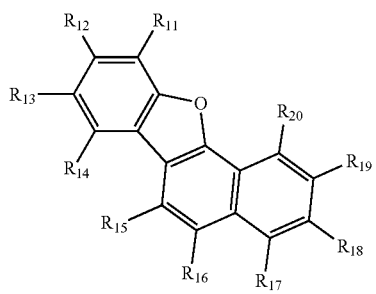

(3)

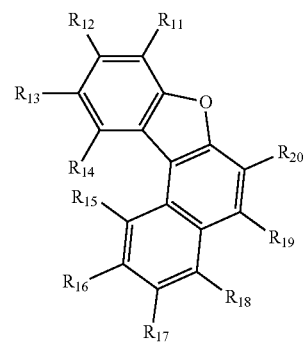

(4)

wherein in the formulas (2) to (4), one or more pairs of two adjacent groups of $R_{15}$ to $R_{20}$ are bonded with each other to form a substituted or unsubstituted, saturated or unsaturated ring, or do not form a substituted or unsubstituted, saturated or unsaturated ring;

when one or more pairs of two adjacent groups of $R_{15}$ to $R_{20}$ are not bonded with each other and do not form a substituted or unsubstituted, saturated or unsaturated ring, one of $R_{11}$ to $R_{20}$ is a single bond bonding to $L_2$;

when one or more pairs of two adjacent groups of $R_{15}$ to $R_{20}$ are bonded with each other to form a substituted or unsubstituted, saturated or unsaturated ring, one of $R_{15}$ to $R_{20}$ which does not form a substituted or unsubstituted, saturated or unsaturated ring and $R_{11}$ to $R_{14}$ is a single bond bonding to $L_2$;

$R_{11}$ to $R_{20}$ that do not form the substituted or unsubstituted, saturated or unsaturated ring and that are not a single bond bonding to $L_2$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1);

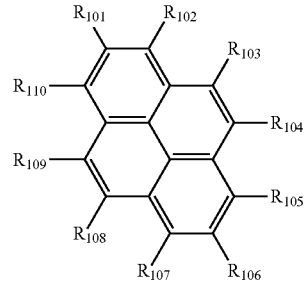

(11)

wherein, in the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{101}$ to $R_{110}$ is a monovalent group represented by the formula (12);

$R_{101}$ to $R_{110}$ that do not form the substituted or unsubstituted, saturated or unsaturated ring and that are not a monovalent group represented by the following formula (12) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{9001}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

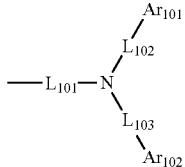

(12)

wherein, in the formula (12), Ar$_{101}$ and Ar$_{102}$ are independently
a substituted or unsubstituted aryl group having 6 to 50 ring carbon atoms, or
a substituted or unsubstituted monovalent heterocyclic group having 5 to 50 ring atoms; L$_{101}$ to L$_{103}$ are independently
a single bonded,
a substituted or unsubstituted arylene group having 6 to 30 ring carbon atoms, or
a substituted or unsubstituted divalent heterocyclic group having 5 to 30 ring atoms;

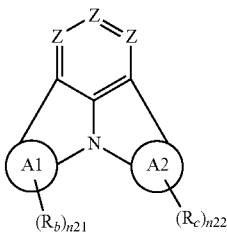

(21)

wherein, in the formula (21),
Zs are independently CR$_a$ or N;
A1 ring and A2 ring are independently a substituted or unsubstituted aromatic hydrocarbon ring having 6 to 50 ring carbon atoms, or a substituted or unsubstituted heterocyclic ring having 5 to 50 ring atoms;
when plural R$_a$s exist, one or more pairs of two or more adjacent groups of R$_a$ are bonded with each other to form a substituted or unsubstituted, saturated or unsaturated ring, or do not form a substituted or unsubstituted, saturated or unsaturated ring;
when plural R$_b$s exist, one or more pairs of two or more adjacent groups of R$_b$ are bonded with each other to form a substituted or unsubstituted, saturated or unsaturated ring, or do not form a substituted or unsubstituted, saturated or unsaturated ring;
when plural R$_c$s exist, one or more pairs of two or more adjacent groups of R$_c$ are bonded with each other to form a substituted or unsubstituted, saturated or unsaturated ring, or do not form a substituted or unsubstituted, saturated or unsaturated ring;
n21 and n22 are independently an integer of 0 to 4;
R$_a$ to R$_c$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
R$_{901}$ to R$_{907}$ are as defined in the formula (1);

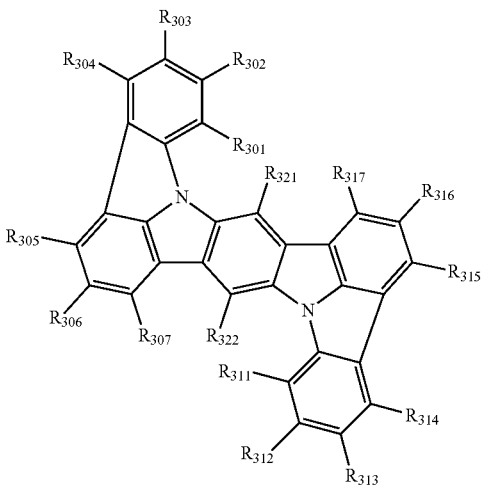

(31)

wherein, in the formula (31),
one or more pairs of two or more adjacent groups of R$_{301}$ to R$_{307}$ and R$_{311}$ to R$_{317}$ form a substituted or unsubstituted, saturated or unsaturated ring, or do not form a substituted or unsubstituted saturated or unsaturated ring;
R$_{301}$ to R$_{307}$ and R$_{311}$ to R$_{317}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
R$_{321}$ and R$_{322}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

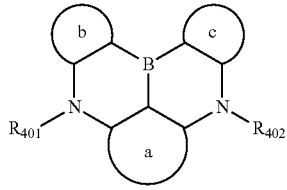
(41)

wherein, in the formula (41), a ring, b ring and c ring are independently a substituted or unsubstituted aromatic hydrocarbon ring having 6 to 50 ring carbon atoms, or a substituted or unsubstituted heterocyclic ring having 5 to 50 ring atoms; $R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

(51)

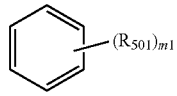
(52)

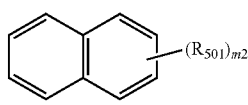
(53)

(54)

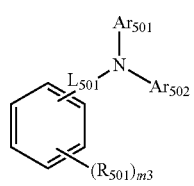
(55)

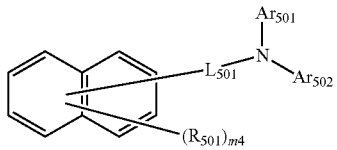
(56)

wherein, in the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{501}$s exist, adjacent plural $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms; $L_{501}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or
a substituted or unsubstituted divalent heterocyclic group having 5 to 50 ring atoms;
m1 is an integer of 0 to 2, m2 is an integer of 0 to 4, m3s are independently an integer of 0 to 3, and m4s are independently an integer of 0 to 5; when plural $R_{501}$s exist, the plural $R_{501}$s may be the same or different;

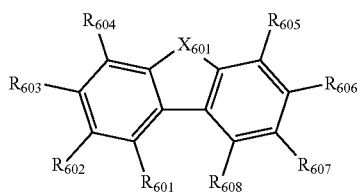

(61)

wherein, in the formula (61),
at least one pair of $R_{601}$ and $R_{602}$, $R_{602}$ and $R_{603}$, and $R_{603}$ and $R_{604}$ are bonded with each other to form a divalent group represented by the formula (62);
at least one pair of $R_{605}$ and $R_{606}$, $R_{606}$ and $R_{607}$, and $R_{607}$ and $R_{608}$ are bonded with each other to form a divalent group represented by formula (63);

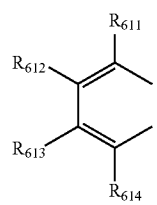

(62)

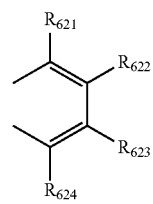

(63)

at least one of $R_{601}$ to $R_{604}$ that does not form the divalent group represented by the formula (62), and $R_{611}$ to $R_{614}$ is a monovalent group represented by the following formula (64);
at least one of $R_{605}$ to $R_{6008}$ that do not form the divalent group represented by the formula (63), and $R_{621}$ to $R_{624}$ is a monovalent group represented by the following formula (64);
$X_{601}$ is an oxygen atom, a sulfur atom, or $NR_{609}$;
$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

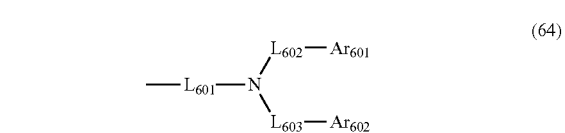

(64)

wherein, in the formula (64), $Ar_{601}$ and $Ar_{602}$ are independently
a substituted or unsubstituted aryl group having 6 to 50 ring carbon atoms, or
a substituted or unsubstituted monovalent heterocyclic group having 5 to 50 ring atoms;
$L_{601}$ to $L_{603}$ are independently
a single bonded,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups;

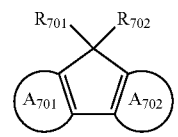

(71)

wherein, in the formula (71),
$A_{701}$ ring and $A_{702}$ ring are independently
a substituted or unsubstituted aromatic hydrocarbon ring having 6 to 50 ring carbon atoms, or
a substituted or unsubstituted heterocyclic ring having 5 to 50 ring atoms;
One or more rings selected from the group consisting of $A_{701}$ ring and $A_{702}$ ring are bonded to the bond * of the structure represented by the following formula (72);

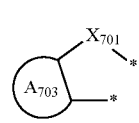

(72)

wherein, in the formula (72),
$A_{703}$ rings are independently
a substituted or unsubstituted aromatic hydrocarbon ring having 6 to 50 ring carbon atoms, or
a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{9001})(R_{902})(R_{903})$,

—$O$—$(R_{904})$,

—$S$—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

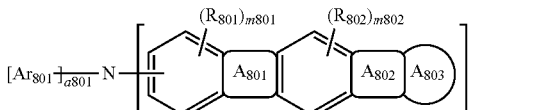 (81)

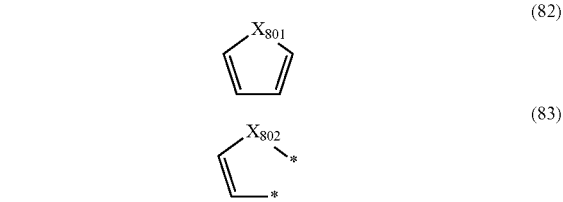

wherein, in the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—$O$—$(R_{904})$,

—$S$—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when these are 2, plural $R_{801}$s or $R_{802}$s may be the same or different;

a801 is an integer of 0 to 2; when a801 is 0 or 1, the structure in the parenthese indicated by "3-a801" may be the same or different from each other; when a801 is 2, $Ar_{801}$s may be the same or different from each other.

2. An electronic apparatus provided with the organic electroluminescence device according to the above 1.

According to the invention, an organic EL device having a long lifetime, and an electronic apparatus provided with the organic EL device can be provided.

BRIEF DESCRIPTION OF THE DRAWINGS

The FIGURE is a view showing a schematic configuration of one embodiment of the organic EL device of the invention.

MODE FOR CARRYING OUT THE INVENTION

Definition

In the present specification, a hydrogen atom means an atom including isotopes different in the number of neutrons, namely, a protium, a deuterium and a tritium.

In the present specification, to a bondable position in which a symbol such as "R", or "D" representing a deuterium atom is not specified in a chemical formula, a hydrogen atom, that is, a light hydrogen atom, a deuterium atom, or a tritium atom is bonded thereto.

In the present specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenyl-fluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In the present specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In the present specification, a term "XX to YY carbon atoms" in an expression of "substituted or unsubstituted ZZ group having XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In the present specification, a term "XX to YY atoms" in an expression of "substituted or unsubstituted ZZ group having XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described herein will be described.

The number of the ring carbon atoms of the "unsubstituted aryl group" described herein is 6 to 50, preferably 6 to 30, and more preferably 6 to 18, unless otherwise specified.

The number of the ring carbon atoms of the "unsubstituted heterocyclic group" described herein is 5 to 50, preferably 5 to 30, and more preferably 5 to 18, unless otherwise specified.

The number of the carbon atoms of the "unsubstituted alkyl group" described herein is 1 to 50, preferably 1 to 20, and more preferably 1 to 6, unless otherwise specified.

The number of the carbon atoms of the "unsubstituted alkenyl group" described herein is 2 to 50, preferably 2 to 20, and more preferably 2 to 6, unless otherwise specified.

The number of the carbon atoms of the "unsubstituted alkynyl group" described herein is 2 to 50, preferably 2 to 20, and more preferably 2 to 6, unless otherwise specified.

The number of the ring carbon atoms of the "unsubstituted cycloalkyl group" described herein is 3 to 50, preferably 3 to 20, and more preferably 3 to 6, unless otherwise specified.

The number of the ring carbon atoms of the "unsubstituted arylene group" described herein is 6 to 50, preferably 6 to 30, and more preferably 6 to 18, unless otherwise specified.

The number of the ring atoms of the "unsubstituted divalent heterocyclic group" described herein is 5 to 50, preferably 5 to 30, and more preferably 5 to 18, unless otherwise specified.

The number of the carbon atoms of the "unsubstituted alkylene group" described herein is 1 to 50, preferably 1 to 20, and more preferably 1 to 6, unless otherwise specified.

Specific examples (specific example group G1) of the "substituted or unsubstituted aryl group" described herein include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed herein are only one example, and the "substituted aryl group" described herein also includes a group in which a group in which "unsubstituted aryl group" has a substituent further has a substituent, and a group in which "substituted aryl group" further has a substituent, and the like.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranethenyl group,
a benzofluoranethenyl group, and
a perylenyl group.

A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described herein is a ring group having at least one hetero atom in the ring atom. Specific examples of the hetero atom include a nitrogen atom, an oxygen atom, a sulfur atom, a silicon atom, a phosphorus atom and a boron atom.

The "heterocyclic group" described herein may be a monocyclic group, or a fused ring group.

The "heterocyclic group" described herein may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocyclic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocyclic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed herein are merely one example, and the "substituted heterocyclic group" described herein also includes a group in which "unsubstituted heterocyclic group" which has a substituent further has a substituent, and a group in which "substituted heterocyclic group" further has a substituent, and the like.

An unsubstituted heterocyclic group having a nitrogen atom:
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group having an oxygen atom:
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzooxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group having a sulfur atom:
a thienyl group,
a thiazolyl group,
an isothiazolyl group,
a thiadiazolyl group,
a benzothiophenyl group,
an isobenzothiophenyl group,
a dibenzothiophenyl group,
a naphthobenzothiophenyl group,
a benzothiazolyl group,
a benzisothiazolyl group,
a phenothiazinyl group,
a dinaphthothiophenyl group,
an azadibenzothiophenyl group, a diazadibenzothiophenyl group,
an azanaphthobenzothiophenyl group, and
a diazanaphthobenzothiophenyl group.

A substituted heterocyclic group having a nitrogen atom:
a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

A substituted heterocyclic group having an oxygen atom:
a phenyldibenzofuranyl group,
a methyldibenzofuranyl group,
a t-butyldibenzofuranyl group, and
a monovalent residue of spiro[9H-xanthene-9,9'-[9H]fluorene].

A substituted heterocyclic group having a sulfur atom:
a phenyldibenzothiophenyl group,
a methyldibenzothiophenyl group,
a t-butyldibenzothiophenyl group, and
a monovalent residue of spiro[9H-thioxantene-9,9'-[9H]fluorene].

A monovalent group derived from the following unsubstituted heterocyclic ring containing at least one of a nitrogen atom, an oxygen atom and a sulfur atom by removal of one hydrogen atom bonded to the ring atoms thereof, and a monovalent group in which a monovalent group derived from the following unsubstituted heterocyclic ring has a substituent by removal of one hydrogen atom bonded to the ring atoms thereof:

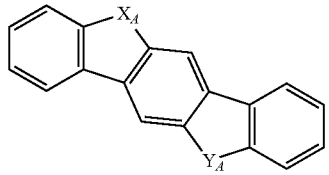
(XY-1)

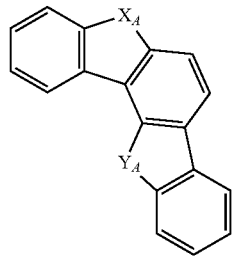
(XY-2)

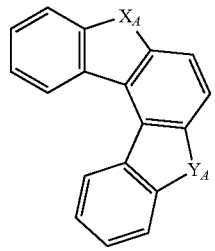
(XY-3)

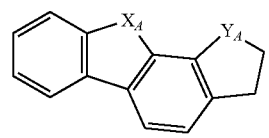
(XY-4)

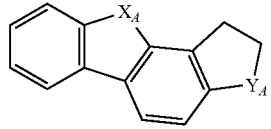
(XY-5)

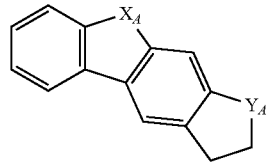
(XY-6)

(XY-7)

(XY-8)

(XY-9)

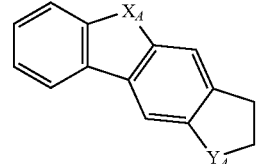
(XY-10)

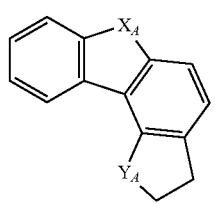
(XY-11)

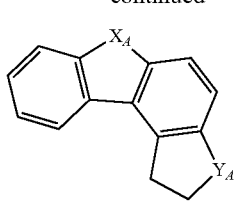
(XY-12)

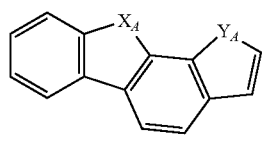
(XY-13)

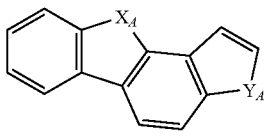
(XY-14)

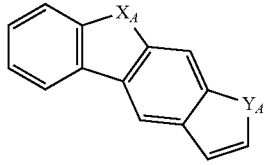
(XY-15)

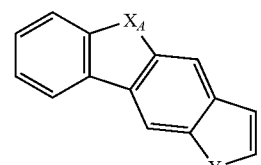
(XY-16)

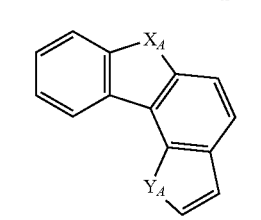
(XY-17)

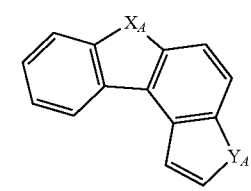
(XY-18)

In the formulas (XY-1) to (XY-18), $X_A$ and $Y_A$ are independently an oxygen atom, a sulfur atom, NH or $CH_2$. However, at least one of $X_A$ and $Y_A$ is an oxygen atom, a sulfur atom or NH.

The heterocyclic ring represented by the formulas (XY-1) to (XY-18) becomes a monovalent heterocyclic group having a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed herein are merely one example, and the "substituted alkyl group" described herein also includes a group in which "unsubstituted alkyl group" has a substituent further has a substituent, a group in which "substituted alkyl group" further has a substituent, and the like.

An unsubstituted alkyl group:
a methyl group,
an ethyl group,
a n-propyl group,
an isopropyl group,
a n-butyl group,
an isobutyl group,
a s-butyl group, and
a t-butyl group.
A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed herein are merely one example, and the "substituted alkenyl group" described herein also includes a group in which "unsubstituted alkenyl group" has a substituent further has a substituent, a group in which "substituted alkenyl group" further has a substituent, and the like.

An unsubstituted alkenyl group and a substituted alkenyl group:
a vinyl group,
an allyl group,
a 1-butenyl group,
a 2-butenyl group,
a 3-butenyl group,
a 1,3-butanedienyl group, a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described herein include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed herein are merely one example, and the "substituted cycloalkyl group" described herein also includes a group in which "unsubstituted cycloalkyl group" has a substituent further has a substituent, a group in which "substituted cycloalkyl group" further has a substituent, and the like.

An unsubstituted aliphatic ring group:
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

A substituted cycloalkyl group:
a 4-methylcyclohexyl group.

Specific examples (specific example group G7) of the group represented by —Si($R_{901}$)($R_{902}$)($R_{903}$) described herein include
—Si(G1)(G1)(G1),
—Si(G1)(G2)(G2),
—Si(G1)(G1)(G2),
—Si(G2)(G2)(G2),
—Si(G3)(G3)(G3),
—Si(G5)(G5)(G5) and
—Si(G6)(G6)(G6).
In which,
G1 is the "aryl group" described in the specific example group G1.

G2 is the "heterocyclic group" described in the specific example group G2.
G3 is the "alkyl group" described in the specific example group G3.
G5 is the "alkynyl group" described in the specific example group G5.
G6 is the "cycloalkyl group" described in the specific example group G6.

Specific examples (specific example group G8) of the group represented by —O—($R_{904}$) described herein include
—O(G1),
—O(G2),
—O(G3) and
—O(G6).
In which,
G1 is the "aryl group" described in the specific example group G1.
G2 is the "heterocyclic group" described in the specific example group G2.
G3 is the "alkyl group" described in the specific example group G3.
G6 is the "cycloalkyl group" described in the specific example group G6.

Specific examples (specific example group G9) of the group represented by —S—($R_{905}$) described herein include
—S(G1),
—S(G2),
—S(G3) and
—S(G6).
In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G10) of the group represented by —N($R_{906}$)($R_{907}$) described herein include
—N(G1)(G1),
—N(G2)(G2),
—N(G1)(G2),
—N(G3)(G3) and
—N(G6) (G6).
In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G11) of the "halogen atom" described herein include a fluorine atom, a chlorine atom, a bromine atom and an iodine atom.

Specific examples of the "alkoxy group" described herein include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthio group" described herein include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described herein include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described herein include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described herein include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described herein is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described herein is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

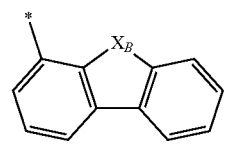

(XY-76)

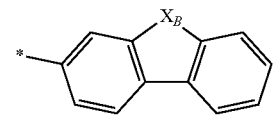

(XY-77)

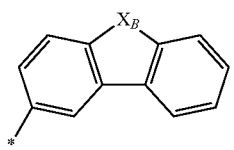

(XY-78)

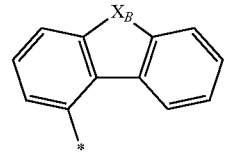

(XY-79)

In the formulas (XY-76) to (XY-79), $X_B$ is an oxygen atom or a sulfur atom.

The substituted or unsubstituted alkyl group described herein is, unless otherwise specified, preferably a methyl group, an ethyl group, a propyl group, an isopropyl group, a n-butyl group, an isobutyl group, a t-butyl group, or the like.

The "substituted or unsubstituted arylene group" descried herein refers to a group in which the above-described "aryl group" is converted into divalence, unless otherwise specified. Specific examples (specific example group G12) of the "substituted or unsubstituted arylene group" include a group in which the "aryl group" described in the specific example group G1 is converted into divalence. Namely, specific examples (specific example group G12) of the "substituted or unsubstituted arylene group" refer to a group derived from the "aryl group" described in specific example group G1 by removal of one hydrogen atom bonded to the ring carbon atoms thereof.

Specific examples (specific example group G13) of the "substituted or unsubstituted divalent heterocyclic group" include a group in which the "heterocyclic group" described in the specific example group G2 is converted into divalence. Namely, specific examples (specific example group G13) of the "substituted or unsubstituted divalent heterocyclic group" refer to a group derived from the "heterocyclic group" described in specific example group G2 by removal of one hydrogen atom bonded to the ring atoms thereof.

Specific examples (specific example group G14) of the "substituted or unsubstituted alkylene group" include a group in which the "alkyl group" described in the specific example group G3 is converted into divalence. Namely, specific examples (specific example group G14) of the "substituted or unsubstituted alkylene group" refer to a group derived from the "alkyl group" described in specific example group G3 by removal of one hydrogen atom bonded to the carbon atoms constituting the alkane structure thereof.

The substituted or unsubstituted arylene group described herein is any group described below, unless otherwise specified.

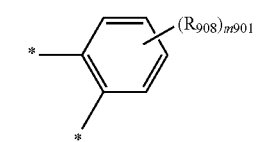
(XY-20)

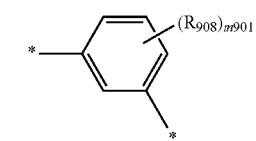
(XY-21)

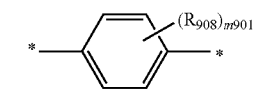
(XY-22)

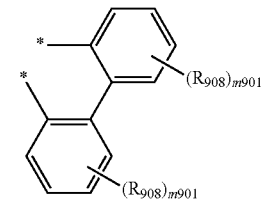
(XY-23)

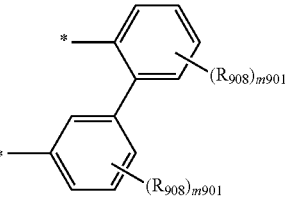
(XY-24)

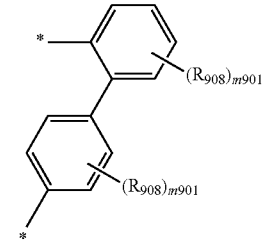
(XY-25)

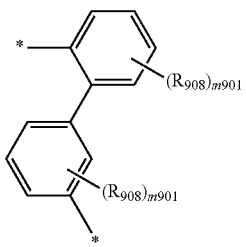
(XY-26)

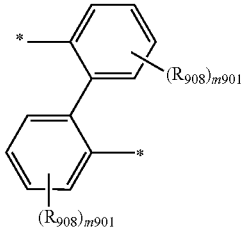
(XY-27)

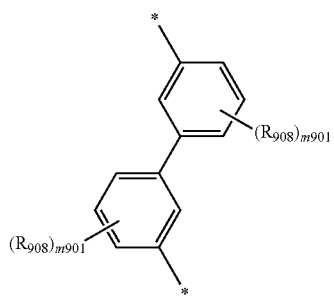
(XY-28)

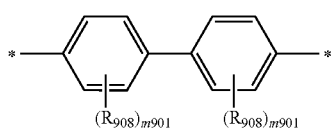
(XY-29)

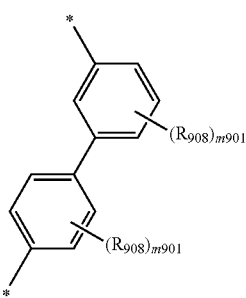
(XY-83)

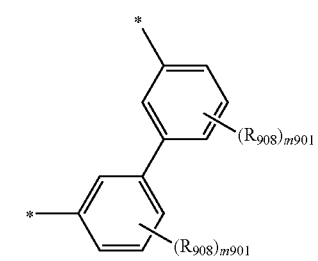
(XY-84)

In the formulas (XY-20) to (XY-29), (XY-83) and (XY-84), $R_{908}$ is a substituent.

Then, m901 is an integer of 0 to 4, and when m901 is 2 or more, a plurality of $R_{908}$ may be the same with or different from each other.

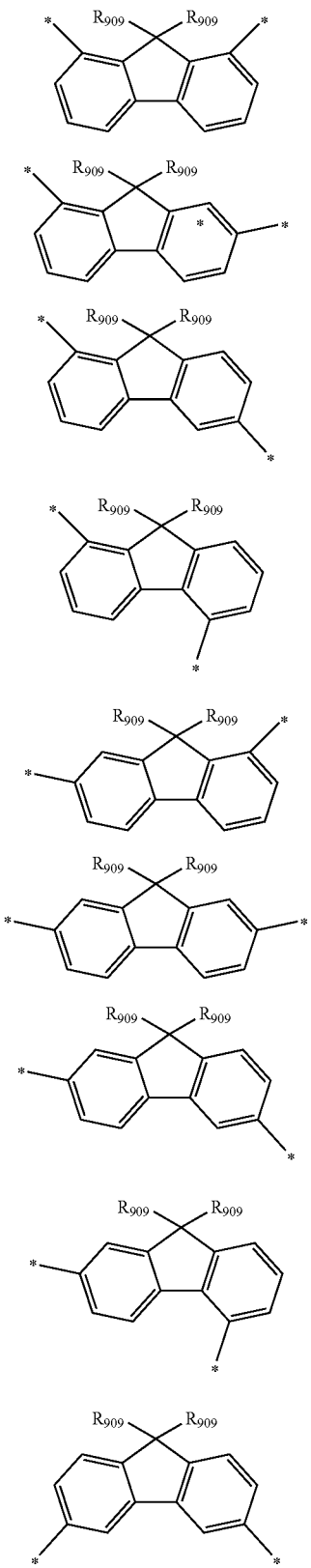

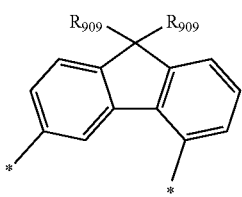

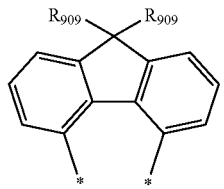

In the formulas (XY-30) to (XY-40), $R_{909}$ is independently a hydrogen atom or a substituent. Two of $R_{909}$ may be bonded with each other through a single bond to form a ring.

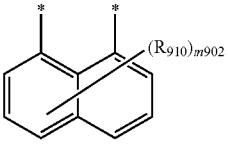

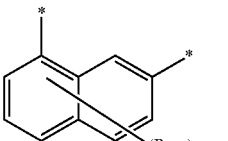

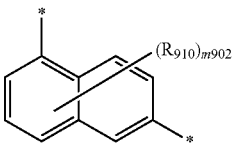

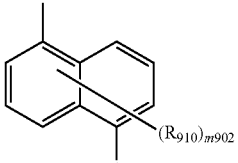

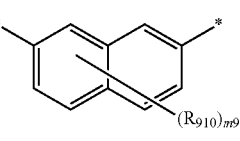

In the formulas (XY-41) to (XY-46), $R_{910}$ is a substituent. Then, m902 is an integer of 0 to 6. When m902 is 2 or more, a plurality of $R_{910}$ may be the same with or different from each other.

The substituted or unsubstituted divalent heterocyclic group described herein is preferably any group described below, unless otherwise specified.
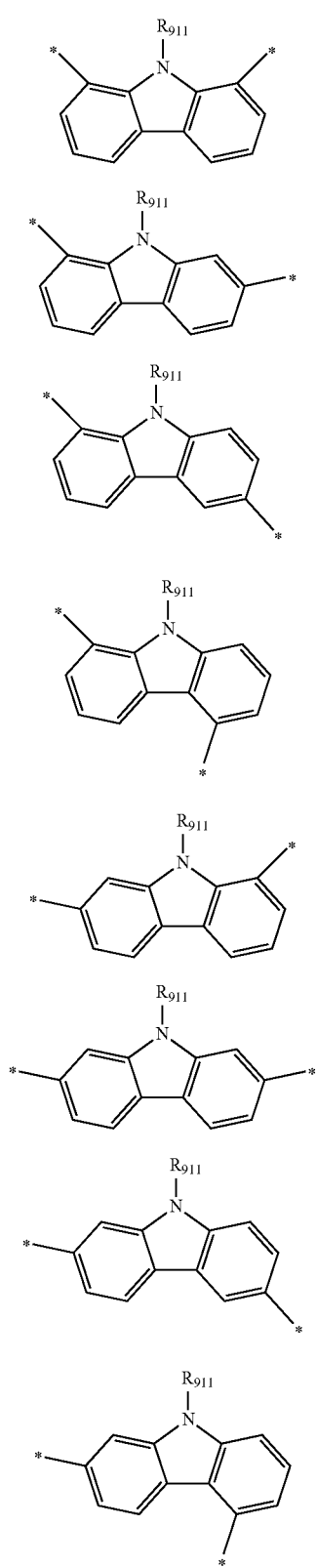
(XY-50)
(XY-51)
(XY-52)
(XY-53)
(XY-54)
(XY-55)
(XY-56)
(XY-57)
-continued
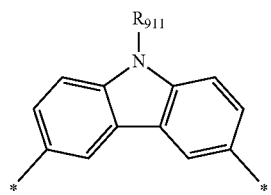
(XY-58)
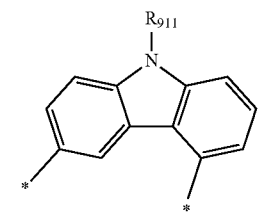
(XY-59)
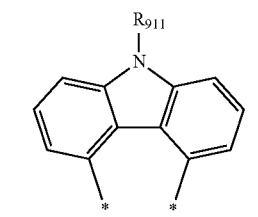
(XY-60)
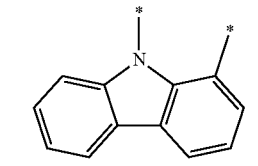
(XY-61)
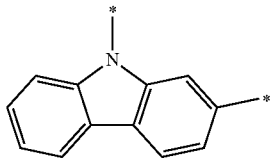
(XY-62)
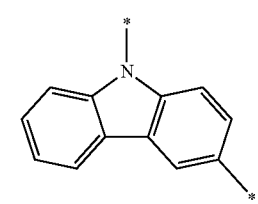
(XY-63)
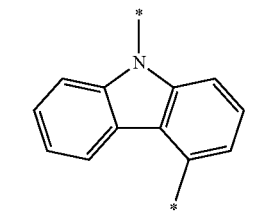
(XY-64)
In the formulas (XY-50) to (XY-60), $R_{911}$ is a hydrogen atom or a substituent.

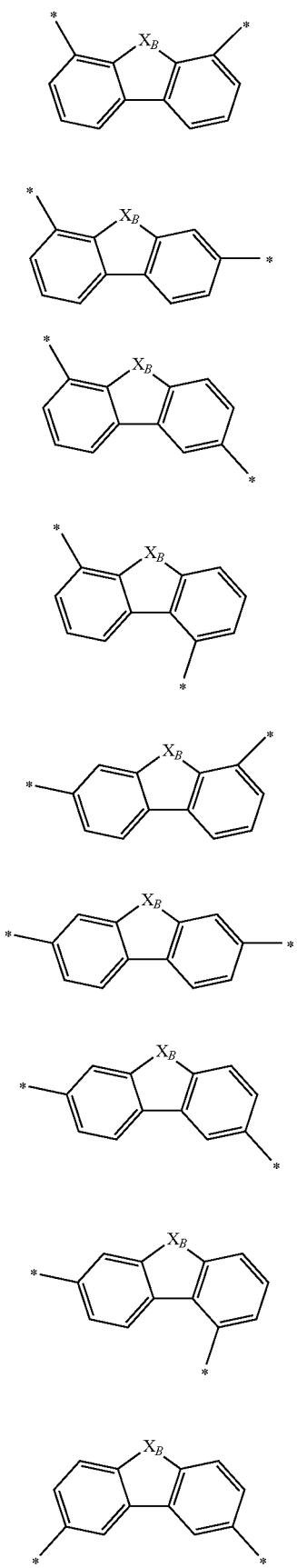

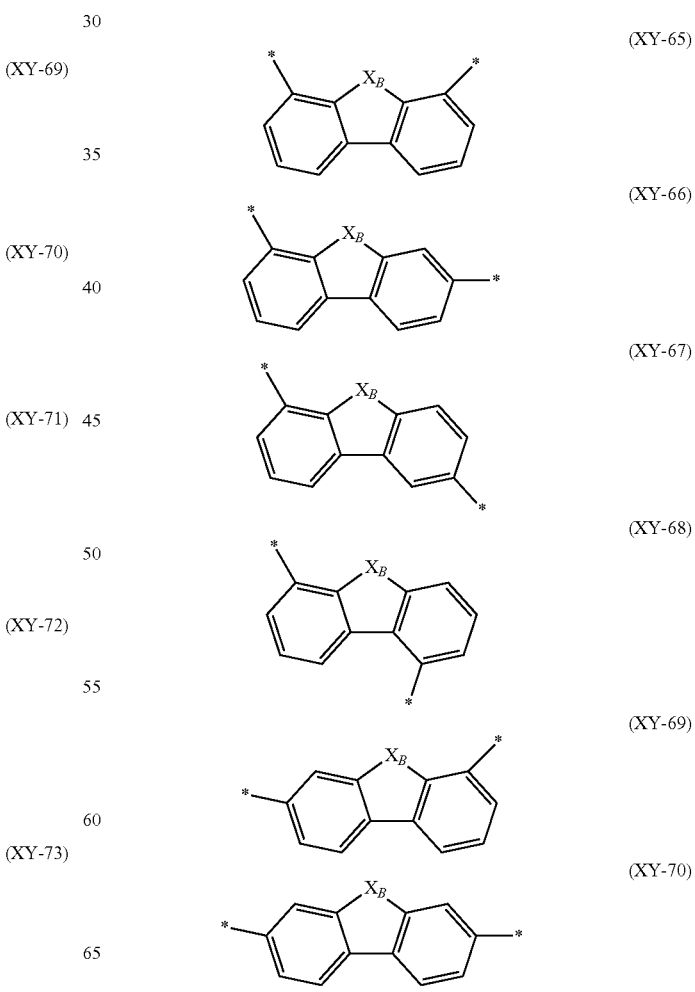

In the formulas (XY-65) to (XY-75), $X_B$ is an oxygen atom or a sulfur atom.

Herein, a case where "one or more sets of two or more groups adjacent to each other are bonded with each other to form a substituted or unsubstituted and saturated or unsaturated ring" will be described by taking, as an example, a case of an anthracene compound represented by the following formula (XY-80) in which a mother skeleton is an anthracene ring.

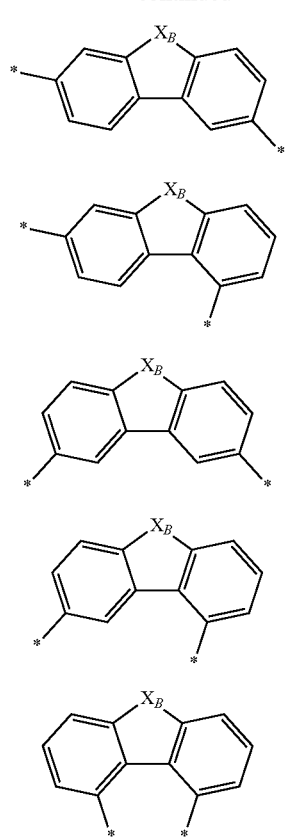

(XY-71)

(XY-72)

(XY-73)

(XY-74)

(XY-75)

For example, two adjacent to each other into one set when "one or more sets of two or more groups adjacent to each other are bonded with each other to form the ring" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ are bonded with each other to form a ring A, and simultaneously $R_{925}$ and $R_{926}$ are bonded with each other to form a ring B is represented by the following formula (XY-81).

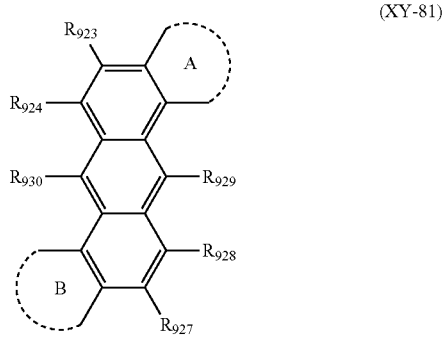

(XY-81)

A case where "two or more groups adjacent to each other" form a ring means that, for example, $R_{921}$ and $R_{922}$ are bonded with each other to form a ring A, and $R_{922}$ and $R_{923}$ are bonded with each other to form a ring C. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

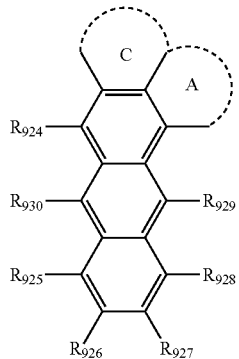

(XY-82)

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the bond(s) that is(are) not involved in the formation of the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

As specific examples of the aromatic hydrocarbon ring, a structure in which the aryl group described in specific example group G1 is terminated with a hydrogen atom may be mentioned.

As specific examples of the aromatic heterocyclic ring, a structure in which the aromatic heterocyclic group described in specific example group G2 is terminated with a hydrogen atom may be mentioned.

As specific examples of the aliphatic hydrocarbon ring, a structure in which the cycloalkyl group described in specific example group G6 is terminated with a hydrogen atom may be mentioned.

When the above-described "saturated or unsaturated ring" has a substituent, the substituent is an "arbitrary substituent" as described below, for example. When the above-mentioned "saturated or unsaturated ring" has a substituent, specific examples of the substituent refer to the substituents described in above-mentioned "the substituent described herein".

In one embodiment of the present specification, the substituent (hereinafter, referred to as an "arbitrary substituent" in several cases) in the case of the "substituted or unsubstituted" is a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$),
—O—($R_{904}$),
—S—($R_{905}$)
—N($R_{906}$)($R_{907}$)
wherein,
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms; and when two or more of $R_{901}$ to $R_{907}$ exist, two or more of $R_{901}$ to $R_{907}$ may be the same with or different from each other,
a halogen atom, a cyano group, a nitro group,
an unsubstituted aryl group having 6 to 50 ring carbon atoms, and
an unsubstituted monovalent heterocyclic group having 5 to 50 ring atoms.

In one embodiment, the substituent in the case of "substituted or unsubstituted" is a group selected from the group consisting of
an alkyl group having 1 to 50 carbon atoms,
an aryl group having 6 to 50 ring carbon atoms, and
a monovalent heterocyclic group having 5 to 50 ring atoms.

In one embodiment, the substituent in the case of "substituted or unsubstituted" is a group selected from the group consisting of
an alkyl group having 1 to 18 carbon atoms,
an aryl group having 6 to 18 ring carbon atoms, and
a monovalent heterocyclic group having 5 to 18 ring atoms.

Specific examples of each group of the arbitrary substituent described above are as described above.

Herein, unless otherwise specified, the saturated or unsaturated ring (preferably substituted or unsubstituted and saturated or unsaturated five-membered or six-membered ring, more preferably a benzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[Organic EL Device]

The organic EL device according to one aspect of the invention comprises a cathode, an anode and an emitting layer disposed between the cathode and the anode, and it is characterized in that the emitting layer comprises a compound represented by the following formula (1) and one or more compounds selected from the group consisting of compounds represented by formulas (11), (21), (31), (41), (51), (61), (71) and (81).

Each compound is described later.

The organic EL device according to one aspect of the invention exhibits high device performance by possessing the above-mentioned constitution. Specifically, it is possible to provide an organic EL device with longer life.

According to one aspect of the present invention, a method for improving a performance of an organic EL device can also be provided. the method is characterized in that the compound represented by the formula (1) and one or more compounds selected from the group consisting of the formulas (11) to (81) are used in combination in the emitting layer of the organic EL device. Specifically, the method can improve an organic EL device performance as compared with the case where a compound having the same structure as formula (1) except that only protium atoms are contained as hydrogen atoms (hereinafter also referred to as "protium compound") is used as a host material. The case where the protium compound is used means that a host material in an emitting layer consists essentially of the protium compound (the ratio of the protium compound to the sum of the protium compound and the compound represented by formula (1) is 90 mol % or more, 95 mol % or more, or 99 mol % or more).

That is, it is possible to increase a performance of an organic EL device by, instead of a protium compound or in addition to a protium compound, using a compound obtained by replacing at least one protium atoms on an anthracene skeleton of the protium compound with a deuterium atom (a compound represented by formula (1)) as a host material.

A schematic outline of the organic EL device of one aspect of the invention is explained by reference to the FIGURE.

The organic EL device 1 according to one aspect of the invention comprises substrate 2, anode 3, emitting layer 5, cathode 10, organic layer 4 disposed between the anode 3 and the emitting layer 5, and organic layer 6 disposed between the emitting layer 5 and the cathode 10.

The compound represented by the formula (1) and one or more compounds selected from a group consisting of compounds represented by the formula (11), (21), (31), (41), (51), (61), (71) and (81) are contained in emitting layer 5 disposed between the anode 3 and the cathode 10. Each compound contained in the emitting layer 5 may be used singly or in combination of two or more.

(Compound Represented by Formula (1))

The compound represented by the formula (1) is explained below.

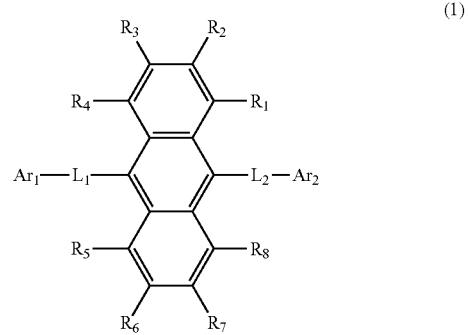

(1)

wherein in the formula (1),
$R_1$ to $R_8$ are independently
a hydrogen atom,
a substituted or unsubstituted alkyl group having 1 to 50 carbon atoms, a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;
$Ar_1$ is
a substituted or unsubstituted aryl group having 6 to 50 ring carbon atoms, or
a substituted or unsubstituted monovalent heterocyclic group having 5 to 50 ring atoms;
$Ar_2$ is a monovalent group represented by the following formula (2), (3) or (4);

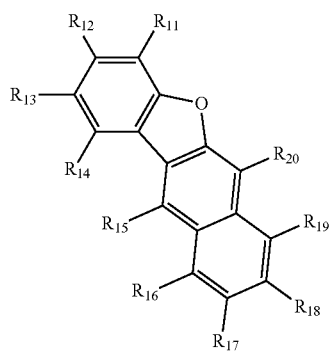

(2)

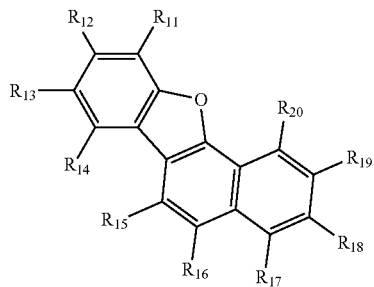

(3)

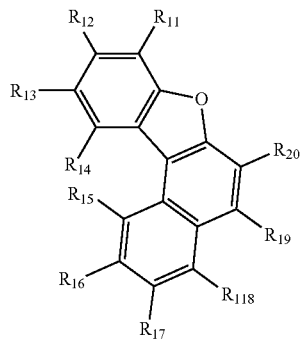

(4)

wherein in the formulas (2) to (4),
one or more pairs of two adjacent groups of $R_{15}$ to $R_{20}$ are bonded with each other to form a substituted or unsubstituted, saturated or unsaturated ring, or do not form a substituted or unsubstituted, saturated or unsaturated ring;
when one or more pairs of two adjacent groups of $R_{15}$ to $R_{20}$ are not bonded with each other and do not form a substituted or unsubstituted, saturated or unsaturated ring, one of $R_{11}$ to $R_{20}$ is a single bond bonding to $L_2$;
when one or more pairs of two adjacent groups of $R_{15}$ to $R_{20}$ are bonded with each other to form a substituted or unsubstituted, saturated or unsaturated ring, one of $R_{15}$ to $R_{20}$ which does not form a substituted or unsubstituted, saturated or unsaturated ring and $R_{11}$ to $R_{14}$ is a single bond bonding to $L_2$;
$R_{11}$ to $R_{20}$ that do not form the substituted or unsubstituted, saturated or unsaturated ring and that are not a single bond bonding to $L_2$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1);
All of $R_1$ to $R_8$ may be deuterium atoms or a part of them (e.g., one, two or more of $R_1$ to $R_8$) may be deuterium atoms.

$R_1$ to $R_8$ that are not deuterium atoms are preferably hydrogen atoms (protium atoms).

In one embodiment, at least one hydrogen atom contained in one or more groups selected from a group consisting of $L_1$ and $L_2$ is a deuterium atom. In more detail, in one embodiment, one or more groups selected from the group consisting of $L_1$ and $L_2$ are an unsubstituted arylene group having 6 to 30 ring carbon atoms in which at least one hydrogen atom is a deuterium atom, or an unsubstituted divalent heterocyclic group having 5 to 30 ring atoms in which at least one hydrogen atom is a deuterium atom.

In one embodiment, $L_1$ and $L$ 2 are independently a single bond, or a substituted or unsubstituted arylene group having 6 to 14 ring carbon atoms. It is preferable that at least one of $L_1$ and $L$ 2 is a single bond.

In one embodiment, any one of $R_{11}$ to $R_{14}$ in formulas (2) to (4) is a single bond bonding to $L_2$.

In one embodiment, one or more pairs of two adjacent groups of $R_{15}$ to $R_{20}$ in formulas (2) to (4) are not bonded with each other and do not form a substituted or unsubstituted, saturated or unsaturated ring.

In one embodiment, among $R_{11}$ to $R_{20}$ in the formulas (2) to (4), those which are not a single bond bonding to $L_2$ and do not contribute to ring formation are preferably hydrogen atoms.

In one embodiment, among $R_{11}$ to $R_{20}$ in the formulas (2) to (4), at least one which is not a single bond bonding to $L_2$ and does not contribute to ring formation is a deuterium atom.

In one embodiment, at least one hydrogen atom contained in one or more $Ar_1$ is a deuterium atom. In more detail, in one embodiment, $Ar_1$ is an unsubstituted aryl group having 6 to 50 ring carbon atoms in which at least one hydrogen atom is a deuterium atom, or an unsubstituted monovalent heterocyclic group having 5 to 50 ring atoms in which at least one hydrogen atom is a deuterium atom.

Existence of a deuterium atom in the compound is confirmed by Mass Spectrometry or $^1$H-NMR Spectrometry. The bonding position of a deuterium atom in the compound is identified by $^1$H-NMR Spectrometry. In concrete terms, it is confirmed as follows.

If it is identified that, by Mass Spectrometry, a molecular weight of a target compound is greater by "one" than a molecular weight of a corresponding compound in which all hydrogen atoms are protium atoms, it is confirmed that one deuterium atom exists in the target compound. Further, the number of deuterium atoms in a molecule can be confirmed by an integration value obtained by $^1$H-NMR analysis on the target compound, since no signal is observed by performing $^1$H-NMR analysis on a deuterium atom. The bonding position of a deuterium can be identified by performing $^1$H-NMR analysis on the target compound and assigning signals.

In the organic EL device according to one aspect of the invention, the content ratio of the protium compound to the total of the compound represented by formula (1) and the protium compound in the emitting layer is preferably 99 mol % or less. The content ratio of the protium compound is confirmed by Mass Spectrometry.

In one embodiment, the emitting layer of the organic EL device according to one aspect of the invention includes the compound represented by the formula (1) and a protium compound, and the content ratio of the former to the total thereof is 30 mol % or more, 50 mol % or more, 70 mol % or more, 90 mol % or more, 95 mol % or more, 99 mol % or more, or 100 mol %.

$Ar_1$ is preferably a substituted or unsubstituted aryl group having 6 to 50 ring carbon atoms, more preferably selected from groups represented by the following formulas (a1) to (a4).

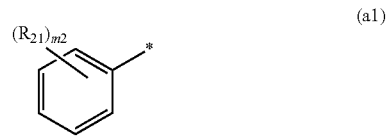

(a1)

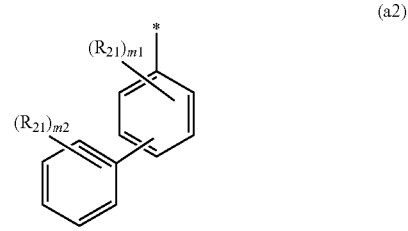

(a2)

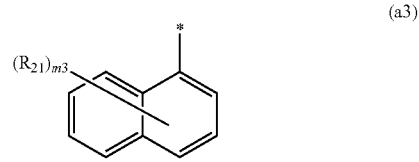

(a3)

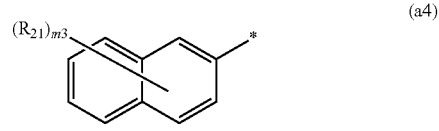

(a4)

wherein in the formulas (a1) to (a4),
* is a single bond bonding to $L_1$;
$R_{21}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
m1 is an integer of 0 to 4;
m2 is an integer of 0 to 5;
m3 is an integer of 0 to 7;
when each of m1 to m3 is 2 or more, the plural $R_{21}$s may be the same or different; and
when each of m1 to m3 is 2 or more, adjacent plural $R_{21}$s are bonded with each other to form a substituted or unsubstituted, saturated or unsaturated ring, or do not form a substituted or unsubstituted, saturated or unsaturated ring.

Preferably, $L_1$ and $L$ 2 are independently a single bond, or a substituted or unsubstituted arylene group having 6 to 14 ring carbon atoms. It is preferable that at least one of $L_1$ and $L$ 2 is a single bond.

In one embodiment, the compound represented by the formula (1) is a compound represented by any one of following formulas (1-1) to (1-3).

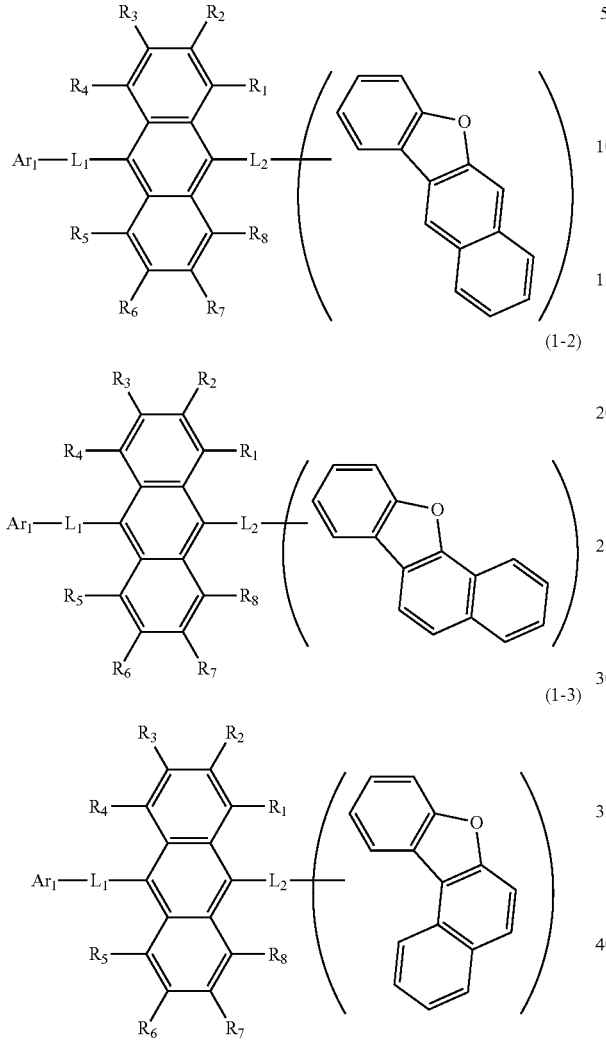

wherein in the formulas (1-1) to (1-3), $R_1$ to $R_8$, $Ar_1$, $L_1$ and $L_2$ are as defined in the formula (1).

In one embodiment, the compound represented by the formula (1) is a compound represented by any one of following formulas (1-11) to (1-13).

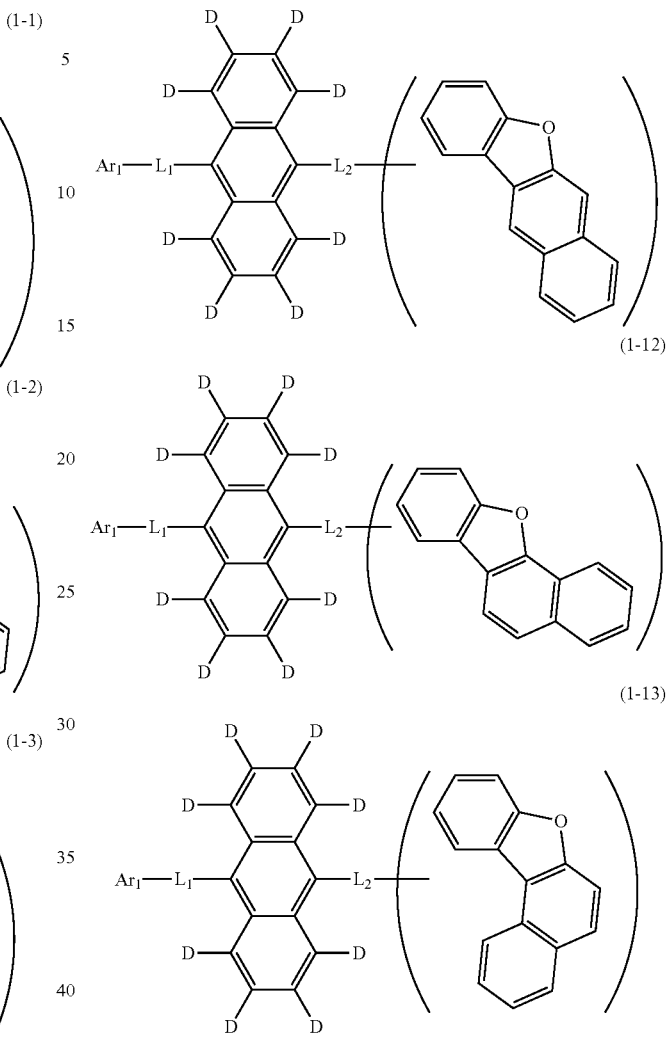

wherein in the formulas (1-11) to (1-13), $Ar_1$, $L_1$ and $L_2$ are as defined in the formula (1).

The compound represented by the formula (1) can be synthesized in accordance with the synthesis process described in Examples by using publicly known alternative reactions or materials corresponding to a target compound.

Examples of the compound represented by formula (1) include the following compounds.

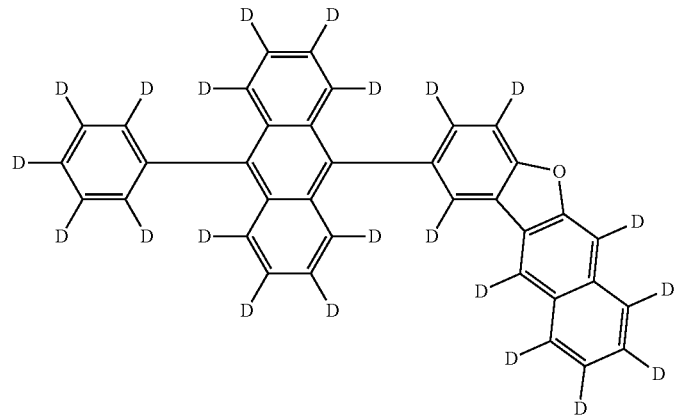

-continued
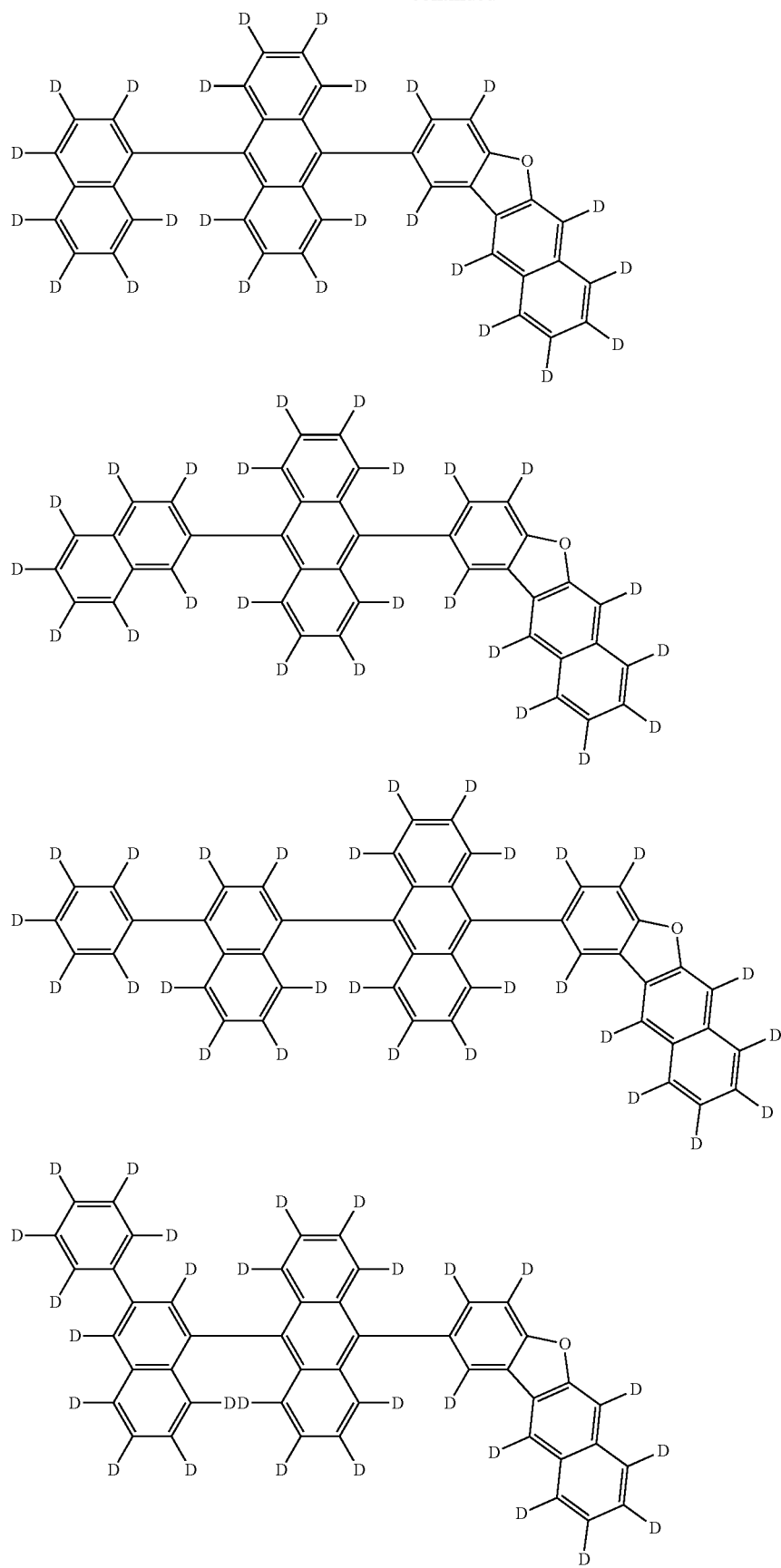

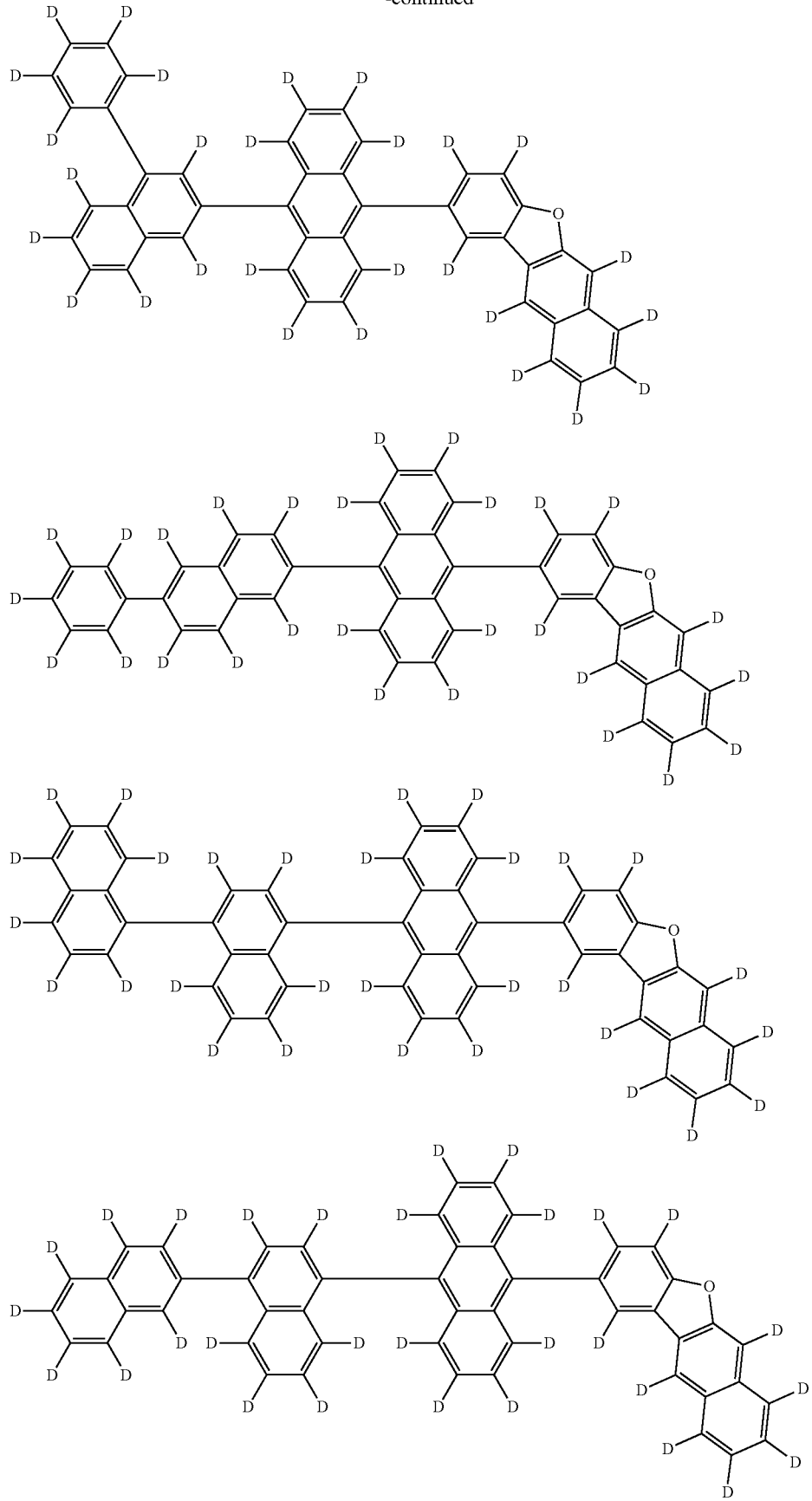

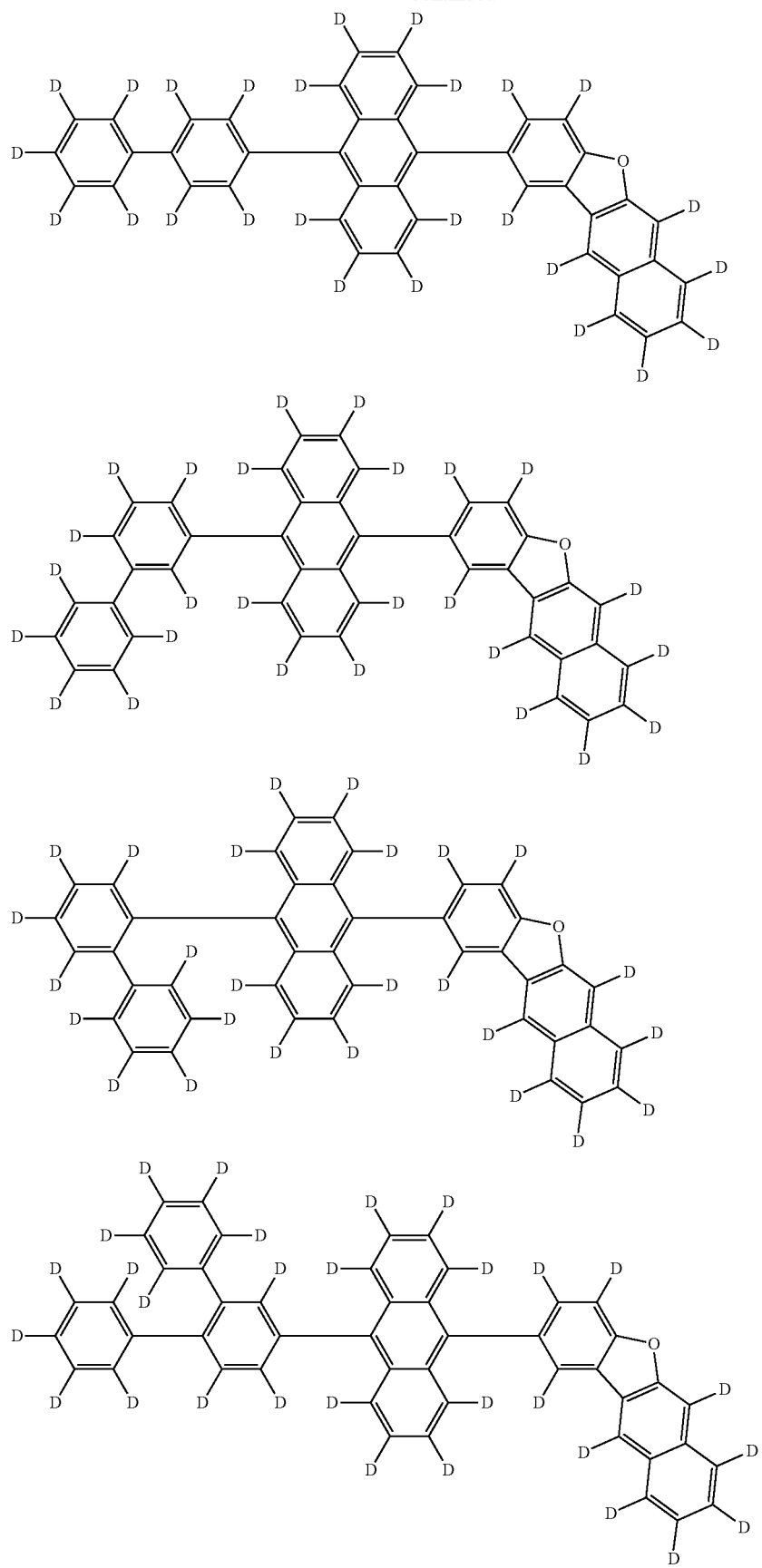

-continued
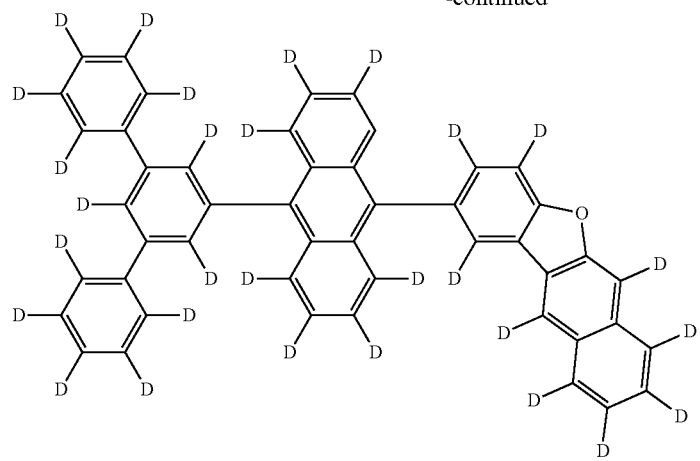
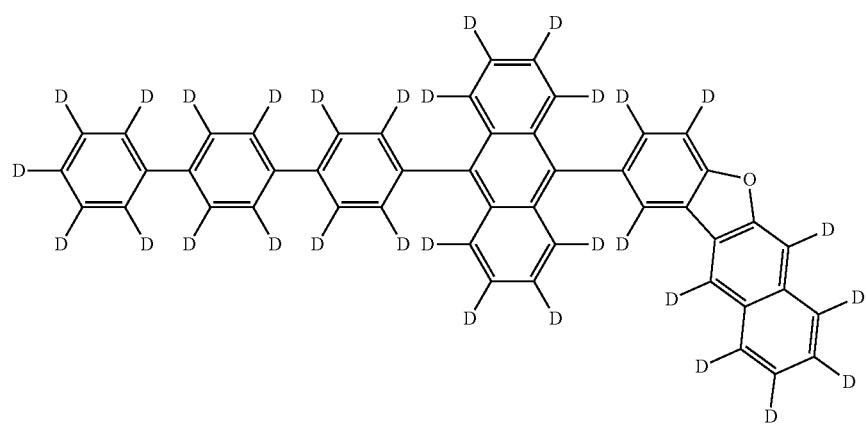
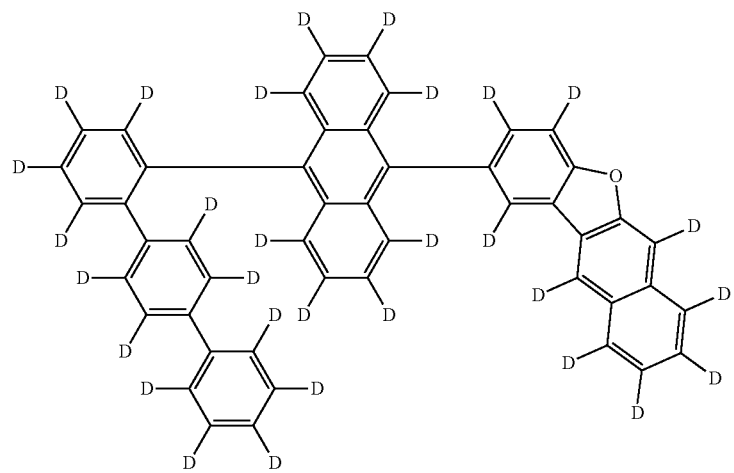

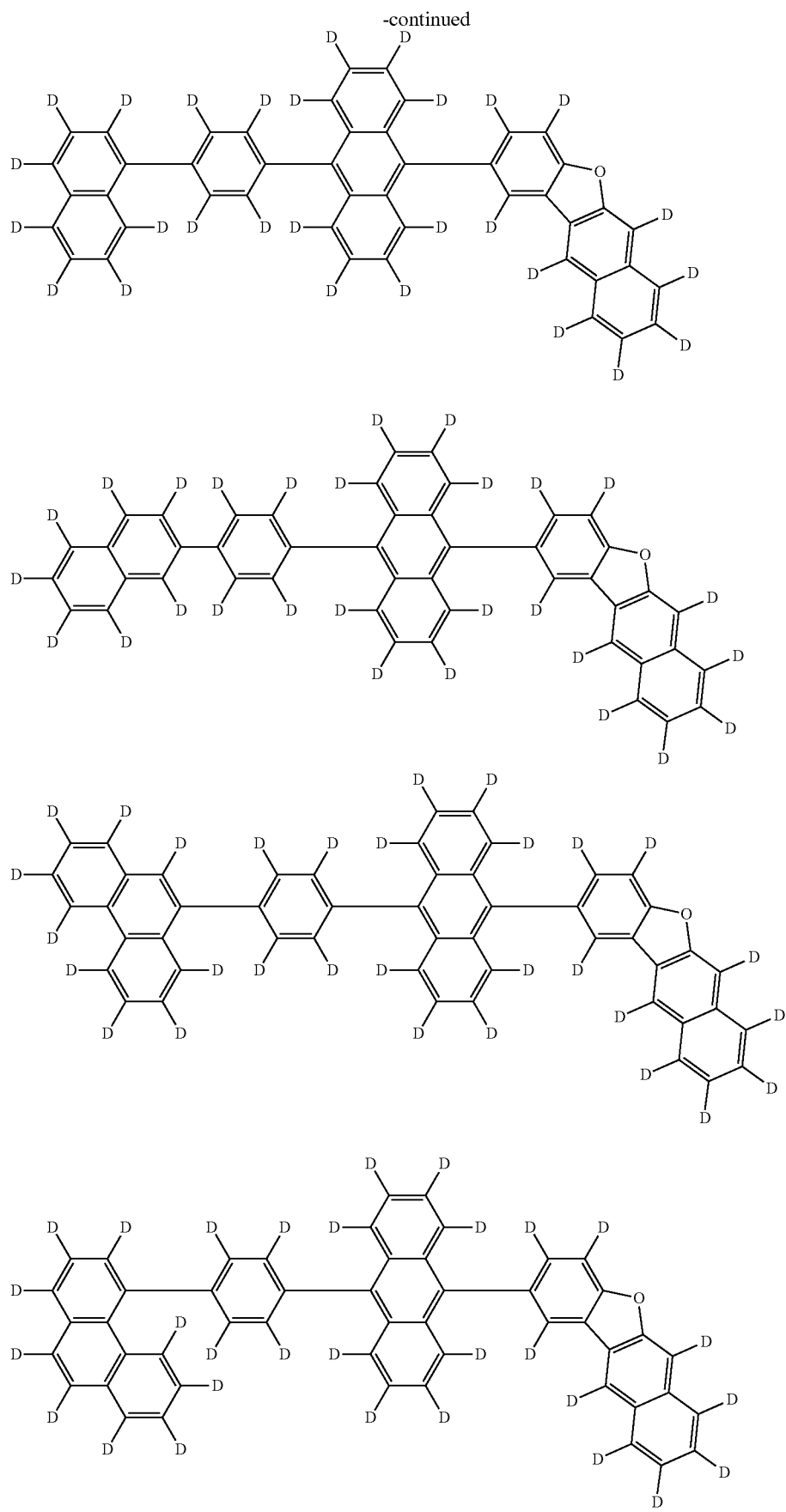

-continued
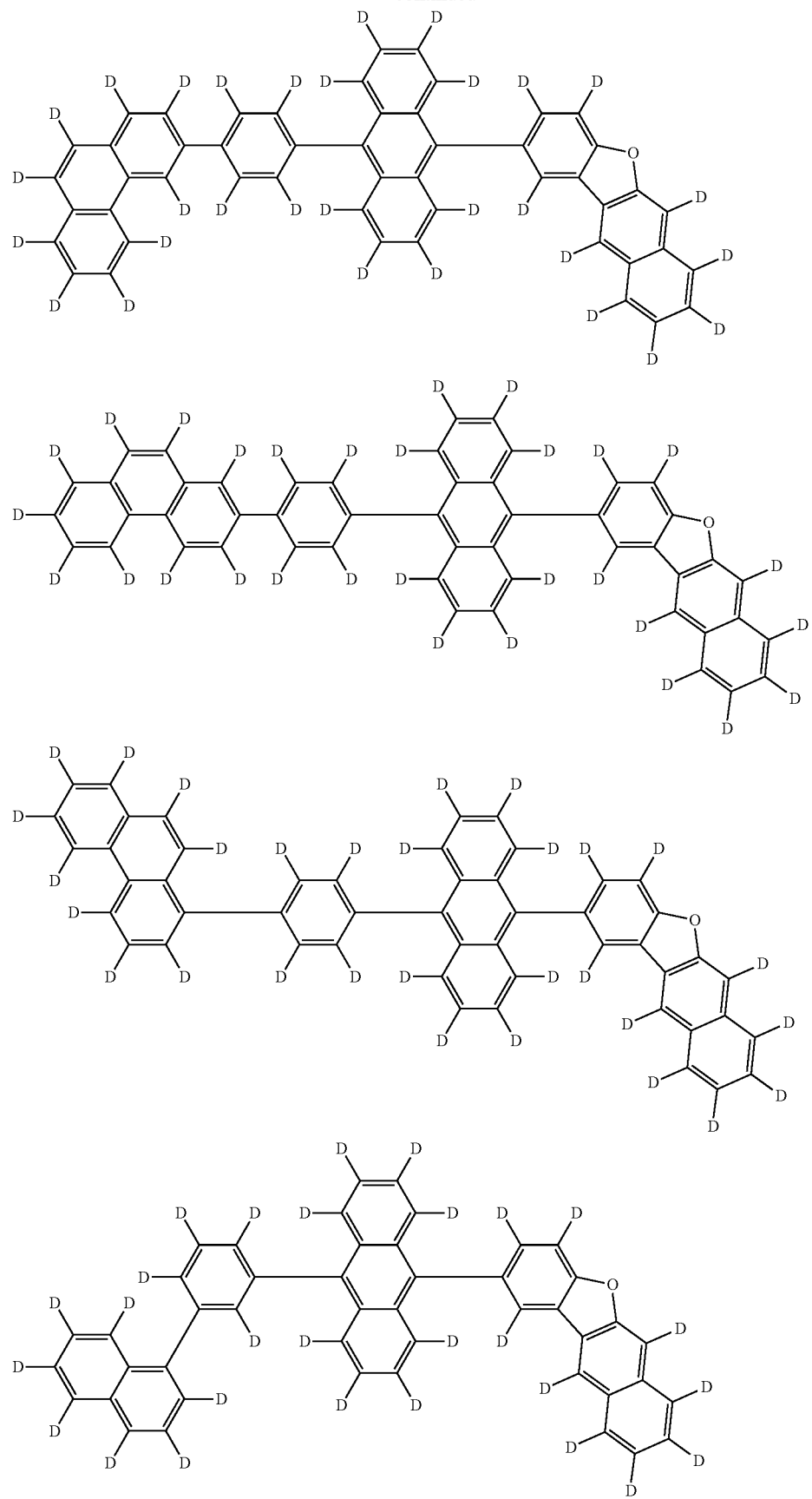

-continued
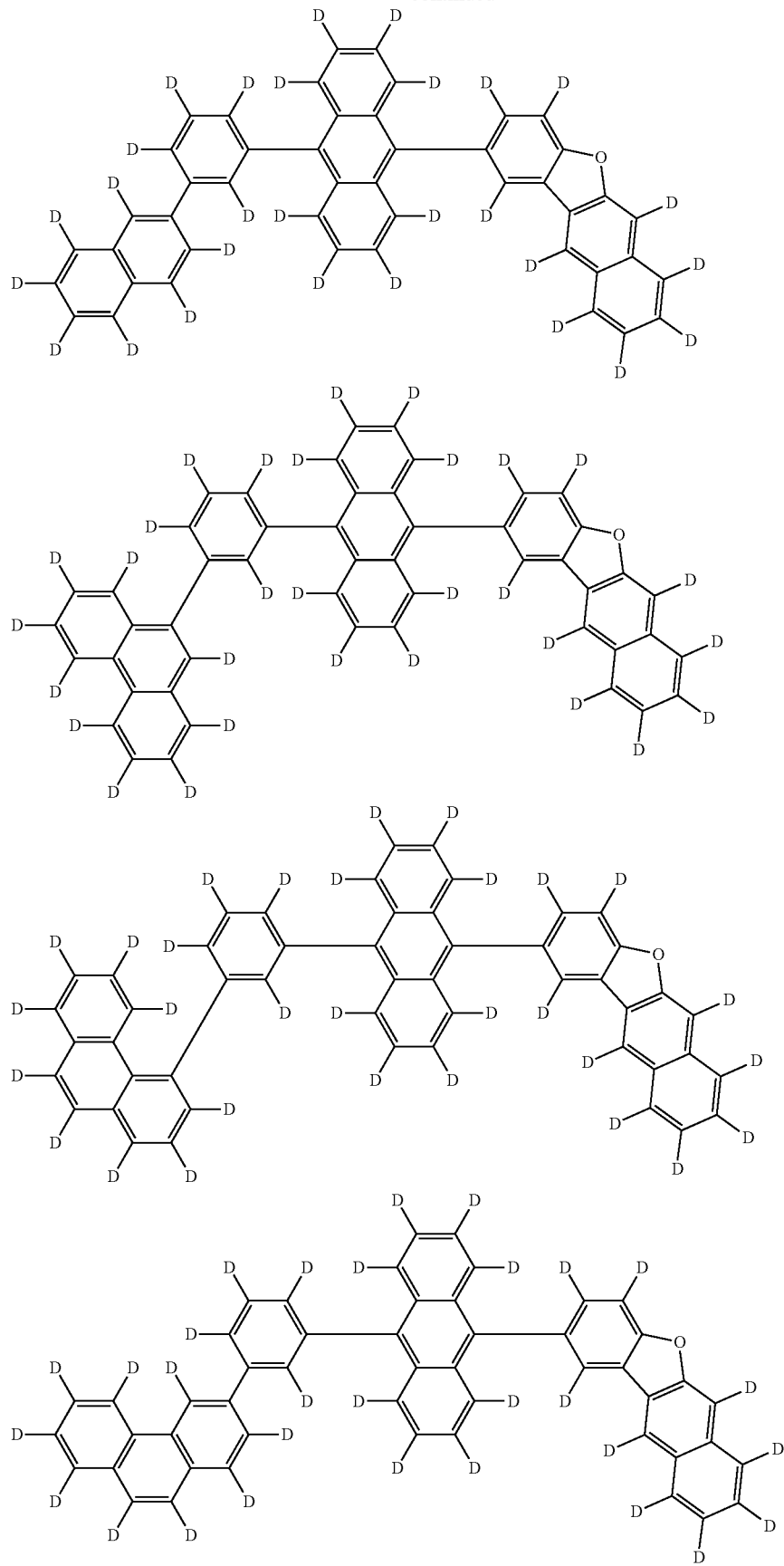

-continued
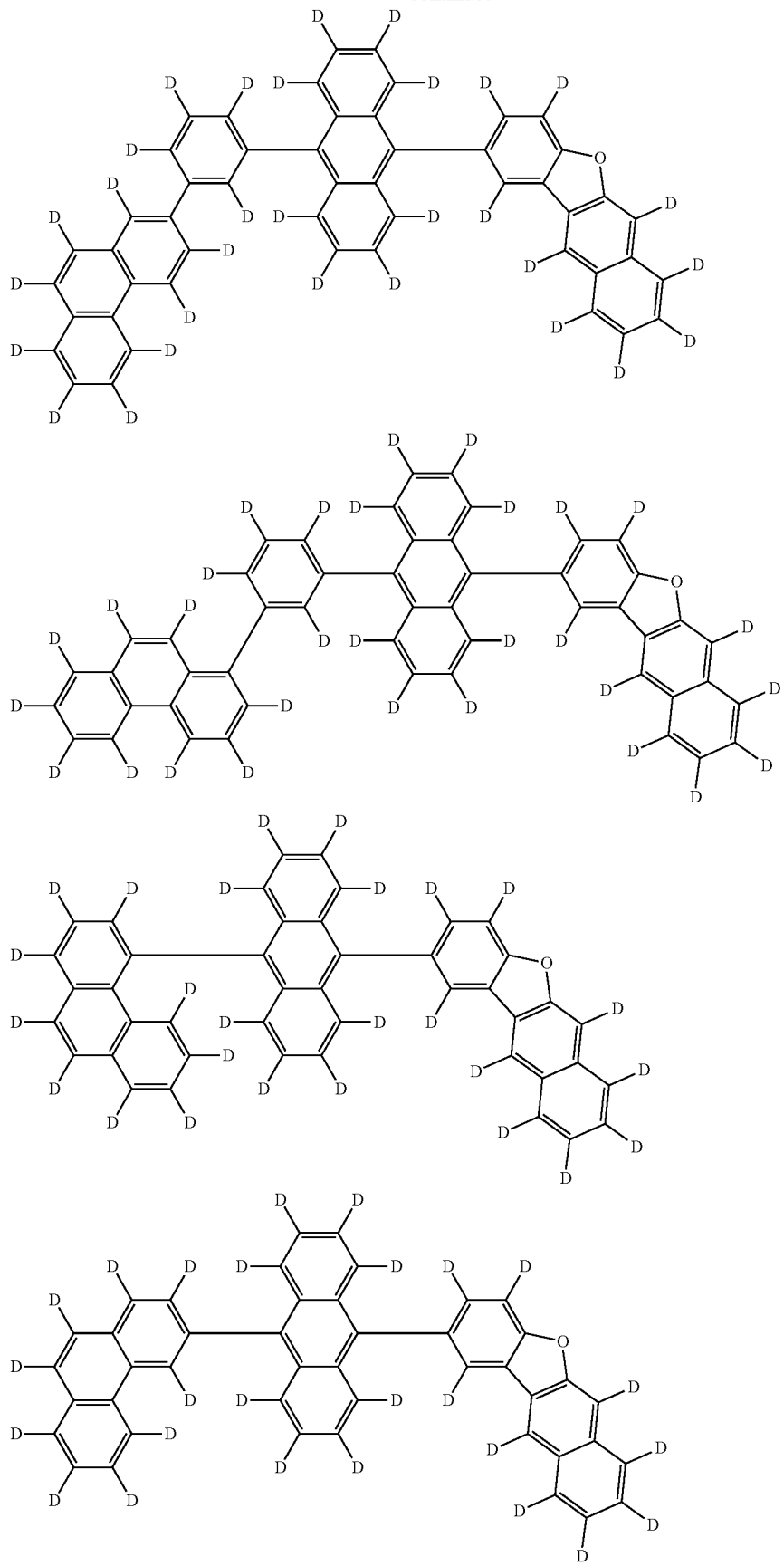

-continued
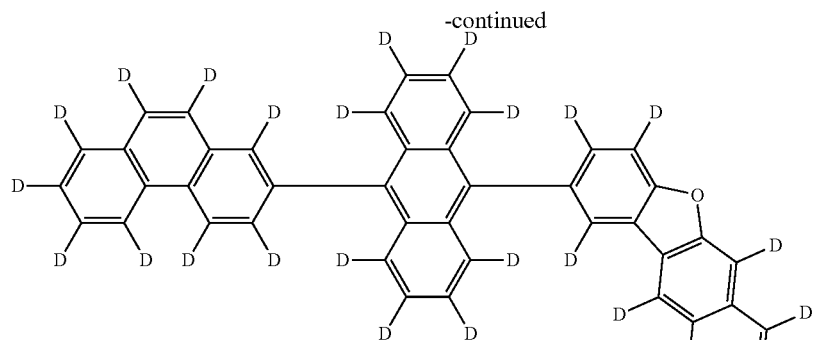
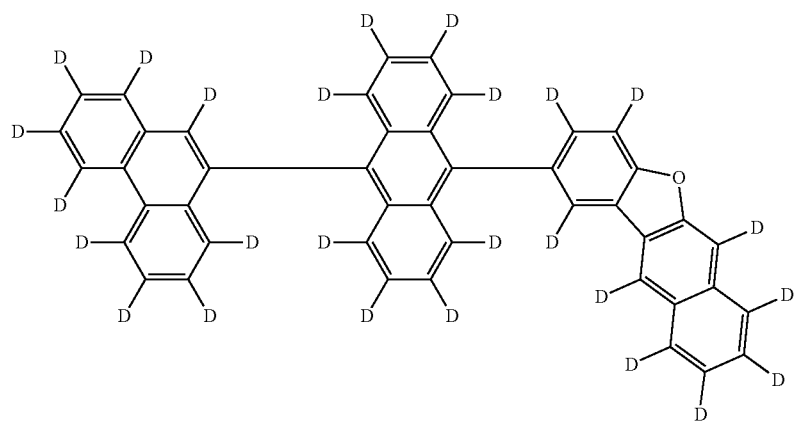
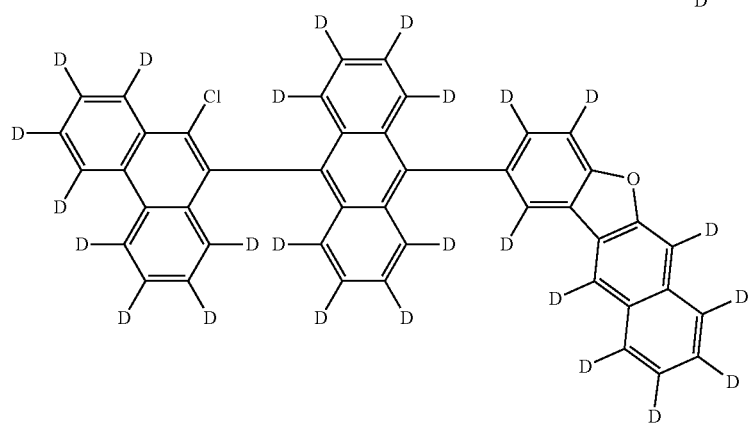
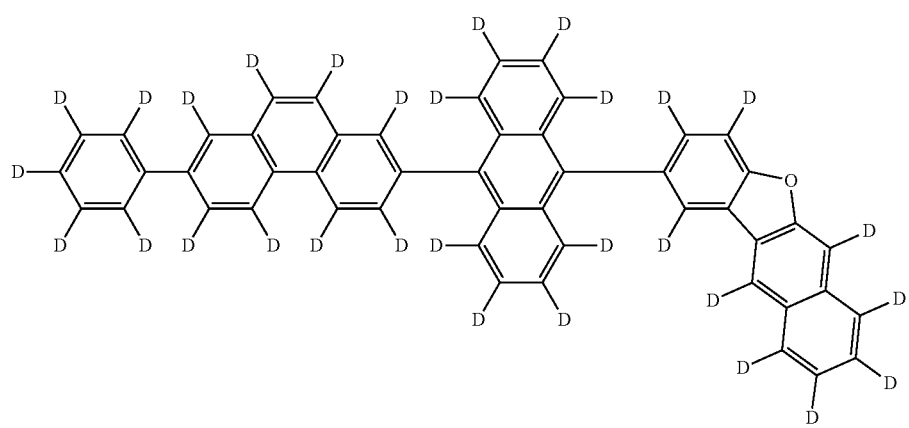

-continued
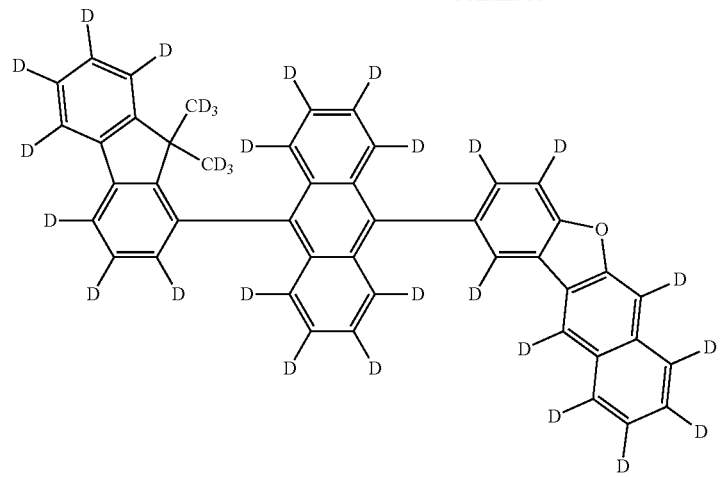
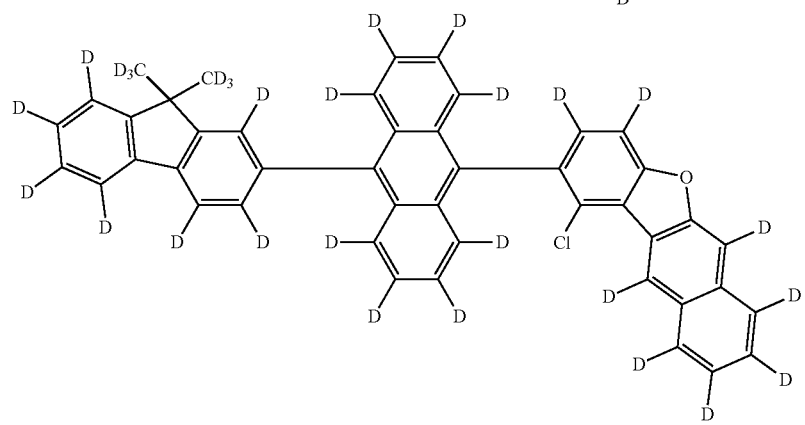
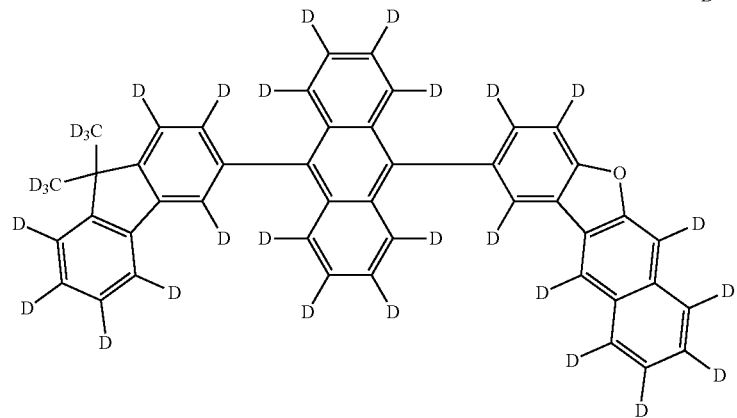
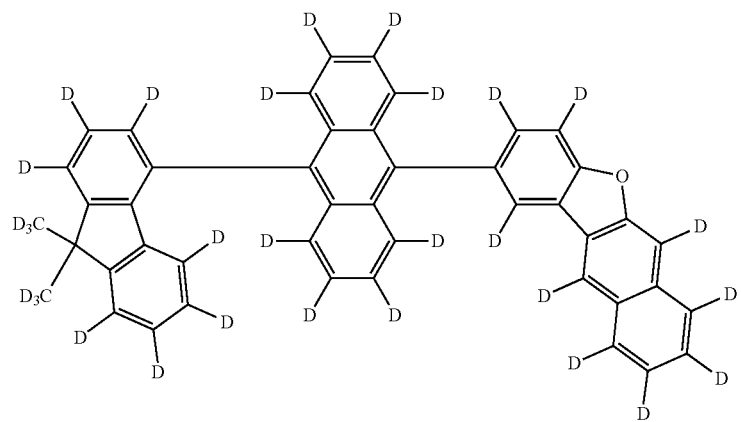

-continued
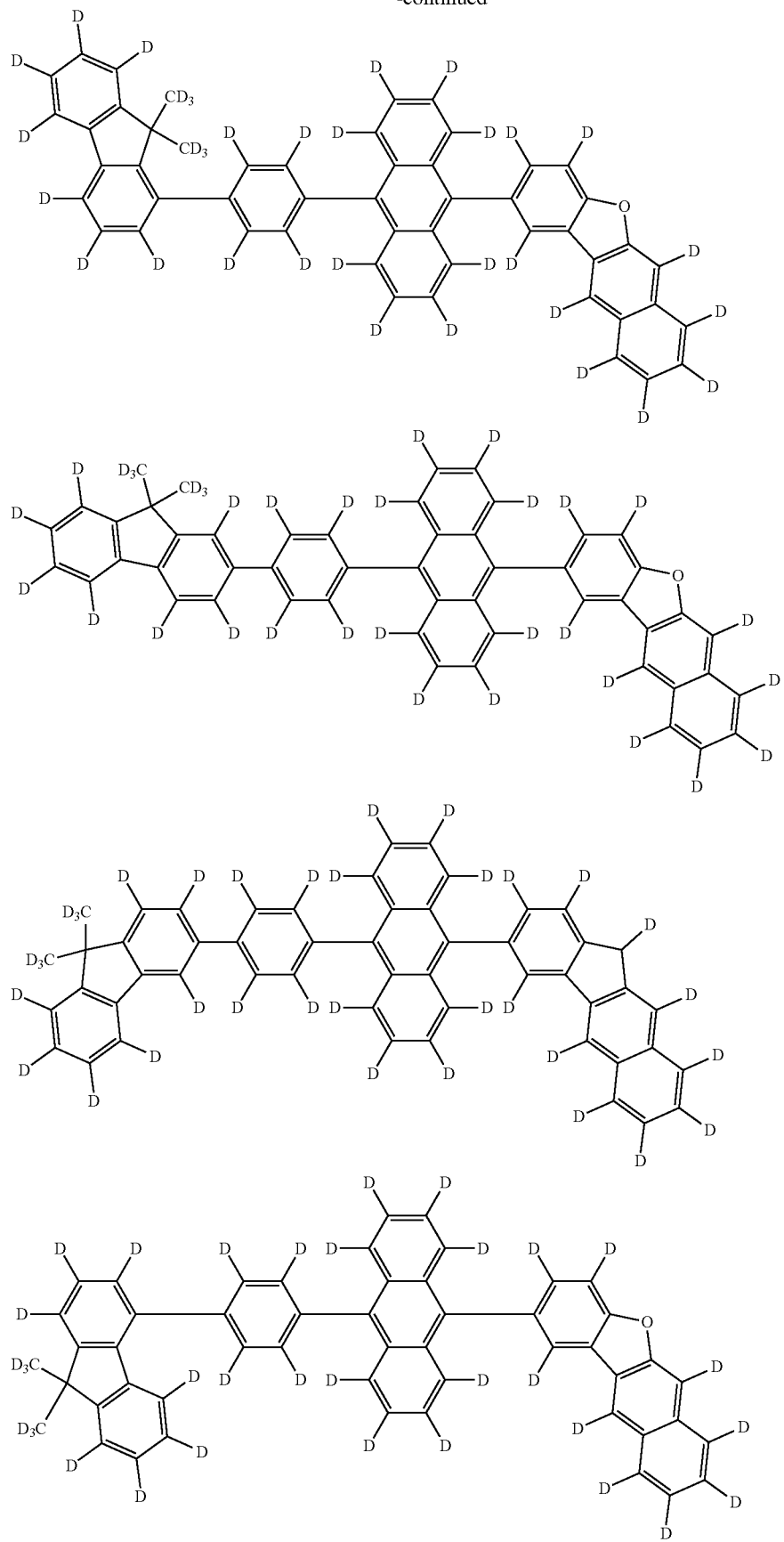

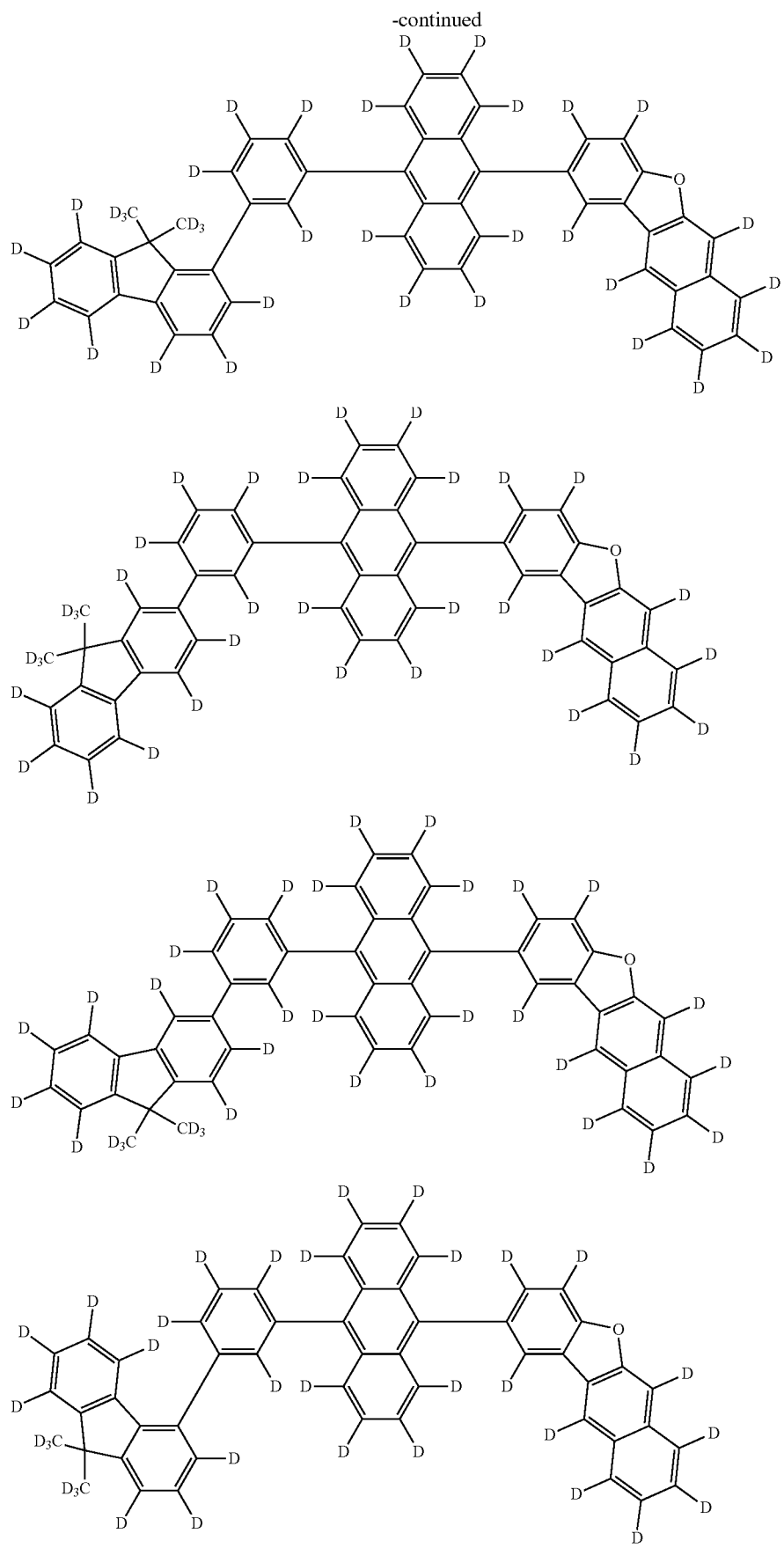

-continued
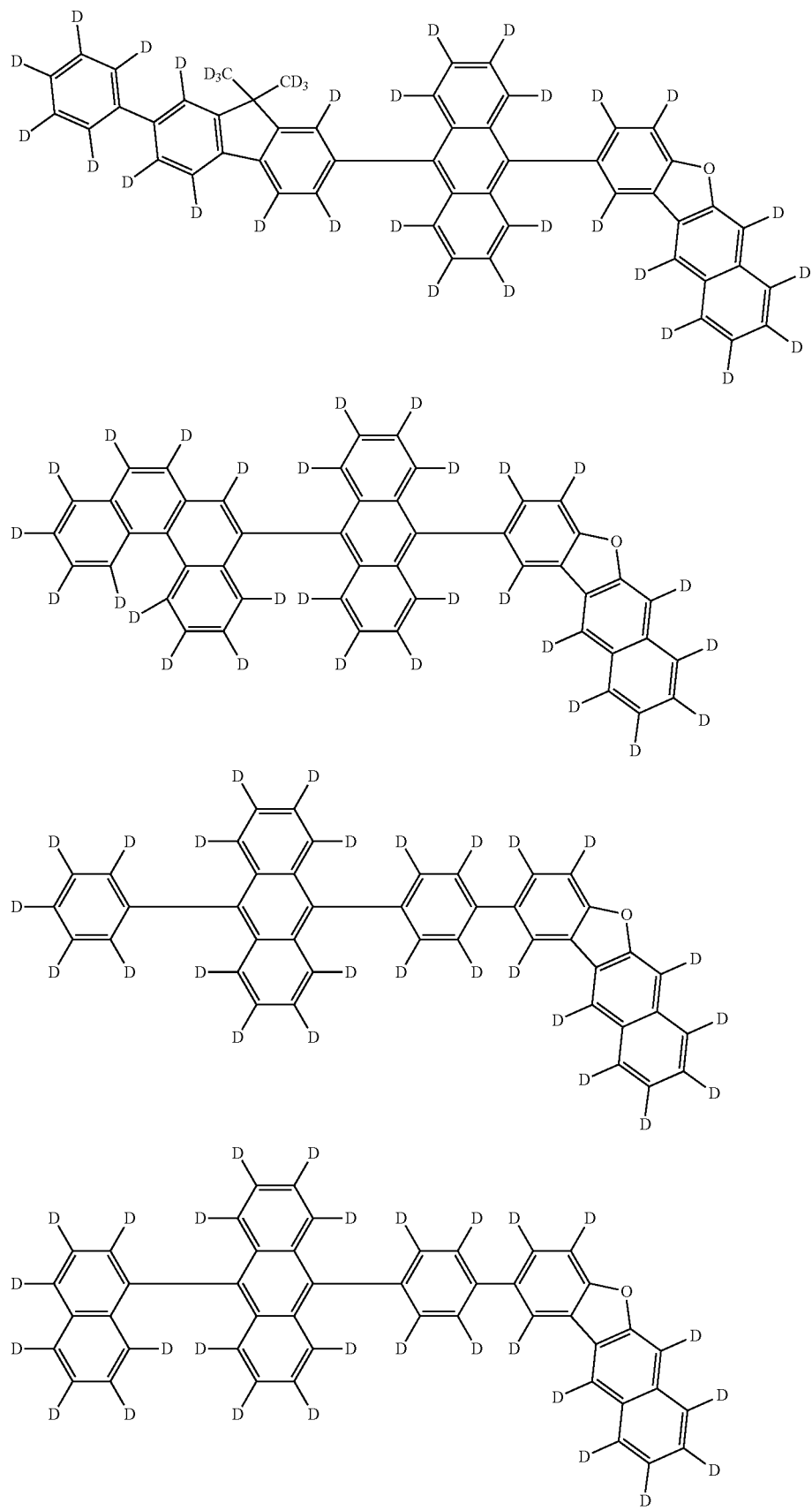

-continued
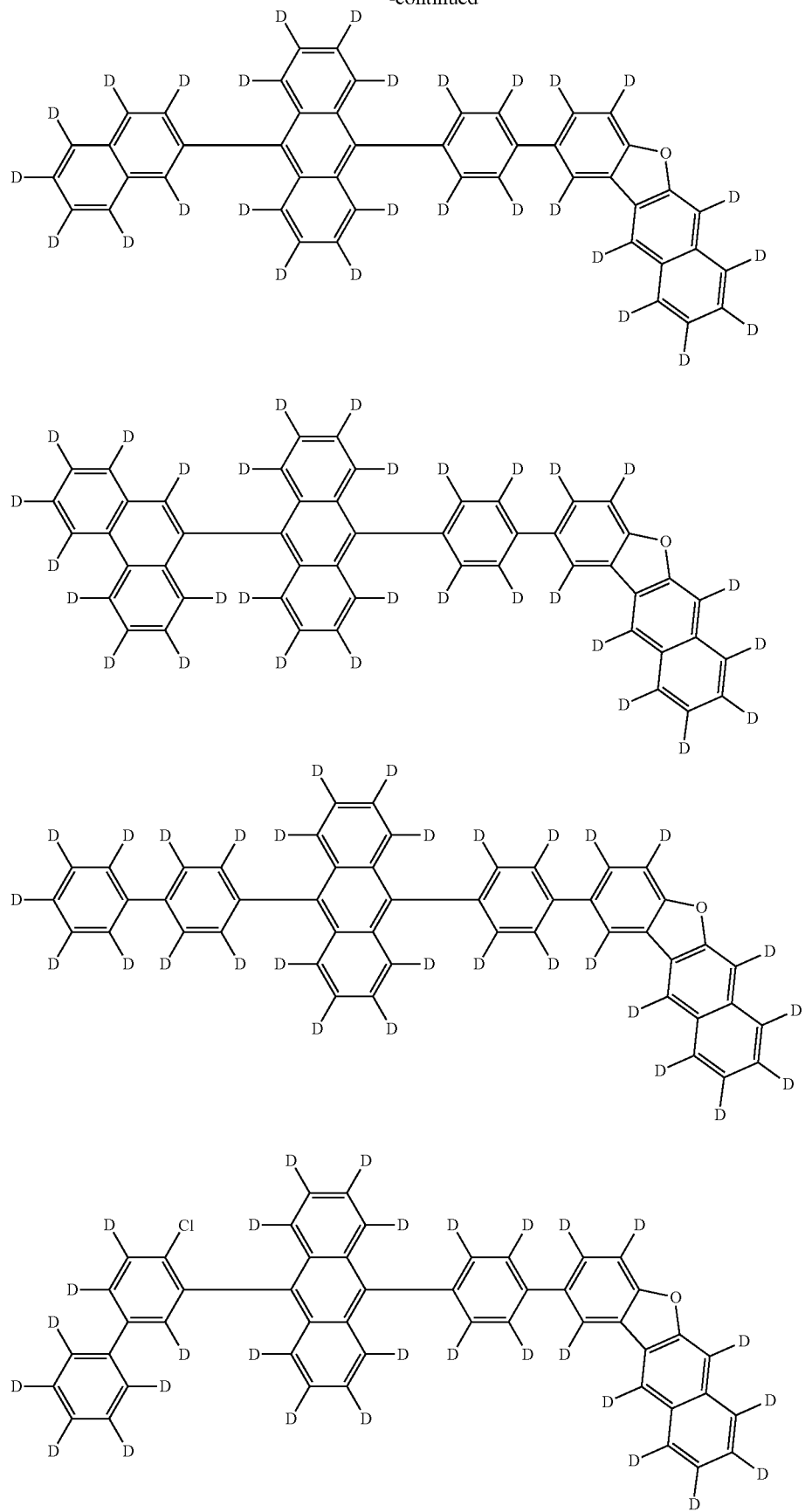

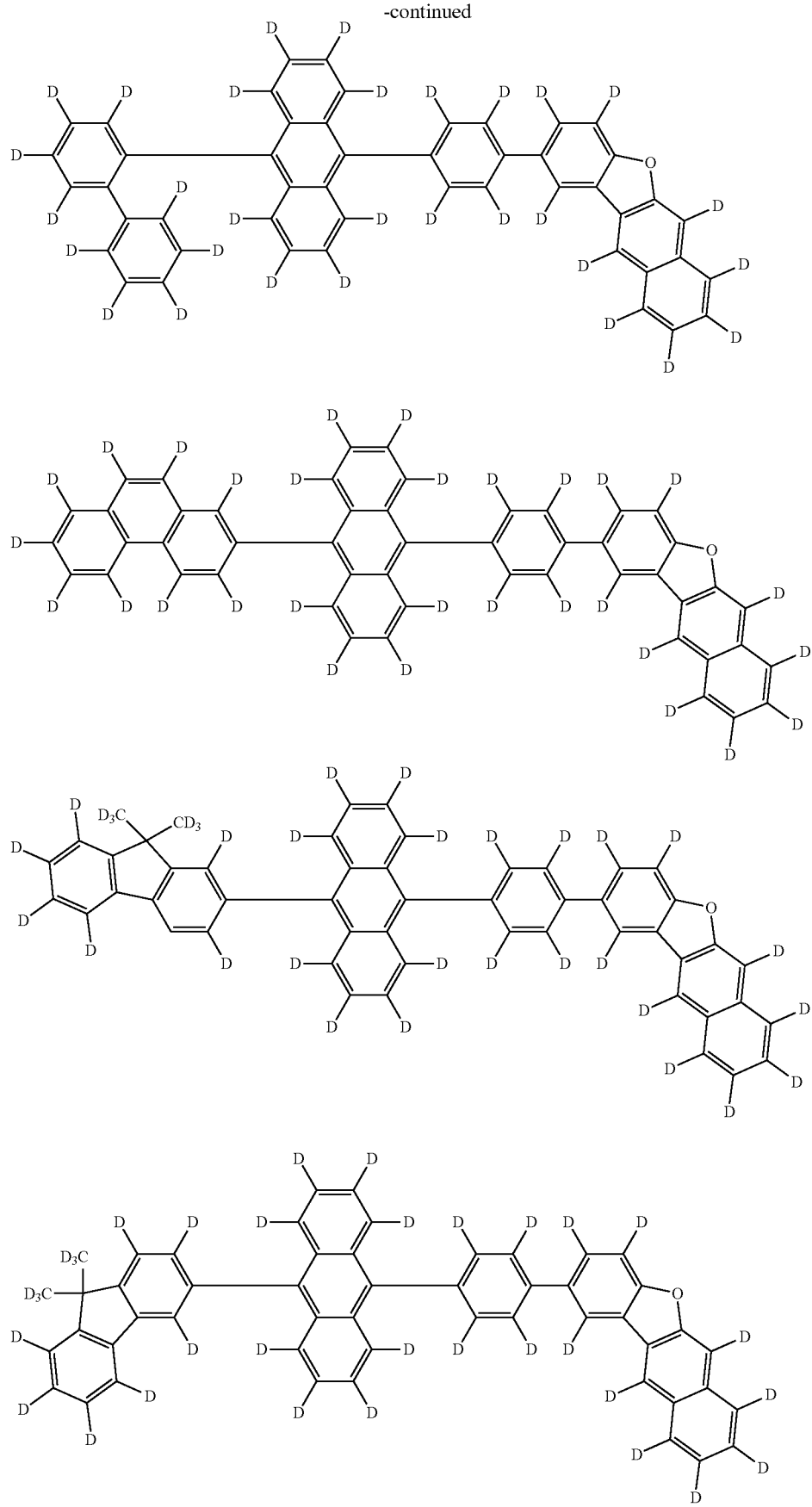

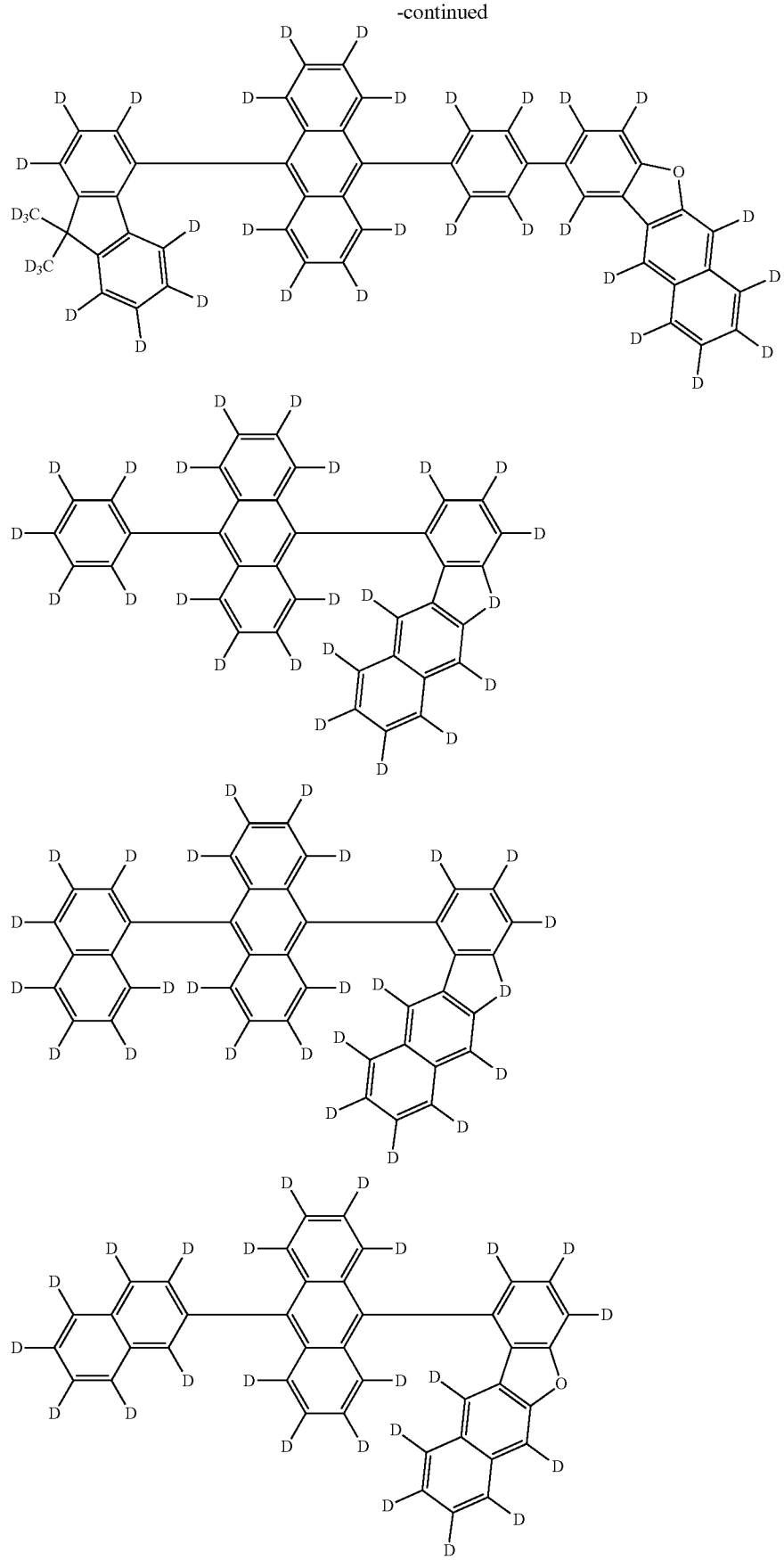

-continued
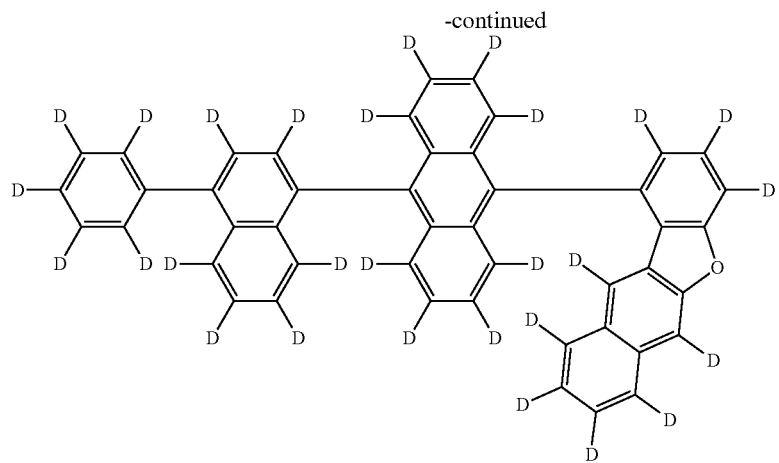
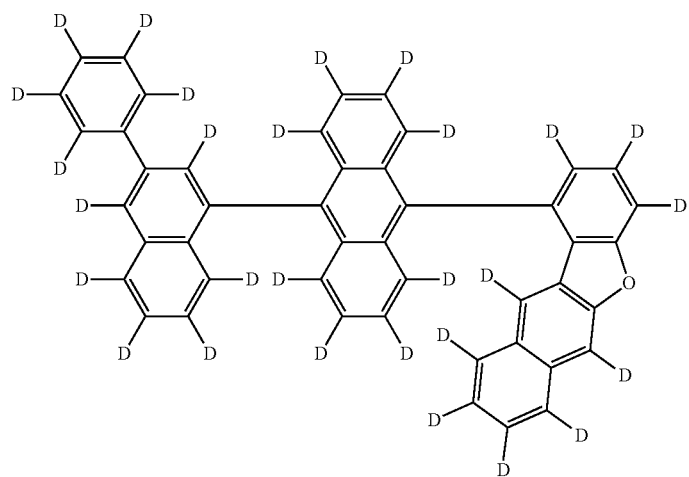
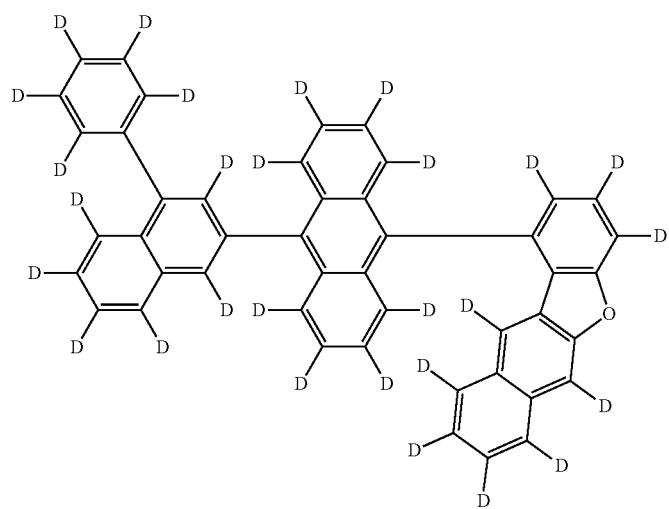

-continued
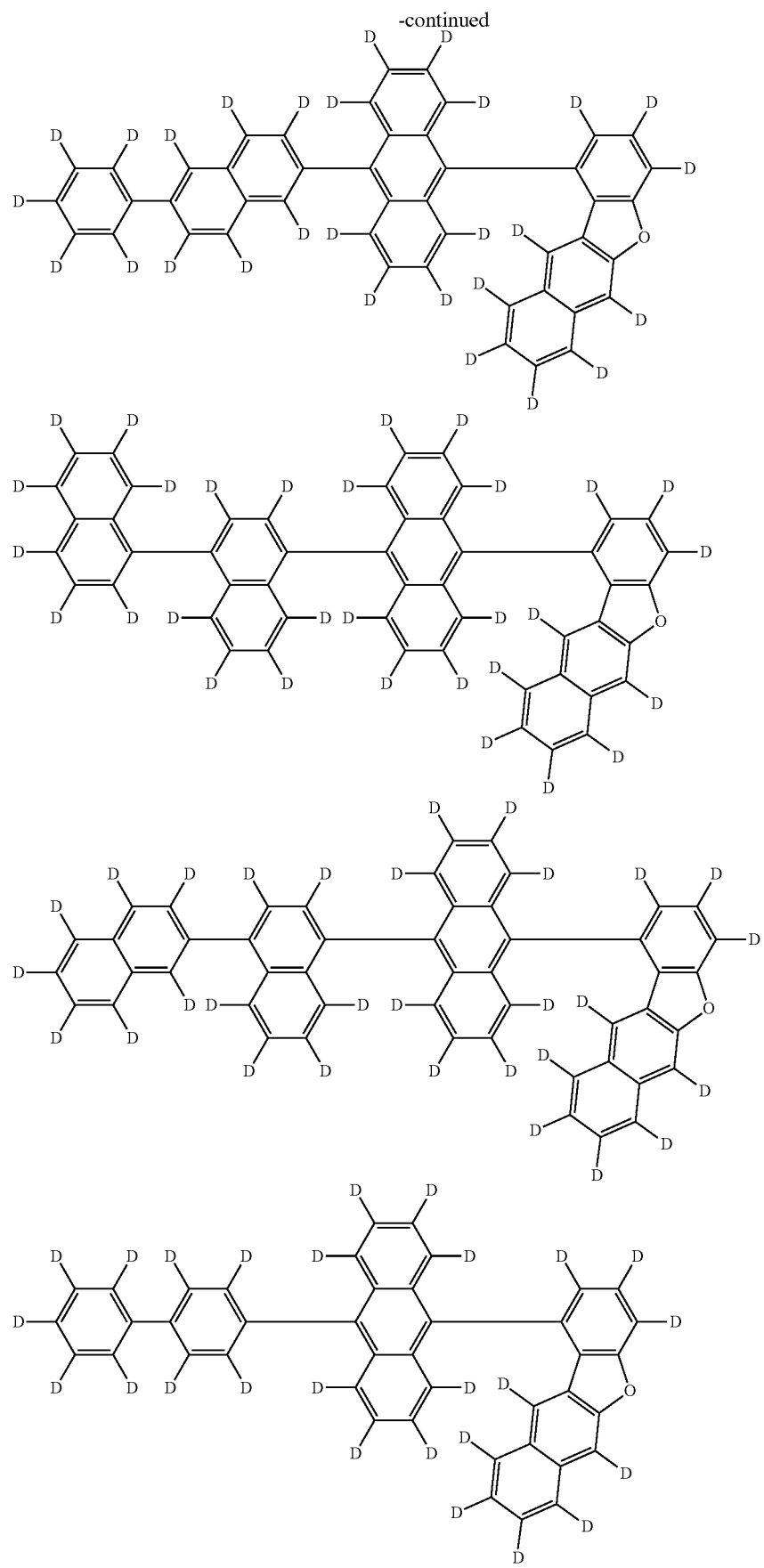

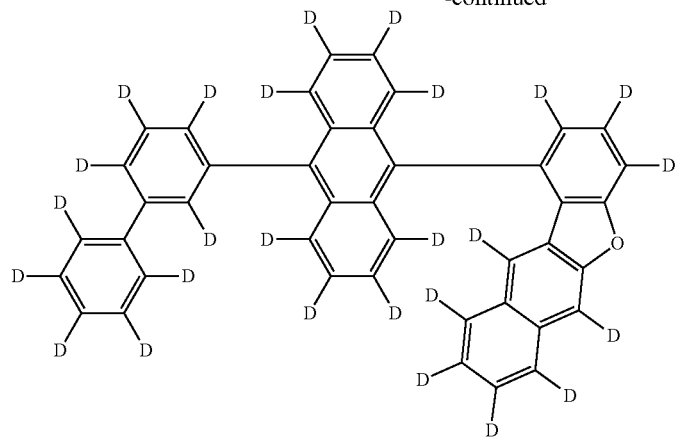
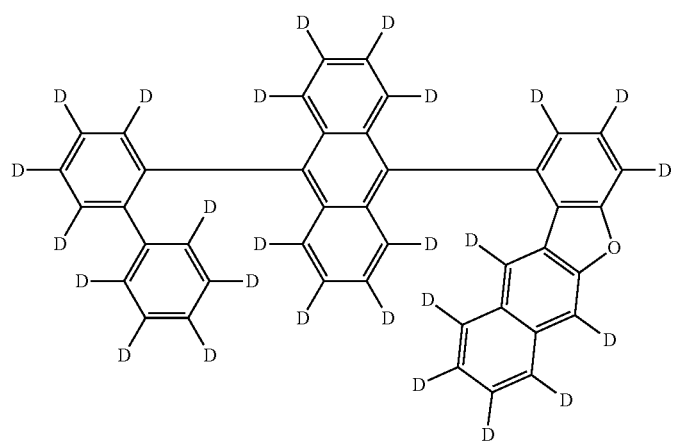
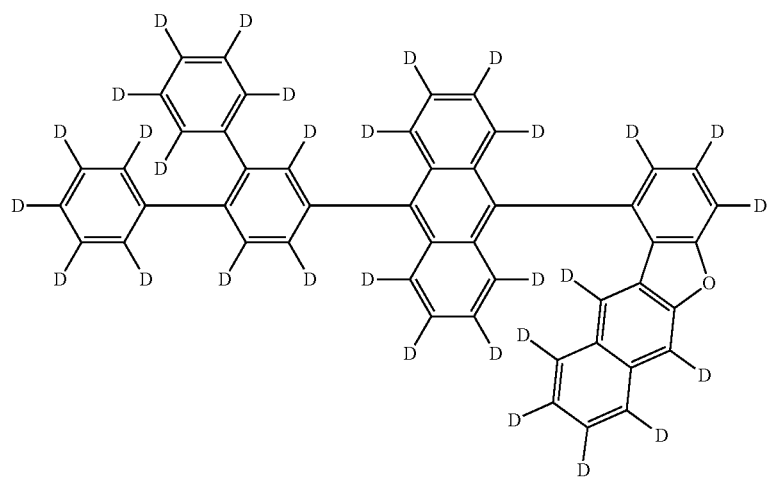

-continued
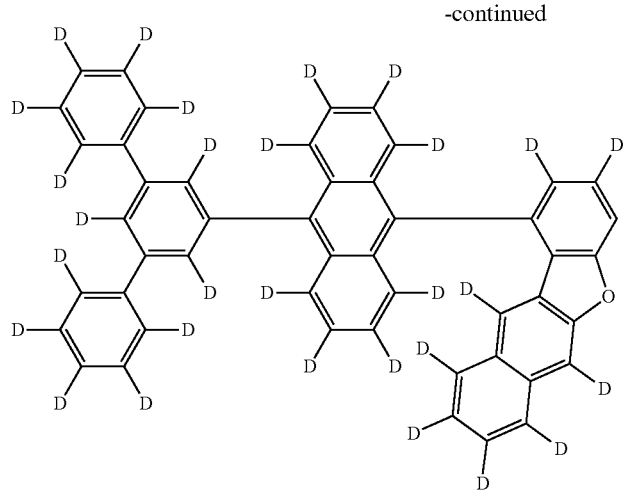
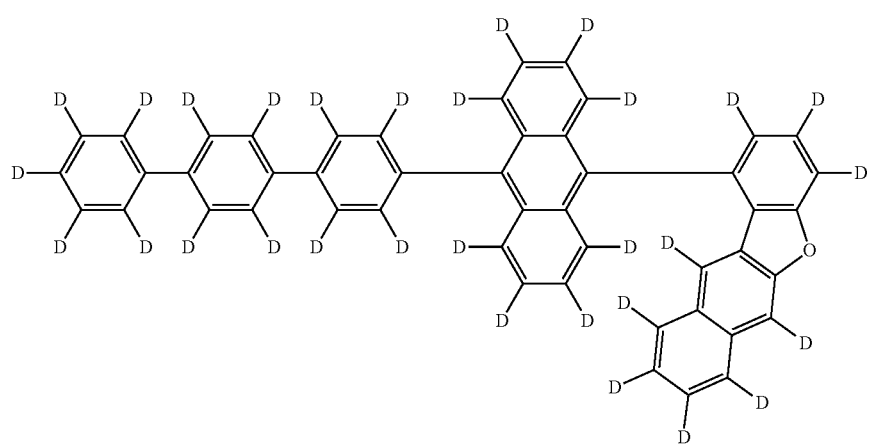
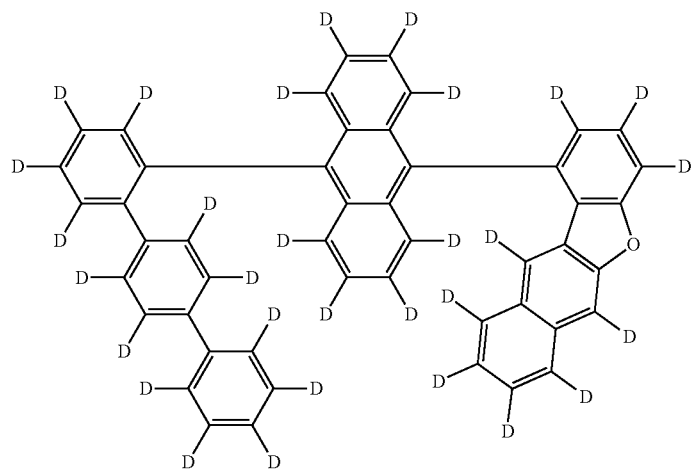

-continued
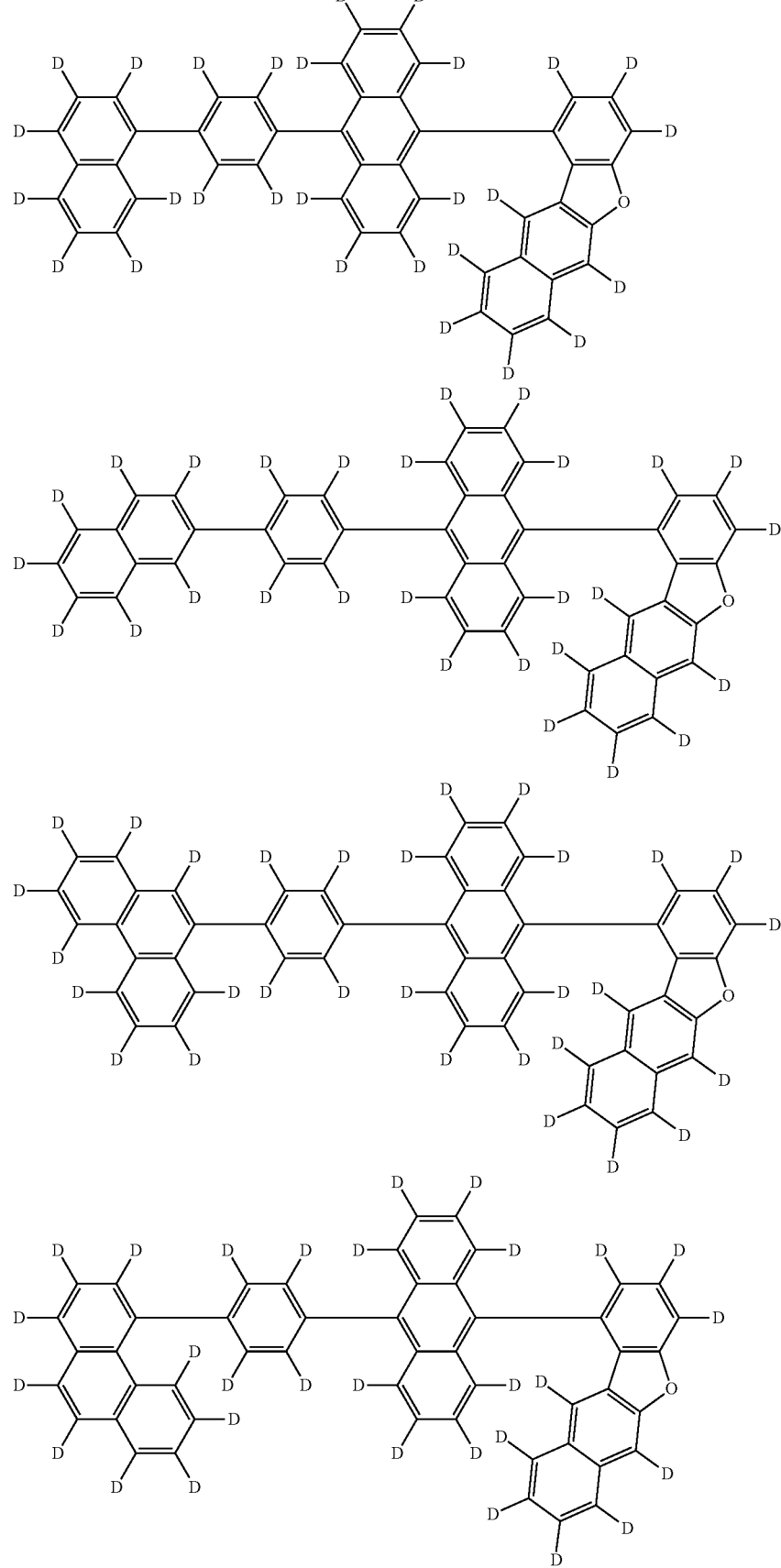

-continued
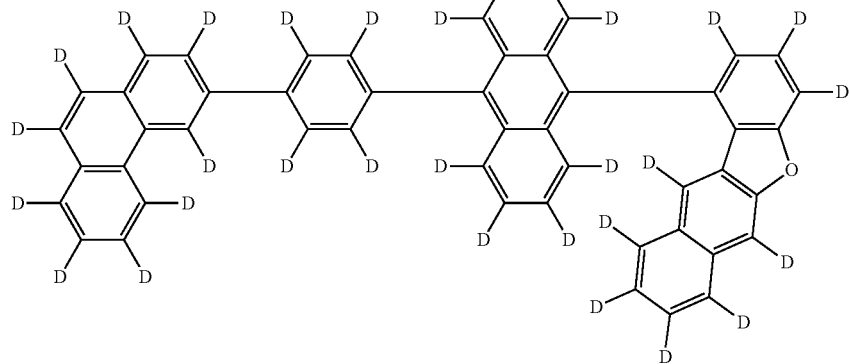
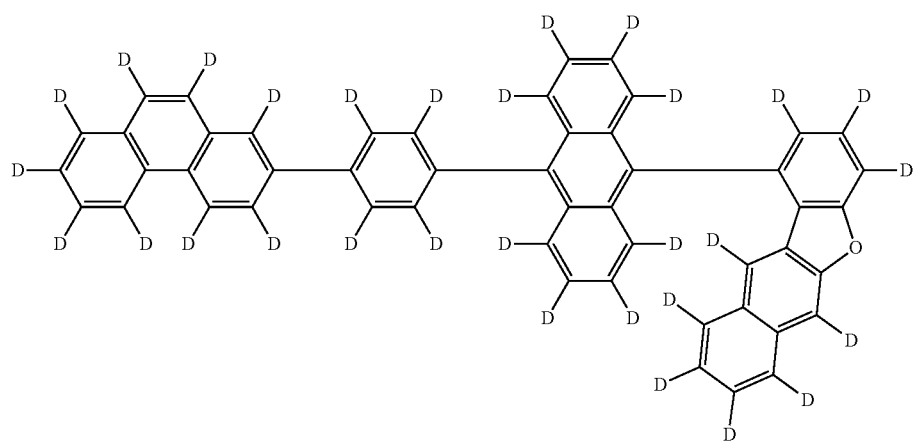
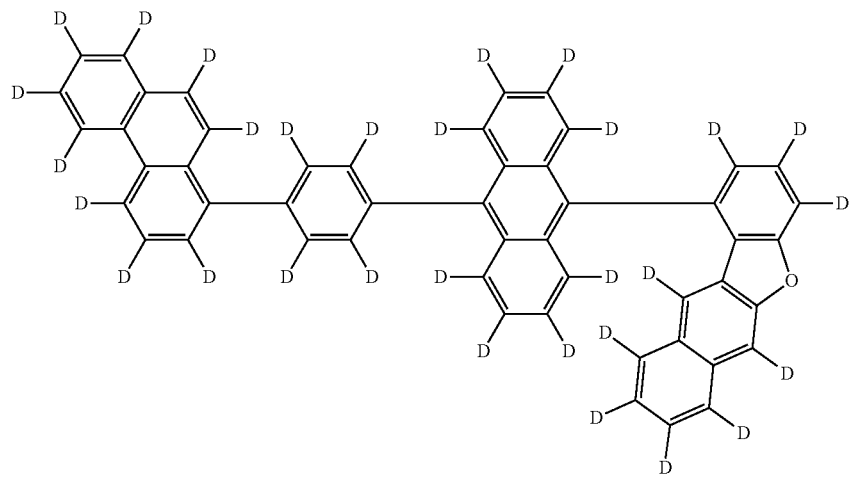

-continued
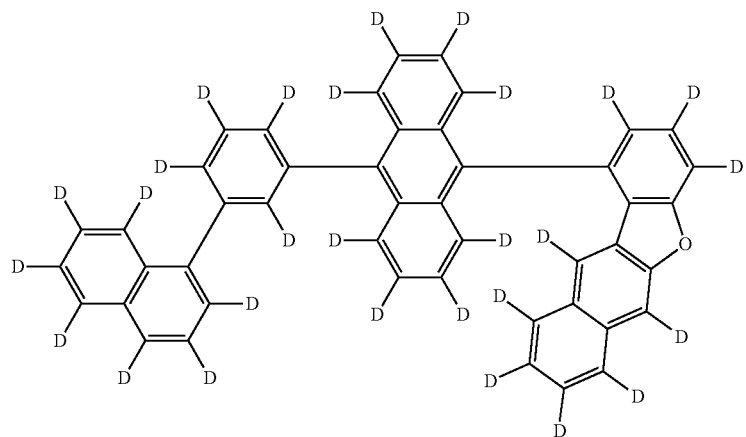
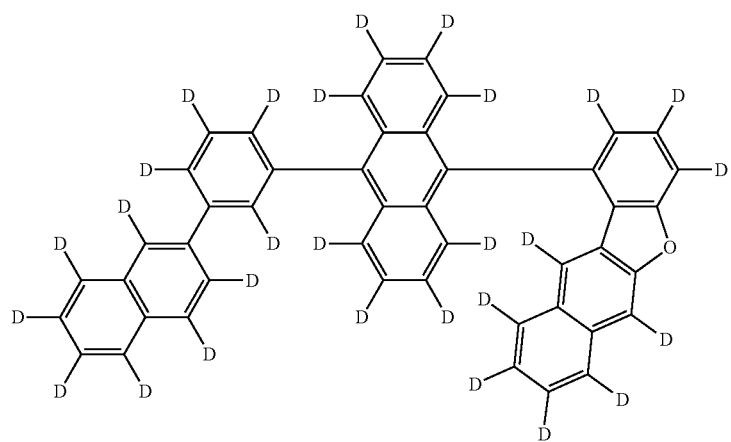
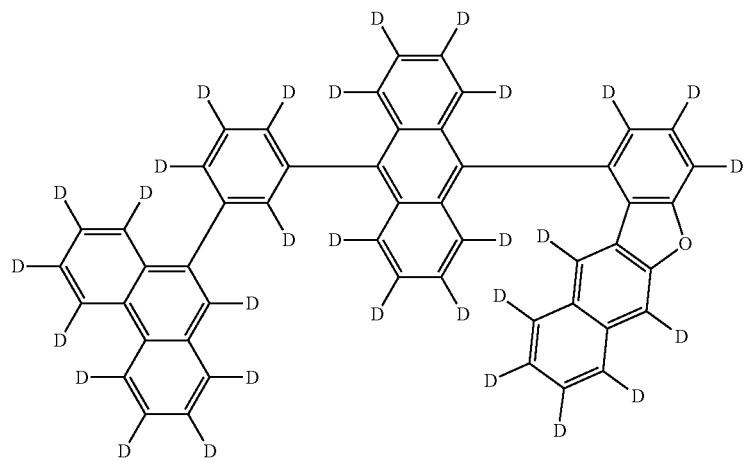

-continued
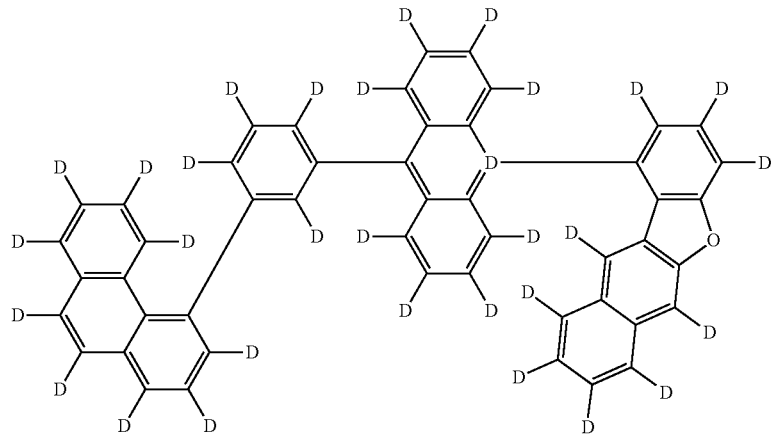
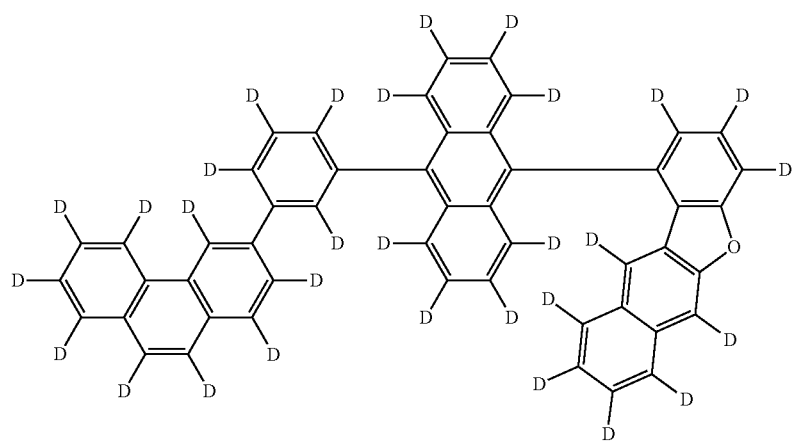
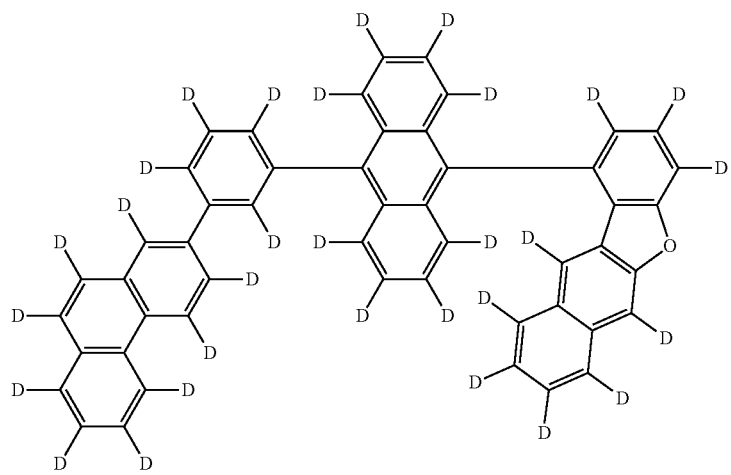

-continued
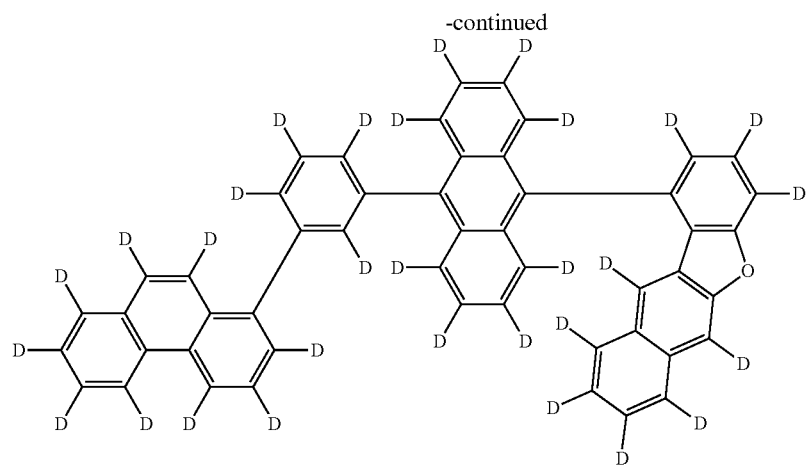
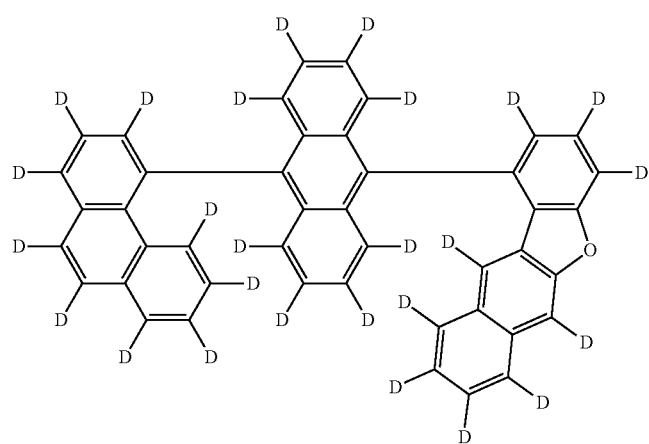
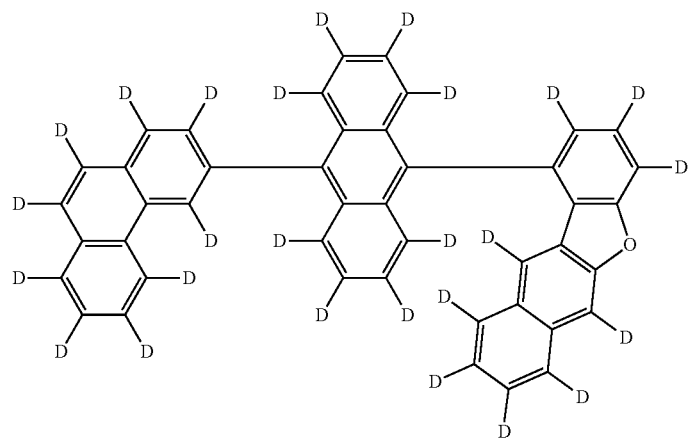

-continued
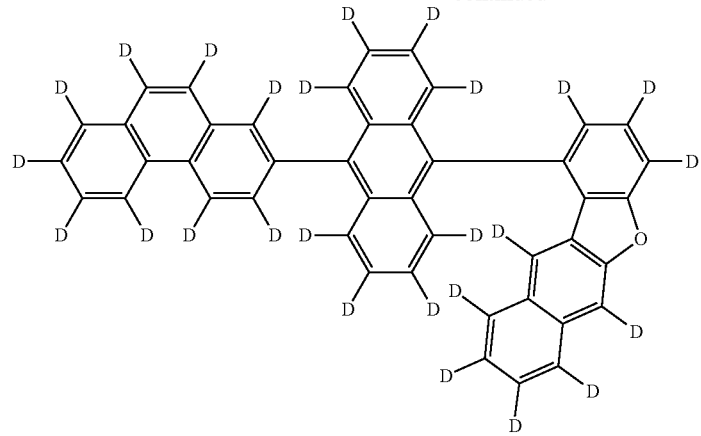
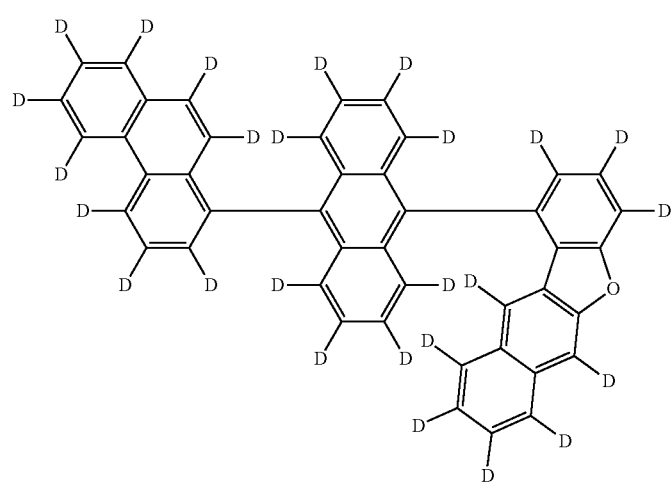
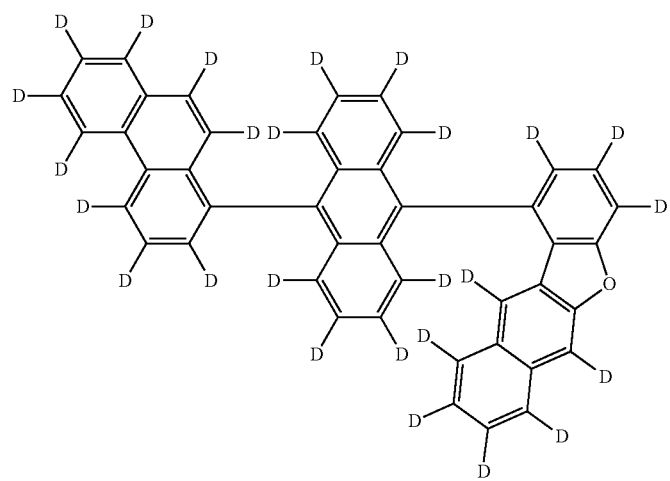

-continued
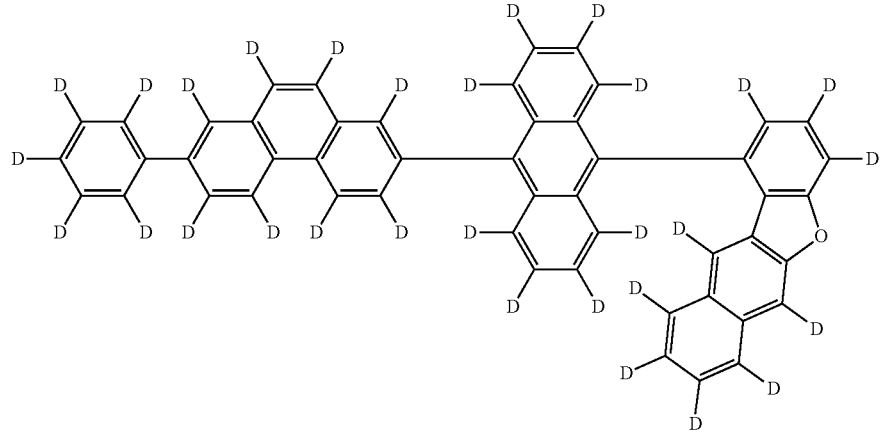
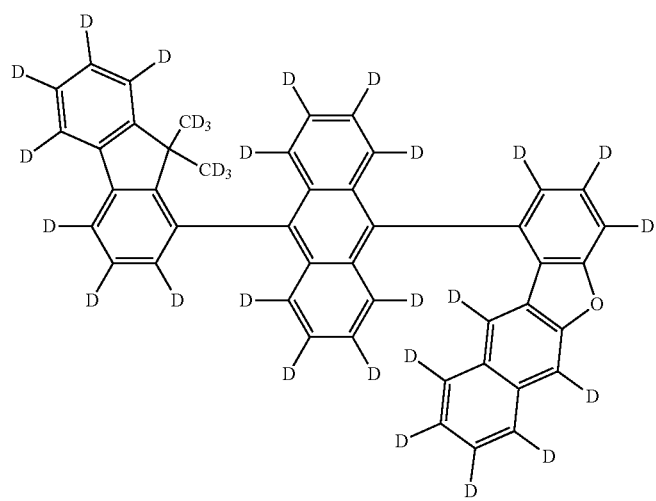
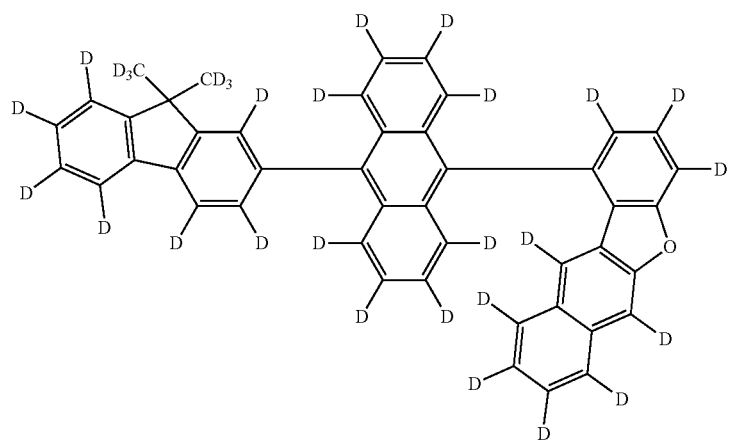

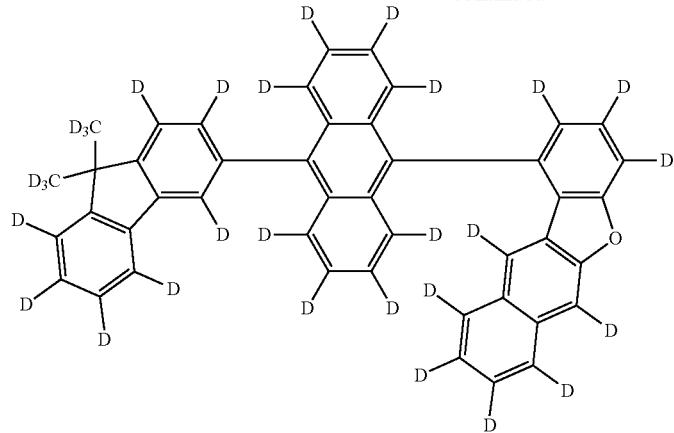
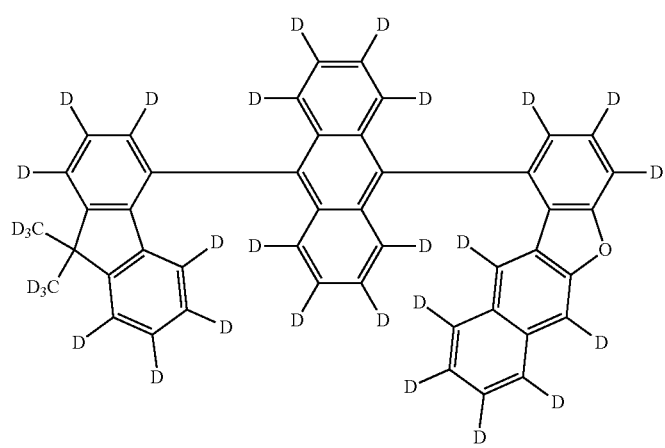
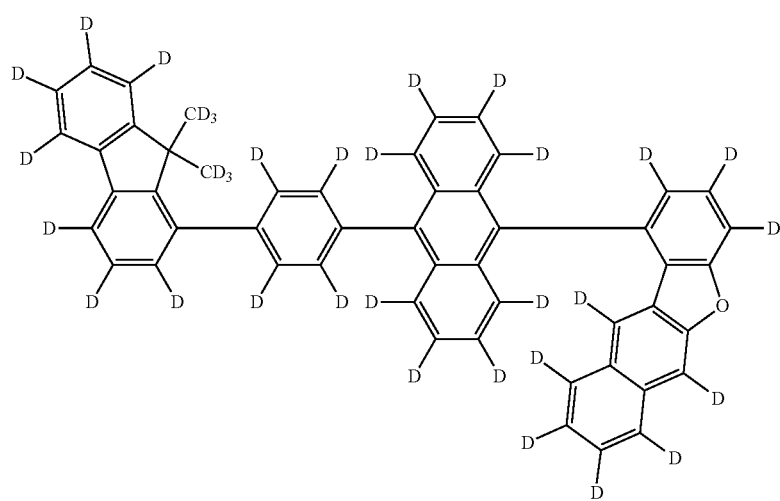

-continued
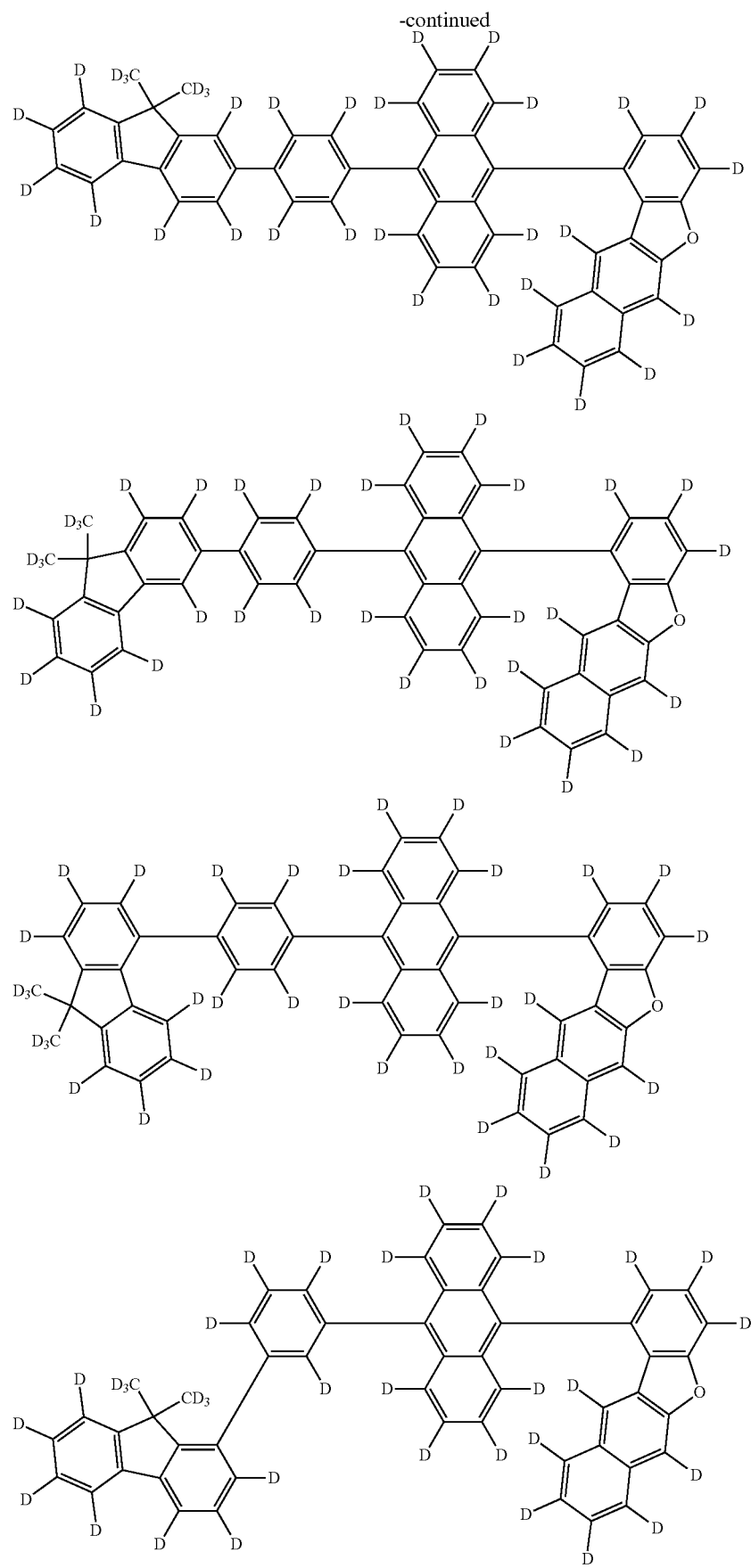

-continued
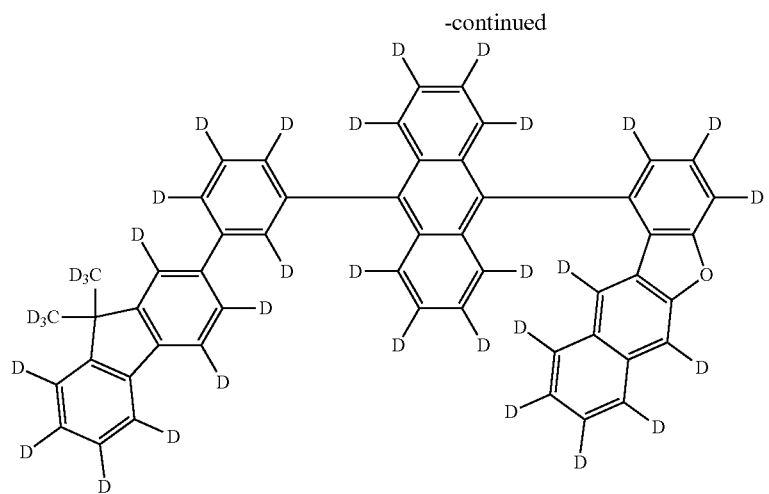
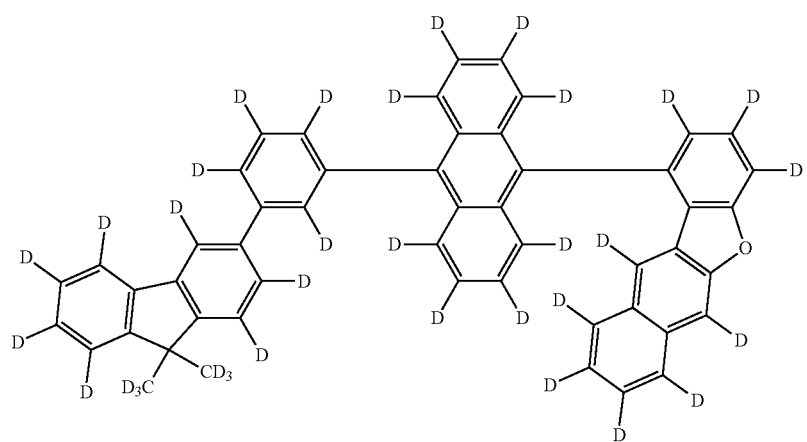
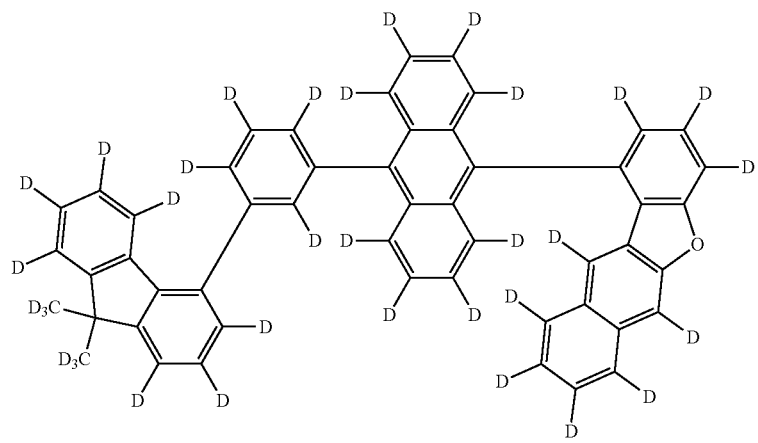

-continued
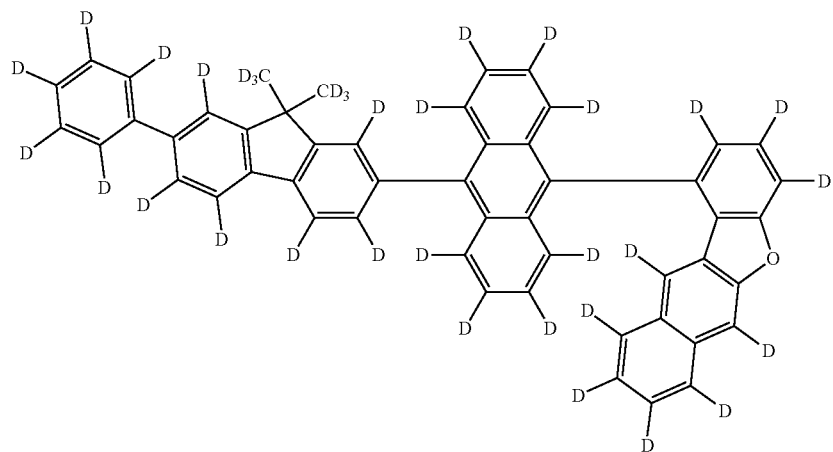
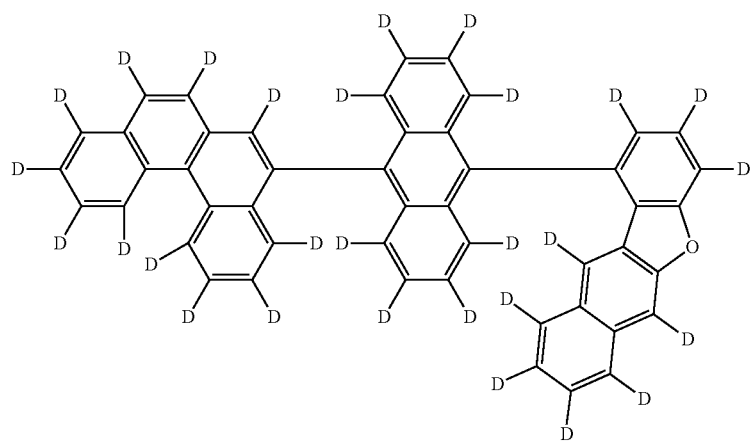
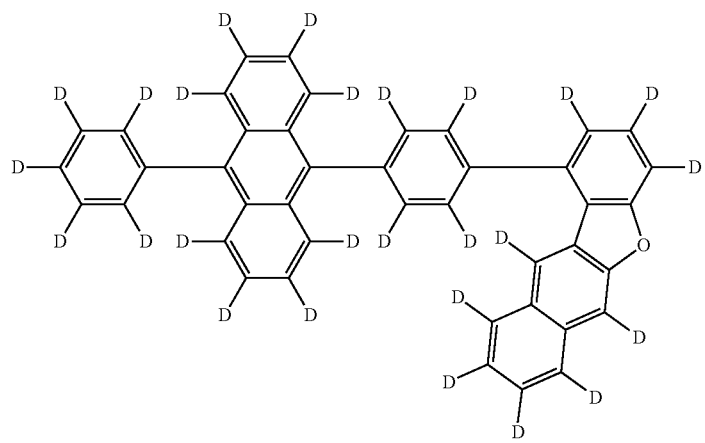

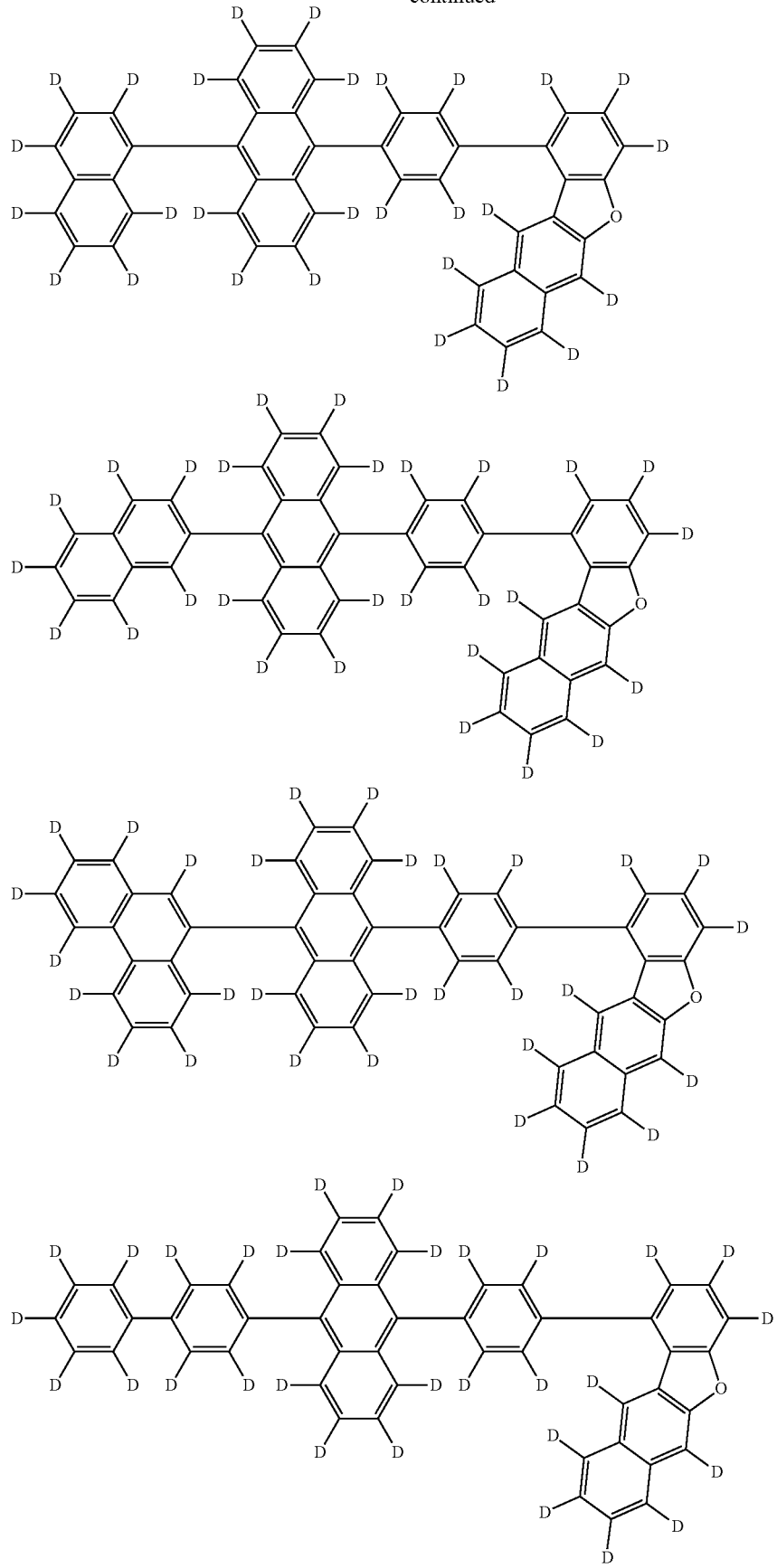

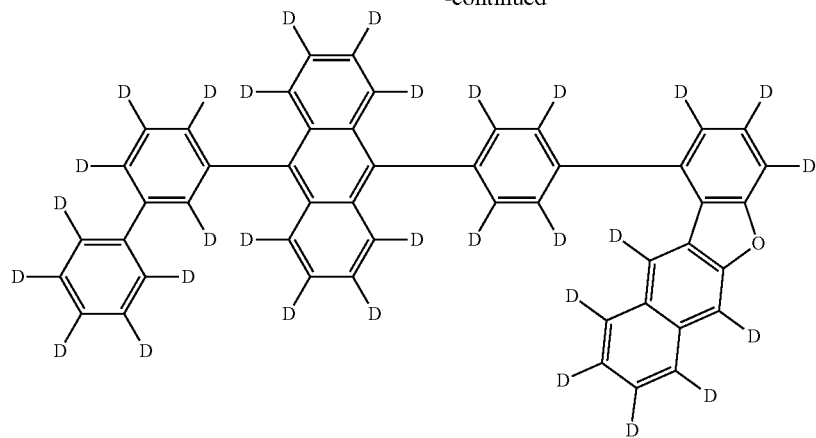
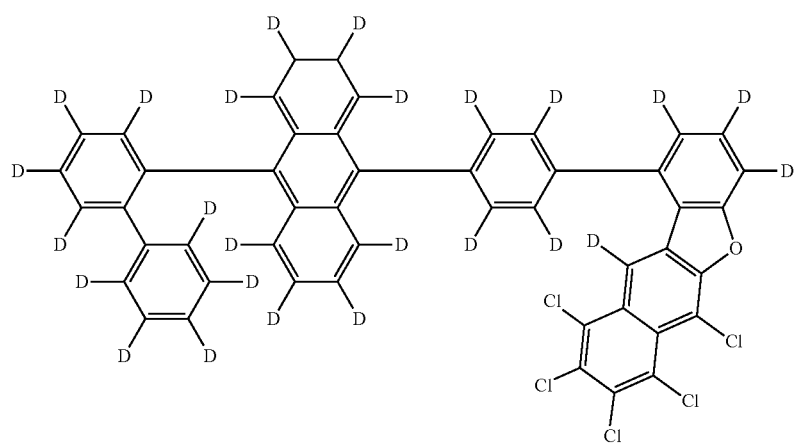
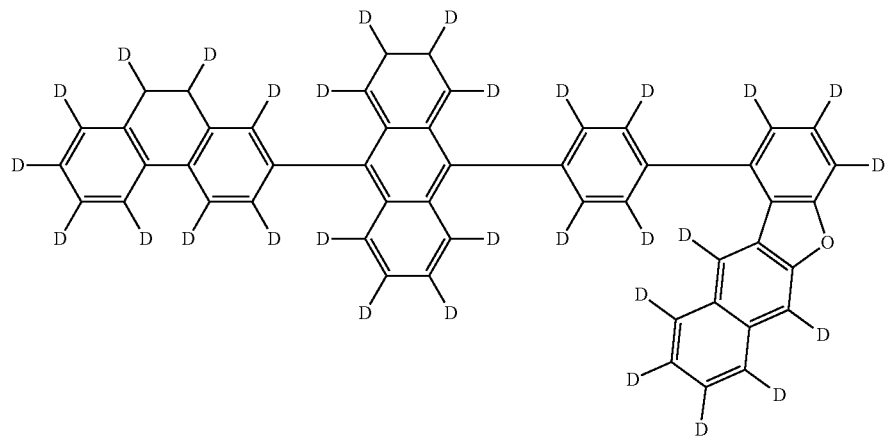

-continued
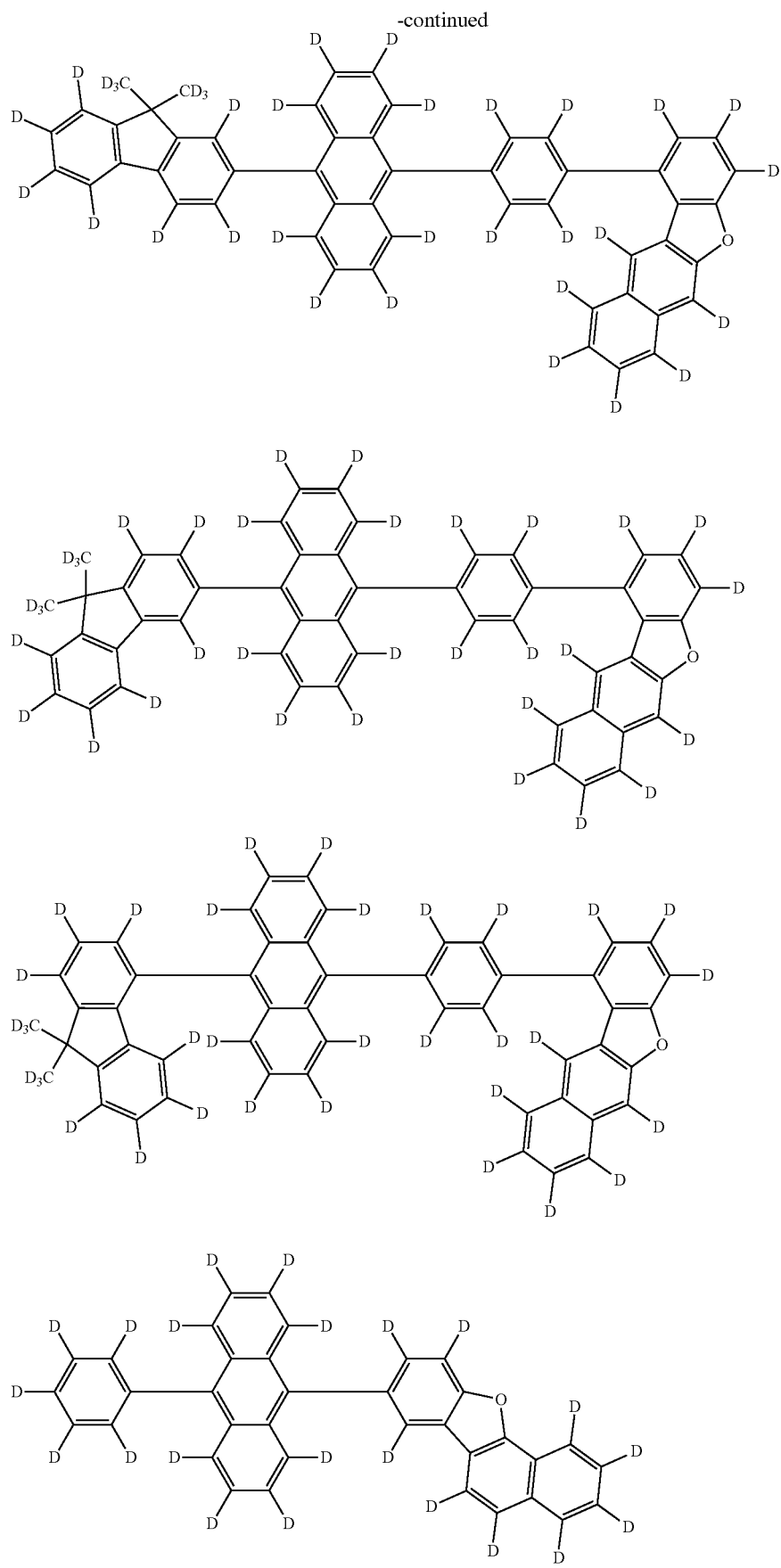

-continued
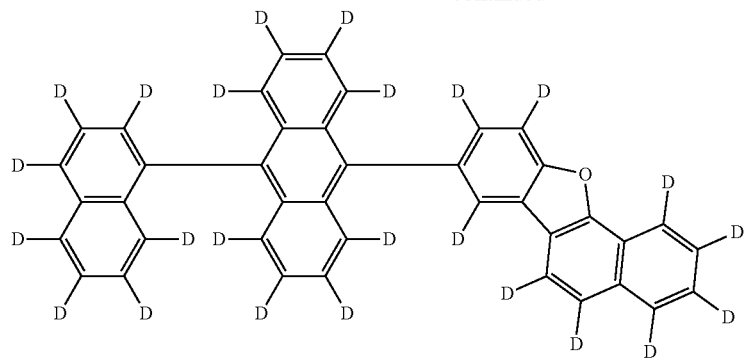
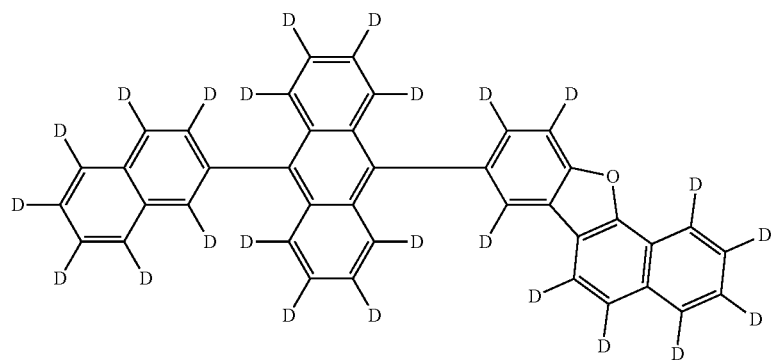
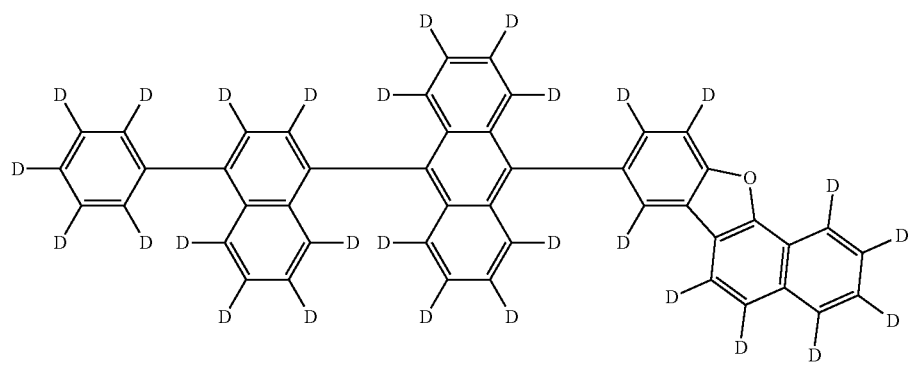
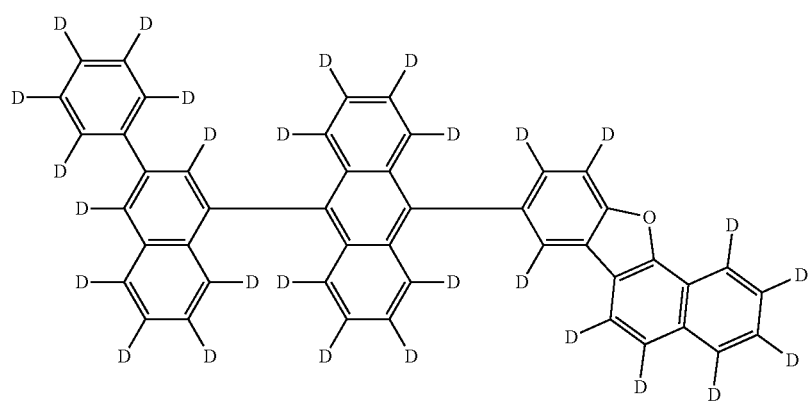

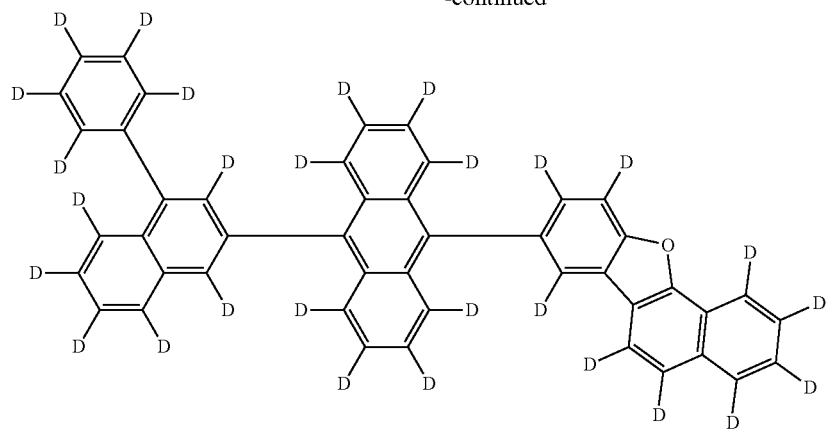
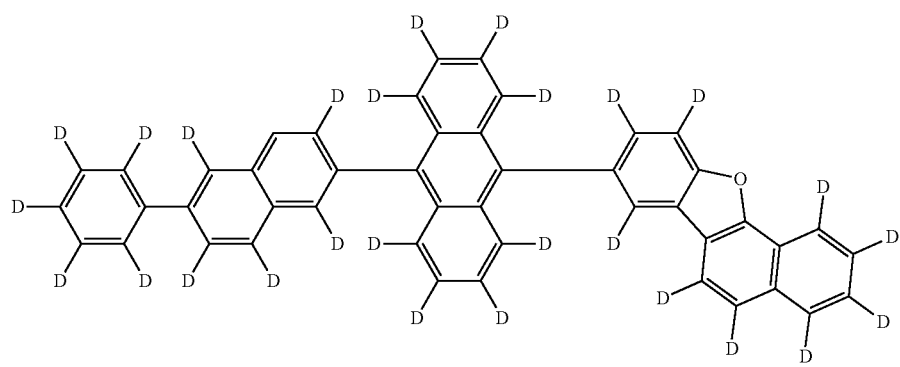
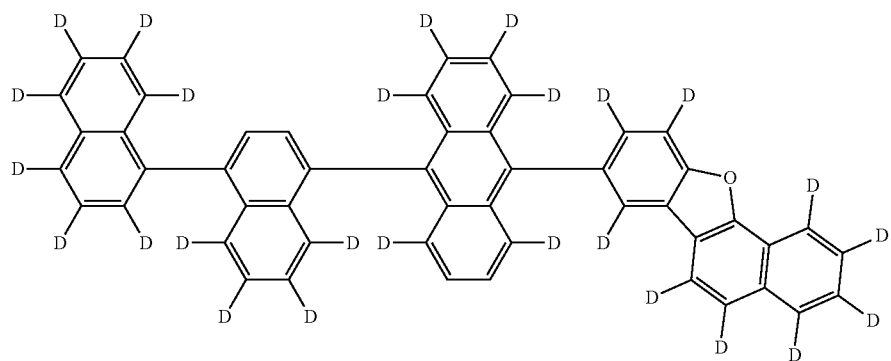
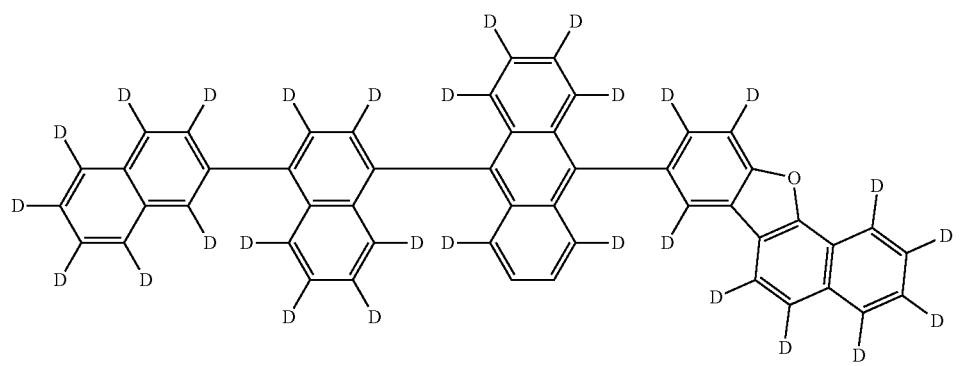

-continued
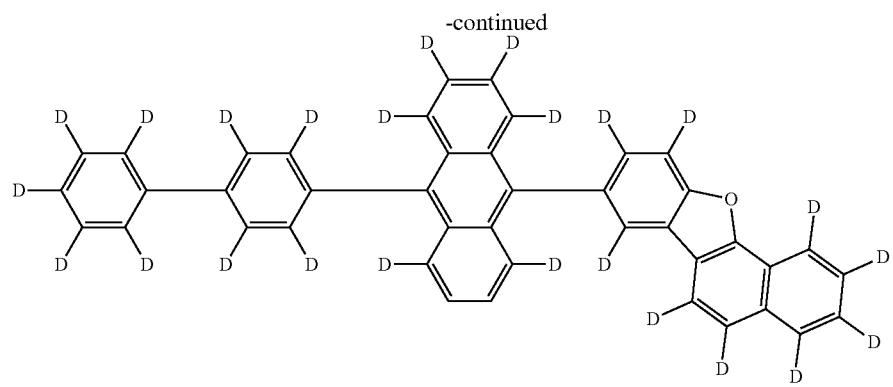
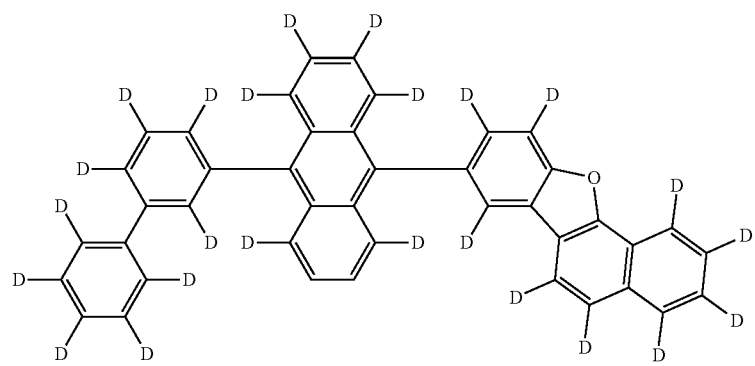
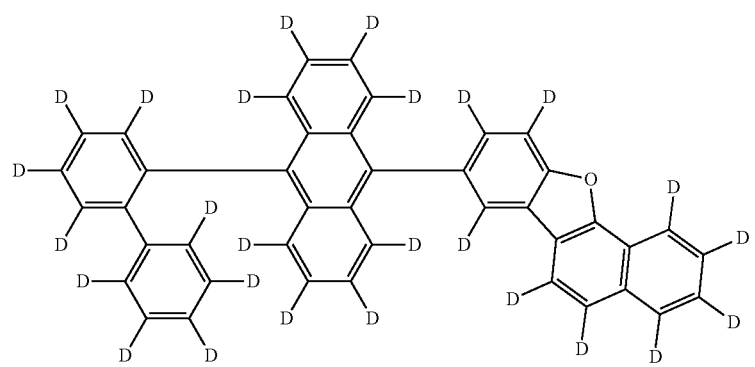
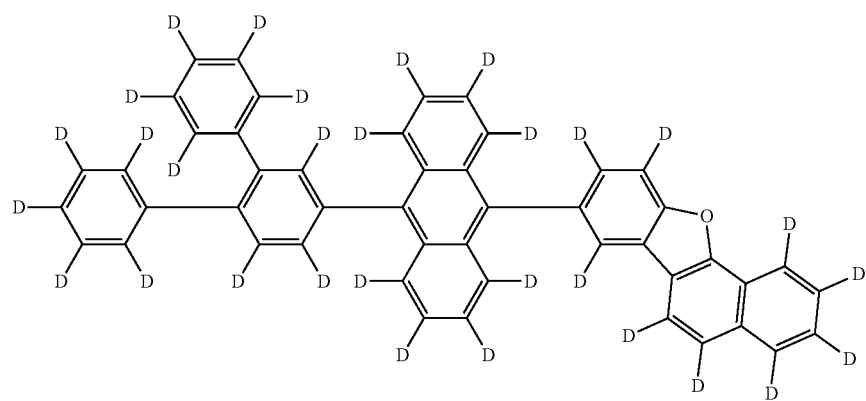

-continued
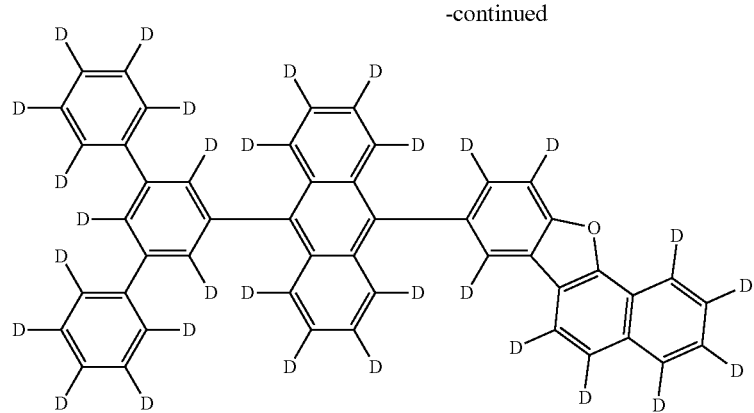
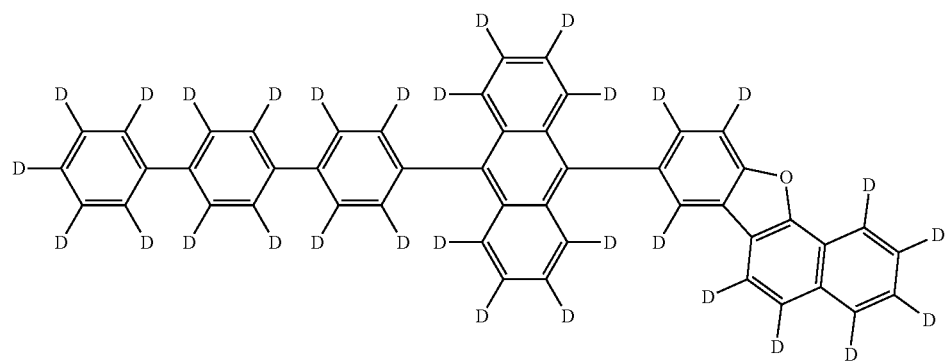
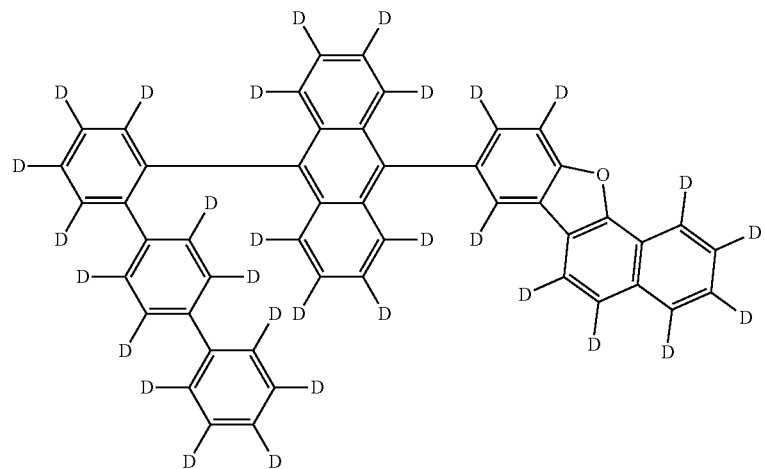
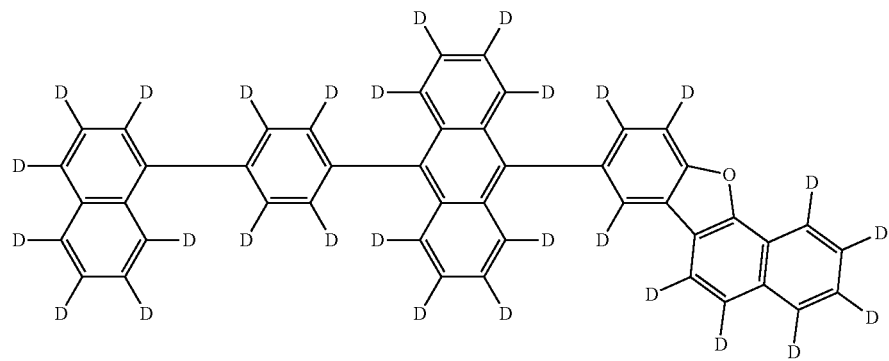

-continued
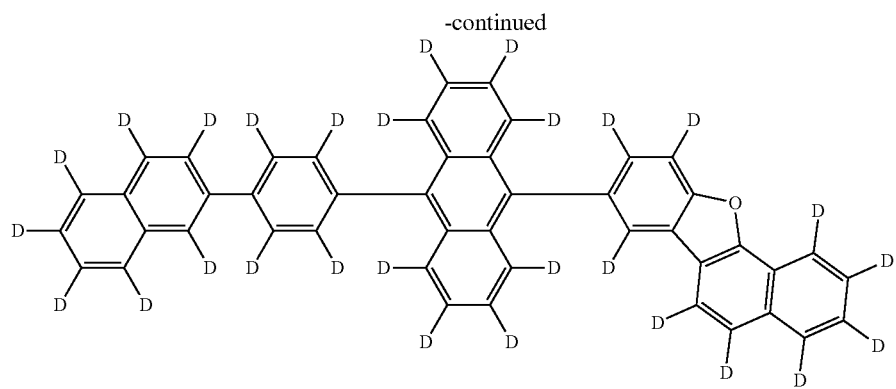
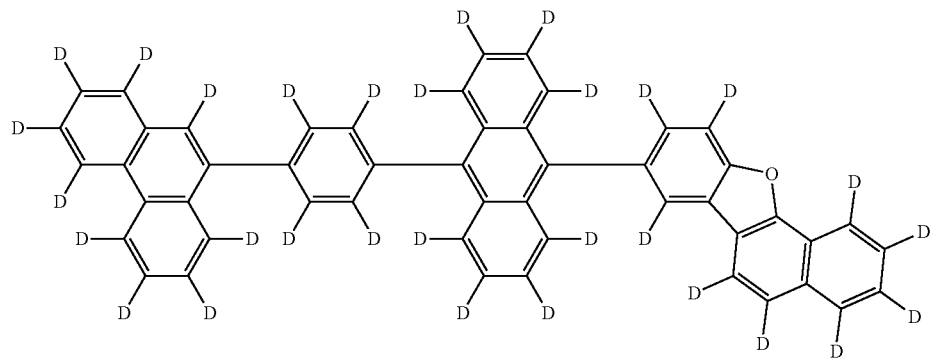
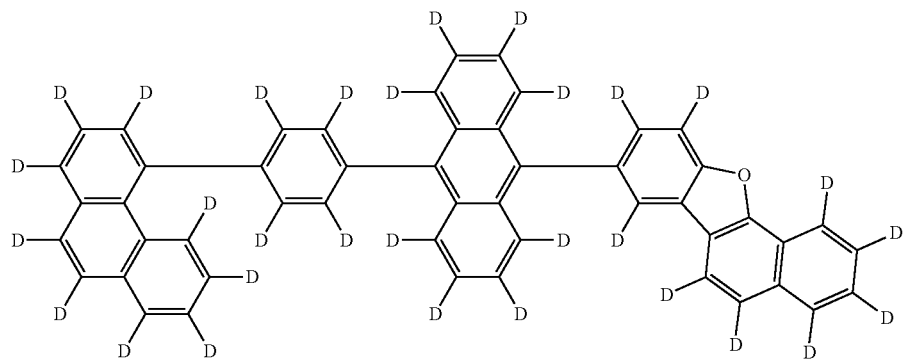
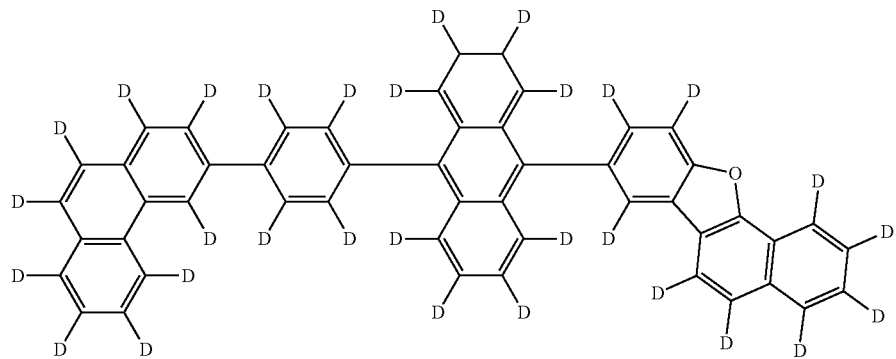

-continued
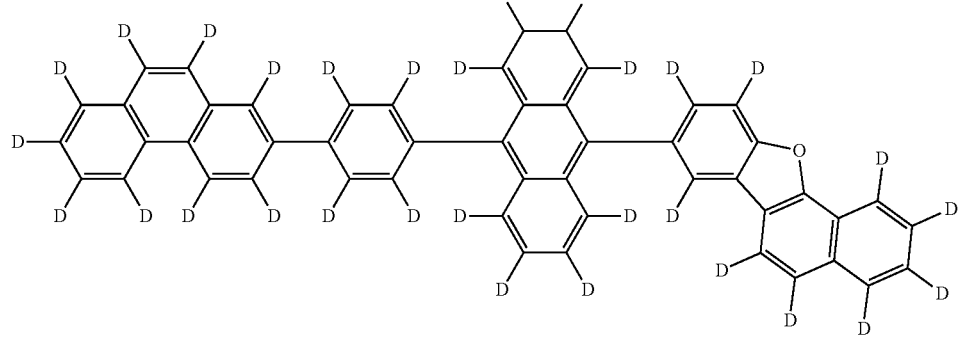
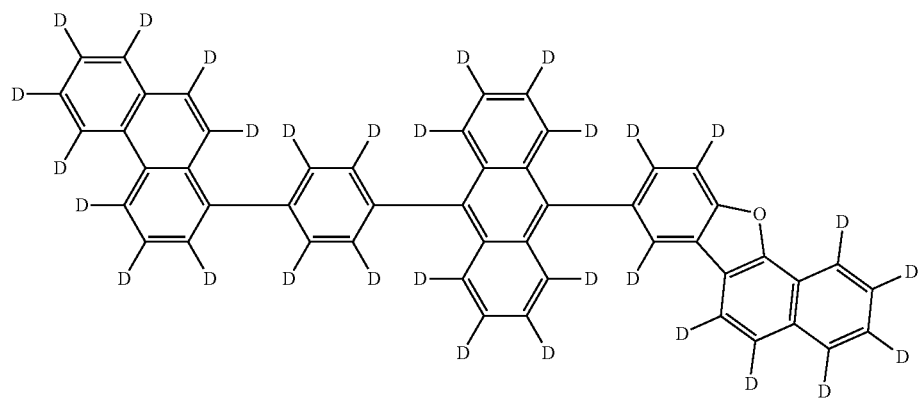
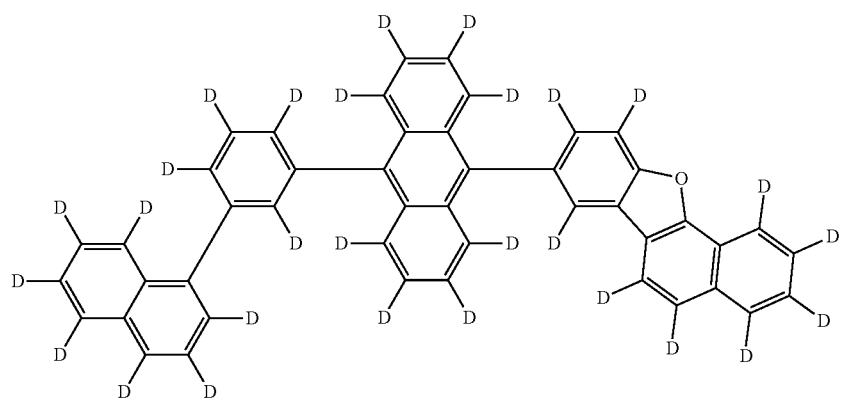
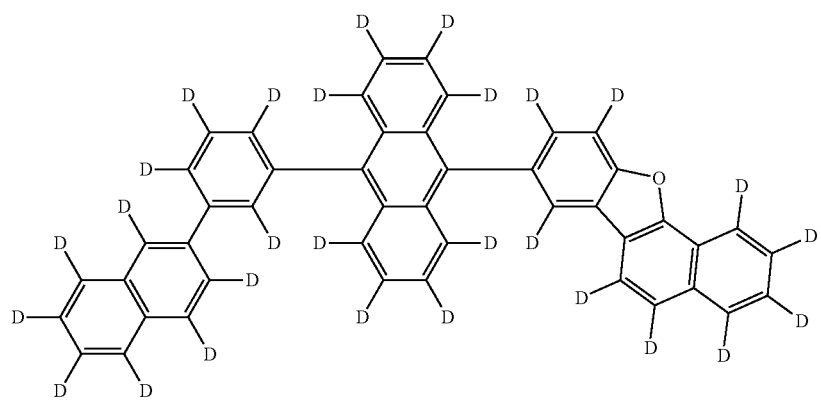

-continued
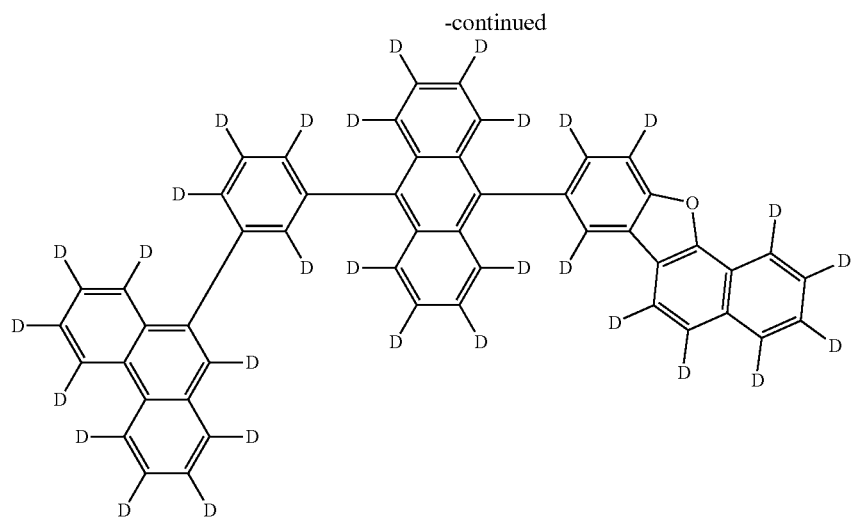
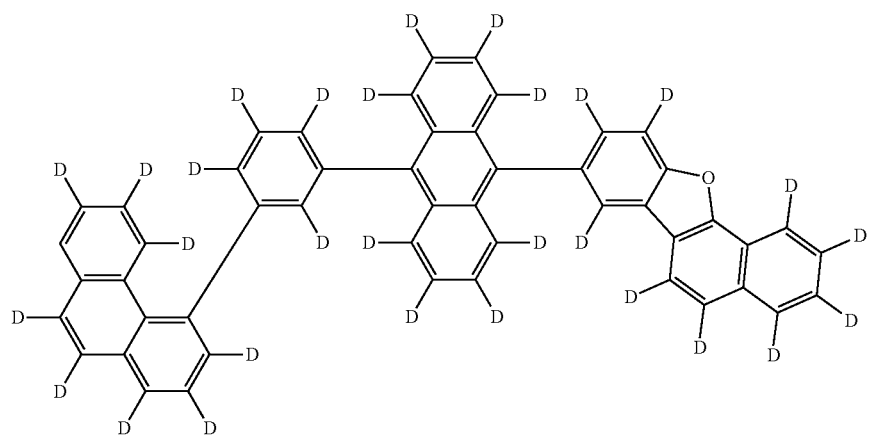
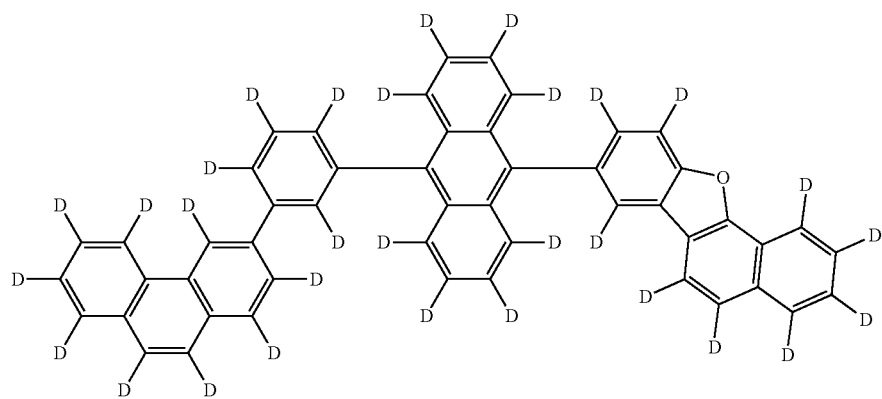

-continued
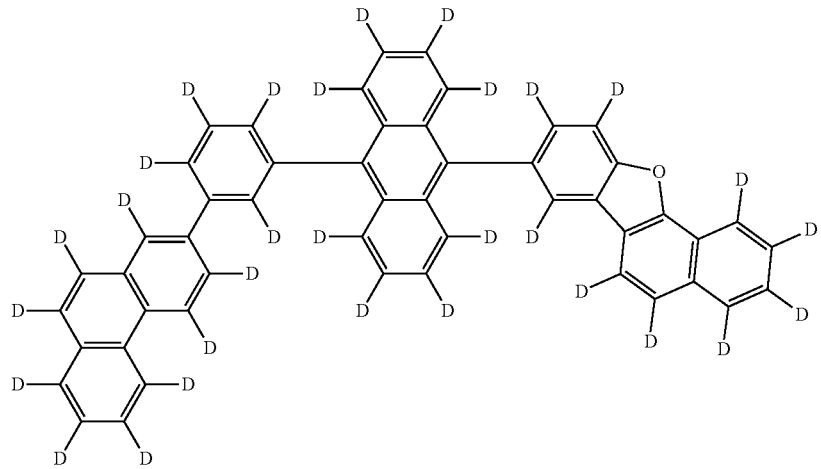
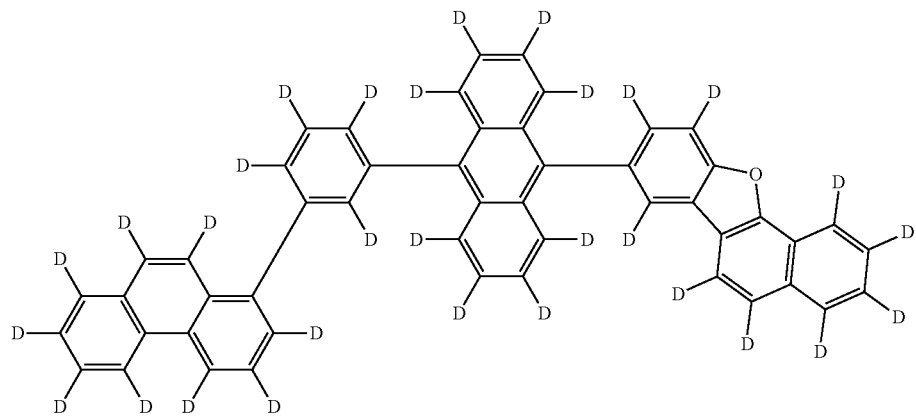
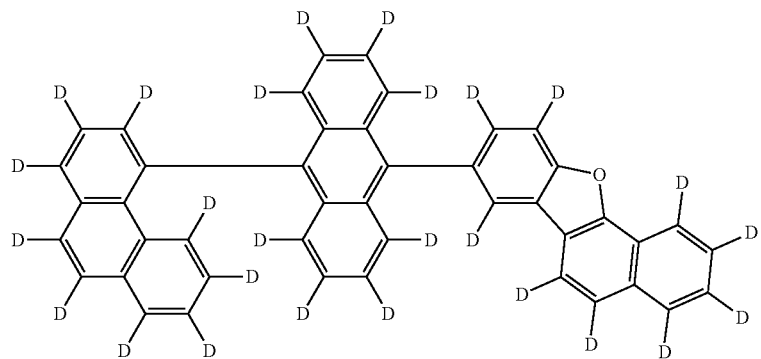
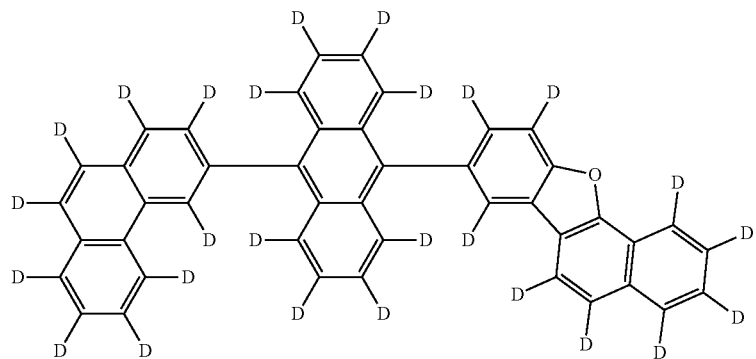

-continued
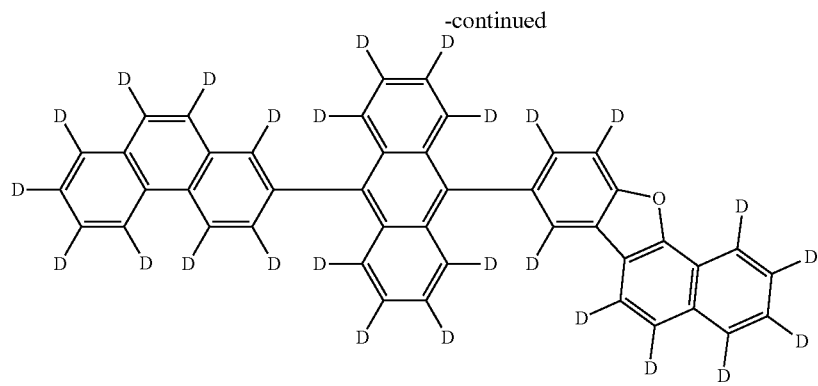
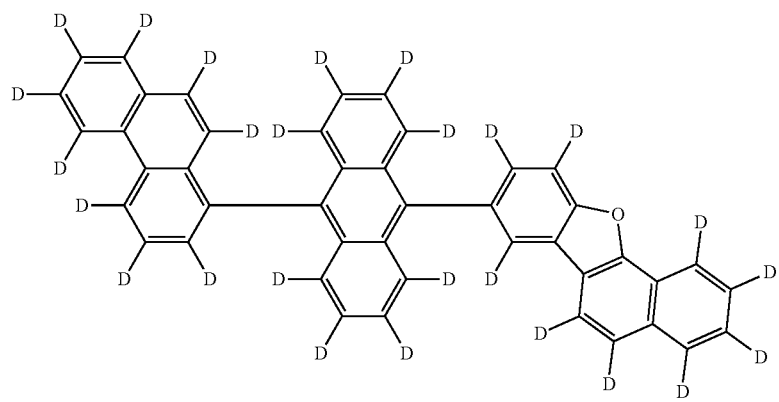
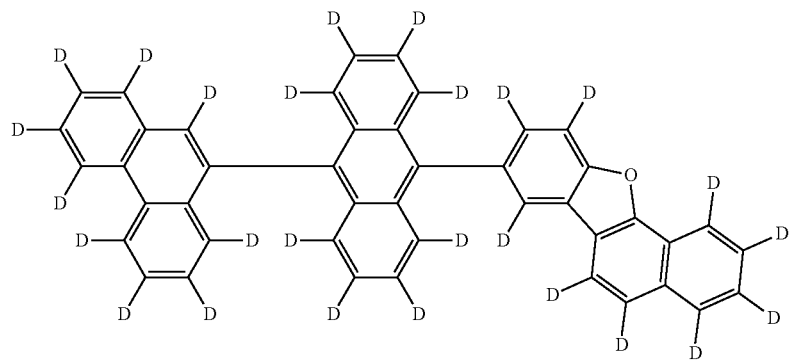
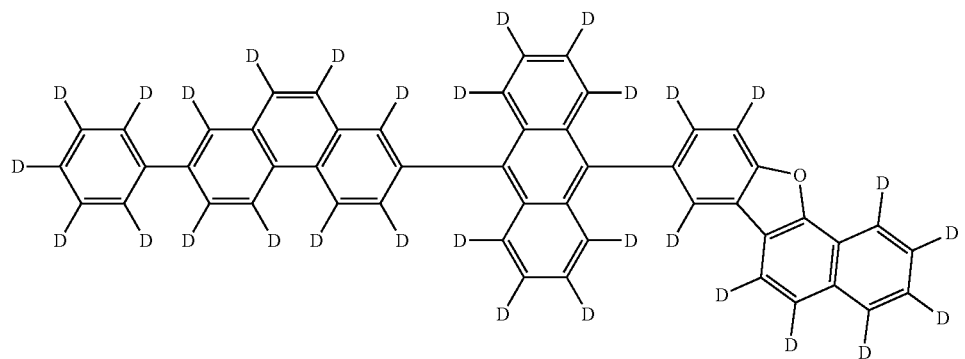

-continued
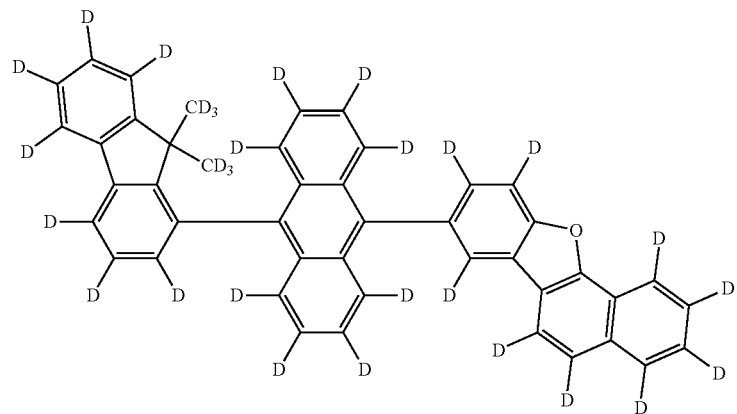
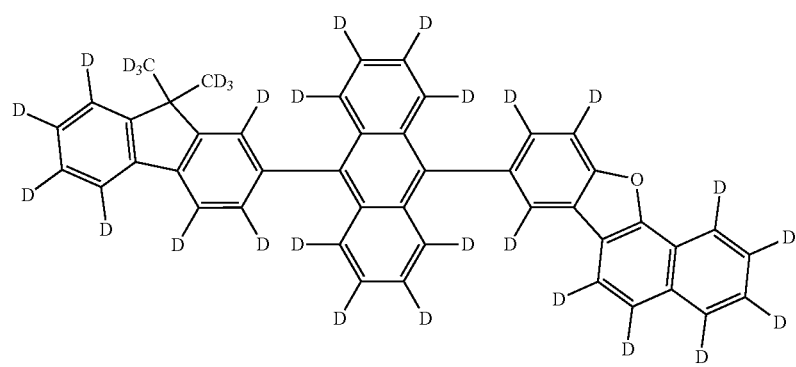
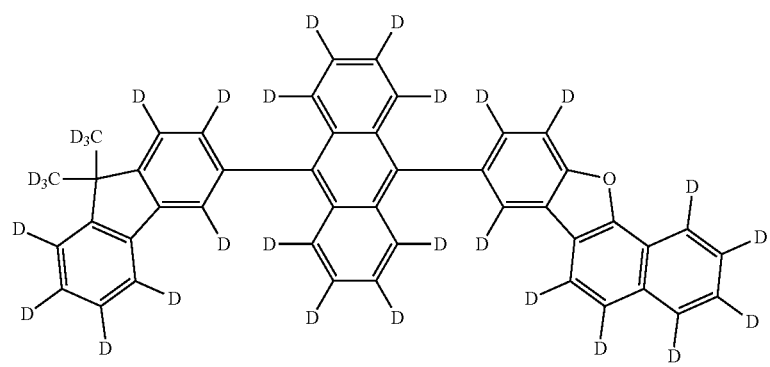
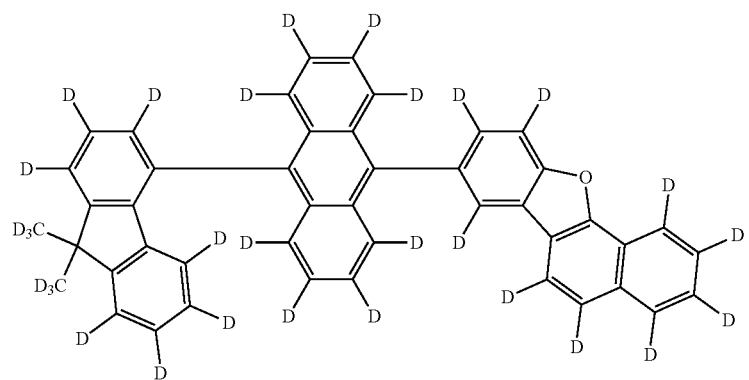

-continued
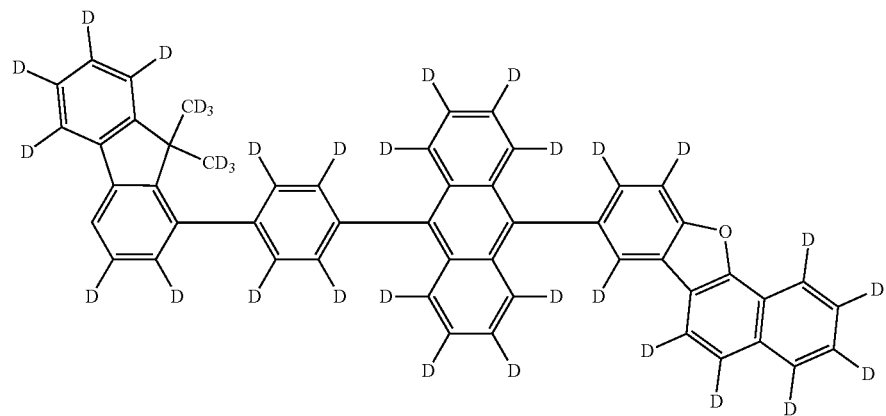
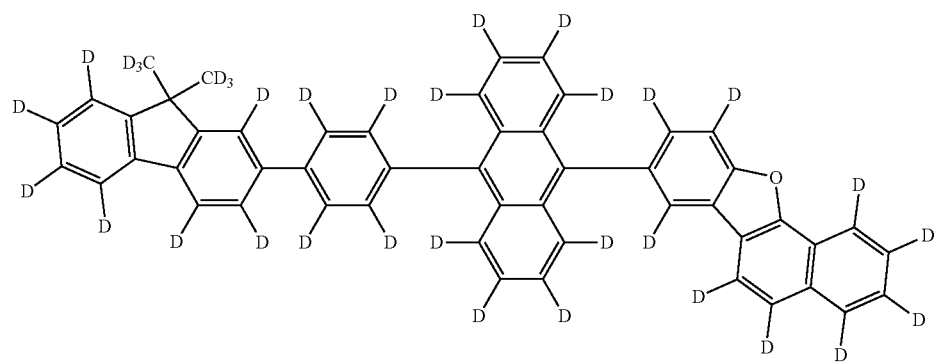
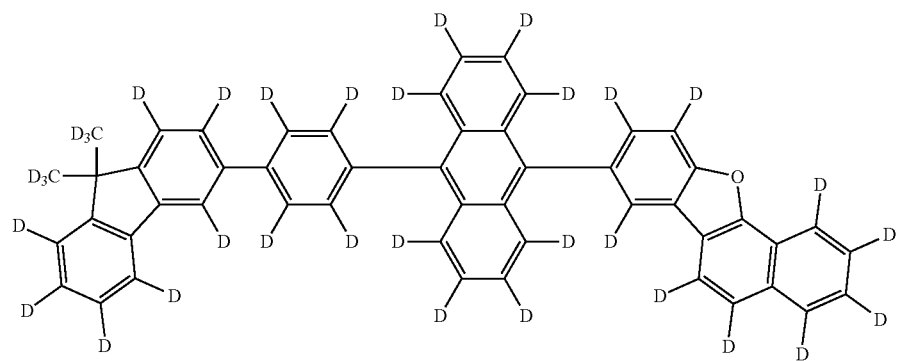
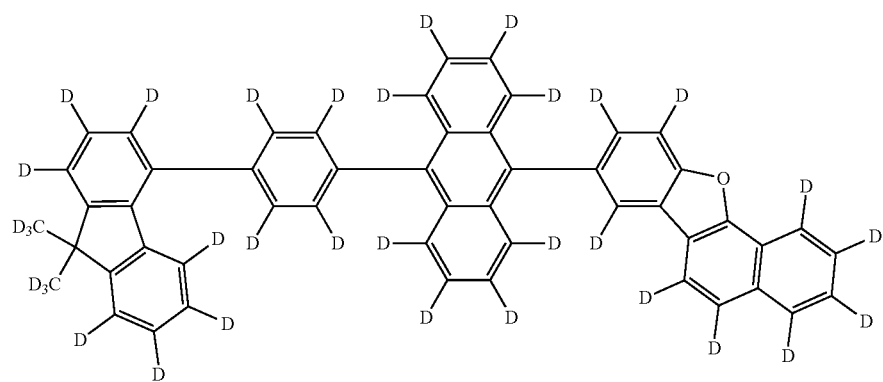

-continued
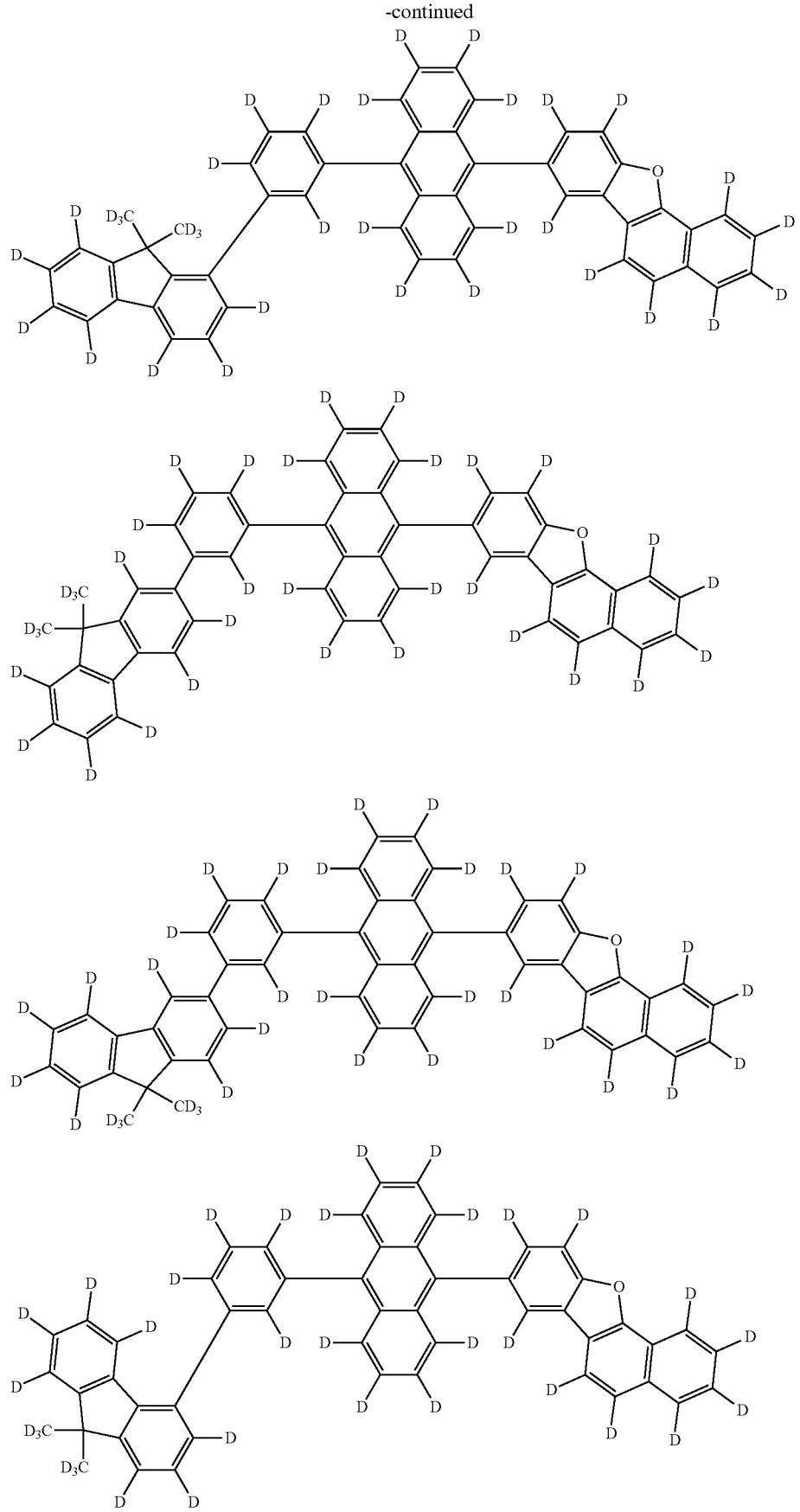

-continued
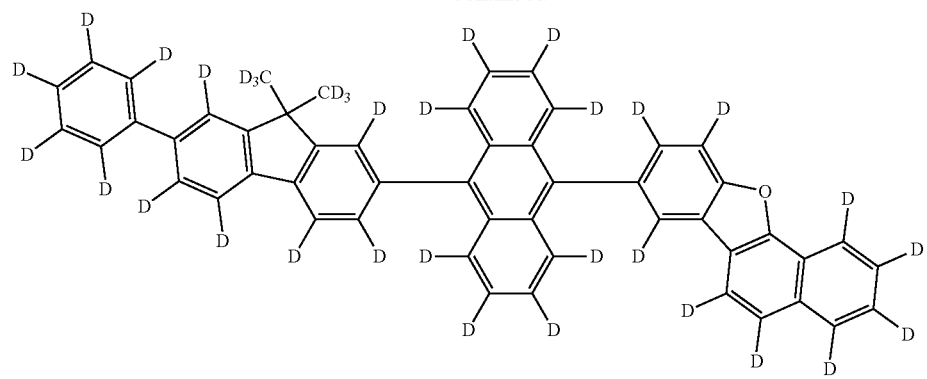
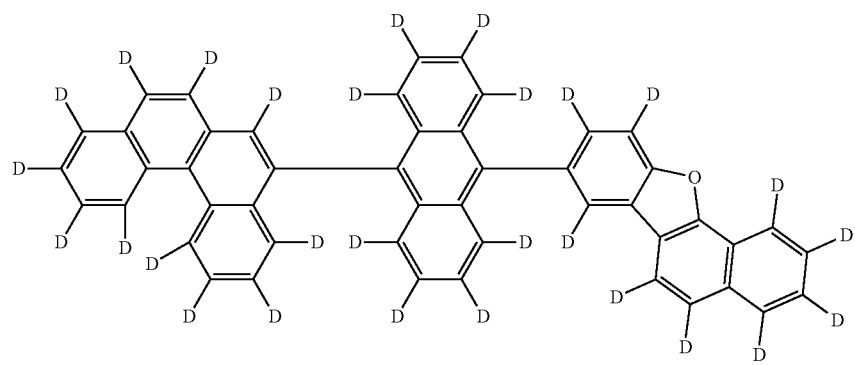
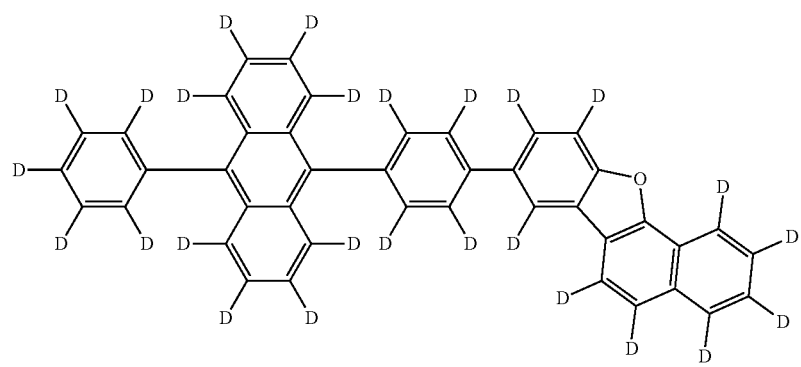
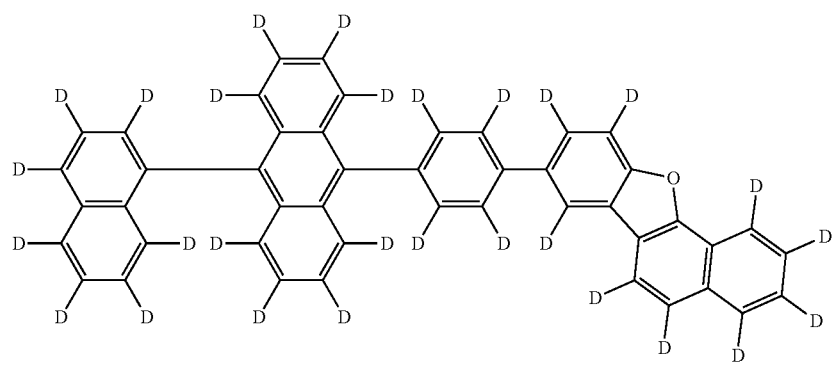

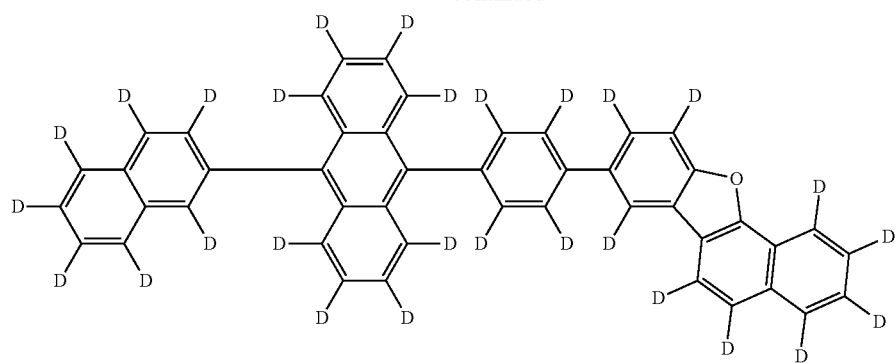
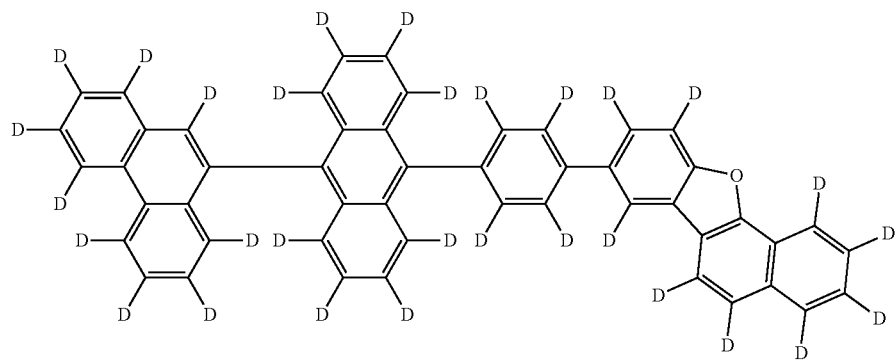
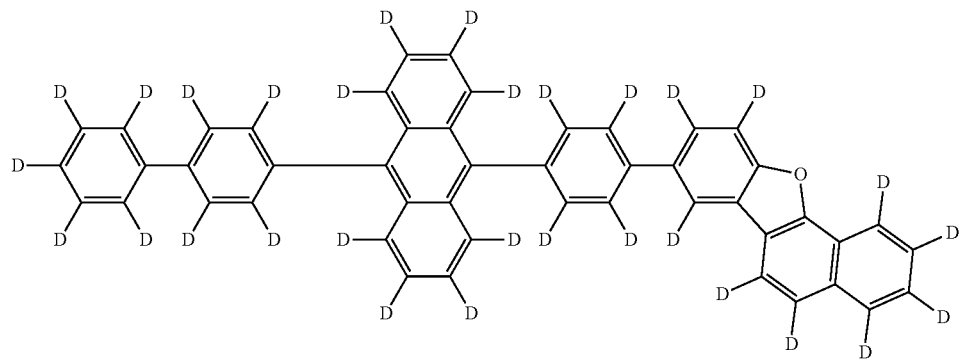
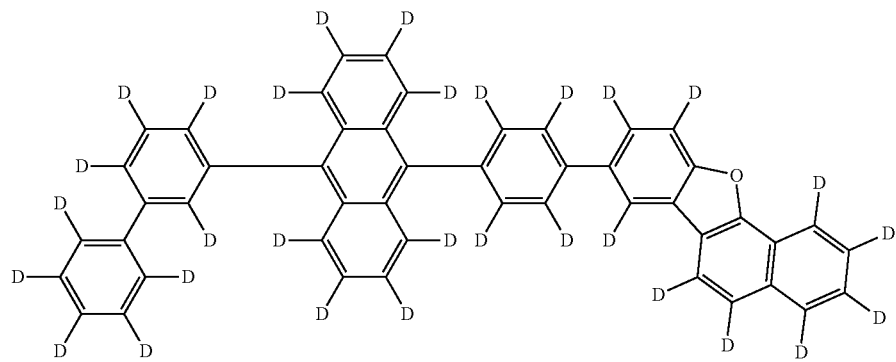

-continued
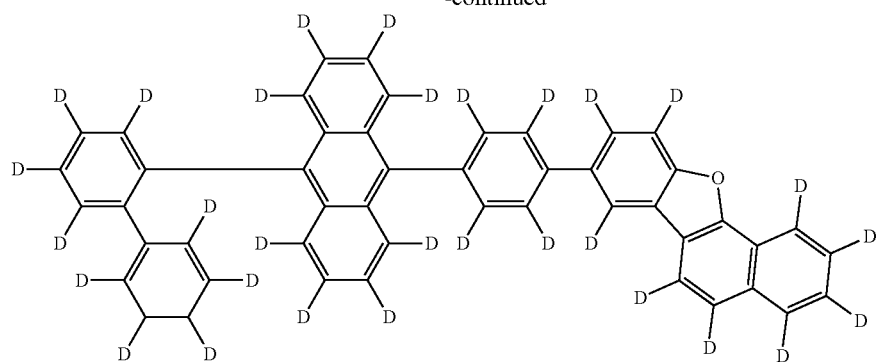
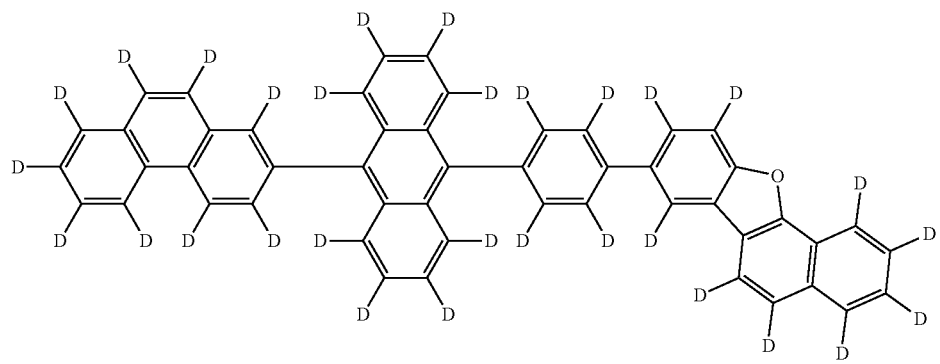
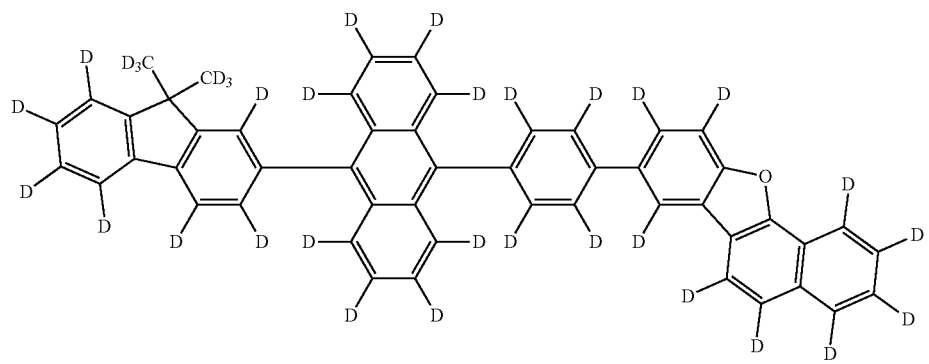
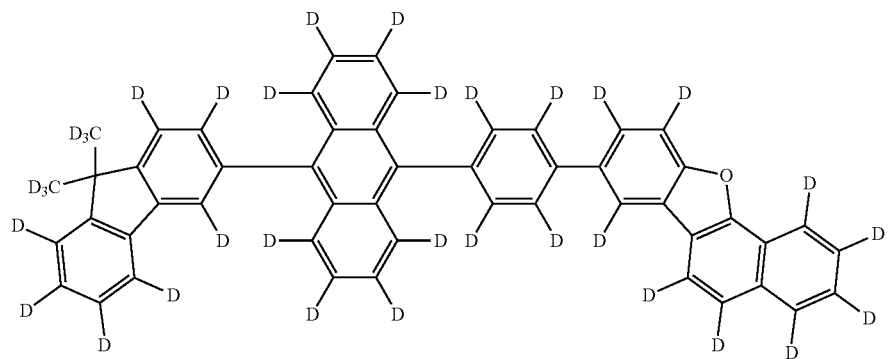

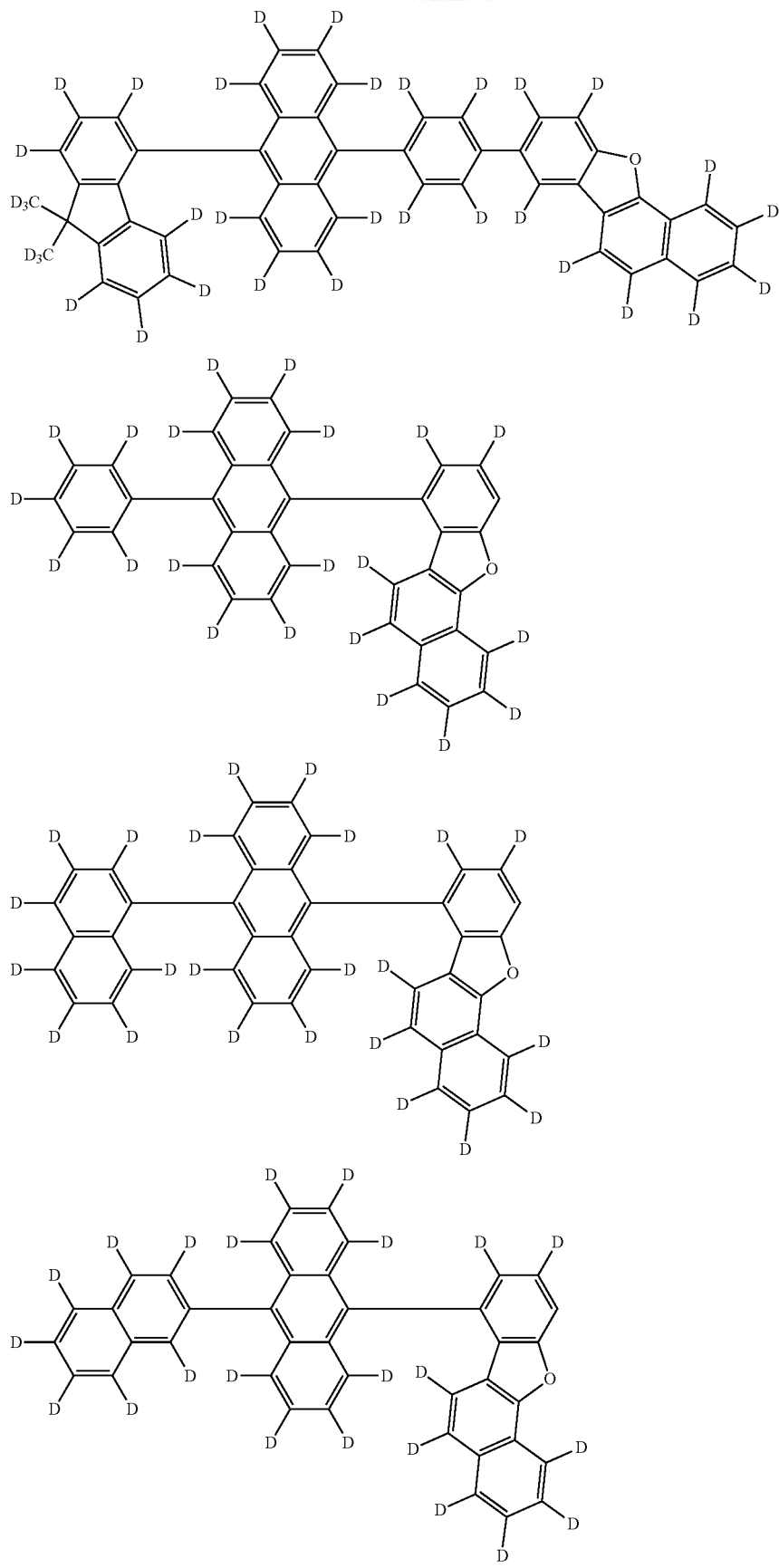

-continued
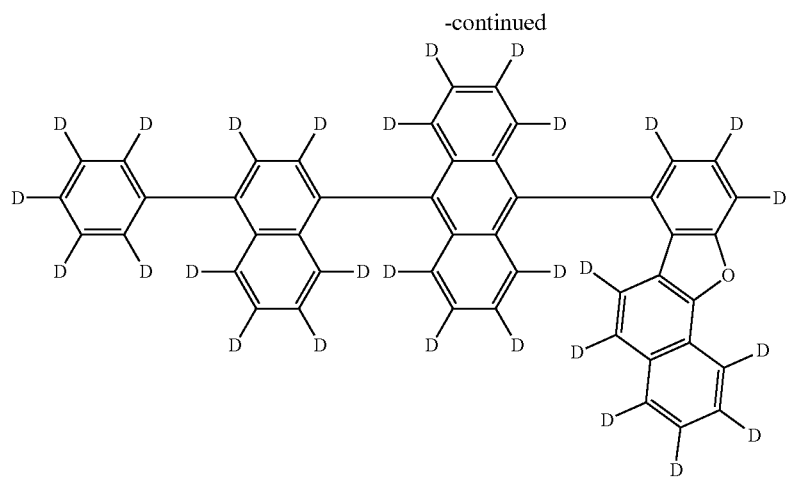
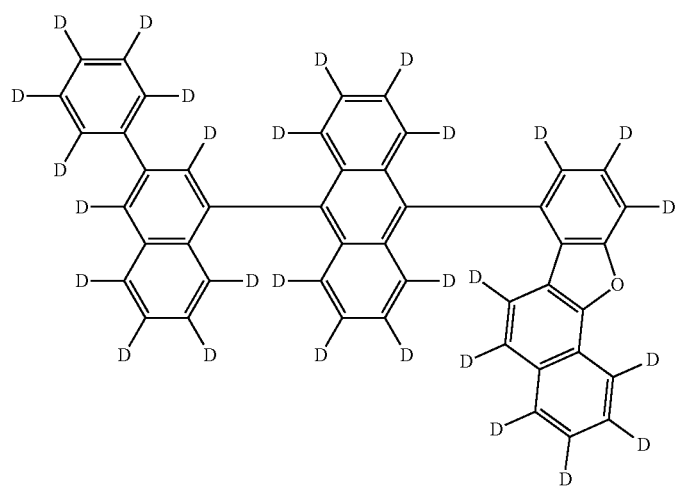
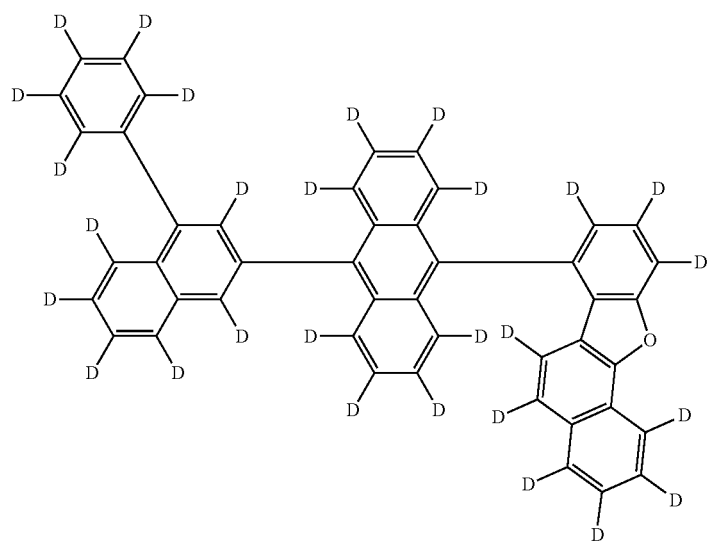

-continued
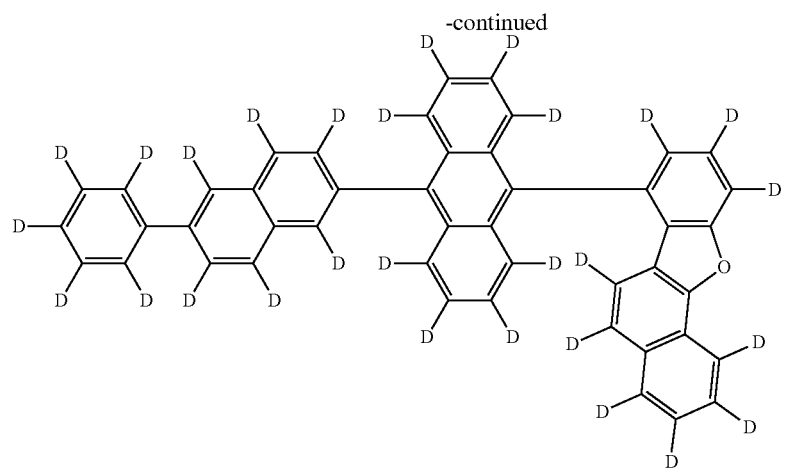
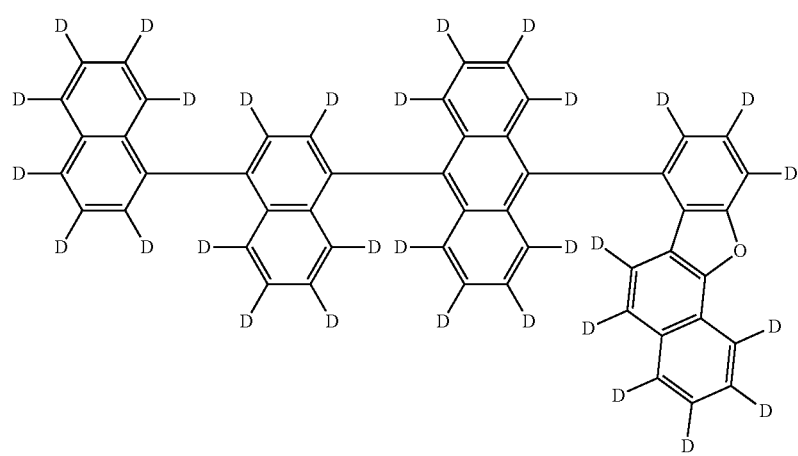
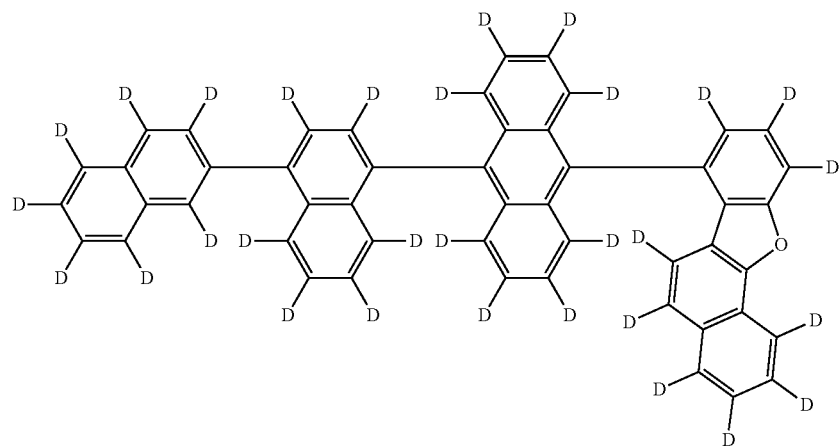

-continued
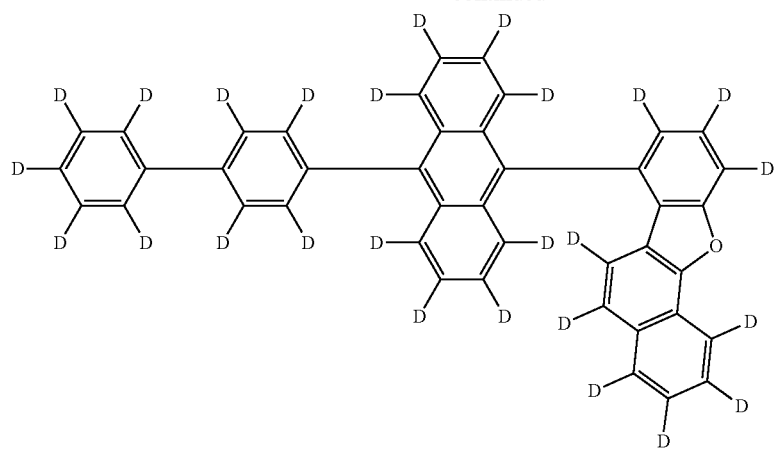
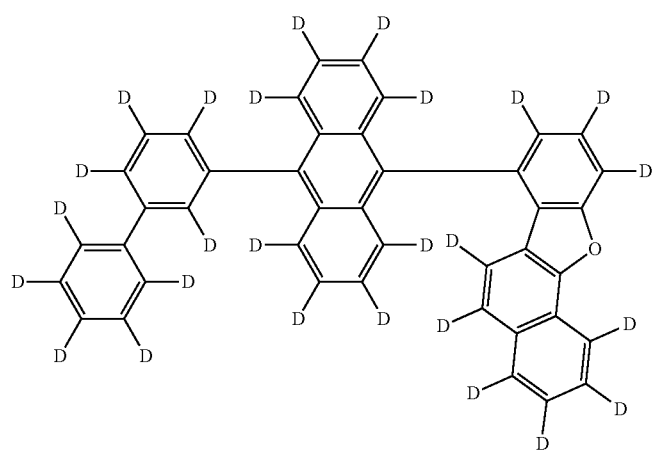
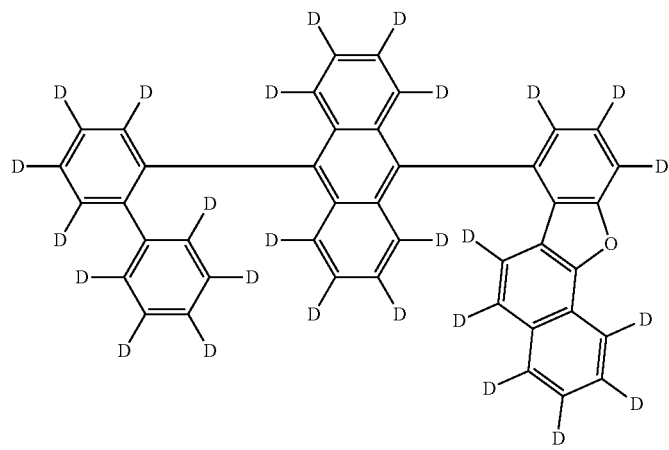

-continued
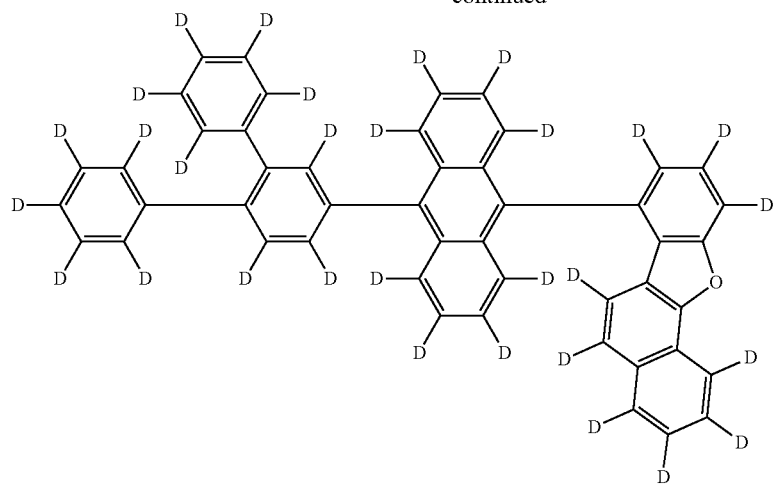
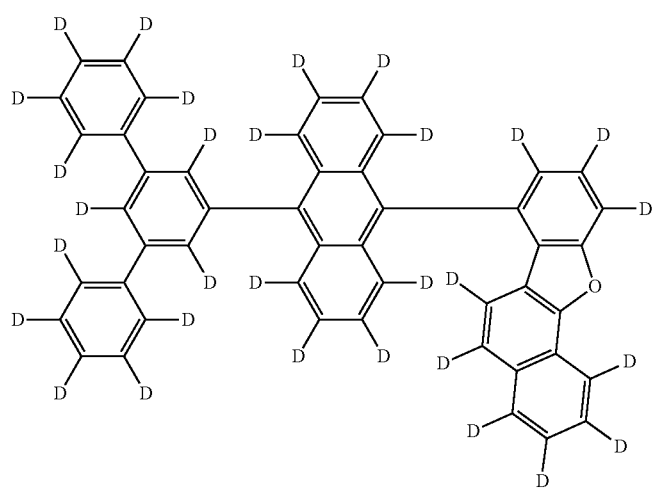
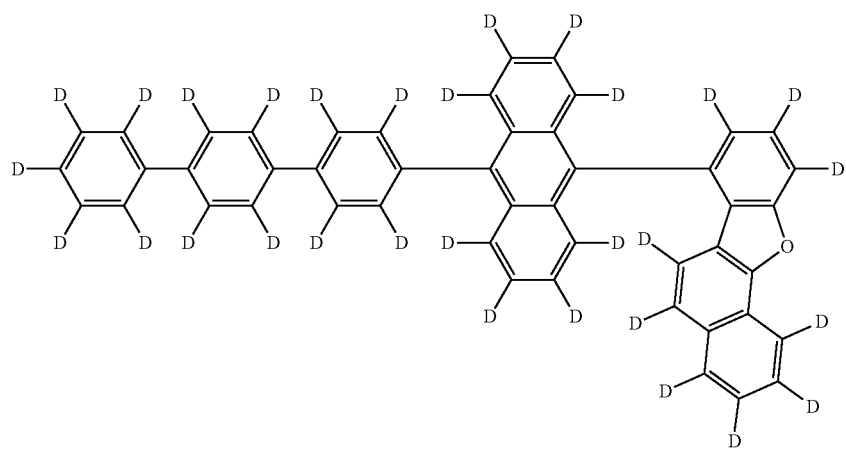

-continued
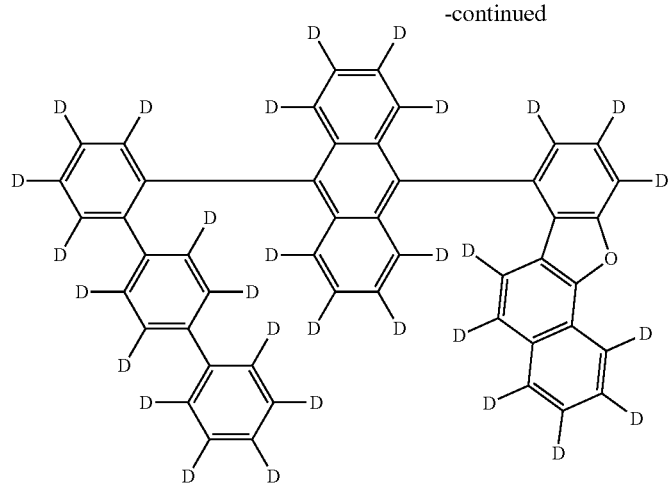
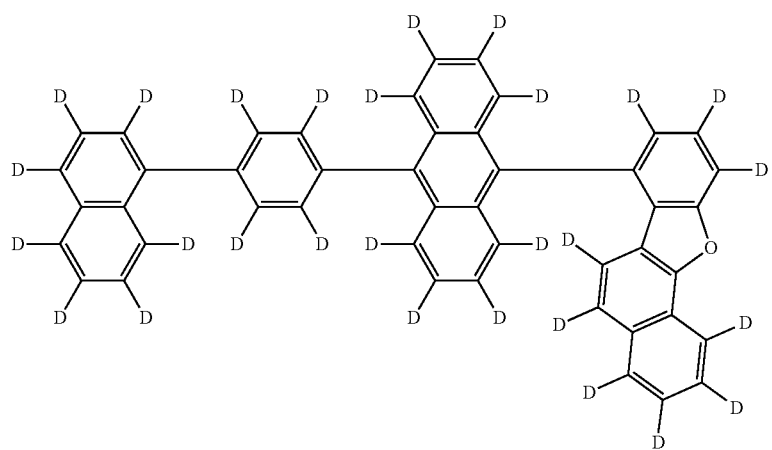
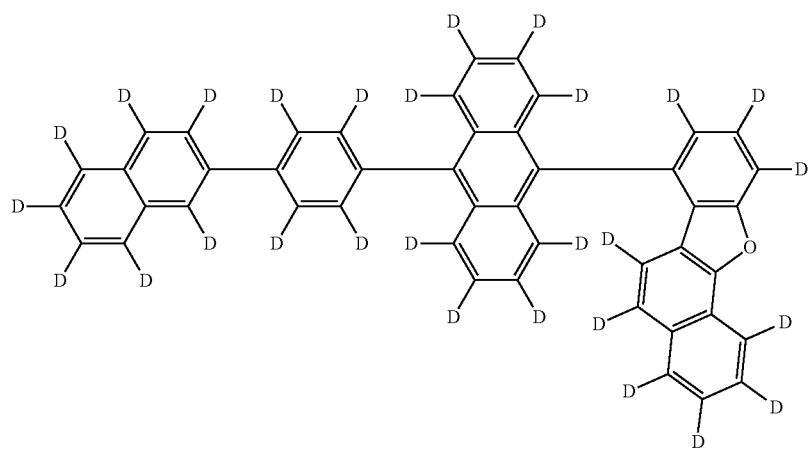

-continued
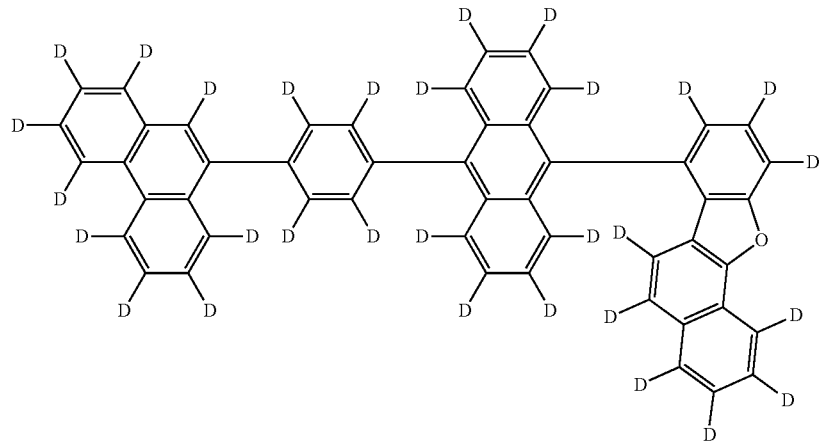

-continued
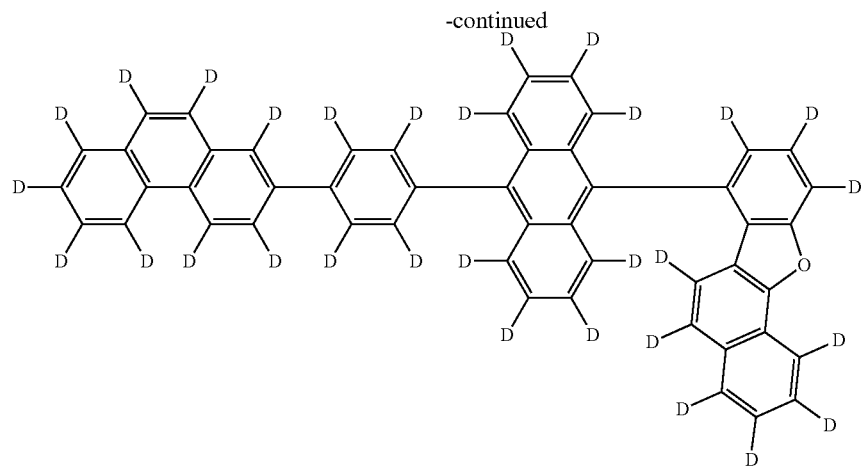
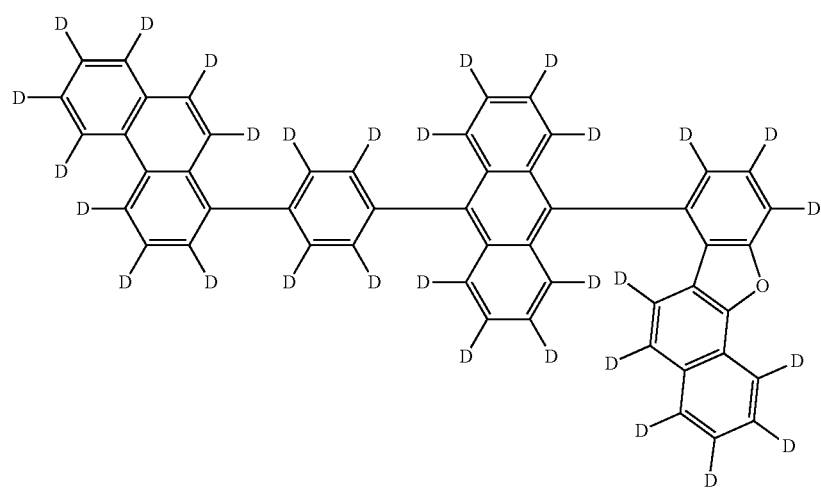
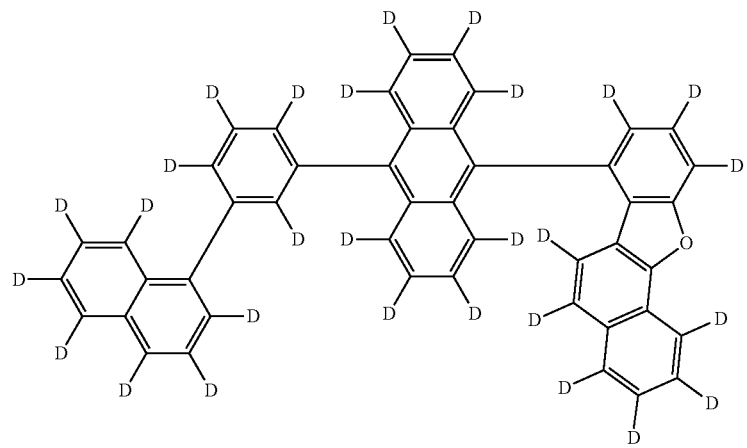

-continued
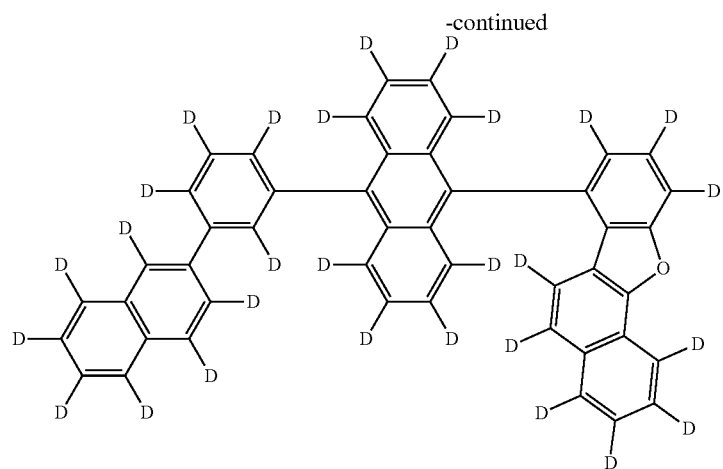
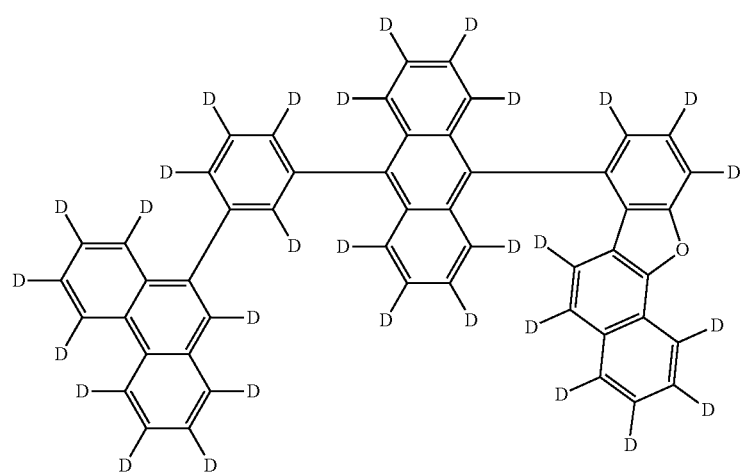
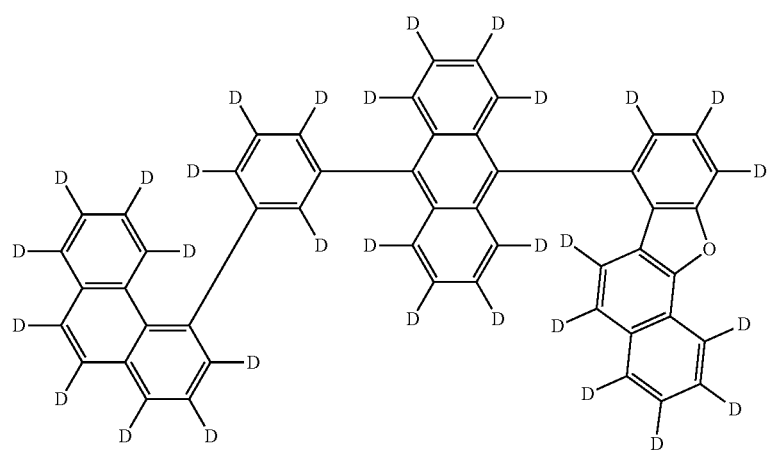

-continued
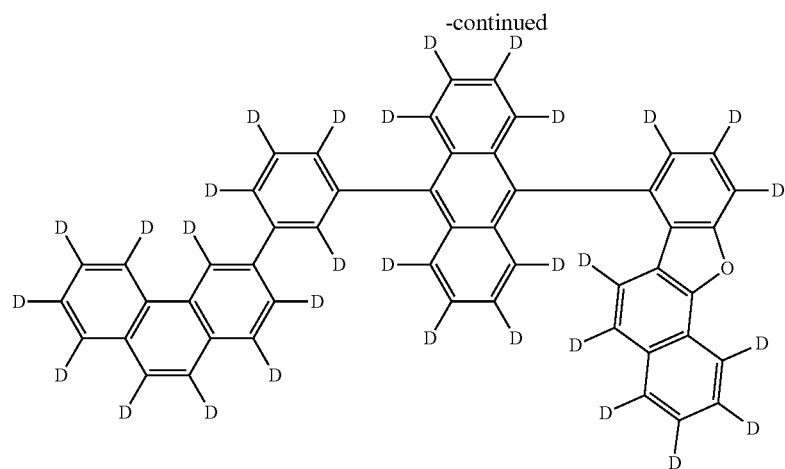
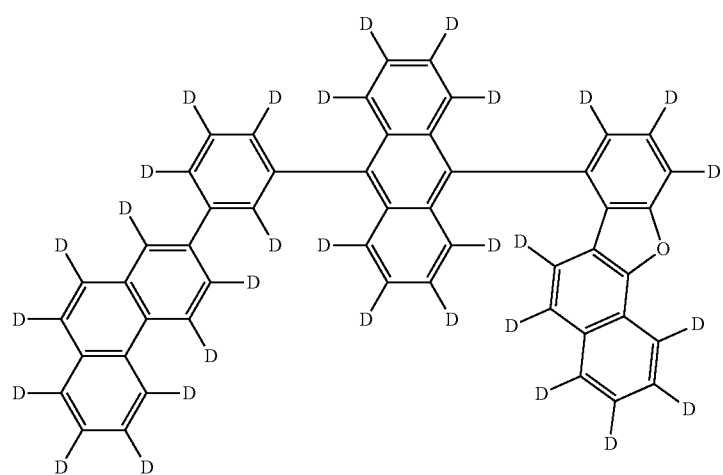
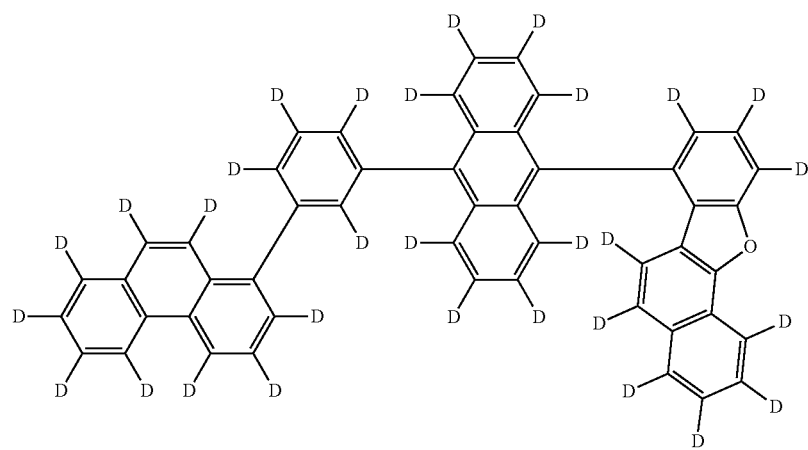

-continued
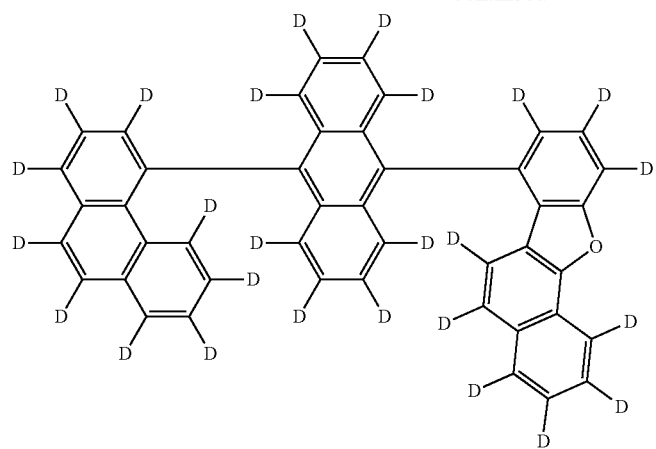
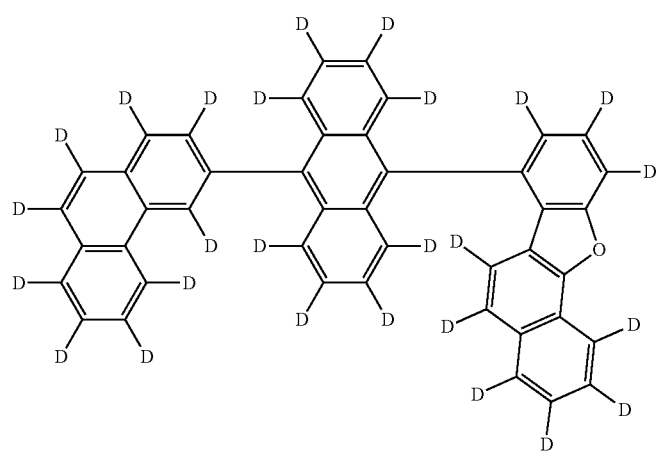
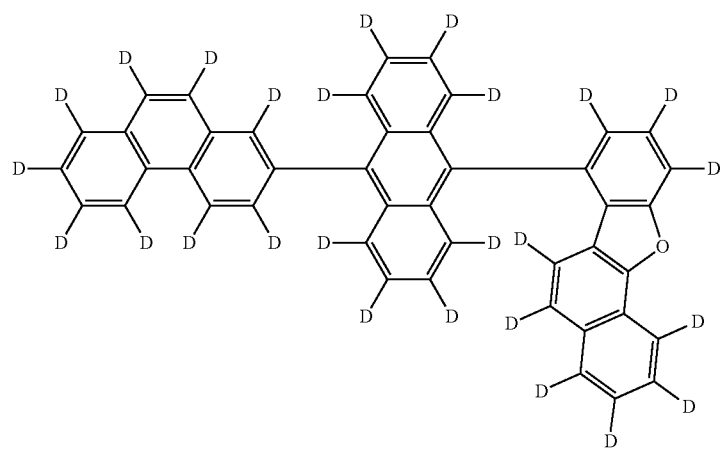

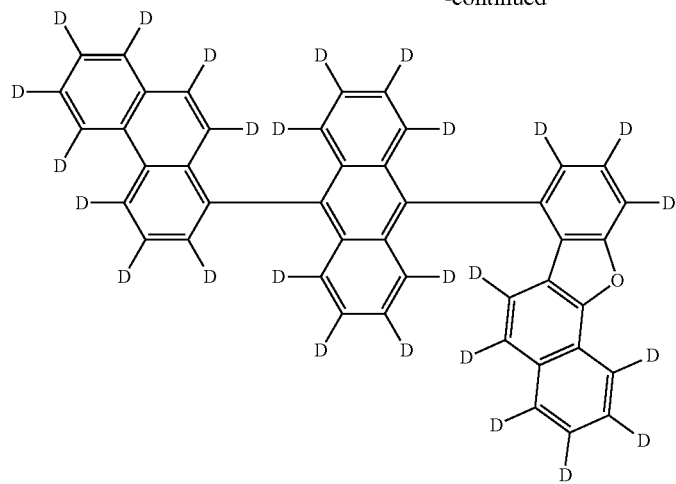
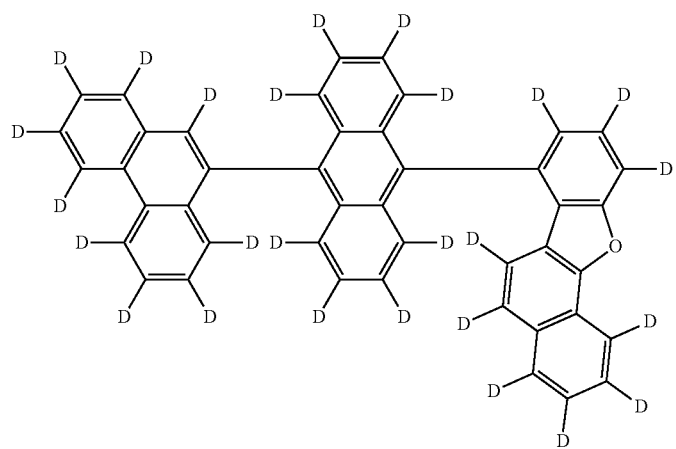
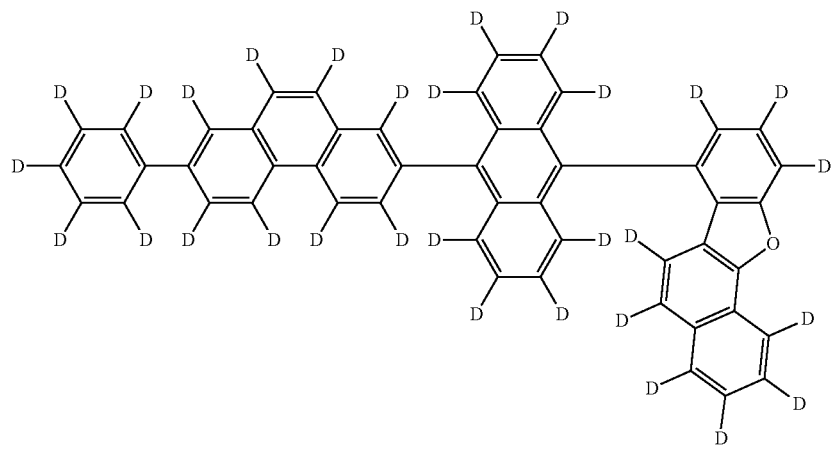

-continued
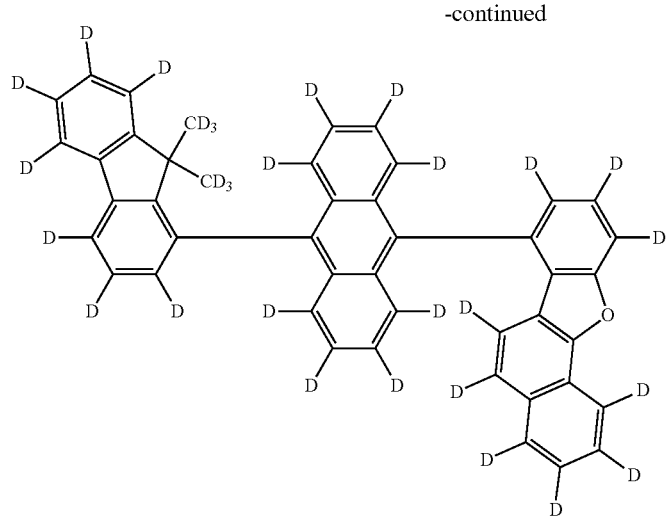
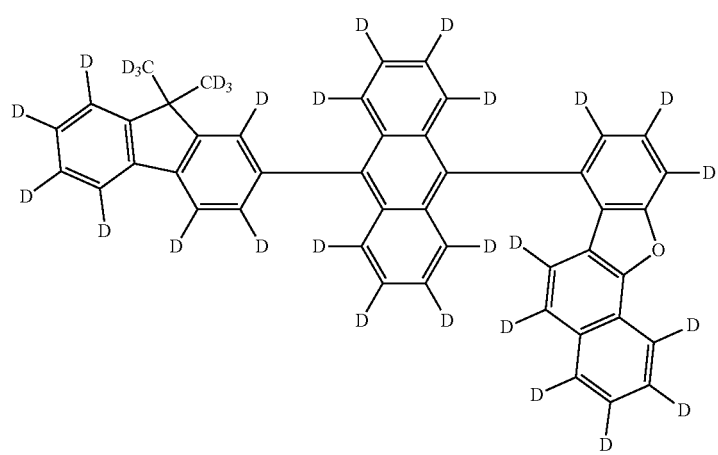
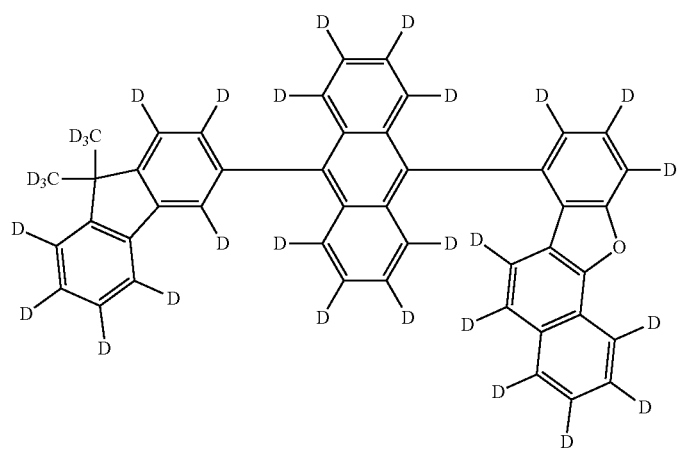

-continued
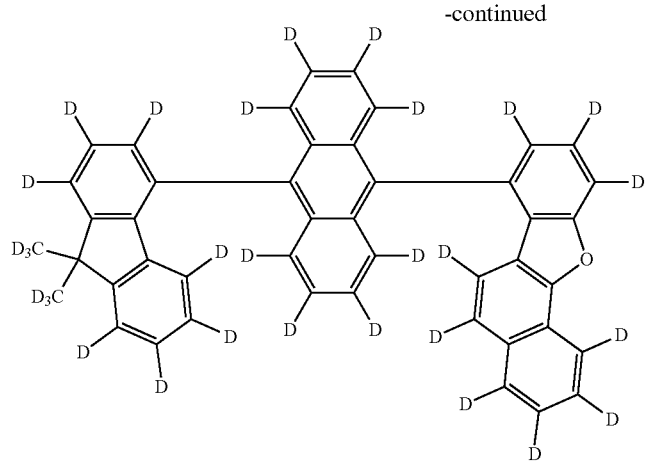
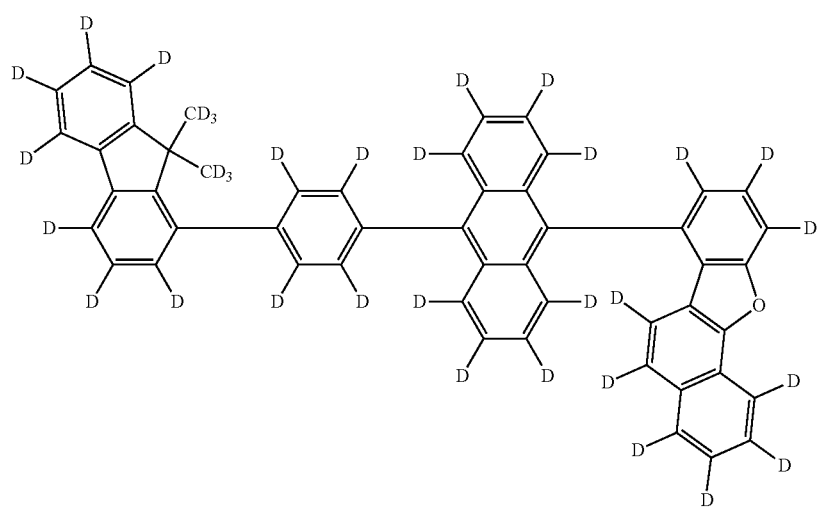
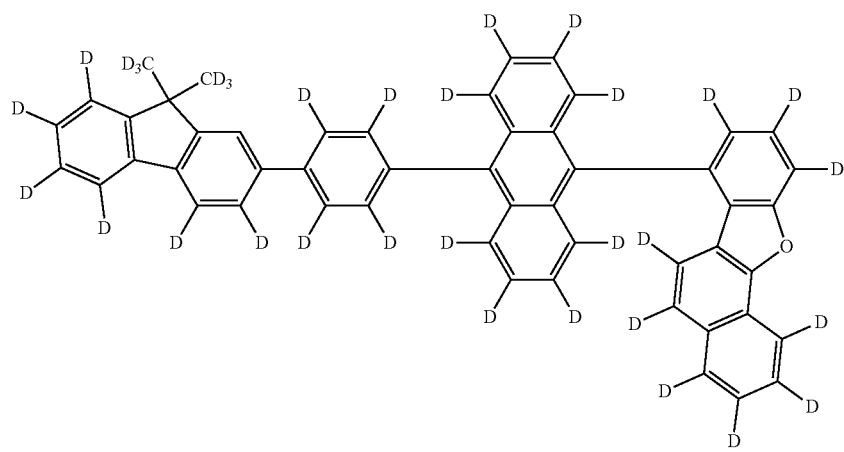

-continued
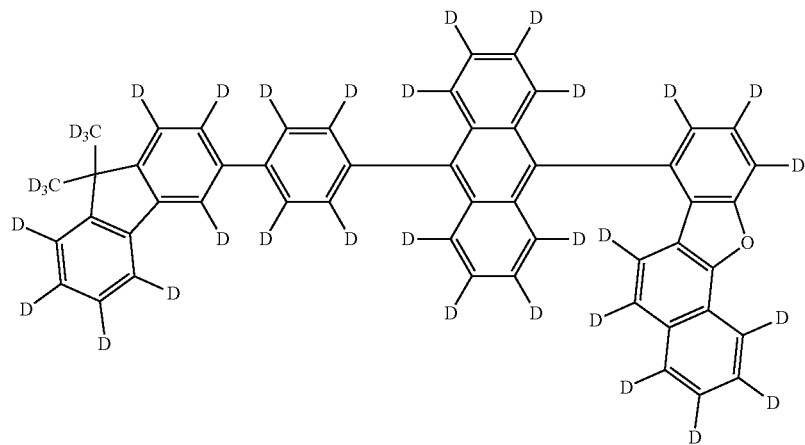
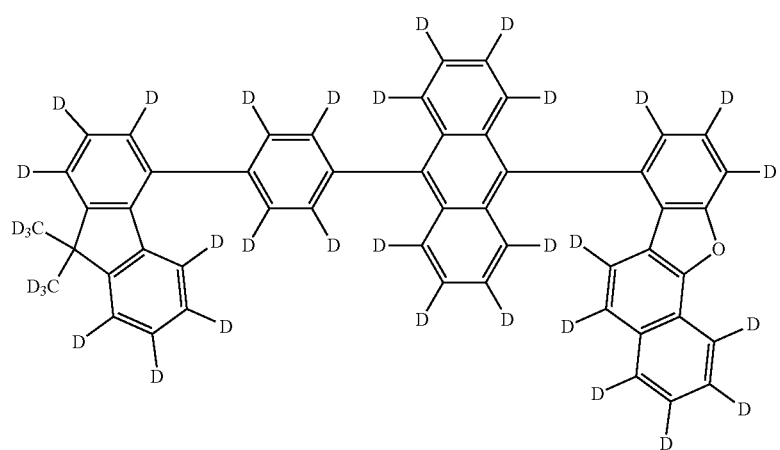
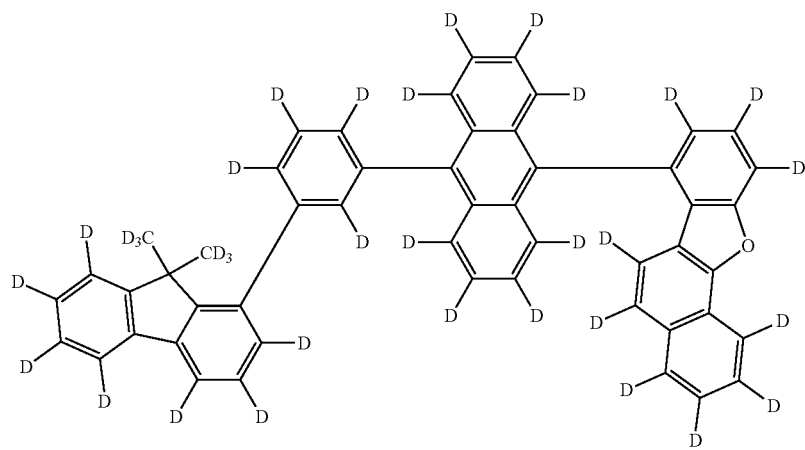

-continued
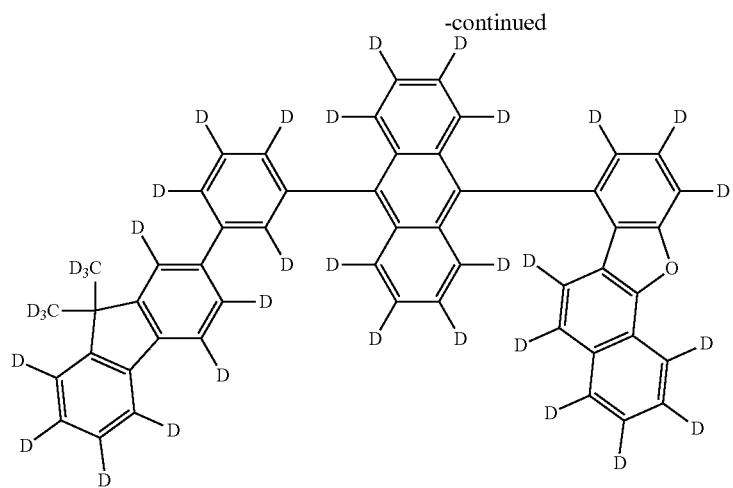
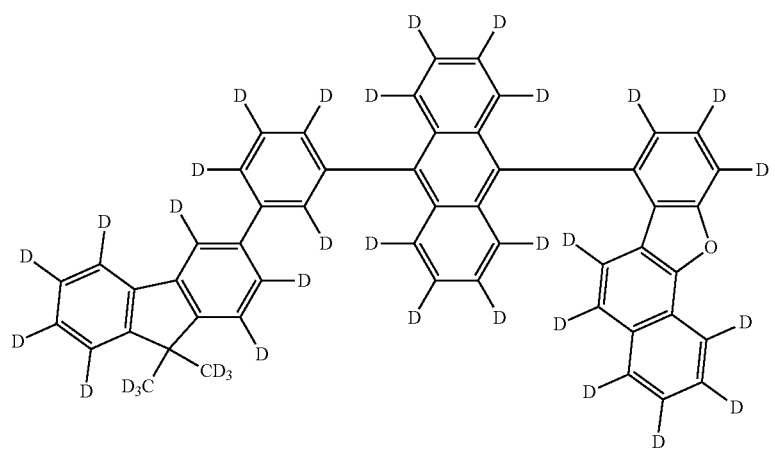
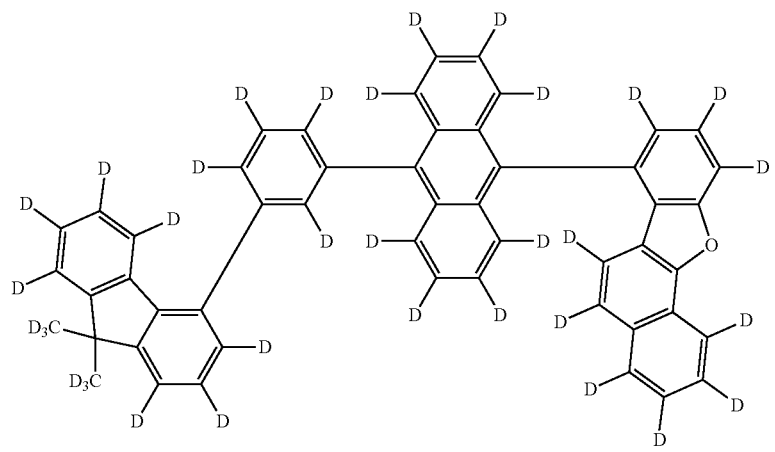

-continued
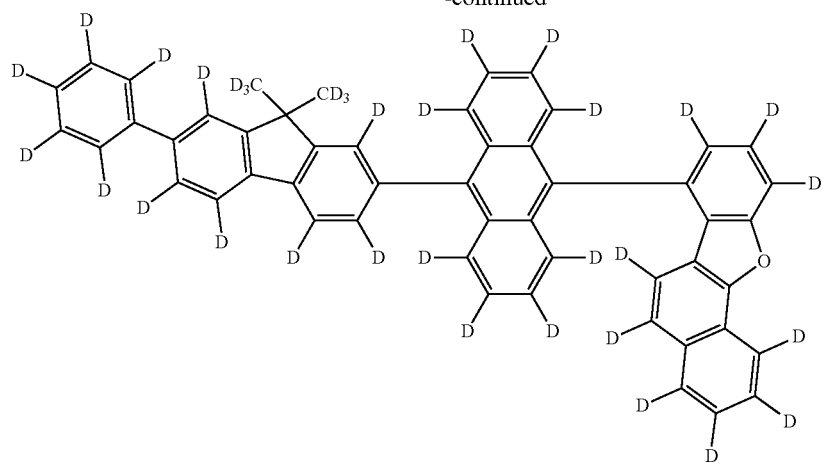
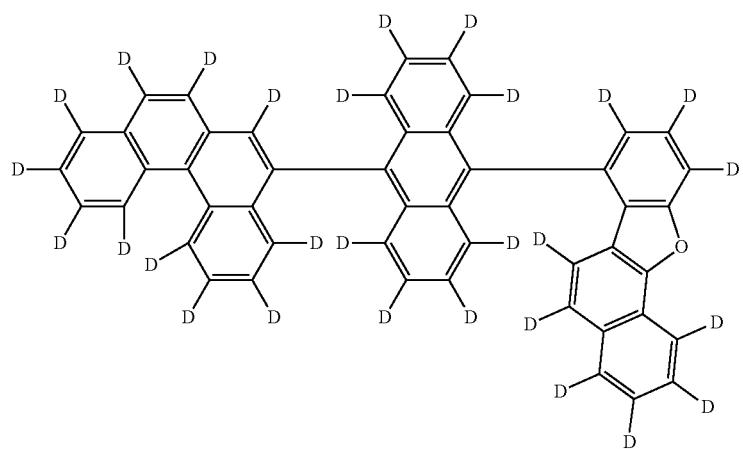
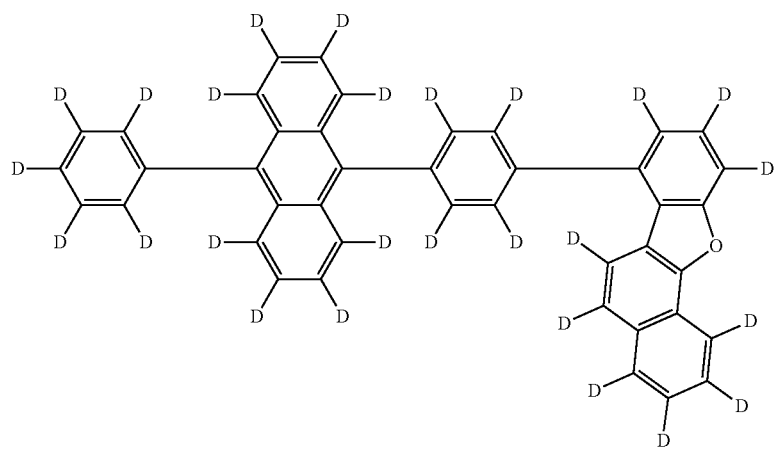

-continued
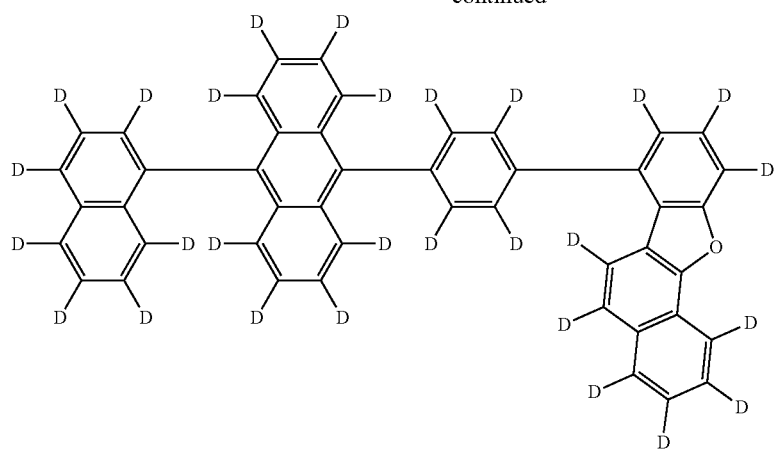
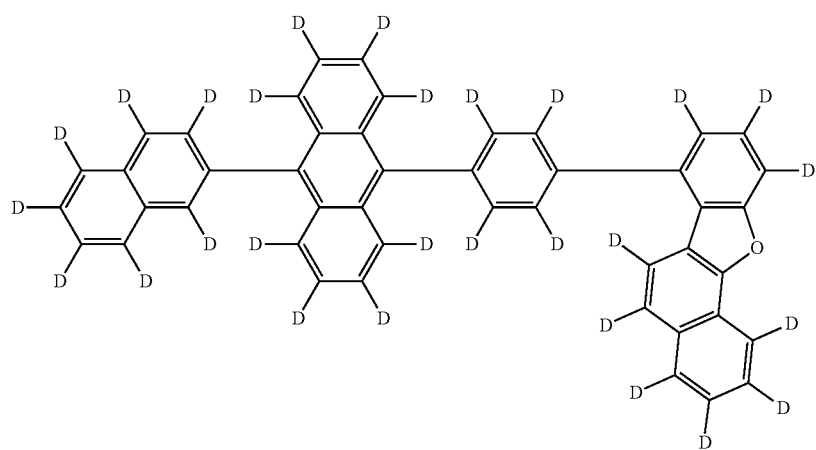
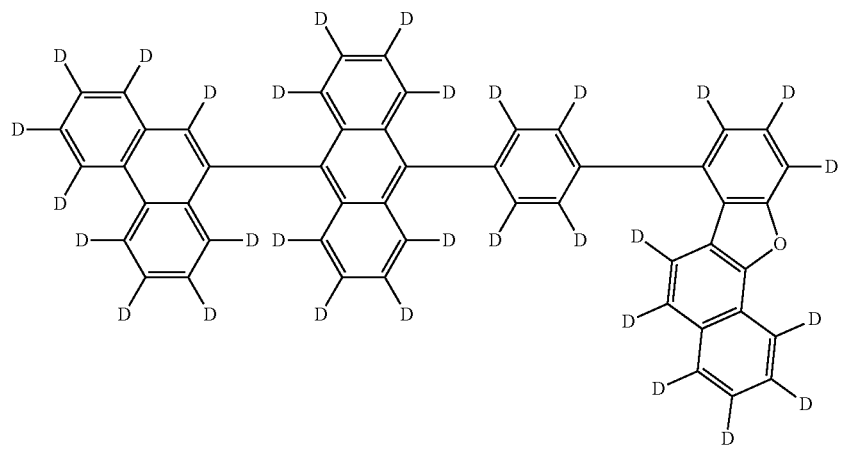

-continued
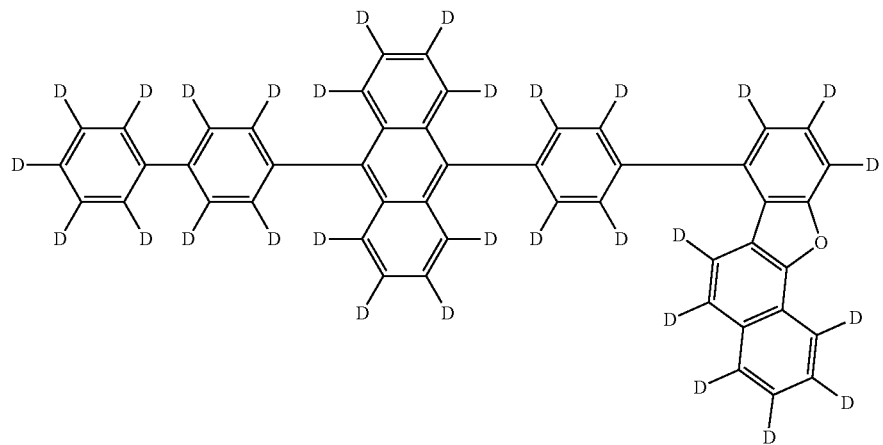
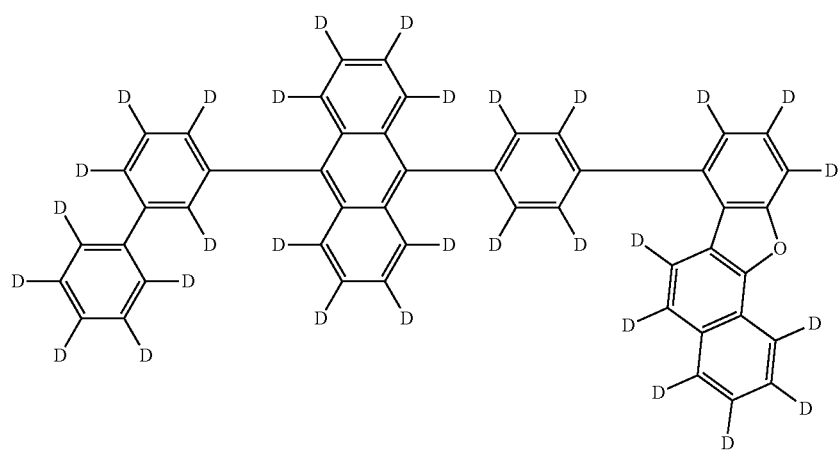
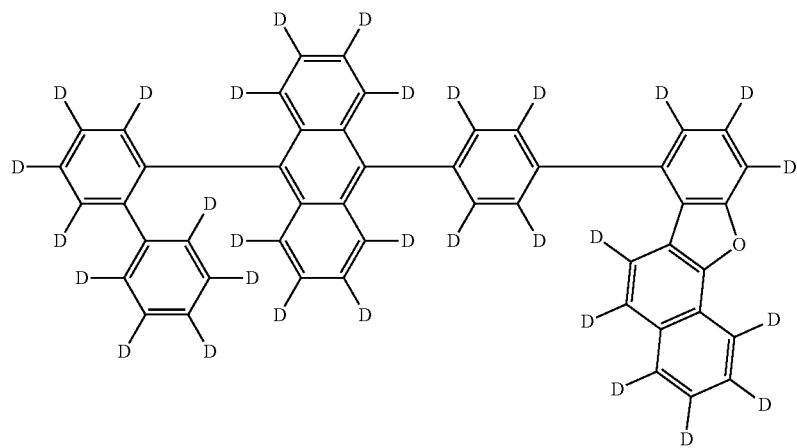

-continued
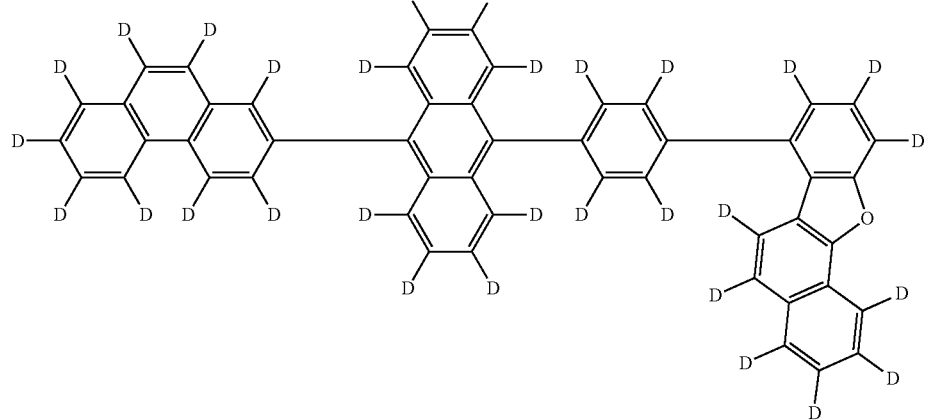
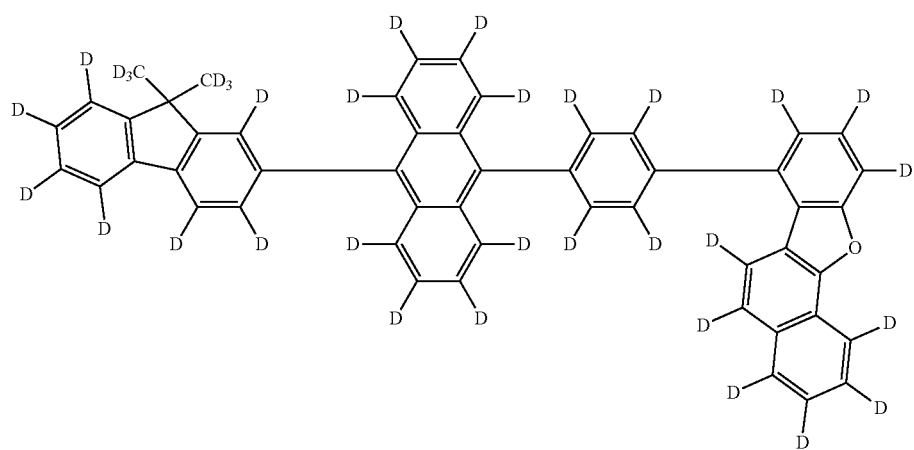
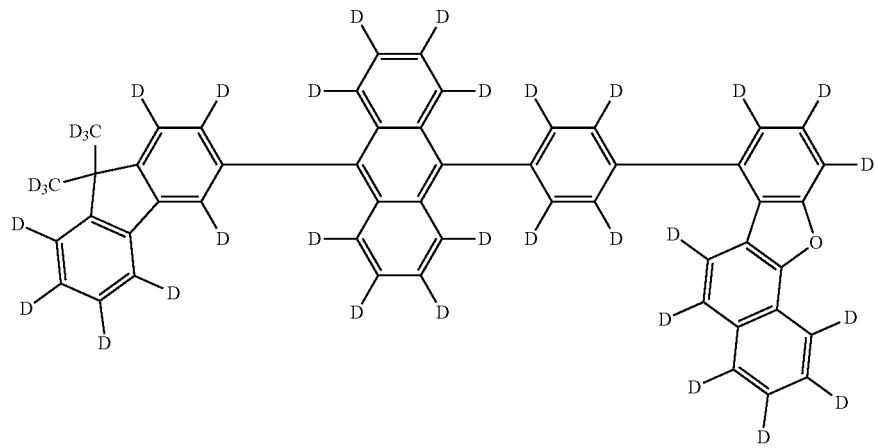

-continued
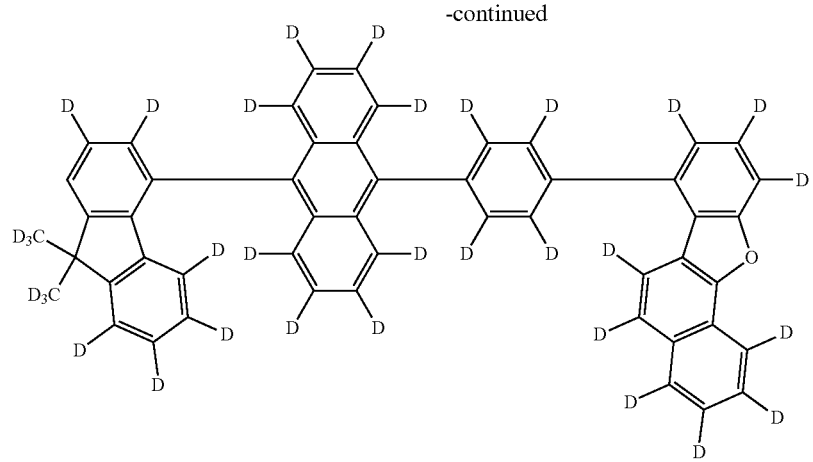
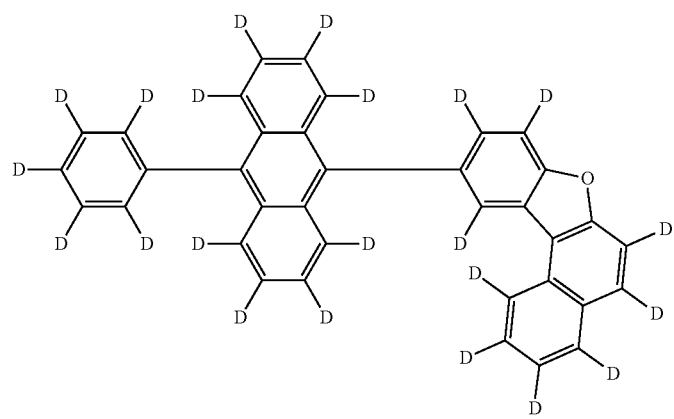
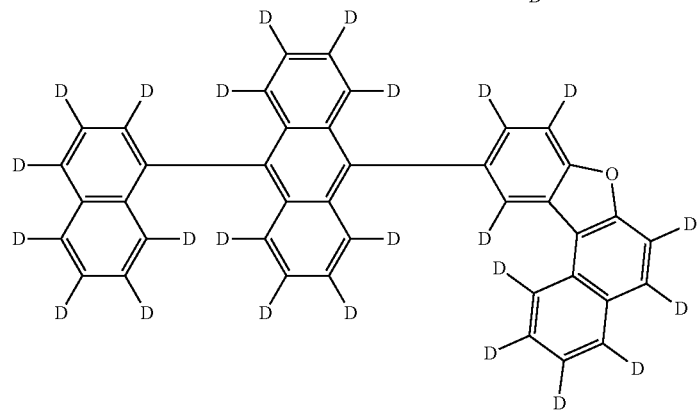
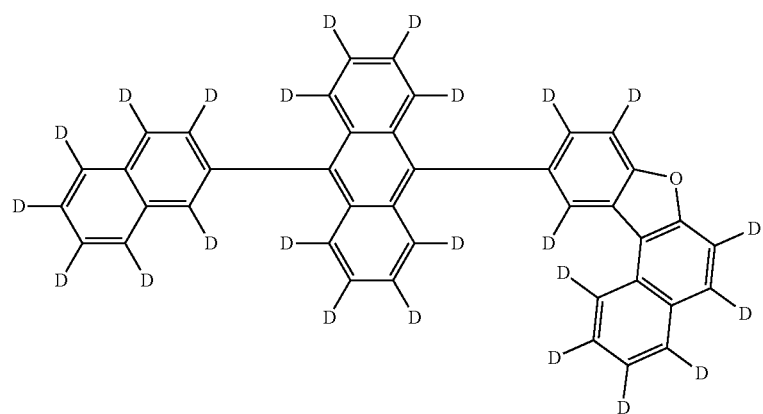

-continued
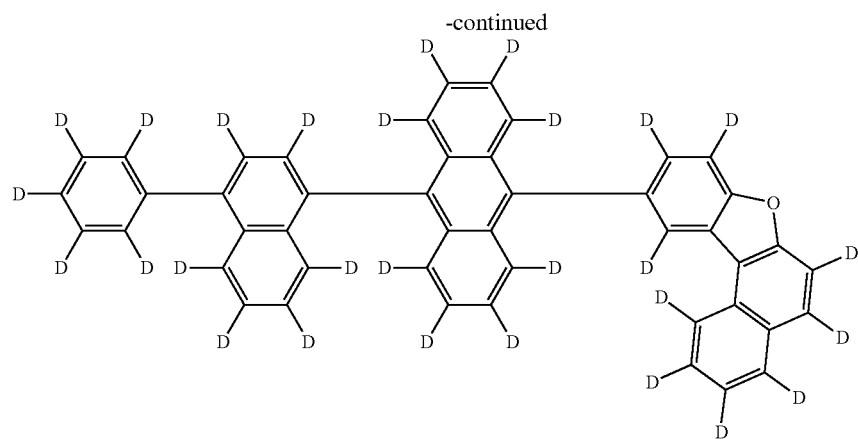
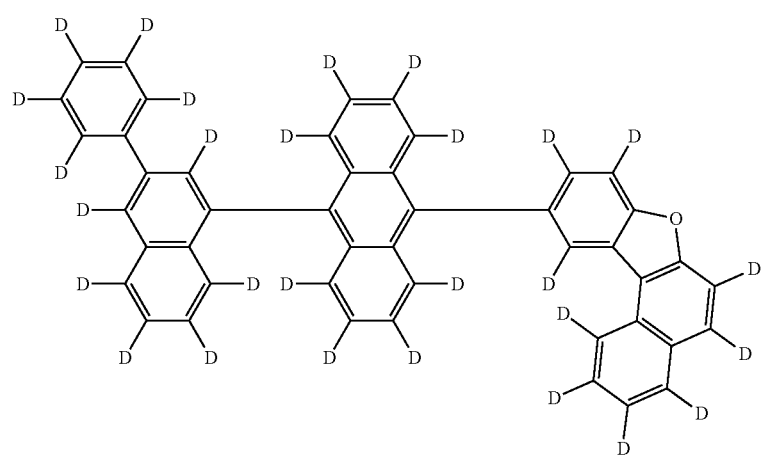
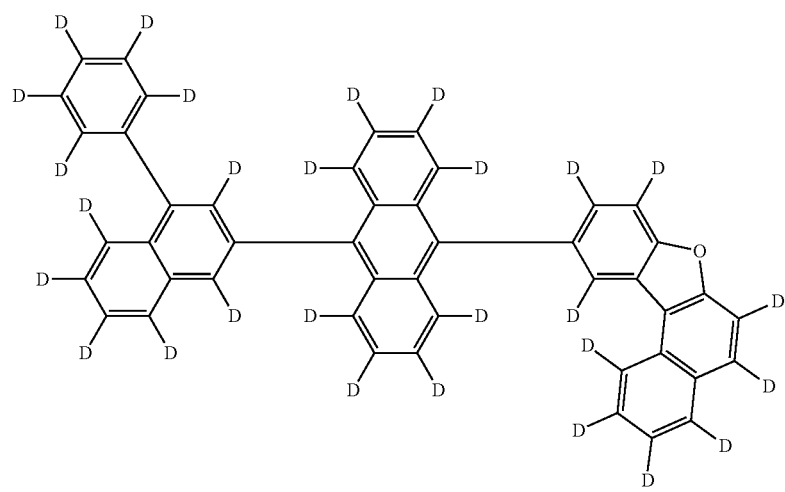

-continued
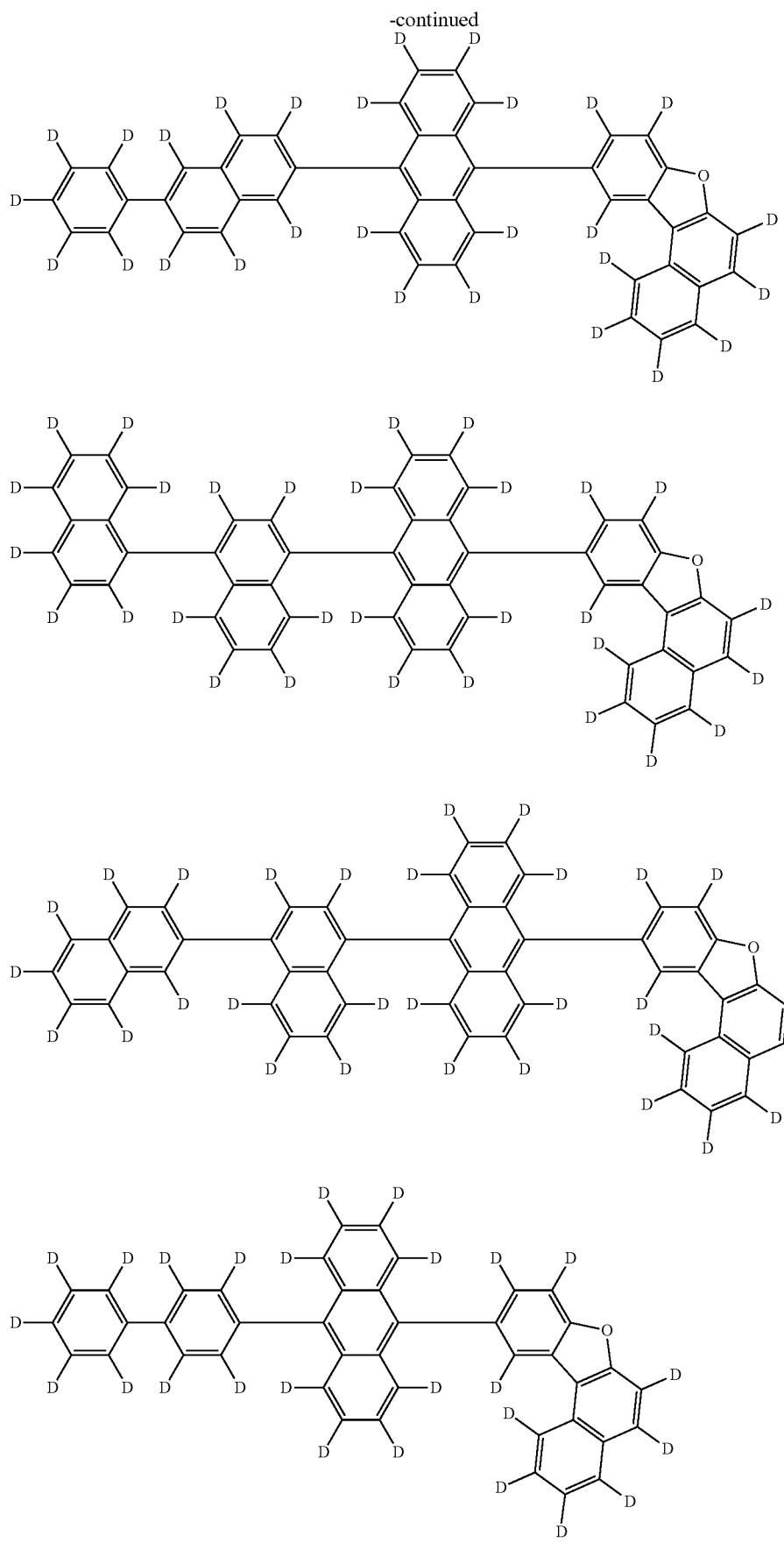

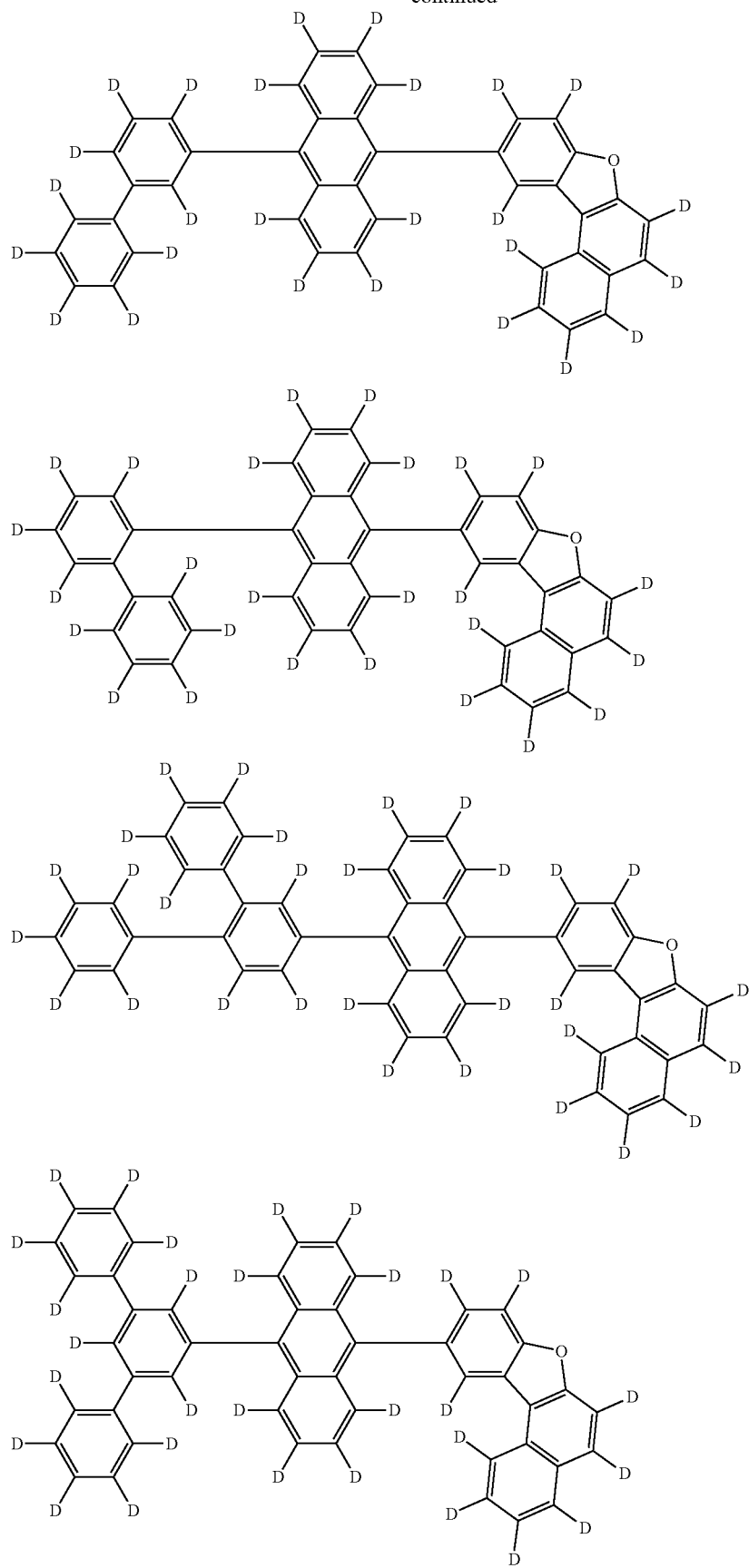

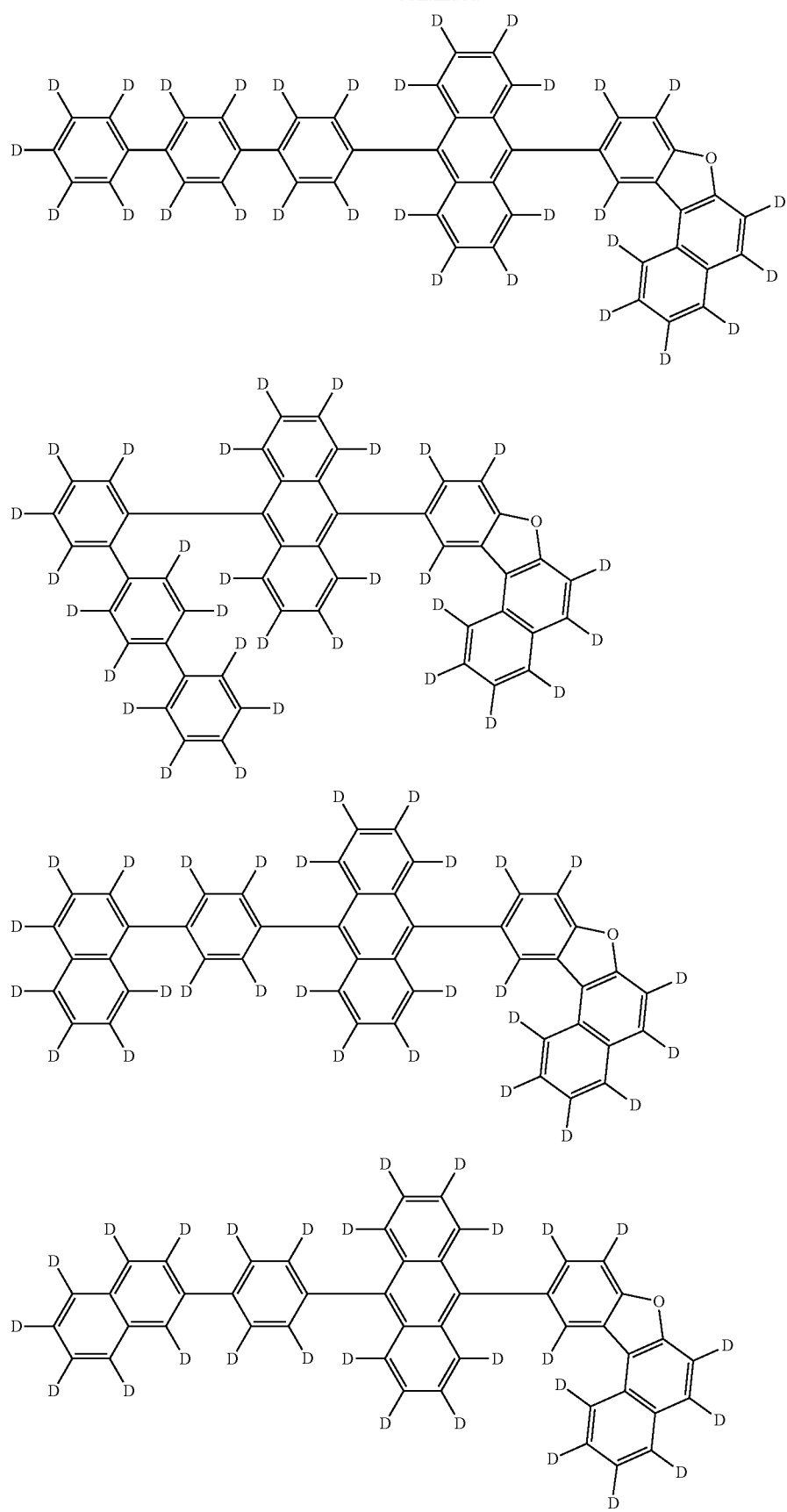

-continued
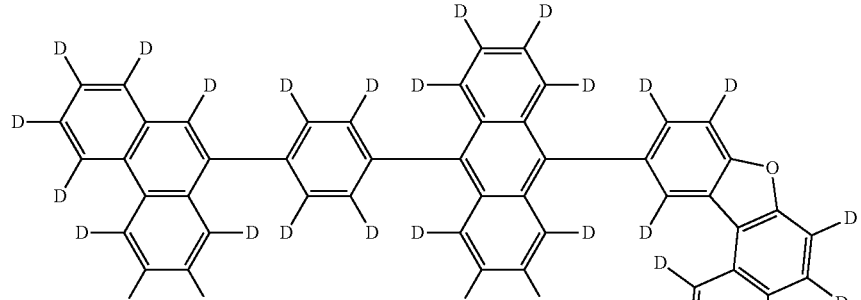
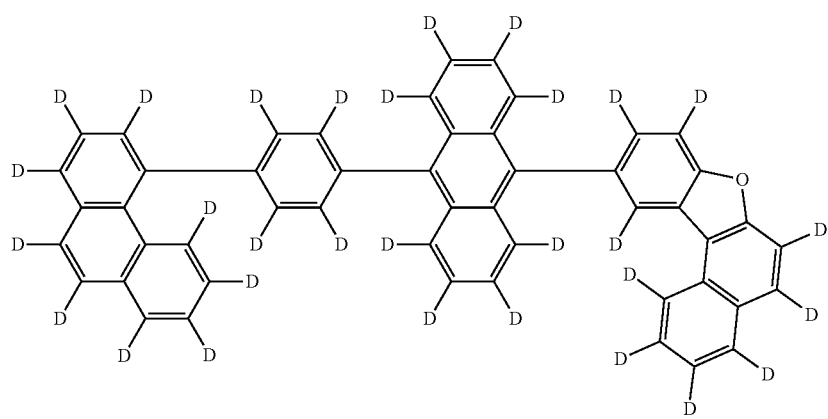
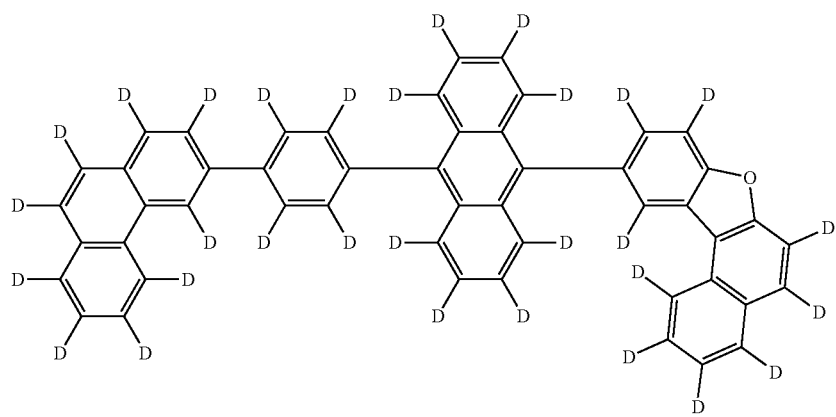
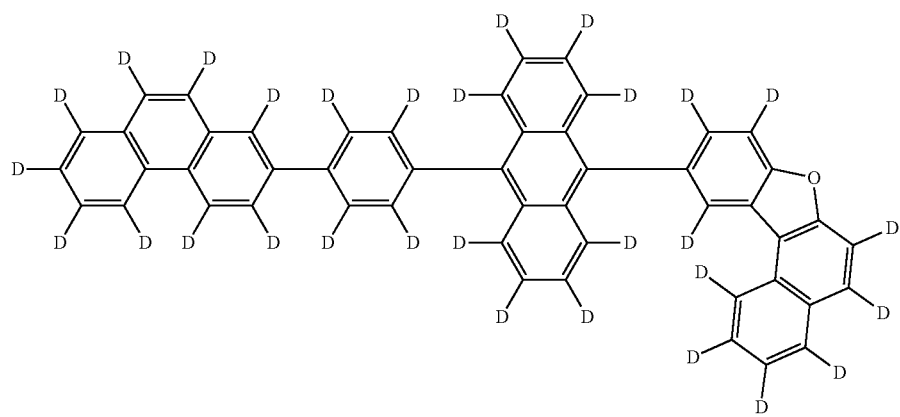

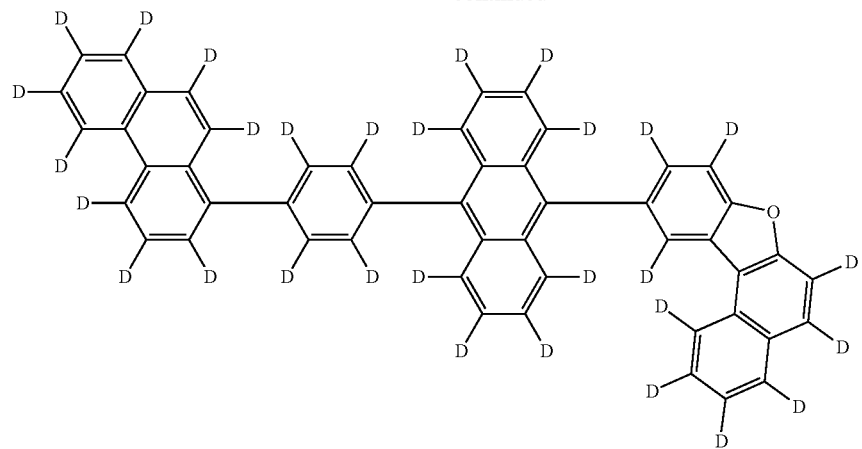
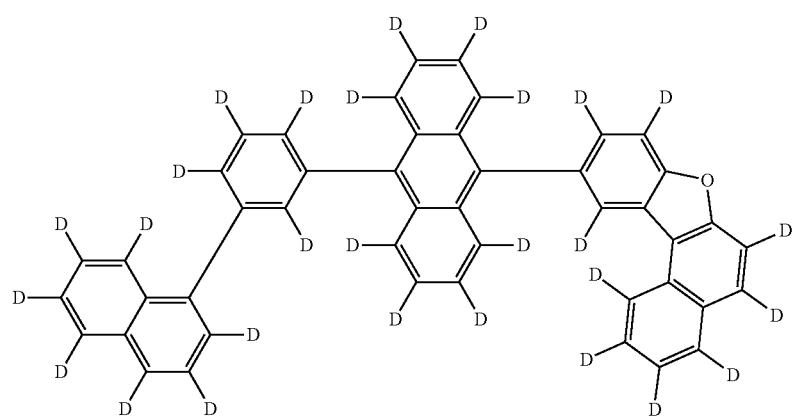
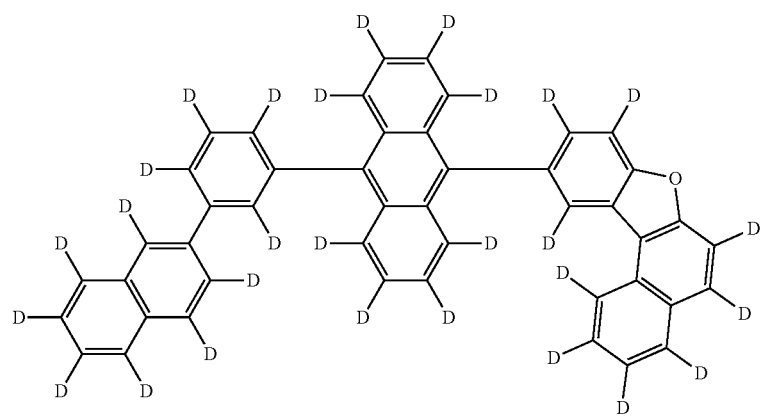

-continued
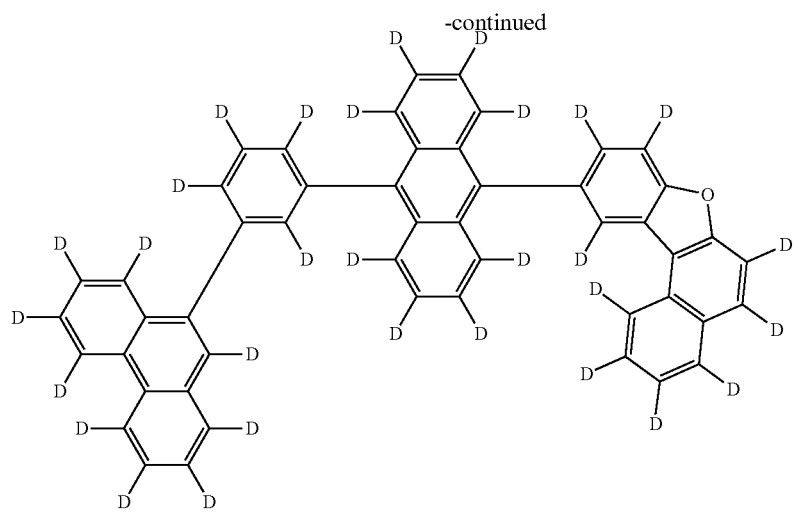
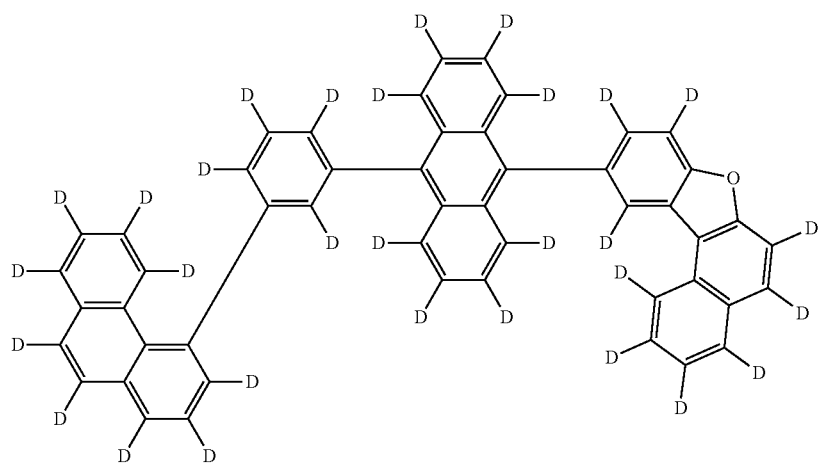
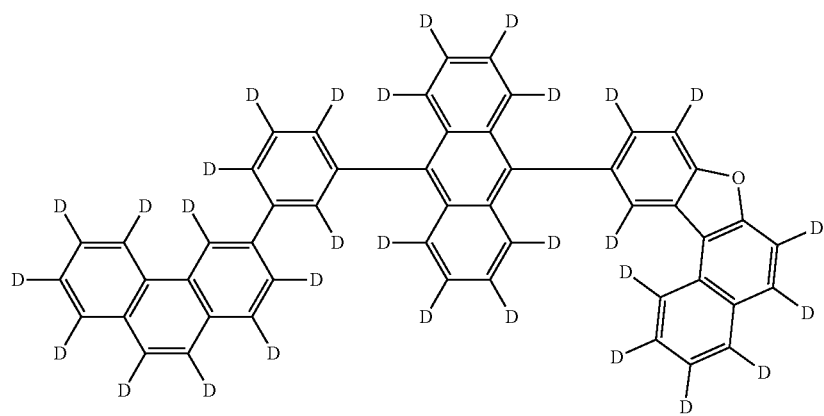

-continued
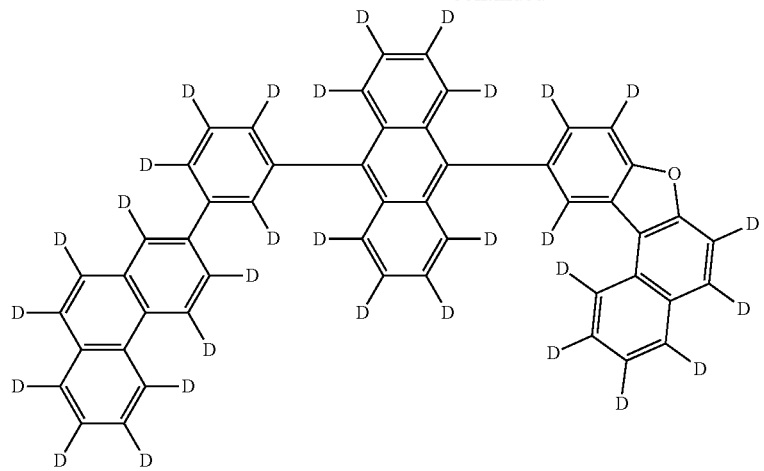
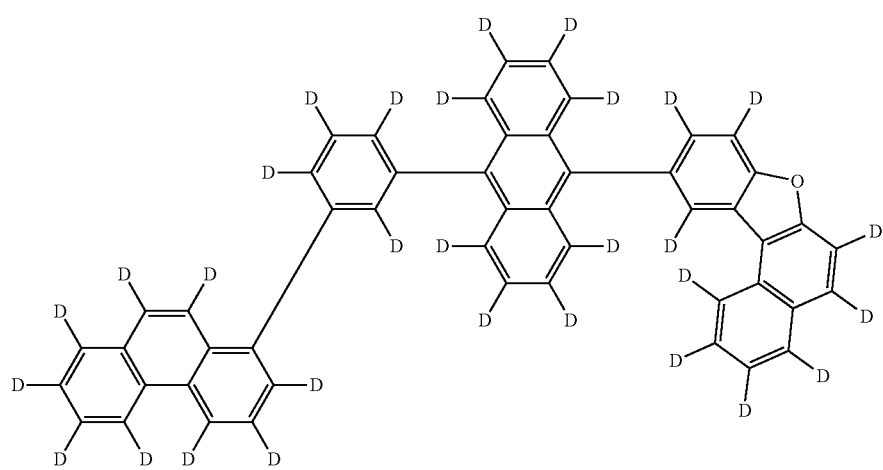
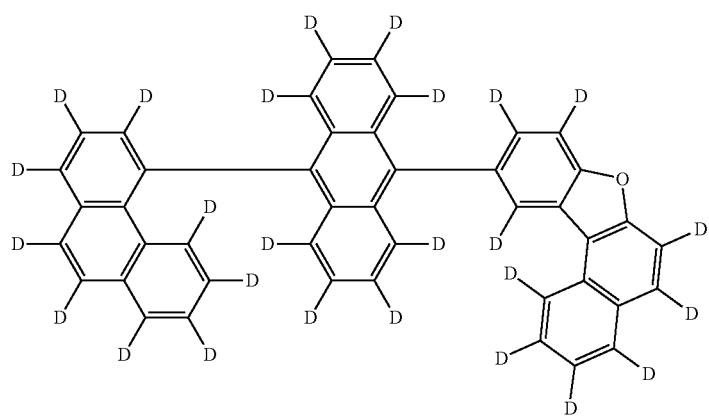

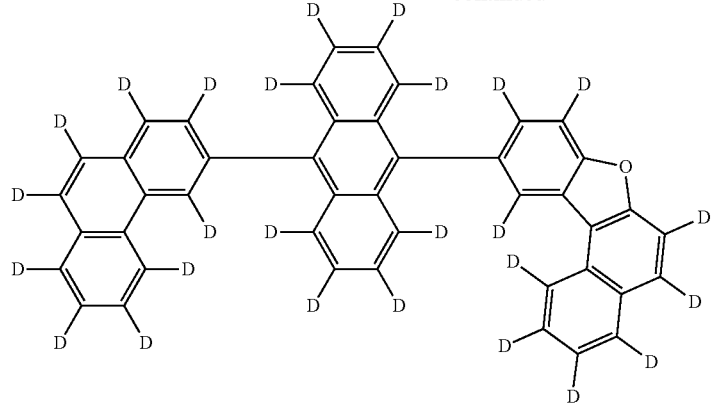
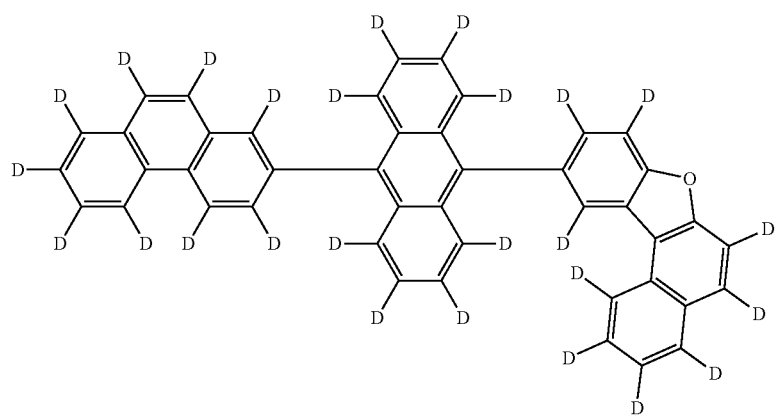
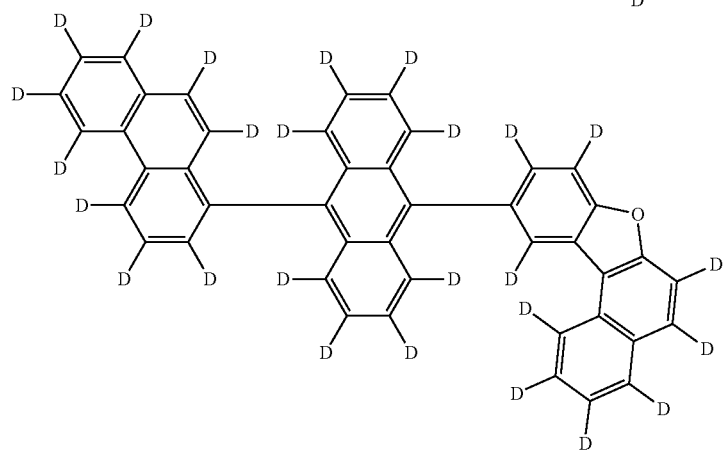
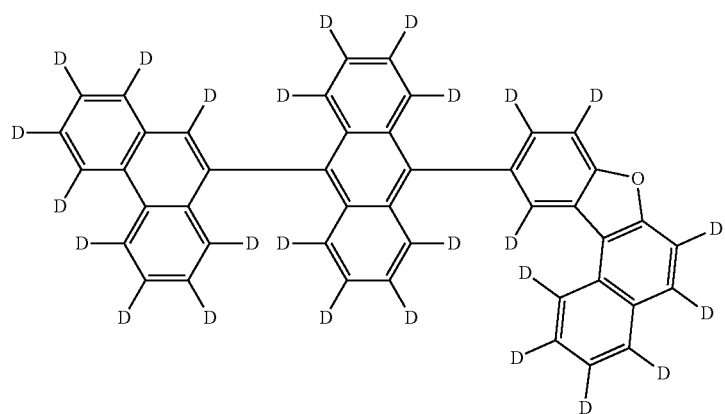

-continued
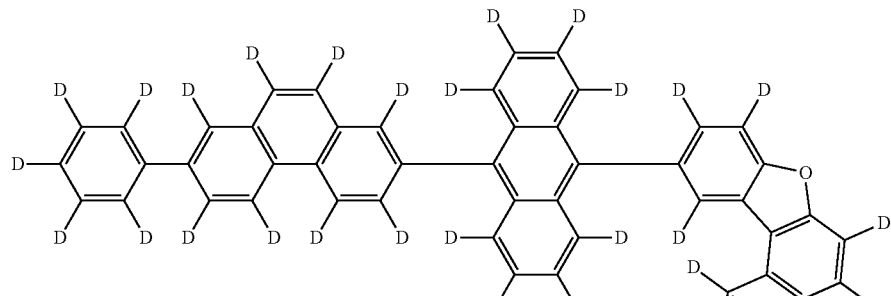
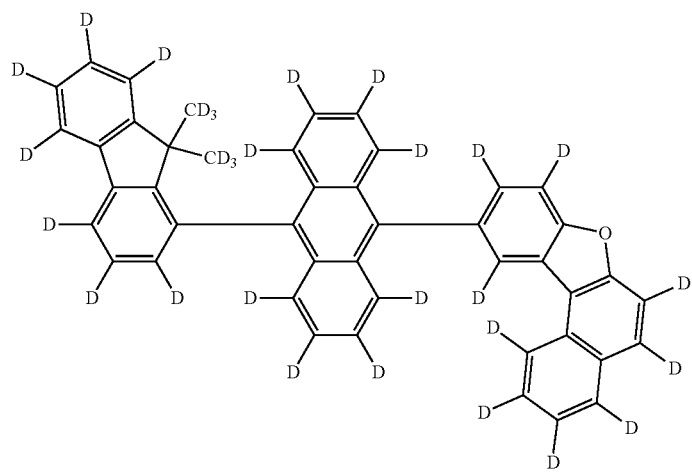
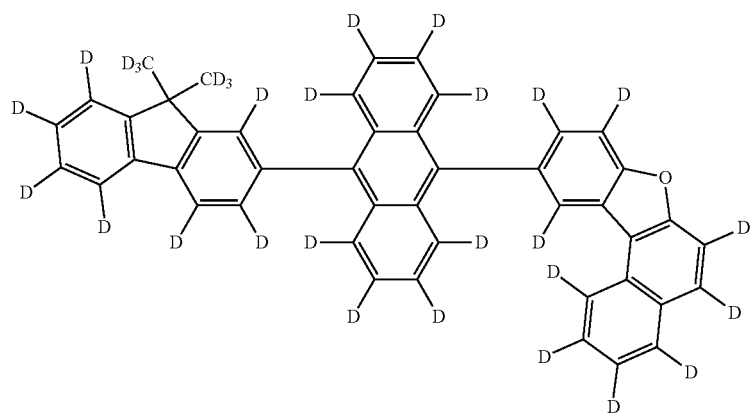
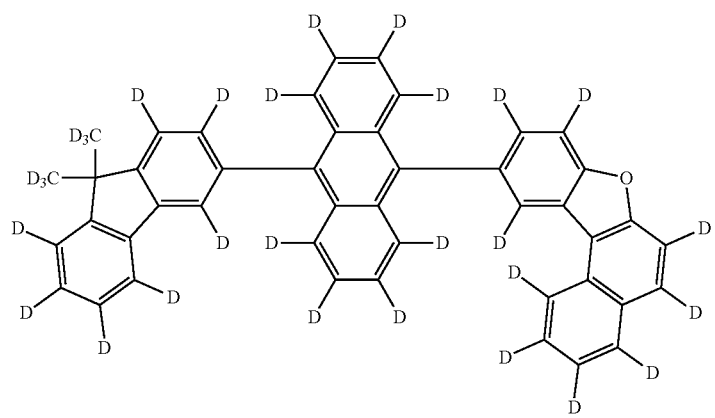

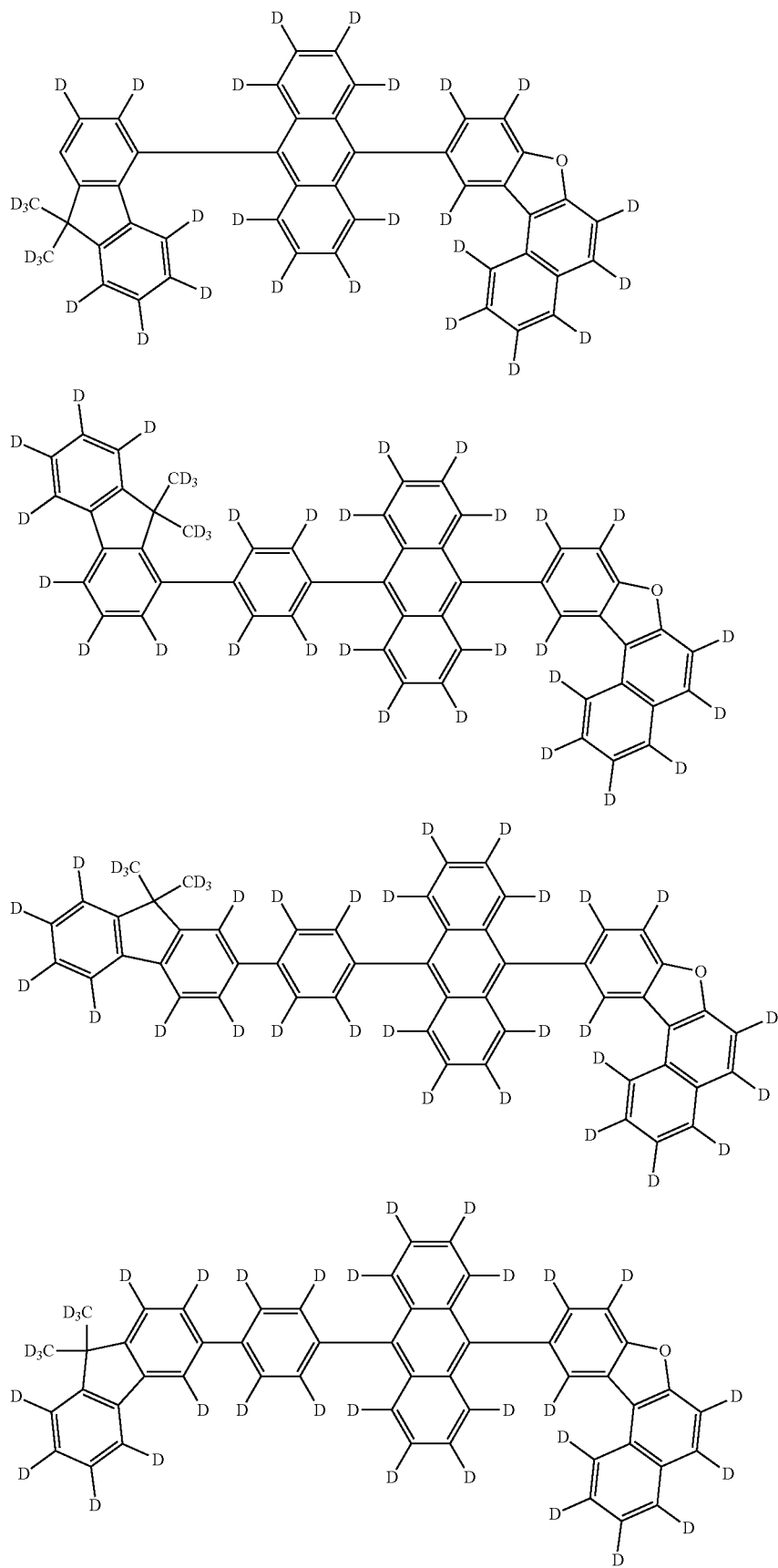

-continued
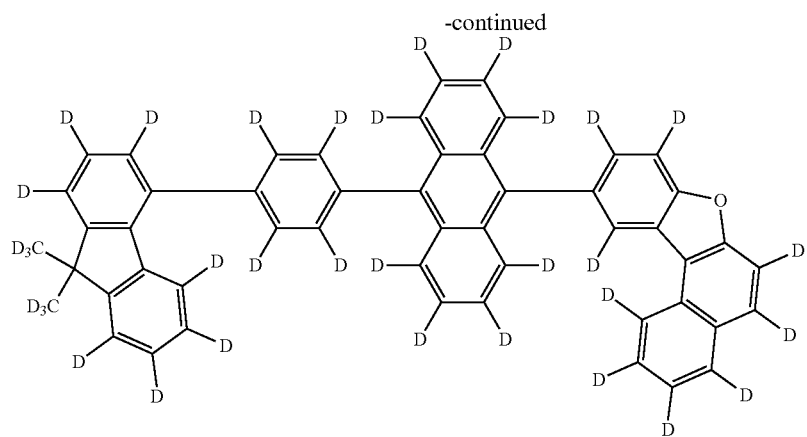
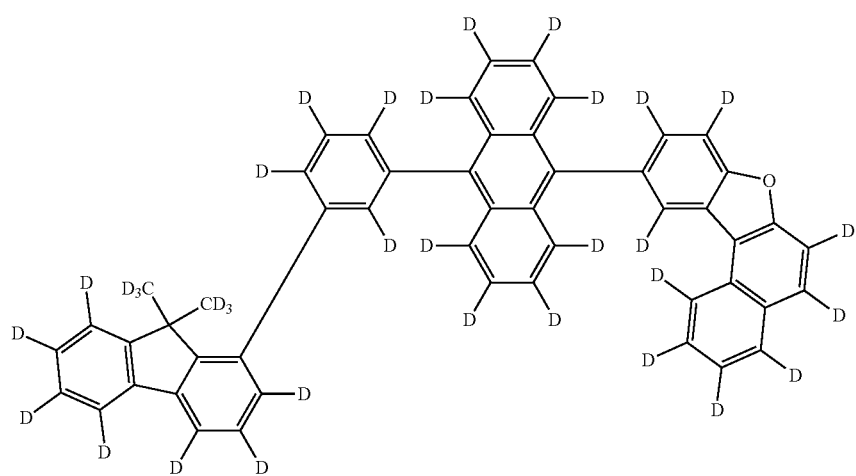
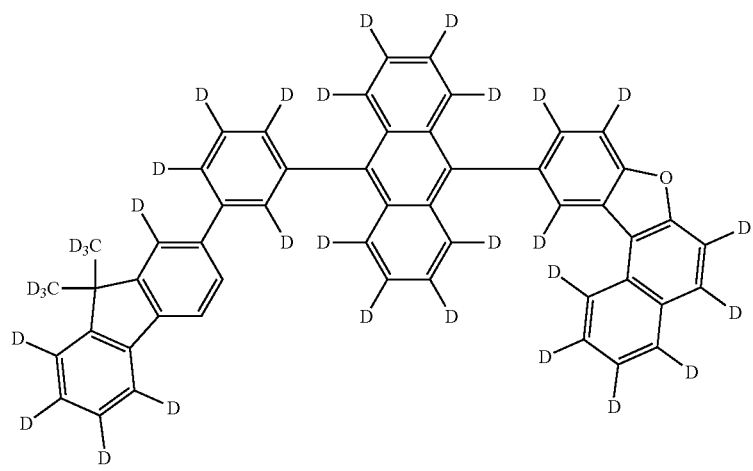

-continued
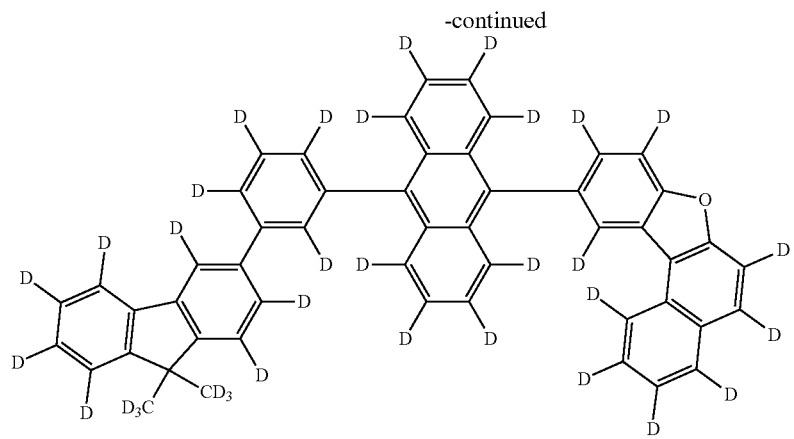
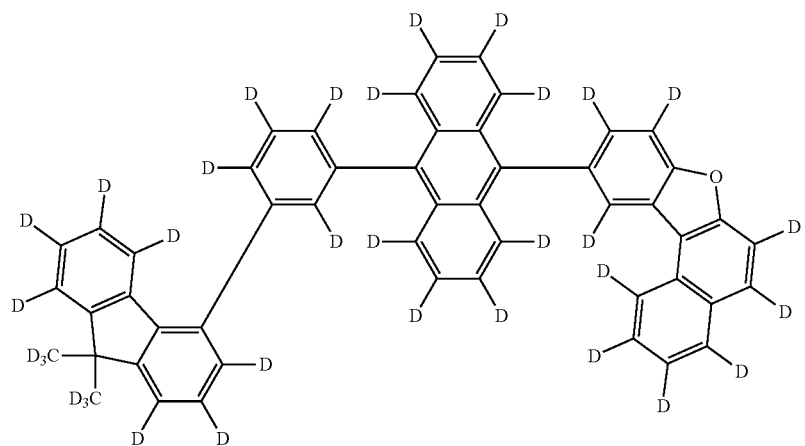
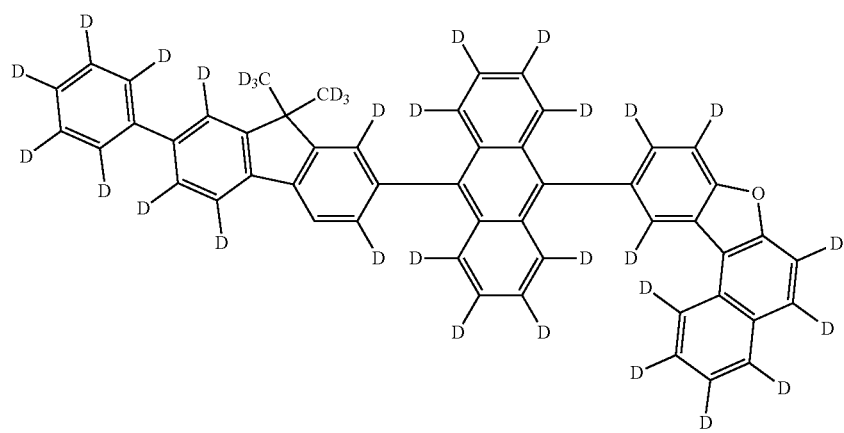
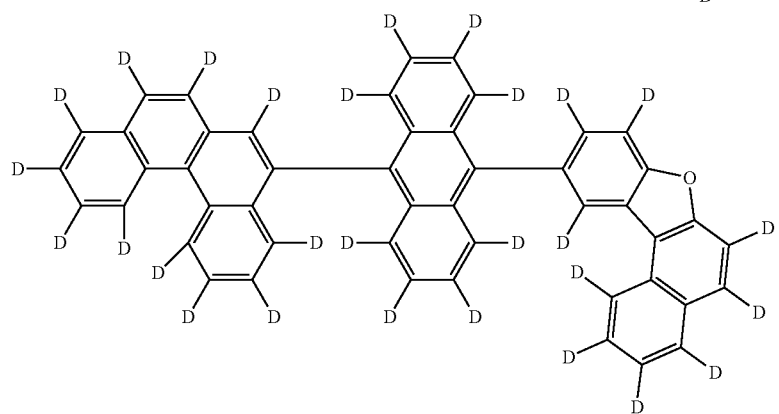

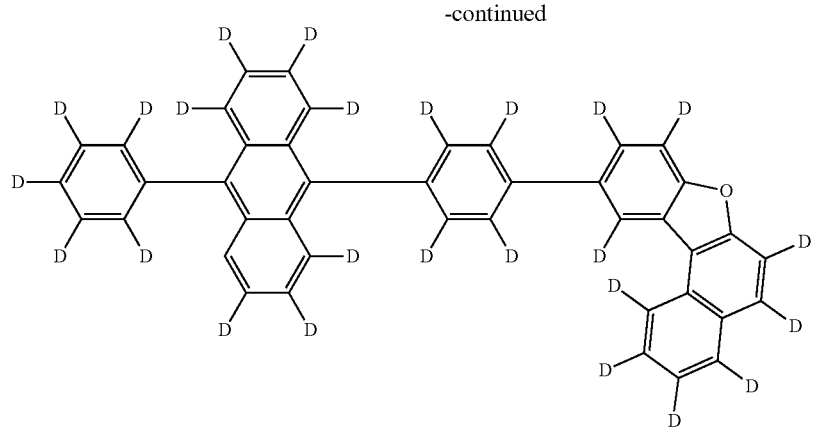
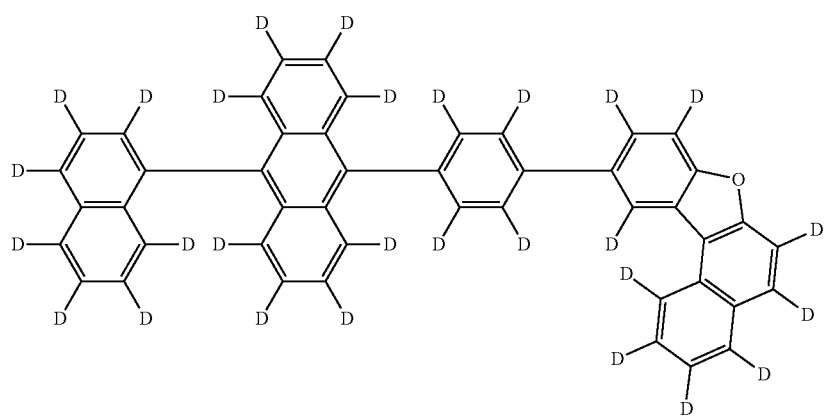
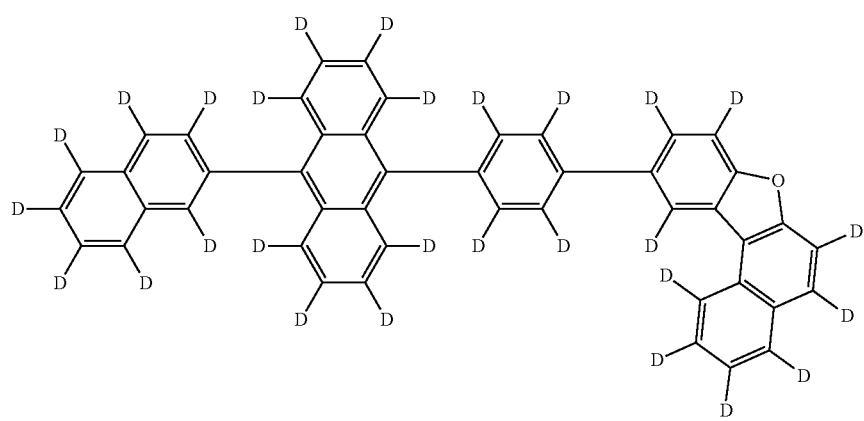
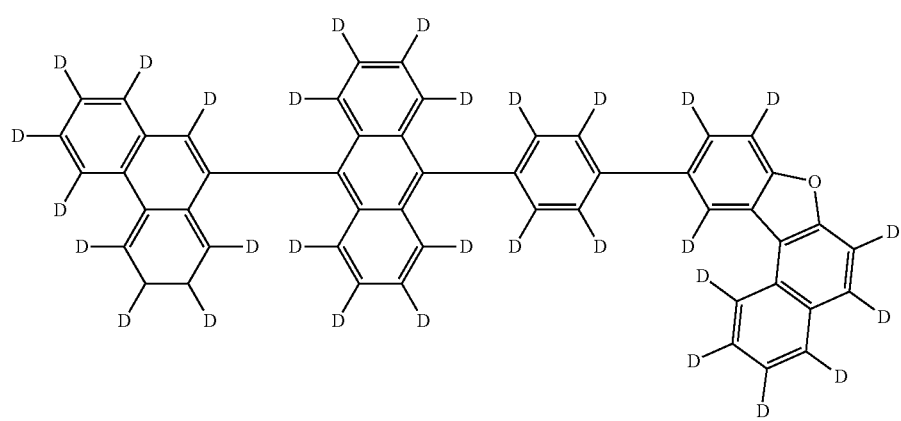

-continued
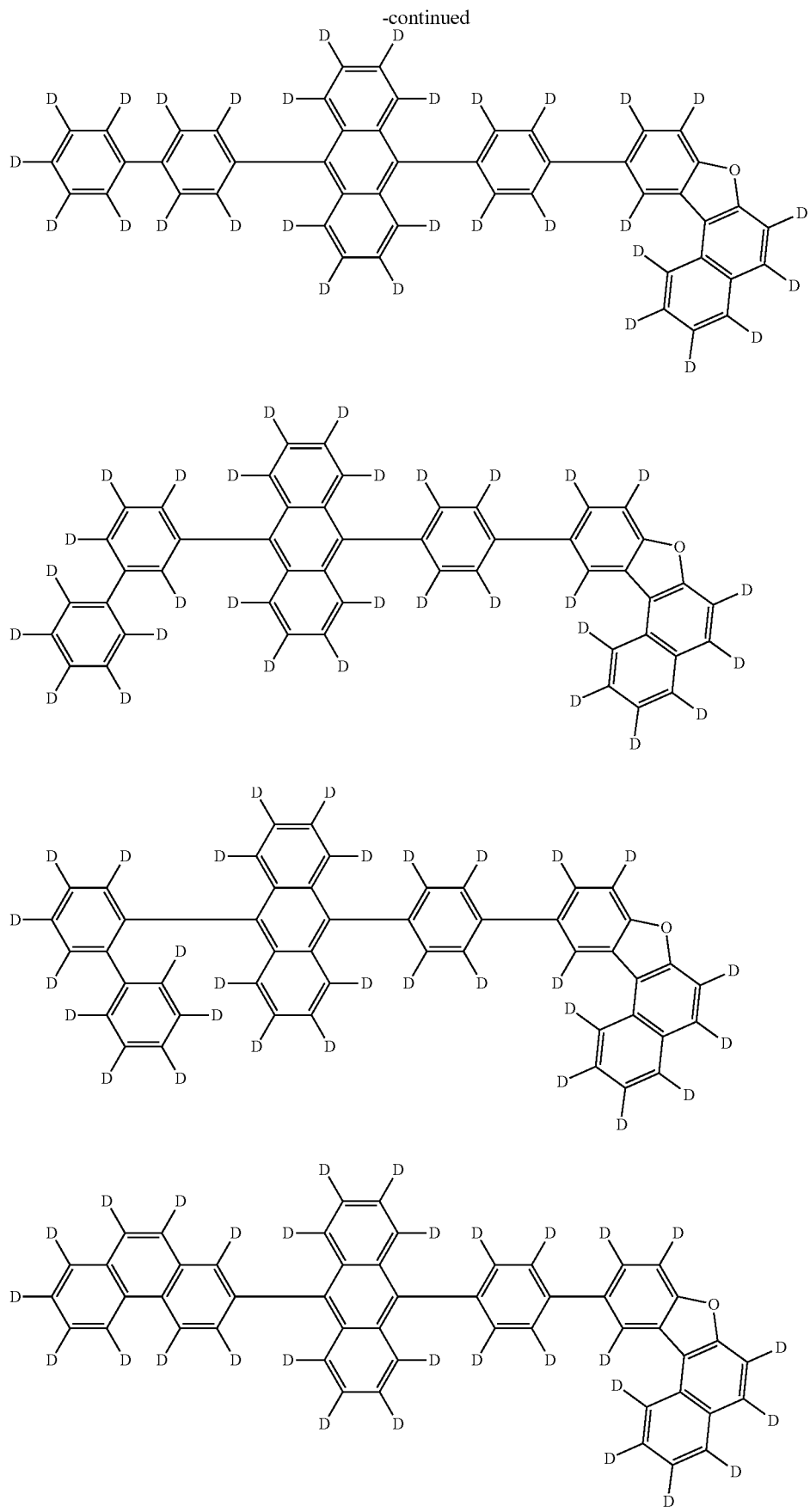

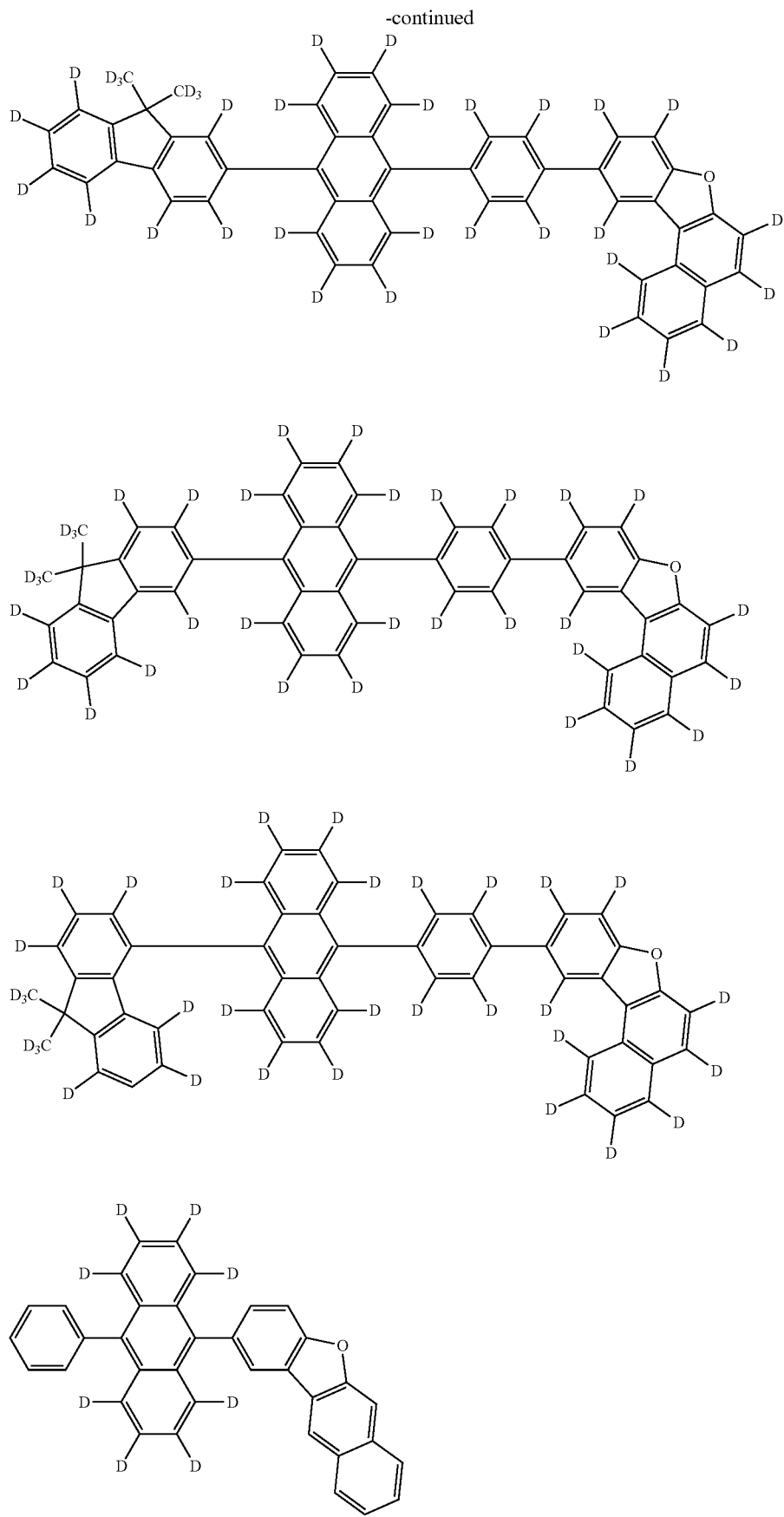

-continued
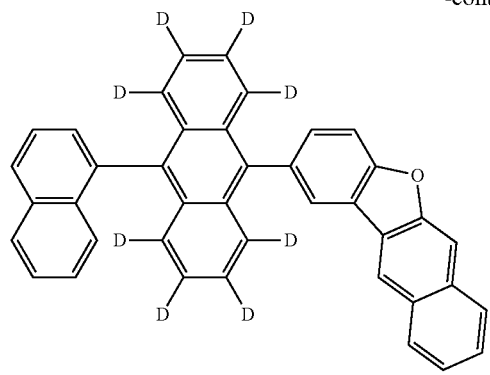
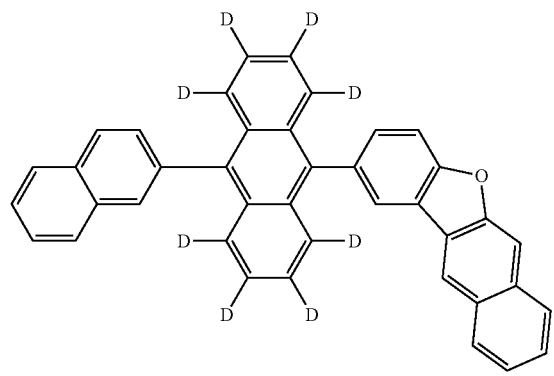
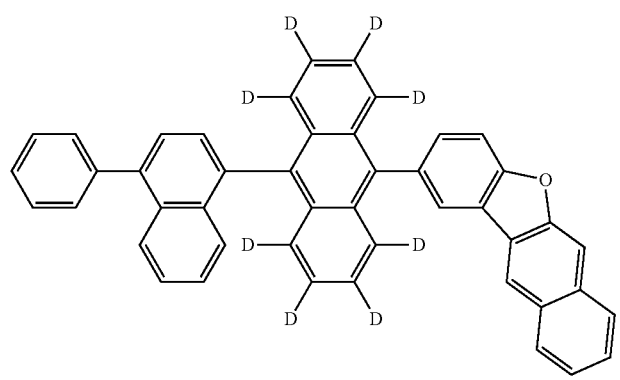
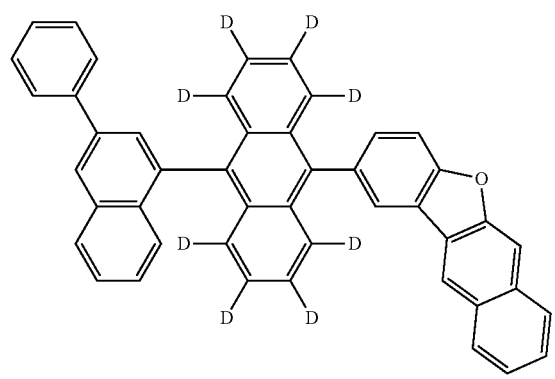

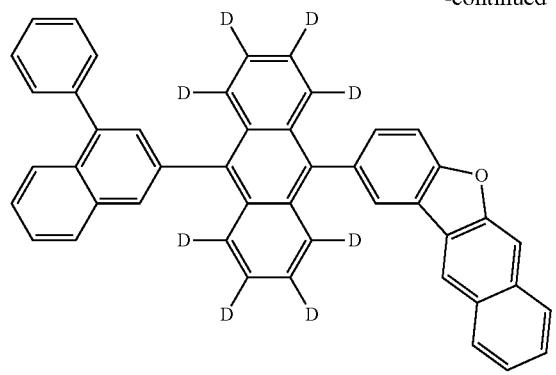
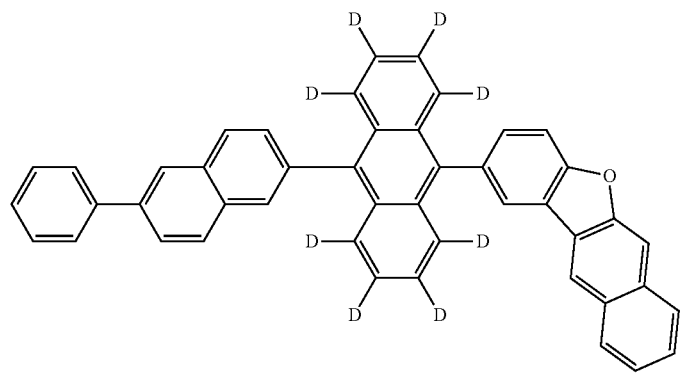
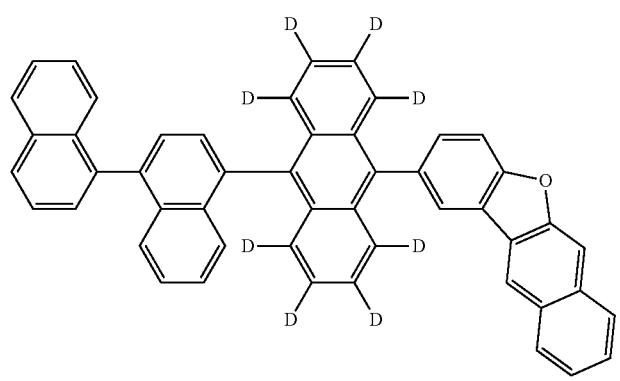
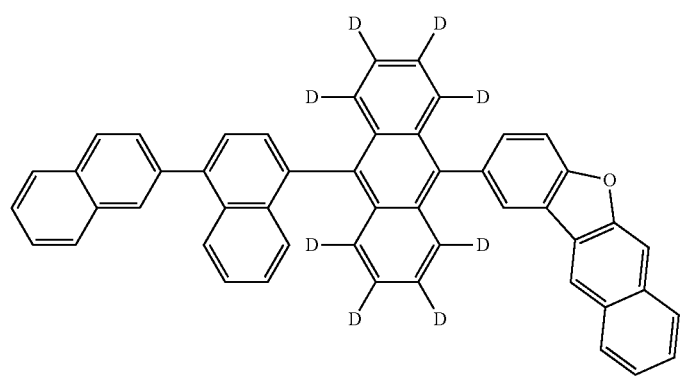

-continued
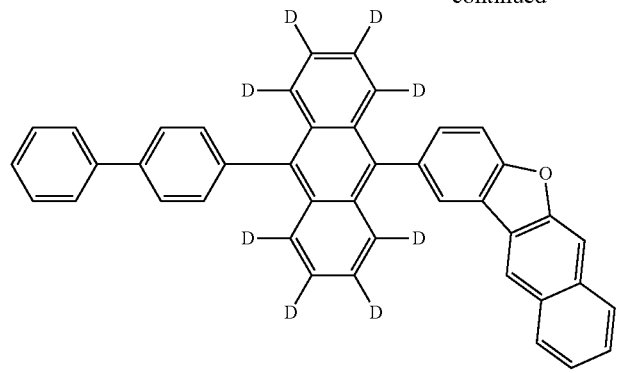
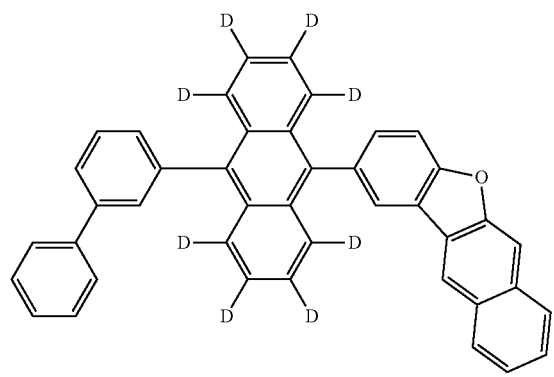
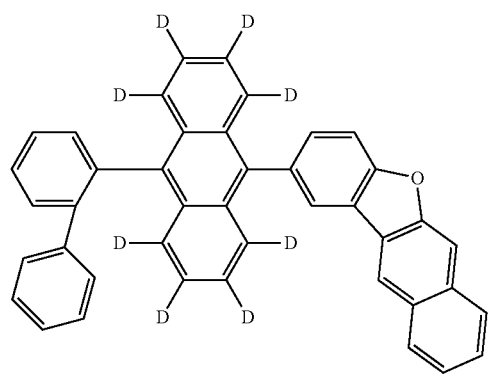
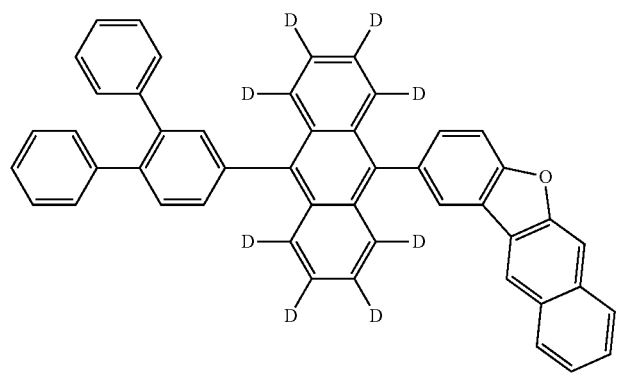

-continued
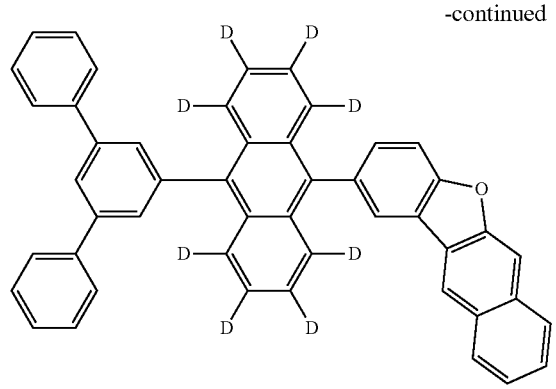
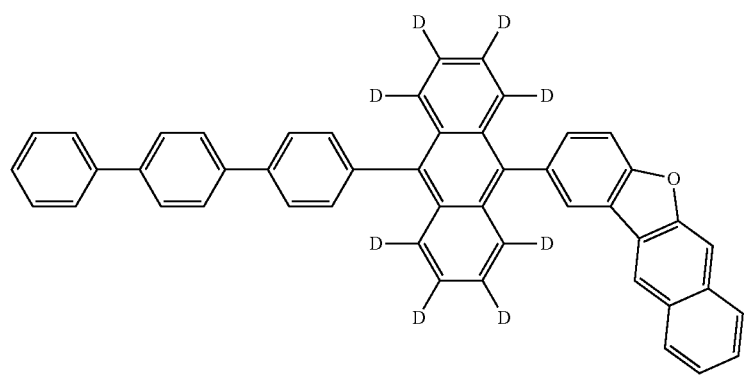
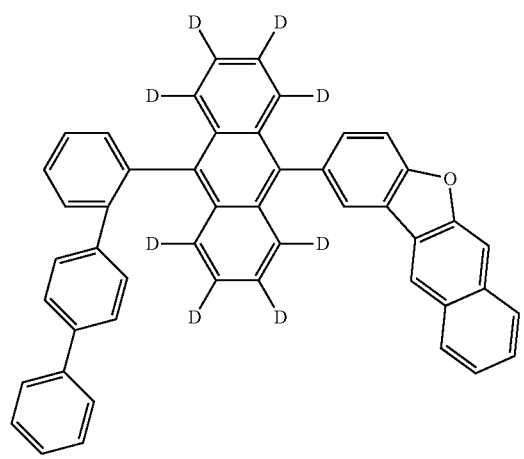
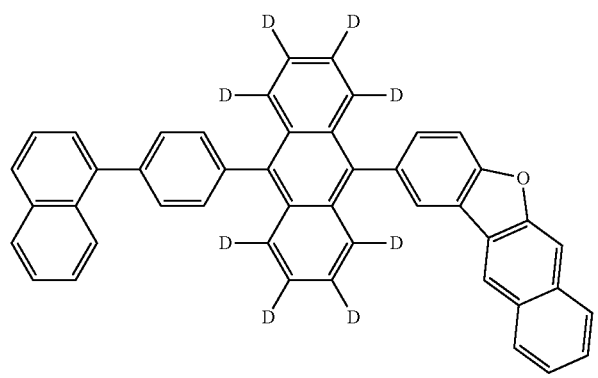

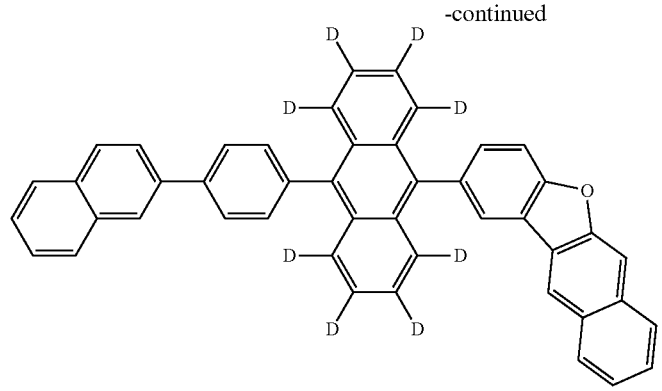
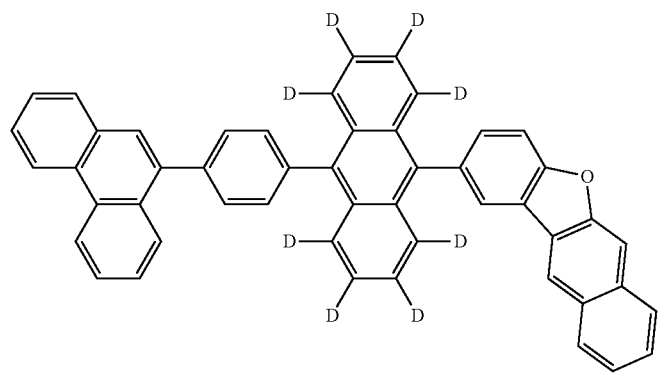
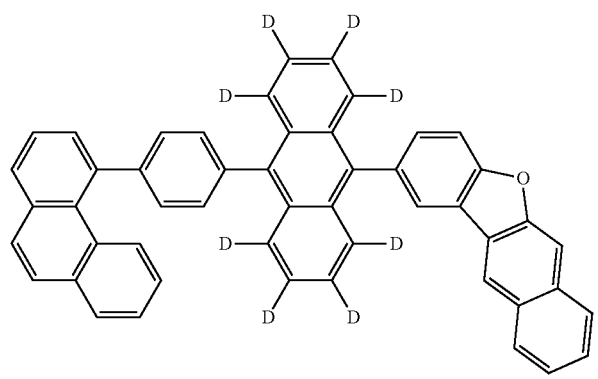
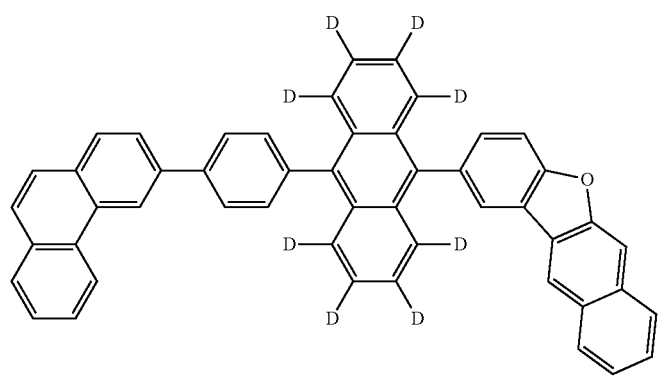

-continued
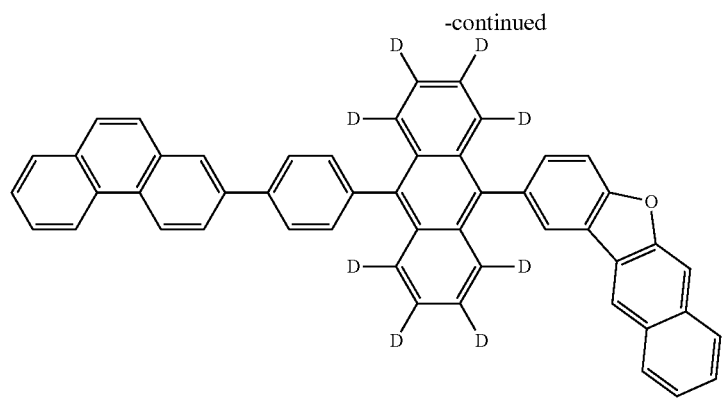
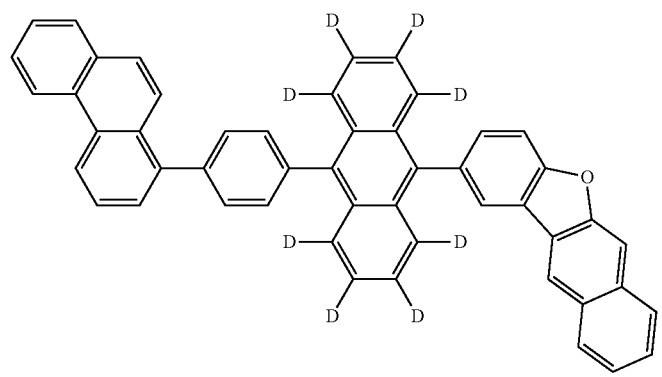
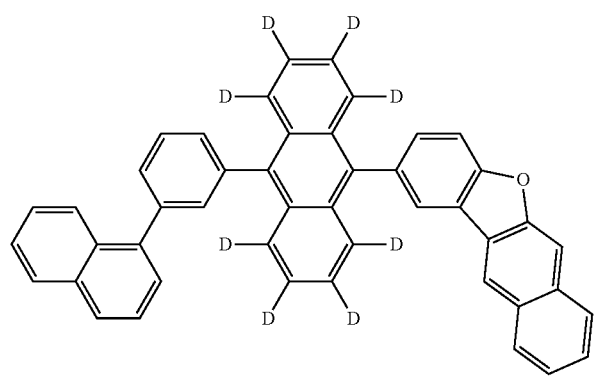
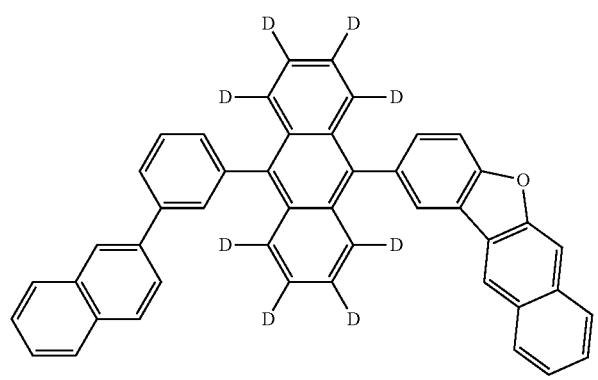

-continued
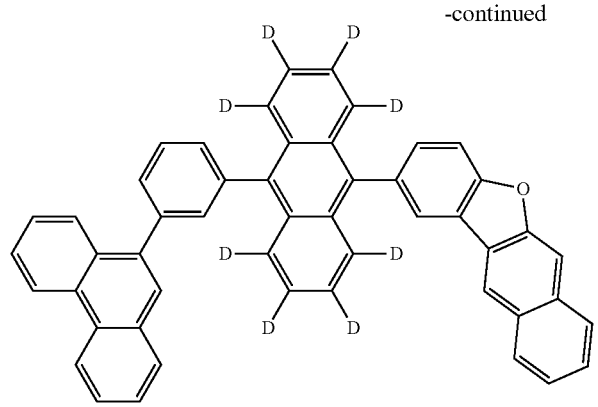
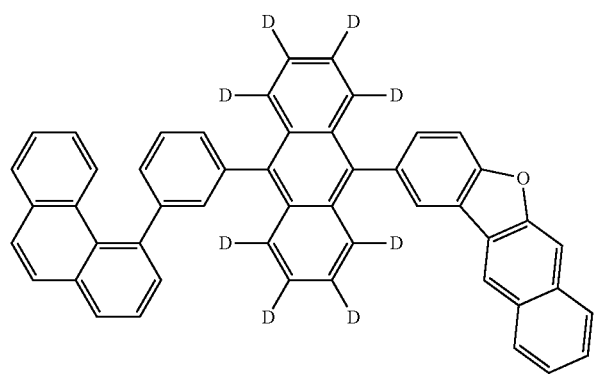
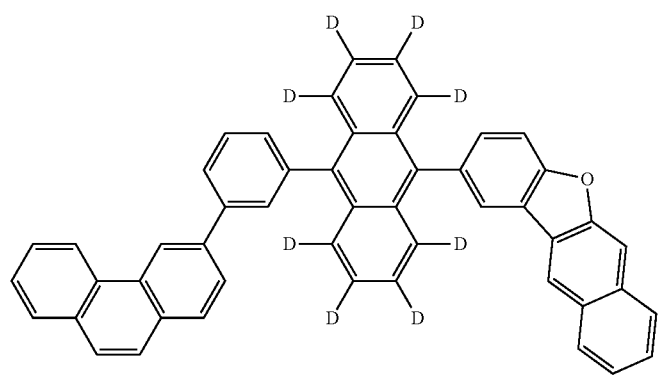
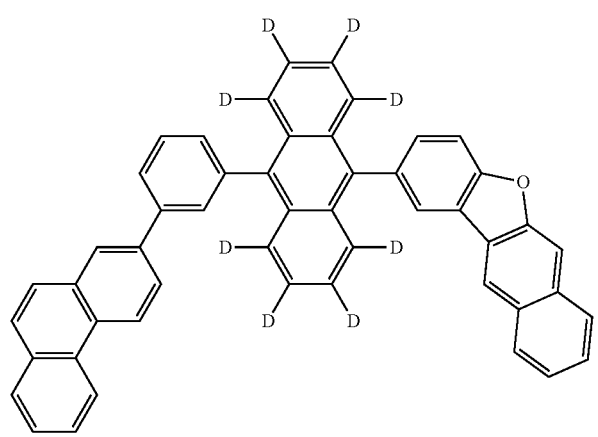

-continued
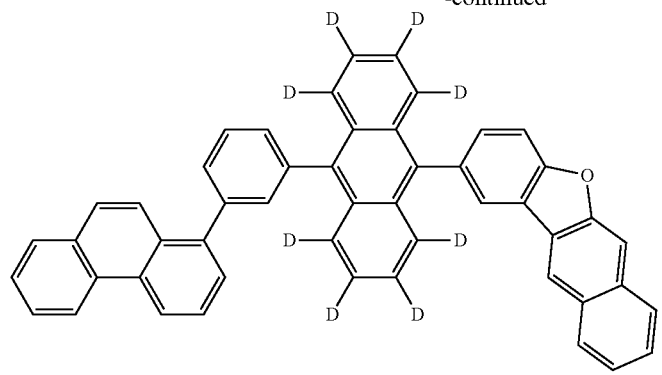
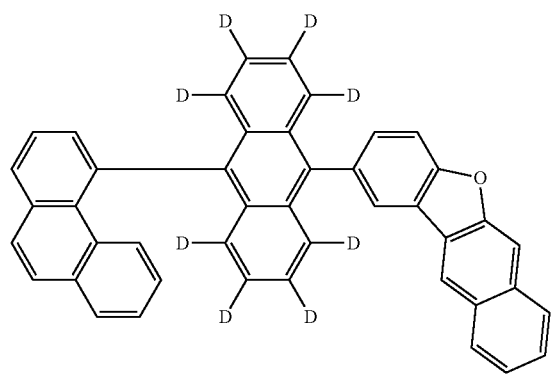
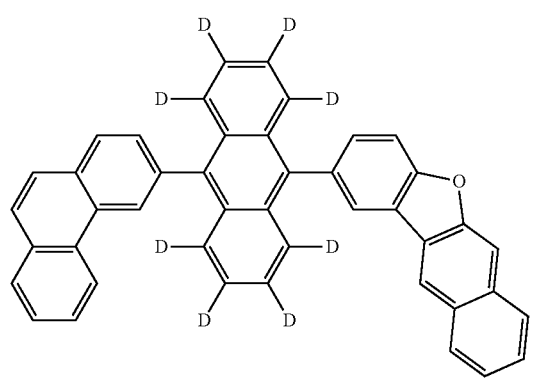
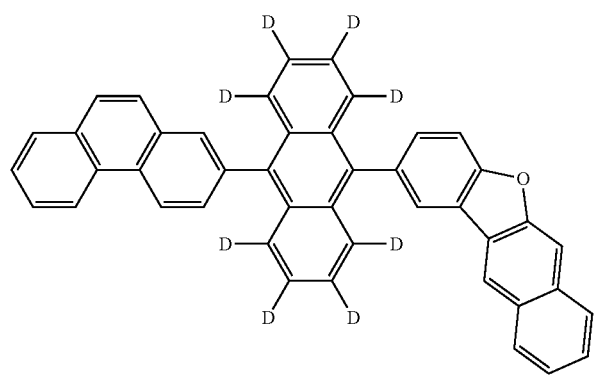

231
-continued
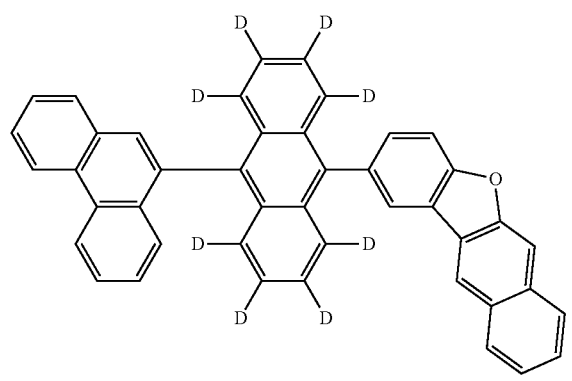
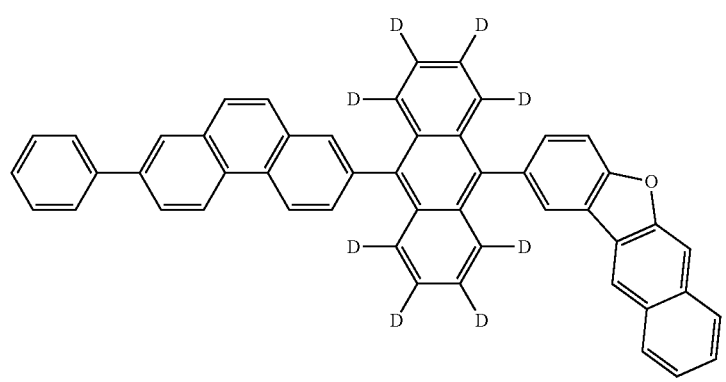
232
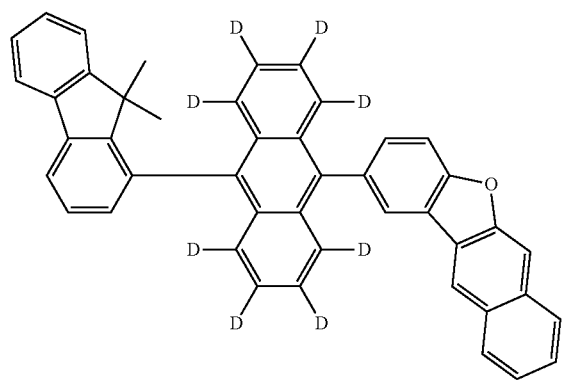

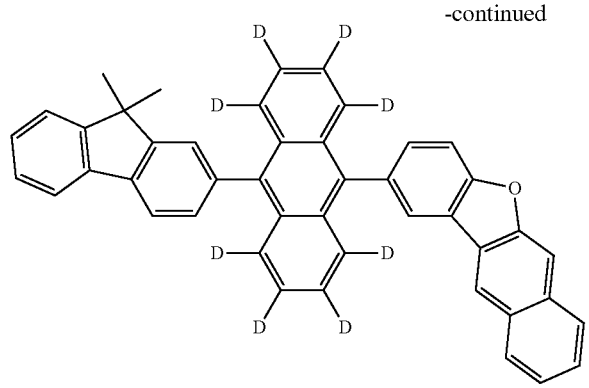

-continued
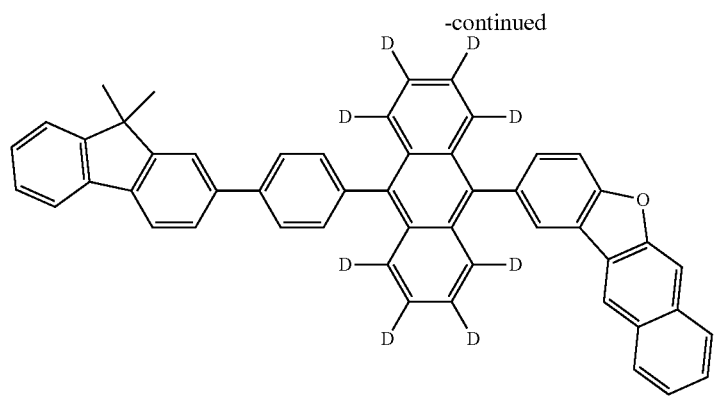
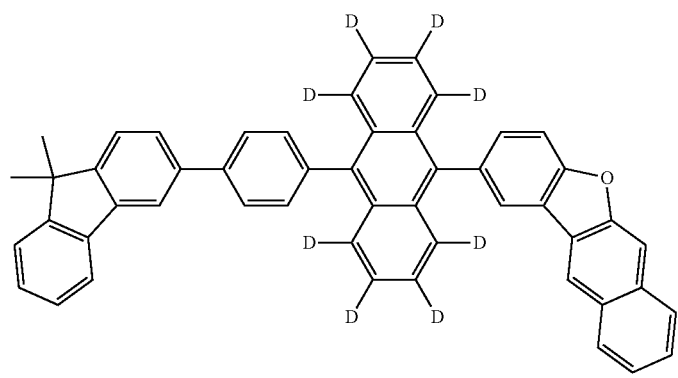
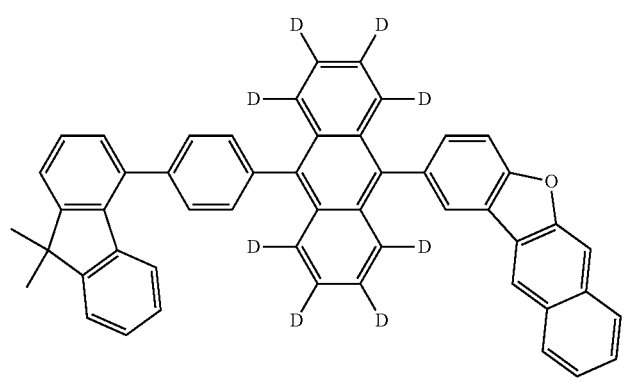
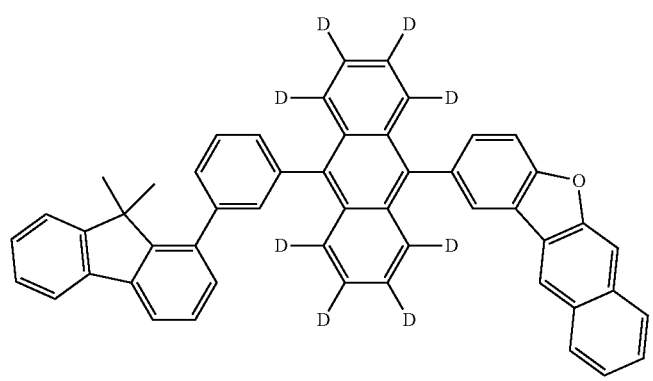

-continued
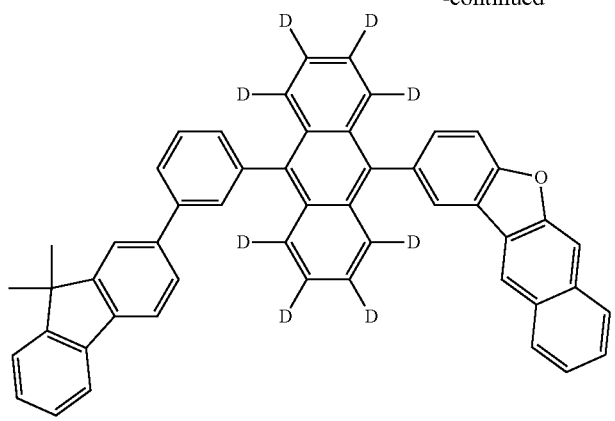
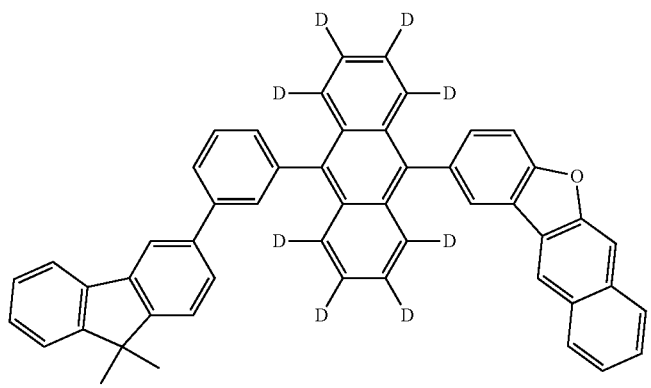
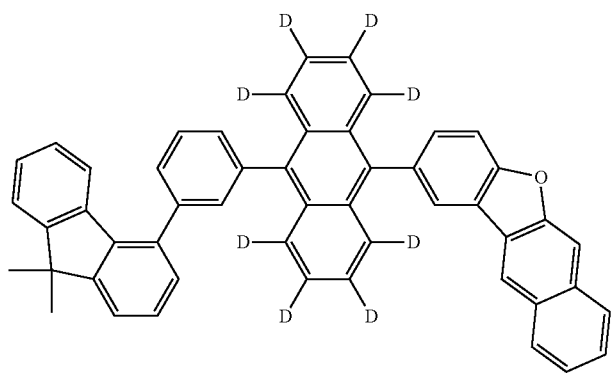
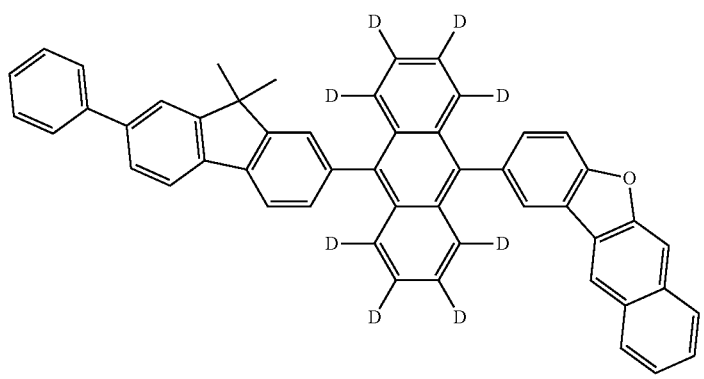

-continued
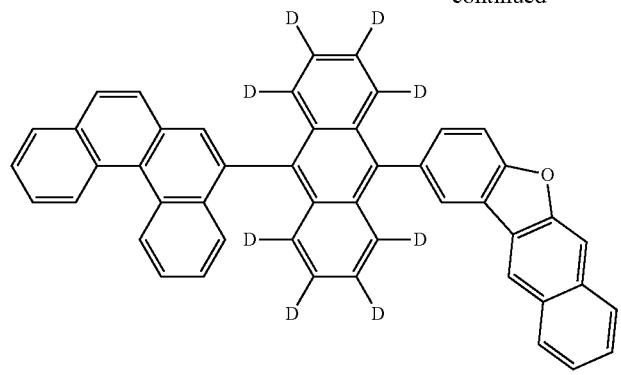
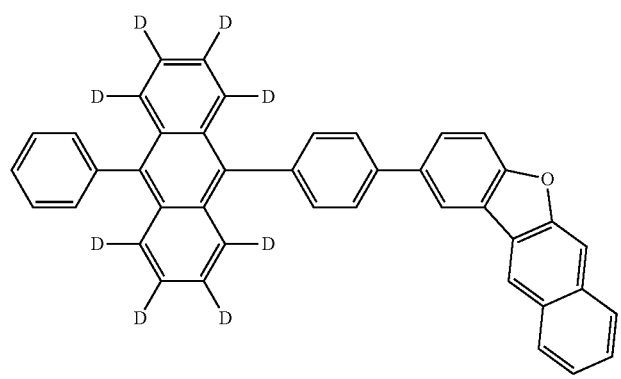
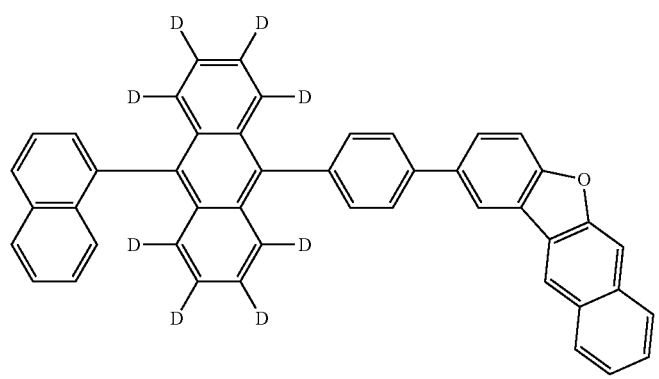
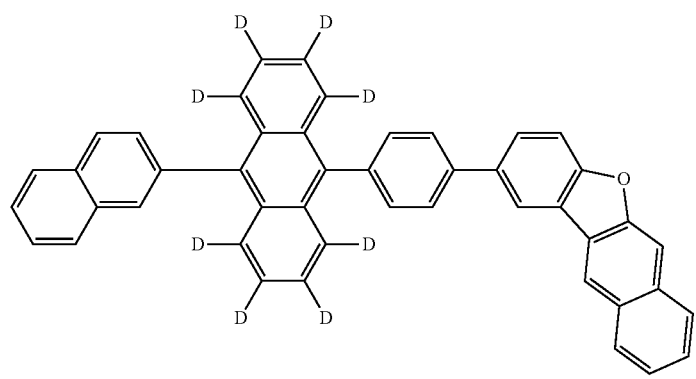

-continued
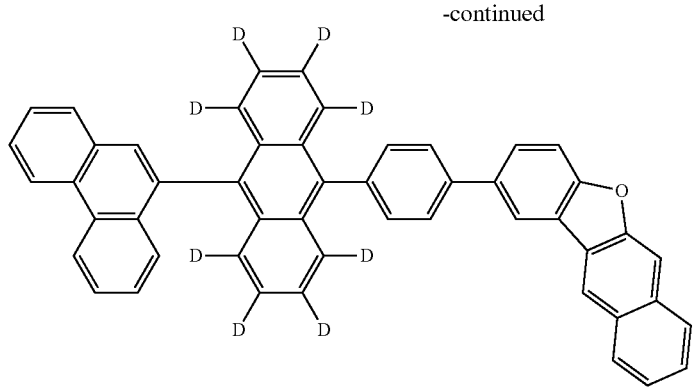
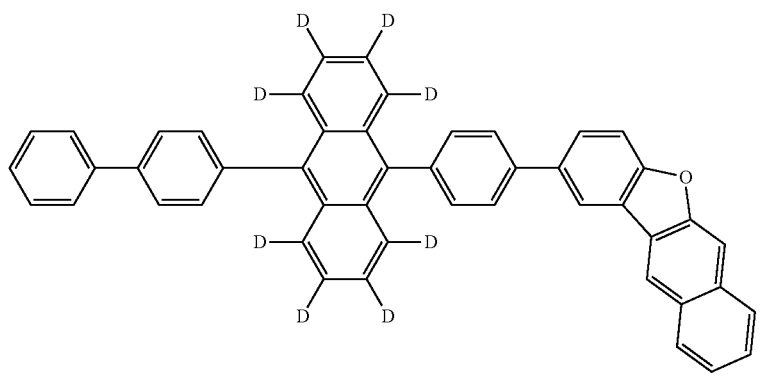
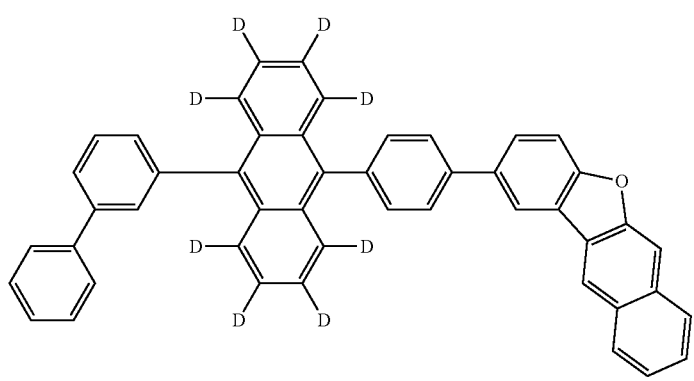
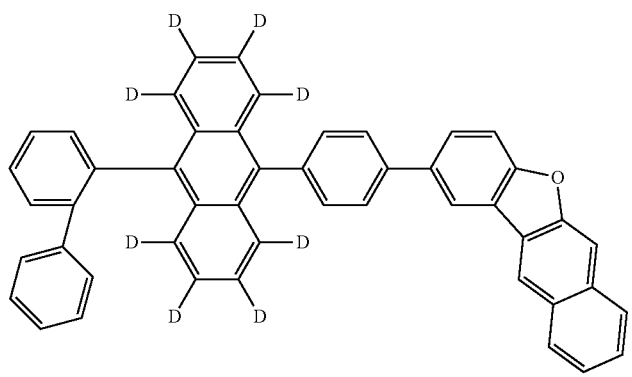

243
-continued
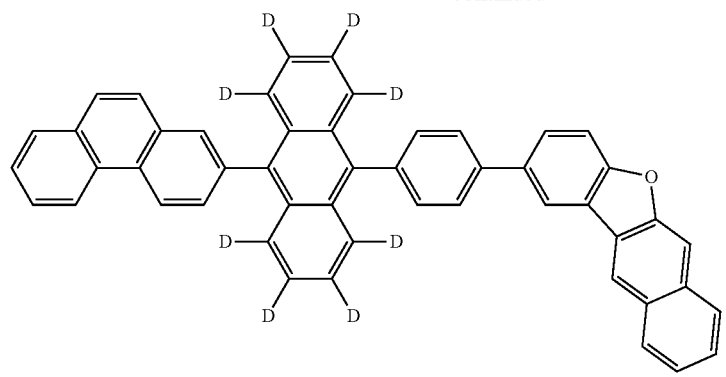
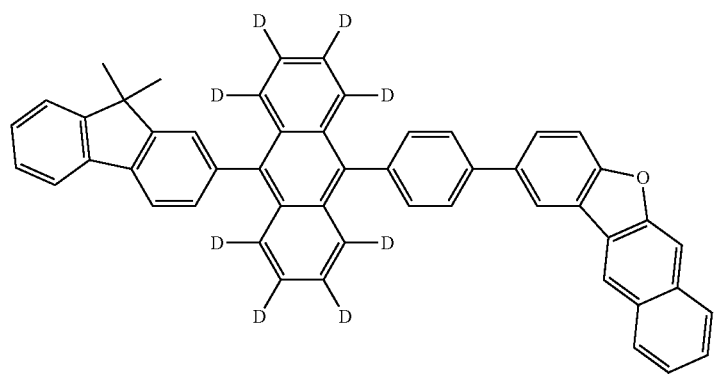
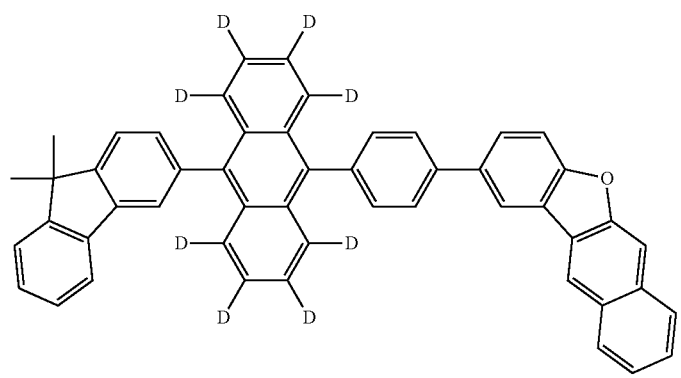
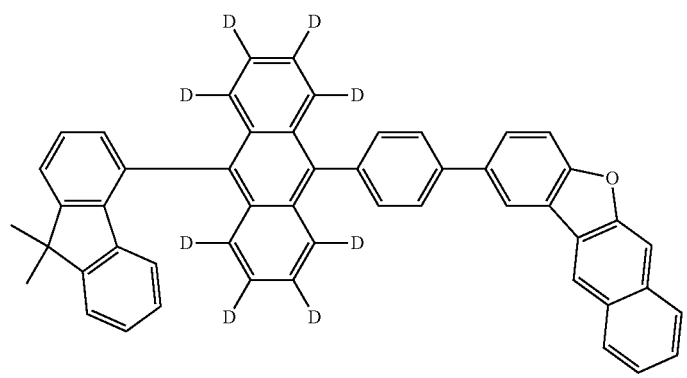
244

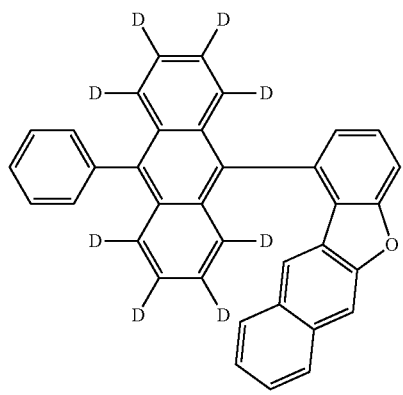
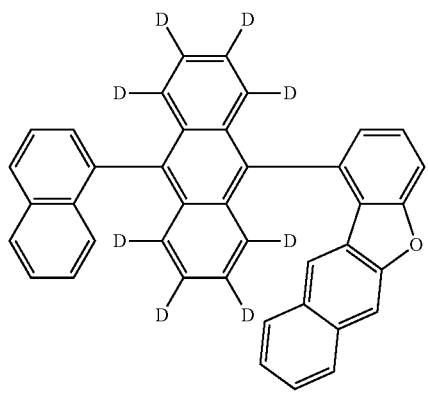
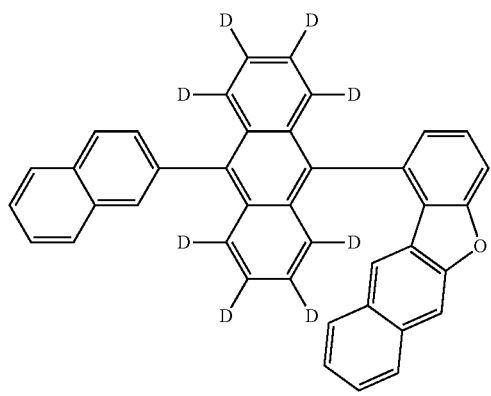
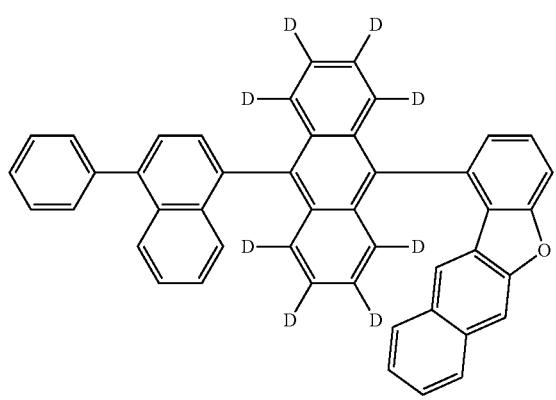

-continued
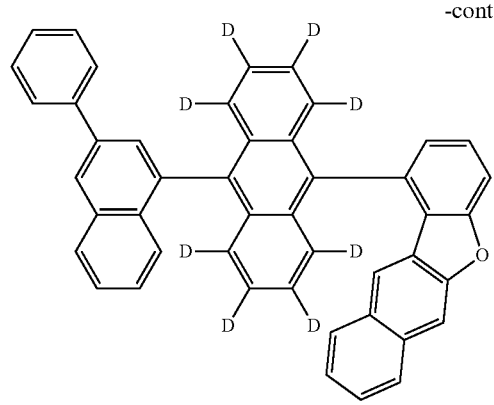
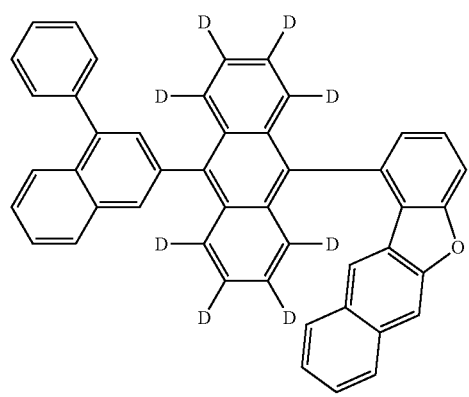
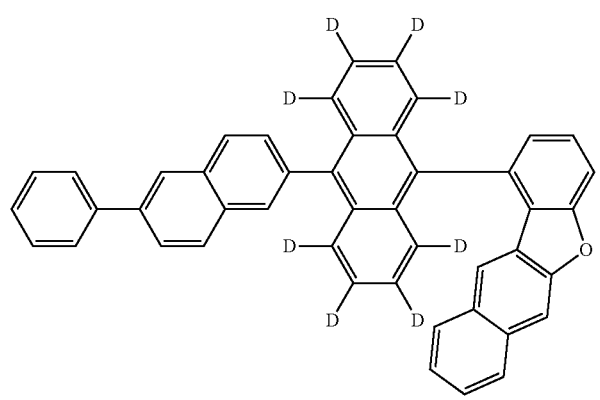
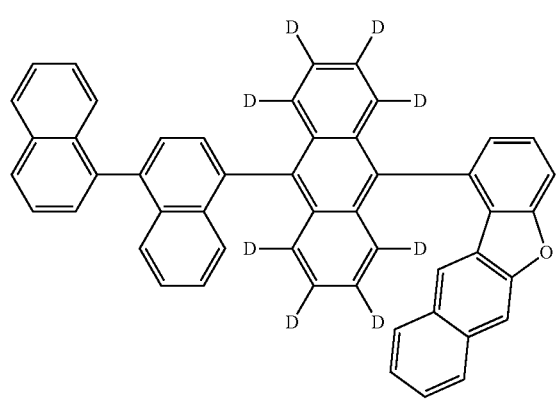

-continued
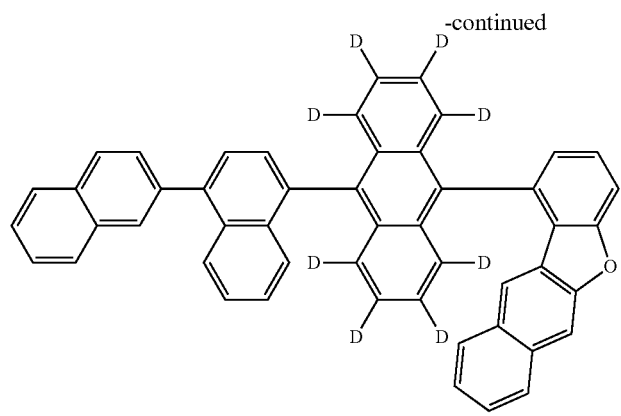
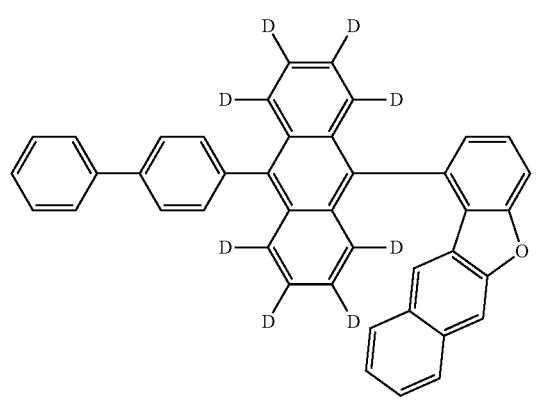
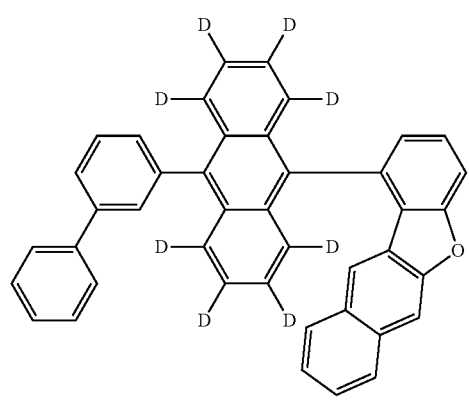
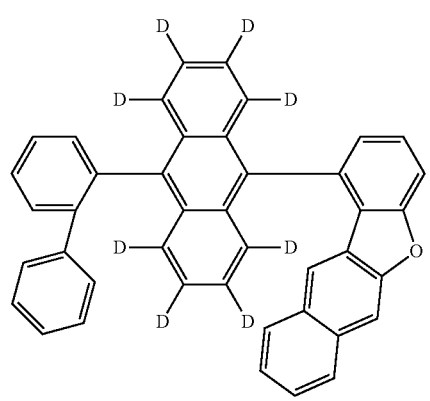

-continued
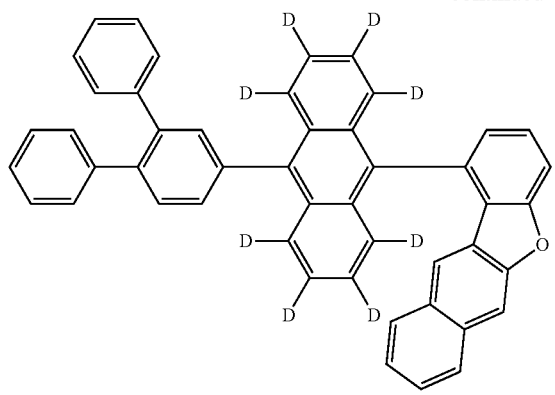
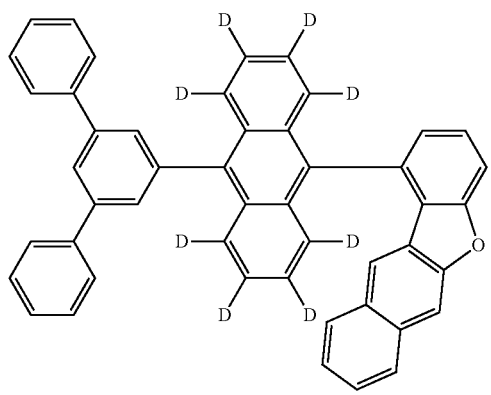
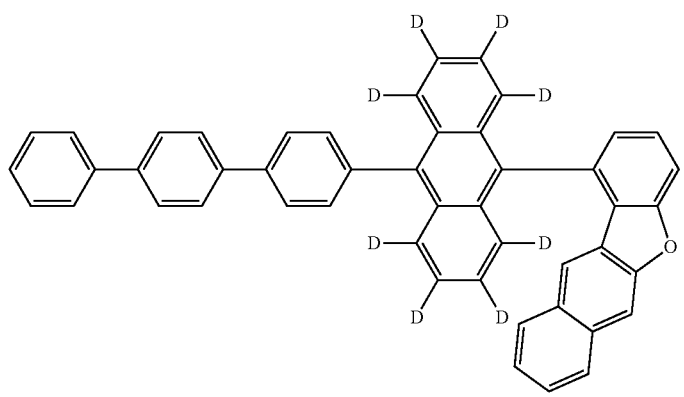
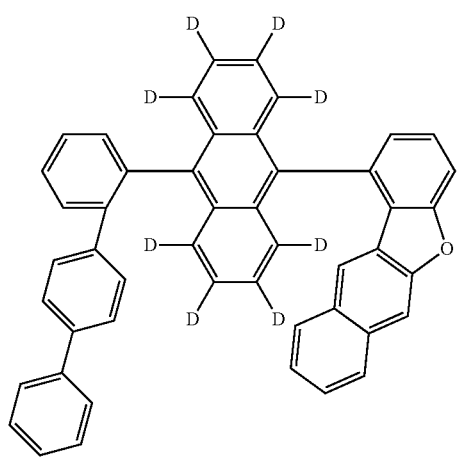

-continued
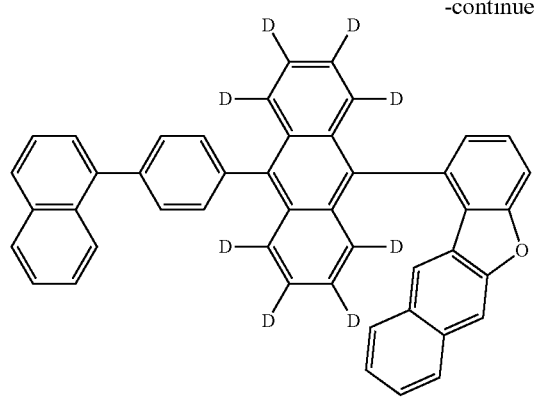
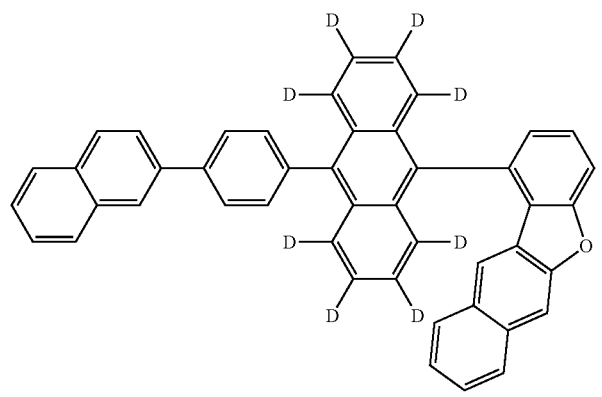
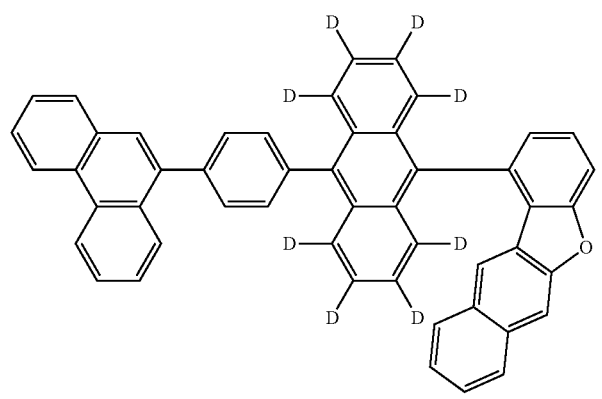
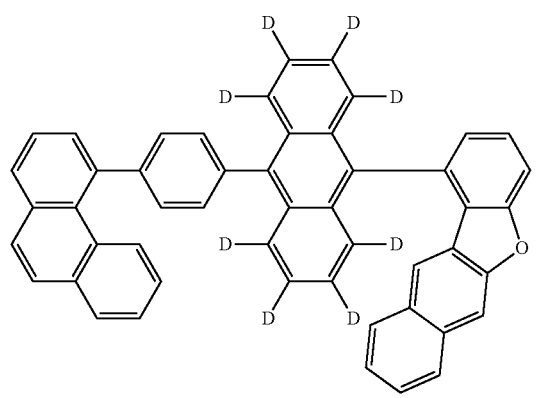

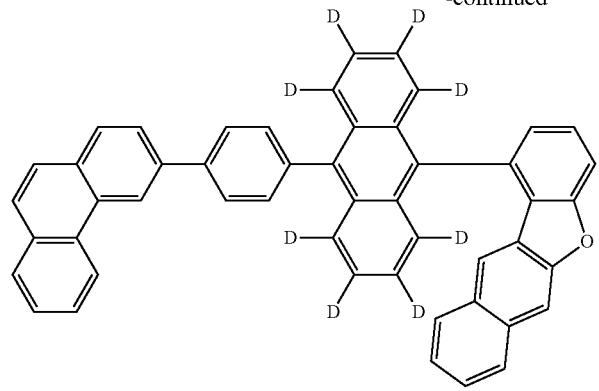

-continued
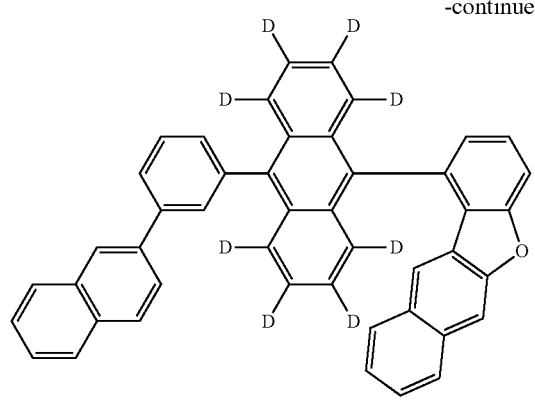
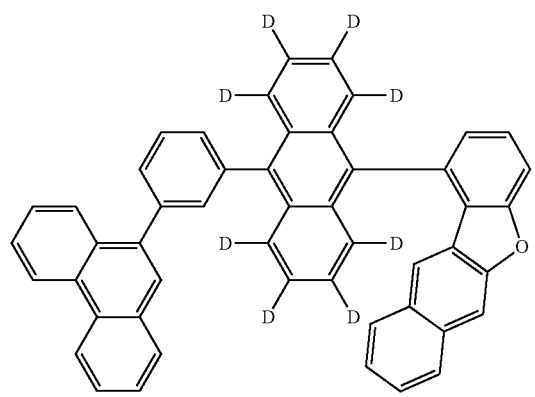
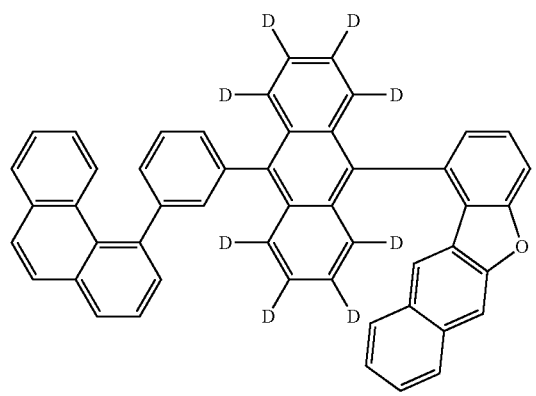
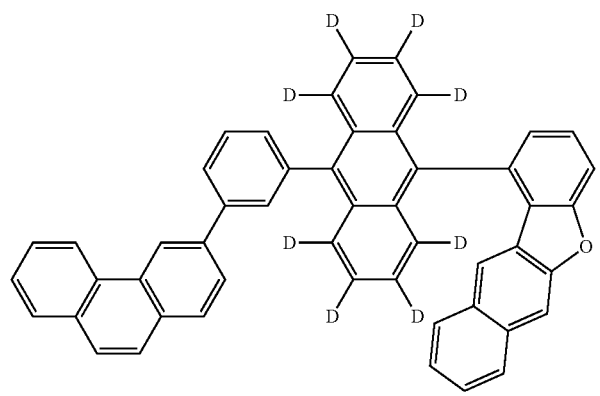

-continued
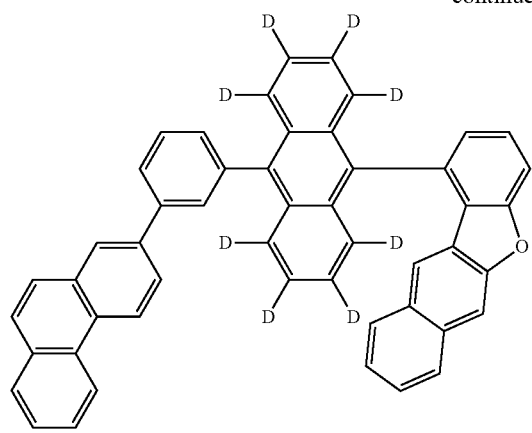
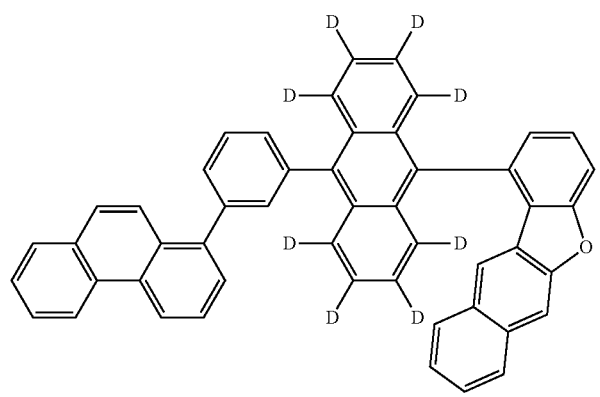
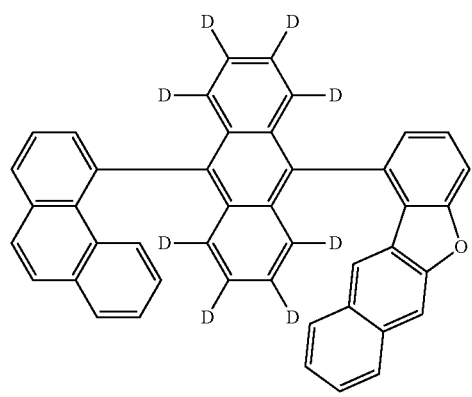
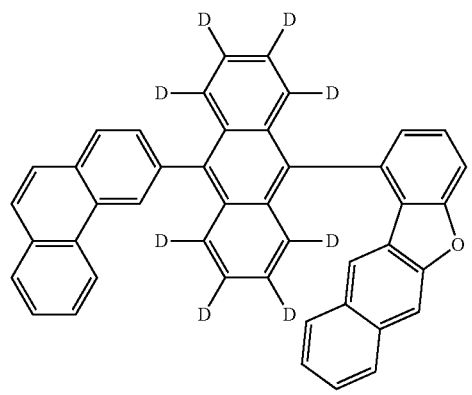

-continued

-continued
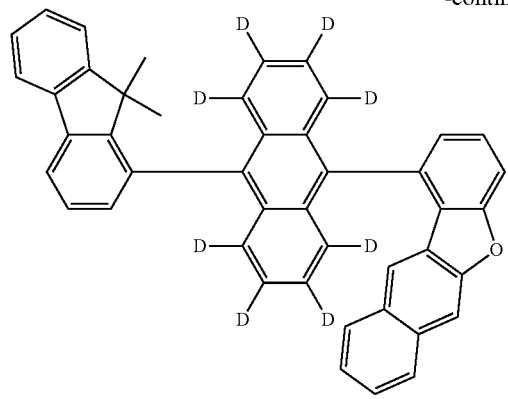
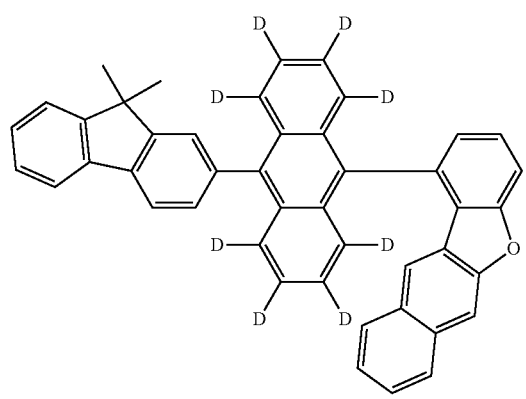
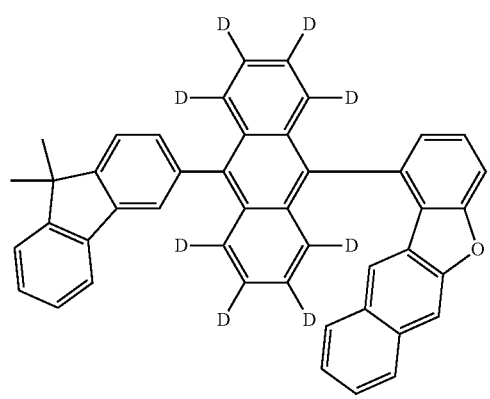
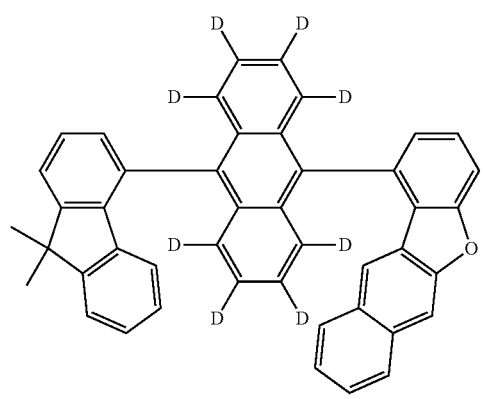

-continued
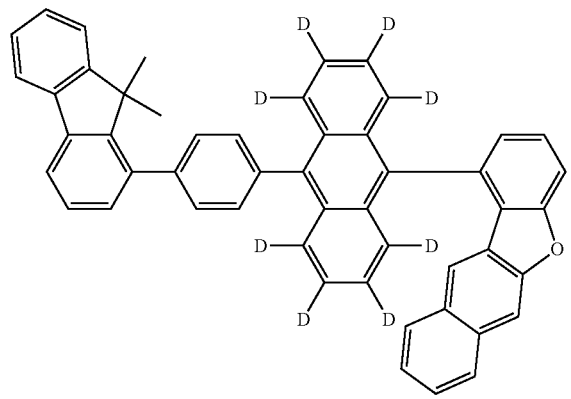
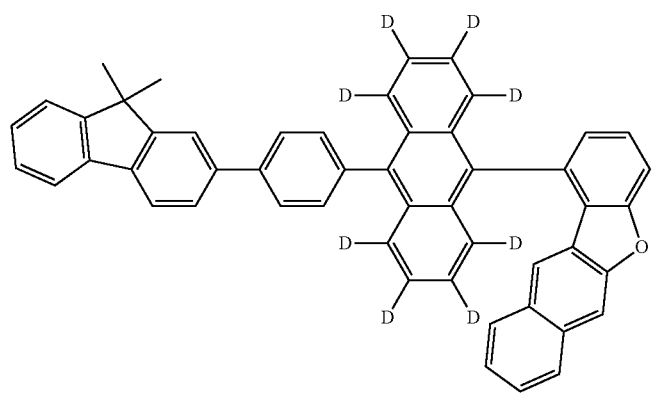
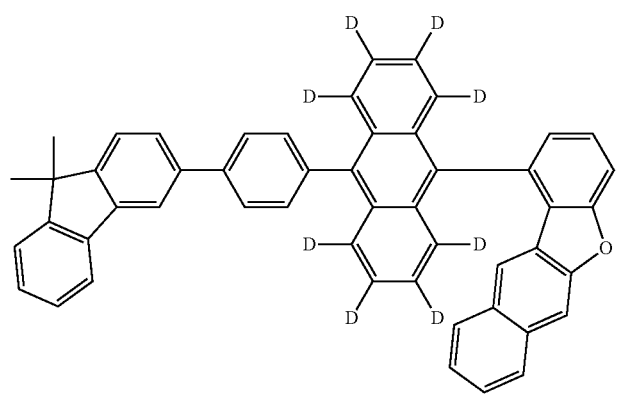
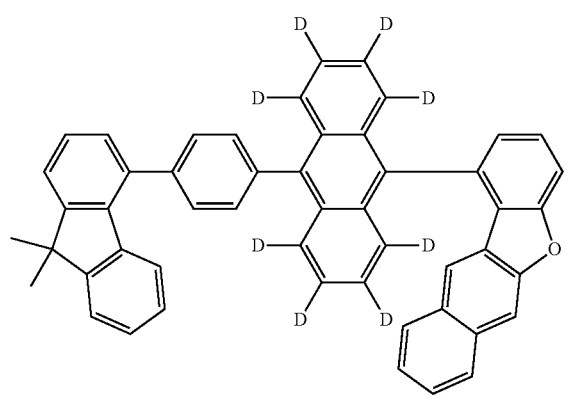

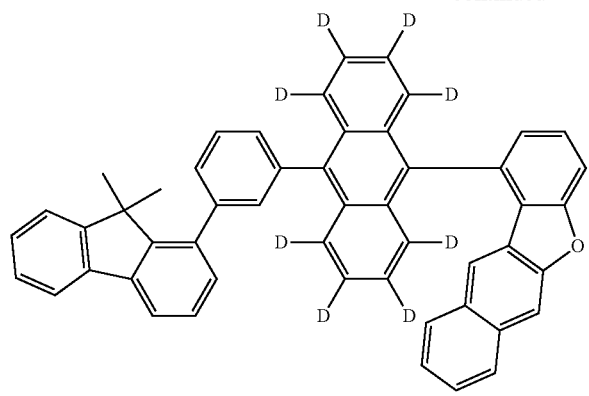
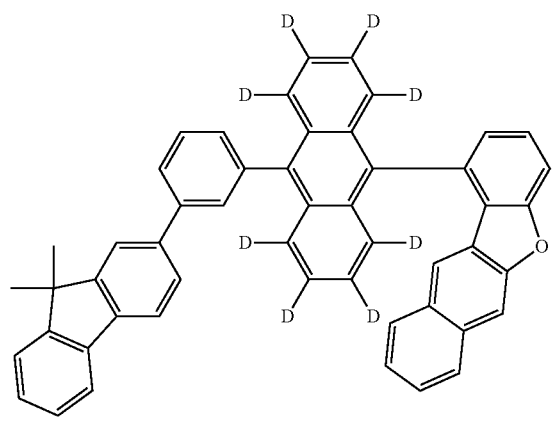
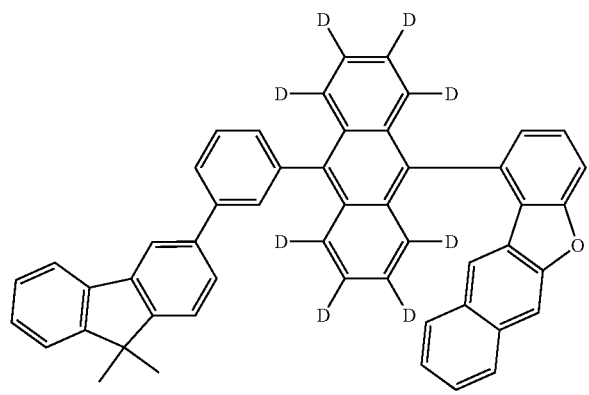
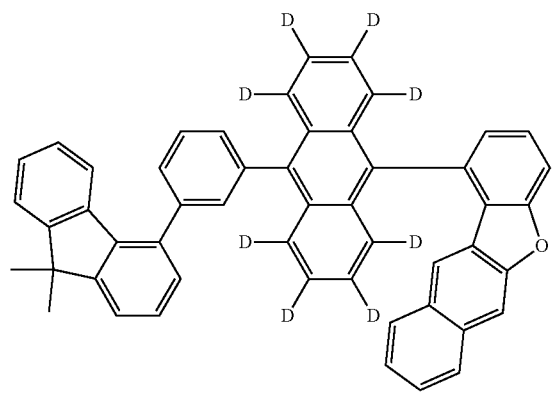

-continued
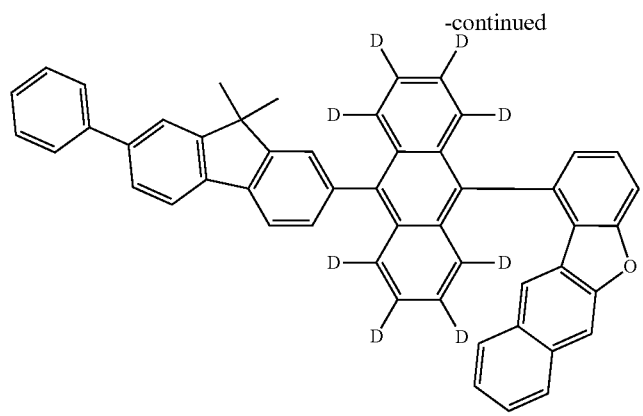
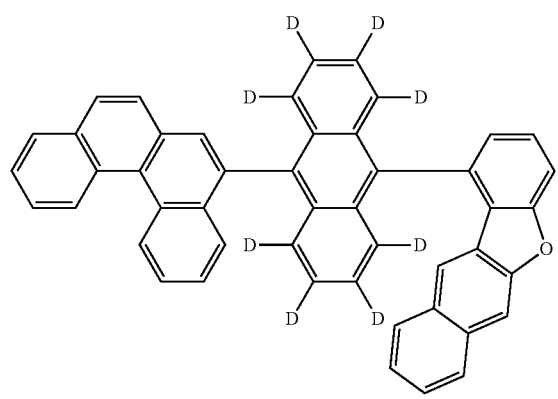
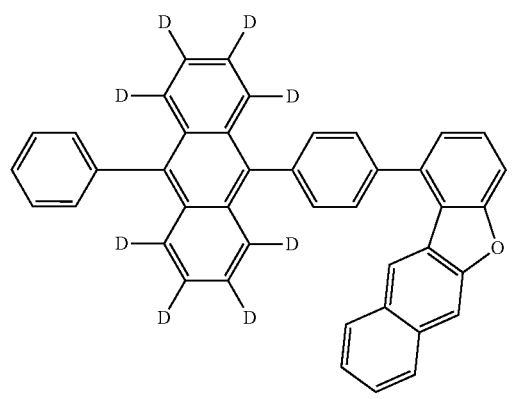
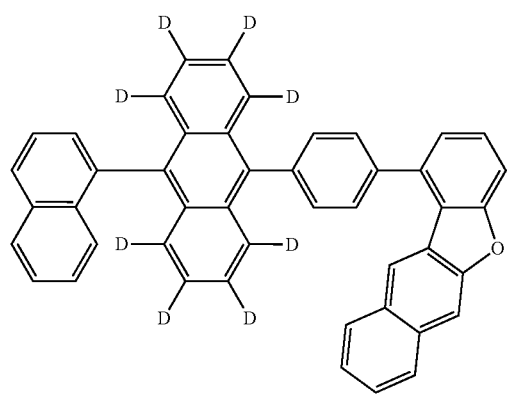

-continued
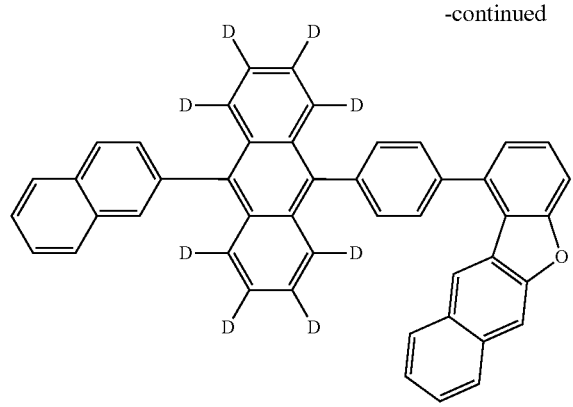
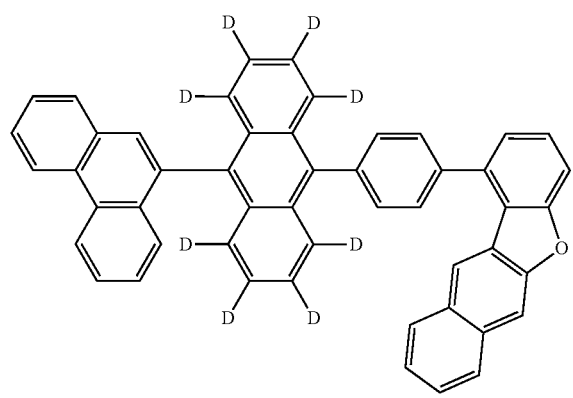
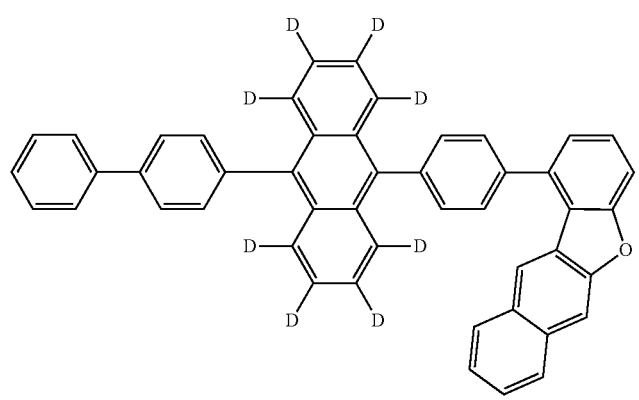
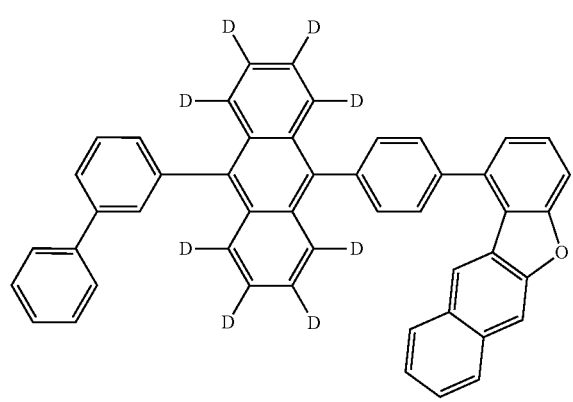

-continued
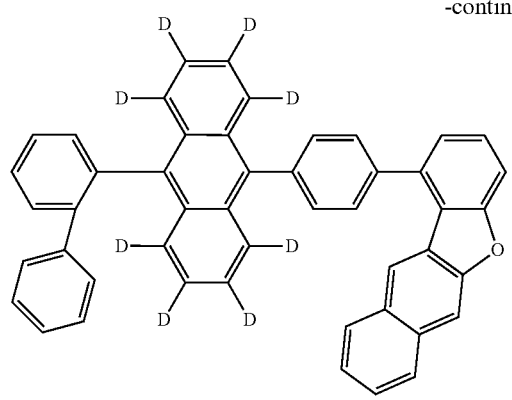
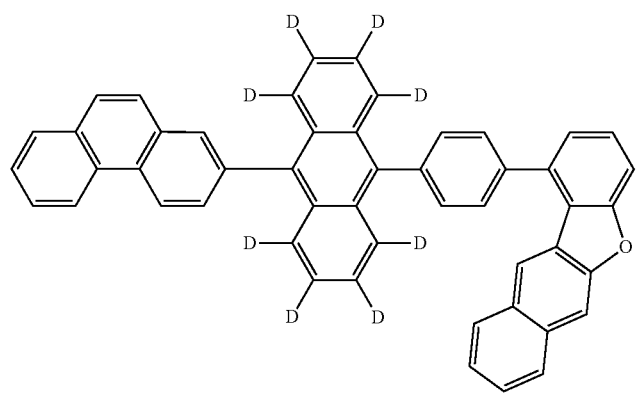
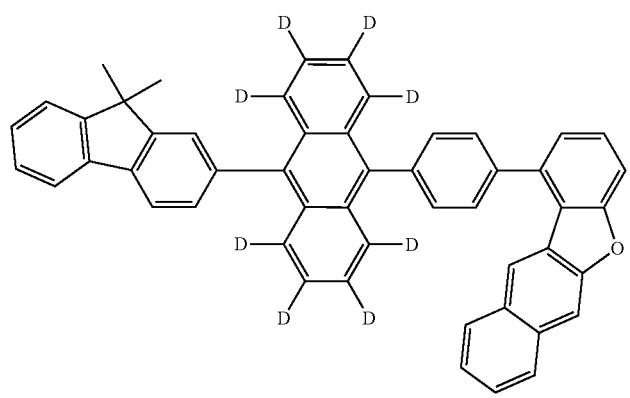
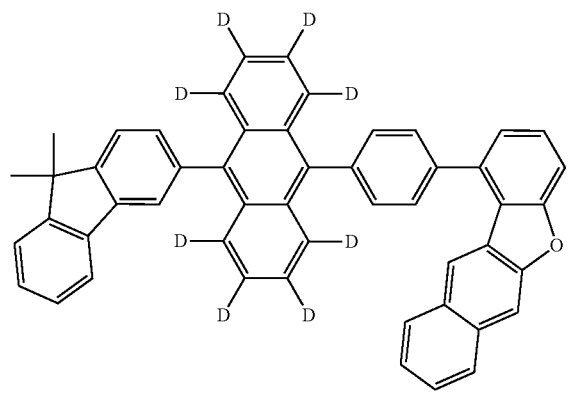

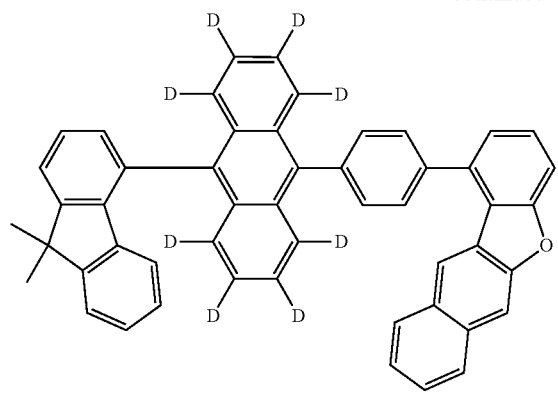
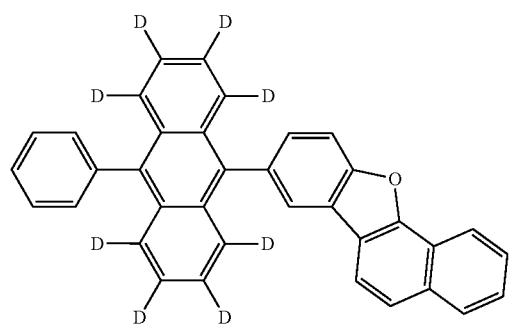
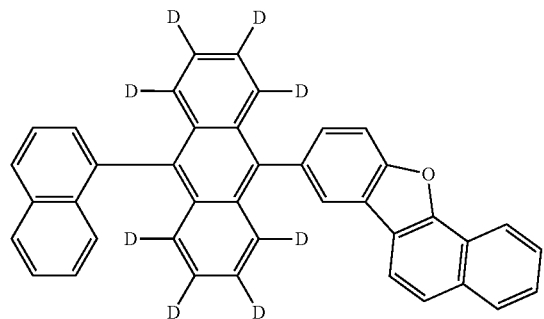
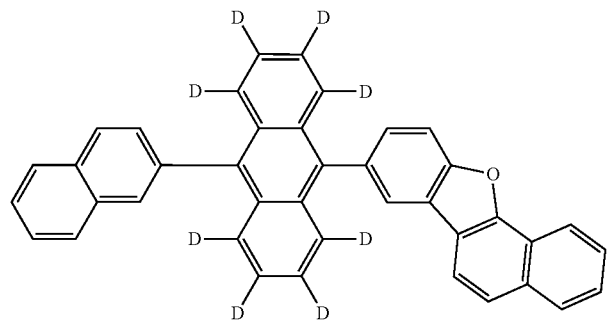
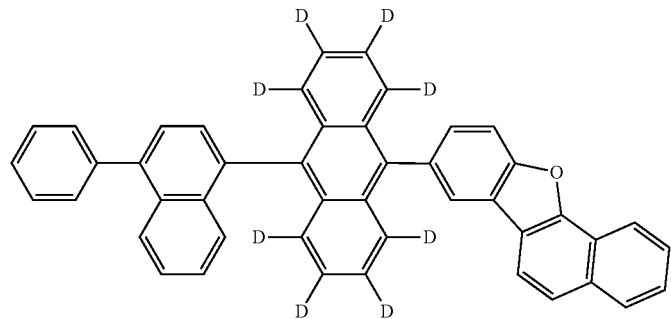

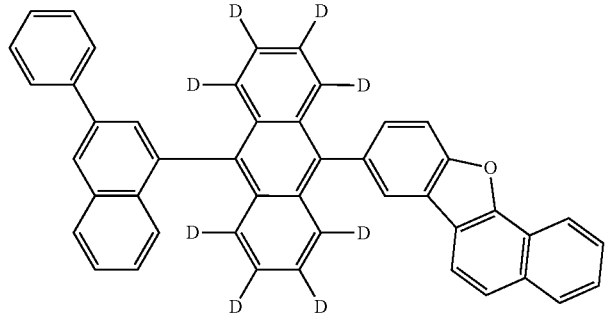
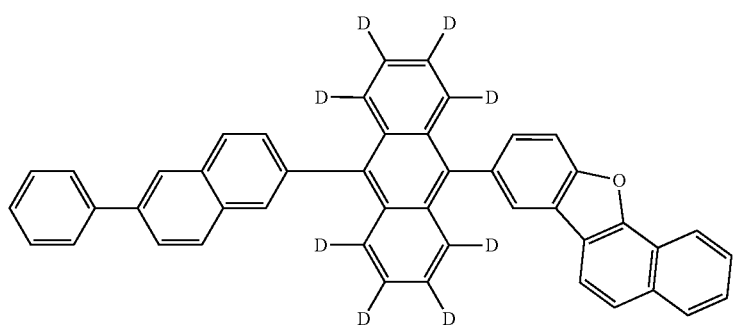
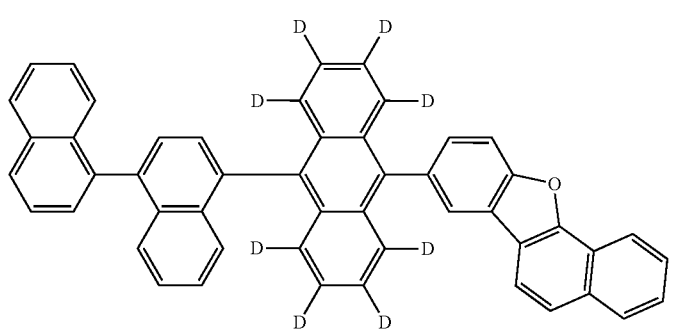
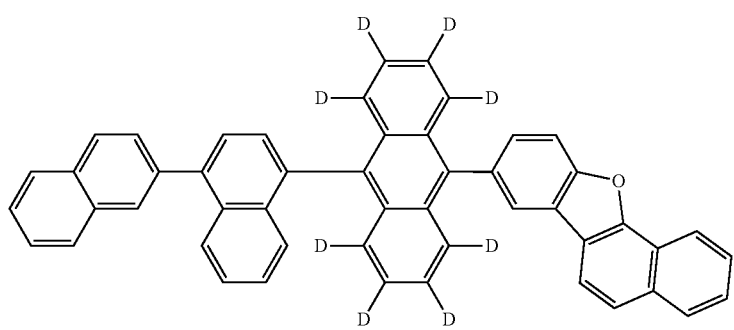

-continued
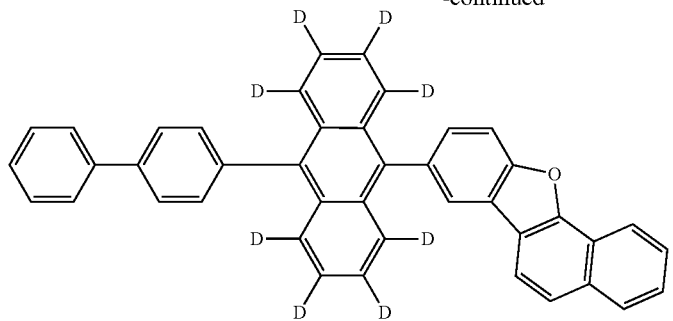
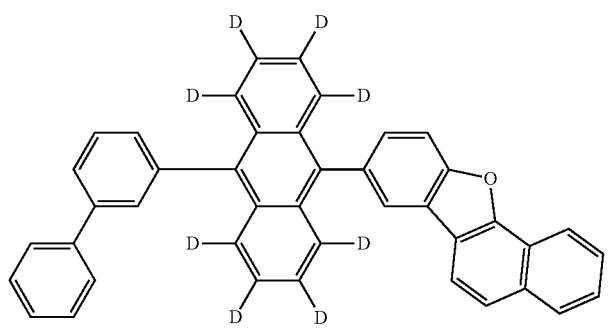
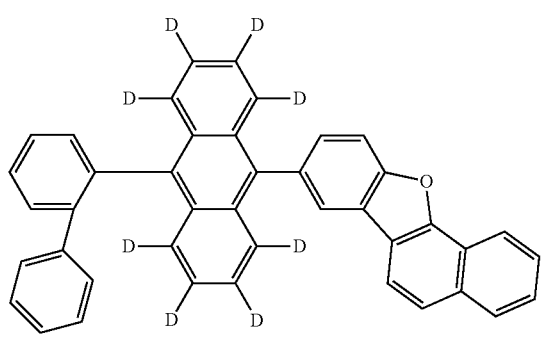
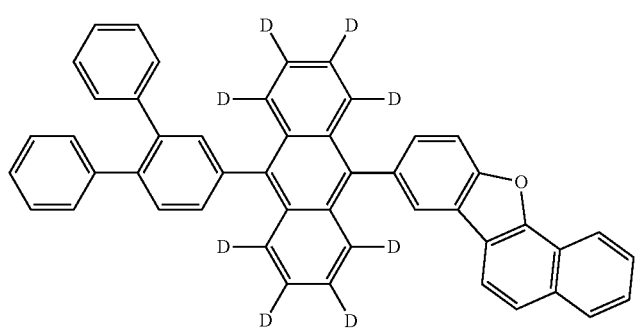
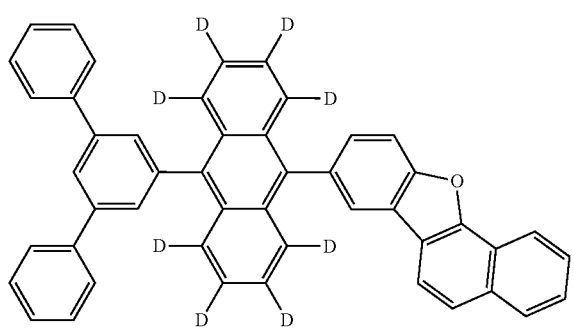

-continued
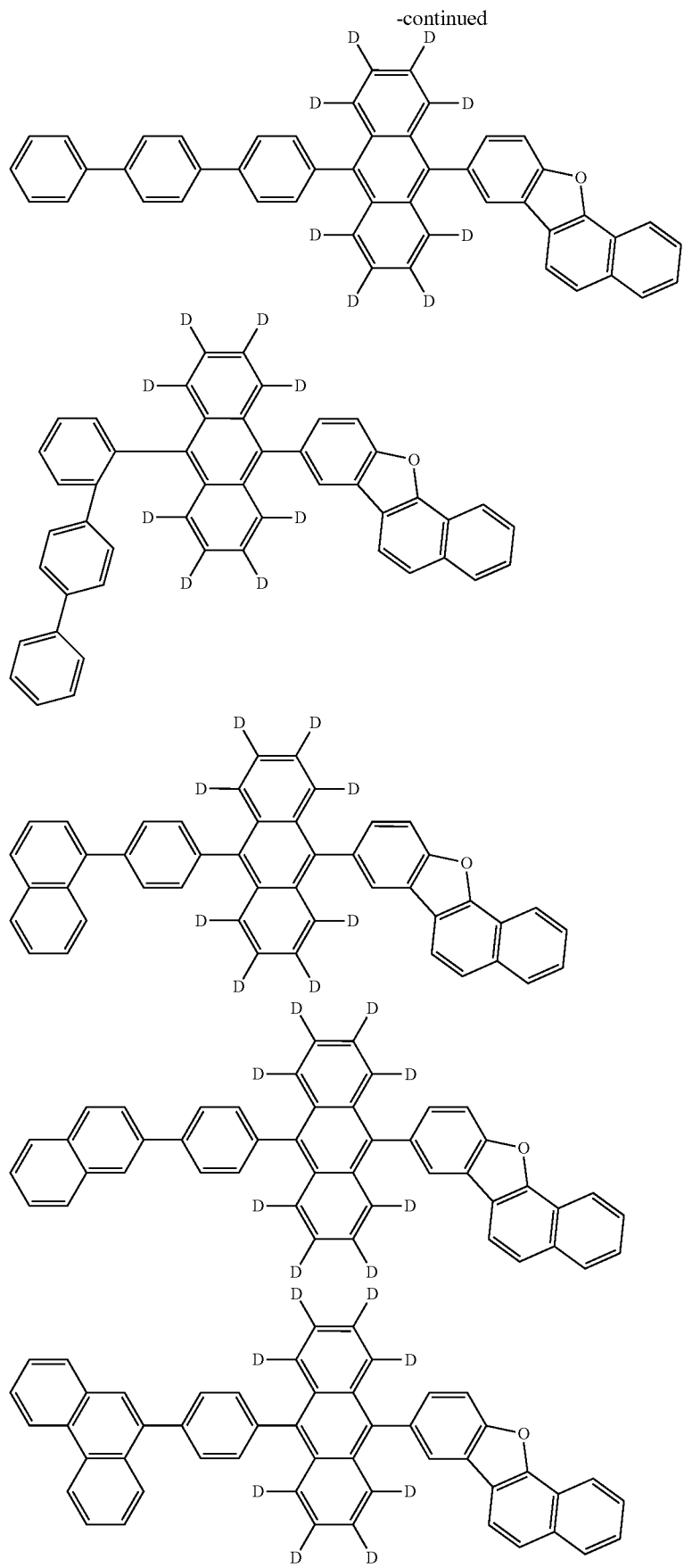

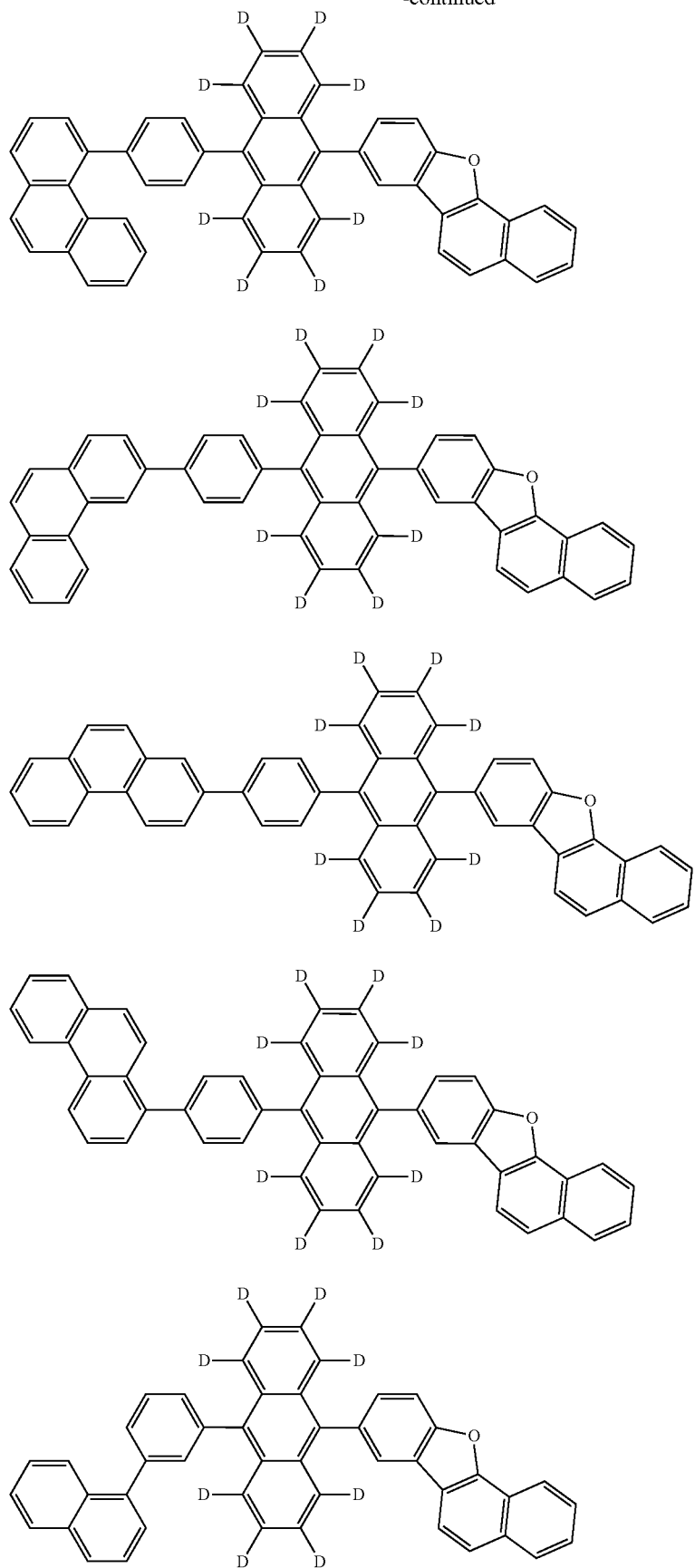

-continued
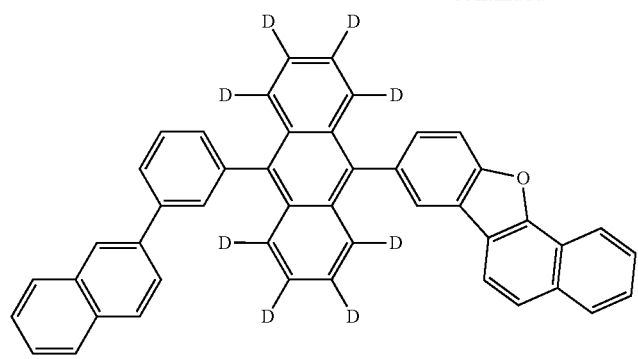
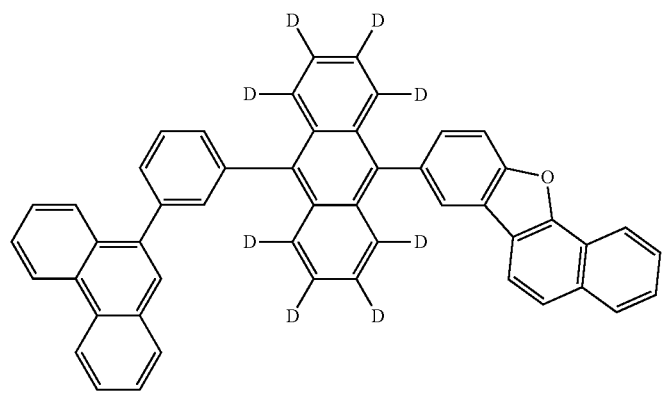
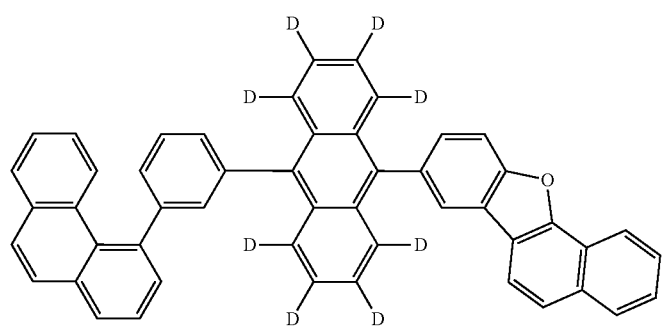
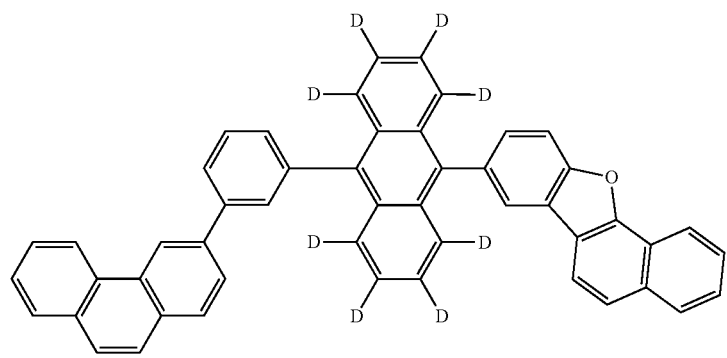

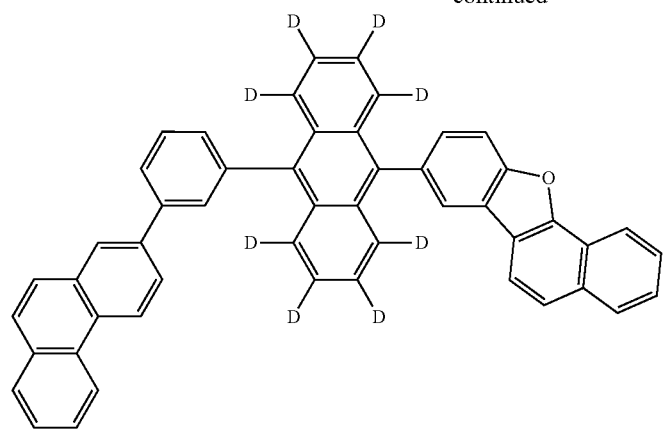
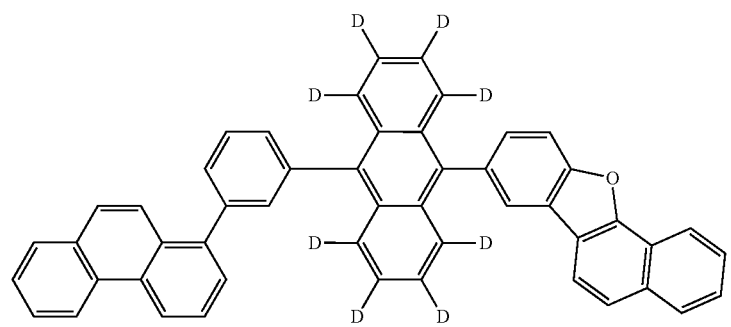
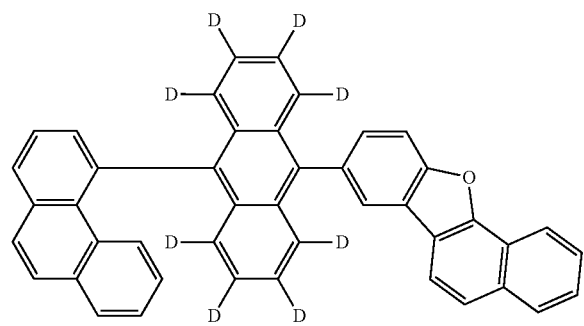
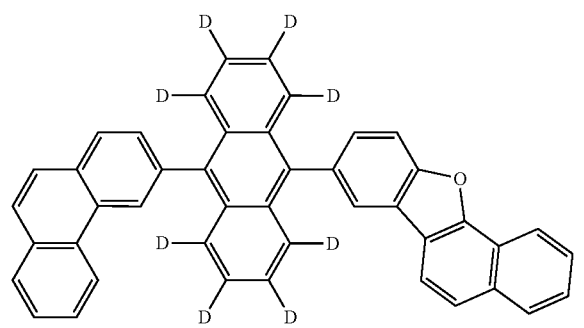
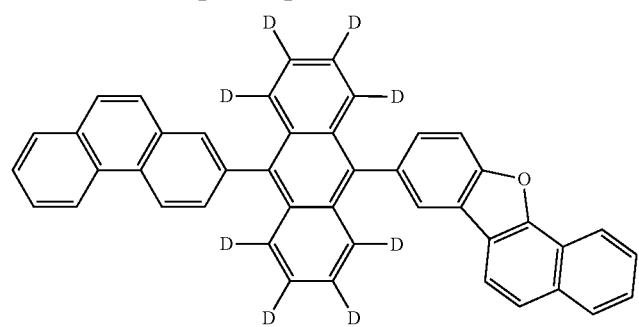

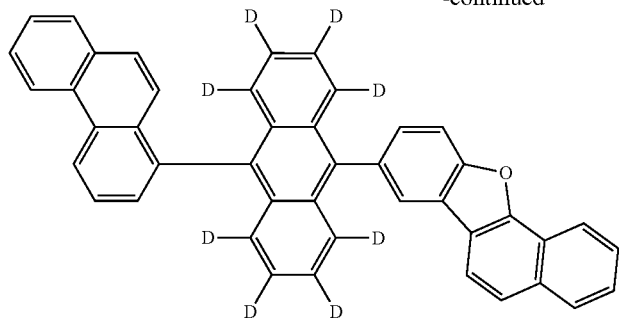
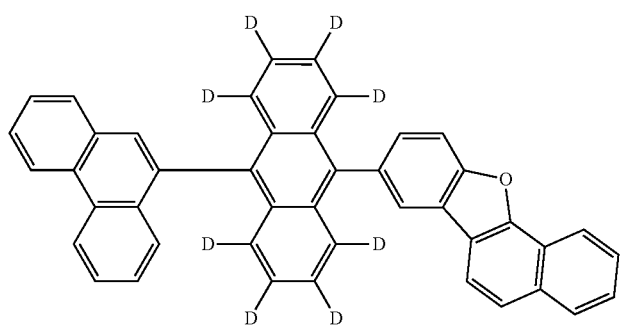
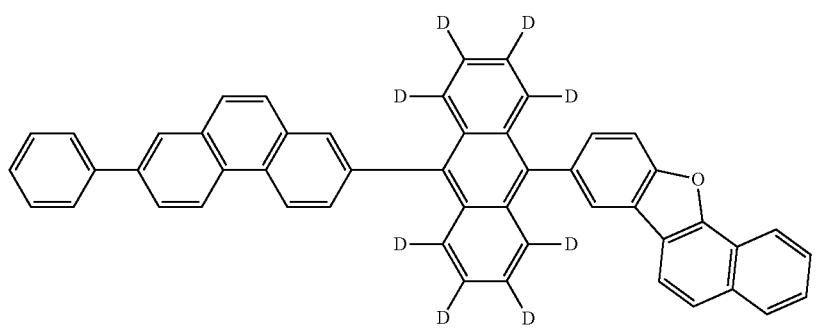
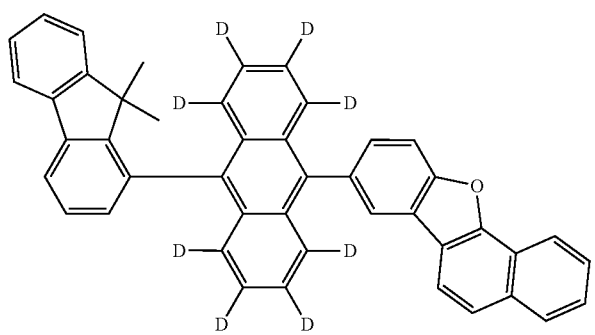
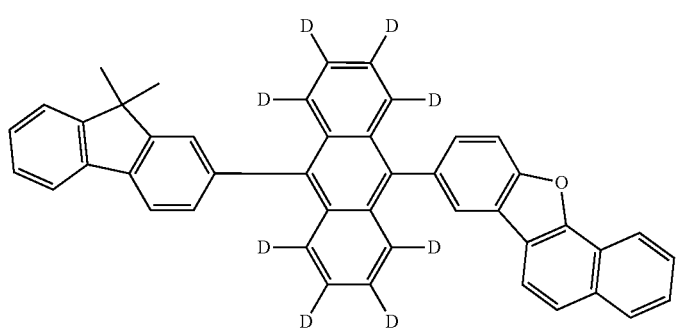

-continued
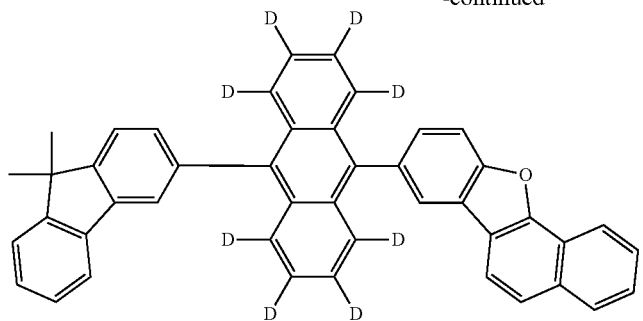
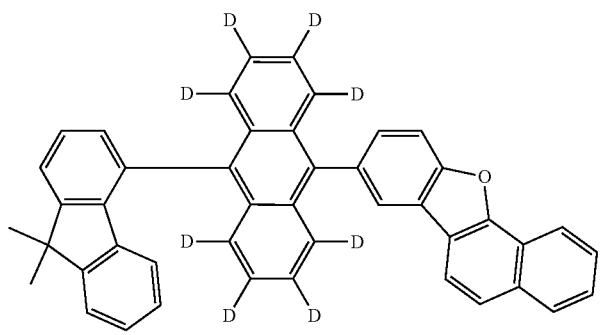
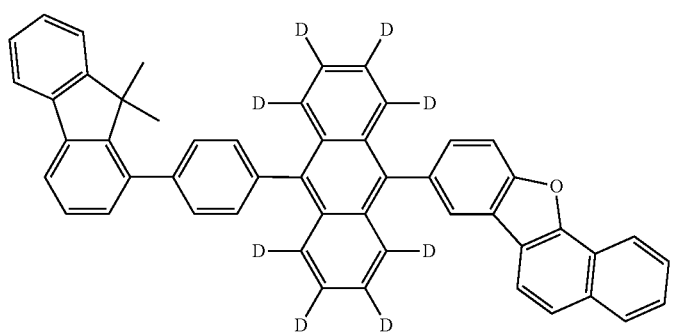
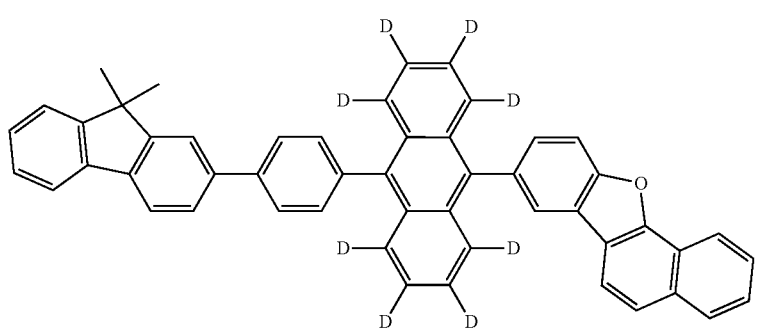
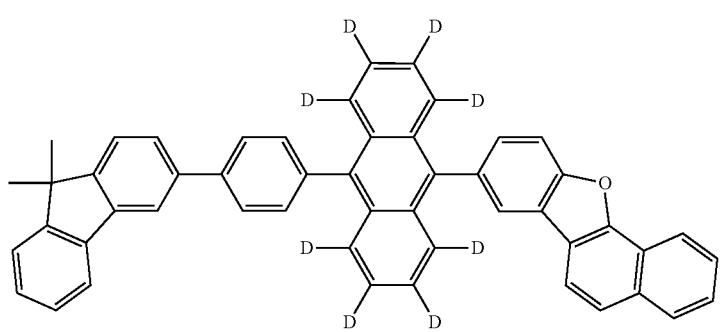

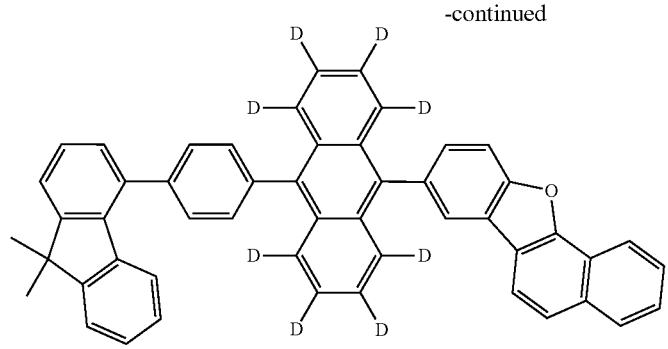
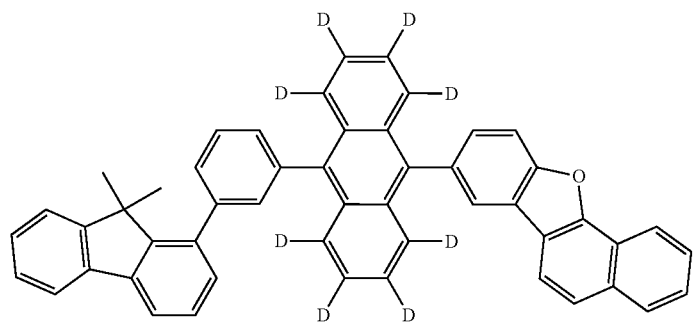
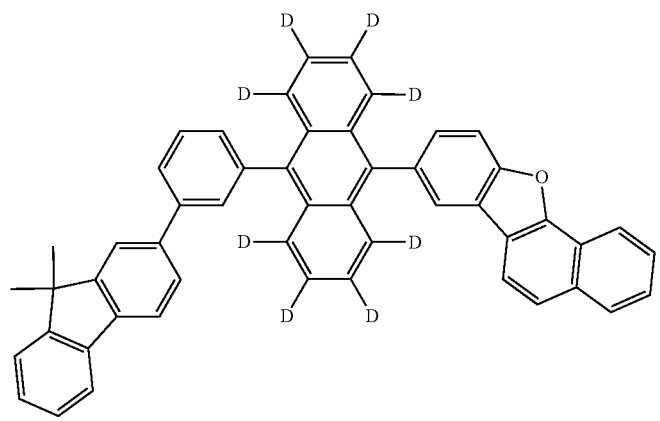
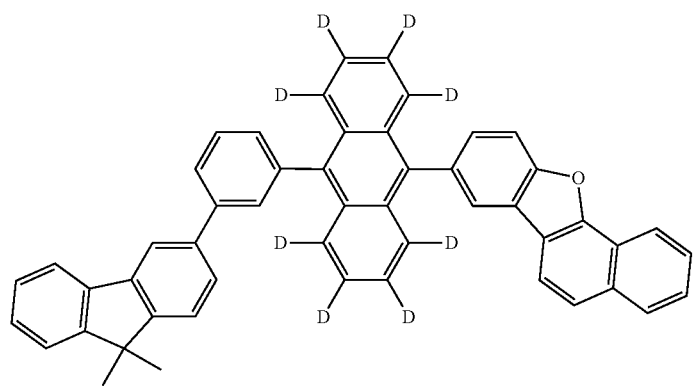

-continued
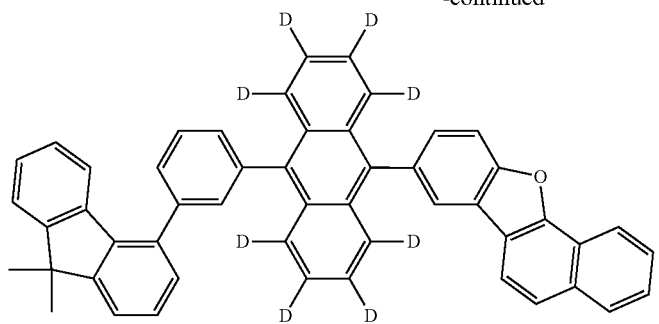
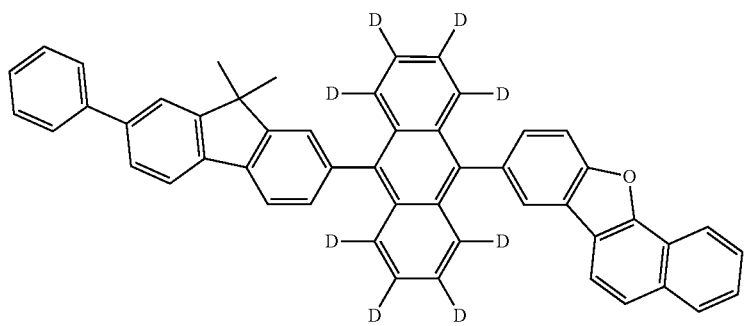
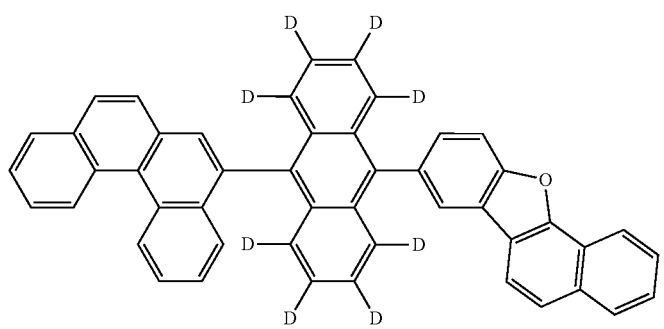
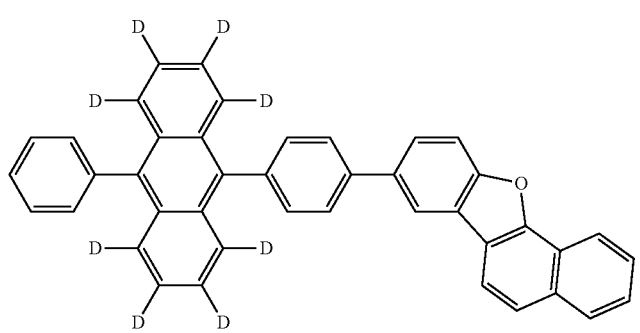
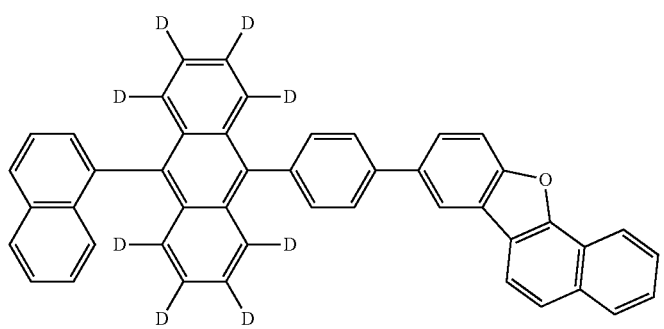

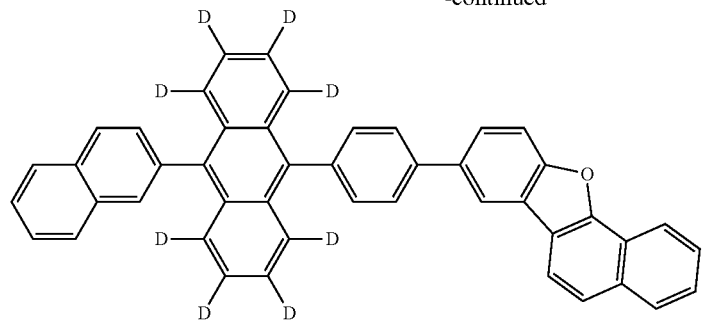
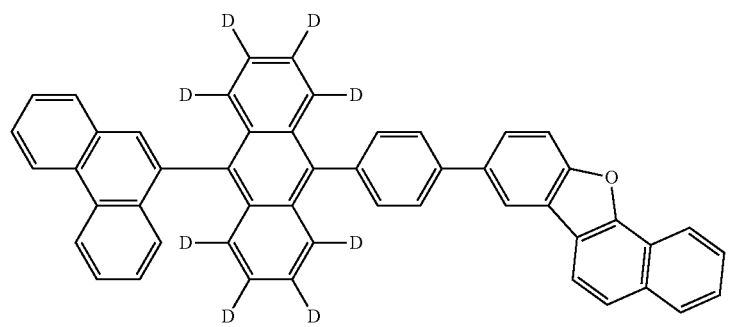
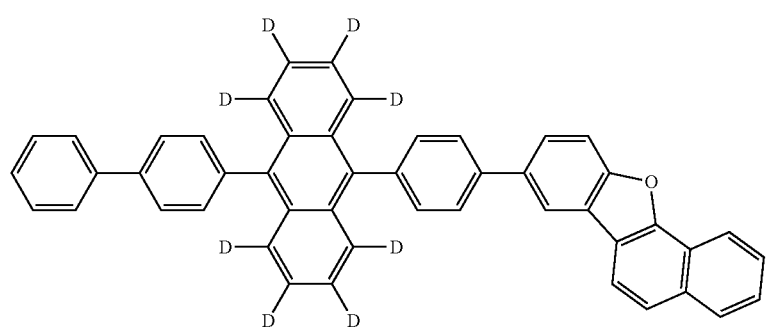
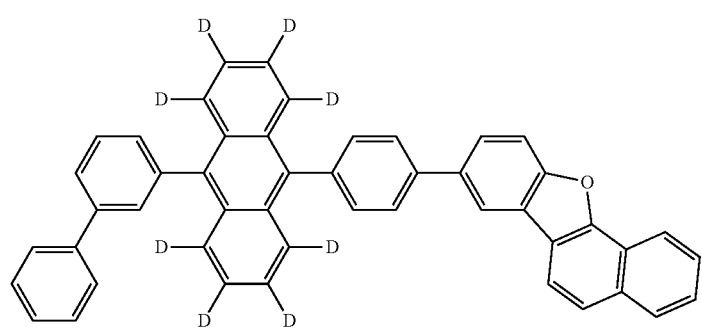
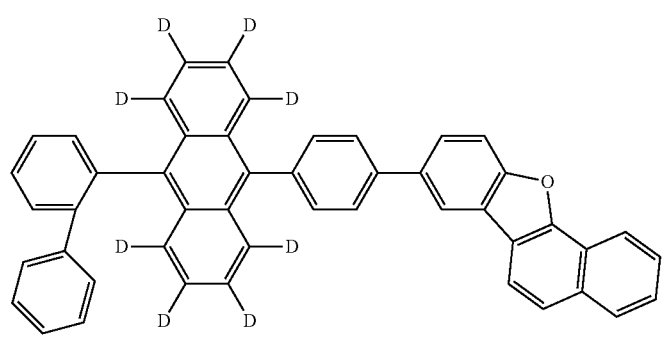

-continued
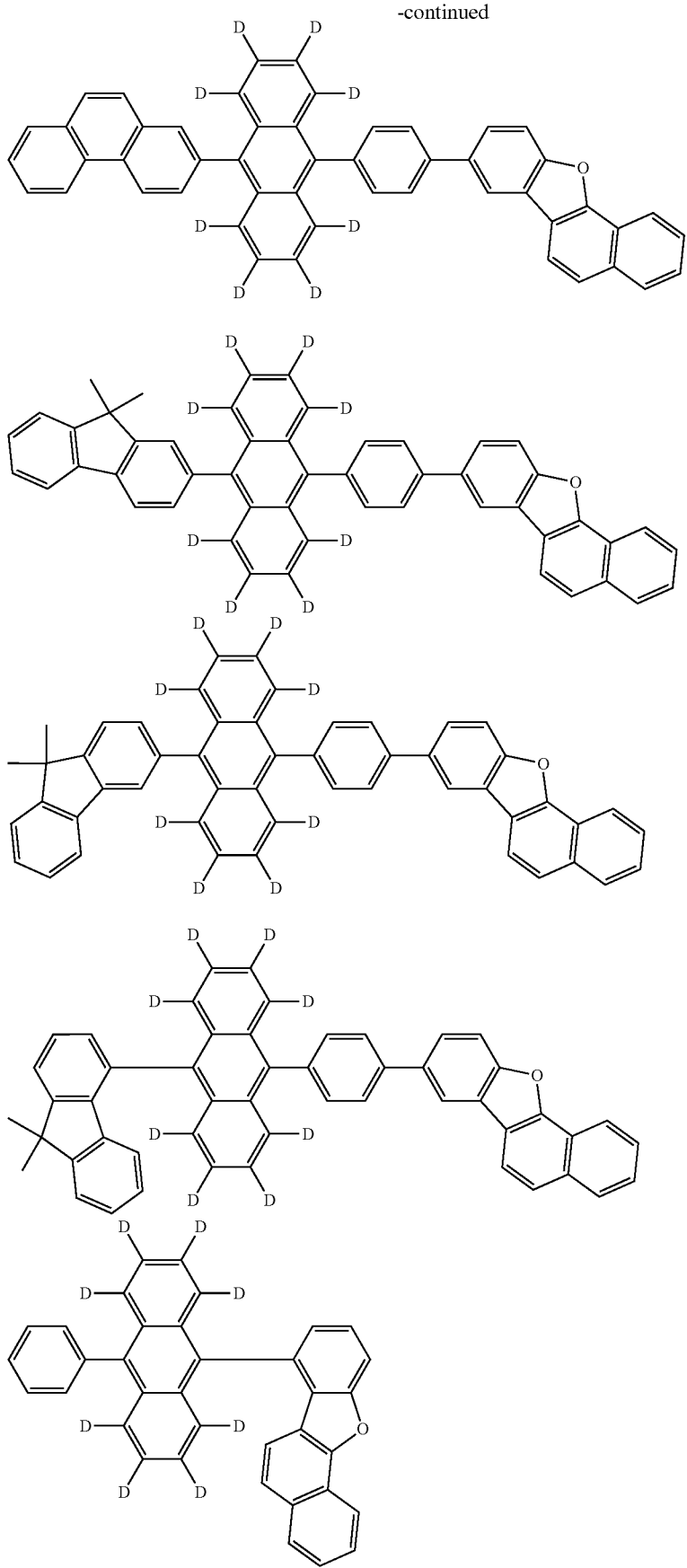

301
-continued
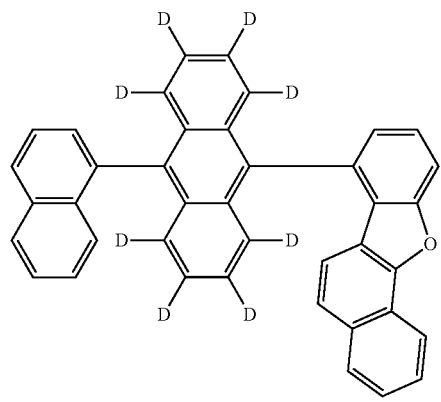
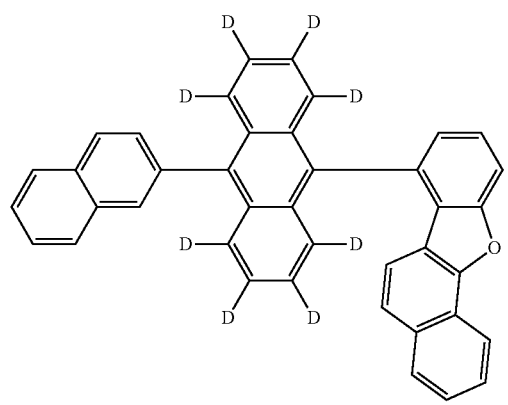
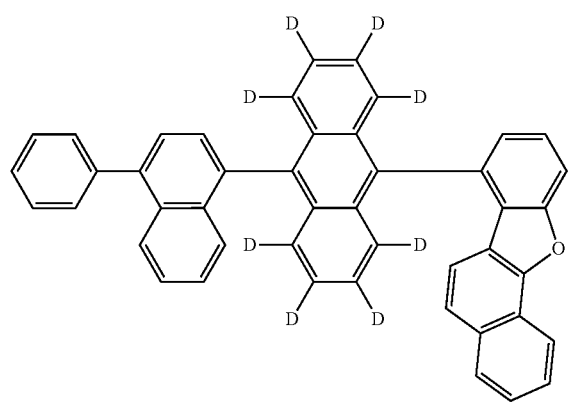
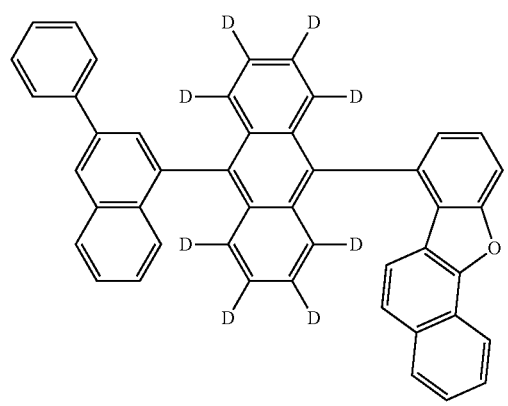
302

-continued
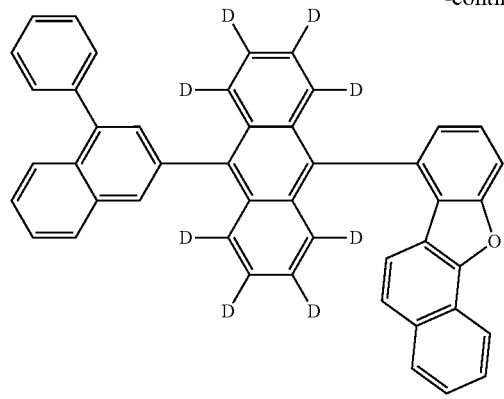
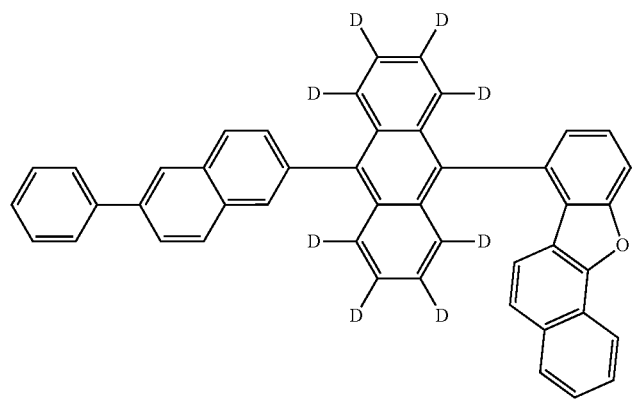
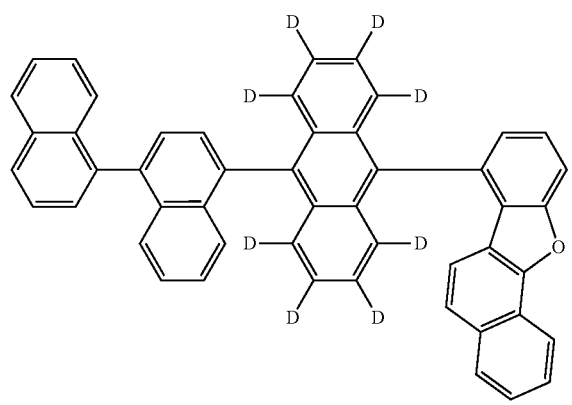
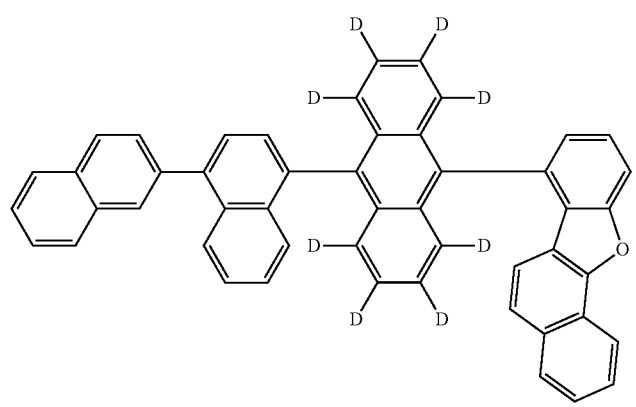

-continued
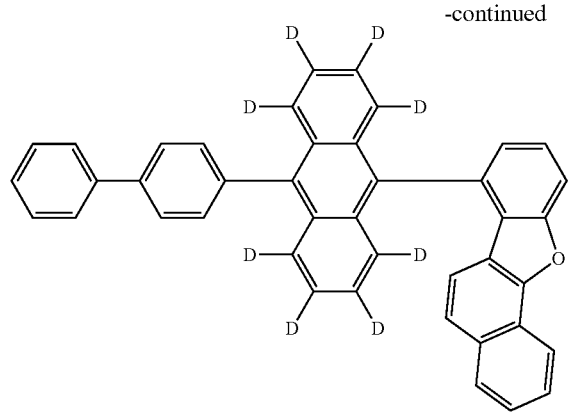
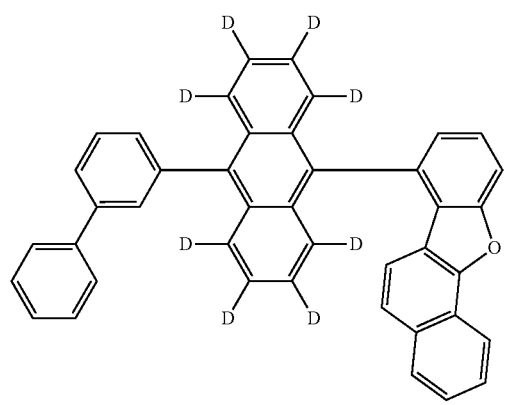
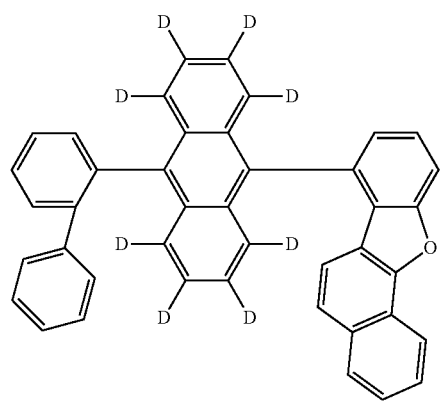
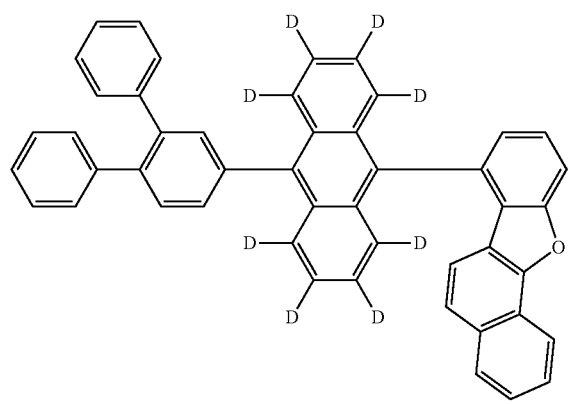

-continued
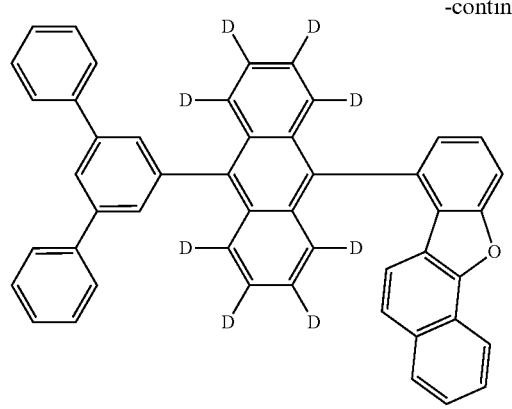
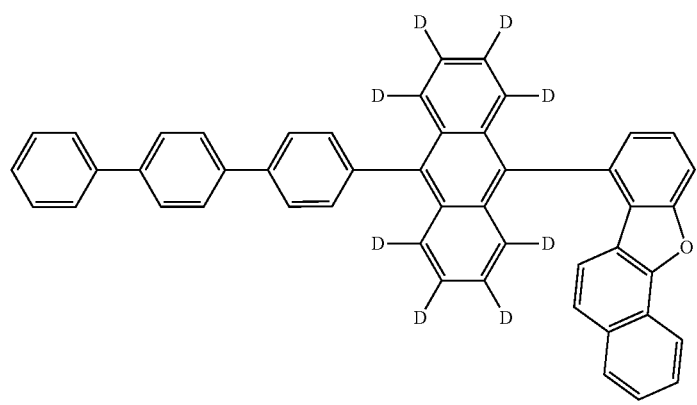
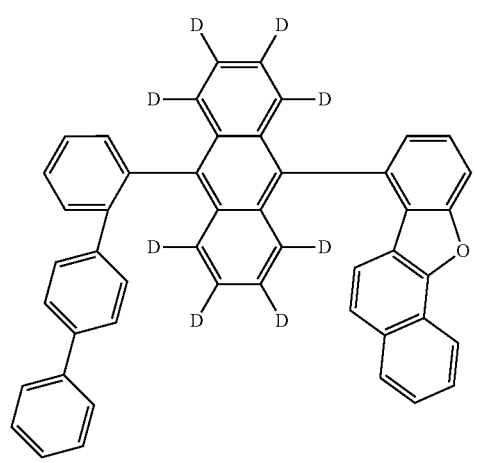
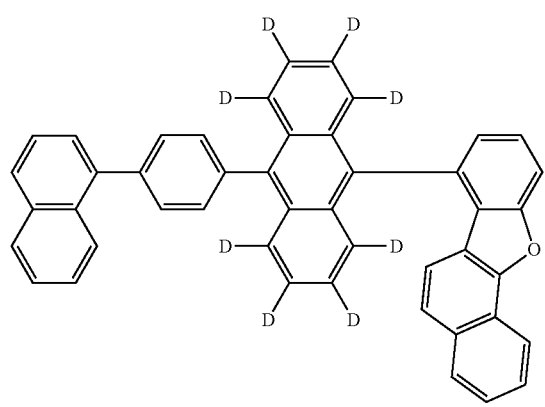

-continued
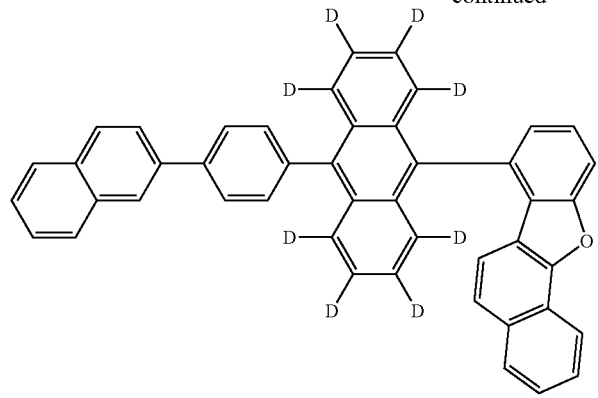
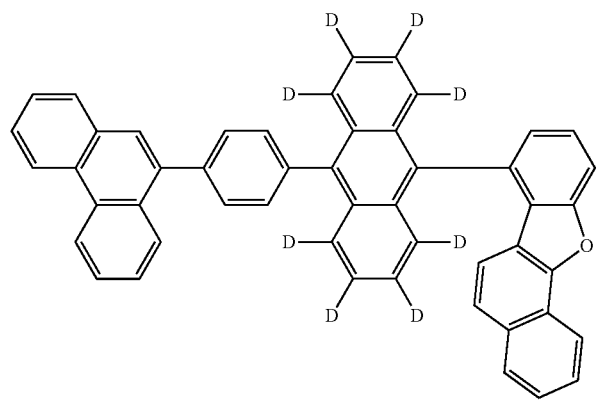
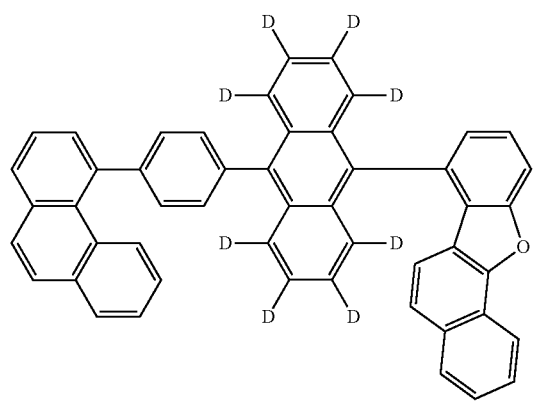
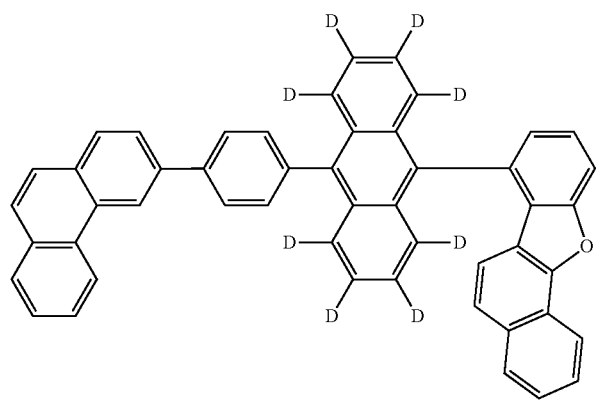

-continued
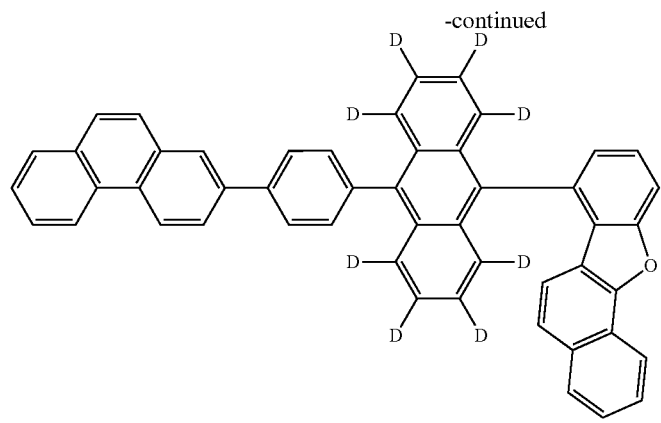
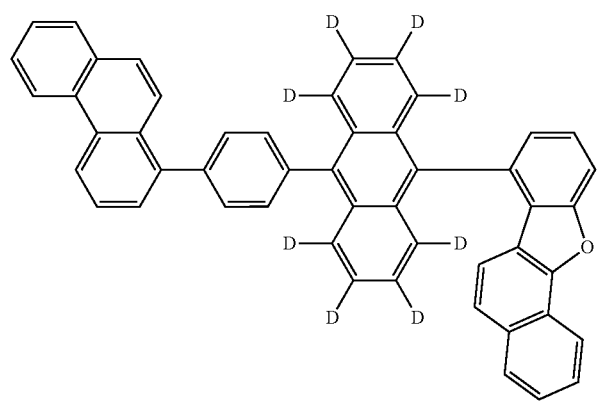
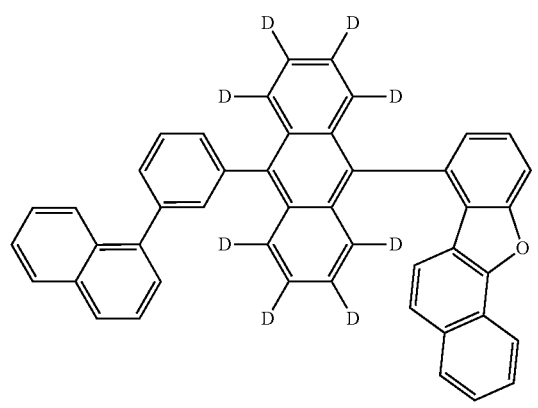
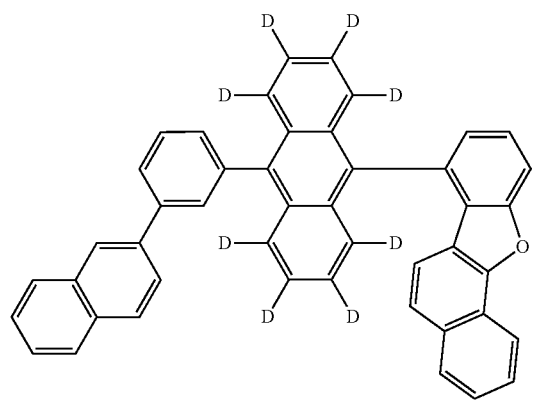

-continued
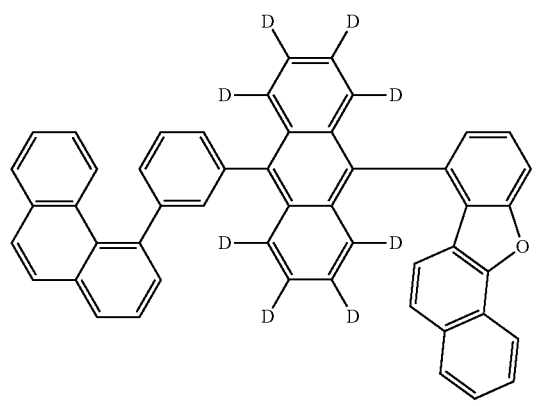
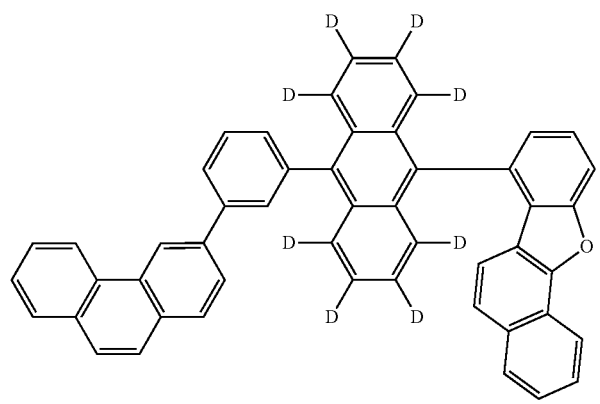
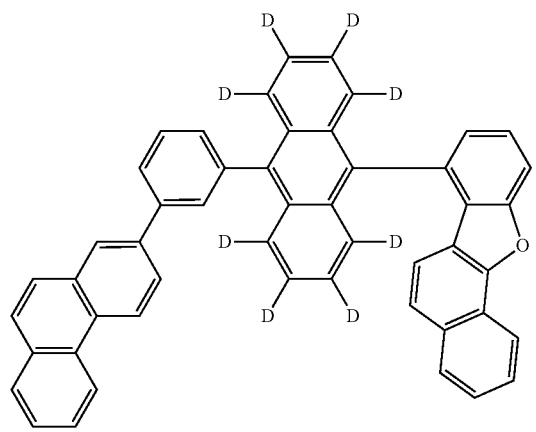

-continued
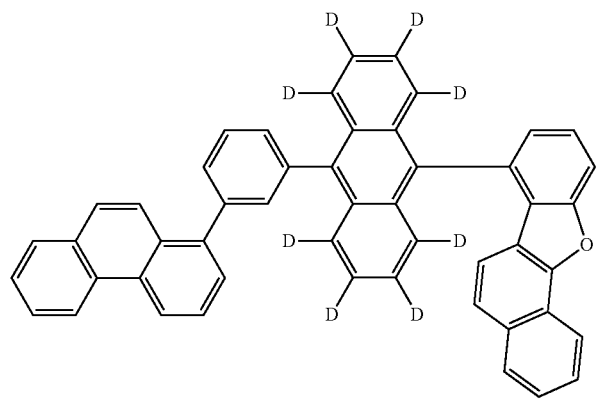
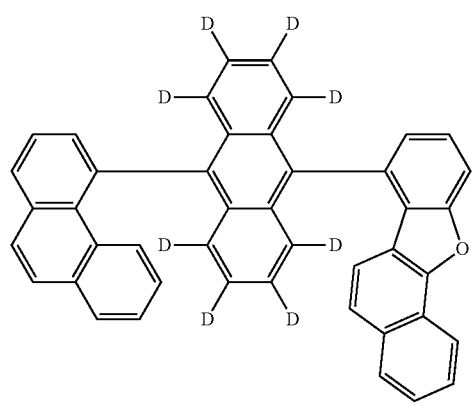
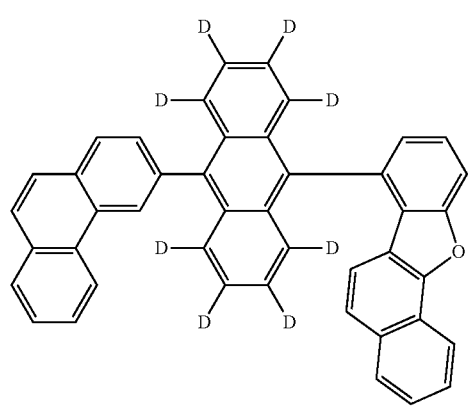
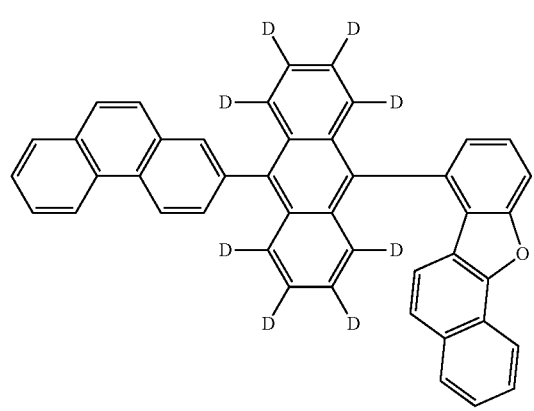

-continued
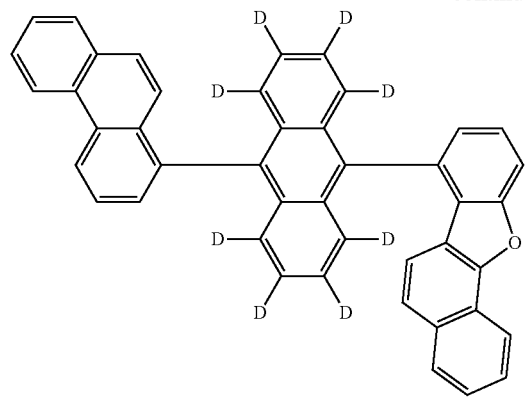
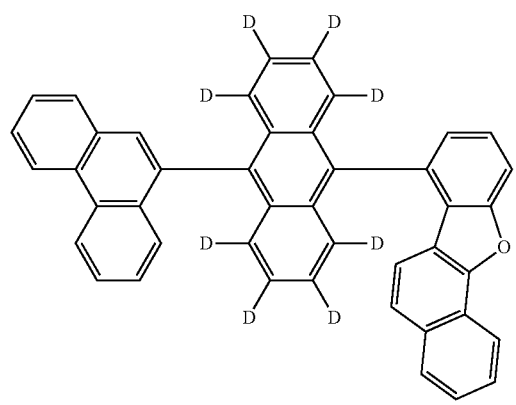
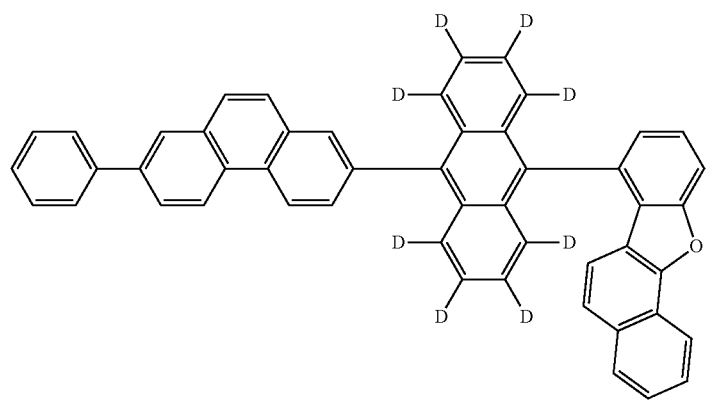
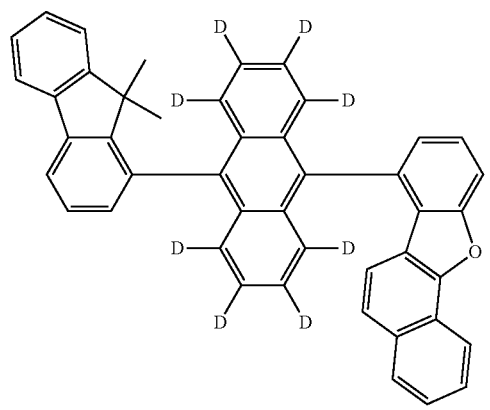

-continued
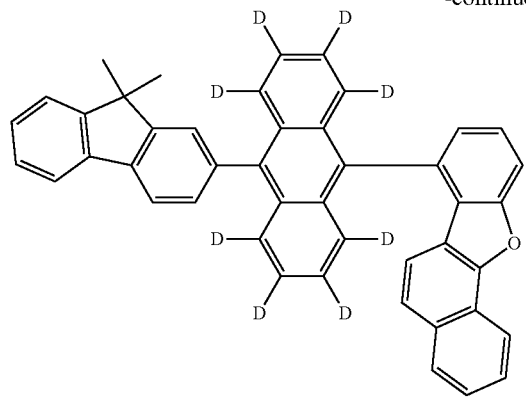
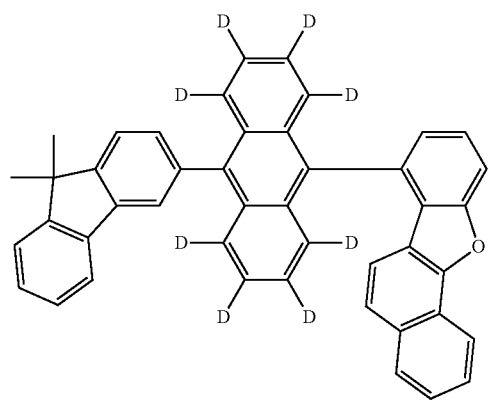
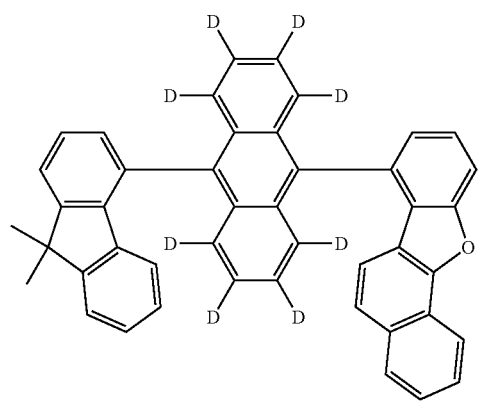
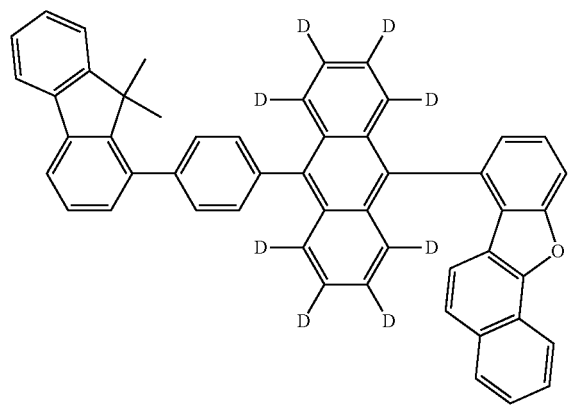

-continued
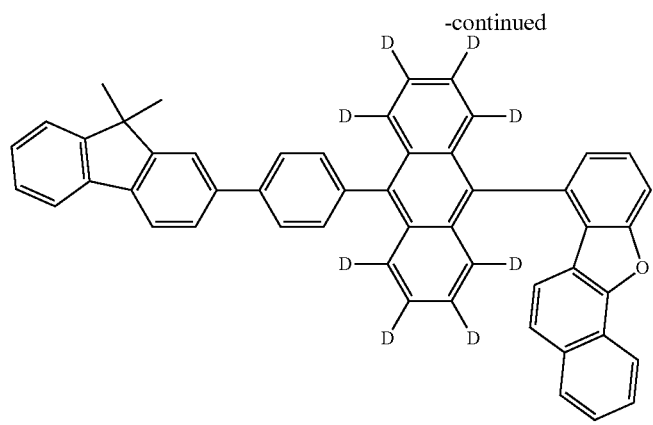
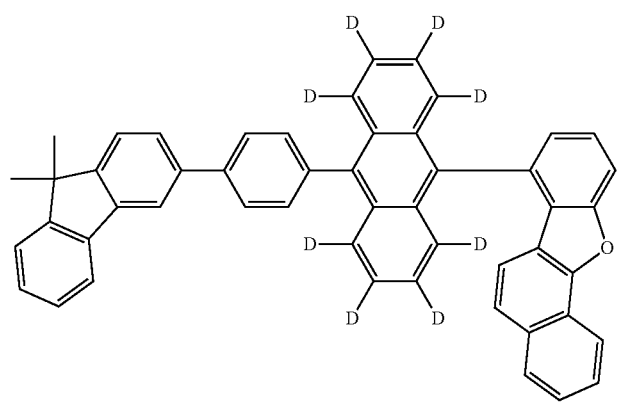
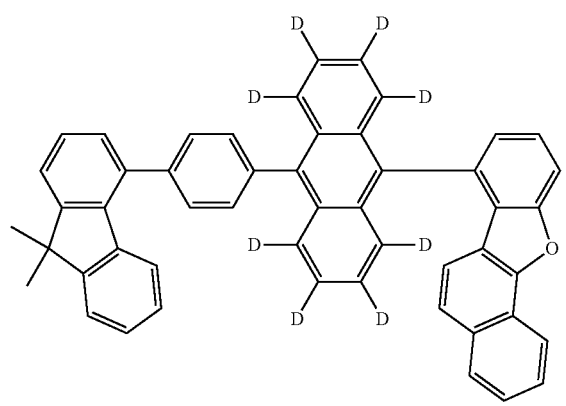
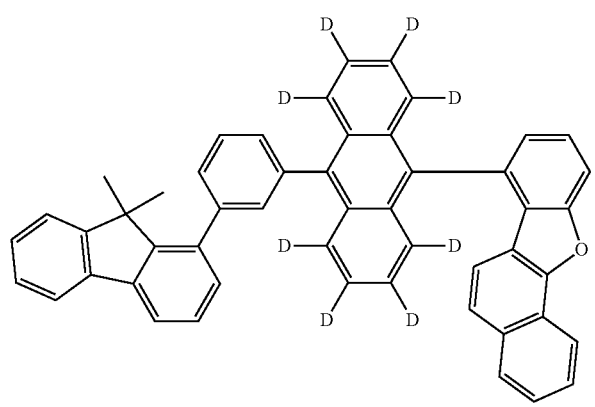

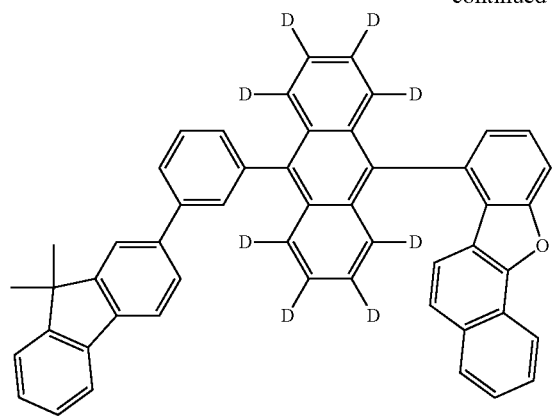
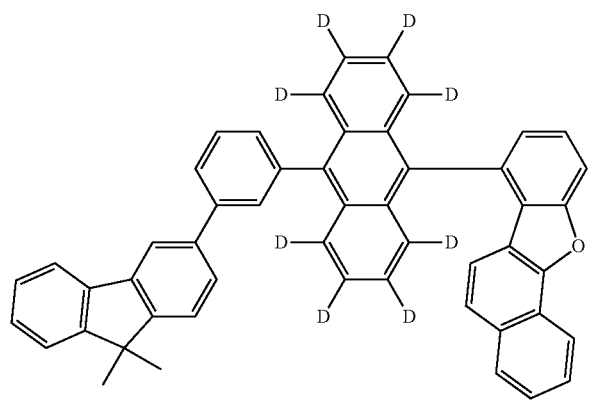
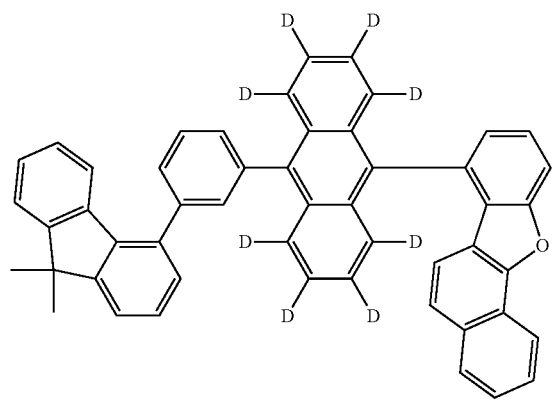
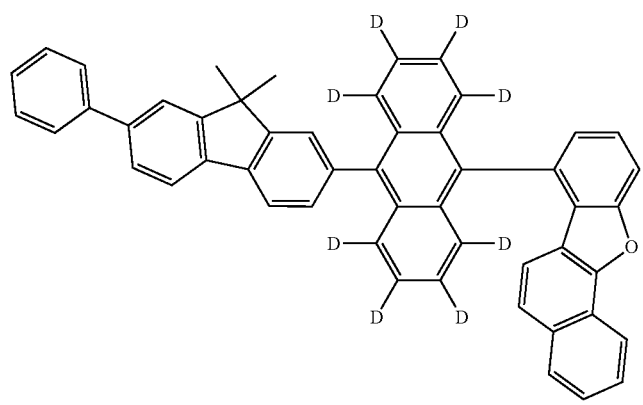

-continued
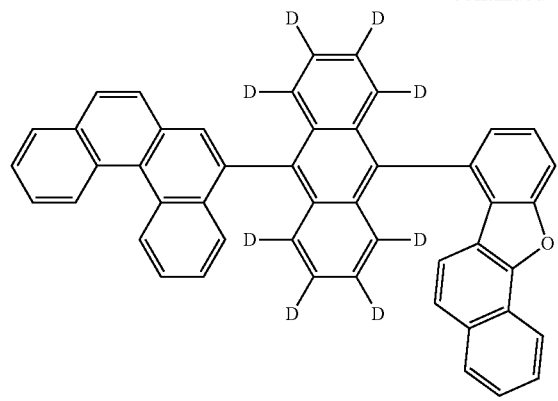
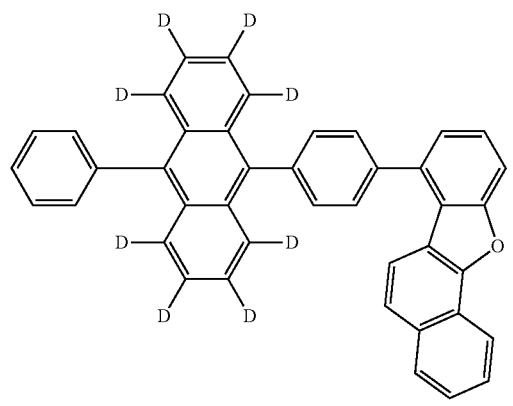
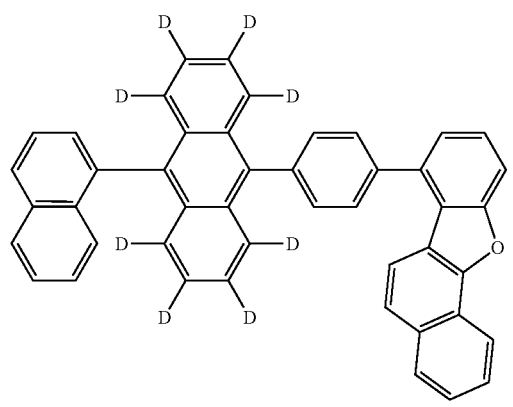
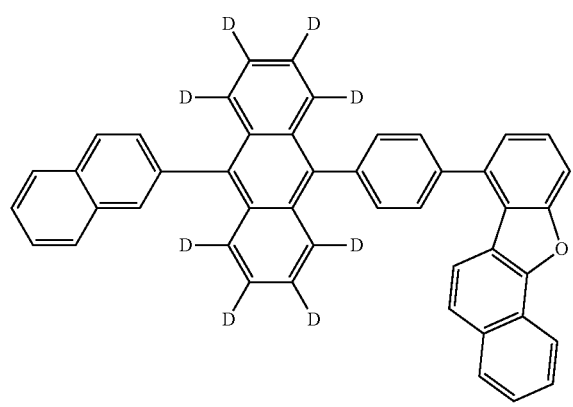

327
328
-continued
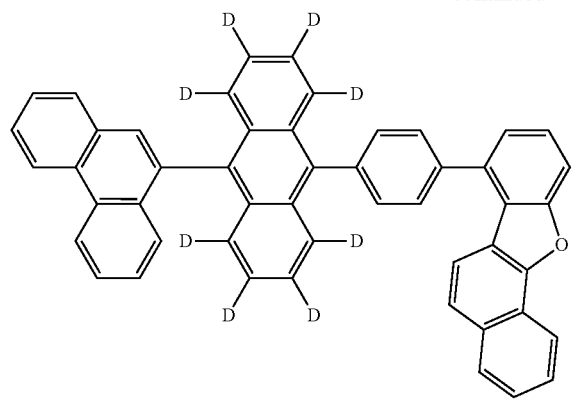
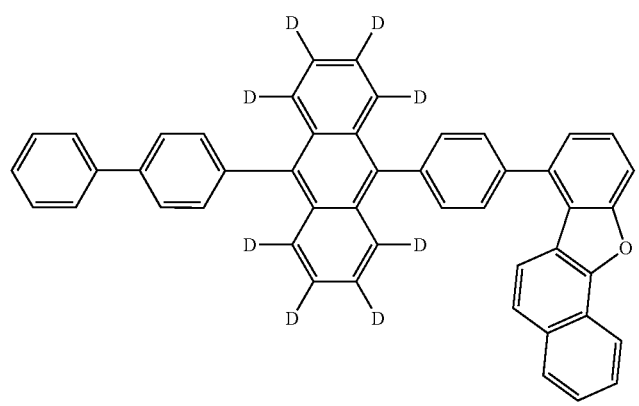
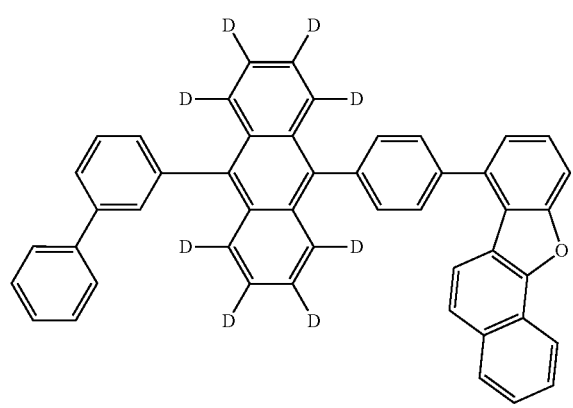
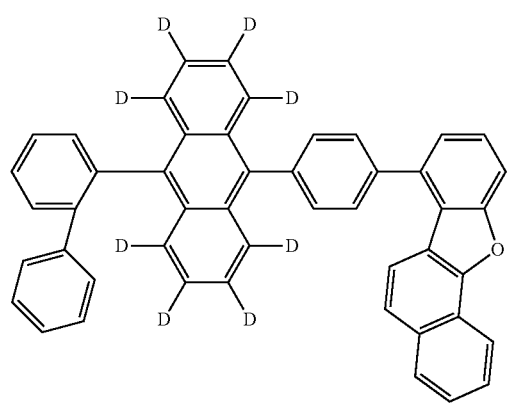

-continued
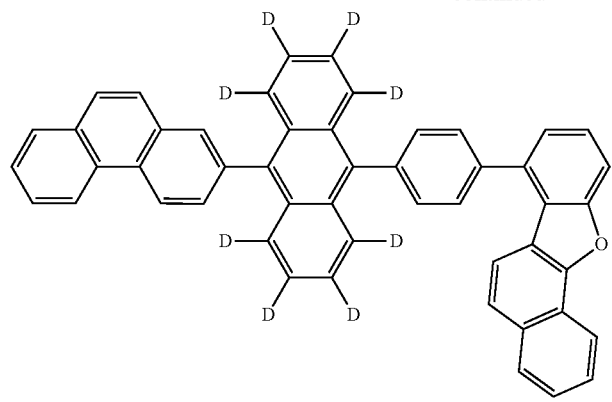
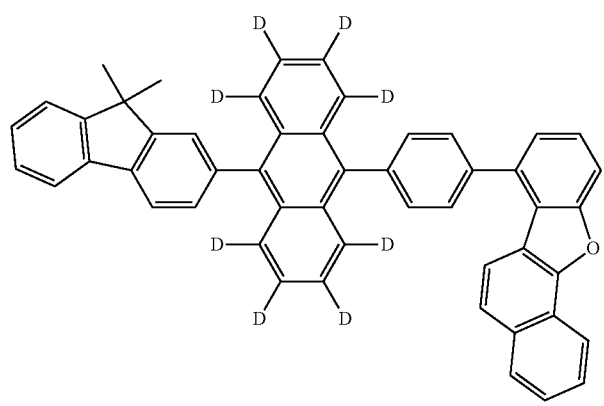
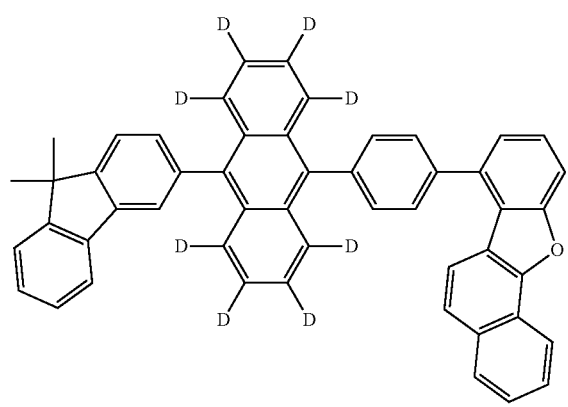
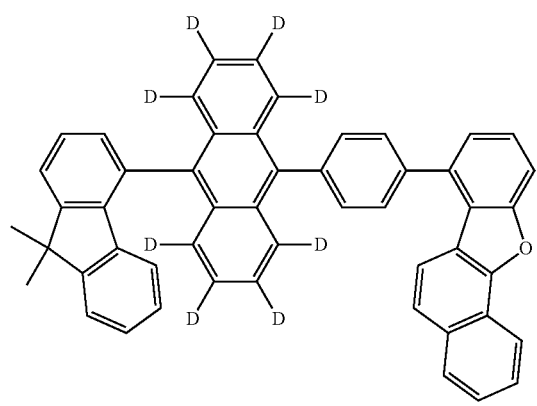

-continued
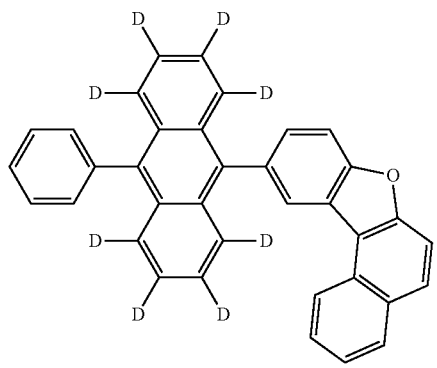
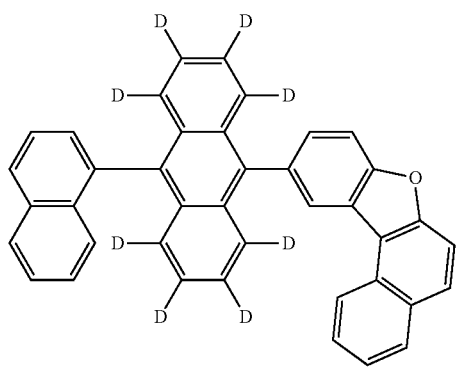
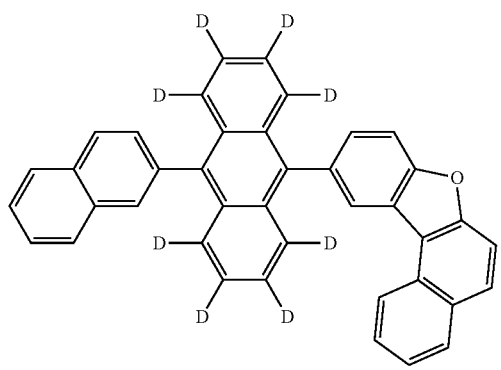
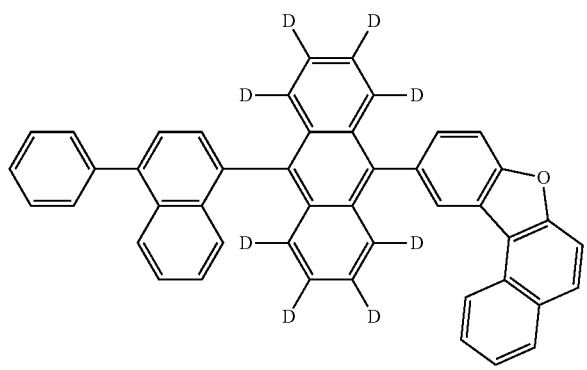

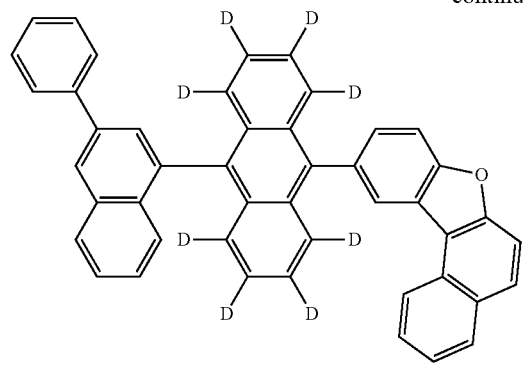
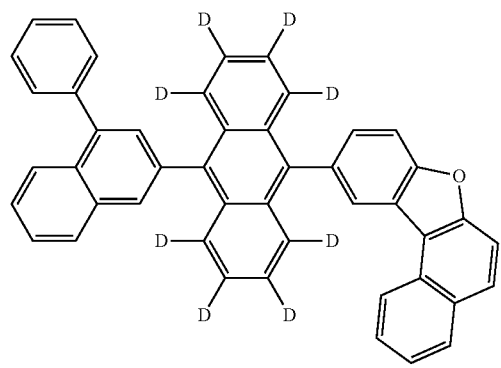
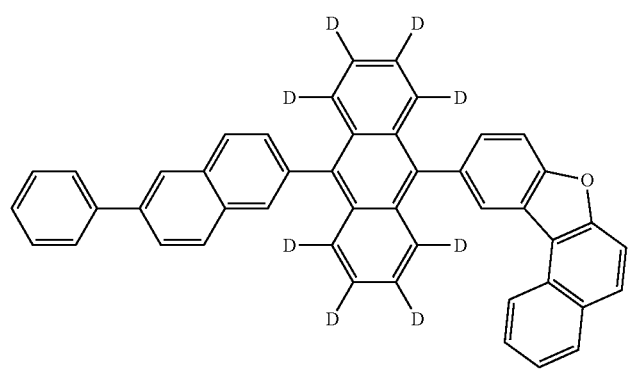
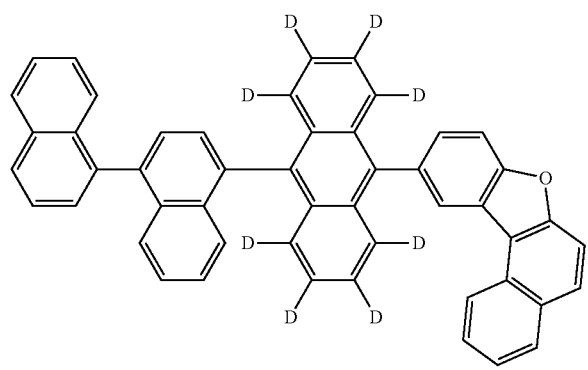

-continued
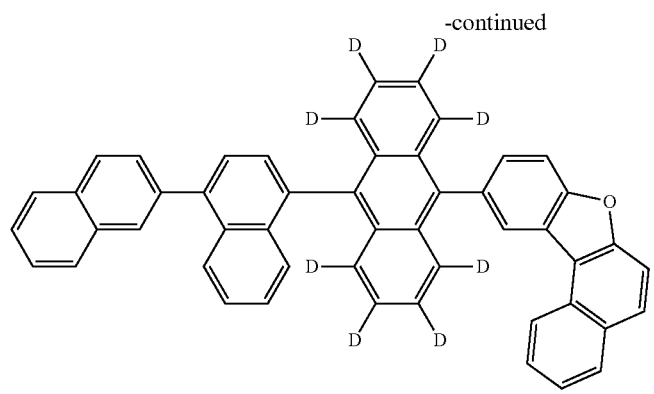
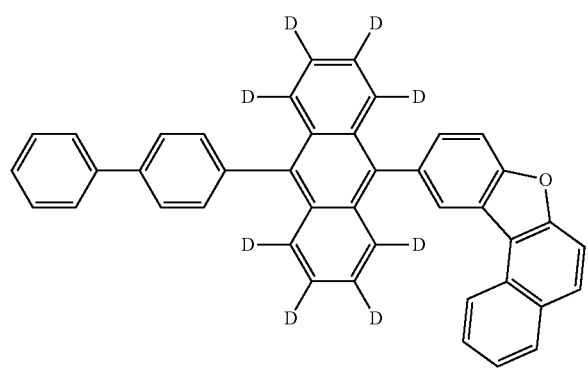
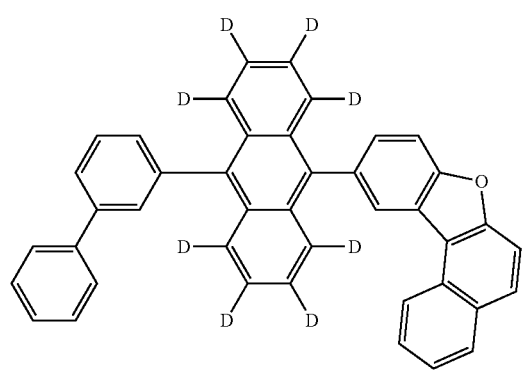
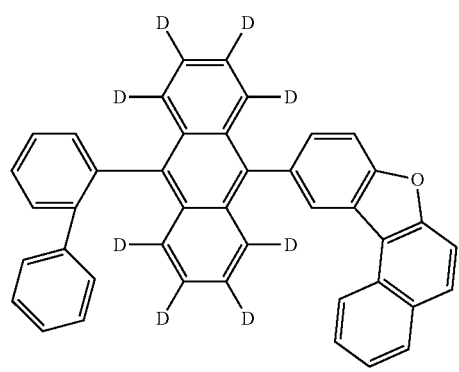

-continued
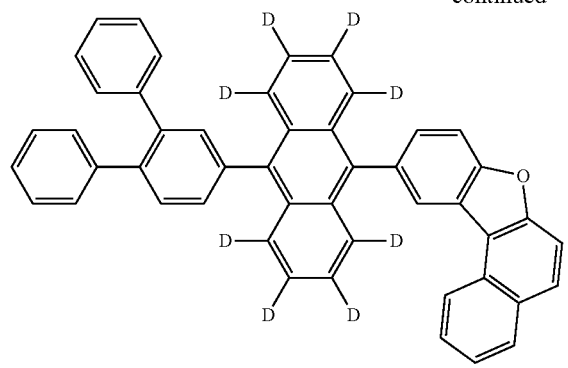
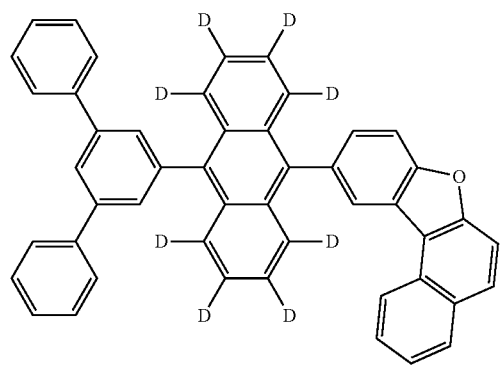
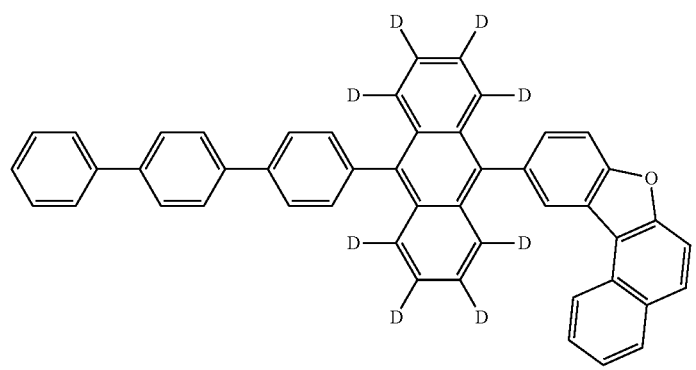
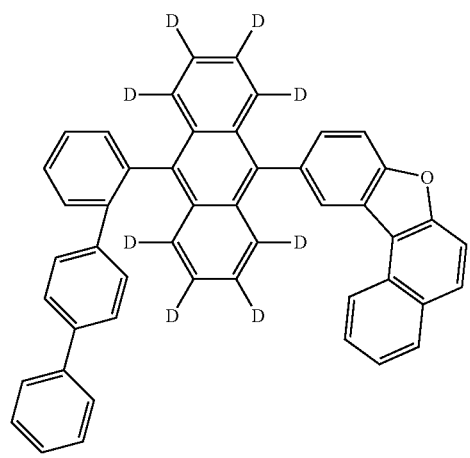

-continued
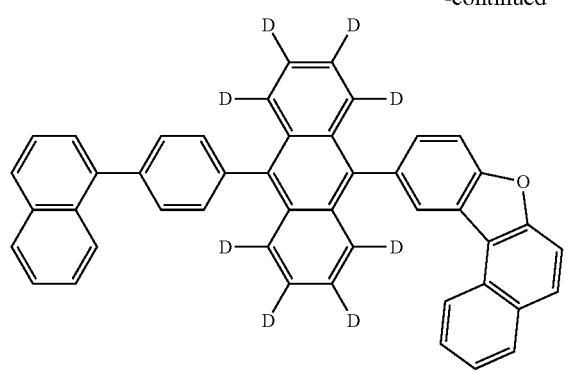
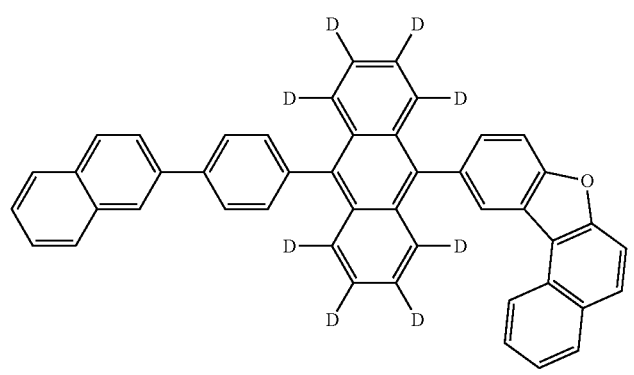
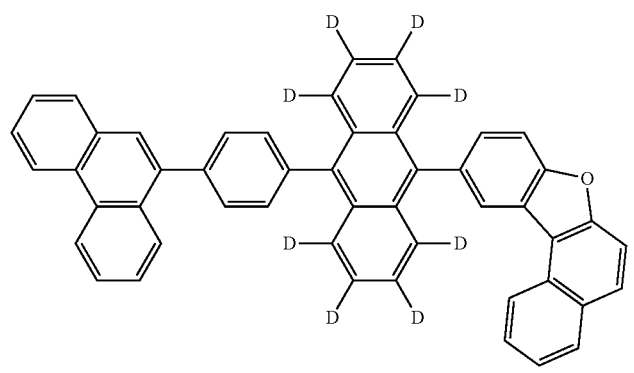
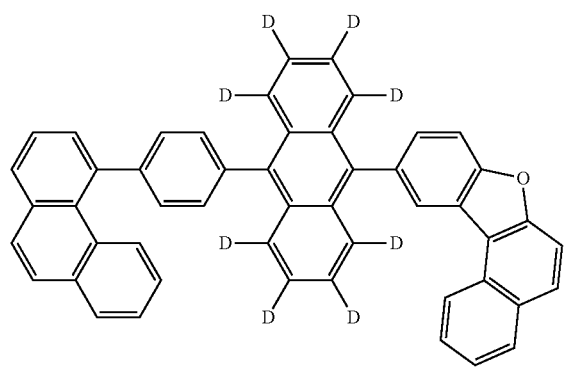

-continued
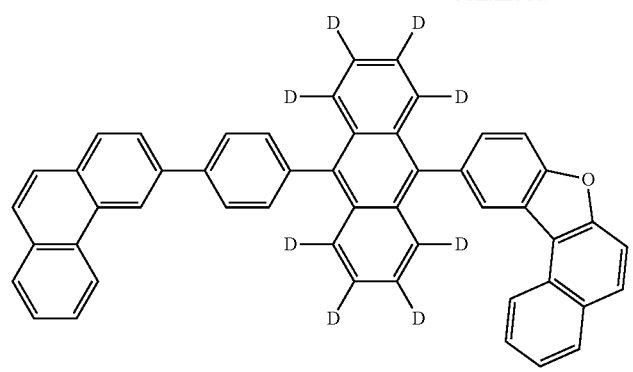
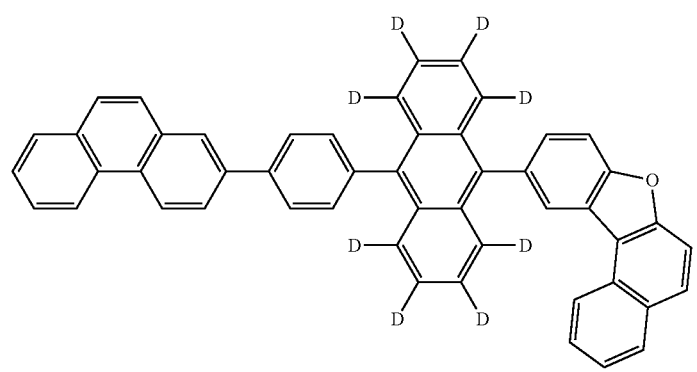
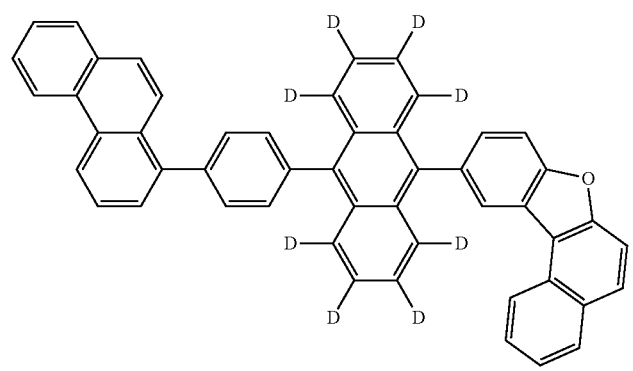
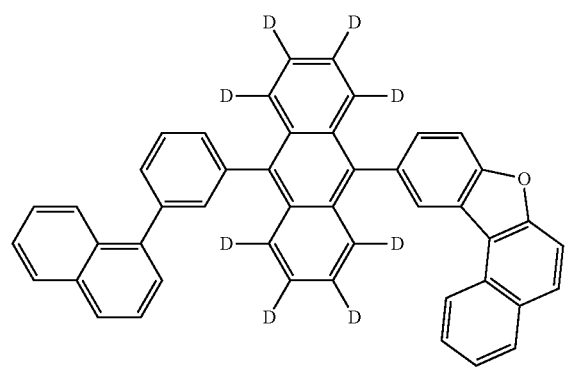

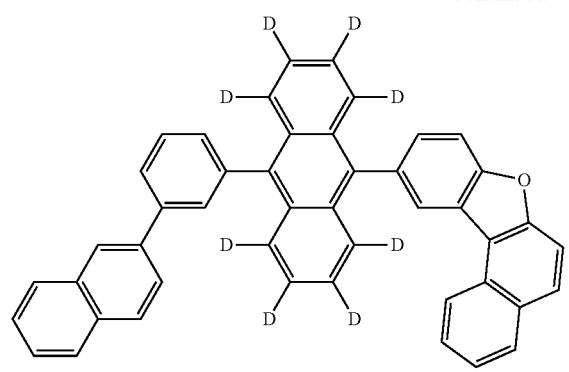
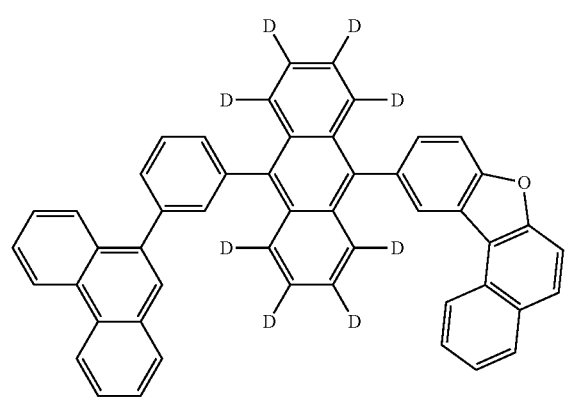
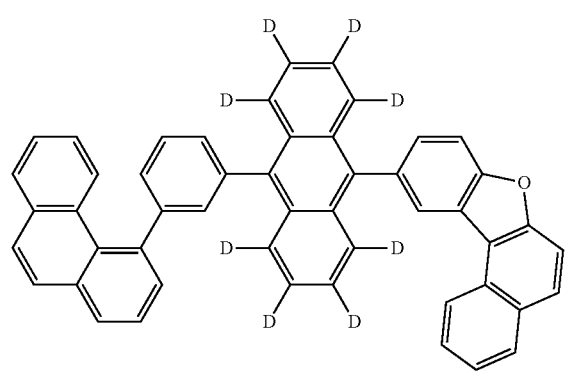
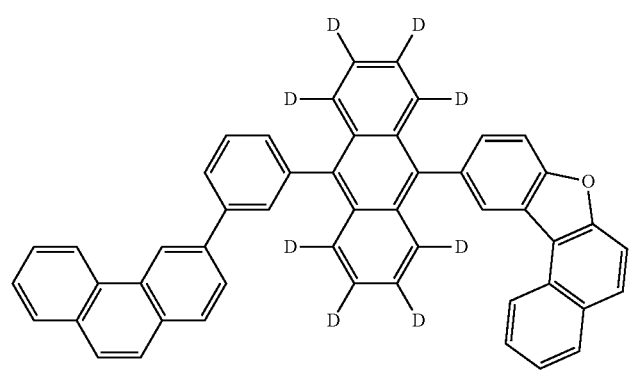

-continued
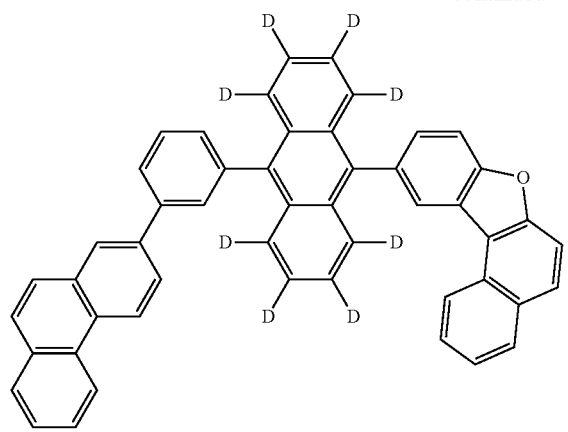
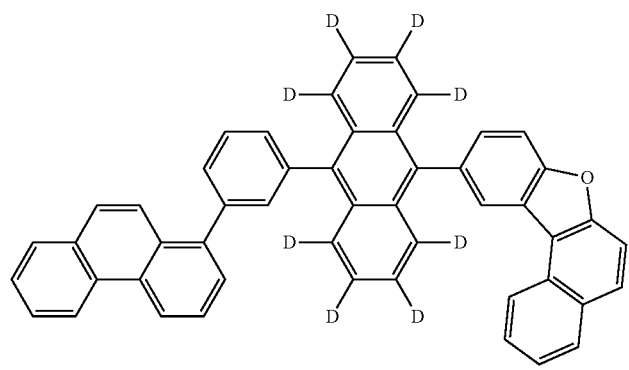
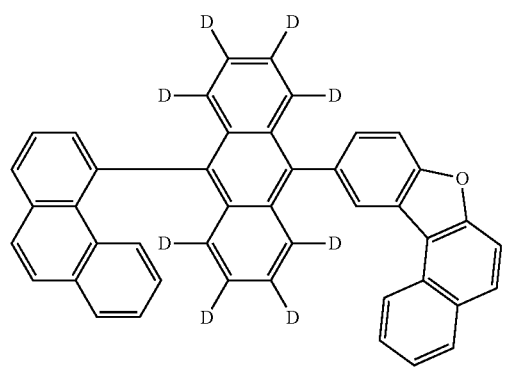
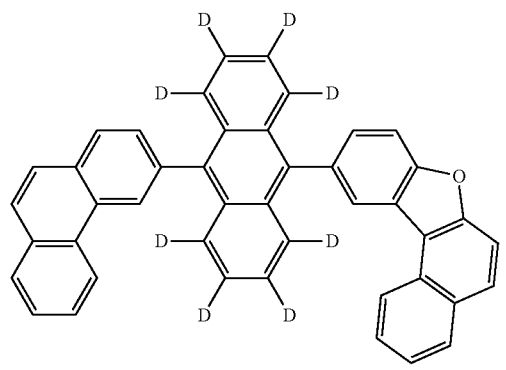

347
348
-continued
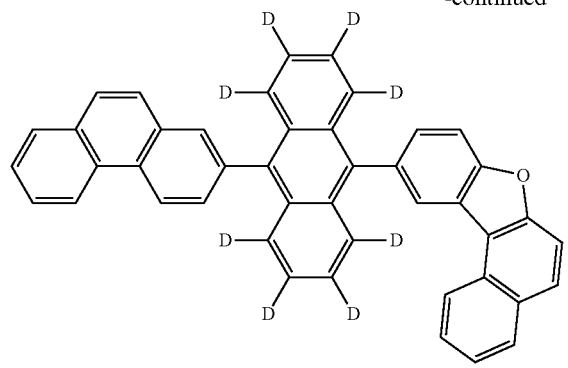
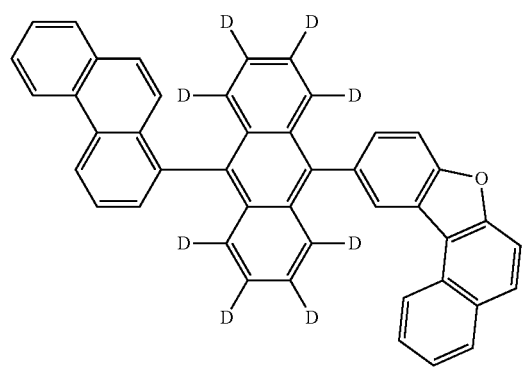
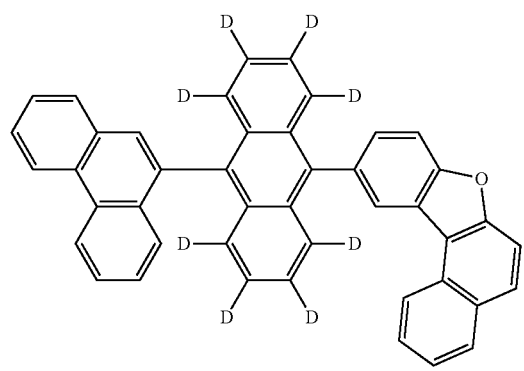
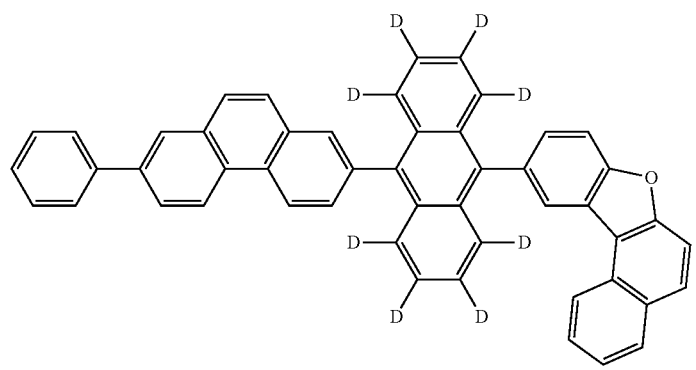

-continued
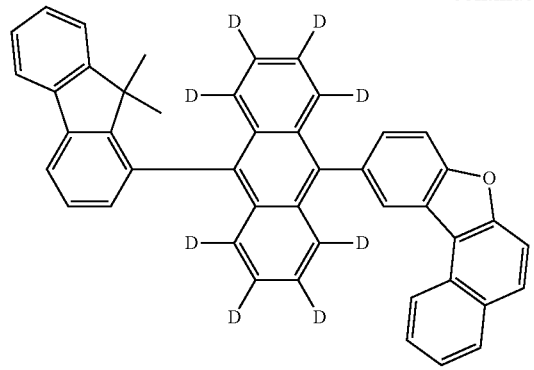
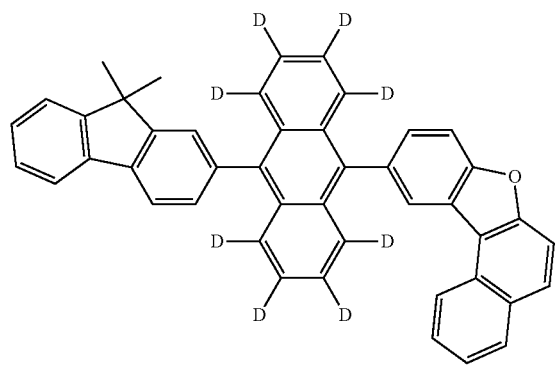
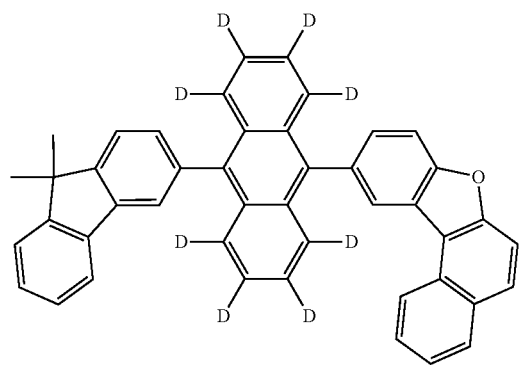
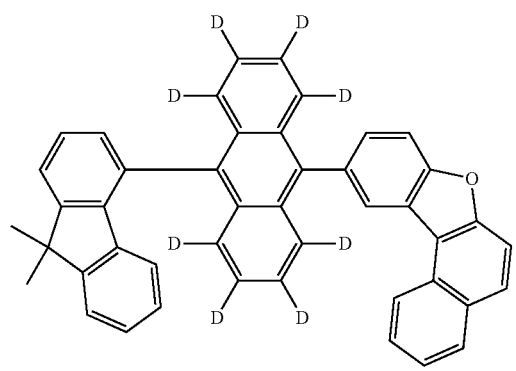

-continued
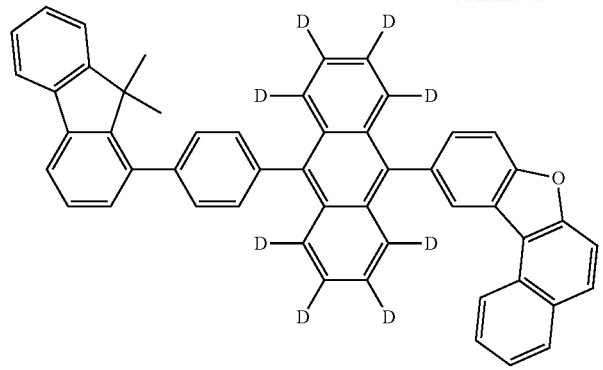
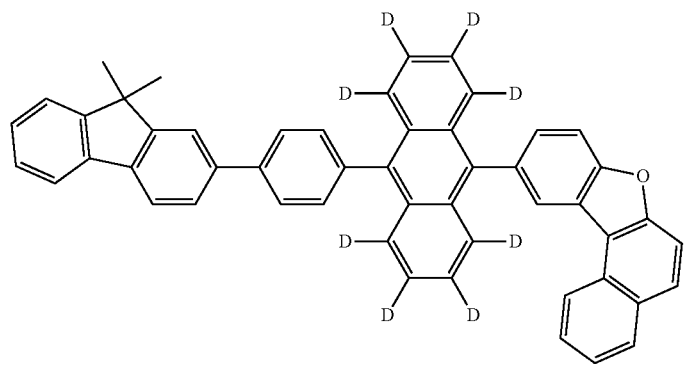
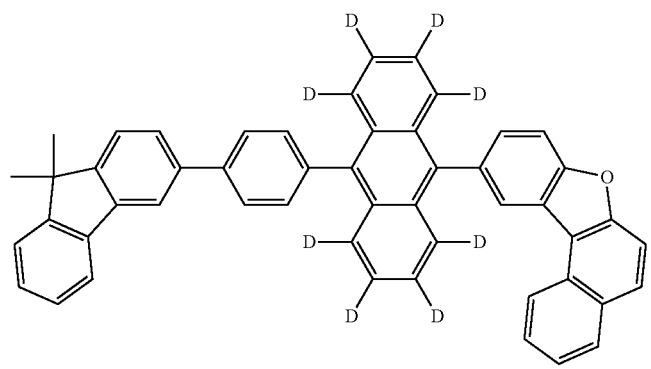
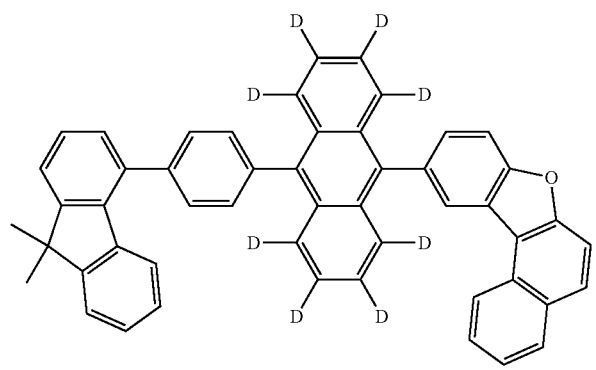

-continued
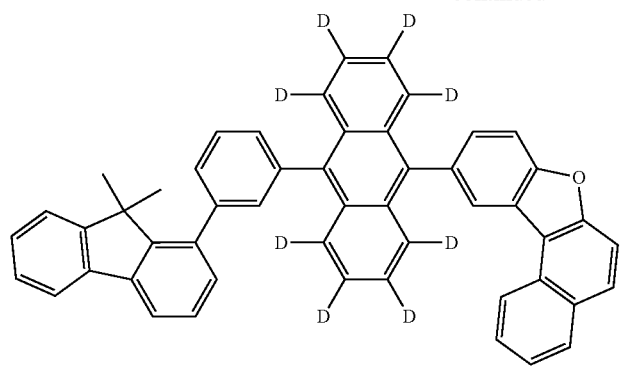
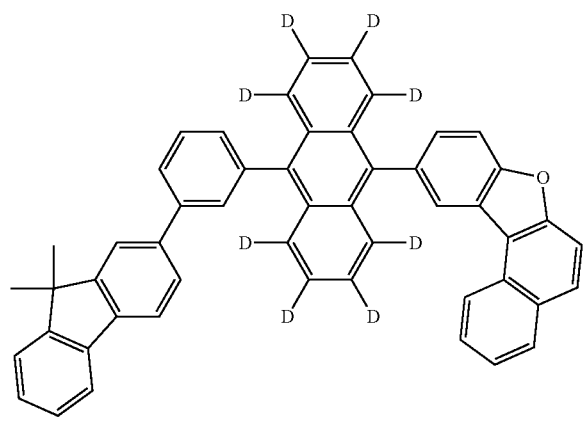
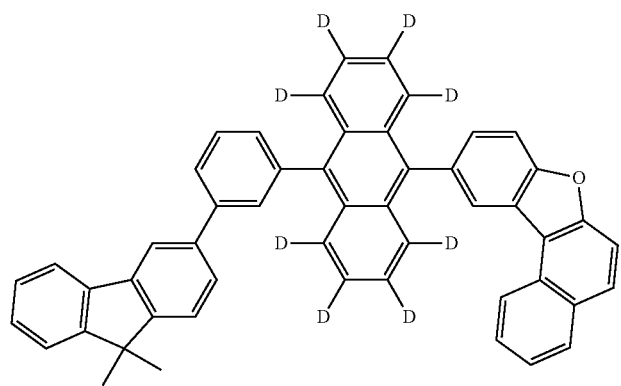
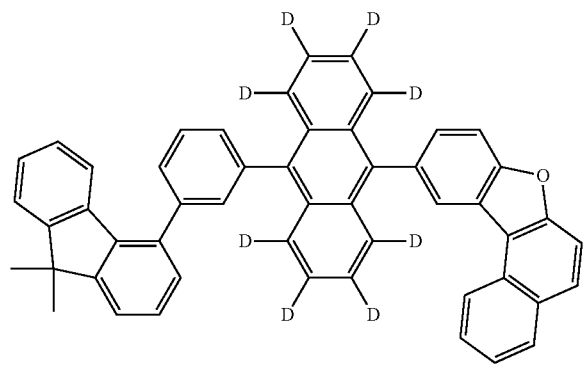

-continued
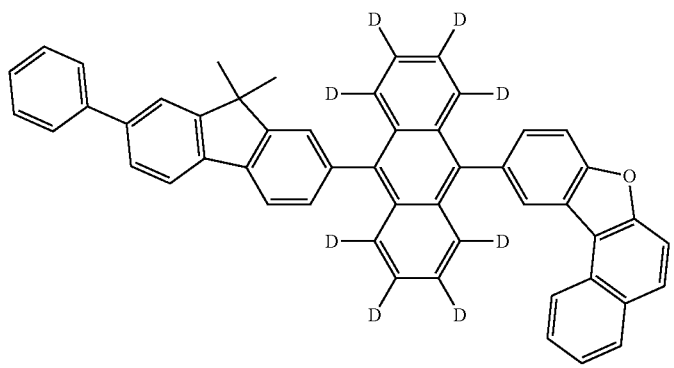
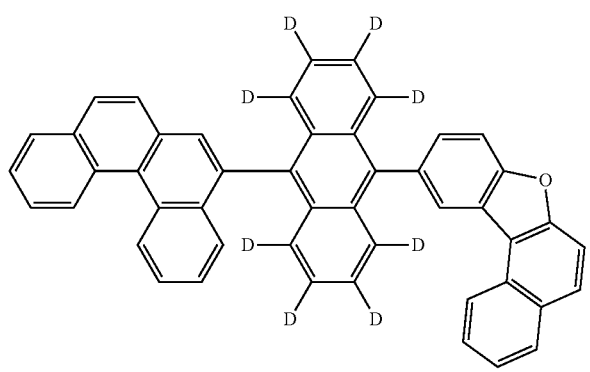
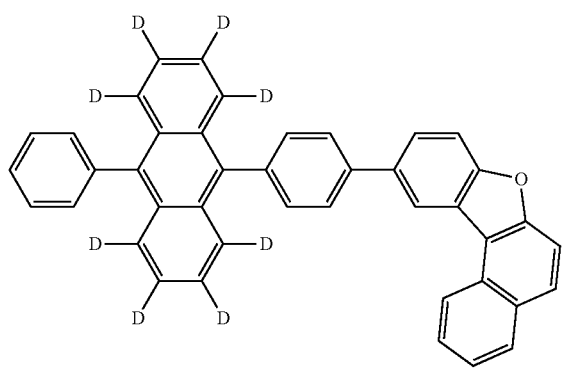
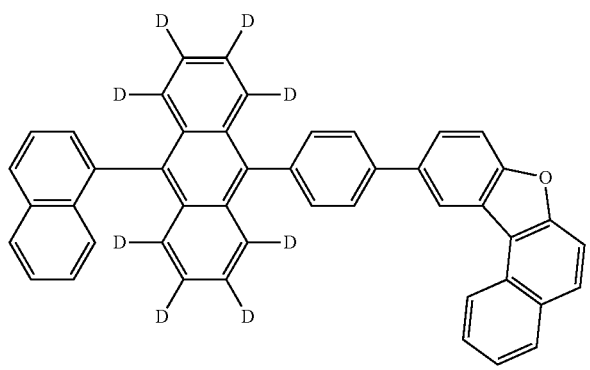

-continued
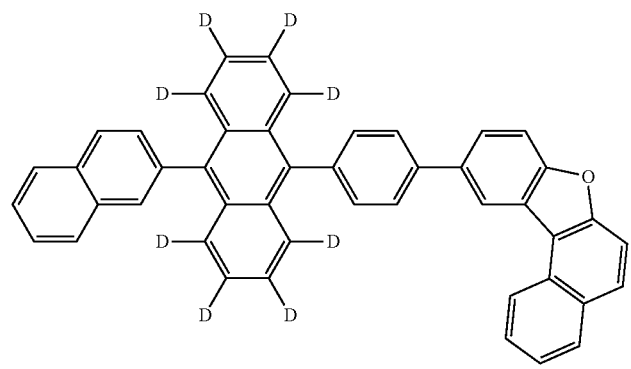

-continued
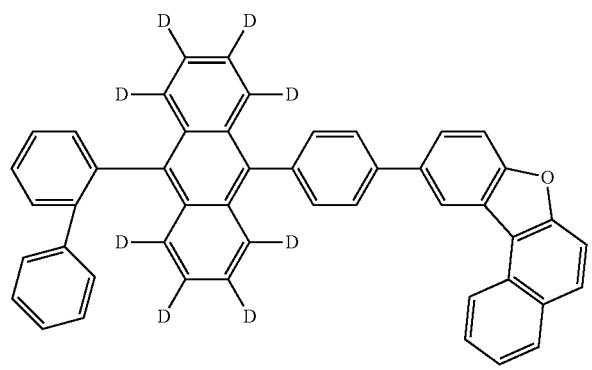
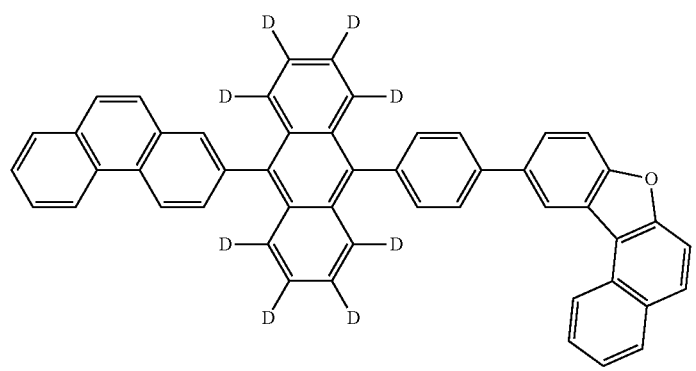
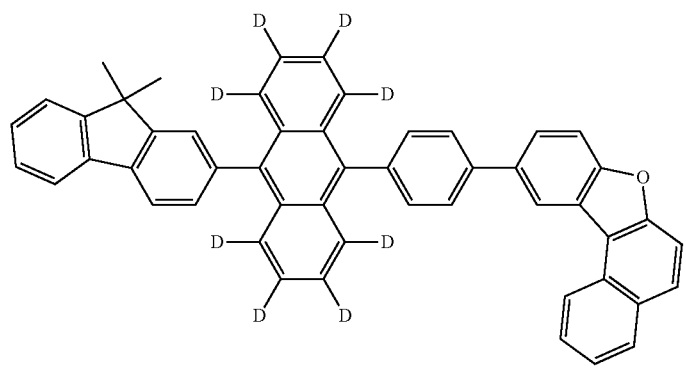
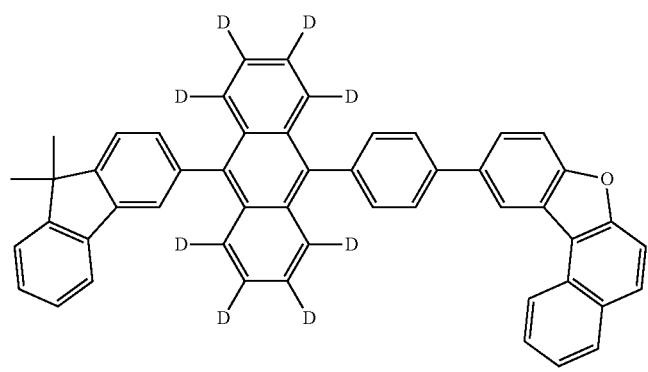

-continued
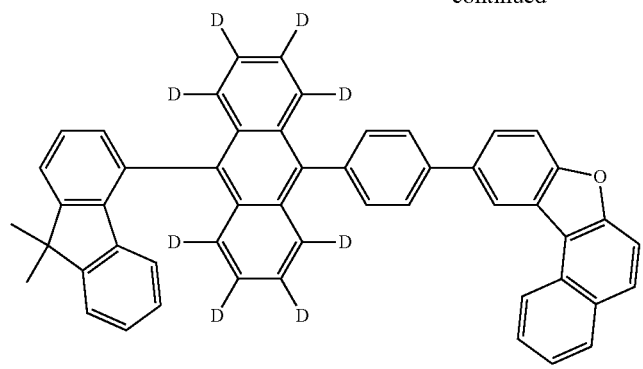
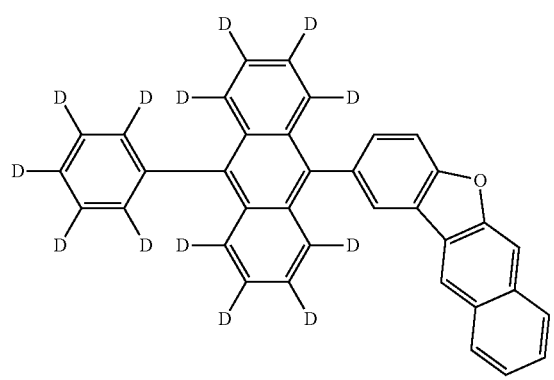
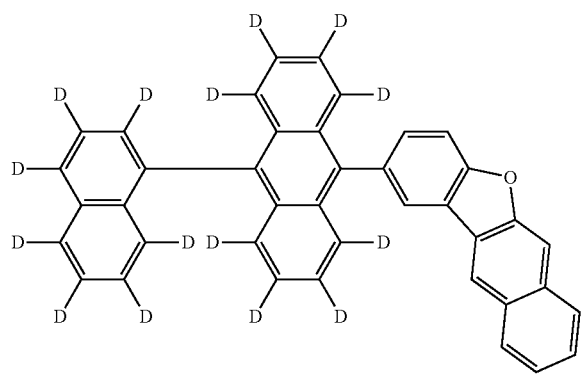
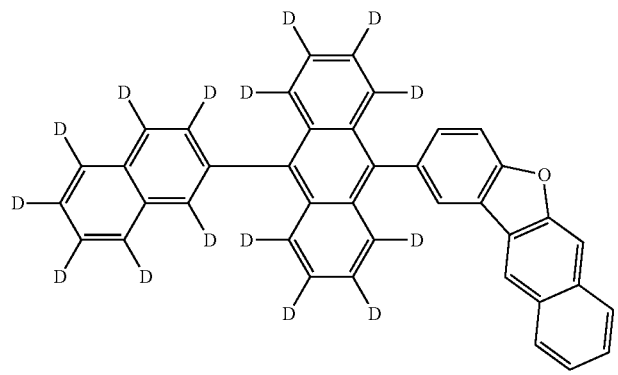

-continued
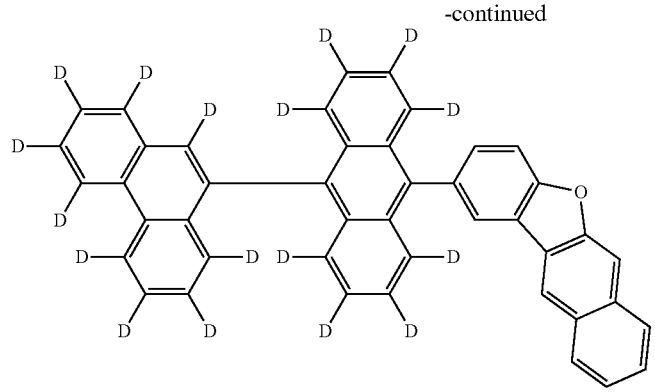
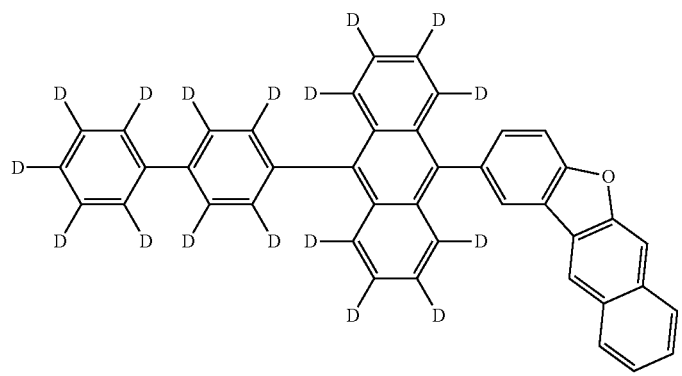
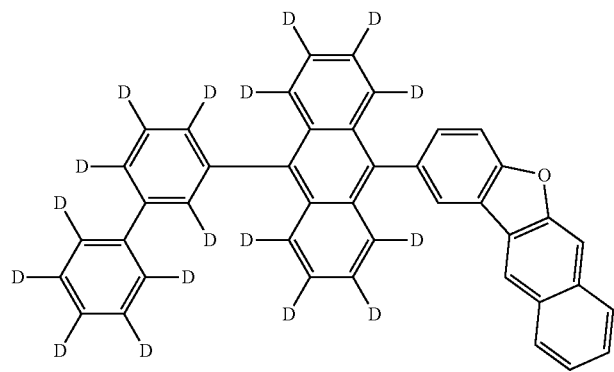
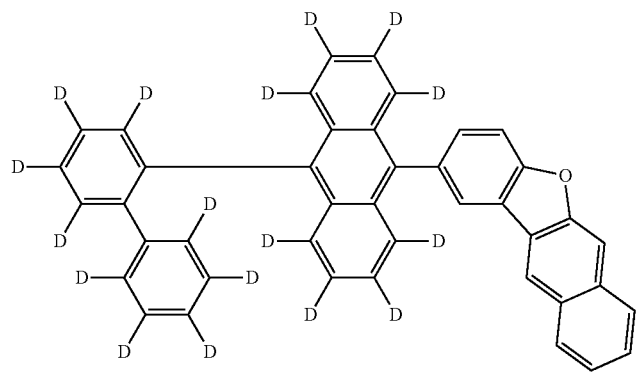

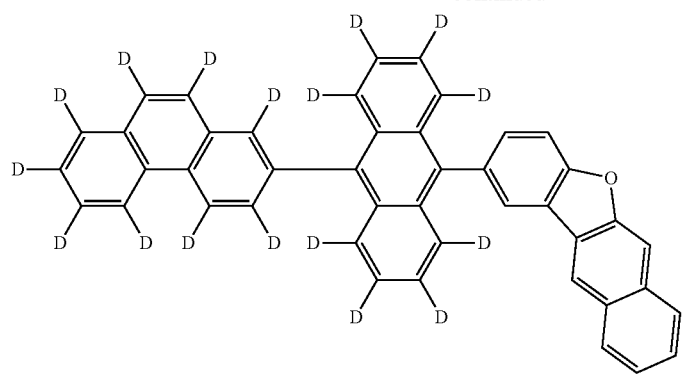
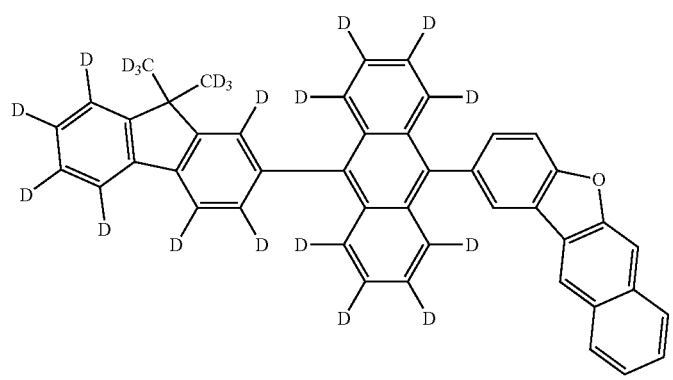
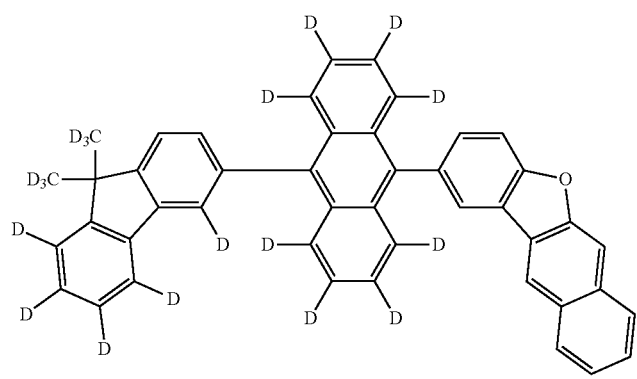
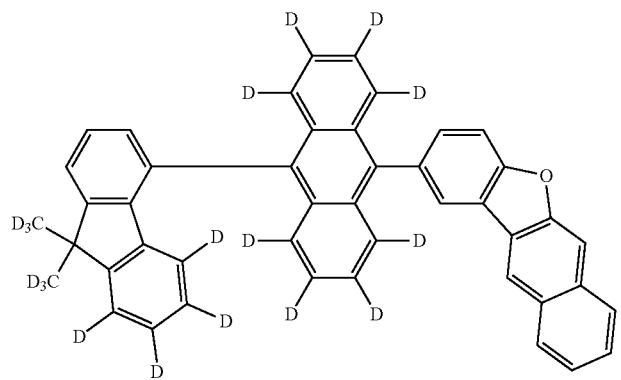

-continued
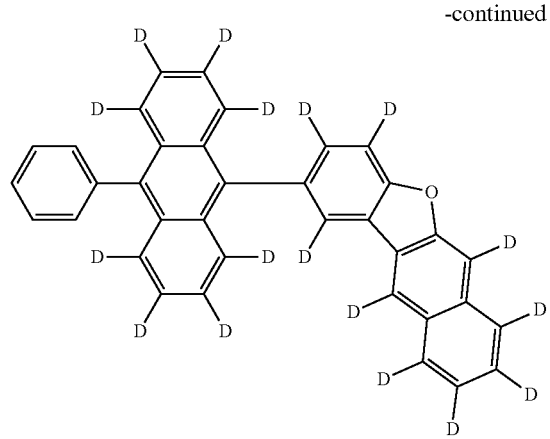
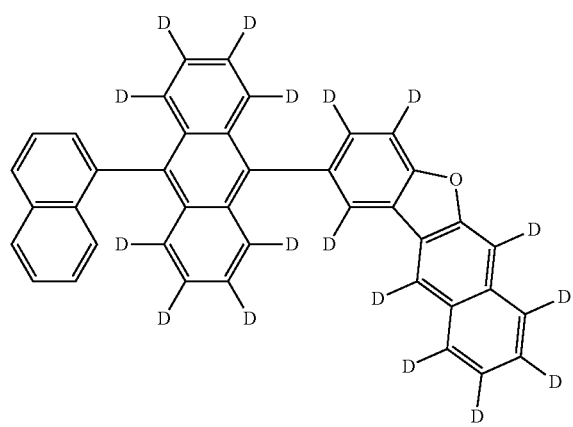
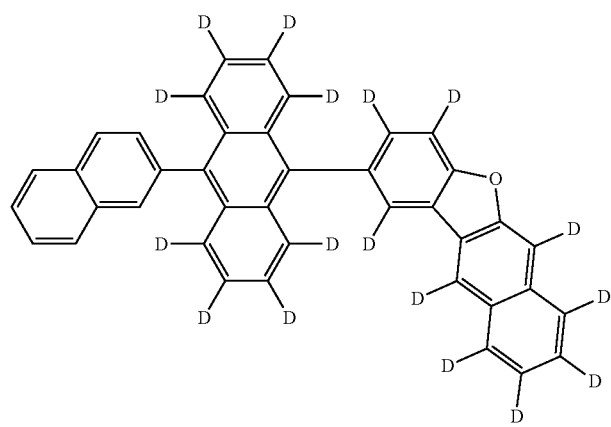
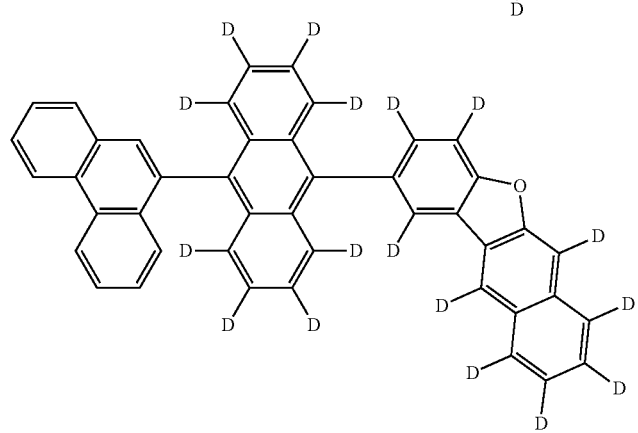

-continued
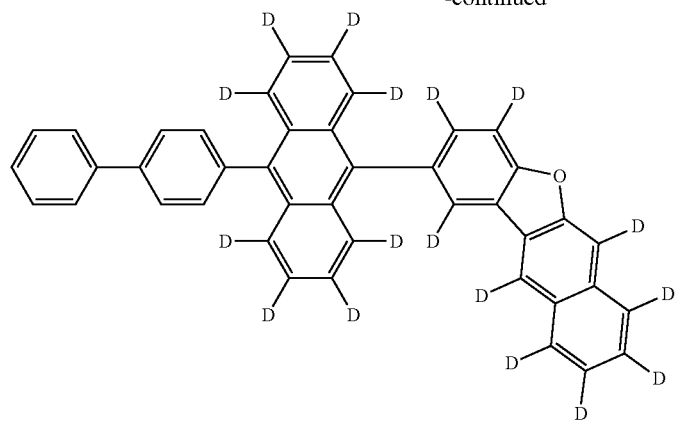
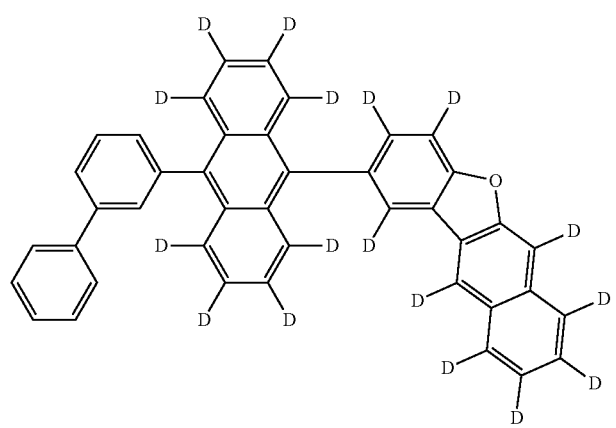
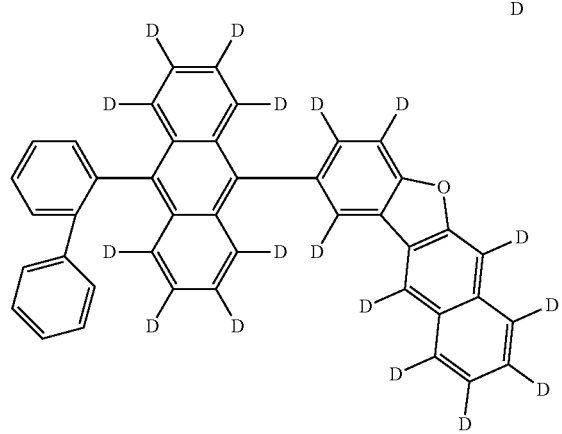
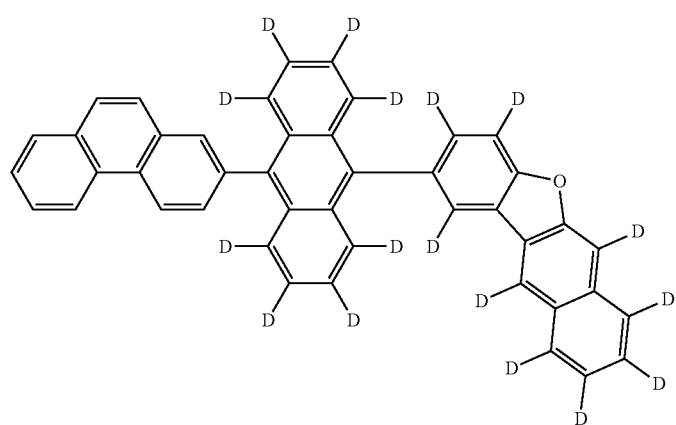

371
372
-continued
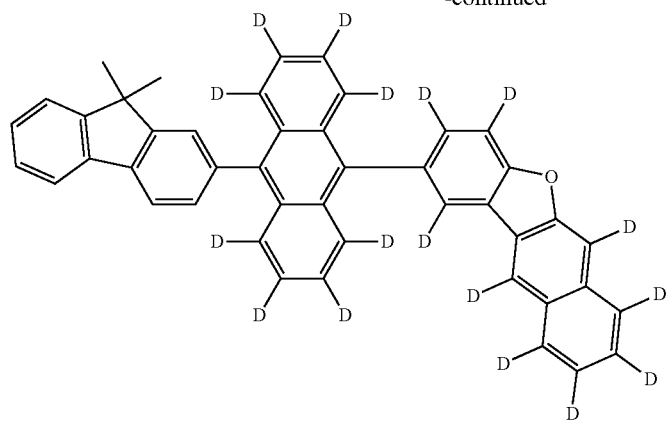
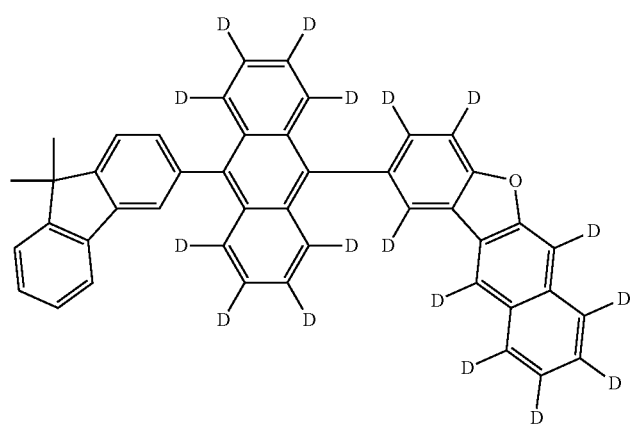
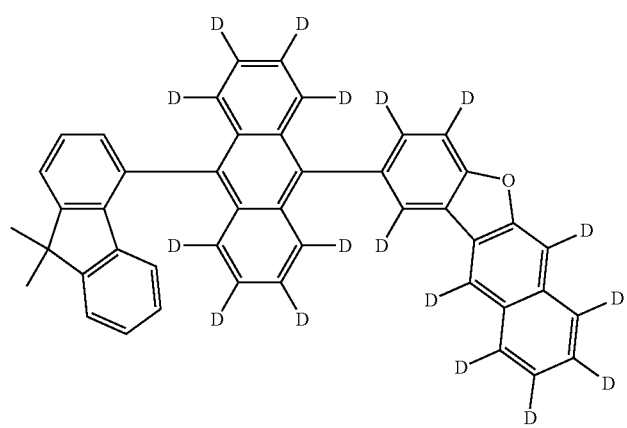
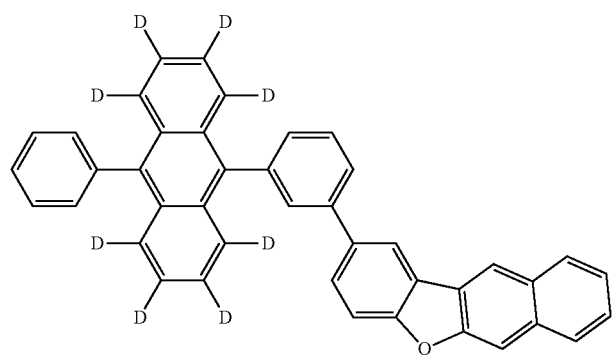

-continued
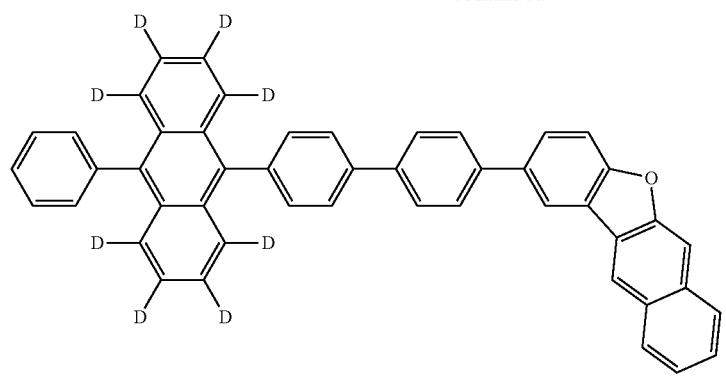
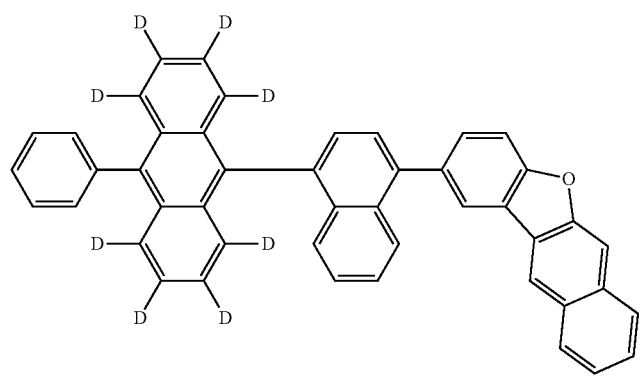
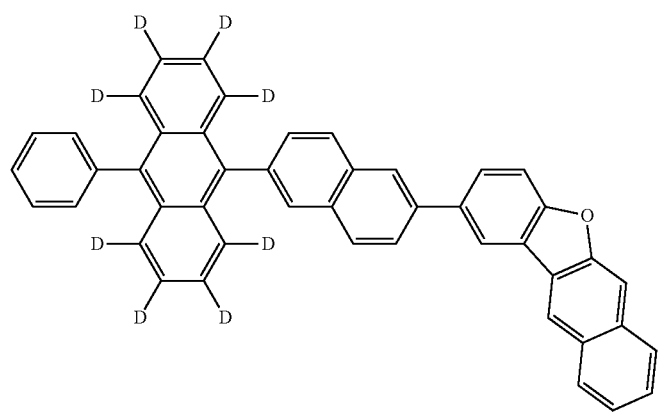
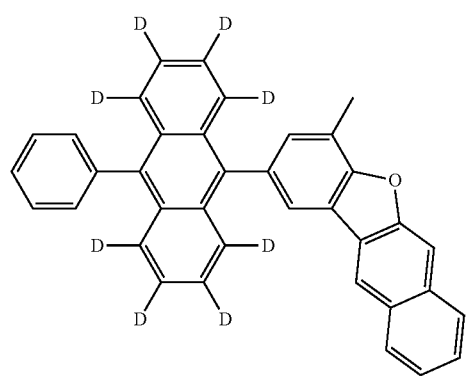

-continued
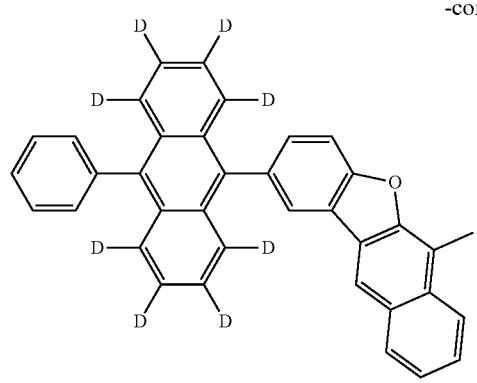
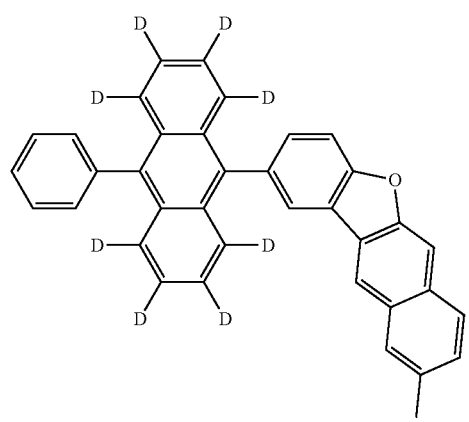
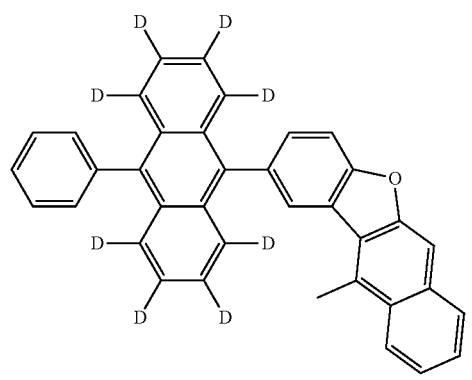
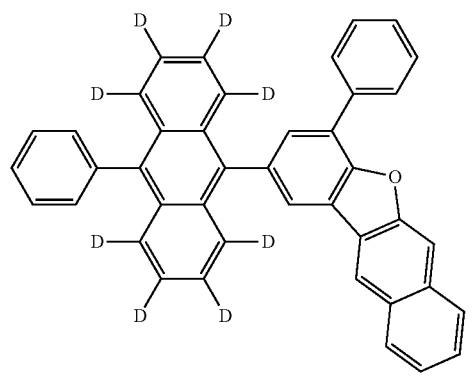

-continued
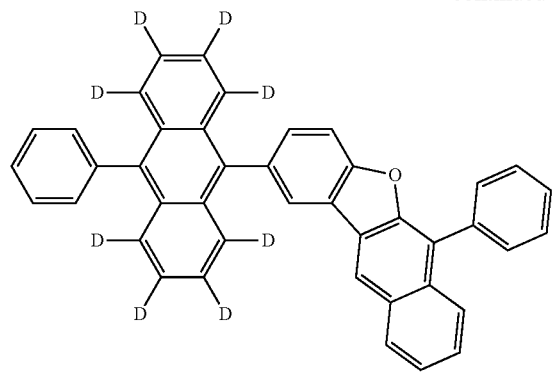
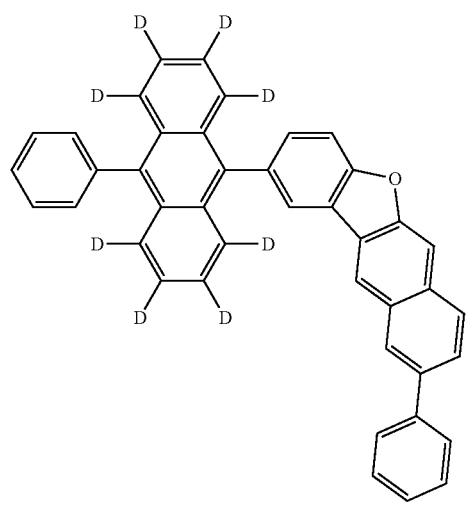
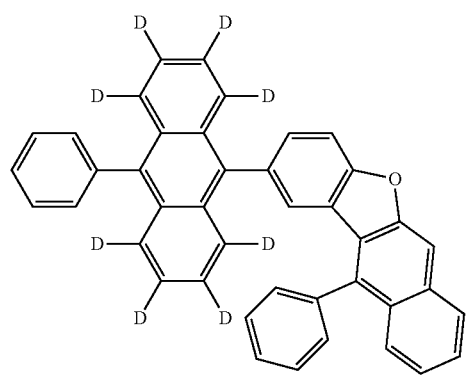
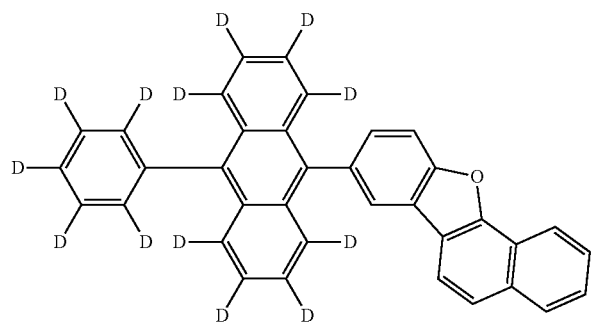

-continued
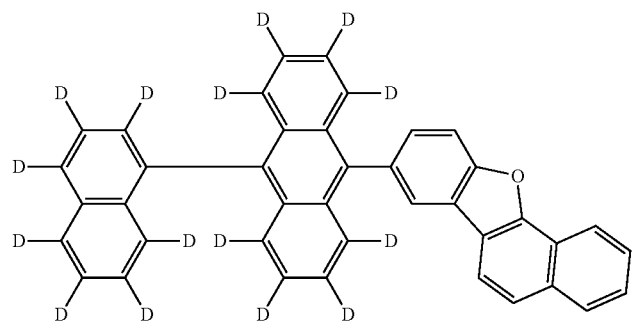
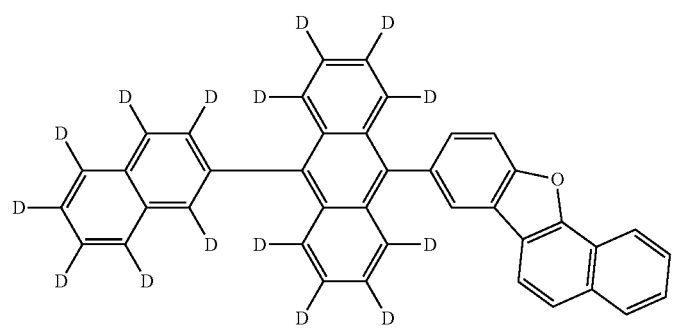
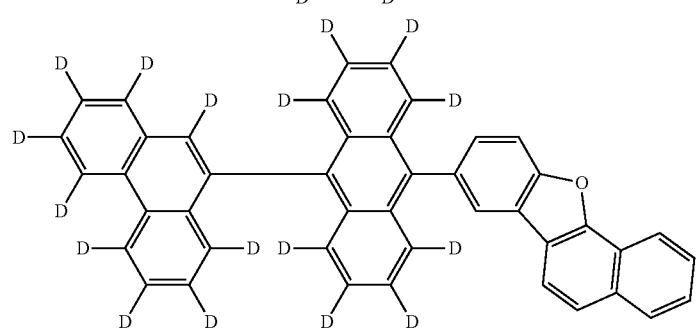
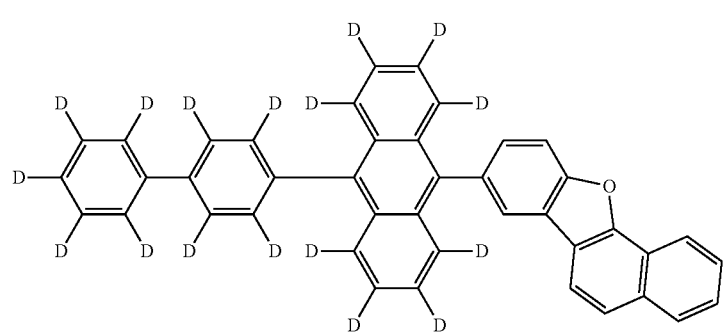
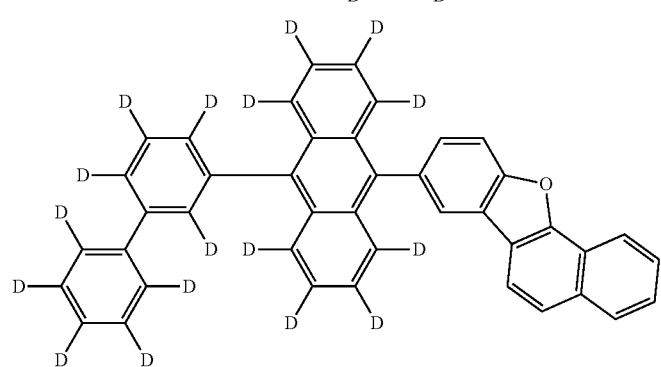

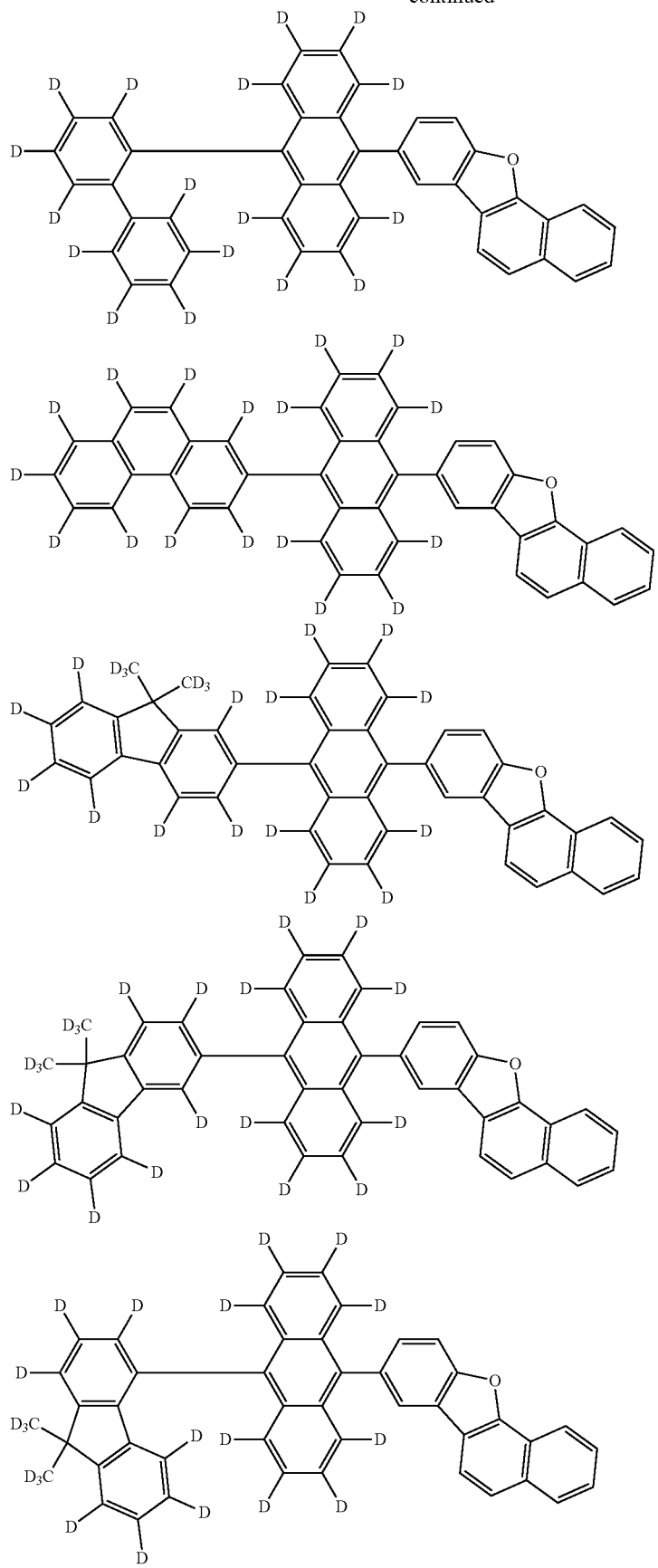

-continued
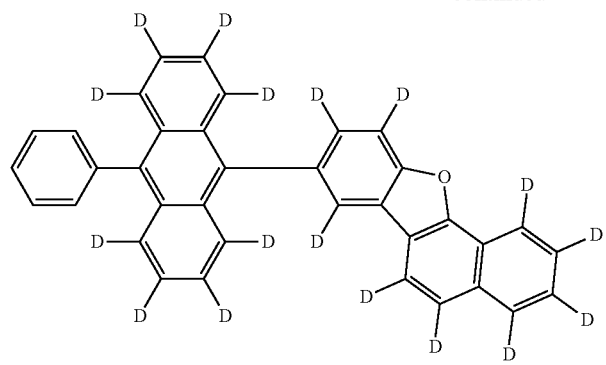
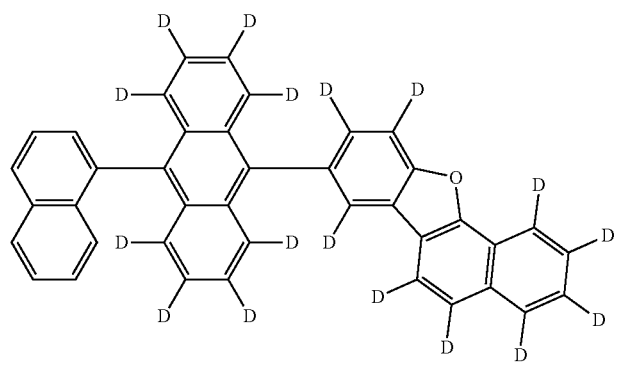
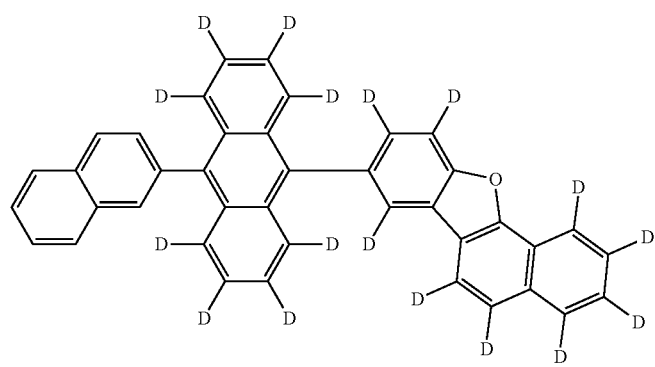
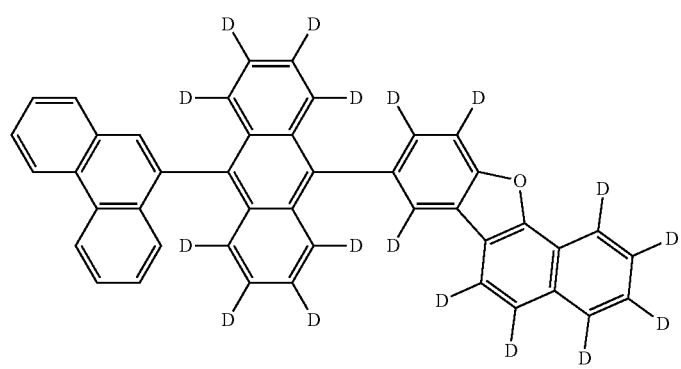

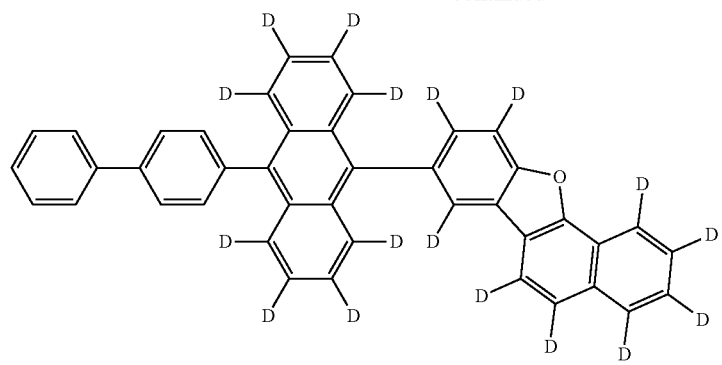
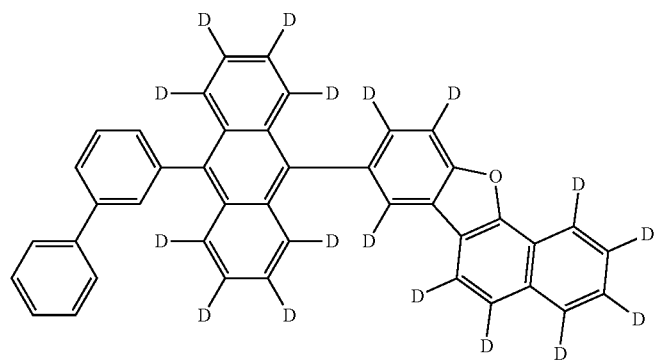
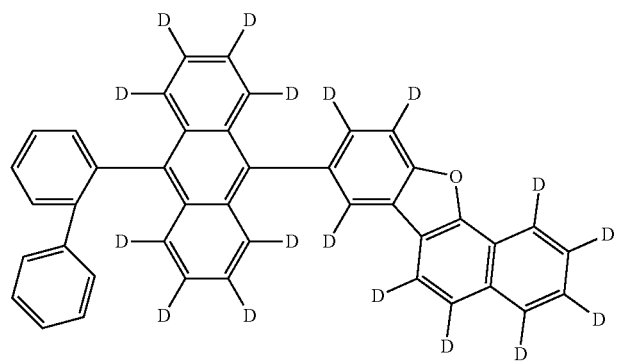
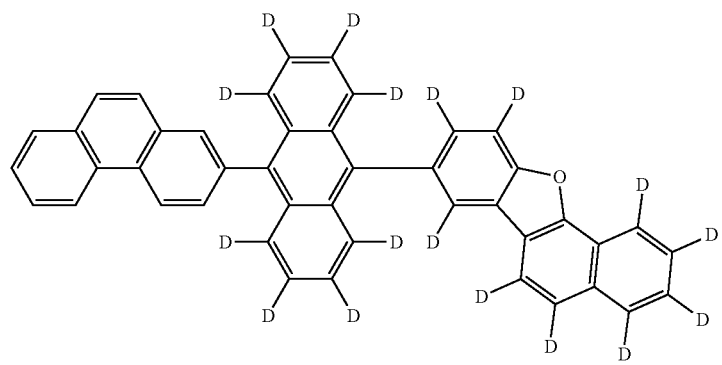

-continued
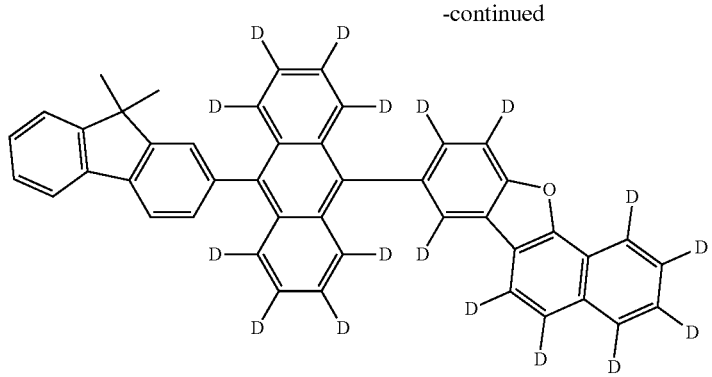
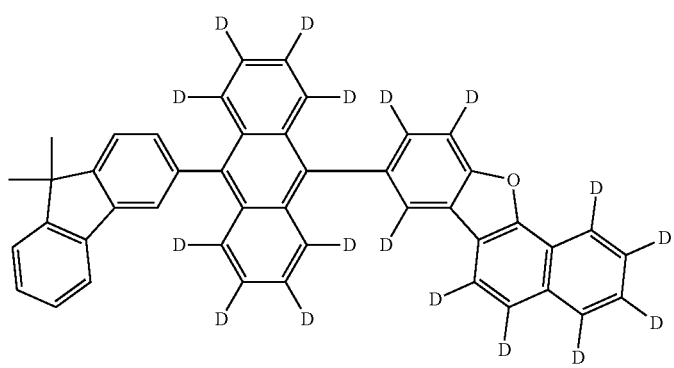
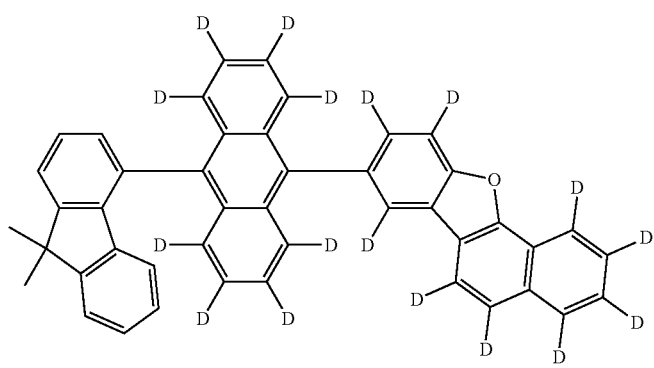
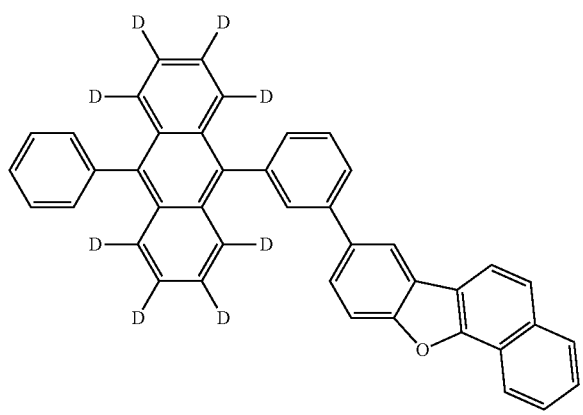

-continued
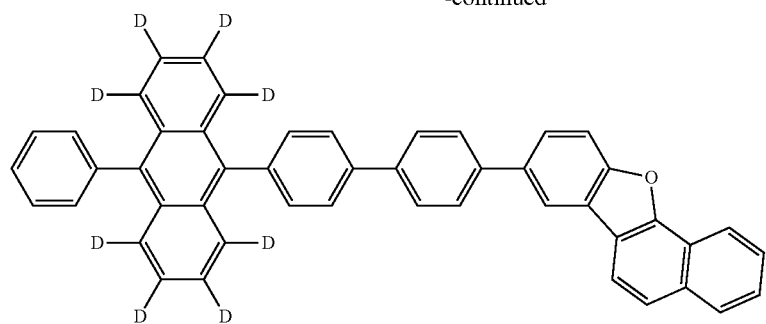
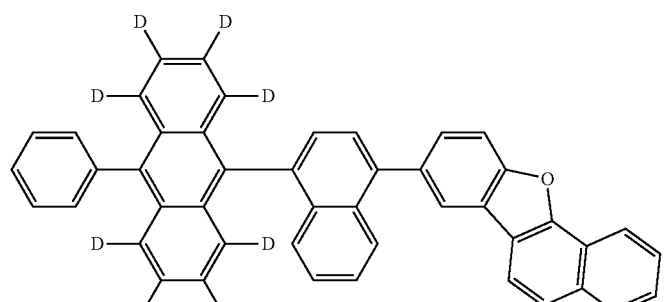
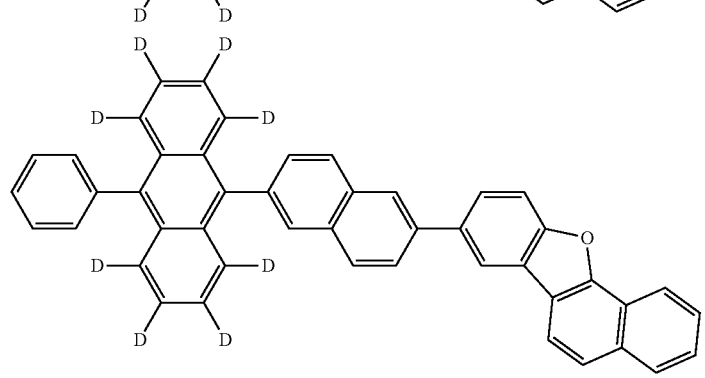
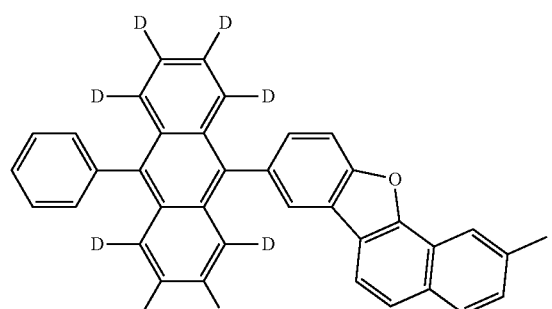
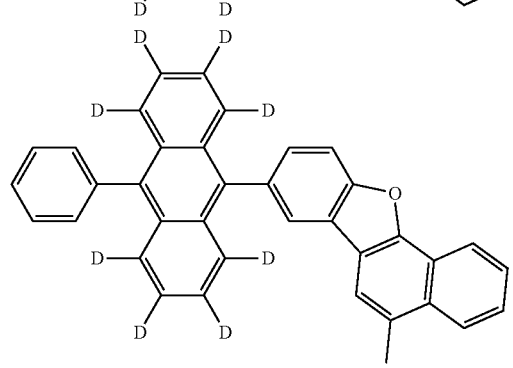

-continued
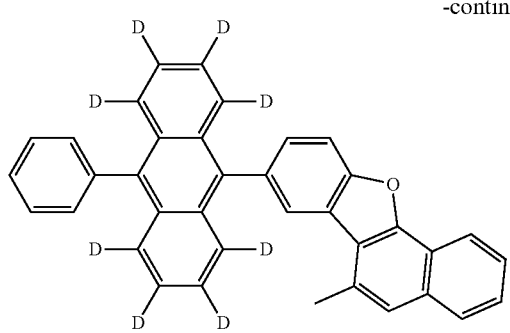
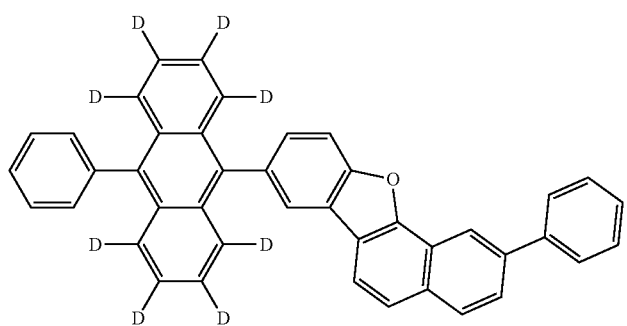
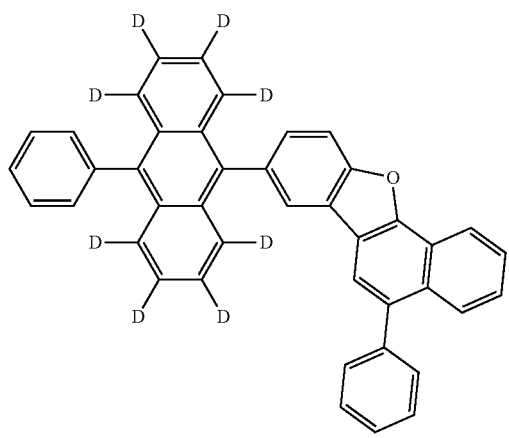
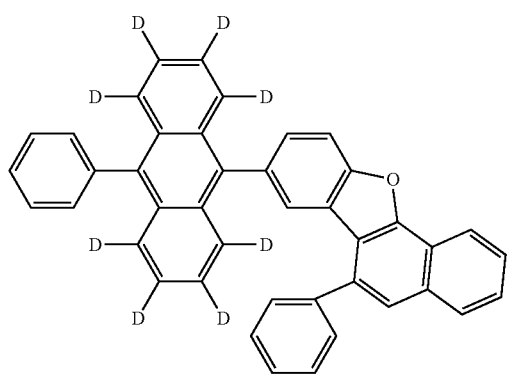

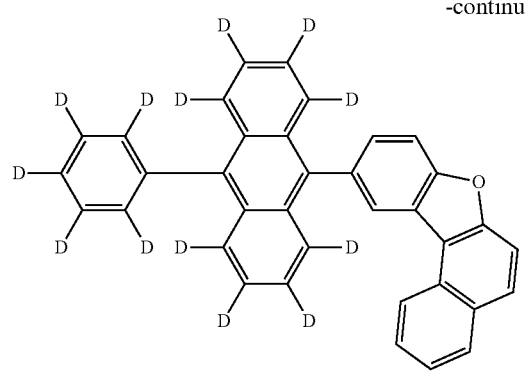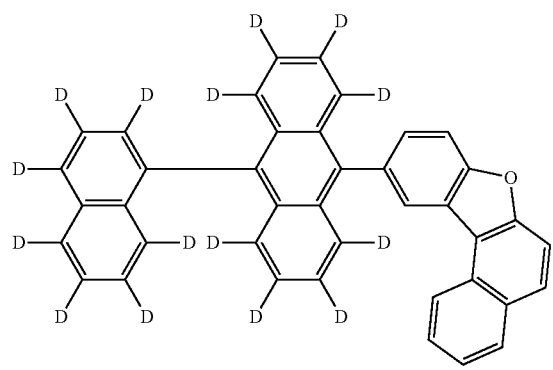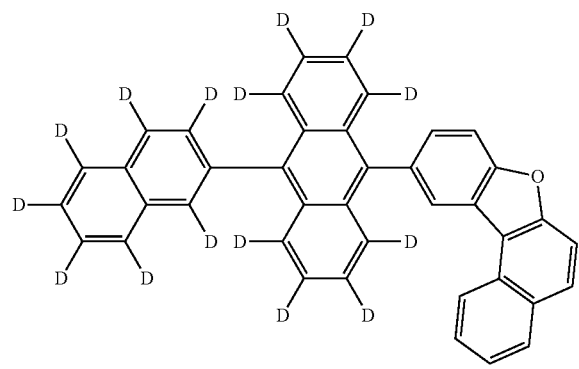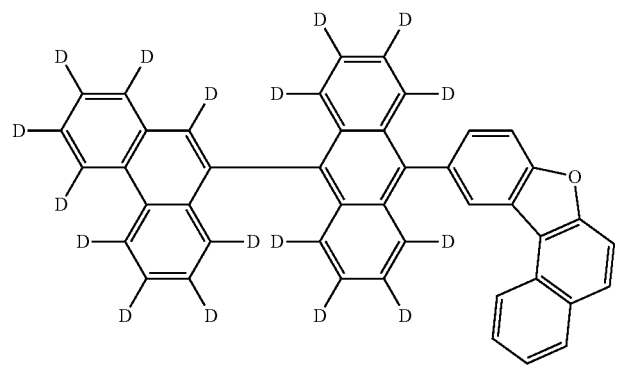

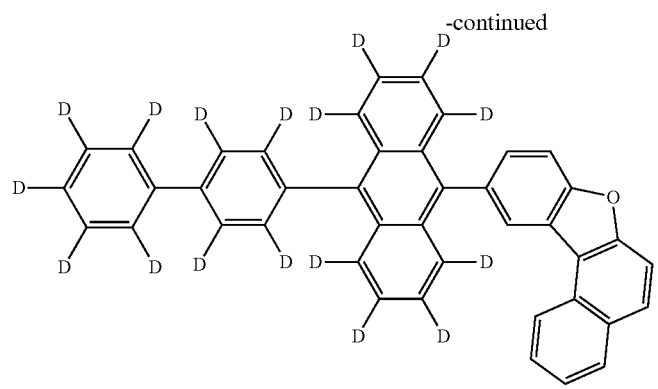

-continued
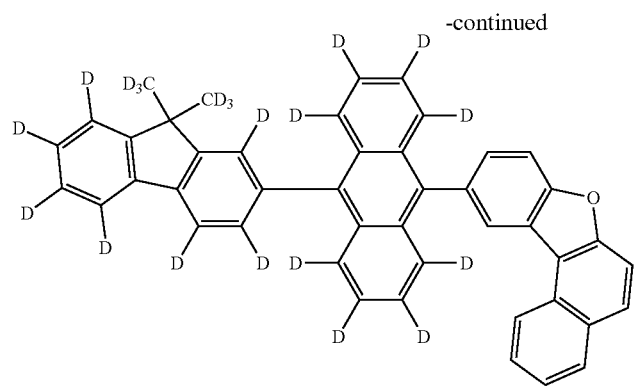
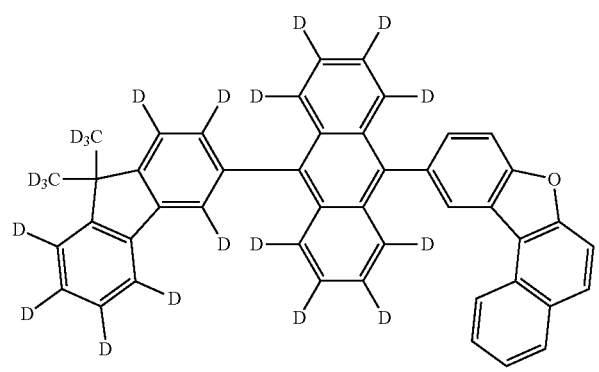
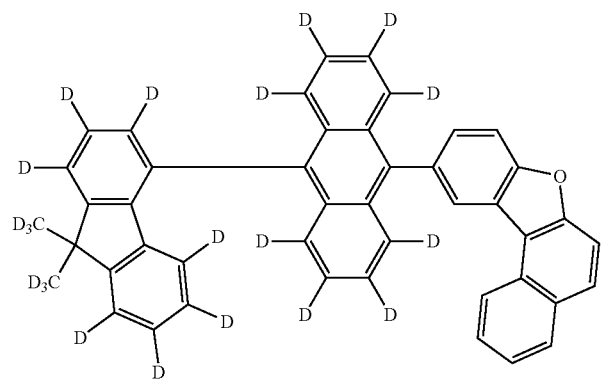
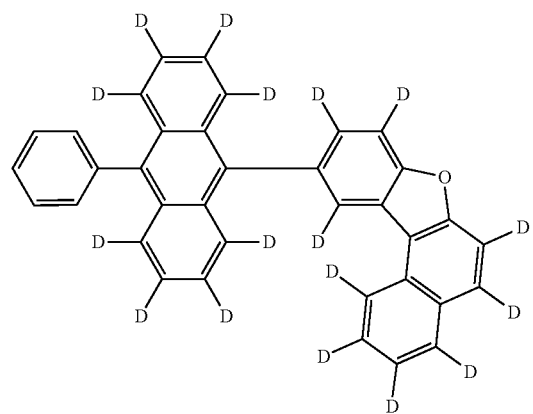

-continued
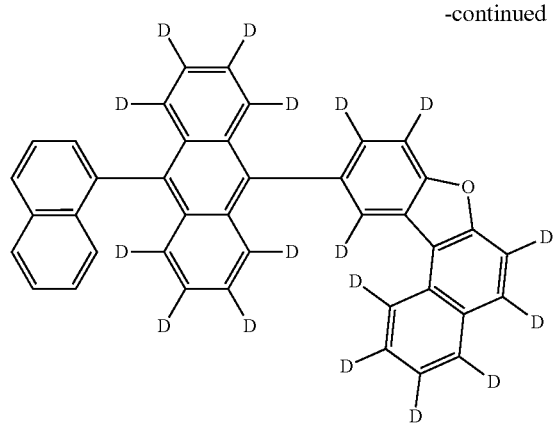
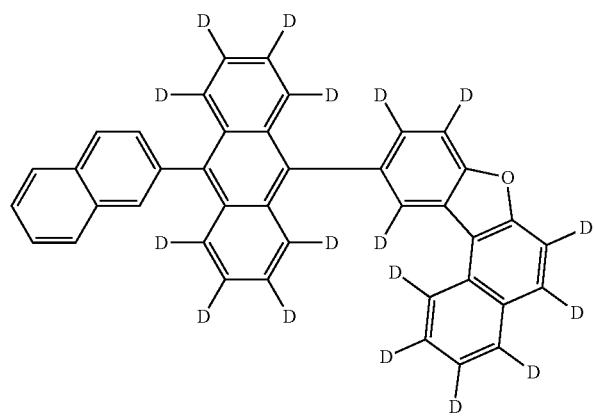
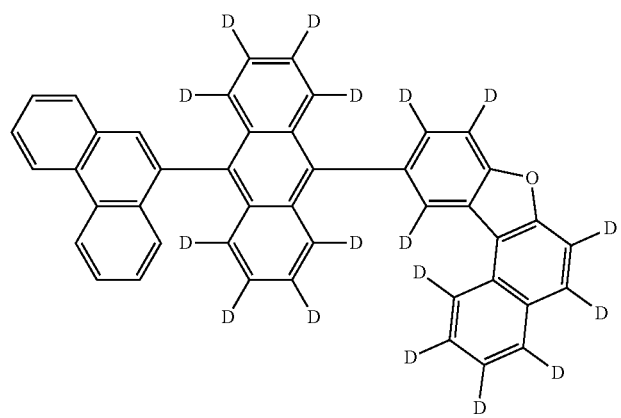
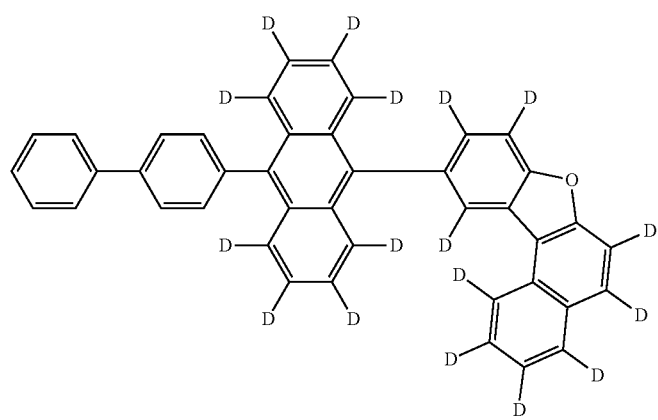

-continued
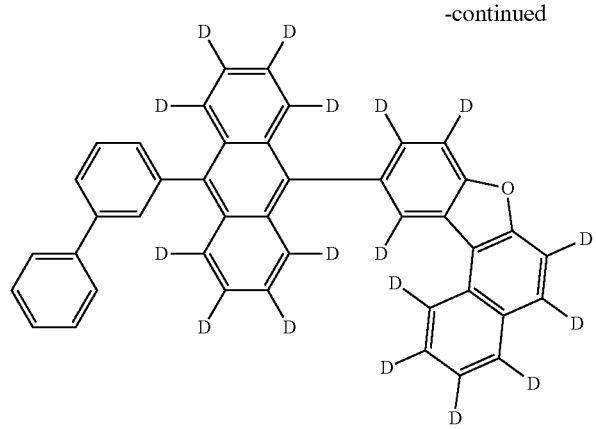
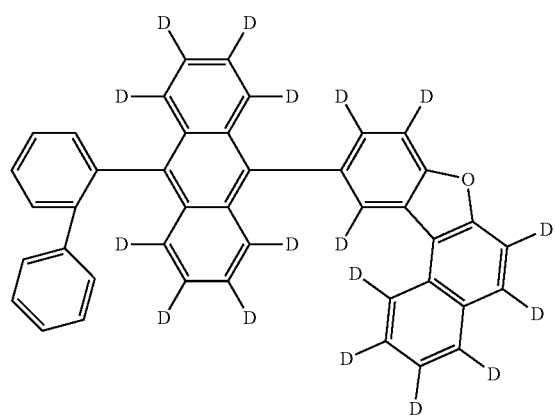
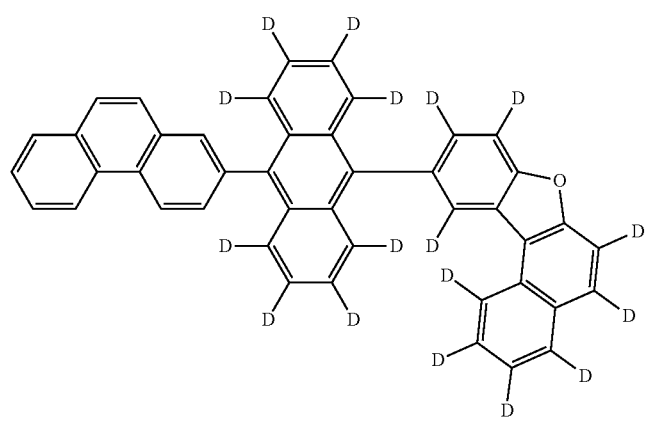
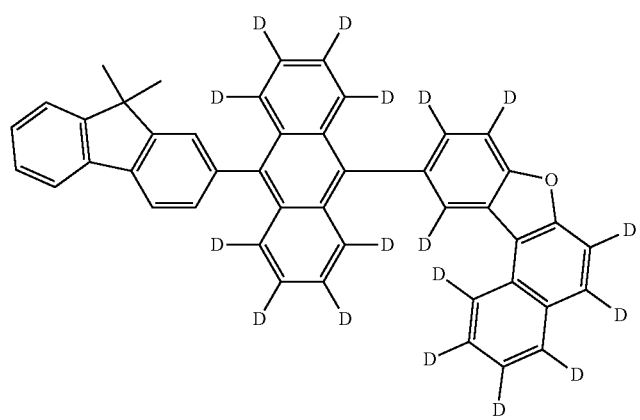

403
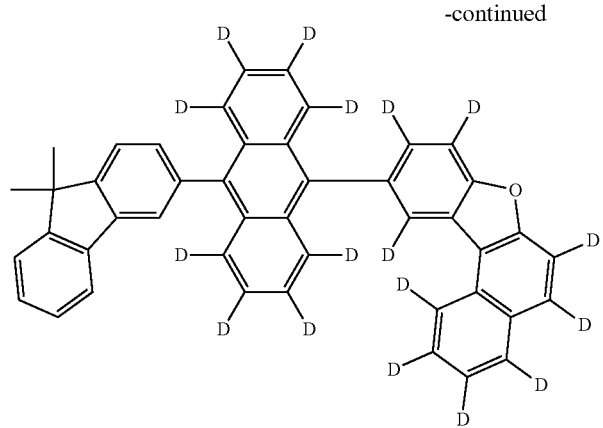
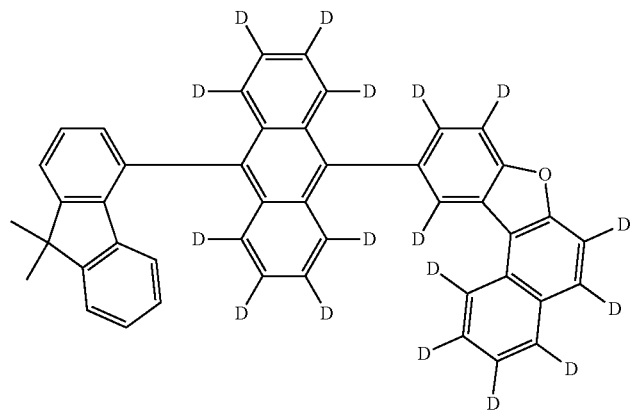
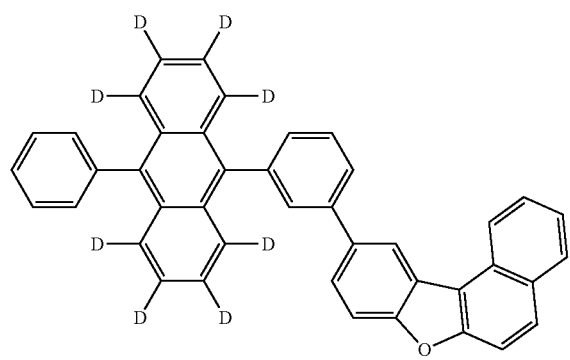
404
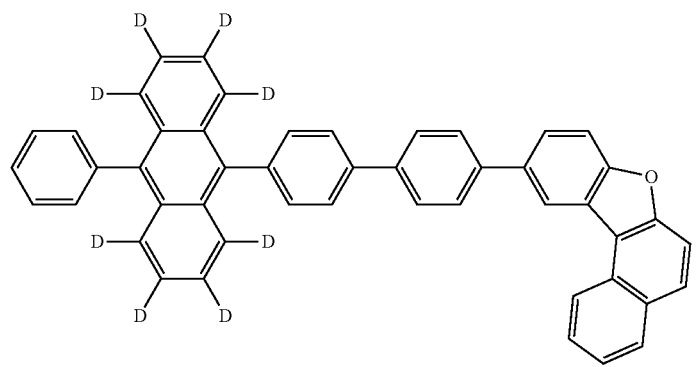

-continued
405
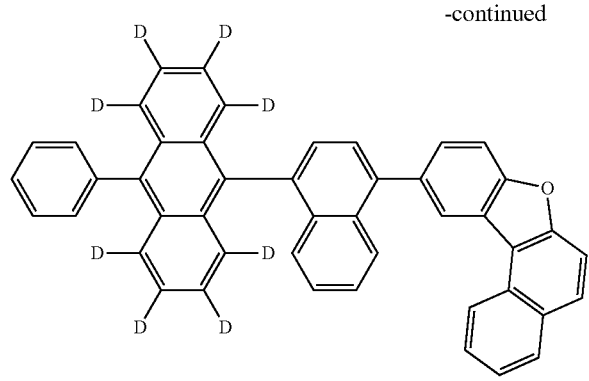
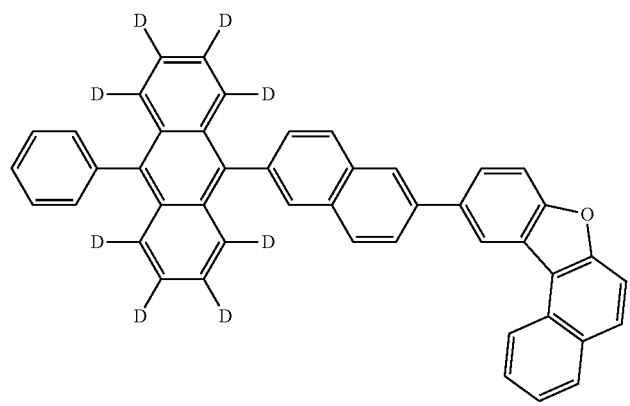
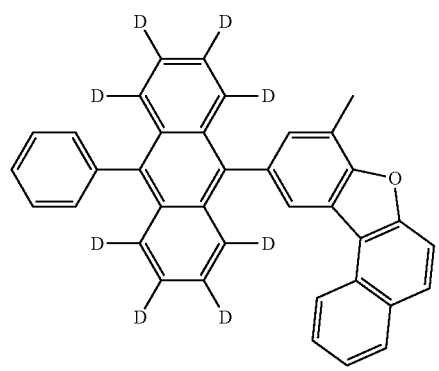
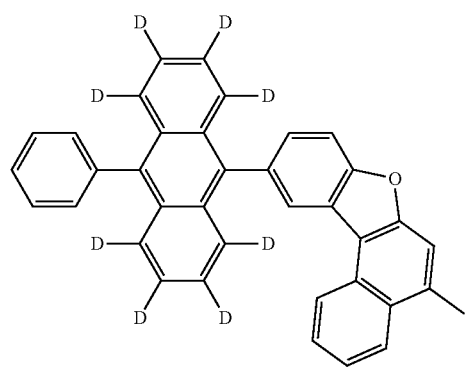
406

-continued
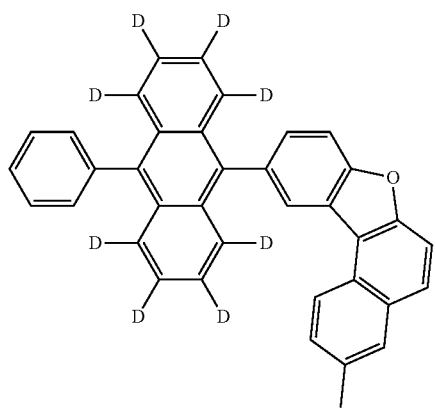
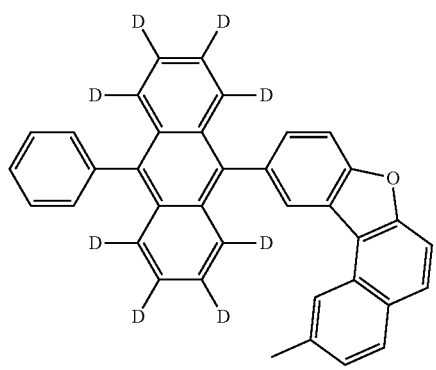
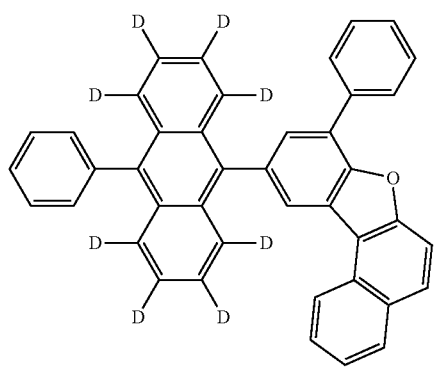
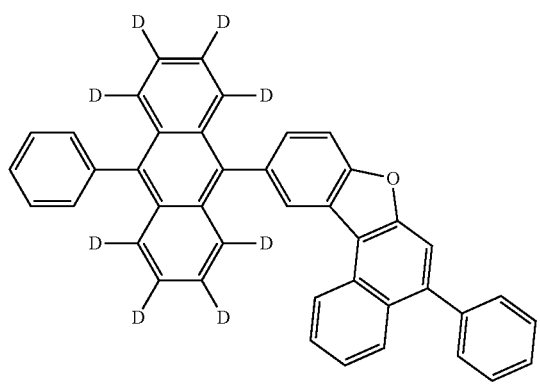

-continued

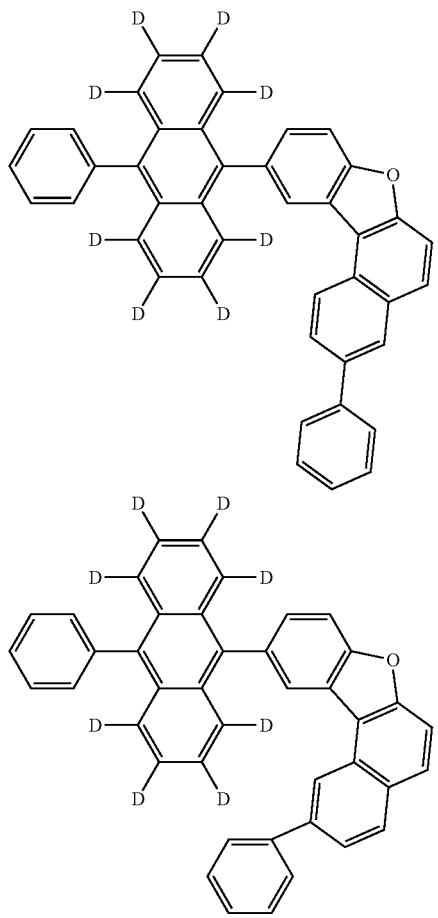

(Compound Represented by Formula (11))

The compound represented by the formula (11) is explained below.

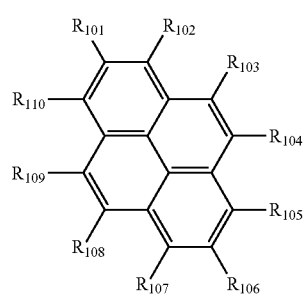

In the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{101}$ to $R_{110}$ is a monovalent group represented by the formula (12);

$R_{101}$ to $R_{110}$ that do not form the substituted or unsubstituted, saturated or unsaturated ring and that are not a monovalent group represented by the following formula (12) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

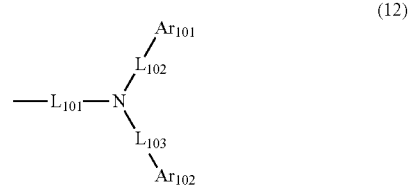

wherein, in the formula (12), $Ar_{101}1$ and $Ar_{102}$ are independently a substituted or unsubstituted aryl group having 6 to 50 ring carbon atoms, or a substituted or unsubstituted monovalent heterocyclic group having 5 to 50 ring atoms;

$L_{101}$ to $L_{103}$ are independently a single bonded, a substituted or unsubstituted arylene group having 6 to 30 ring carbon atoms, or a substituted or unsubstituted divalent heterocyclic group having 5 to 30 ring atoms;

In the formula (11), it is preferable that two of $R_{101}$ to $R_{110}$ are the group represented by the formula (12).

In one embodiment, the compound represented by the formula (11) is represented by the following formula (13):

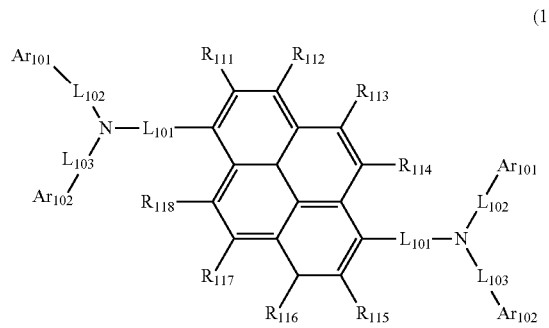

(13)

wherein in the formula (13), $R_{111}$ to $R_{118}$ are the same as $R_{101}$ to $R_{110}$ that is not a monovalent group represented by the formula (12) in the formula (11). $Ar_{101}$, $Ar_{102}$, $L_{101}$, $L_{102}$ and $L_{103}$ are as defined in the formula (12).

In the formula (11), $L_{101}$ is preferably a single bond and $L_{102}$ and $L_{103}$ are preferably a single bond.

In one embodiment, the compound represented by the formula (11) is represented by the formula (14) or (15).

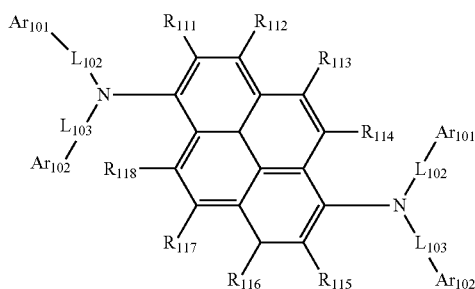

(14)

wherein in the formula (14), $R_{111}$ to $R_{110}$ are as defined in the formula (13). $Ar_{101}$, $Ar_{102}$, $L_{102}$ and $L_{103}$ are as defined in the formula (12).

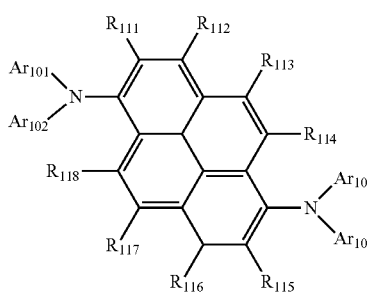

(15)

wherein in the formula (15), $R_{111}$ to $R_{118}$ are as defined in the formula (13). $Ar_{101}1$ and $Ar_{102}$ are as defined in the formula (12).

In the formula (11) (formula (12)), it is preferable that at least one of $Ar_{101}1$ and $Ar_{102}$ is the group represented by the following formula (16).

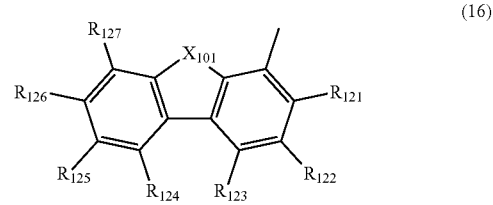

(16)

wherein in the formula (16), $X_{101}$ is an oxygen atom or a sulfur atom;

One or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring:

$R_{121}$ to $R_{127}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

It is preferable that $X_{101}$ is an oxygen atom.

It is preferable that at least one of $R_{121}$ to $R_{127}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

It is preferable that in the formula (11) (formula (12), $Ar_{101}$ is a group represented by the formula (16) and $Ar_{102}$ is a substituted or unsubstituted aryl group having 6 to 50 ring carbon atoms.

In one embodiment, the compound represented by the formula (11) is represented by the following formula (17).

(17)

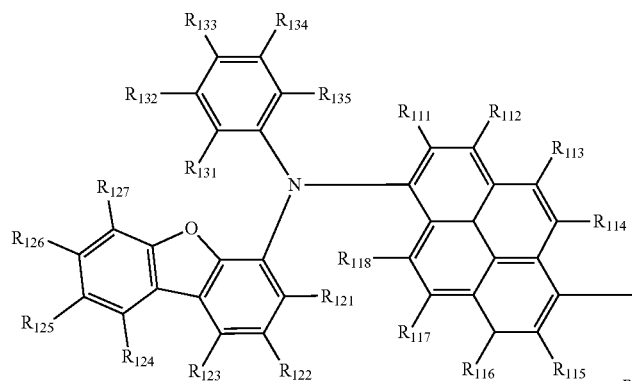

wherein in the formula (17), $R_{111}$ to $R_{118}$ are as defined in the formula (13), and $R_{121}$ to $R_{127}$ are as defined in the formula (16);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

As the compound represented by the formula (11), the following compounds can be given as specific examples, for example.

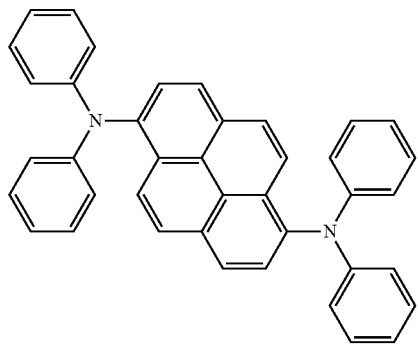

-continued

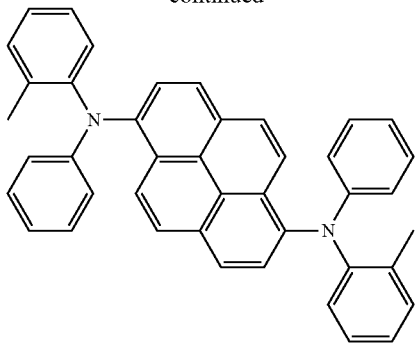

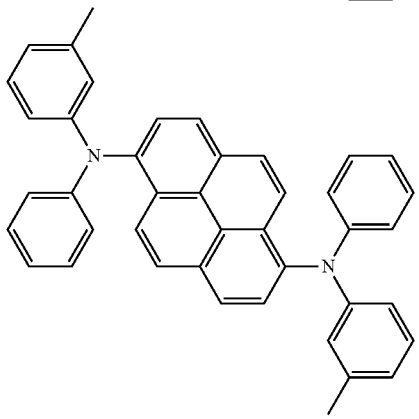

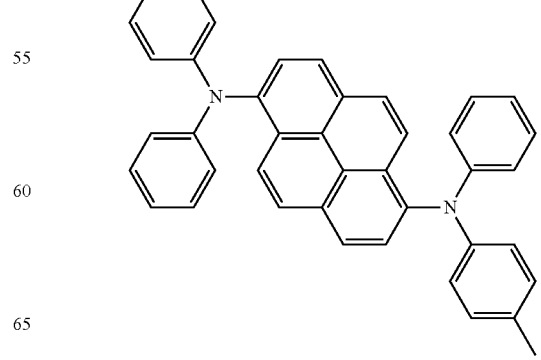

415
-continued
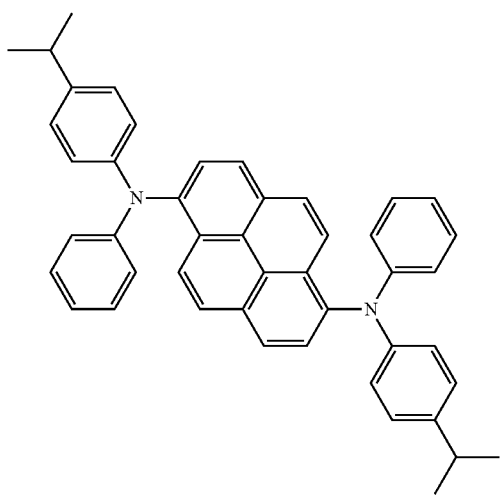
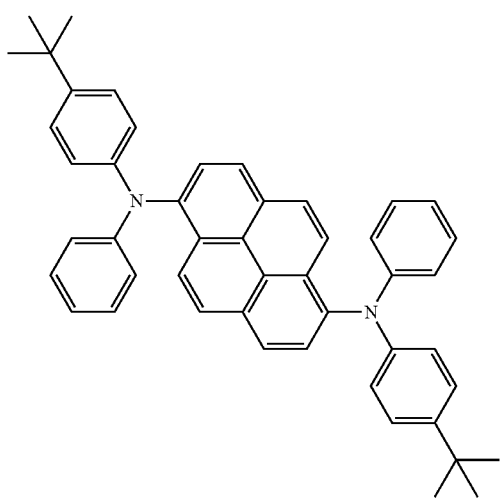
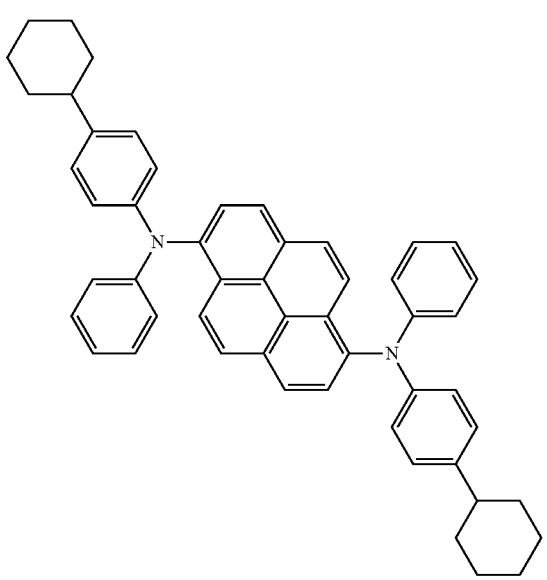
416
-continued
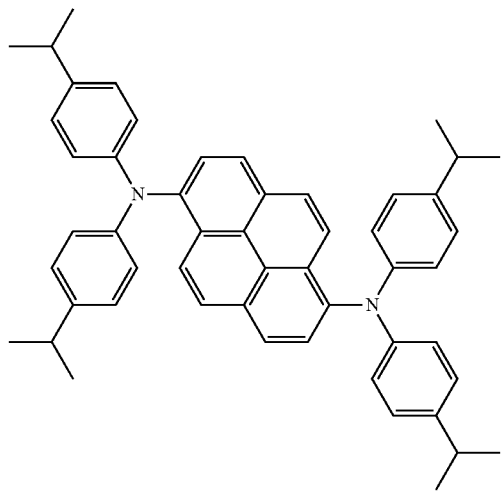
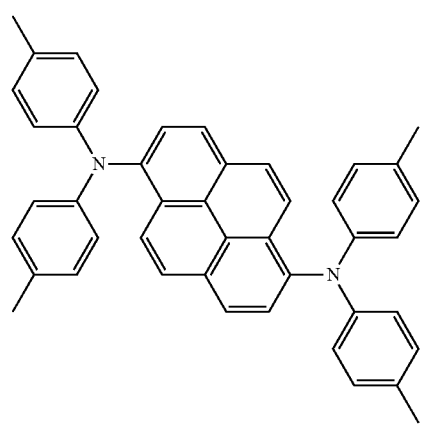
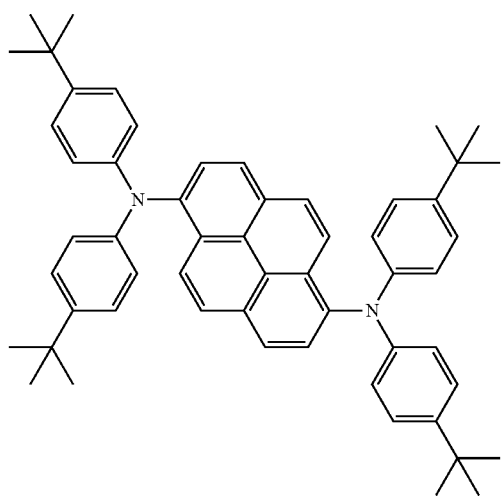

417
-continued
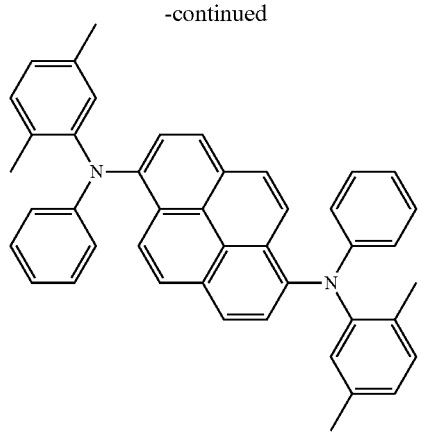
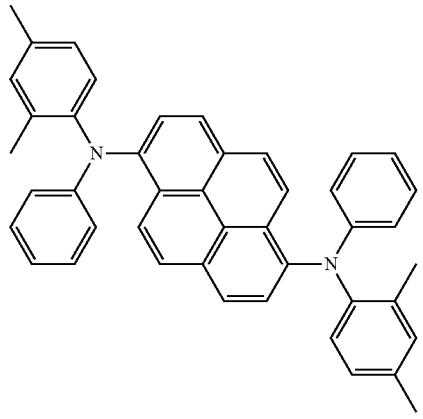
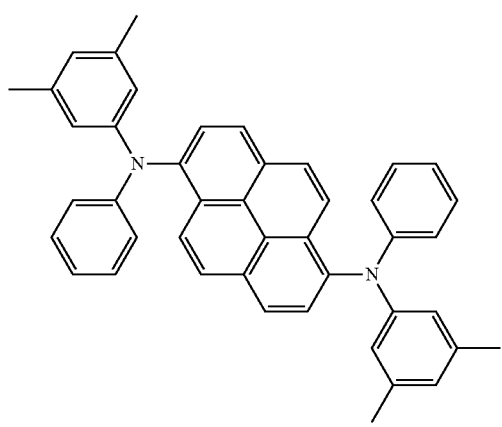
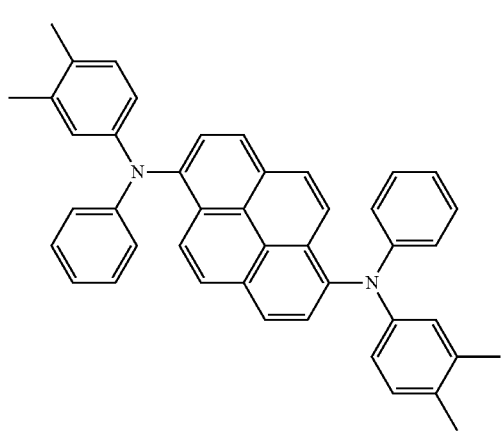
418
-continued

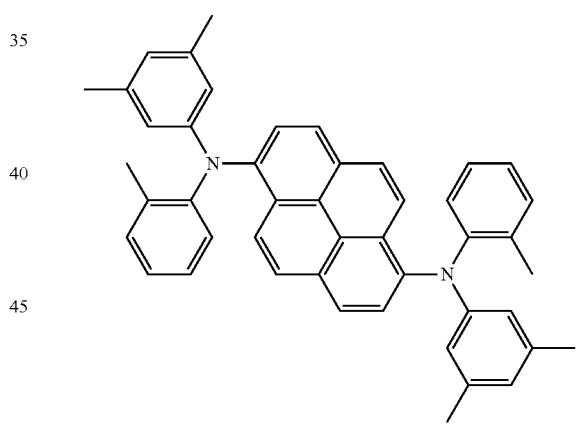
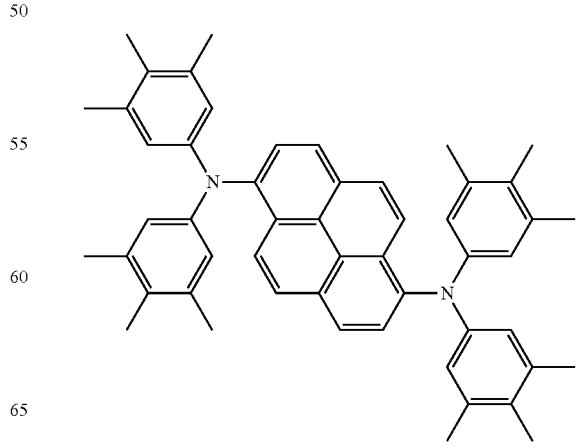

419
-continued
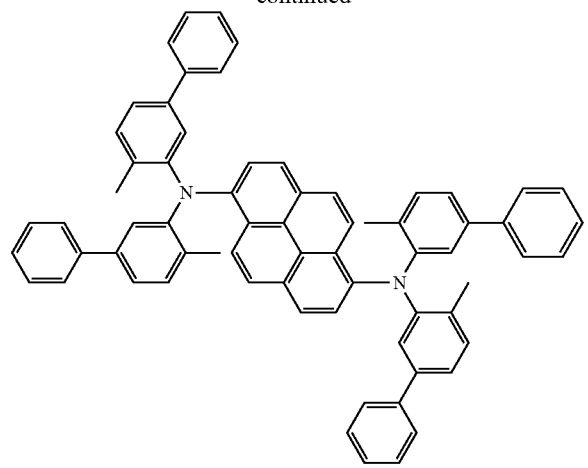
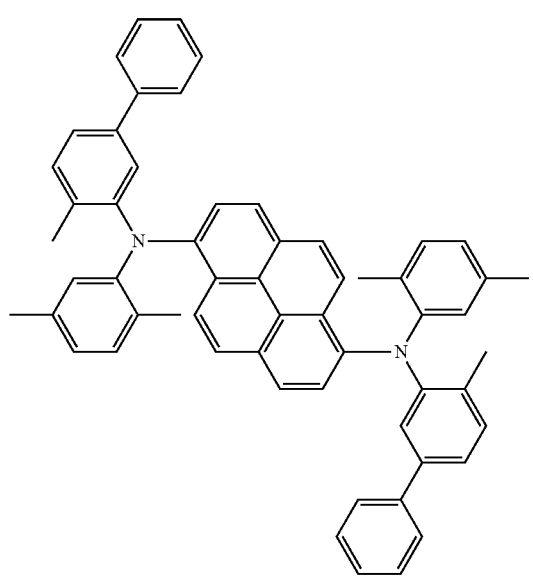
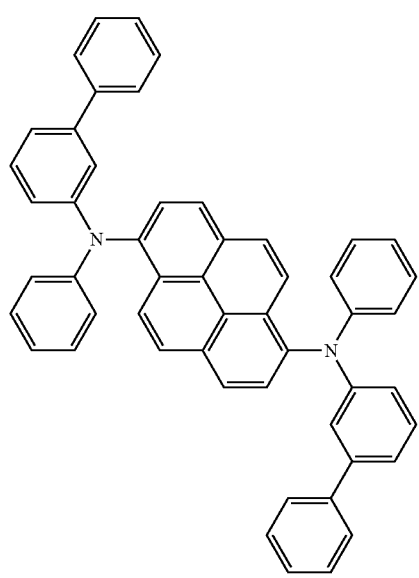
420
-continued
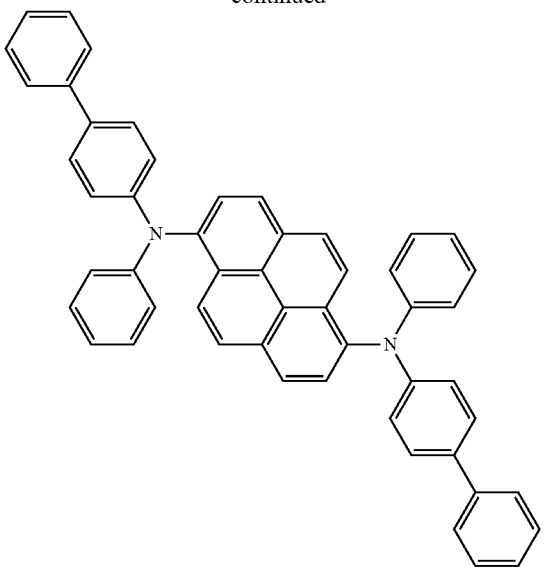

421
-continued
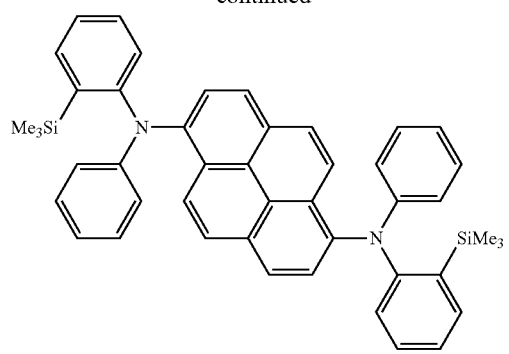
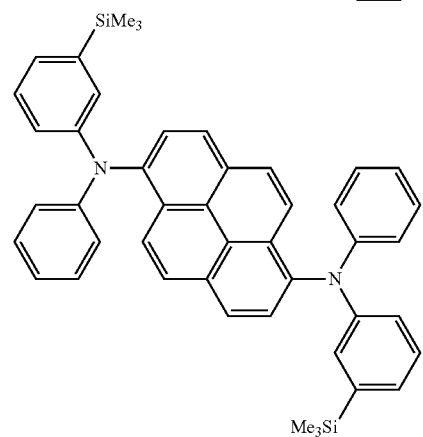
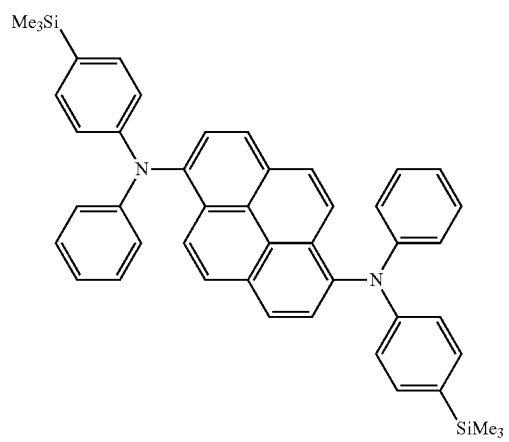
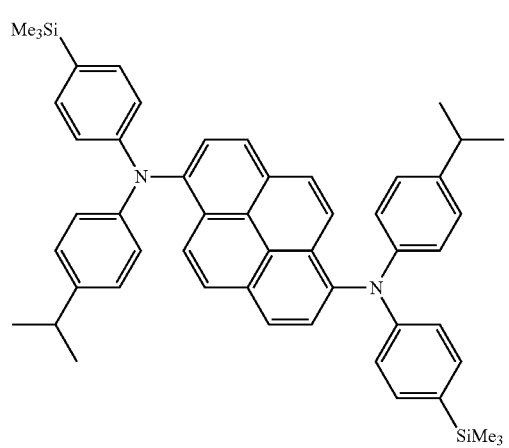
422
-continued
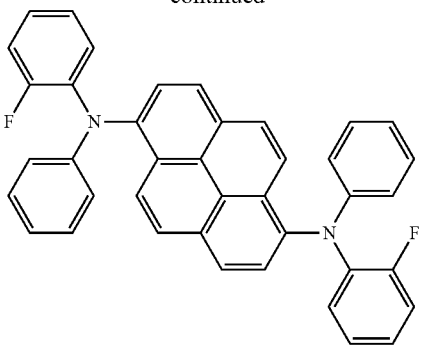
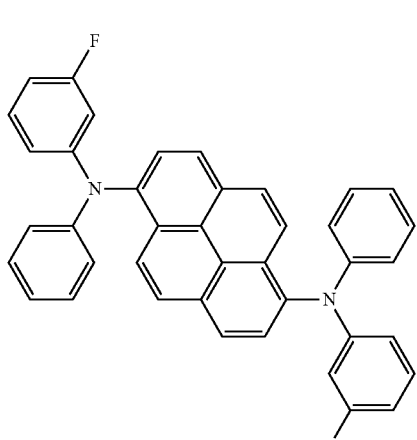
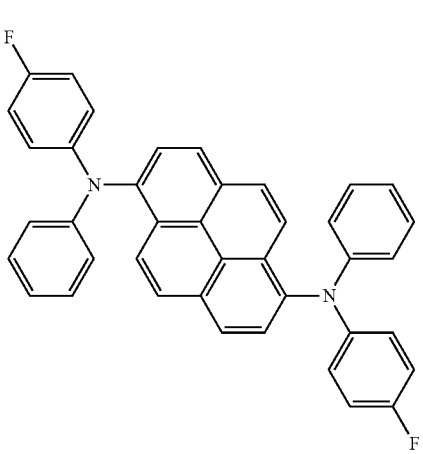
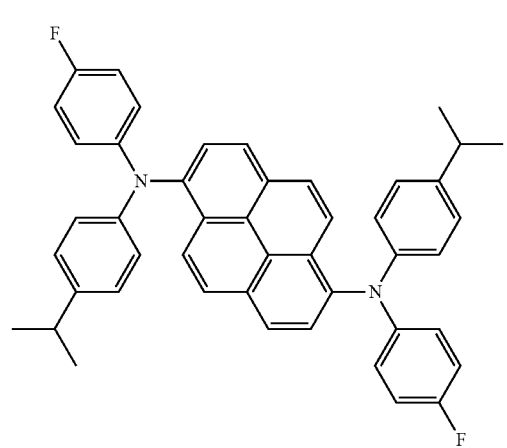

423
-continued
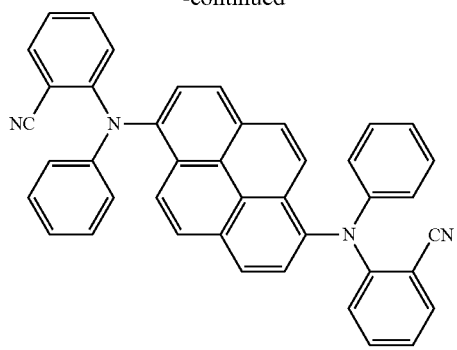
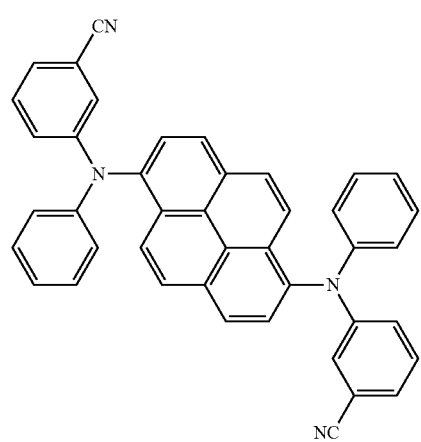
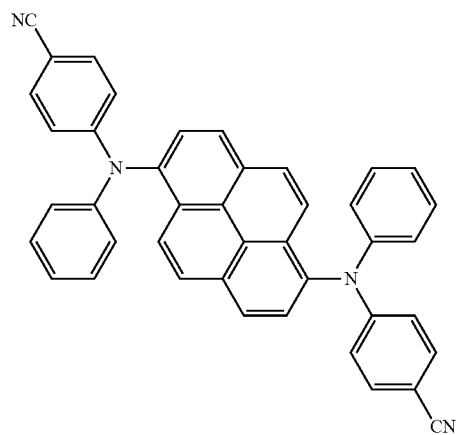
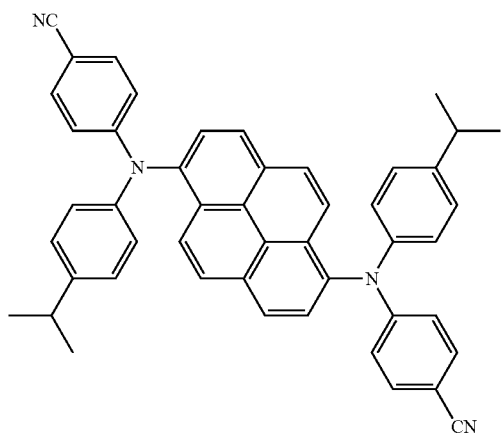
424
-continued
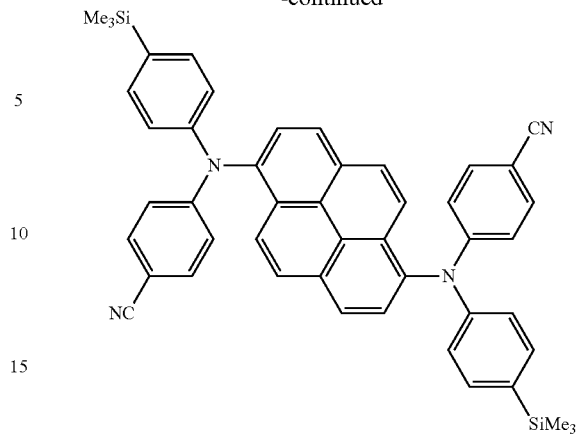
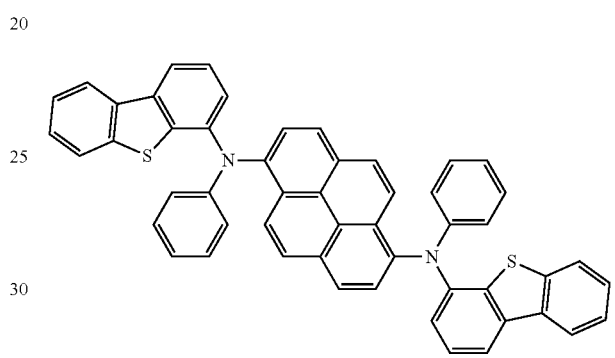
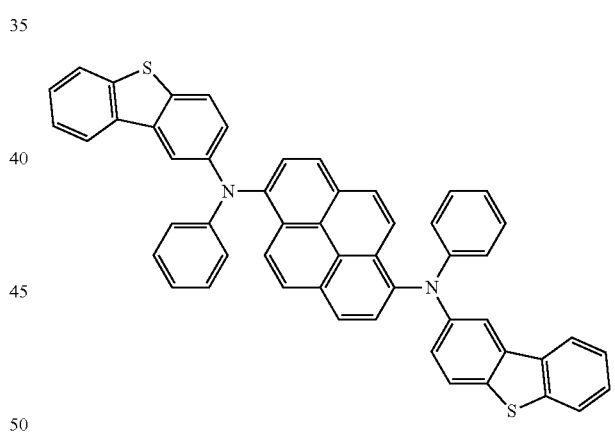
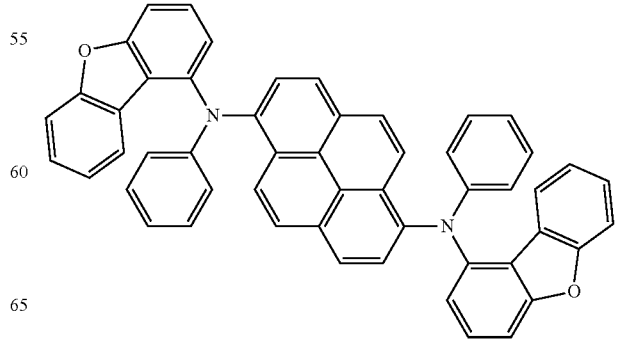

425
-continued
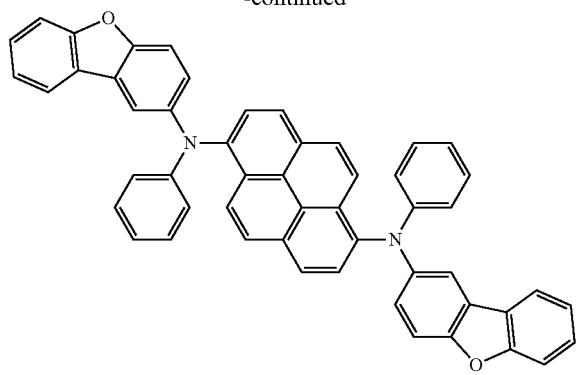
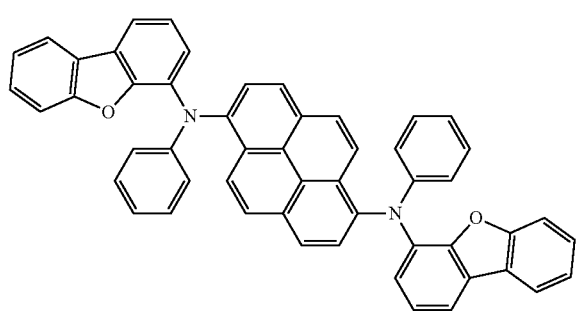
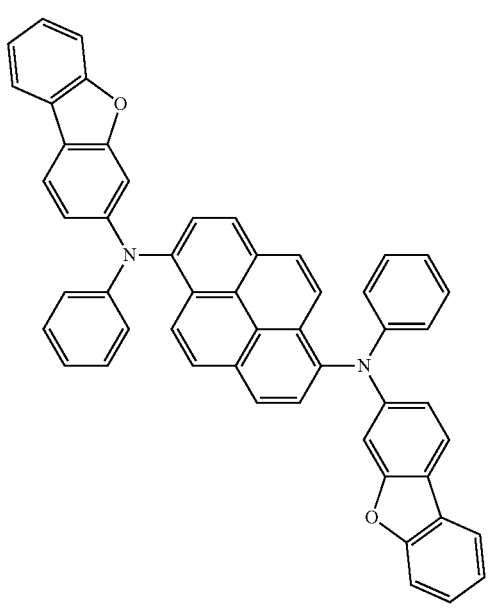
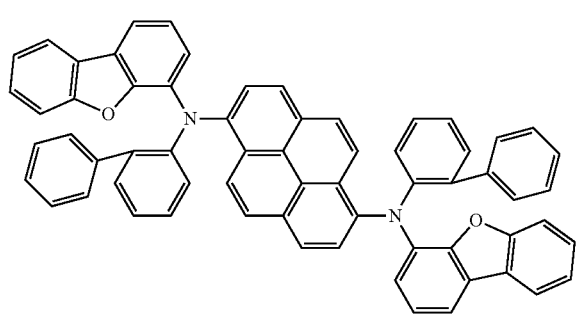
426
-continued
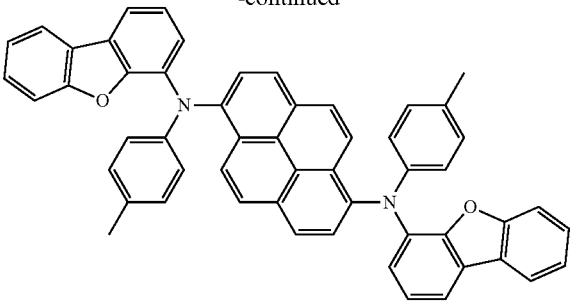
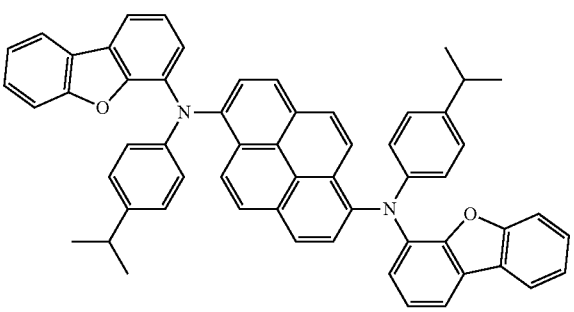
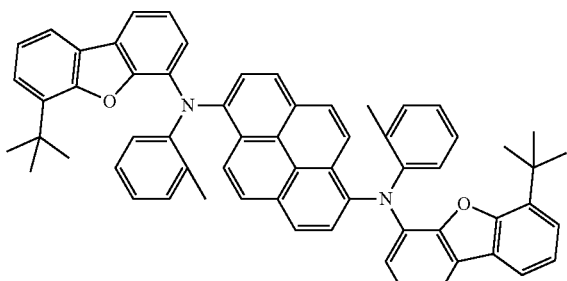
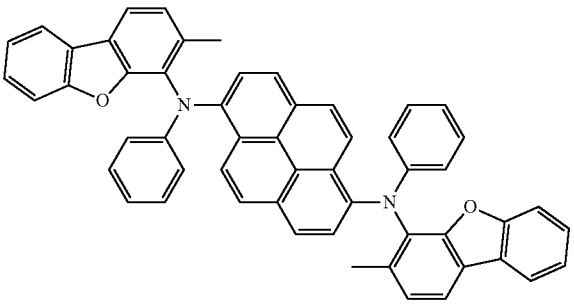
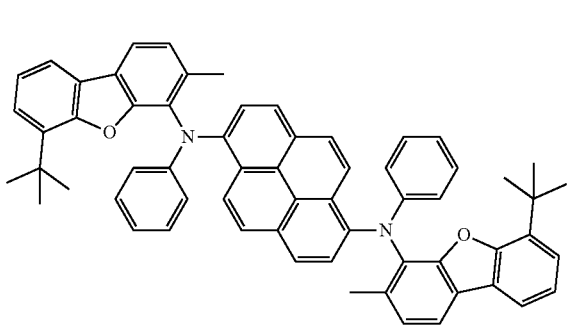

427
-continued
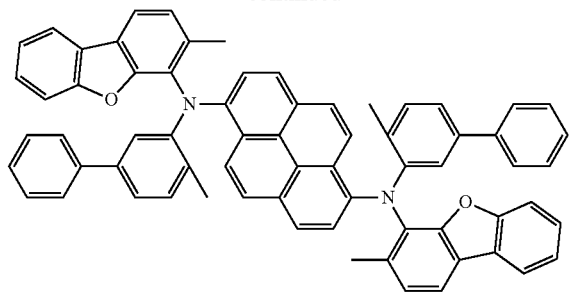
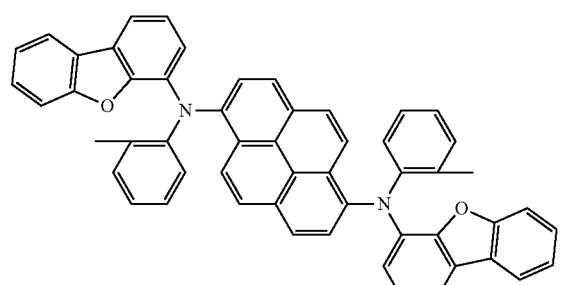
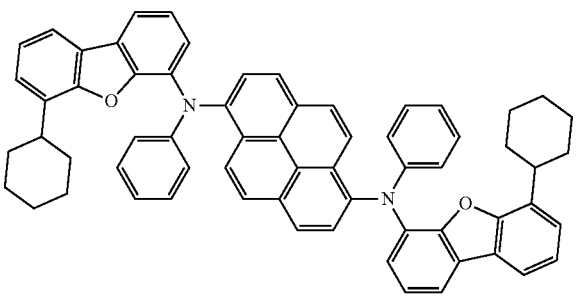
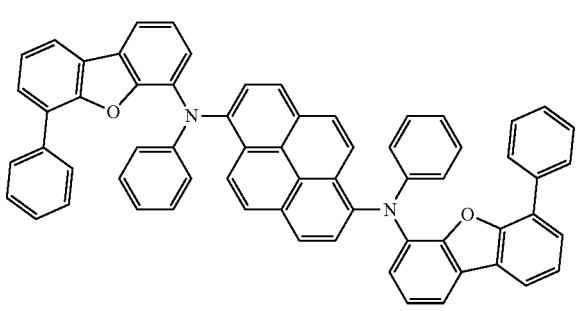
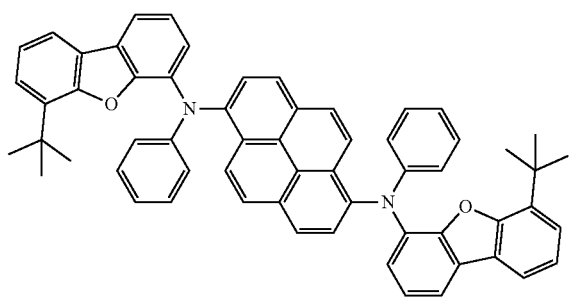
428
-continued
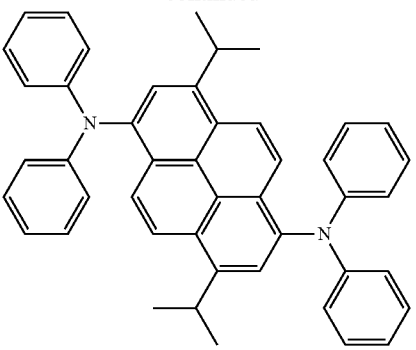
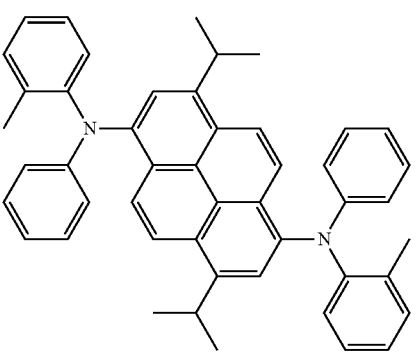
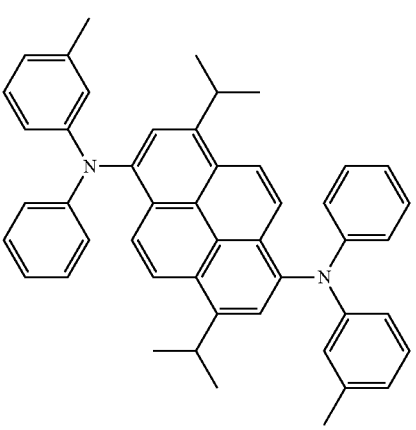
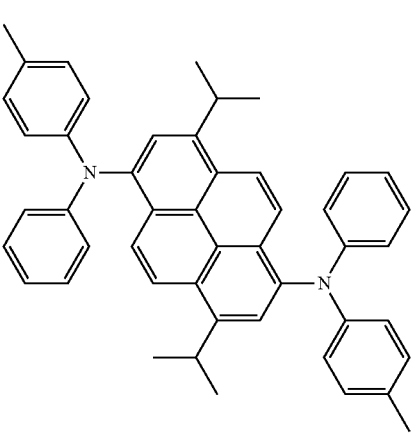

429
-continued
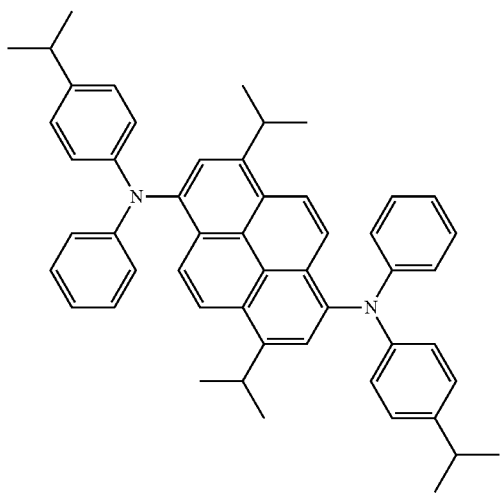
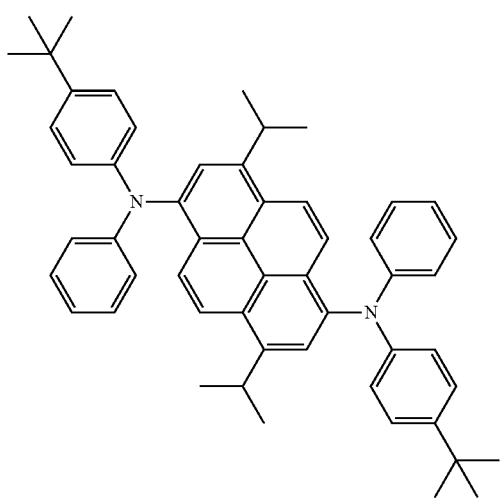
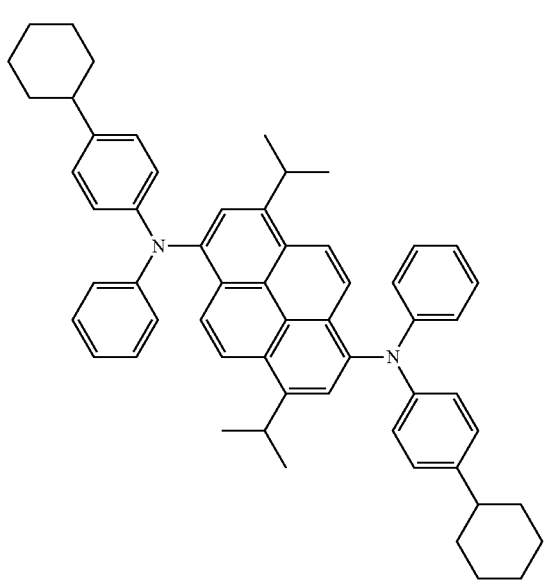
430
-continued
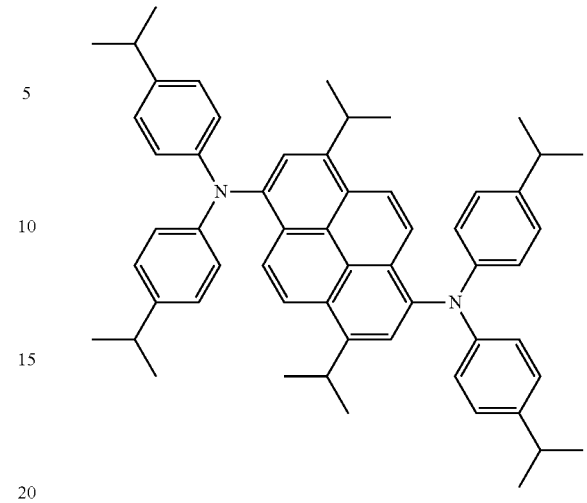
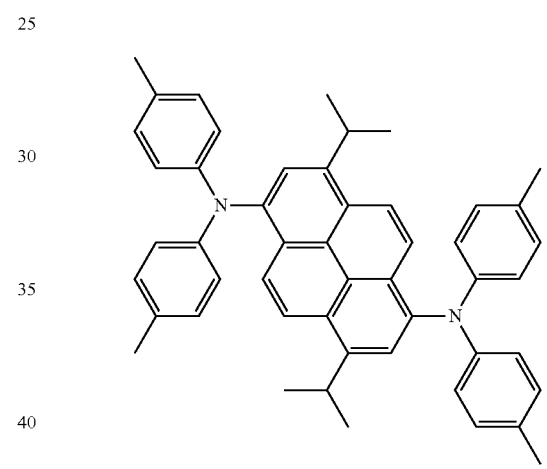
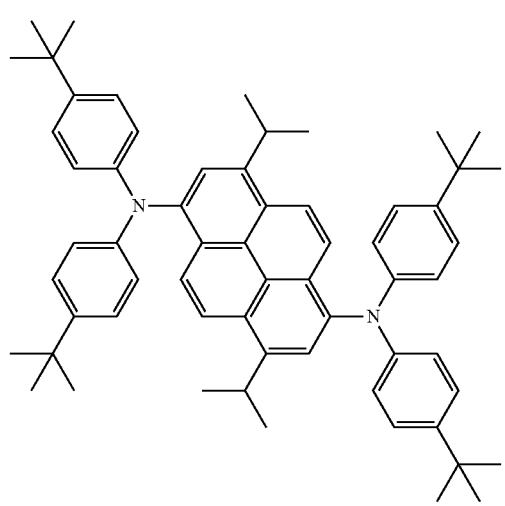

431
-continued
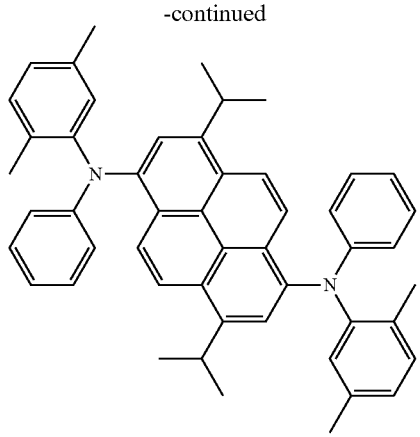
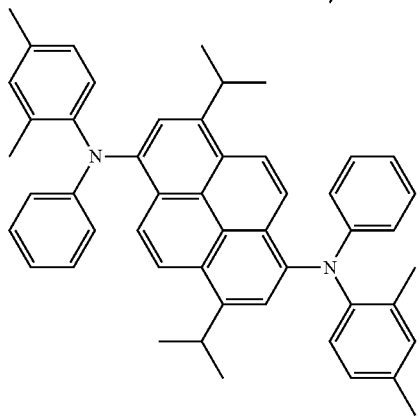
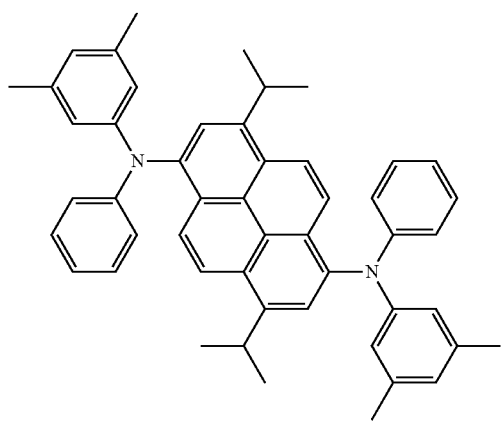
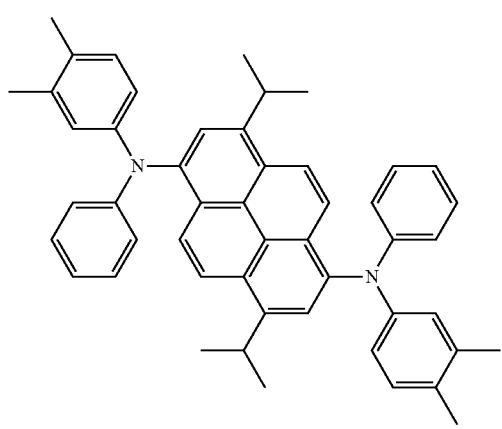
432
-continued
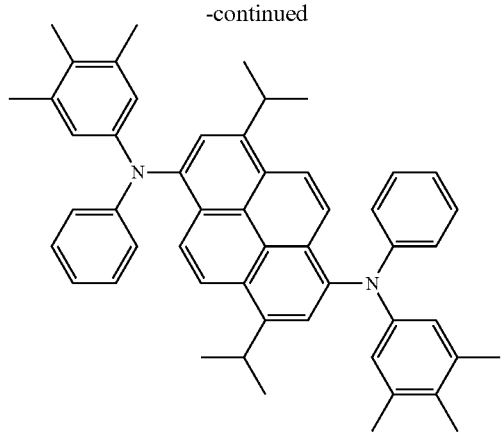
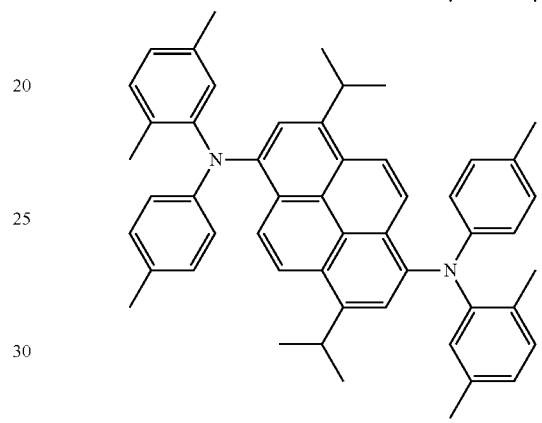
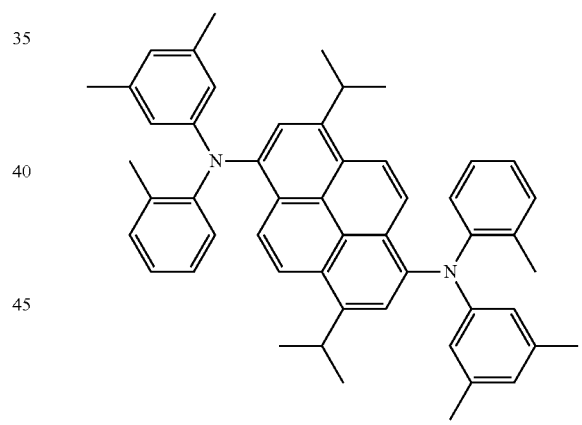
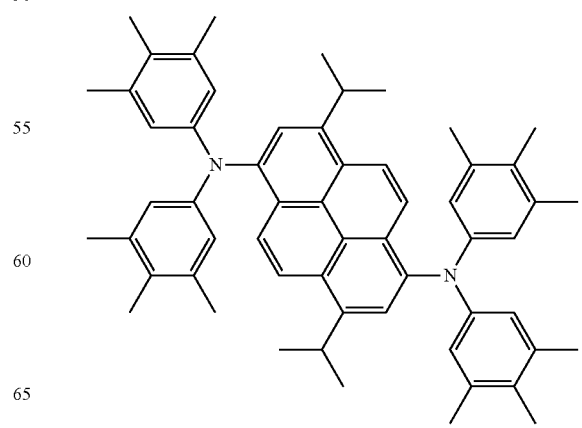

433
-continued
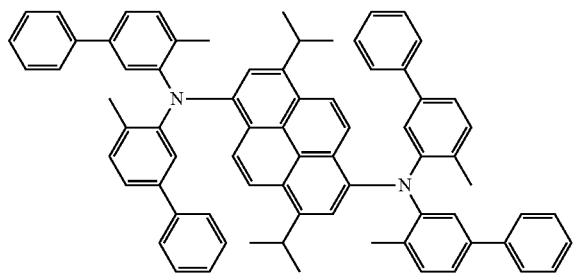
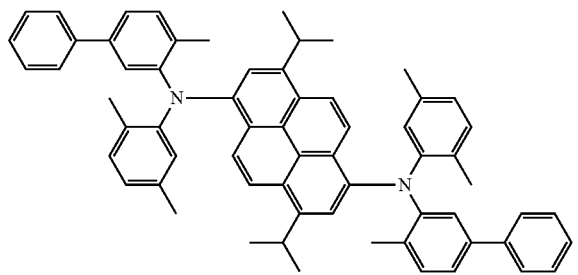
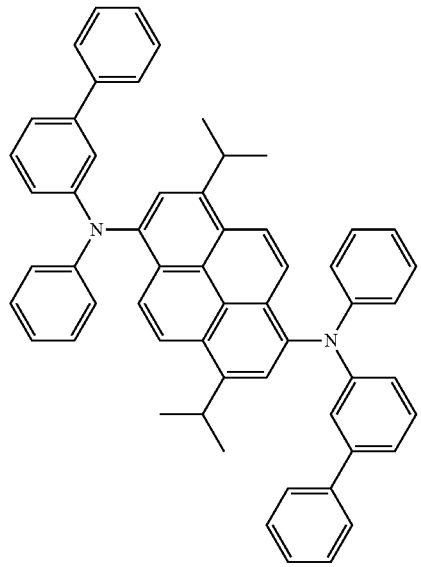
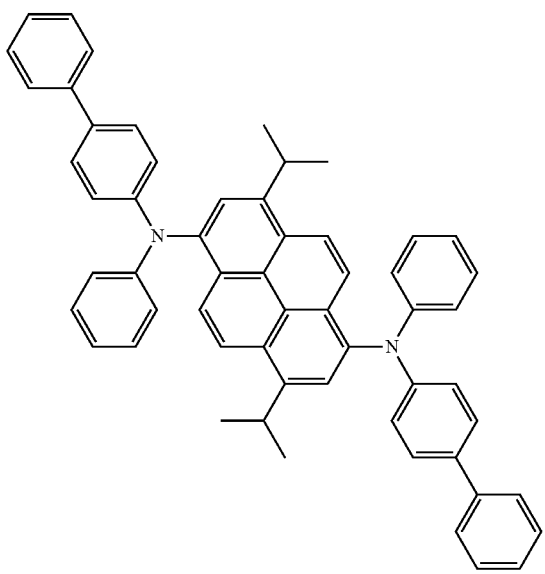
434
-continued
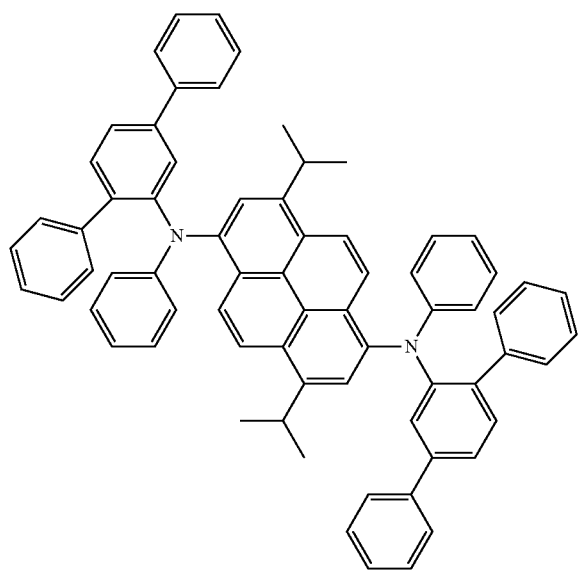
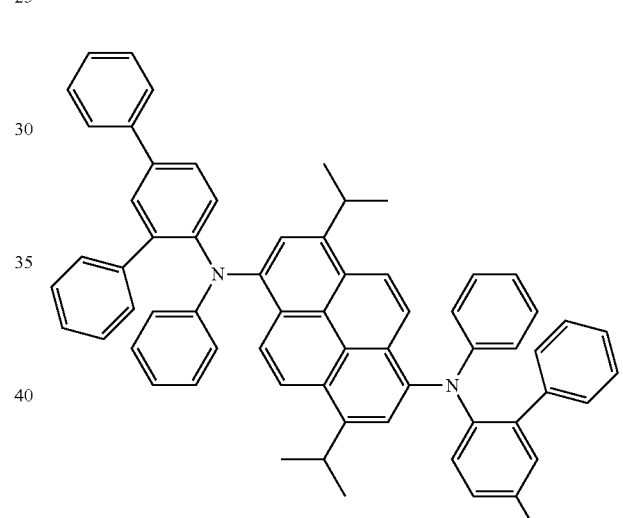
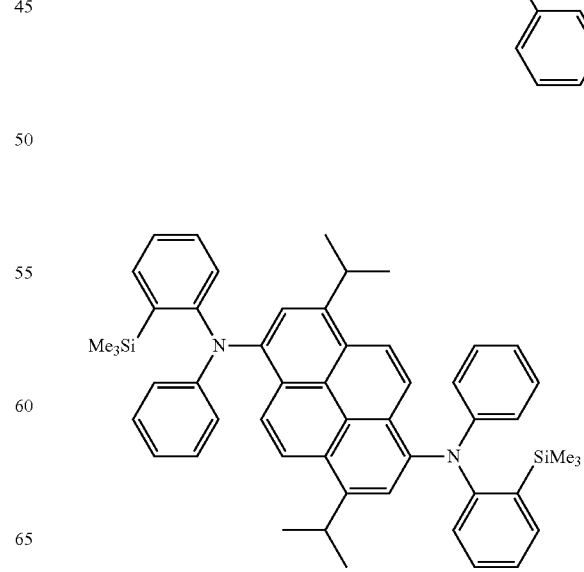

435
-continued
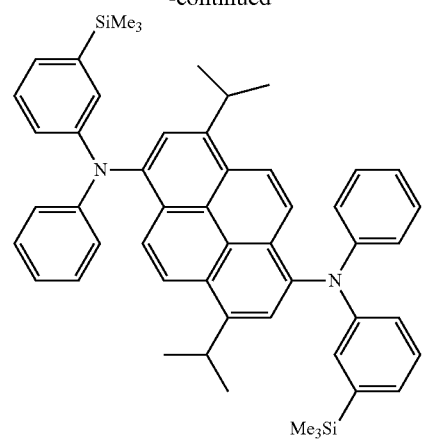
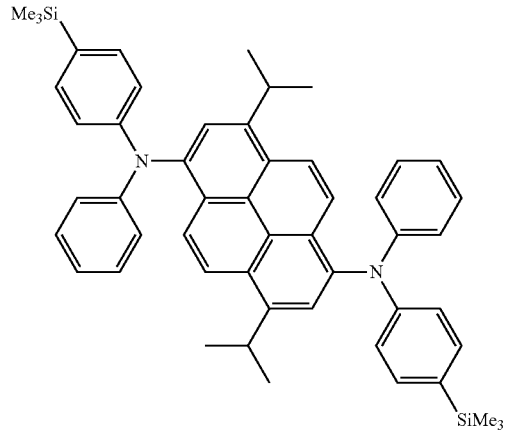
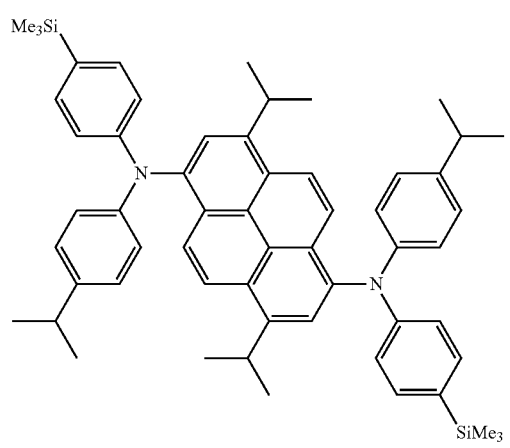
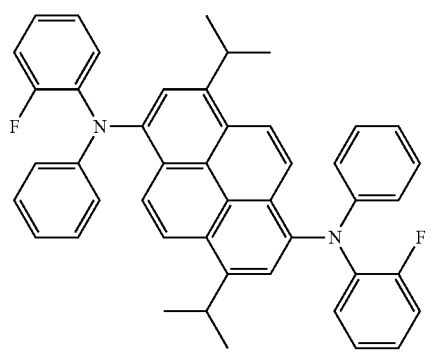
436
-continued
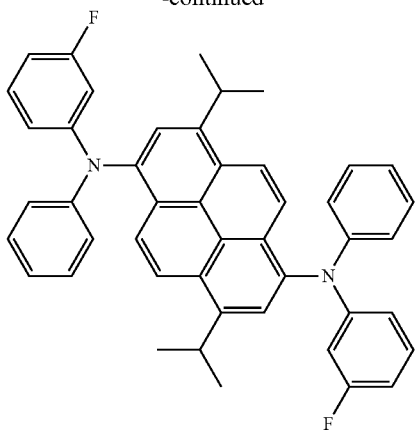
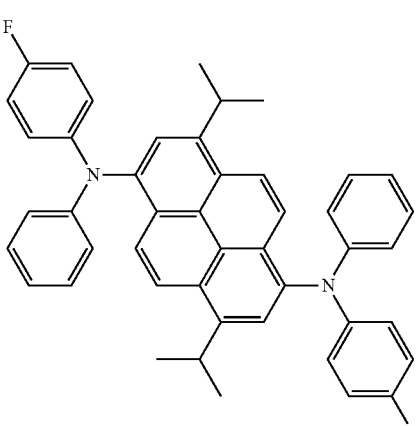
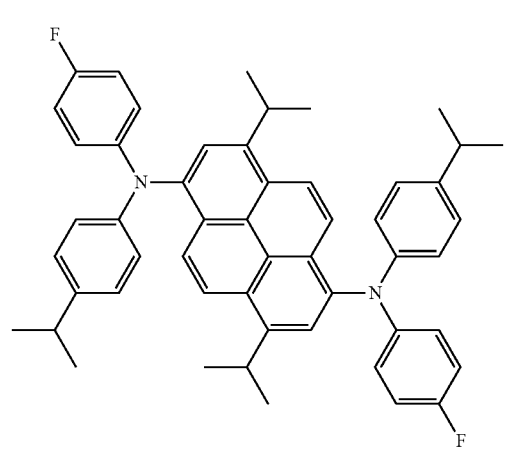
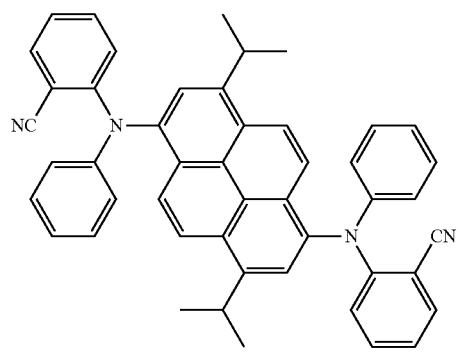

-continued
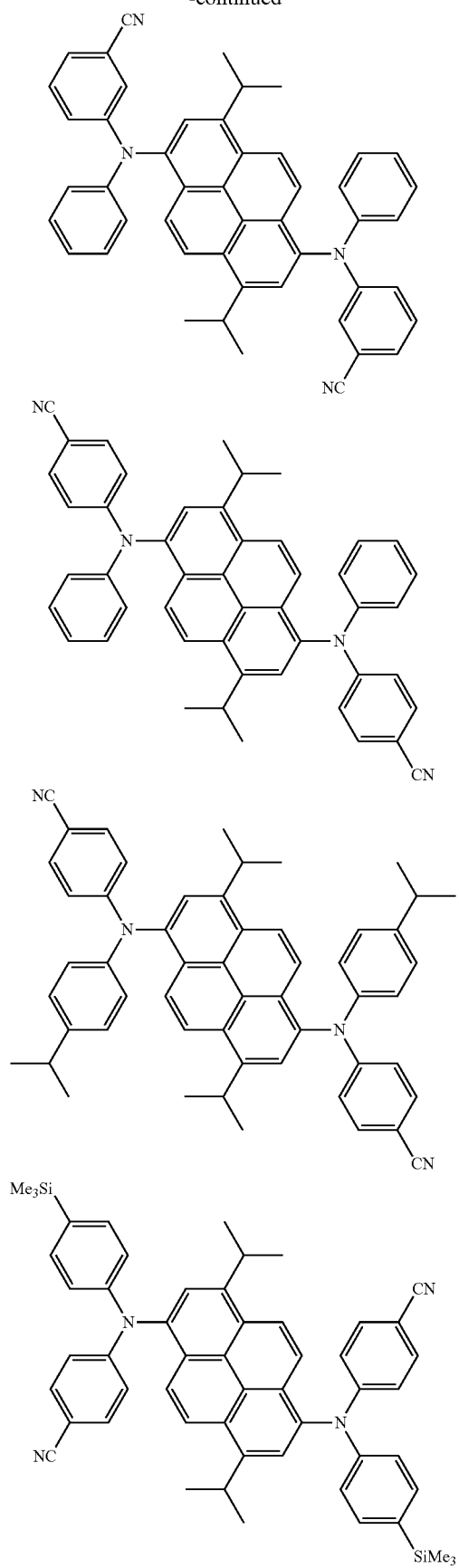
-continued
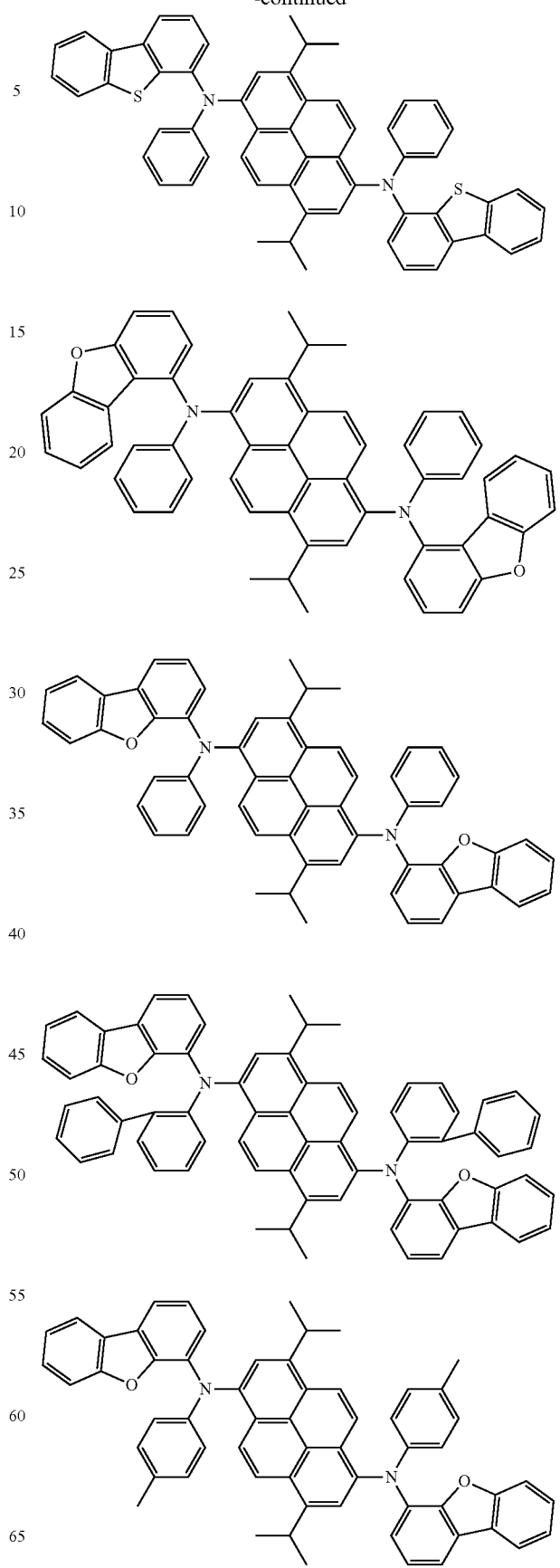

439
-continued
440
-continued
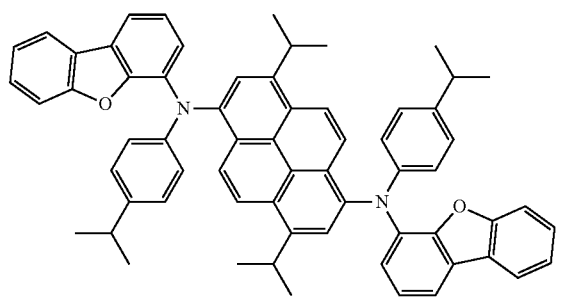
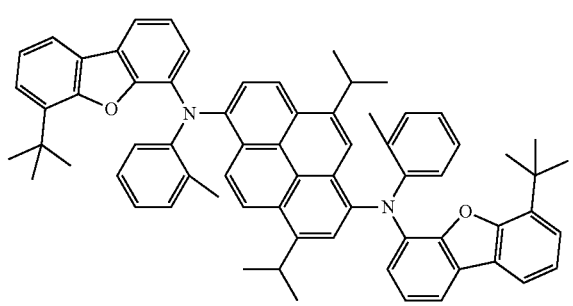
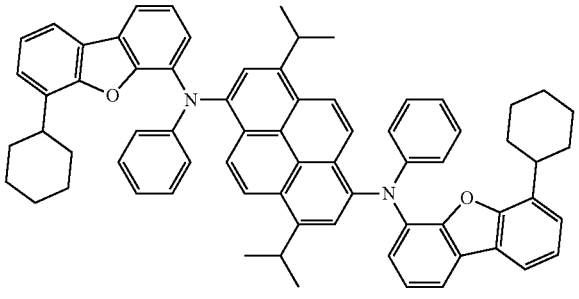
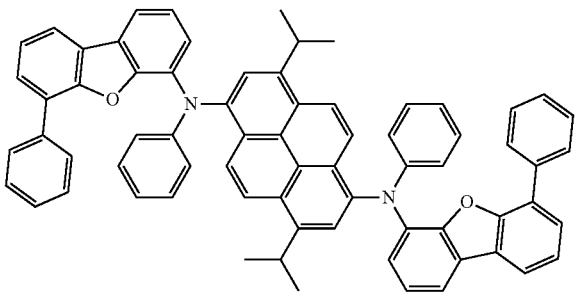
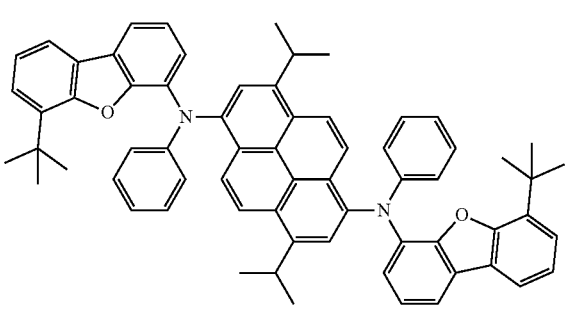
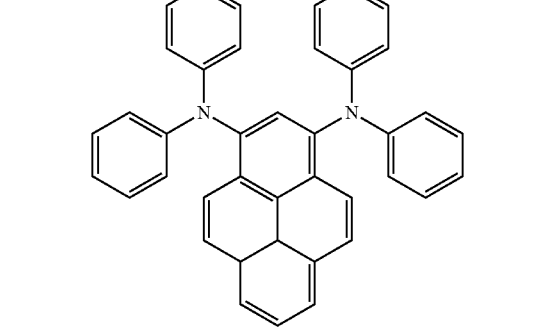

441
-continued
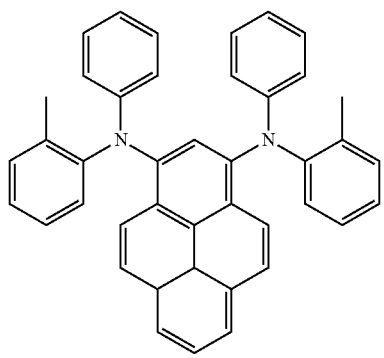
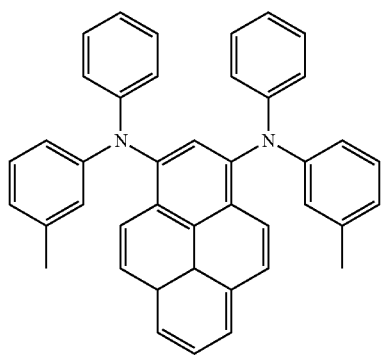
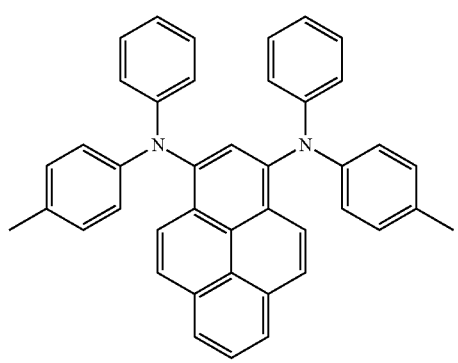
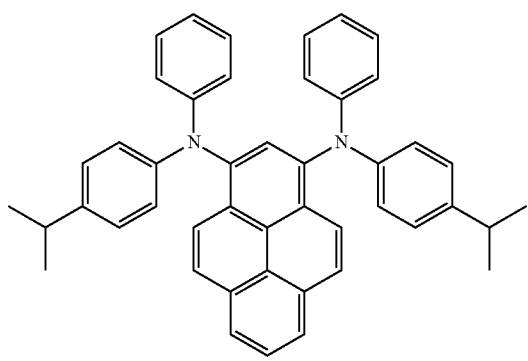
442
-continued
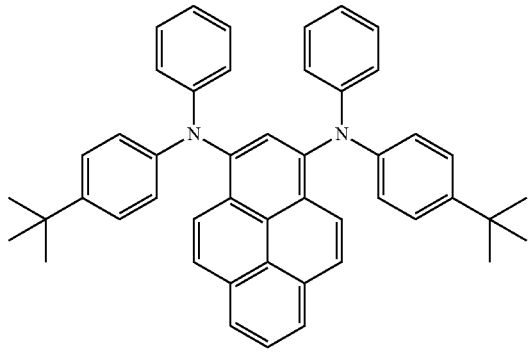
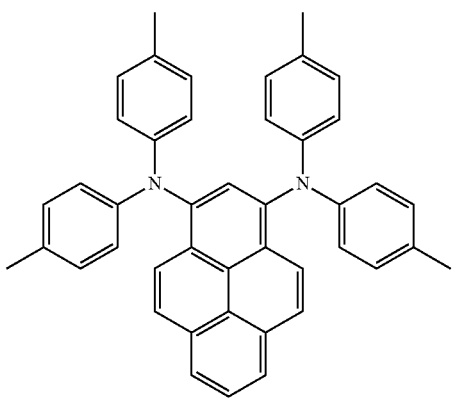
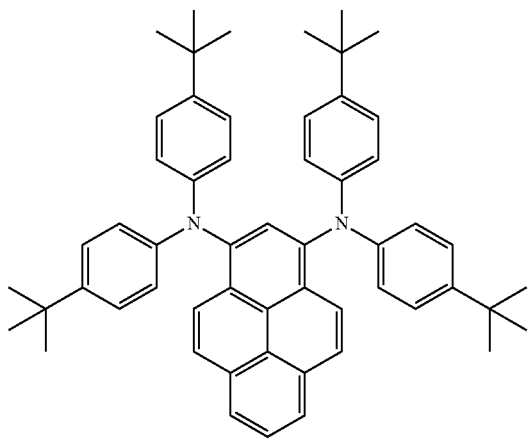
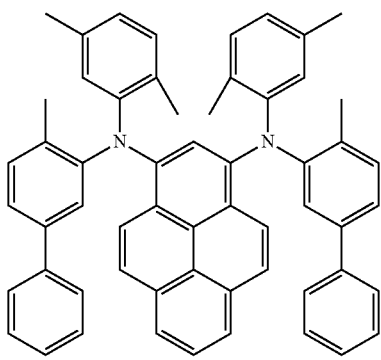

443
-continued
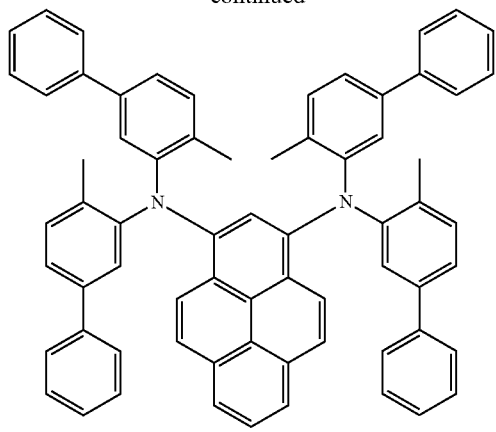
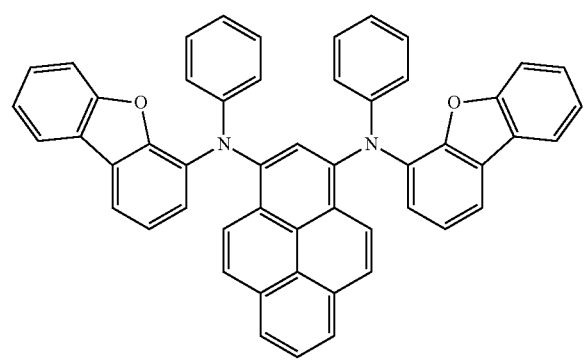
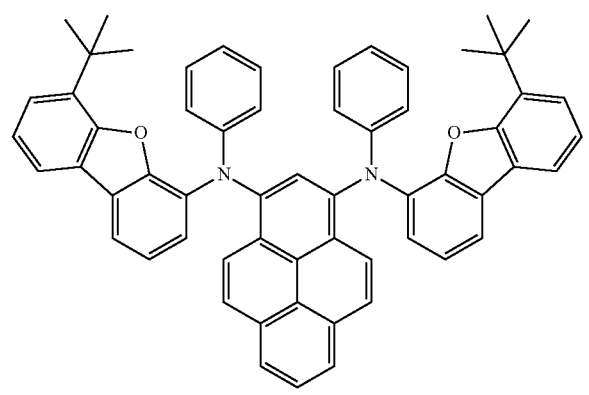
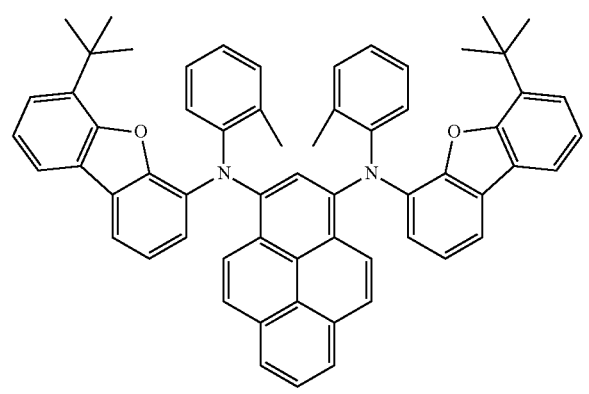
444
-continued
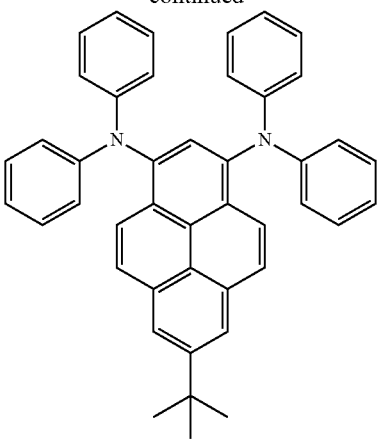
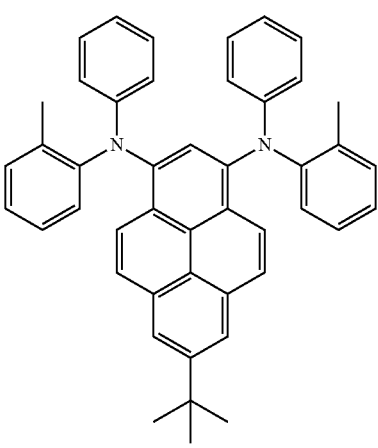
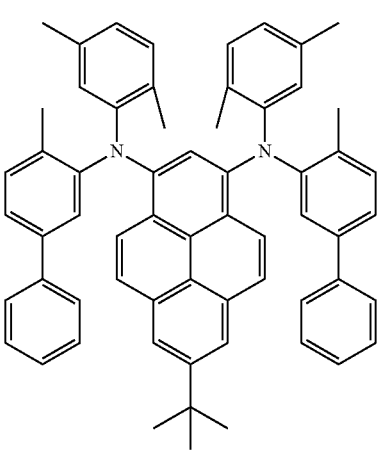

445
-continued
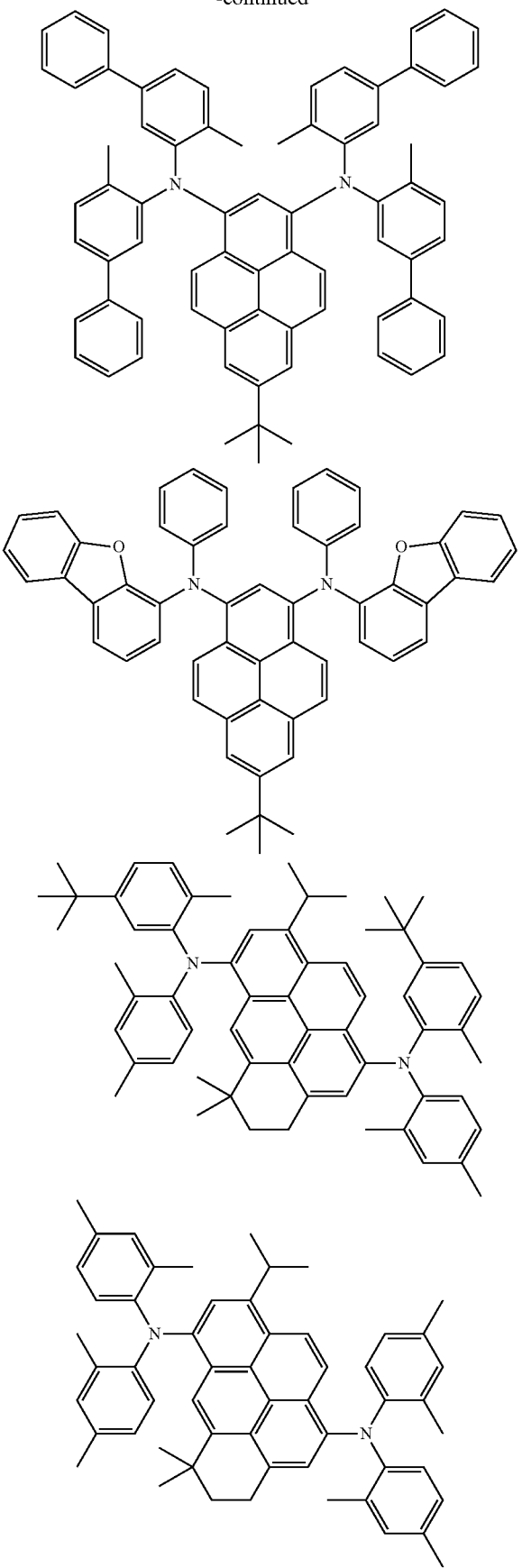
446
-continued
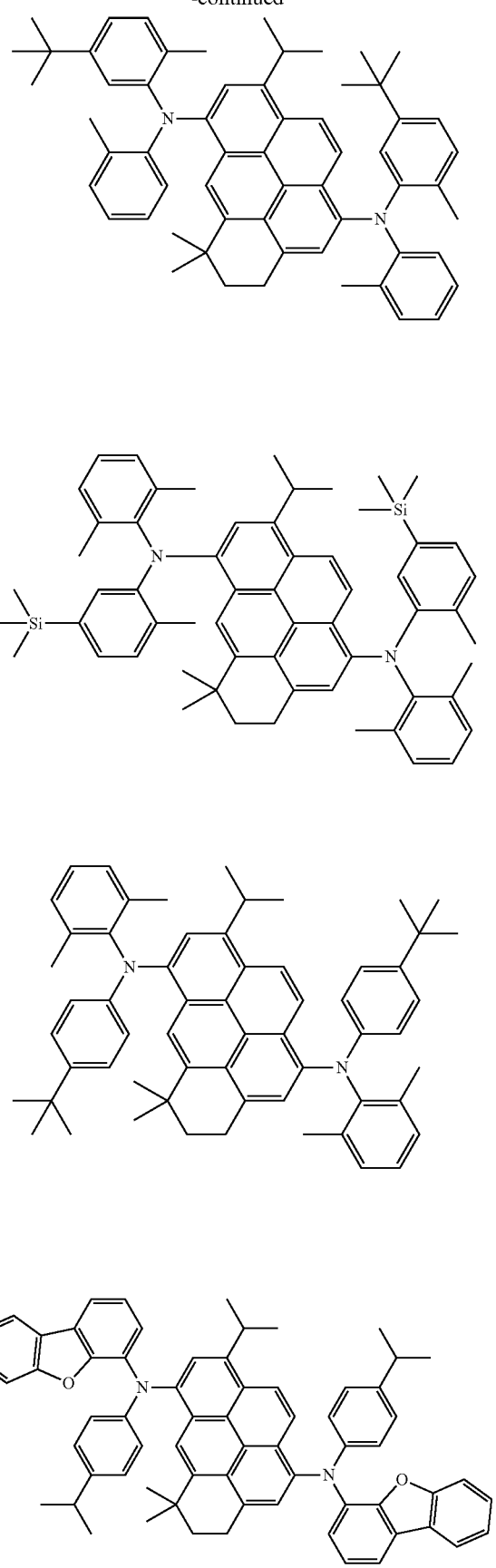

447
-continued
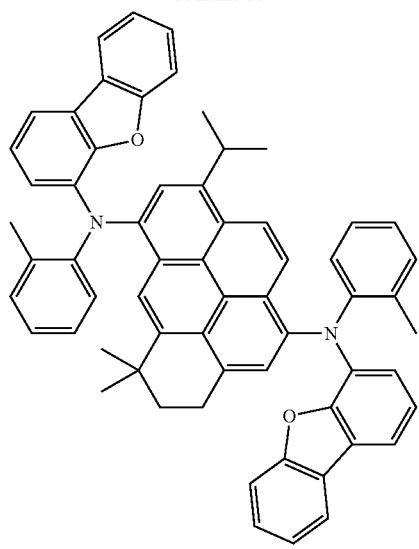
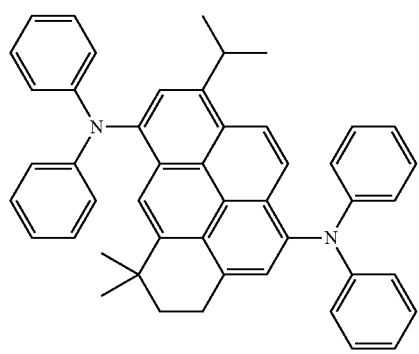
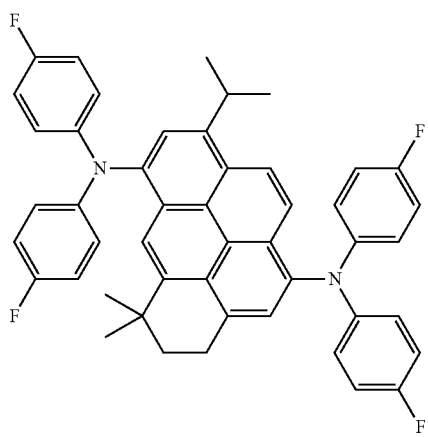
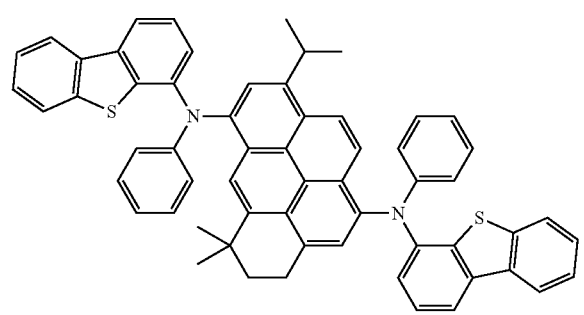
448
-continued
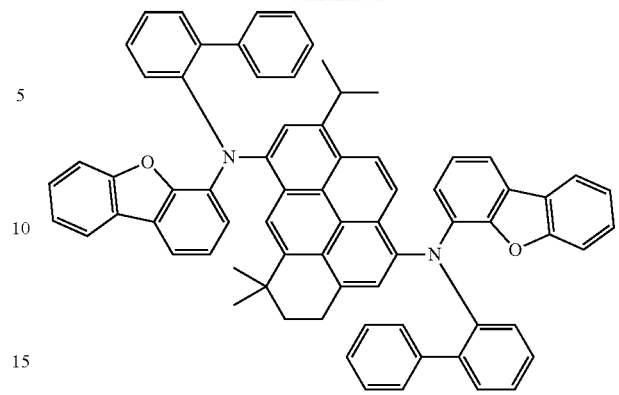
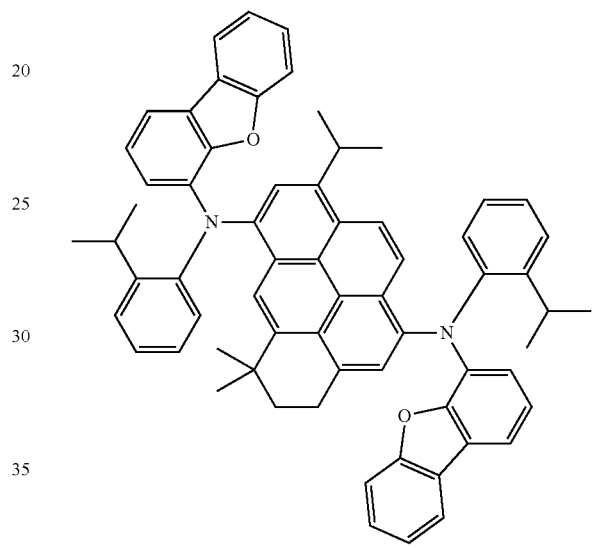
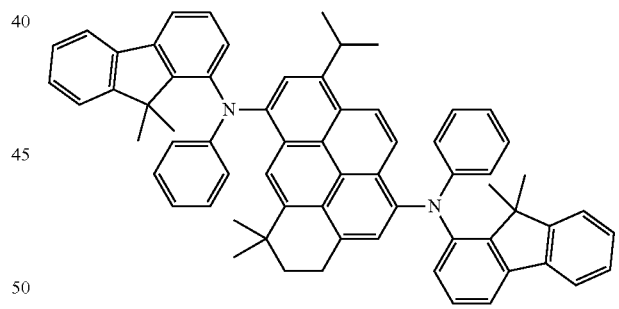
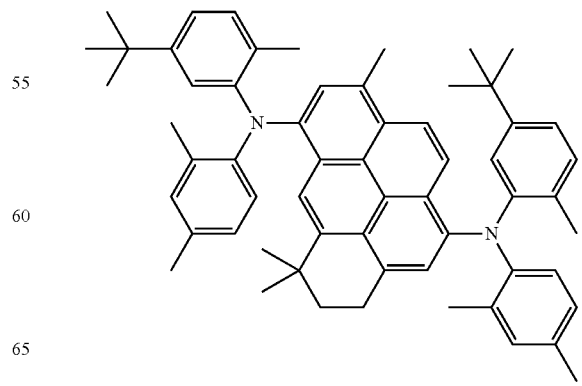

-continued

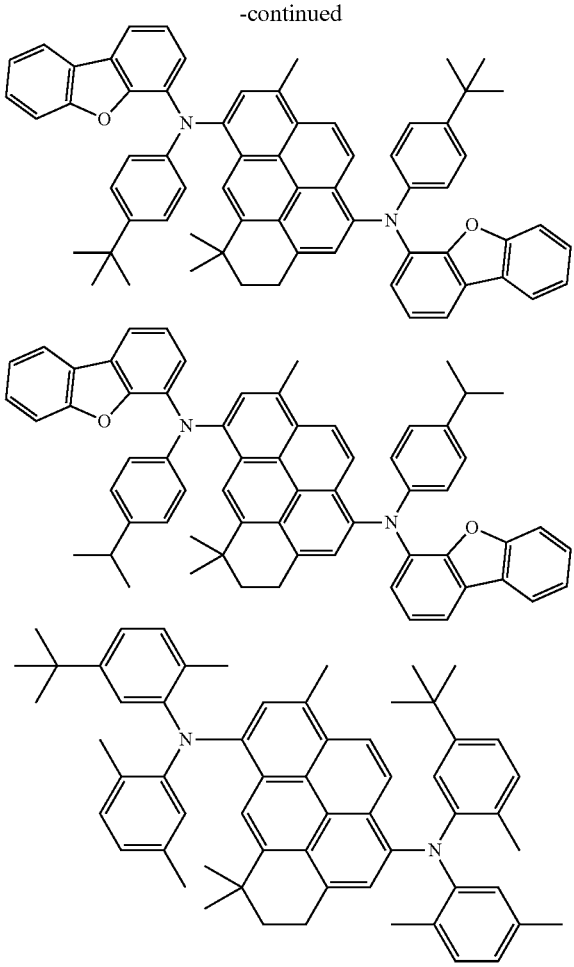

(Compound Represented by Formula (21))

The compound represented by the formula (21) is explained below.

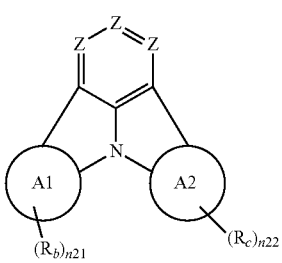

(21)

wherein, in the formula (21),

Zs are independently $CR_a$ or N;

A1 ring and A2 ring are independently a substituted or unsubstituted aromatic hydrocarbon ring having 6 to 50 ring carbon atoms, or a substituted or unsubstituted heterocyclic ring having 5 to 50 ring atoms;

when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;

when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;

when plural $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;

n21 and n22 are independently an integer of 0 to 4;

$R_a$ to $R_c$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

The "aromatic hydrocarbon ring" of A1 ring and A2 ring has the same structure as the compound obtained by introducing a hydrogen atom into the "aryl group" described above. The "aromatic hydrocarbon ring" of the A1 ring and the A2 ring contains two carbon atoms in the fused bicyclic structure at the center of the formula (21) as ring atoms. Examples of "substituted or unsubstituted aromatic hydrocarbon ring having 6 to 50 ring carbon atoms" include compounds in which a hydrogen atom is introduced into the "aryl group" described in the example group G1.

The "heterocyclic ring" of A1 ring and A2 ring has the same structure as the compound obtained by introducing a hydrogen atom into the "heterocyclic group" described above. The "heterocyclic ring" of the A1 ring and the A2 ring contains two carbon atoms in the fused bicyclic structure at the center of the formula (21) as ring atoms. Examples of "substituted or unsubstituted heterocyclic ring having 5 to 50 ring atoms" include compounds in which a hydrogen atom is introduced into the "heterocyclic group" described in the example group G2.

$R_b$ is bonded to one of carbon atoms which form the aromatic hydrocarbon ring of A1 ring, or one of atoms which form the heterocycle of A1 ring.

$R_c$ is bonded to one of carbon atoms which form the aromatic hydrocarbon ring of A2 ring, or one of atoms which form the heterocycle of A2 ring.

It is preferable that at least one (preferably two) of $R_a$ to $R_c$ is a group represented by the following formula (21a).

-$L_{201}$-$Ar_{201}$ (21a)

wherein in the formula (21a), $L_{201}$ is a single bond, a substituted or unsubstituted arylene group having 6 to 30 ring carbon atoms, or a substituted or unsubstituted bivalent heterocyclic group having 5 to 30 ring atoms;

Ar$_{201}$ is
a substituted or unsubstituted arylene group having 6 to 50 ring carbon atoms,
a substituted or unsubstituted monovalent heterocyclic group having 5 to 50 ring atoms, or
a group represented by the following formula (21 b):

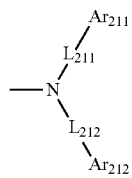
(21b)

wherein in the formula (21 b),
L$_{211}$ and L$_{212}$ are independently
a single bond,
a substituted or unsubstituted arylene group having 6 to 30 ring carbon atoms, or
a substituted or unsubstituted divalent heterocyclic group having 5 to 30 ring atoms;
Ar$_{211}$ and Ar$_{212}$ are bonded with each other to form a substituted or unsubstituted, saturated or unsaturated ring, or do not form a substituted or unsubstituted, saturated or unsaturated ring; and
Ar$_{211}$ and Ar$_{212}$ that do not form a substituted or unsubstituted, saturated or unsaturated ring are independently
a substituted or unsubstituted aryl group having 6 to 50 ring carbon atoms or
a substituted or unsubstituted monovalent heterocyclic group having 5 to 50 ring atoms.
In one embodiment, the compound represented by the formula (21) is represented by the following formula (22).

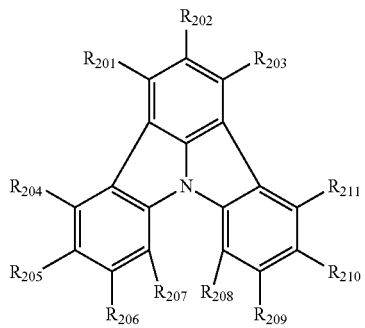
(22)

wherein in the formula (22),
one or more pairs of two or more adjacent groups of R$_{201}$ to R$_{211}$ are bonded with each other to form a substituted or unsubstituted, saturated or unsaturated ring, or do not form a substituted or unsubstituted saturated or unsaturated ring;
R$_{201}$ to R$_{211}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
R$_{9001}$ to R$_{907}$ are as defined in the formula (1))
It is preferable that at least one (preferably two) of R$_{201}$ to R$_{211}$ is the group represented by the formula (21a). It is preferable that R$_{204}$ and R$_{211}$ are the group represented by the formula (21a).
In one embodiment, the compound represented by the formula (21) is a compound obtained by bonding the structure represented by the following formula (21-1) or (21-2) to A1 ring. In one embodiment, the compound represented by the formula (22) is a compound obtained by bonding the structure represented by the following formula (21-1) or (21-2) to the ring to which R$_{204}$ to R$_{207}$ bonds to.

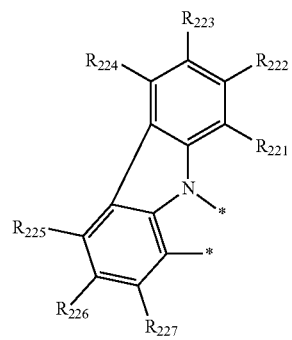
(21-1)

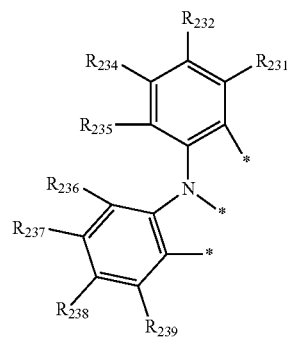
(21-2)

wherein in the formula (21-1), two bonds shown by * independently bond to a ring carbon atom in the aromatic hydrocarbon ring or a ring atom in the heterocyclic group in A1 ring in the formula (21), or bond to one of R$_{204}$ to R$_{207}$ in the formula (22);
wherein in the formula (21-2), three bonds shown by * independently bond to a ring carbon atom in the aromatic hydrocarbon ring or a ring atom in the heterocyclic group in A1 ring in the formula (22), or bond to one of R$_{204}$ to R$_{207}$ in the formula (22);
One or more pairs of two or more adjacent groups of R$_{221}$ to R$_{227}$ and R$_{221}$ to R$_{239}$ are bonded with each other to form a substituted or unsubstituted, saturated or unsaturated ring, or do not form a substituted or unsubstituted, saturated or unsaturated ring;

$R_{221}$ to $R_{227}$ and $R_{231}$ to $R_{239}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1)

In one embodiment, the compound represented by the formula (21) is a compound represented by the following formula (21-3), (21-4), or (21-5).

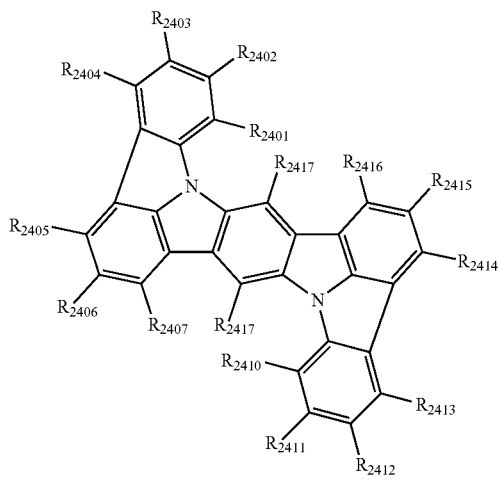

(21-3)

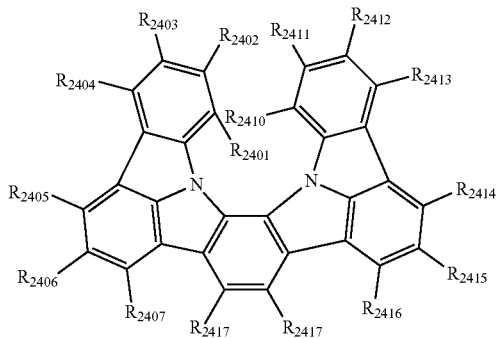

(21-4)

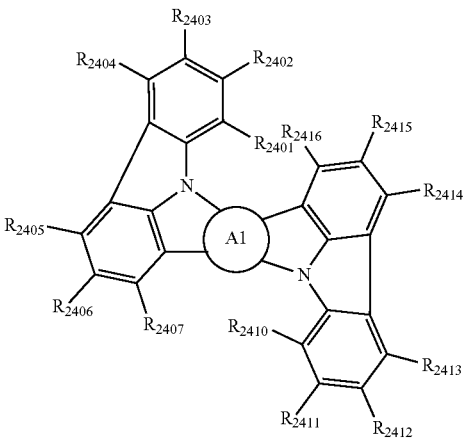

(21-5)

wherein in the formulas (21-3), (21-4) and (21-5),

A1 ring is as defined in the formula (21);

$R_{2401}$ to $R_{2407}$ are the same as $R_{221}$ to $R_{227}$ in the formulas (21-1) and (21-2); and $R_{2410}$ to $R_{2417}$ are the same as $R_{201}$ to $R_{211}$ in the formula (22).

In one embodiment, the substituted or unsubstituted aromatic hydrocarbon ring having 6 to 50 ring carbon atoms of A1 ring in the formula (21-5) is a substituted or unsubstituted napthalene ring, or a substituted or unsubstituted fluorene ring.

In one embodiment, the substituted or unsubstituted heterocycle having 5 to 50 ring atoms of A1 ring in the formula (21-5) is a substituted or unsubstituted dibenzofuran ring, a substituted or unsubstituted carbazole ring, or a substituted or unsubstituted dibenzothiophene ring.

In one embodiment, the compound represented by the formula (21) or (22) is selected from the group consisting of the compounds represented by the following formulas (21-6-1) to (21-6-7).

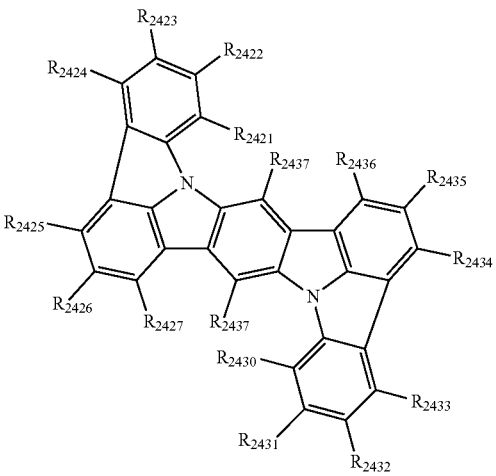

(21-6-1)

(21-6-2)

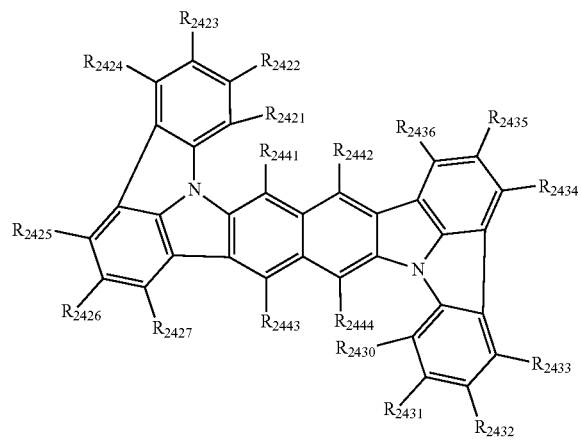

(21-6-3)

(21-6-4)

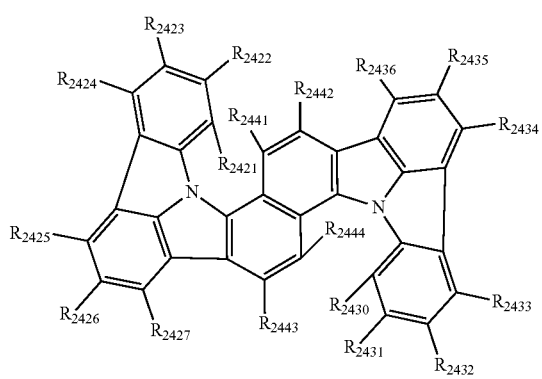

(21-6-5)

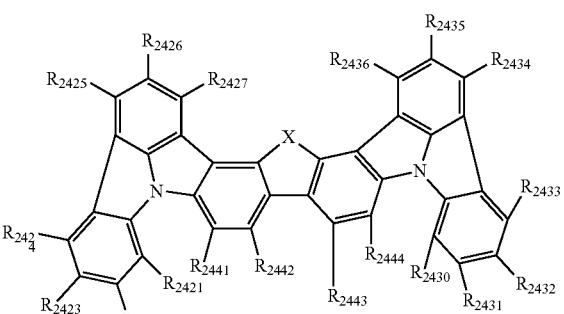

(21-6-6)

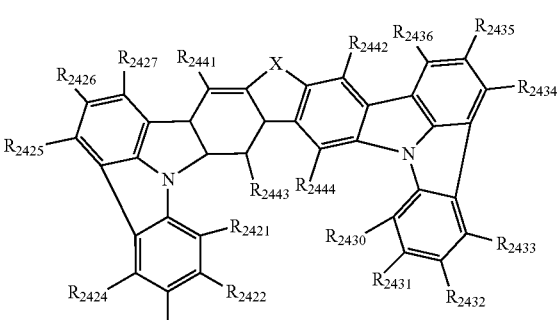

(21-6-7)

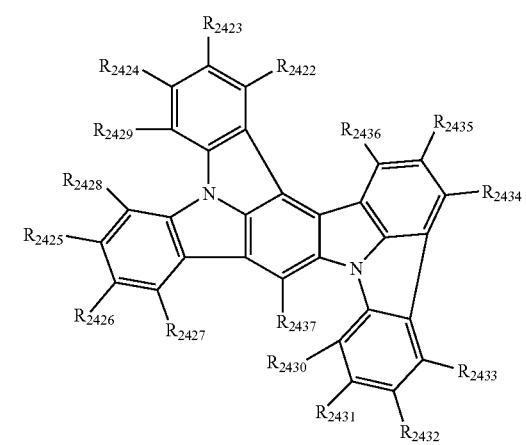

wherein in the formulas (21-6-1) to (21-6-7), $R_{2421}$ to $R_{2427}$ are the same as $R_{221}$ to $R_{227}$ in the formulas (21-1) and (21-2);

$R_{2430}$ to $R_{2437}$ and $R_{2441}$ to $R_{2444}$ are the same as $R_{201}$ to $R_{211}$ in the formula (22);

X is O, $NR_{901}$, or $C(R_{902})(R_{903})$; and $R_{901}$ to $R_{903}$ are as defined in the formula (1).

In one embodiment, in the compound represented by the formula (22), one or more pairs of two or more adjacent groups of $R_{201}$ to $R_{211}$ are bonded with each other to form a substituted or unsubstituted, saturated or unsaturated ring. This embodiment is described in the following formula (25).

(Compound Represented by Formula (25))

The compound represented by the formula (25) is explained below.

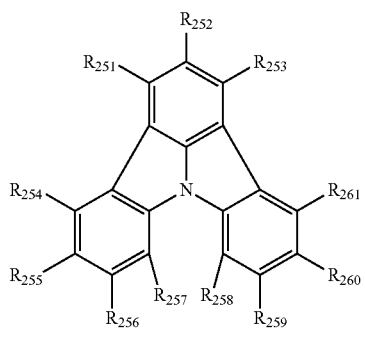

(25)

wherein in the formula (25), two or more pairs selected from a group consisting of $R_{251}$ and $R_{252}$, $R_{252}$ and $R_{253}$, $R_{254}$ and $R_{255}$, $R_{255}$ and $R_{256}$, $R_{256}$ and $R_{257}$, $R_{258}$ and $R_{259}$, $R_{259}$ and $R_{260}$, and $R_{260}$ and $R_{261}$ bond with each other to form a substituted or unsubstituted, saturated or unsaturated ring; Provided that the pair of $R_{251}$ and $R_{252}$ and the pair of $R_{252}$ and $R_{253}$ do not form a ring simultaneously; the pair of $R_{254}$ and $R_{255}$ and the pair of $R_{255}$ and $R_{256}$ do not form a ring simultaneously; the pair of $R_{255}$ and $R_{256}$ and the pair of $R_{256}$ and $R_{257}$ do not form a ring simultaneously; the pair of $R_{258}$ and $R_{259}$ and the pair of $R_{259}$ and $R_{260}$ do not form a ring simultaneously; and the pair of $R_{259}$ and $R_{260}$ and the pair of $R_{260}$ and $R_{261}$ do not form a ring simultaneously;

When two or more rings are formed by $R_{251}$ to $R_{261}$, the rings may be the same or different;

$R_{251}$ to $R_{261}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or —Si($R_{9001}$)($R_{902}$)($R_{903}$),
—O—($R_{904}$),
—S—($R_{905}$),
—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{9001}$ to $R_{907}$ are as defined in the formula (1).

In the formula (25), $R_n$ and $R_{n+1}$ (n is an integer selected from 251, 252, 254 to 256 and 258 to 260) bond with each other to form a substituted or unsubstituted, saturated or unsaturated ring together with two ring carbon atoms to which $R_n$ and $R_{n+1}$ bond with. The ring is preferably configured with atoms selected from C atom, O atom, S atom and N atom, and the number of atoms is preferably 3 to 7, more preferably 5 or 6.

The number of the above-described ring structures in the compound represented by the formula (25) is, for example, 2, 3 or 4. Two or more ring structures may exist in the same benzene ring of the main skeleton in the formula (25), or may exist in different benzene rings. For example, the compound has three ring structures, one ring structure may exist in each of the three benzene rings in the formula (25).

As the above-mentioned ring structure in the compound represented by the formula (25), structures represented by the following formulas (251) to (260) can be given, for example.

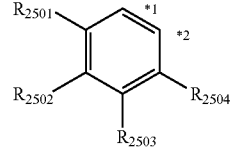
(251)

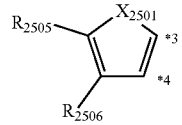
(252)

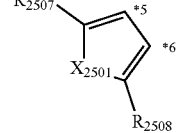
(253)

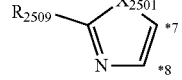
(254)

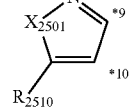
(255)

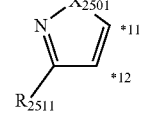
(256)

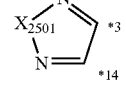
(257)

wherein in the formulas (251) to (257), each of *1 and *2, *3 and *4, *5 and *6, *7 and *8, *9 and *10, *11 and *12, and *13 and *14 represents two ring carbon atoms to which $R_n$ and $R_{n+1}$ bond, and $R_n$ may bond to either one of the two ring carbon atoms of *1 and *2, *3 and *4, *5 and *6, *7 and *8, *9 and *10, *11 and *12, and *13 and *14;

$X_{2501}$ is C($R_{2512}$) ($R_{2513}$), N$R_{2514}$, O or S;

One or more pairs of two or more adjacent groups of $R_{2501}$ to $R_{2506}$ and $R_{2512}$ to $R_{2513}$ are bonded with each other to form a substituted or unsubstituted, saturated or unsaturated ring, or do not form a substituted or unsubstituted saturated or unsaturated ring; and $R_{2501}$ to $R_{2514}$ that do not form a substituted or unsubstituted saturated or unsaturated ring are the same as $R_{251}$ to $R_{261}$.

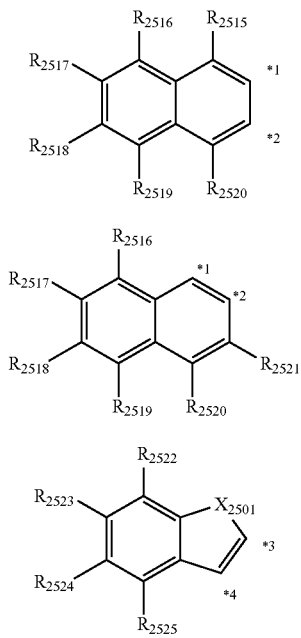

(258)

(259)

(260)

wherein in the formulas (258) to (260), each of *1 and *2, and *3 and *4 represents two ring carbon atoms to which $R_n$ and $R_{n+1}$ bond, and $R_n$ may bond to either one of the two ring carbon atoms of *1 and *2, or 3 and *4;

$X_{2501}$ is $C(R_{2512})(R_{2513})$, $NR_{2514}$, O or S;

One or more pairs of two or more adjacent groups of $R_{2515}$ to $R_{2525}$ bond to each other to form a substituted or unsubstituted, saturated or unsaturated ring, or do not form a substituted or unsubstituted saturated or unsaturated ring; and $R_{2515}$ to $R_{2521}$ and $R_{2522}$ to $R_{2525}$ that do not form a substituted or unsubstituted saturated or unsaturated ring are the same as $R_{251}$ to $R_{261}$.

In the formula (25), it is preferable that at least one of $R_{252}$, $R_{254}$, $R_{255}$, $R_{260}$ and $R_{261}$ (preferably at least one of $R_{252}$, $R_{255}$, and $R_{260}$, more preferably $R_{252}$) is a group which does not form a ring.

(i) Substituent in the case where the ring structure formed by $R_n$ and $R_{n+1}$ has a substituent in the formula (25),
(ii) $R_{251}$ to $R_{261}$ that do not form a ring structure in the formula (25), and
(iii) $R_{2501}$ to $R_{2514}$ and $R_{2515}$ to $R_{2525}$ in the formulas (251) to (260) are preferably independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$N(R_{906})(R_{907})$,
a substituted or unsubstituted aryl group having 6 to 50 ring carbon atoms,
a substituted or unsubstituted monovalent heterocyclic group having 5 to 50 ring atoms, or a group selected from the following groups.

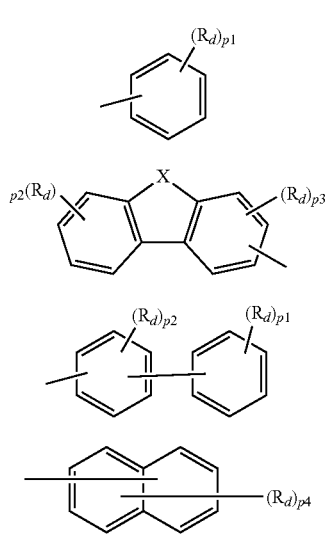

(261)

(262)

(263)

(264)

wherein in the formulas (261) to (264),
$R_d$s are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
X is $C(R_{901})(R_{902})$, $NR_{903}$, O, or S;
$R_{901}$ to $R_{907}$ are as defined in the formula (1); and
p1 is an integer of 0 to 5, p2 is an integer of 0 to 4, p3 is an integer of 0 to 3, and p4 is an integer of 0 to 7.

In one embodiment, the compound represented by the formula (25) is represented by the following formulas (25-1) to (25-6).

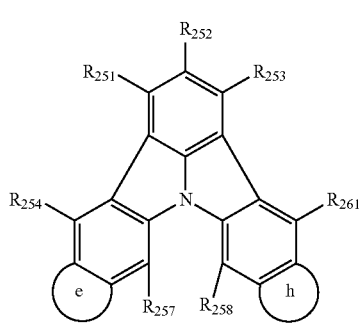

(25-1)

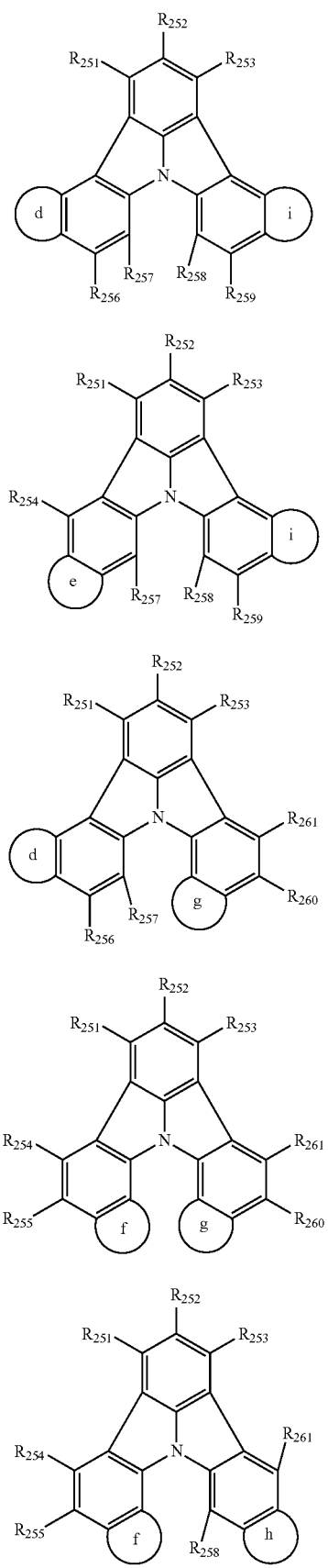
wherein in the formulas (25-1) to (25-6), ring d to ring i are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-7) to (25-12).

(25-11)
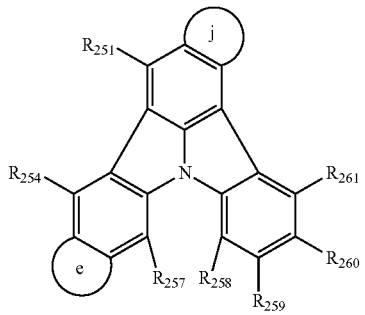
(25-12)
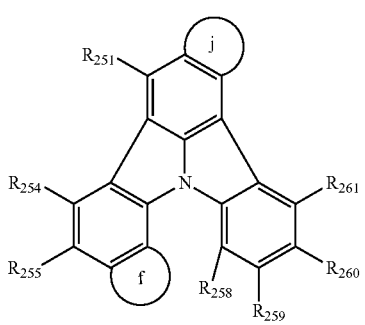
wherein in the formulas (25-7) to (25-12), ring d to ring f, ring k, and ring j are independently a substituted or unsubstituted, saturated or unsaturated ring; and $R_{251}$ to $R_{261}$ are the same as defined in the formula (25).
[0140] In one embodiment, the compound represented by the formula (25) is represented by the following formulas (25-13) to (25-21).
(25-13)
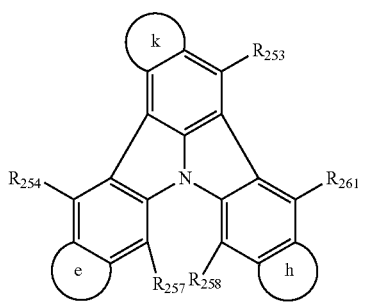
(25-14)
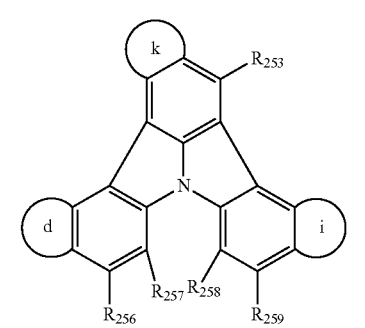
(25-15)
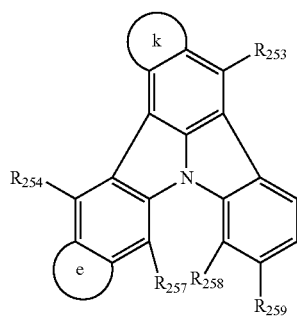
(25-16)
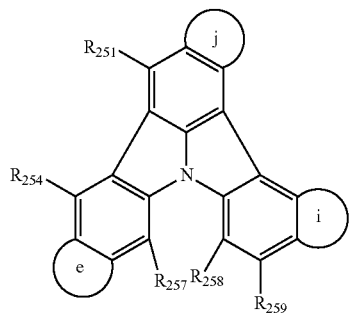
(25-17)
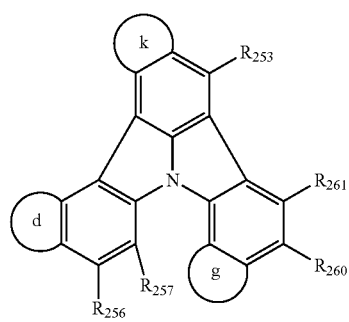
(25-18)
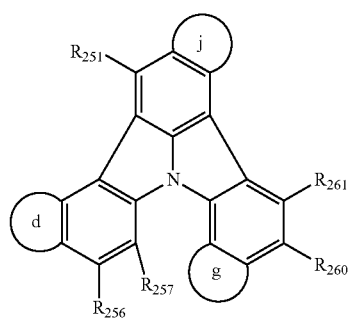
(25-19)
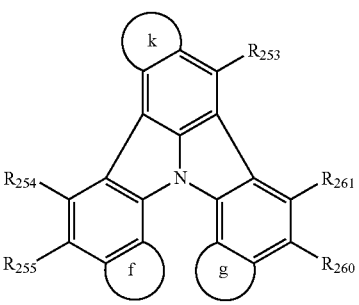

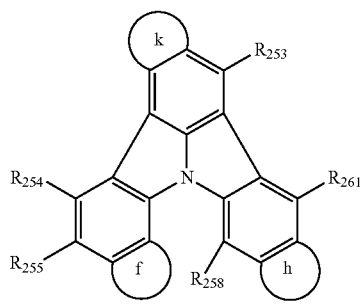

(25-20)

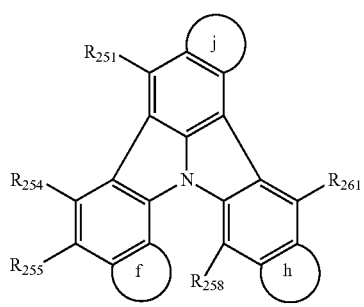

(25-21)

wherein in the formulas (25-13) to (25-21), ring d to ring k are independently a substituted or unsubstituted, saturated or unsaturated ring; and $R_{251}$ to $R_{261}$ are the same as defined in the formula (25).

As a substituent in the case where the ring g or ring h further has a substituent, a substituted or unsubstituted alkyl group having 1 to 50 carbon atoms, a substituted or unsubstituted aryl group having 6 to 50 ring carbon atoms, or a group represented by the formula (261), (263) or (264) can be given for example.

In one embodiment, the compound represented by the formula (25) is represented by one of the following formulas (25-22) to (25-25).

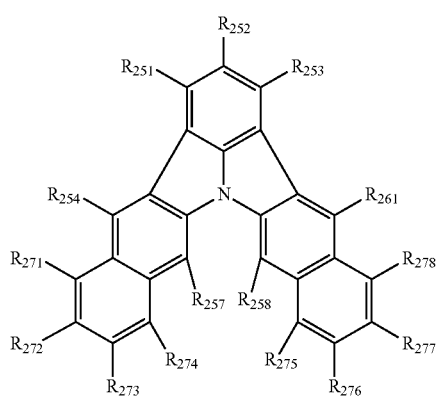

(25-22)

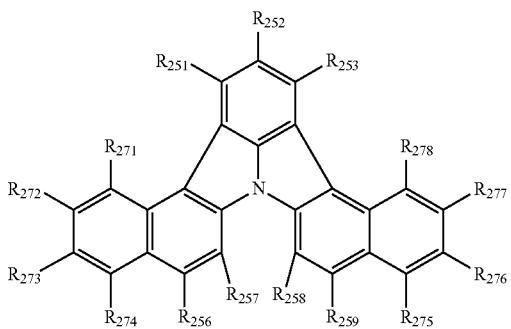

(25-23)

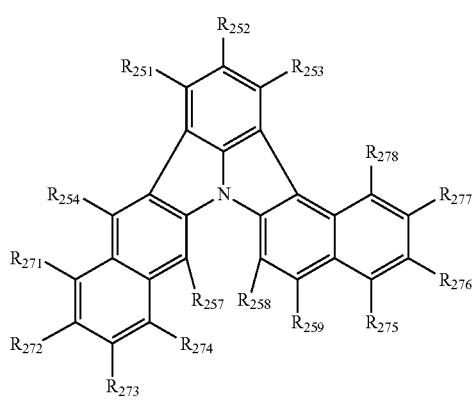

(25-24)

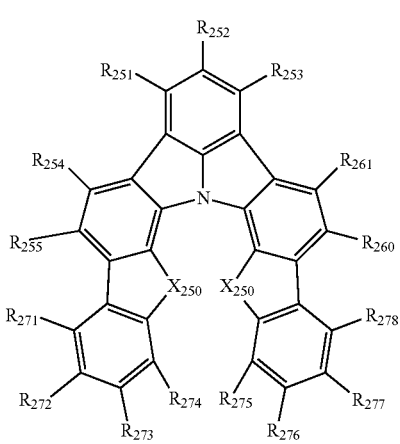

(25-25)

wherein in the formulas (25-22) to (25-25), $X_{250}$ is $C(R_{901})(R_{902})$, $NR_{903}$, O or S; $R_{251}$ to $R_{261}$, and $R_{271}$ to $R_{278}$ are the same as $R_{251}$ to $R_{261}$ in the formula (25); and $R_{901}$ to $R_{903}$ are as defined in the formula (1).

In one embodiment, the compound represented by the formula (25) is represented by the following formula (25-26).

(25-26)
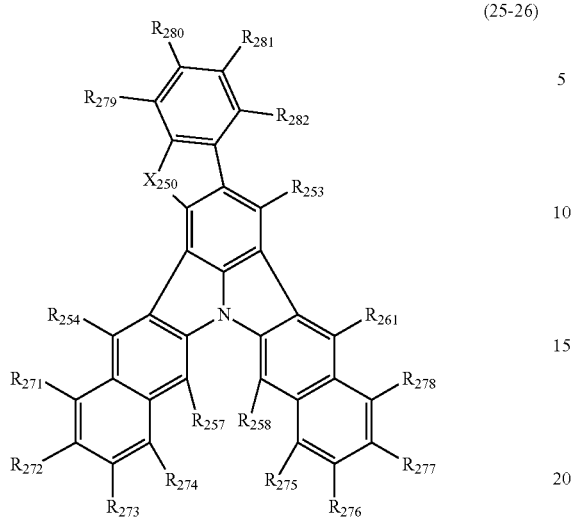
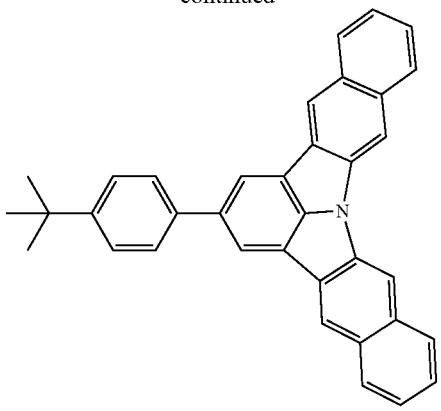
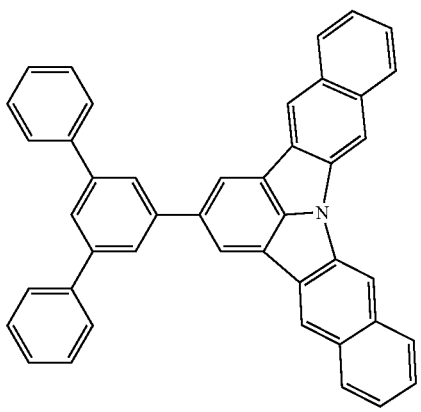
wherein in the formula (25-26), $X_{250}$ is $C(R_{901})(R_{902})$, $NR_{903}$, O or S; $R_{253}$, $R_{254}$, $R_{257}$, $R_{258}$, $R_{261}$, and $R_{271}$ to $R_{282}$ are the same as $R_{251}$ to $R_{261}$ in the formula (25); and $R_{901}$ to $R_{903}$ are as defined in the formula (1).
As the compound represented by the formula (21), the following compounds can be shown for example. In the following example compounds, Ph represents phenyl group and D represents deuterium atom.
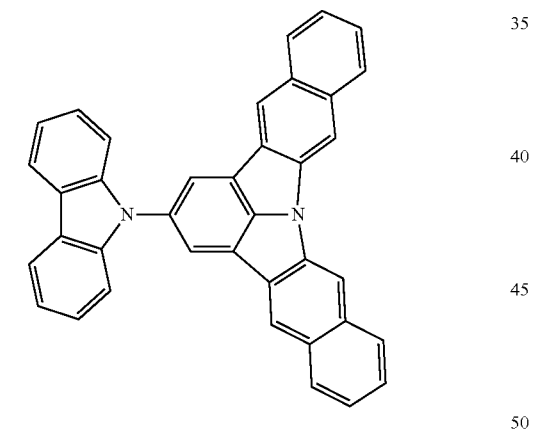
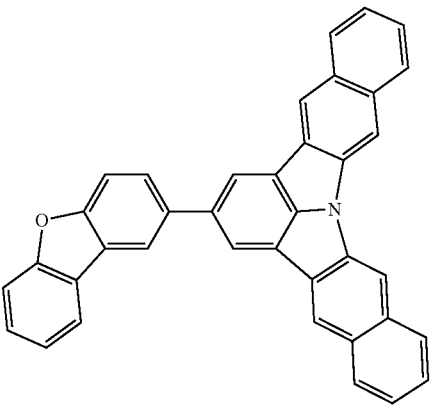
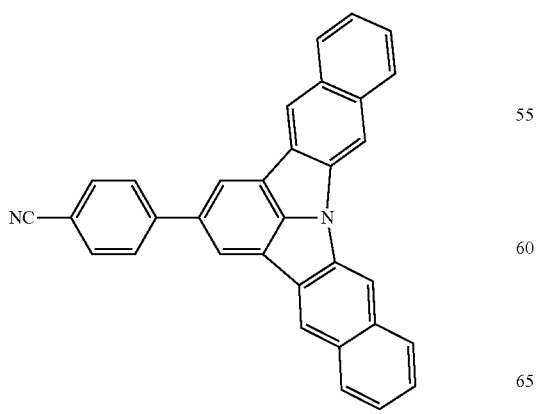
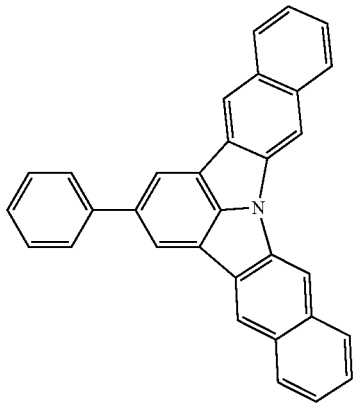

469
-continued
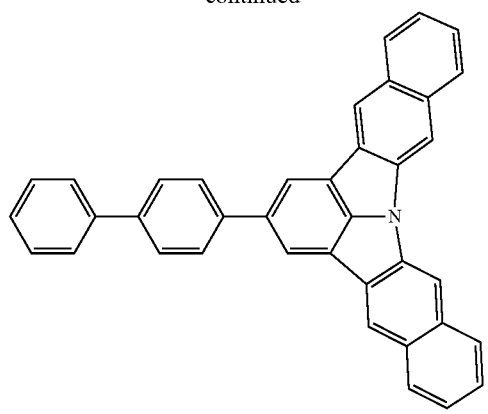
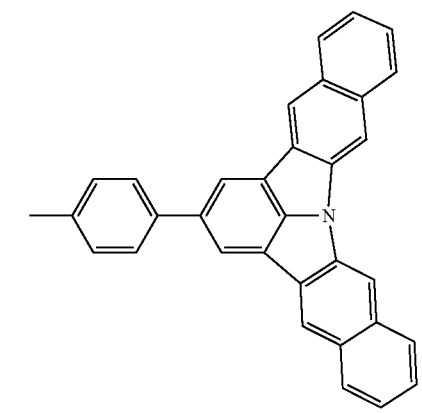
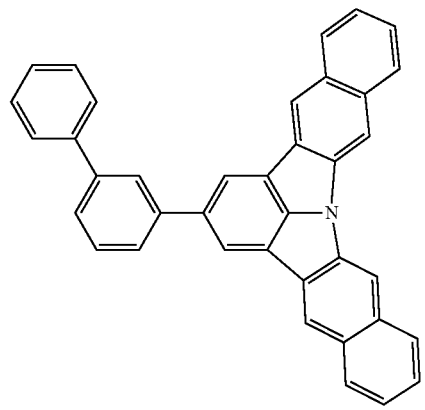
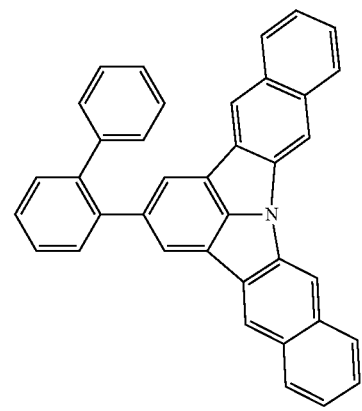
470
-continued
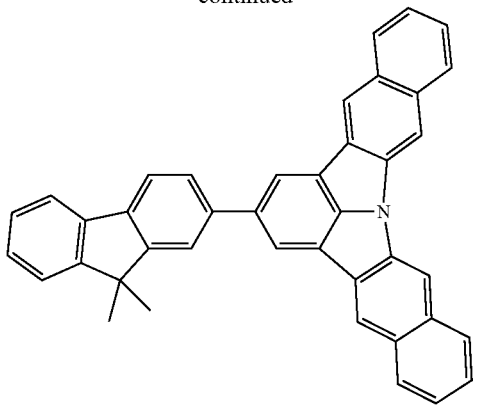
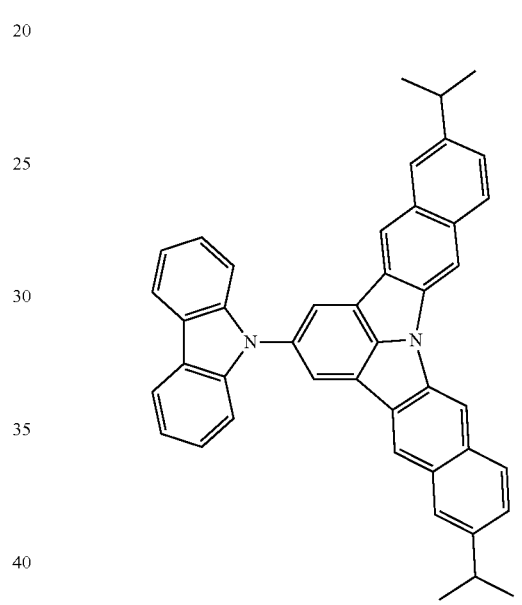
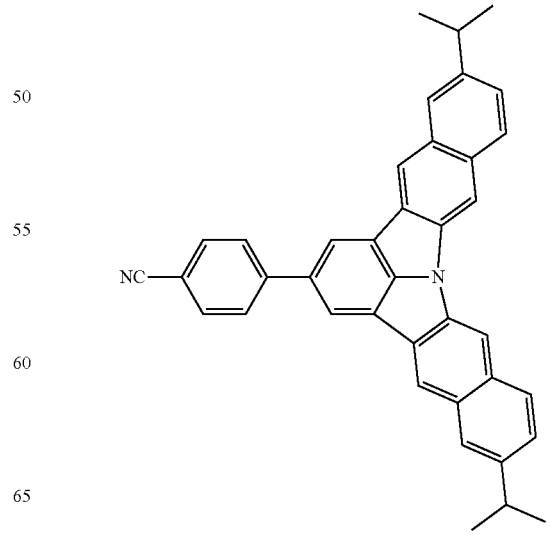

471
-continued
472
-continued
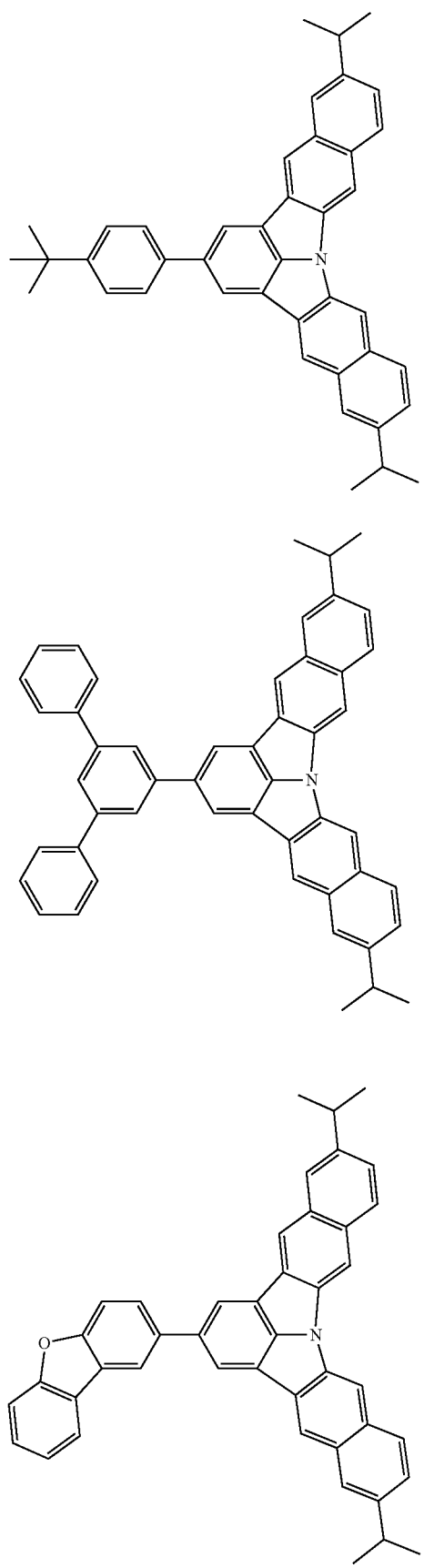
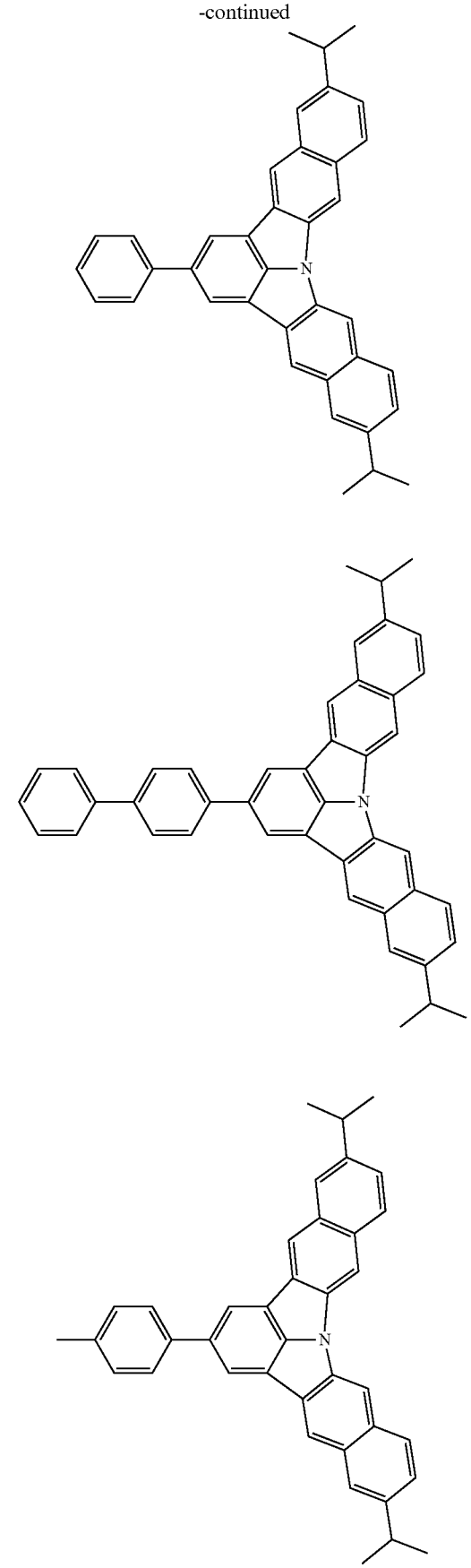

473
-continued
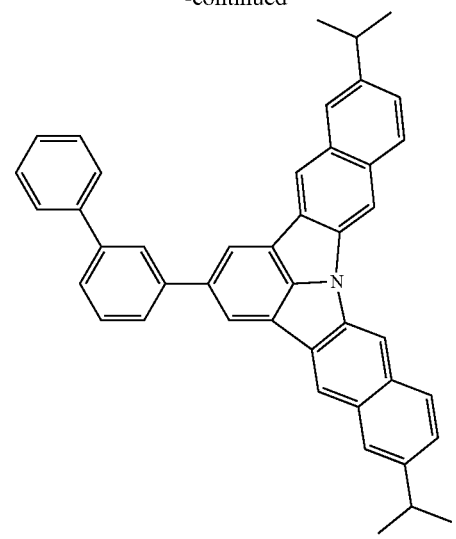
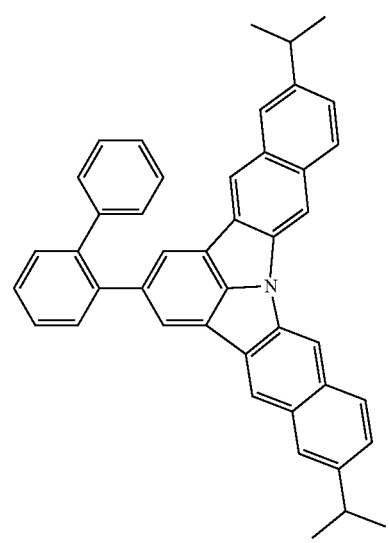
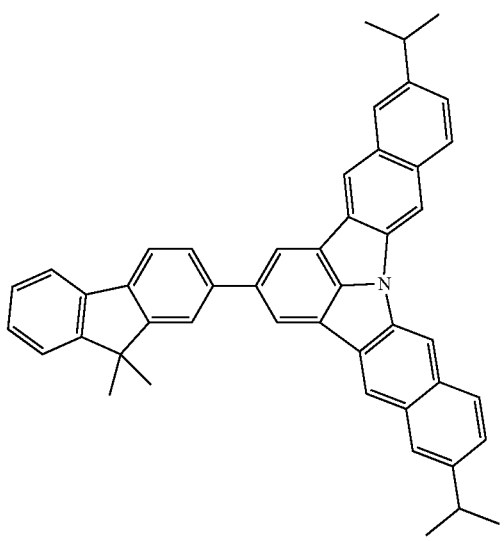
474
-continued
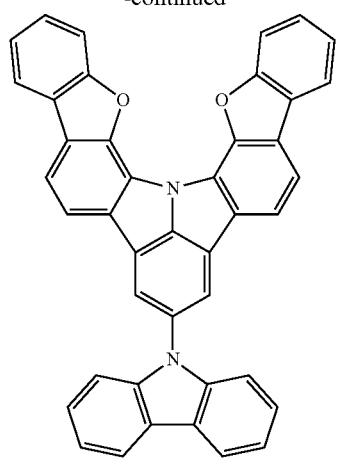
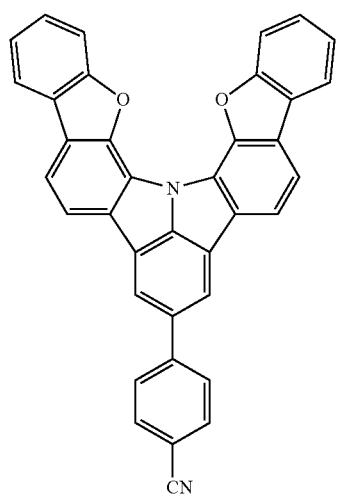
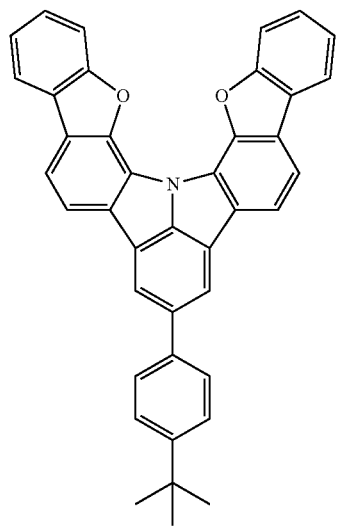

475
-continued
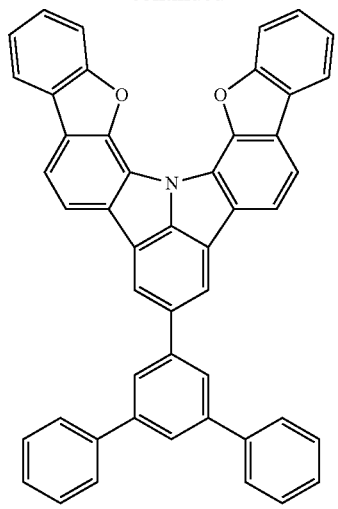
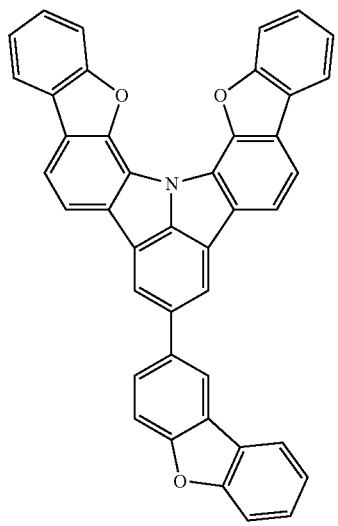
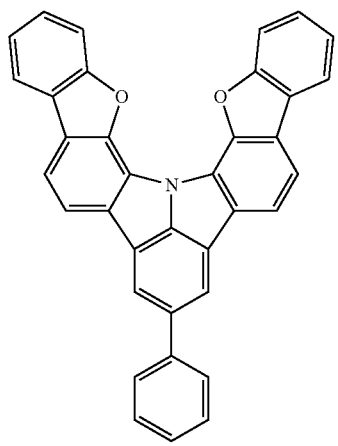
476
-continued
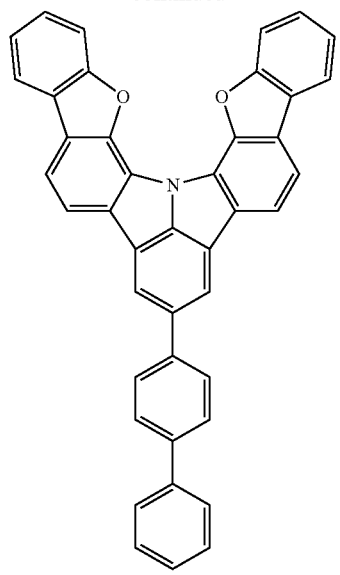
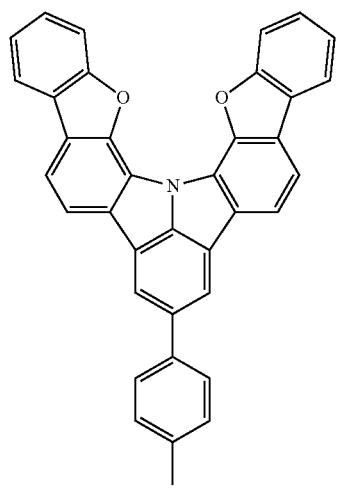
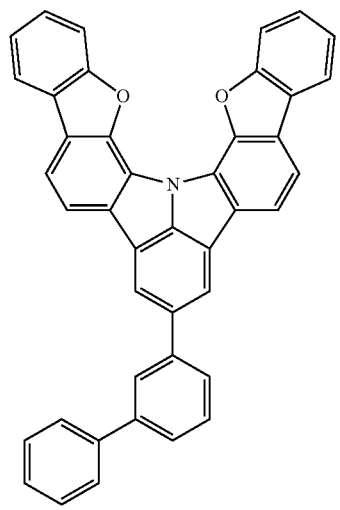

477
-continued
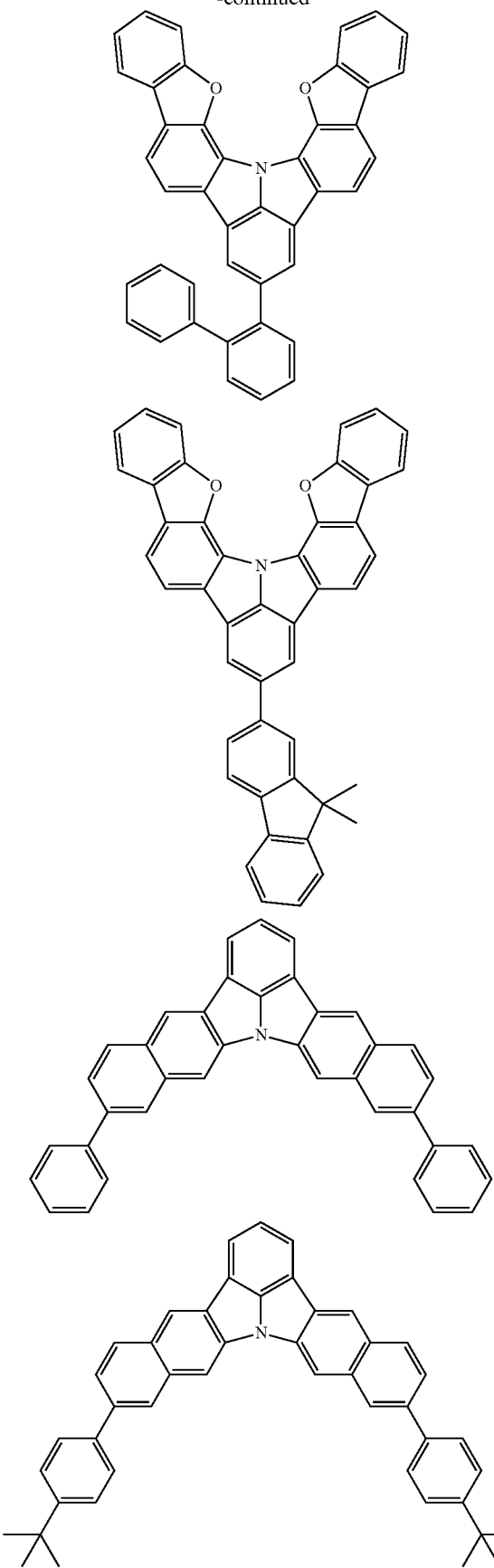
478
-continued
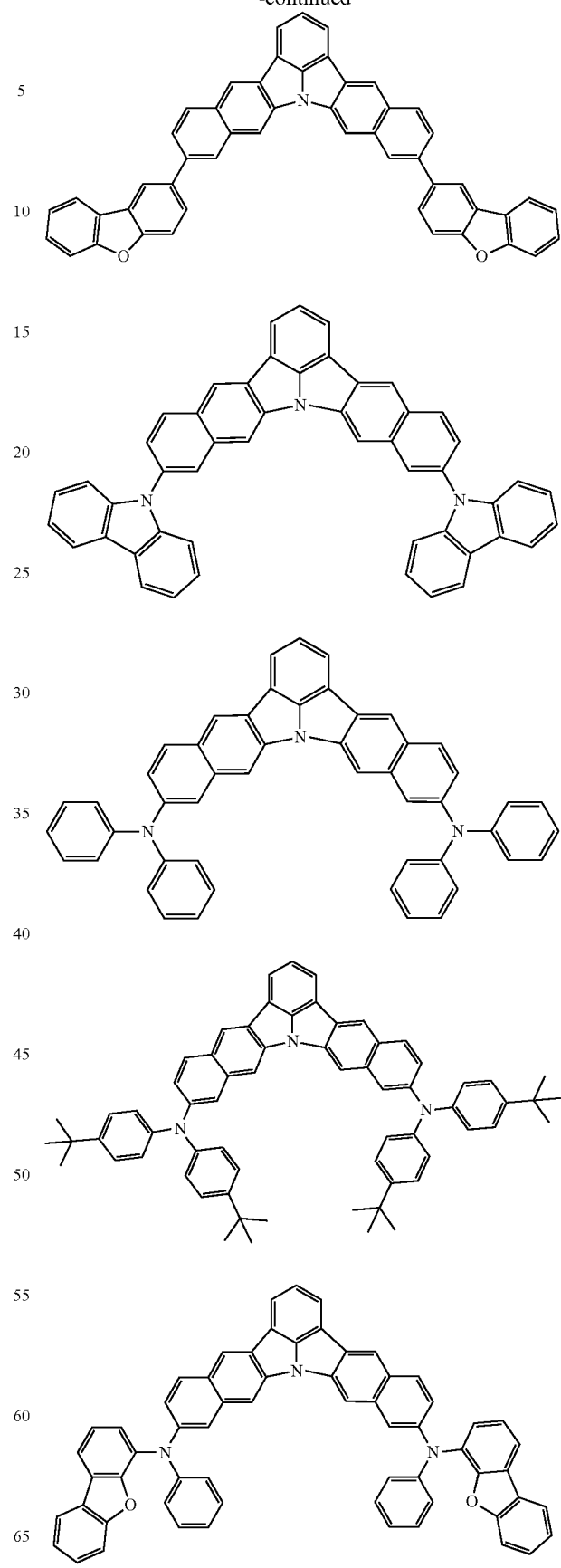

-continued
479
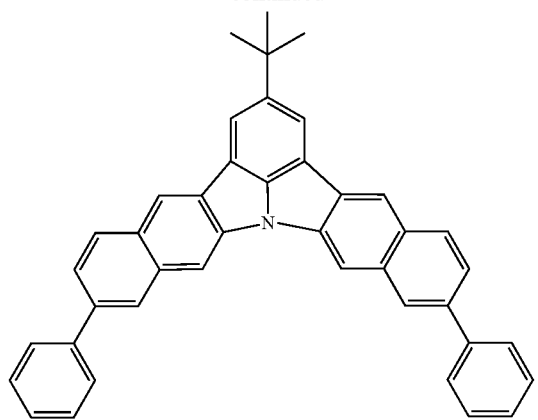
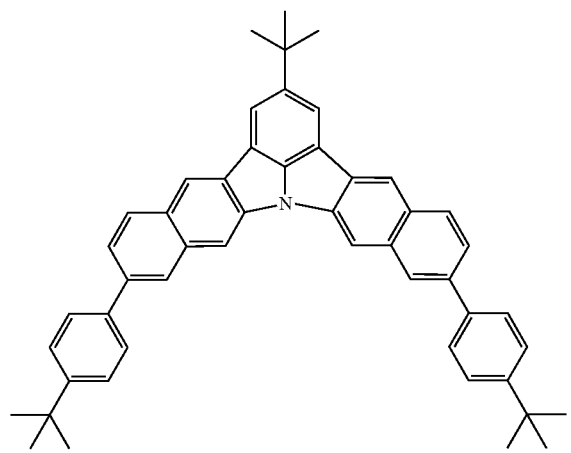
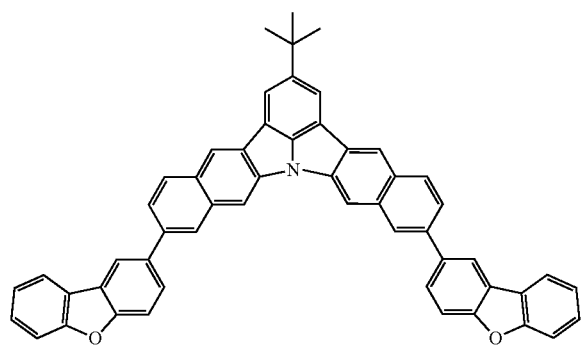
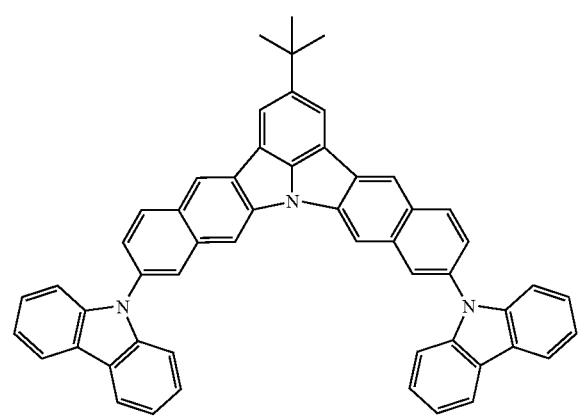
480
-continued
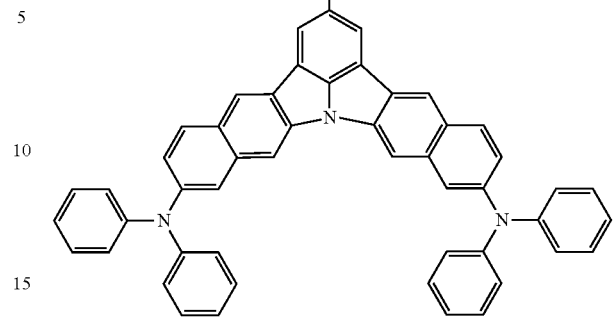
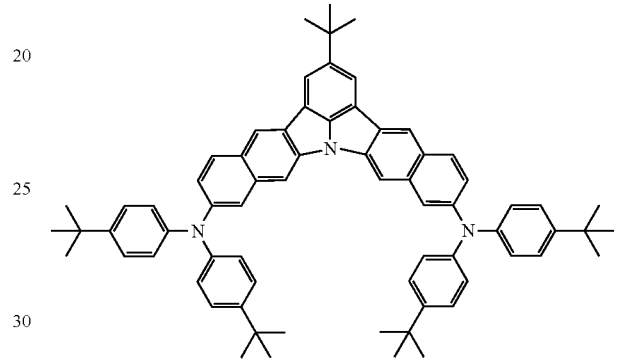
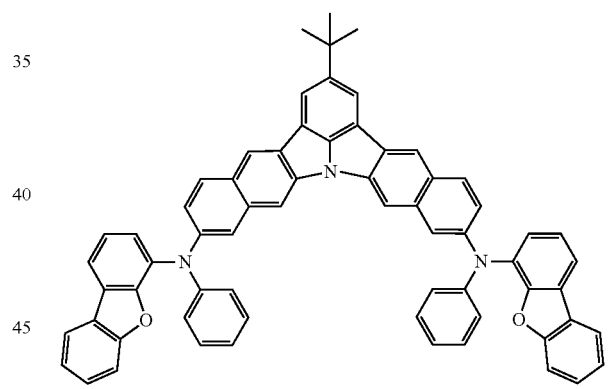
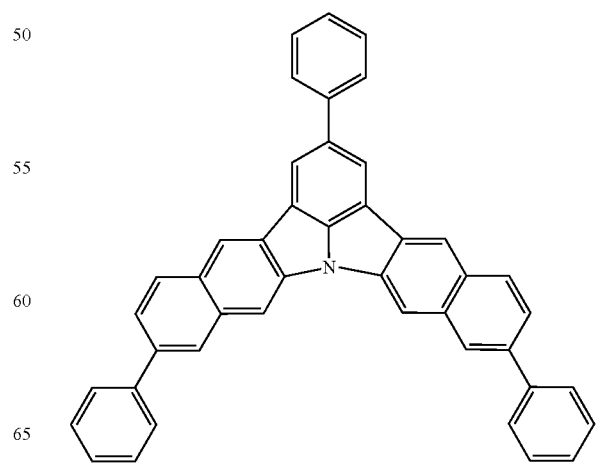

481
-continued
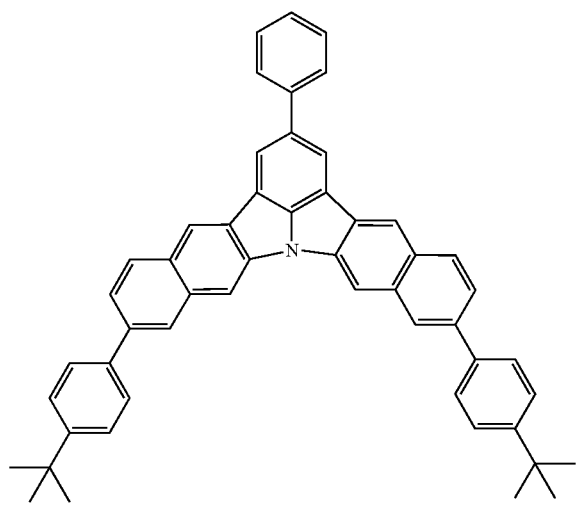
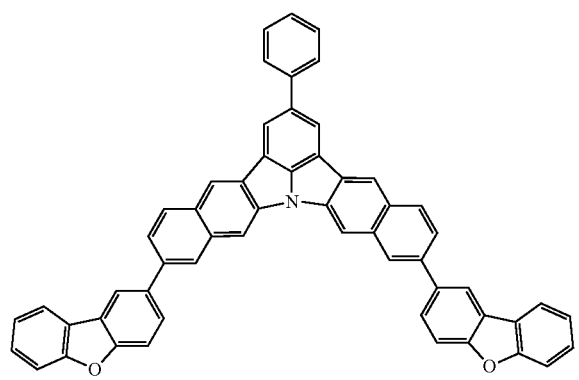
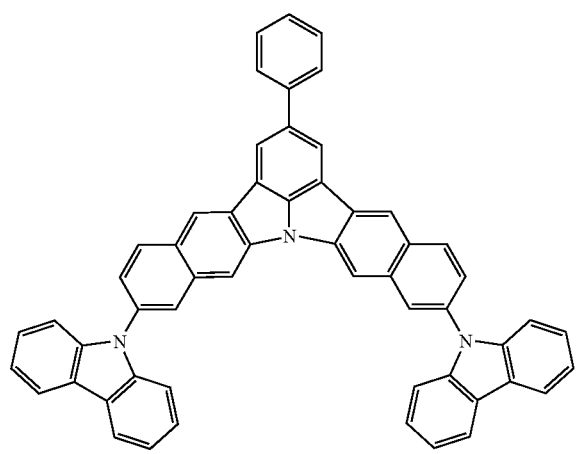
482
-continued
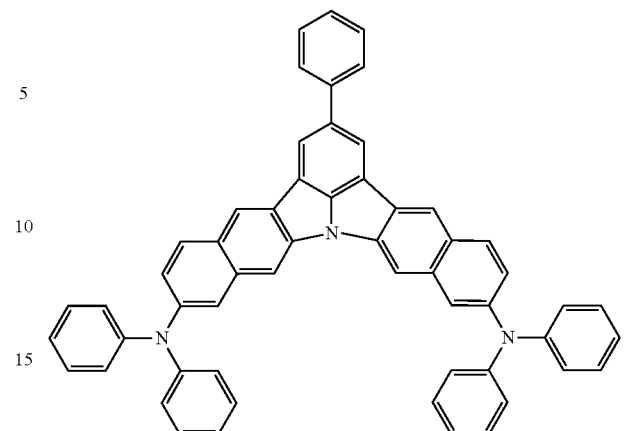
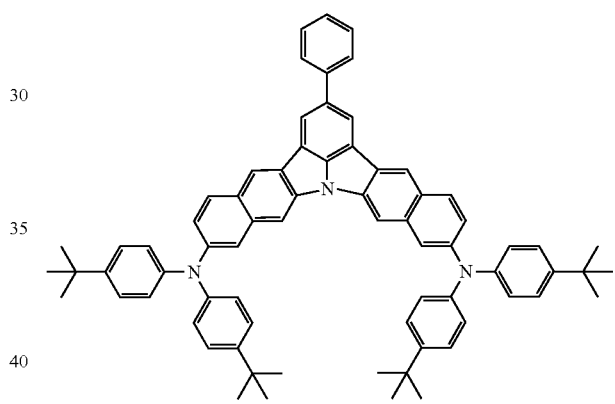
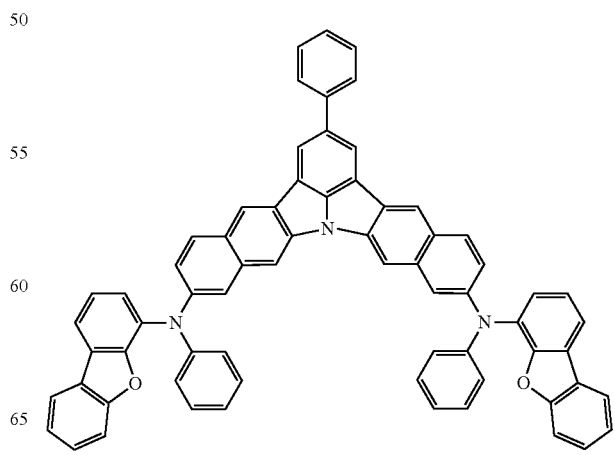

483
-continued
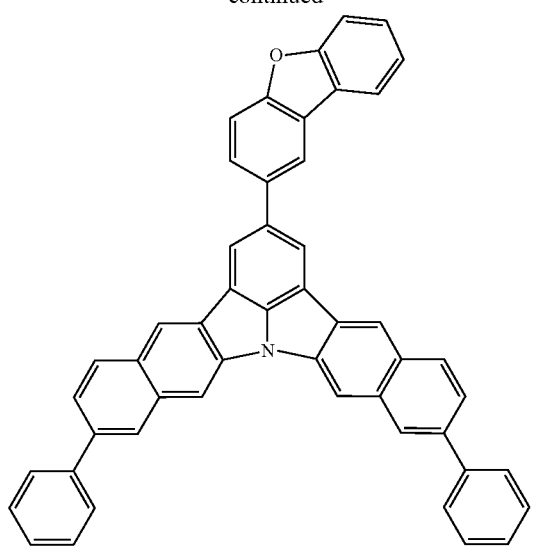
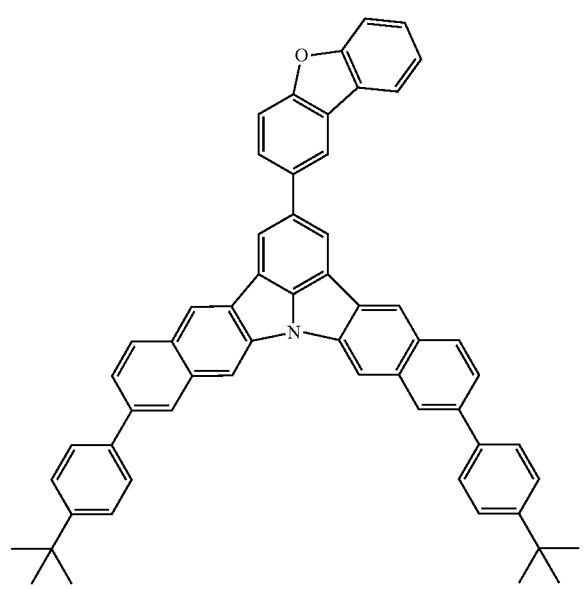
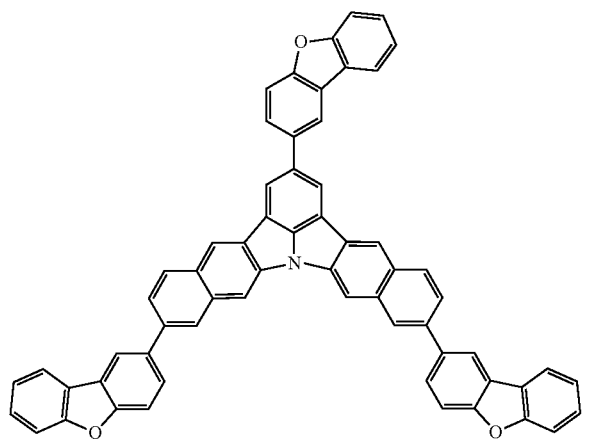
484
-continued
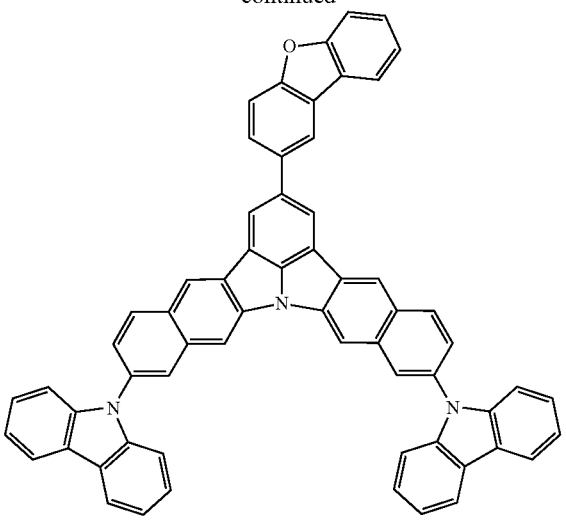
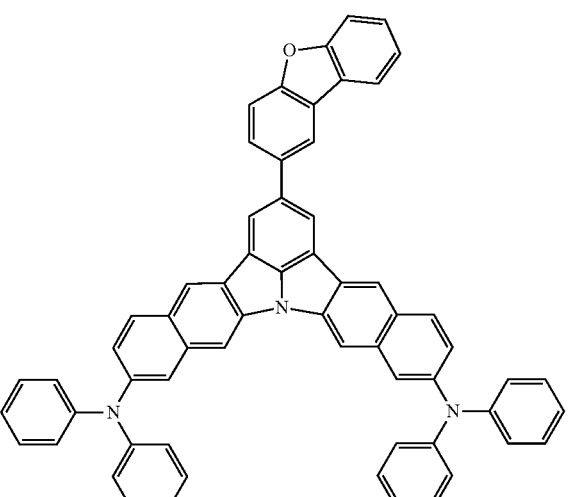
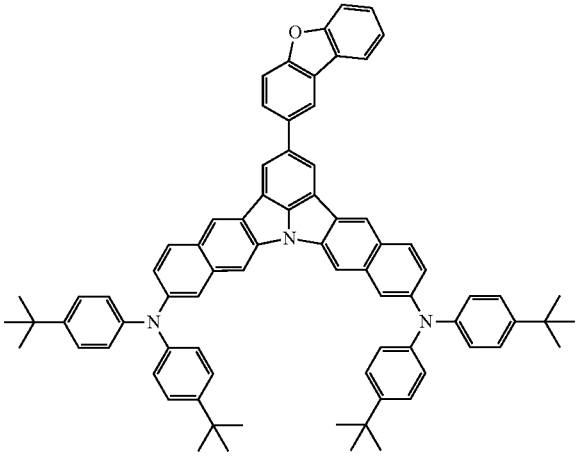

485
-continued
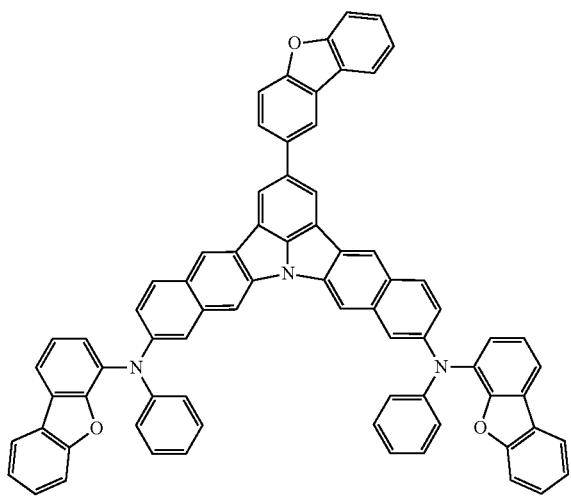
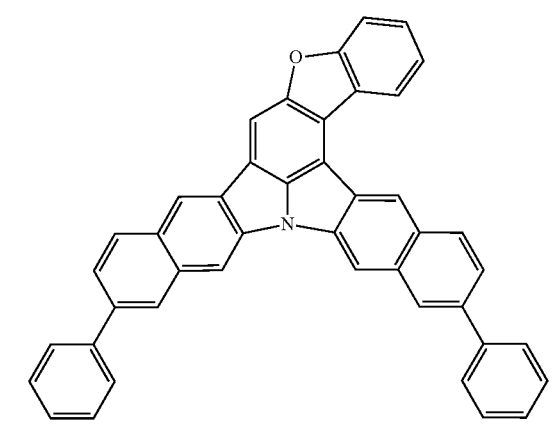
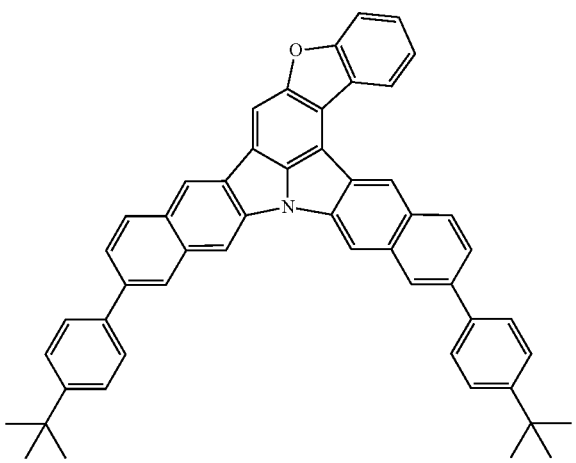
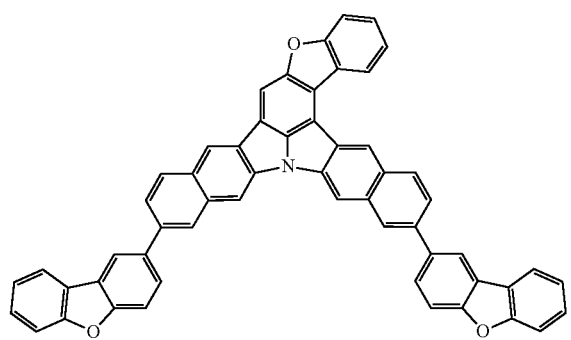
486
-continued
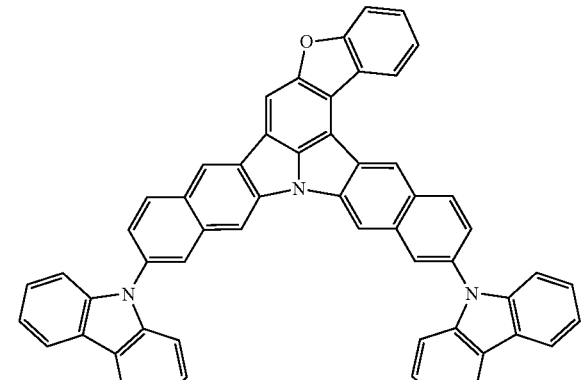
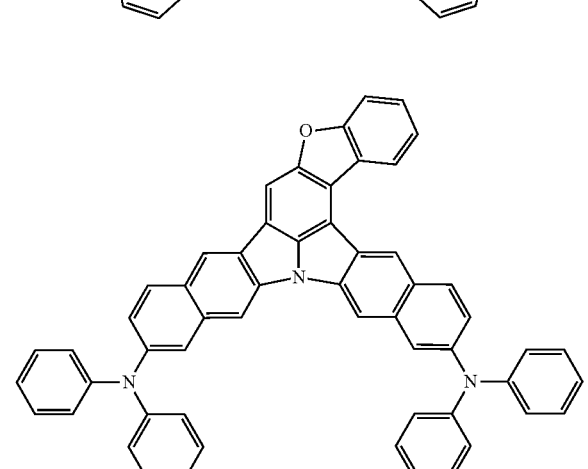
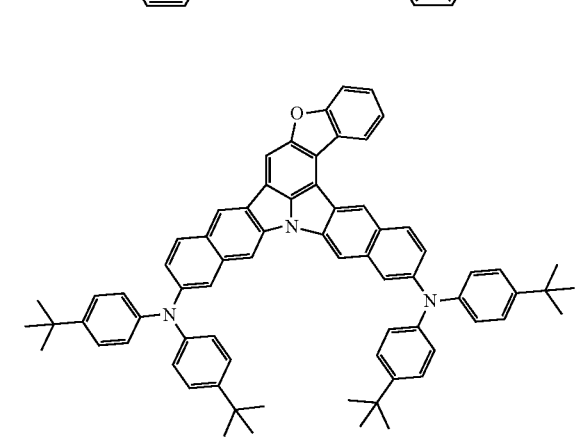
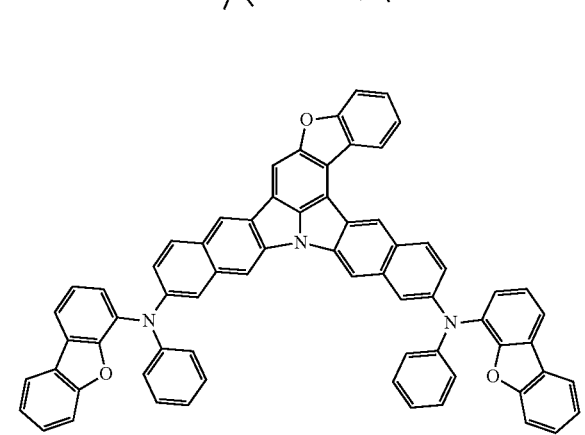

487
-continued
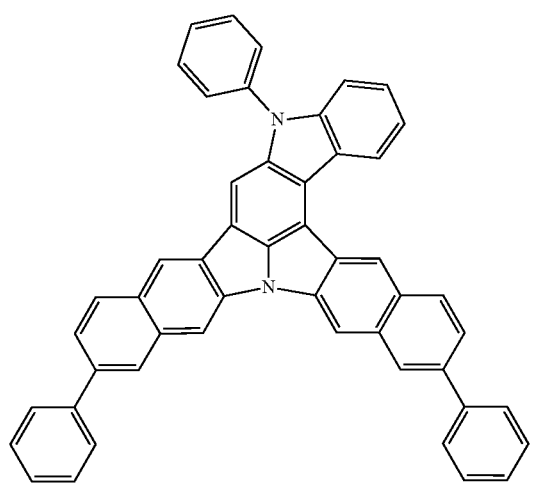
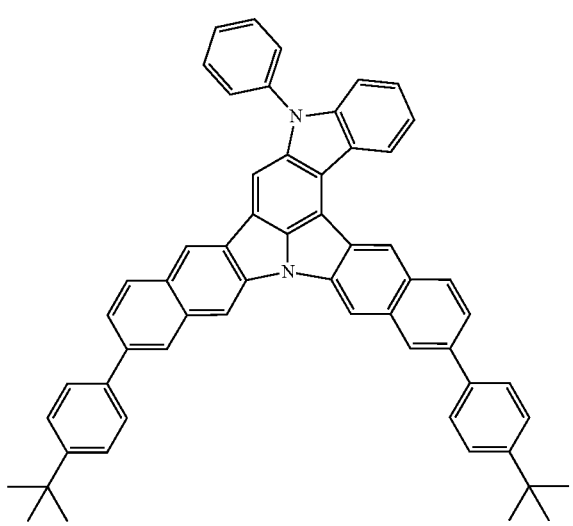
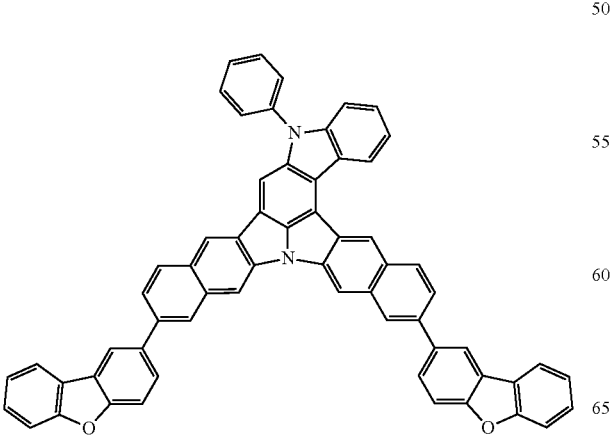
488
-continued
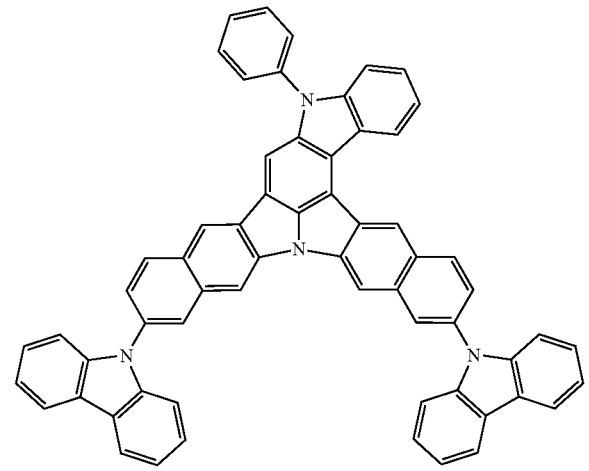
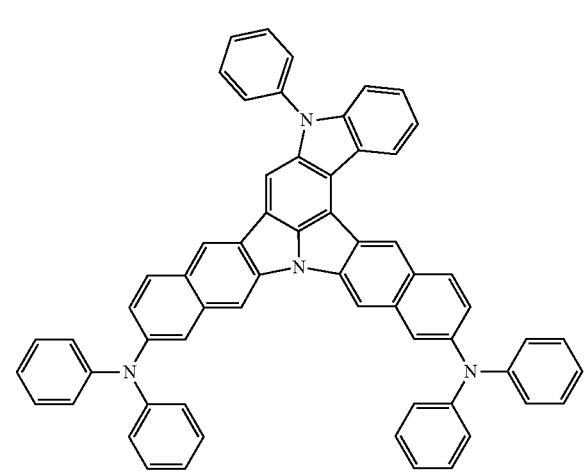
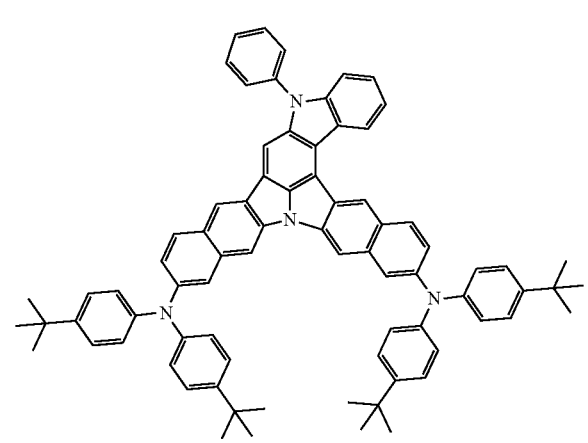

489
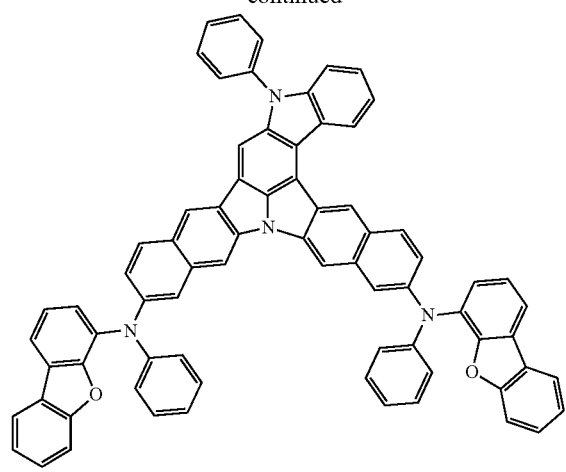
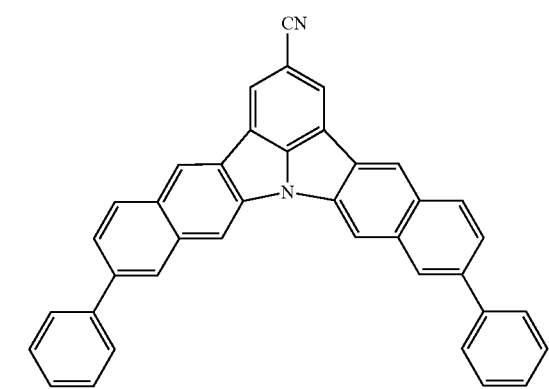
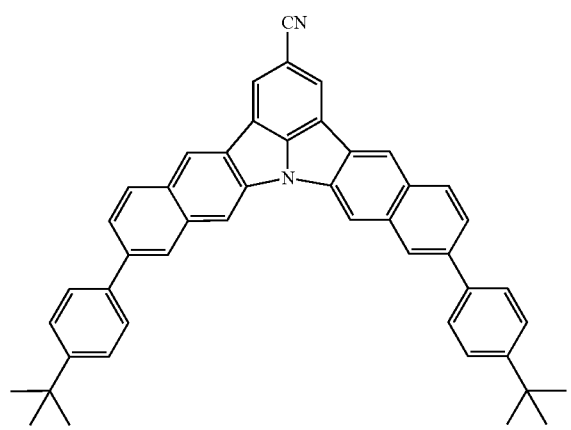
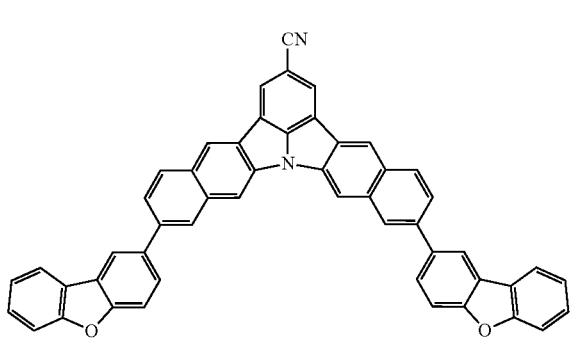
490
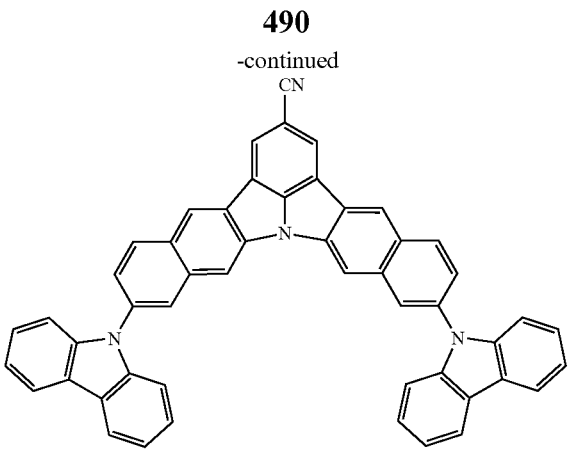
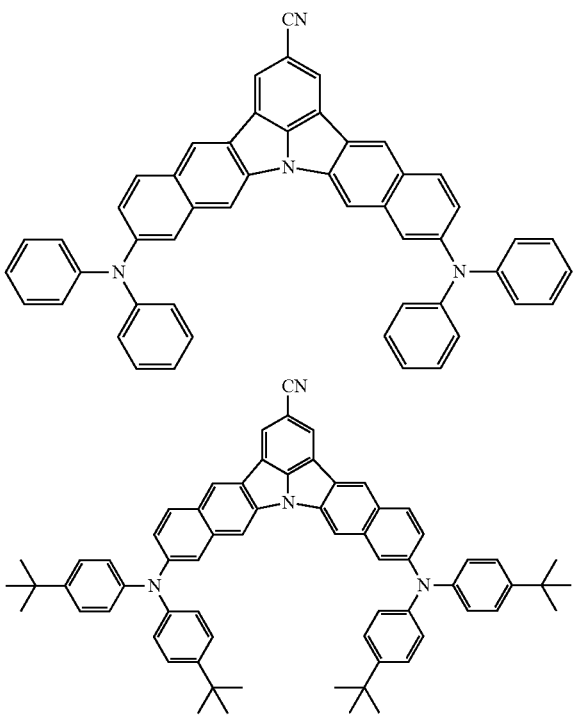
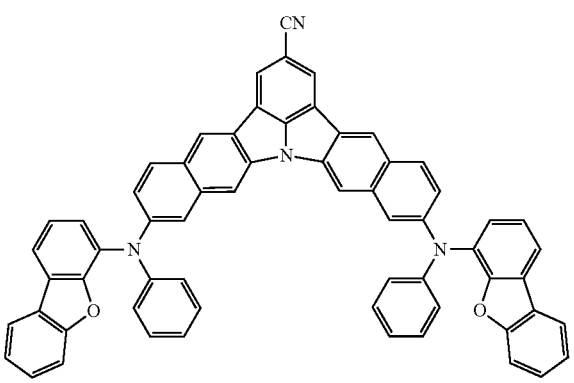
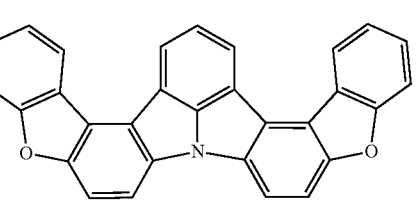

491
-continued
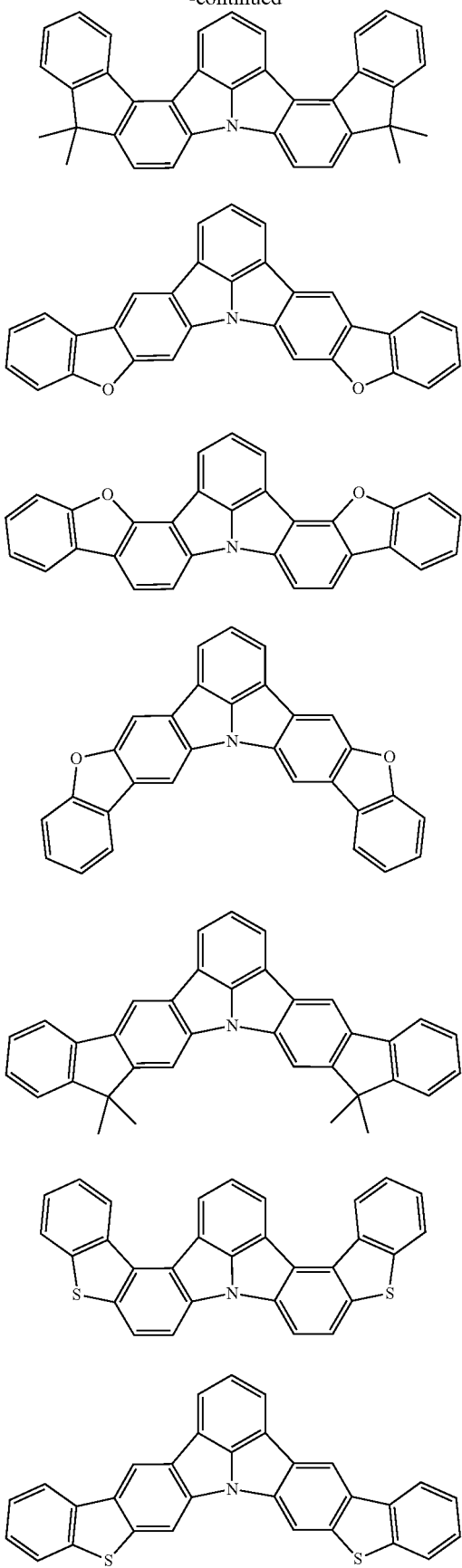
492
-continued
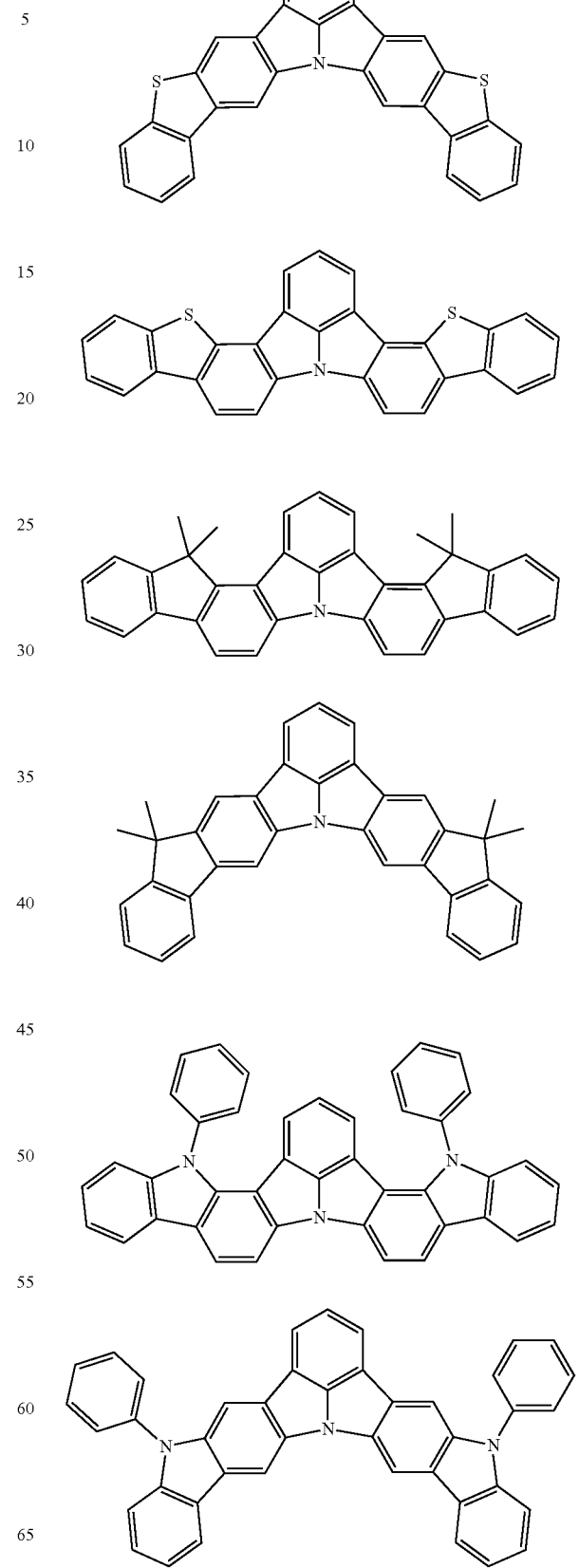

493
-continued
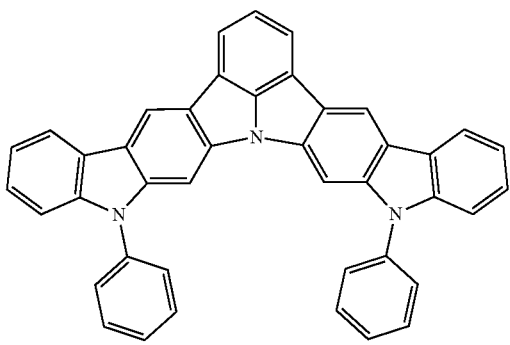
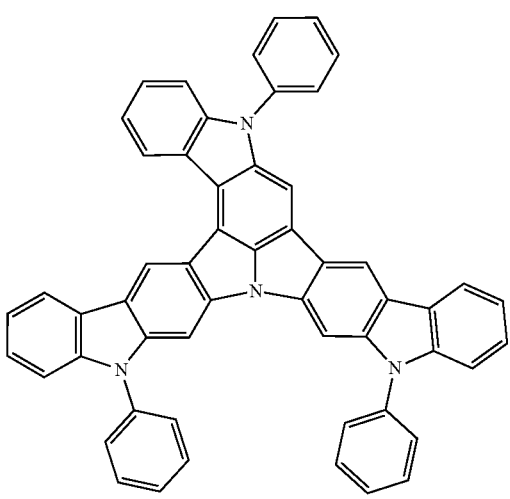
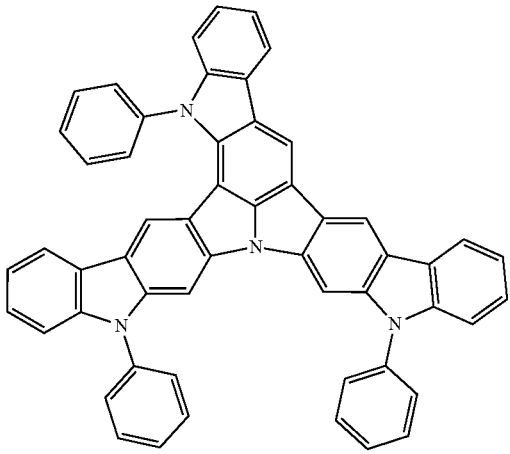
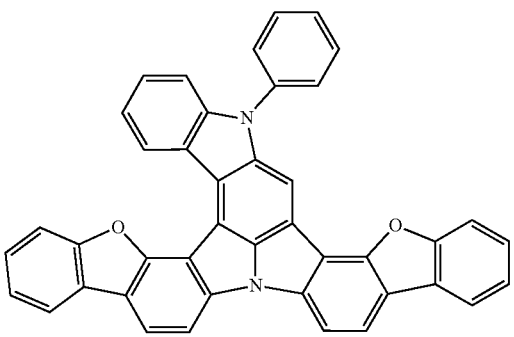
494
-continued
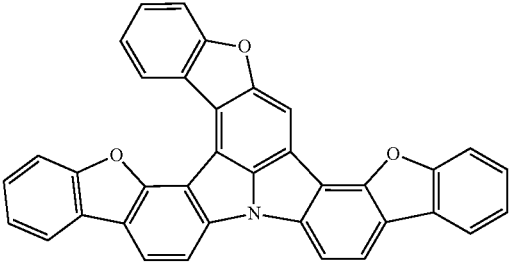
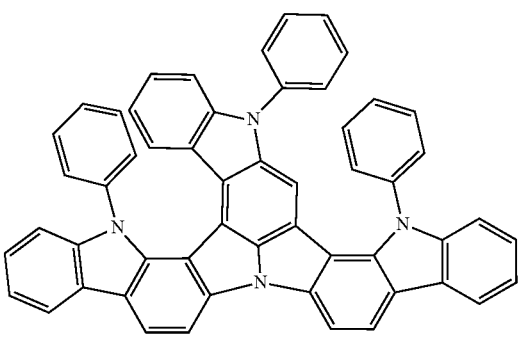
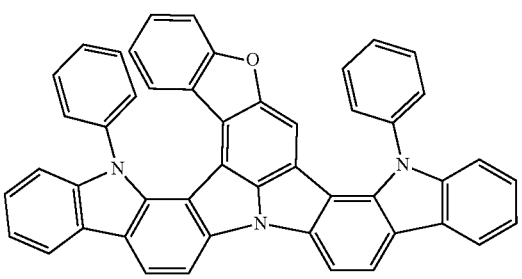
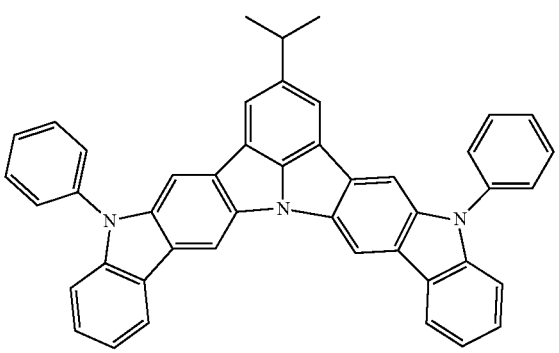
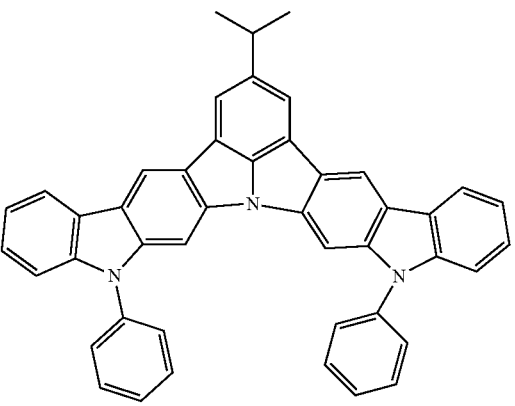

-continued
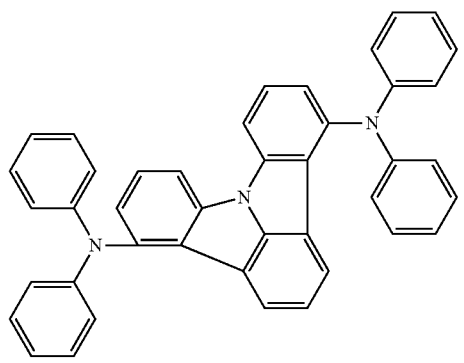
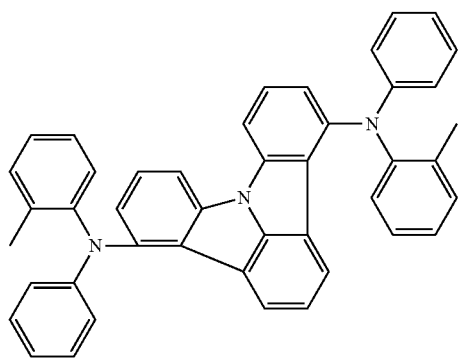
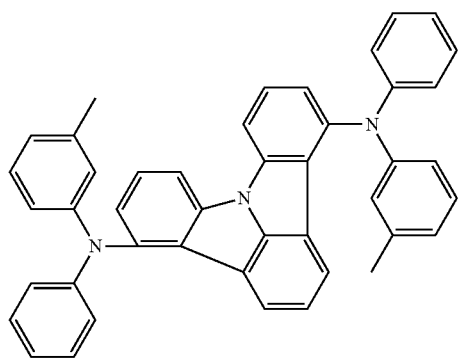
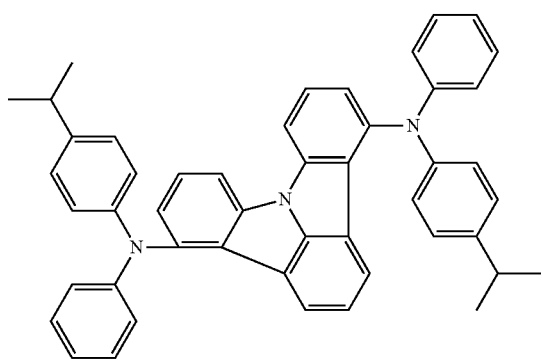
-continued
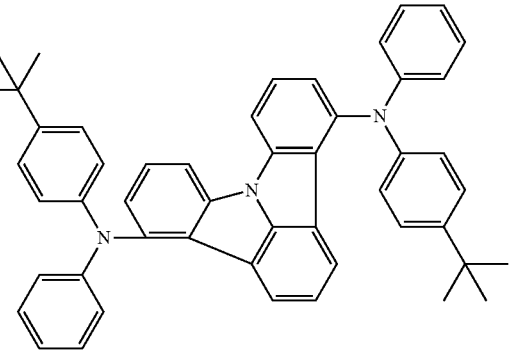
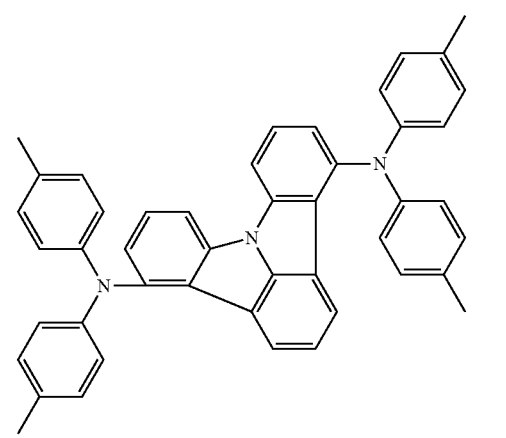
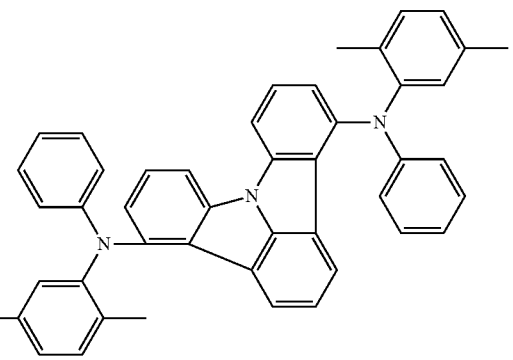
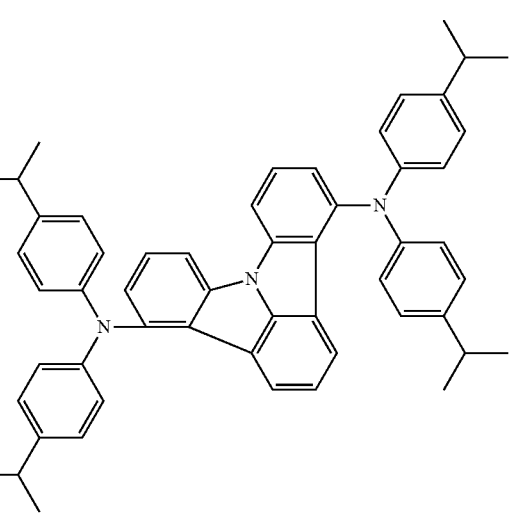

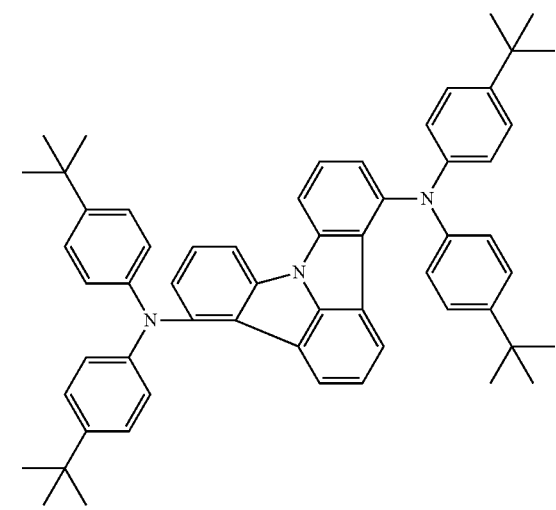
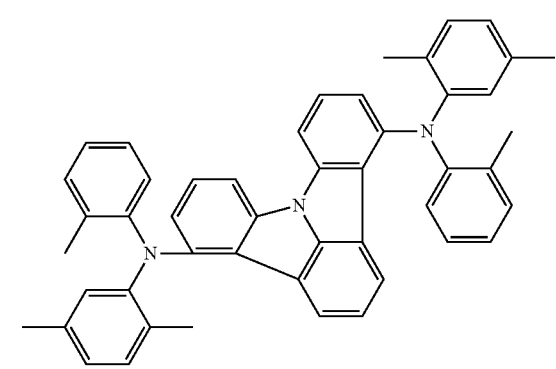
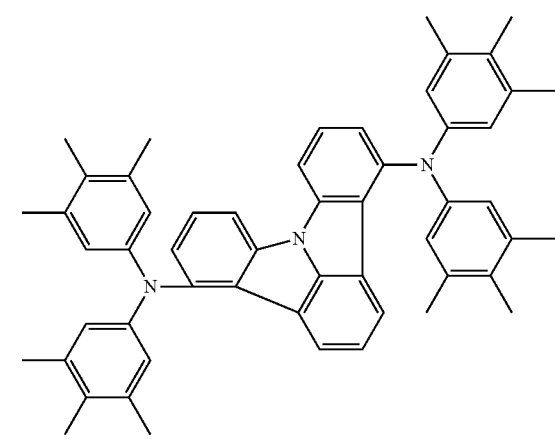
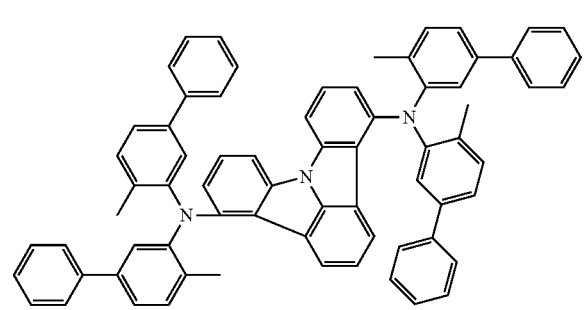
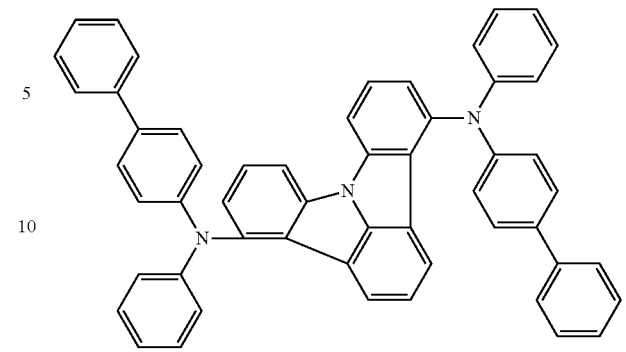
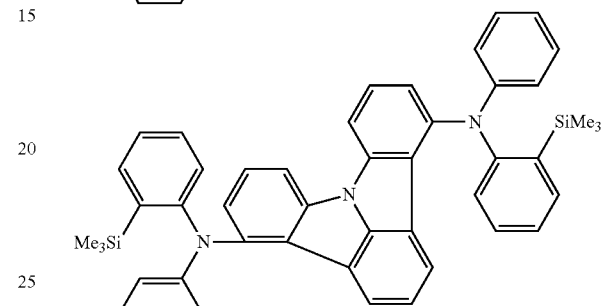
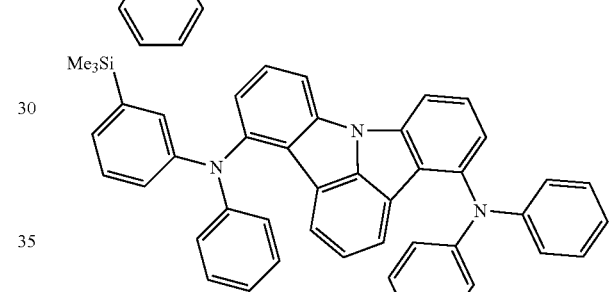
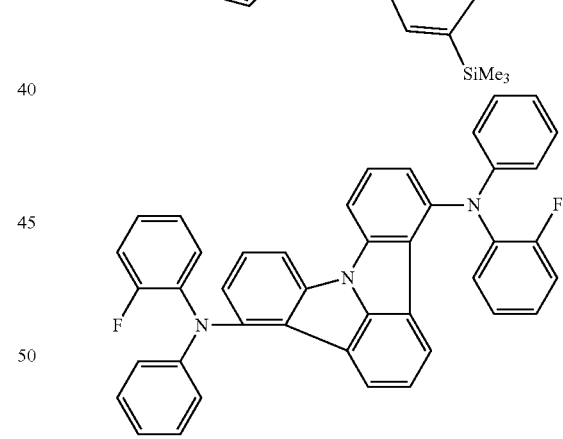
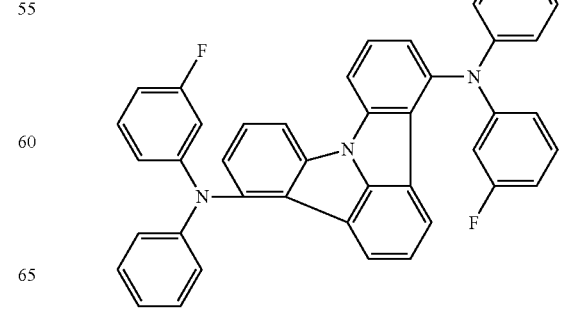

499
-continued
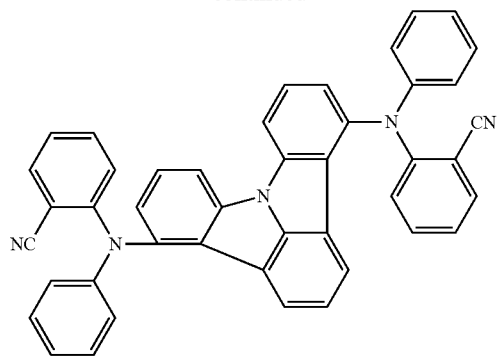
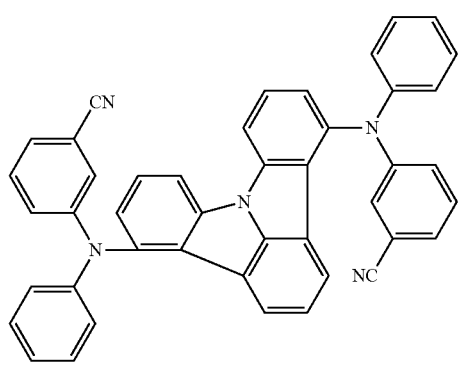
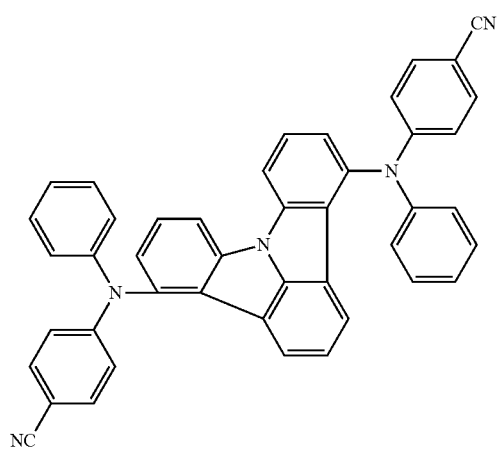
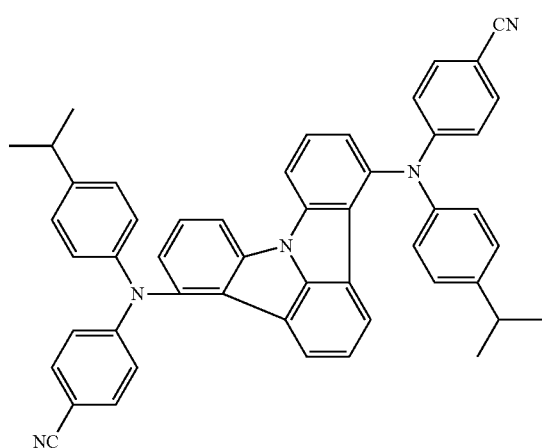
500
-continued
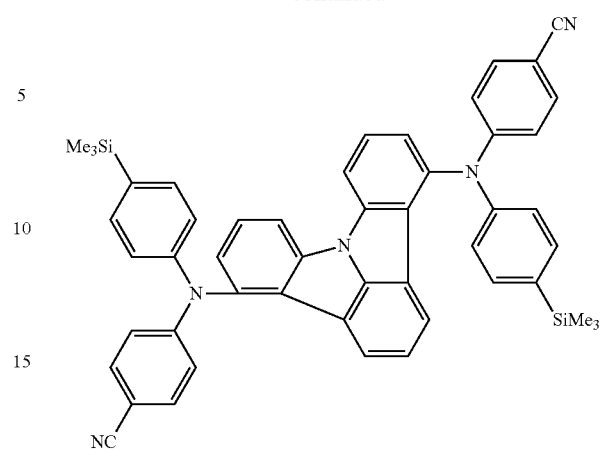
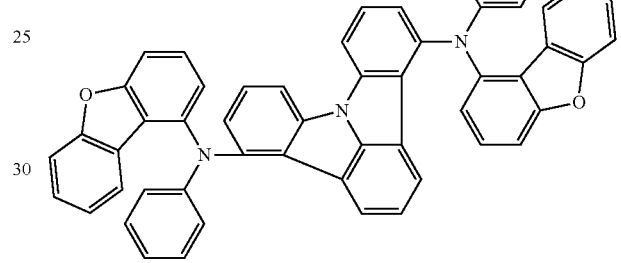
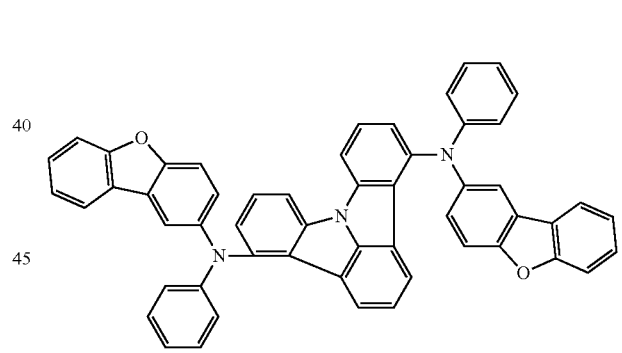
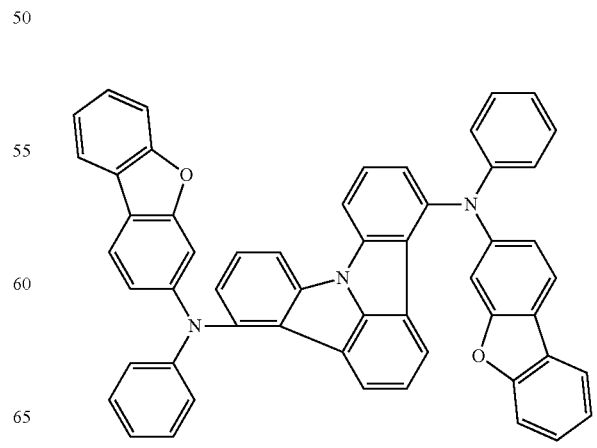

501
-continued
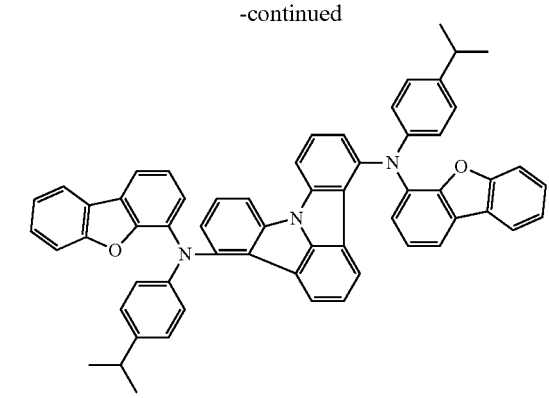
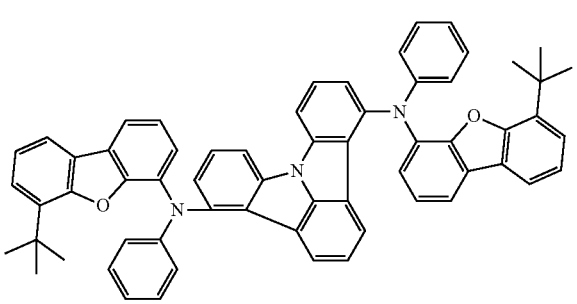
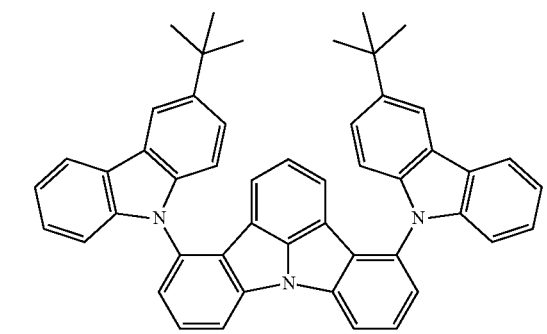
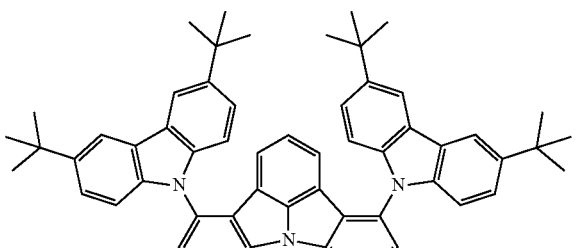
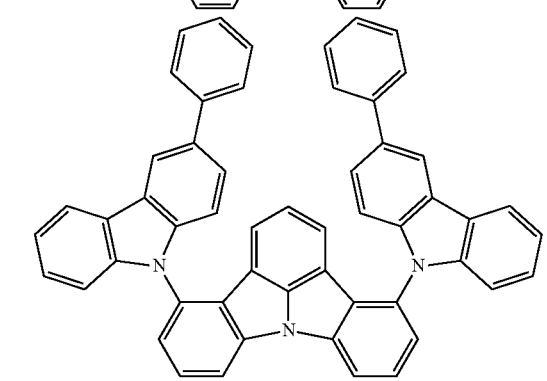
502
-continued
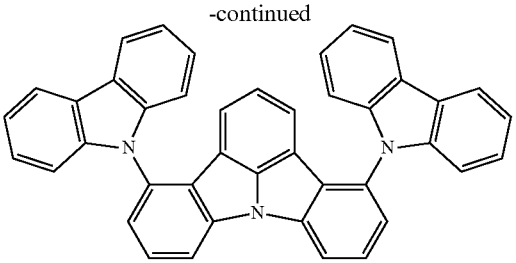
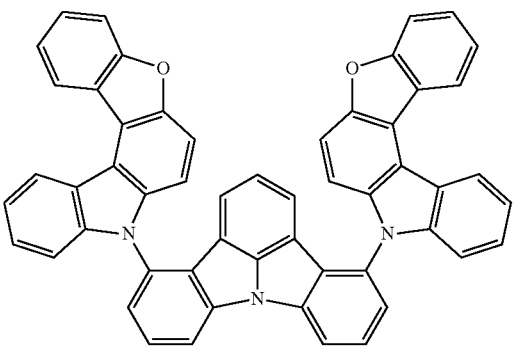
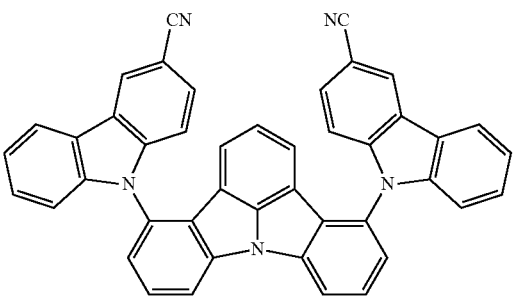
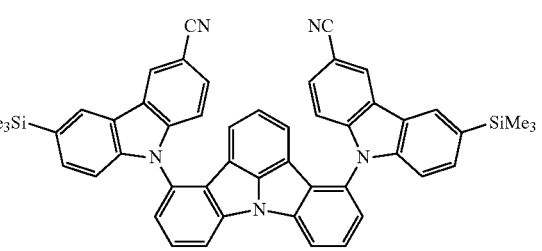
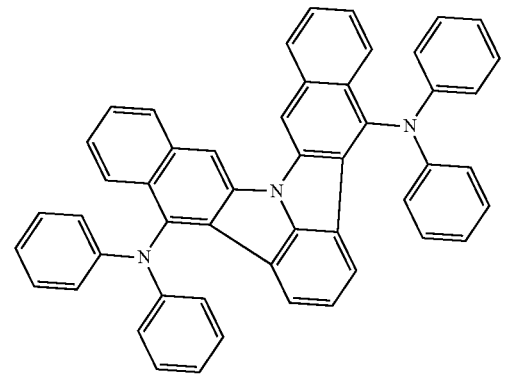

503
-continued
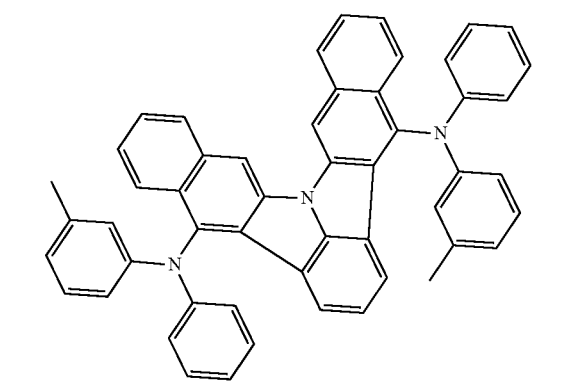
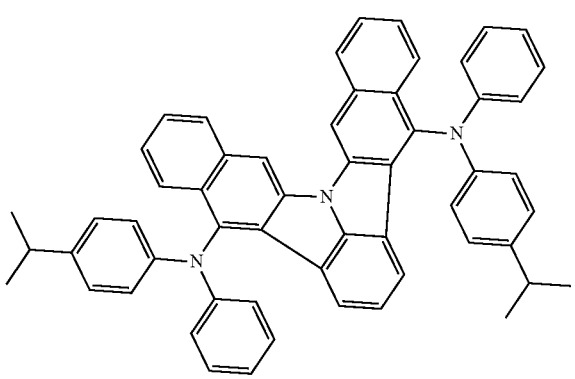
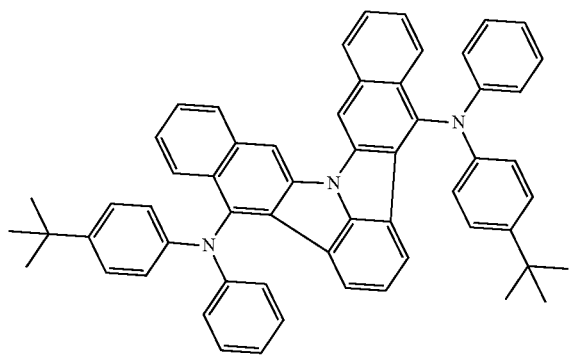
504
-continued
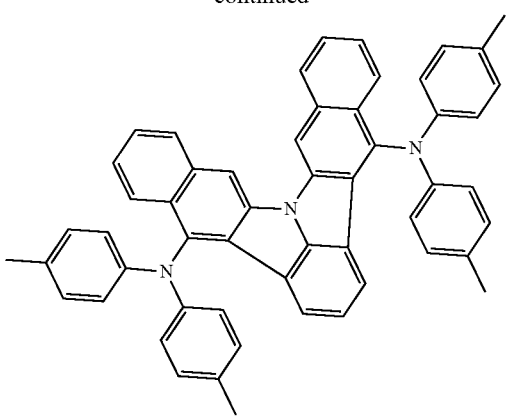
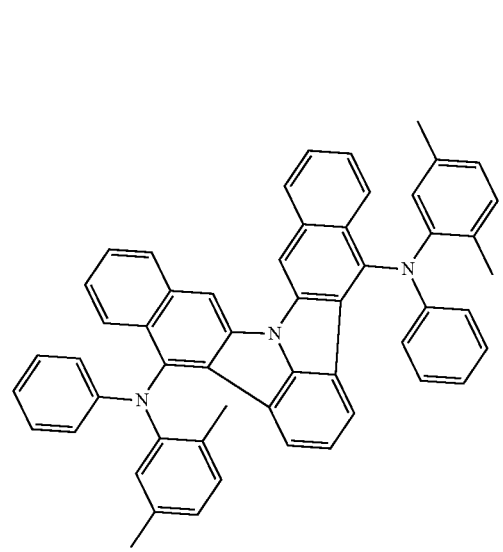
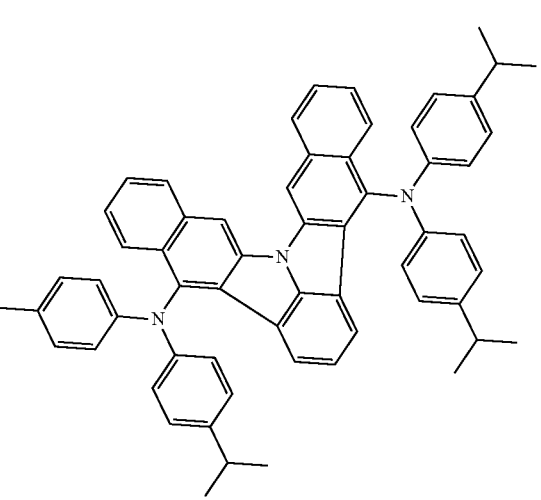

505
-continued
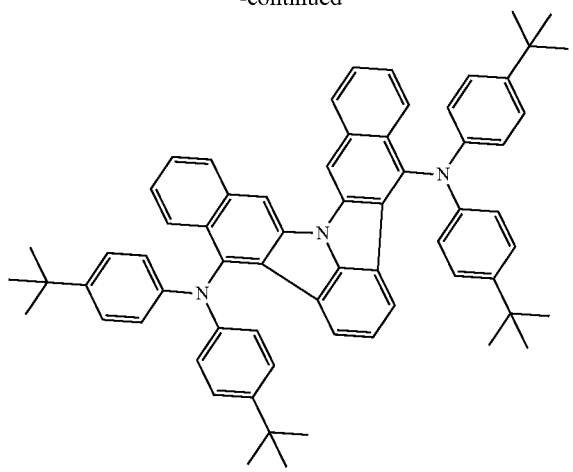
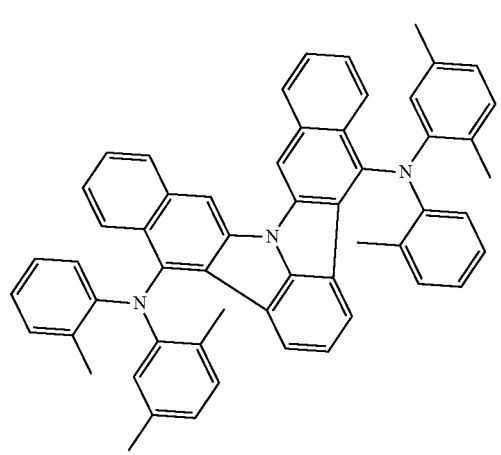 [SMILES: Cc1ccc(C)c(N(c2ccccc2C)c2c3ccccc3cc3c2c2cccc4c5c(N(c6ccccc6C)c6cc(C)ccc6C)c6ccccc6cc5n3c24)c1]
506
-continued
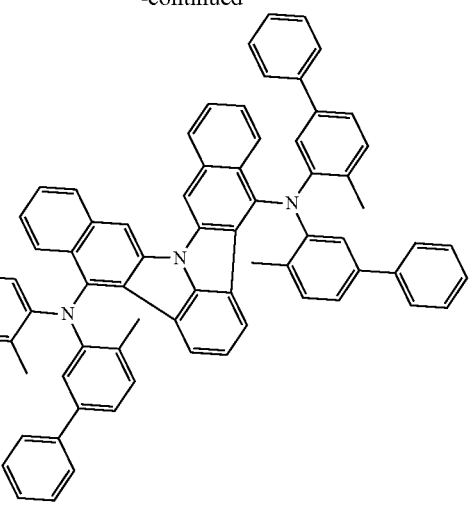
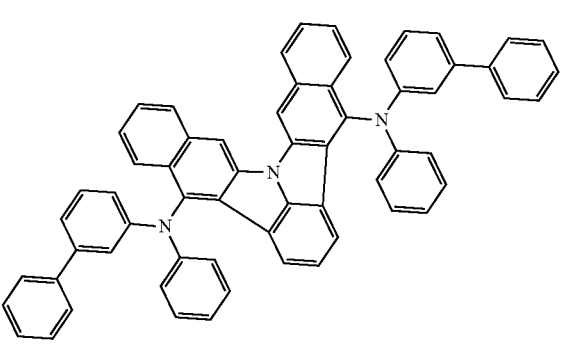
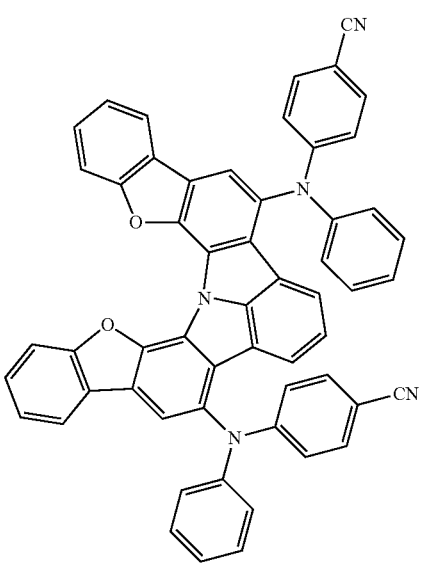

507
-continued
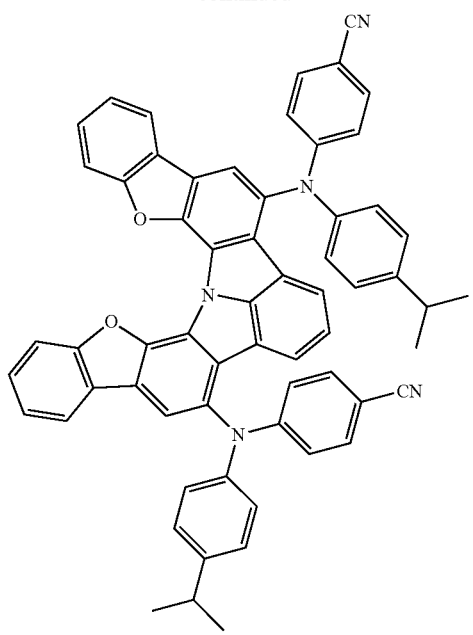
508
-continued
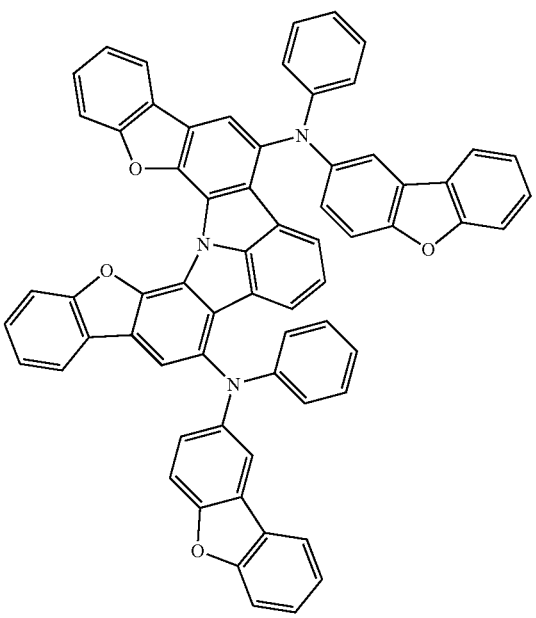
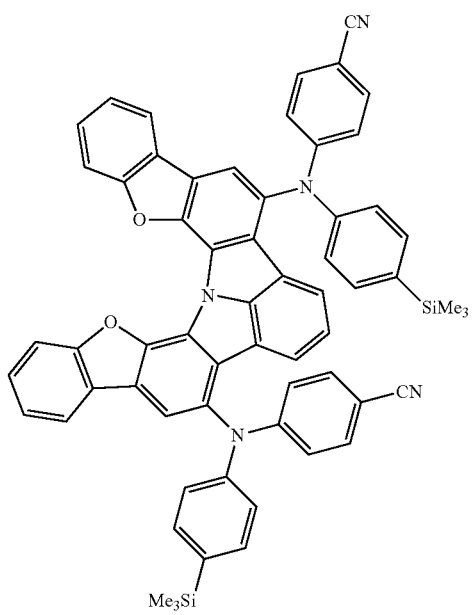
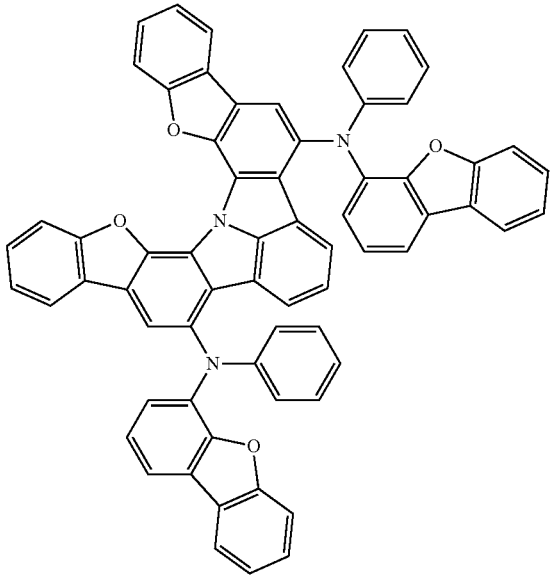

509
-continued
510
-continued
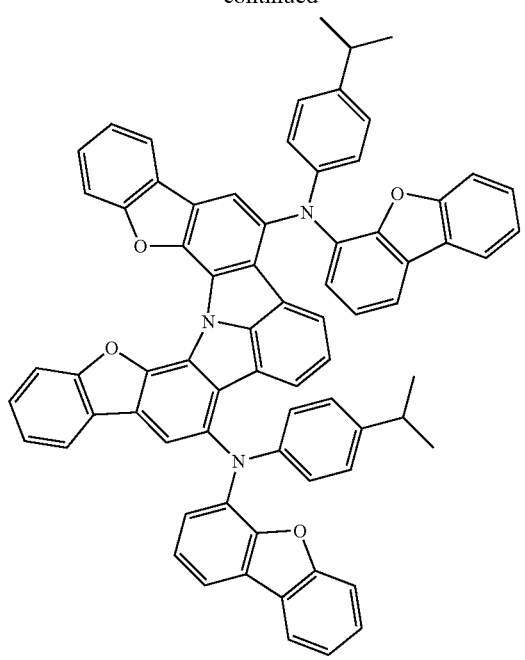
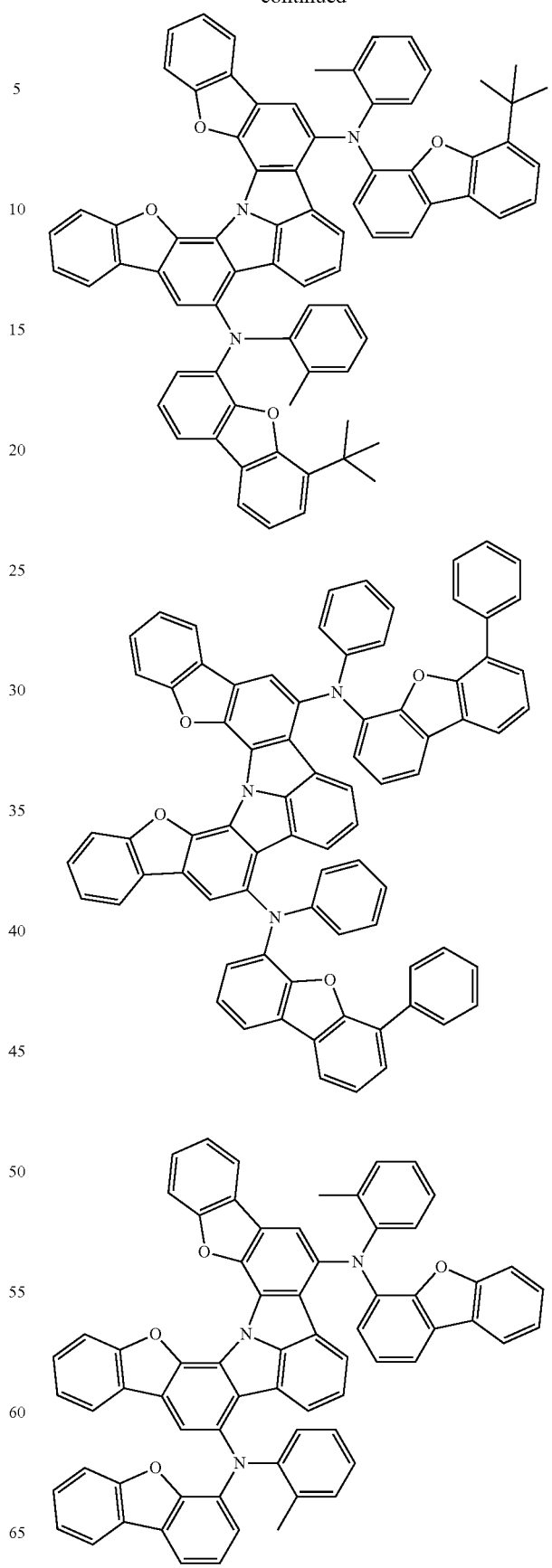

511
-continued
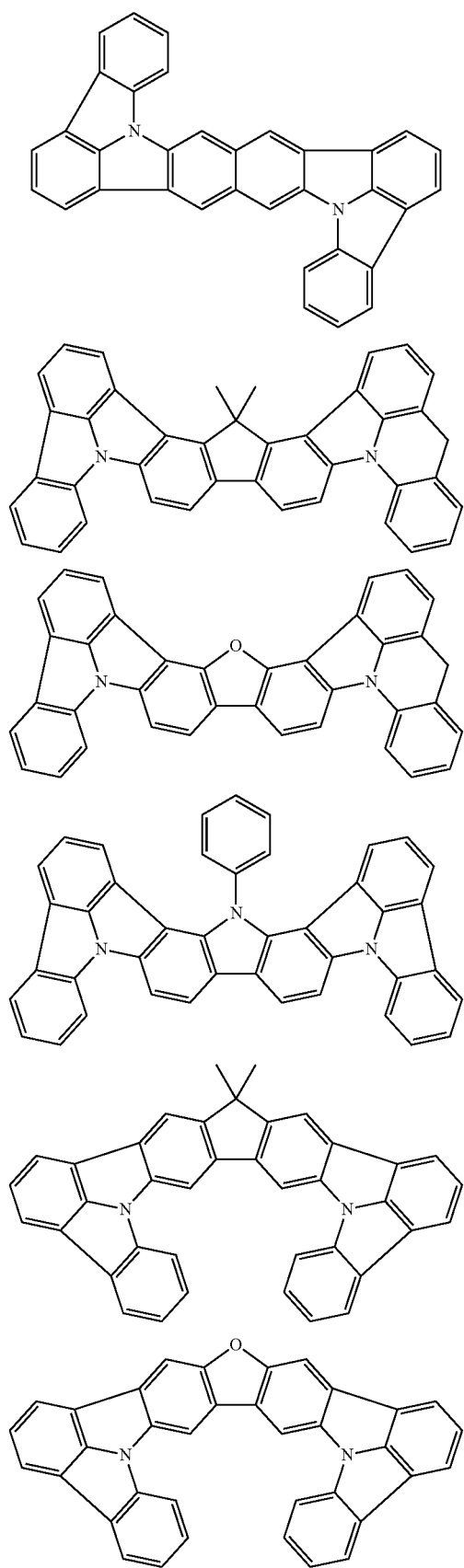
512
-continued
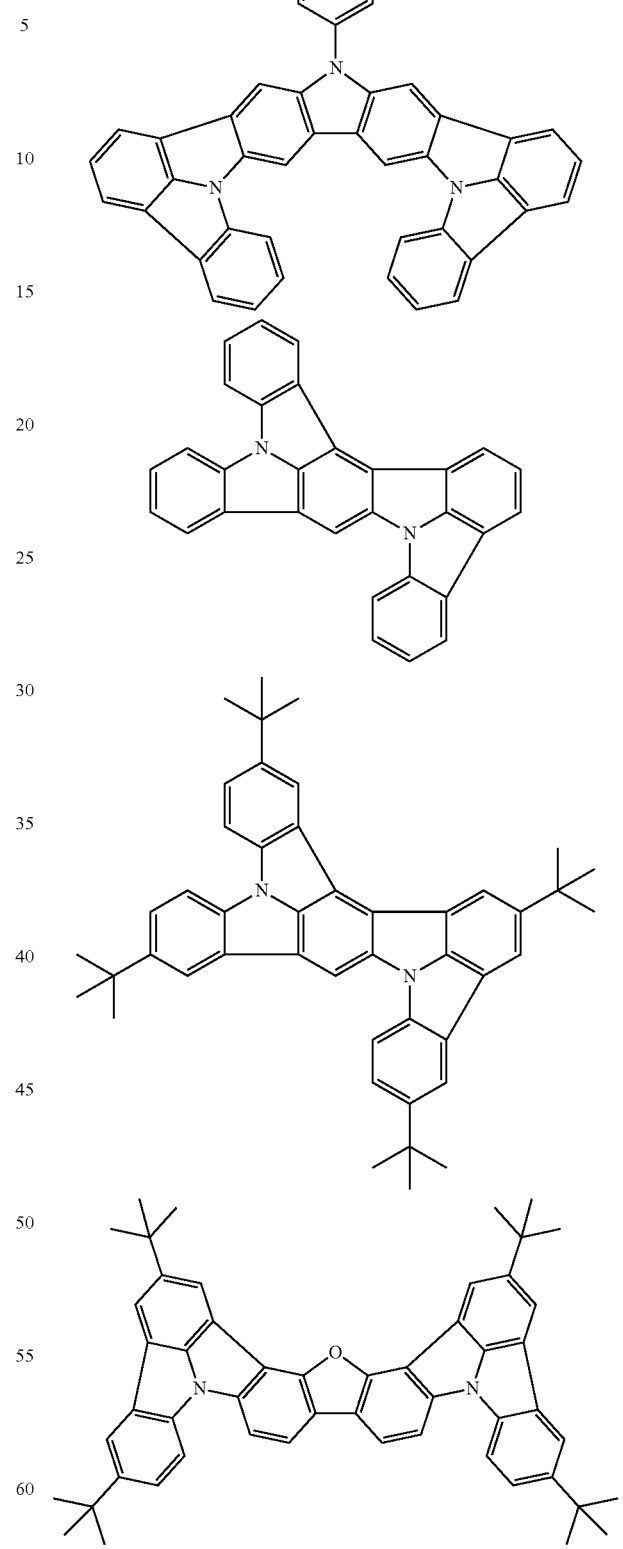
(Compound Represented by Formula (31))
The compound represented by the formula (31) is explained below.

The compound represented by formula (31) is a compound corresponding to the compound represented by the formula (21-3).

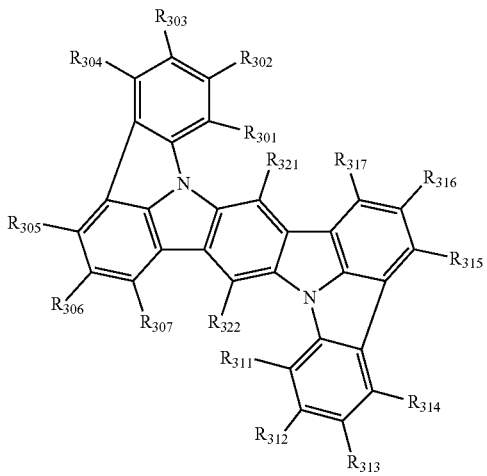

(31)

wherein in the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

Example of "One pair of two or more adjacent groups of $R_{3001}$ to $R_{307}$ and $R_{311}$ to $R_{317}$" is pairs of $R_{301}$ and $R_{302}$, $R_{302}$ and $R_{303}$ $R_{303}$ and $R_{304}$, $R_{305}$ and $R_{306}$, $R_{306}$ and $R_{307}$, and $R_{301}$, $R_{302}$ and $R_{303}$, and the like.

In one embodiment, at least one of $R_{301}$ to $R_{307}$ and $R_{311}$ to $R_{317}$, preferably two of $R_{301}$ to $R_{307}$ and $R_{311}$ to $R_{317}$ is a group represented by —N($R_{906}$)($R_{907}$).

In one embodiment, $R_{301}$ to $R_{307}$ and $R_{311}$ to $R_{317}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the following formula (32).

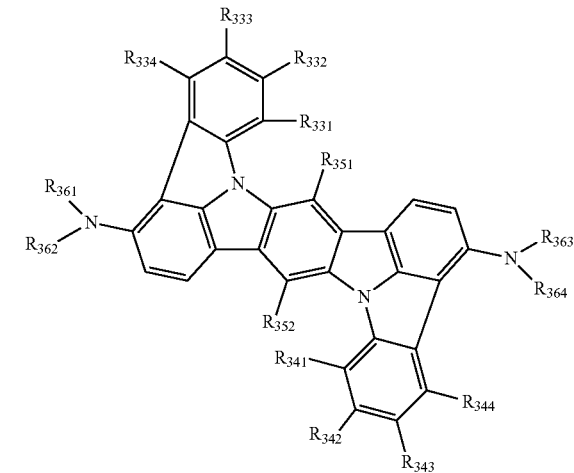

(32)

wherein in the formula (32), one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted saturated or unsaturated ring;

$R_{331}$ to $R_{334}$ and $R_{341}$ to $R_{344}$ that do not form the substituted or unsubstituted, saturated or unsaturated ring and $R_{351}$ and $R_{352}$ are independently a hydrogen atom, a substituted or unsubstituted aryl group having 6 to 50 ring carbon atoms, or a substituted or unsubstituted monovalent heterocyclic group having 5 to 50 ring atoms; and $R_{361}$ to $R_{364}$ are independently a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the formula (33).

(33)

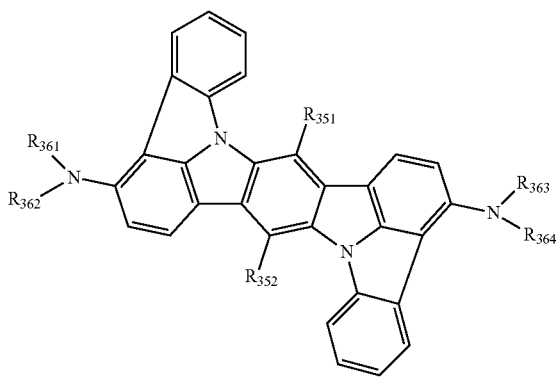

wherein in the formula (33), $R_{351}$, $R_{352}$, and $R_{361}$ to $R_{364}$ are as defined in the formula (32).

In one embodiment, the compound represented by the formula (31) is a compound represented by the formula (34) or (35).

(34)

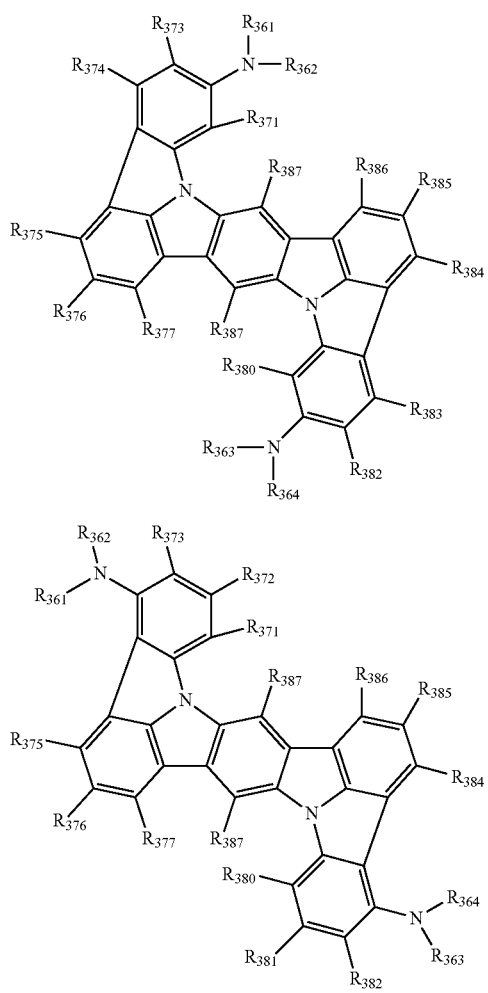

(35)

wherein in the formulas (34) and (35), $R_{361}$ to $R_{364}$ are as defined in the formula (32);

one or more pairs of two or more adjacent groups of $R_{371}$ to $R_{377}$ and $R_{380}$ to $R_{386}$ form a substituted or unsubstituted, saturated or unsaturated ring, or do not form a substituted or unsubstituted saturated or unsaturated ring; and $R_{371}$ to $R_{377}$ and $R_{380}$ to $R_{386}$ that do not form the substituted or unsubstituted, saturated or unsaturated ring and $R_{387}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the formula (34-2) or (35-2).

(34-2)

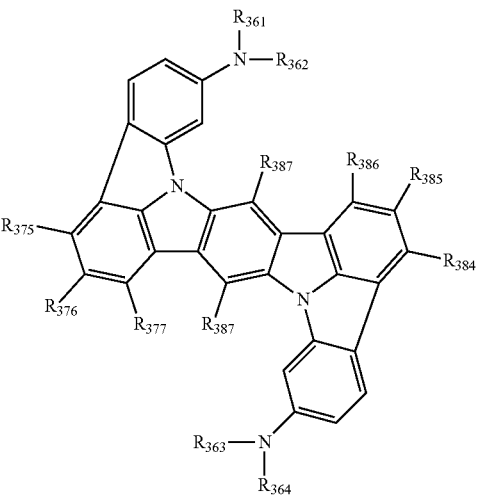

(35-2)

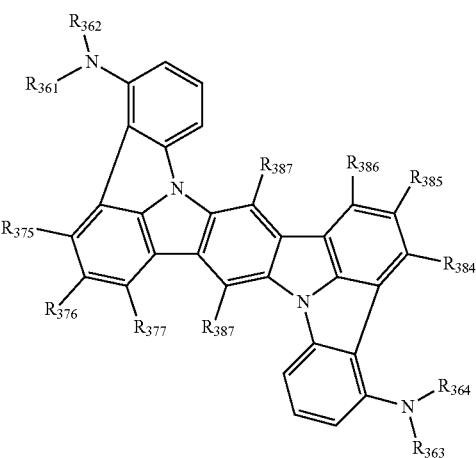

wherein in the formulas (34-2) and (35-2), $R_{361}$ to $R_{364}$, $R_{375}$ to $R_{377}$ and $R_{384}$ to $R_{387}$ are as defined in the formulas (34) and (35).

In one embodiment, $R_{361}$ to $R_{364}$ in the formulas (32), (33), (34), (35), (34-2) and (35-2) are independently a substituted or unsubstituted aryl group having 6 to 50 ring carbon atoms (preferably a substituted or unsubstituted phenyl group).

In one embodiment, $R_{321}$ and $R_{322}$ in the formula (31) and $R_{351}$, $R_{352}$ and $R_{387}$ in the formulas (32), (33), (34), (35), (34-2) and (35-2) are independently a hydrogen atom or a substituted or unsubstituted aryl group having 6 to 50 ring carbon atoms (preferably a substituted or unsubstituted phenyl group).

In one embodiment, the compound represented by the formula (31) is one or more compounds selected from the group consisting of the following formulas (32-11), (34-11) and (35-11).

(32-11)

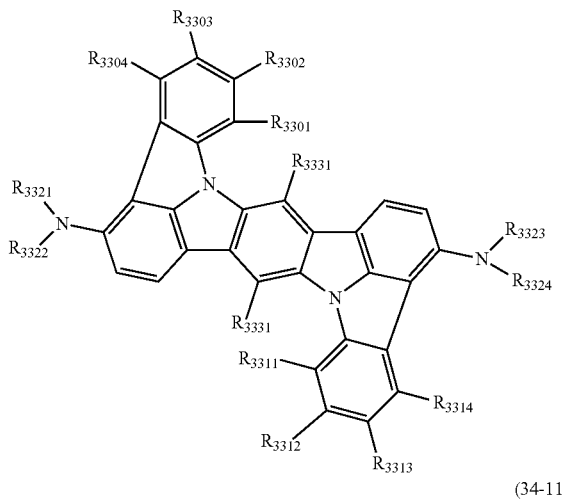

(34-11)

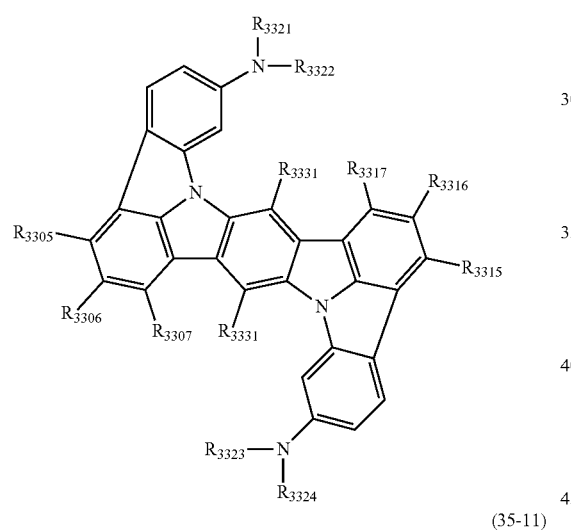

(35-11)

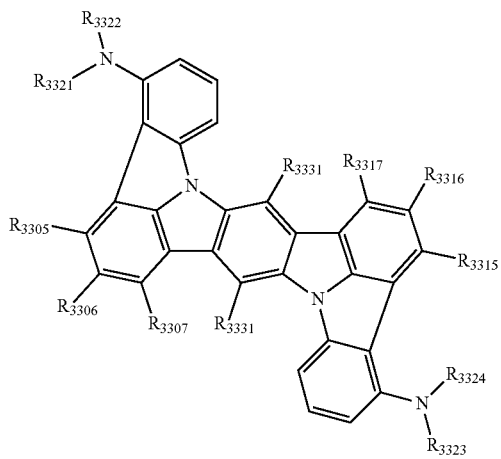

wherein in the formulas (32-11), (34-11) and (35-11), one or more pairs of two or more adjacent groups of $R_{3301}$ to $R_{3307}$ and $R_{3311}$ to $R_{3317}$ form a substituted or unsubstituted, saturated or unsaturated ring, or do not form a substituted or unsubstituted, saturated or unsaturated ring;

$R_{3301}$ to $R_{3307}$ and $R_{3311}$ to $R_{3317}$ that do not form the substituted or unsubstituted, saturated or unsaturated ring, and $R_{3331}$ are independently a hydrogen atom, a substituted or unsubstituted aryl group having 6 to 20 ring carbon atoms, or a substituted or unsubstituted monovalent heterocyclic group having 5 to 20 ring atoms;

two $R_{3331}$s may be the same with or different from each other; and $R_{3321}$ to $R_{3324}$ are independently a substituted or unsubstituted aryl group having 6 to 20 ring carbon atoms, or a substituted or unsubstituted monovalent heterocyclic group having 5 to 20 ring atoms.

In one embodiment, the one or more compounds selected from the group consisting of the formulas (32-11), (34-11) and (35-11) is one or more compounds selected from a group consisting of the following formulas (32-12), (34-12) and (35-12).

(32-12)

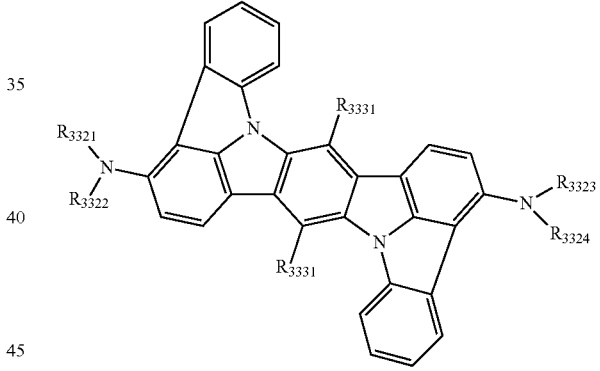

(34-12)

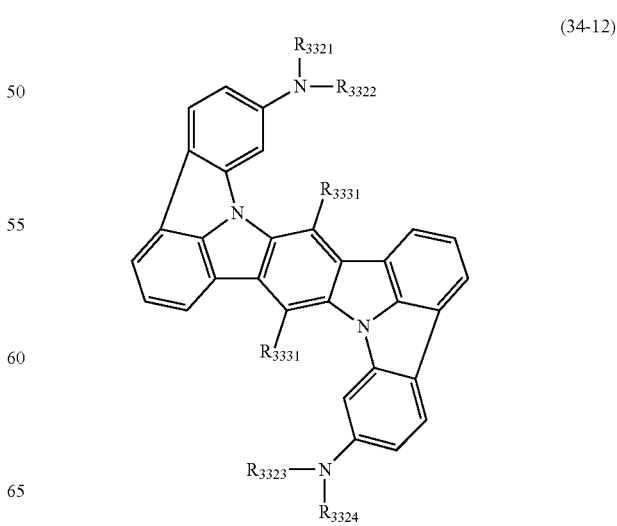

(35-12)

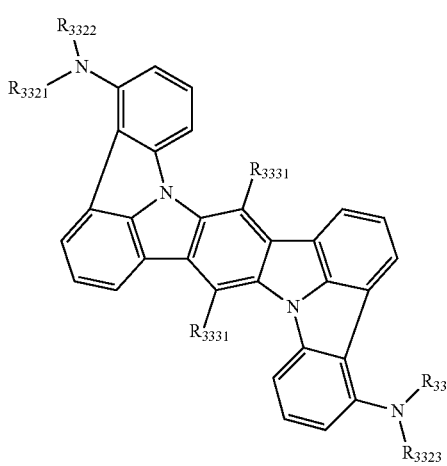

(36-1)

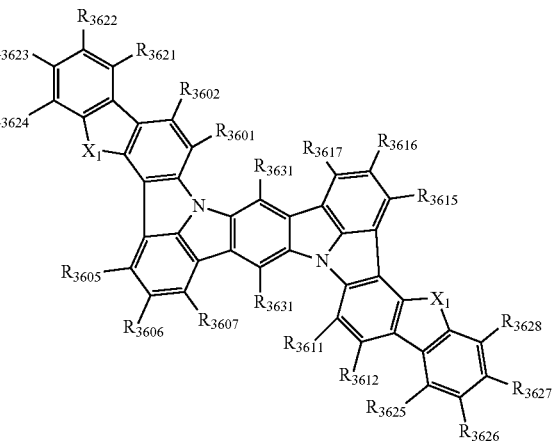

wherein in the formulas (32-12), (34-12) and (35-12), $R_{3321}$ to $R_{3324}$ and $R_{3331}$ are as defined in the formulas (32-11), (34-11) and (35-11).

In one embodiment, in the formulas (32-11), (34-11), (35-11), (32-12), (34-12) and (35-12), $R_{3321}$ to $R_{3324}$ are independently a substituted or unsubstituted phenyl group.

In one embodiment, in the formulas (32-11), (34-11), (35-11), (32-12), (34-12) and (35-12), two $R_{3331}$s are independently a hydrogen atom.

In one embodiment, in the formulas (32-11), (34-11), (35-11), (32-12), (34-12) and (35-12), the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), the substituent in the case of "substituted or unsubstituted" is an alkyl group having 1 to 5 carbon atoms.

In one embodiment, in the formulas (32-11), (34-11), (35-11), (32-12), (34-12) and (35-12), $R_{3321}$ to $R_{3324}$ are independently a substituted or unsubstituted phenyl group, and two $R_{3331}$s are independently a hydrogen atom.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is an alkyl group having 1 to 5 carbon atoms.

In one embodiment, in the compound represented by the formula (31), one or more pairs of two or more adjacent groups of $R_{301}$ to $R_{307}$ and $R_{311}$ to $R_{317}$ form a substituted or unsubstituted, saturated or unsaturated ring.

In one embodiment, the compound represented by the formula (31) is one or more compounds selected from the group consisting of the following formulas (36-1) to (36-6).

(36-2)

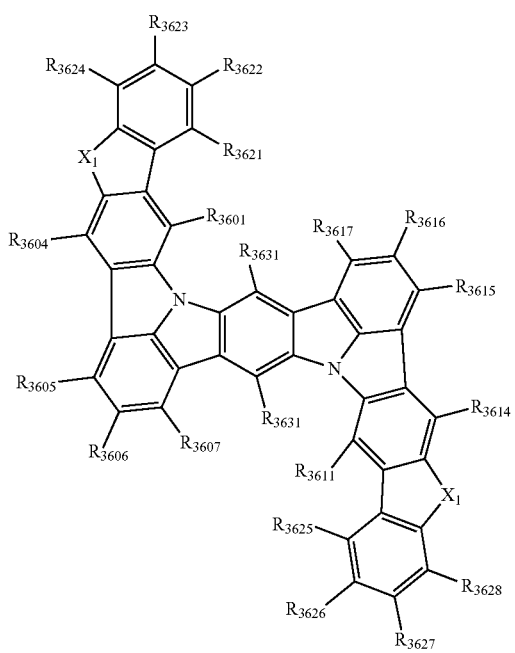

(36-3)

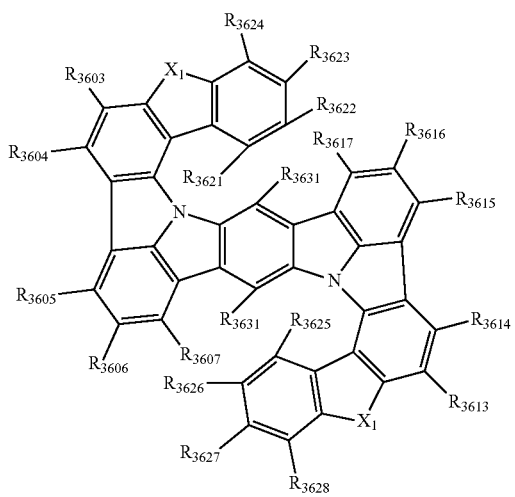

-continued (36-4)

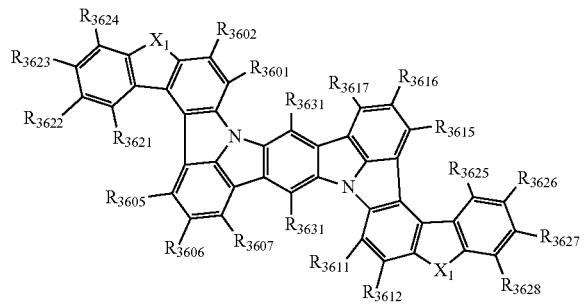

(36-5)

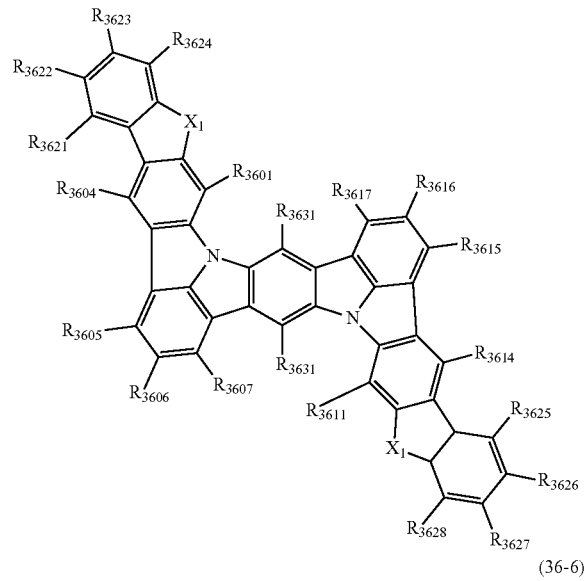

(36-6)

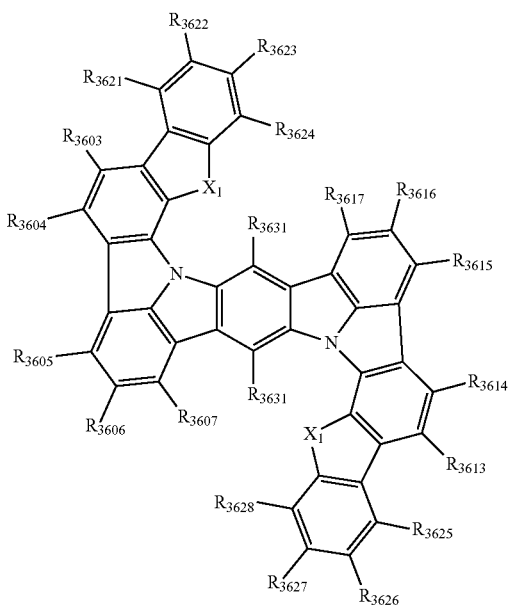

wherein in the formulas (36-1) to (36-6),
one or more pairs of two or more adjacent groups of $R_{3605}$ to $R_{3607}$, $R_{3615}$ to $R_{3617}$ and $R_{3631}$ bond with each other to form a substituted or unsubstituted, saturated or unsaturated ring or do not form the ring;

one or more pairs of two or more adjacent groups of $R_{3601}$ to $R_{3604}$, $R_{3611}$ to $R_{3614}$ and $R_{3621}$ to $R_{3628}$ bond with each other to form a substituted or unsubstituted, saturated or unsaturated ring or do not form the ring;

$R_{3601}$ to $R_{3607}$, $R_{3611}$ to $R_{3617}$, $R_{3621}$ to $R_{3628}$ and $R_{3631}$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or
a substituted or unsubstituted monovalent heterocyclic group having 5 to 50 ring atoms; $R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
$X_1$ is selected from O, S and N($R_{3641}$), and two $X_1$s may be the same with or different from each other;
$R_{3641}$ and one or more groups selected from $R_{3601}$ to $R_{3604}$, $R_{3611}$ to $R_{3614}$, $R_{3624}$ and $R_{3628}$ bond with each other to form a substituted or unsubstituted, saturated or unsaturated ring or do not form the ring; and
$R_{3641}$ that do not form the ring is a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

In one embodiment, the compound represented by the formula (31) is a compound represented by the formula (36-1) or (36-2). In one embodiment, the compound represented by the formula (31) is a compound represented by the formula (36-1).

In one embodiment, in the compound represented by the formulas (36-1) to (36-6), two $R_{3631}$s are phenyl groups.

In one embodiment, in the compound represented by the formulas (36-1) to (36-6), $X_1$ is N($R_{3641}$).

In one embodiment, in the compound represented by the formulas (36-1) to (36-6), $R_{3641}$ is a substituted or unsubstituted aryl group having 6 to 50 ring carbon atoms.

In one embodiment, the compound represented by the formula (31) is a compound represented by the following formula (36-1-1).

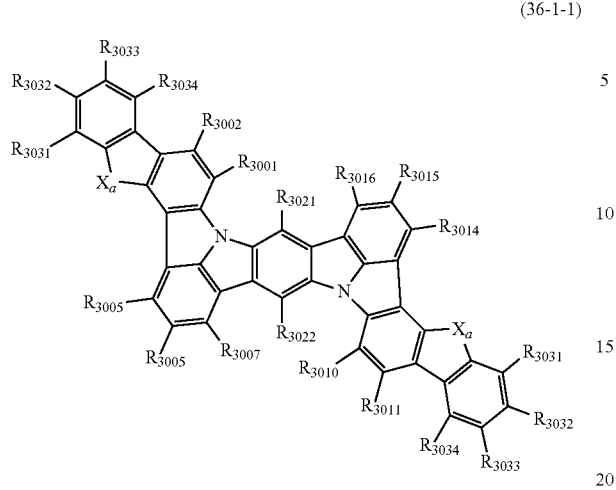

(36-1-1)

wherein in the formula (36-1-1), one or more pairs of two or more adjacent groups of $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3034}$ bond with each other to form a substituted or unsubstituted, saturated or unsaturated ring or do not form the ring;

$X_a$s are independently selected from O, S and N($R_{3035}$);

$R_{3035}$ and $R_{3031}$ bond with each other to form a substituted or unsubstituted, saturated or unsaturated ring or do not form the ring; and $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3035}$ that do not form the ring and $R_{3021}$ and $R_{3022}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, a substituent in the case of "substituted or unsubstituted" in the formulas (31) to (35), (34-2), (35-2), (32-11), (34-11), (35-11), (32-12), (34-12), (35-12), (36-1) to (36-6) and (36-1-1) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

As the compound represented by the formula (31), the following compounds can be given for example.

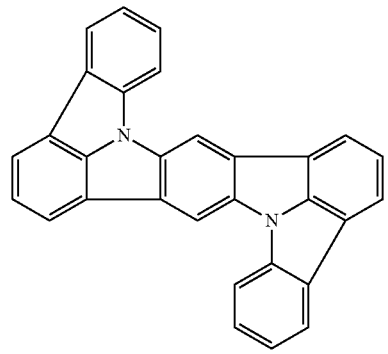

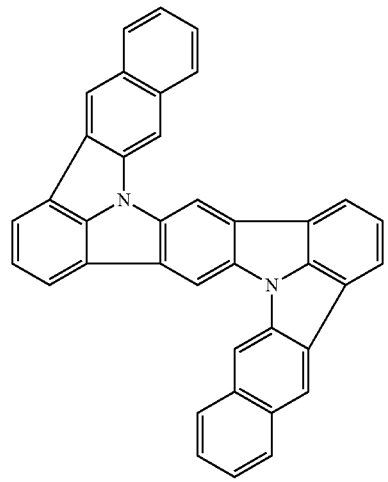

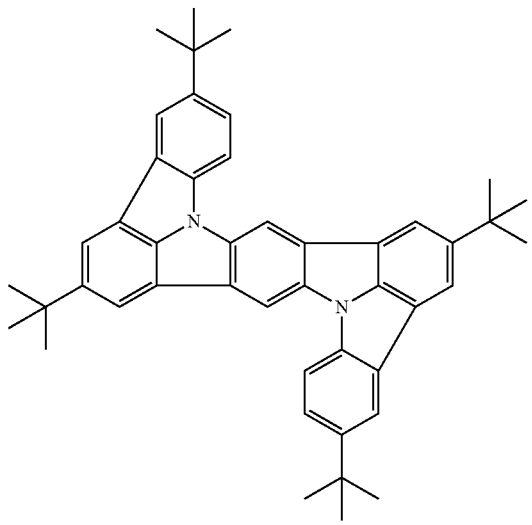

525
-continued
526
-continued
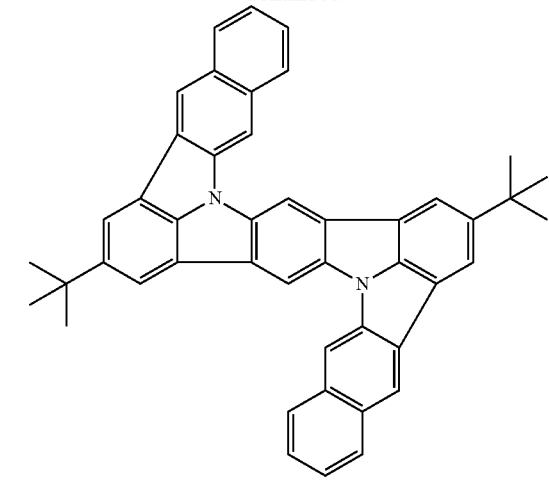
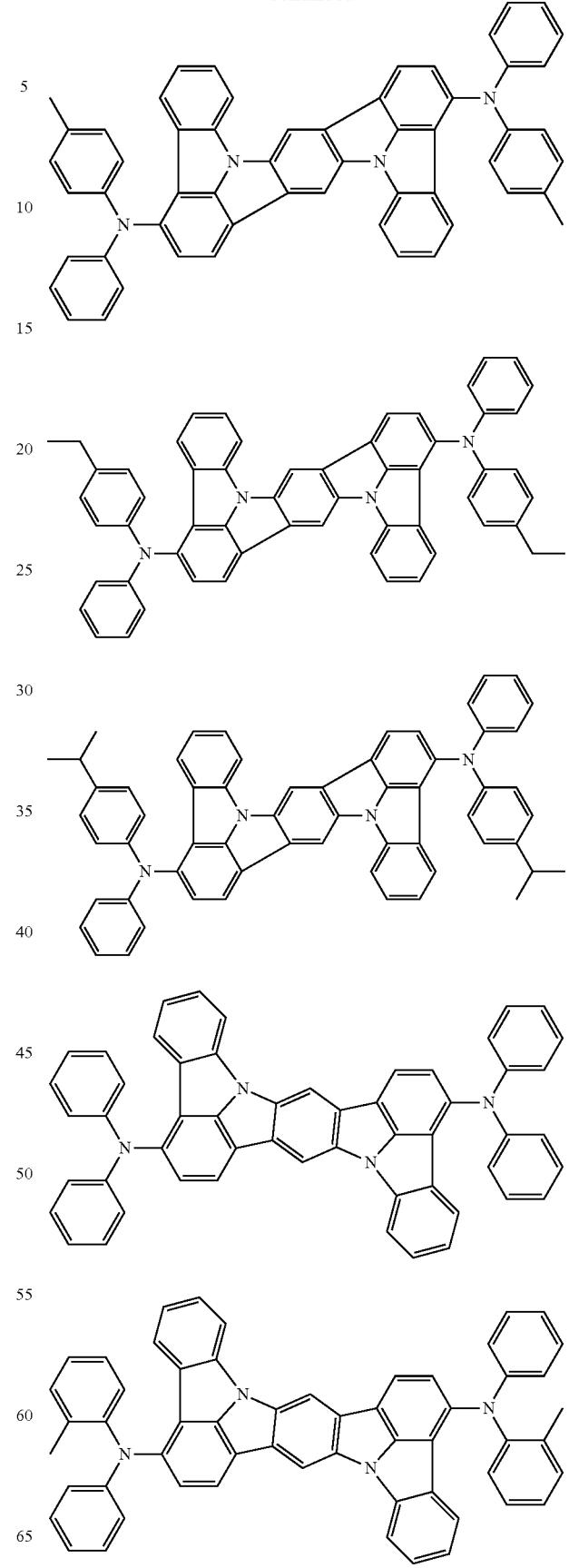

527
-continued
528
-continued
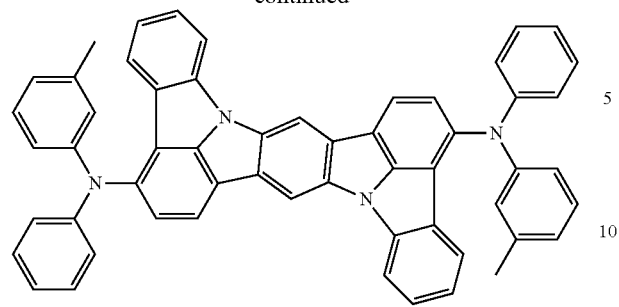
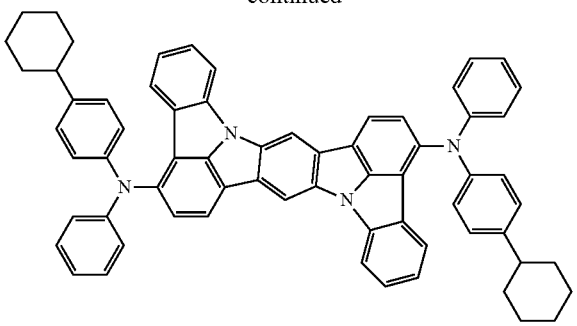
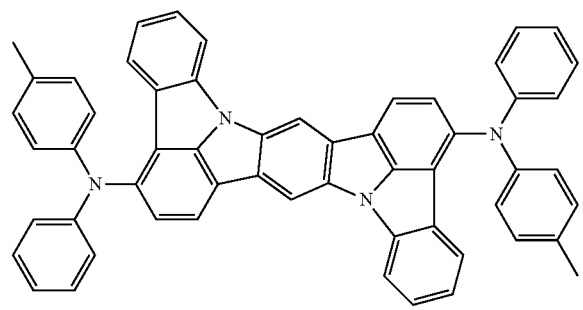
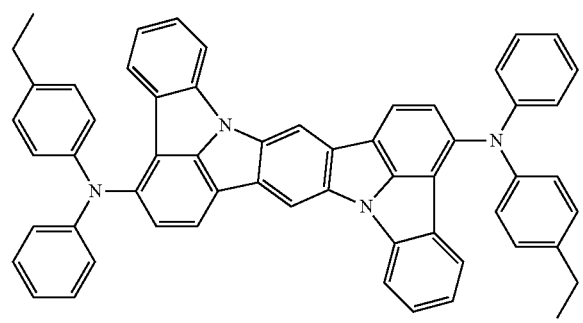
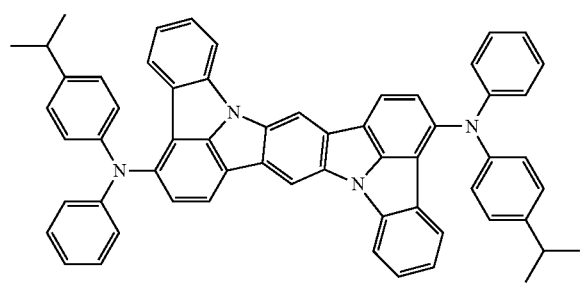
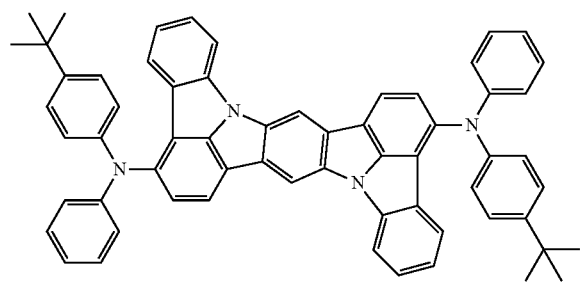

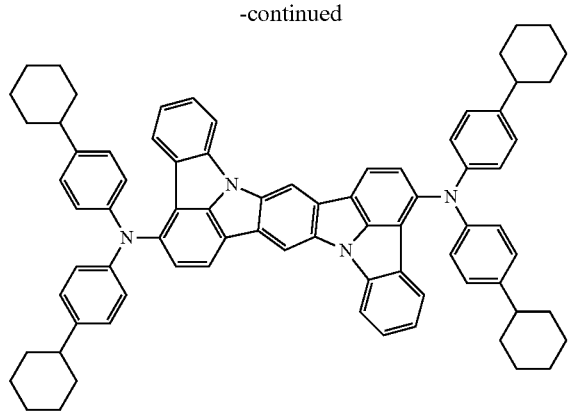
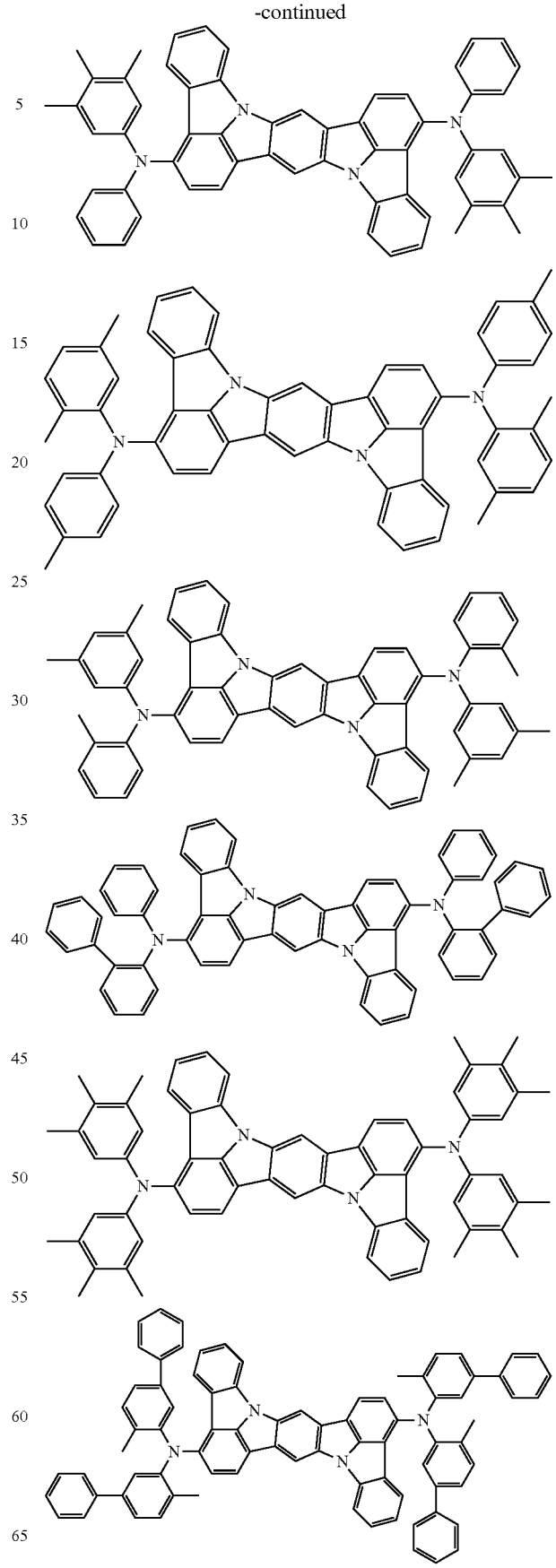

531
-continued
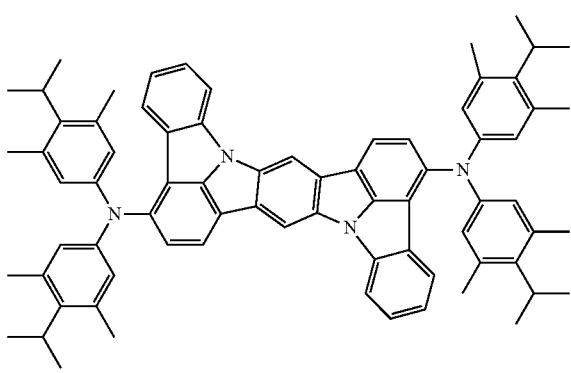
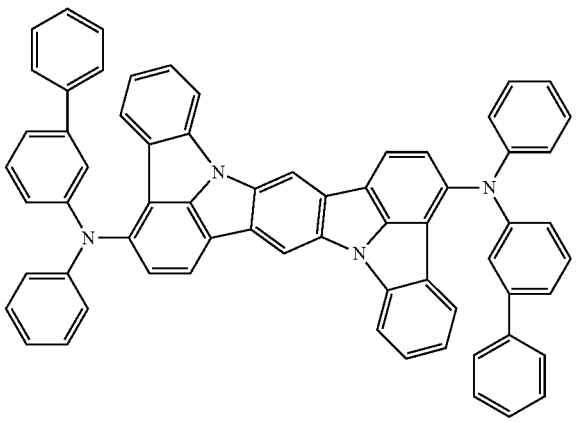
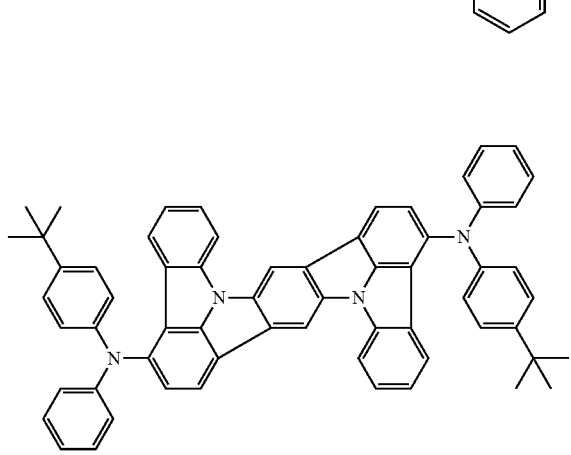
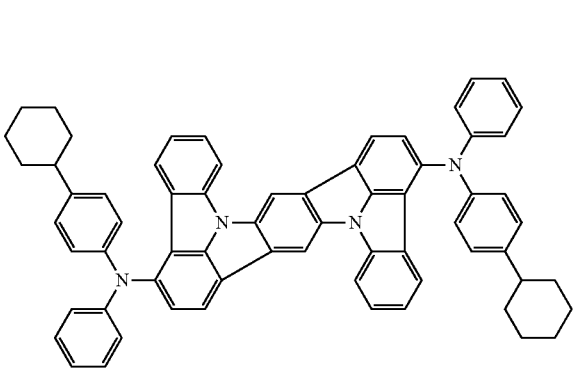
532
-continued
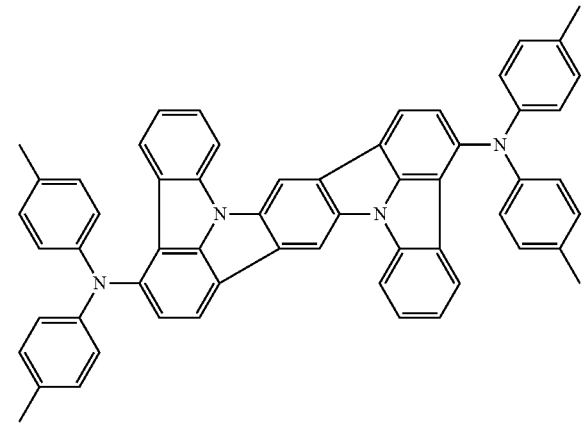
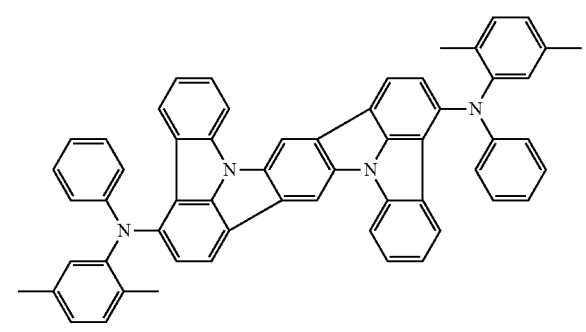
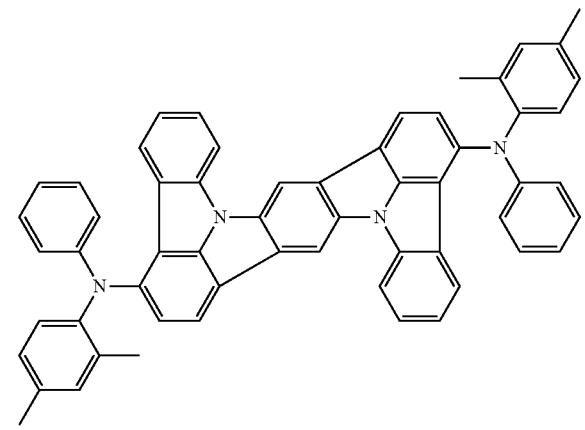
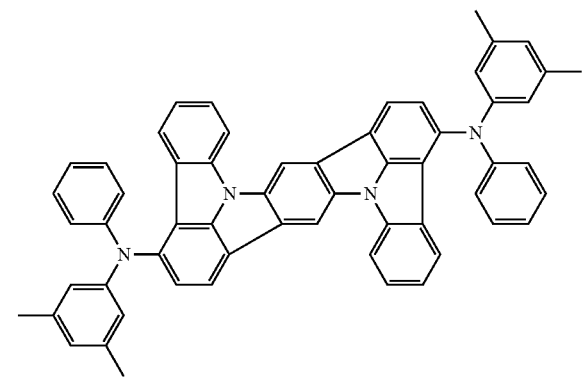

533
-continued
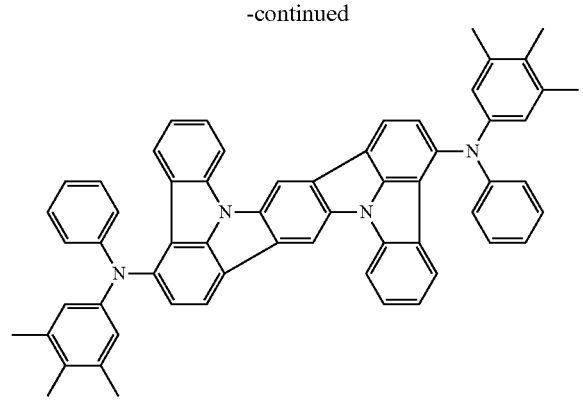
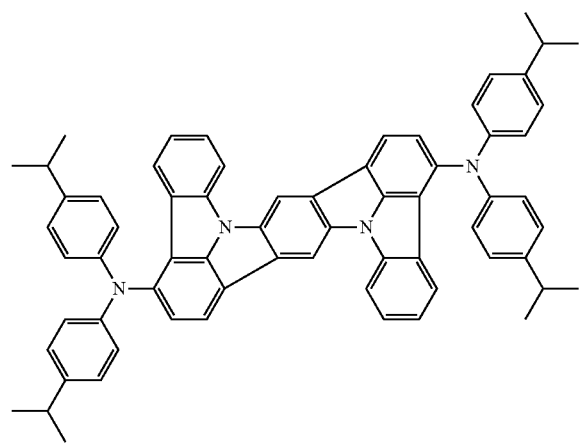
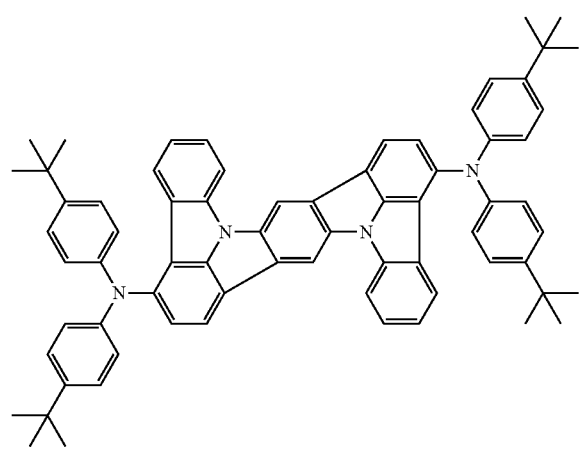
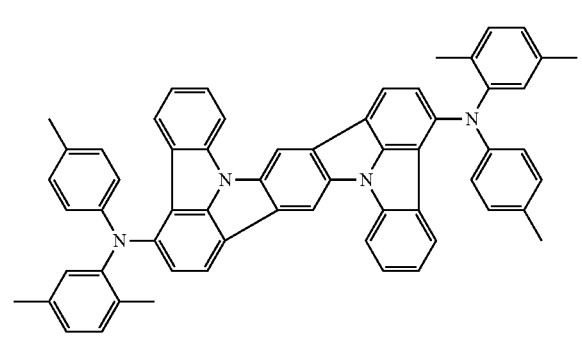
534
-continued
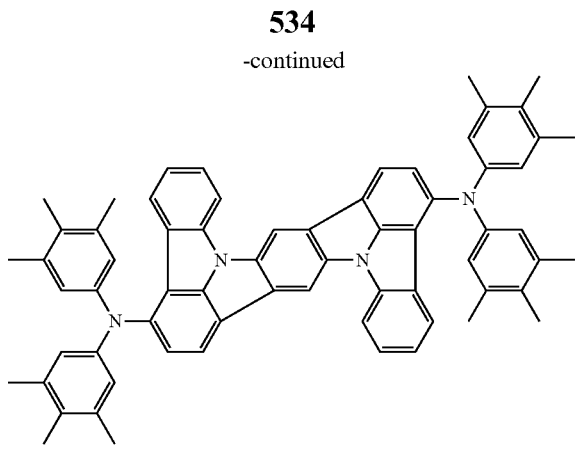
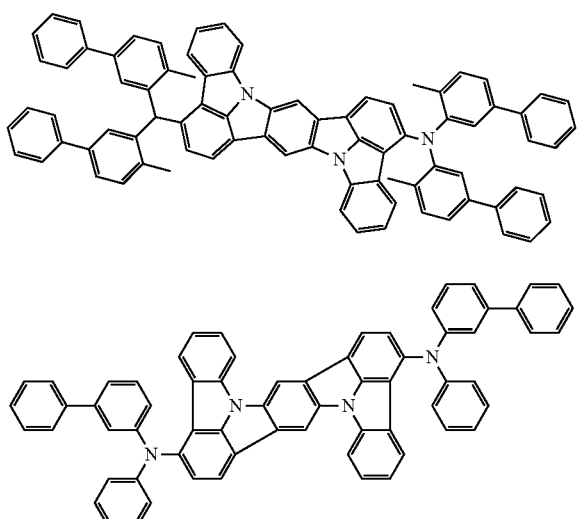
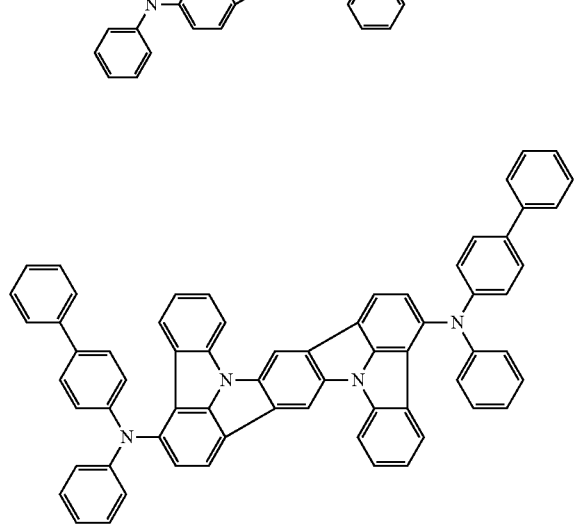
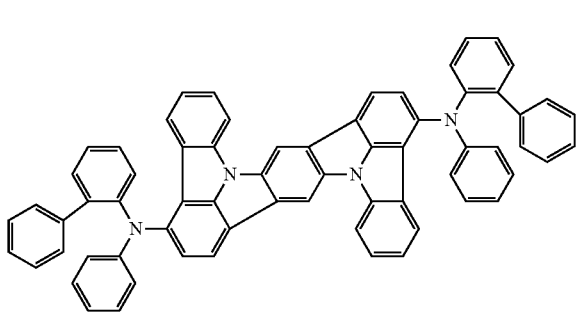

535
-continued
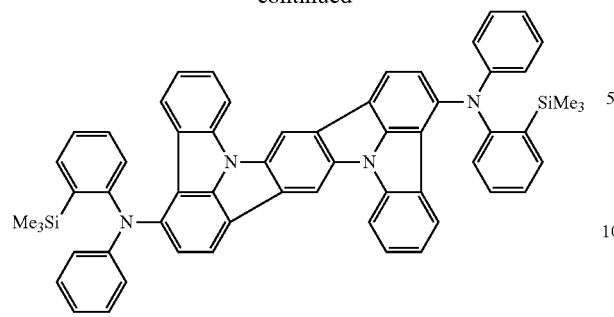
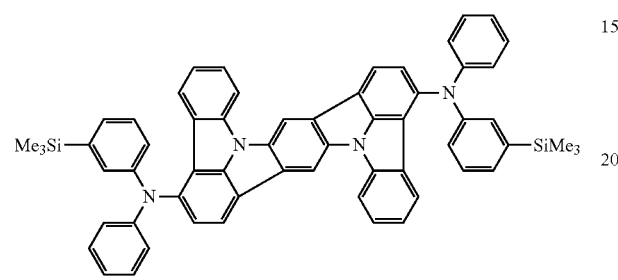
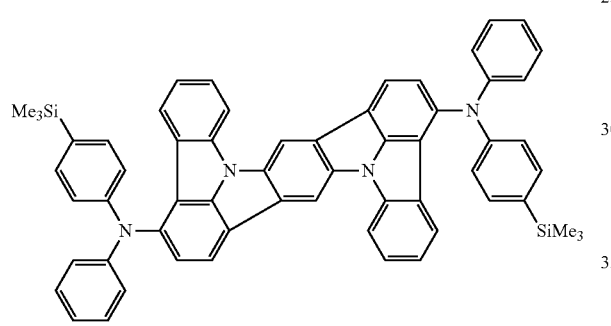
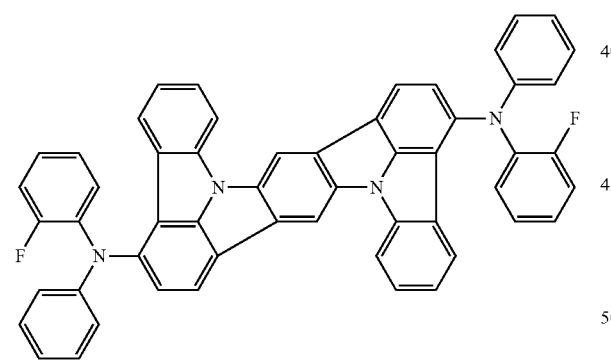
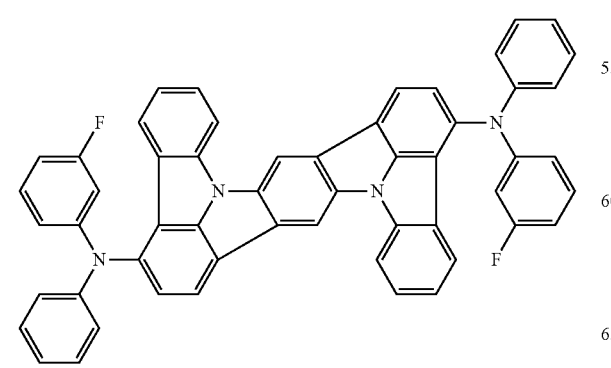
536
-continued
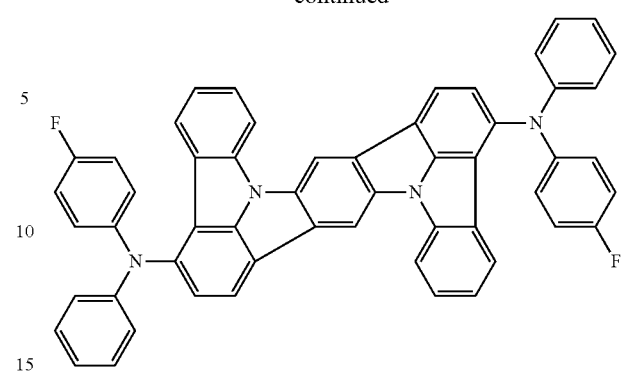
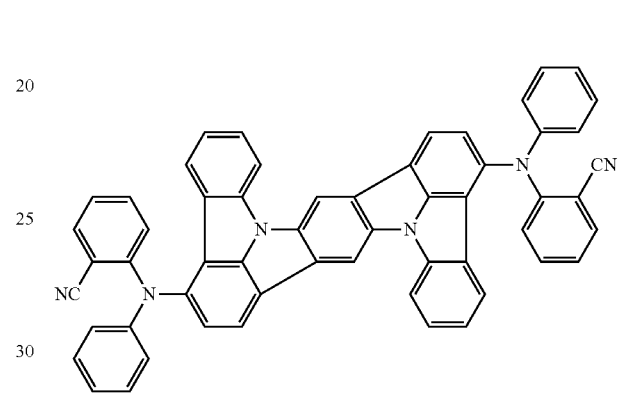
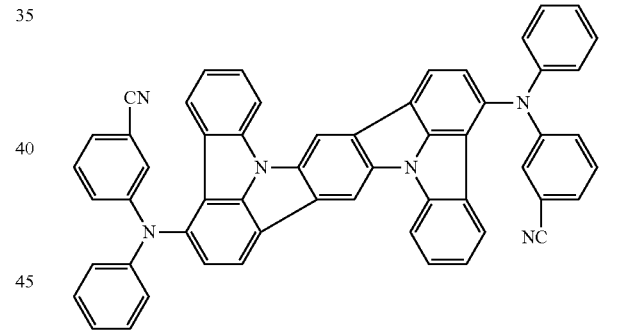
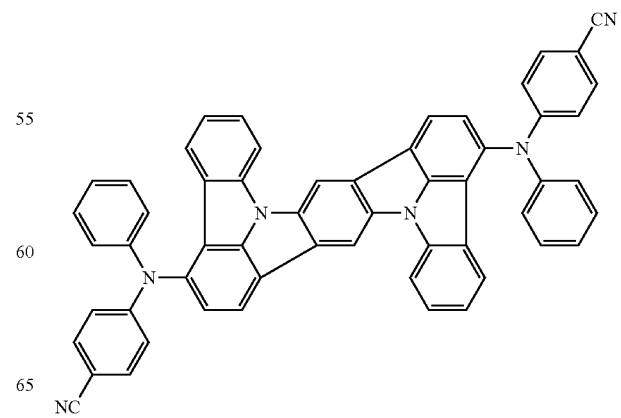

537
-continued
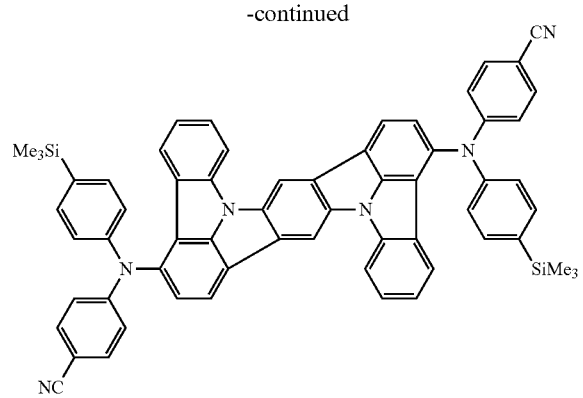
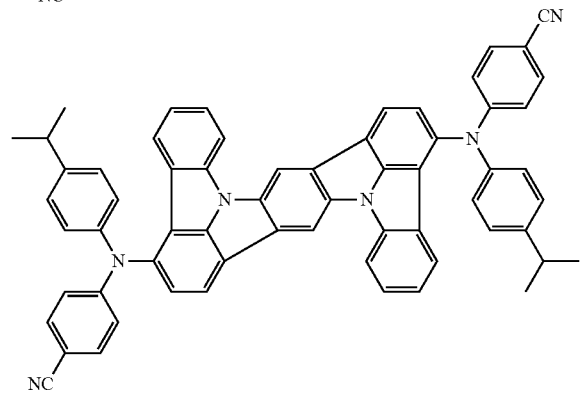
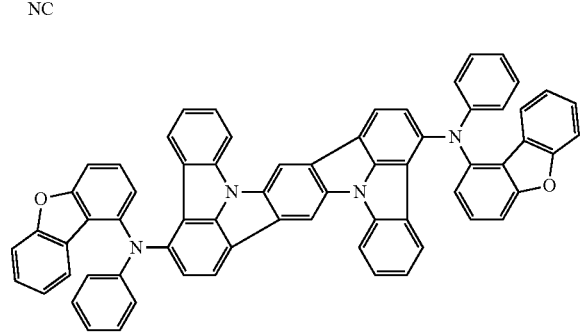
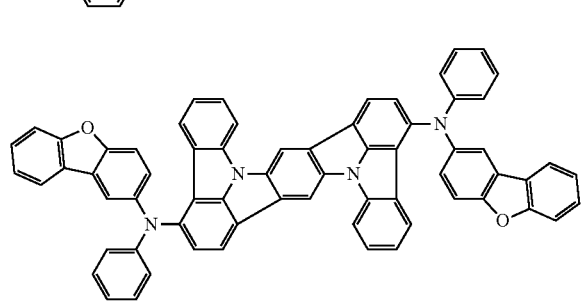
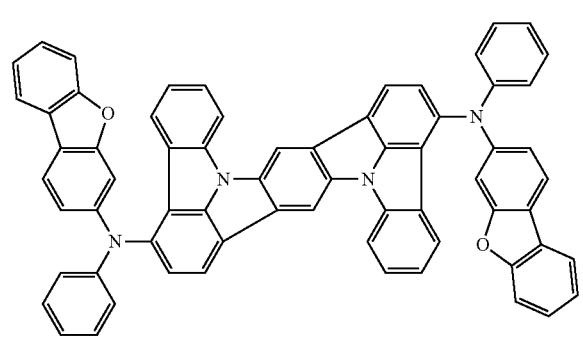
538
-continued
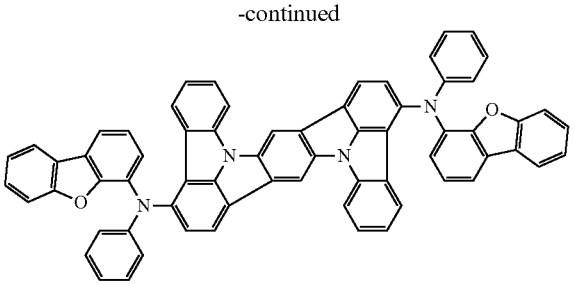
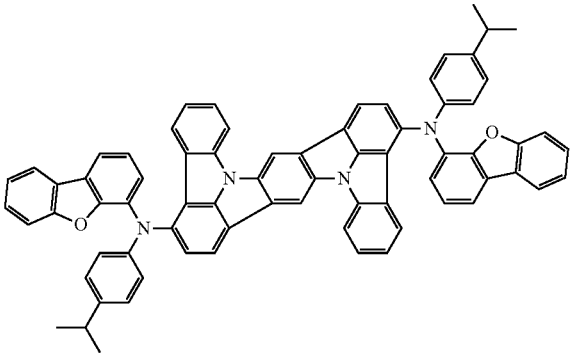
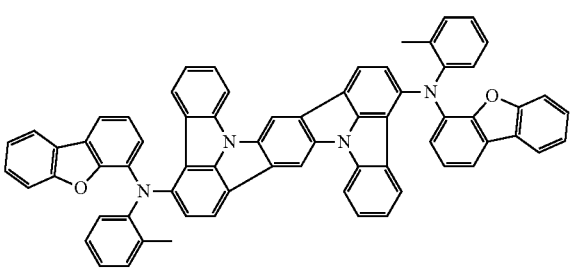
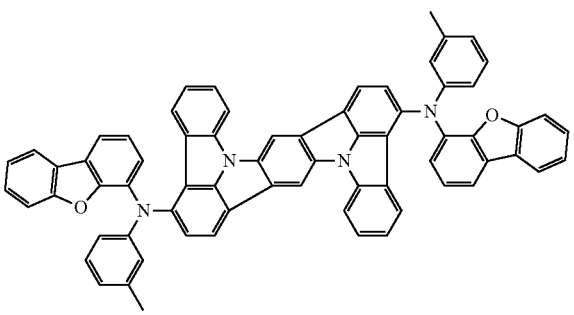
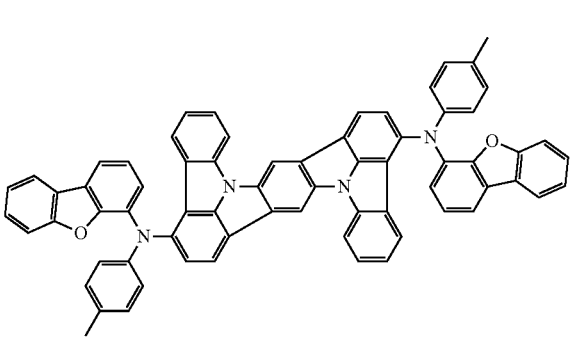

539
-continued
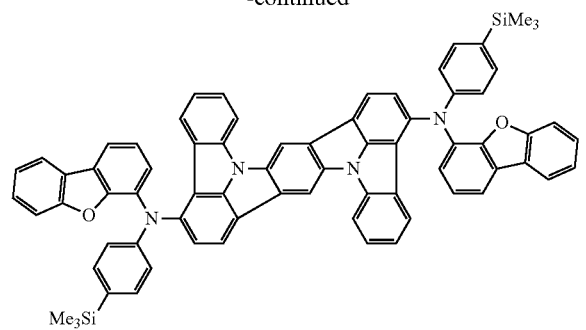
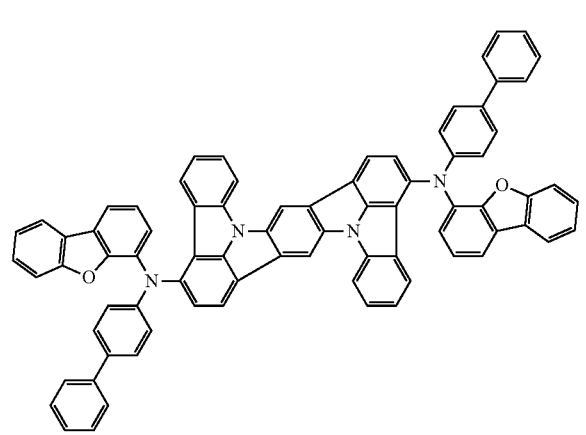
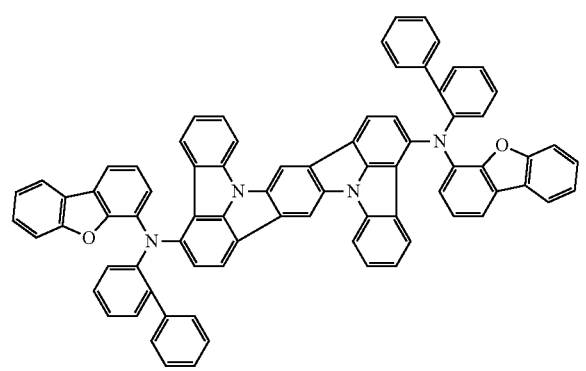
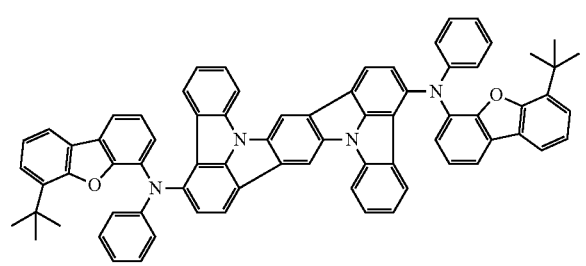
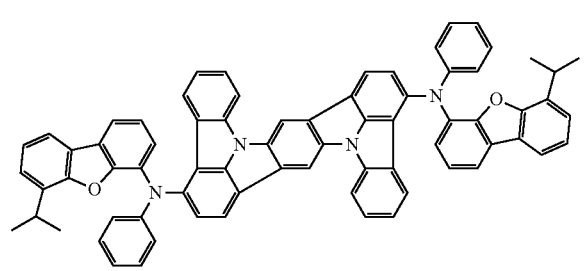
540
-continued
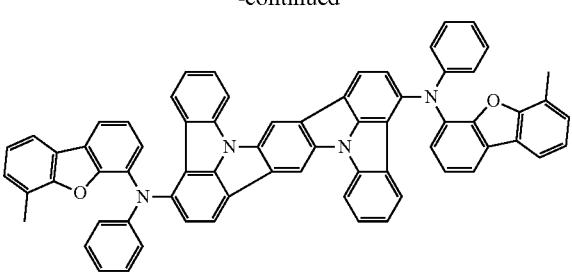
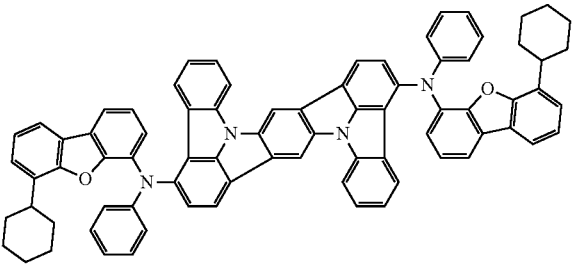
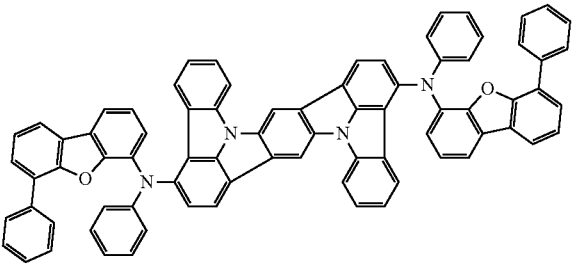
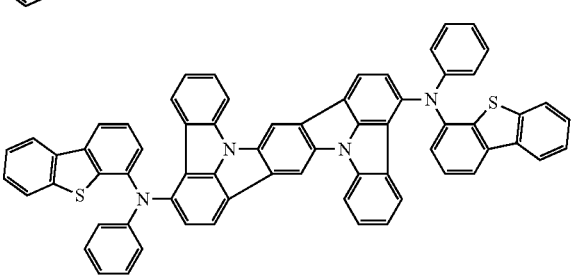
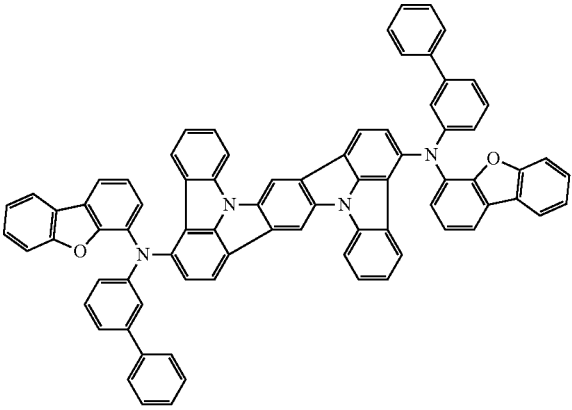
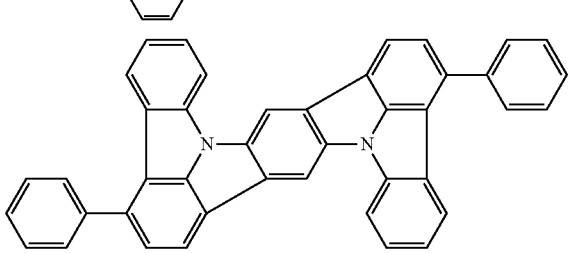

541
-continued
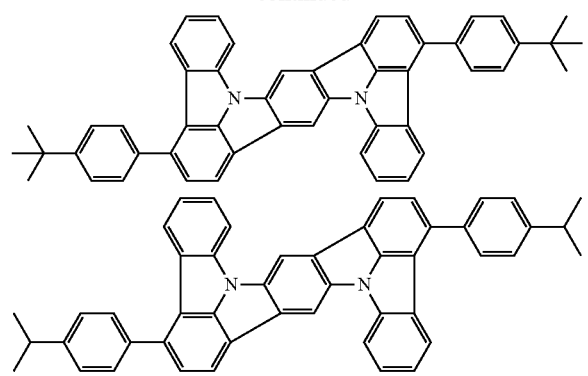
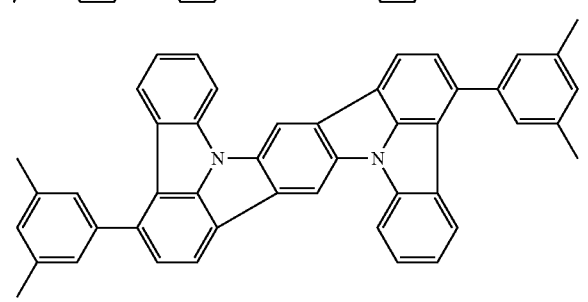
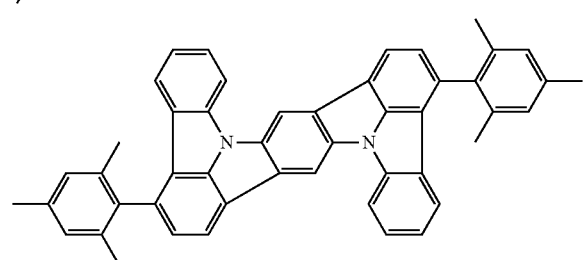
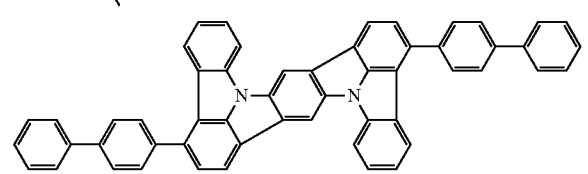
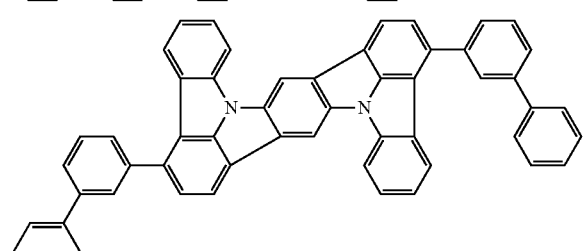
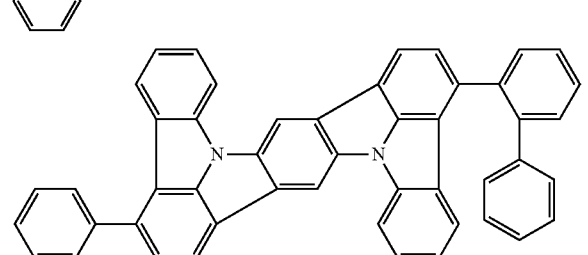
542
-continued
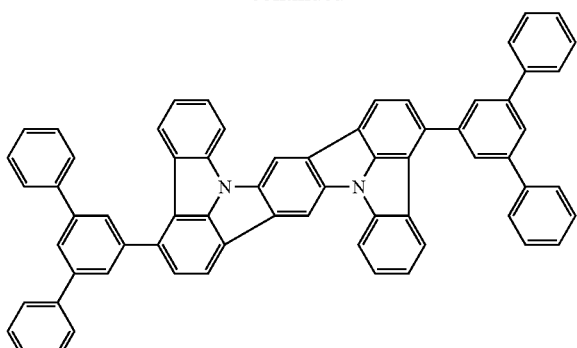
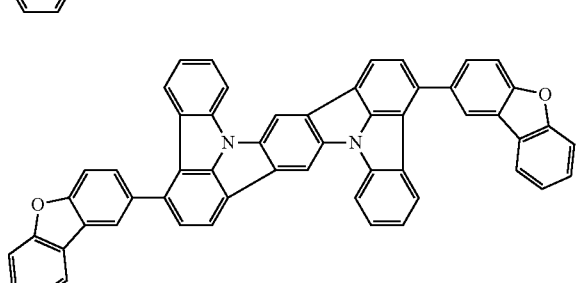
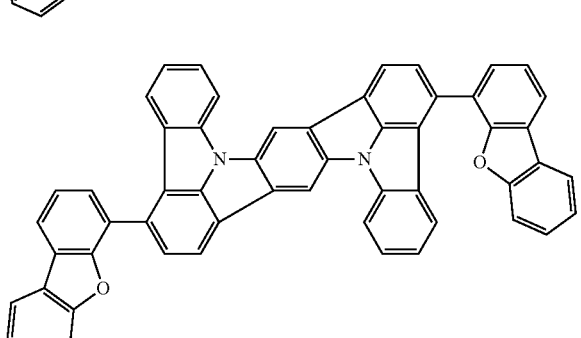
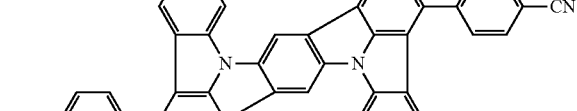

543
-continued
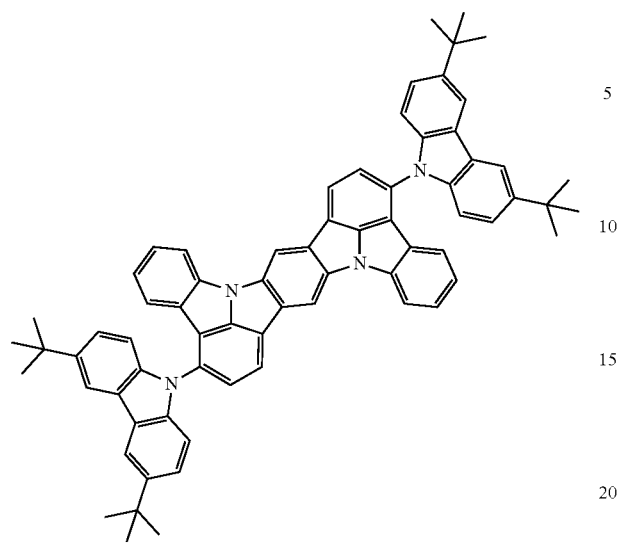
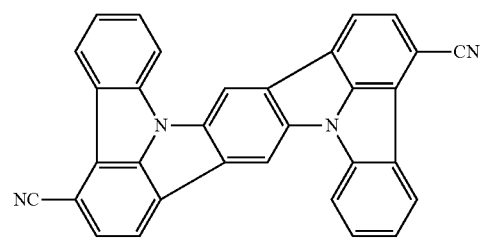
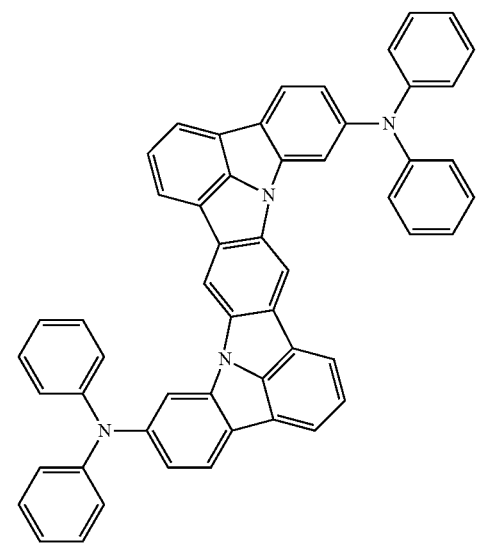
544
-continued
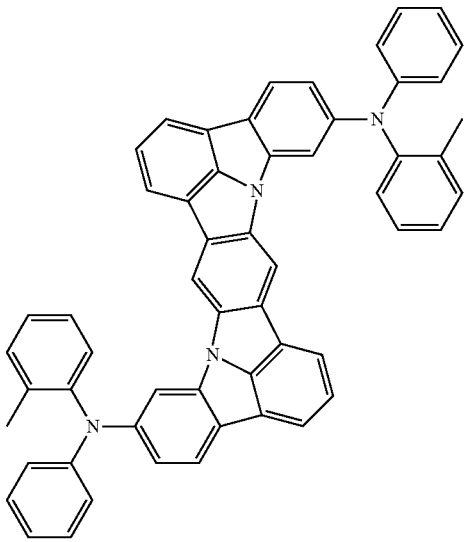
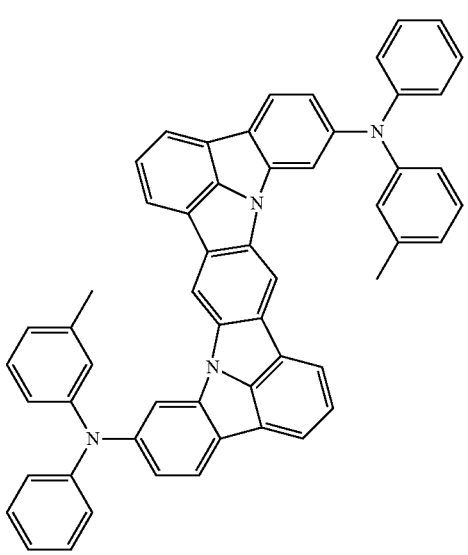
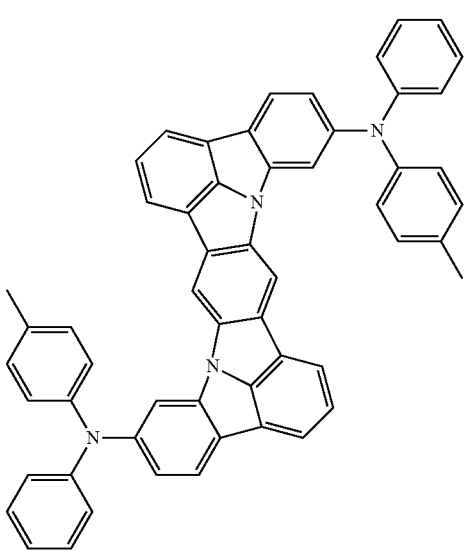

545
-continued
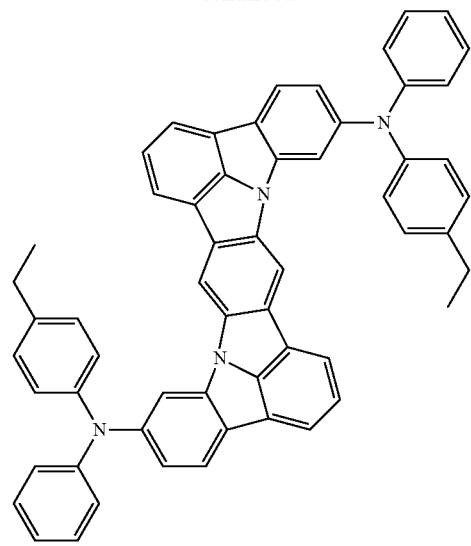
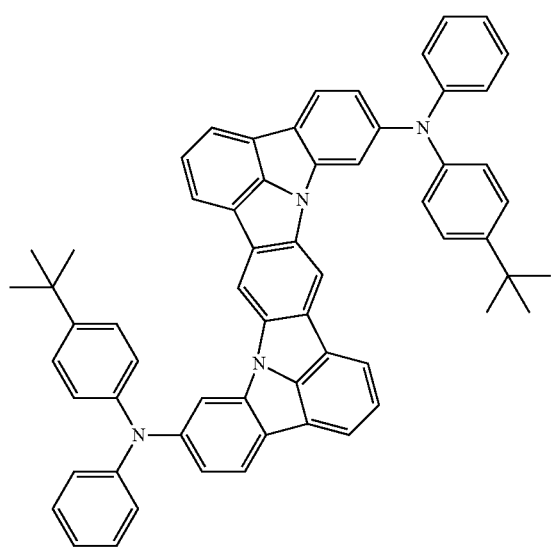
546
-continued
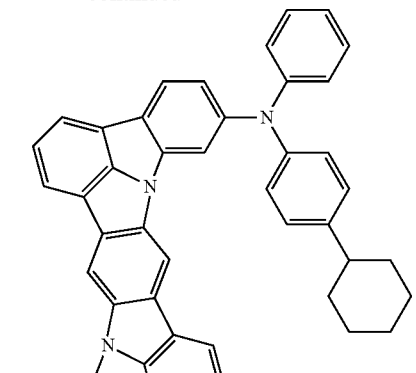
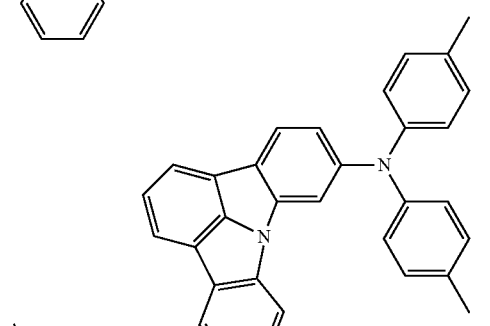
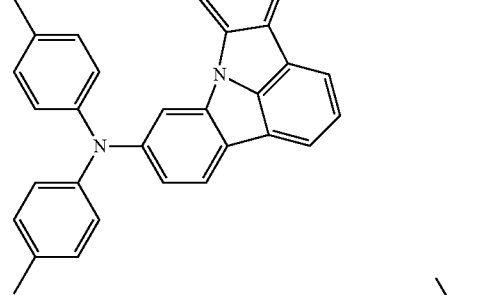
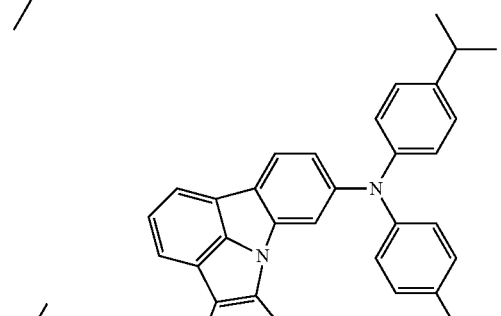
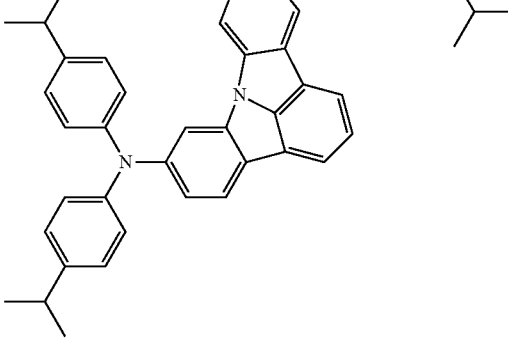

547
-continued
548
-continued
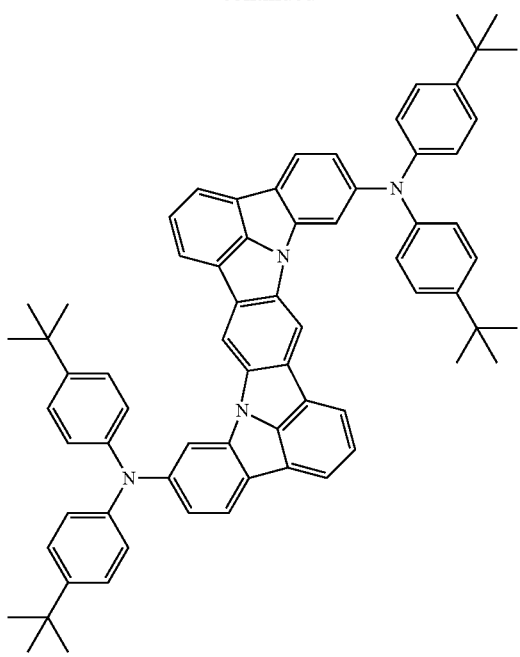
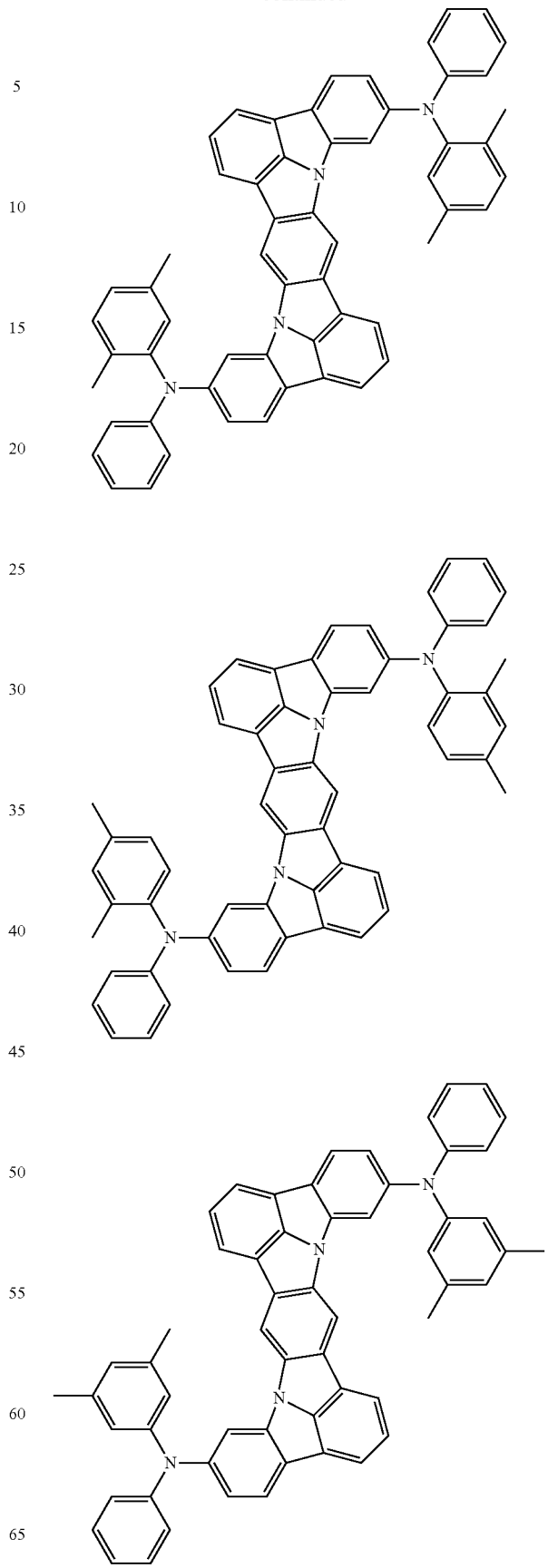

549
-continued
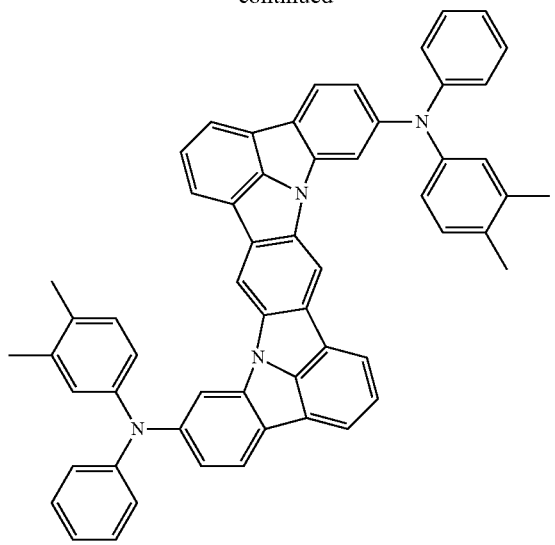
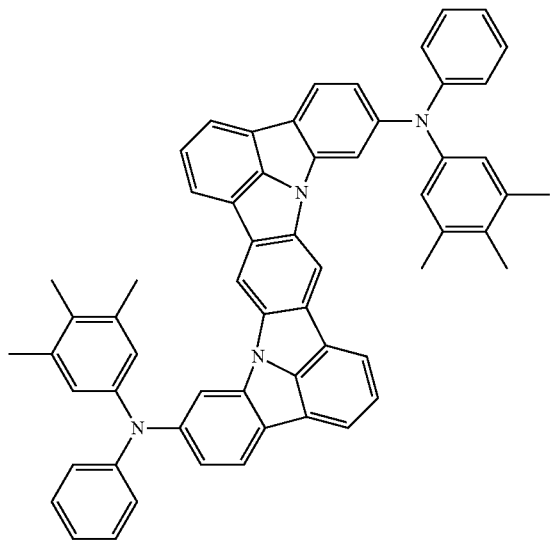
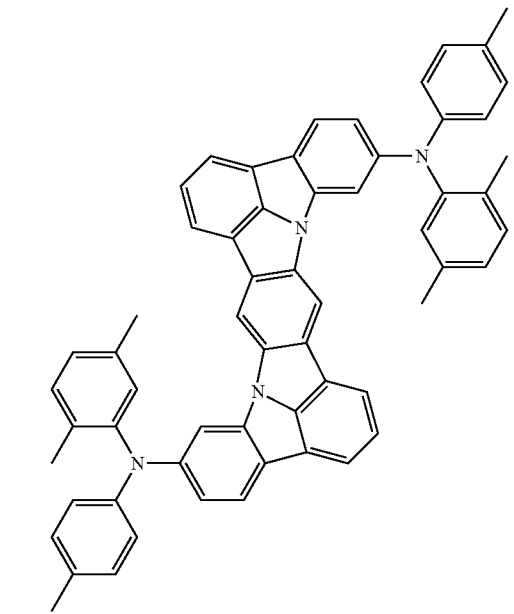
550
-continued
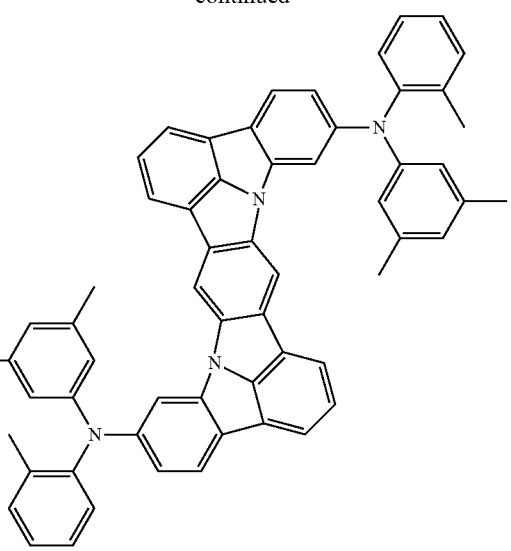
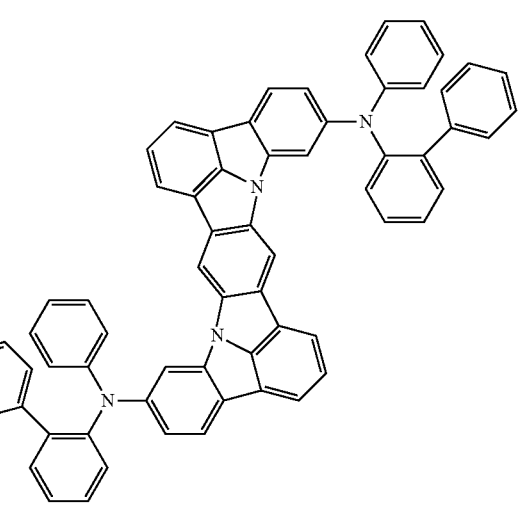
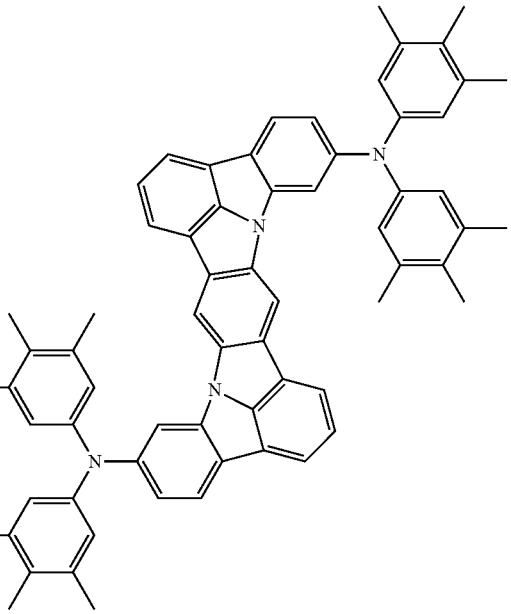

551
-continued
552
-continued
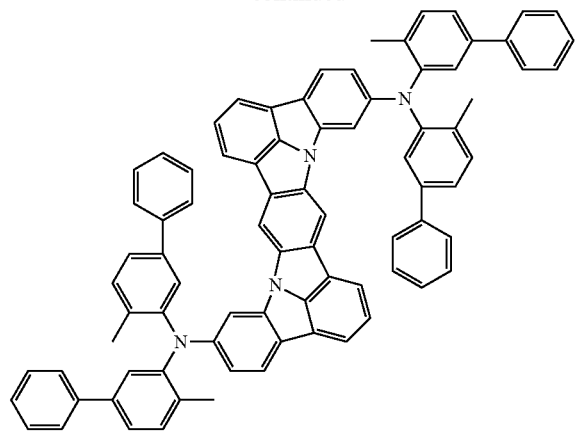
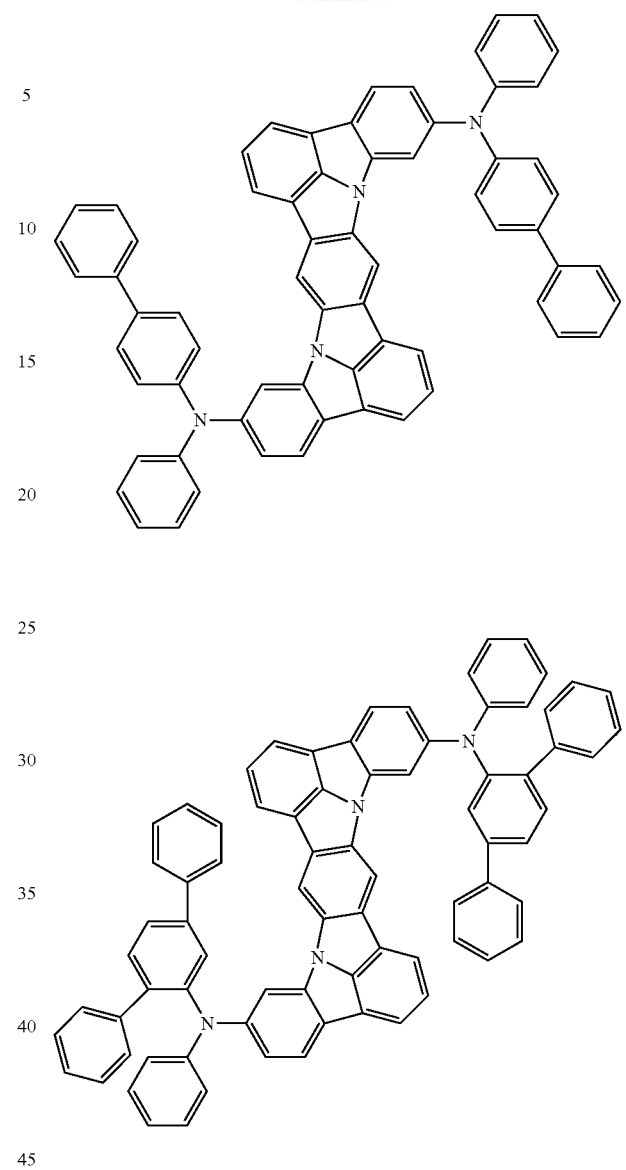
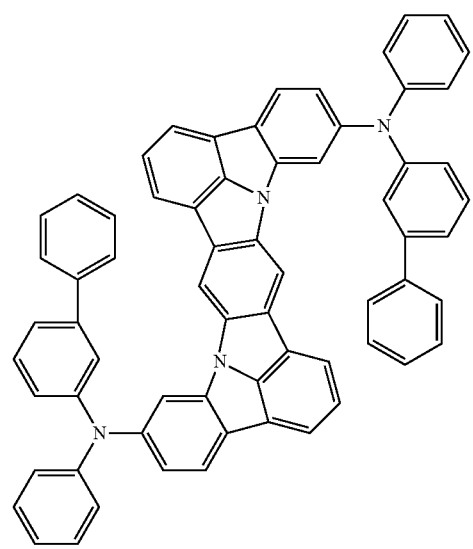

553
-continued
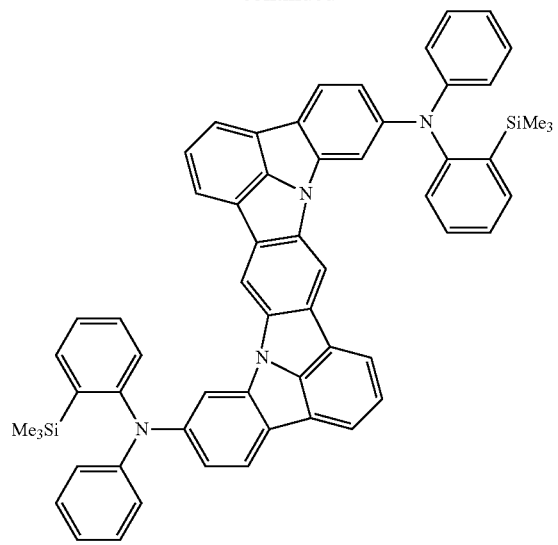
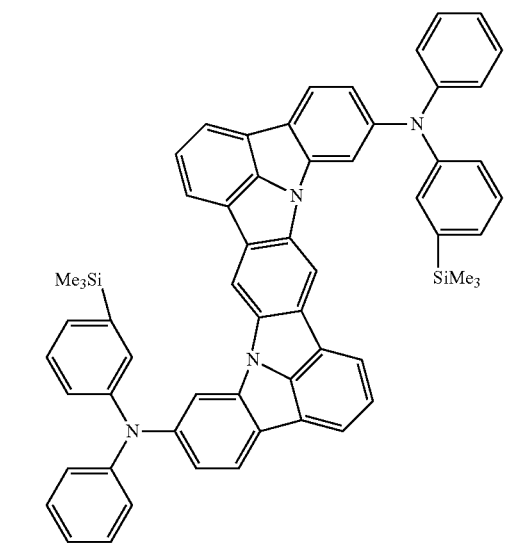
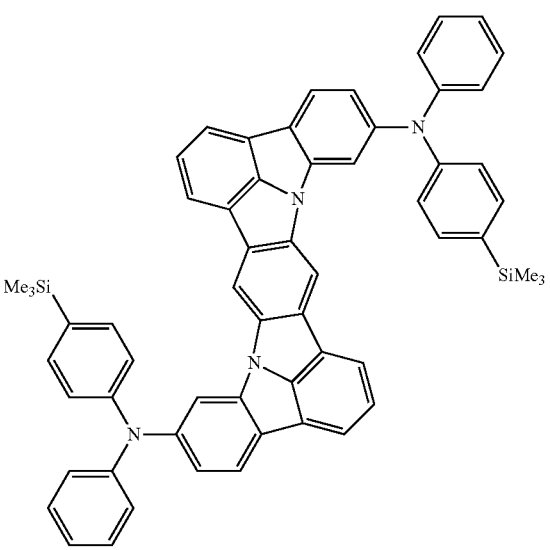
554
-continued
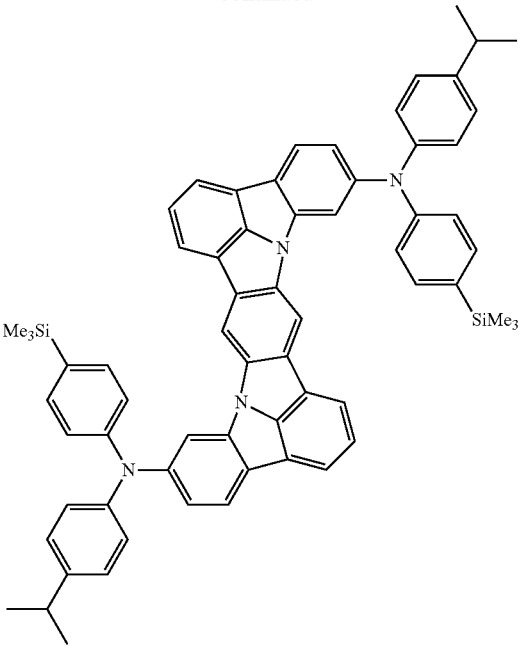
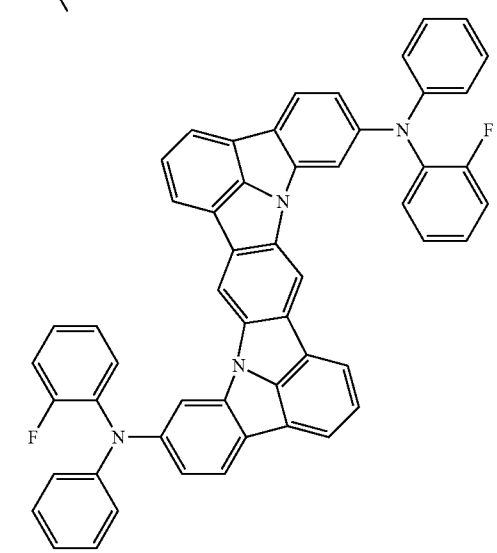
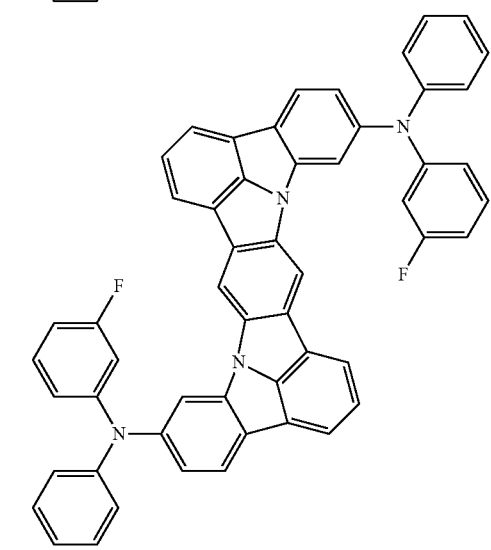

555
-continued
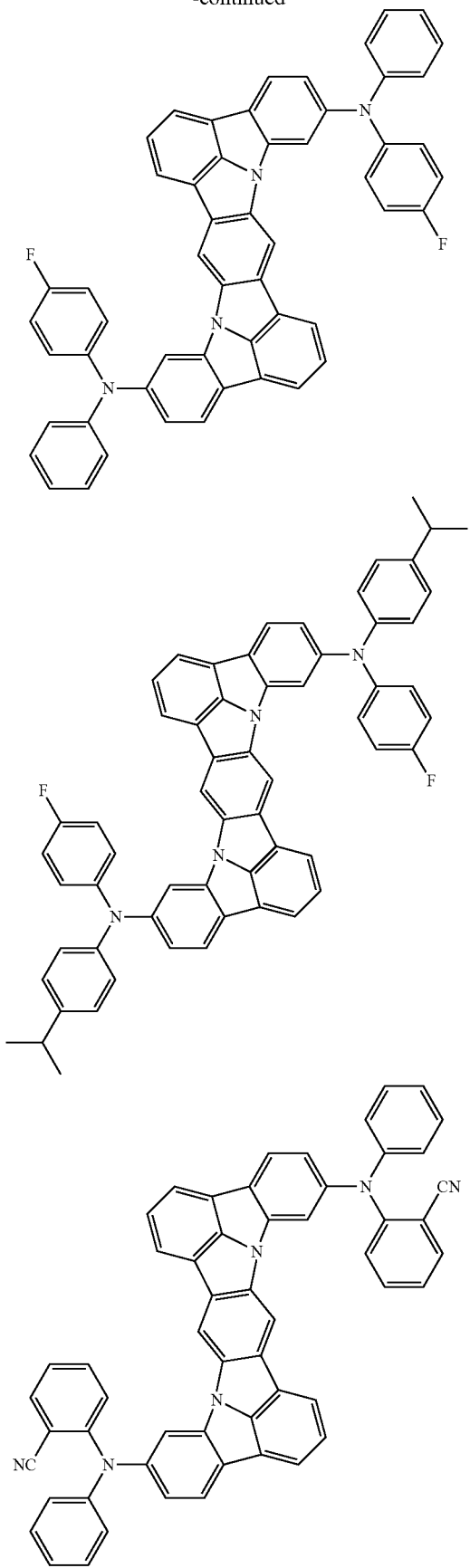
556
-continued
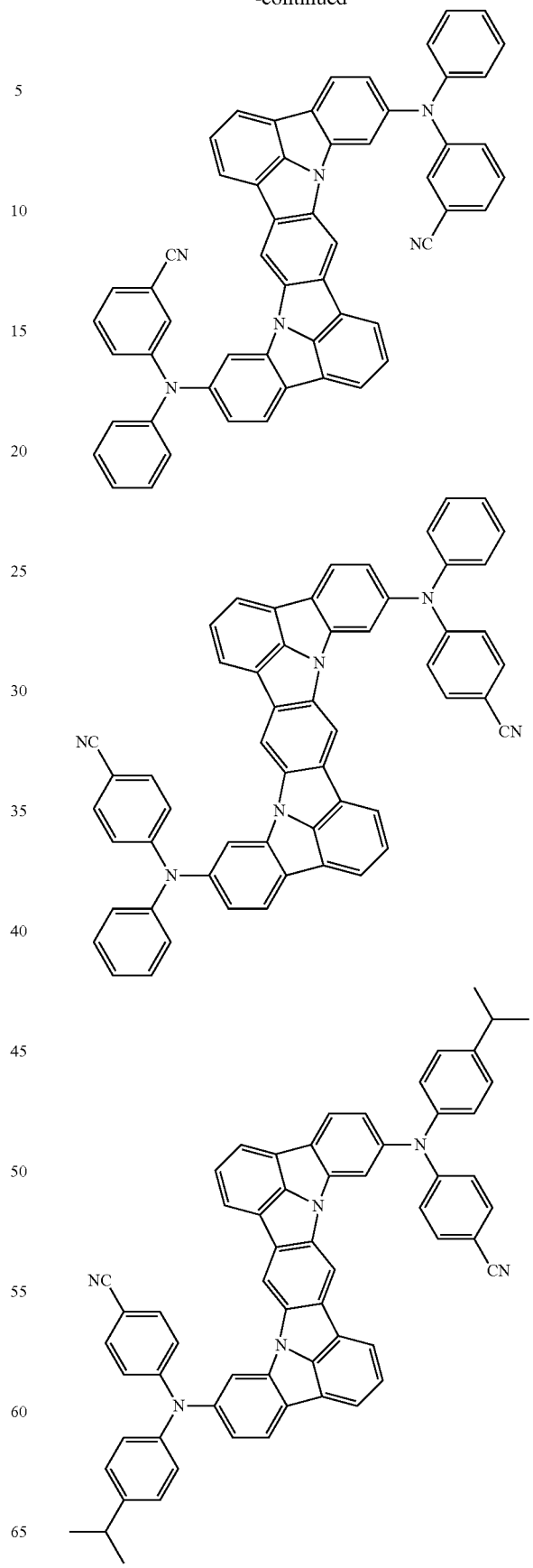

557
-continued
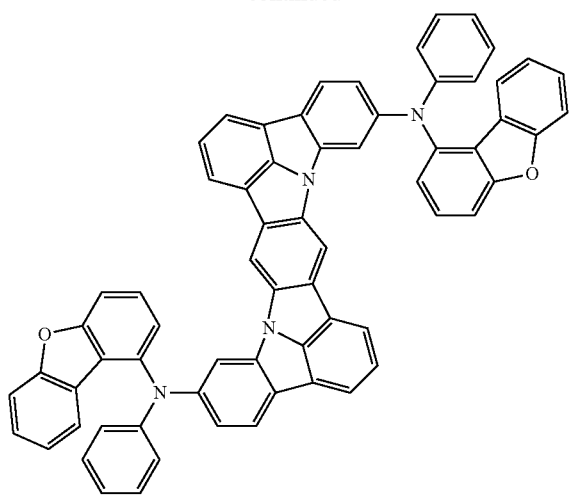
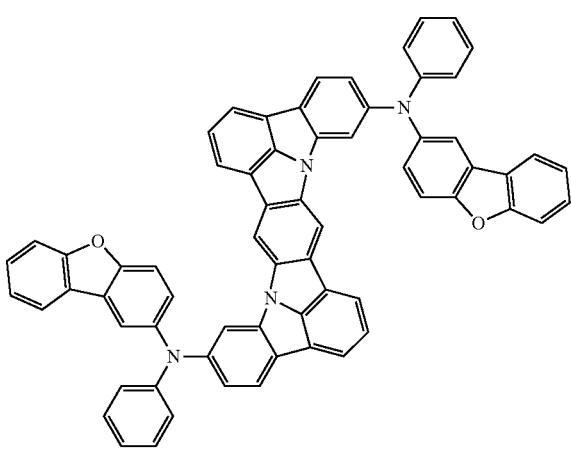
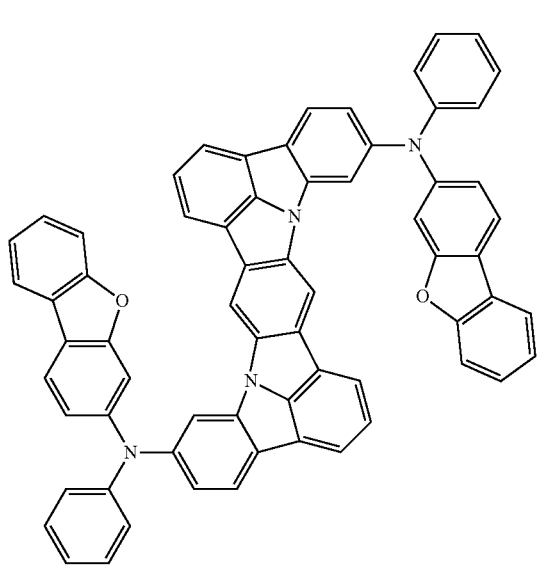
558
-continued
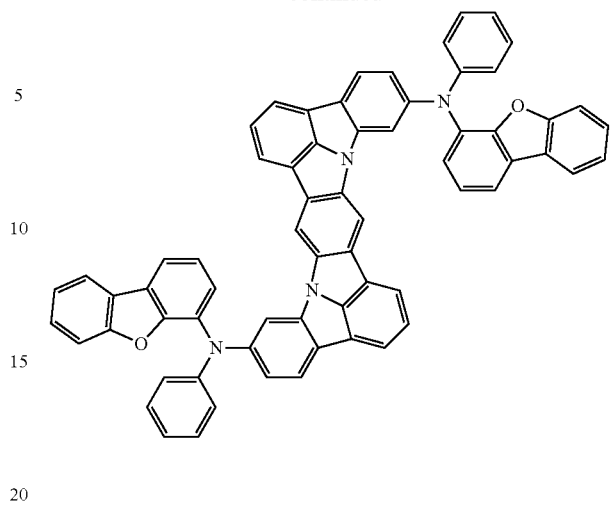
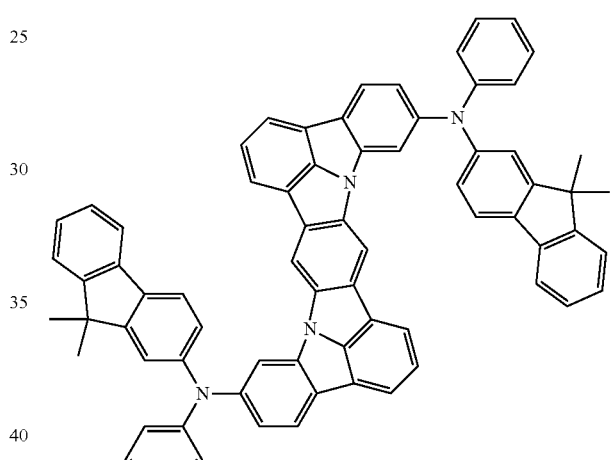
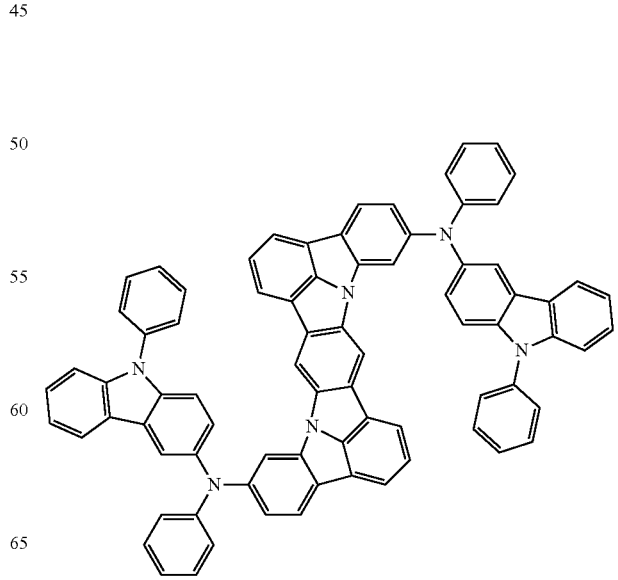

559
-continued
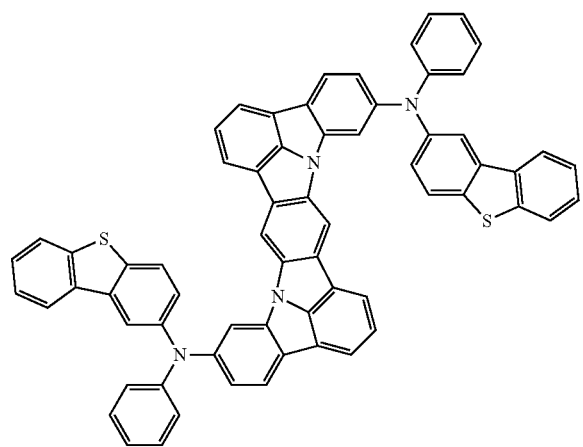
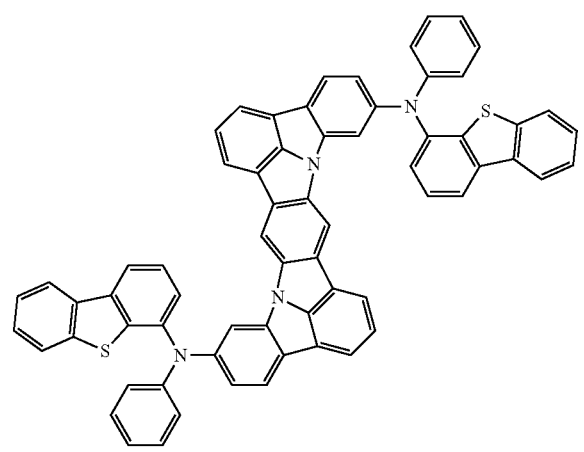
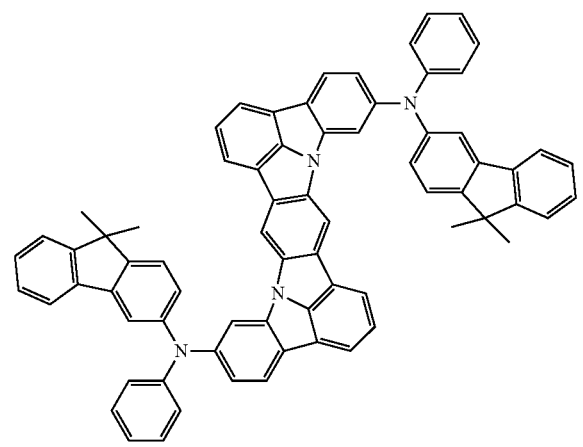
560
-continued
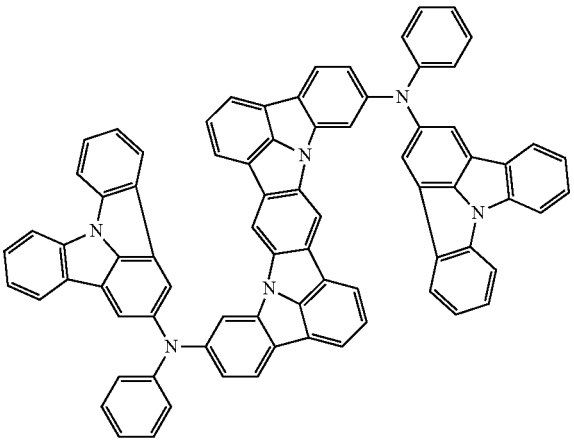
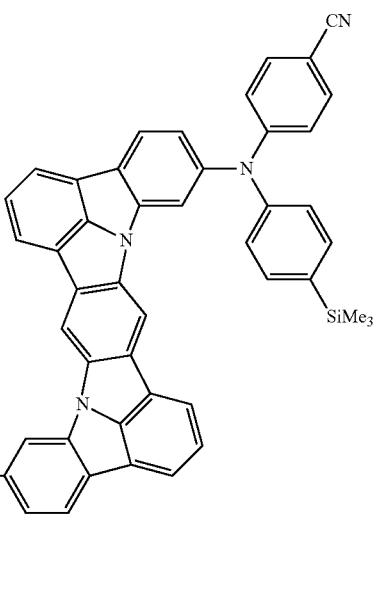
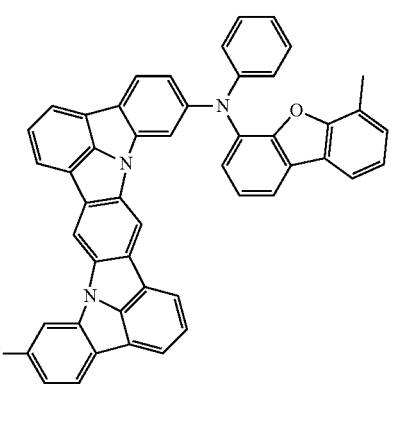

561
-continued
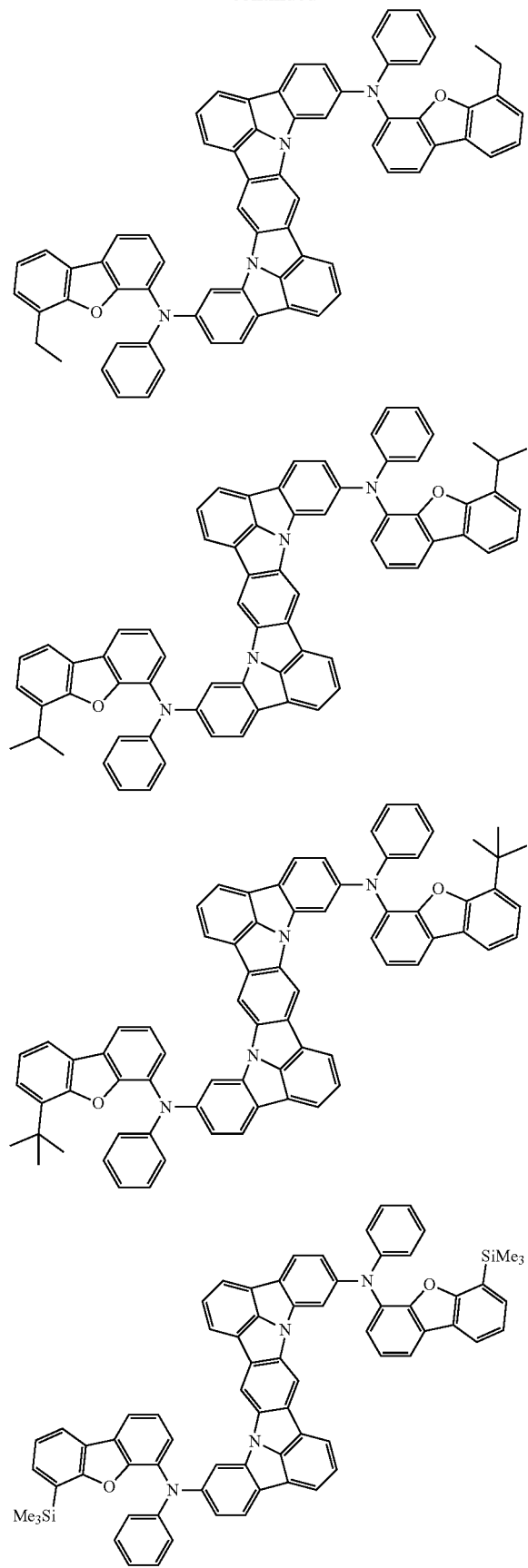
562
-continued
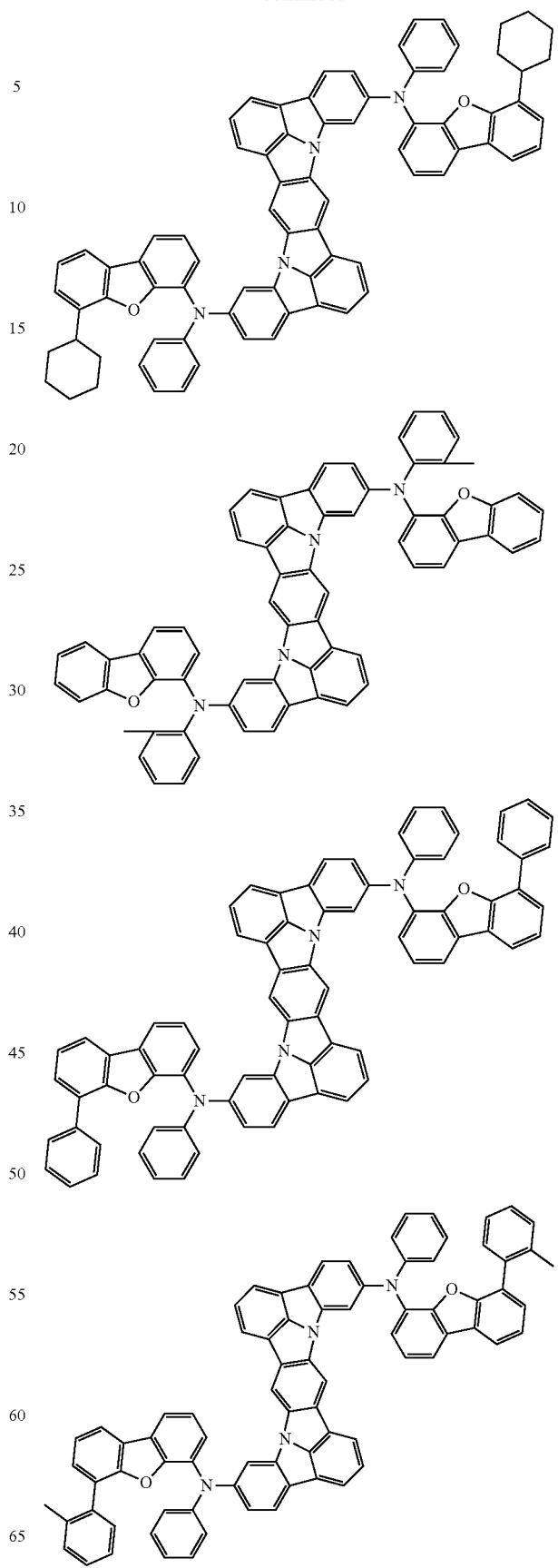

563
-continued
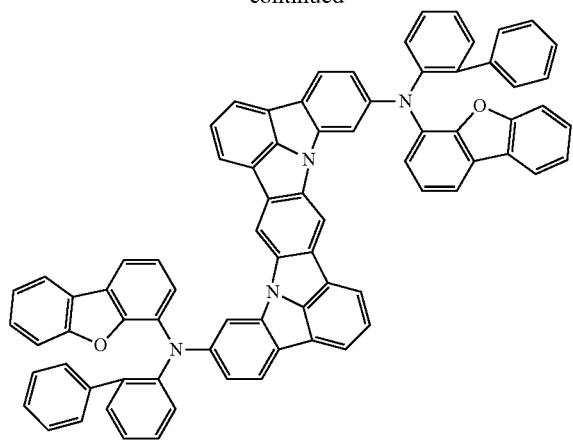
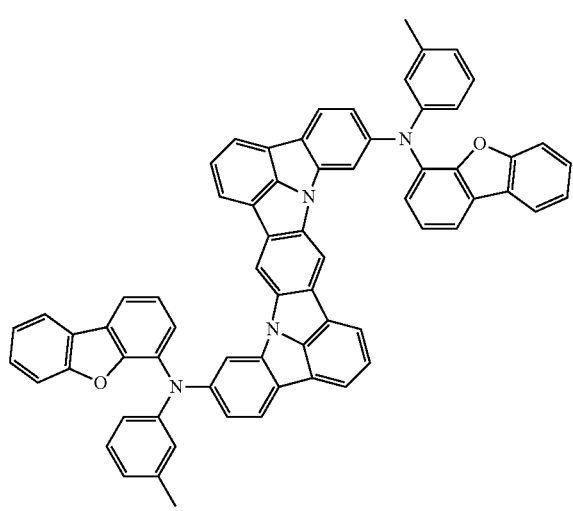
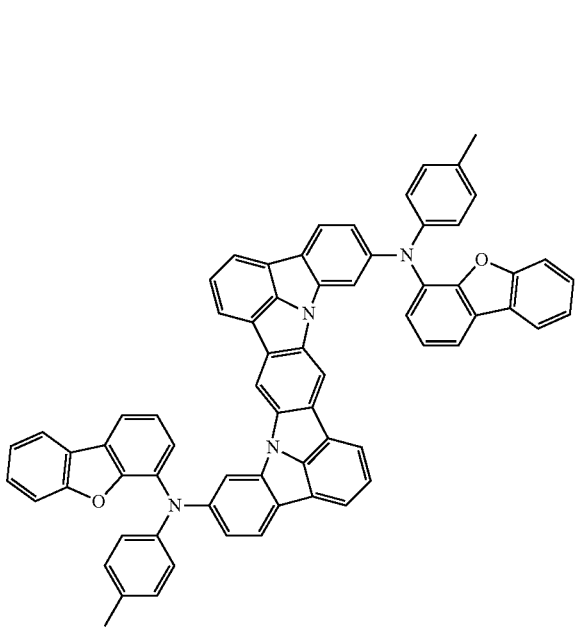
564
-continued
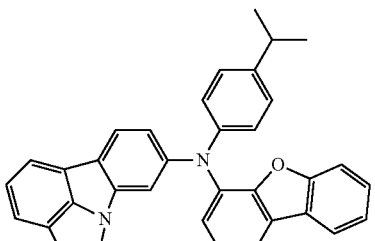
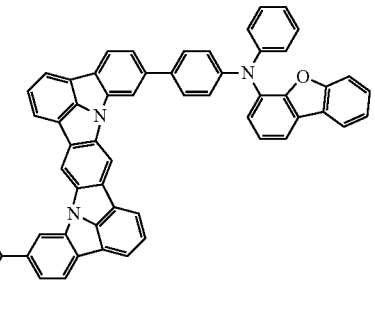
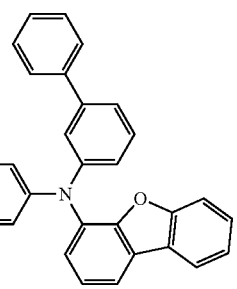
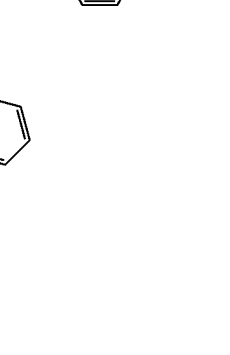

565
-continued
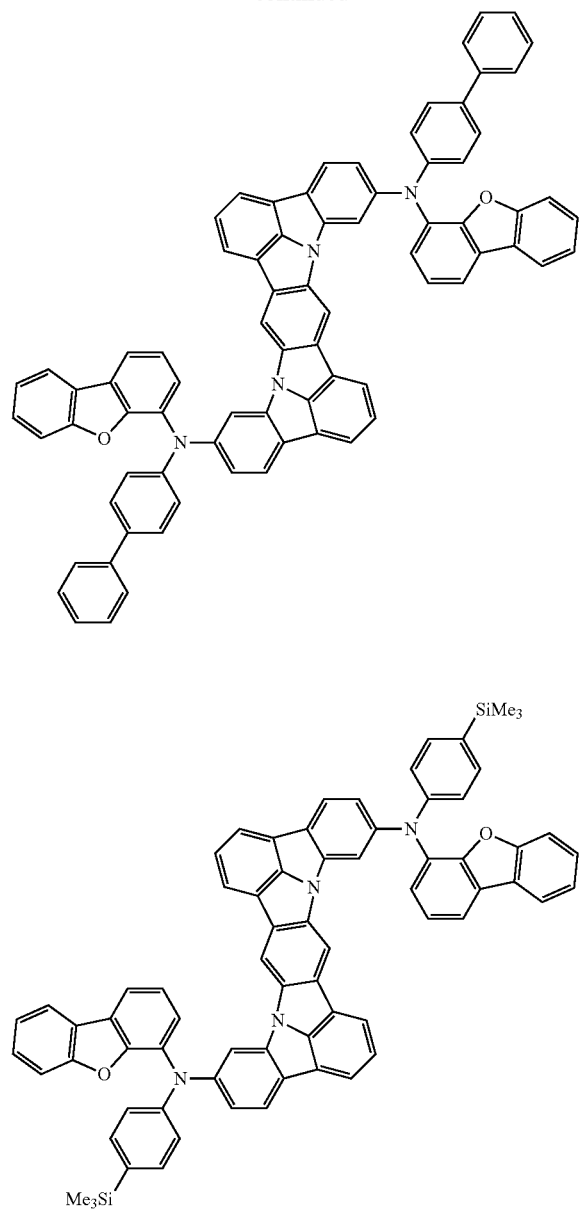
566
-continued
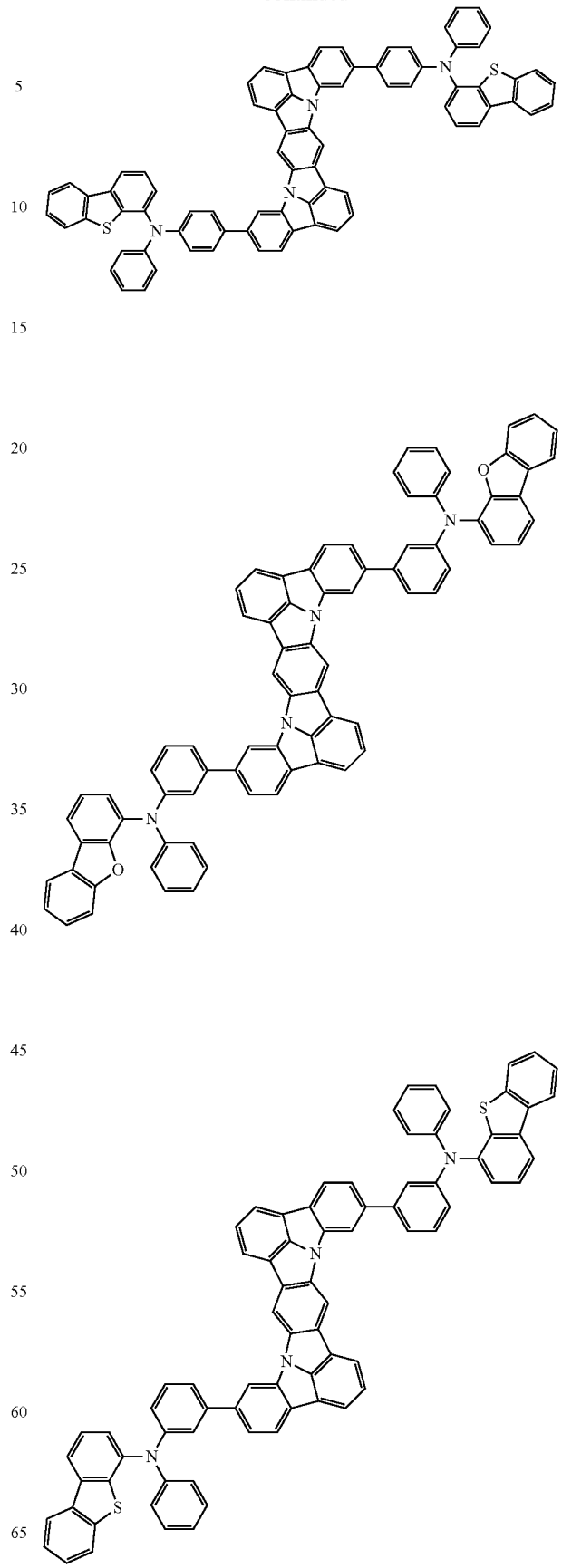

567
-continued
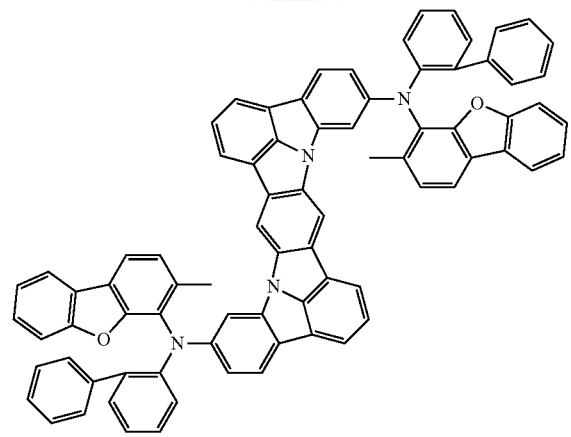
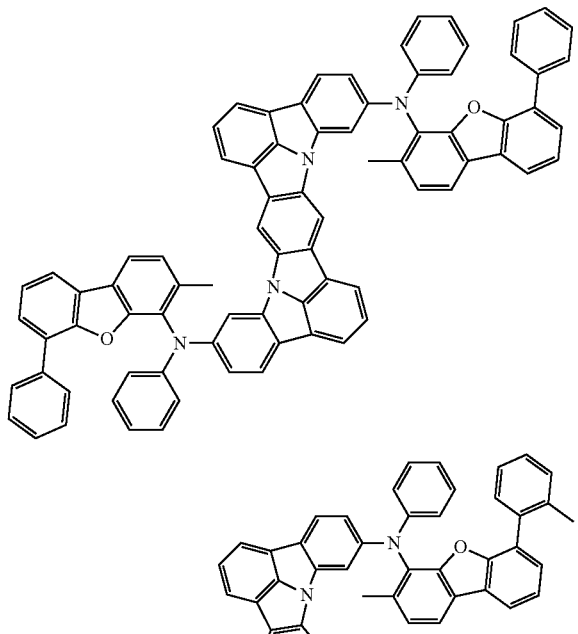
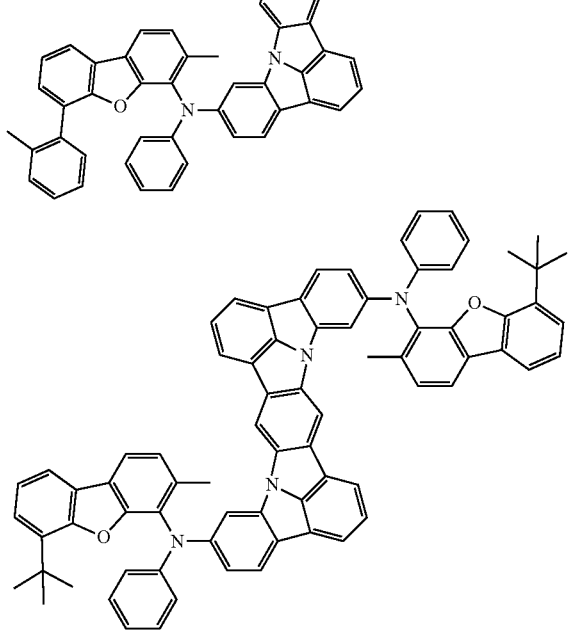
568
-continued
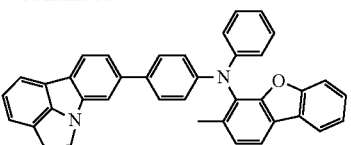
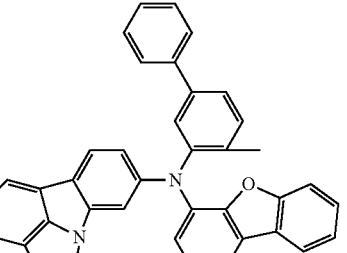

569
-continued
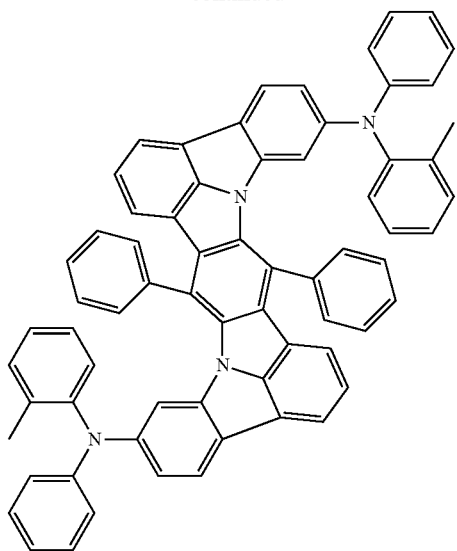
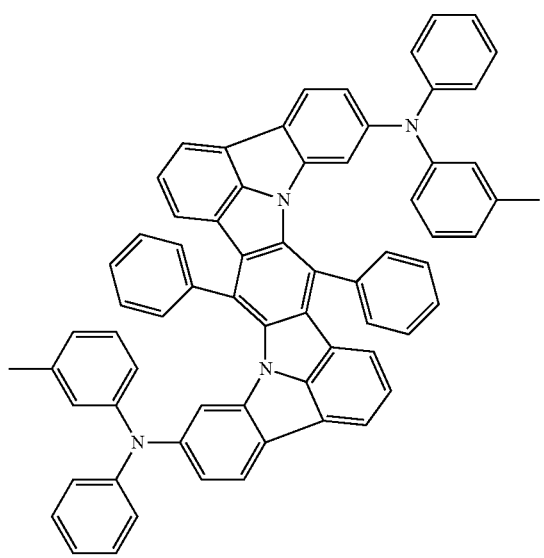
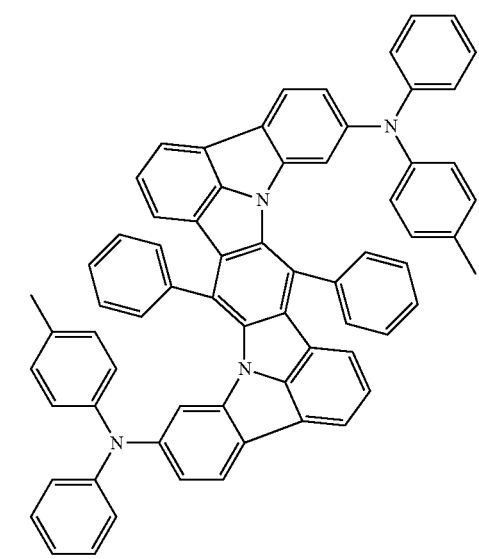
570
-continued
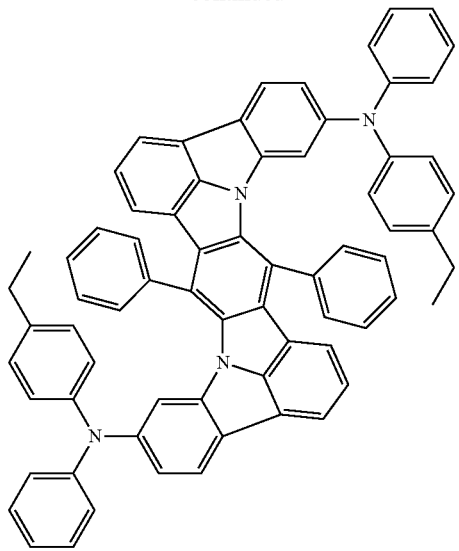
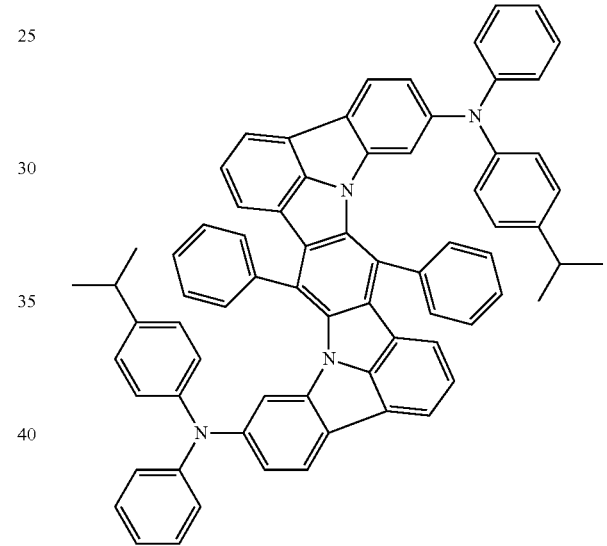
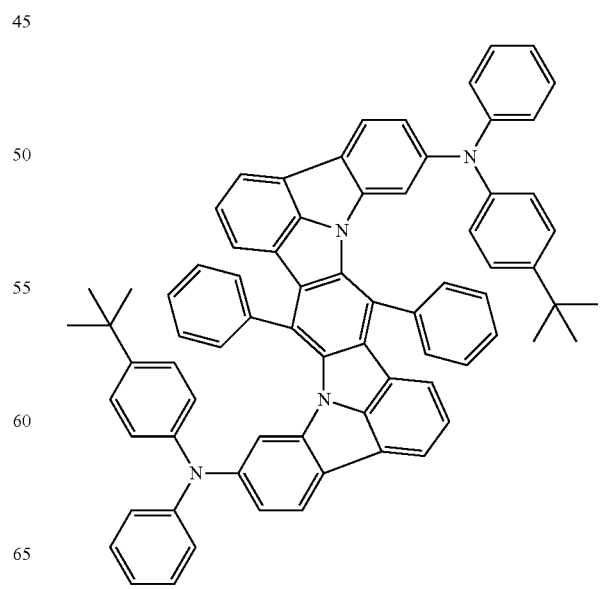

571
-continued
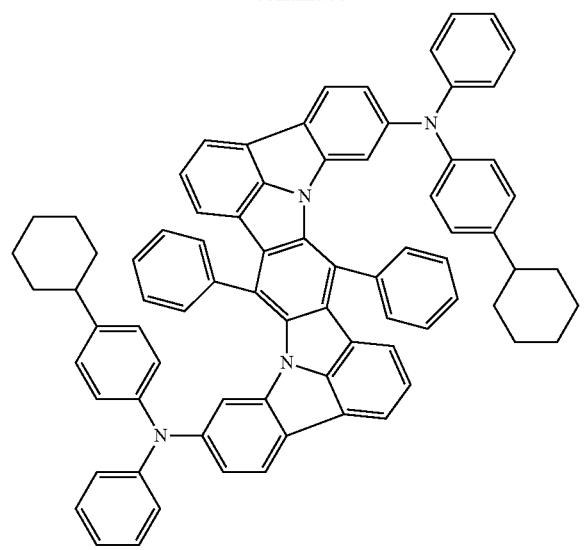
572
-continued
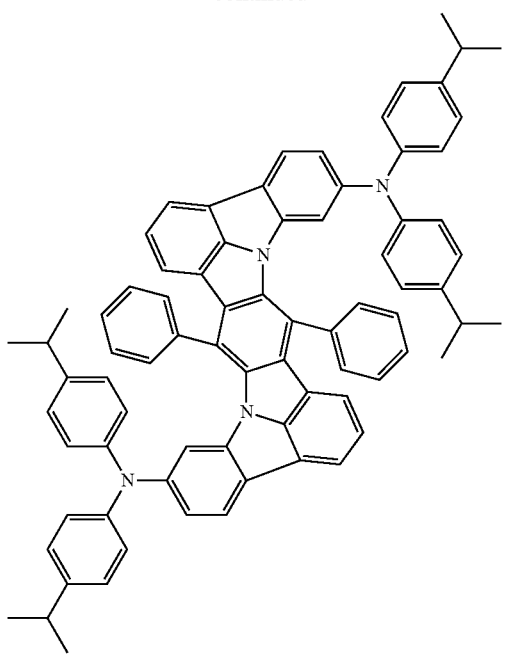
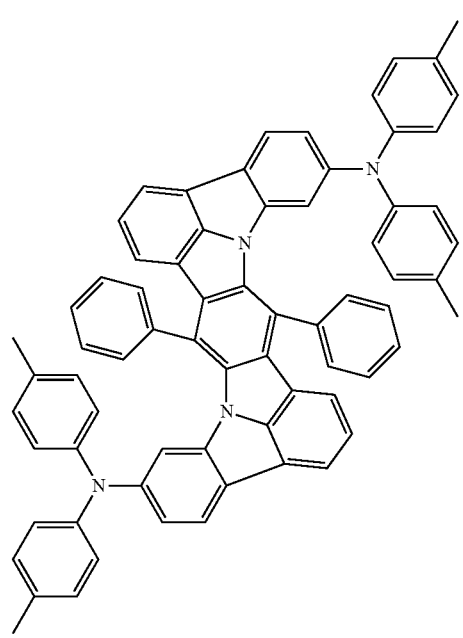
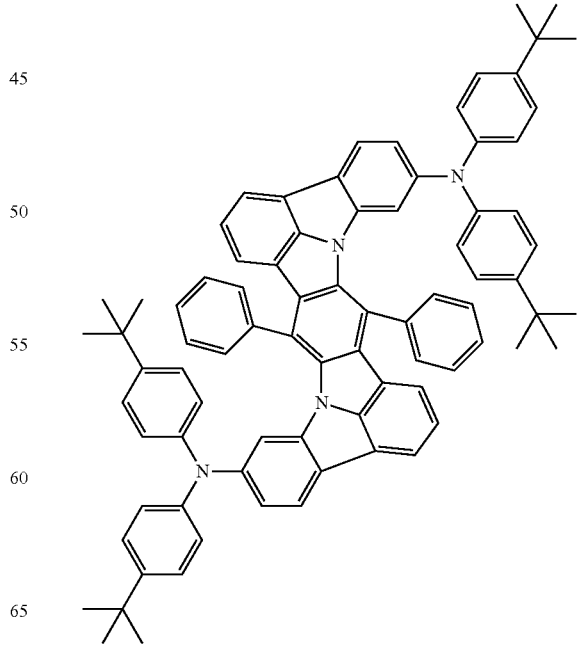

573
-continued
574
-continued
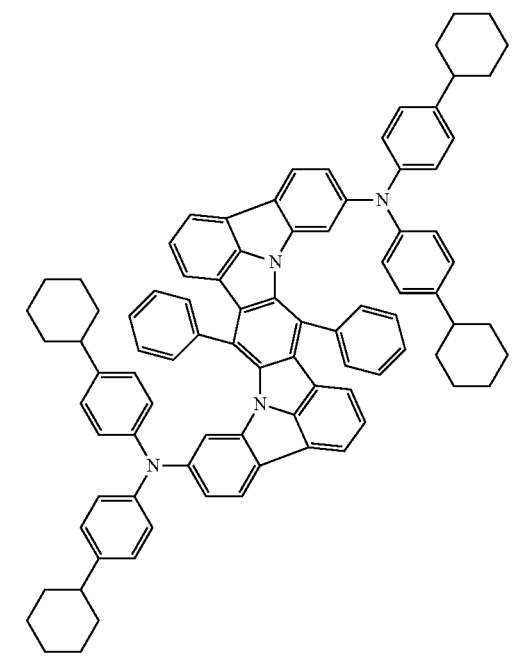
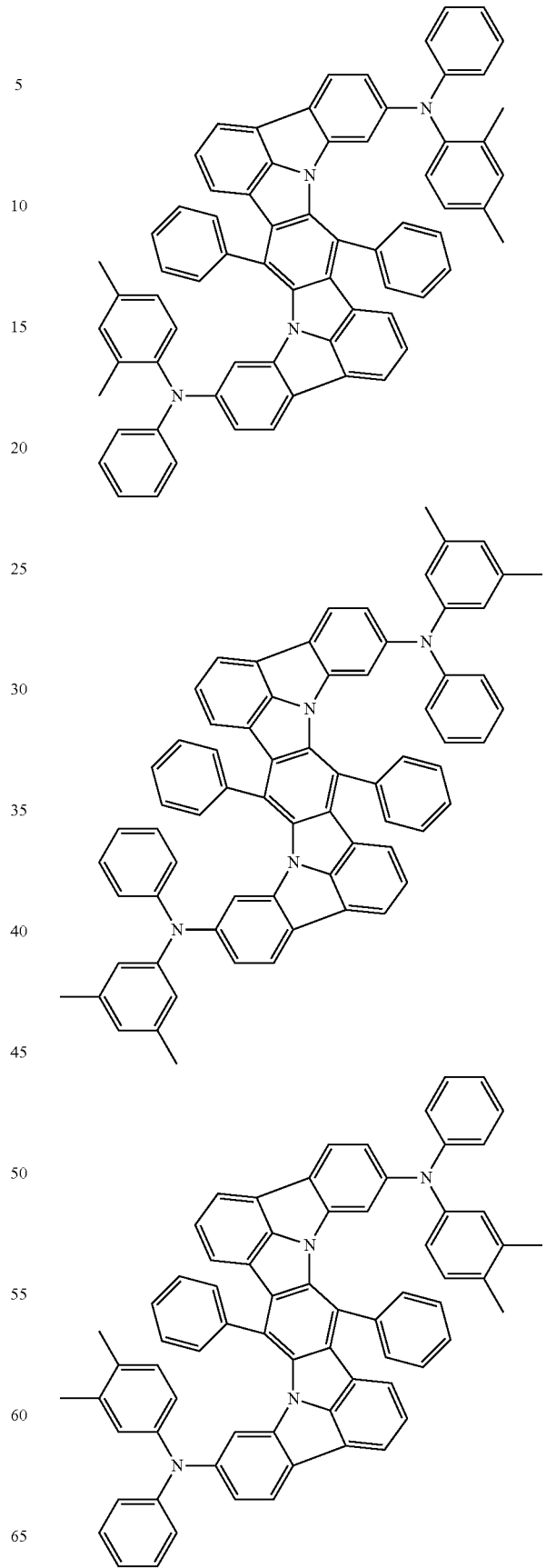

575
-continued
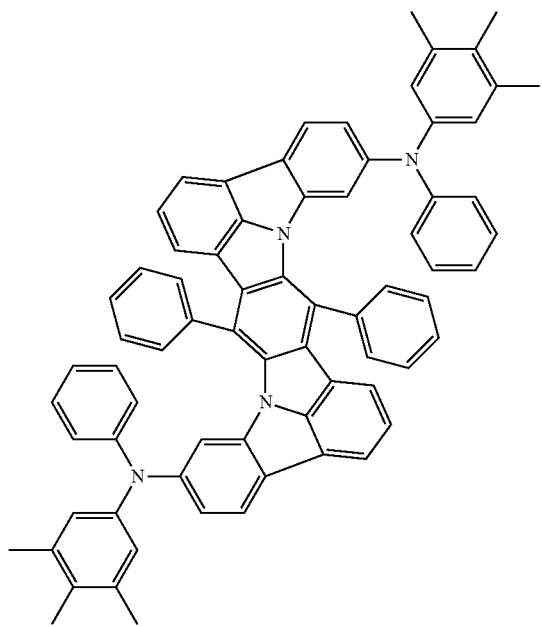
576
-continued
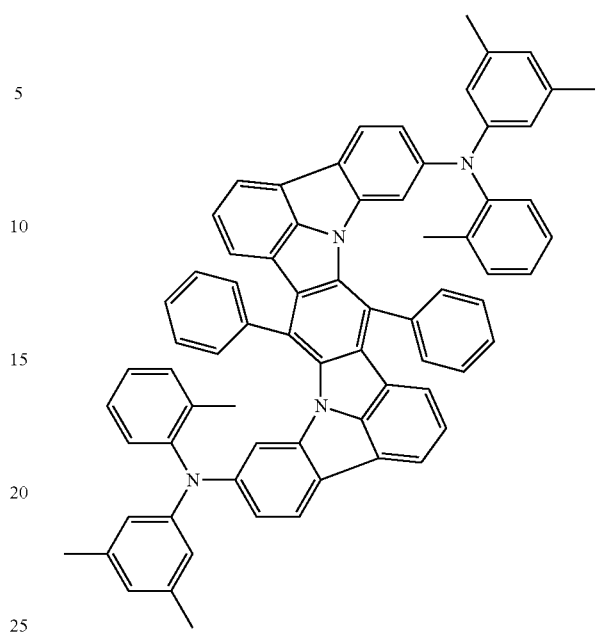
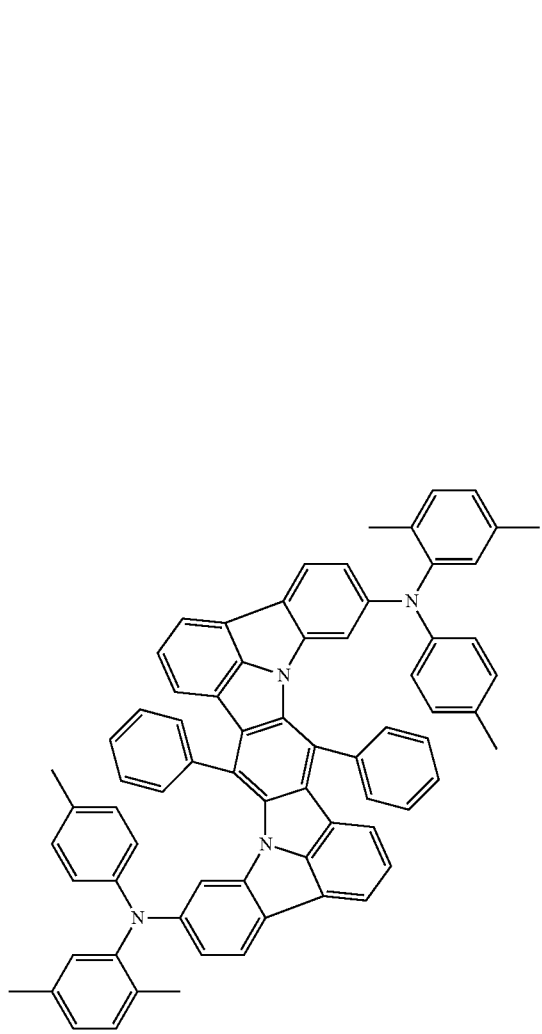
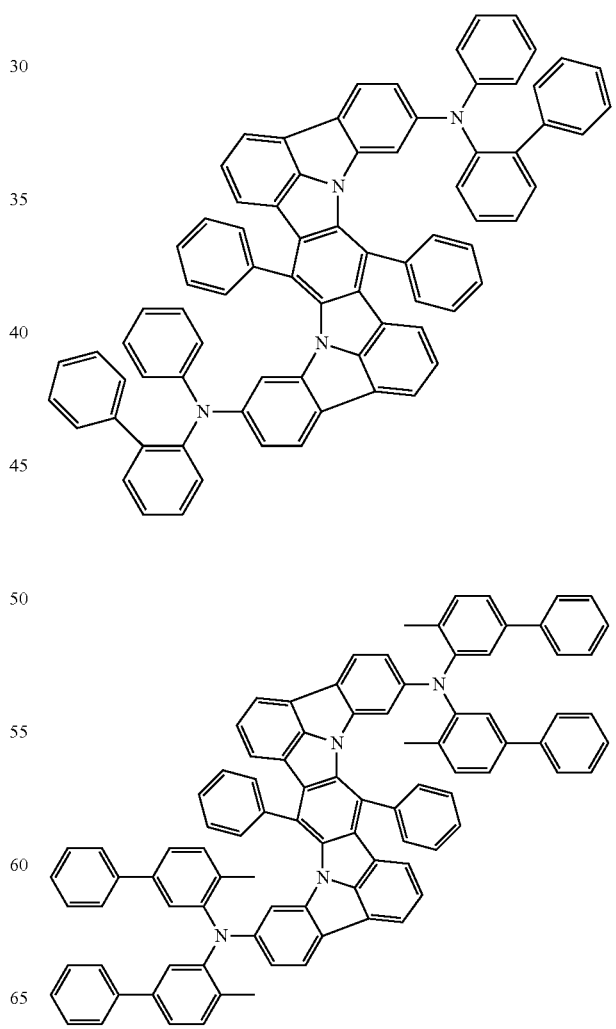

577
-continued
578
-continued
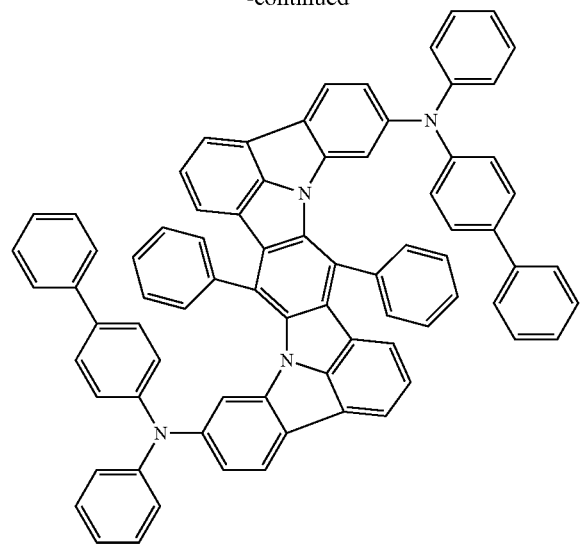
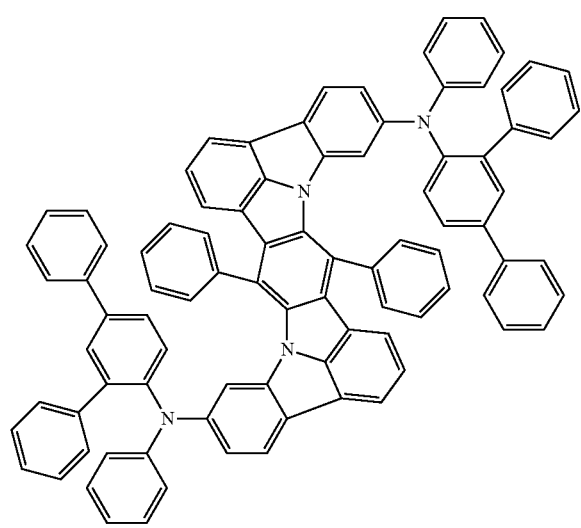
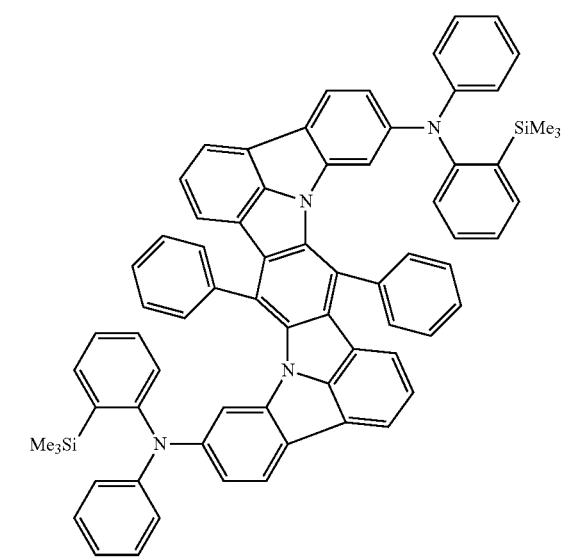
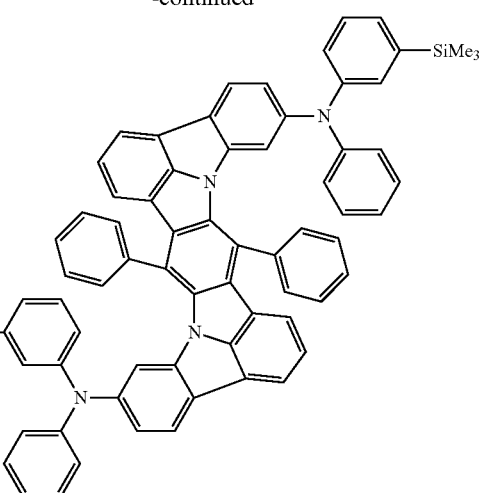
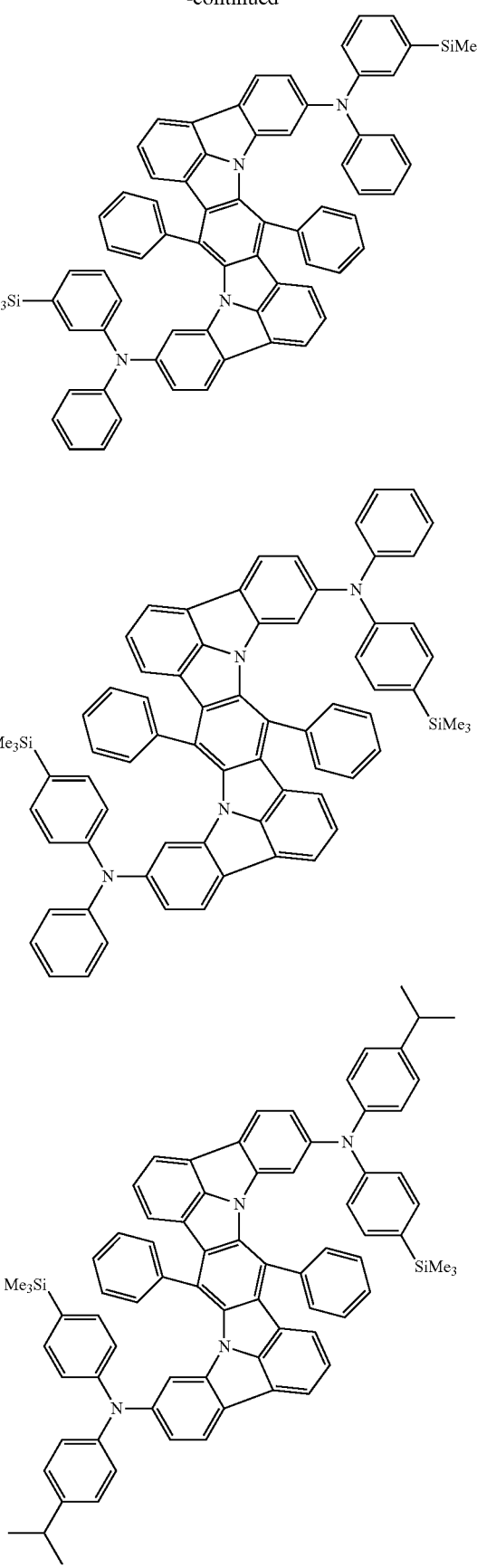

579
-continued
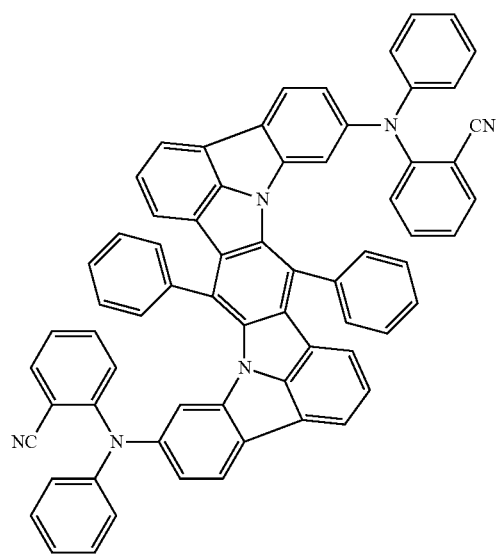
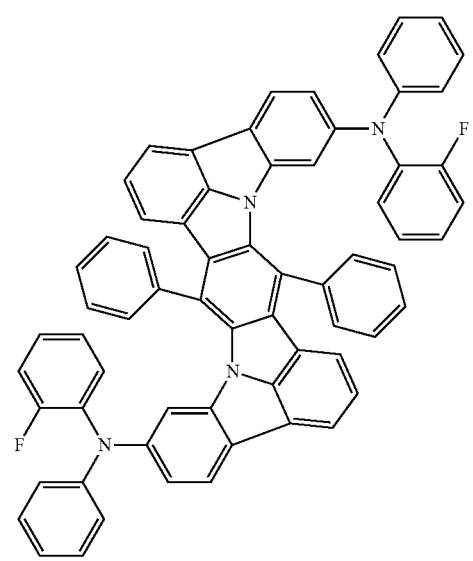
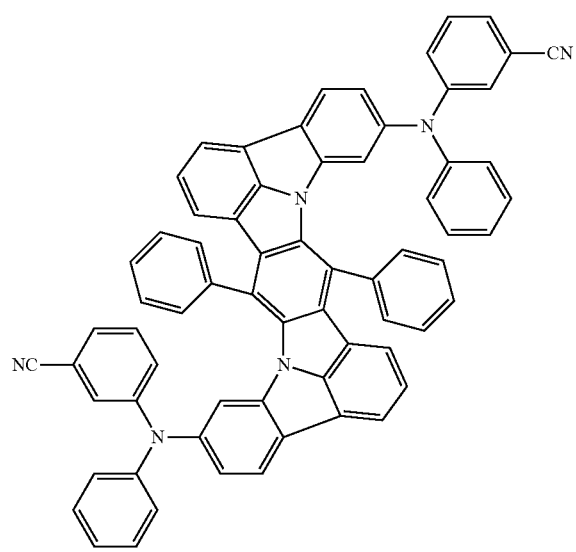
580
-continued
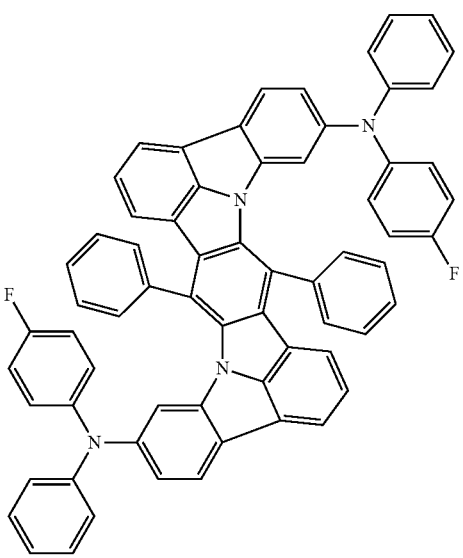
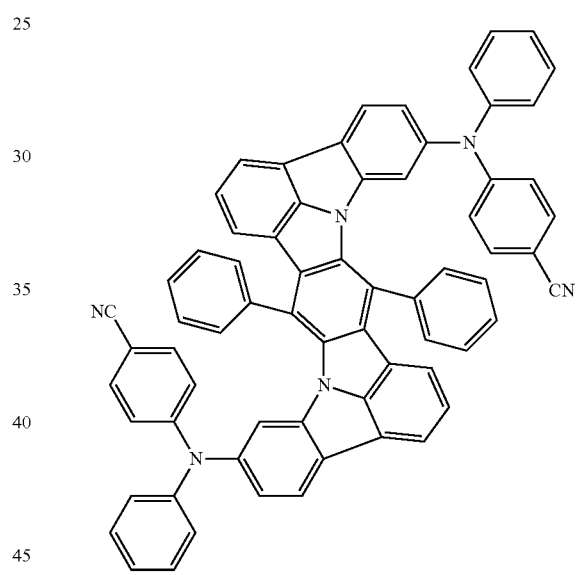
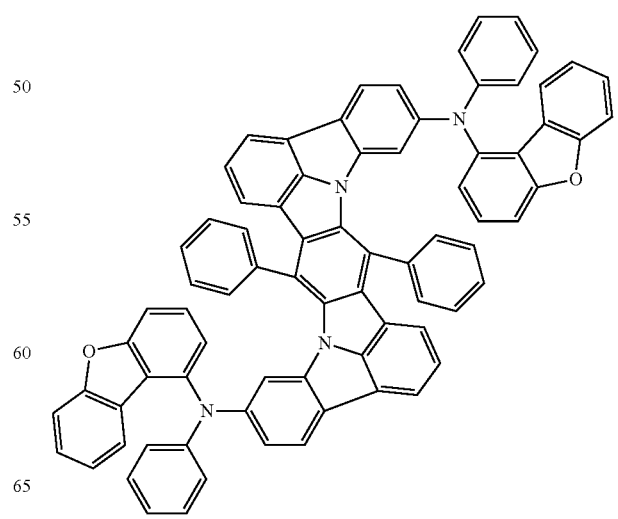

581
-continued
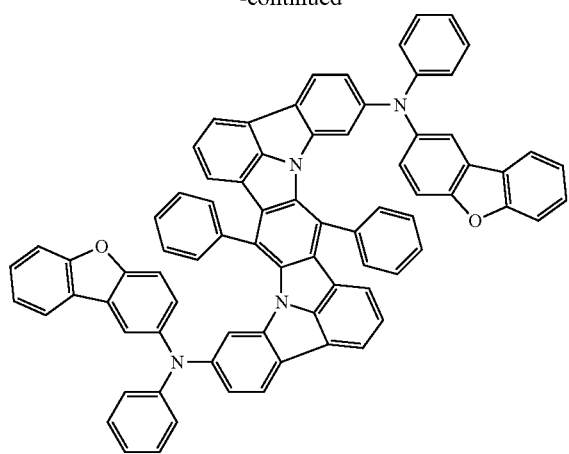
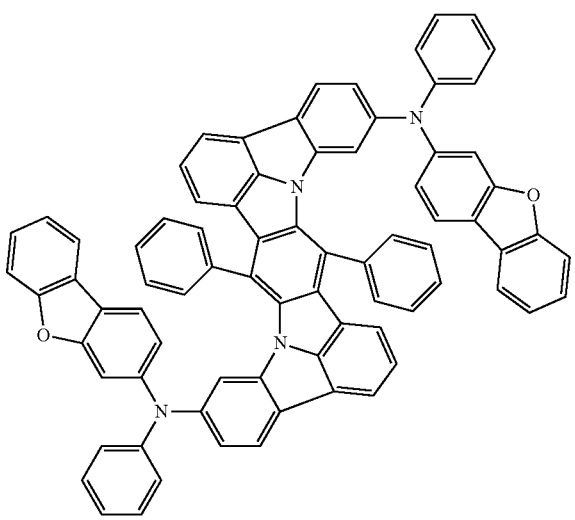
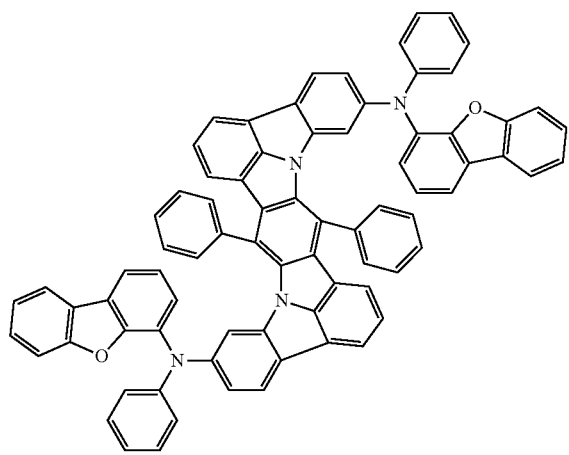
582
-continued
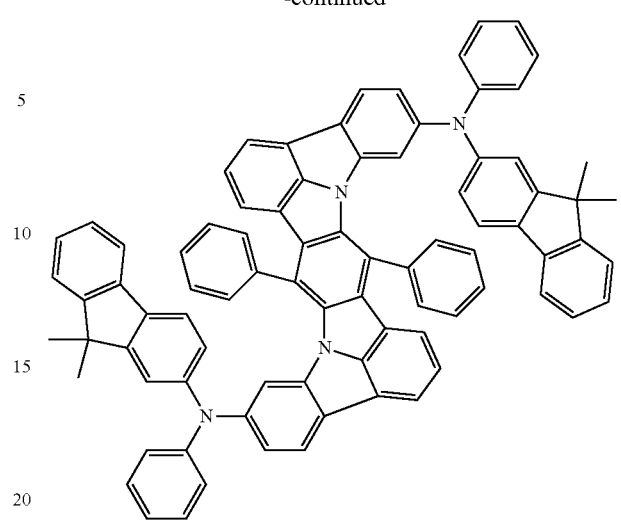
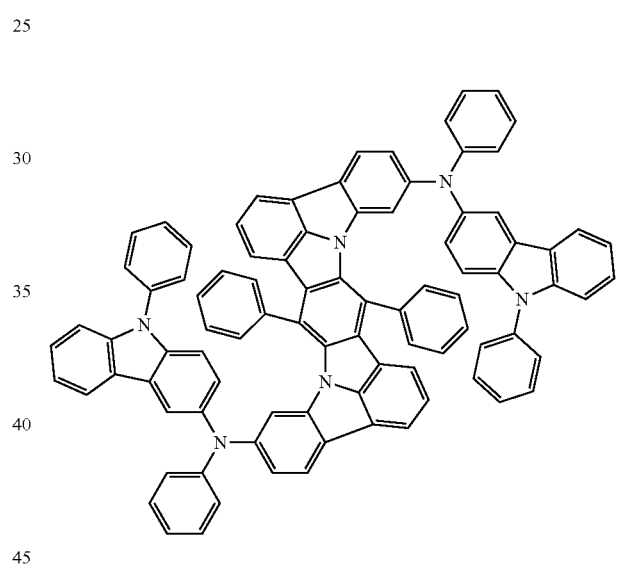
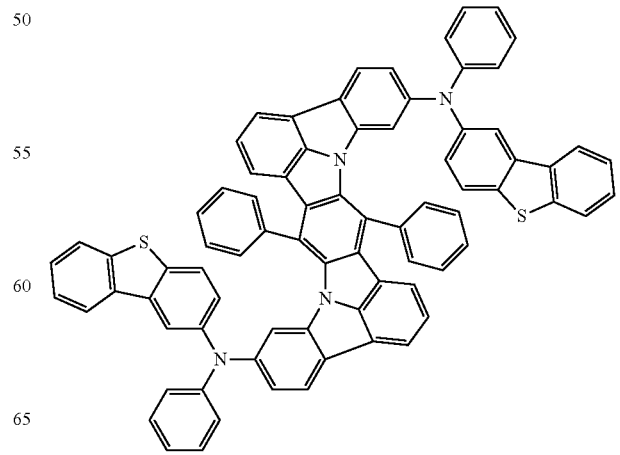

583
-continued
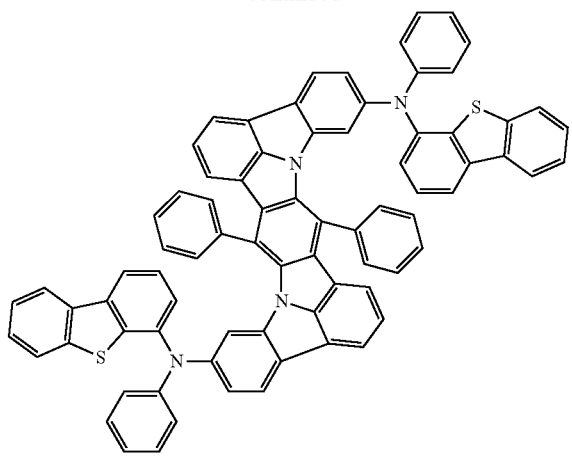
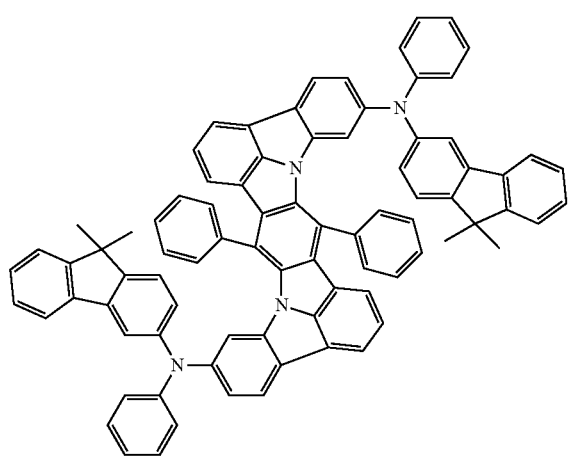
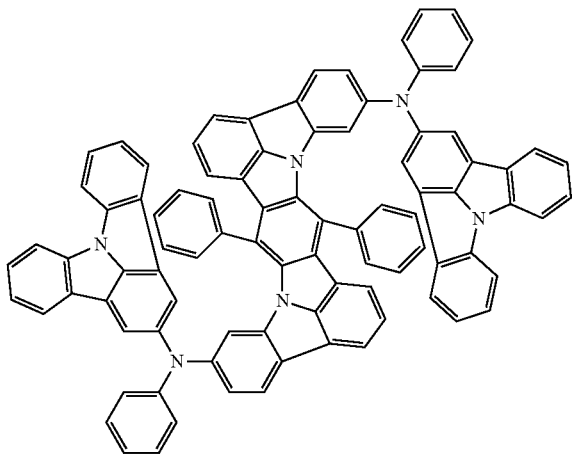
584
-continued
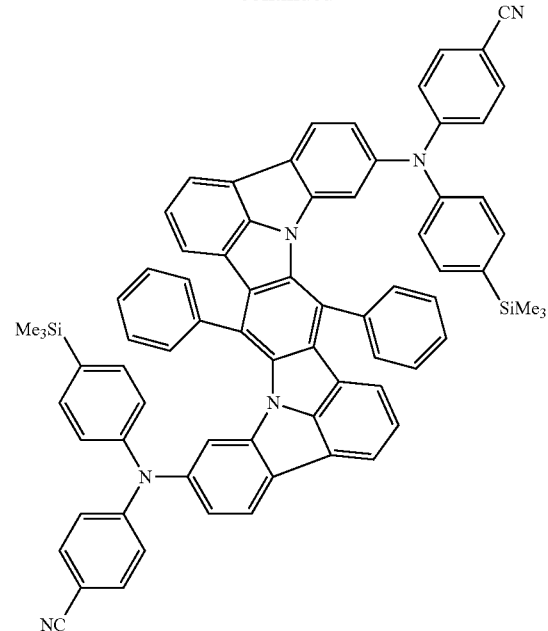
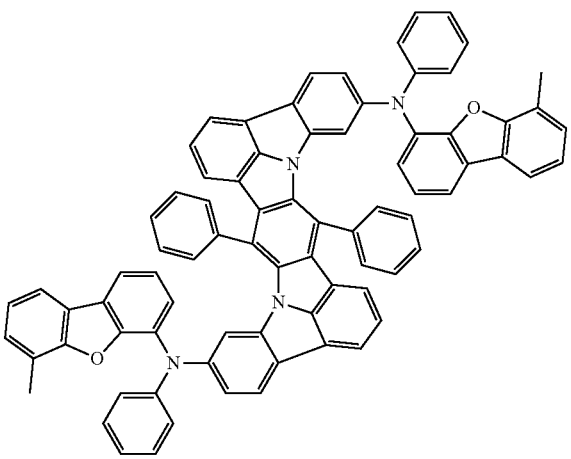
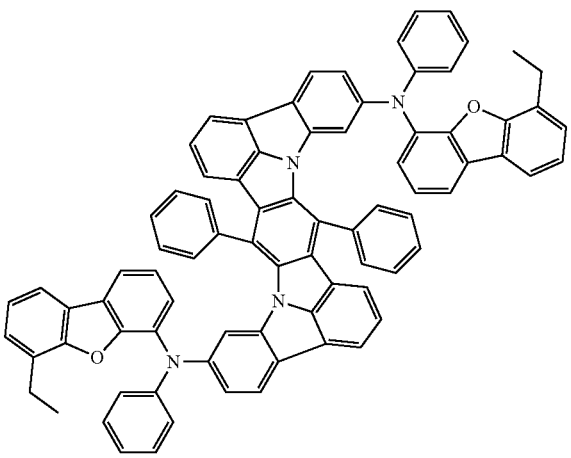

585
-continued
586
-continued
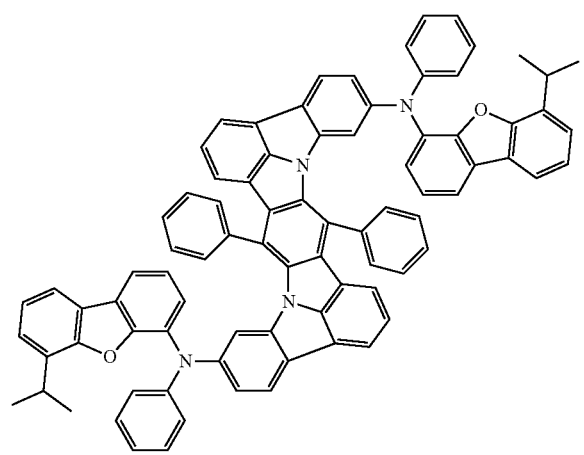
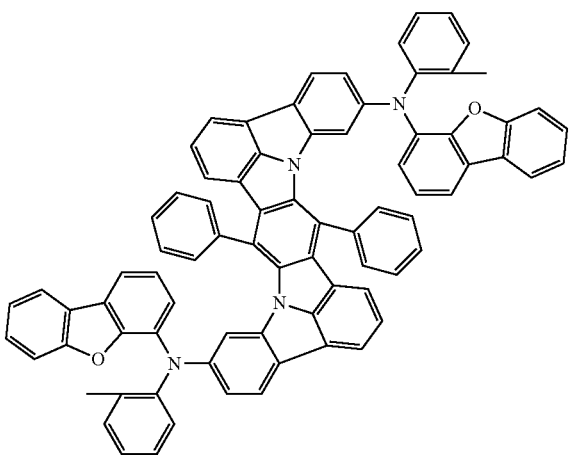
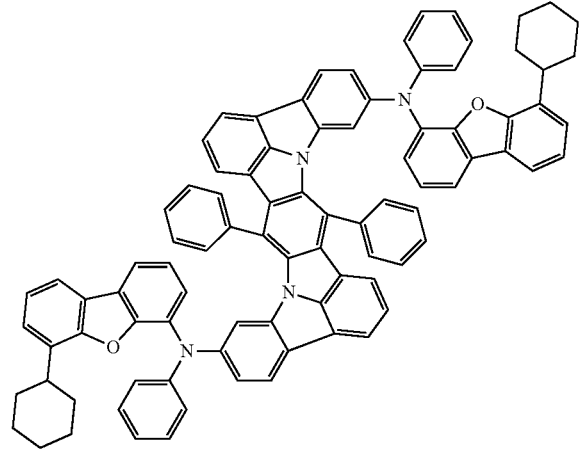
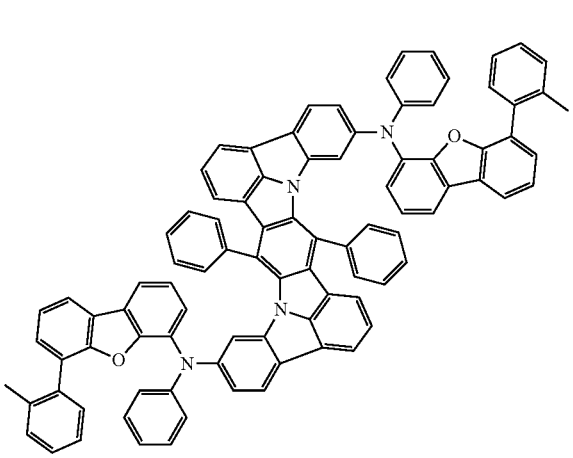

587
-continued
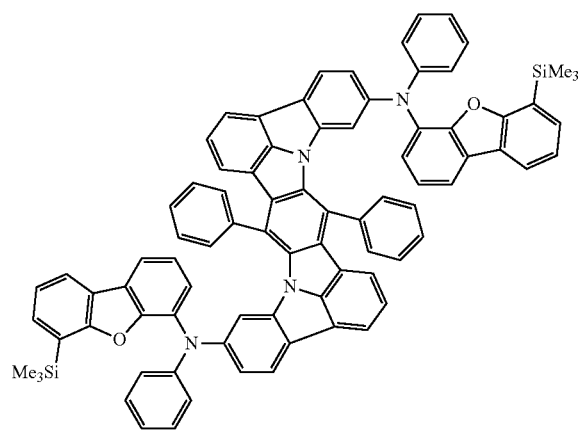
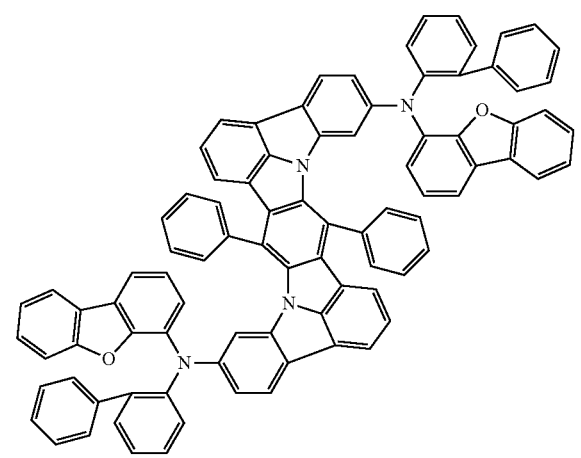
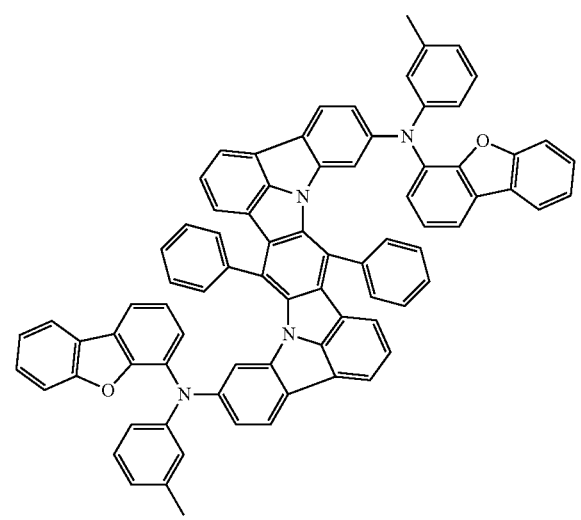
588
-continued
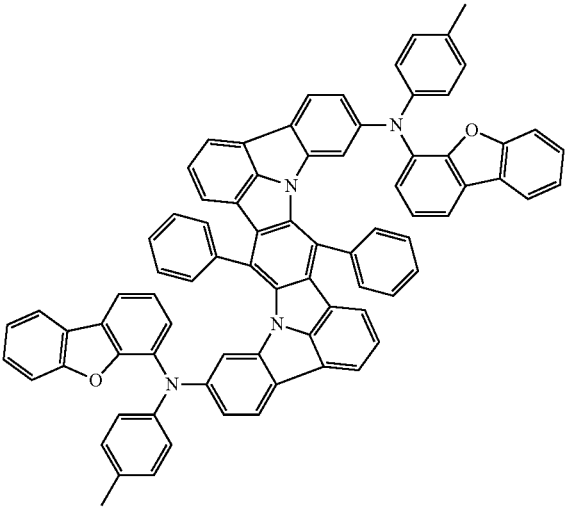
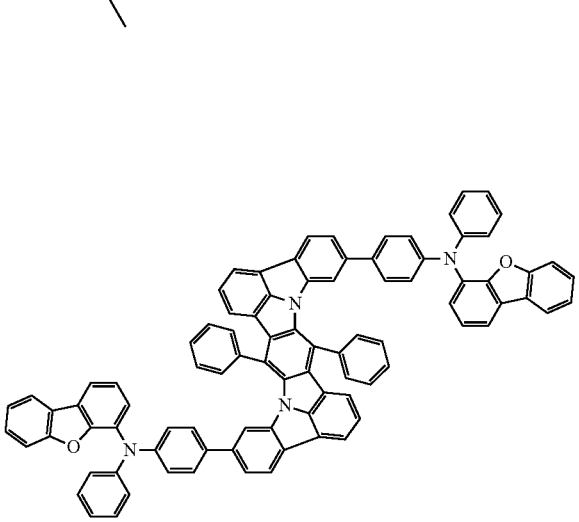

589
-continued
590
-continued
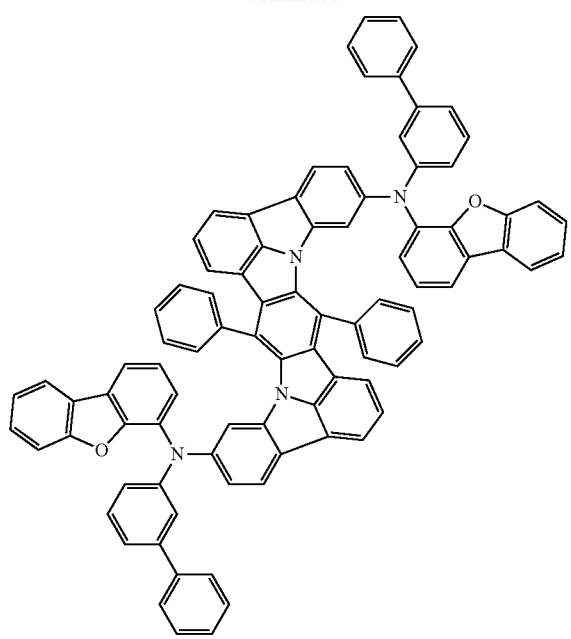
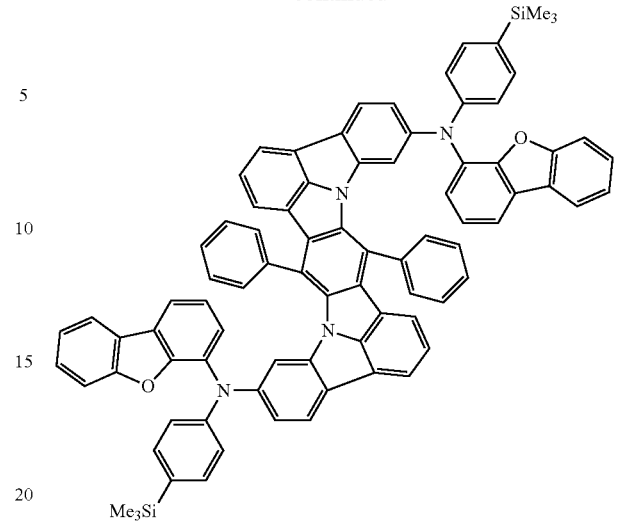
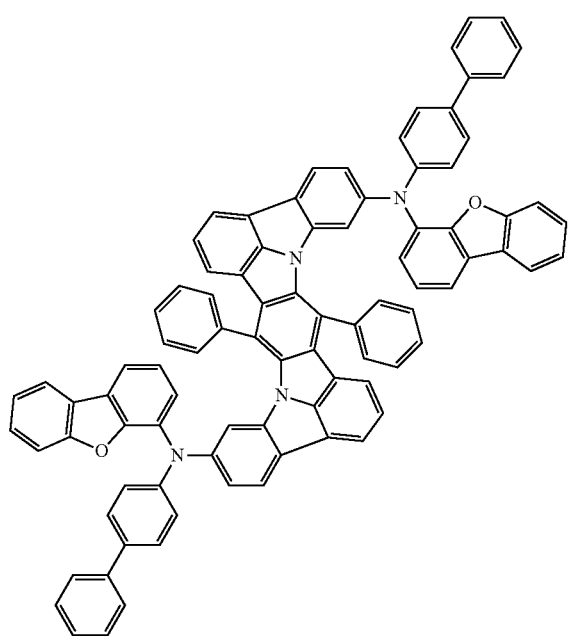
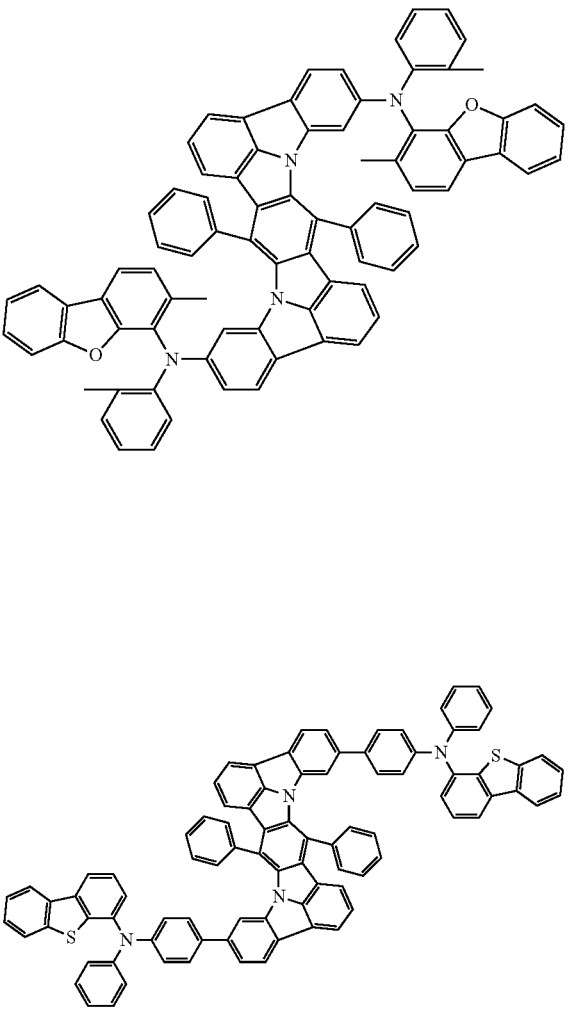

591
-continued
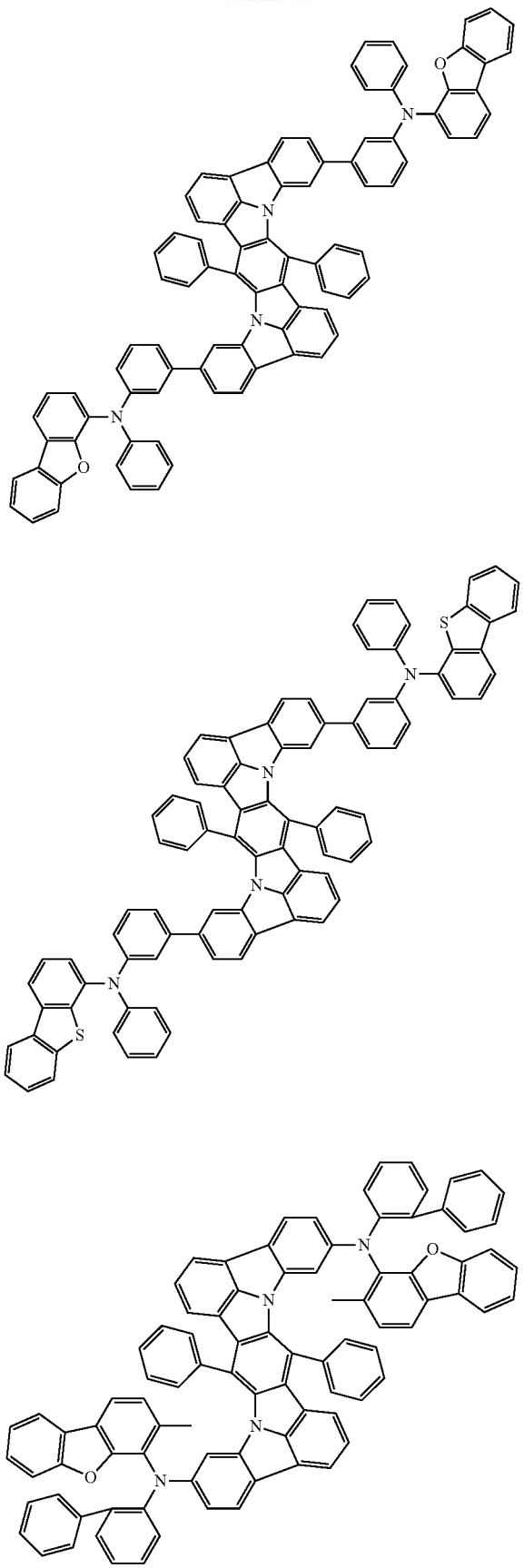
592
-continued
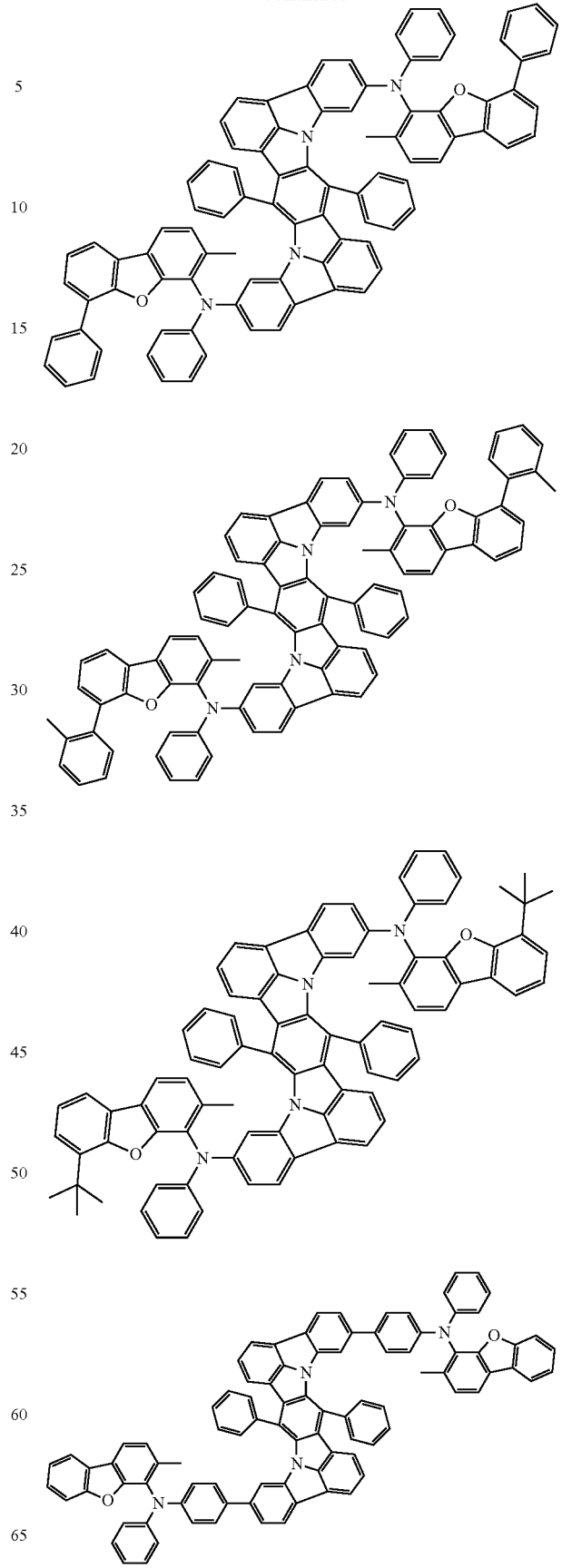

593
-continued
594
-continued
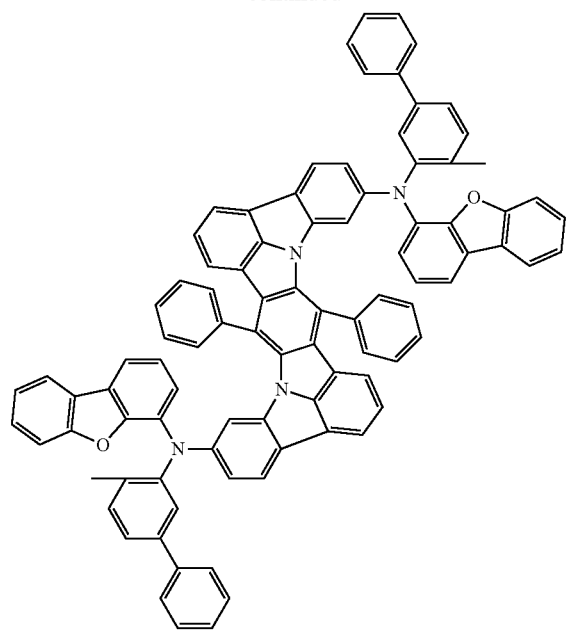
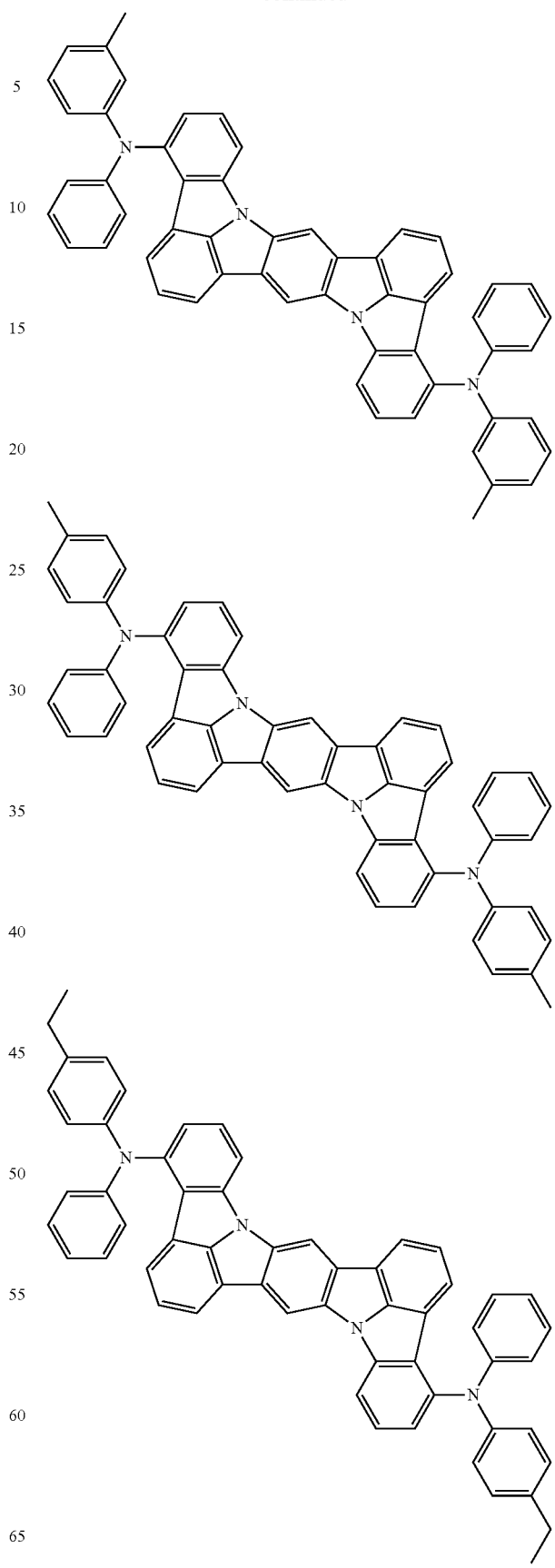

595
-continued
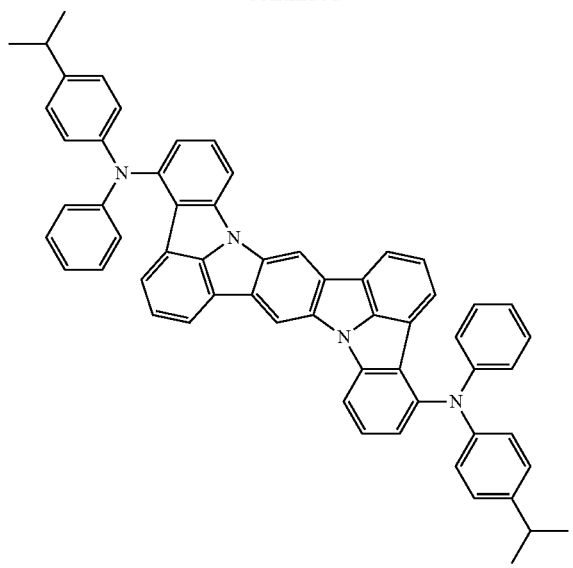
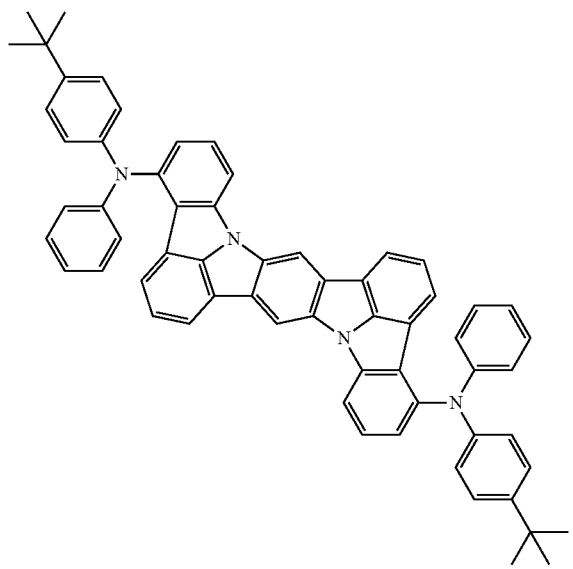
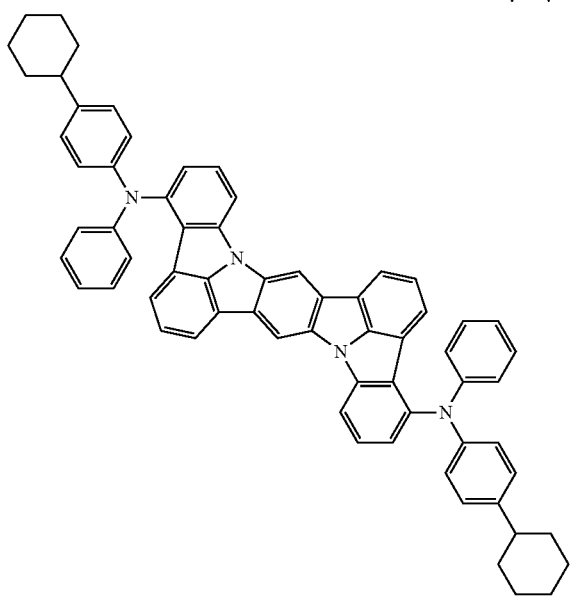
596
-continued
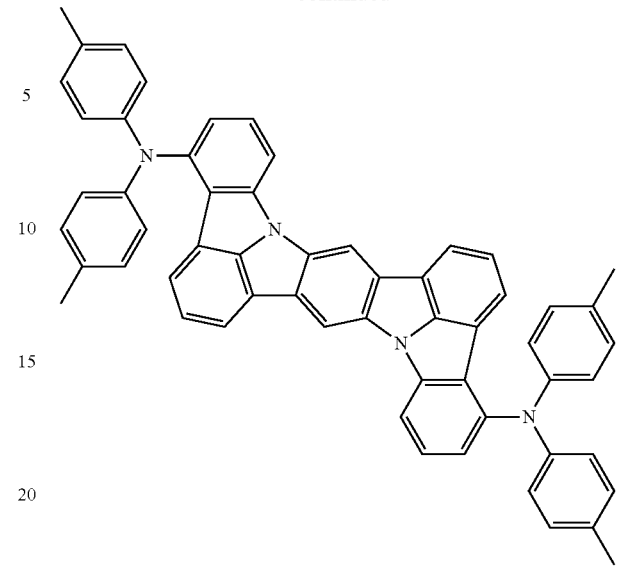
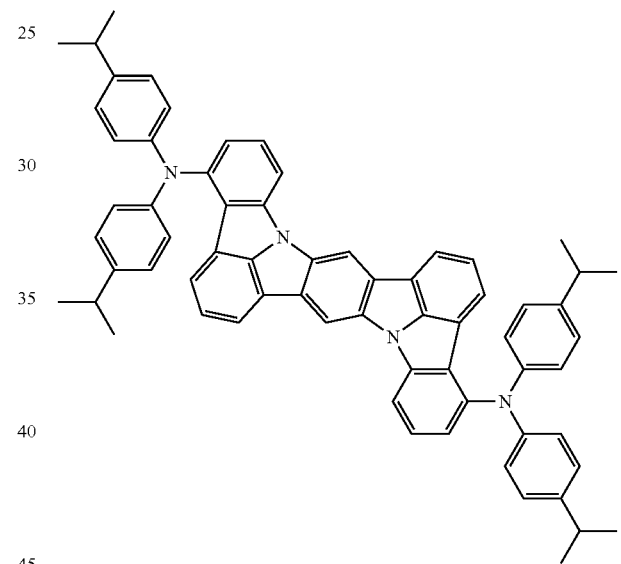
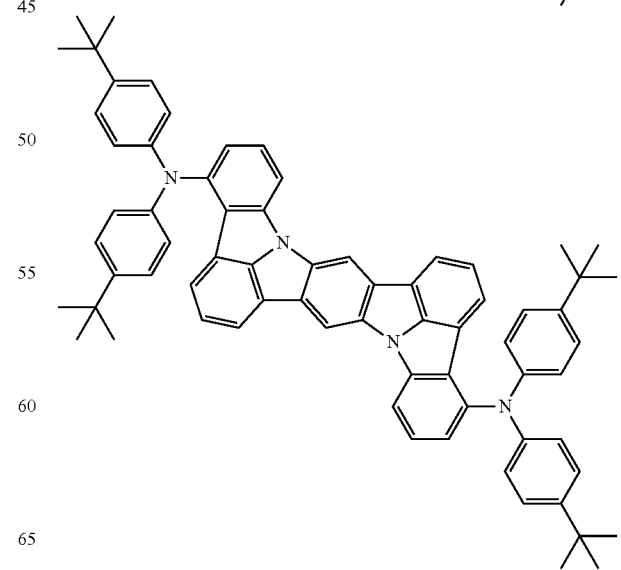

597
-continued
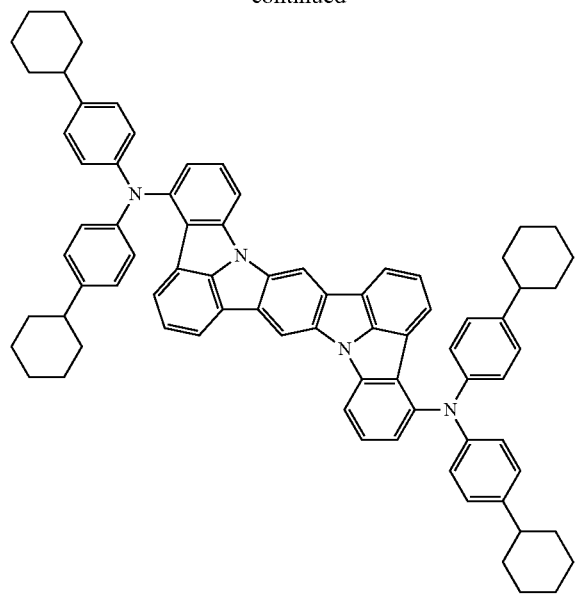
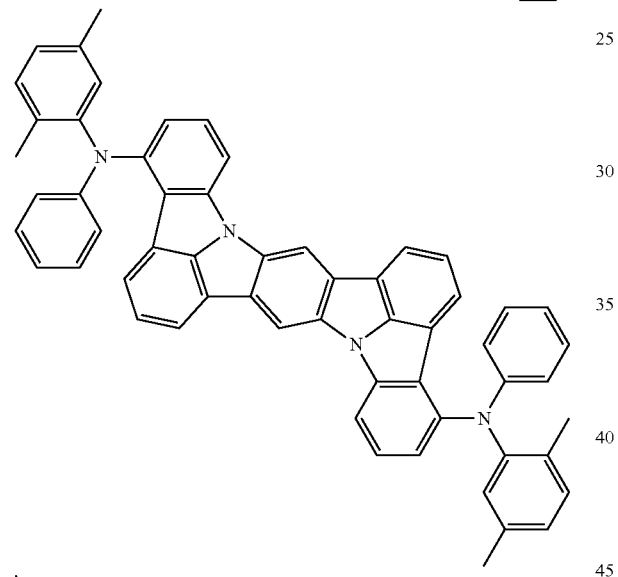
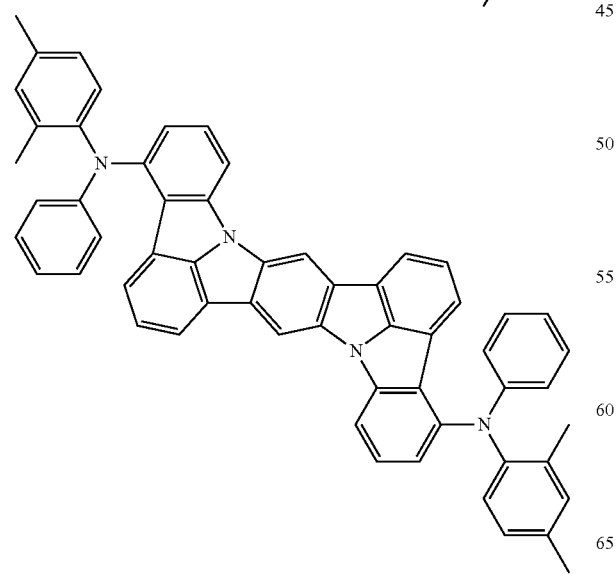
598
-continued

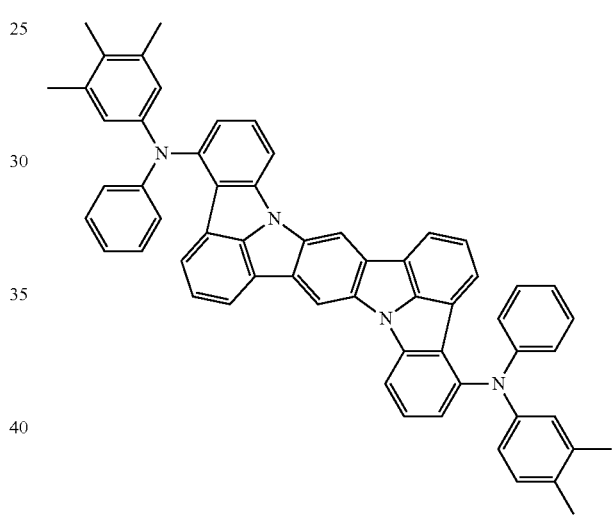
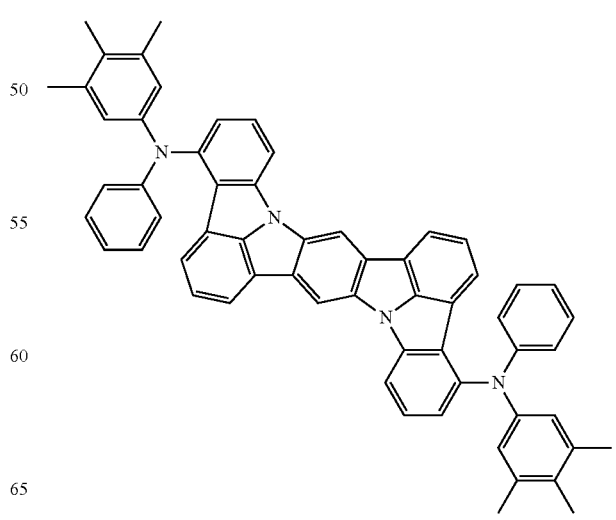

599
-continued
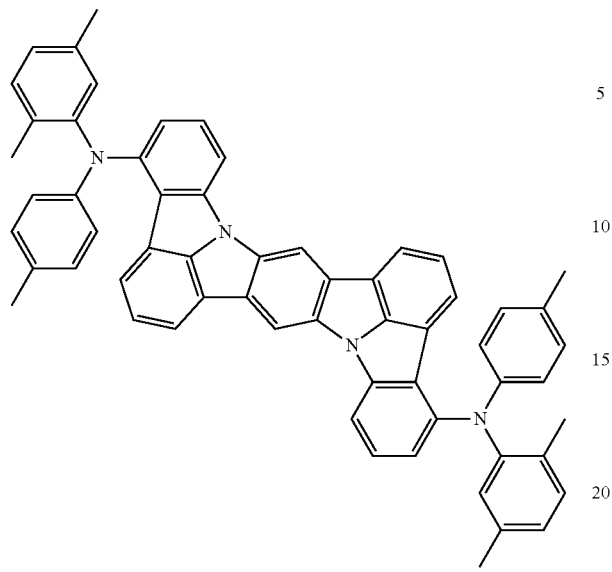
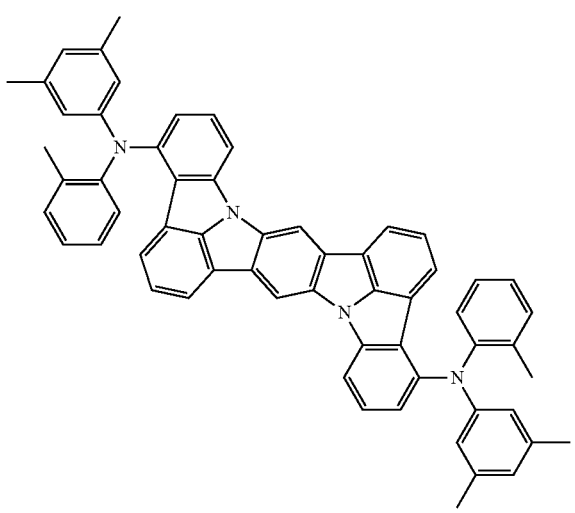
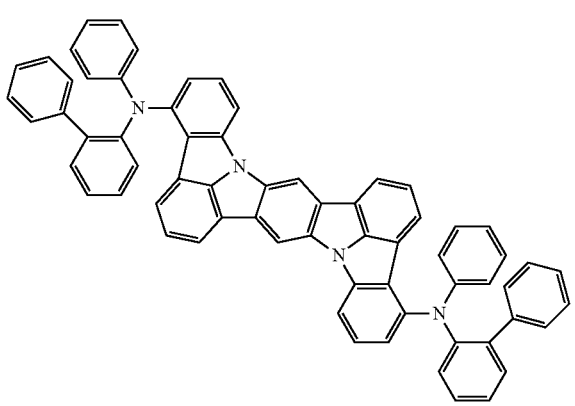
600
-continued

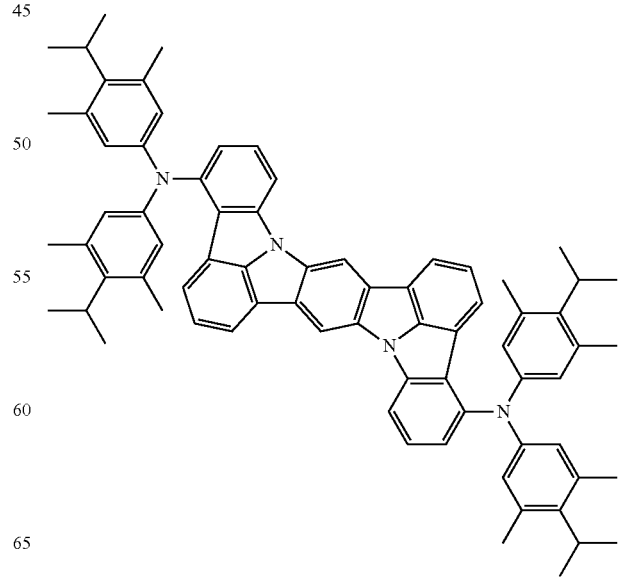

601
-continued
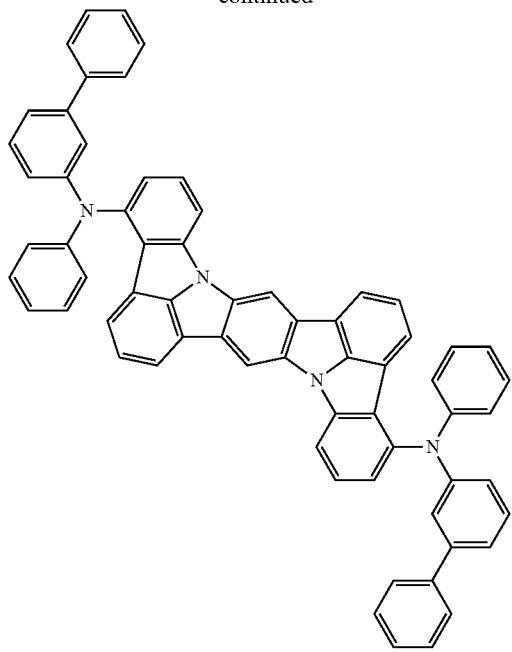
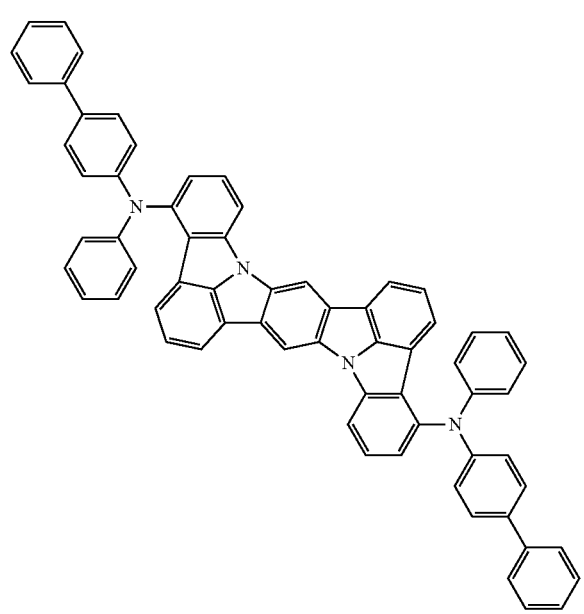
602
-continued
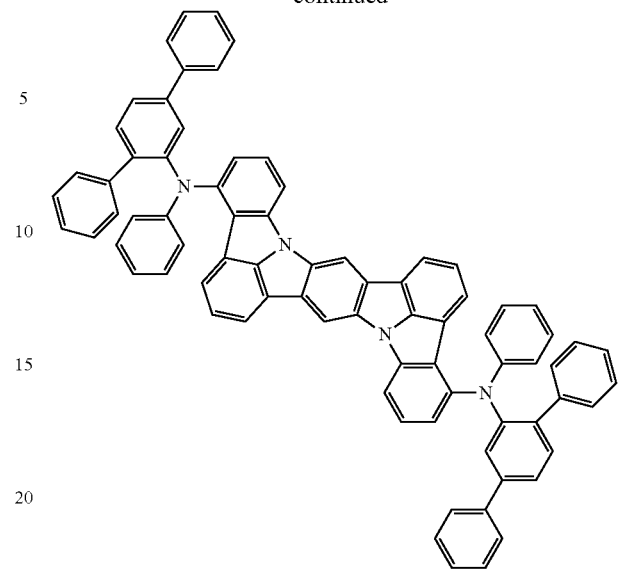
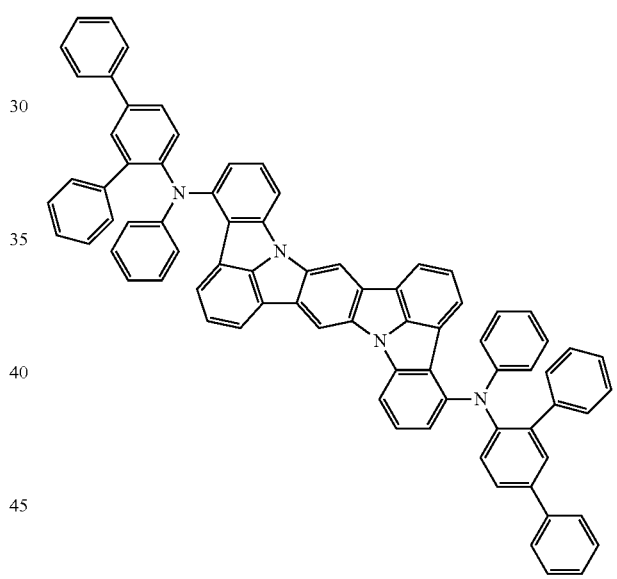
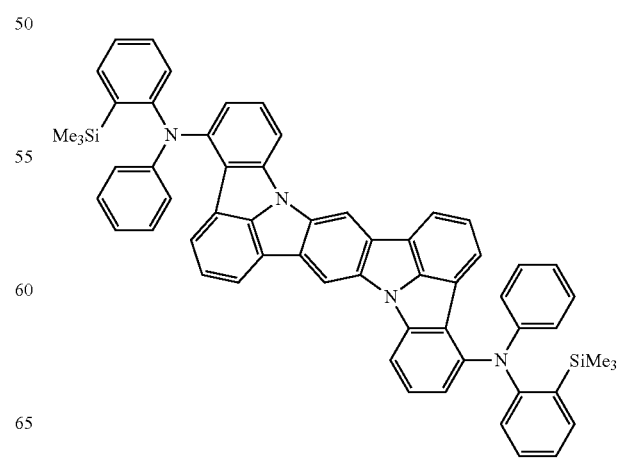

603
-continued
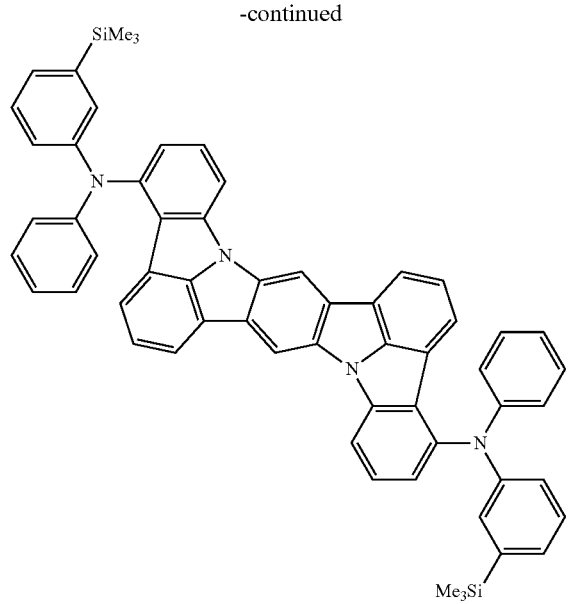
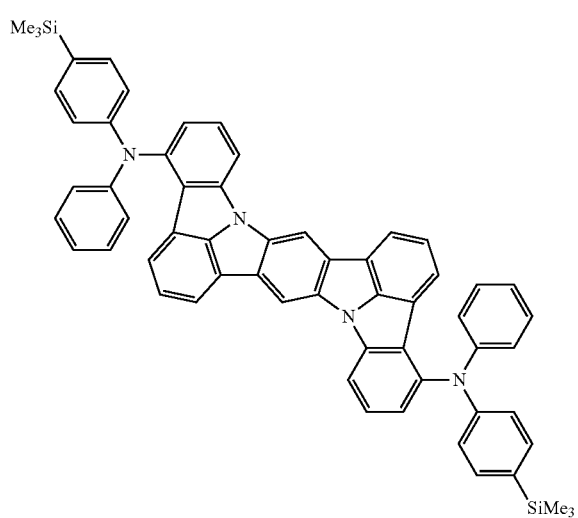
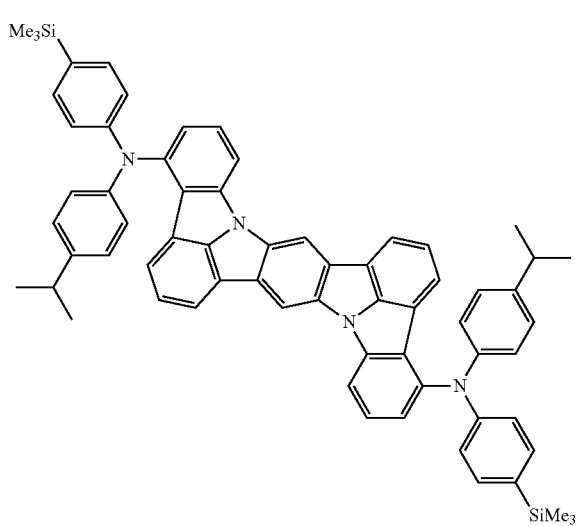
604
-continued
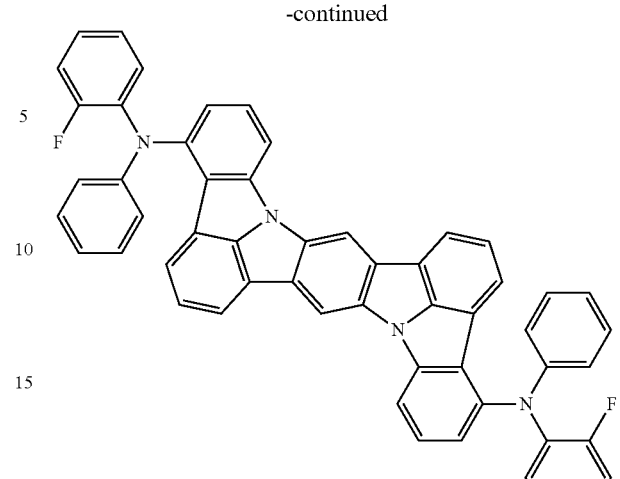
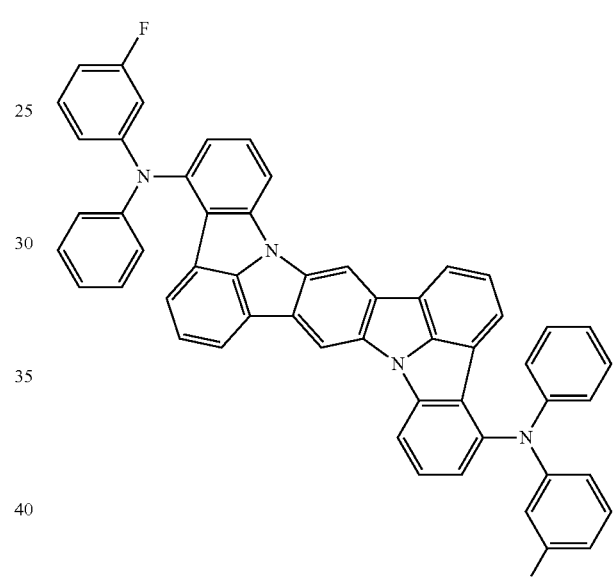
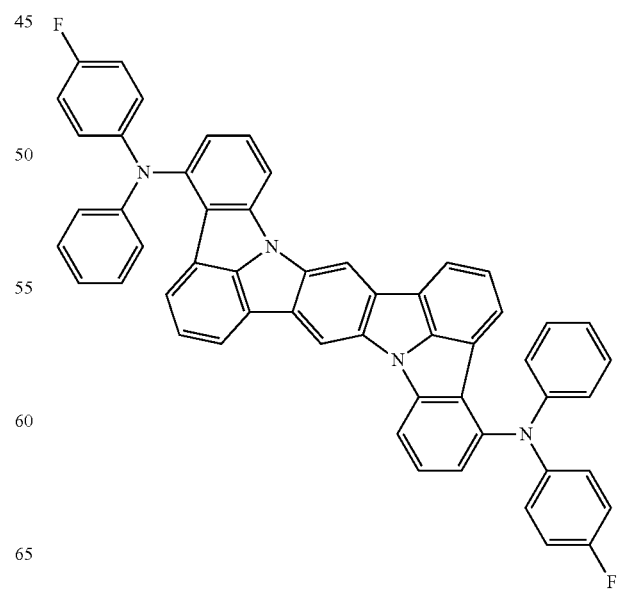

605
-continued
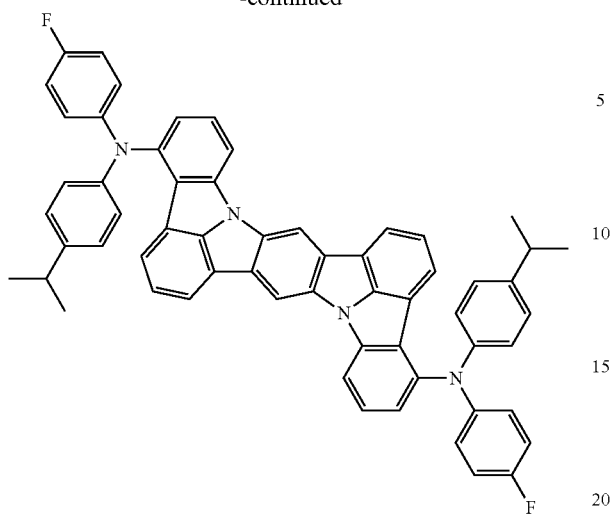
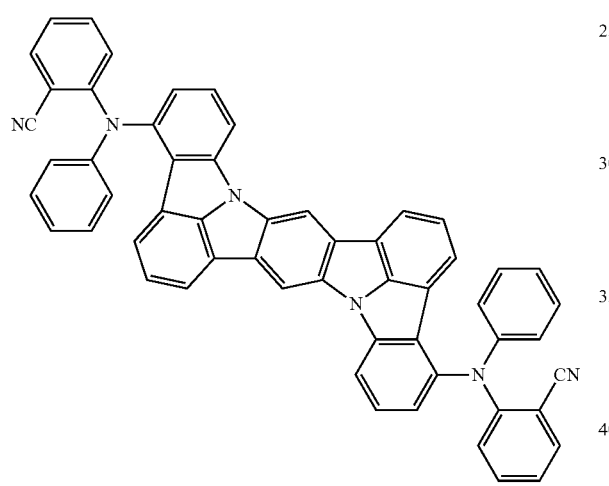
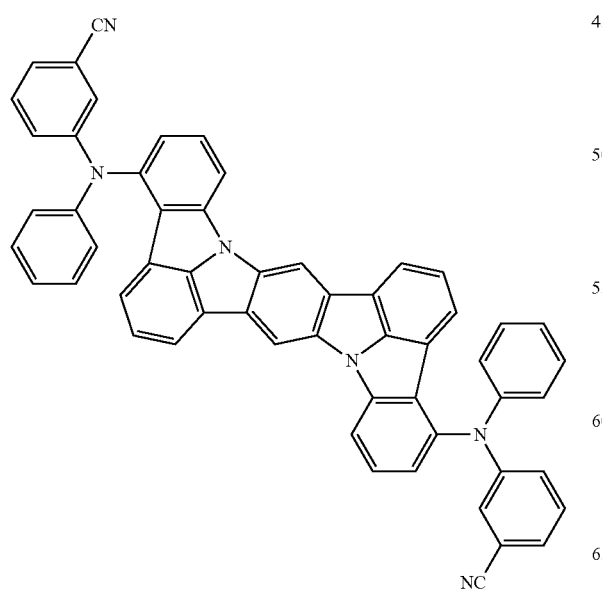
606
-continued
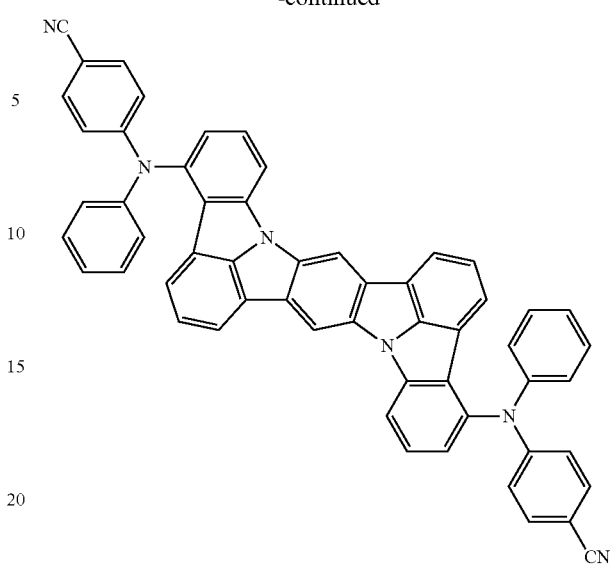
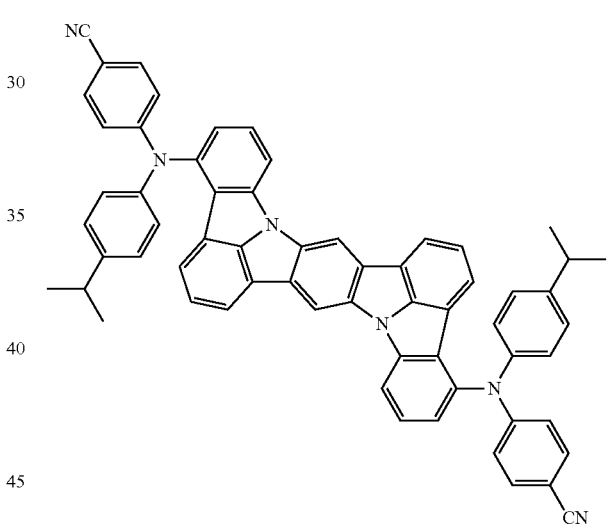
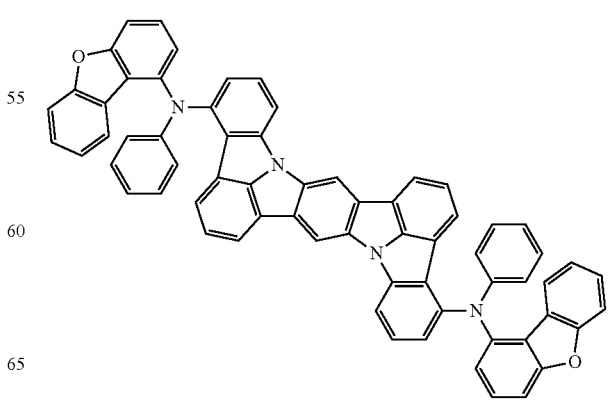

607
-continued
608
-continued
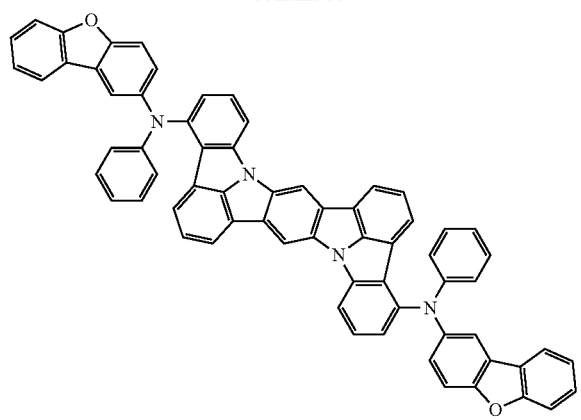
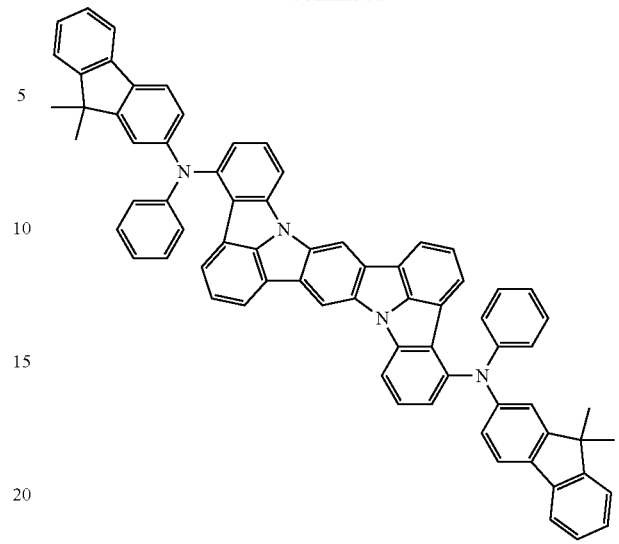
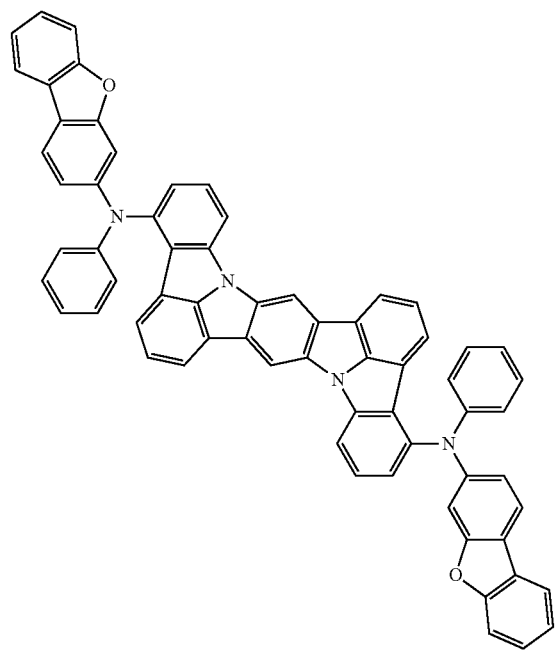
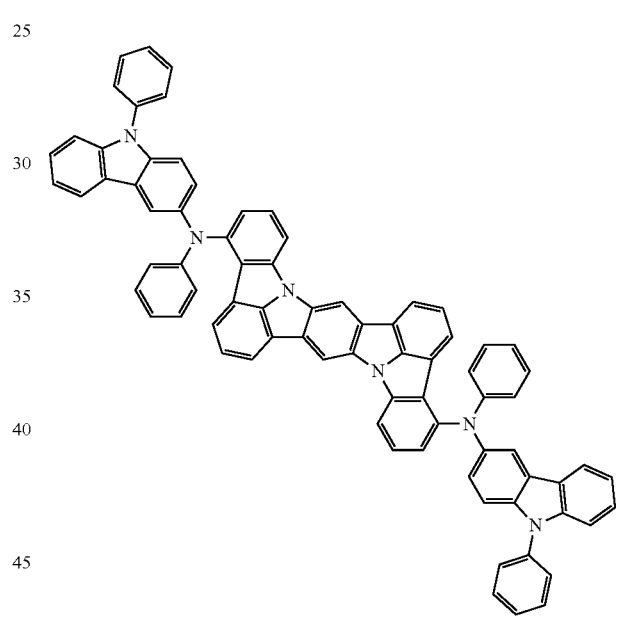
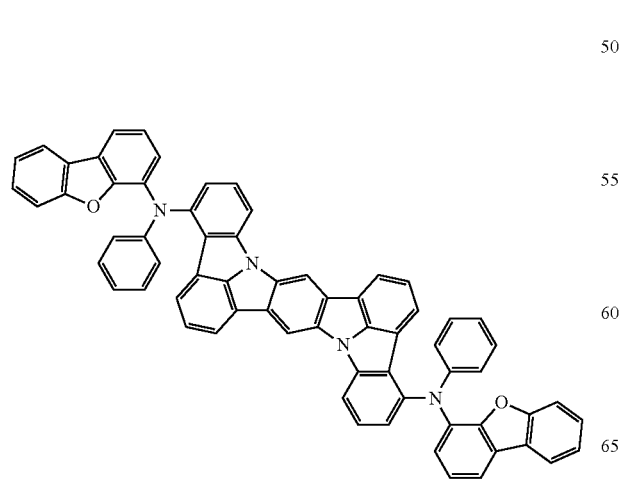
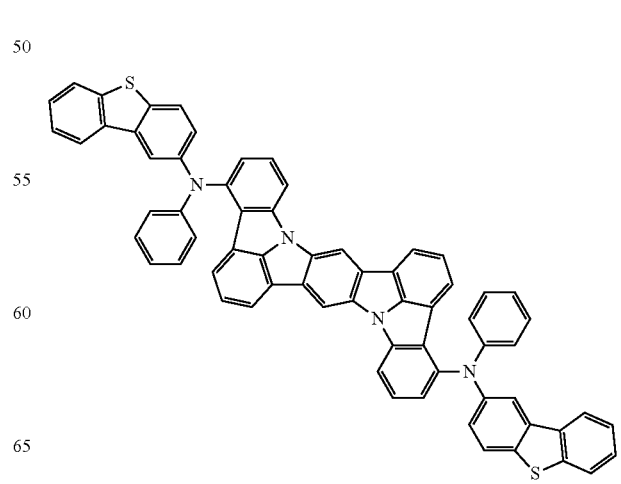

609
-continued
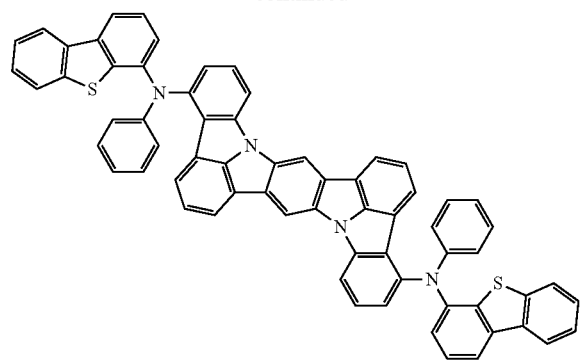
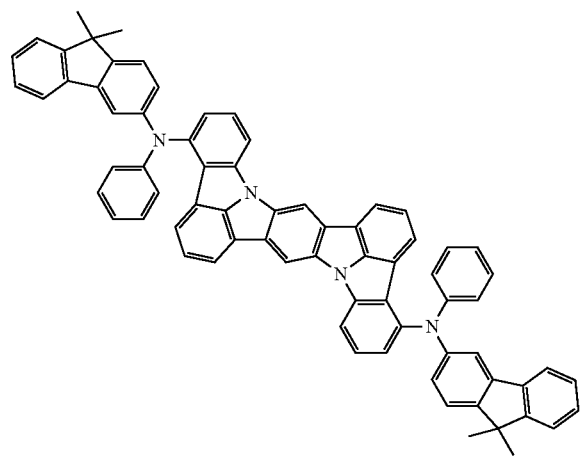
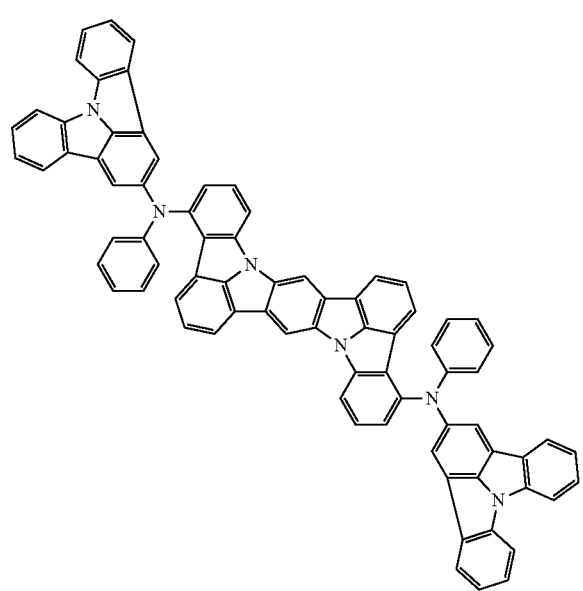
610
-continued
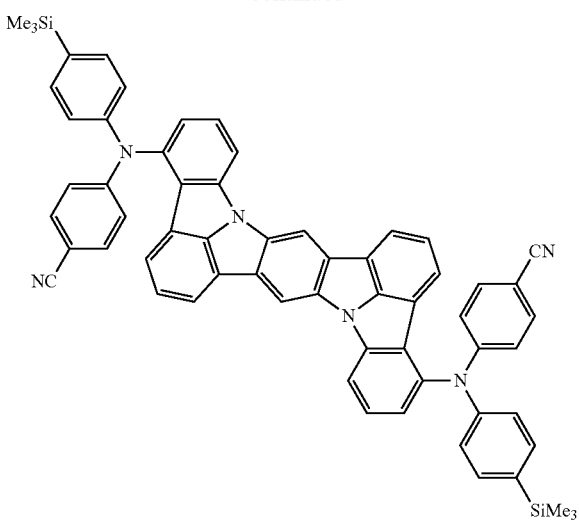

611
-continued
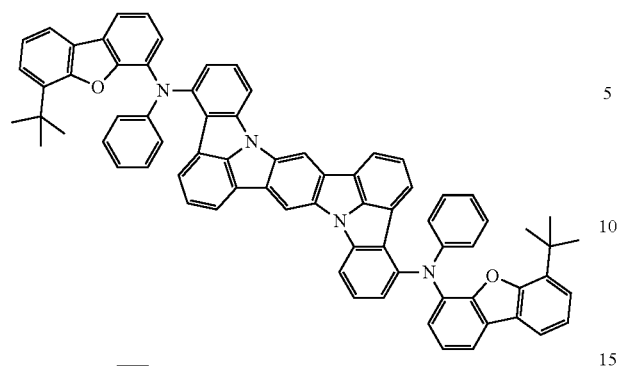
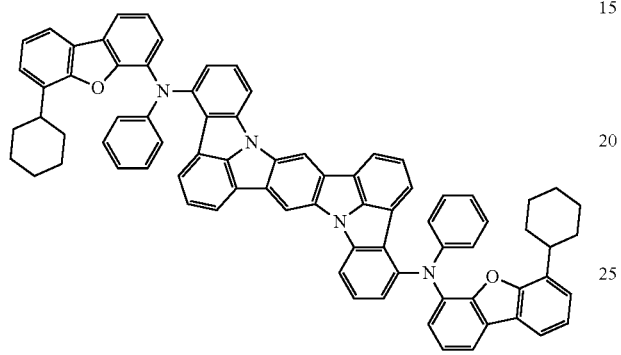
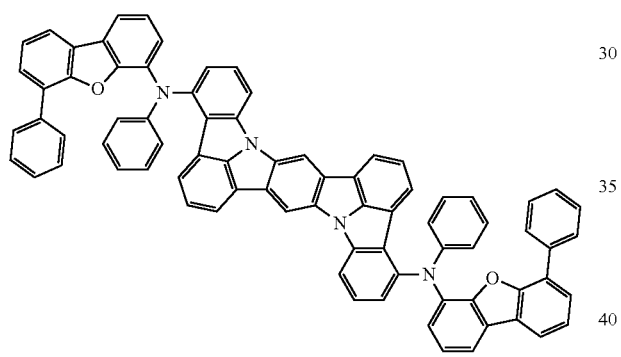
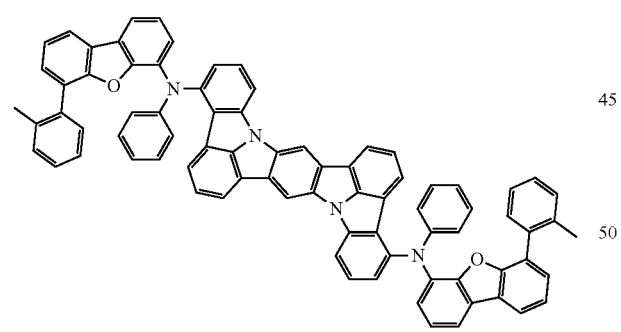
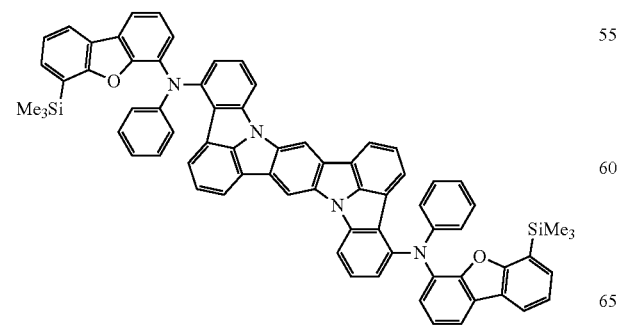
612
-continued
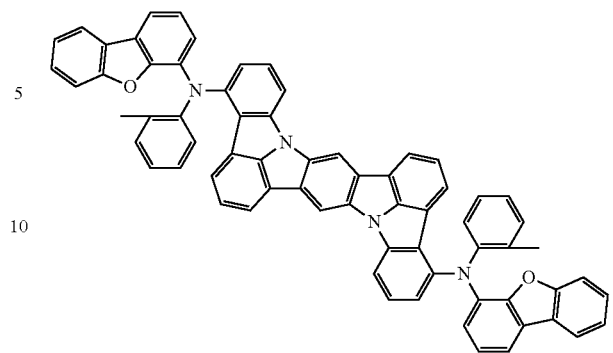
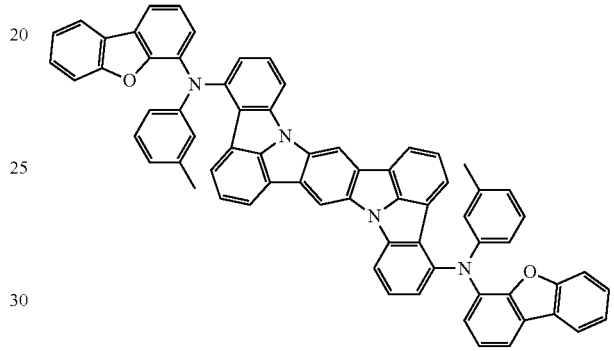
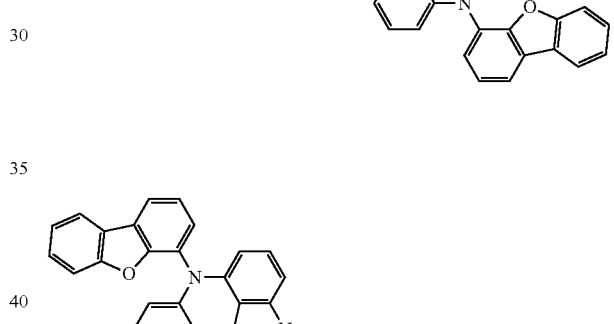
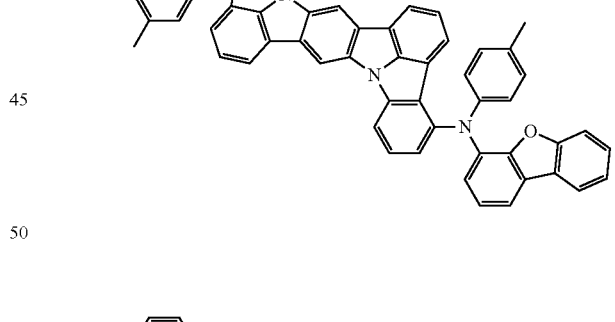
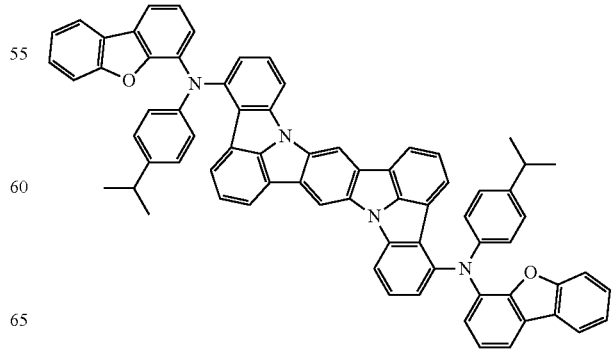

613
-continued
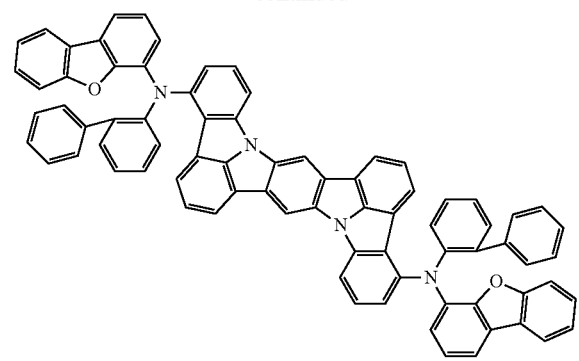
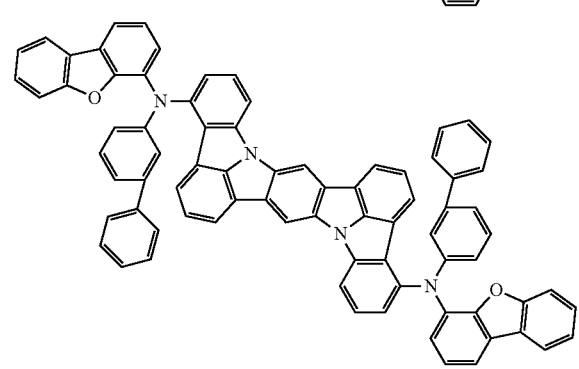
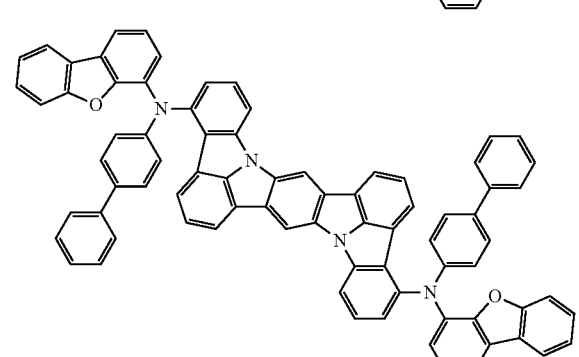
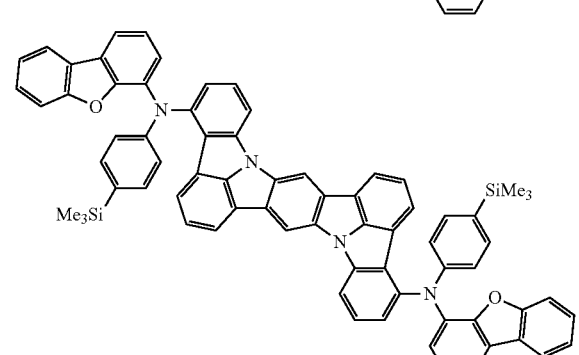
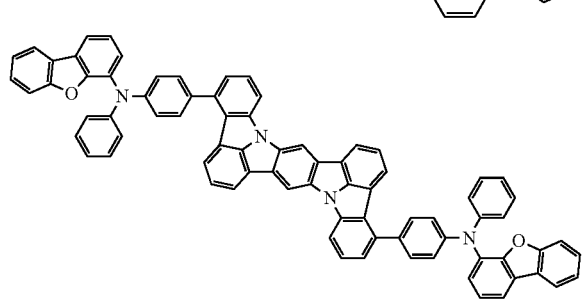
614
-continued
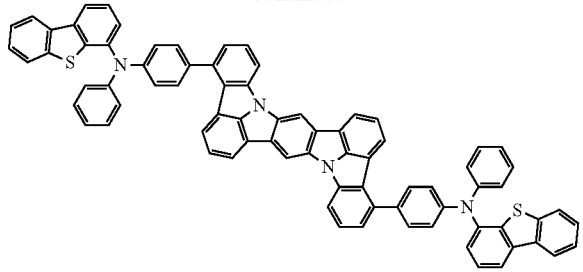
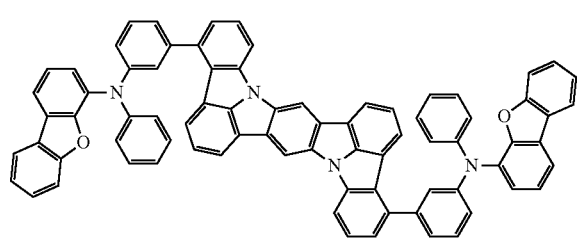
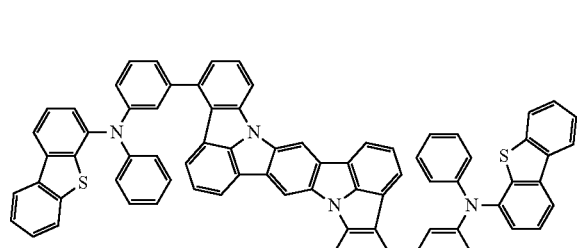
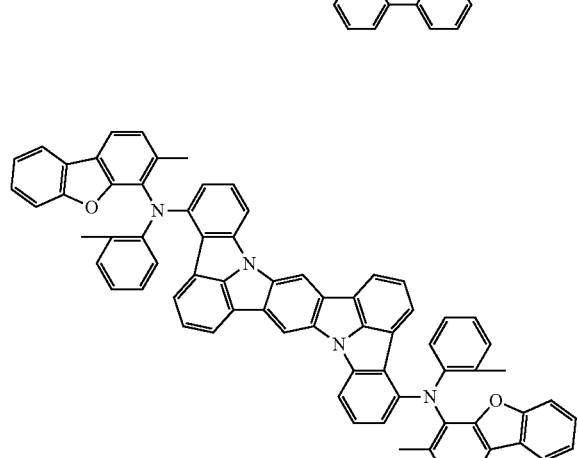
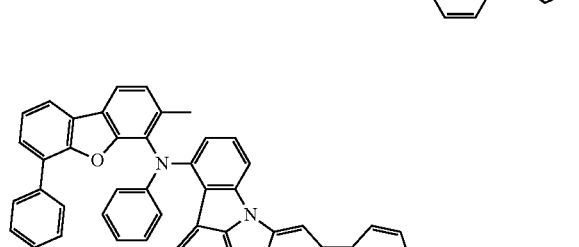
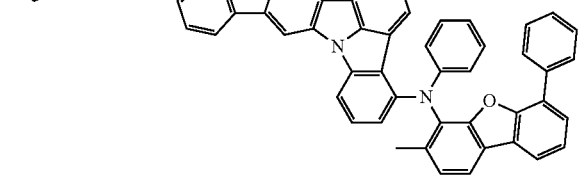

615
-continued
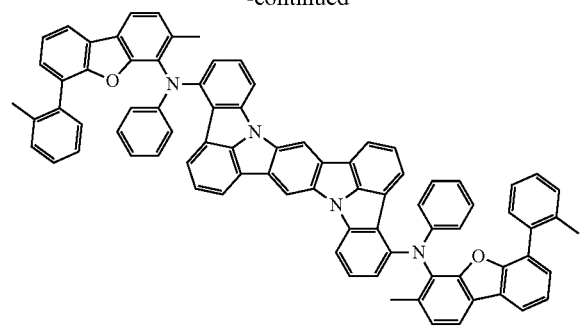
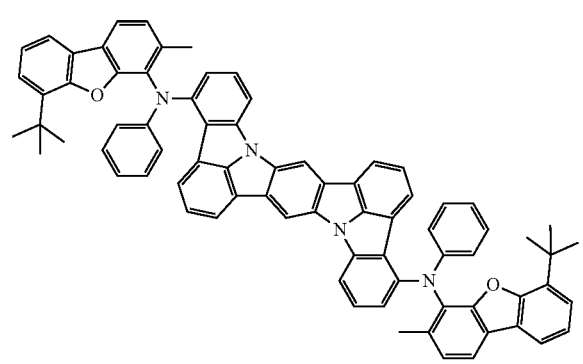
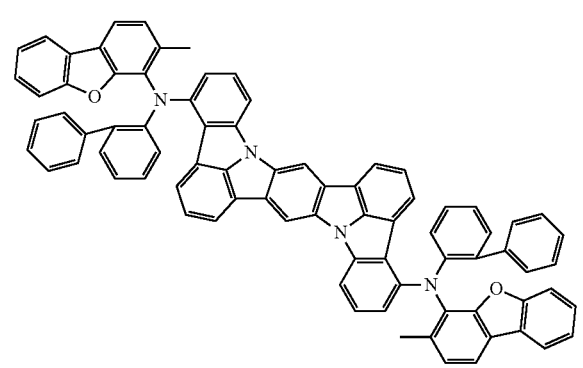
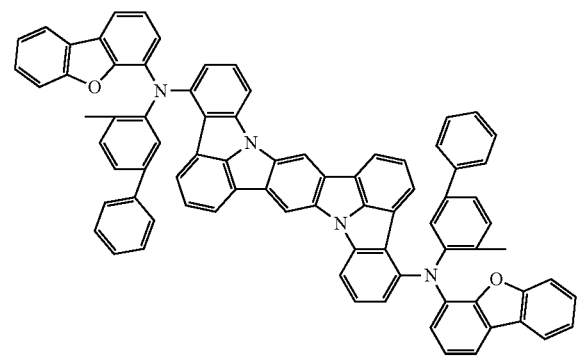
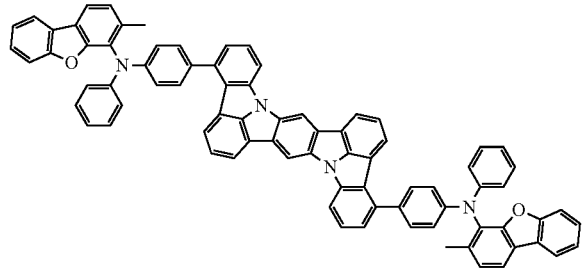
616
-continued
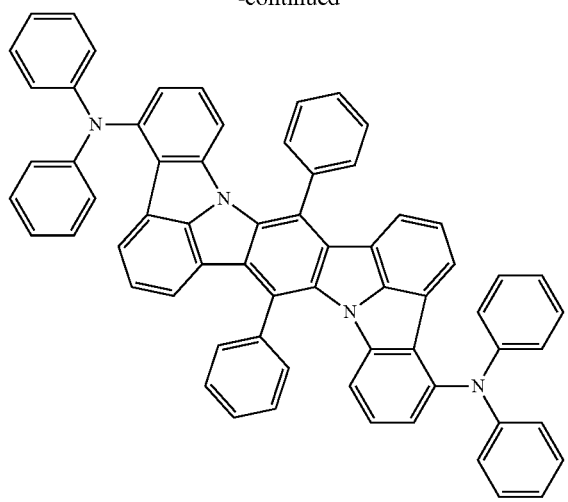
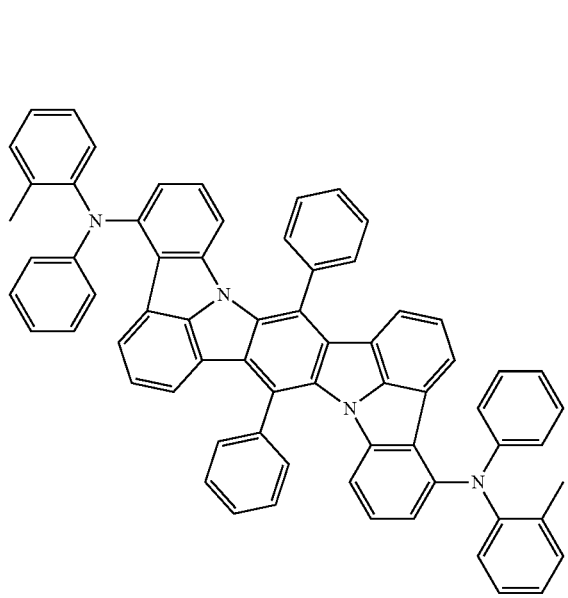
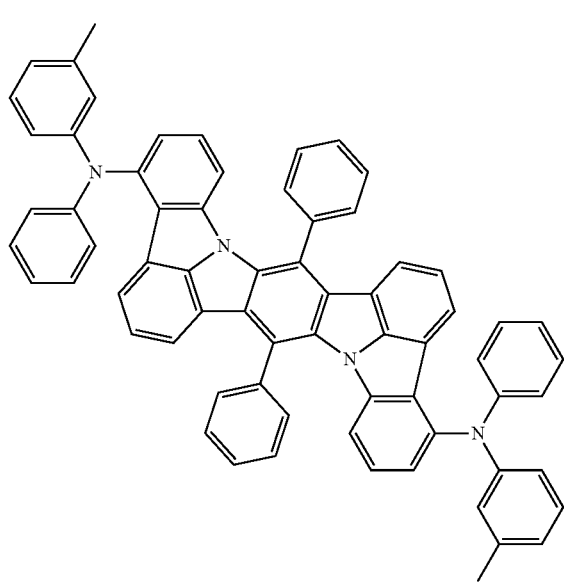

617
-continued
618
-continued
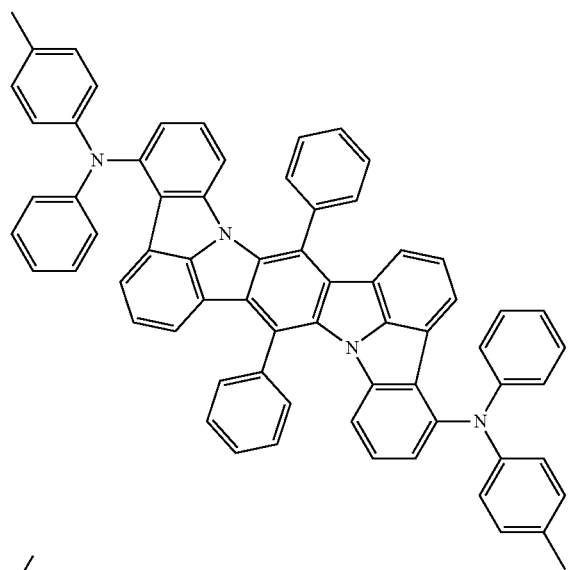
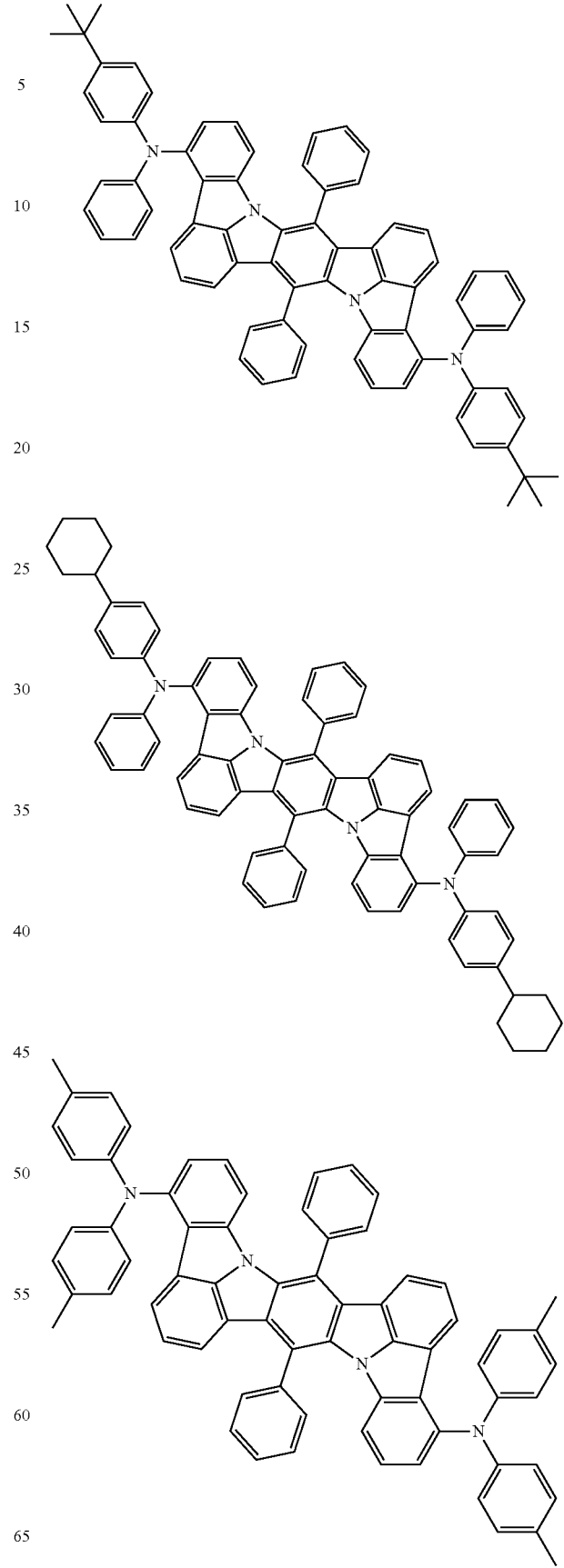

619
-continued
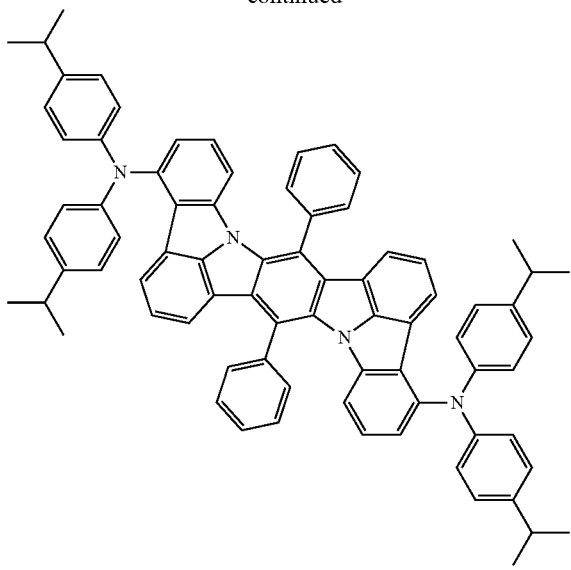
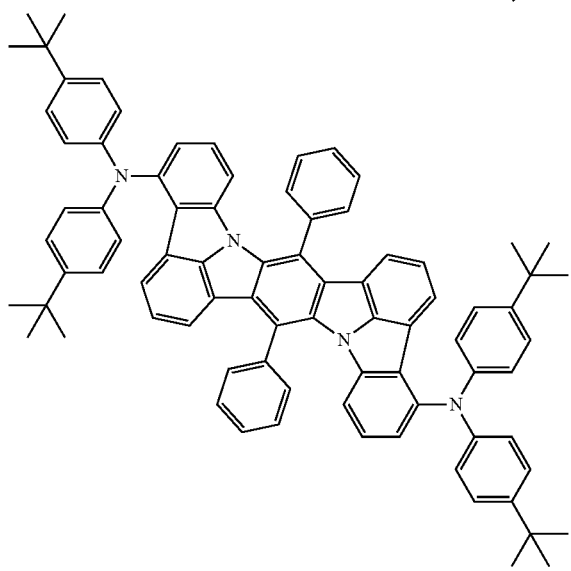
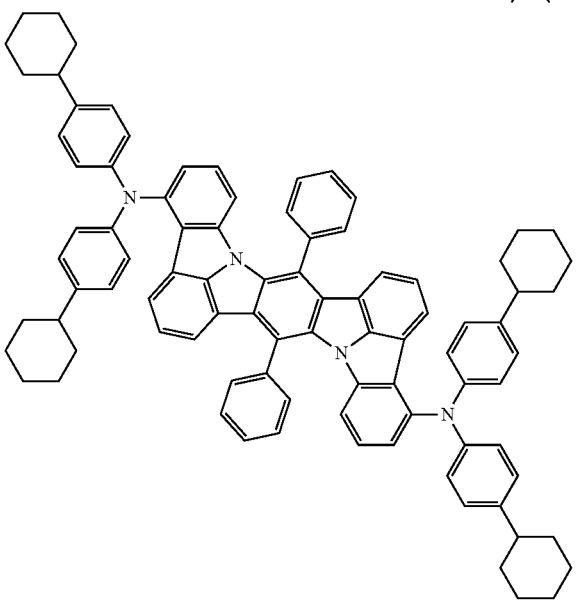
620
-continued
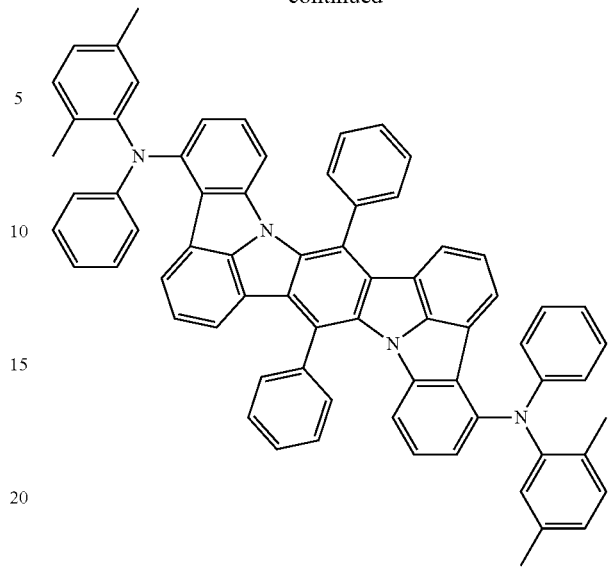
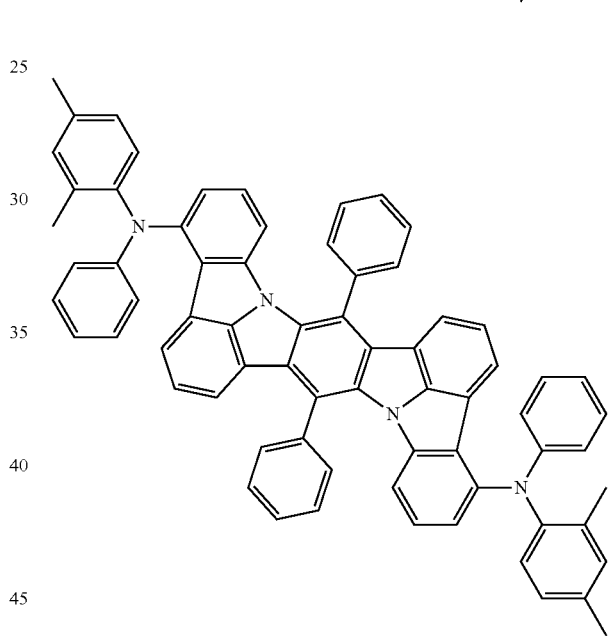

621
-continued
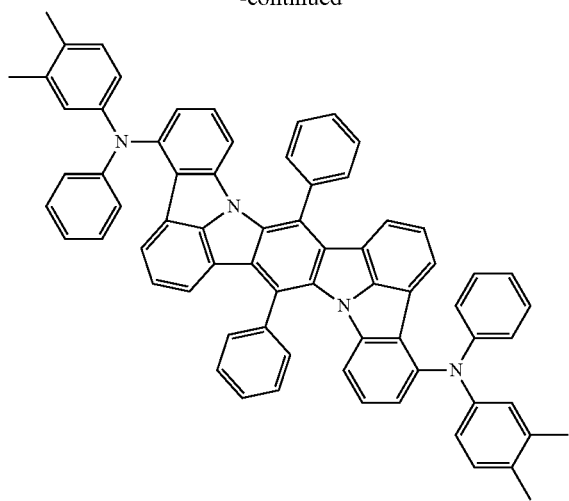
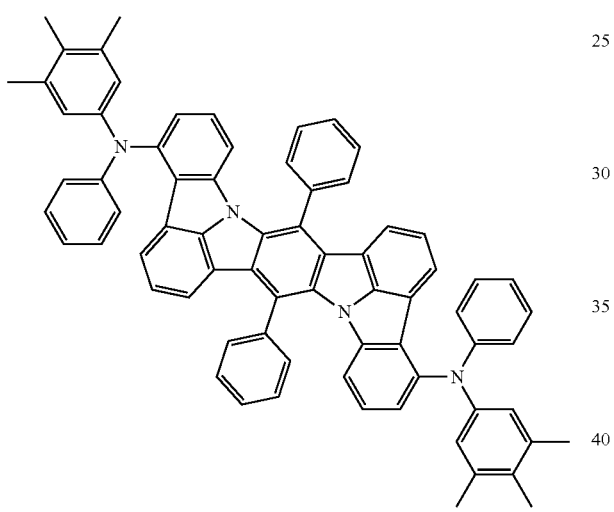
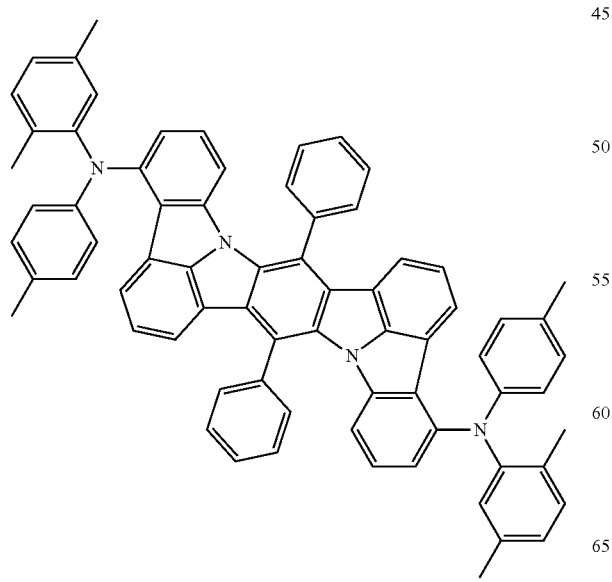
622
-continued
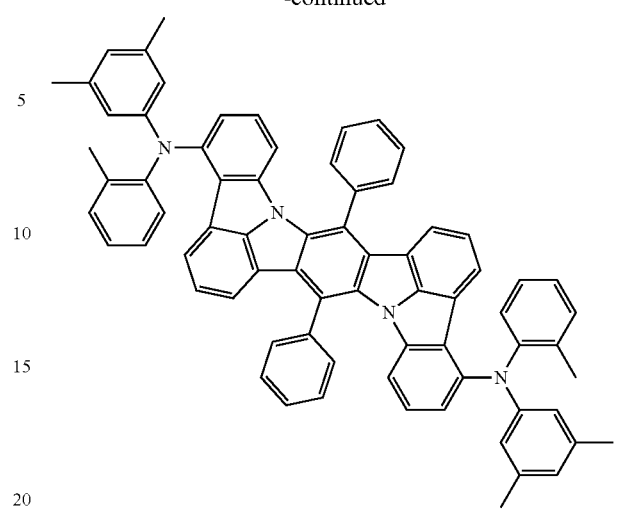
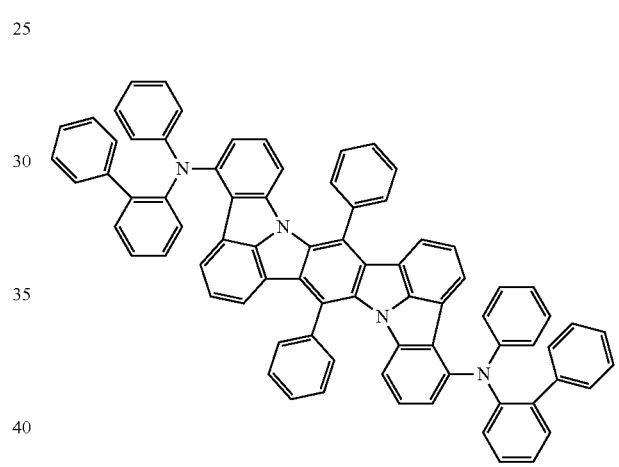
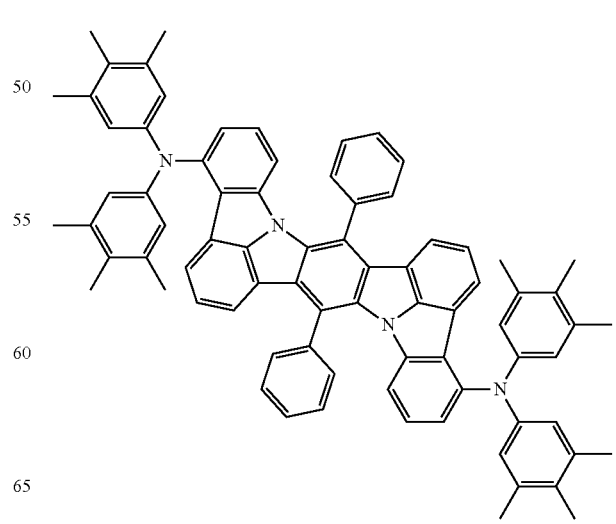

623
-continued
624
-continued
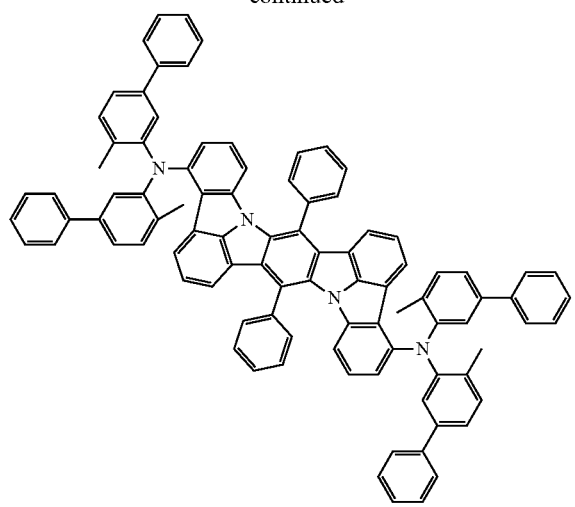
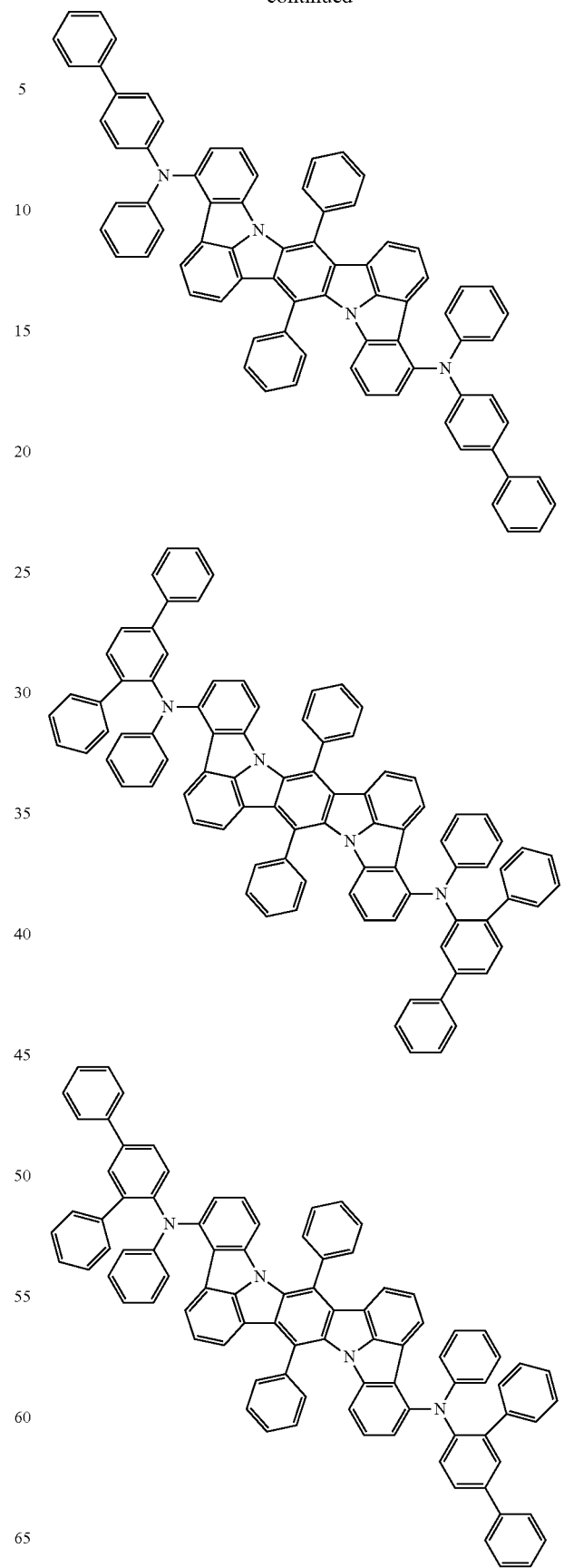

625
-continued
626
-continued
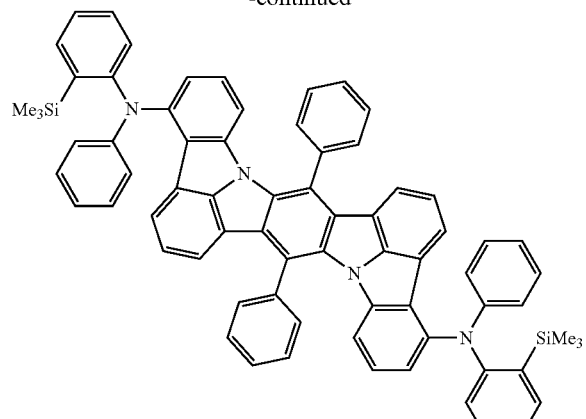
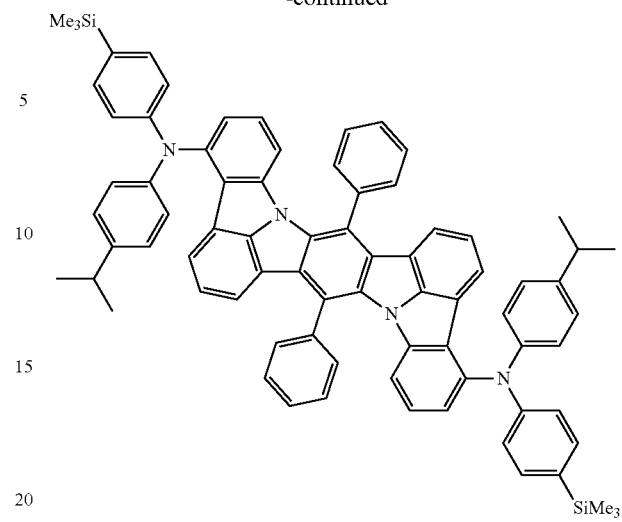
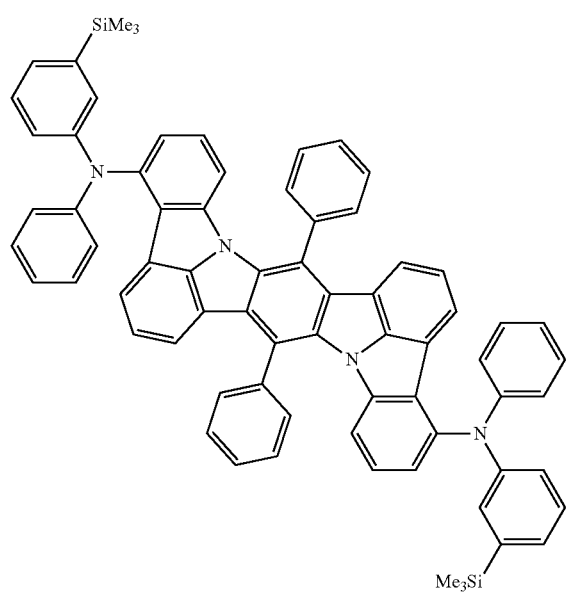
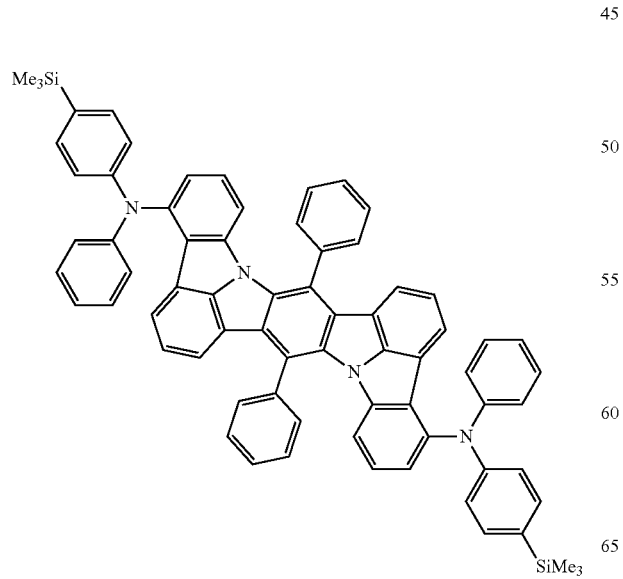
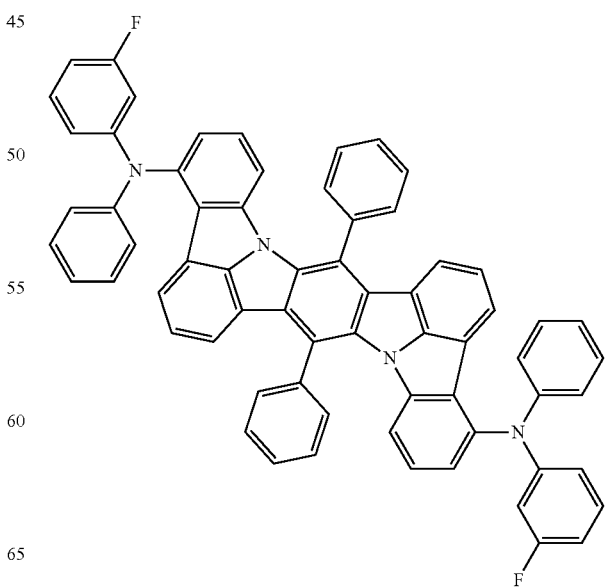

627
-continued
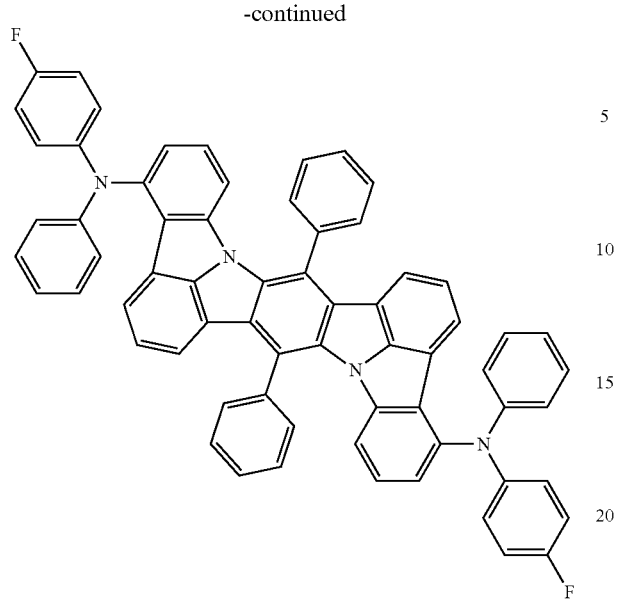
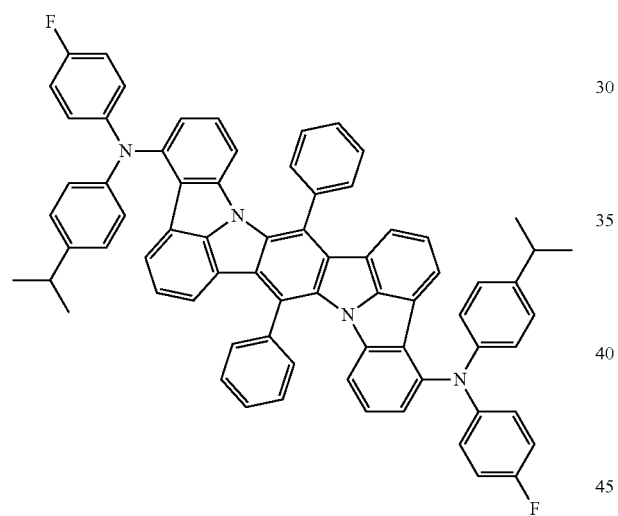
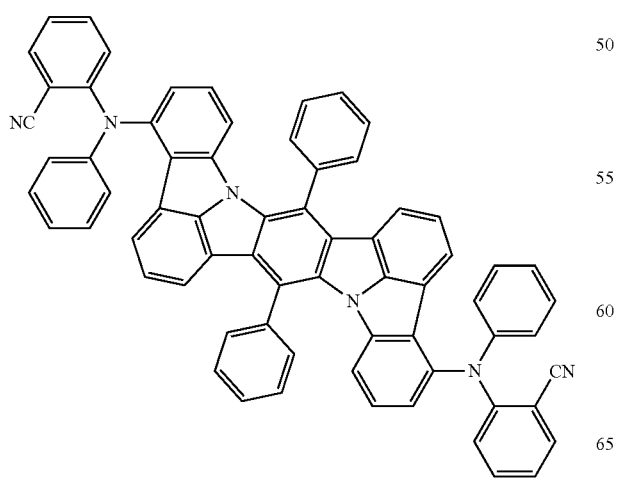
628
-continued
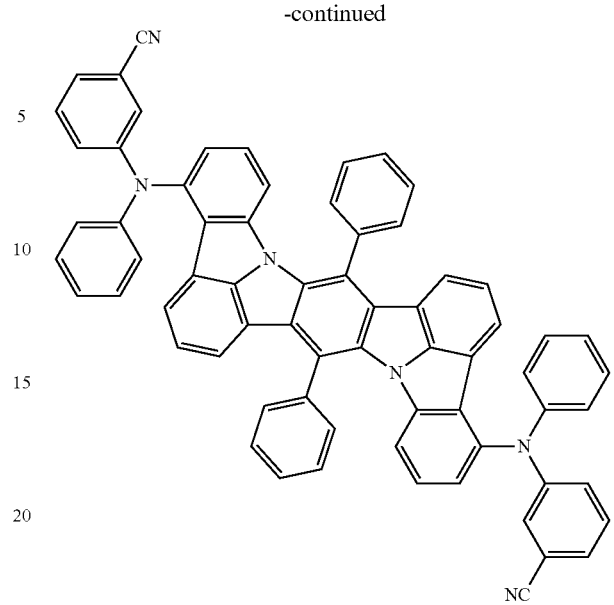
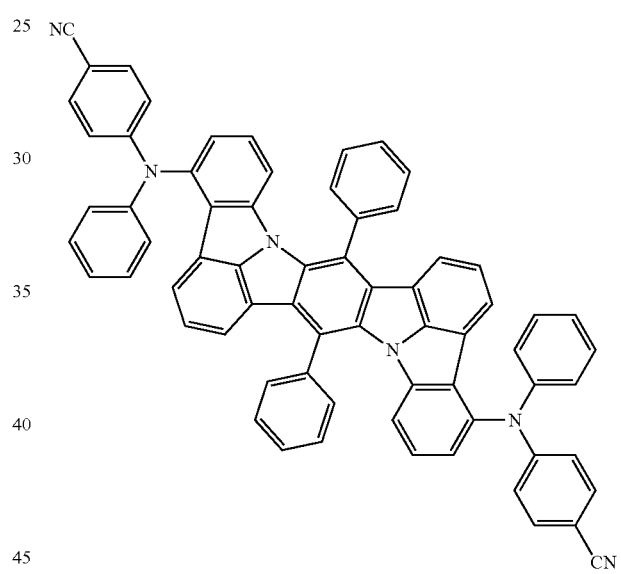
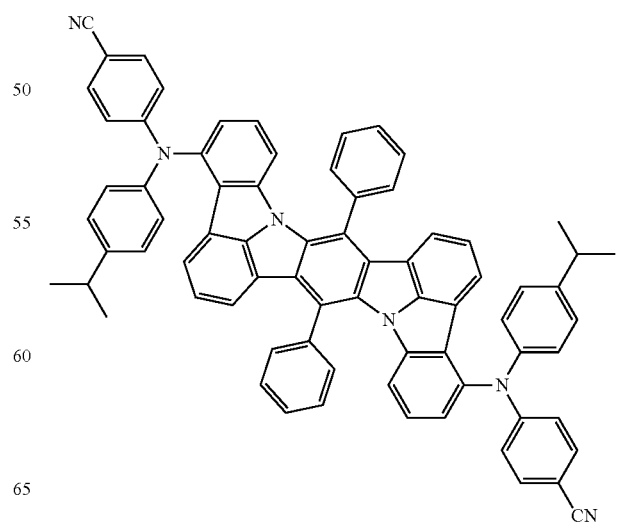

629
-continued
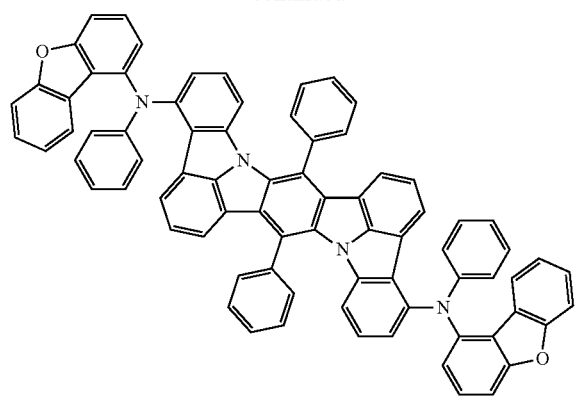
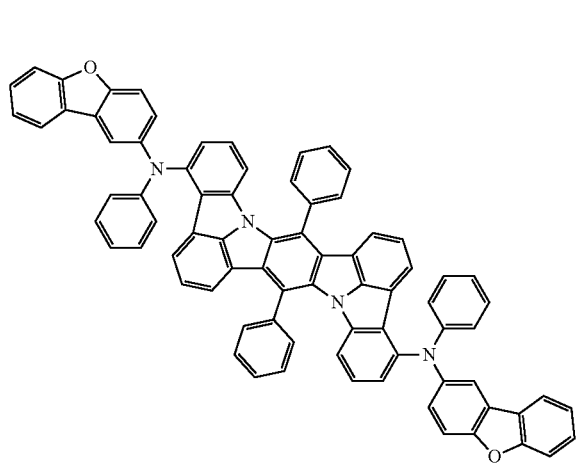
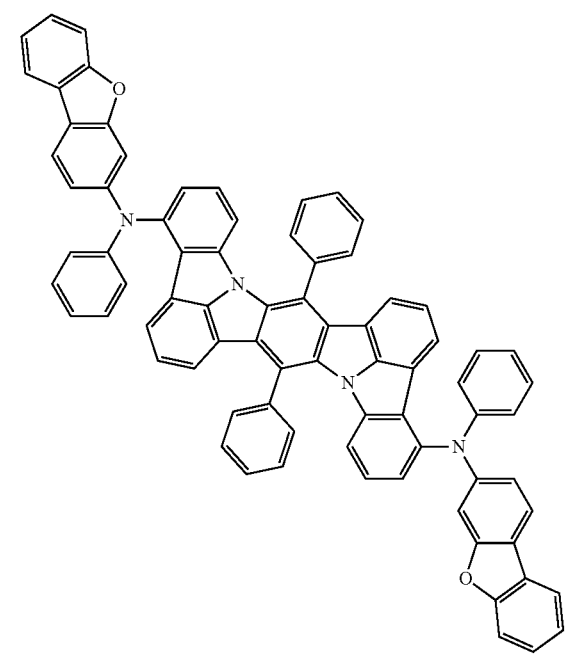
630
-continued
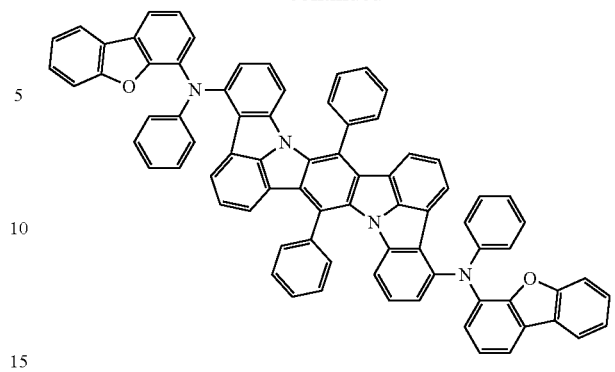
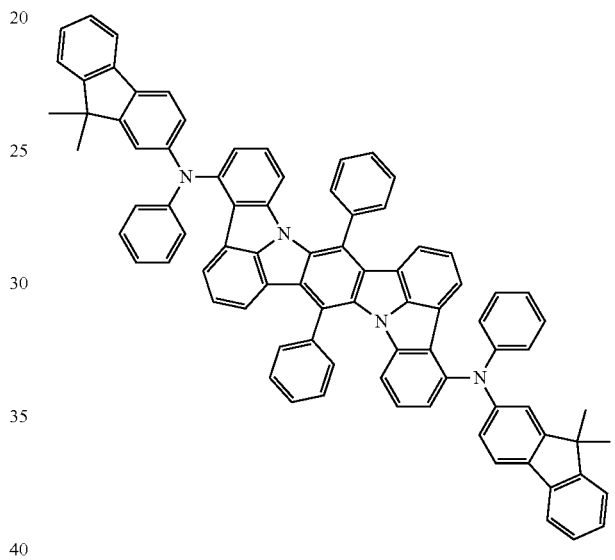
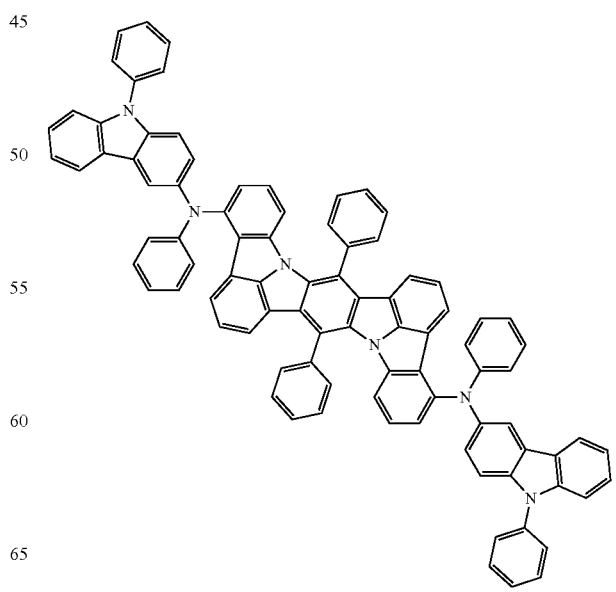

631
-continued
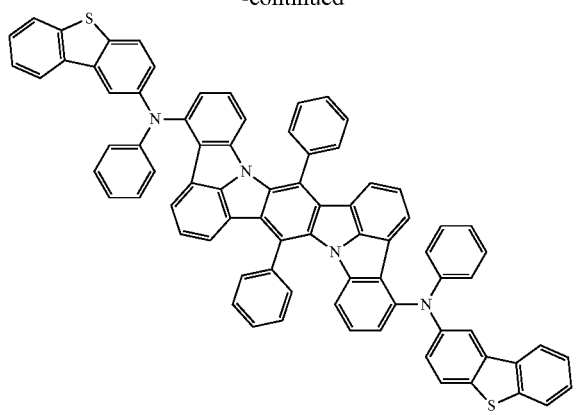
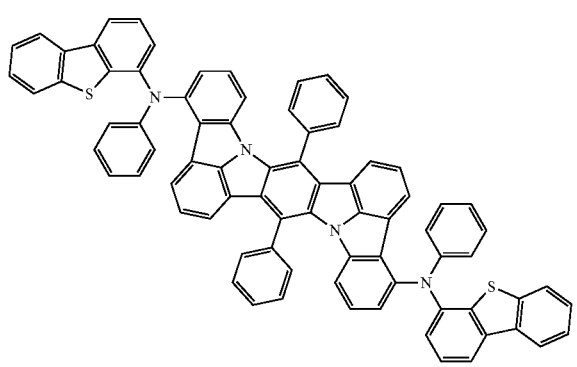
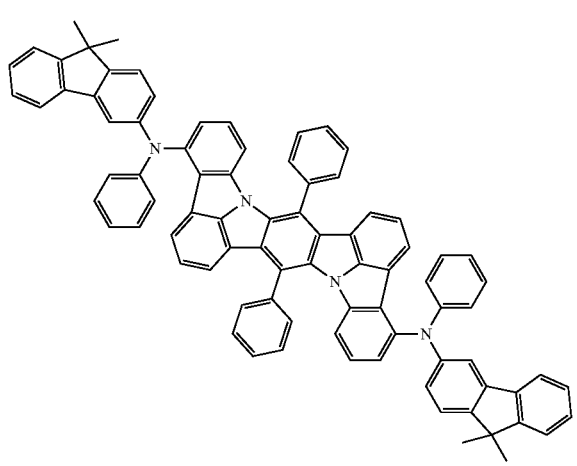
632
-continued
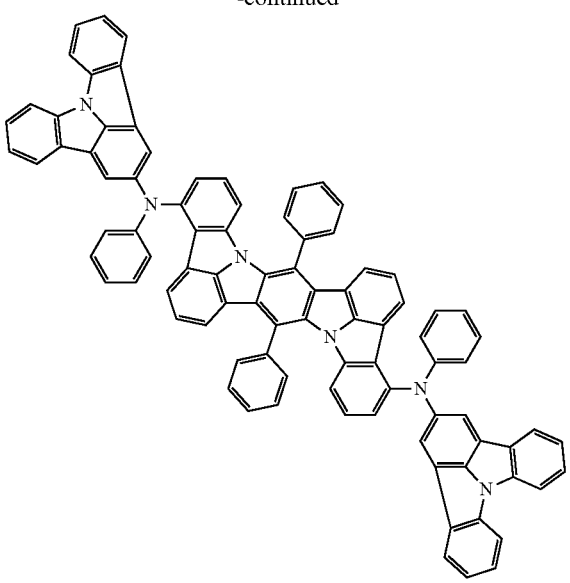
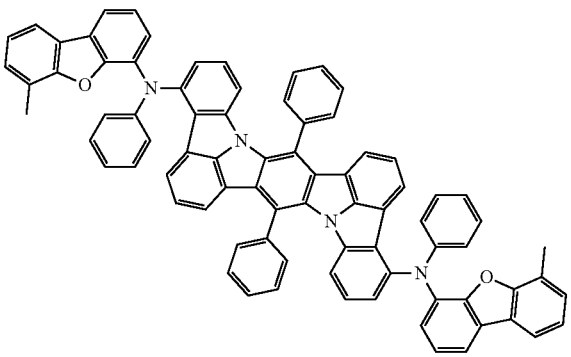

633
-continued
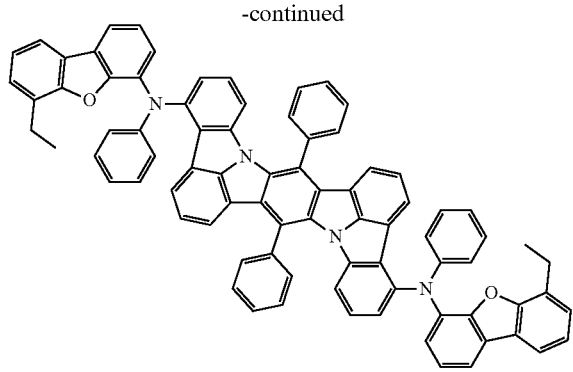
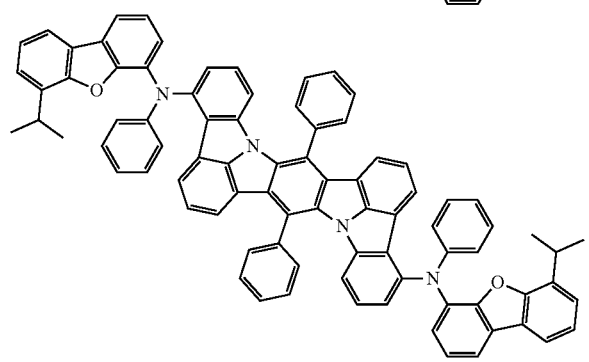
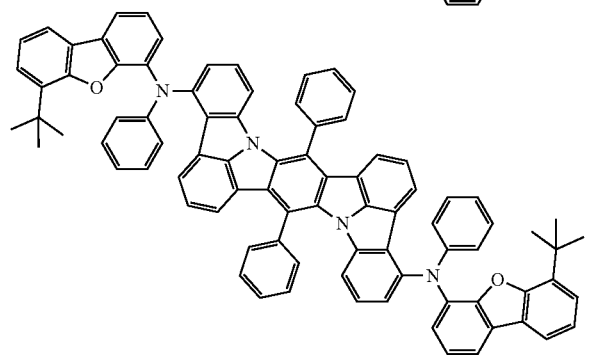
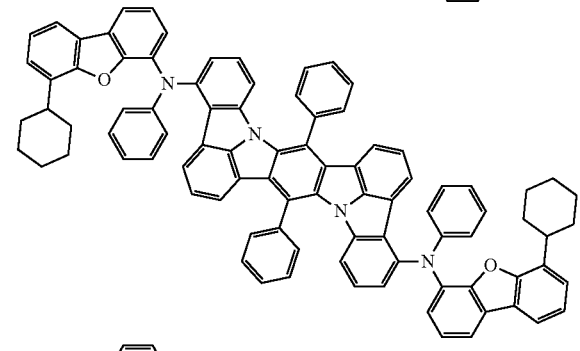
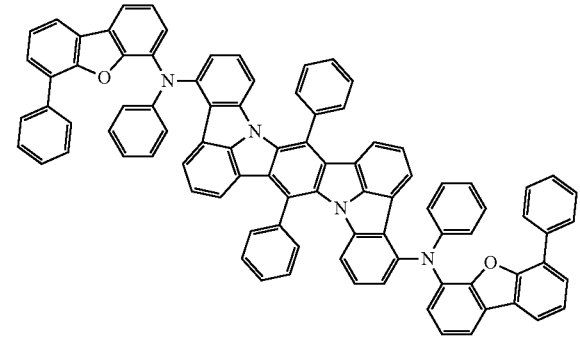
634
-continued
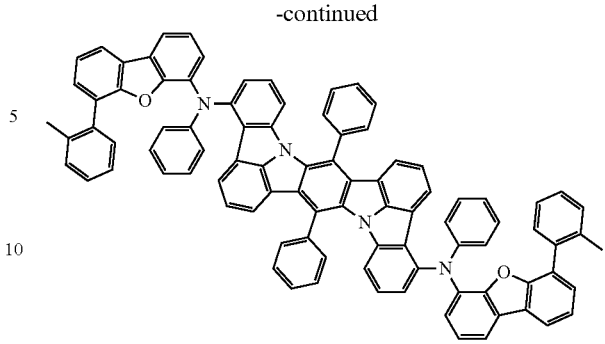
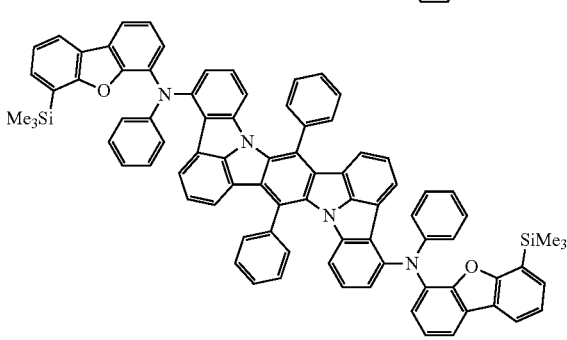
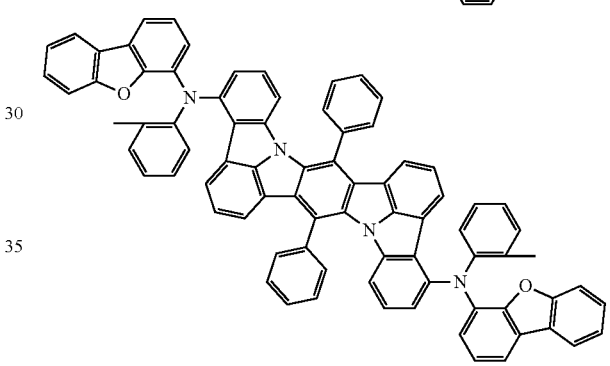
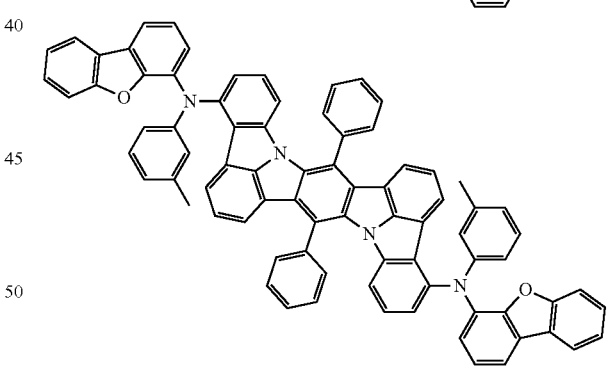
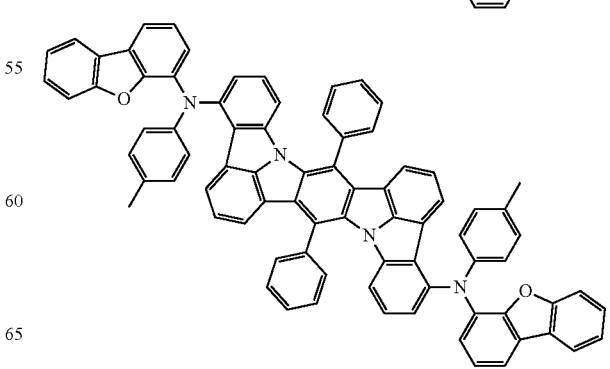

635
-continued
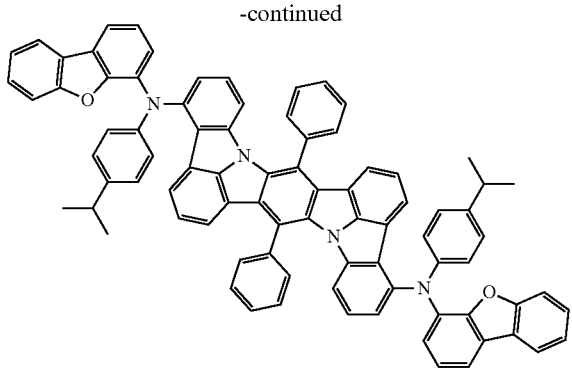
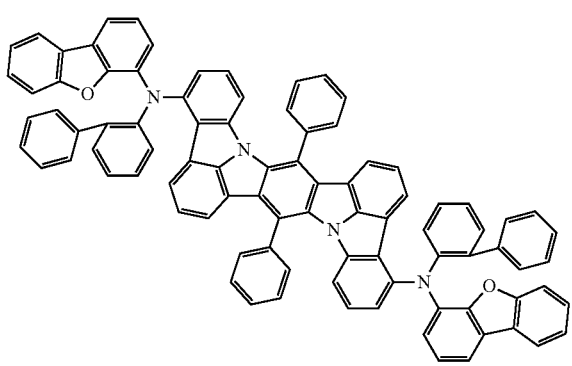
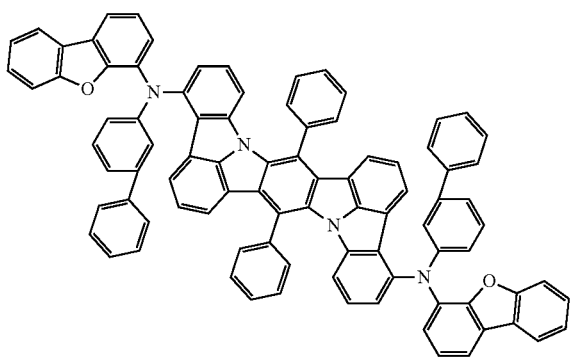
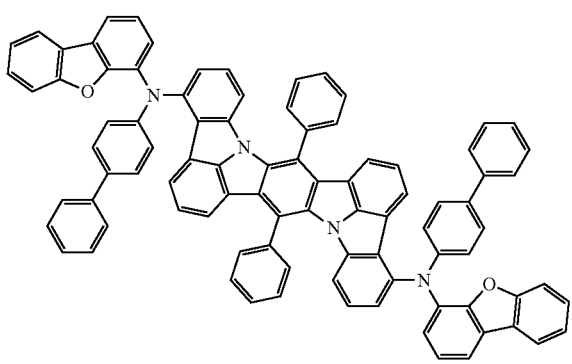
636
-continued
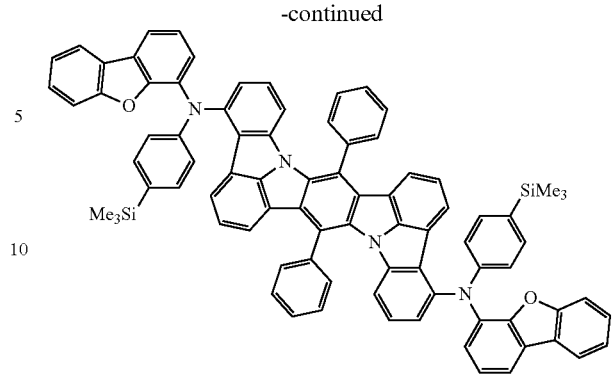
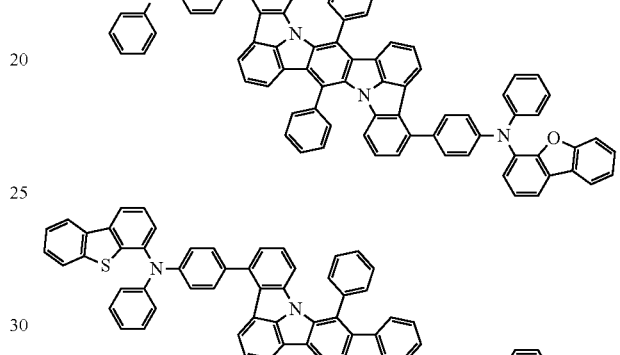
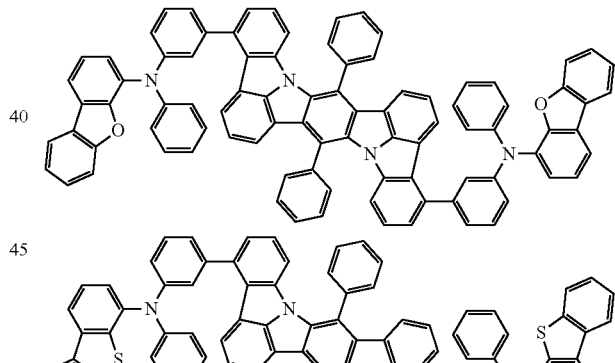
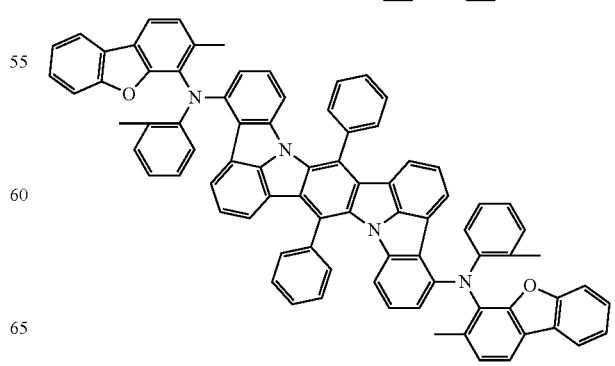

637
-continued
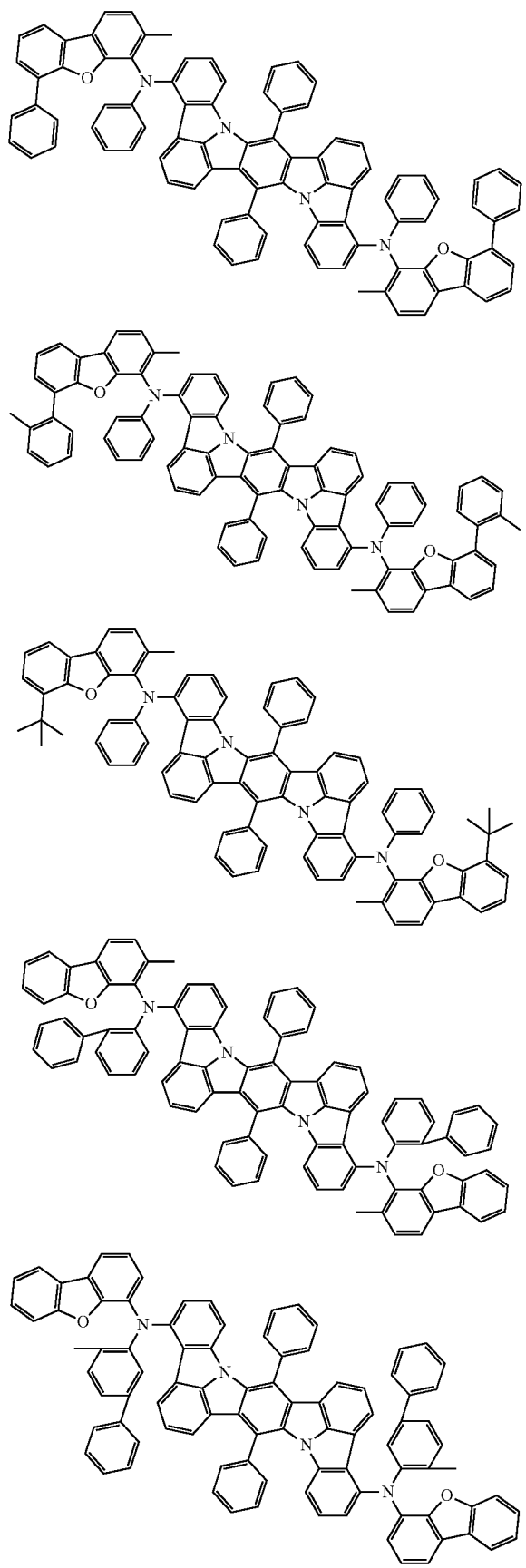
638
-continued
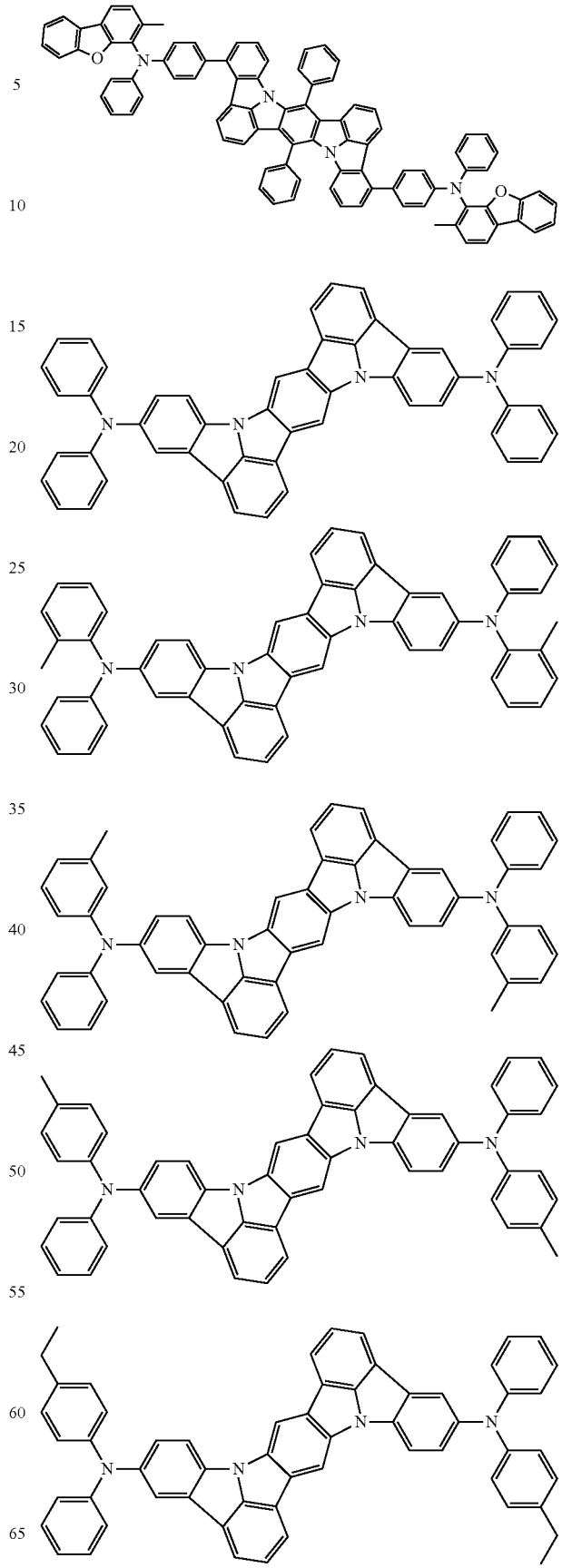

639
-continued
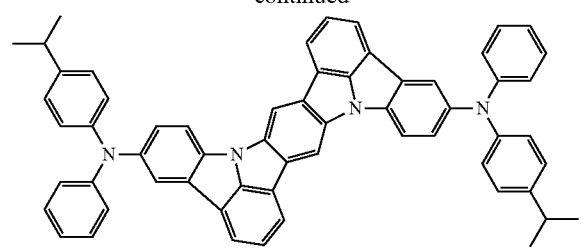
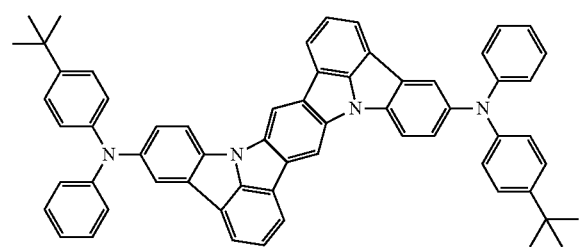
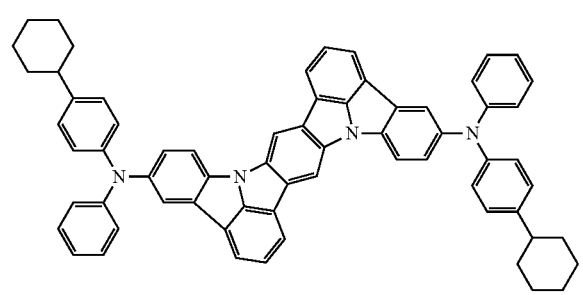
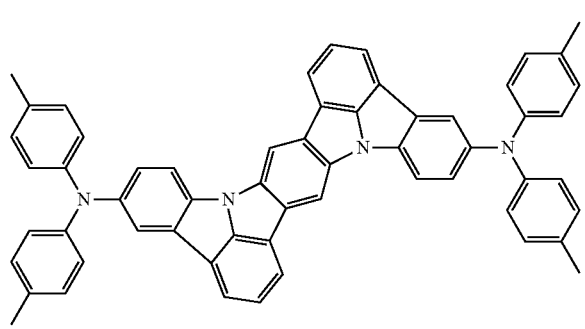
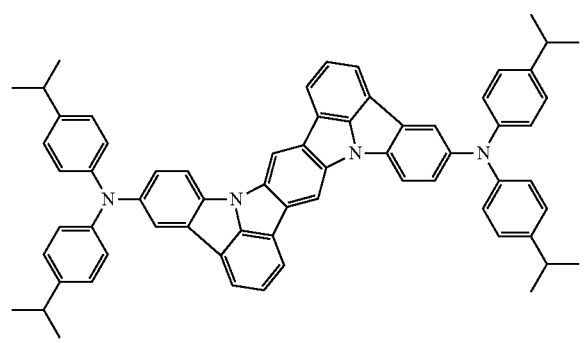
640
-continued
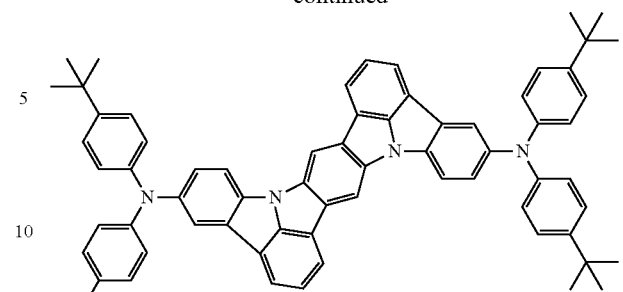
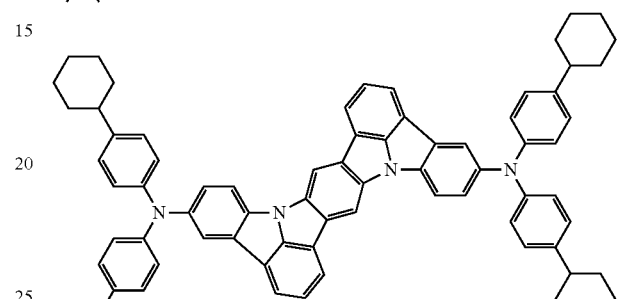
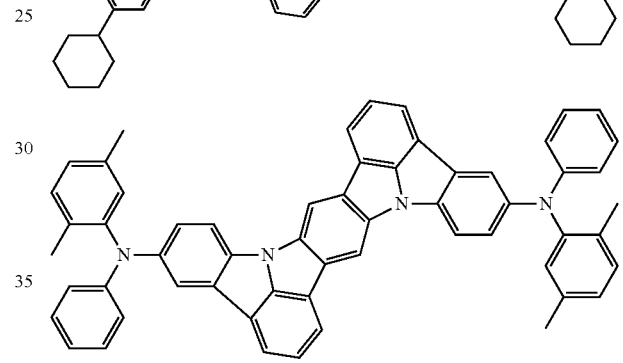
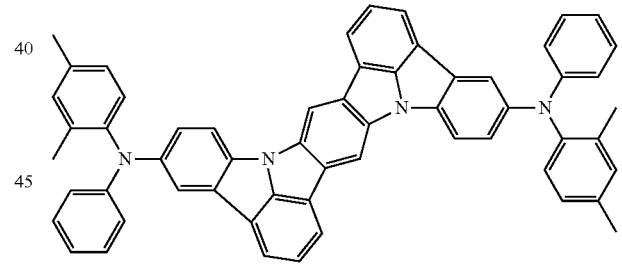
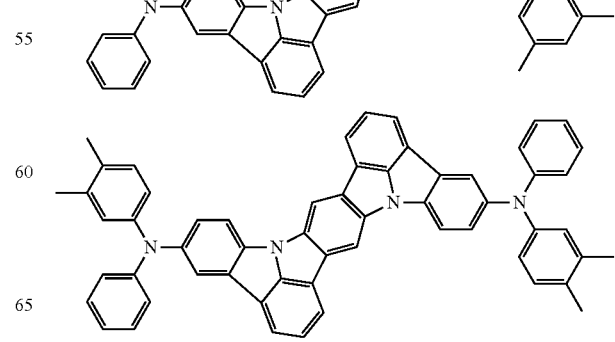

641
-continued
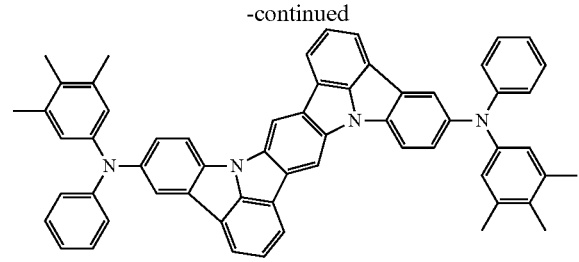
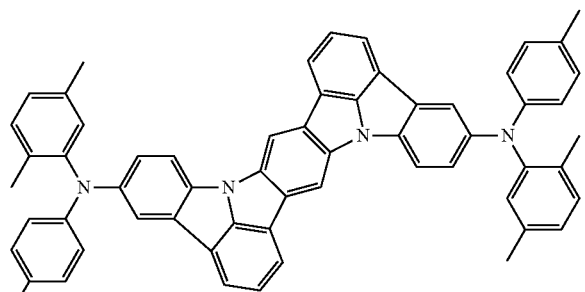
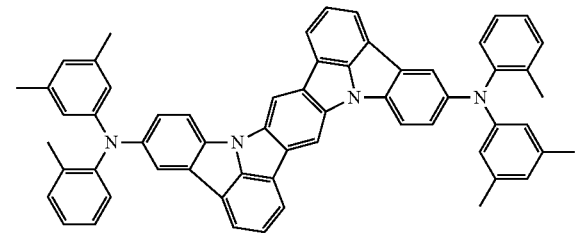
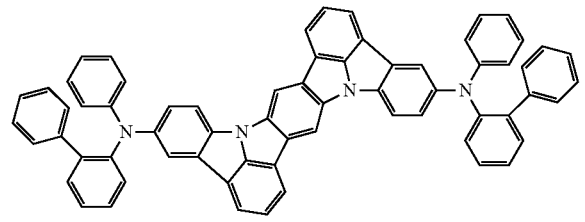
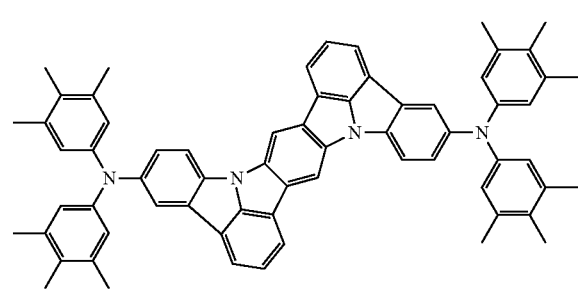
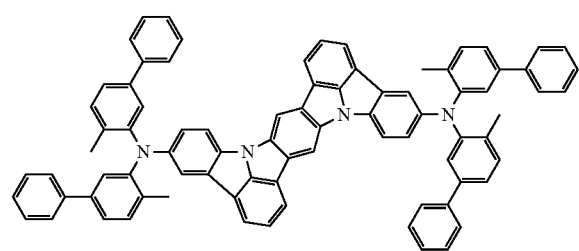
642
-continued
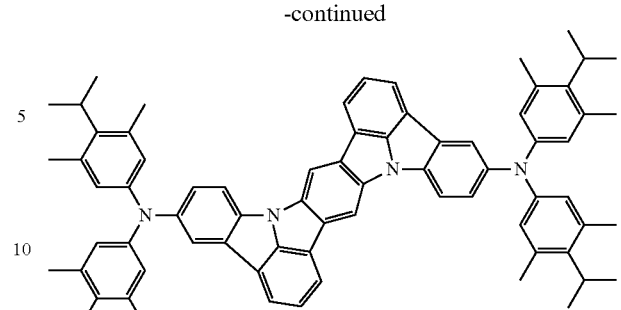
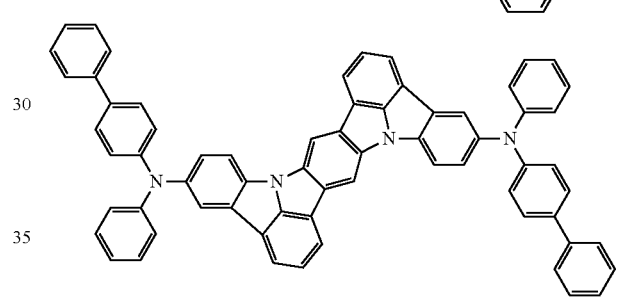
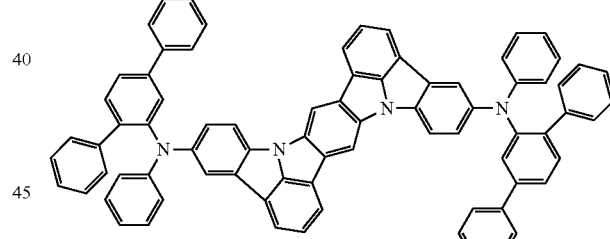
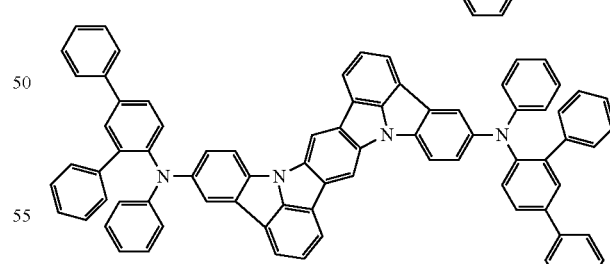
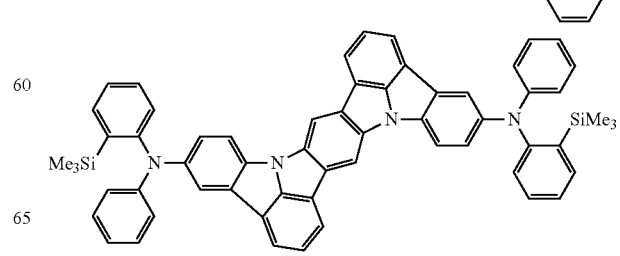

643
-continued
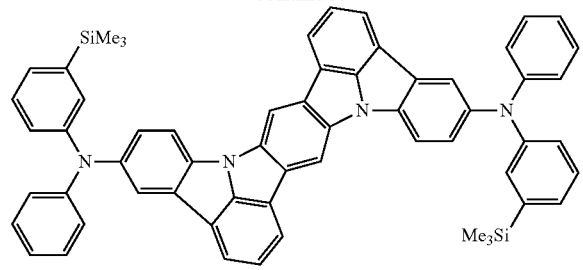
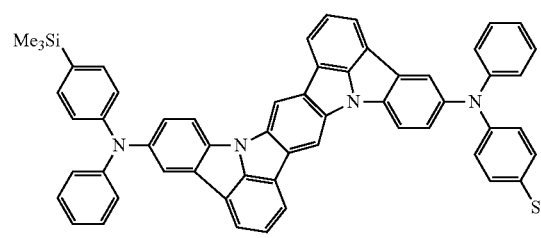
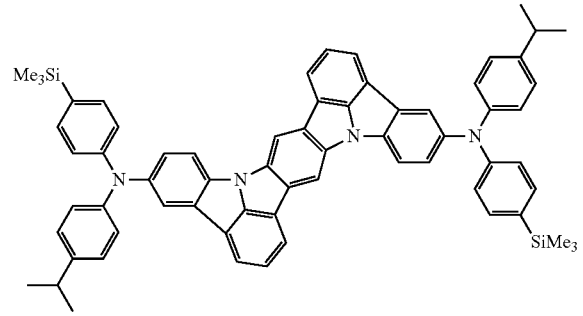
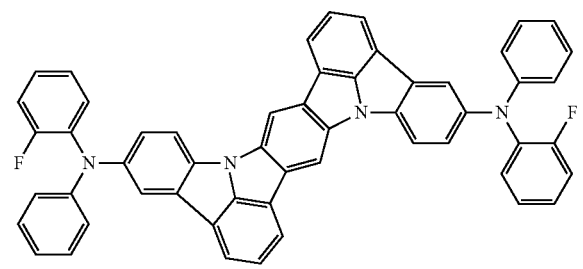
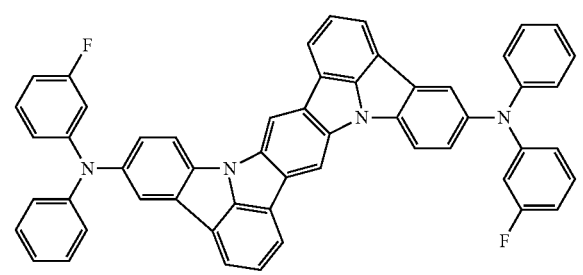
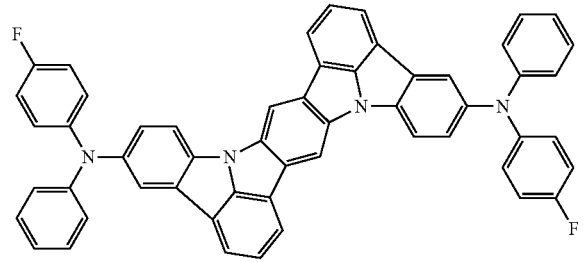
644
-continued
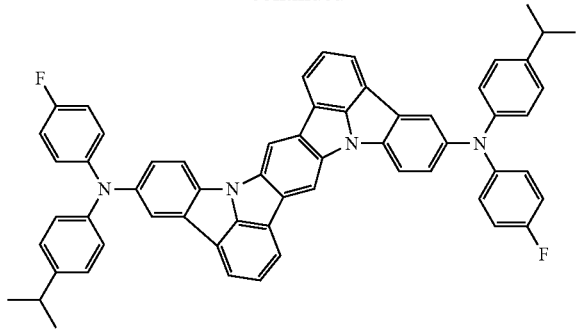
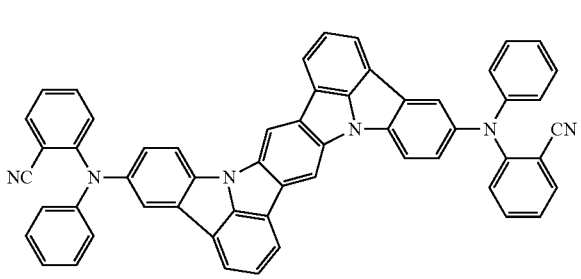
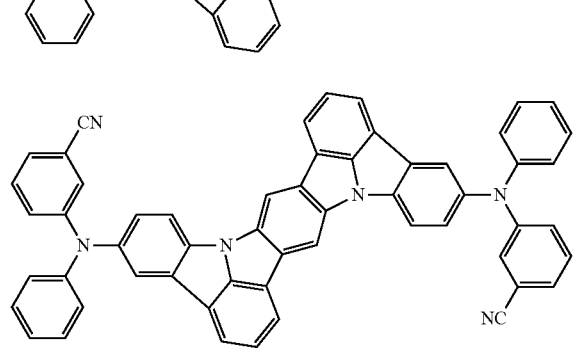
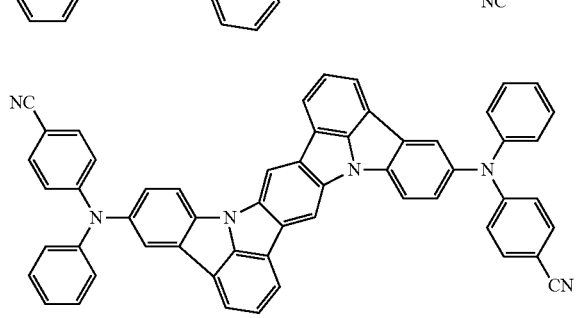
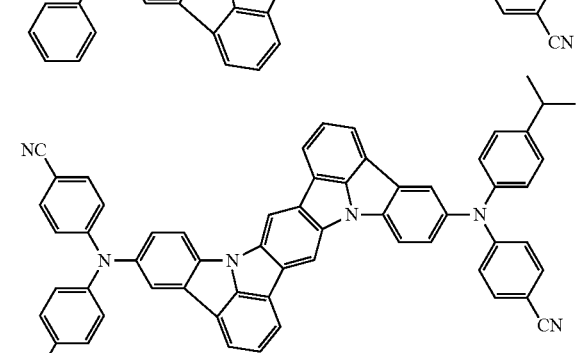
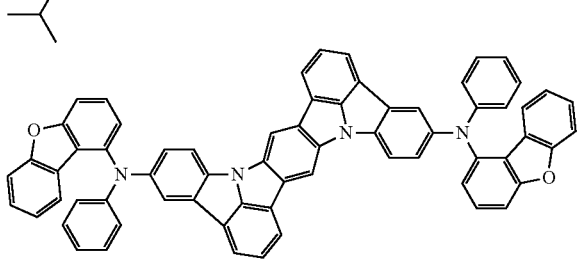

645
-continued
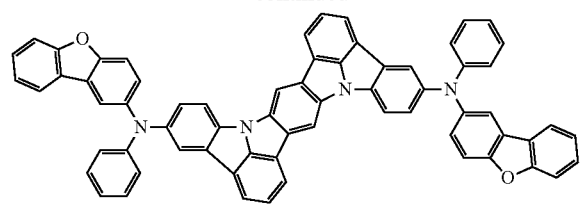
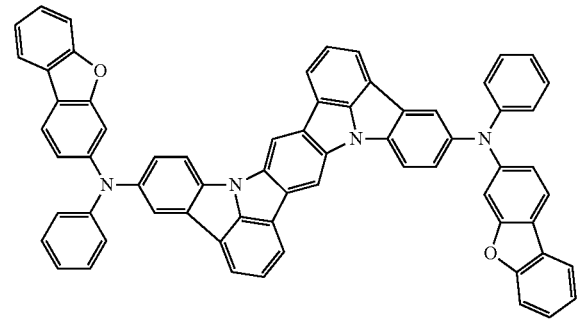
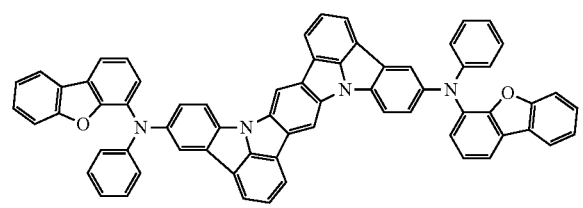
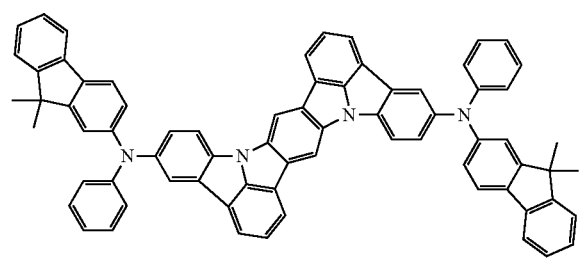
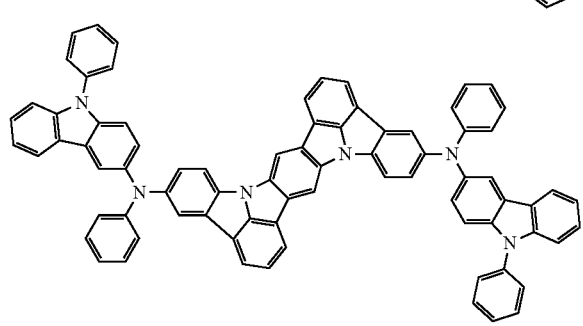
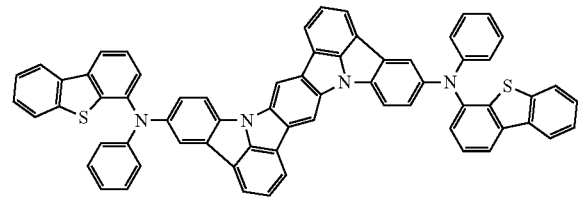
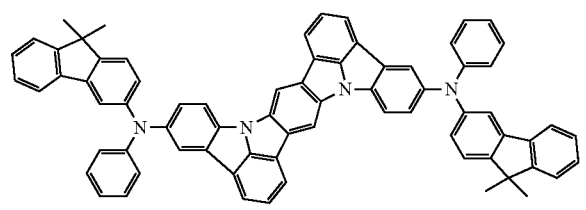
646
-continued
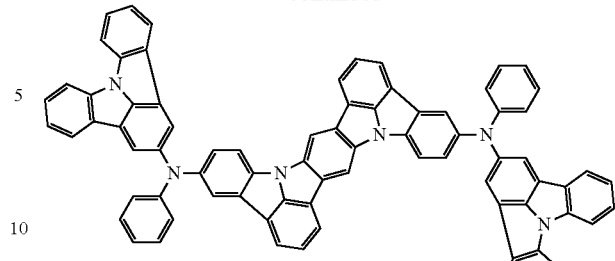
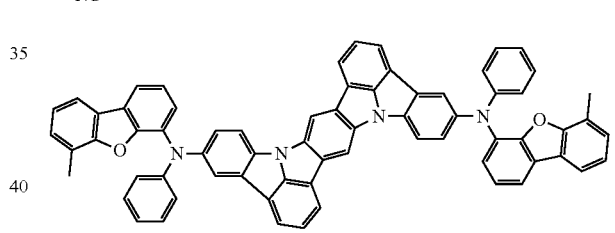
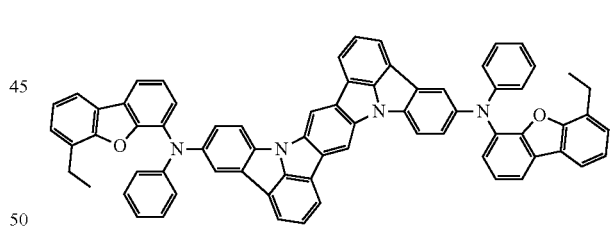
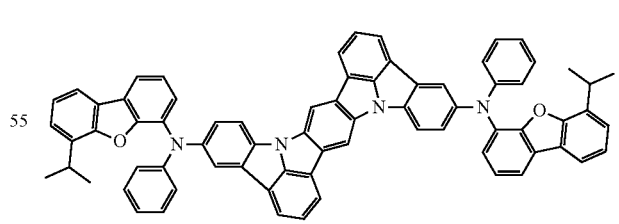
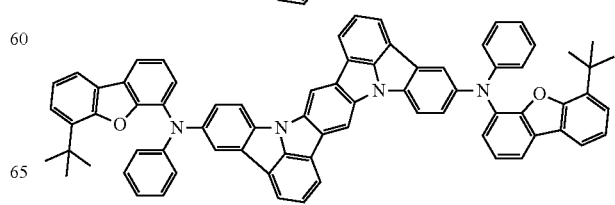

-continued
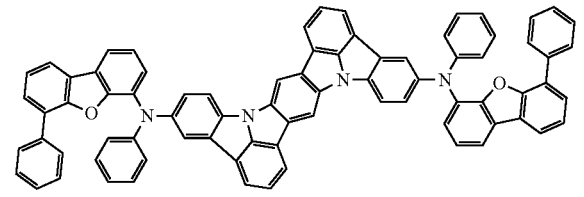
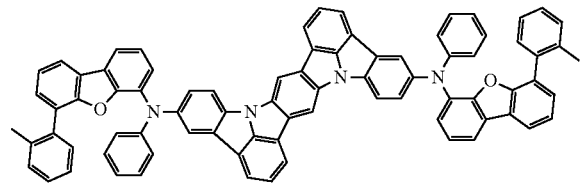
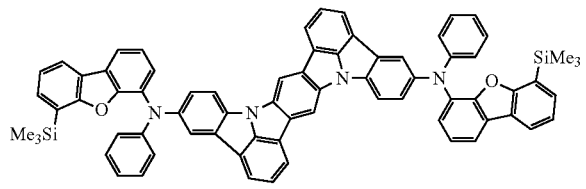
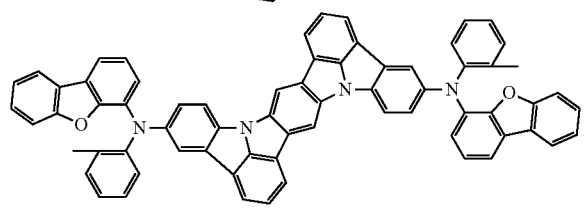
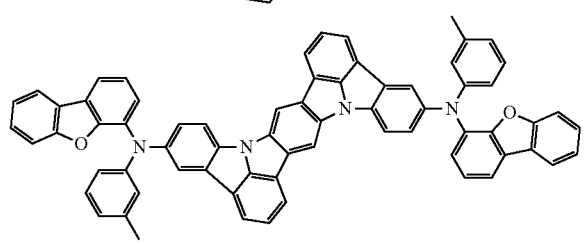
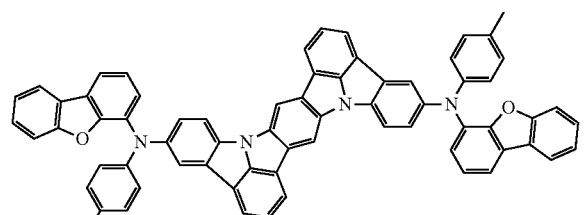
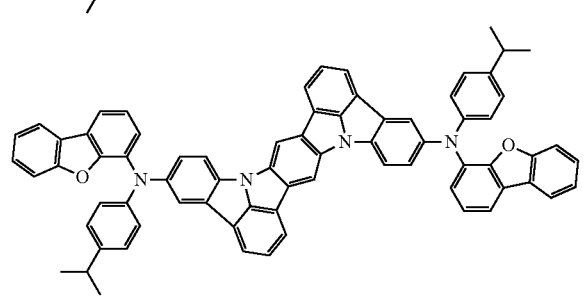
-continued
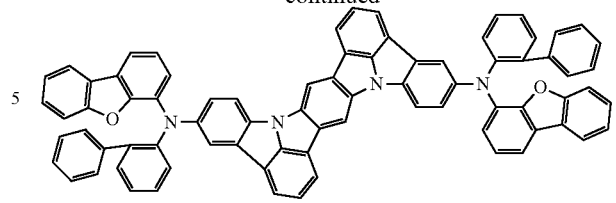
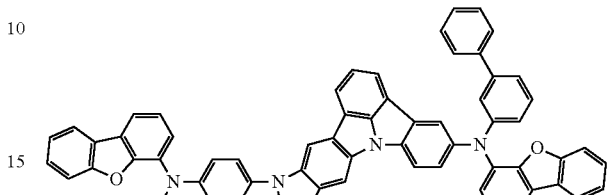
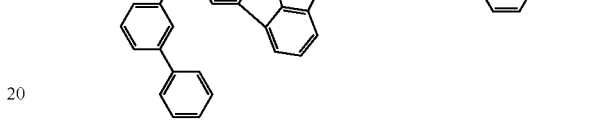
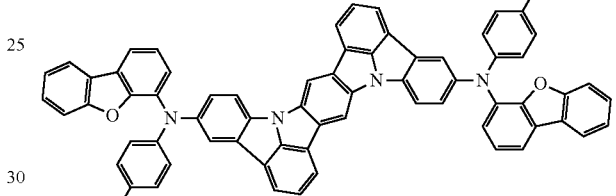
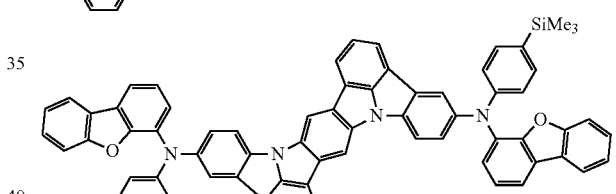
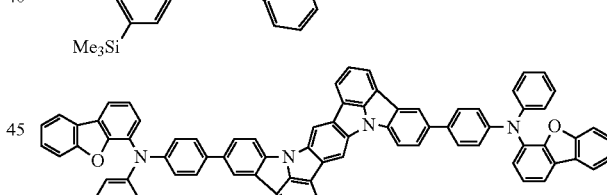
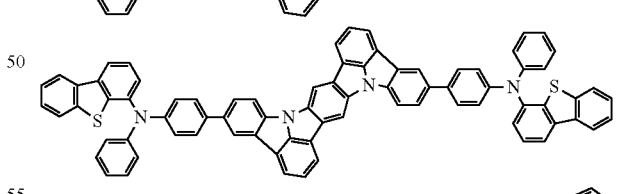
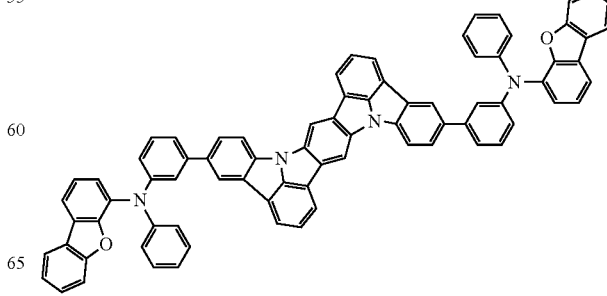

| 649 -continued | 650 -continued |
|---|---|
| 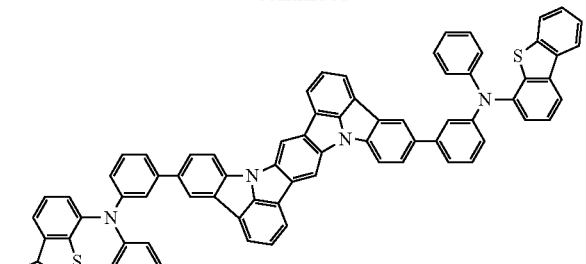 | 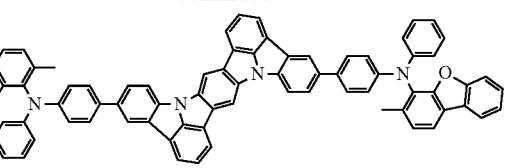 |
| 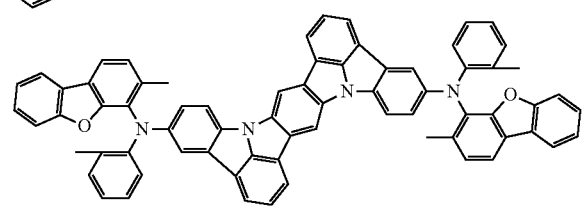 | 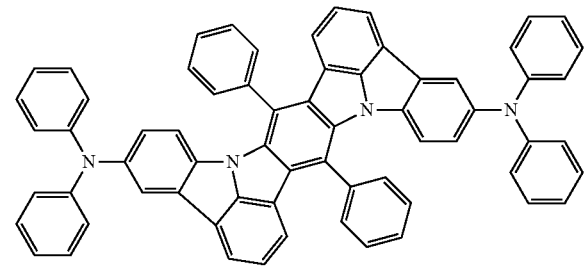 |
| 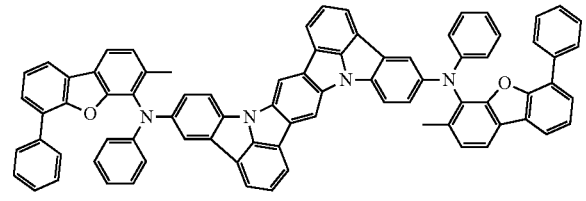 | 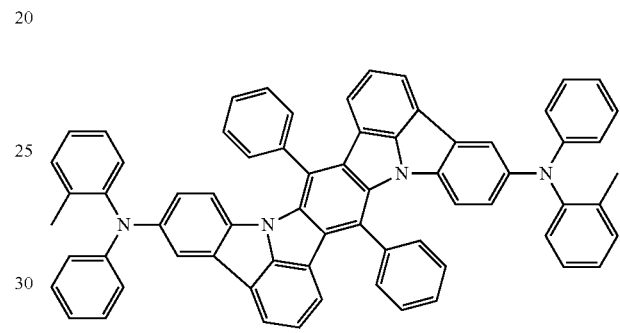 |
| 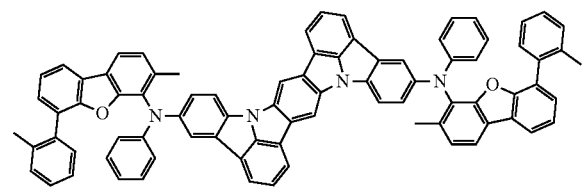 | 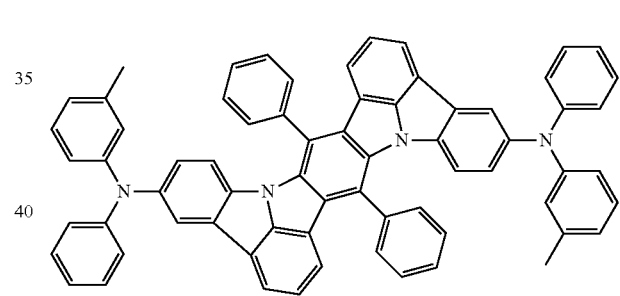 |
| 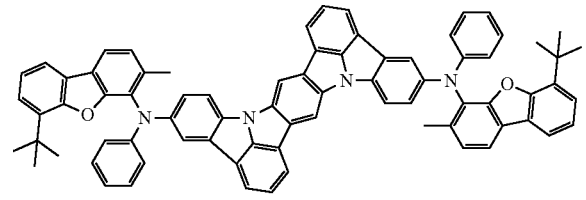 | 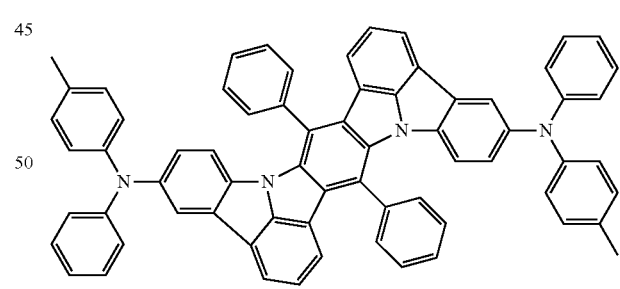 |
| 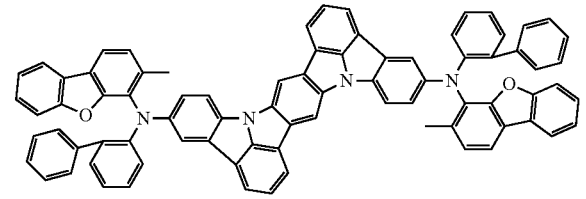 | 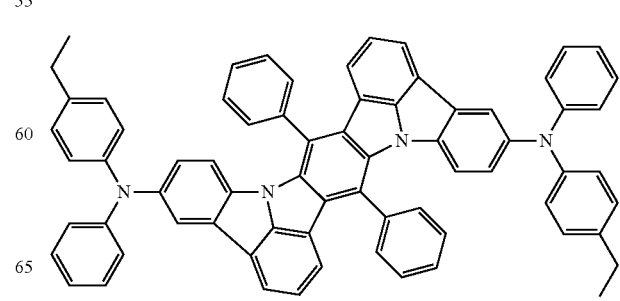 |
| 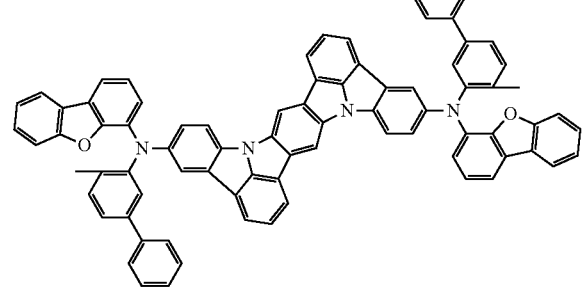 | |

| 651 -continued | 652 -continued |
|---|---|
| 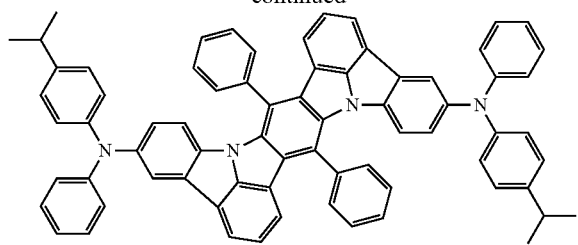 | 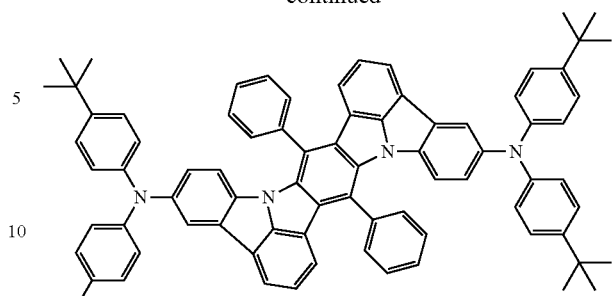 |
| 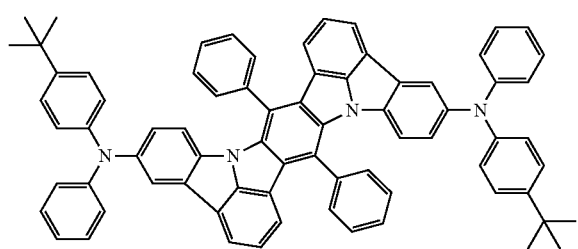 | 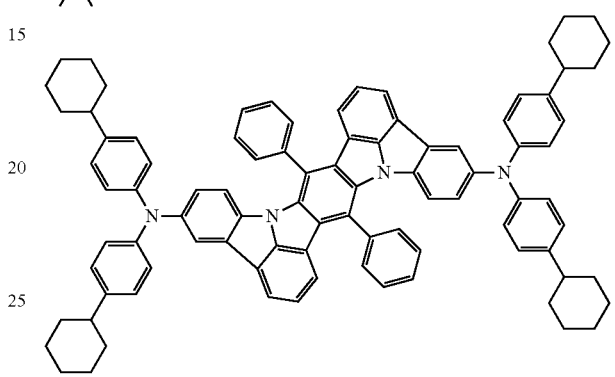 |
| 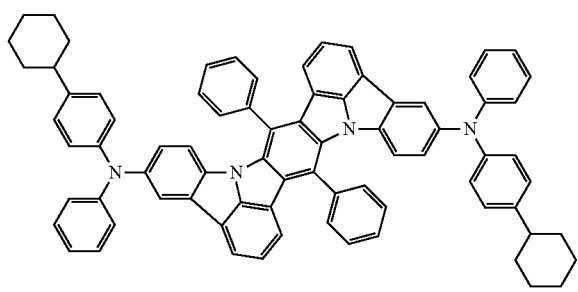 | 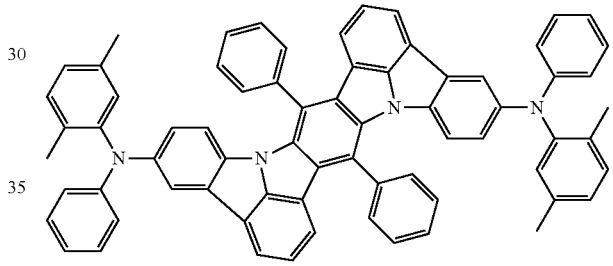 |
| 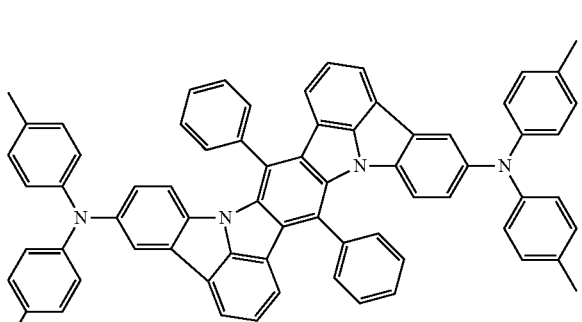 | 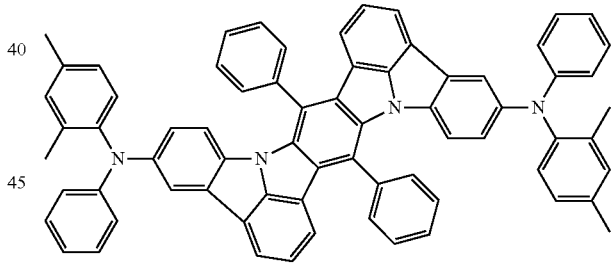 |
| 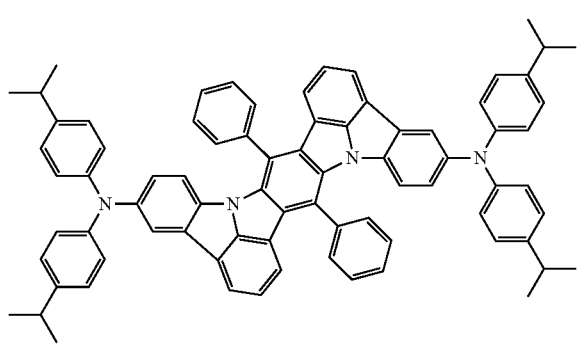 | 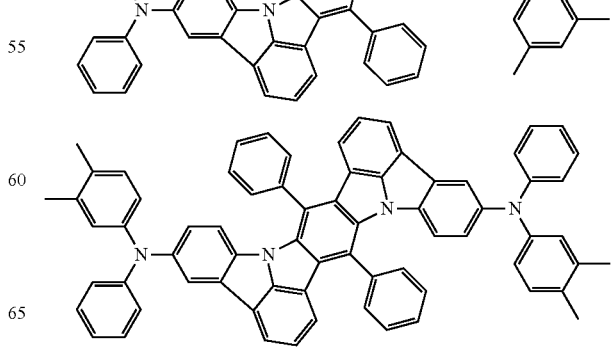 |

653
-continued
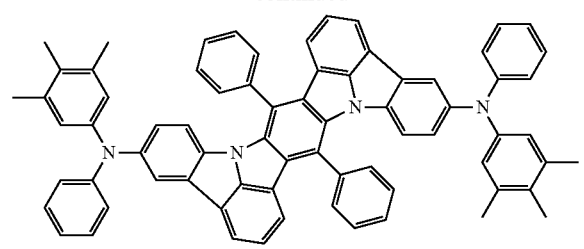
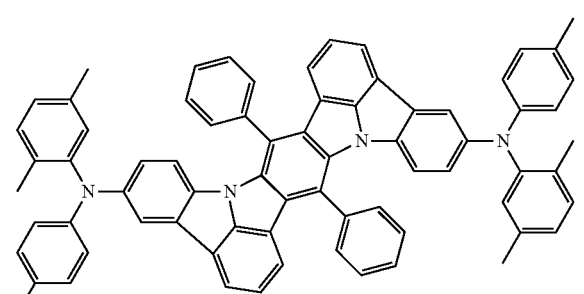
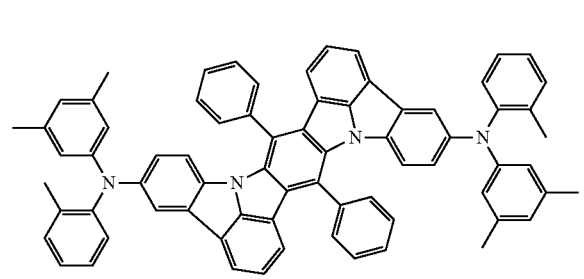
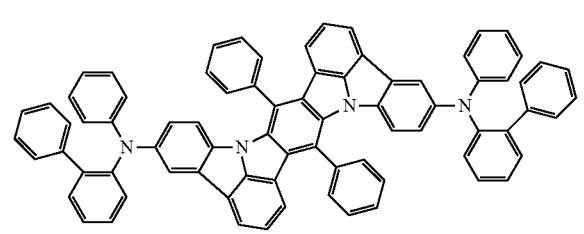
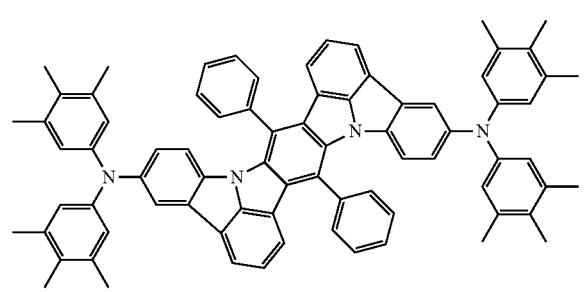
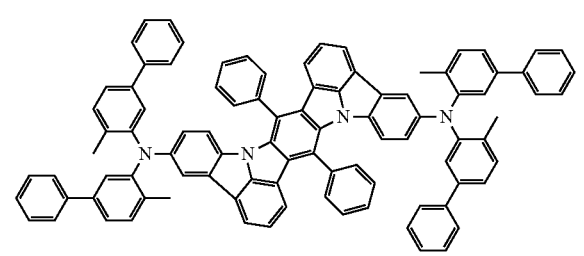
654
-continued
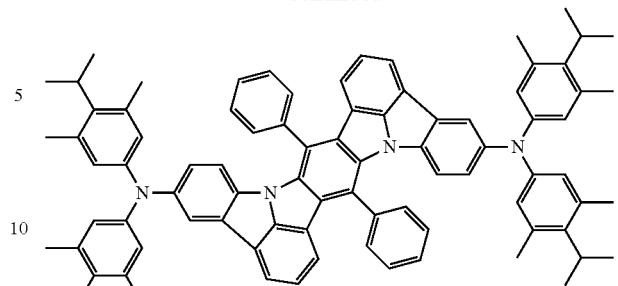
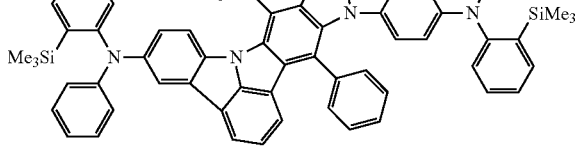

655
-continued
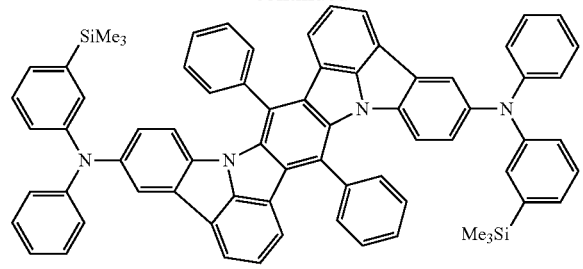
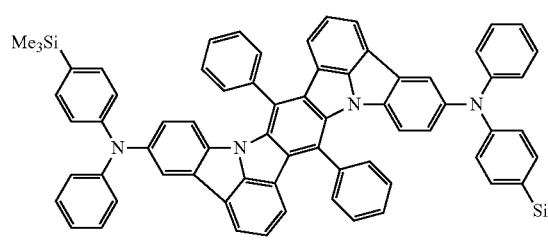
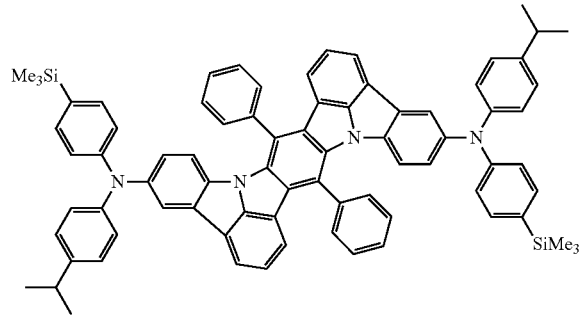
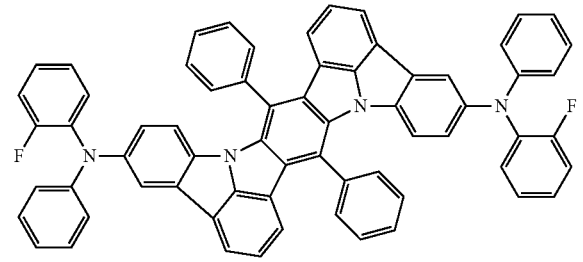
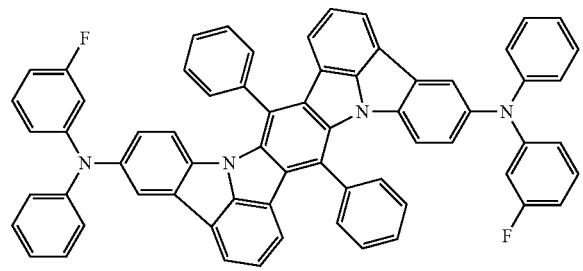
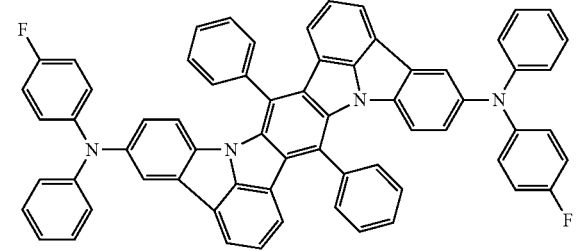
656
-continued
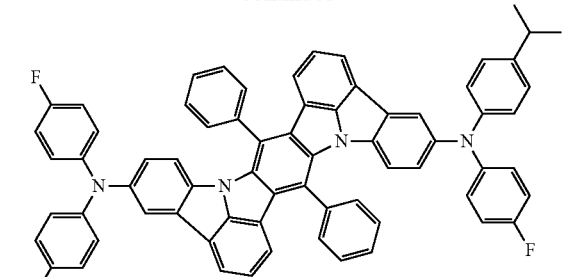
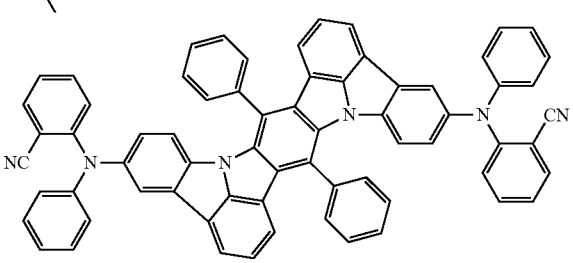
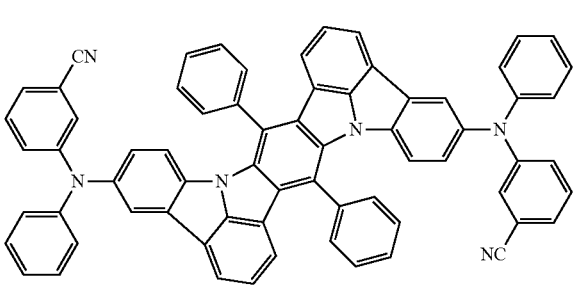
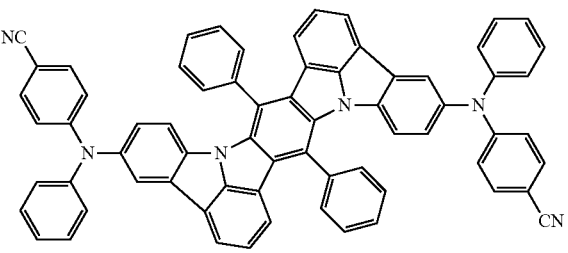
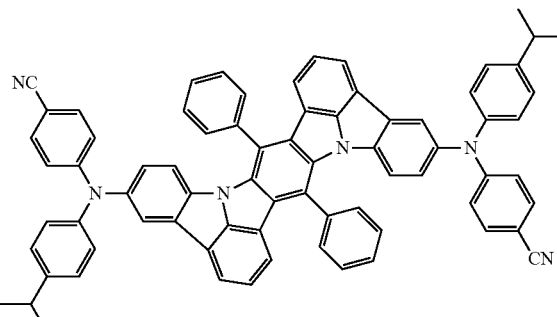
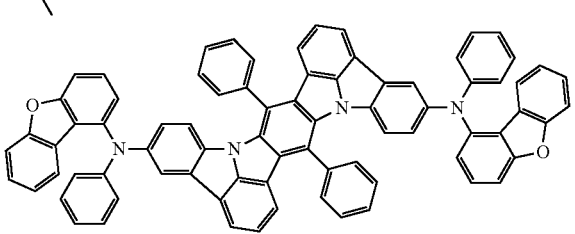

657
-continued
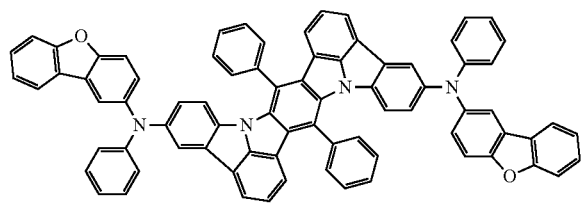
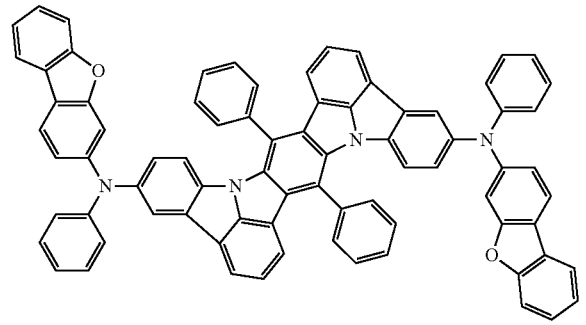
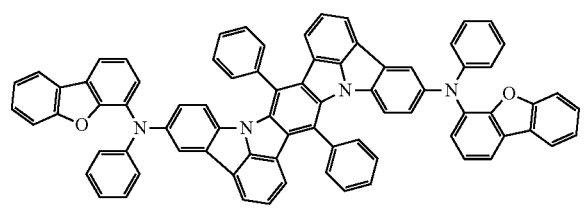
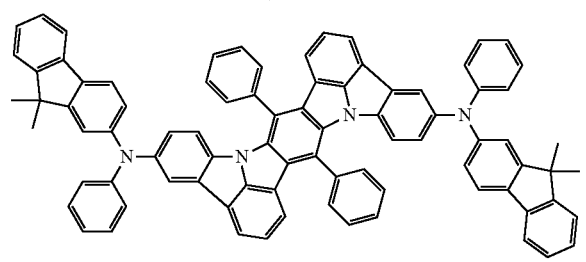
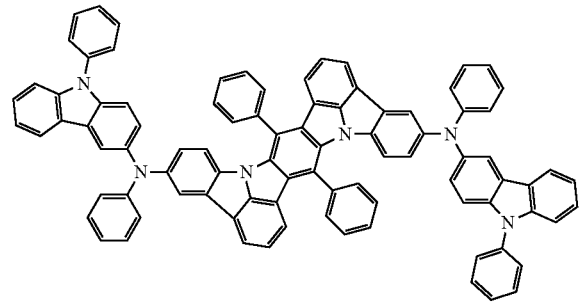
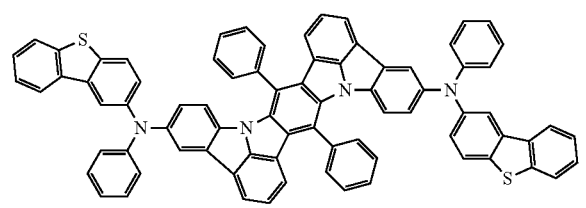
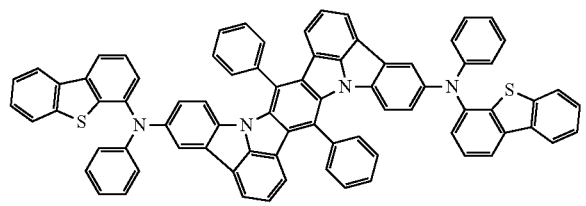
658
-continued
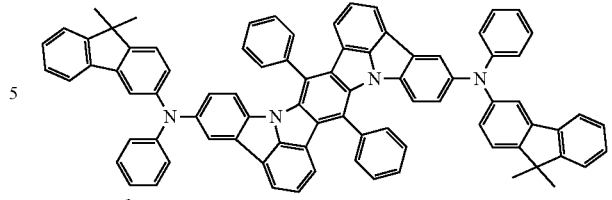
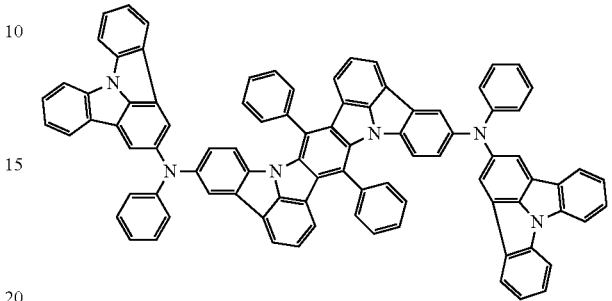
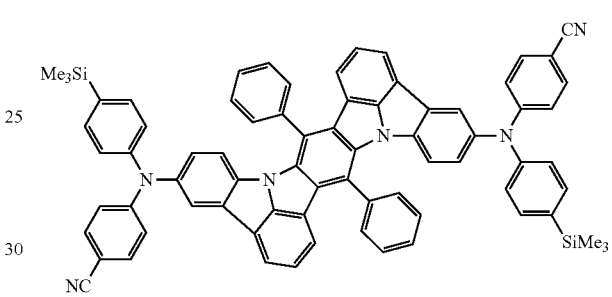
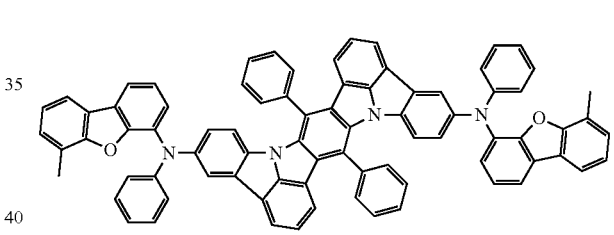
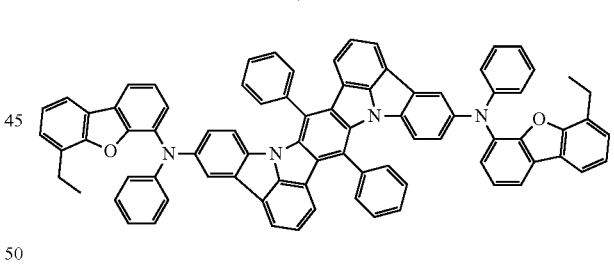
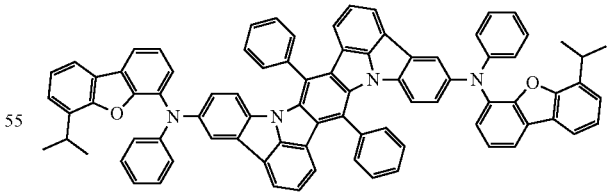
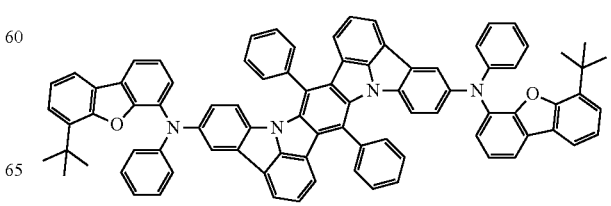

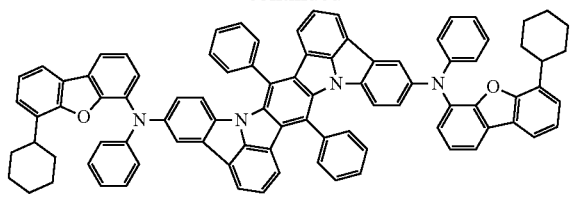
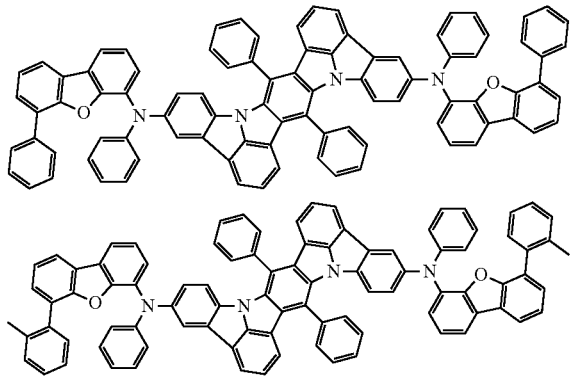
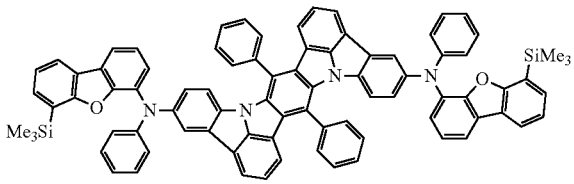
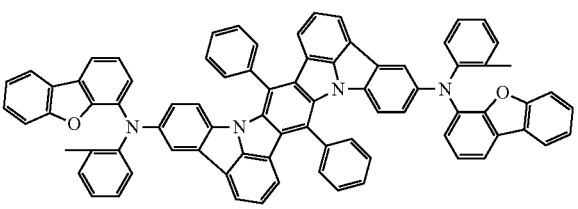
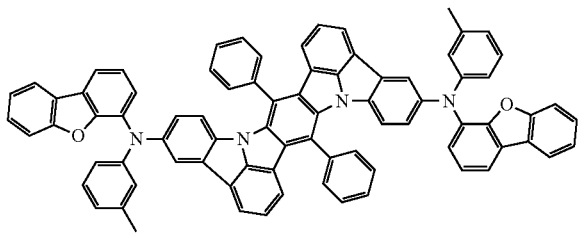
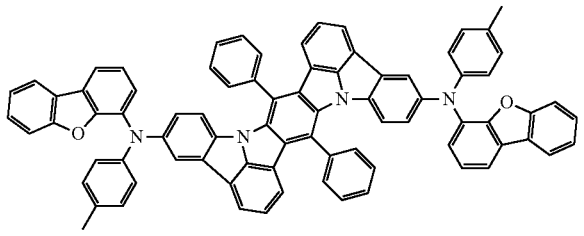
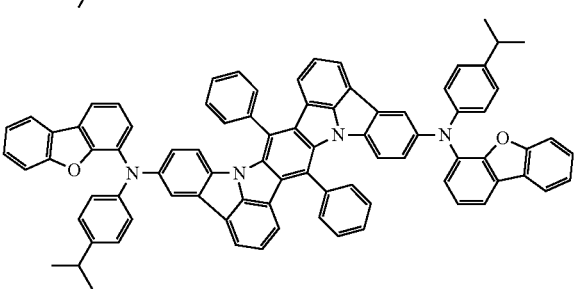
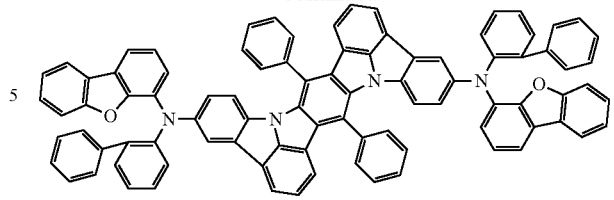
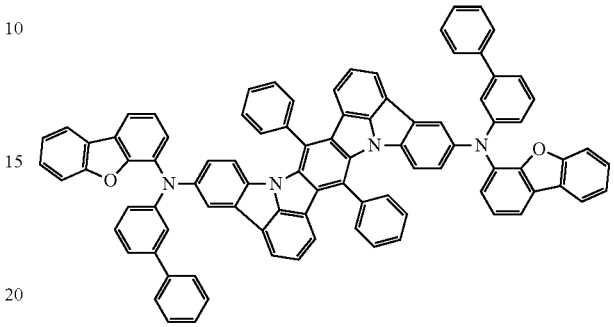
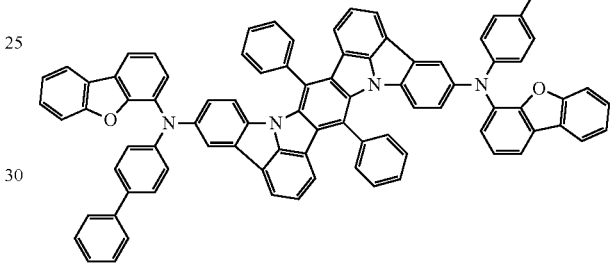
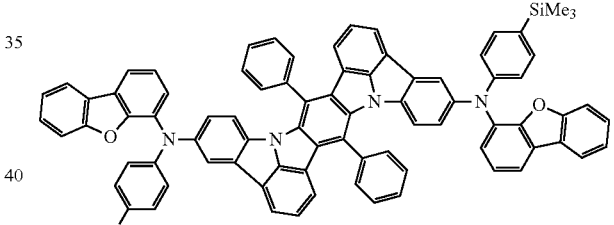
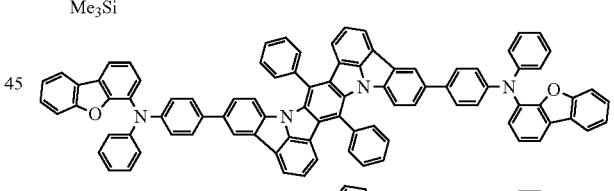
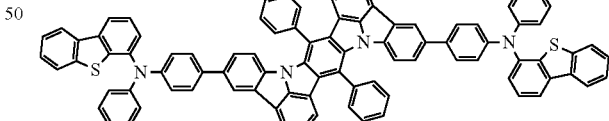
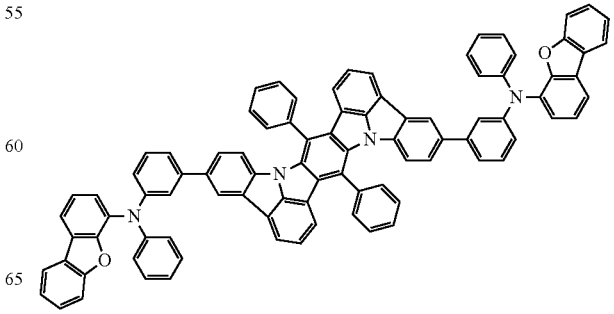

661
-continued
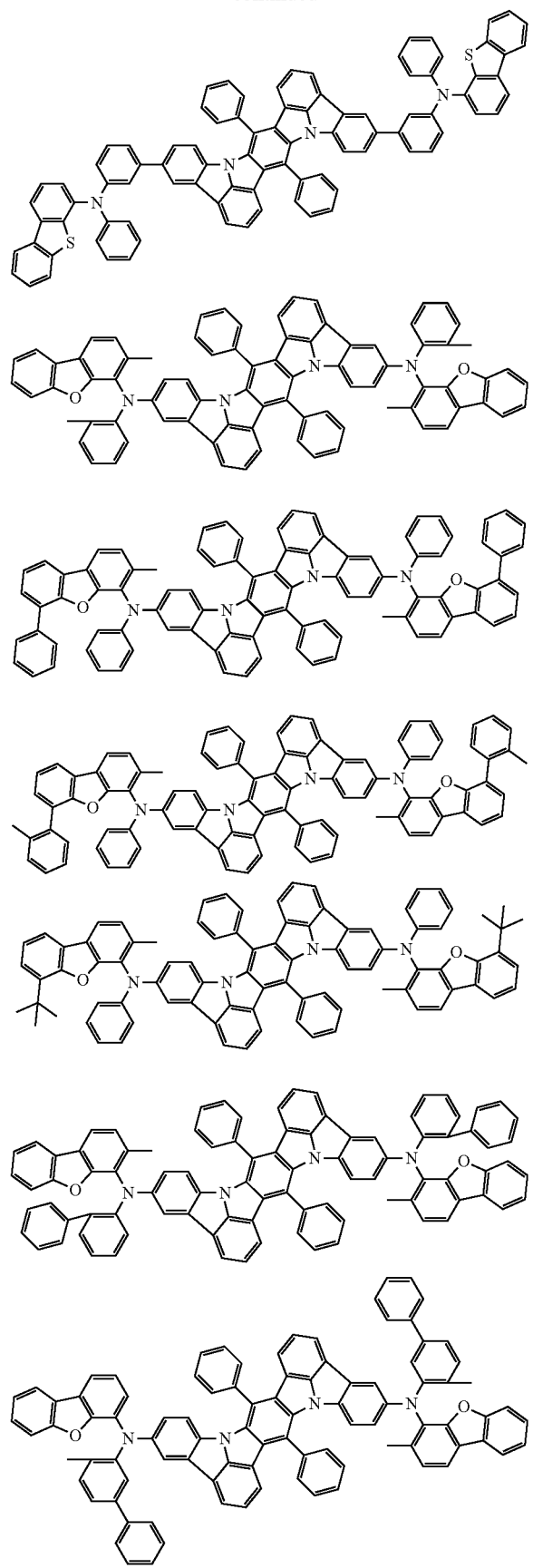
662
-continued
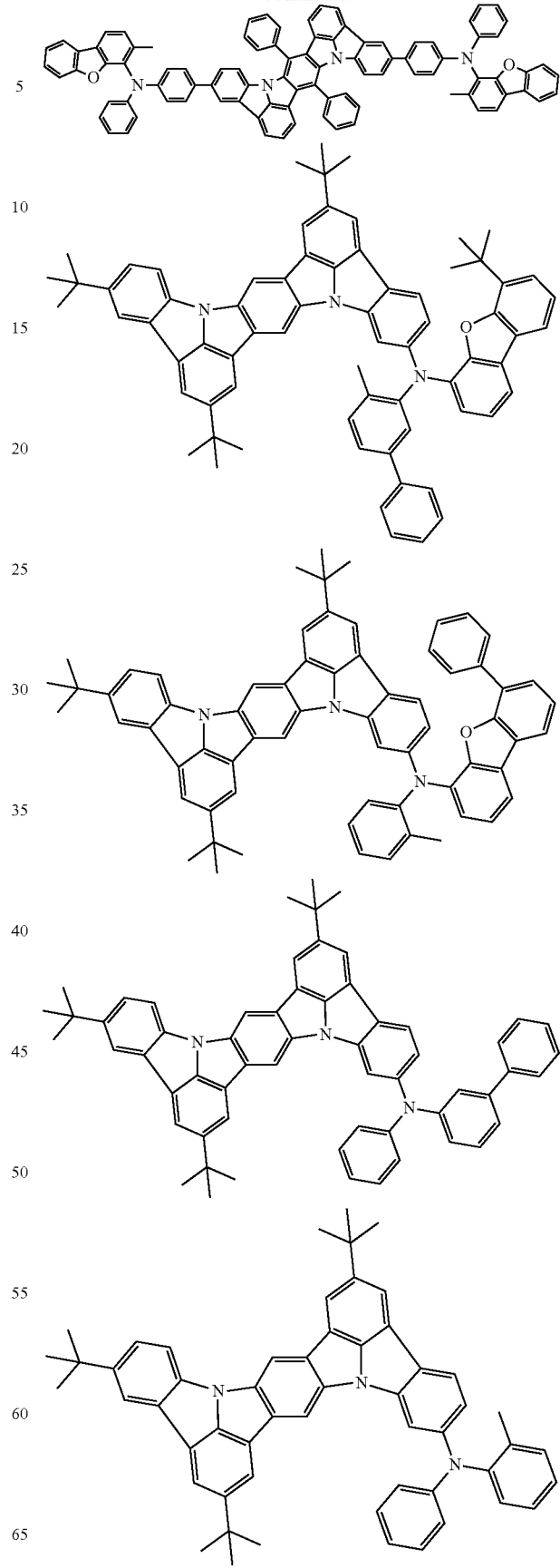

663
-continued
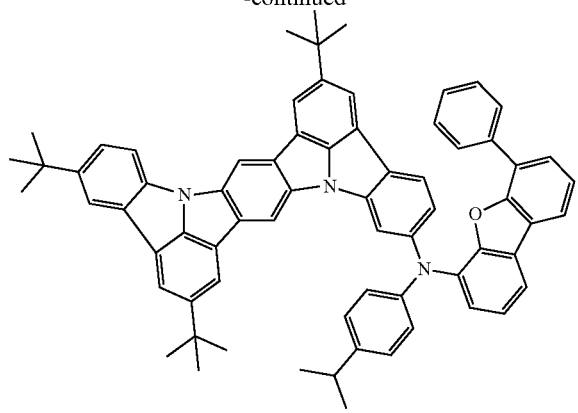
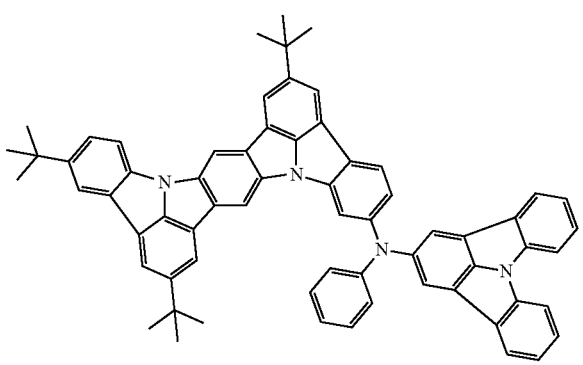
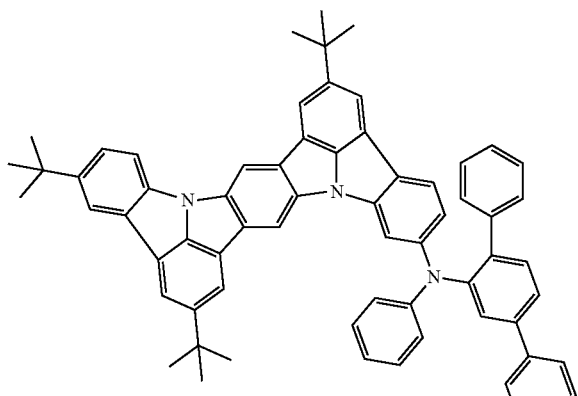
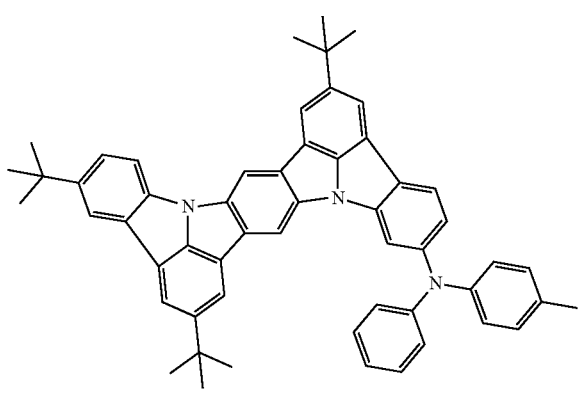
664
-continued
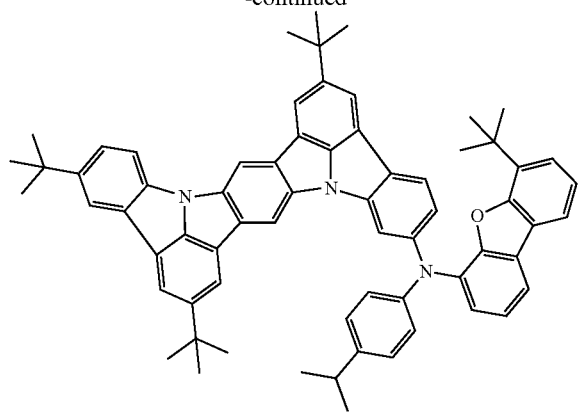
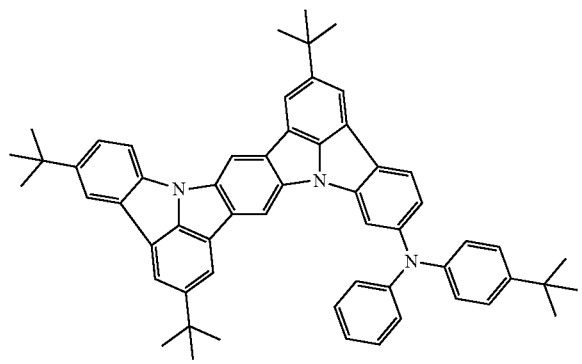
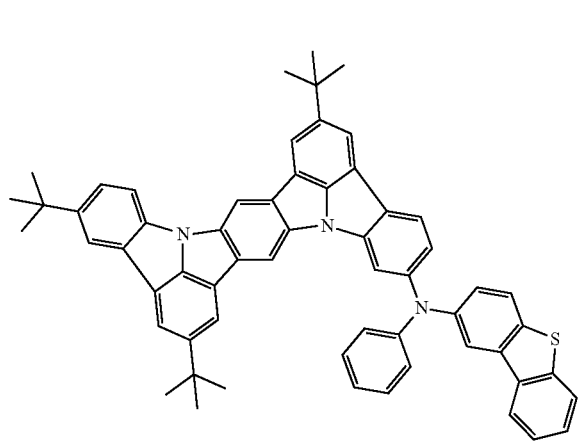
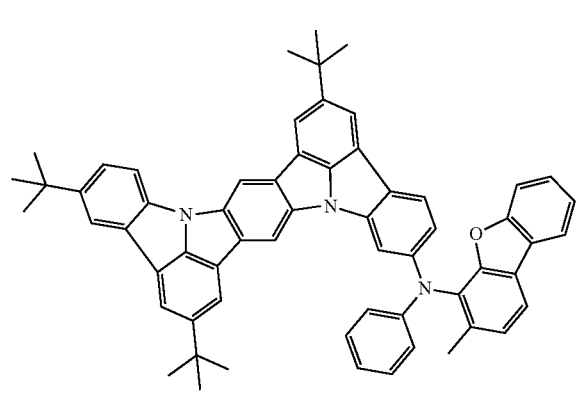

665
-continued
666
-continued
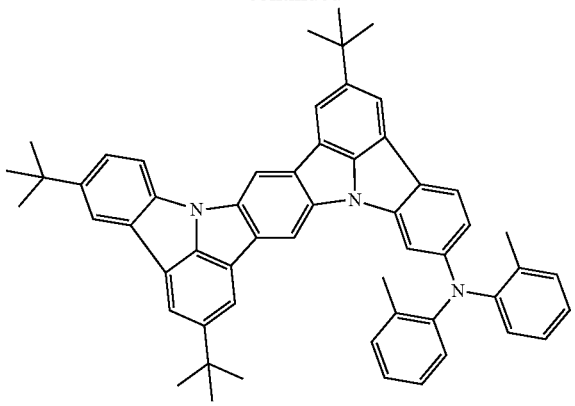
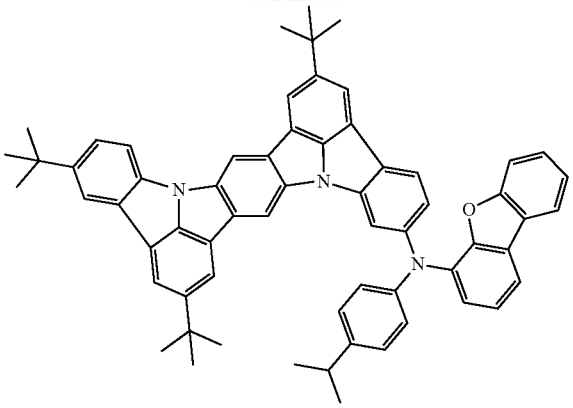
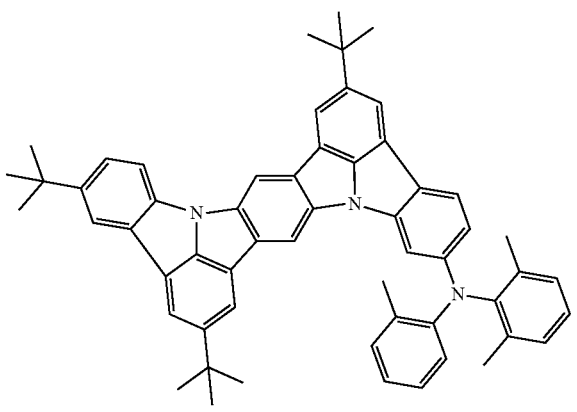
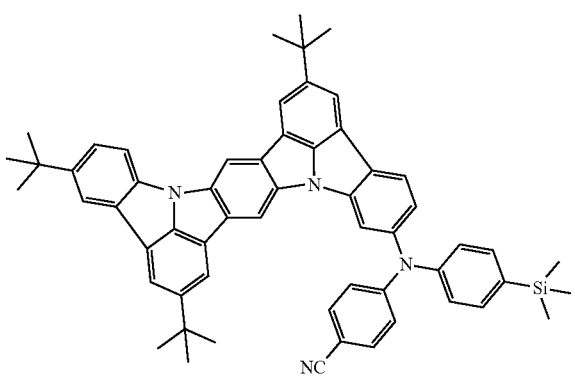
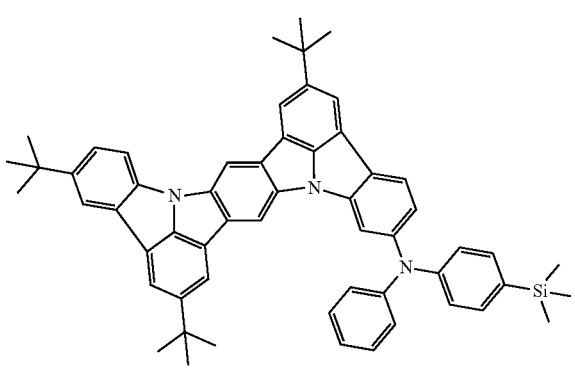
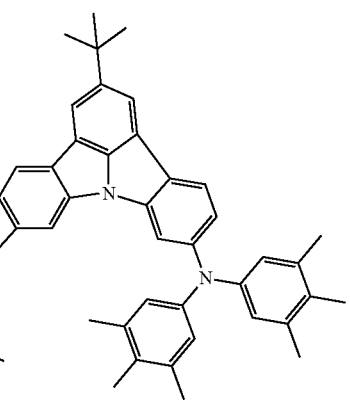

667
-continued
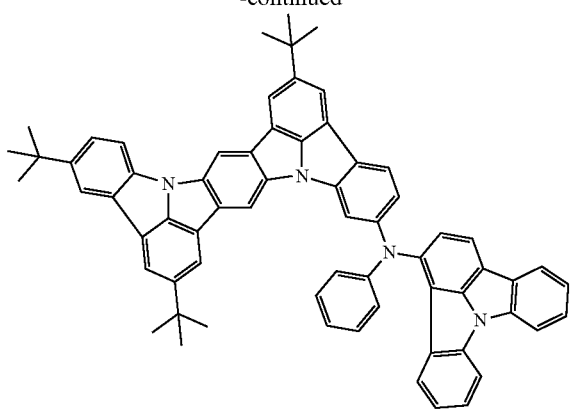
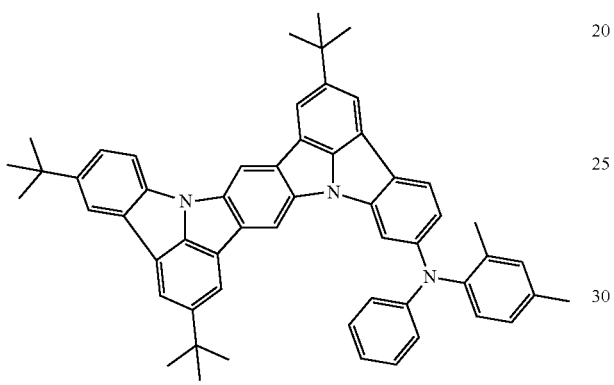
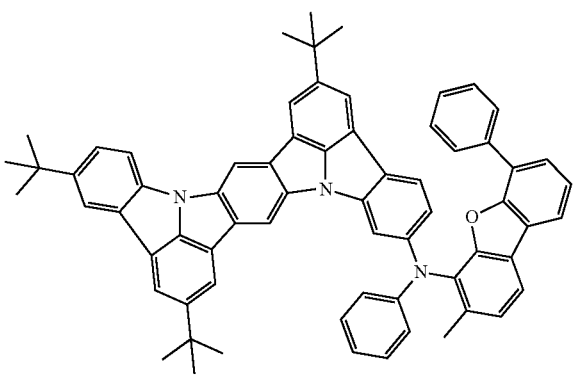
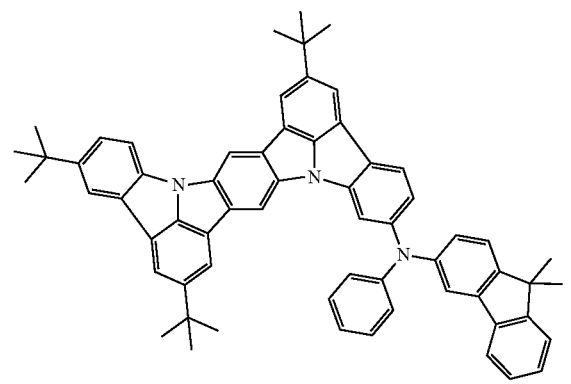
668
-continued
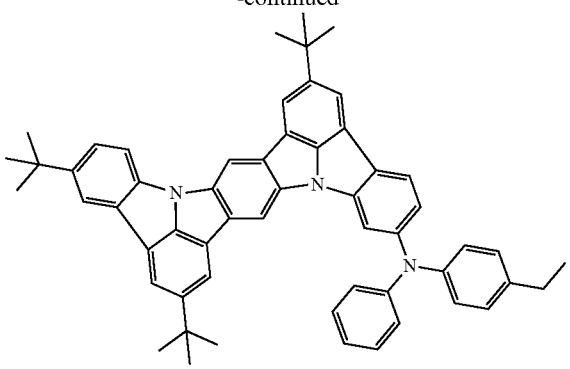
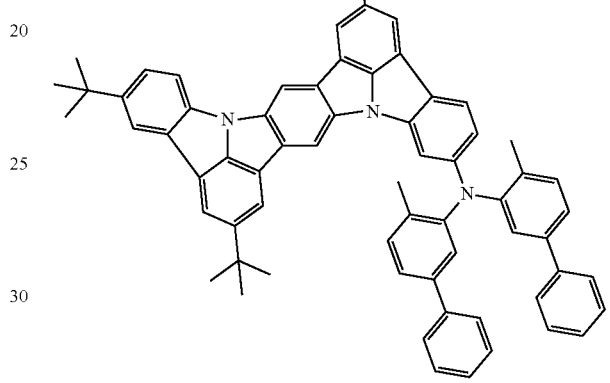
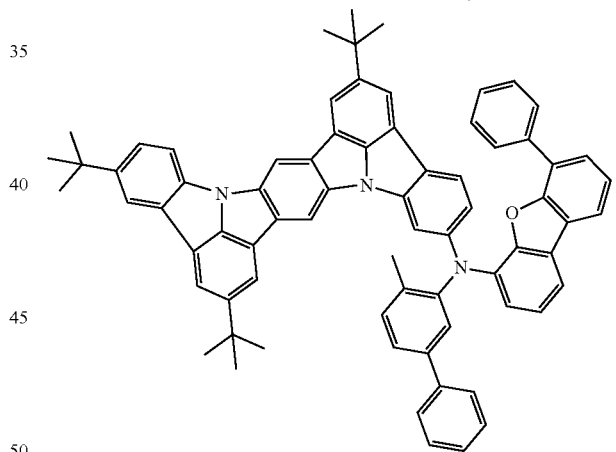
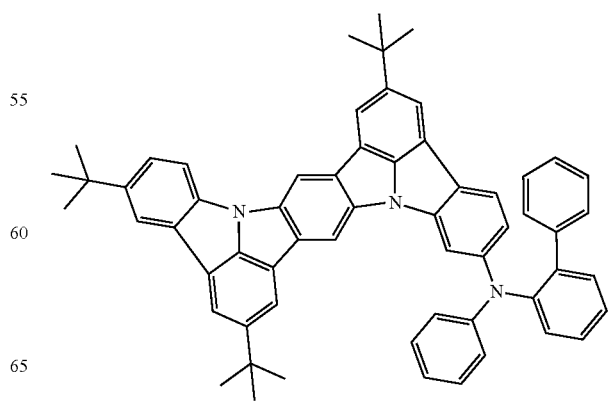

| 669 -continued | 670 -continued |
|---|---|
| 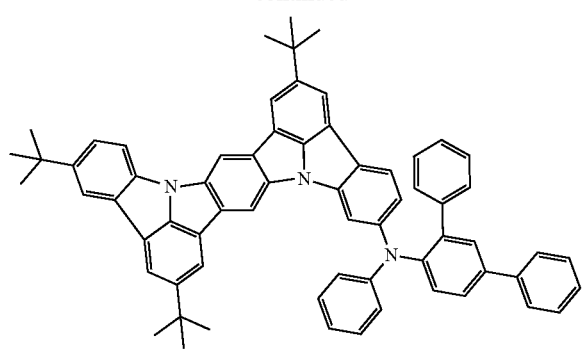 | 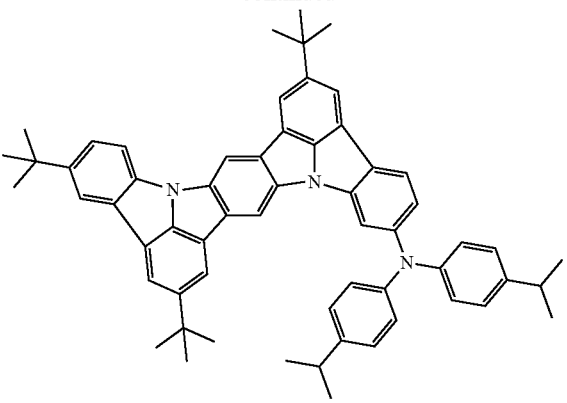 |
| 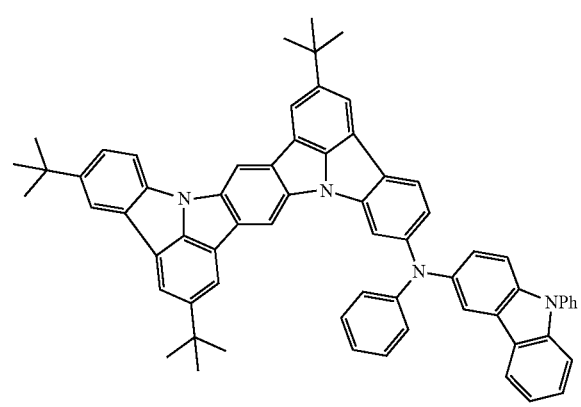 | 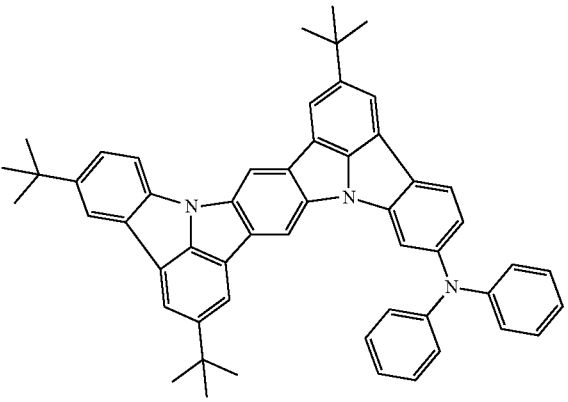 |
| 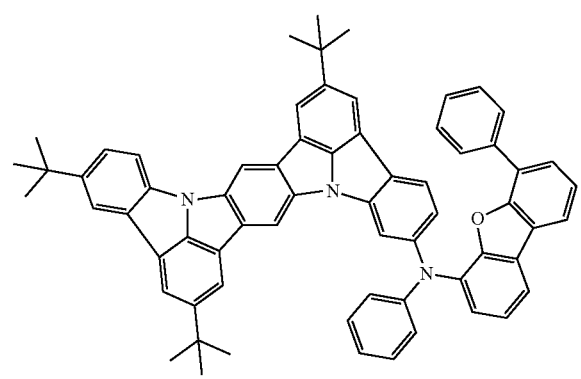 | 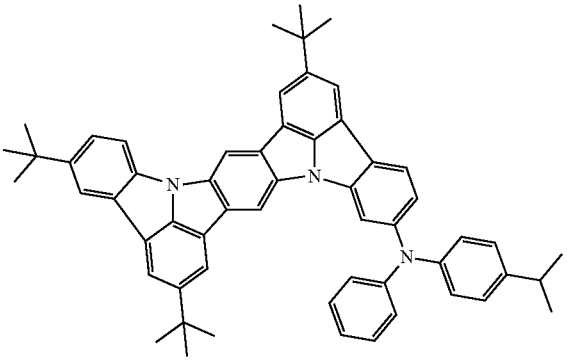 |
| 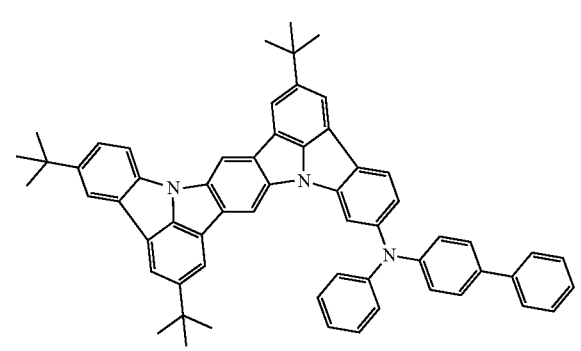 | 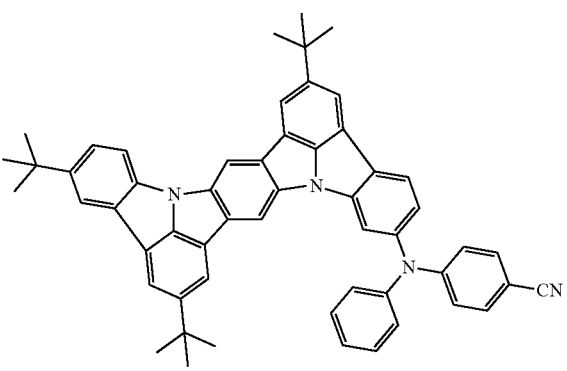 |

671
-continued
672
-continued
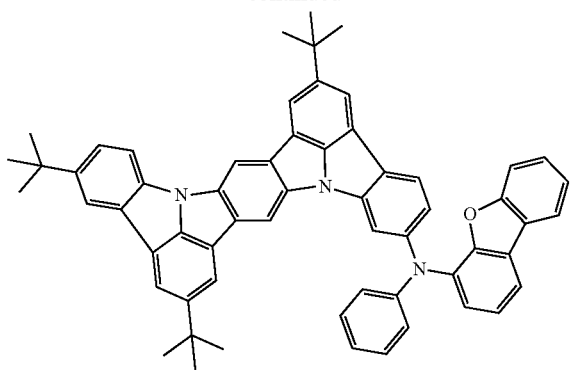
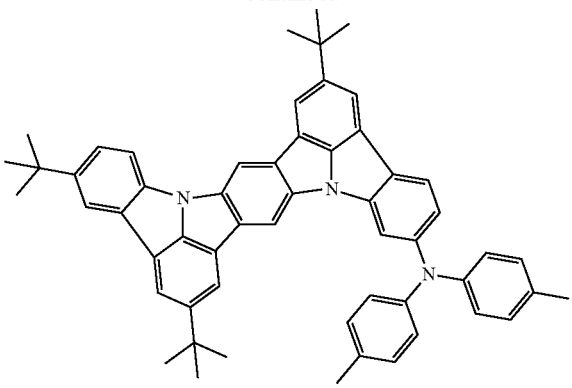

673
-continued
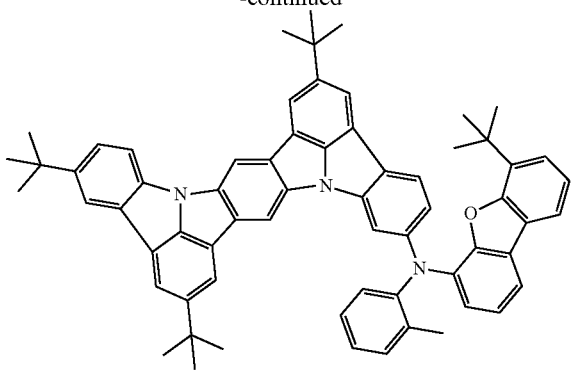
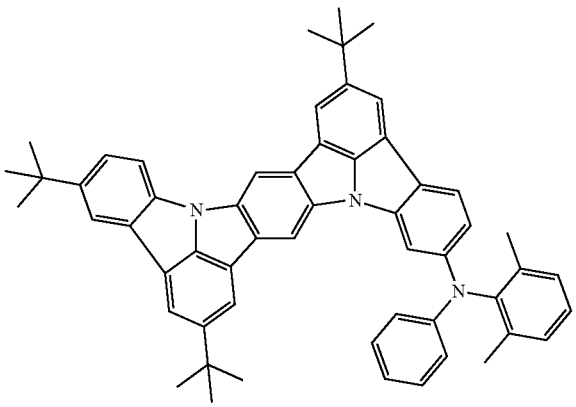
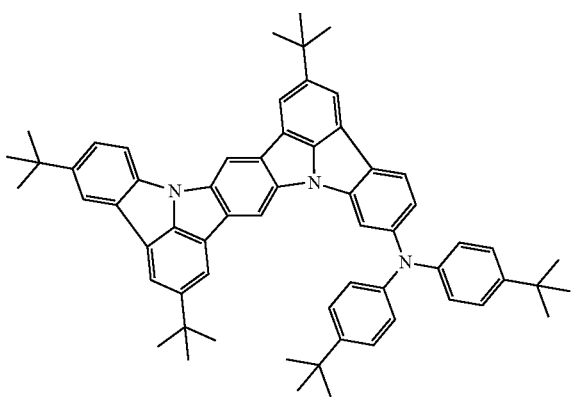
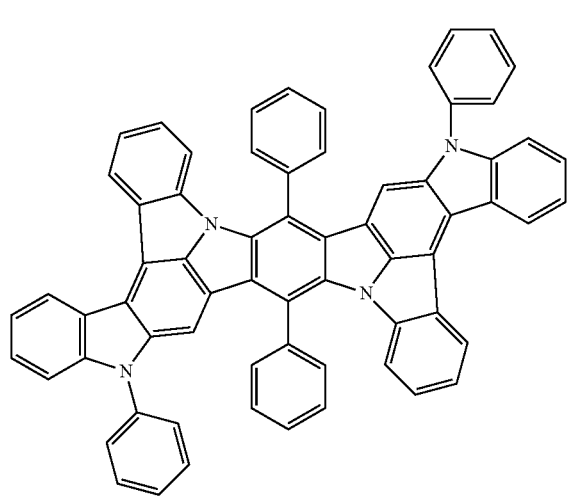
674
-continued
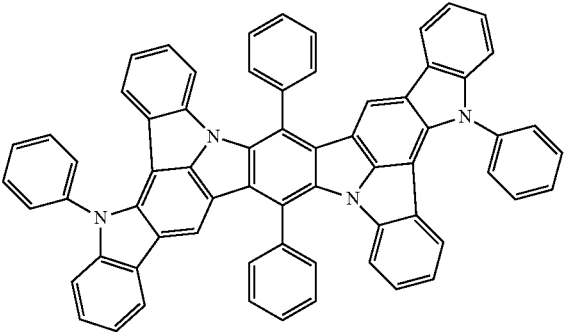
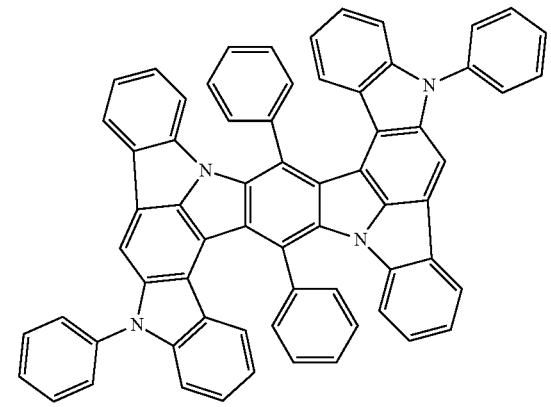
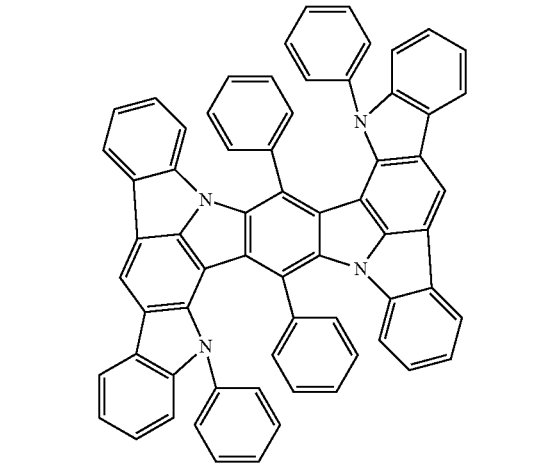
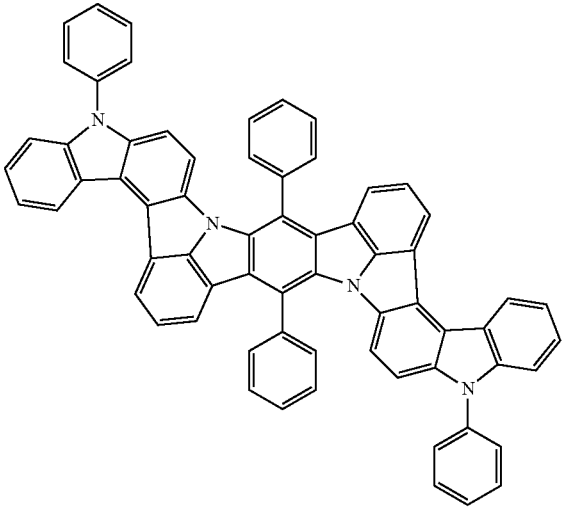

675
-continued
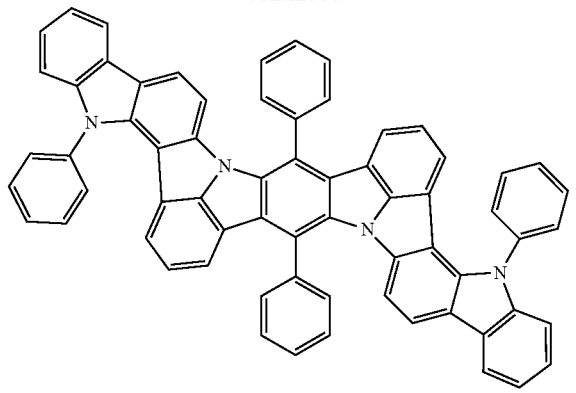
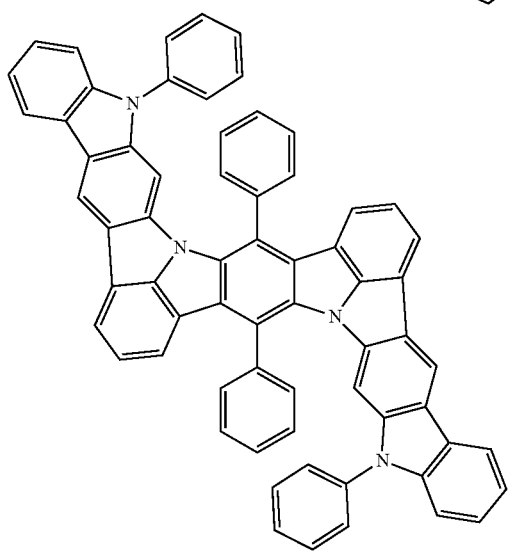

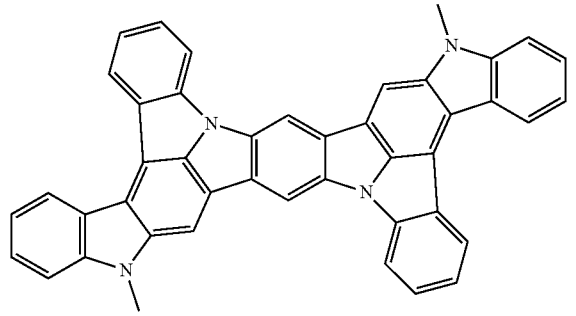
676
-continued
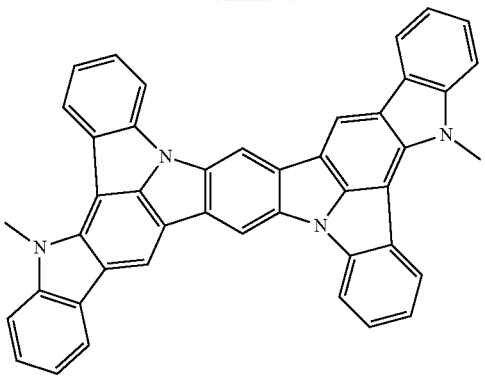
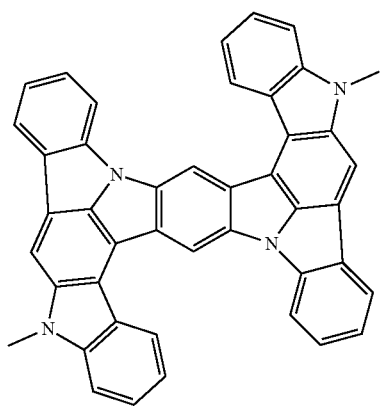
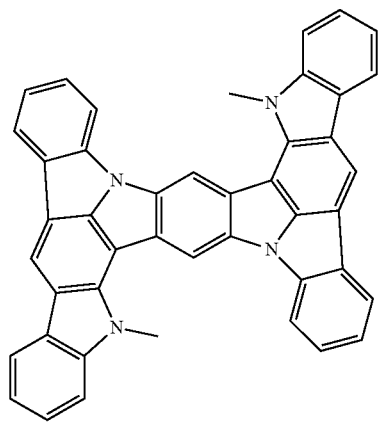
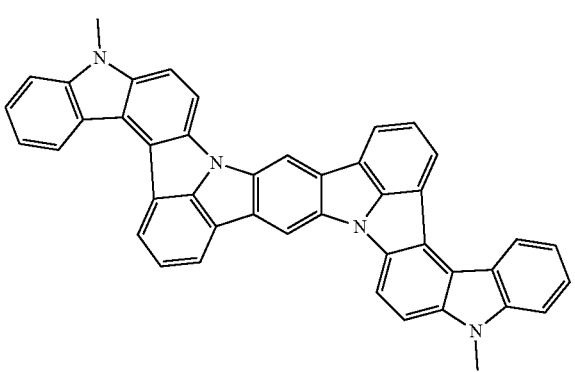

677
-continued
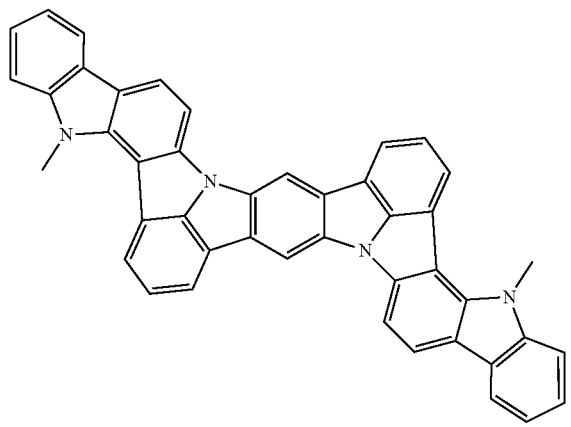
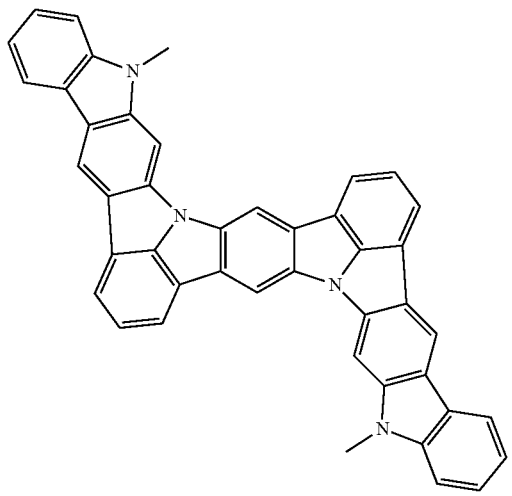
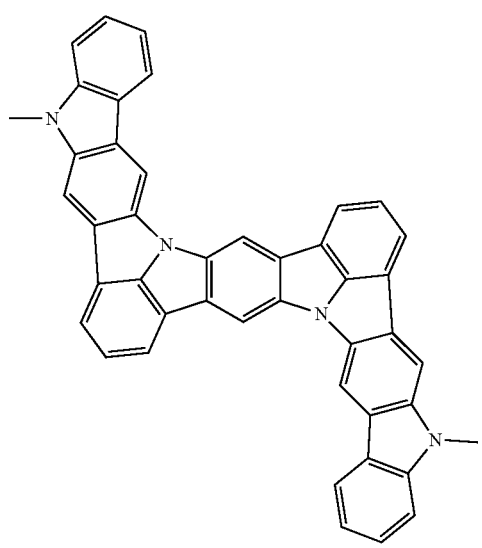
678
-continued
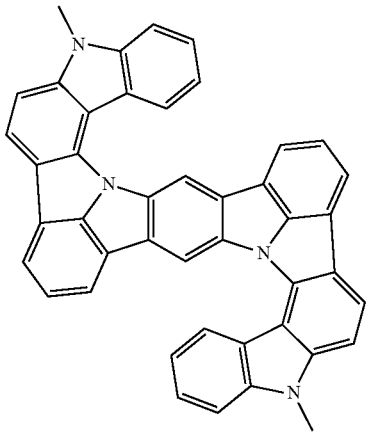
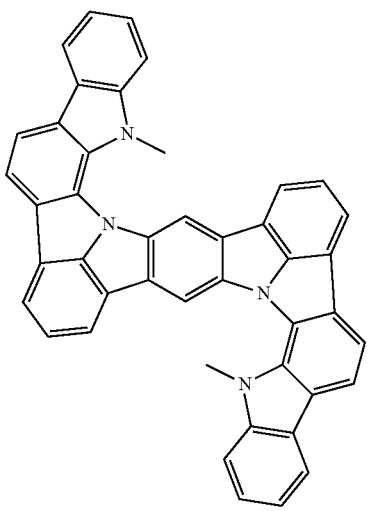
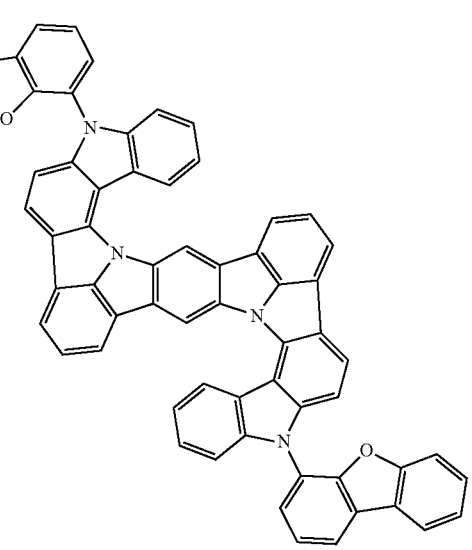

679
-continued
680
-continued
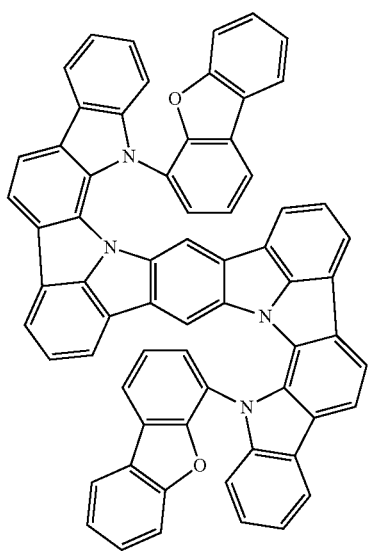
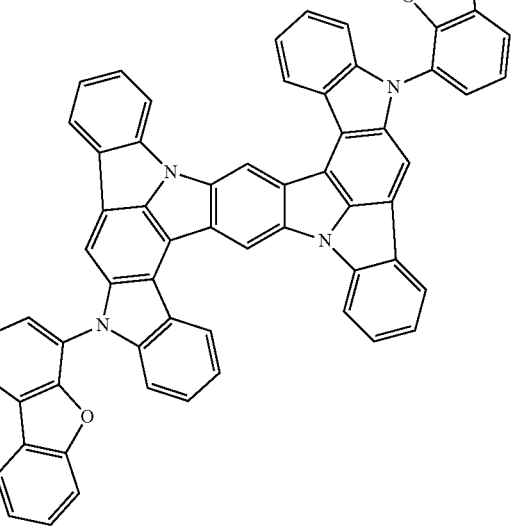
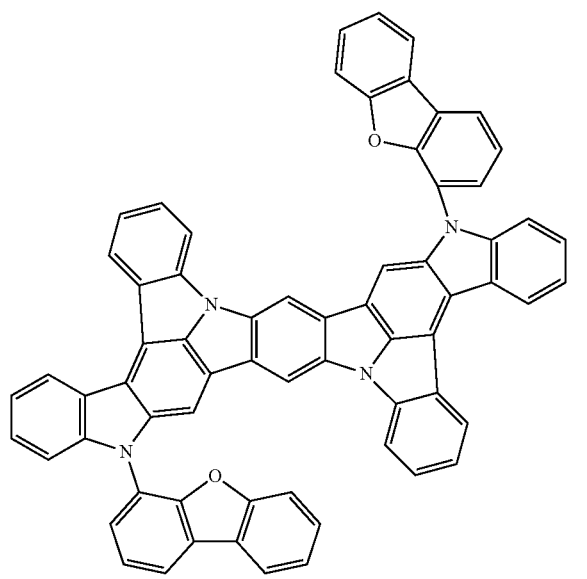
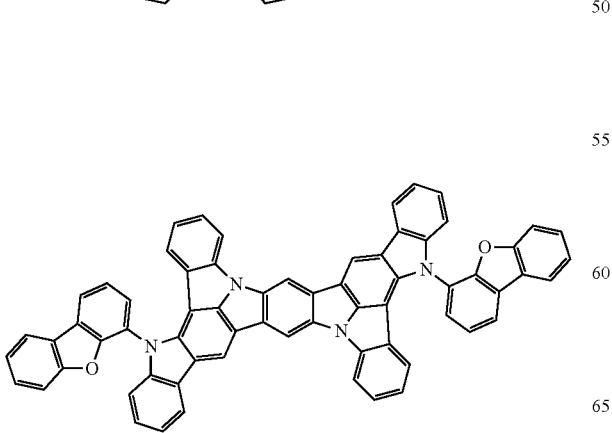

681
-continued
682
-continued
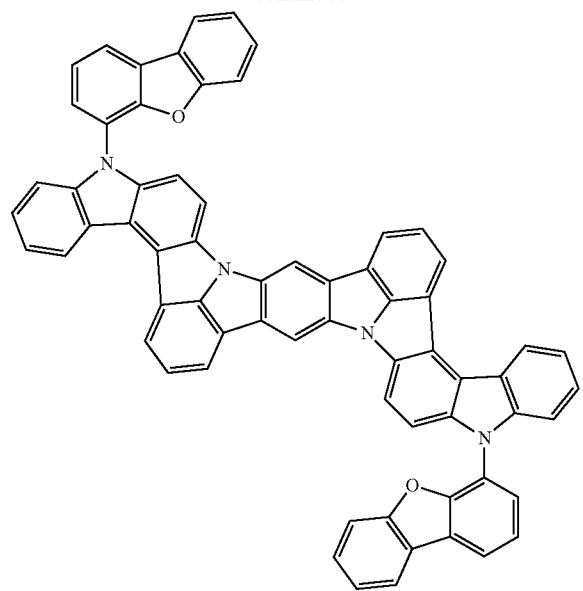
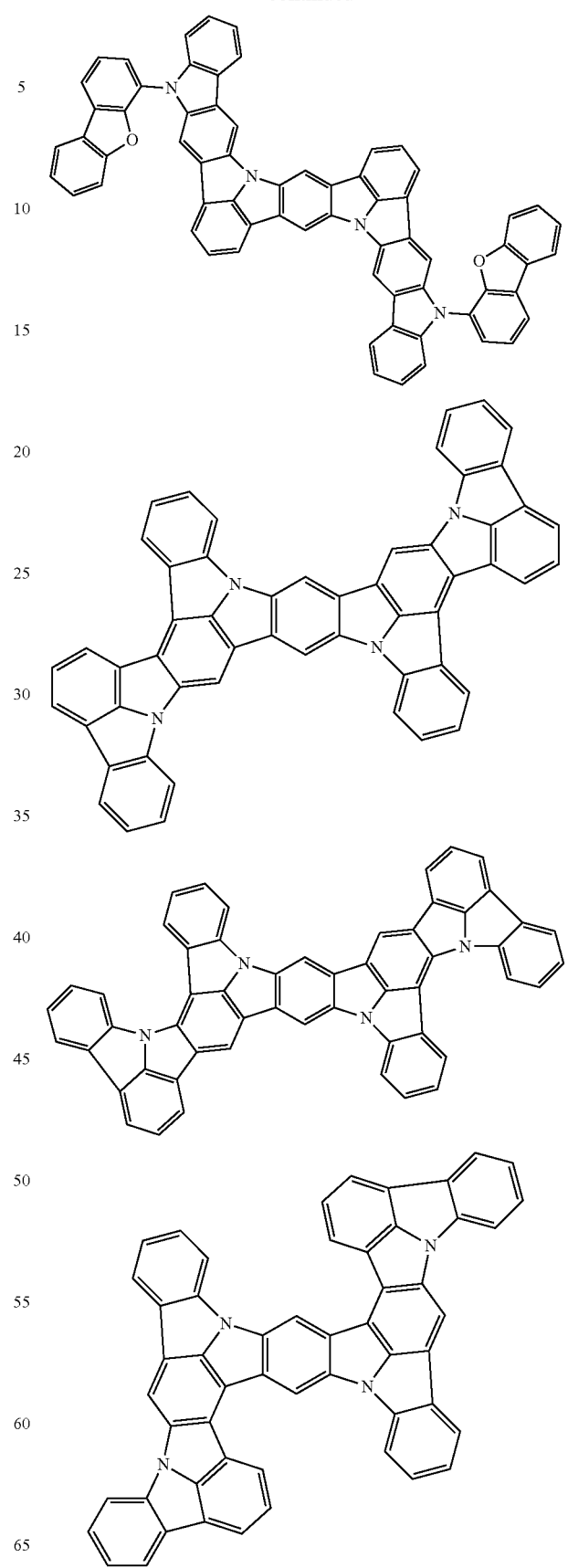

683
-continued
684
-continued
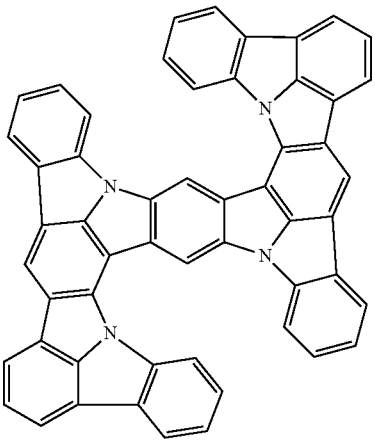
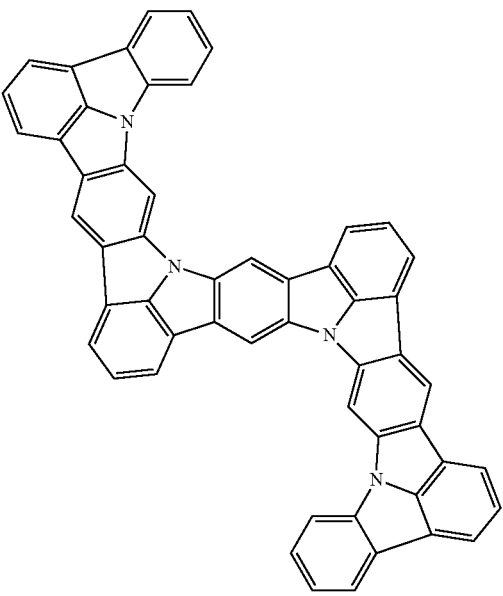
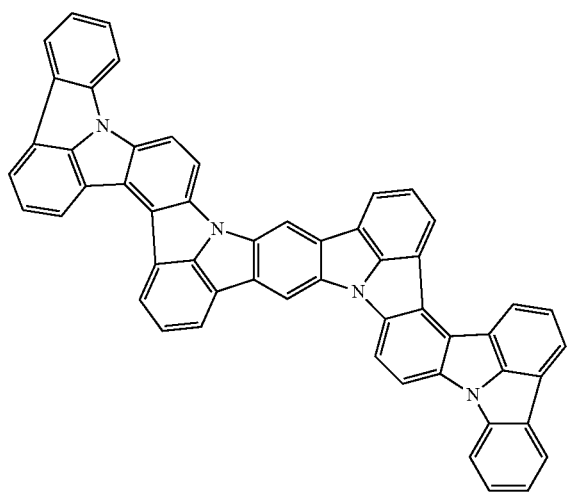
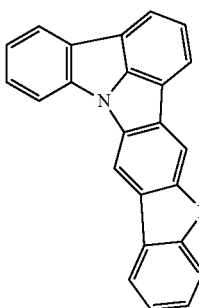
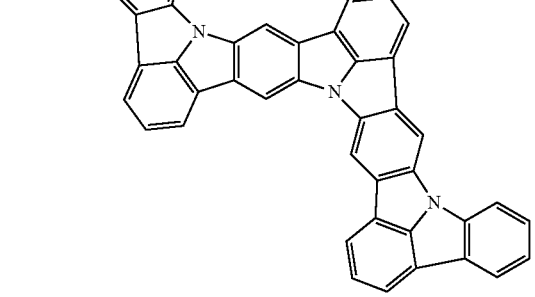
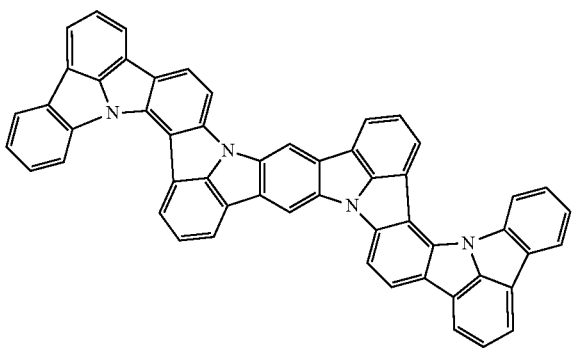
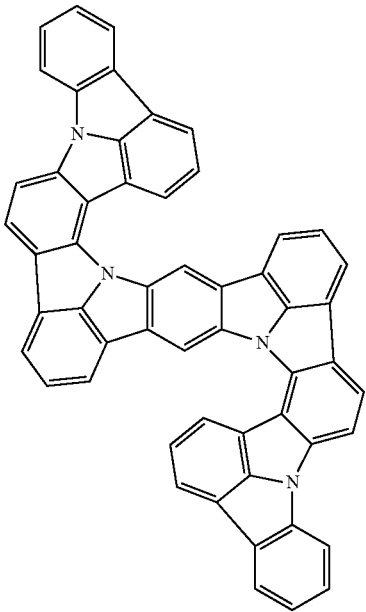

685
-continued
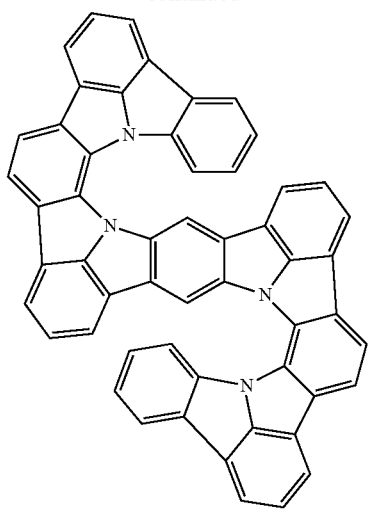
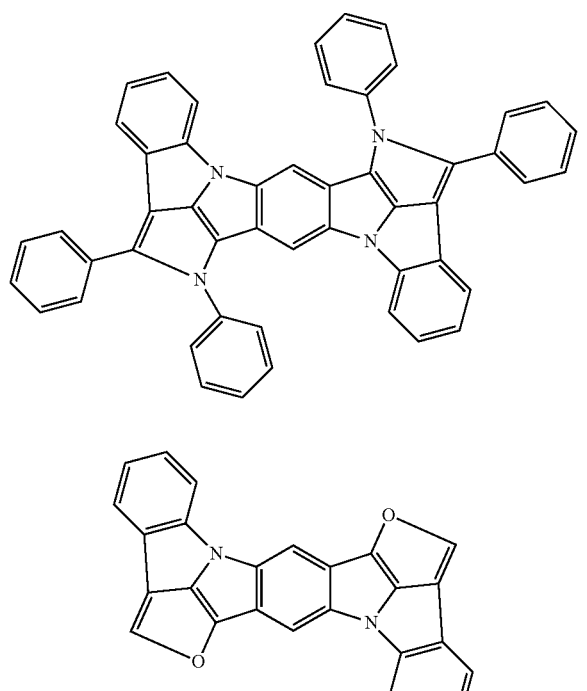
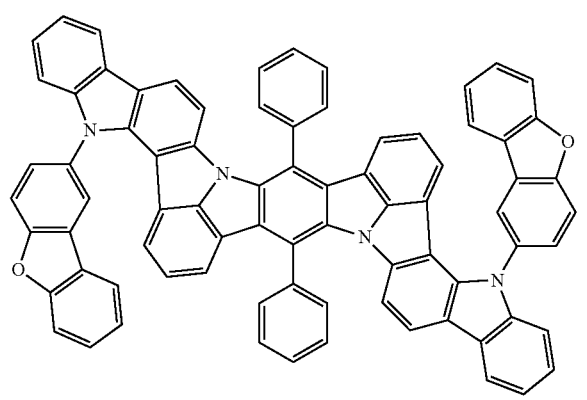
686
-continued
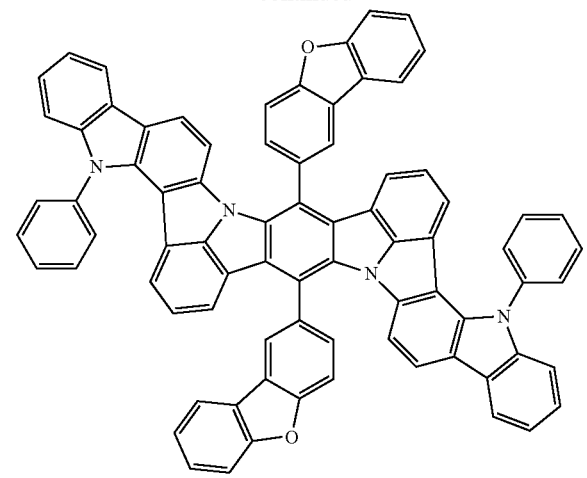
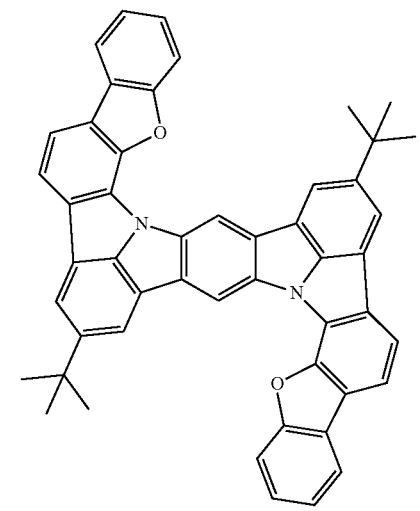
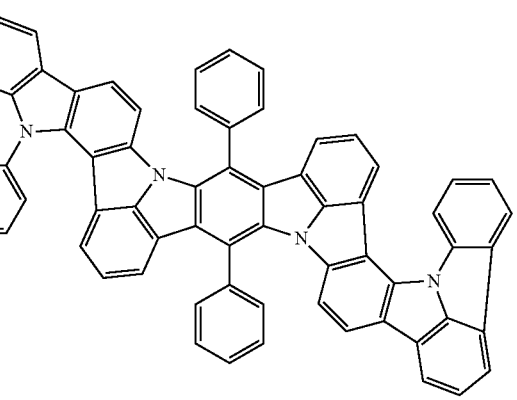

687
-continued
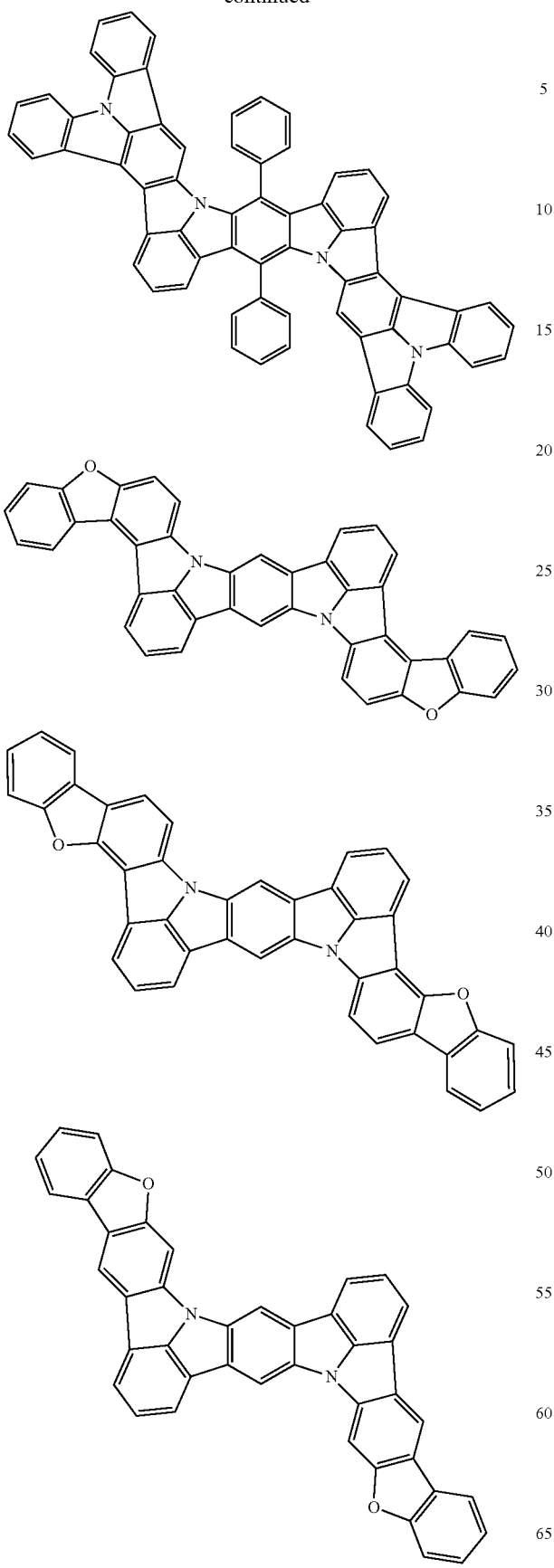
688
-continued
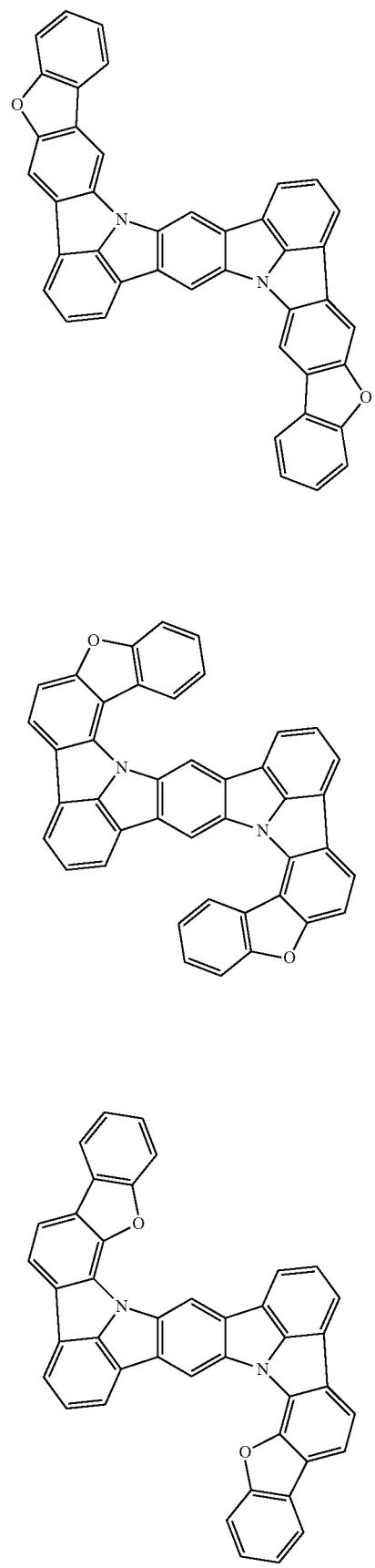

689
-continued
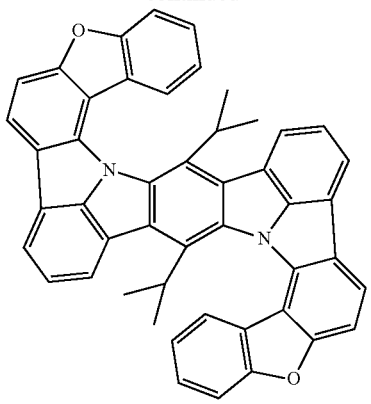
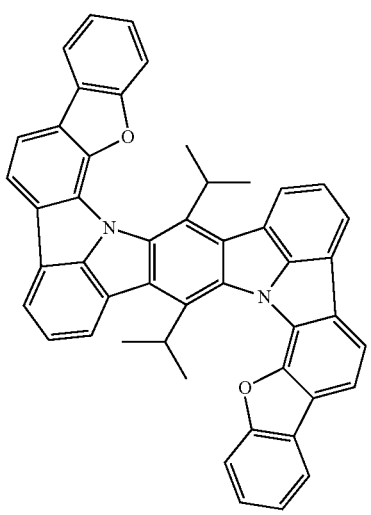
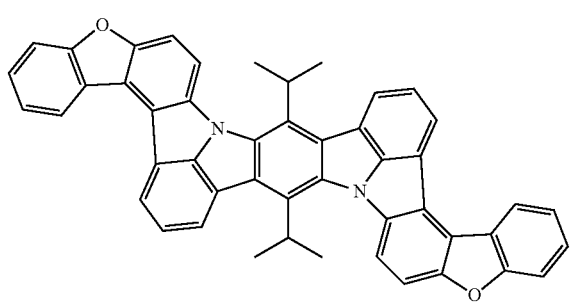
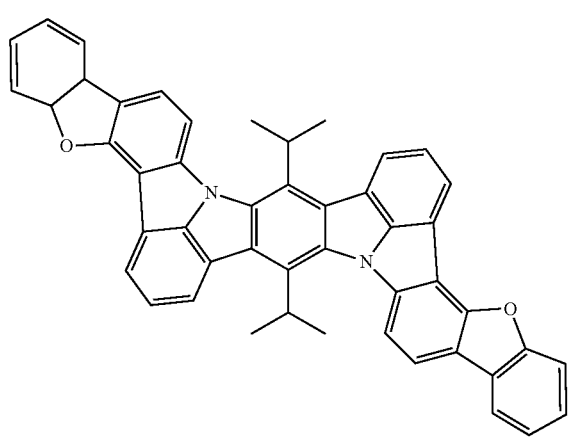
690
-continued
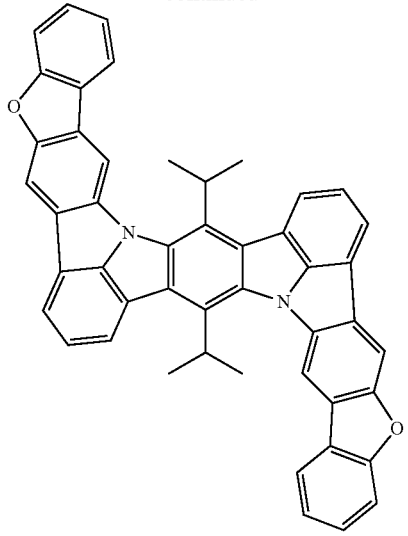
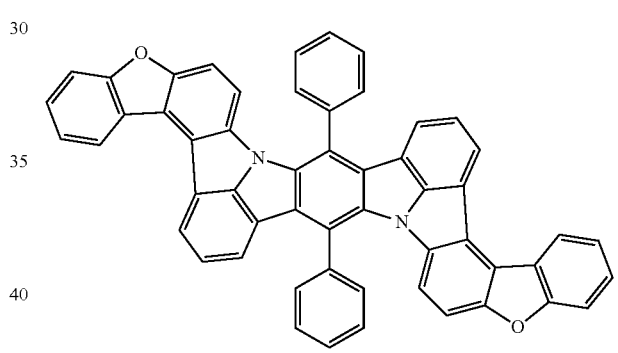
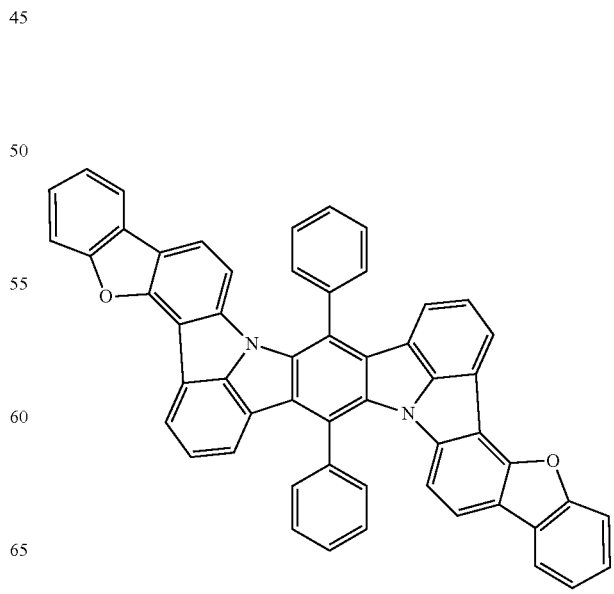

691
-continued
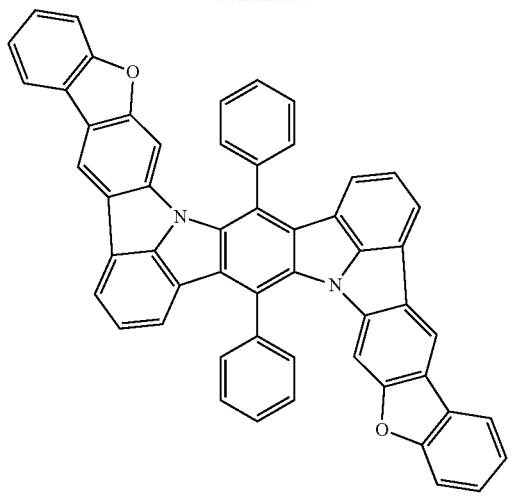
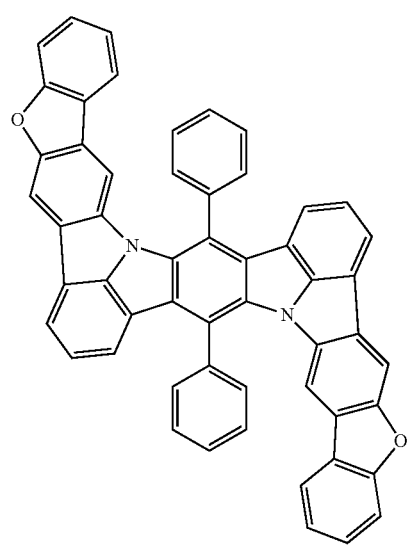
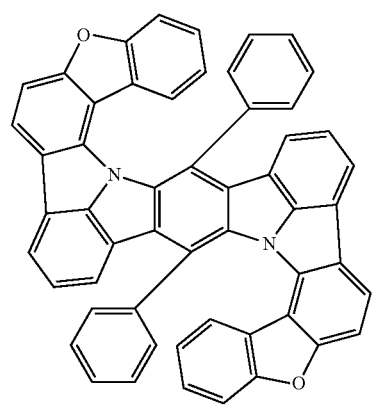
692
-continued
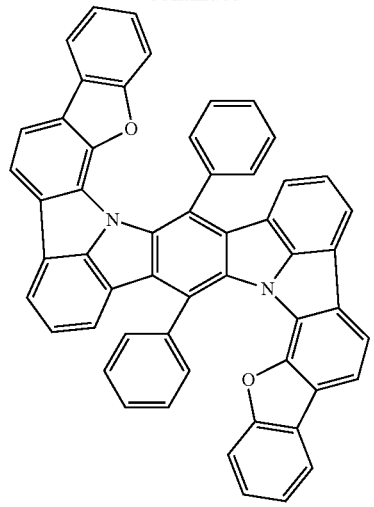
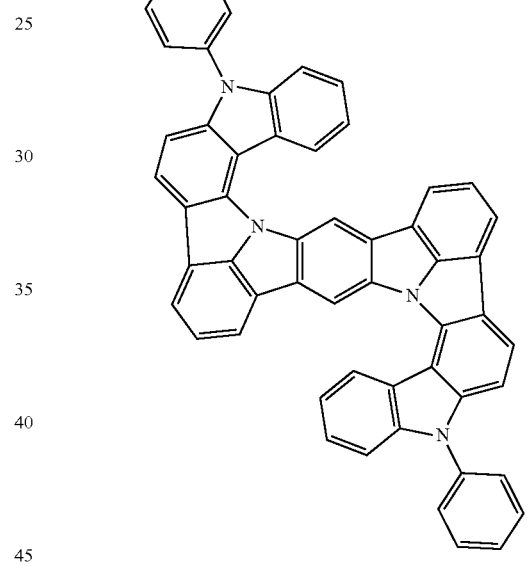
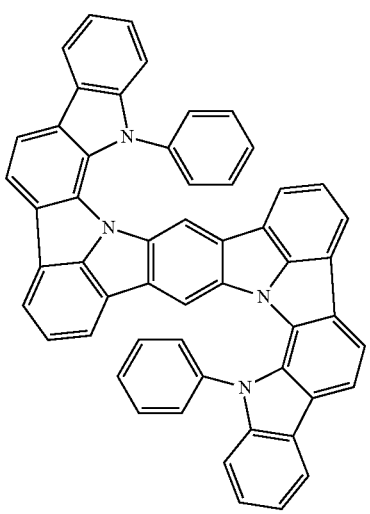

693
-continued
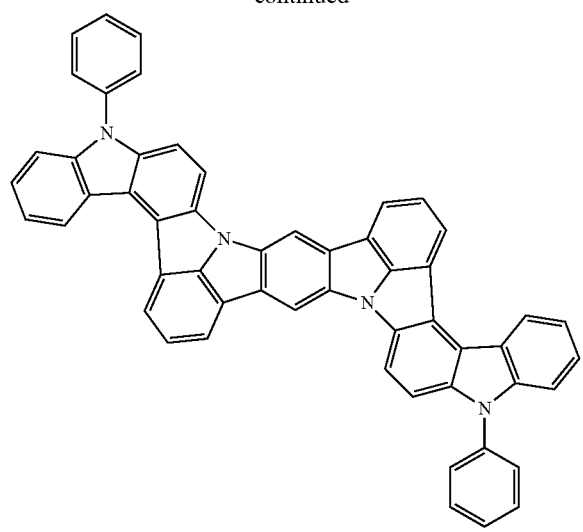
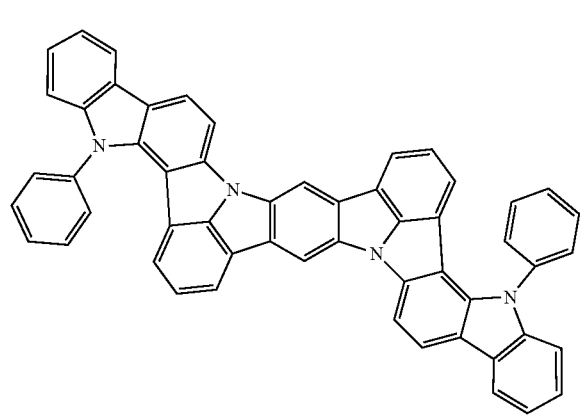
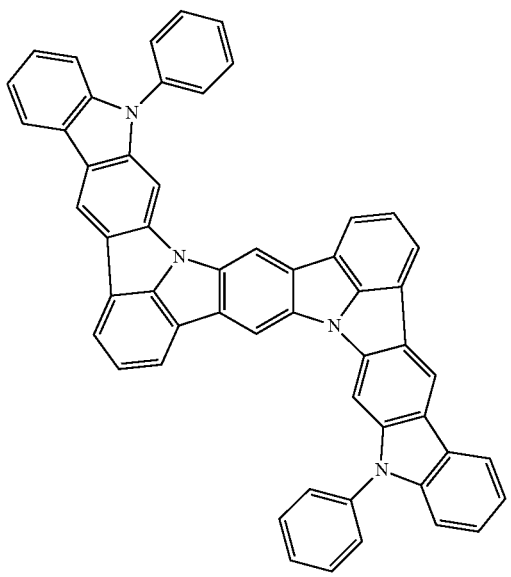
694
-continued
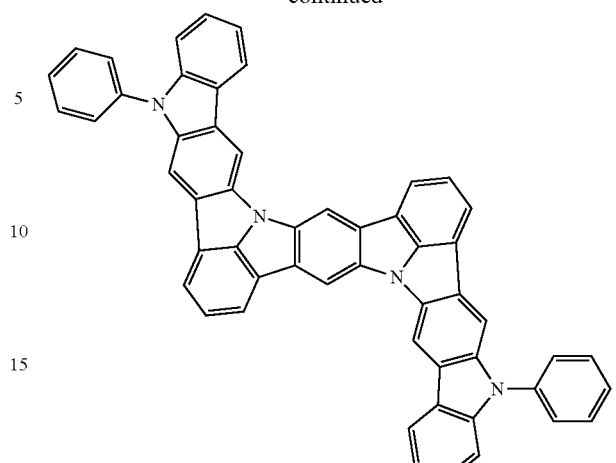
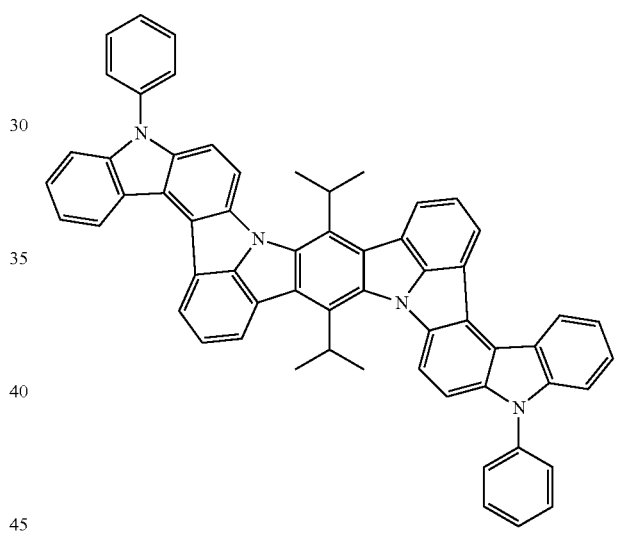
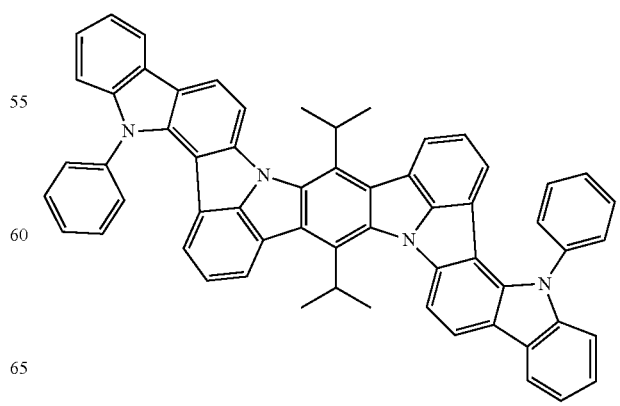

695
-continued
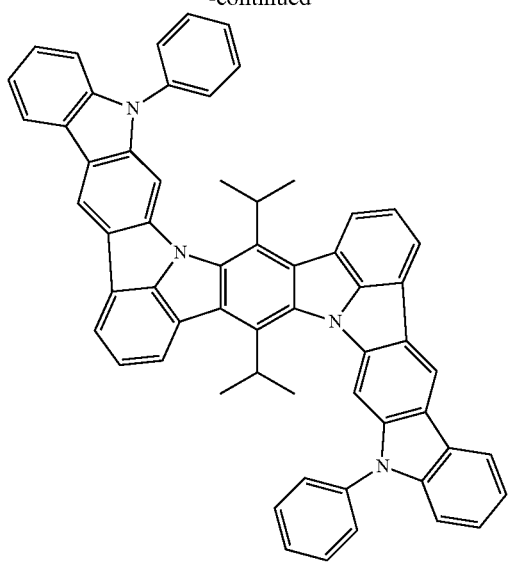
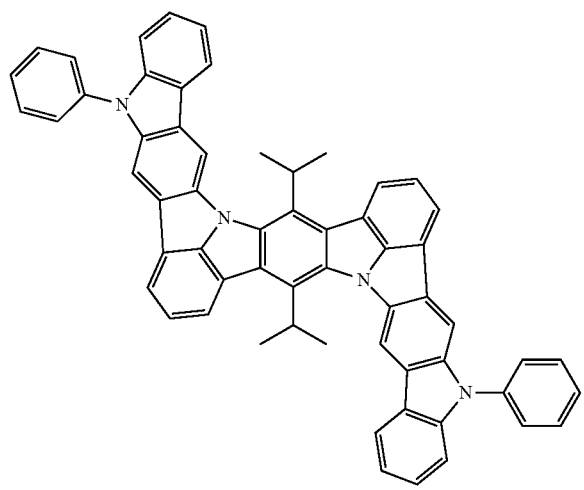
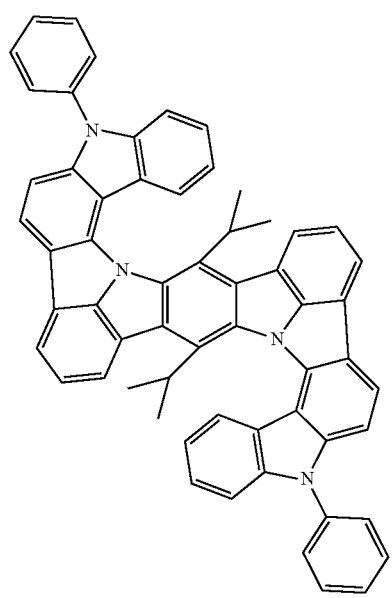
696
-continued
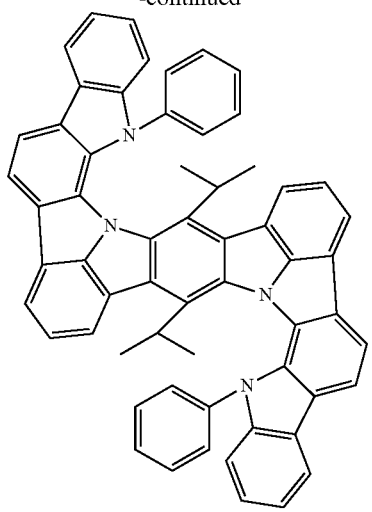
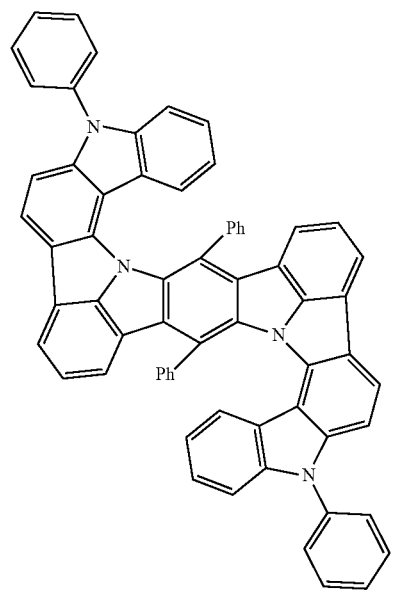
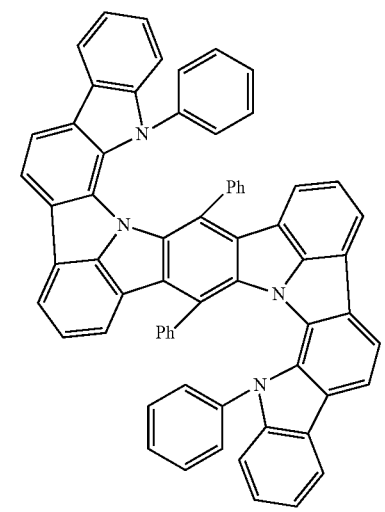 [SMILES: c1ccc(-c2c3c4cccc5c6ccc7c8ccccc8n(-c8ccccc8)c7c6n(c3c(-c3ccccc3)c3c6cccc7c8ccc9c%10ccccc%10n(-c%10ccccc%10)c9c8n(c23)c76)c54)cc1]

697
-continued
698
-continued
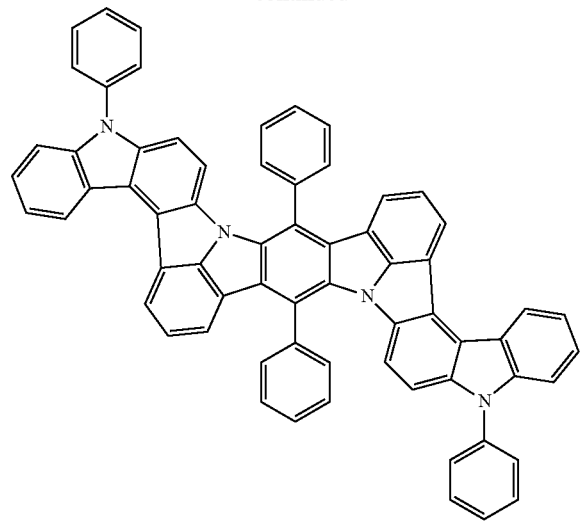
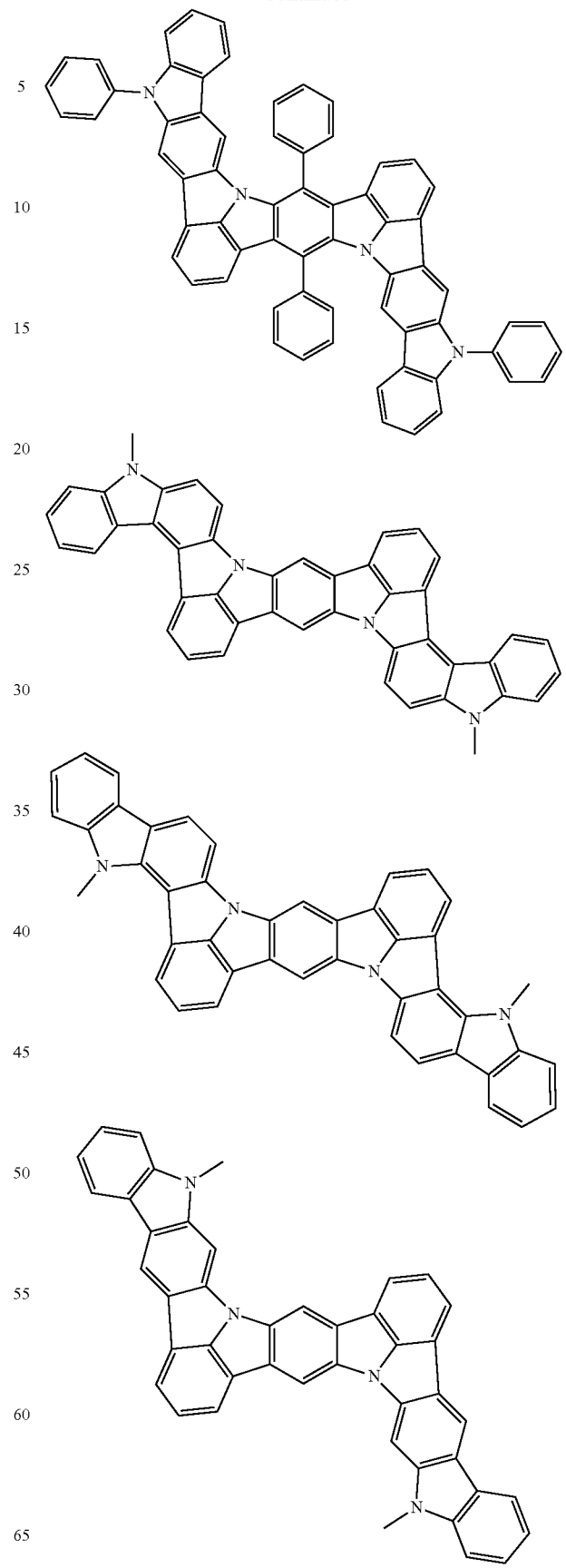

699
-continued
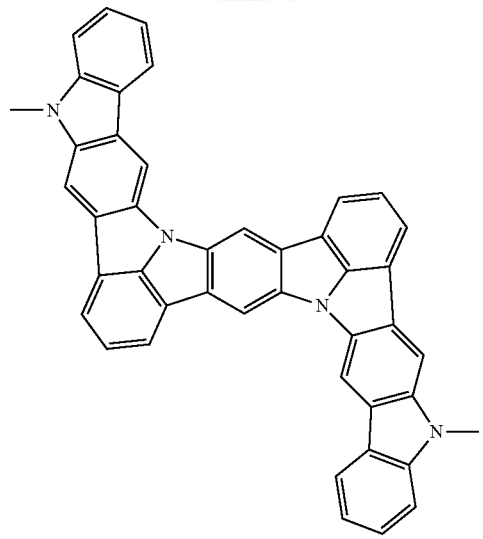
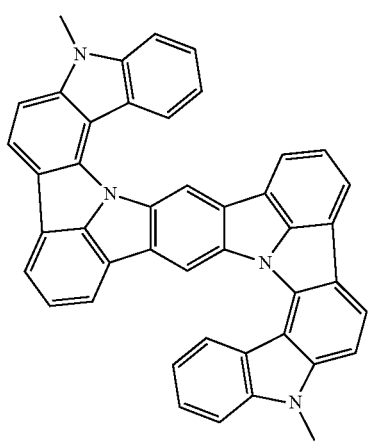
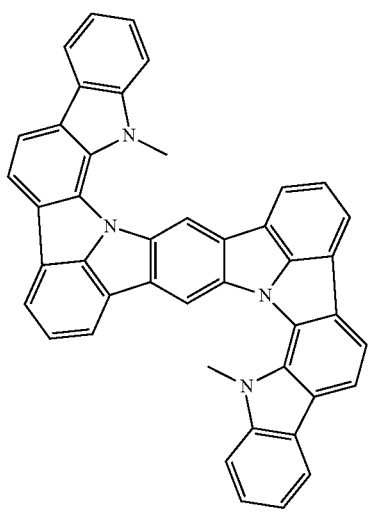
700
-continued
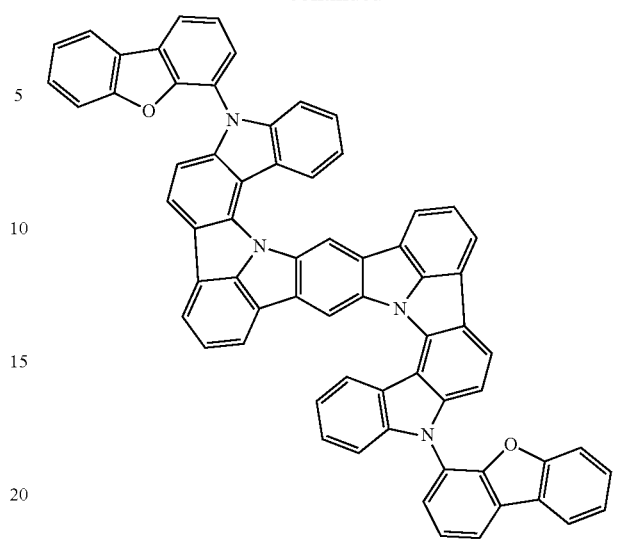
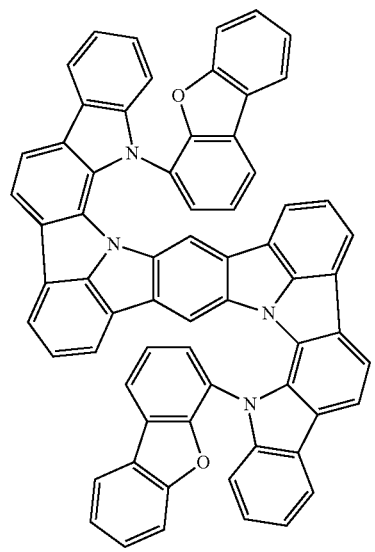
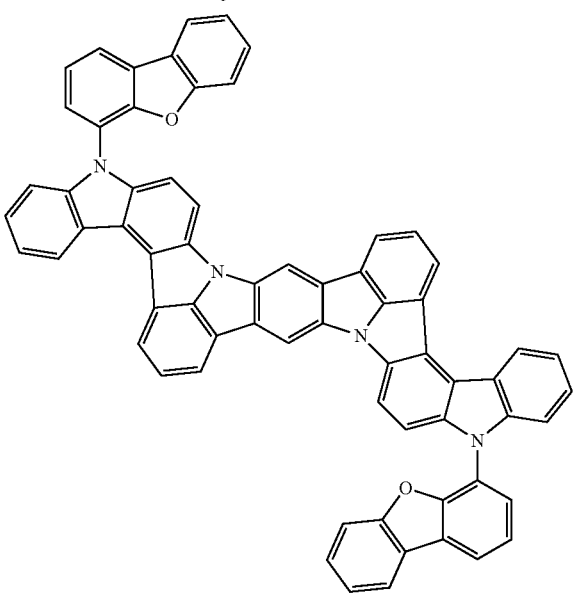

701
-continued
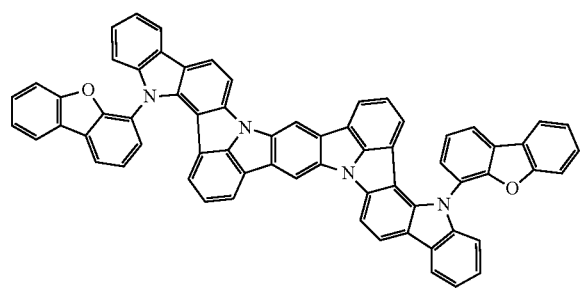
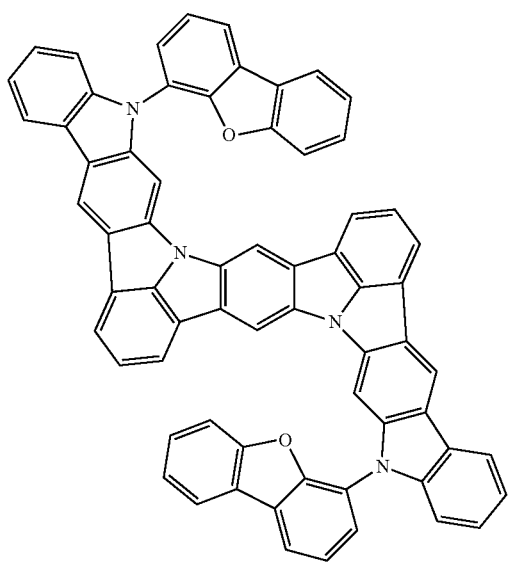
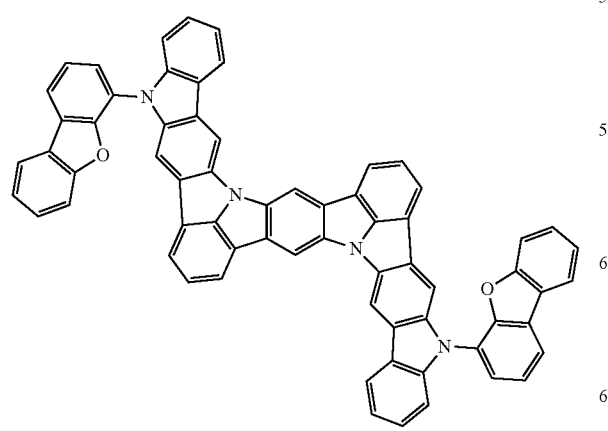
702
-continued
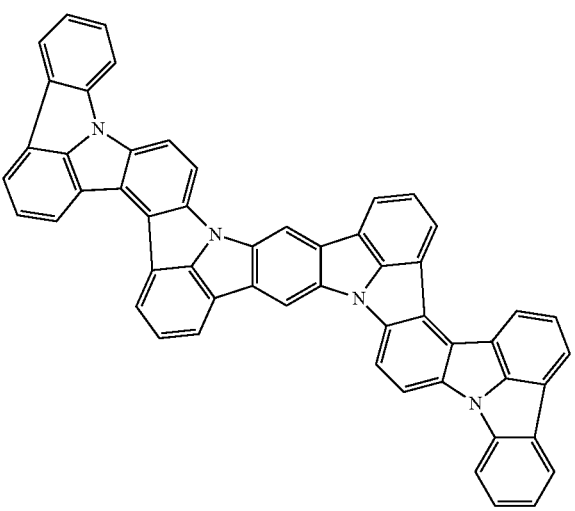
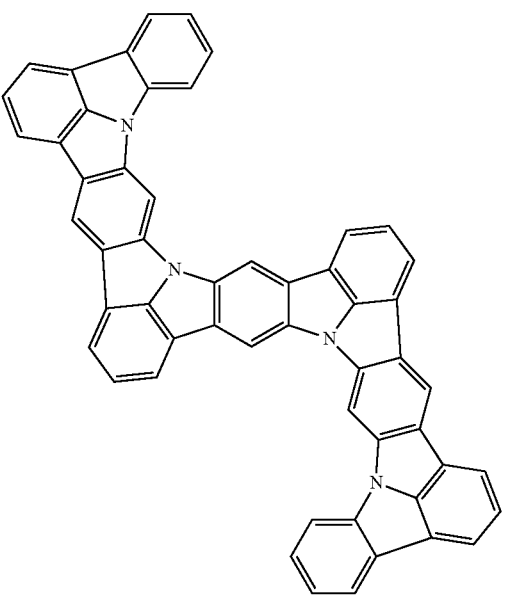

703
-continued
704
-continued
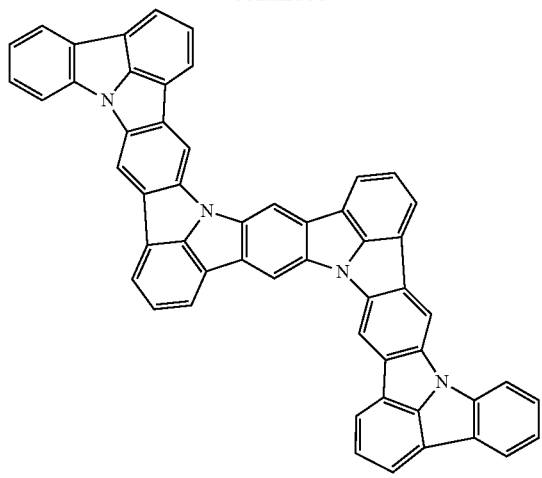
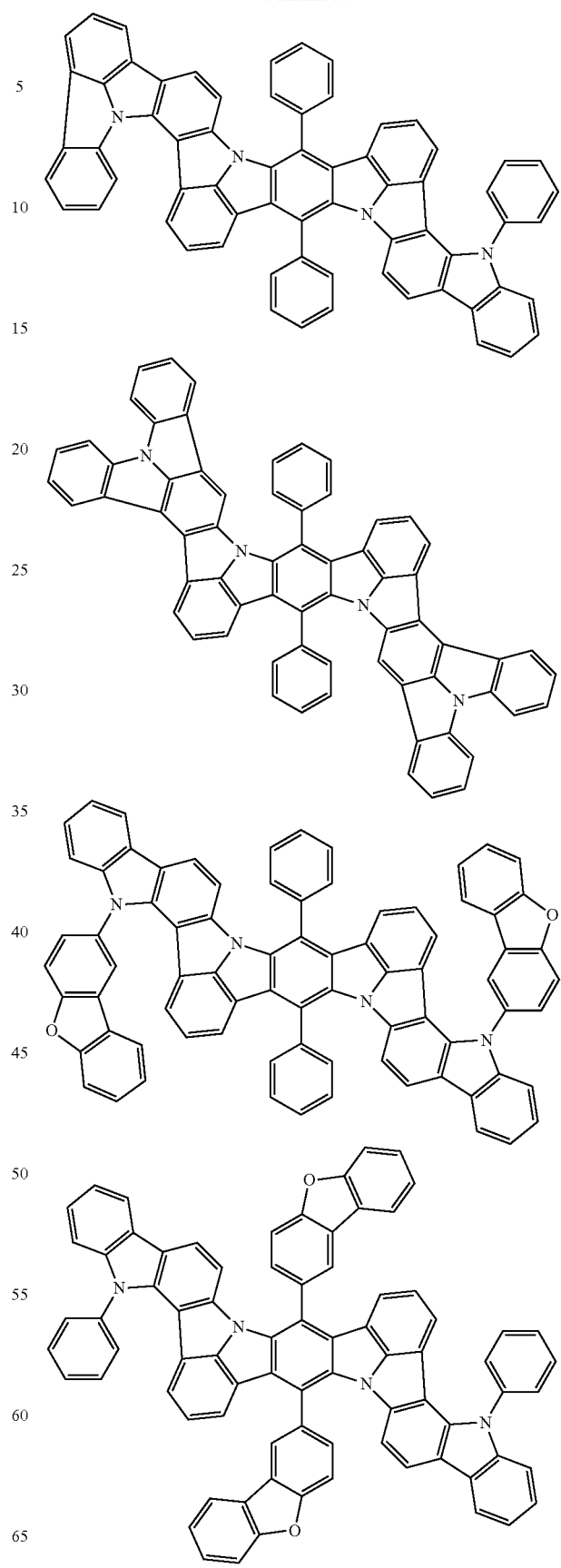

-continued

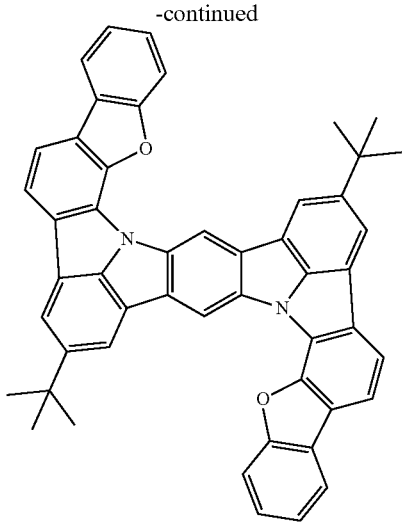

(Compound Represented by Formula (41))

The compound represented by the formula (41) is explained below.

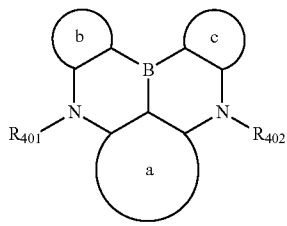

(41)

wherein, in the formula (41), a ring, b ring and c ring are independently a substituted or unsubstituted aromatic hydrocarbon ring having 6 to 50 ring carbon atoms, or a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

The a ring, b ring and c ring are rings (a substituted or unsubstituted aromatic hydrocarbon ring having 6 to 50 ring carbon atoms or a substituted or unsubstituted heterocyclic ring having 5 to 50 ring atoms) fuse to the fused bicyclic structure composed of B atom and two N atoms in the center of the formula (41).

The "aromatic hydrocarbon ring" of the a ring, the b ring and the c ring has the same structure as the compound obtained by introducing a hydrogen atom into the "aryl group" described above. The "aromatic hydrocarbon ring" of the a ring contains three carbon atoms in the fused bicyclic structure in the center of the formula (41) as ring atoms. The "aromatic hydrocarbon ring" of the b ring and the c ring contain two carbon atoms in the fused bicyclic structure in the center of the formula (41) as ring atoms. As examples of "substituted or unsubstituted aromatic hydrocarbon ring having 6 to 50 ring carbon atoms", compounds in which a hydrogen atom is introduced into the "aryl group" described in the group G1 and the like can be given.

The "heterocyclic ring" of the a ring, the b ring and the c ring has the same structure as the compound obtained by introducing a hydrogen atom into the "heterocyclic group" described above. The "heterocyclic ring" of the a ring contains three carbon atoms in the fused bicyclic structure in the center of the formula (41) as ring atoms. The "heterocyclic ring" of the b ring and the c ring contain two carbon atoms in the fused bicyclic structure in the center of the formula (41) as ring atoms. As examples of "substituted or unsubstituted heterocyclic ring having 5 to 50 ring atoms", compounds in which a hydrogen atom is introduced into the "heterocyclic group" described in the group G2.

$R_{401}$ and $R_{402}$ may be independently bonded to the a ring, the b ring or the c ring to form a substituted or unsubstituted heterocyclic ring. This heterocyclic ring contains the nitrogen atom in the fused bicyclic structure in the center of the formula (41). This heterocyclic ring may contain a heteroatom other than the nitrogen atom. "$R_{401}$ and $R_{402}$ are bonded to the a ring, the b ring or the c ring" means, specifically, an atom forming the a ring, the b ring or the c ring is bonded to an atom forming $R_{401}$ and $R_{402}$. For example, it is possible that $R_{401}$ is bonded to the a ring to form a nitrogen-containing heterocyclic ring having a two-ring fused structure (or three or more rings fused structure) in which a ring containing $R_{401}$ and the a ring are fused.

The same applies to the case where $R_{401}$ is bonded to the b ring, $R_{402}$ is bonded to the a ring, and $R_{402}$ is bonded to the c ring.

In one embodiment, the a ring, the b ring and the c ring in the formula (41) are independently a substituted or unsubstituted aromatic hydrocarbon ring having 6 to 50 ring carbon atoms.

In one embodiment, the a ring, the b ring and the c ring in the formula (41) are independently a substituted or unsubstituted benzene ring or a substituted or unsubstituted naphthalene ring.

In one embodiment, $R_{401}$ and $R_{402}$ in the formula (41) are independently a substituted or unsubstituted aryl group having 6 to 50 ring carbon atoms, or a substituted or unsubstituted monovalent heterocyclic group having 5 to 50 ring atoms, and preferably a substituted or unsubstituted aryl group having 6 to 50 ring carbon atoms.

In one embodiment, the compound represented by the formula (41) is a compound represented by the following formula (42).

(42)

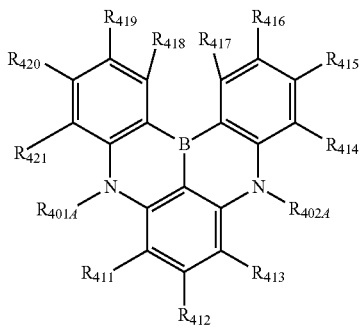

wherein in the formula (42), $R_{401A}$ is bonded with one or more groups selected from $R_{411}$ or $R_{421}$ to form a substituted or unsubstituted heterocyclic ring, or does not form a substituted or unsubstituted heterocyclic ring; $R_{402A}$ is bonded with one or more group selected from $R_{413}$ or $R_{414}$ to form
a substituted or unsubstituted heterocyclic ring, or does not form a substituted or unsubstituted heterocyclic ring;

$R_{401A}$ and $R_{402A}$ that do not form a substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

One or more pairs of two or more adjacent groups of $R_{411}$ to $R_{421}$ are bonded with each other to form a substituted or unsubstituted, saturated or unsaturated ring, or do not form a substituted or unsubstituted, saturated or unsaturated ring;

$R_{411}$ to $R_{421}$ that do not form the substituted or unsubstituted heterocyclic ring or the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

$R_{401A}$ and $R_{402A}$ in the formula (42) correspond to $R_{401}$ and $R_{402}$ in the formula (41).

$R_{401A}$ and $R_{411}$ may be bonded with each other to form a nitrogen-containing heterocyclic ring having two-ring fused structure (or three or more rings fused structure) which is a fused ring of a ring containing $R_{401A}$ and $R_{411}$ and the benzene ring of the a ring, for example. As examples of the nitrogen-containing heterocyclic ring, compounds correspond to nitrogen-containing heterocyclic group having two or more ring fused structure in the group G2 can be given. The same applies to the cases where $R_{401A}$ and $R_{412}$ are bonded, $R_{402A}$ and $R_{413}$ are bonded, and $R_{402A}$ and $R_{414}$ are bonded.

One or more pairs of two or more adjacent groups of $R_{411}$ to $R_{421}$ are bonded with each other to form a substituted or unsubstituted, saturated or unsaturated ring. For example, $R_{411}$ and $R_{412}$ are bonded to form a benzene ring, an indole ring, a pyrrole ring, a benzofuran ring, a benzothiophene ring or the like which fuses to the six-membered ring to which $R_{411}$ and $R_{412}$ bond, and the formed fused ring is a naphthalene ring, a carbazole ring, an indole ring, a dibenzofuran ring or a dibenzothiophene ring.

In one embodiment, $R_{411}$ to $R_{421}$ that do not contribute to form a ring are independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom or a substituted or unsubstituted alkyl group having 1 to 50 carbon atoms.

In one embodiment, $R_{411}$ to $R_{421}$ that do not contribute to form a ring are independently a hydrogen atom, a substituted or unsubstituted alkyl group having 1 to 50 carbon atoms, and at least one of $R_{411}$ to $R_{421}$ is a substituted or unsubstituted alkyl group having 1 to 50 carbon atoms.

In one embodiment, the compound represented by the formula (42) is a compound represented by the following formula (43).

(43)

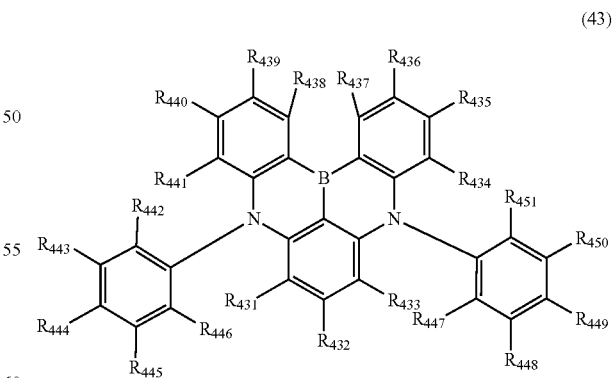

wherein in the formula (43),
$R_{431}$ is bonded with $R_{446}$ to form a substituted or unsubstituted heterocyclic ring, or does not form a substituted or unsubstituted heterocyclic ring; $R_{433}$ is bonded with $R_{447}$ to form a substituted or unsubstituted heterocyclic ring, or does not form a substituted or unsubstituted heterocyclic ring;

$R_{434}$ is bonded with $R_{451}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring;

One or more pairs of two or more adjacent groups of $R_{431}$ to $R_{451}$ are bonded with each other to form a substituted or unsubstituted, saturated or unsaturated ring, or do not form a substituted or unsubstituted, saturated or unsaturated ring;

$R_{431}$ to $R_{451}$ that do not form a substituted or unsubstituted heterocyclic ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

$R_{431}$ may bond to $R_{446}$ to form a substituted or unsubstituted heterocyclic ring. For example, $R_{431}$ may bonds with $R_{446}$ to form a nitrogen-containing heterocyclic ring with three or more fused rings of the benzene ring to which $R_{46}$ bond, a nitrogen-containing ring and the benzene ring of the a ring. As examples of the nitrogen-containing heterocyclic ring, compounds correspond to nitrogen-containing heterocyclic group having three or more ring fused structure in the group G2 can be given. The same applies to the cases where $R_{433}$ and $R_{447}$ are bonded, $R_{434}$ and $R_{451}$ are bonded, and $R_{441}$ and $R_{442}$ are bonded.

In one embodiment, $R_{431}$ to $R_{451}$ that do not contribute to form a ring are independently, a hydrogen atom, a substituted or unsubstituted alkyl group having 1 to 50 carbon atoms, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently, a hydrogen atom, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently a hydrogen atom or a substituted or unsubstituted alkyl group having 1 to 50 carbon atoms.

In one embodiment, $R_{431}$ to $R_{451}$ that do not contribute to form a ring are independently a hydrogen atom, a substituted or unsubstituted alkyl group having 1 to 50 carbon atoms, and at least one of $R_{431}$ to $R_{451}$ is a substituted or unsubstituted alkyl group having 1 to 50 carbon atoms.

In one embodiment, the compound represented by the formula (43) is a compound represented by the following formula (43A).

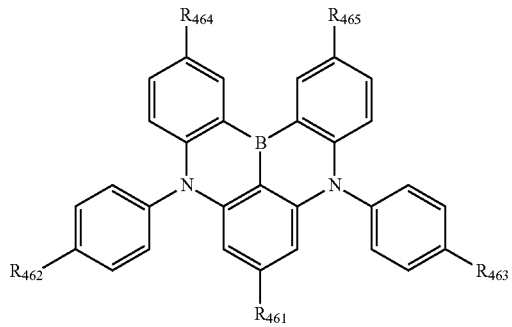

(43A)

wherein in the formula (43A),
$R_{461}$ is
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms; and
$R_{462}$ to $R_{465}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms.

In one embodiment, $R_{461}$ to $R_{465}$ are independently a substituted or unsubstituted alkyl group having 1 to 50 carbon atoms or a substituted or unsubstituted aryl group having 6 to 50 ring carbon atoms.

In one embodiment, $R_{461}$ and $R_{465}$ are independently a substituted or unsubstituted alkyl group having 1 to 50 carbon atoms.

In one embodiment, the compound represented by the formula (43) is a compound represented by the following formula (43B).

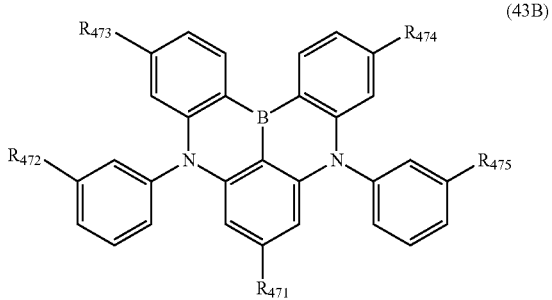

(43B)

wherein in the formula (43B),
$R_{471}$ and $R_{472}$ are independently,
a hydrogen atom,
a substituted or unsubstituted alkyl group having 1 to 50 carbon atoms, a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$) ($R_{907}$), or
a substituted or unsubstituted aryl group having 6 to 50 ring carbon atoms;

$R_{473}$ to $R_{475}$ are independently,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$) ($R_{907}$), or
a substituted or unsubstituted aryl group having 6 to 50 ring carbon atoms; and
$R_{906}$ and $R_{907}$ are as defined in the formula (1).

In one embodiment, the compound represented by the formula (43) is the compound represented by the following formula (43B').

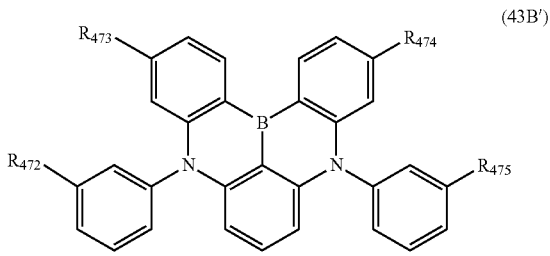

(43B')

wherein in the formula (43B'), $R_{472}$ to $R_{475}$ are as defined in the formula (43B).

In one embodiment, at least one of $R_{471}$ to $R_{475}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$) ($R_{907}$), or
a substituted or unsubstituted aryl group having 6 to 50 ring carbon atoms.

In one embodiment,
$R_{472}$ is
a hydrogen atom,
a substituted or unsubstituted alkyl group having 1 to 50 carbon atoms,
—N($R_{906}$) ($R_{907}$), or
a substituted or unsubstituted aryl group having 6 to 50 ring carbon atoms; and
$R_{471}$ and $R_{473}$ to $R_{475}$ are independently
a substituted or unsubstituted alkyl group having 1 to 50 carbon atoms,
—N($R_{906}$) ($R_{907}$), or
a substituted or unsubstituted aryl group having 6 to 50 ring carbon atoms.

In one embodiment, the compound represented by the formula (43) is a compound represented by the formula (43C).

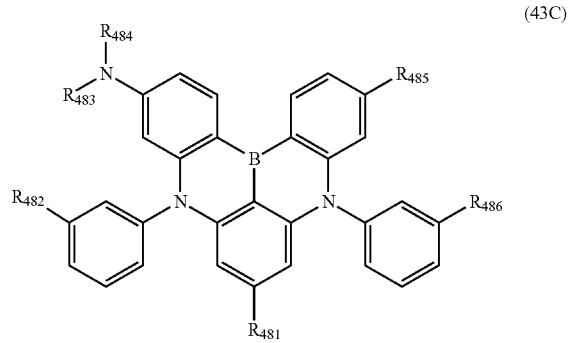

(43C)

wherein in the formula (43C),
$R_{481}$ and $R_{482}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms; and
$R_{483}$ to $R_{486}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms.

In one embodiment, the compound represented by the formula (43) is the compound represented by the following formula (43C').

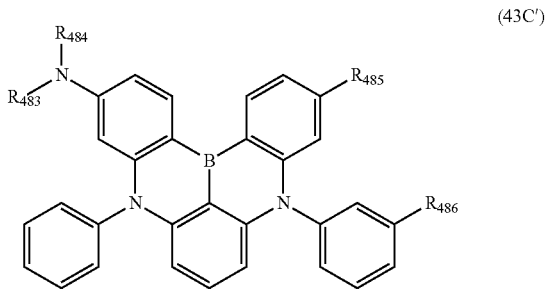

(43C')

wherein in the formula (43C'), $R_{483}$ to $R_{486}$ are as defined in the formula (43C).

In one embodiment, $R_{481}$ to $R_{486}$ are independently a substituted or unsubstituted alkyl group having 1 to 50 carbon atoms or a substituted or unsubstituted aryl group having 6 to 50 ring carbon atoms.

In one embodiment, $R_{481}$ to $R_{486}$ are independently a substituted or unsubstituted aryl group having 6 to 50 ring carbon atoms.

The compound represented by the formula (41) can be synthesized by the following method: An intermediate is obtained by bonding the a ring, the b ring and the c ring with linking groups (a group containing N—$R_1$ and a group containing N—$R_2$) (first reaction), and a final compound is obtained by bonding the a ring, the b ring and the c ring with a linking group (a group containing B) (second reaction). In the first reaction, an amination reaction such as Buchwald-Hartwig reaction can be applied. In the second reaction, tandem hetero-Friedel-Crafts reaction or the like can be applied.

Examples of the compound represented by the formula (41) are described below. They are just exemplified compounds and the compound represented by the formula (41) is not limited to the following examples.

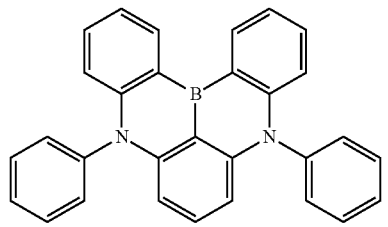

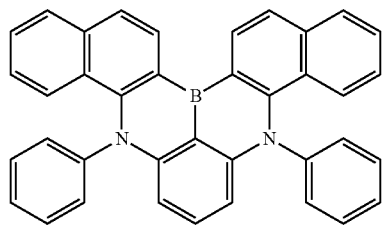

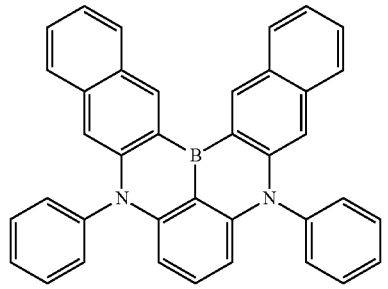

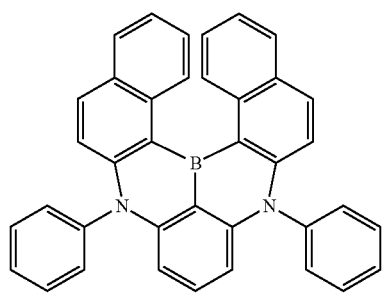

-continued

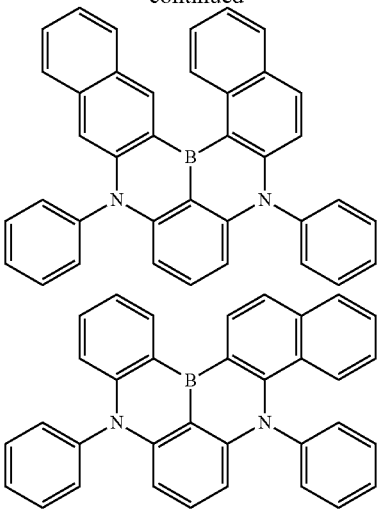

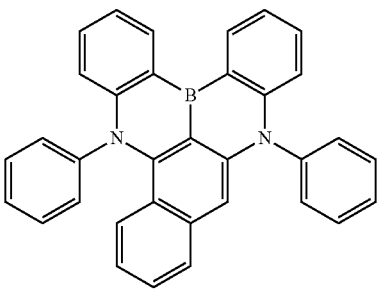

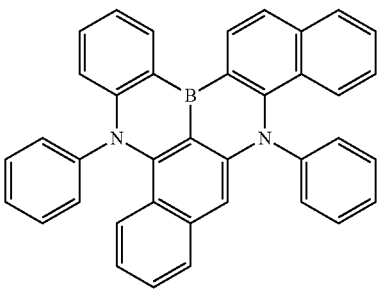

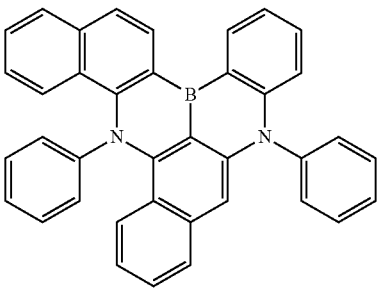

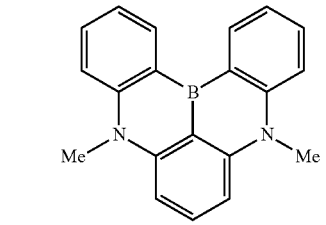

715
-continued
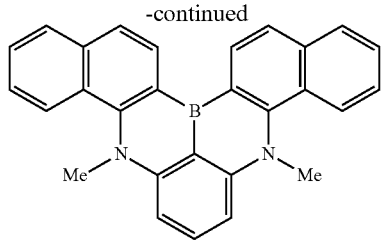
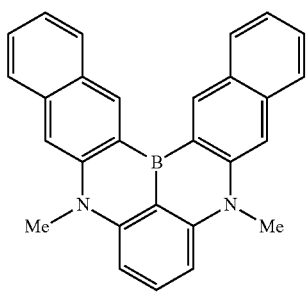
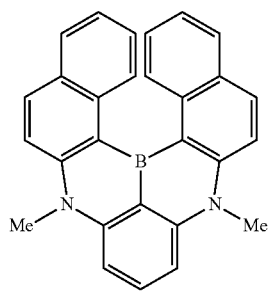
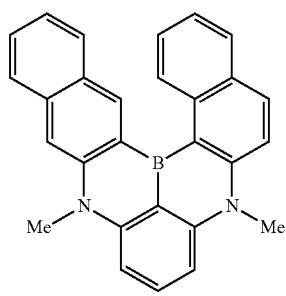
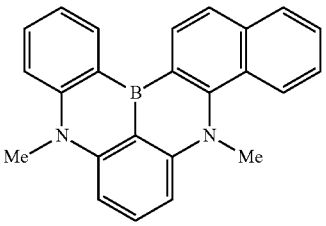
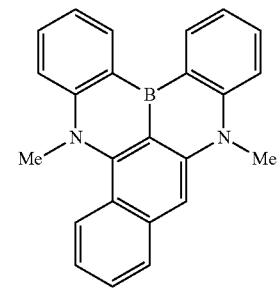
716
-continued
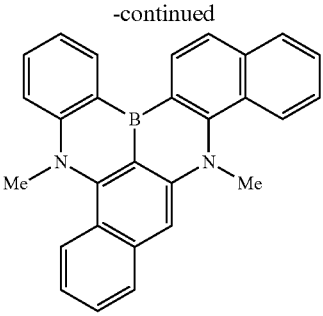
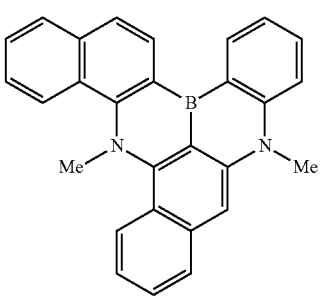
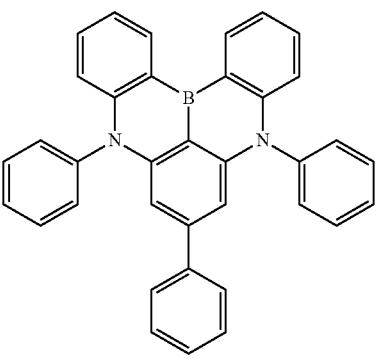
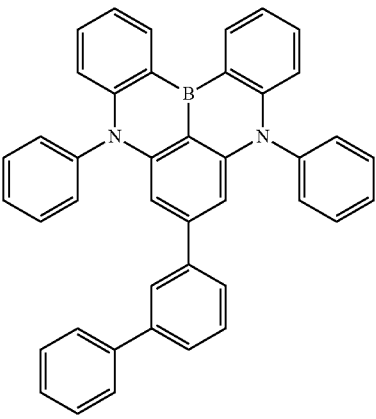

717
-continued
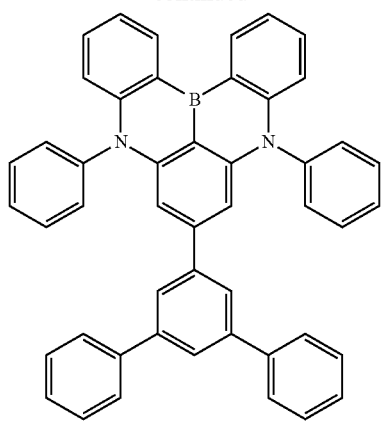
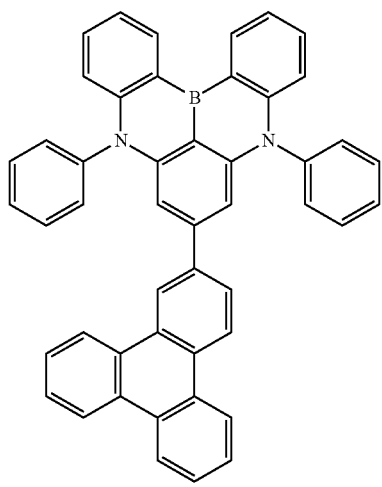
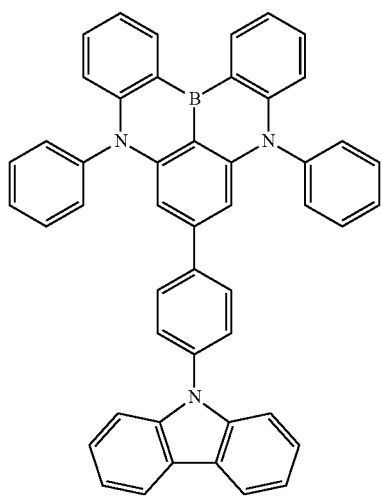
718
-continued
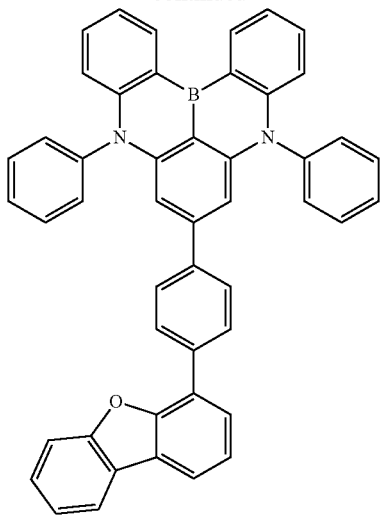
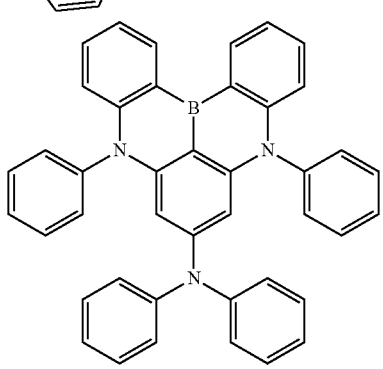
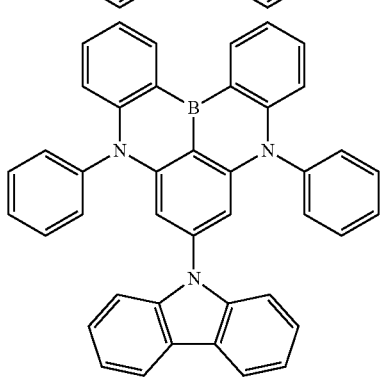
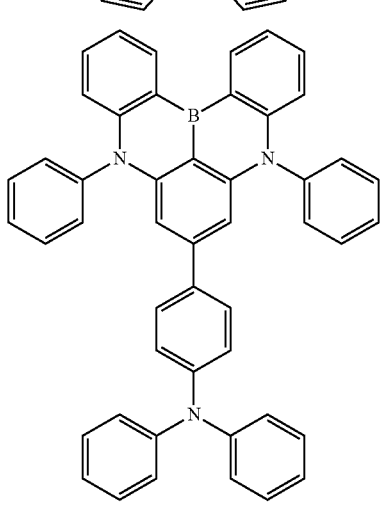

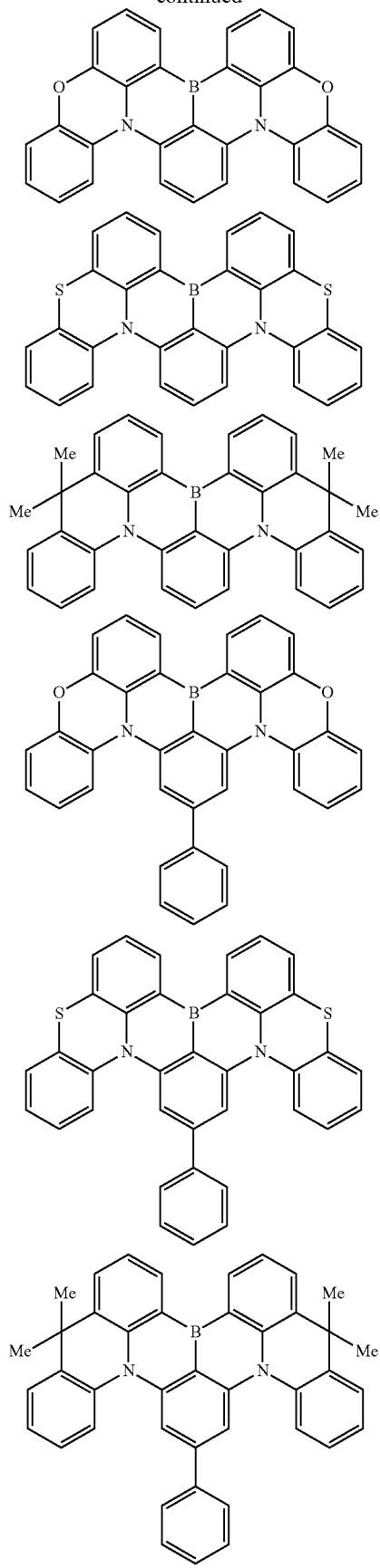
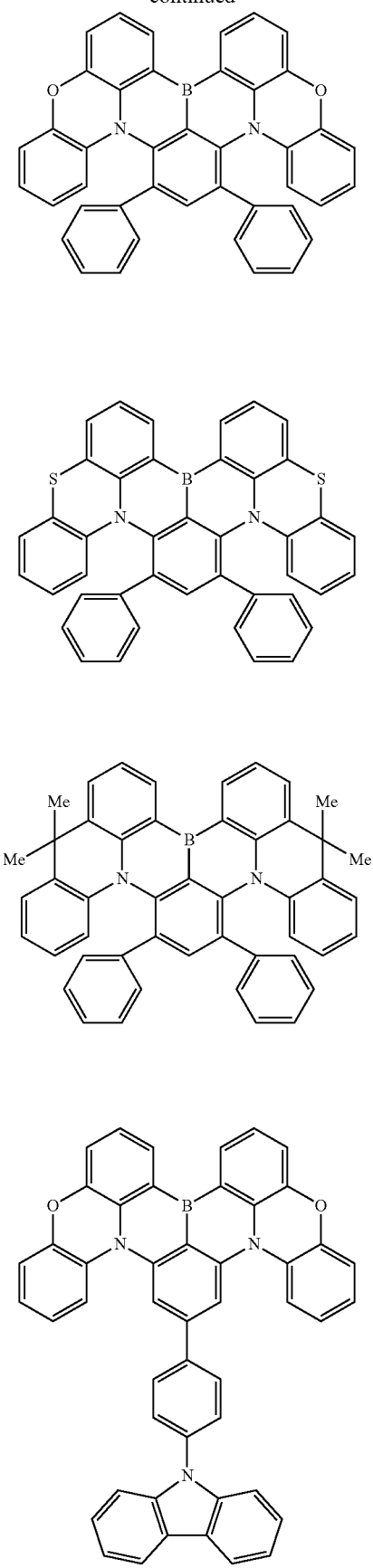

721
-continued
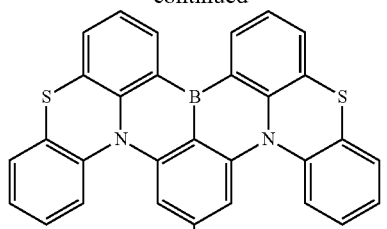
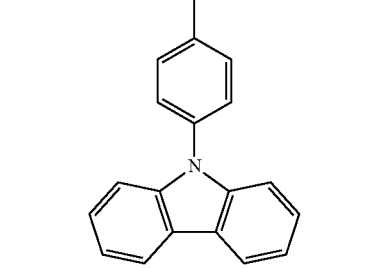
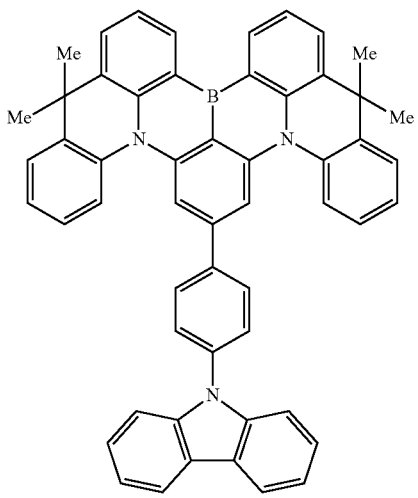
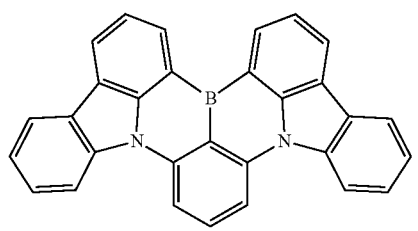
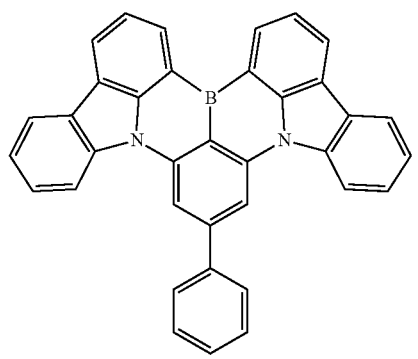
722
-continued
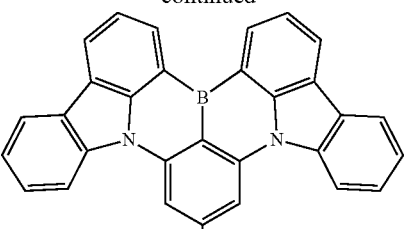
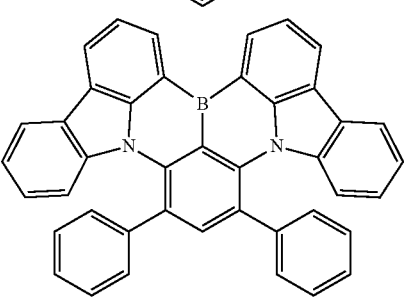
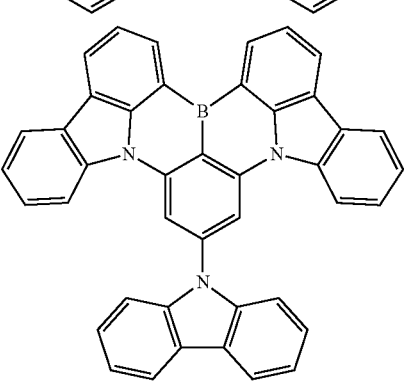
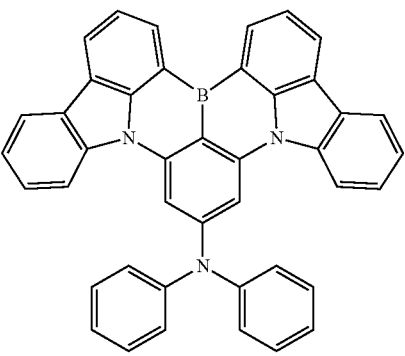
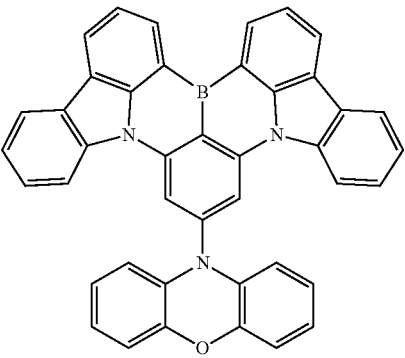

723
-continued
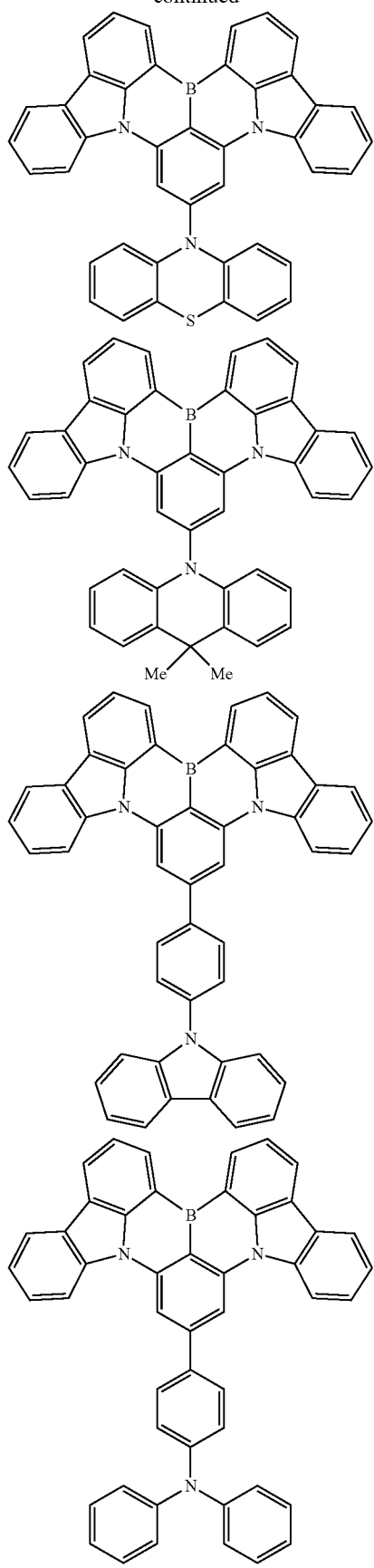
724
-continued
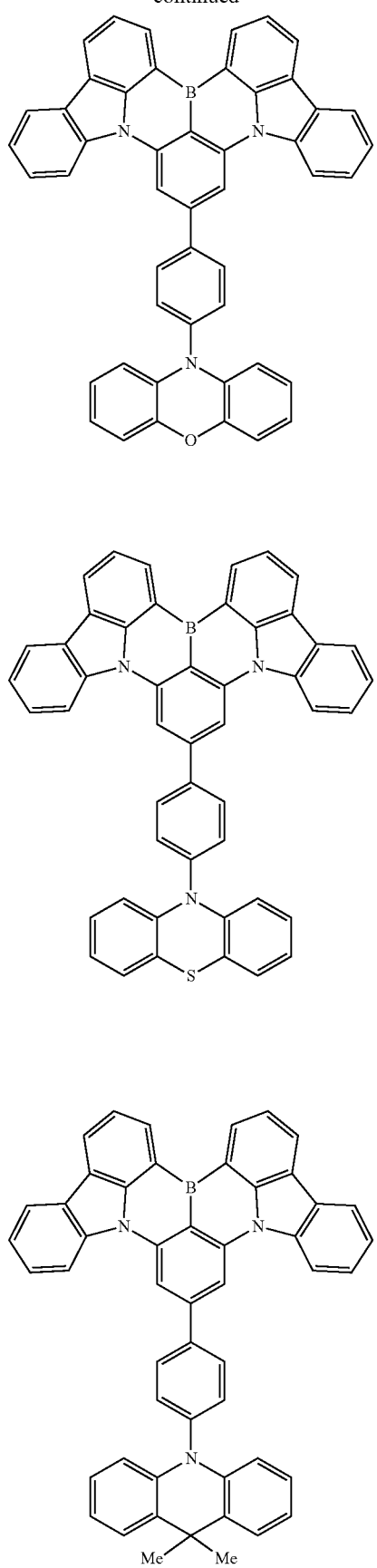

| 725 -continued | 726 -continued |
|---|---|
| 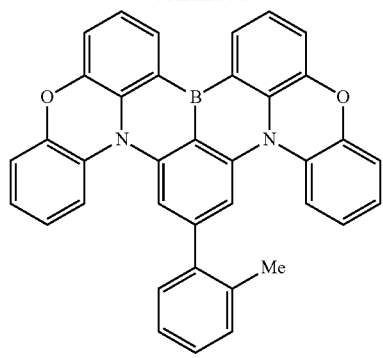 | 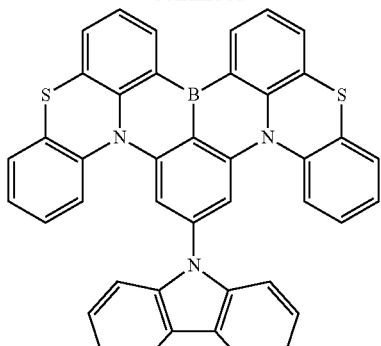 |
| 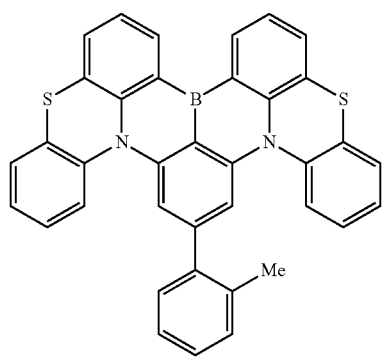 | 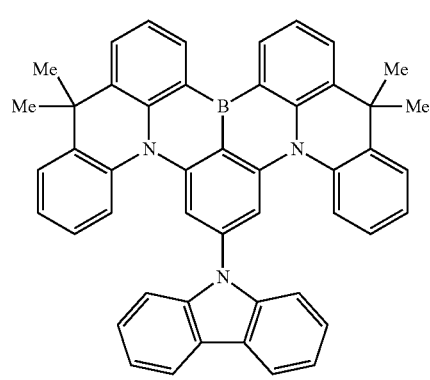 |
| 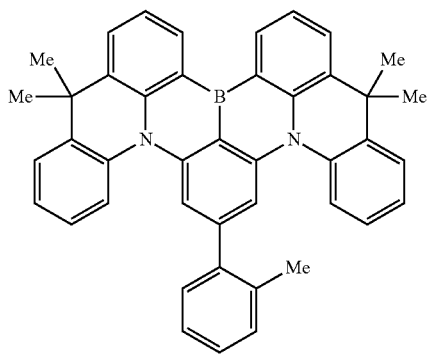 | 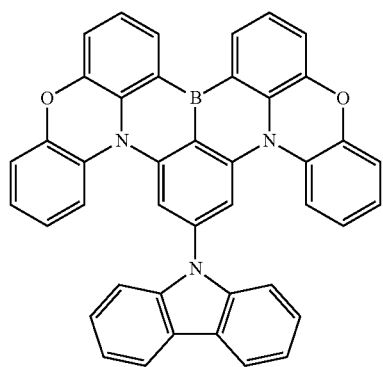 |
| 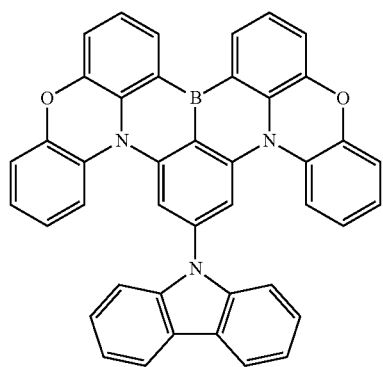 | 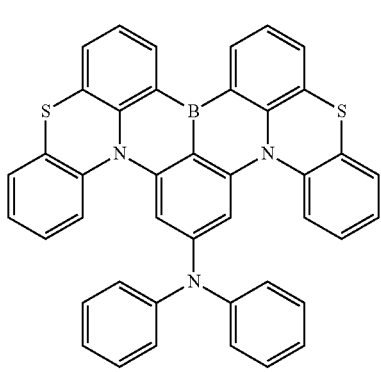 |

727
-continued
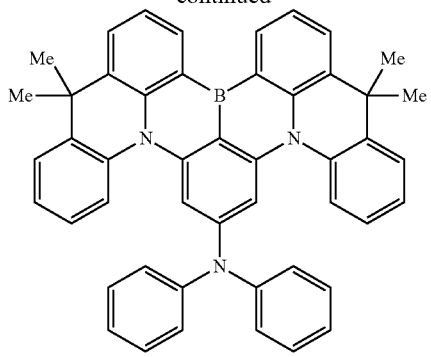
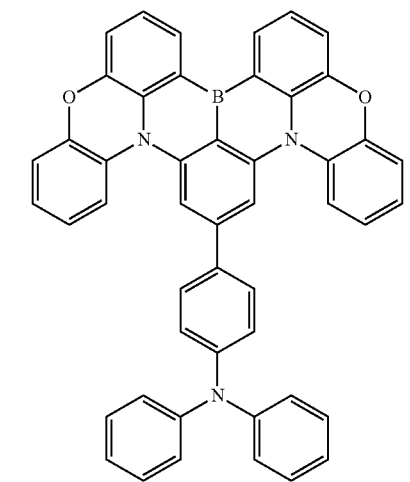
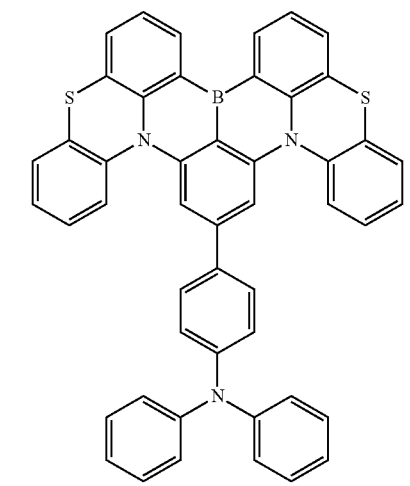
728
-continued
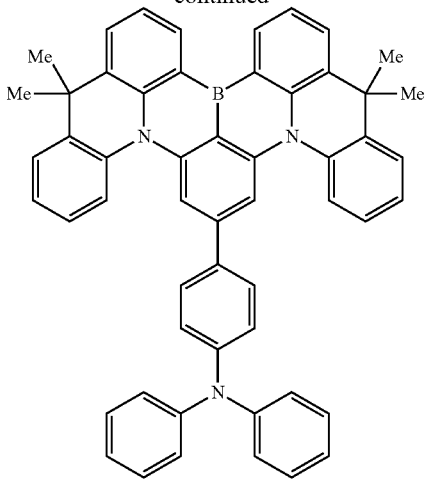
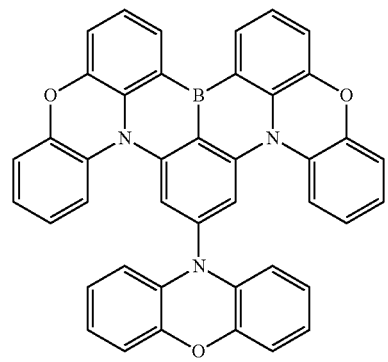
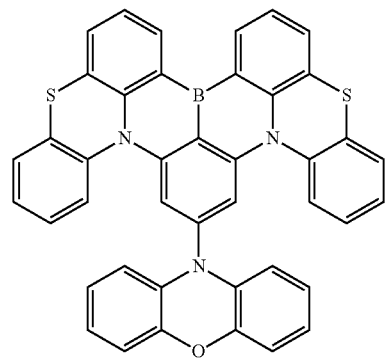
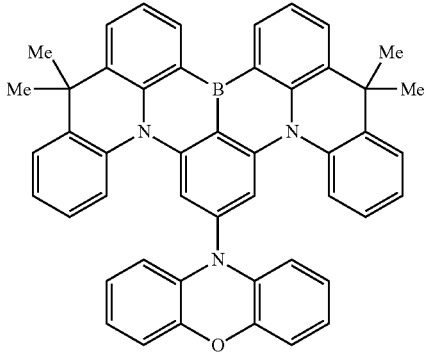

729
-continued
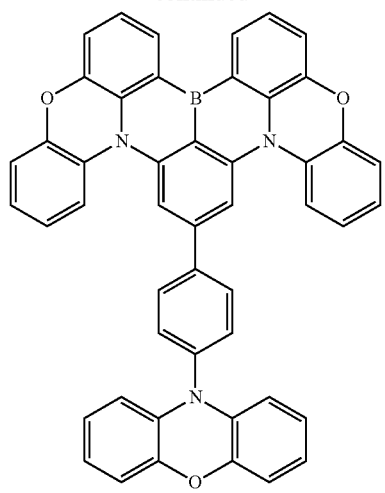
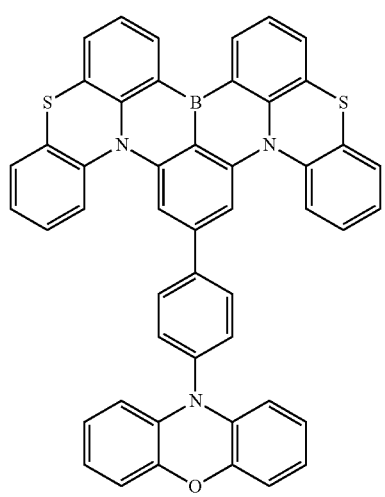
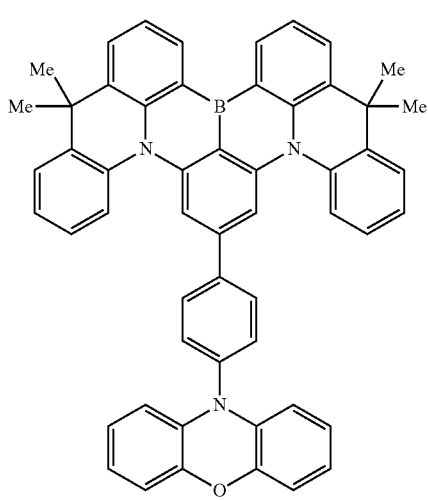
730
-continued
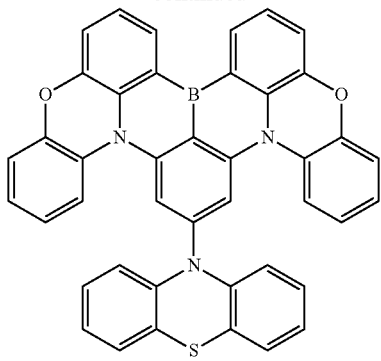
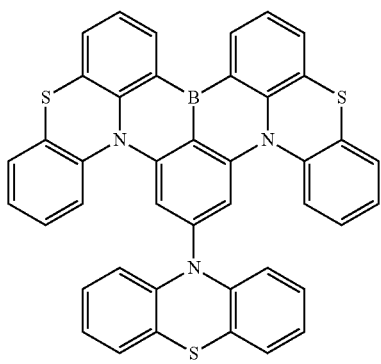
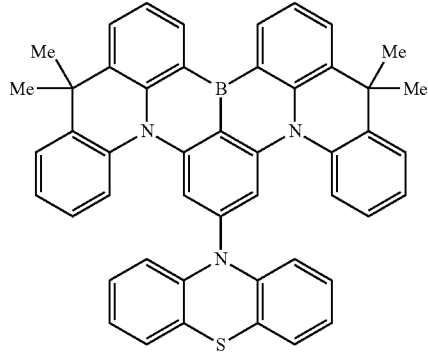
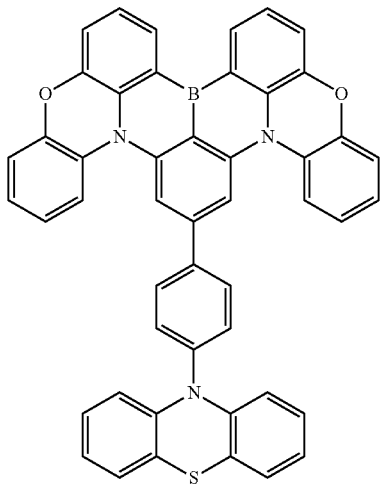

731
-continued
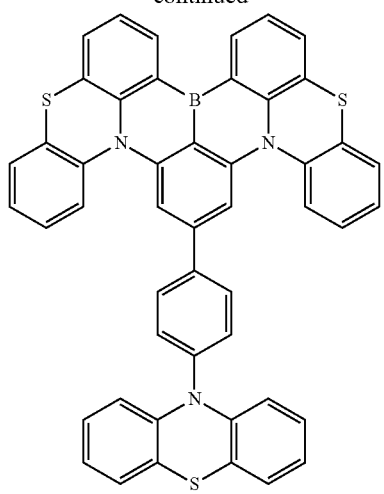
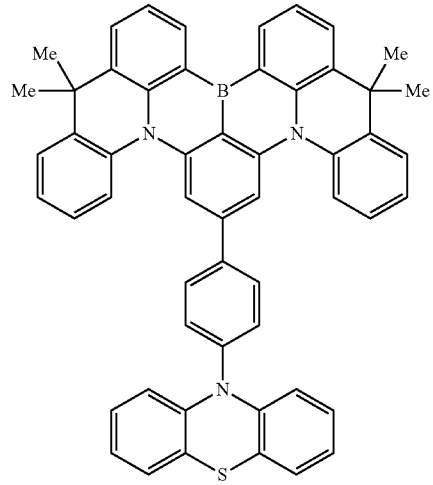
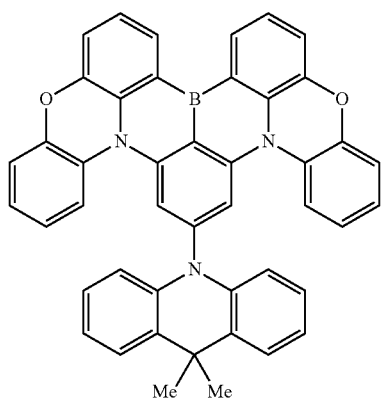
732
-continued
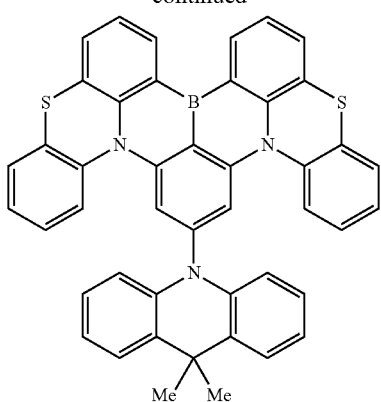
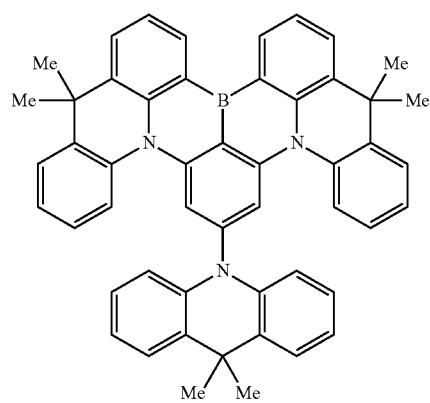
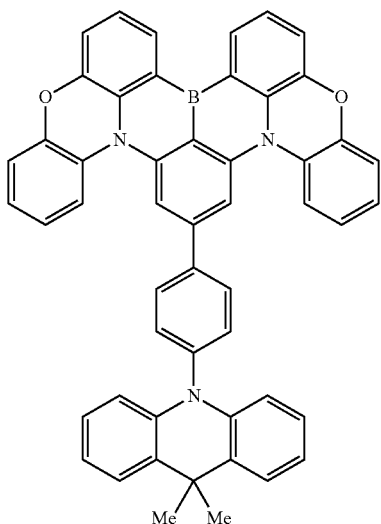

733
-continued
734
-continued
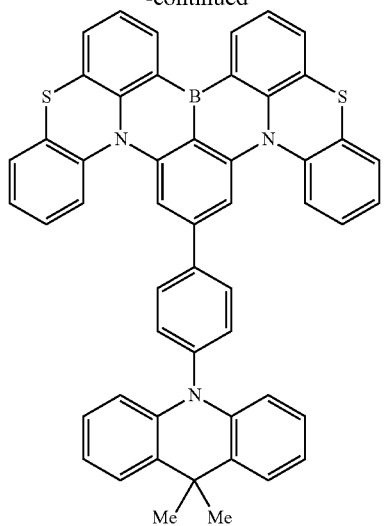
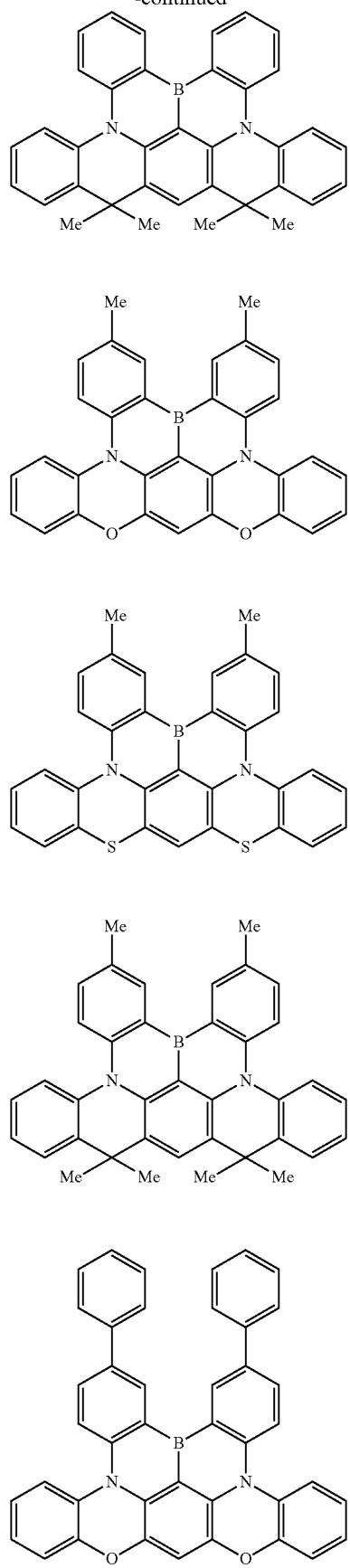

735
-continued
736
-continued
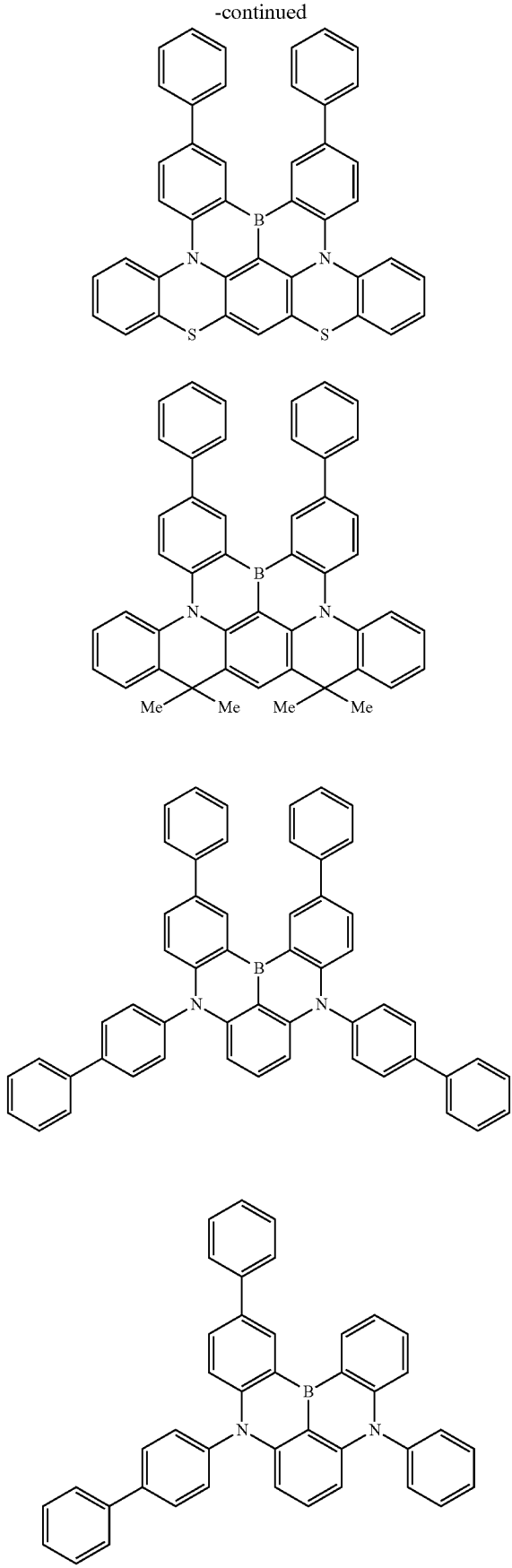
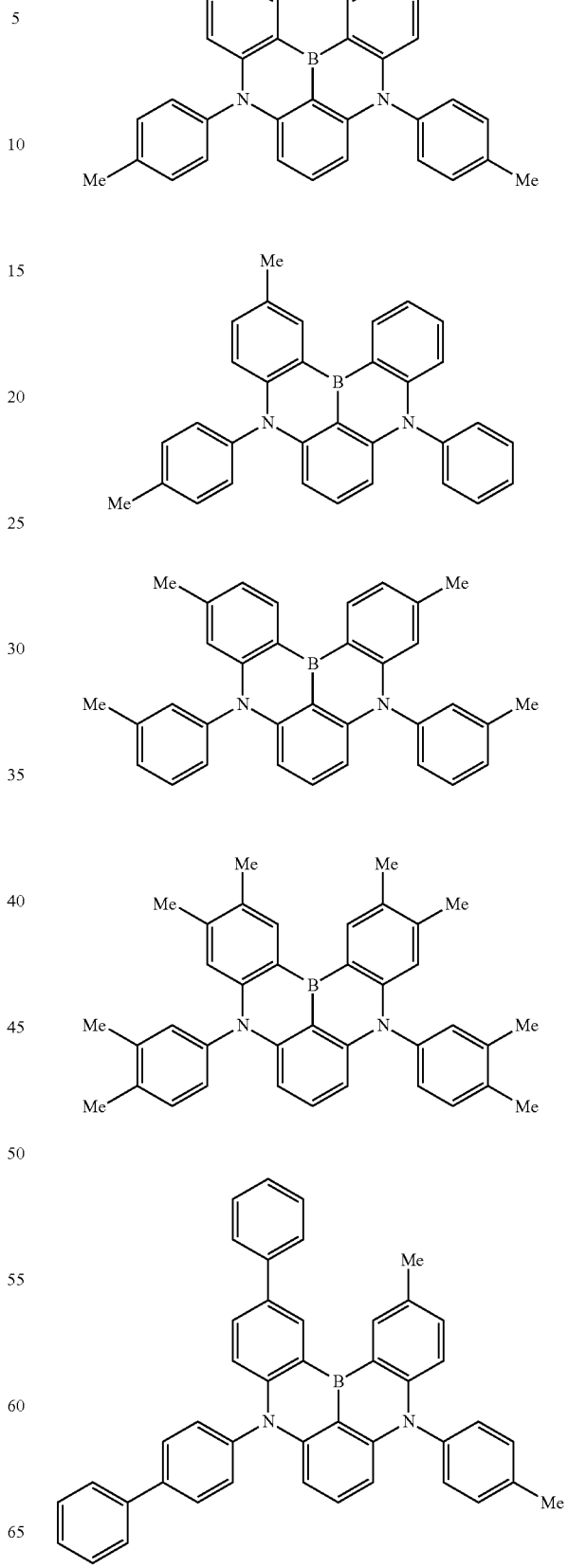

737
-continued
738
-continued
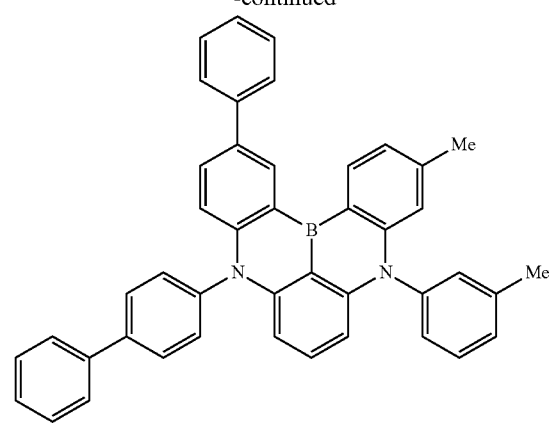
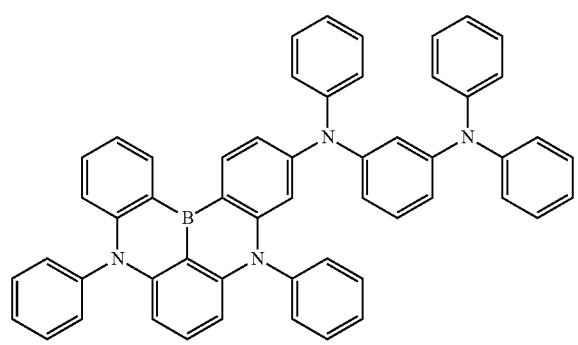
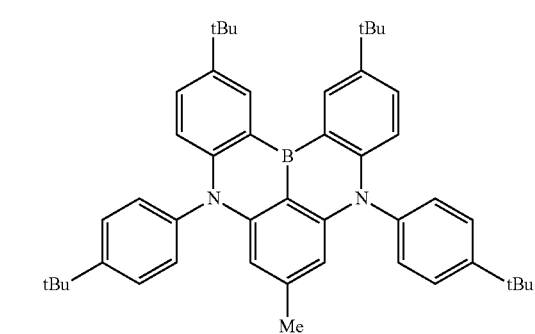
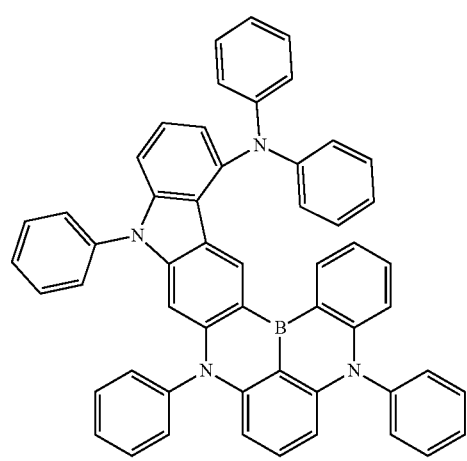
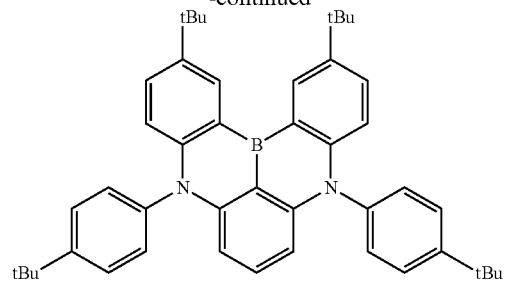
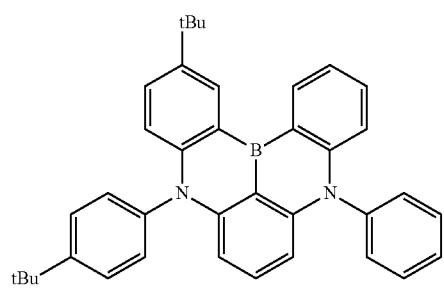
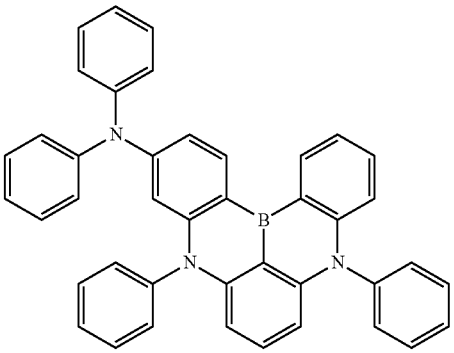
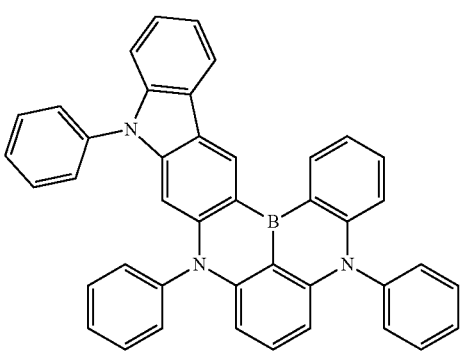
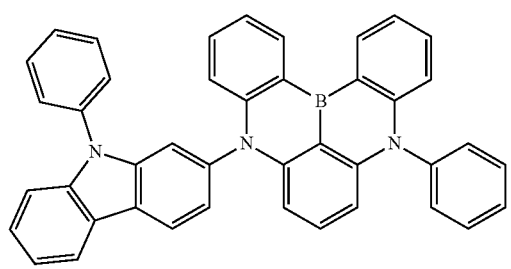

739
-continued
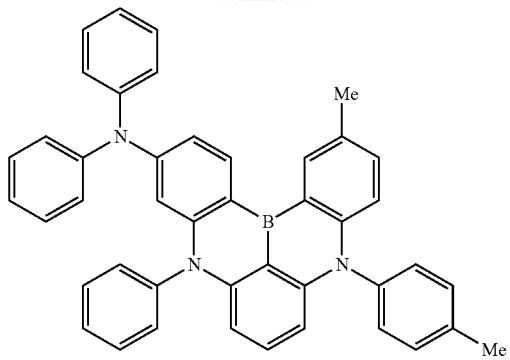
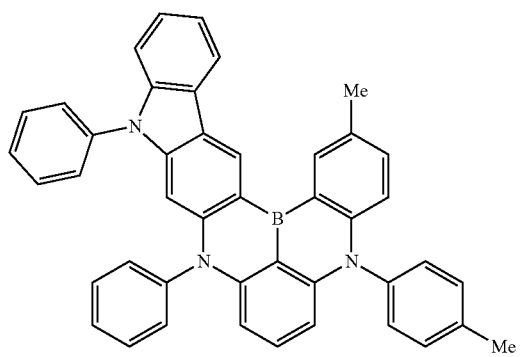
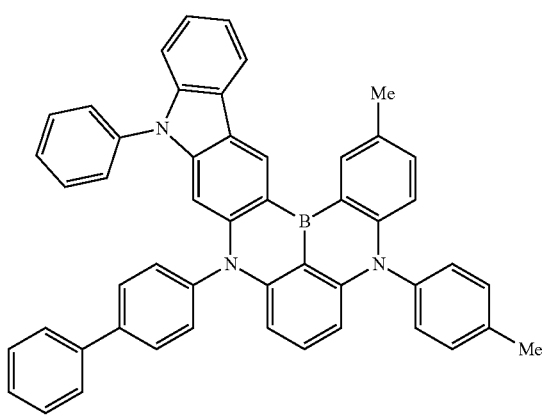
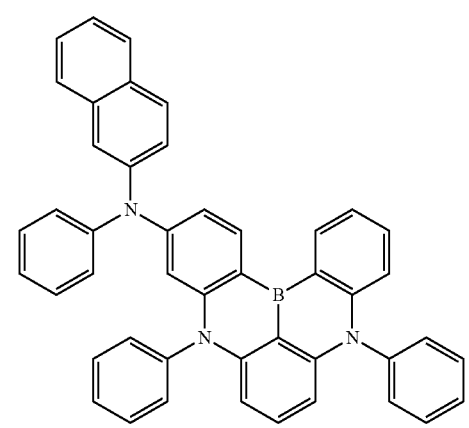
740
-continued
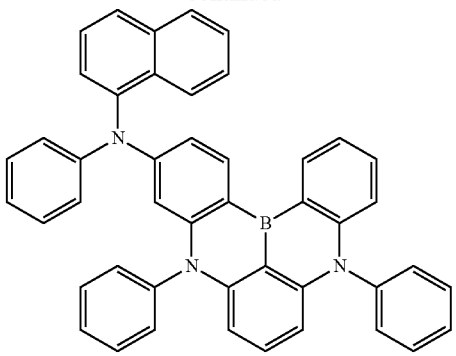
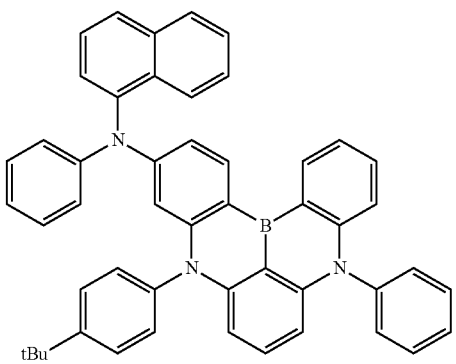
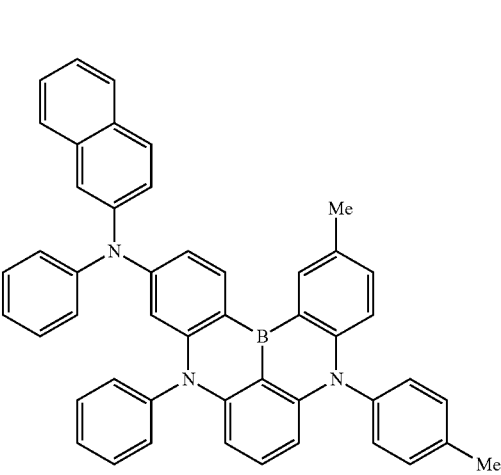
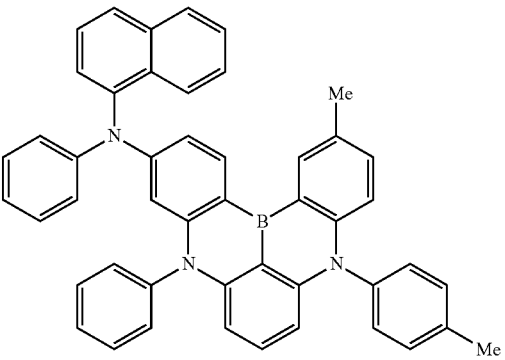

741
-continued
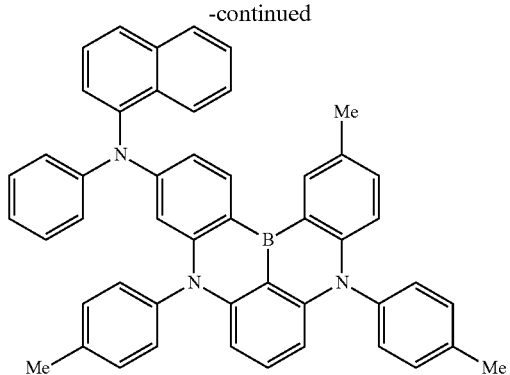
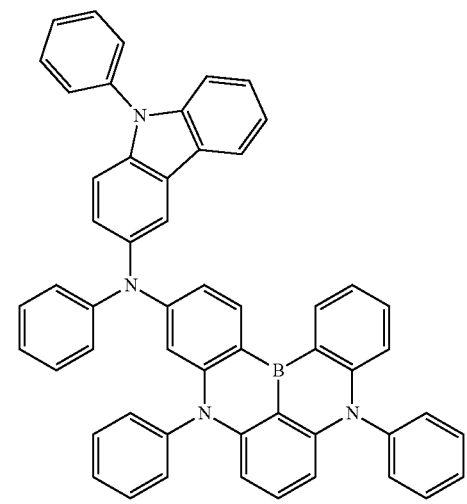
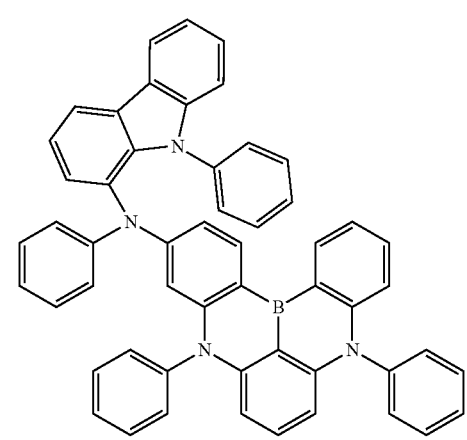
742
-continued
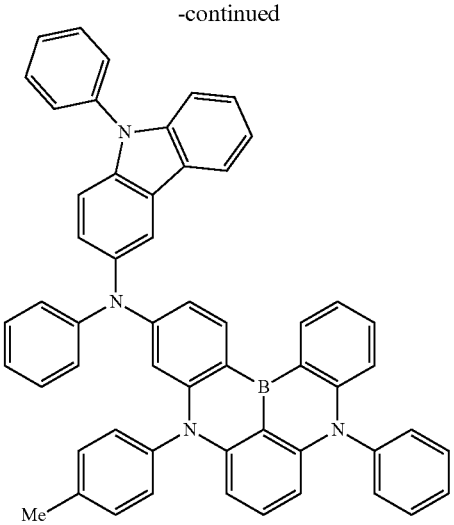
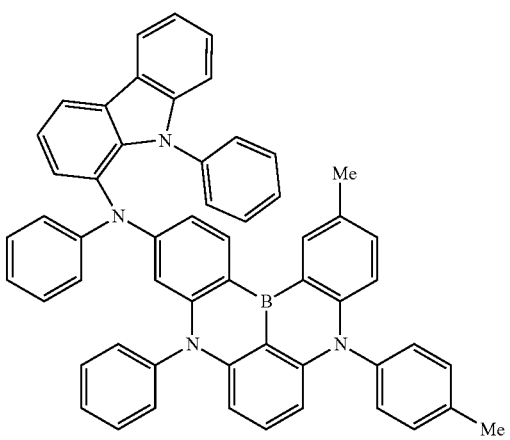

743
-continued
744
-continued
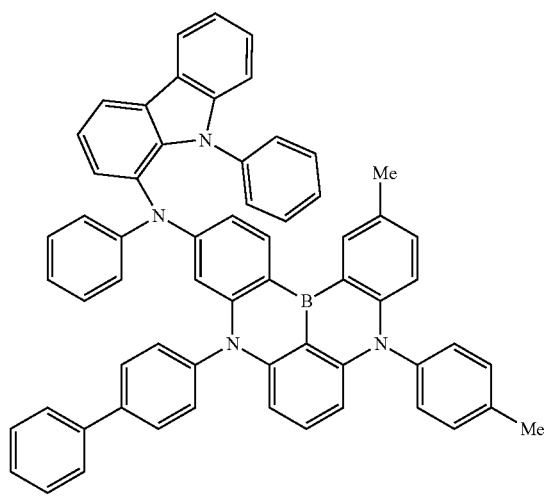
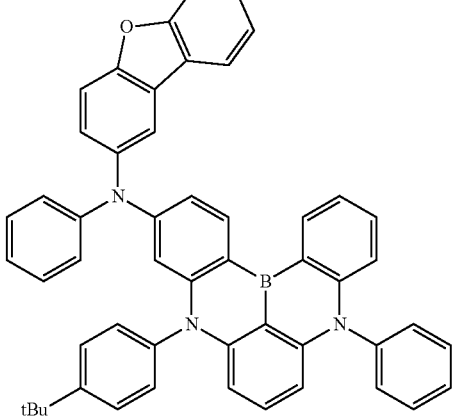
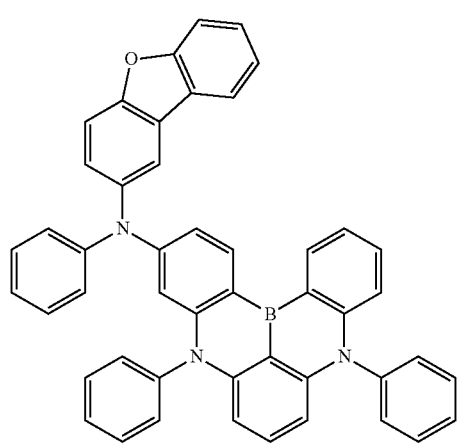
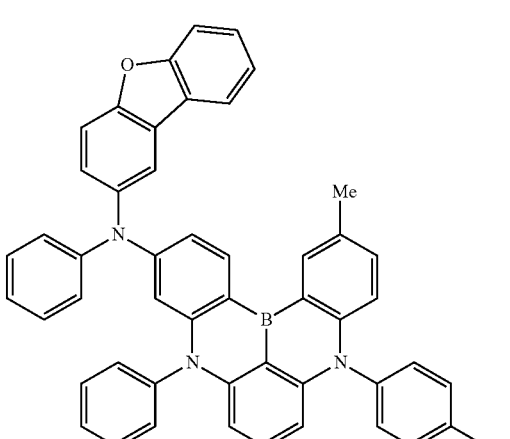
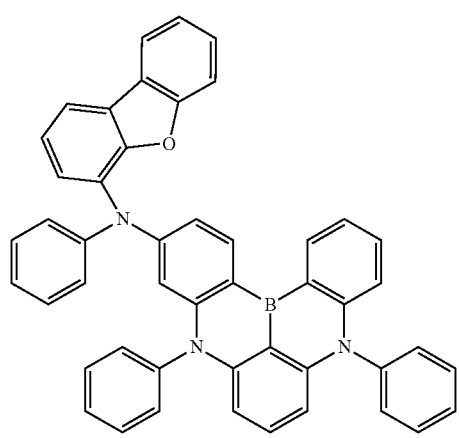
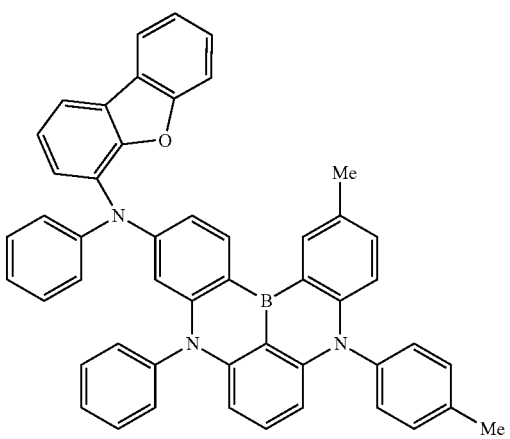

745
-continued
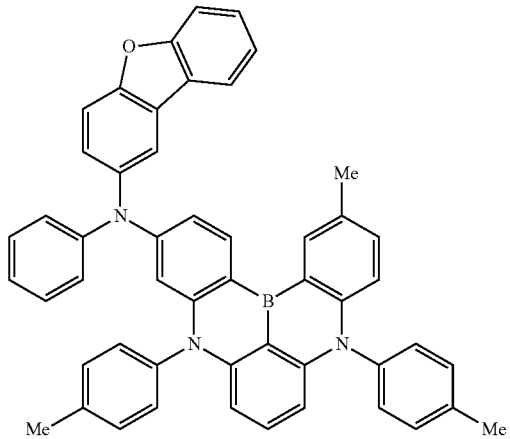
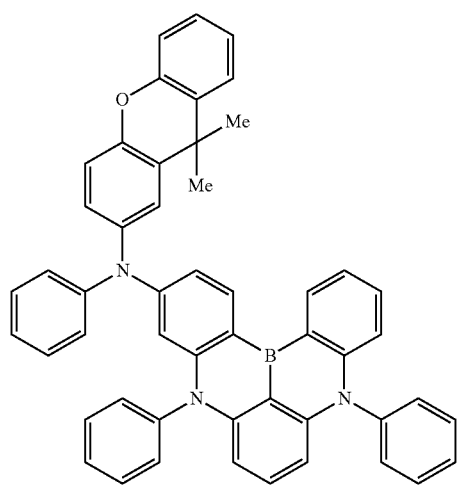
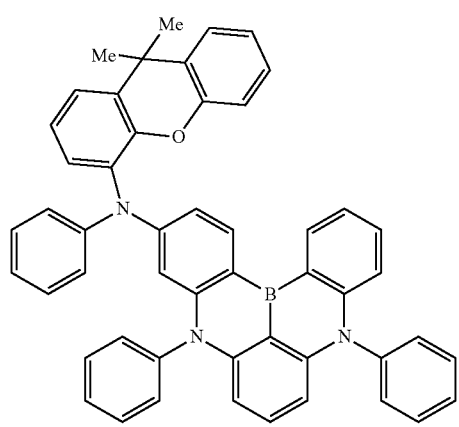
746
-continued
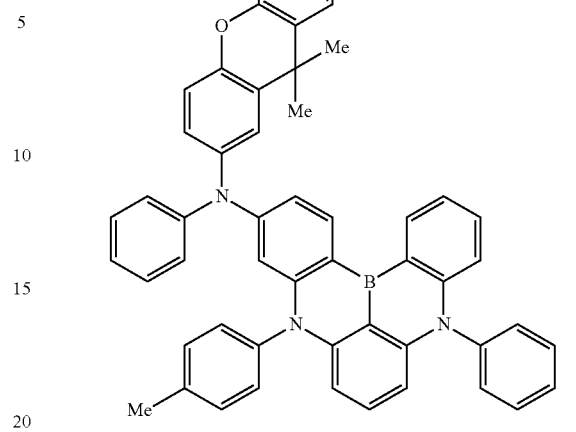
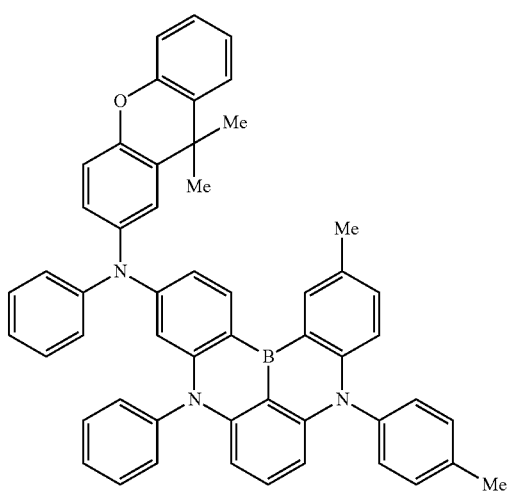
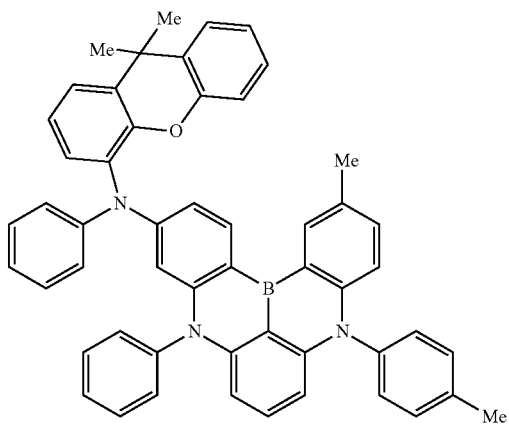

747
-continued
748
-continued
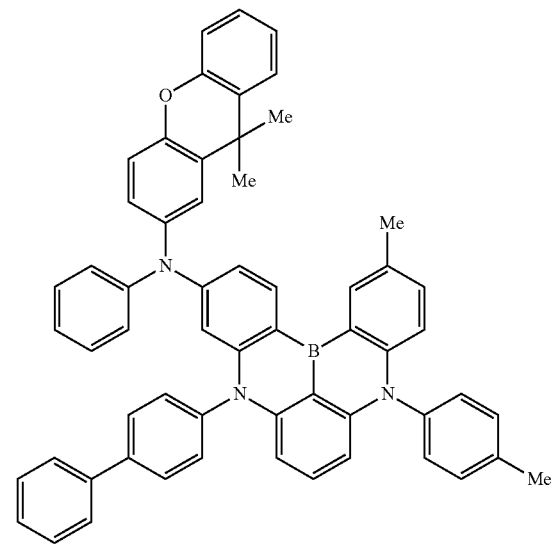
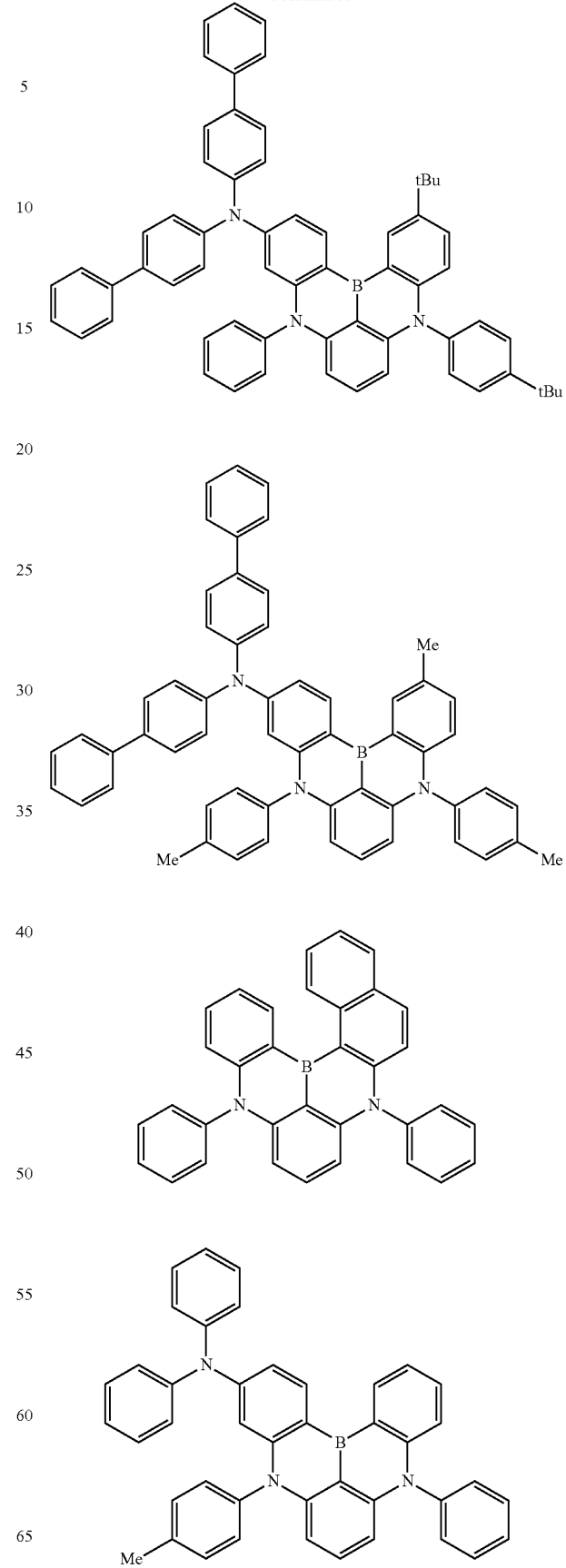

749
-continued
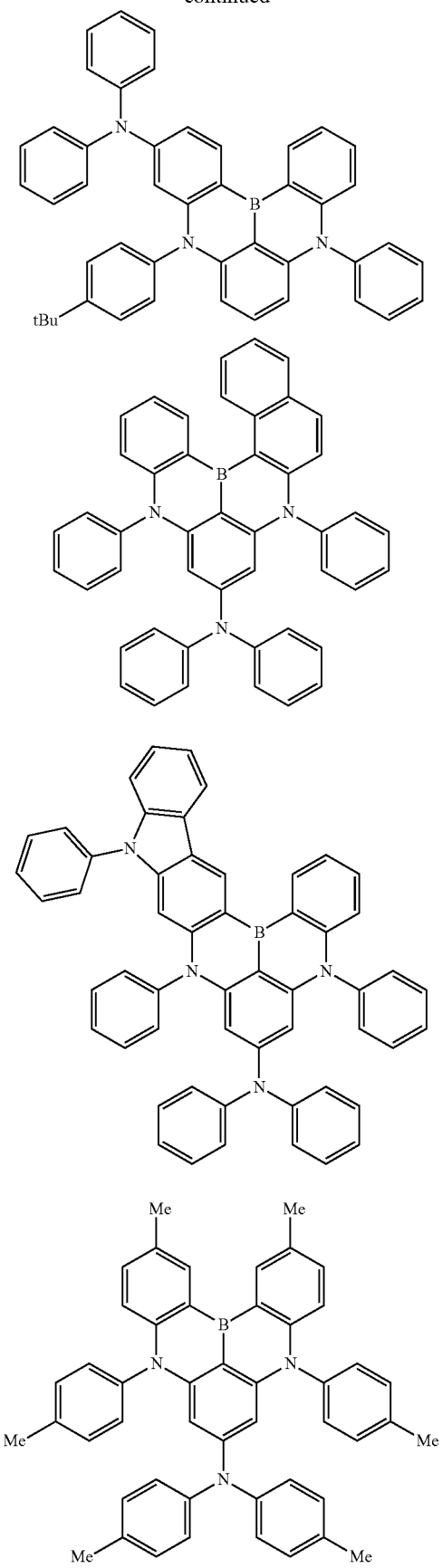
750
-continued
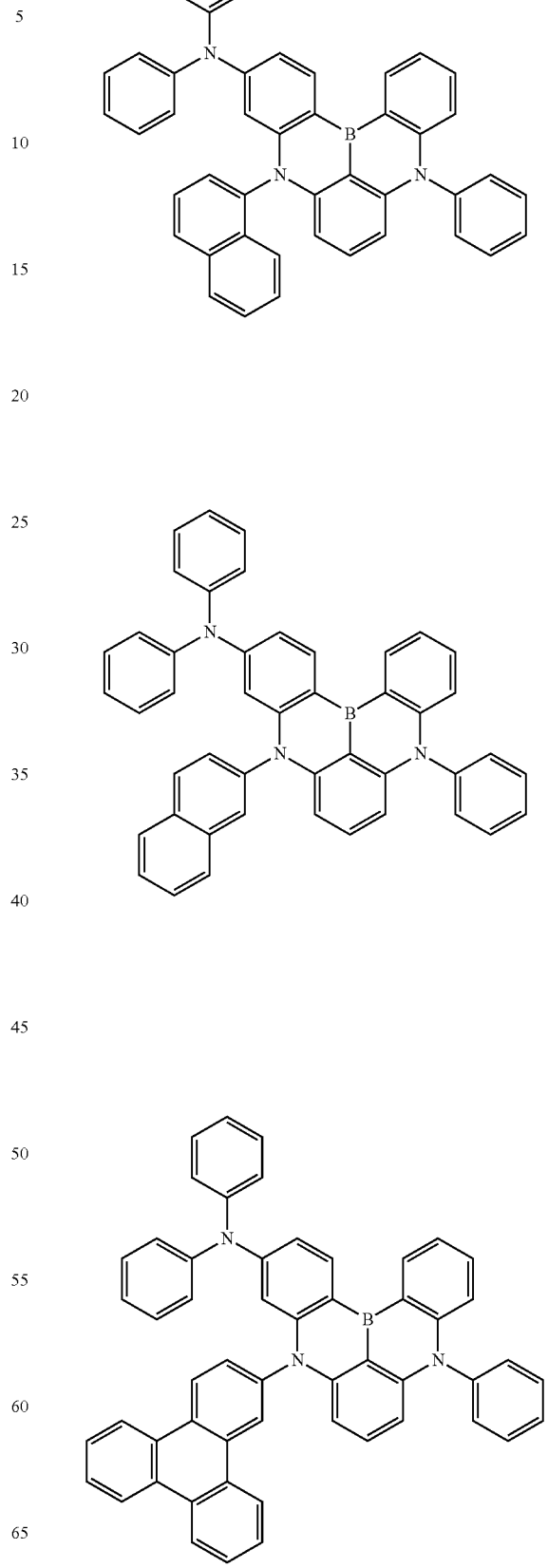

751
-continued
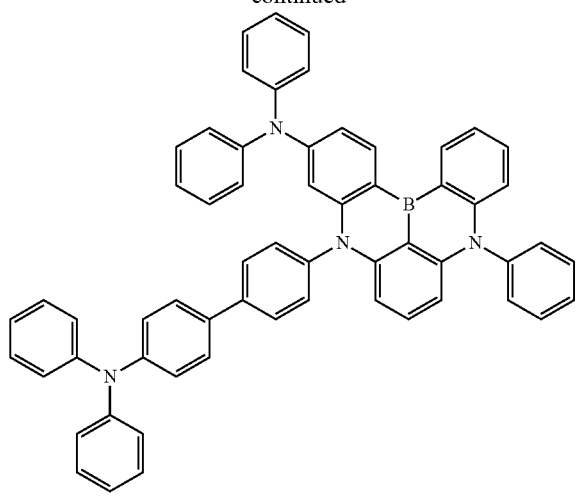
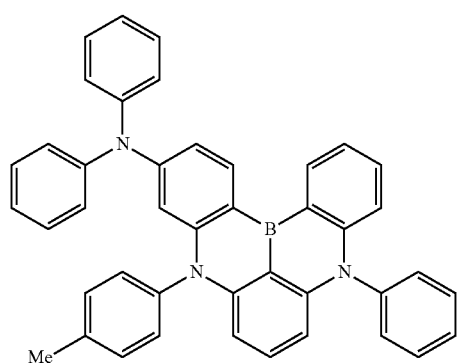
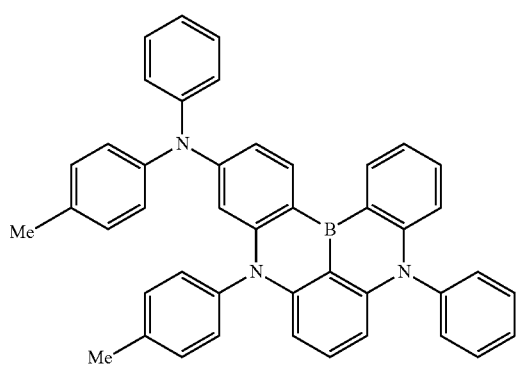
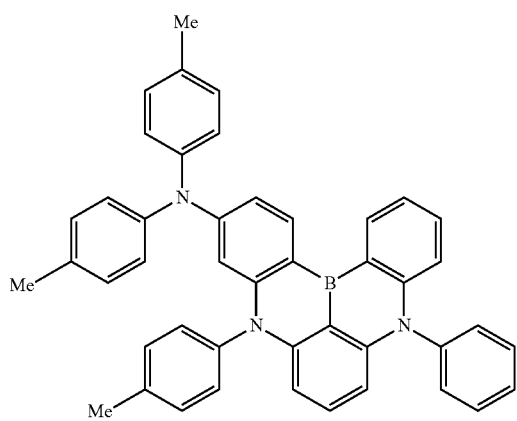
752
-continued
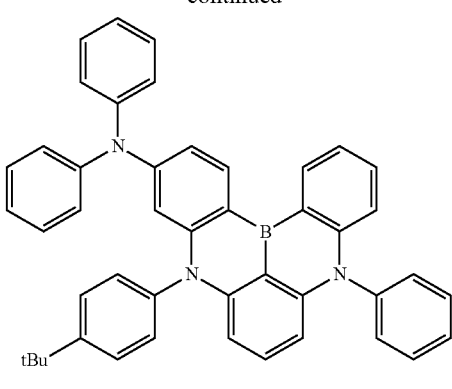
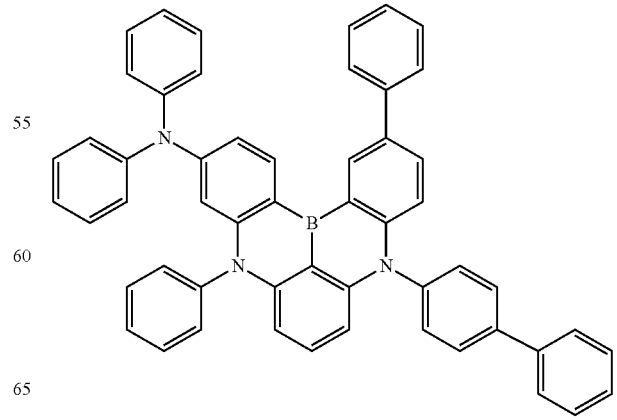

753
-continued
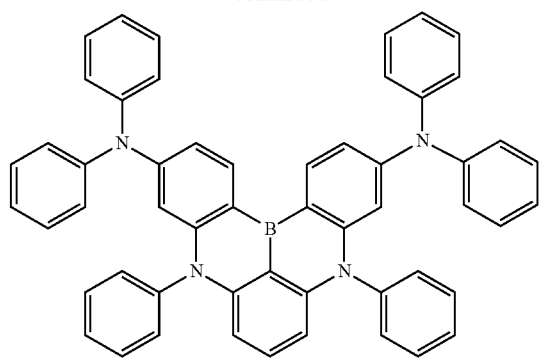
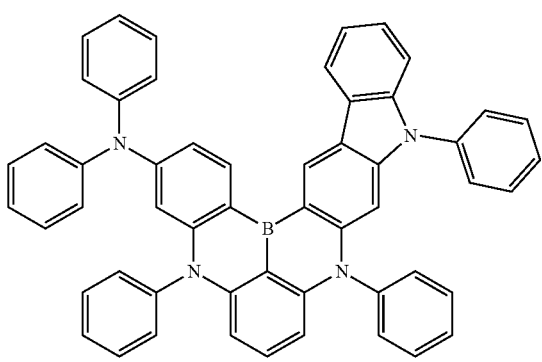
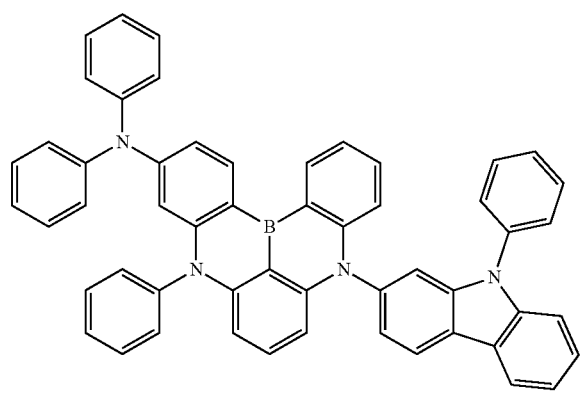
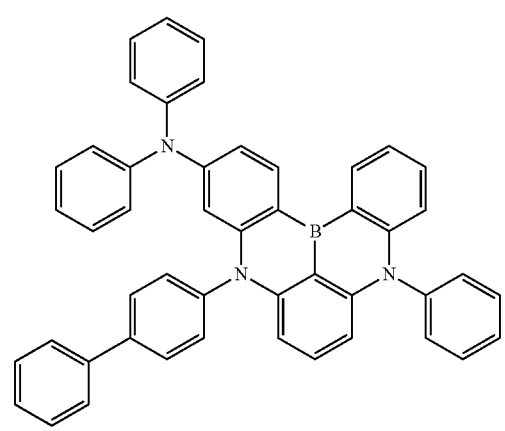
754
-continued
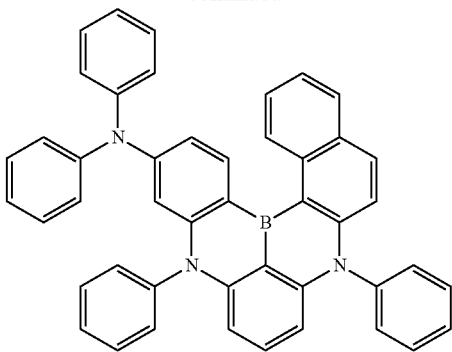
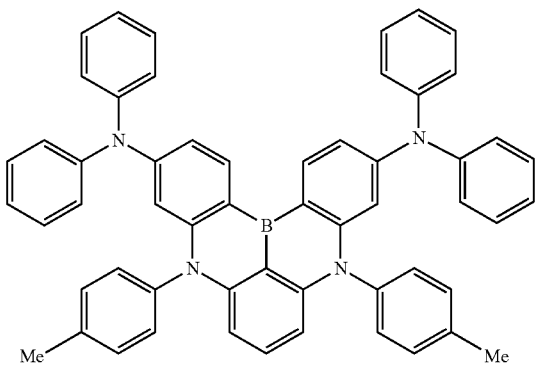
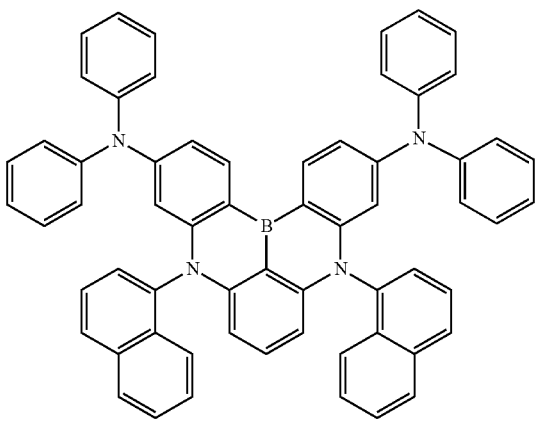
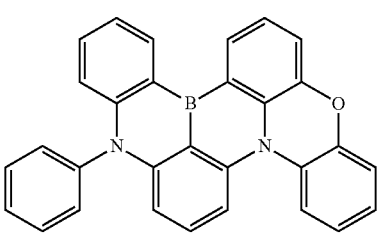
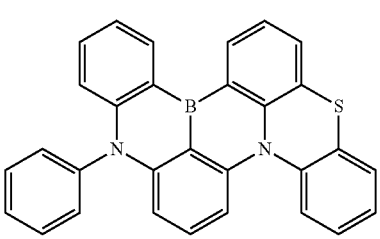

755
-continued
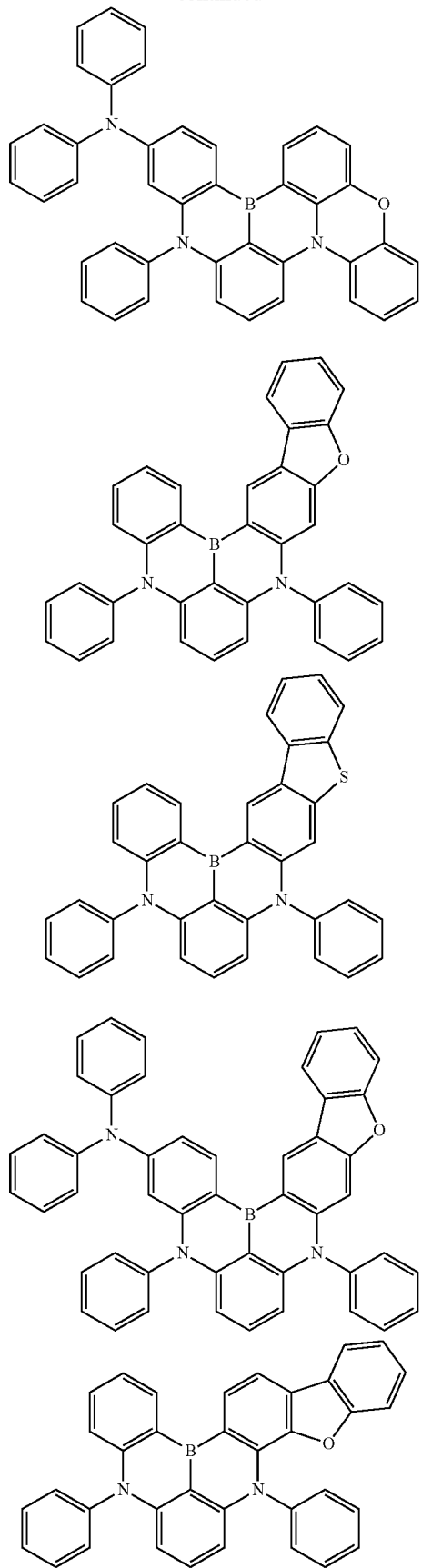
756
-continued
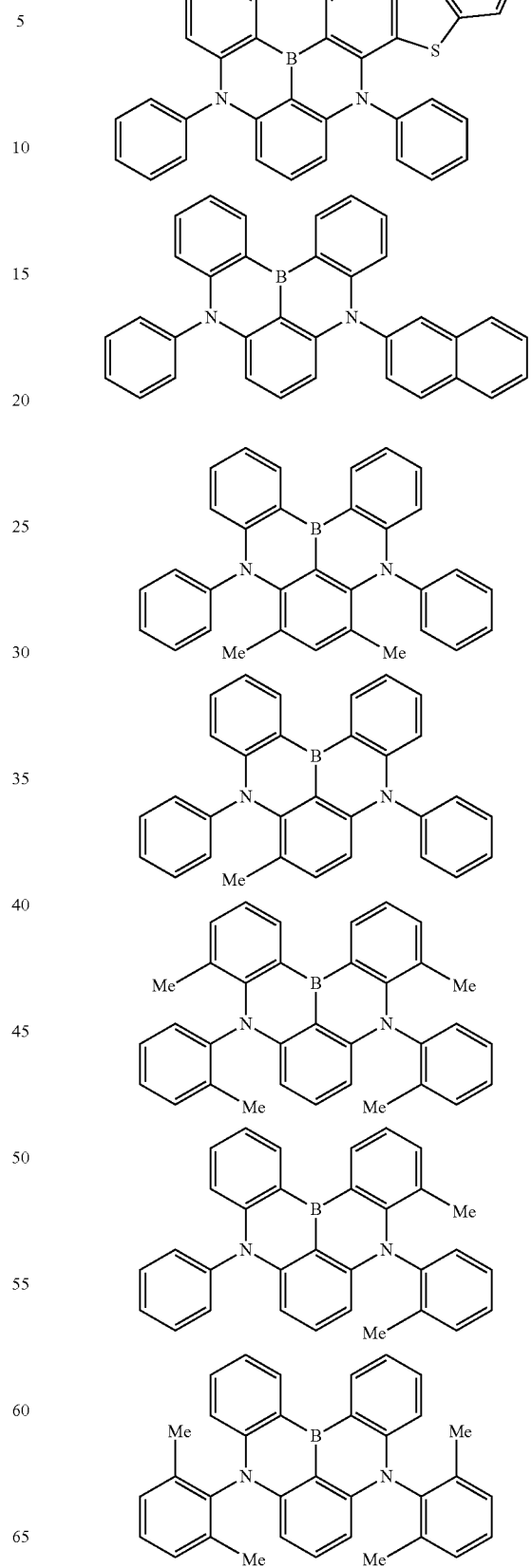

-continued

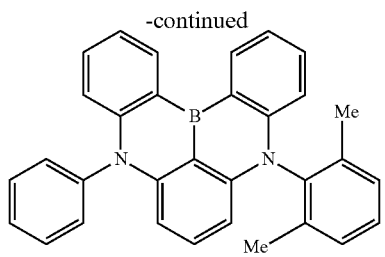

(Compound Represented by Formula (51))

The compound represented by the formula (51) is explained below.

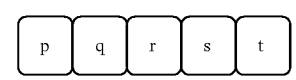 (51)

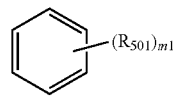 (52)

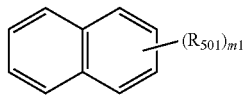 (53)

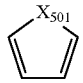 (54)

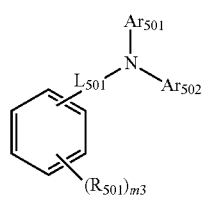 (55)

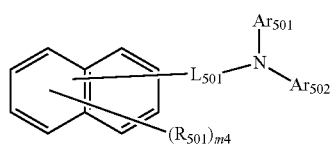 (56)

wherein, in the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{501}$s exist, adjacent plural $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_{501}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is an integer of 0 to 2, m2 is an integer of 0 to 4, m3s are independently an integer of 0 to 3, and m4s are independently an integer of 0 to 5; when plural $R_{501}$s exist, the plural $R_{501}$s may be the same or different;

In the formula (51), each of the p ring to the t ring is fused to an adjacent ring by sharing two carbon atoms. The position and direction of fusing are not limited, and condensation is possible at any position and direction.

In one embodiment, in the formula (52) or (53) of the r ring, $R_{501}$ is a hydrogen atom.

In one embodiment, the compound represented by the formula (51) is represented by any one of the following formulas (51-1) to (51-6).

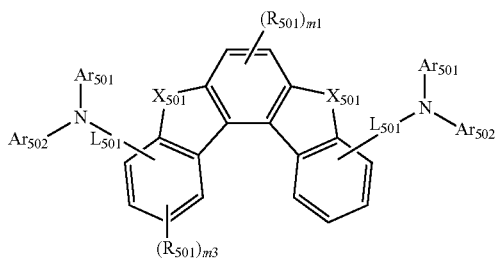 (51-1)

(51-2)
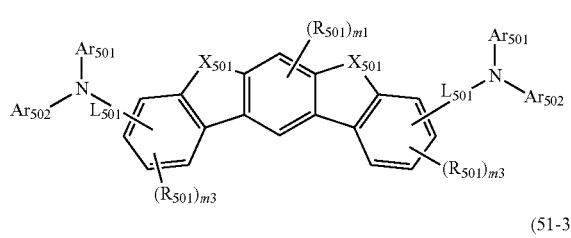

(51-3)
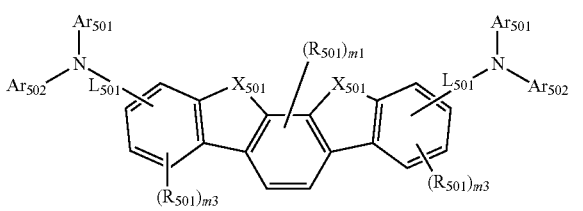

(51-4)
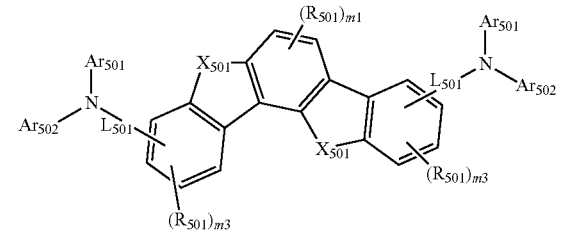

(51-5)
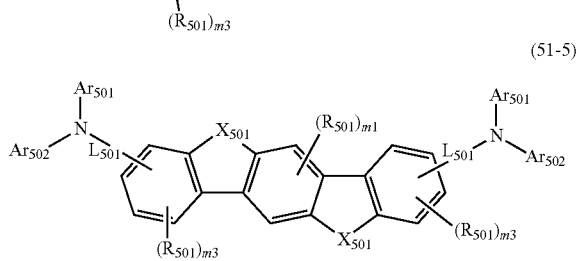

(51-6)
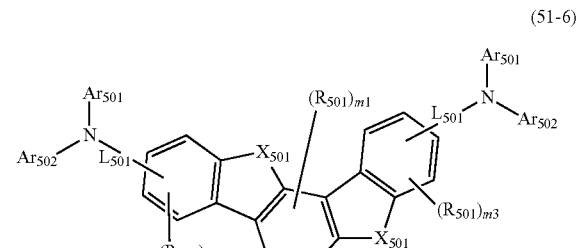

wherein in the formulas (51-1) to (51-6), $R_{501}$, $X_{501}$, $Ar_{501}$, $Ar_{502}$, $L_{501}$, m1 and m3 are as defined in the formula (51).

In one embodiment, the compound represented by the formula (51) is represented by any one of the following formulas (51-11) to (51-13).

(51-11)
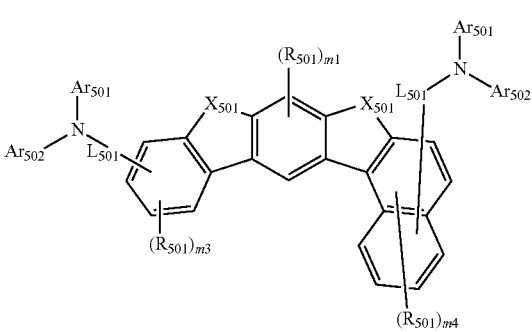

(51-12)
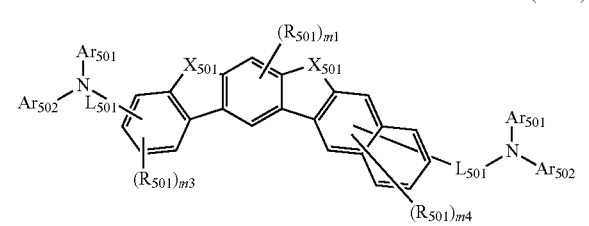

(51-13)
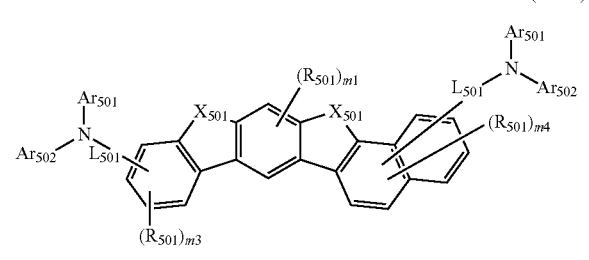

wherein in the formulas (51-11) to (51-13), $R_{501}$, $X_{501}$, $Ar_{501}$, $Ar_{502}$, $L_{501}$, m1, m3 and m4 are as defined in the formula (51).

In one embodiment, the compound represented by the formula (51) is represented by any one of the following formulas (51-21) to (51-25).

(51-21)
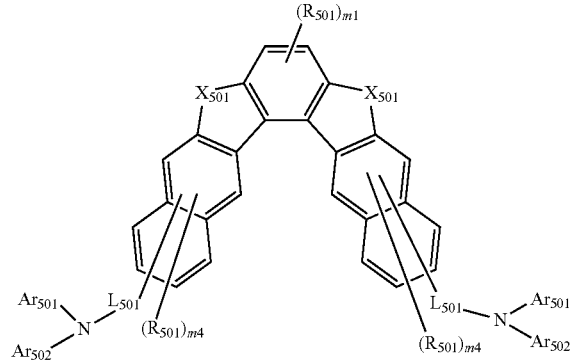

(51-22)
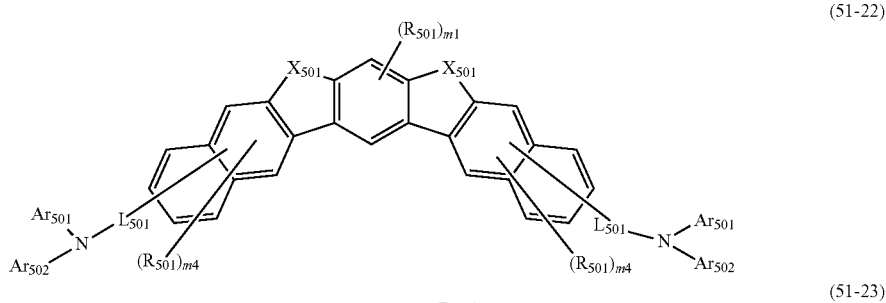
(51-23)
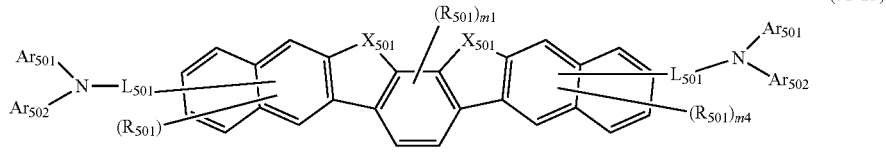
(51-24)
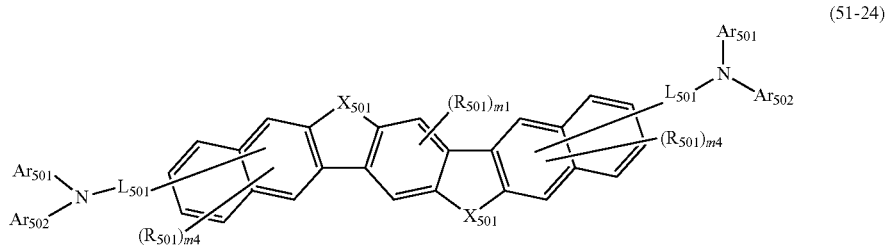
(51-25)
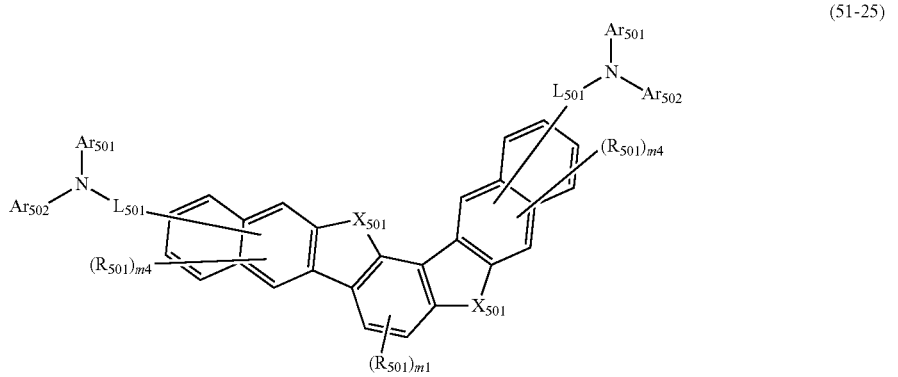
wherein in the formulas (51-21) to (51-25), $R_{501}$, $X_{501}$, $Ar_{501}$, $Ar_{502}$, $L_{501}$, m1, m4 are as defined in the formula (51).
In one embodiment, the compound represented by the formula (51) is represented by any one of the following formulas (51-31) to (51-33).
(51-31)
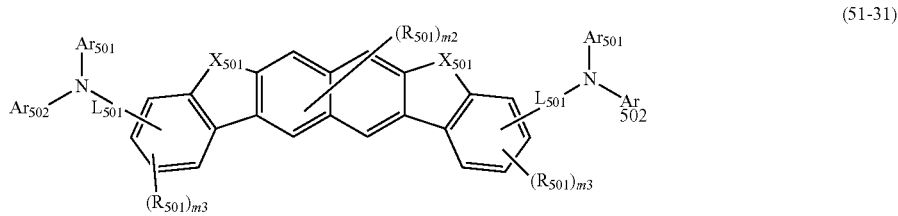
(51-32)
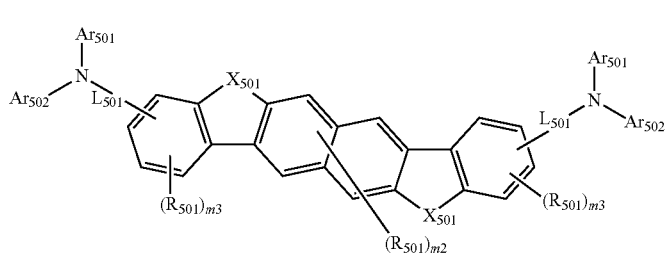

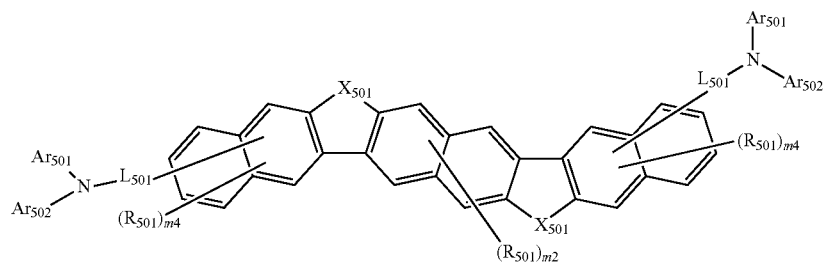

(51-33)

wherein in the formulas (51-31) to (51-33), $R_{501}$, $X_{501}$, $Ar_{501}$, $Ar_{502}$, $L_{501}$, m1 to m4 are as defined in the formula (51).

In one embodiment, $Ar_{501}$ and $Ar_{502}$ are independently a substituted or unsubstituted aryl group having 6 to 50 ring carbon atoms.

In one embodiment, one of $Ar_{501}$ and $Ar_{502}$ is a substituted or unsubstituted aryl group having 6 to 50 ring carbon atoms and the other is a substituted or unsubstituted monovalent heterocyclic ring having 5 to 50 ring atoms.

As examples of the compound represented by the formula (51), the following compounds can be given, for example.

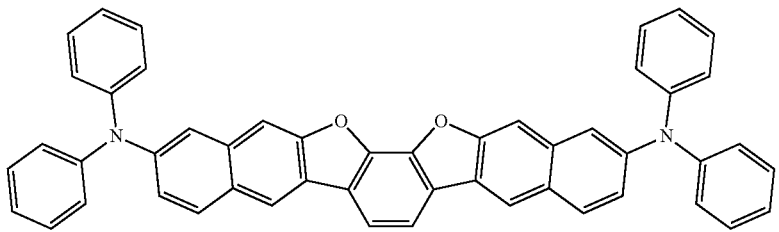

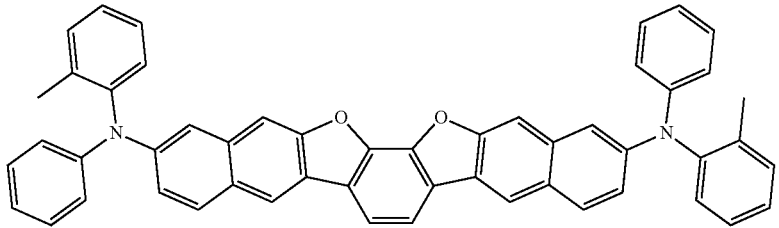

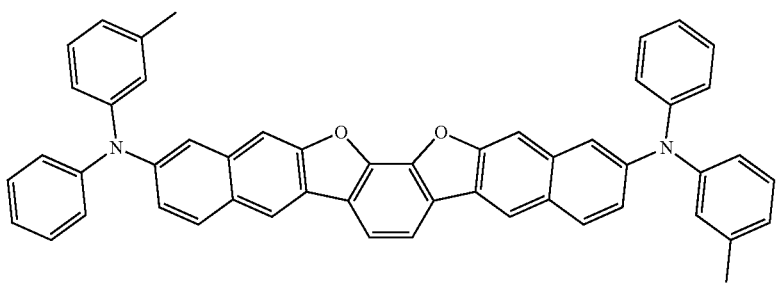

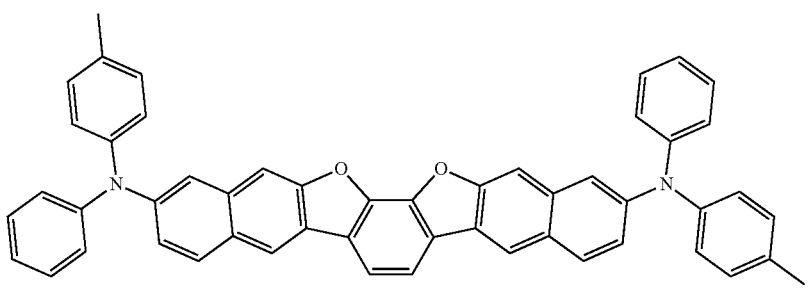

-continued
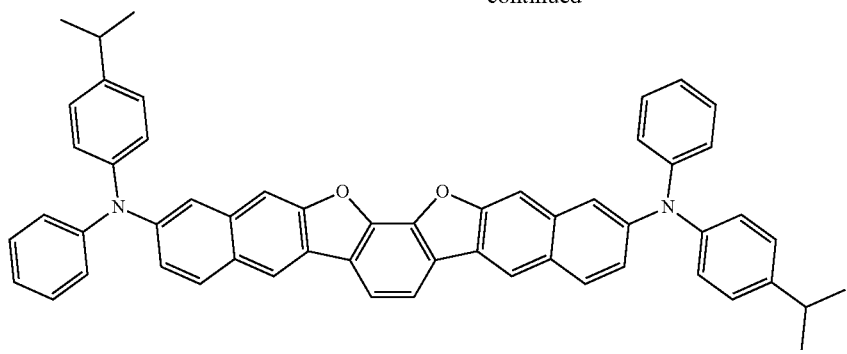
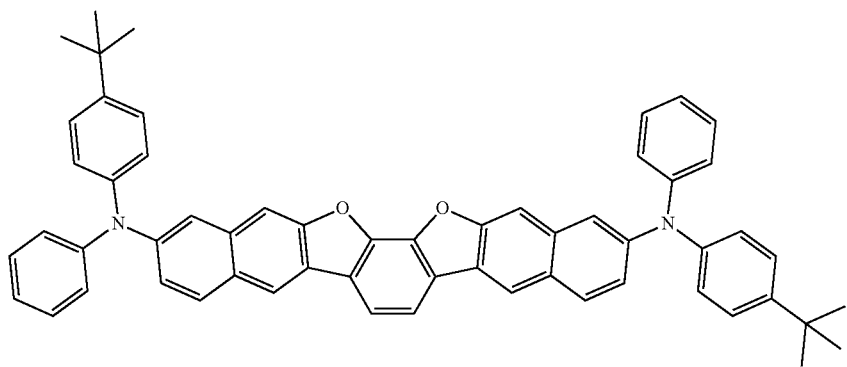
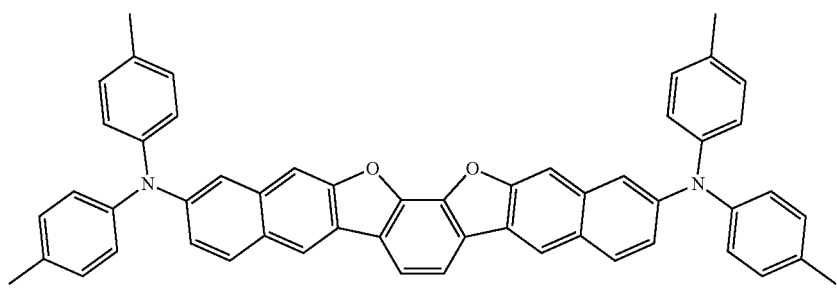
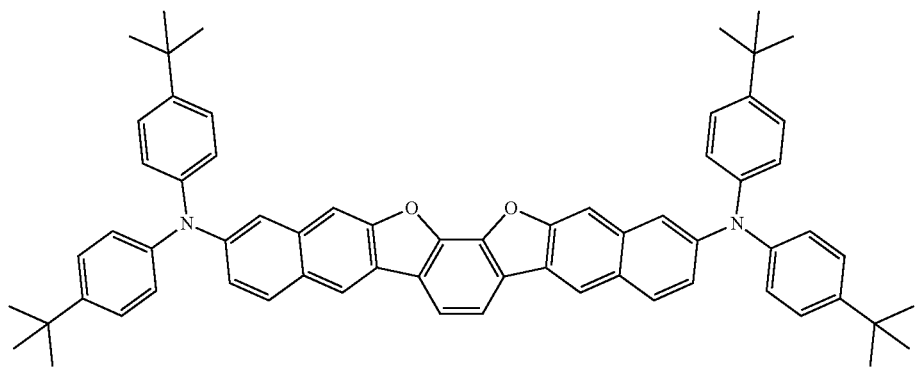
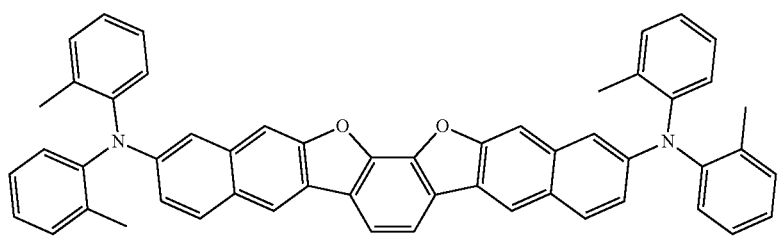

-continued
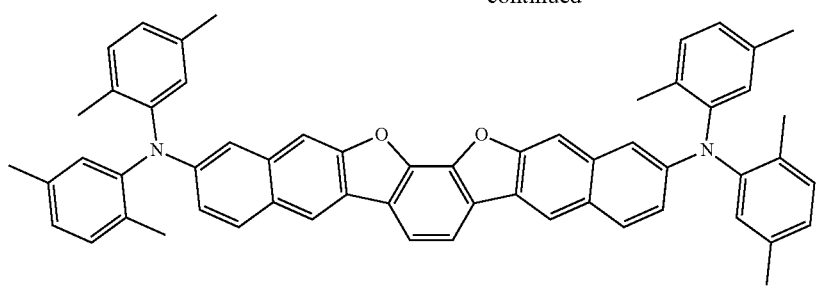
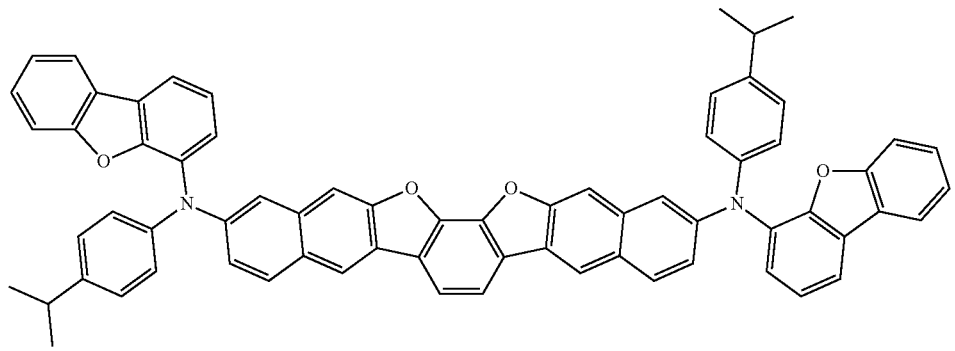
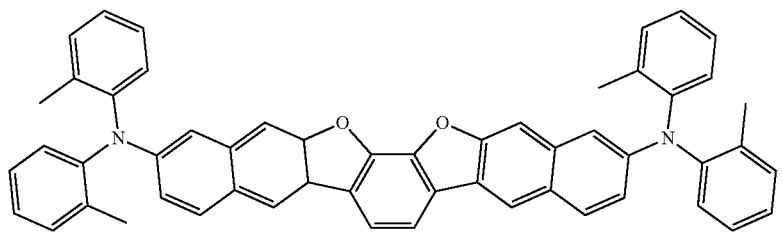
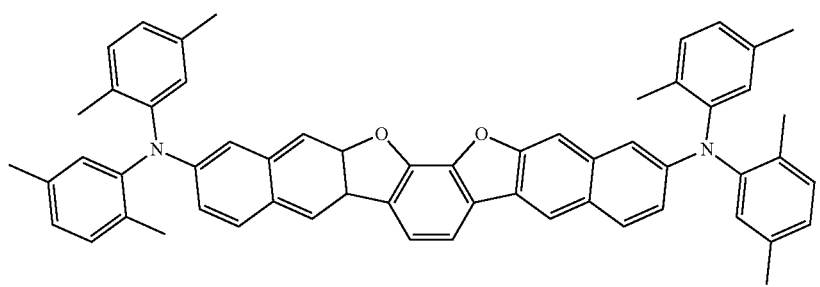
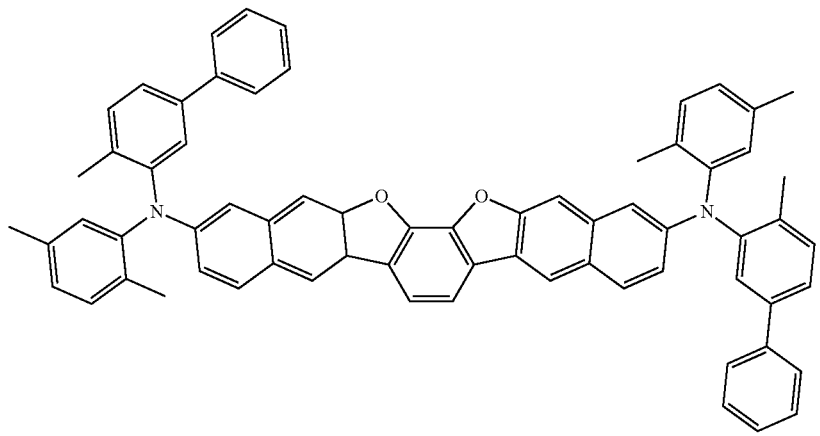

-continued
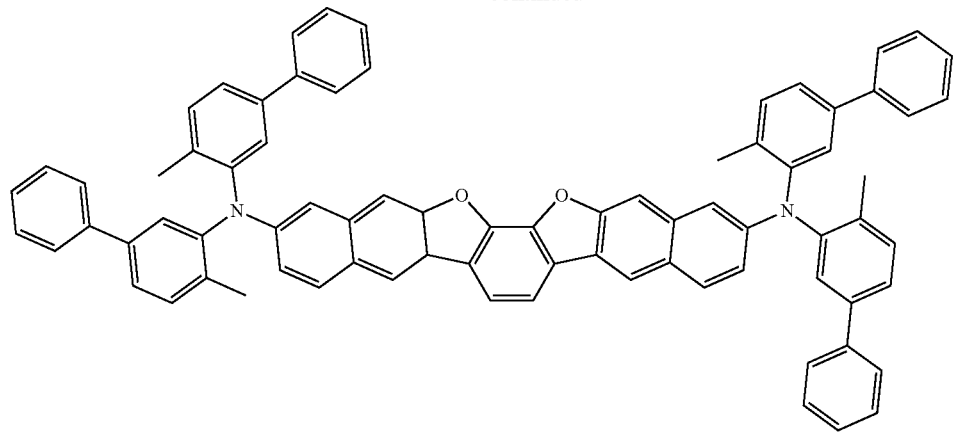
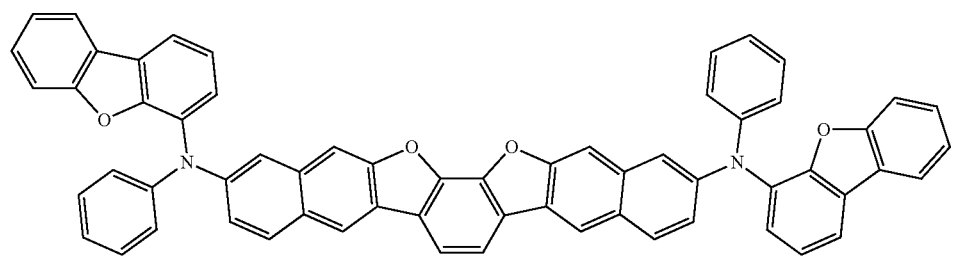
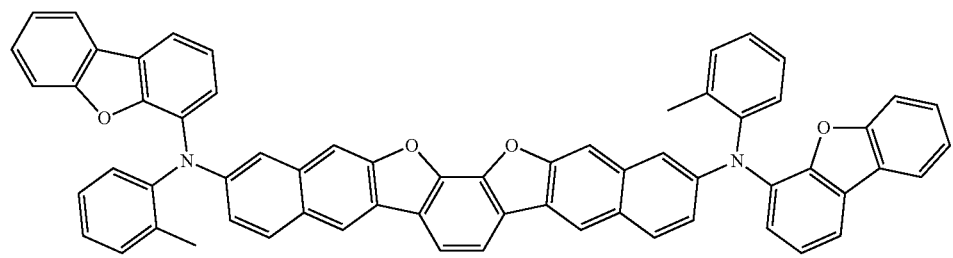
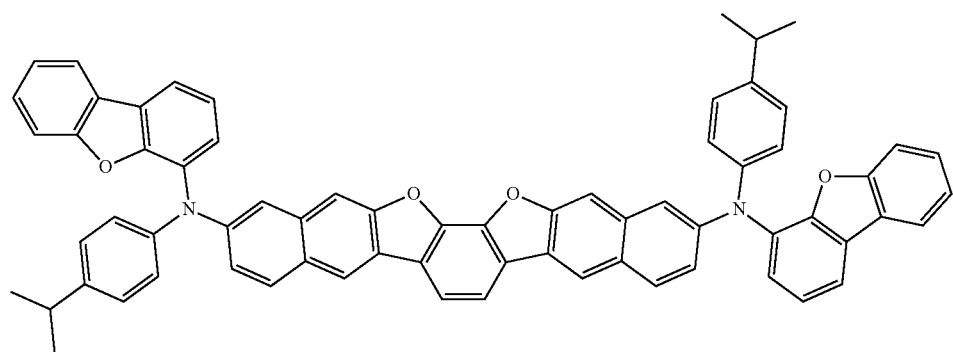
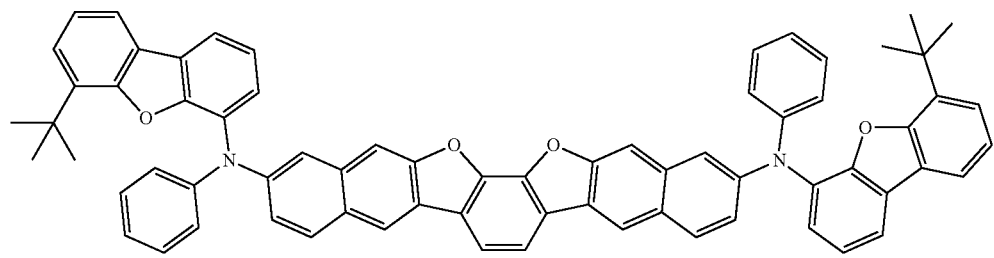

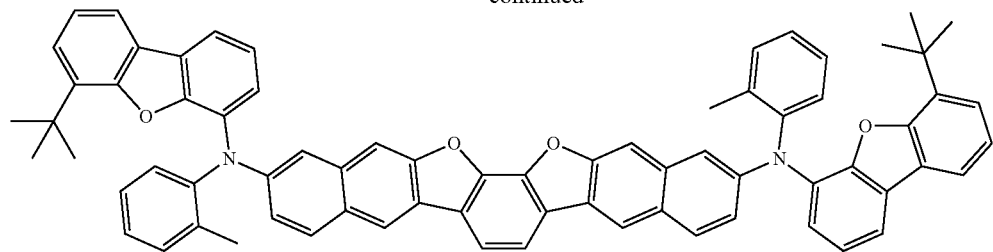
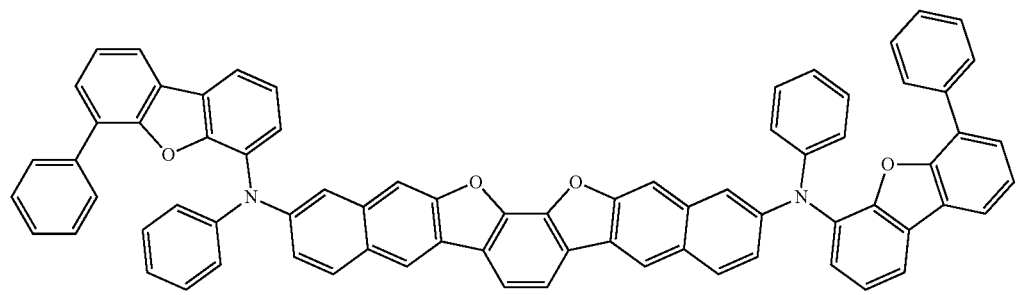
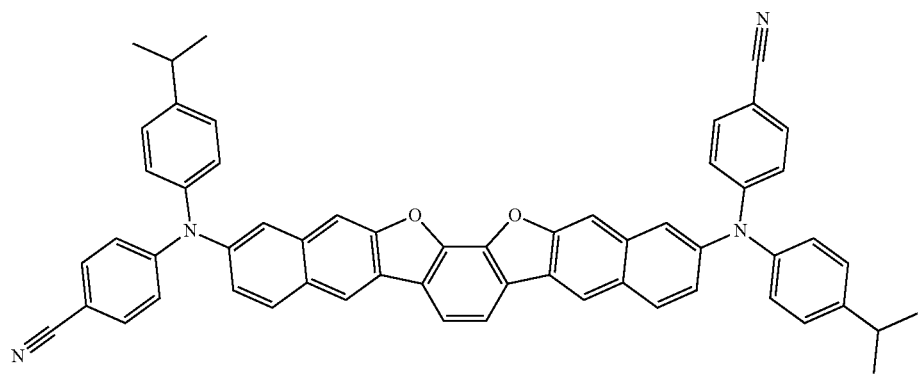
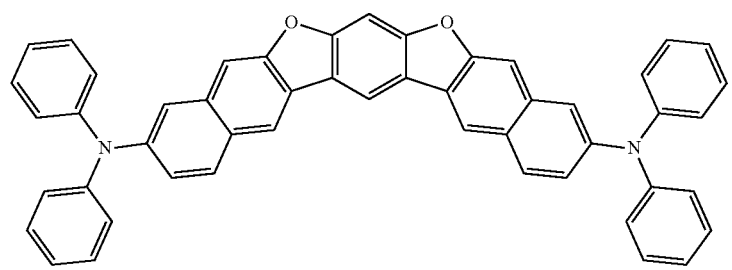
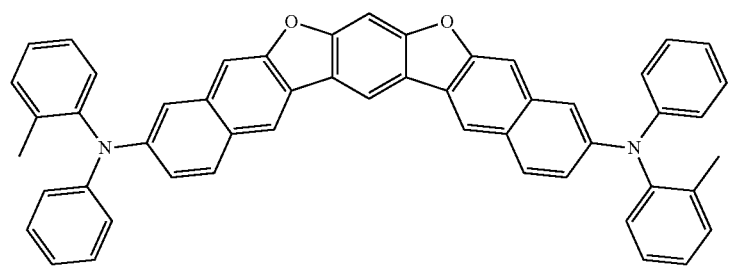

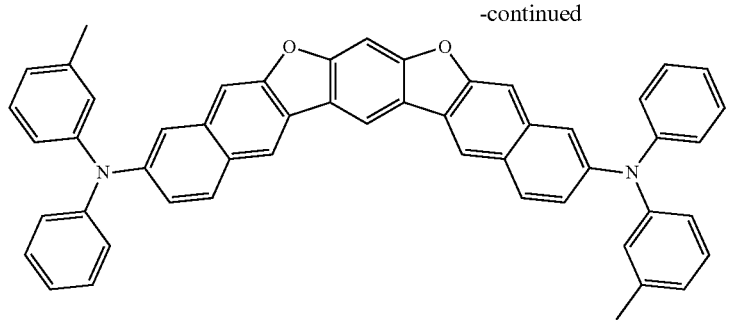
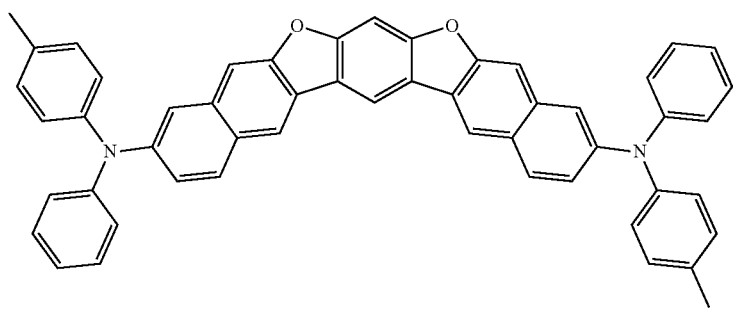
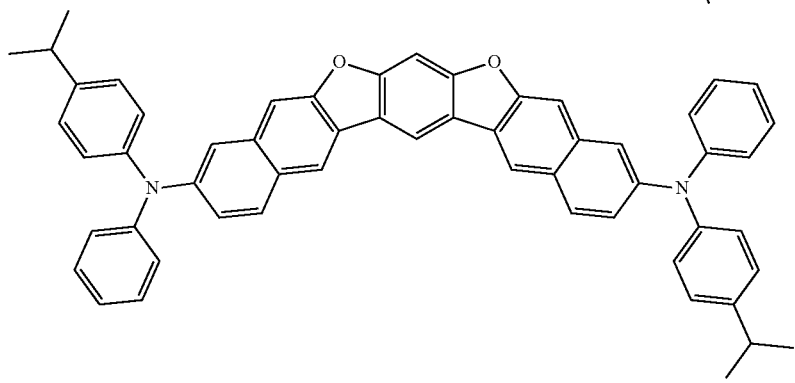
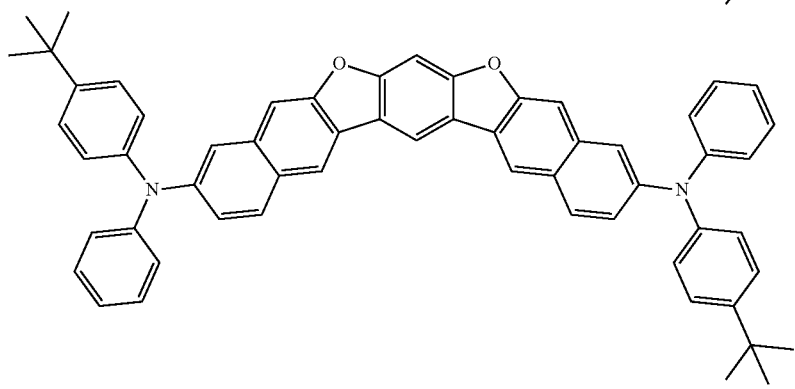
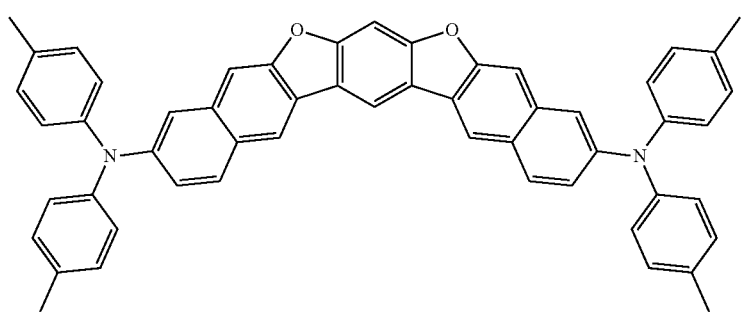

-continued
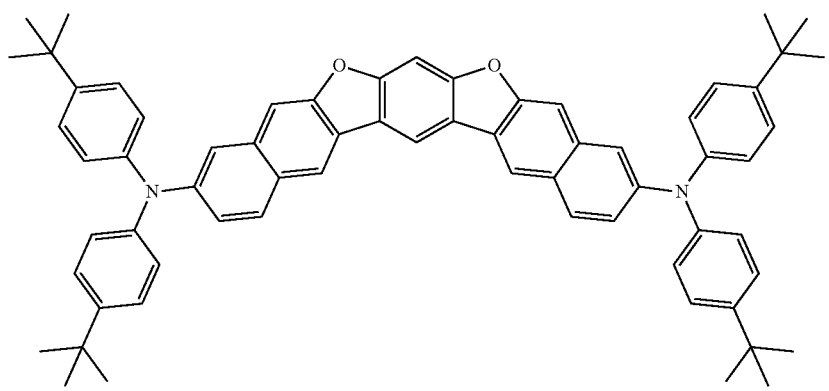
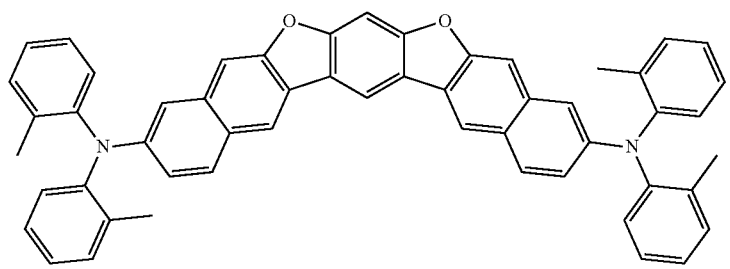
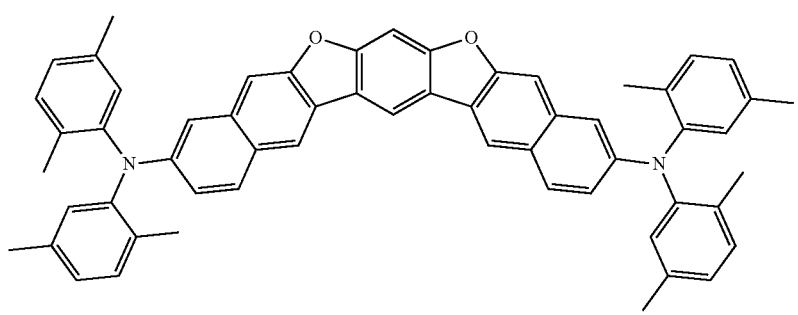
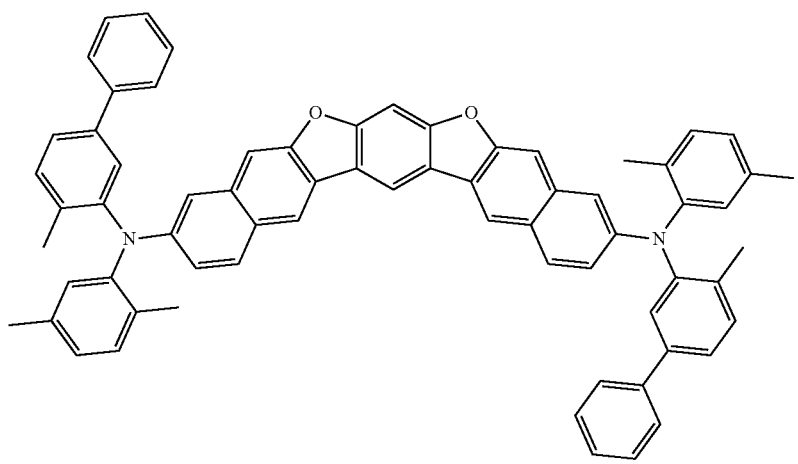

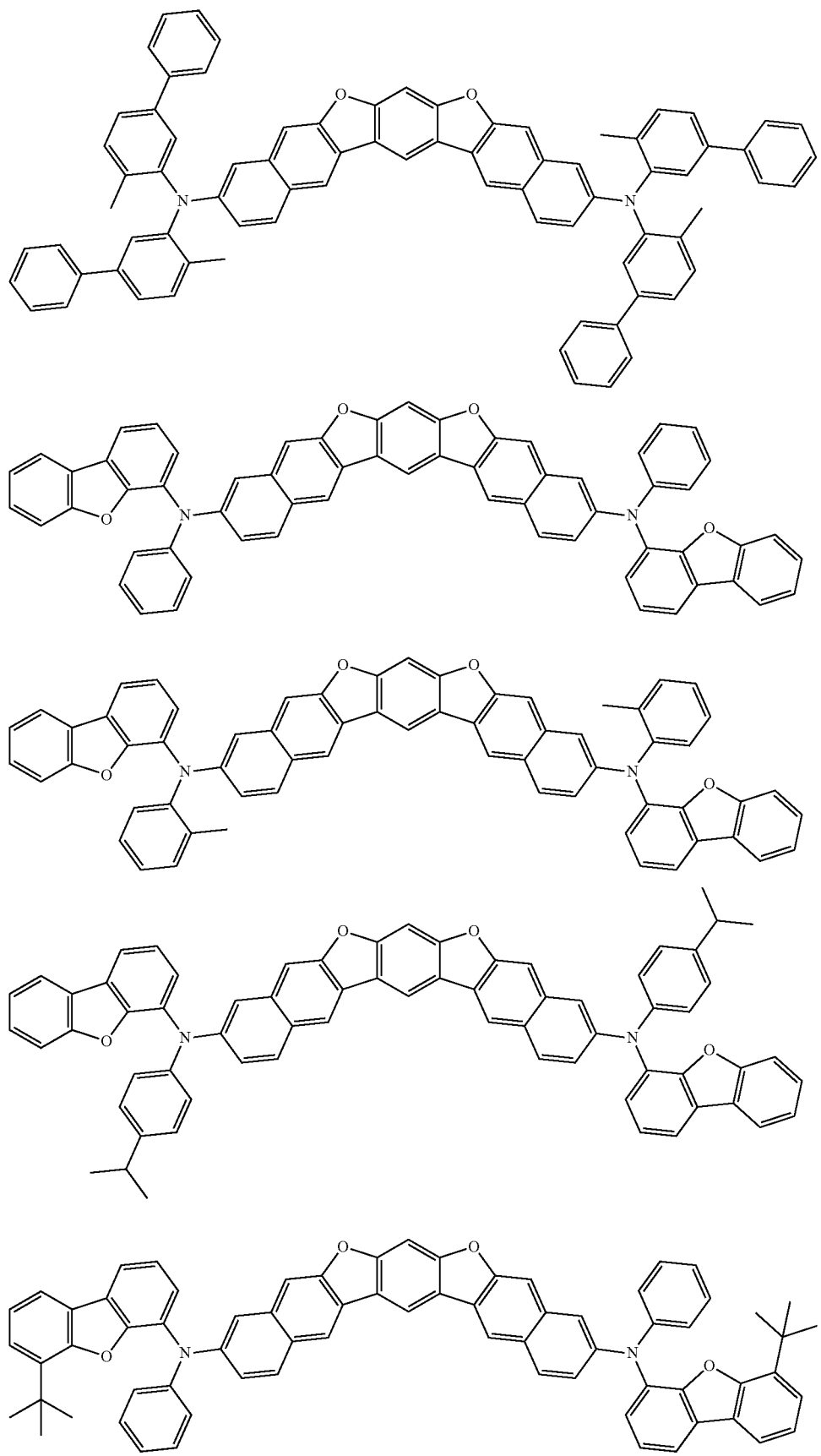

-continued
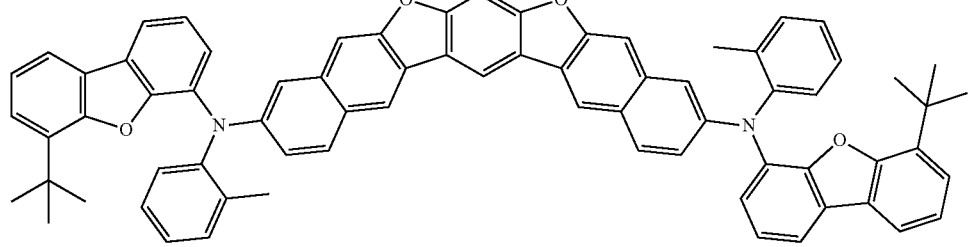
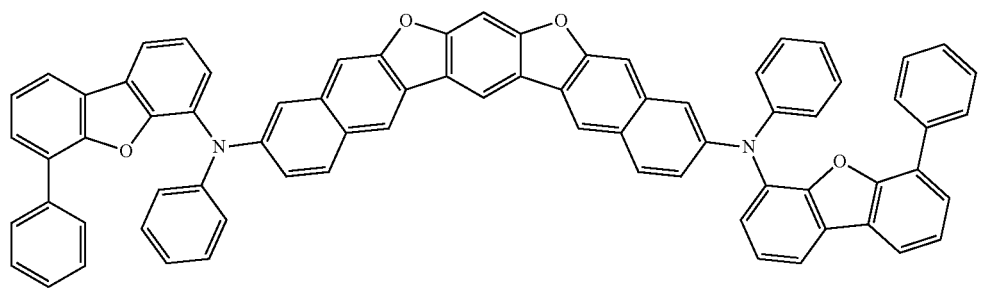
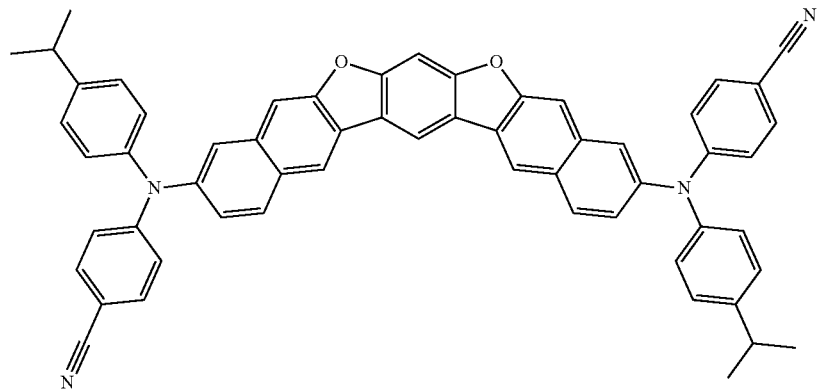
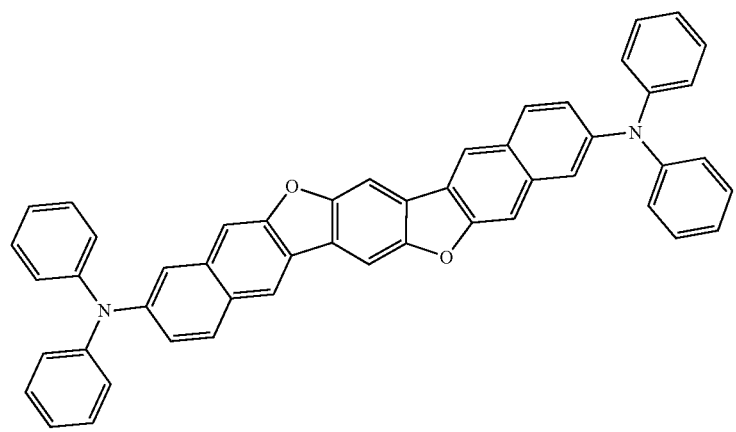

-continued
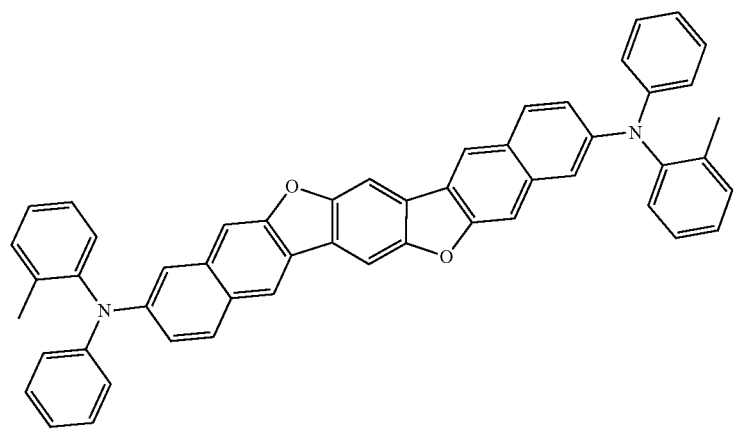
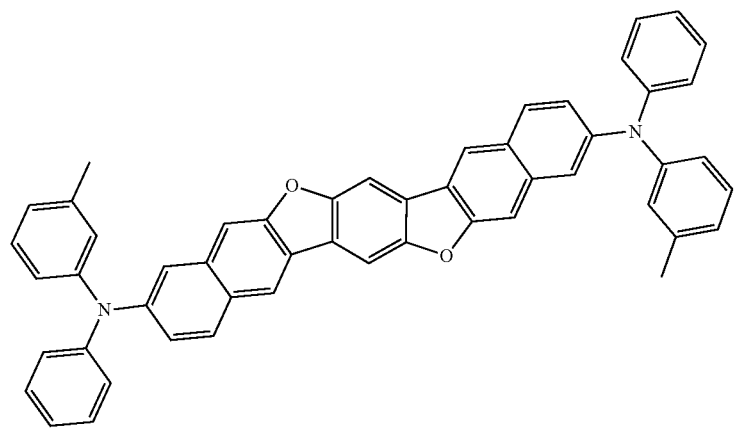
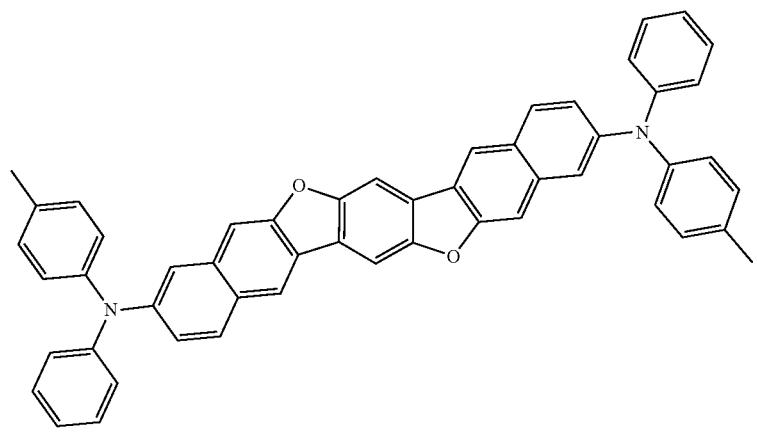
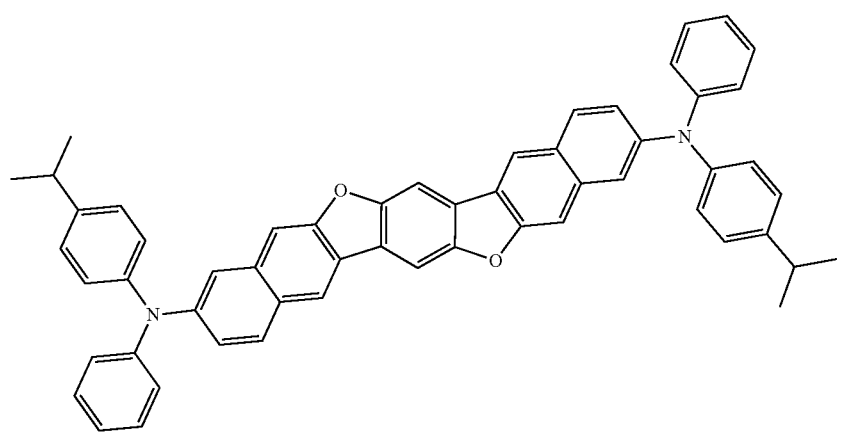

-continued
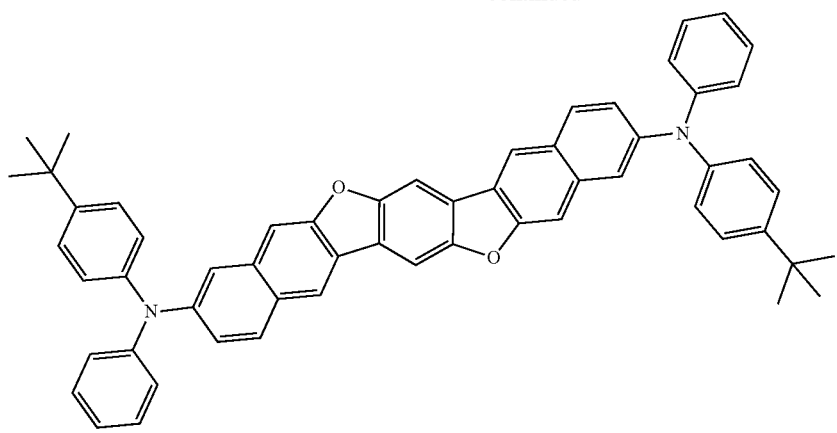
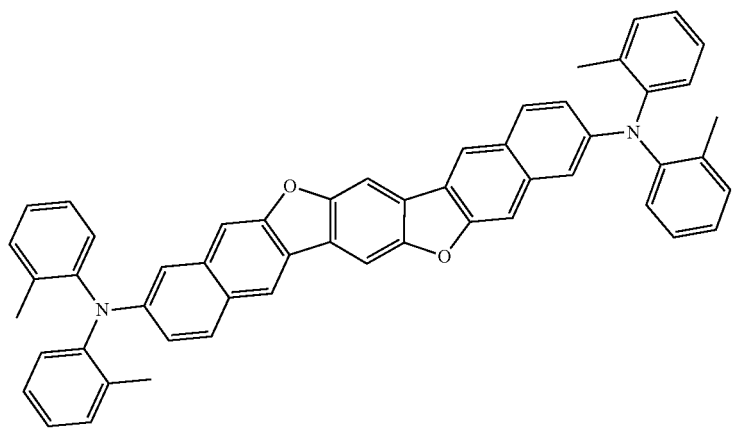
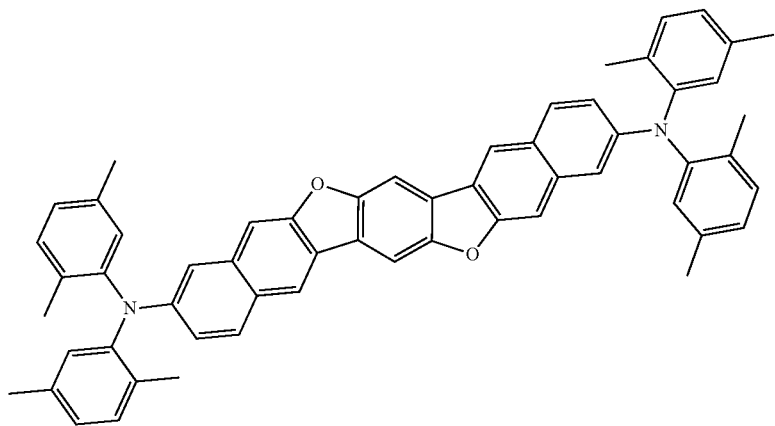
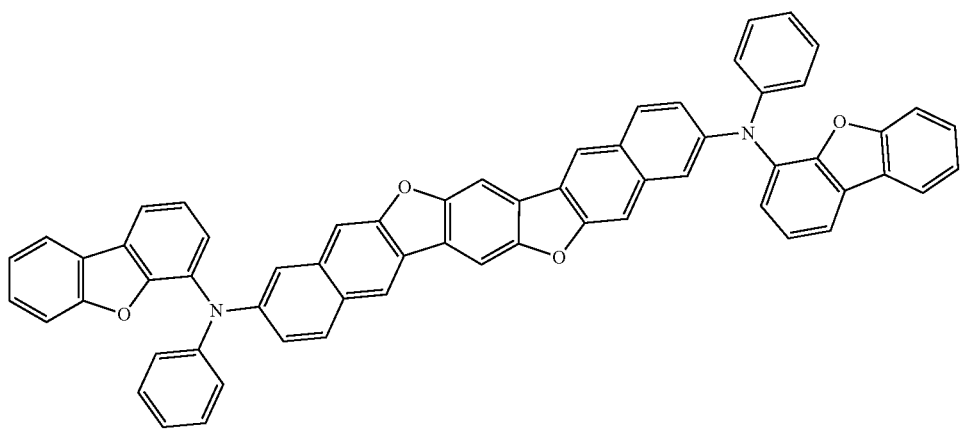

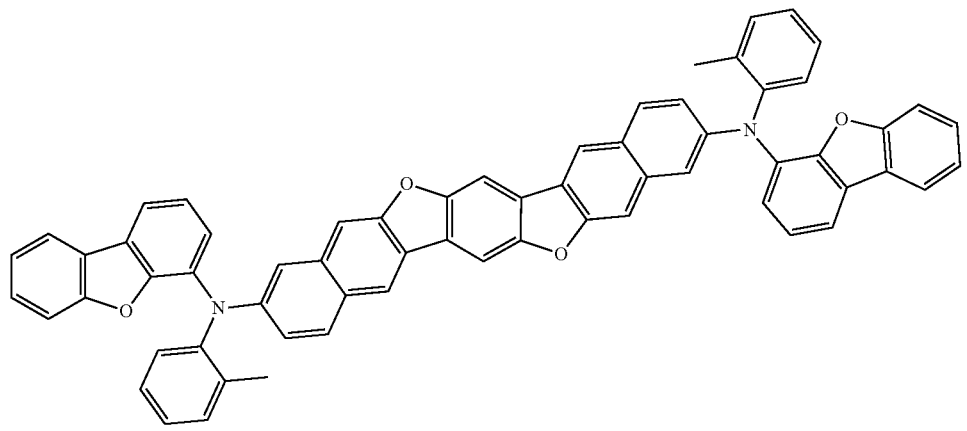
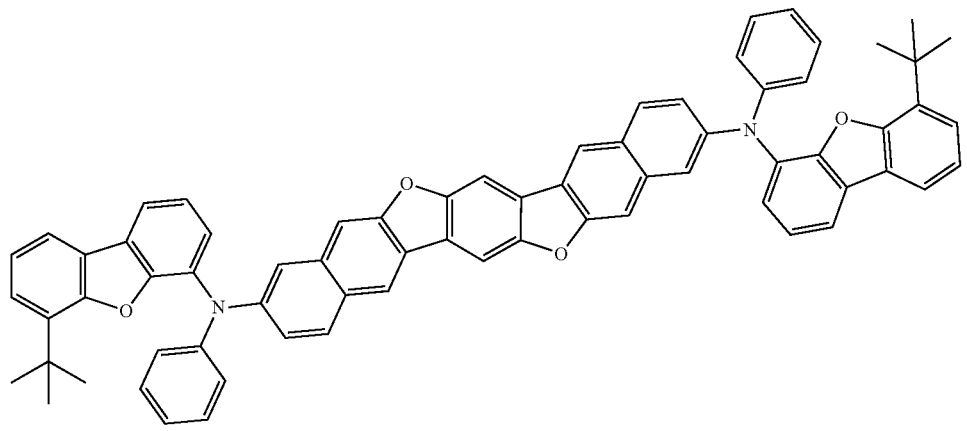
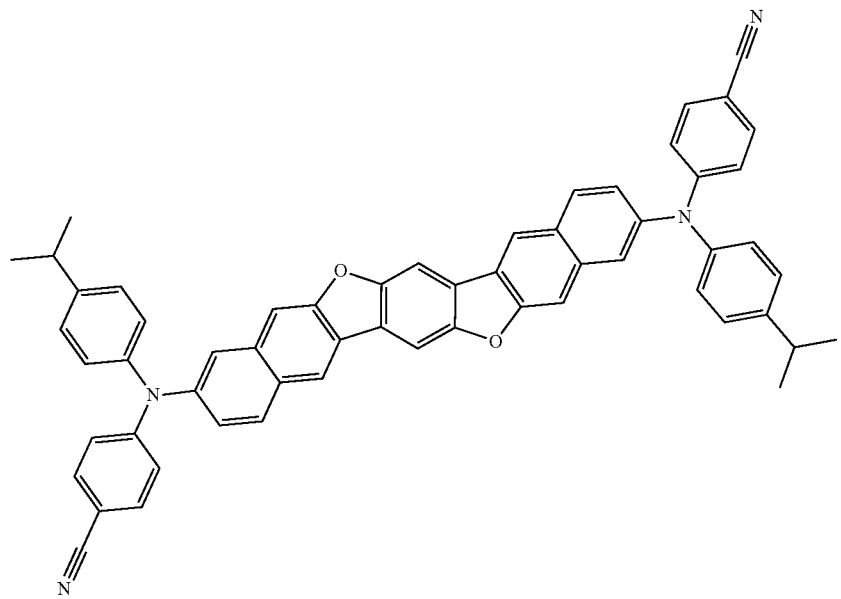

787
788
-continued
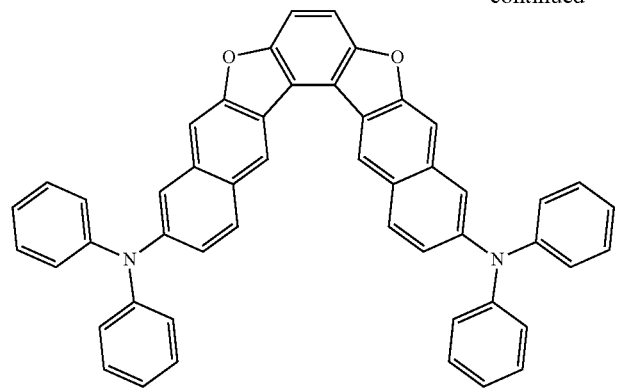
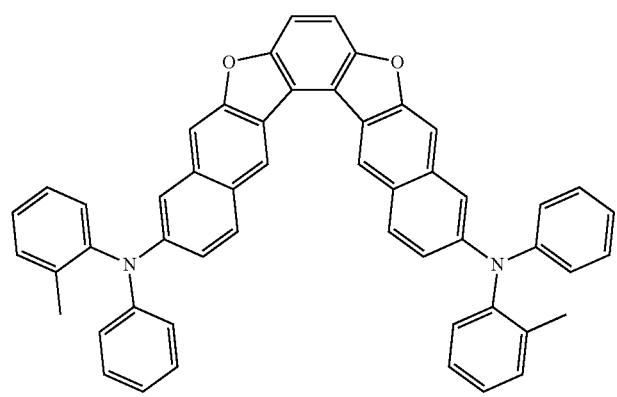
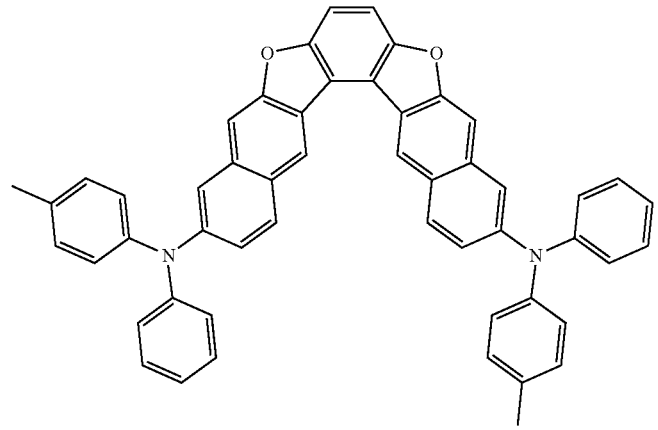
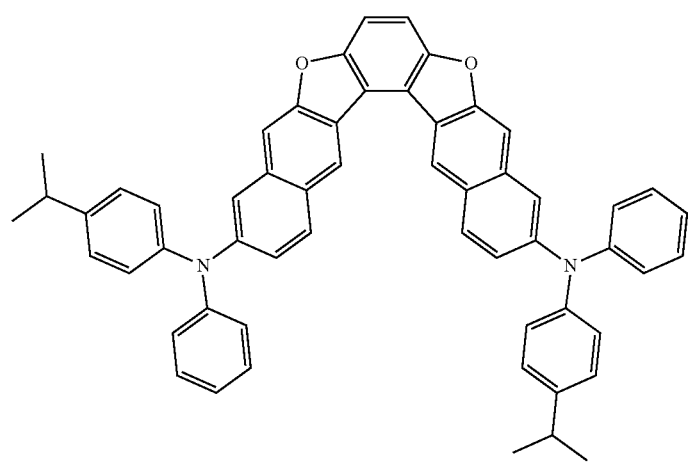

-continued
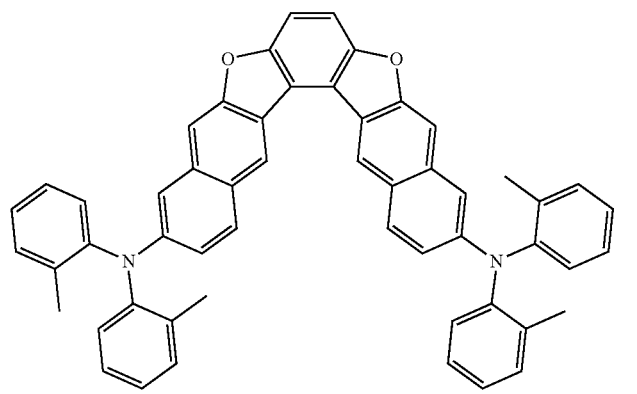
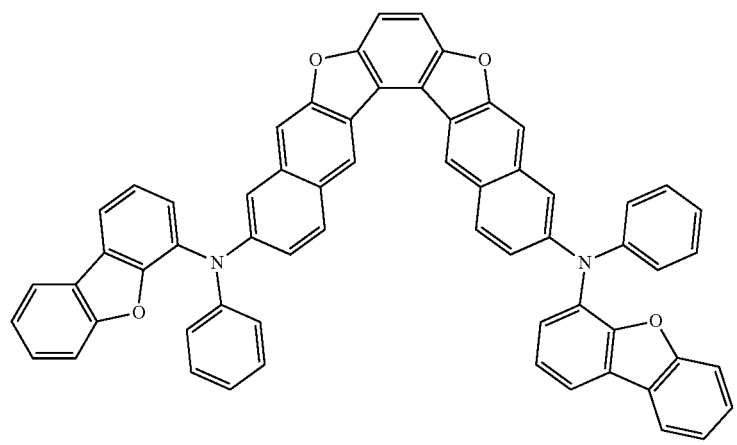
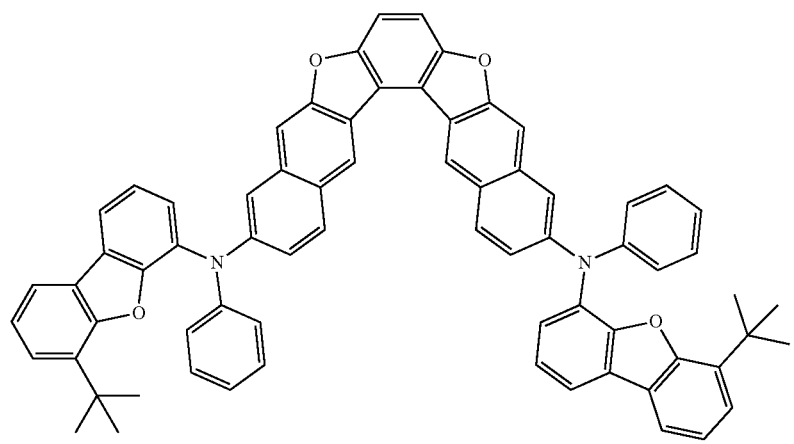
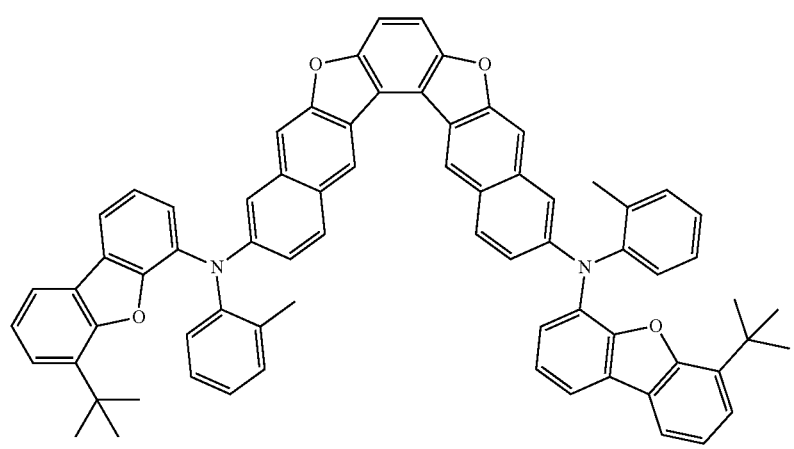

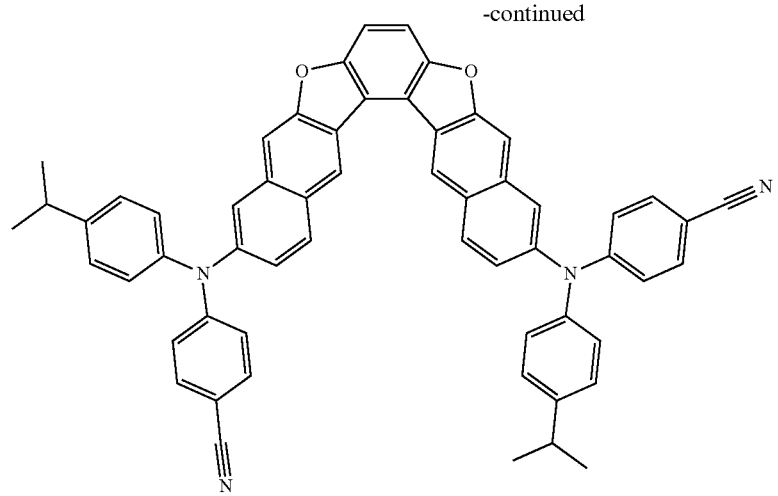
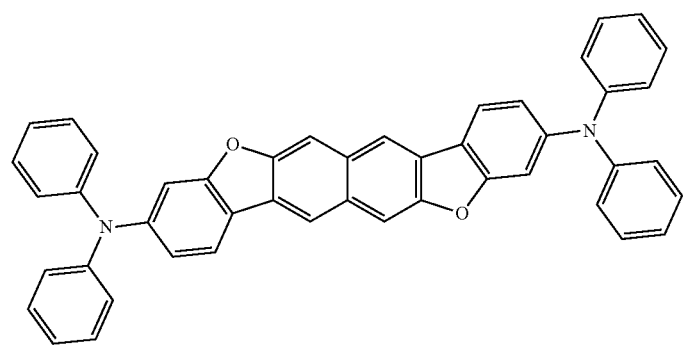
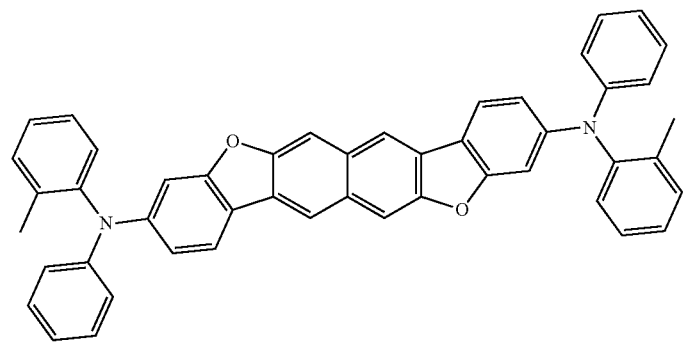
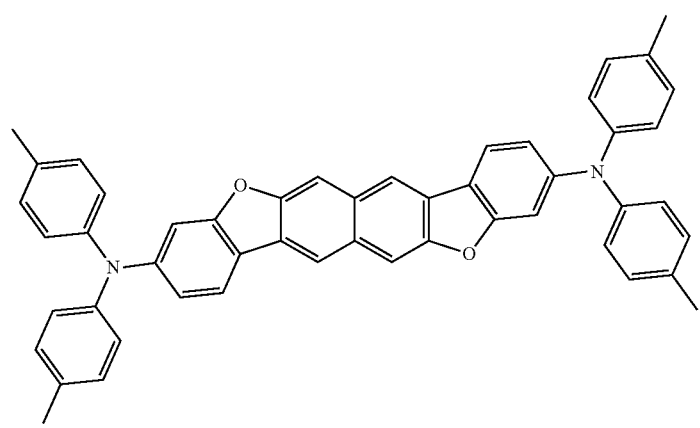

-continued
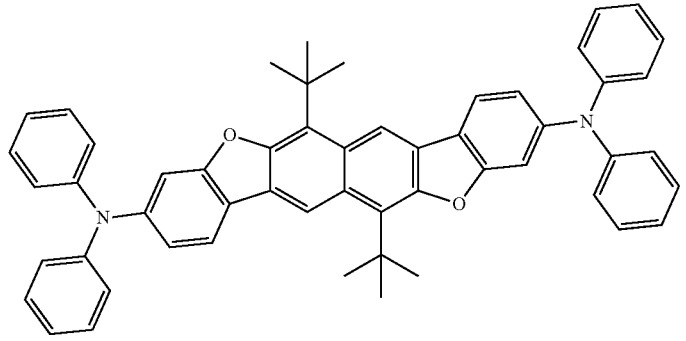
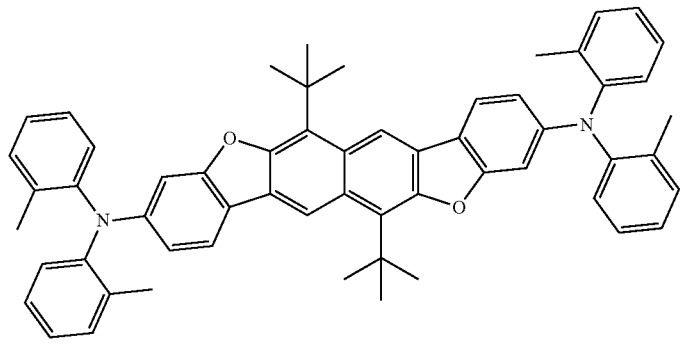
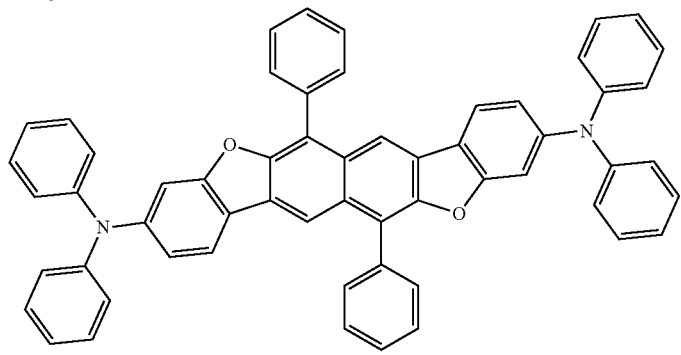
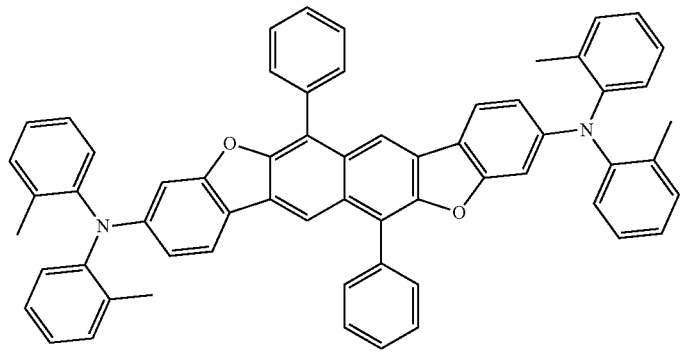
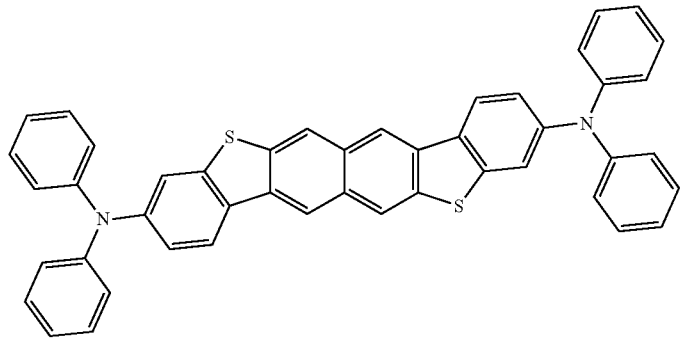

-continued
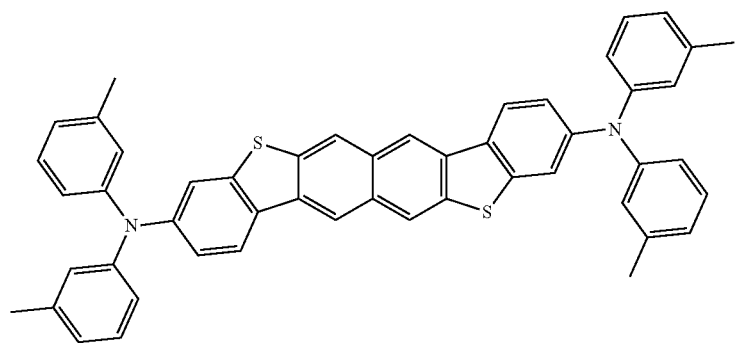
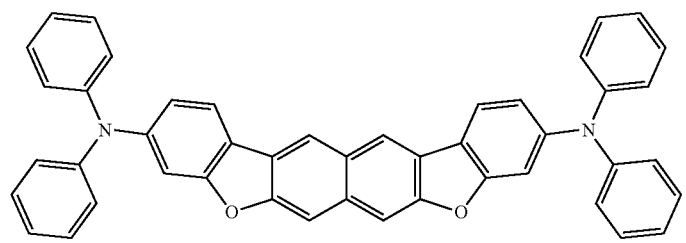
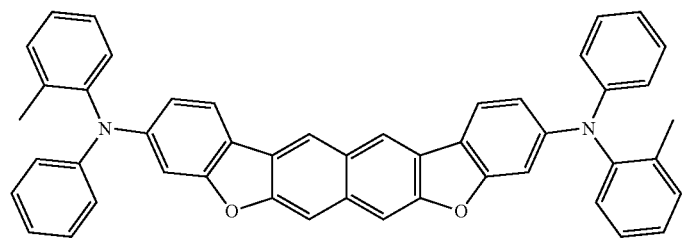
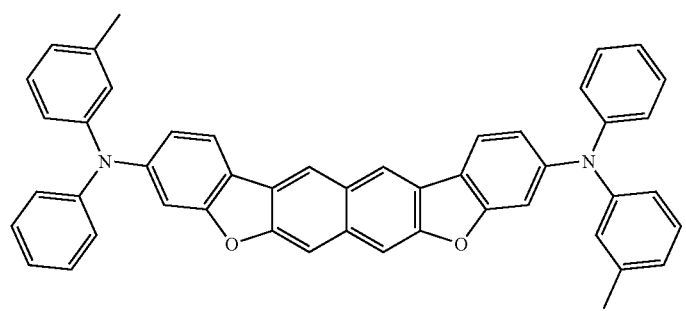
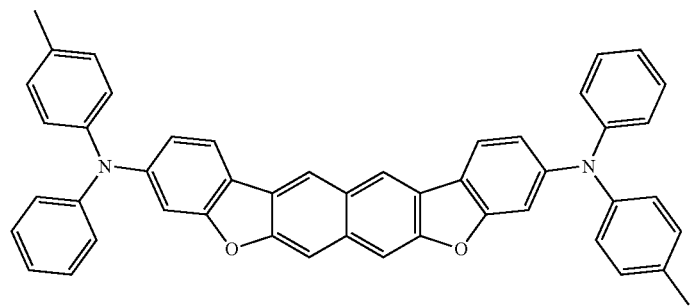

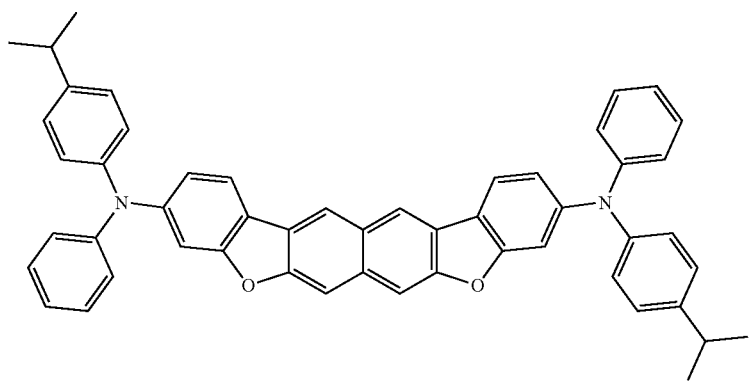
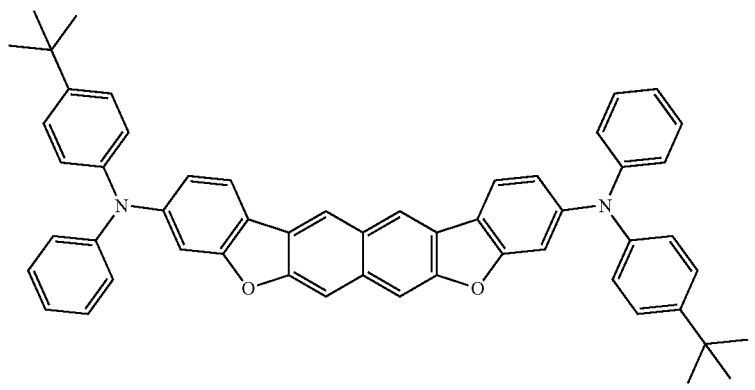
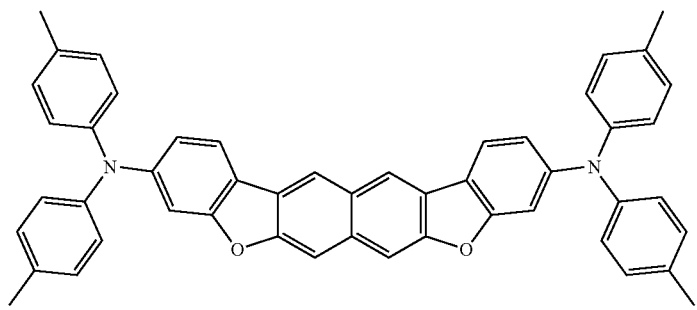
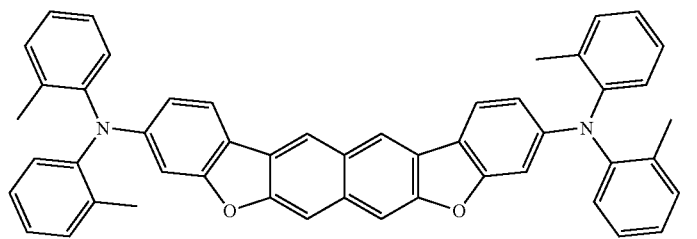
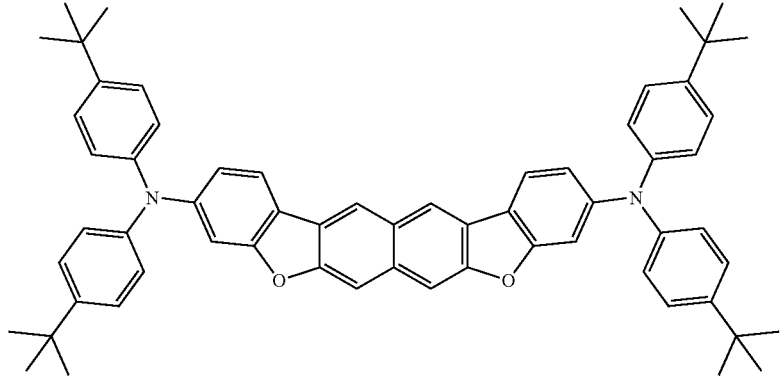

-continued
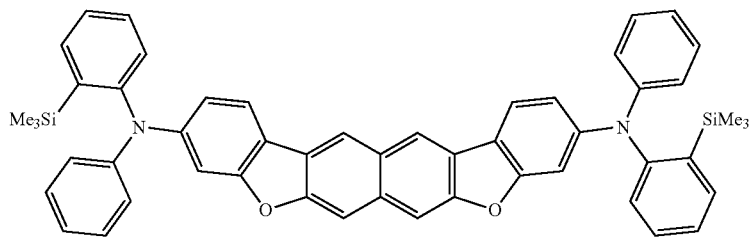
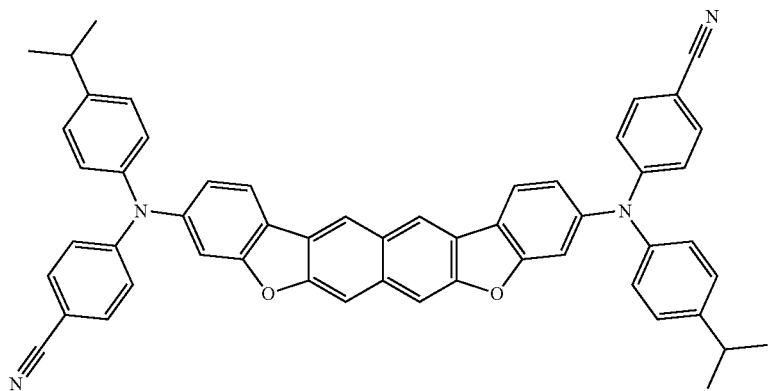
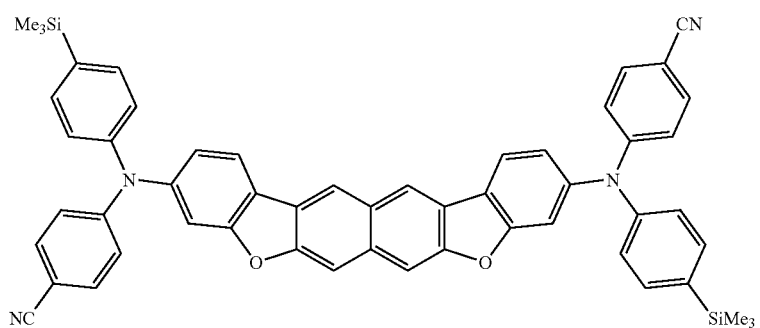
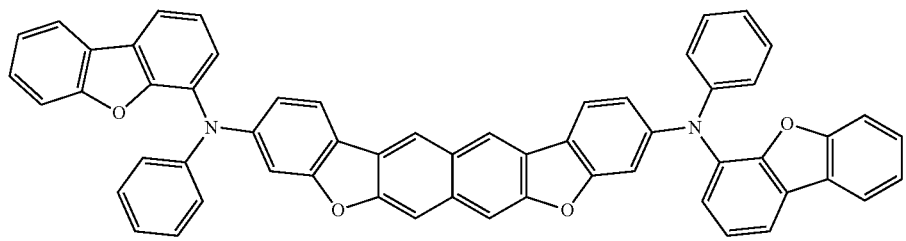
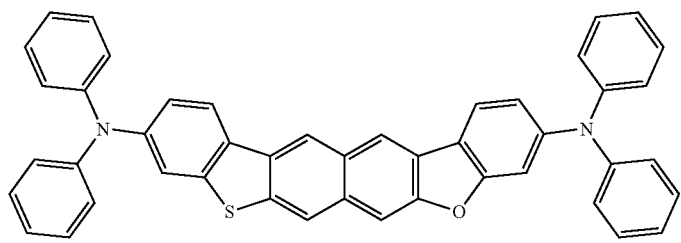

-continued
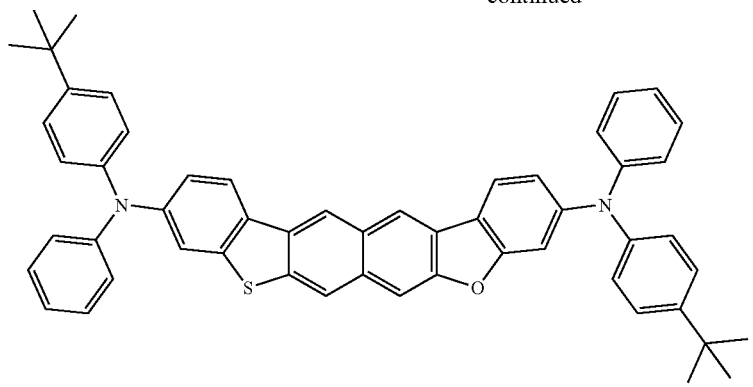
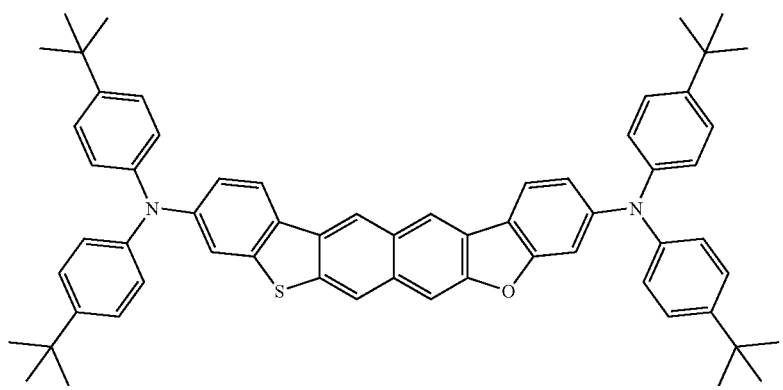
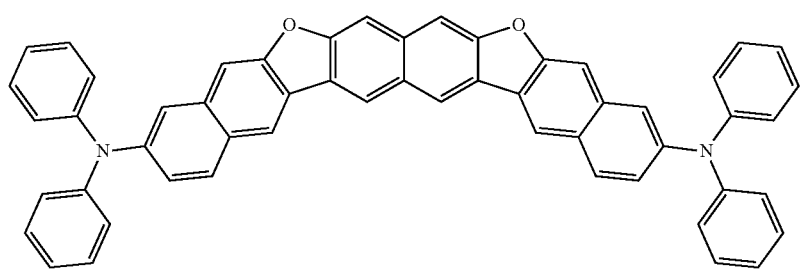
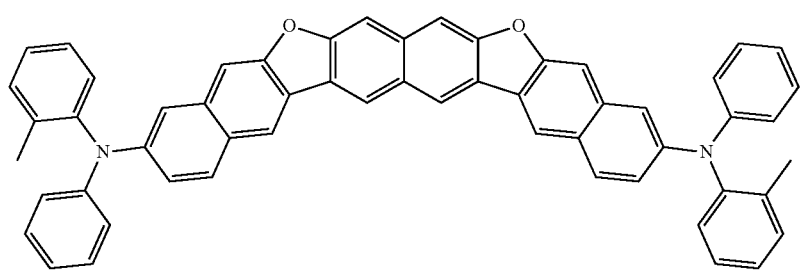
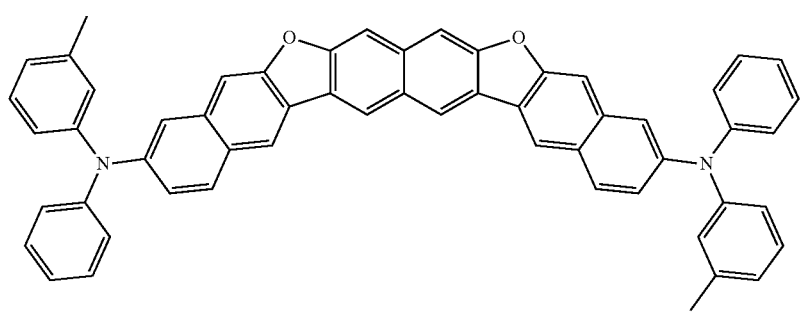

803 804
-continued
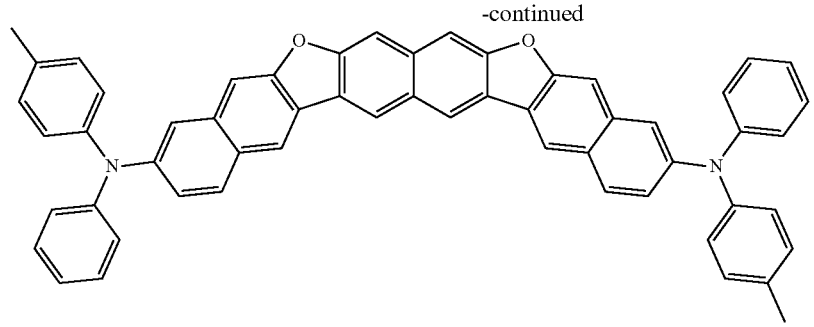
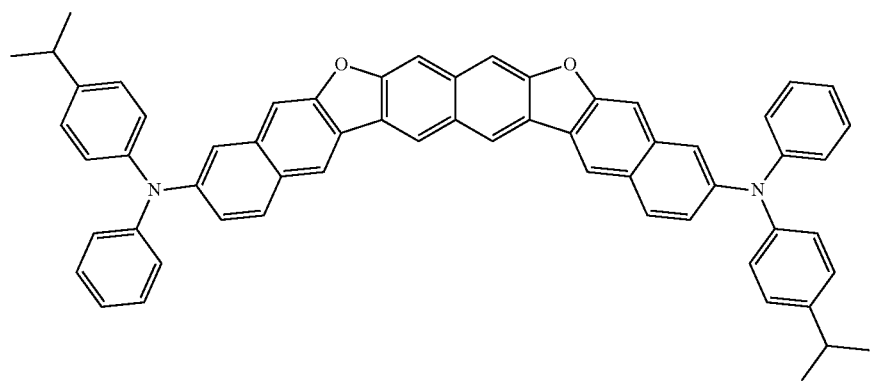
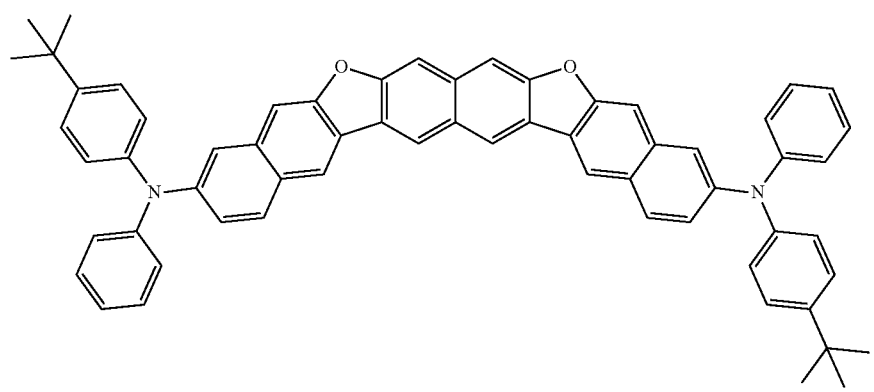
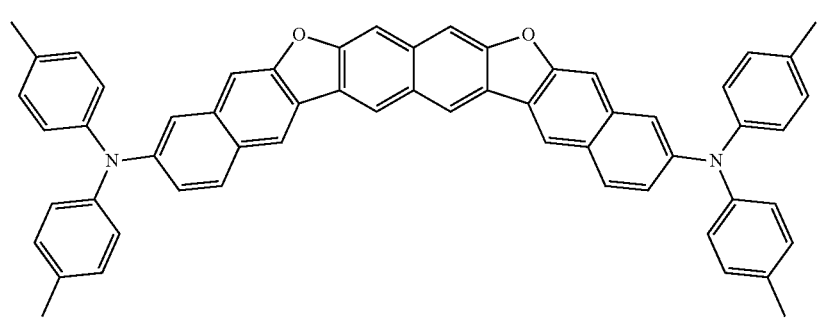
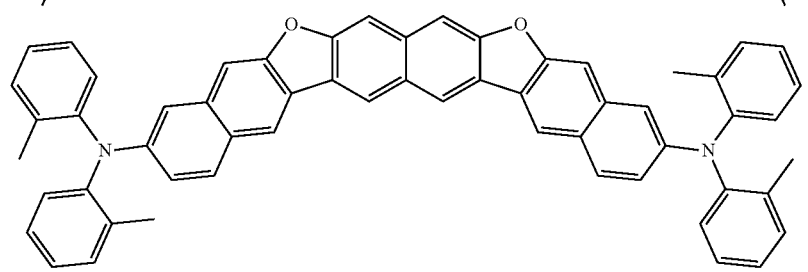

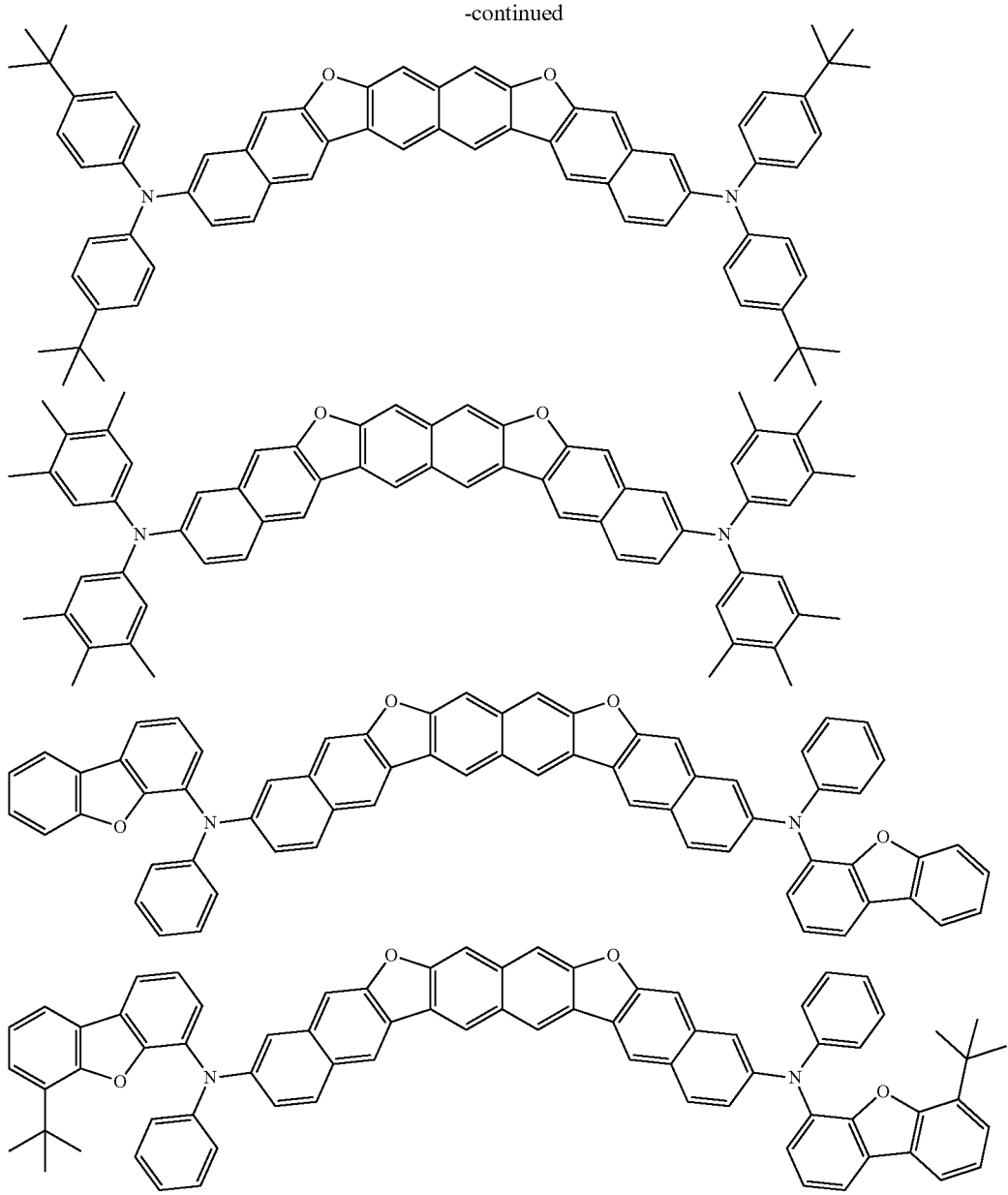

(Compound Represented by Formula (61))

The compound represented by the formula (61) is explained below.

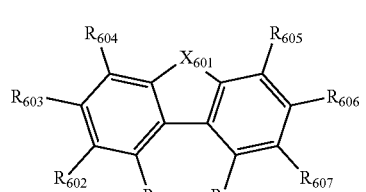

(61)

wherein, in the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

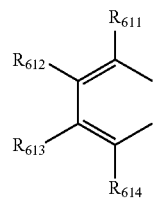

(62)

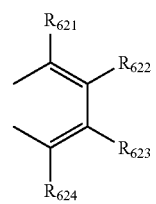

(63)

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

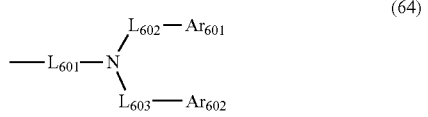

(64)

wherein, in the formula (64), $Ar_{601}$ and $Ar_{602}$ are independently a substituted or unsubstituted aryl group having 6 to 50 ring carbon atoms, or a substituted or unsubstituted monovalent heterocyclic group having 5 to 50 ring atoms;

$L_{601}$ to $L_{603}$ are independently a single bonded, a substituted or unsubstituted arylene group having 6 to 30 ring carbon atoms, a substituted or unsubstituted divalent heterocyclic group having 5 to 30 ring atoms, or a divalent linking group formed by bonding 2 to 4 above mentioned groups;

In the formula (61), positions at which the divalent group represented by the formula (62) and the divalent group represented by the formula (63) are formed are not limited, and said groups can be formed at possible positions in $R_{601}$ to $R_{608}$.

In one embodiment, the compound represented by the formula (61) is represented by any one of the following formulas (61-1) to (61-6).

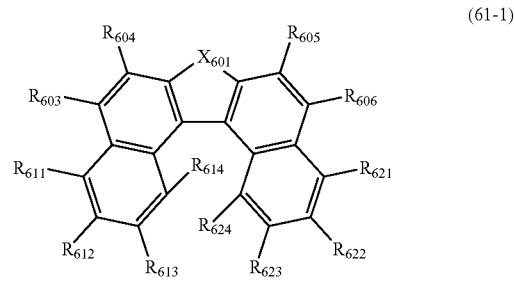
(61-1)

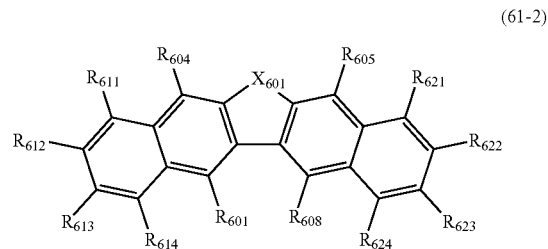
(61-2)

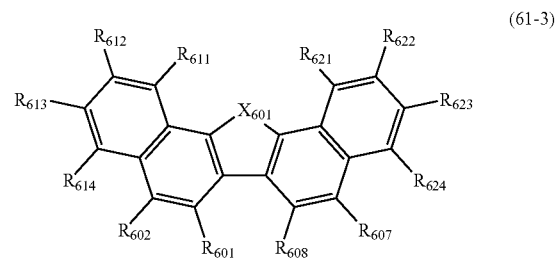
(61-3)

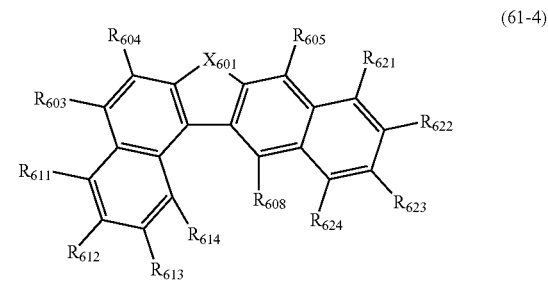
(61-4)

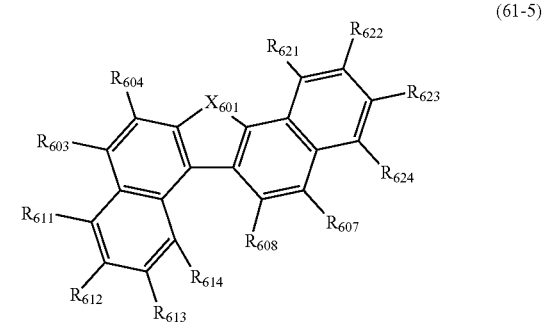
(61-5)

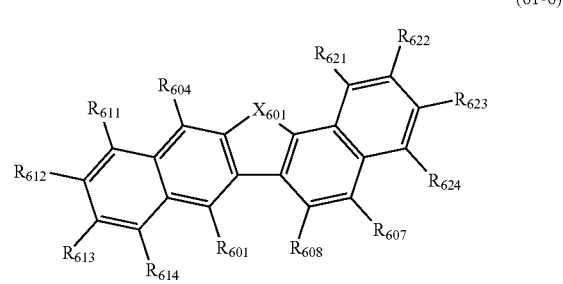
(61-6)

wherein in the formulas (61-1) to (61-6), $X_{601}$ is as defined in the formula (61);

at least two of $R_{601}$ to $R_{624}$ are monovalent groups represented by the formula (64);

$R_{601}$ to $R_{624}$ that are not monovalent groups represented by the formula (64) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In one embodiment, the compound represented by the formula (61) is represented by any one of the following formulas (61-7) to (61-18).

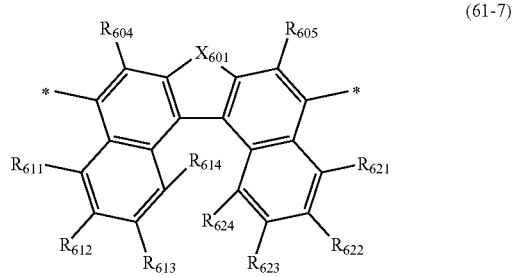
(61-7)

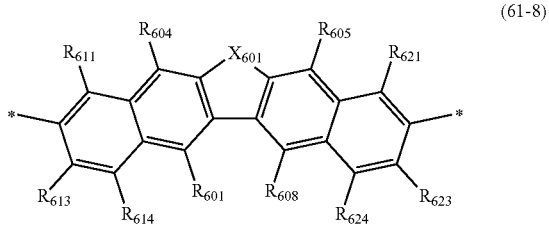
(61-8)

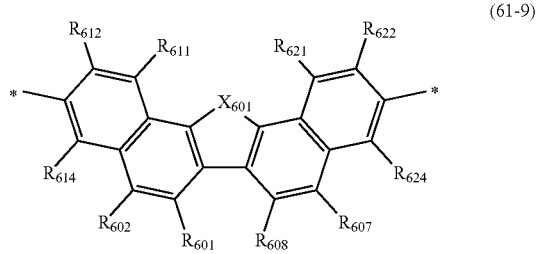
(61-9)

-continued

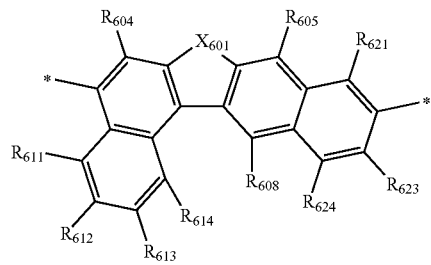
(61-10)

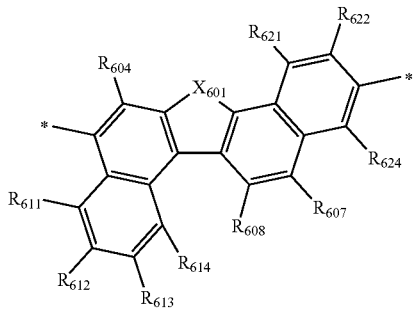
(61-11)

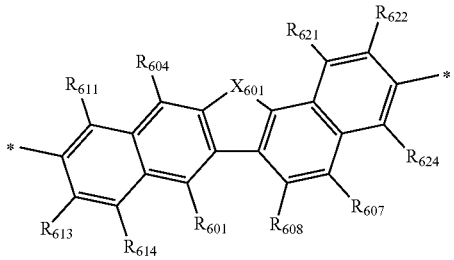
(61-12)

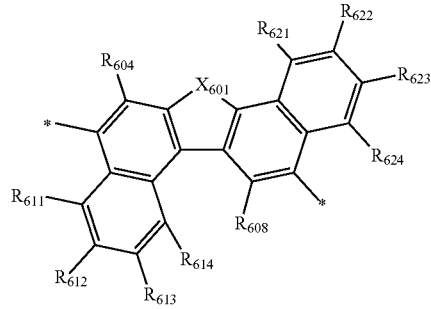
(61-13)

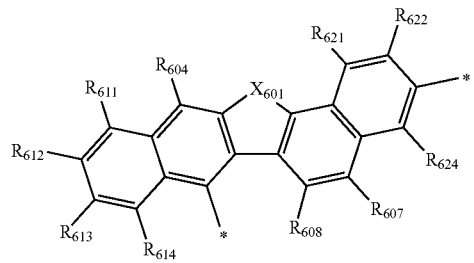
(61-14)

-continued (61-15)
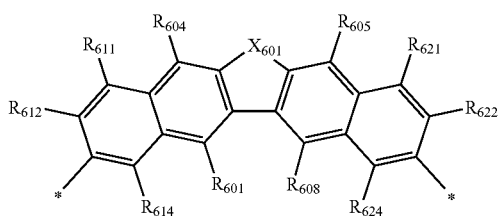

(61-16)
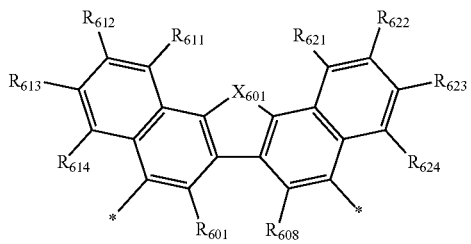

(61-17)
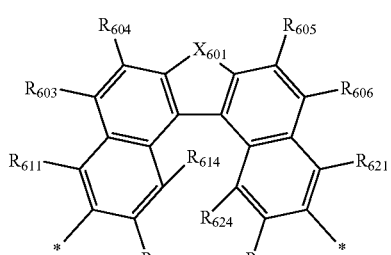

(61-18)
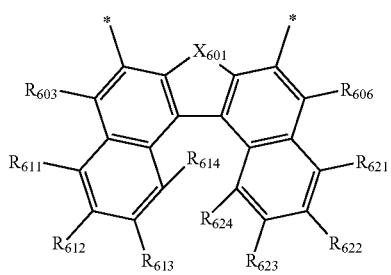

wherein in the formulas (61-7) to (61-18), $X_{601}$ is as defined in the formula (61); * is a single bond bonding to the monovalent group represented by the formula (64); and $R_{601}$ to $R_{624}$ are the same as $R_{601}$ to $R_{624}$ that are not monovalent groups represented by the formula (64).

$R_{601}$ to $R_{608}$ which do not form the divalent group represented by the formula (62) and (63) and are not monovalent groups represented by the formula (64), and $R_{611}$ to $R_{614}$ and $R_{621}$ to $R_{624}$ which are not monovalent groups represented by the formula (64) are preferably independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

The monovalent group represented by the formula (64) is preferably represented by the following formulas (65) or (66).

(65)
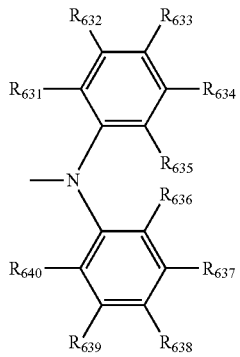

wherein in the formula (65), $R_{631}$ to $R_{640}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

(66)
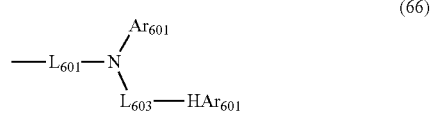

wherein in the formula (66), $Ar_{601}$, $L_{601}$ and $L_{603}$ are as defined in the formula (64); and $HAr_{601}$ is a structure represented by the following formula (67);

(67)
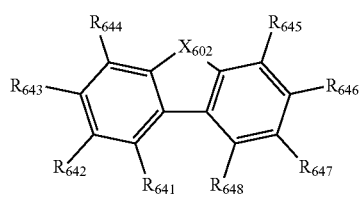

wherein in the formula (67) $X_{602}$ is an oxygen atom or a sulfur atom;

any one of R$_{641}$ to R$_{648}$ is a single bond bonding to L$_{603}$;
R$_{641}$ to R$_{648}$ which are not single bonds are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
R$_{901}$ to R$_{907}$ are as defined in the formula (1).)

As specific example of the compound represented by the formula (61), in addition to the compounds described in WO2014/104144, the following compounds can be given, for example.

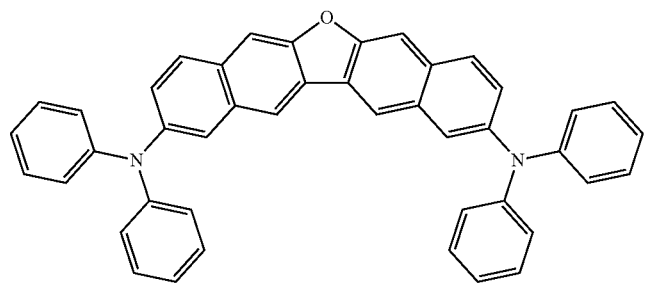

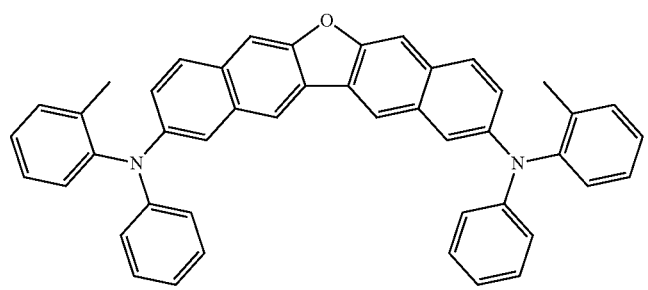

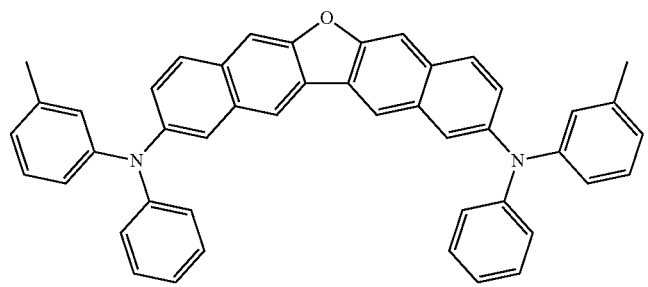

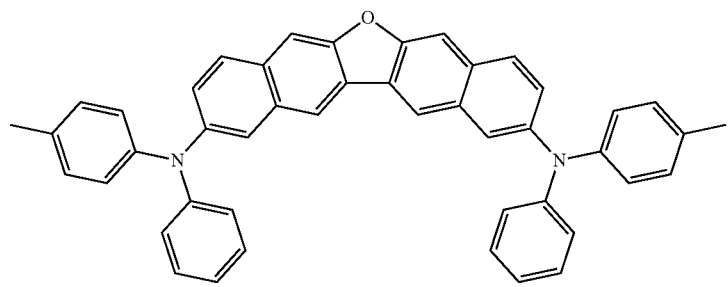

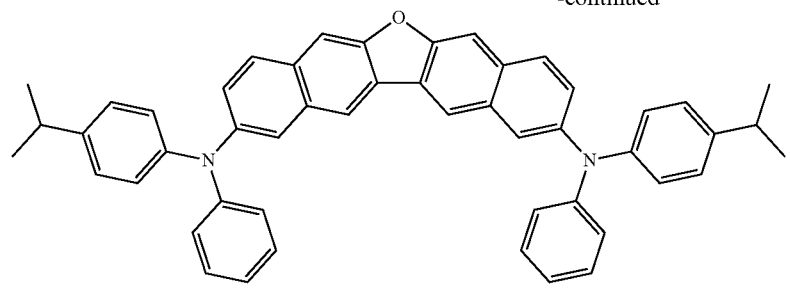
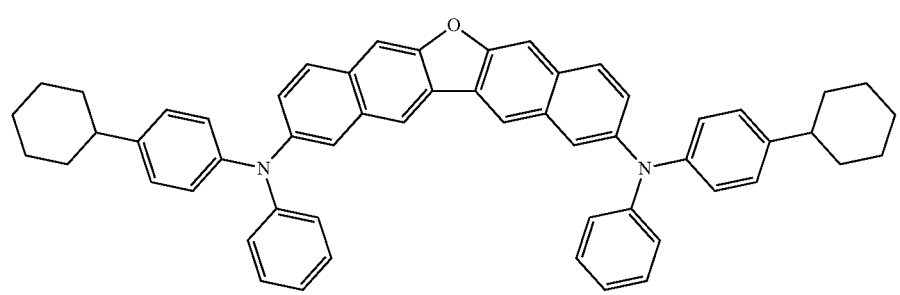
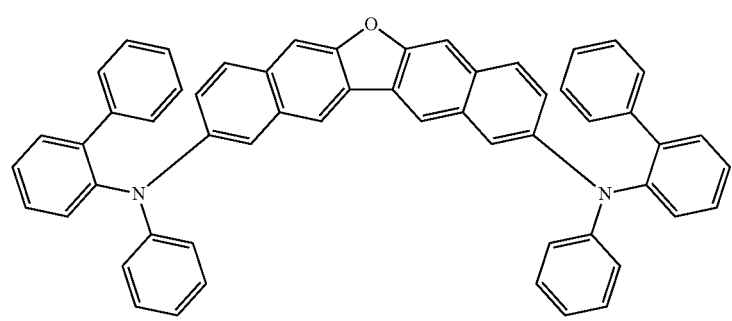
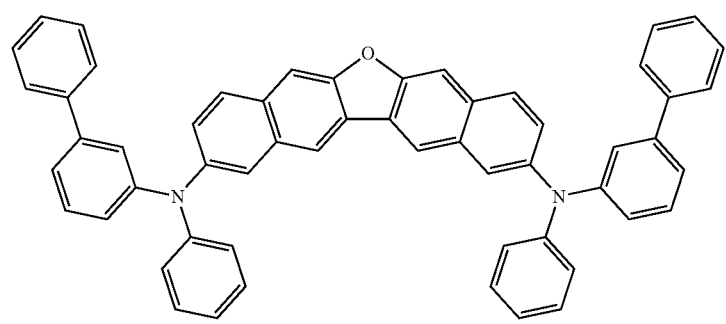
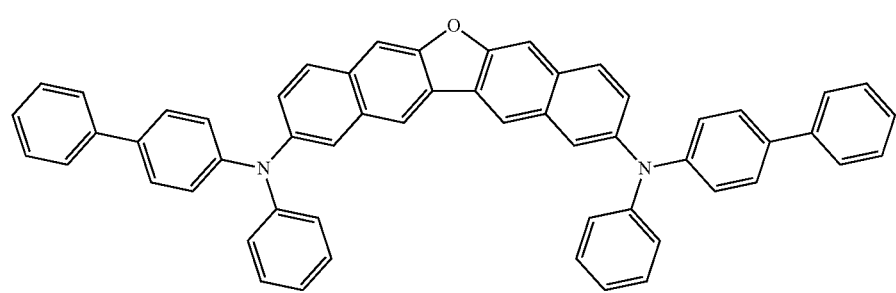

-continued
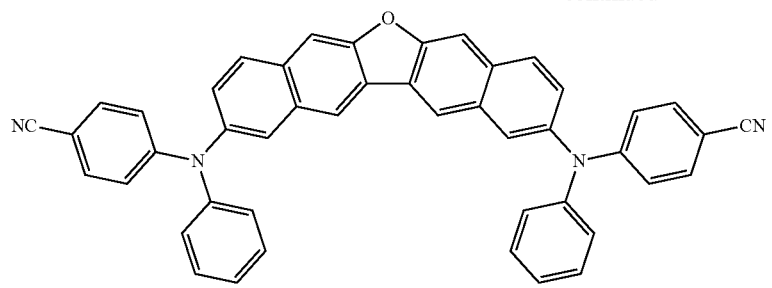
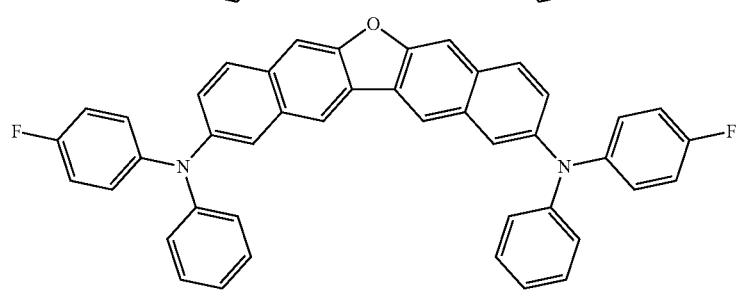
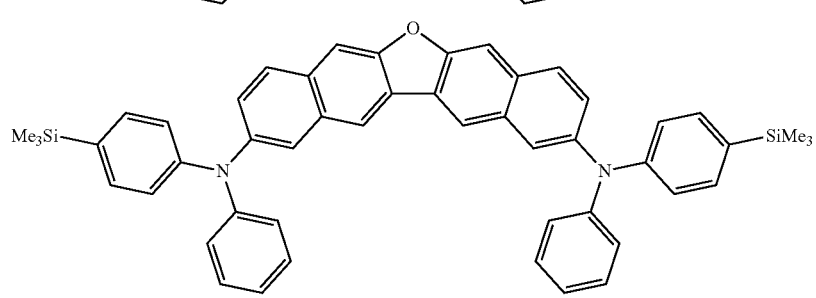
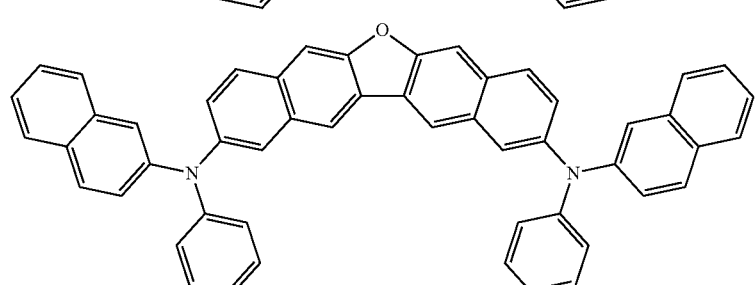
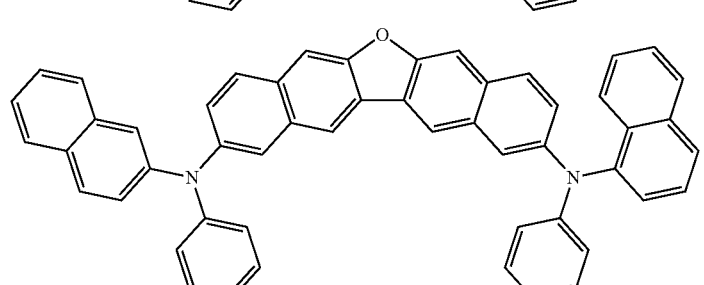
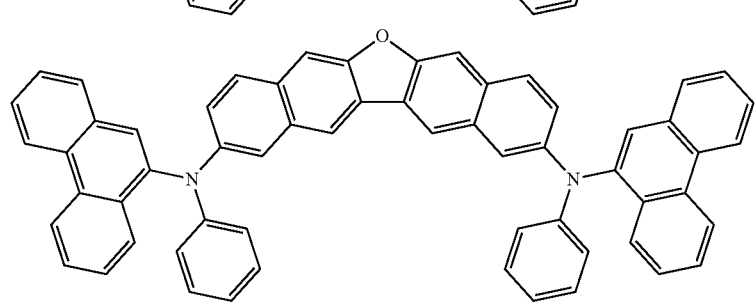

-continued
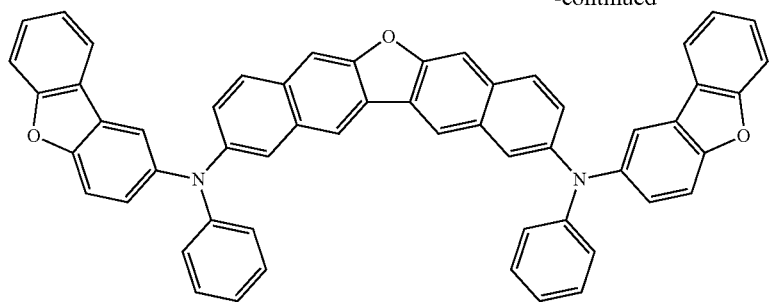
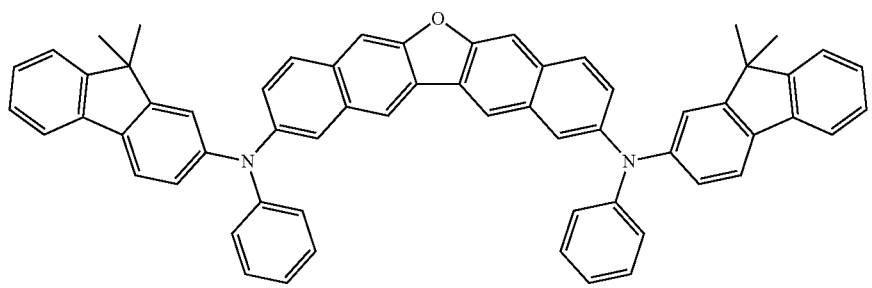
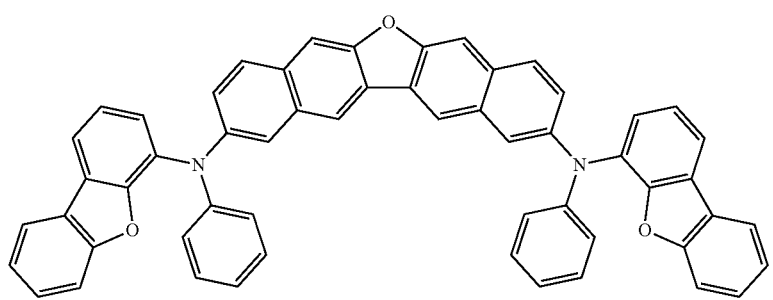
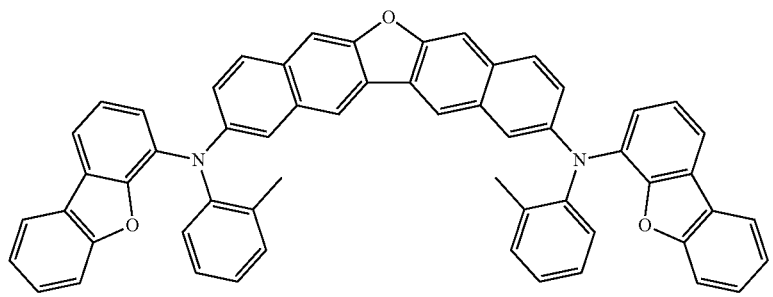
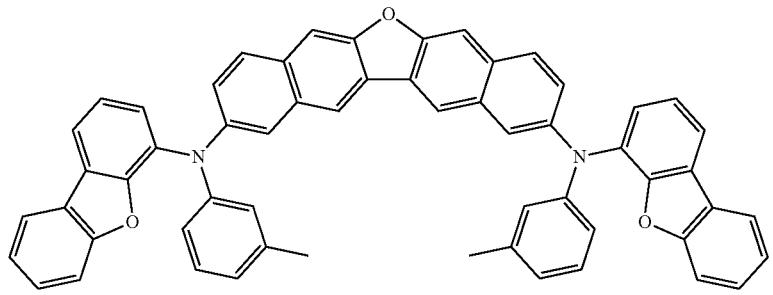

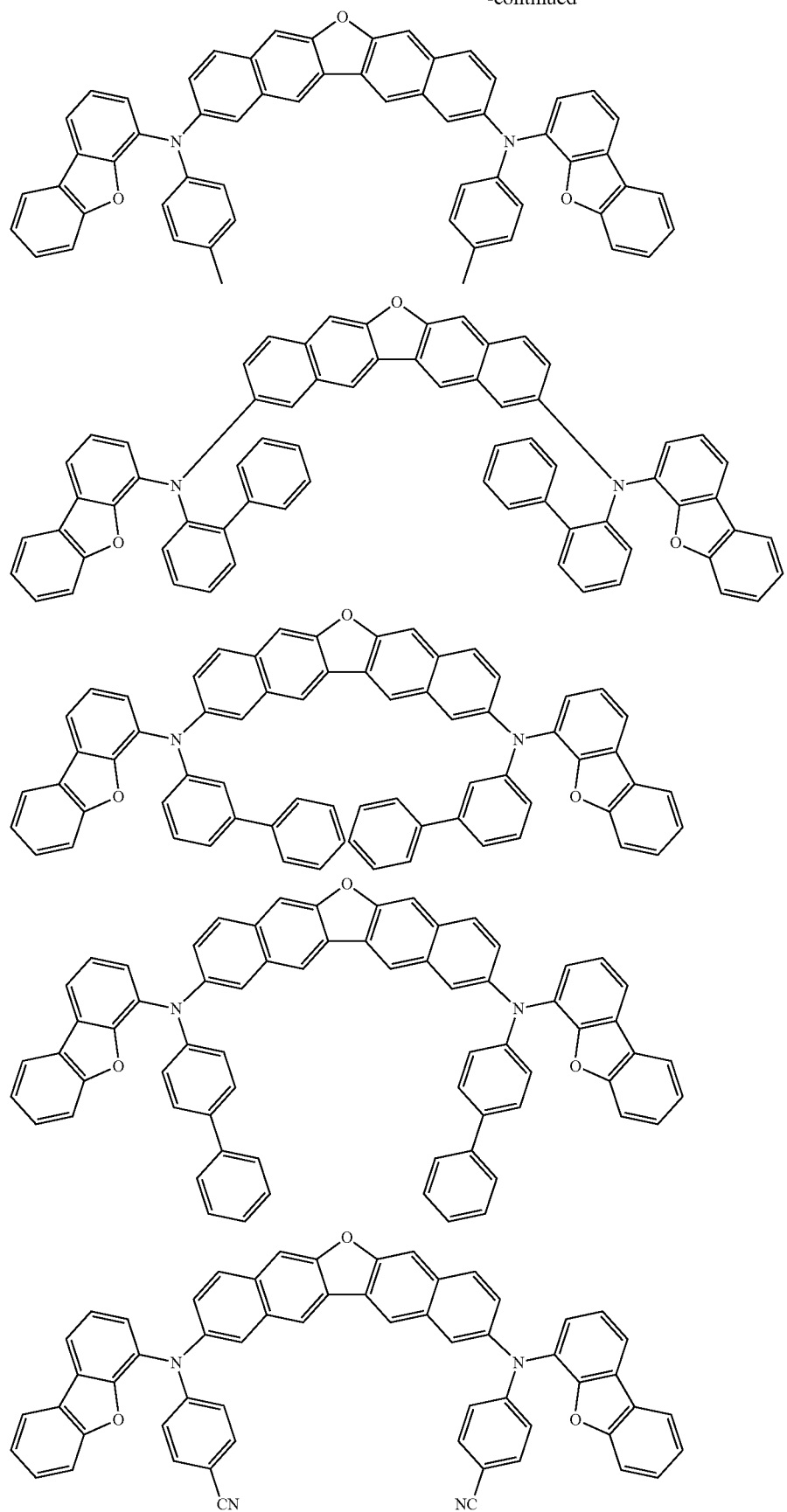

823
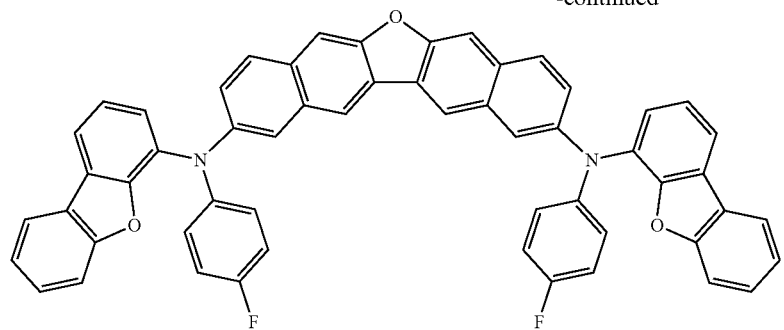
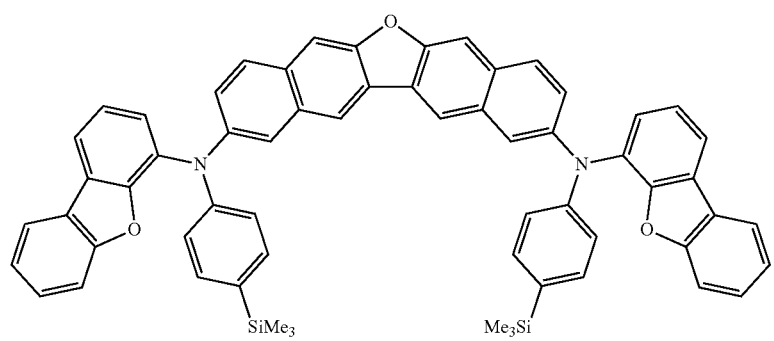
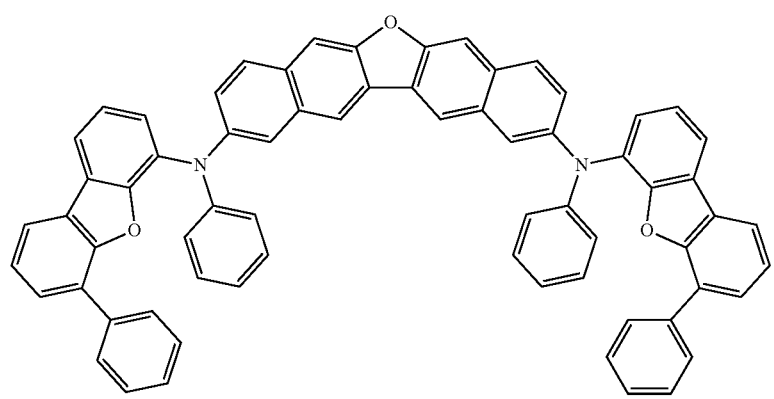
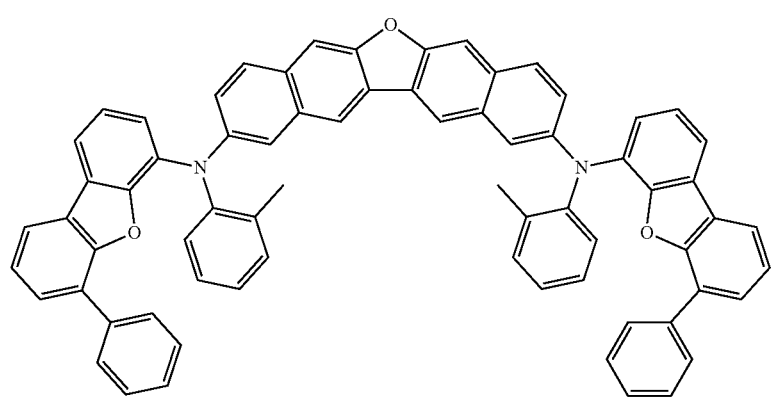
824
-continued

-continued
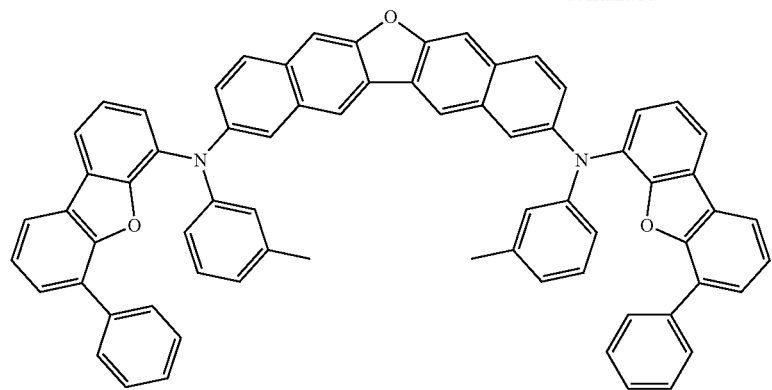
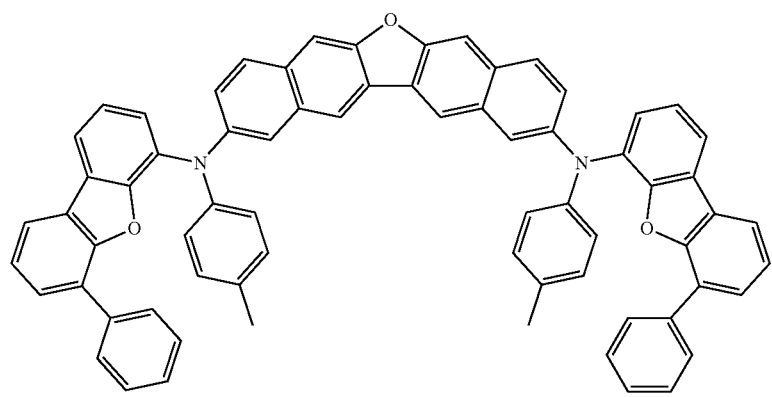
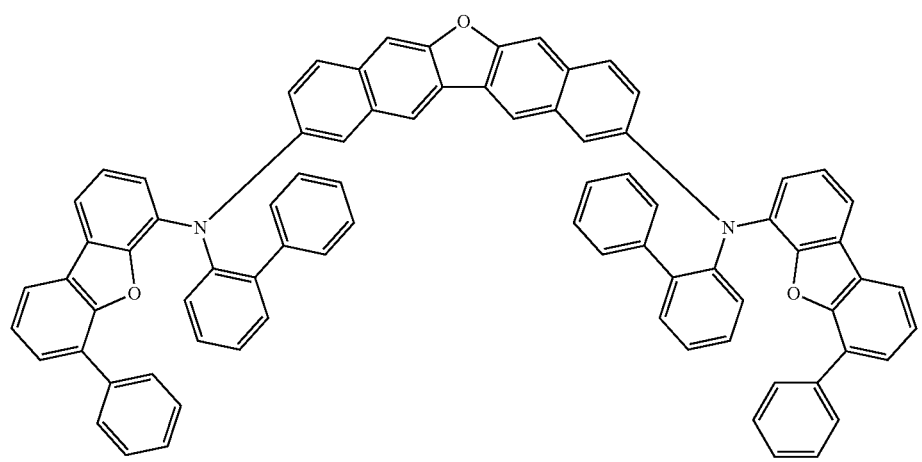
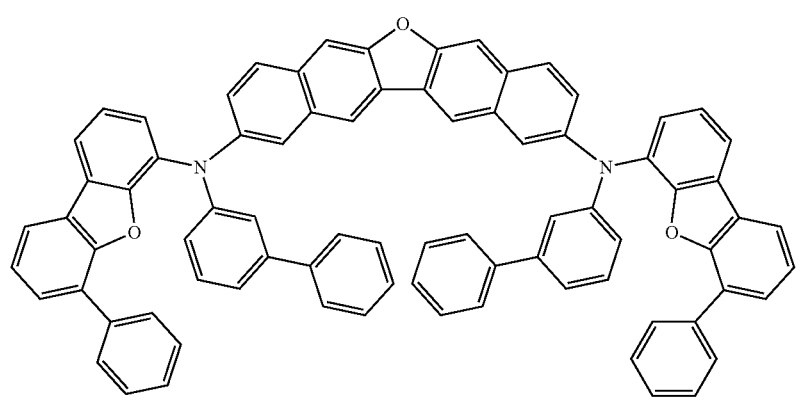

-continued
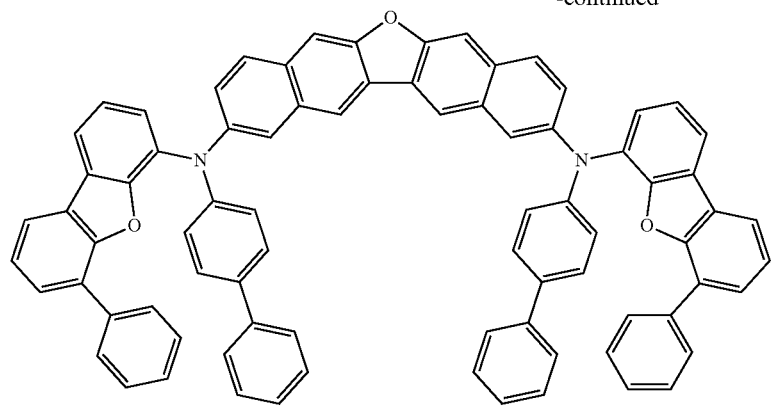
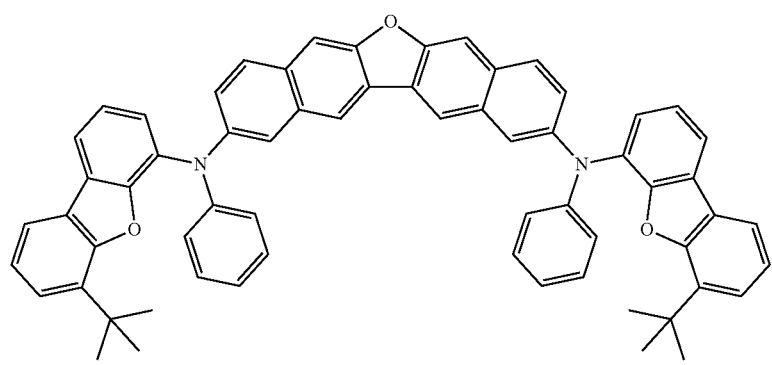
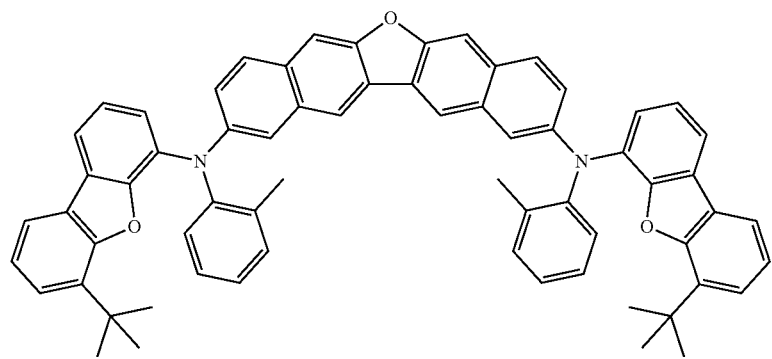
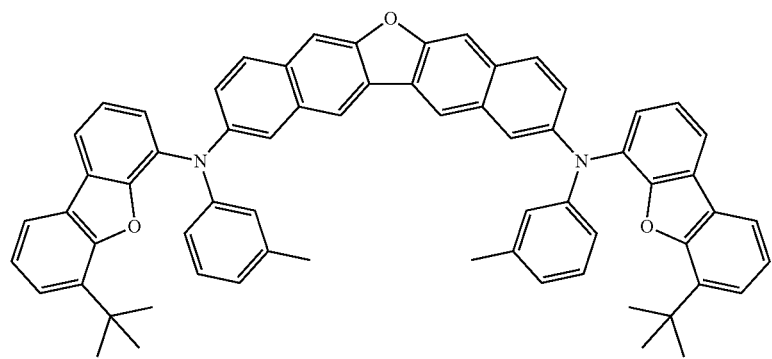

-continued
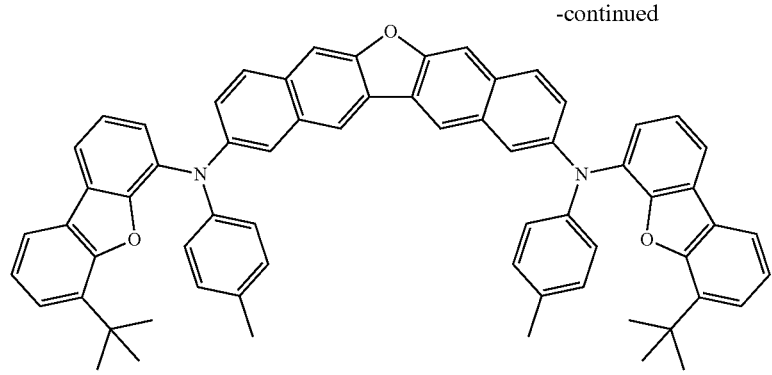
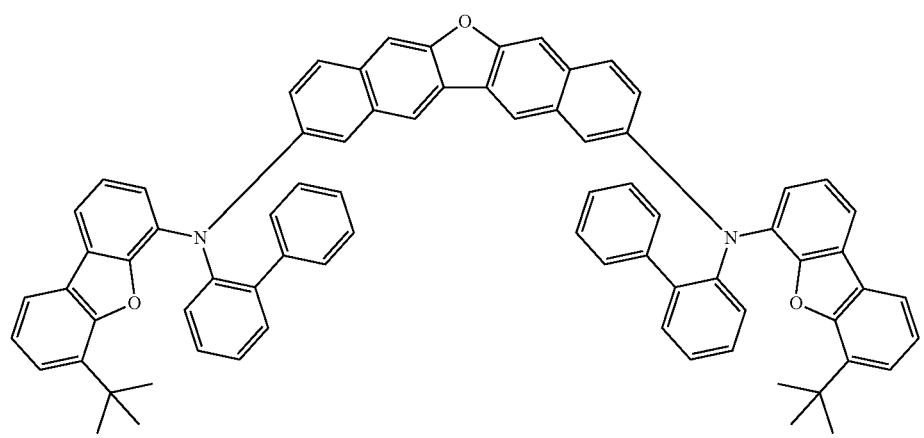
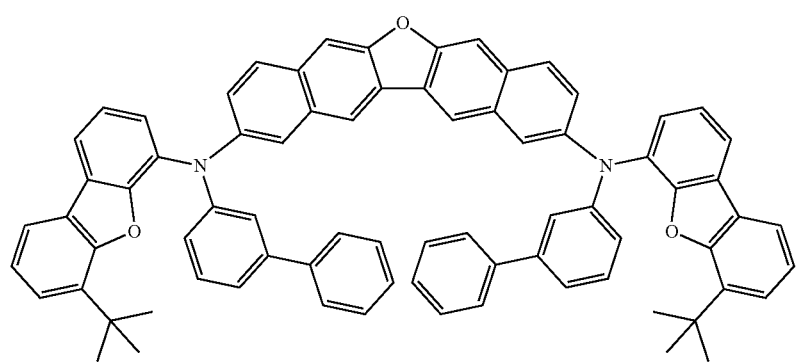
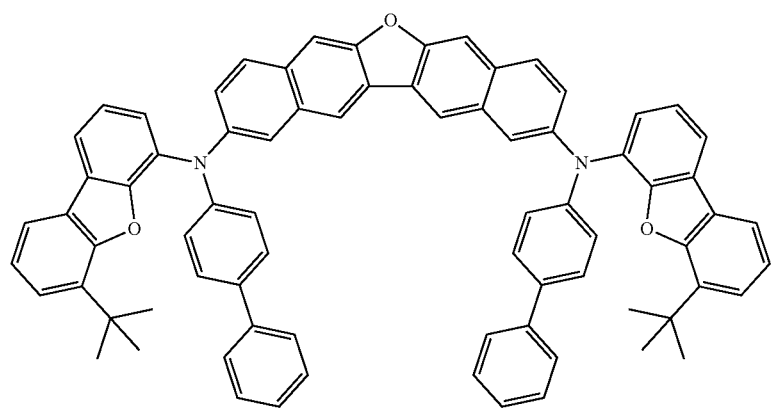

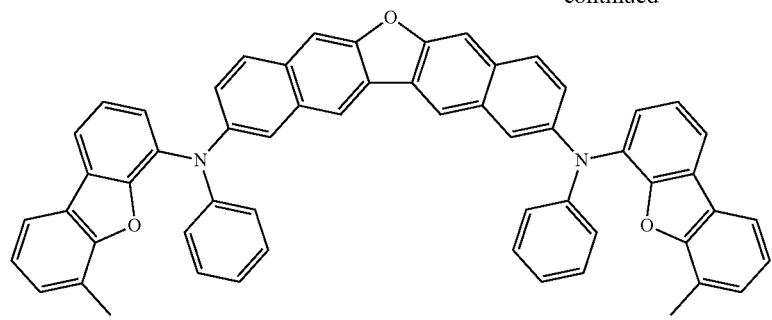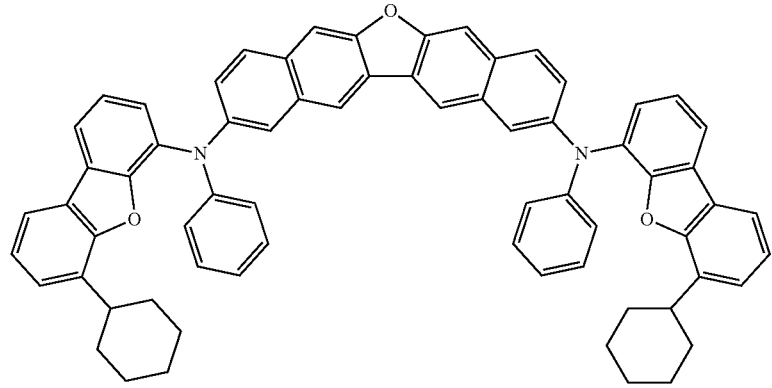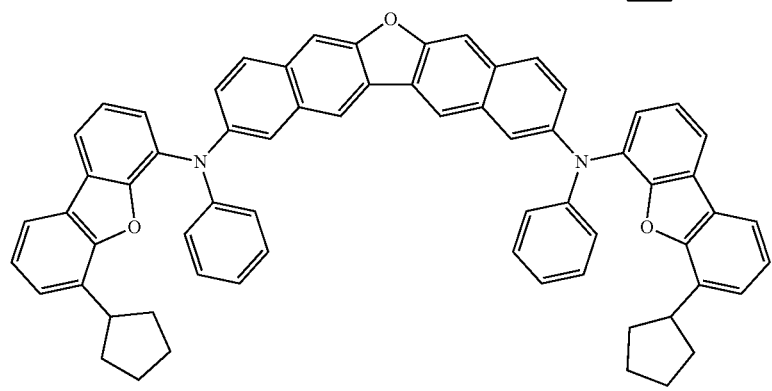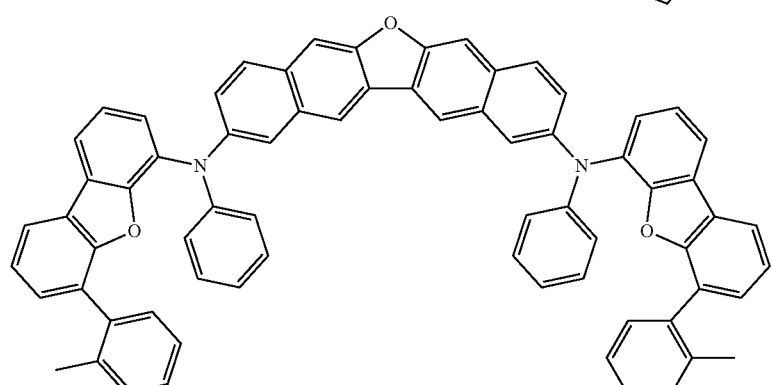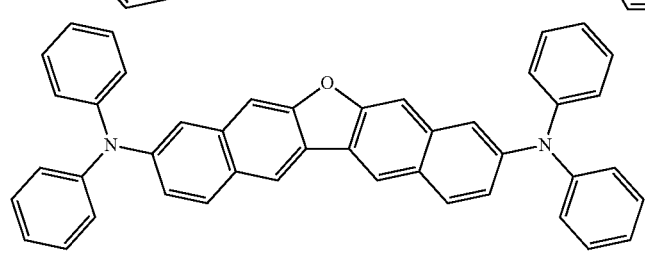

-continued
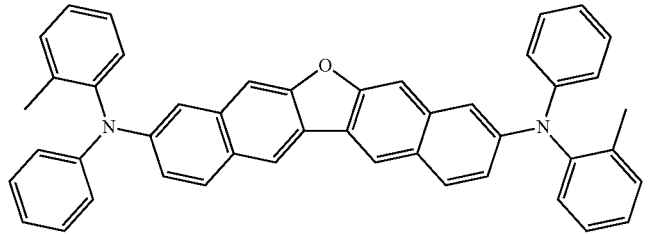
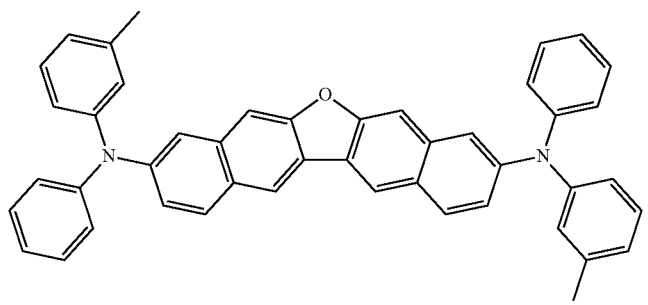
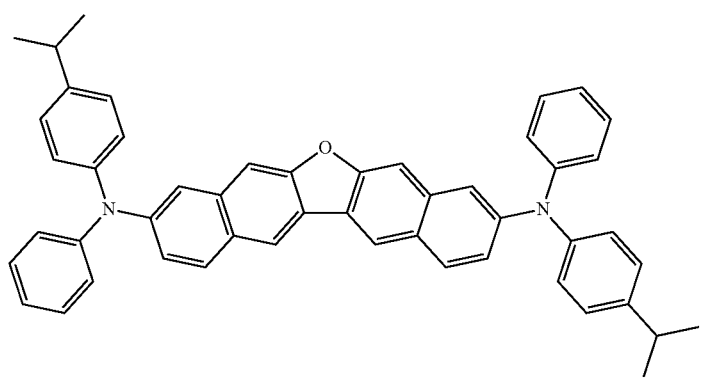
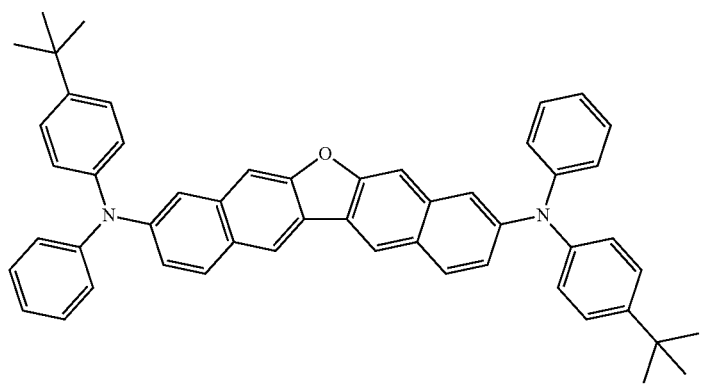
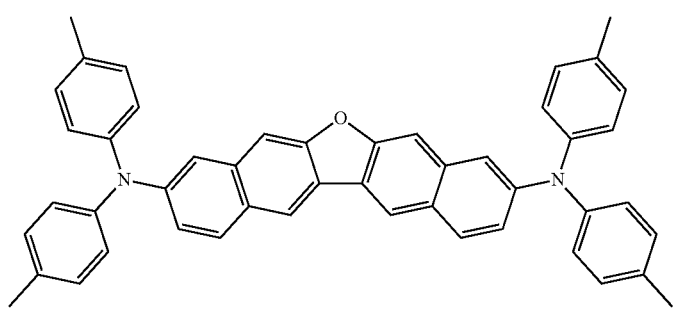

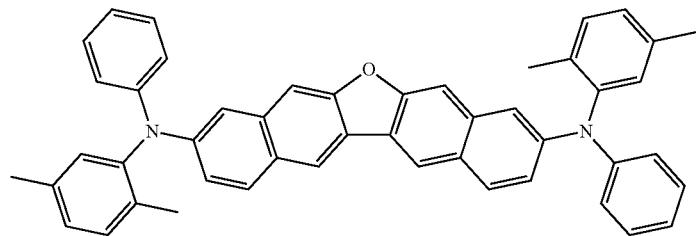
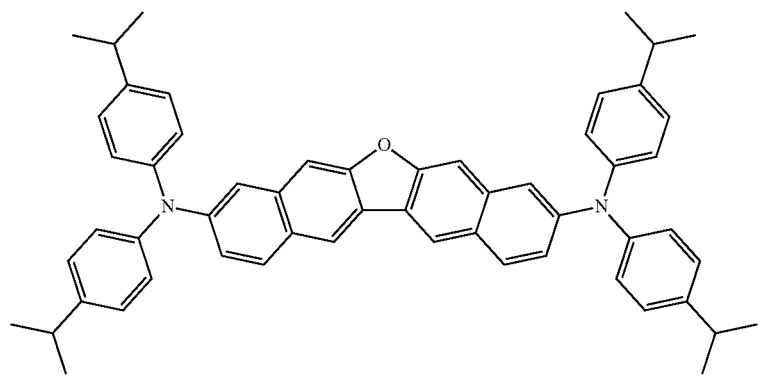
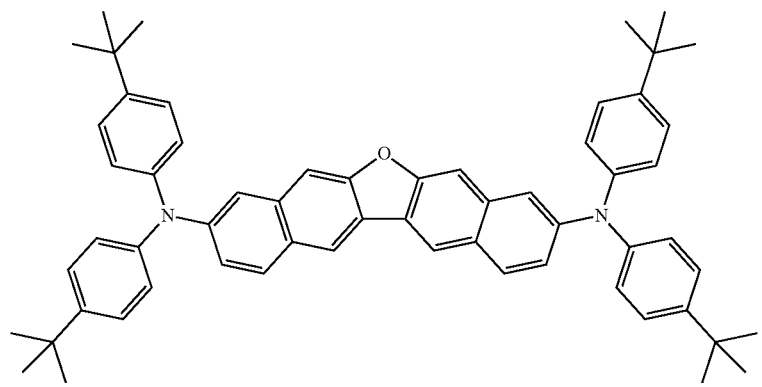
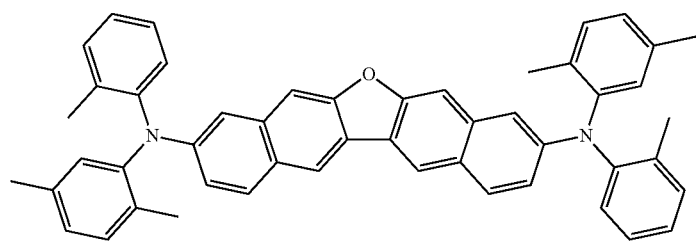
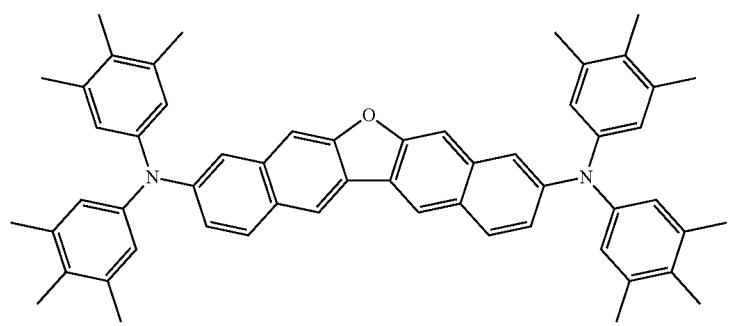

-continued
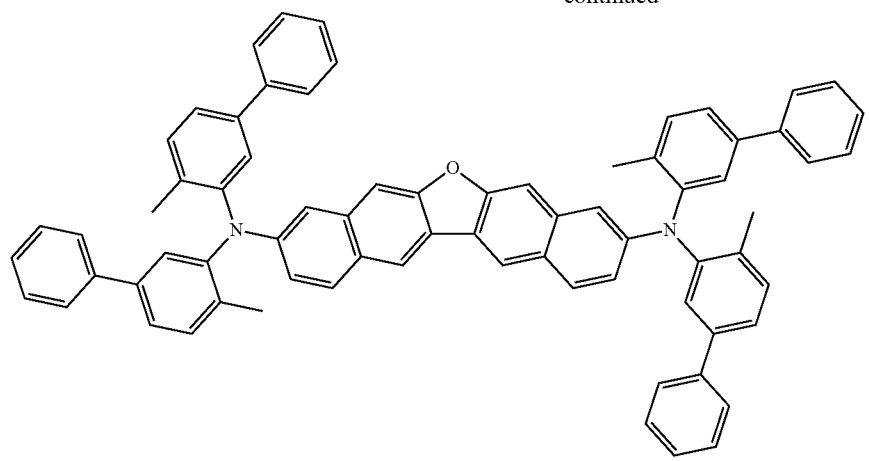
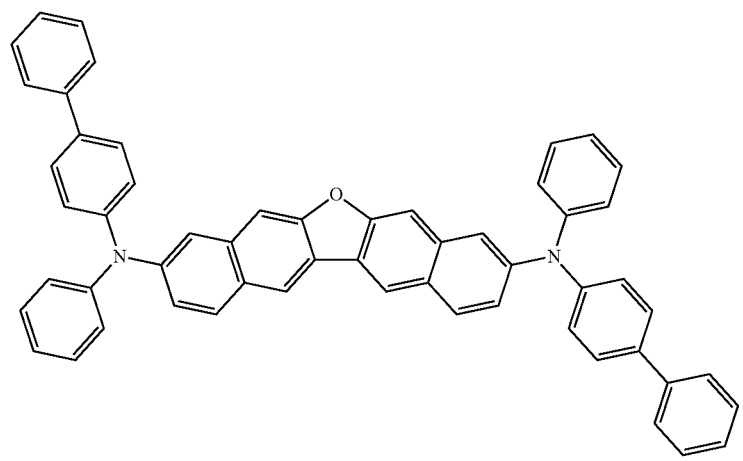
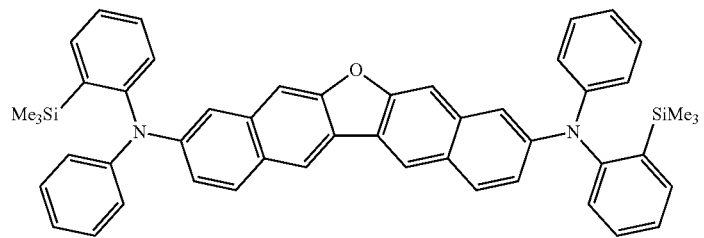
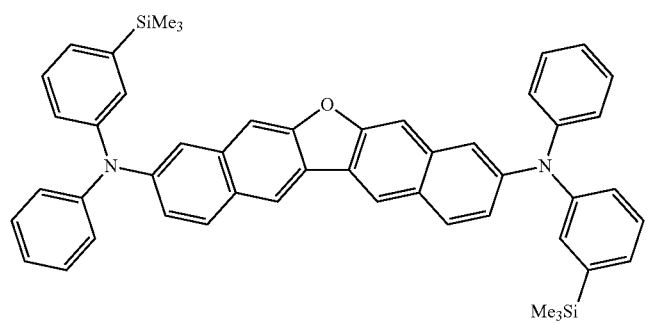
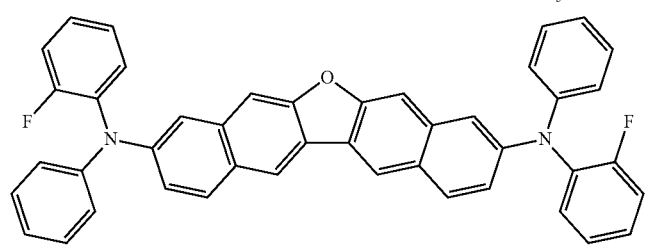

-continued
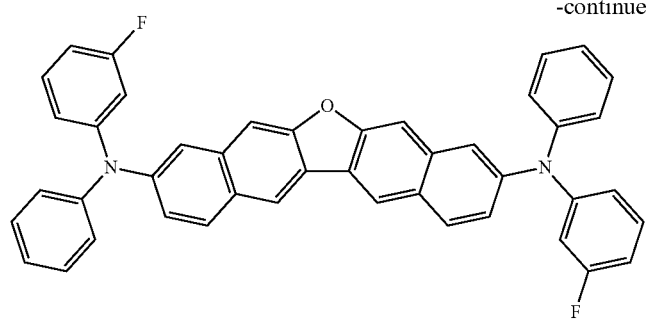
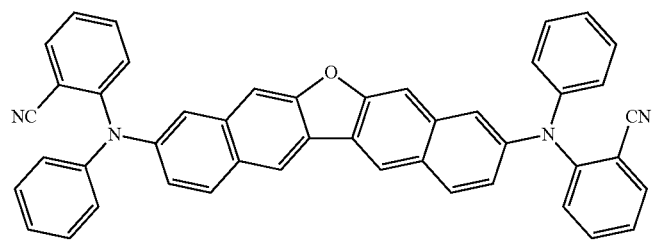
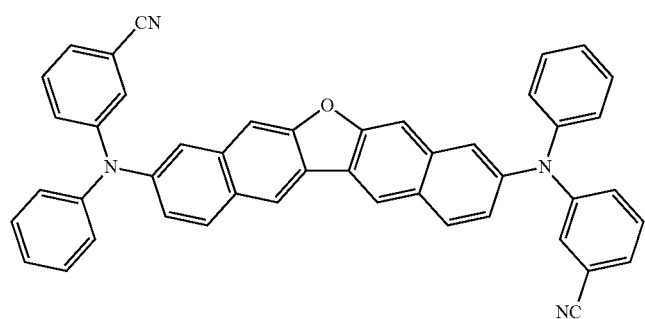
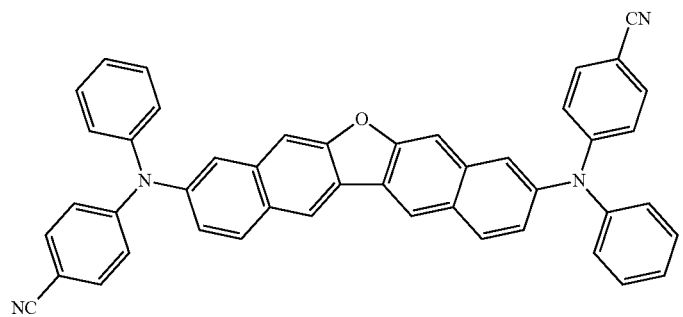
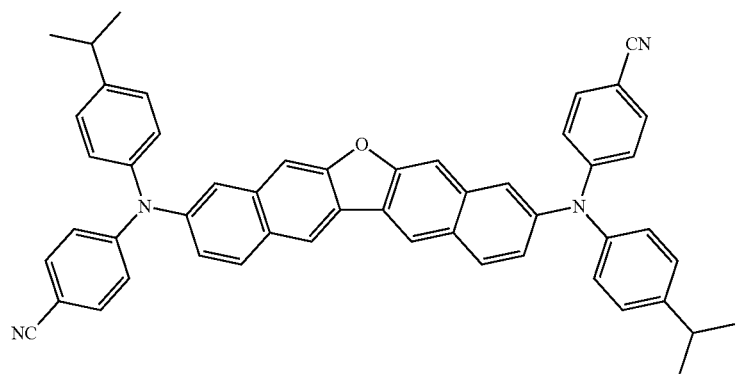

-continued
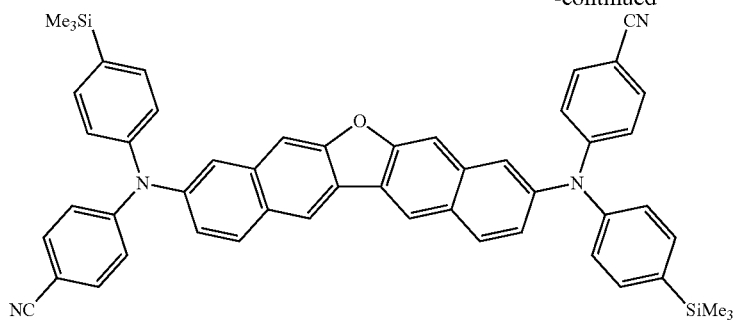
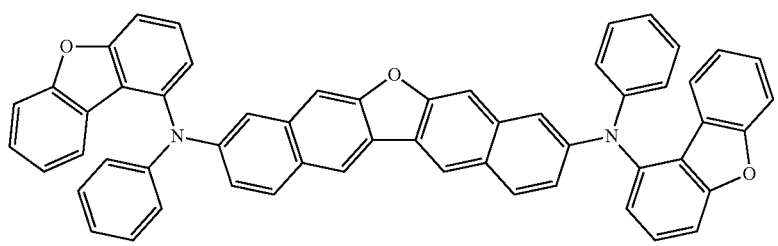
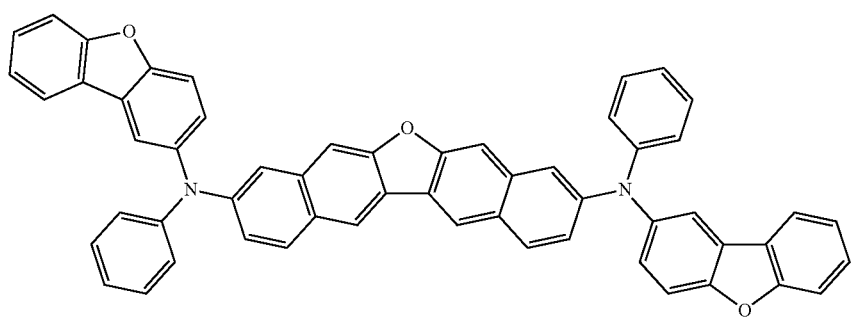
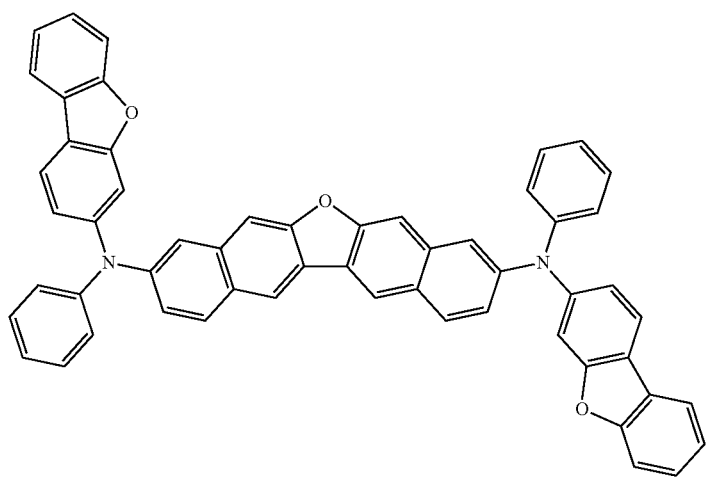
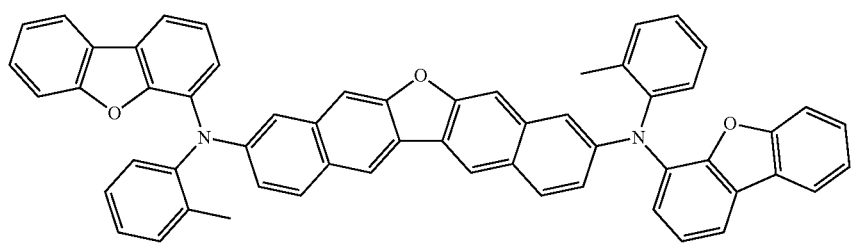

843 844
-continued
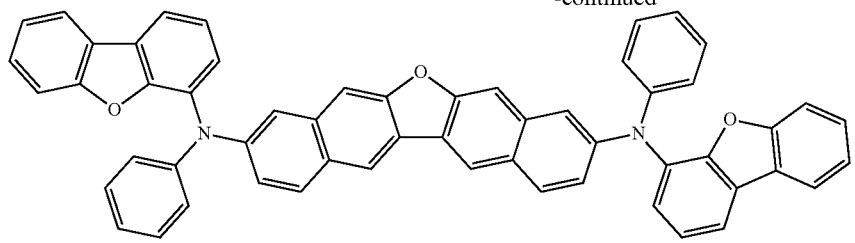
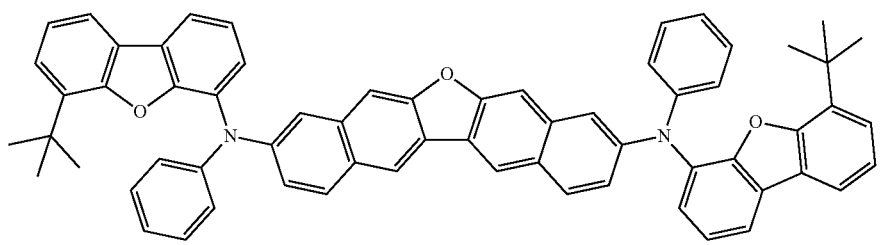
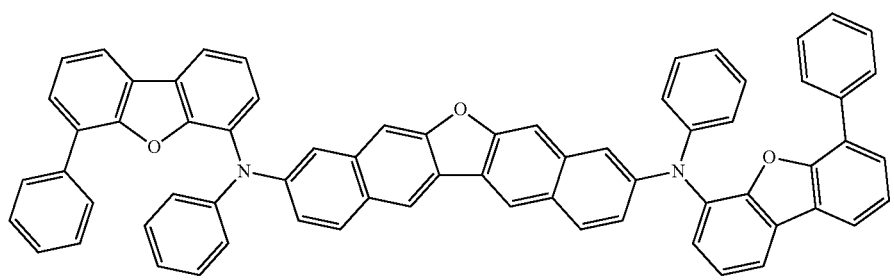
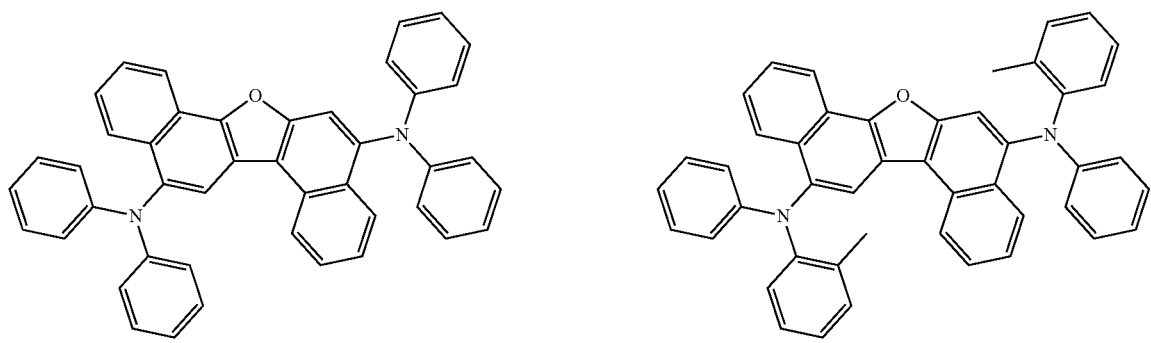
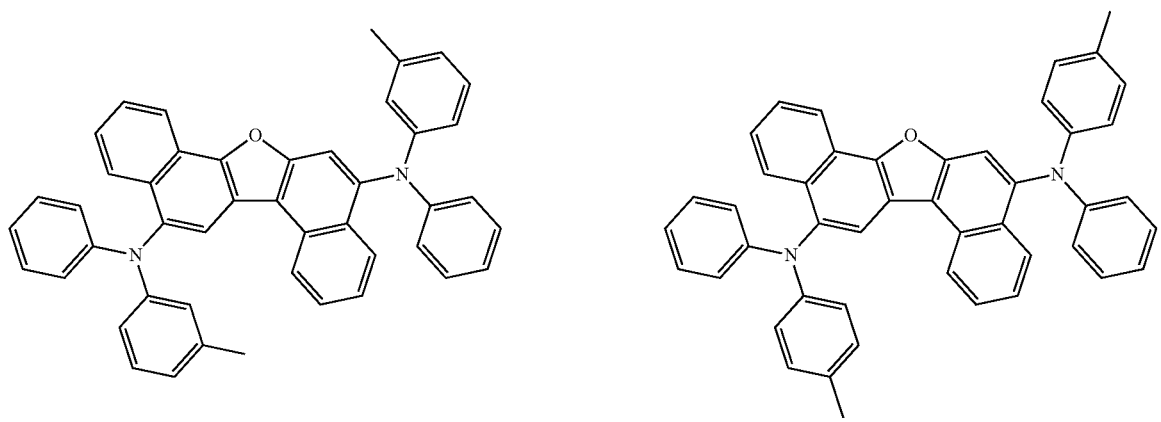

-continued
845 846
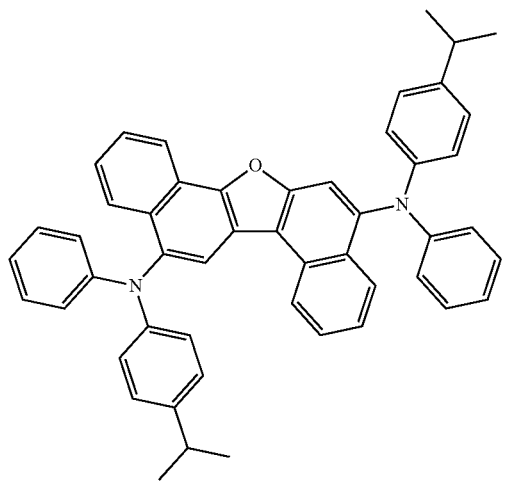 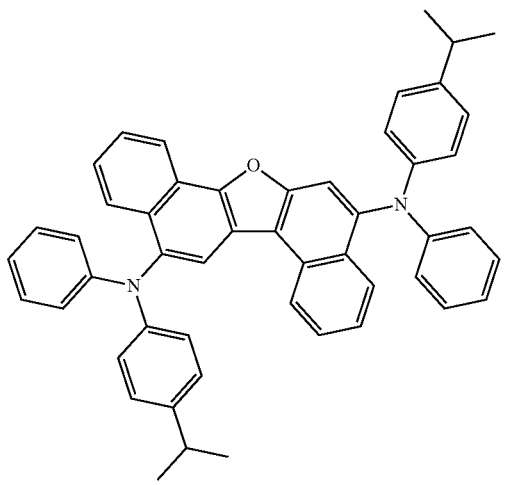
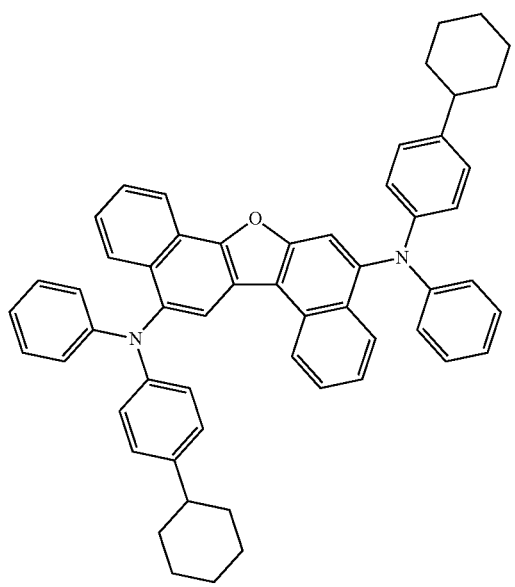 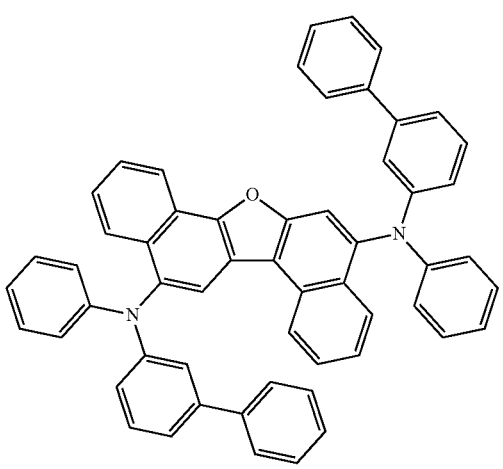
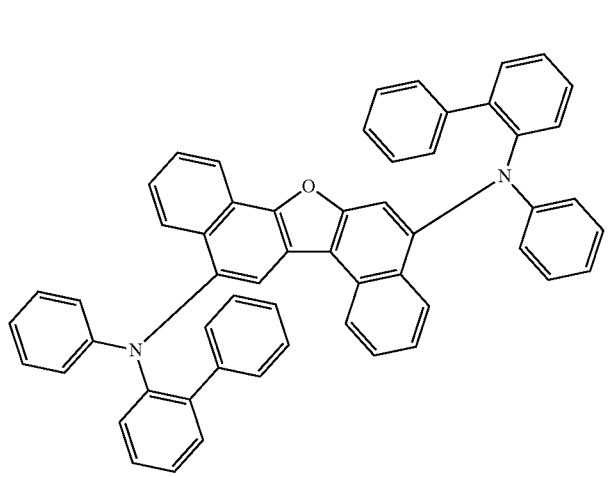 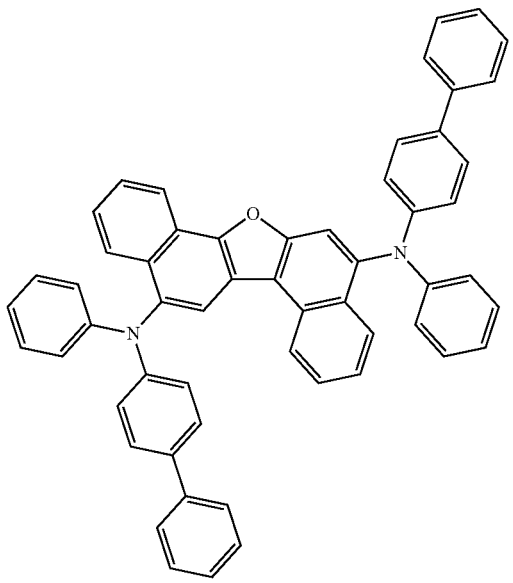

847
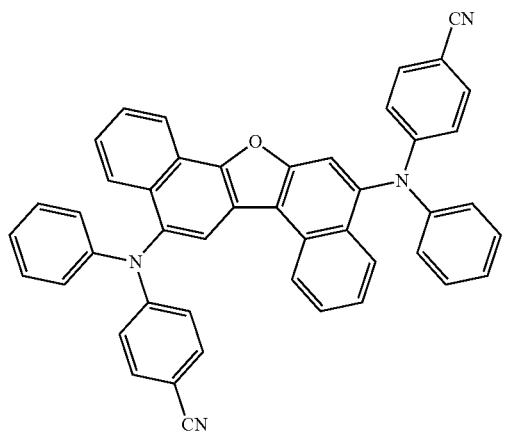
848
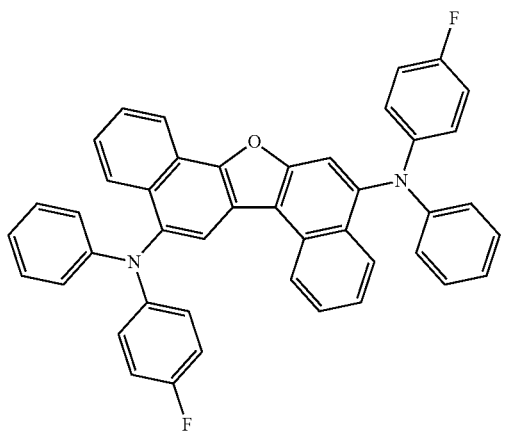
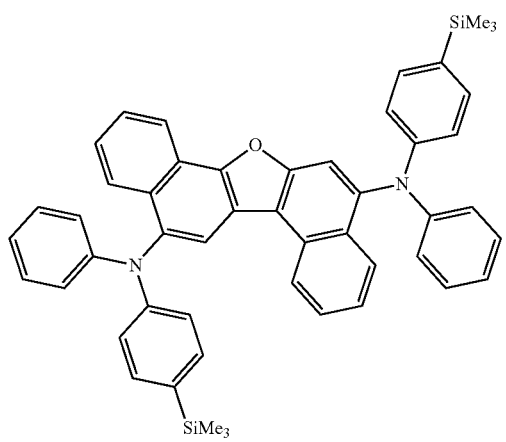
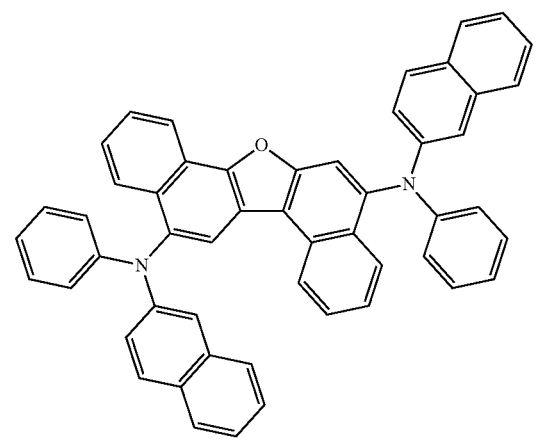
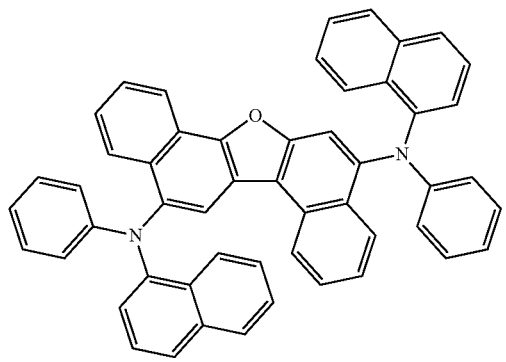
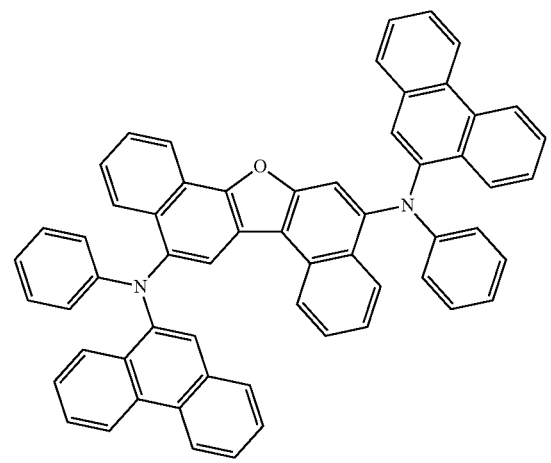

-continued
849
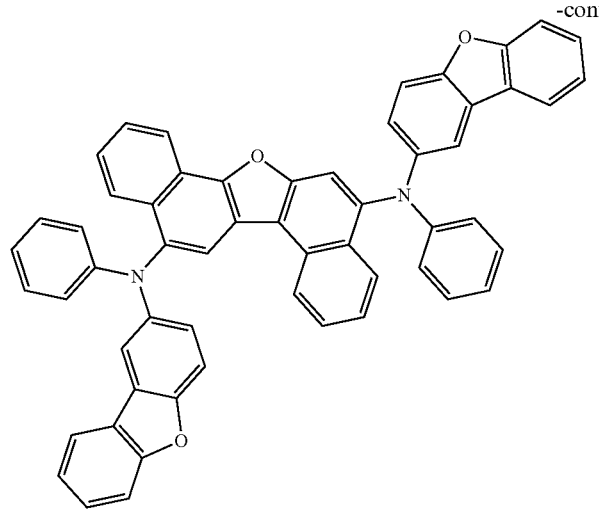
850
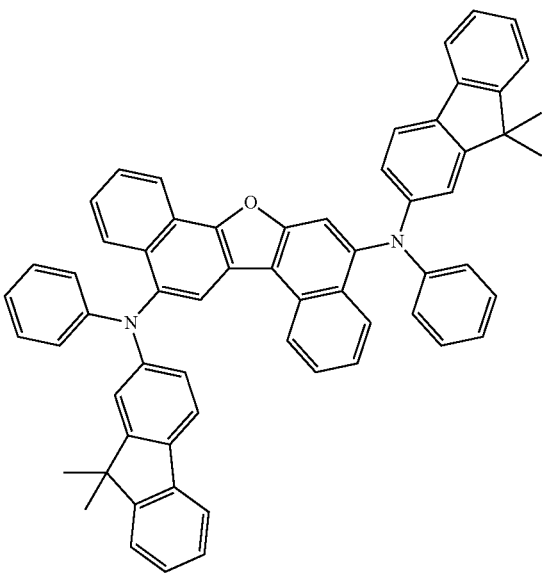
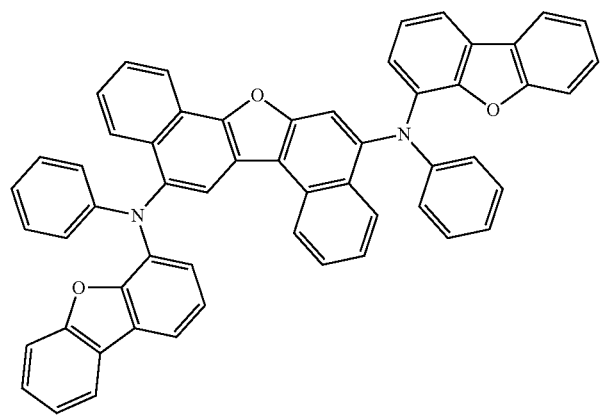
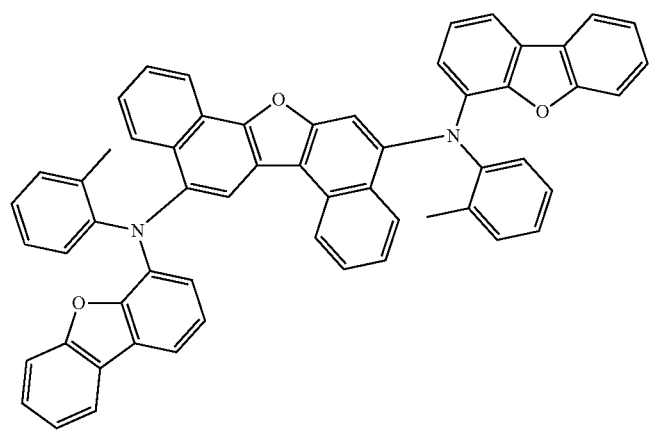

-continued
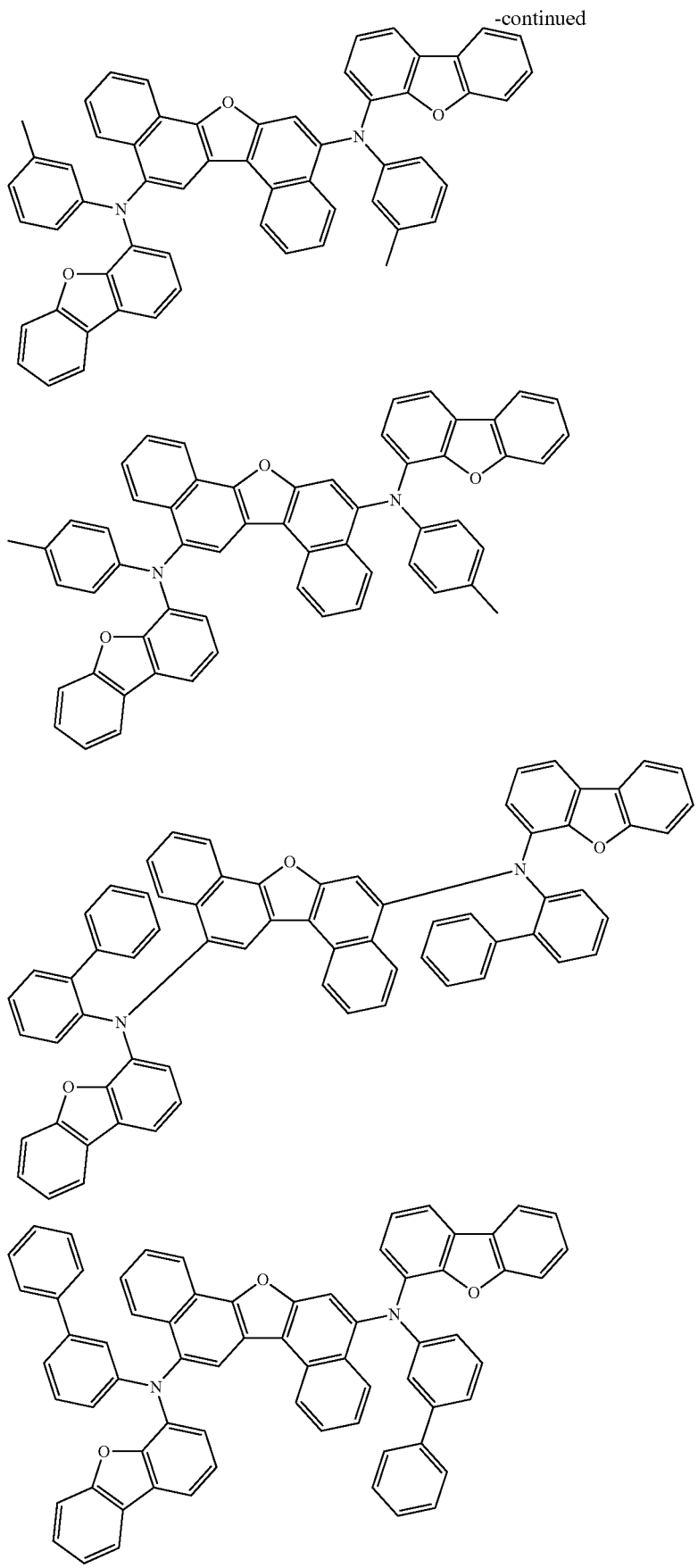

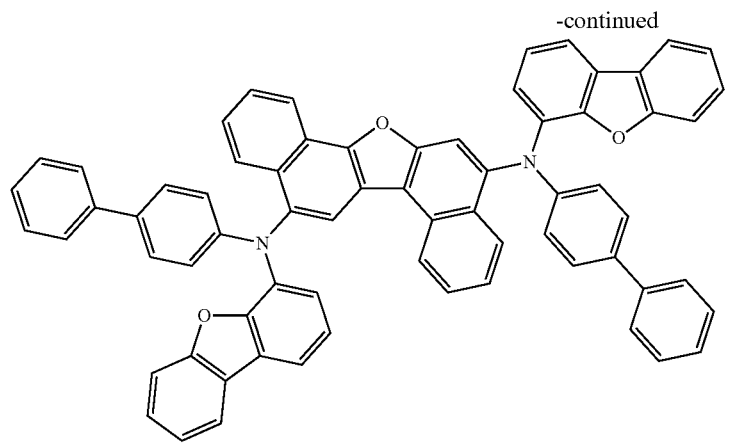
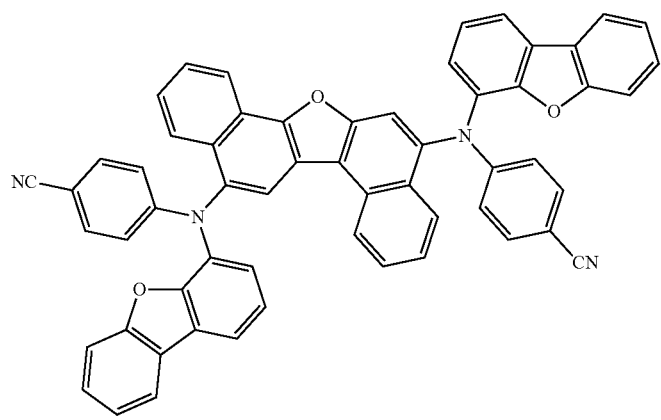
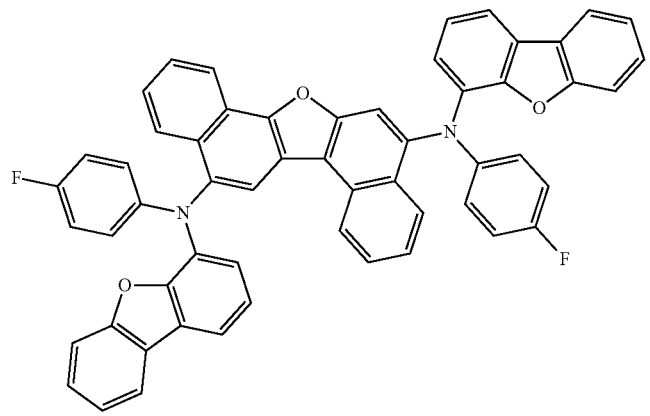
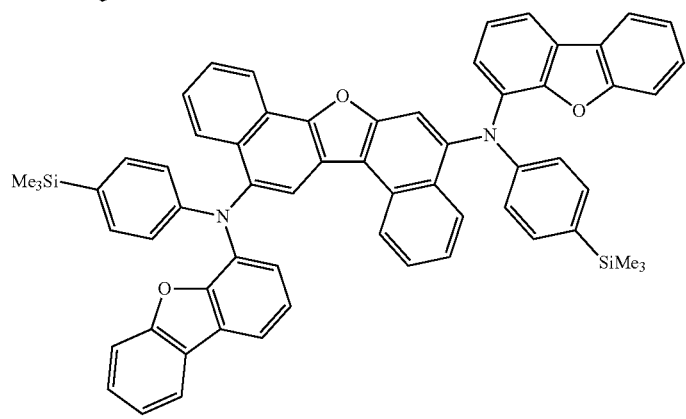

-continued
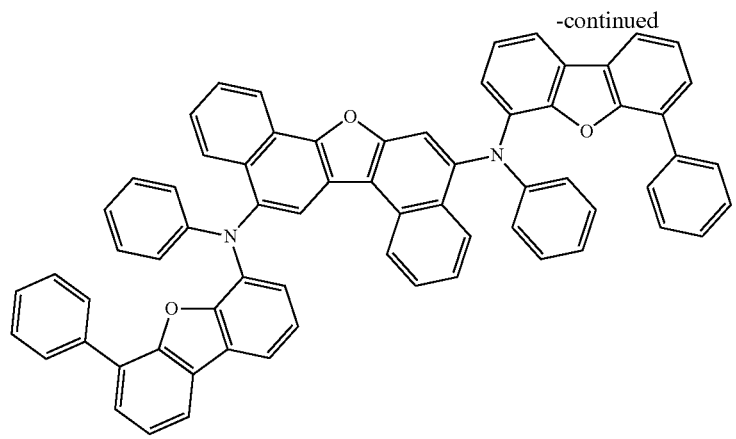
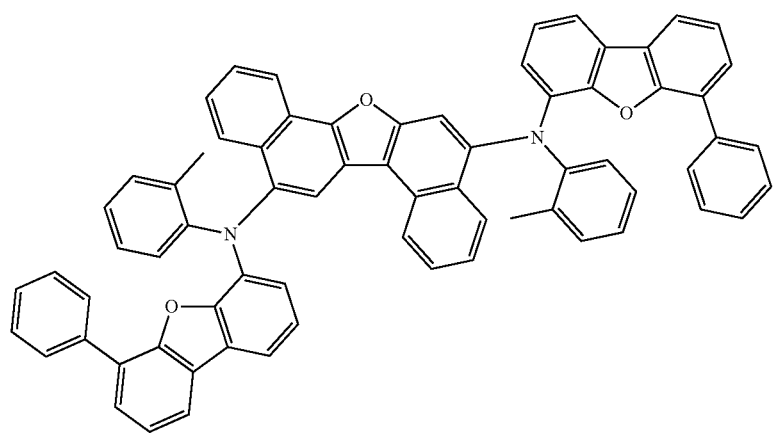
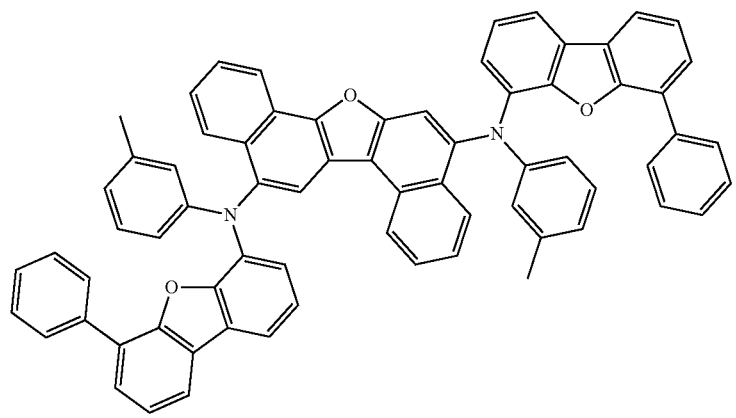
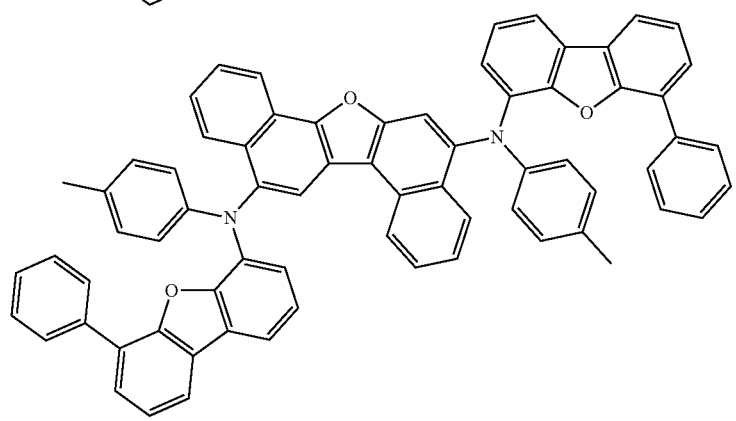

-continued
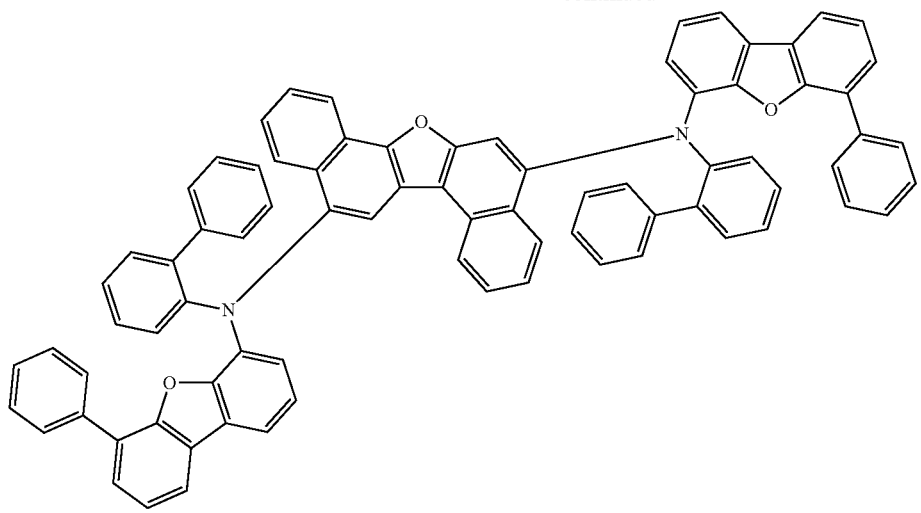
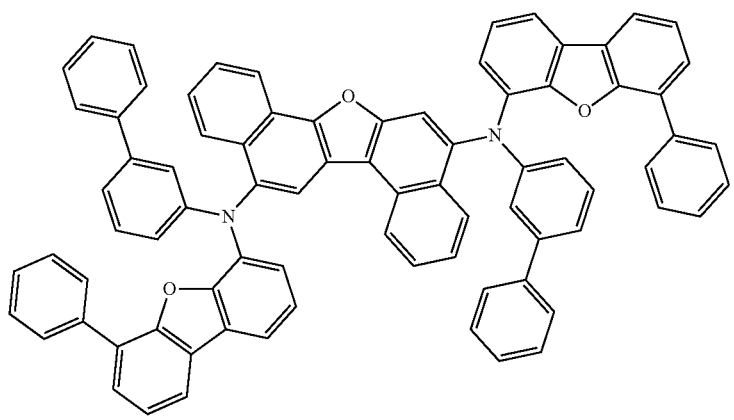
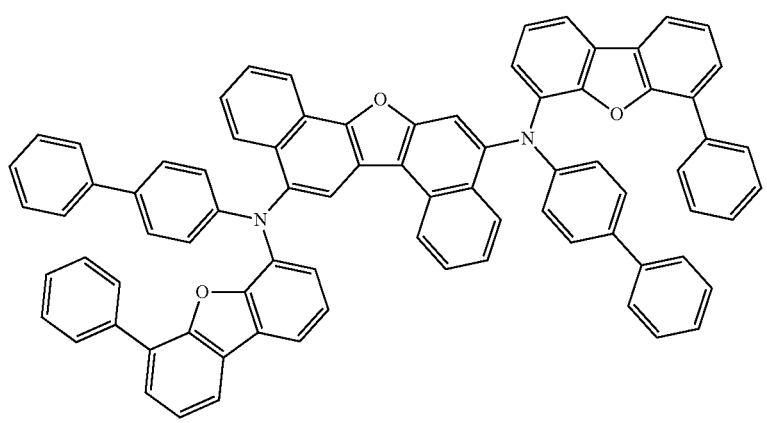

-continued
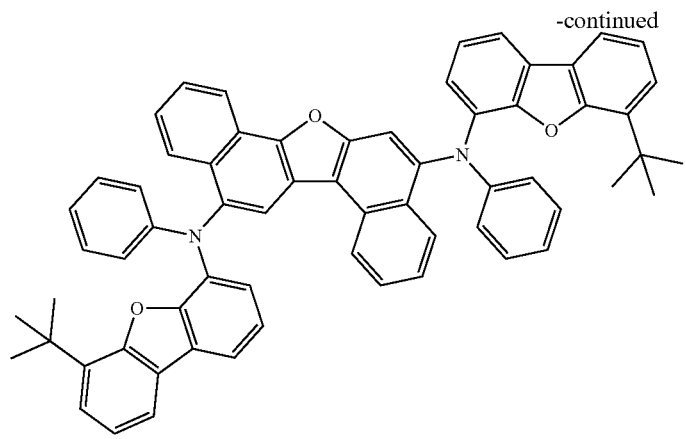
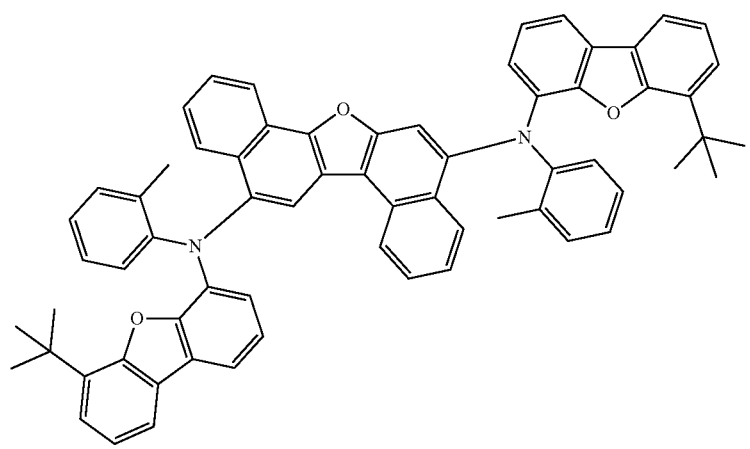
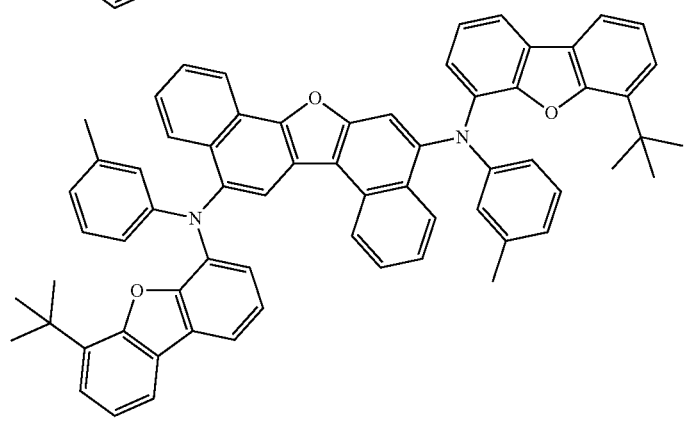
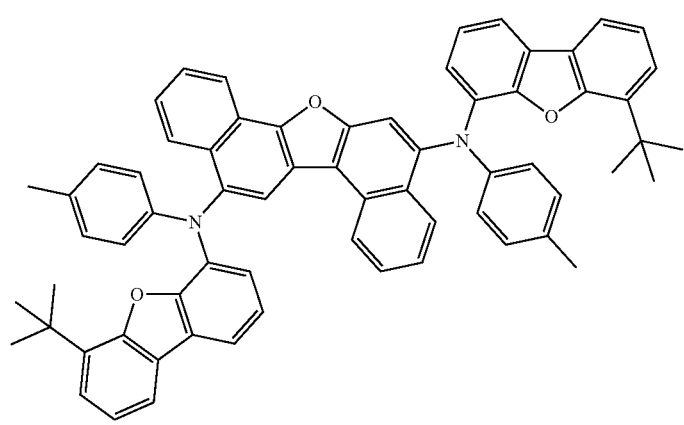

-continued
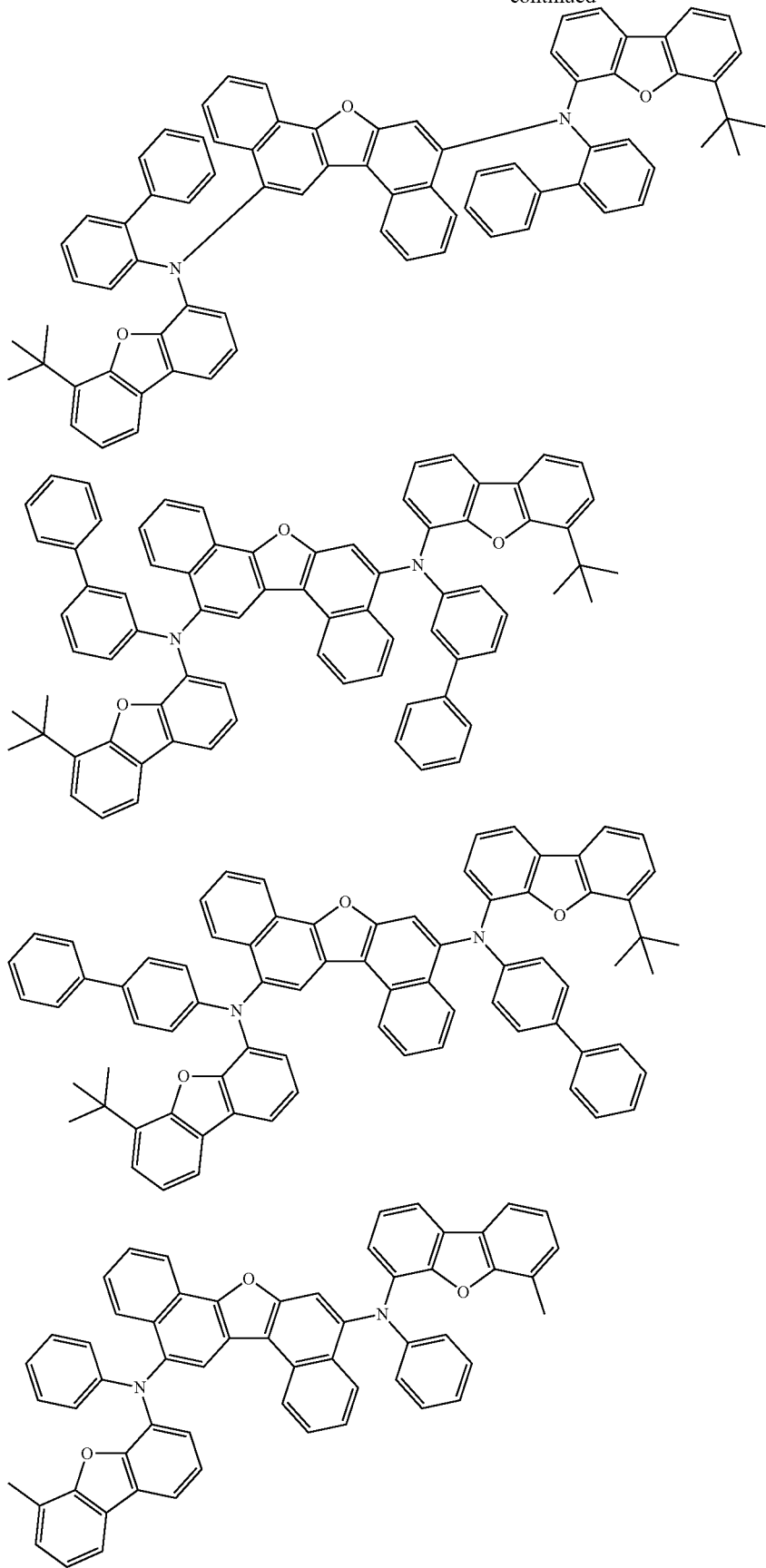

863 864
-continued
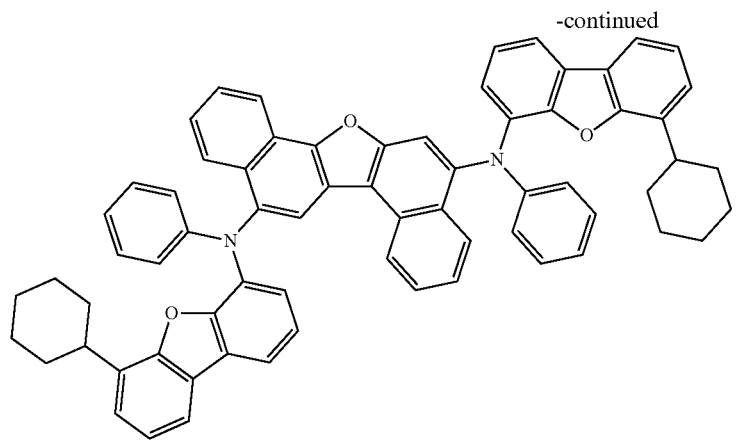
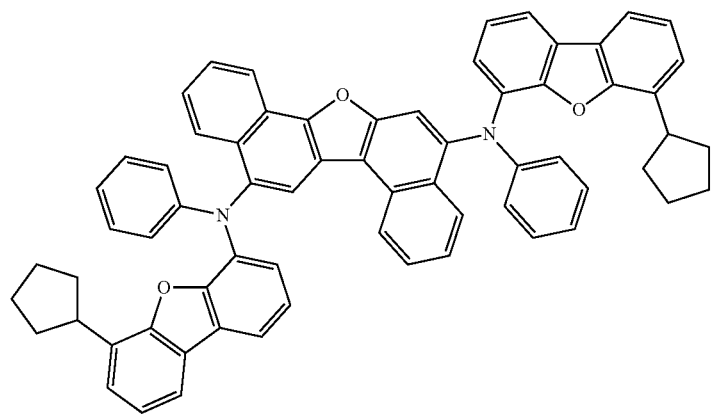
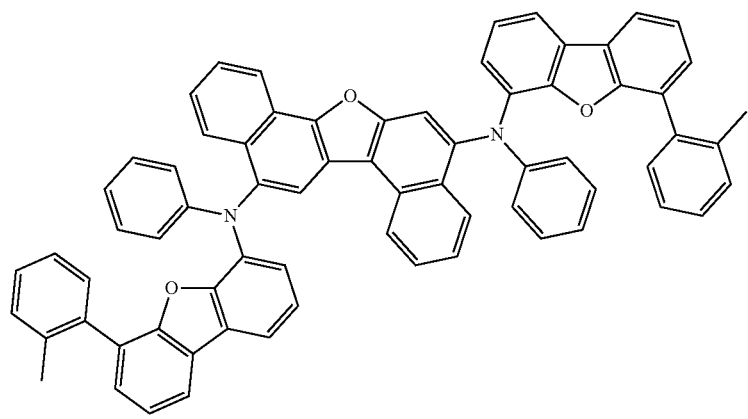
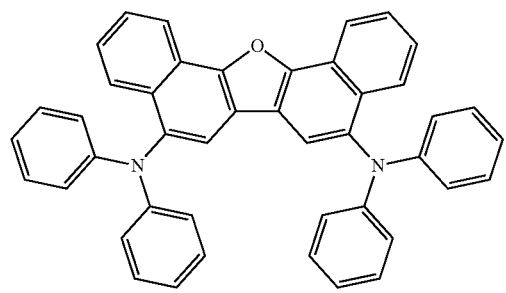
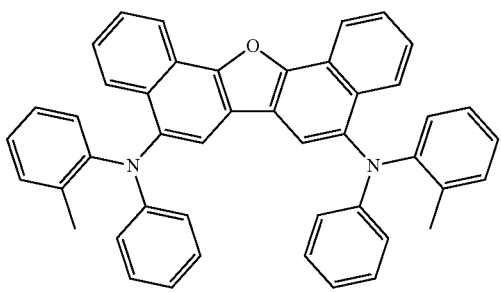

865
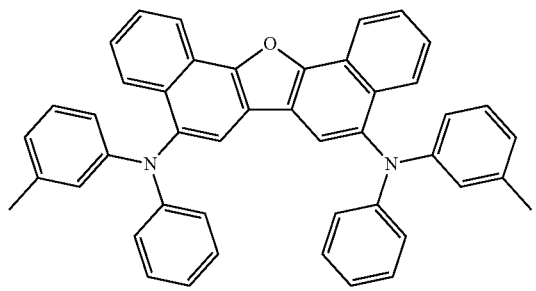
-continued
866
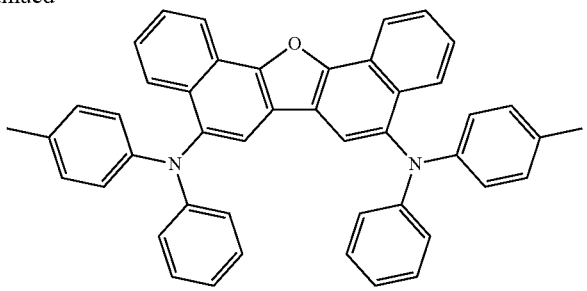
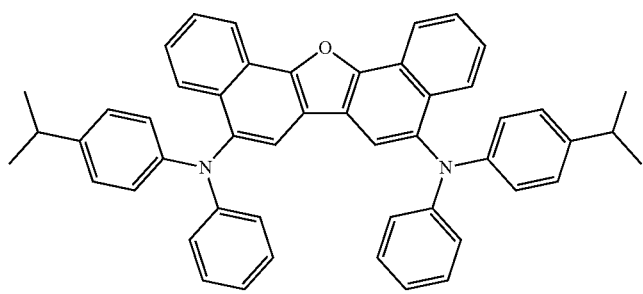
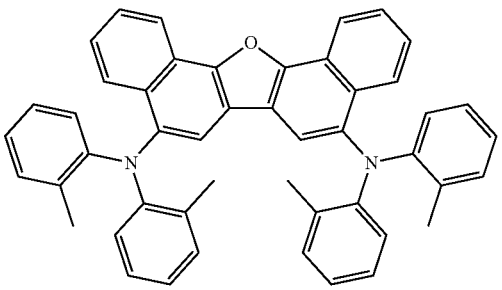
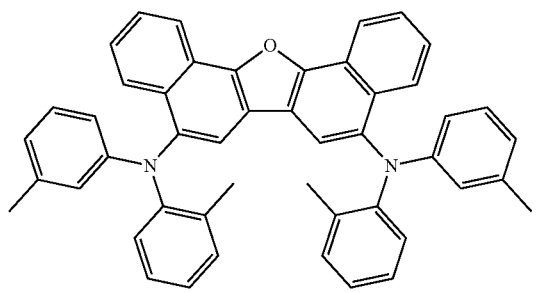
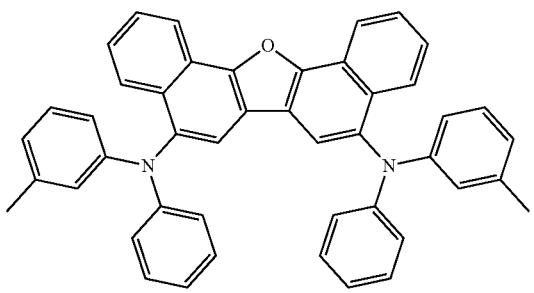
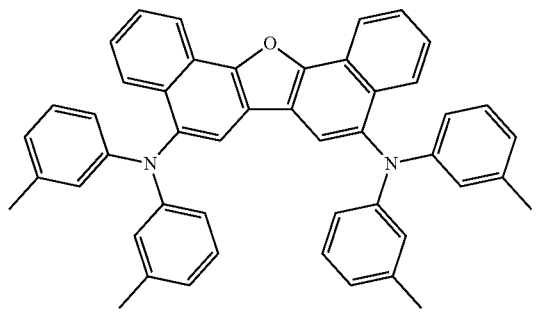
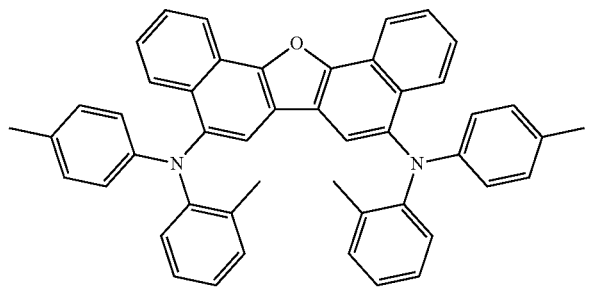
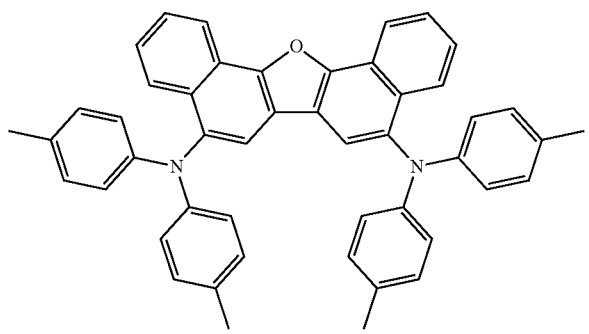
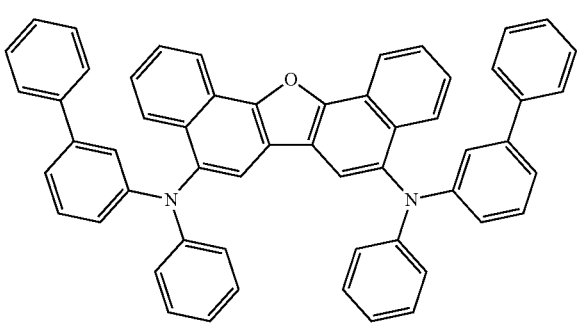

-continued
867
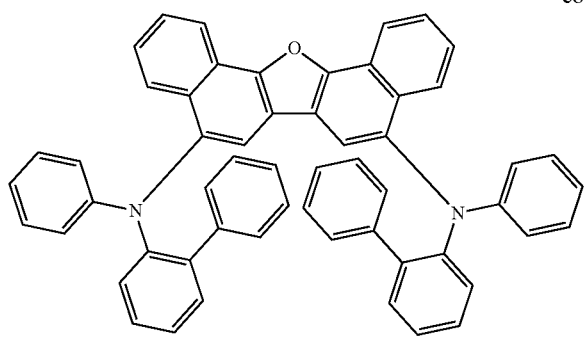
868
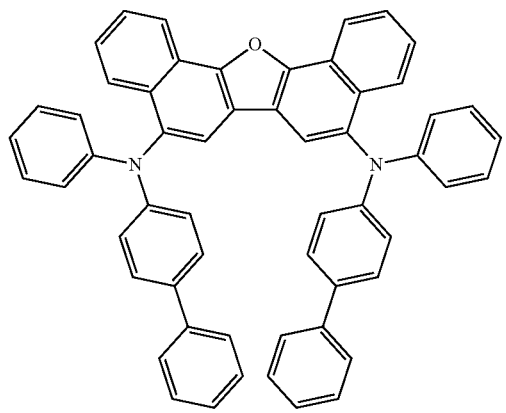
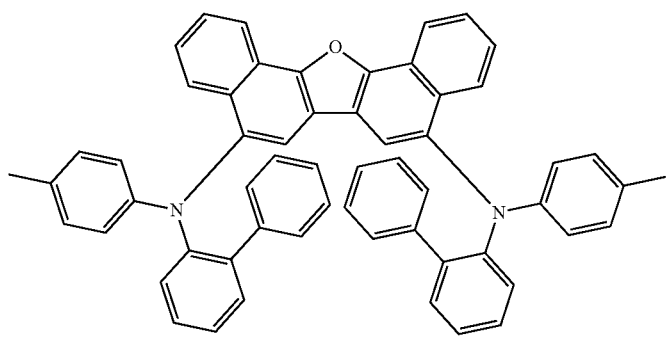
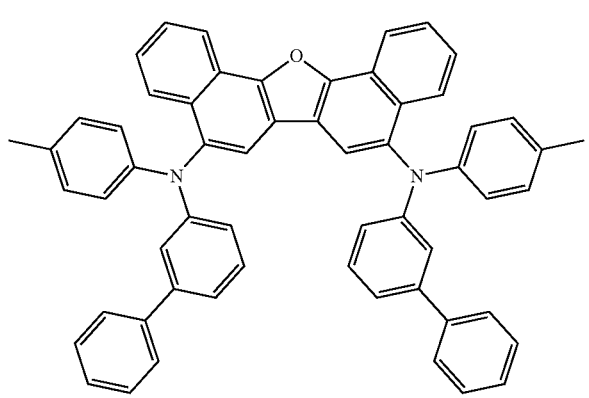
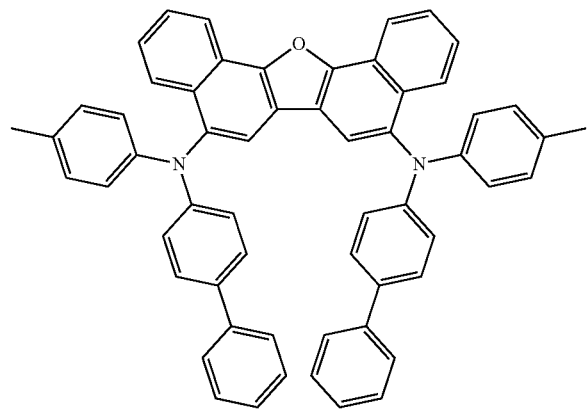
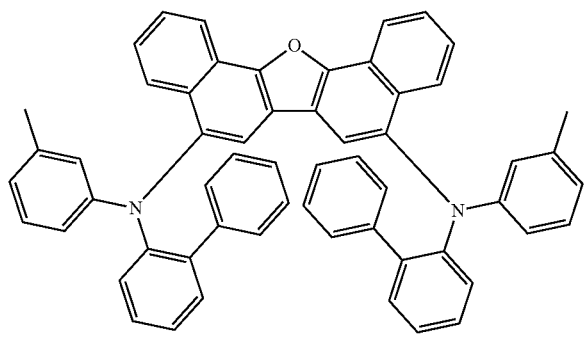
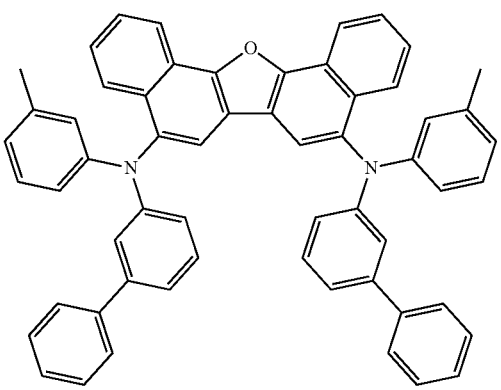

-continued
869
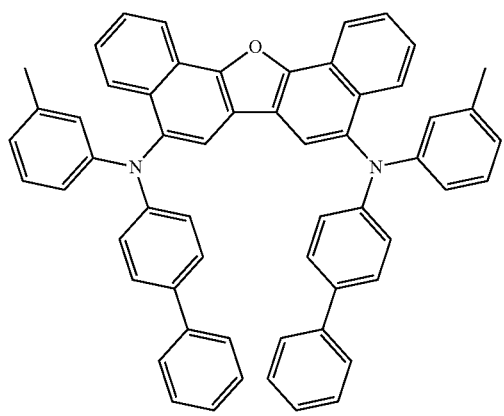
870
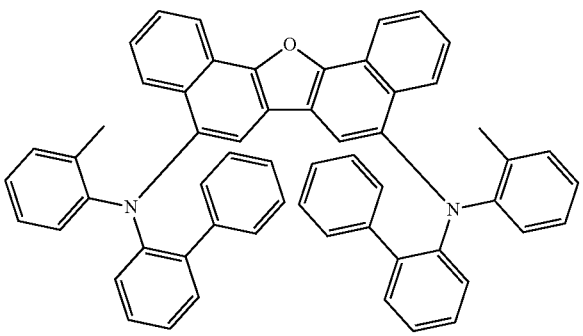
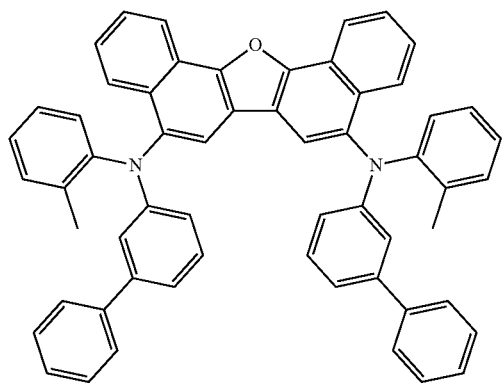
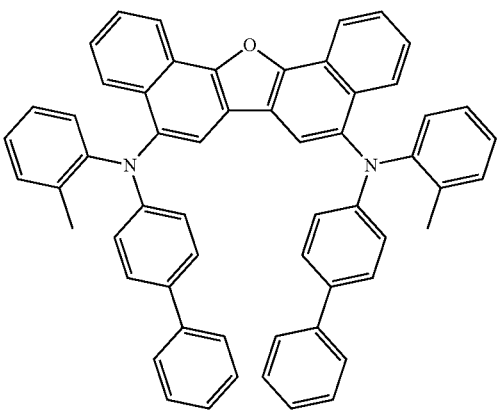
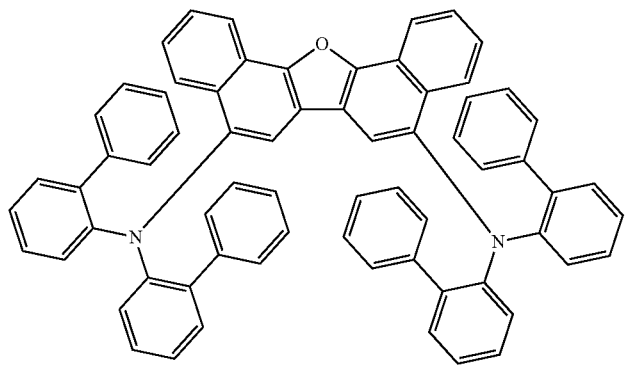
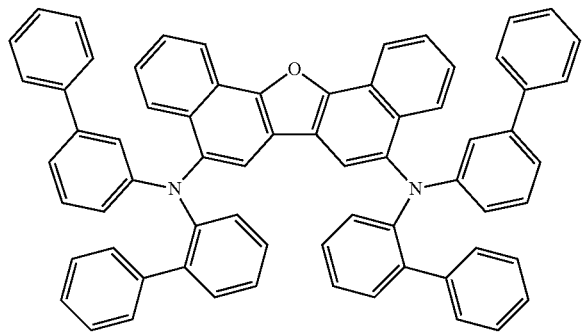
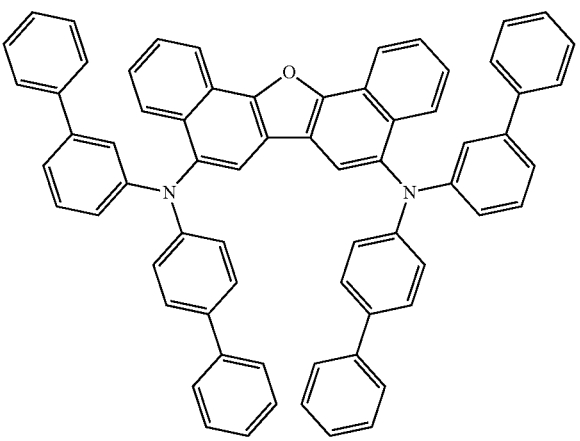

-continued
871
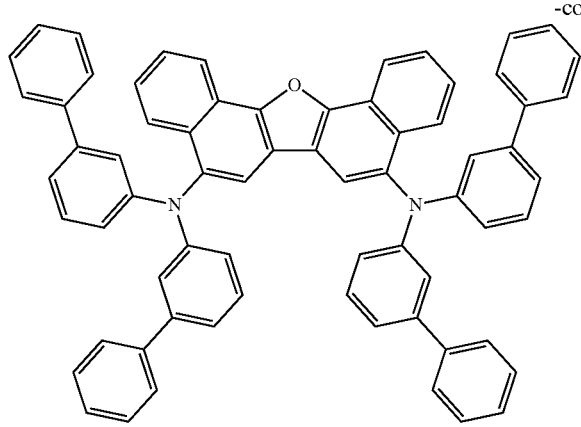
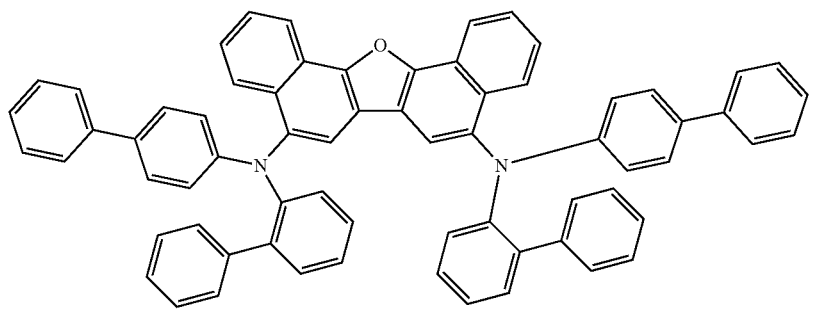
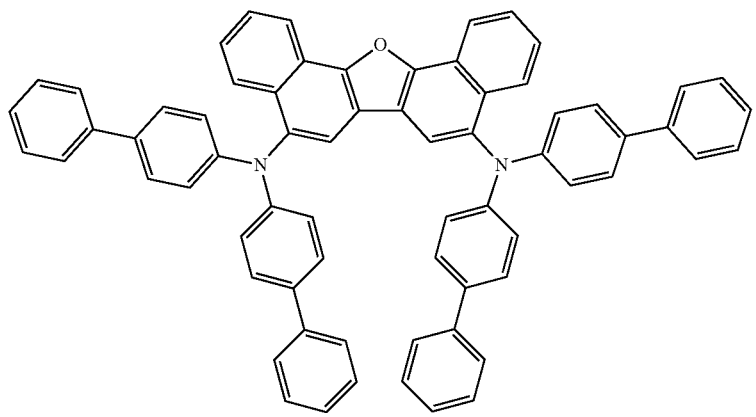
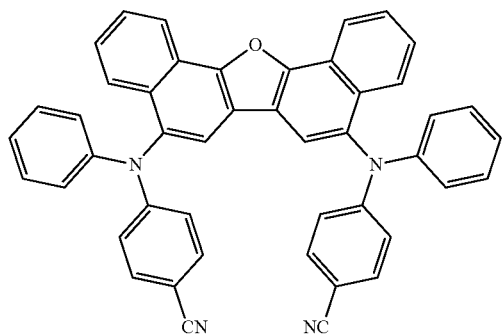
872
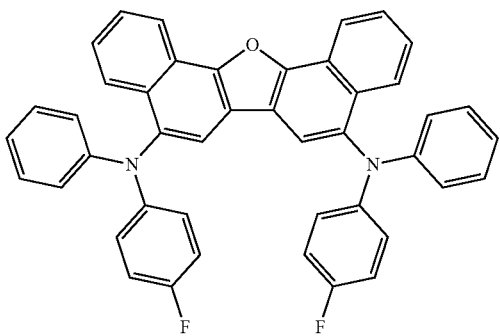

-continued
873
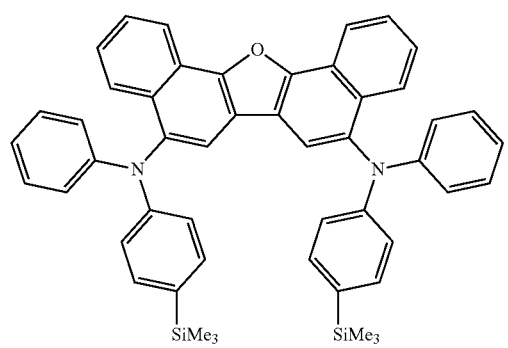
874
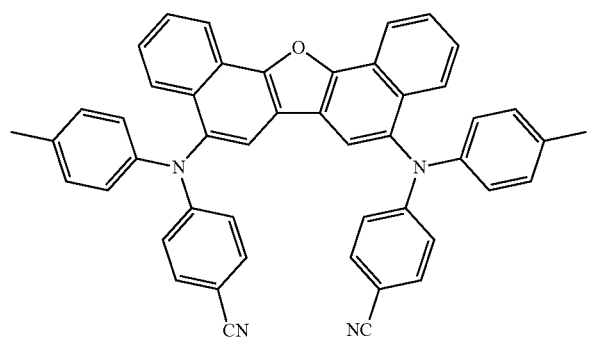
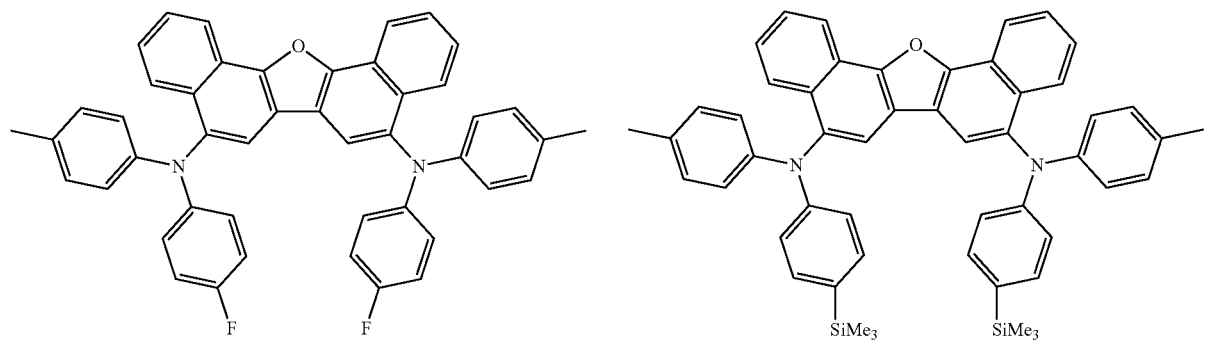
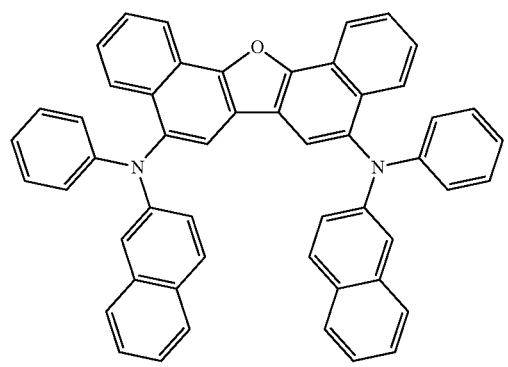
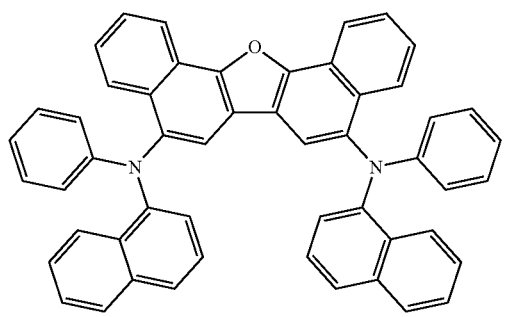
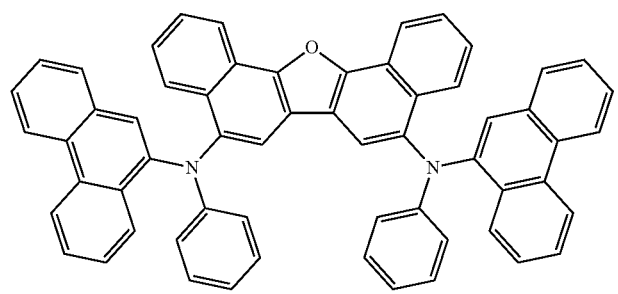
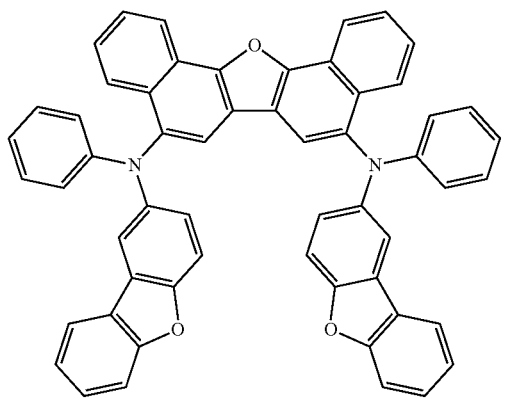

-continued
| 875 | 876 |
|---|---|
| 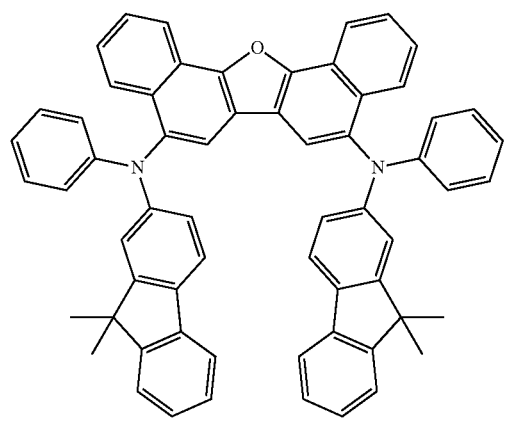 | 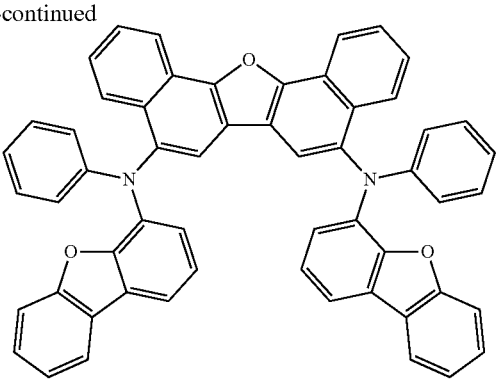 |
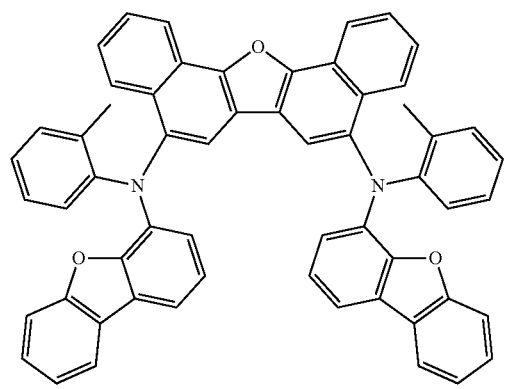
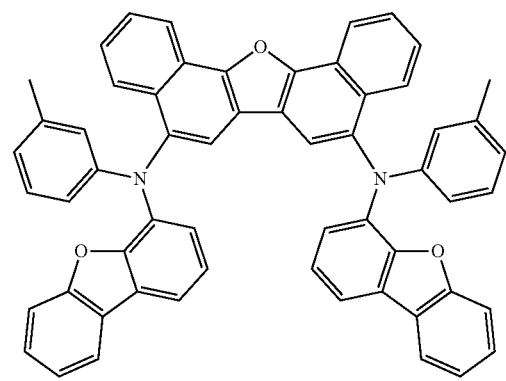
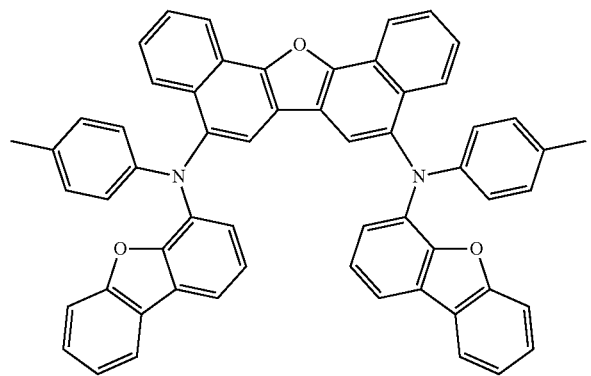
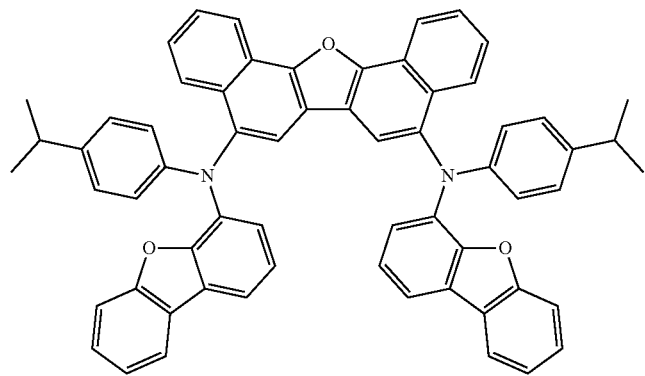

-continued
877
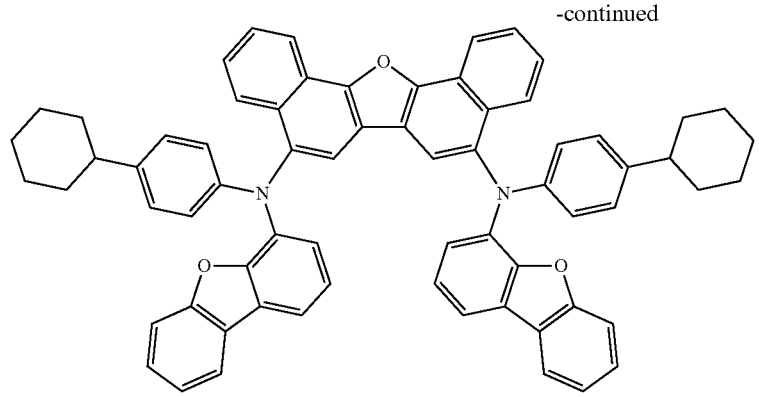
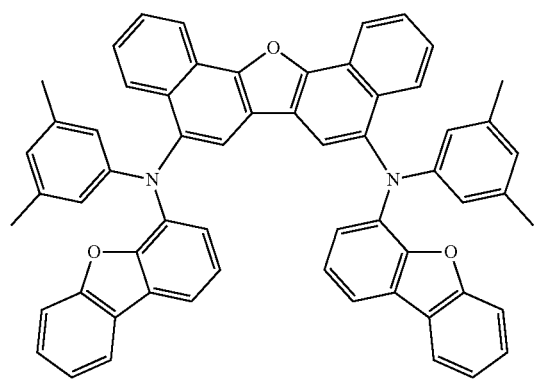
878
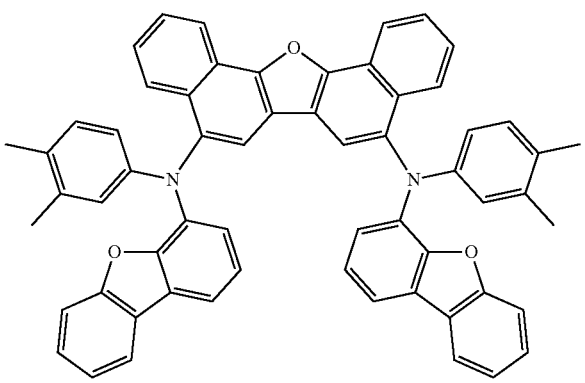
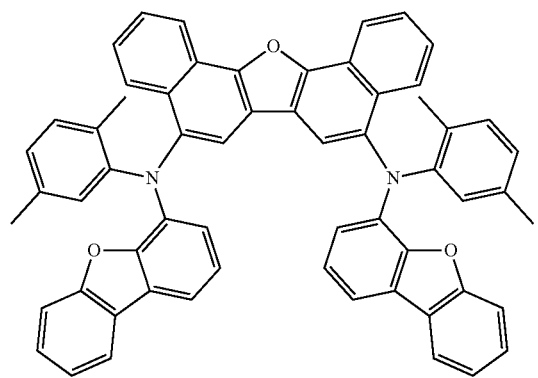
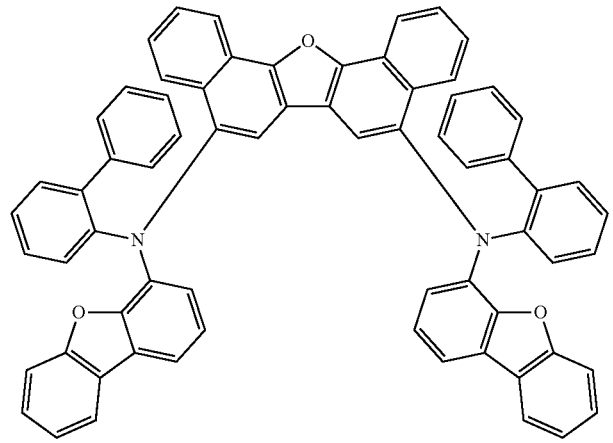
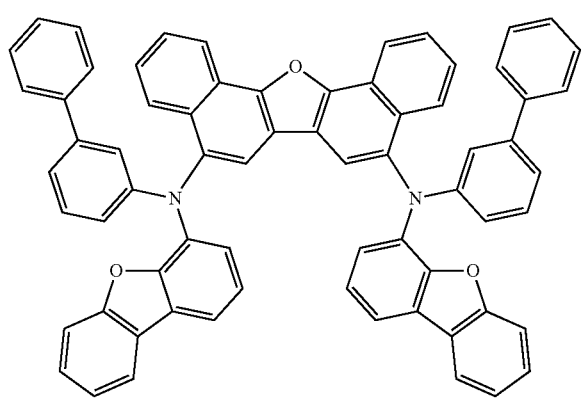

-continued
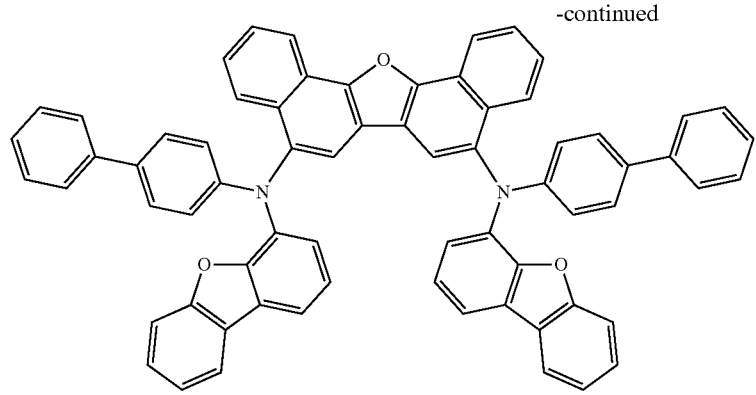
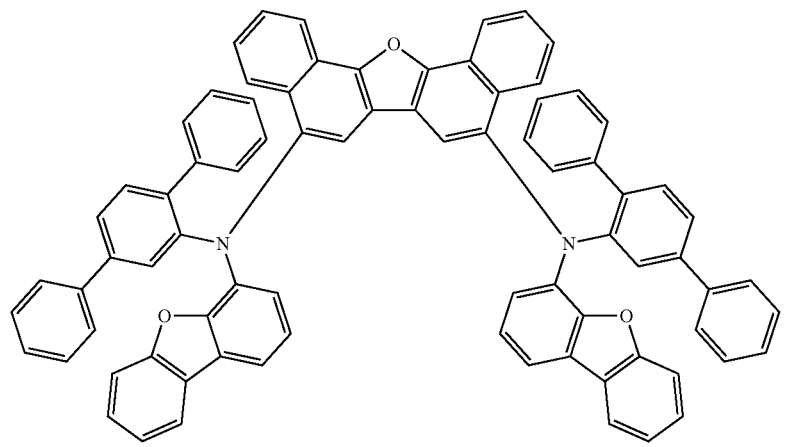
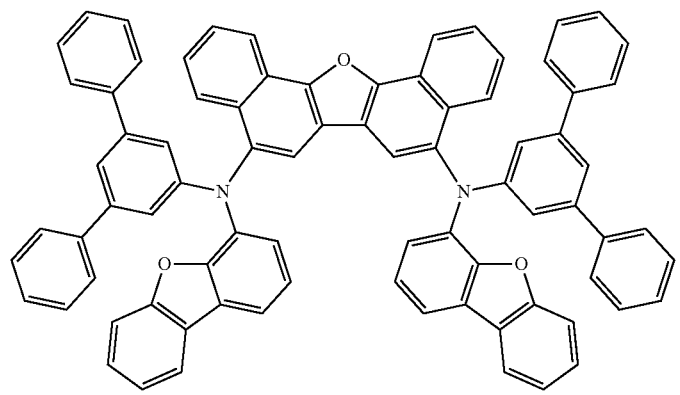
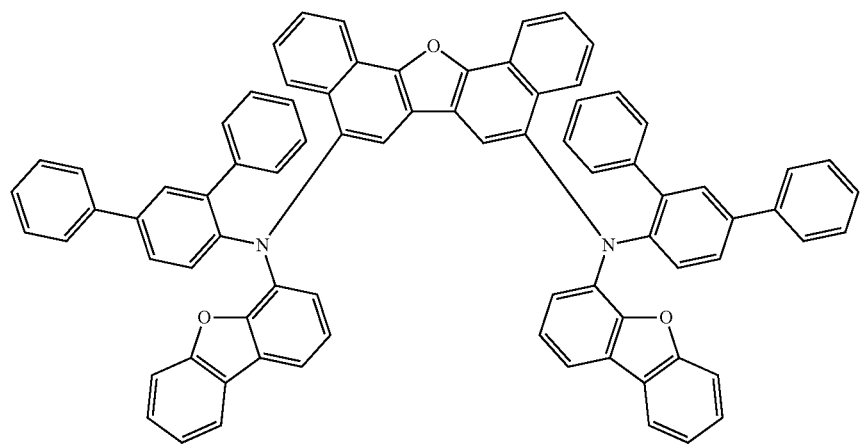

881 882
-continued
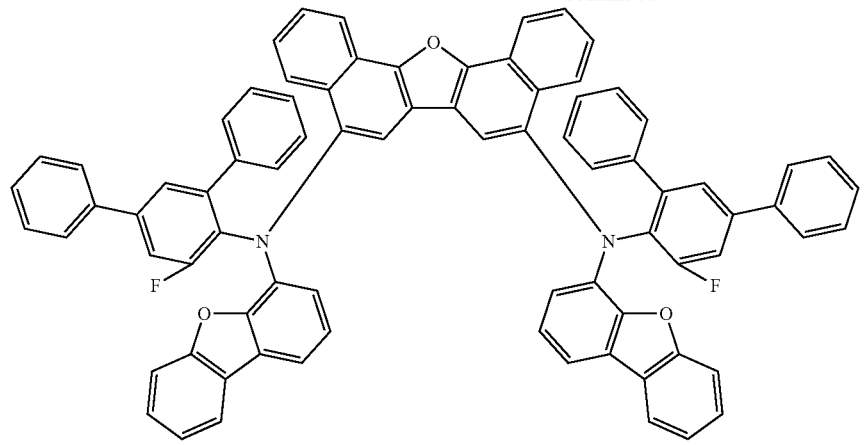
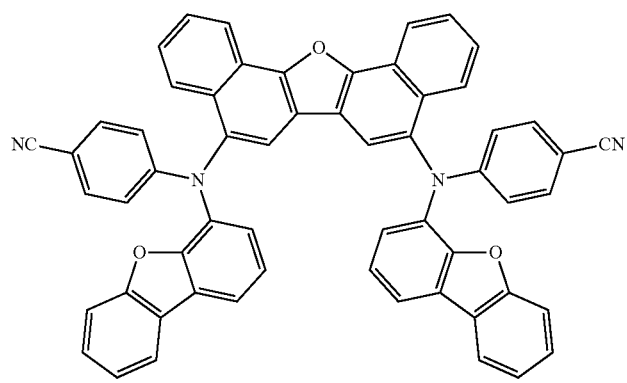
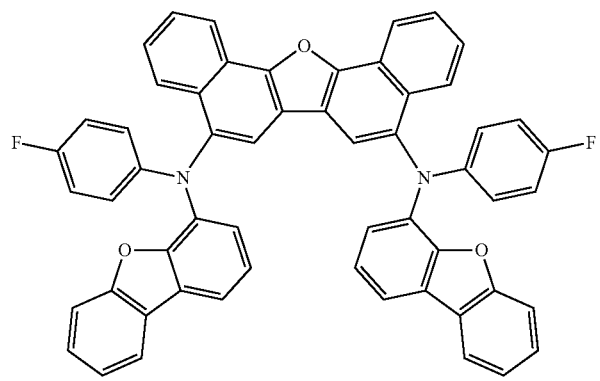
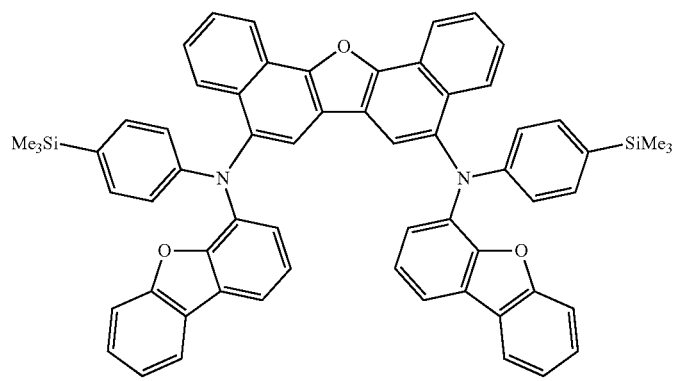

883
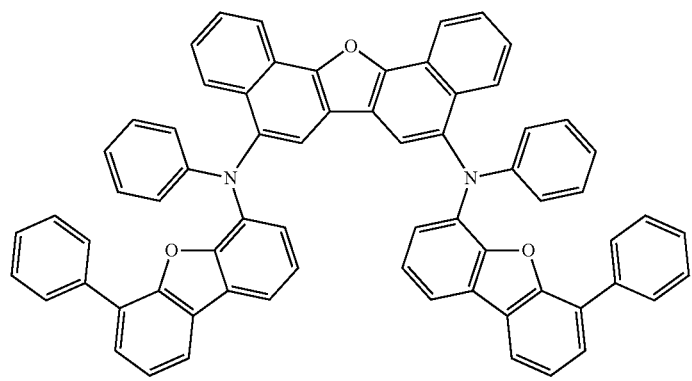
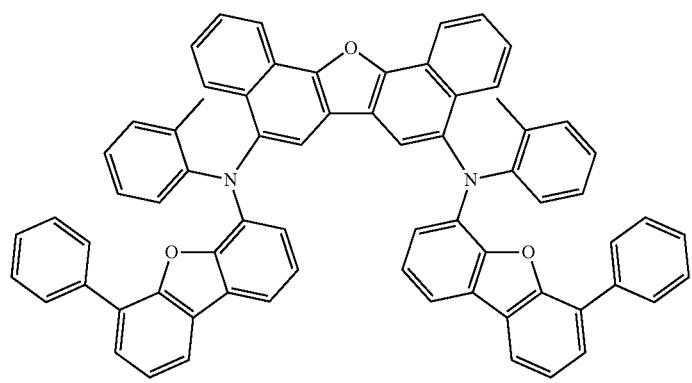
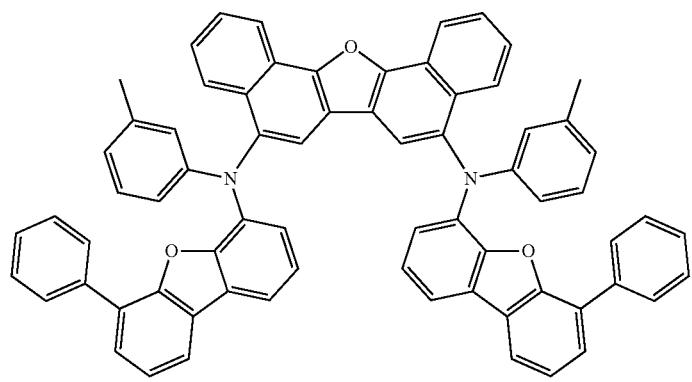
884
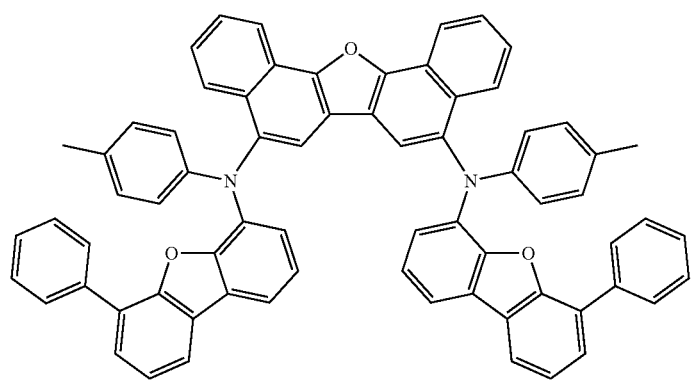

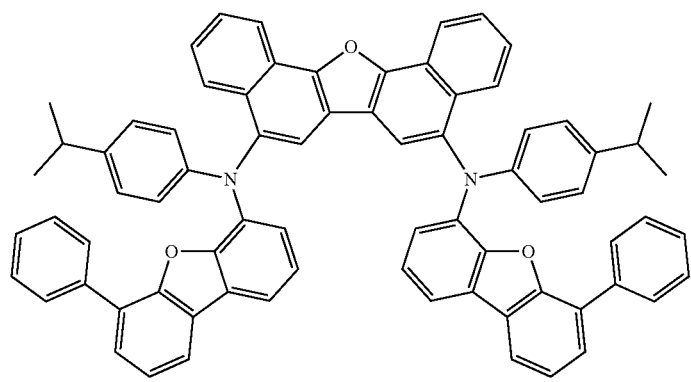
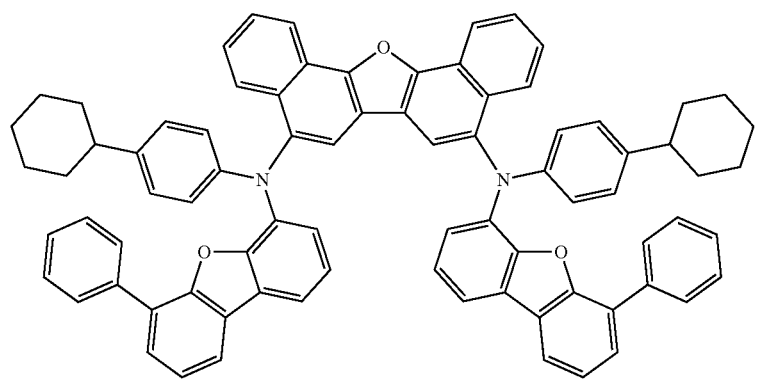
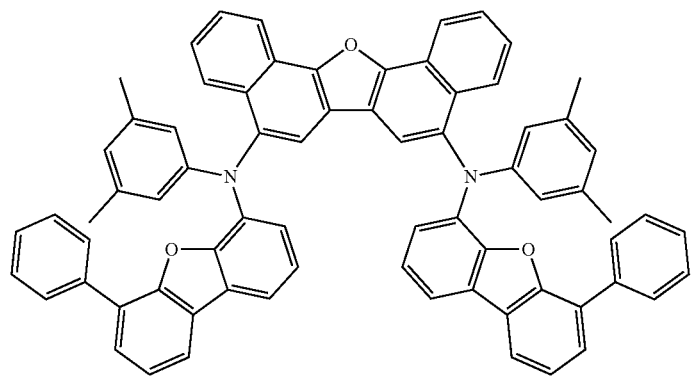
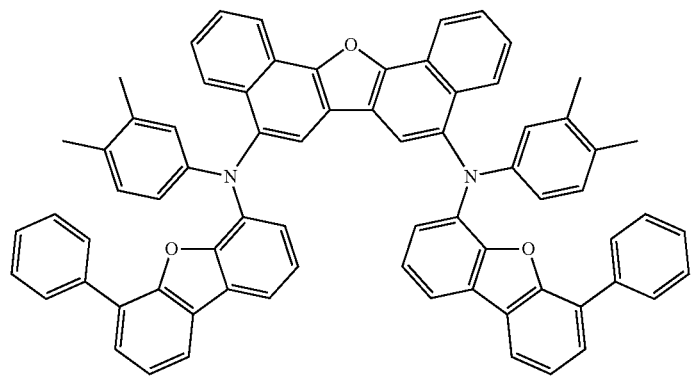

887 888
-continued
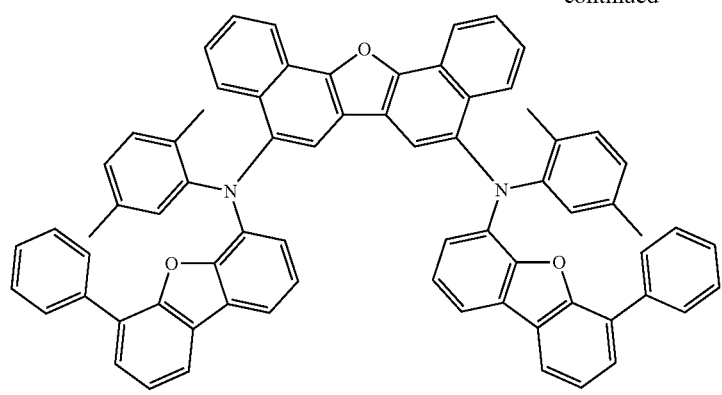
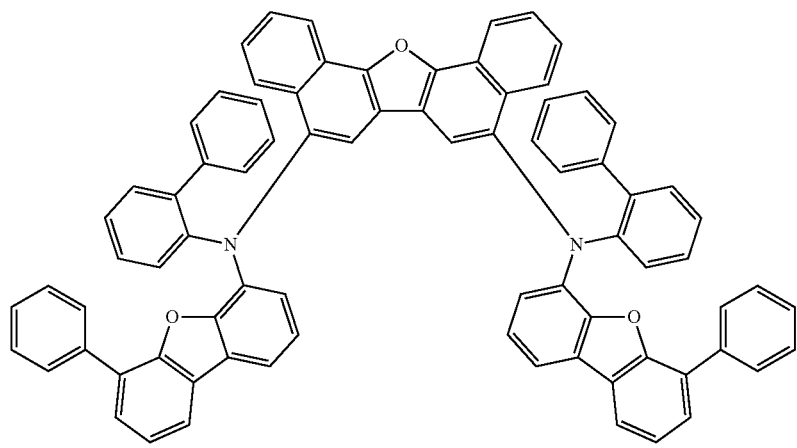
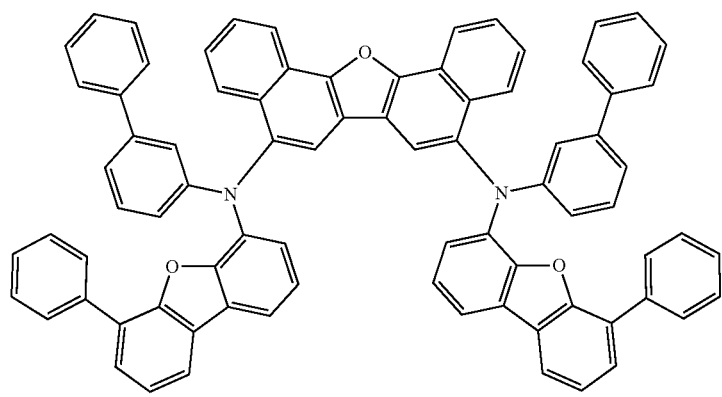
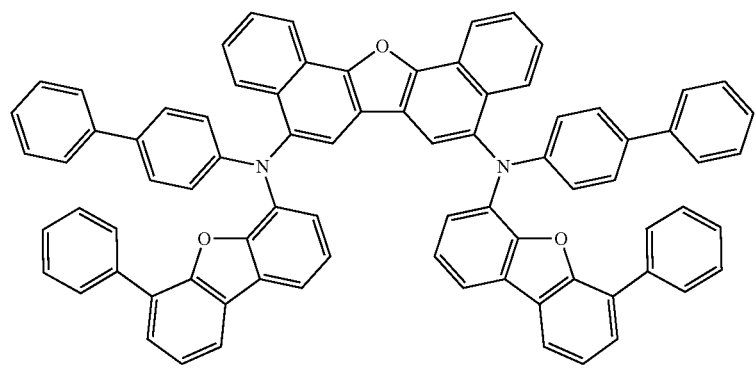

889 890
-continued
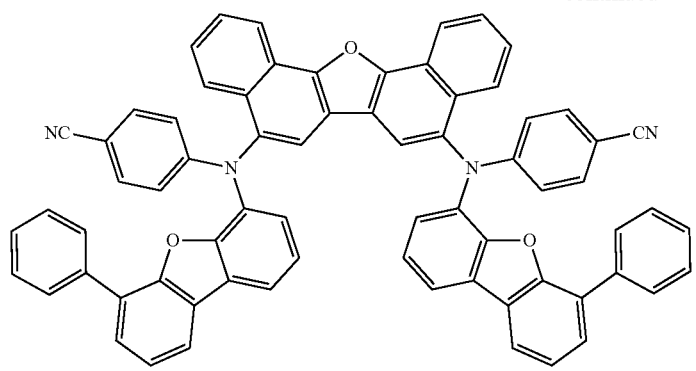
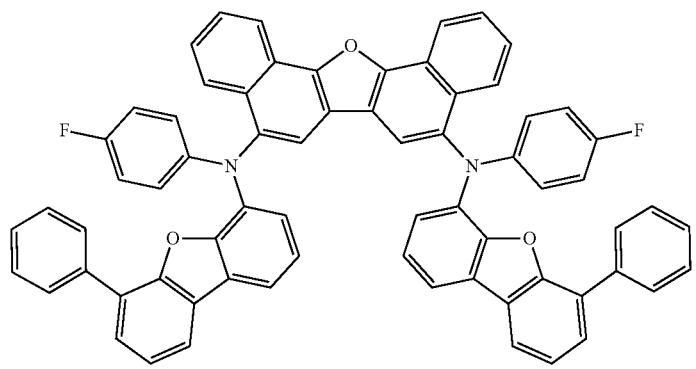
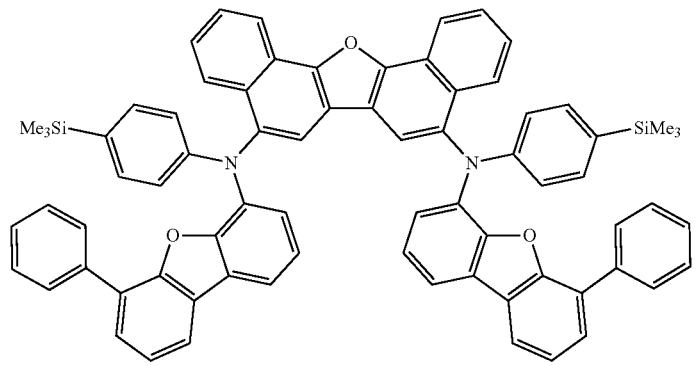
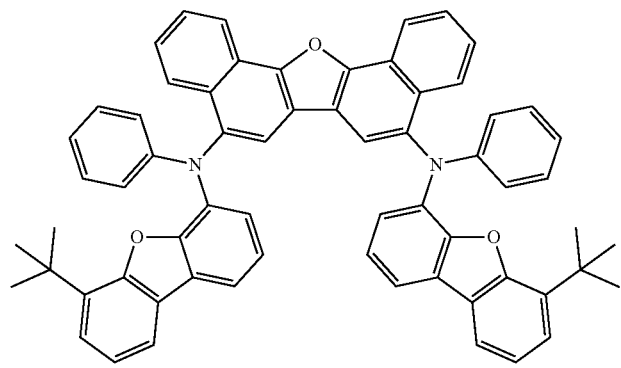

891
-continued
892
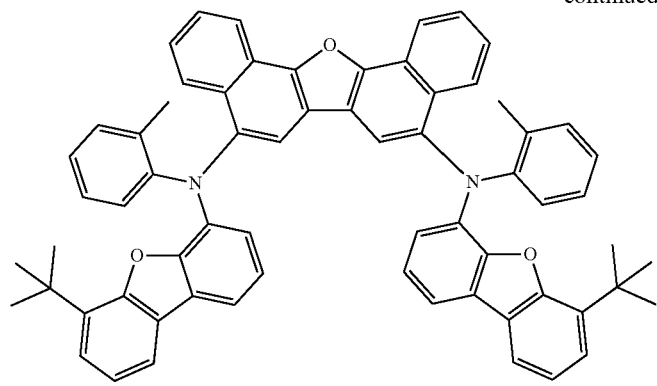
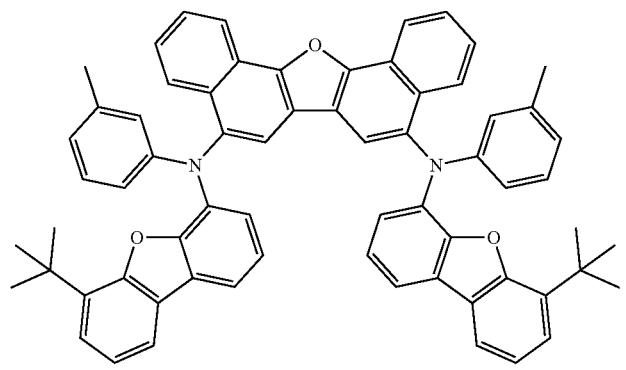
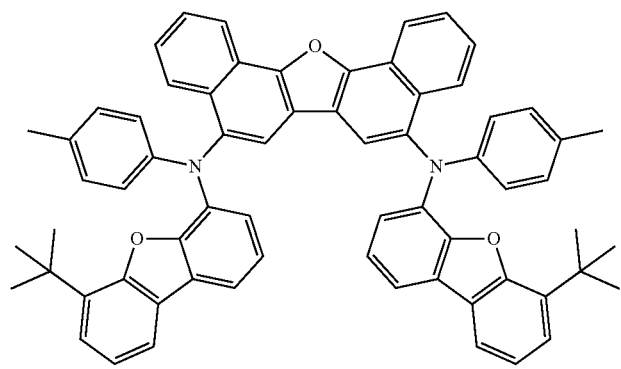
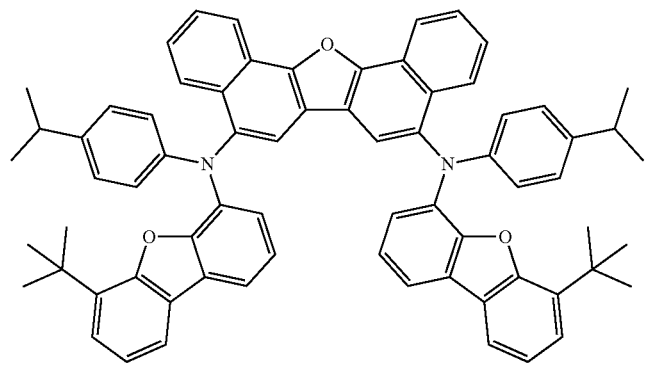

-continued
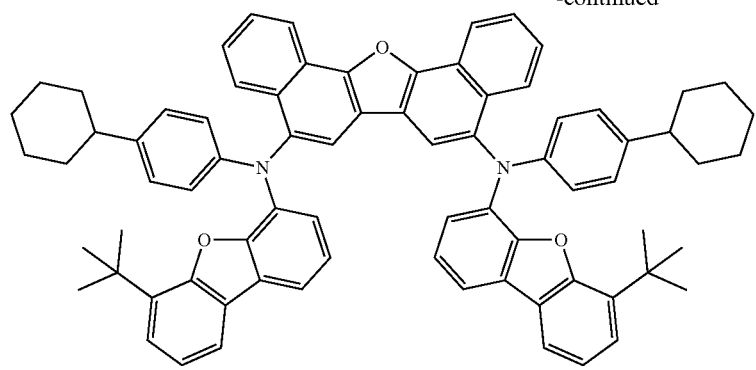
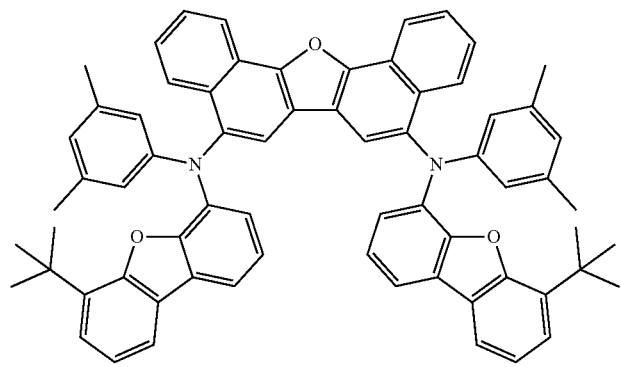
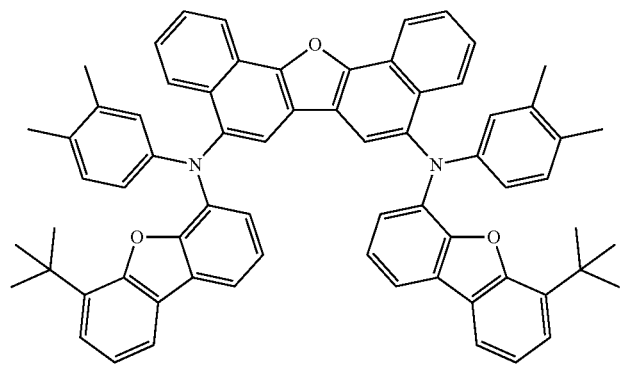
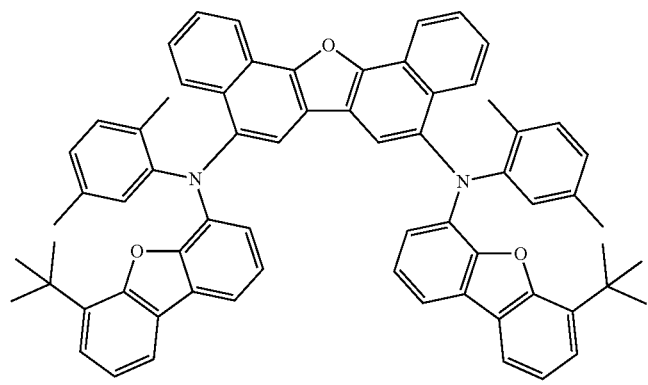

895 896
-continued
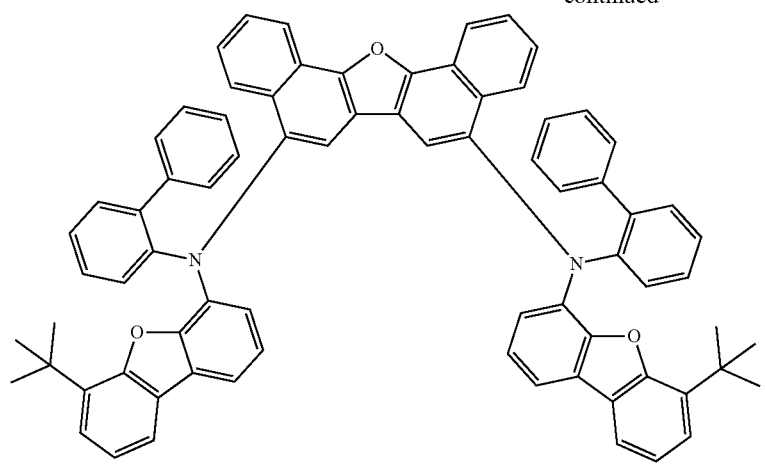
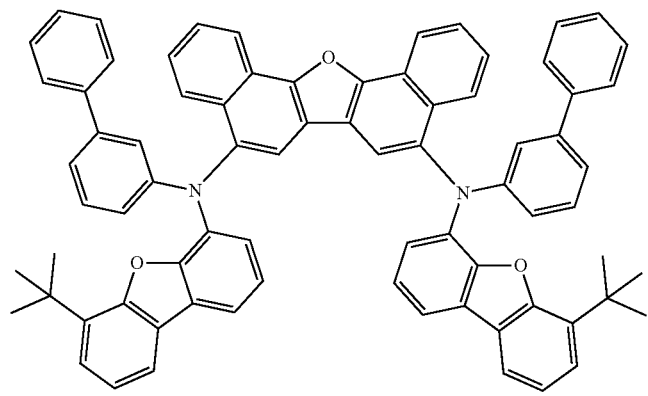
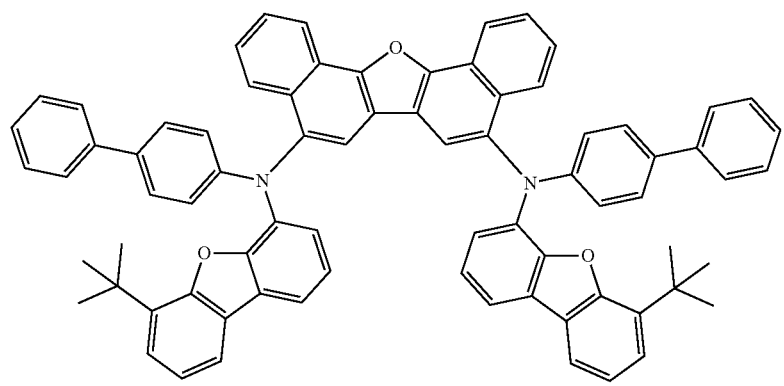
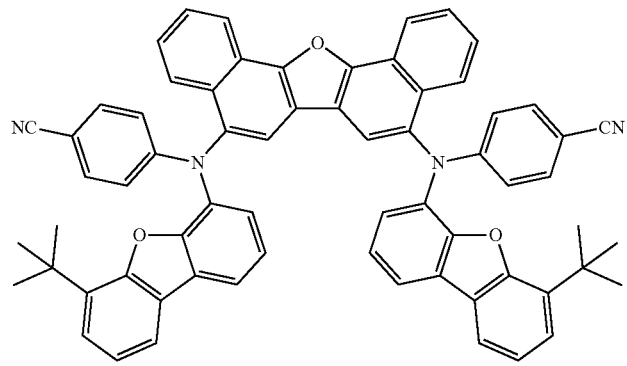

897                                                        898
-continued
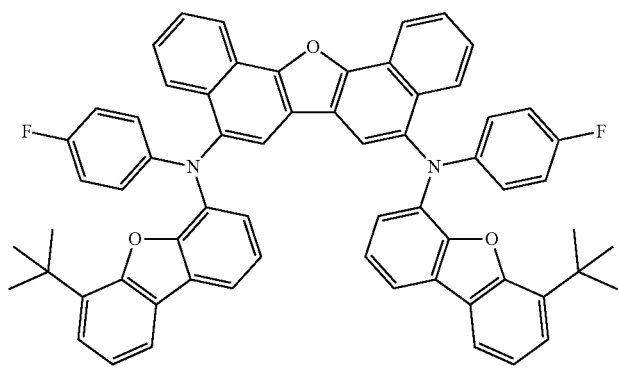
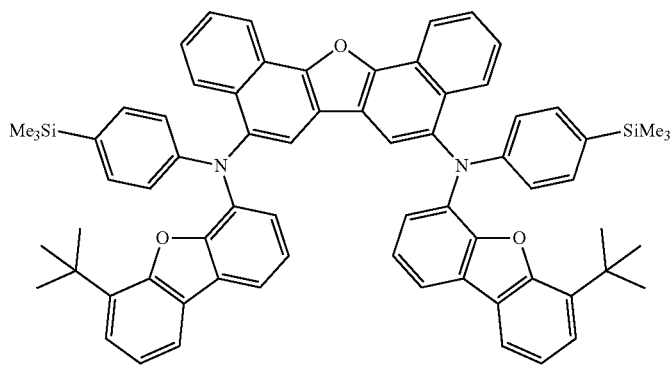
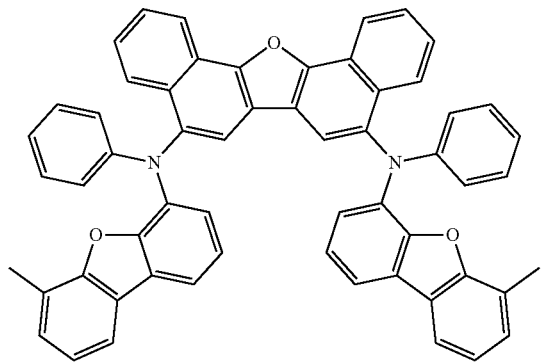
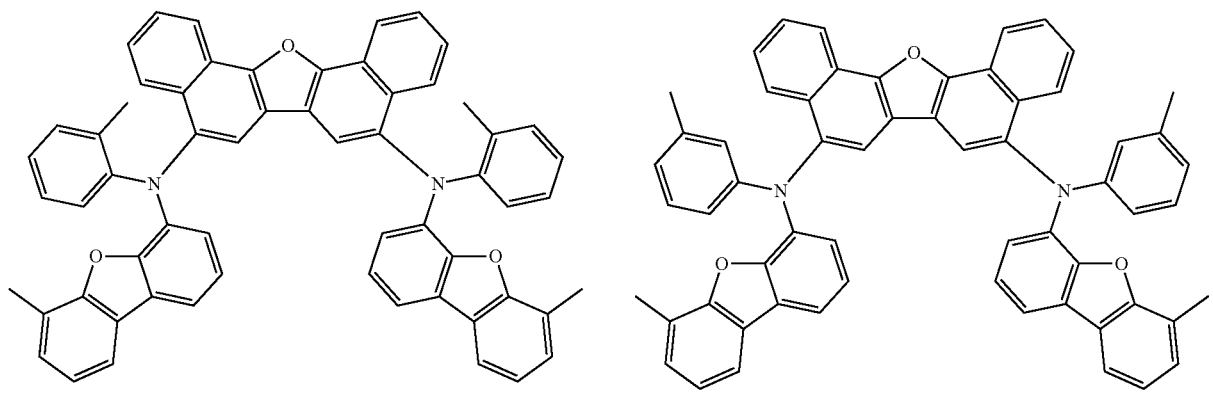

899
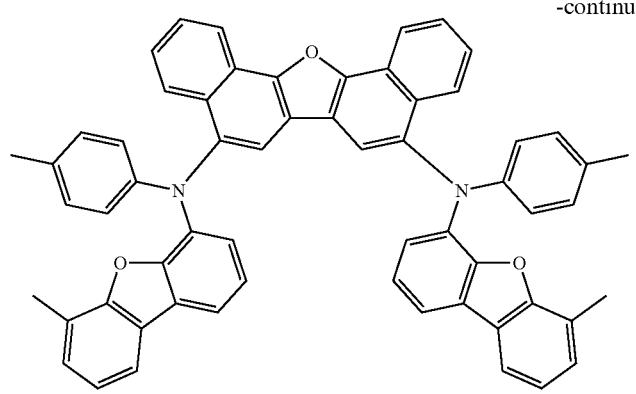
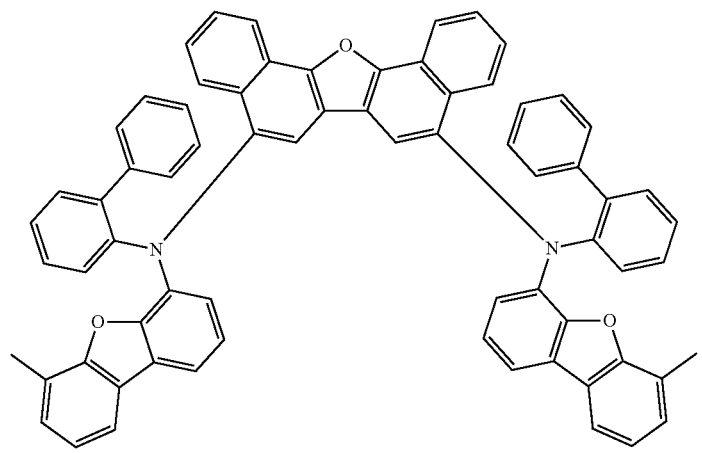
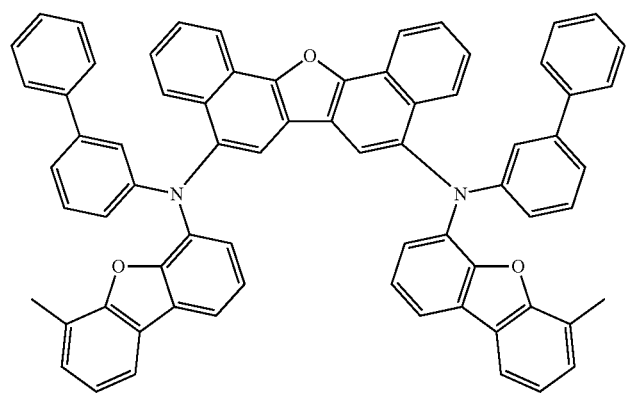
900
-continued
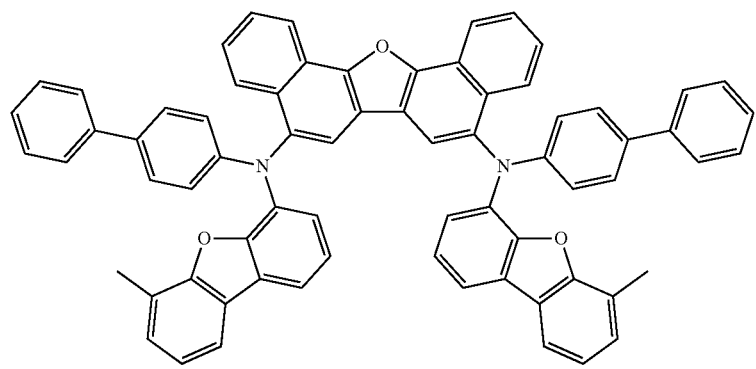

901 902
-continued
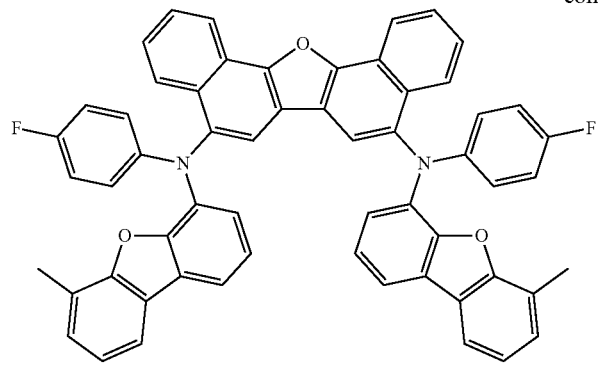
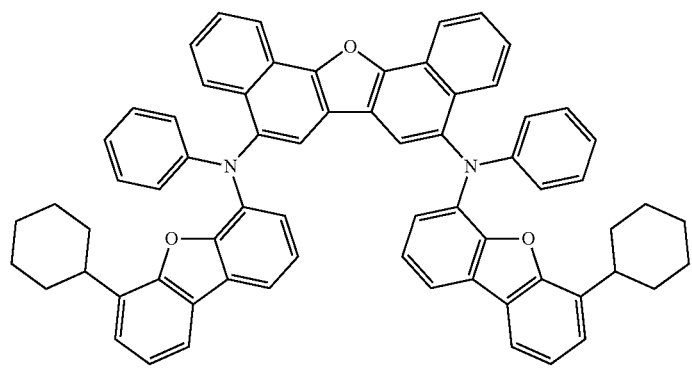
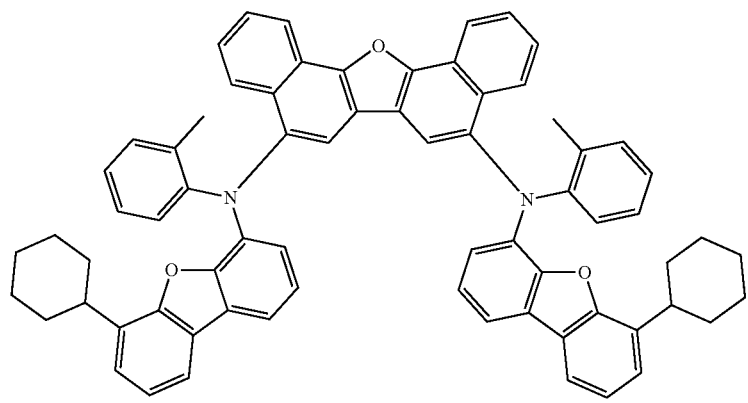
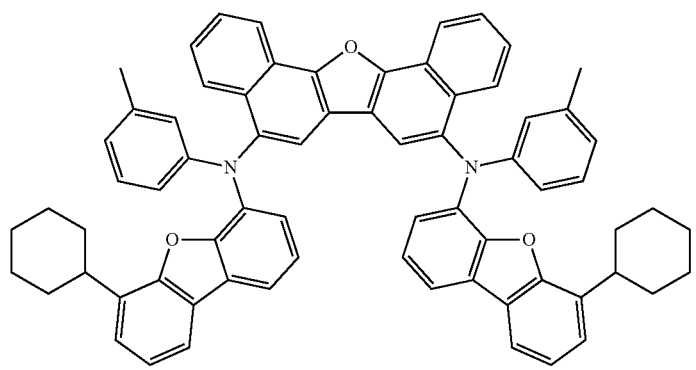

903
-continued
904
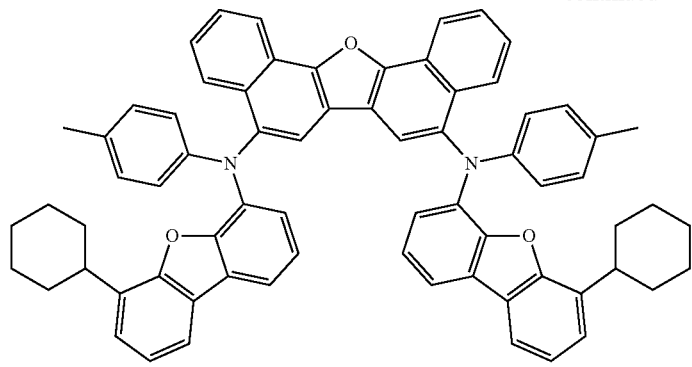
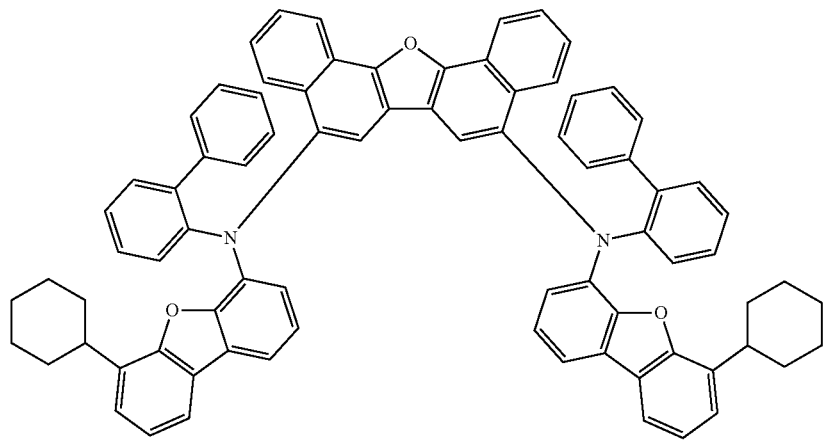
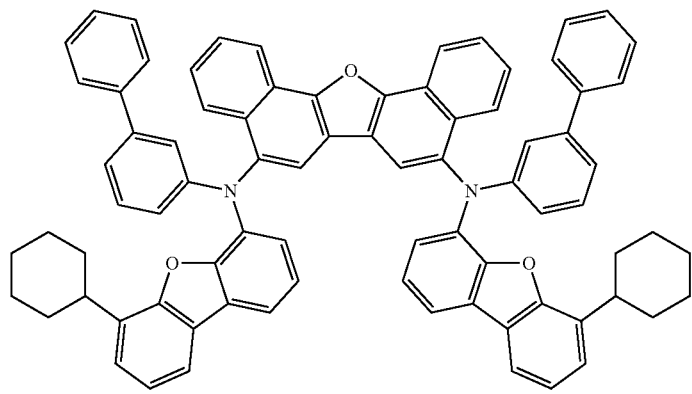
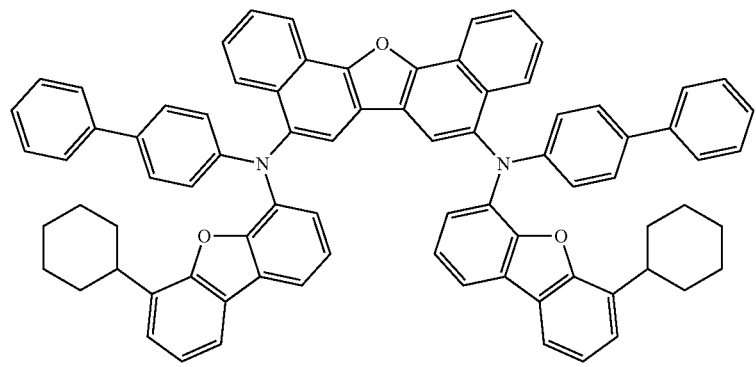

905
906
-continued
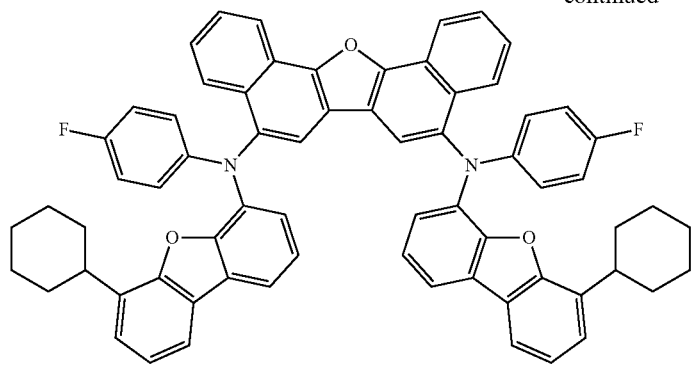
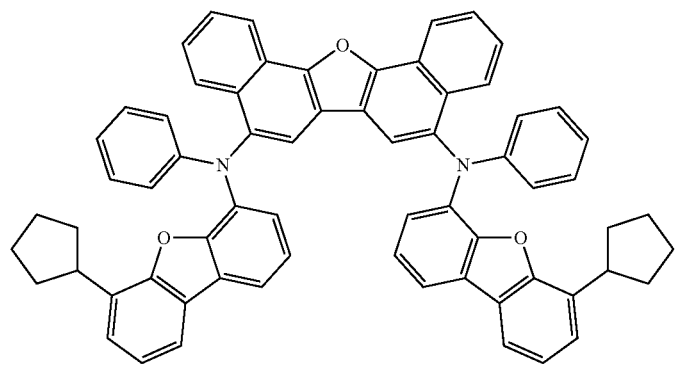
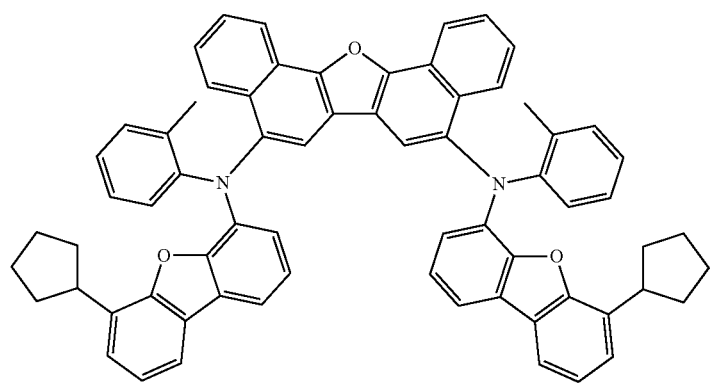
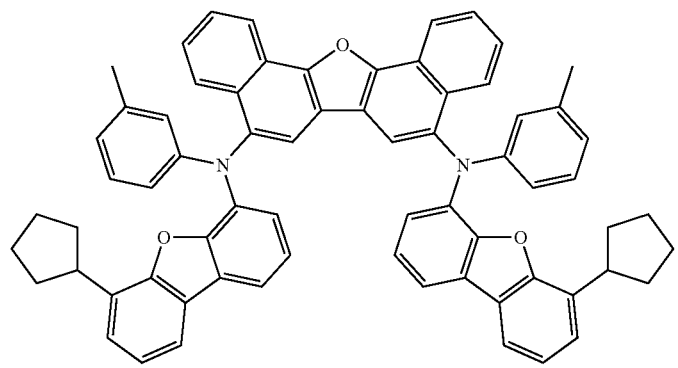

907
-continued
908
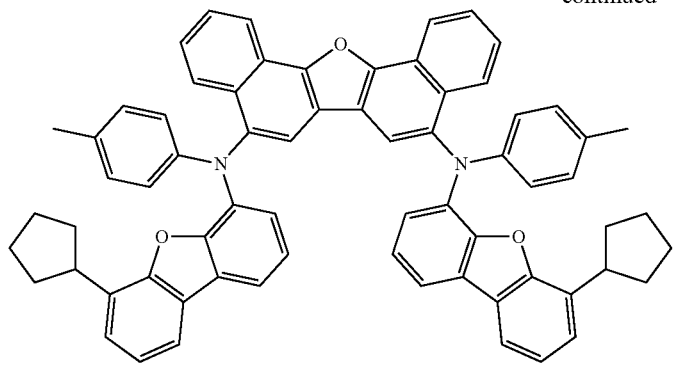
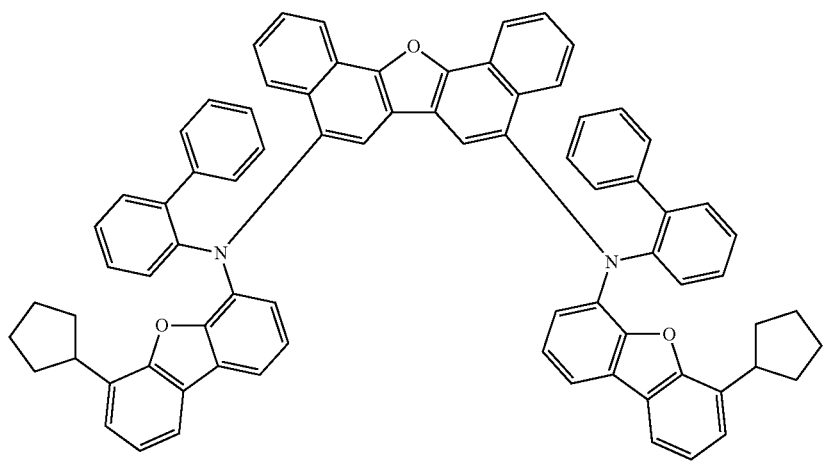
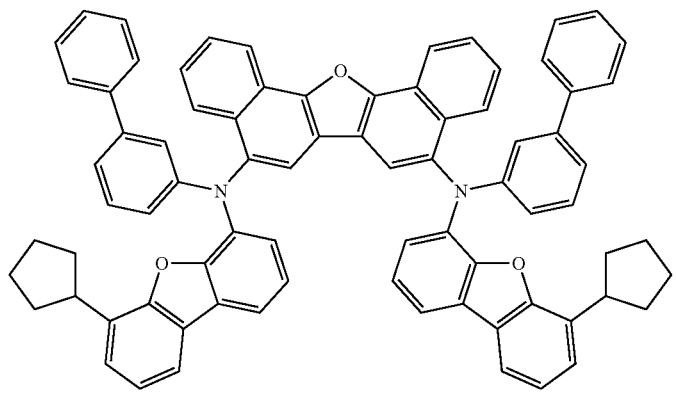
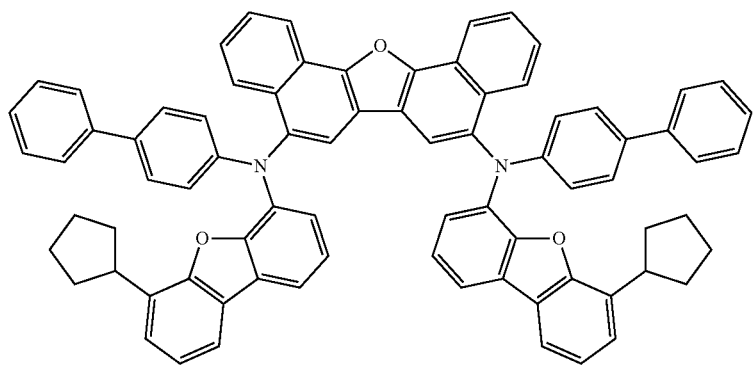

-continued
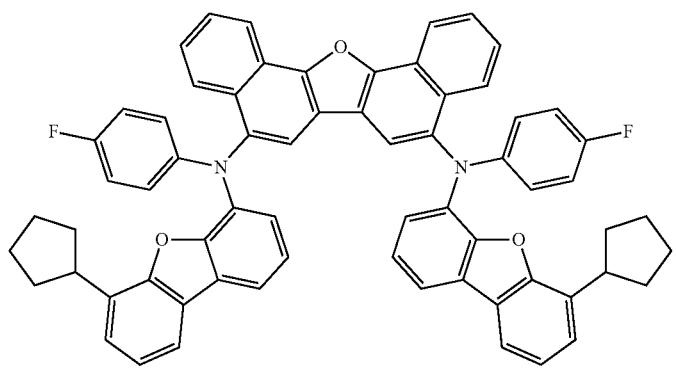
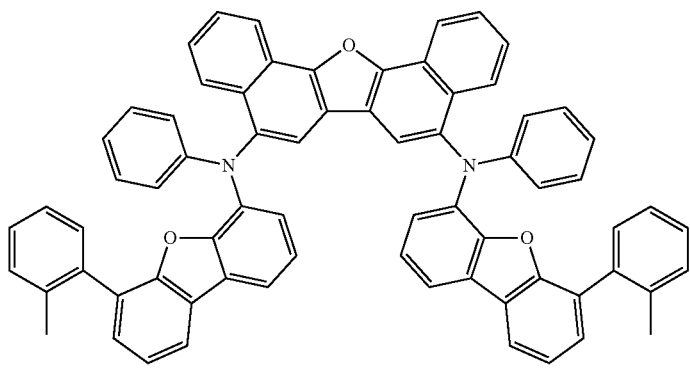
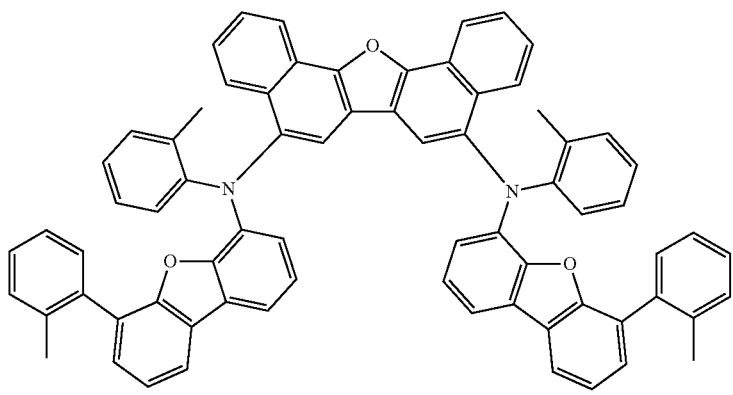
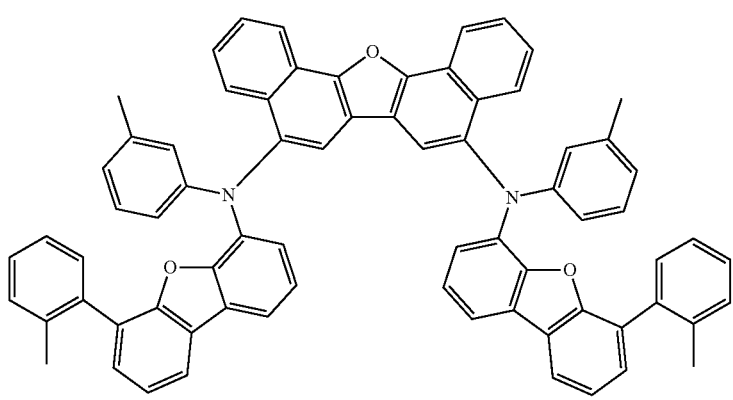

-continued
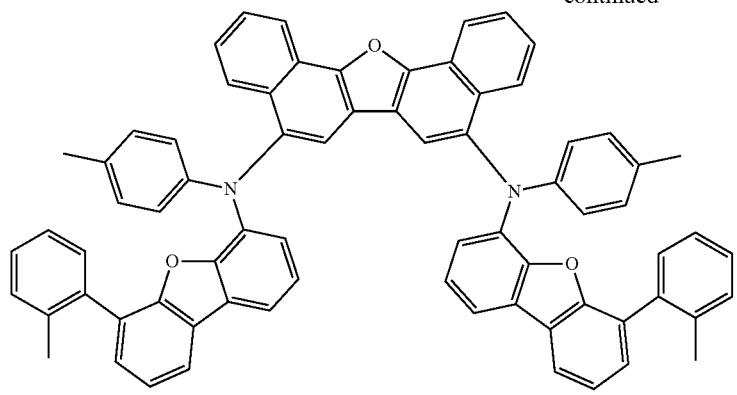
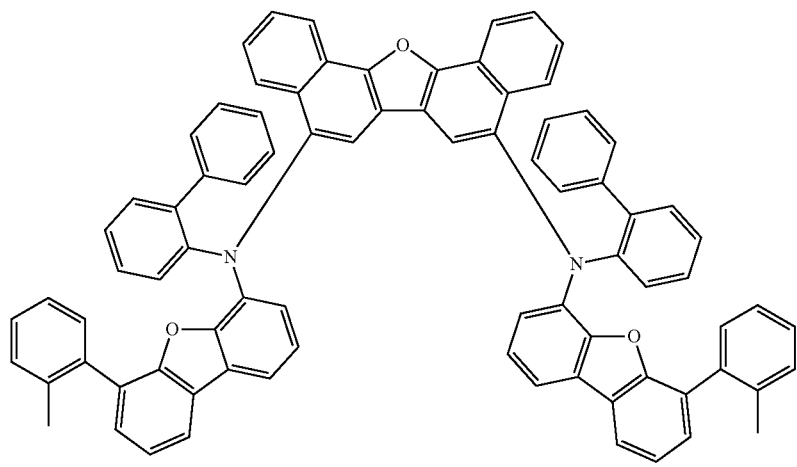
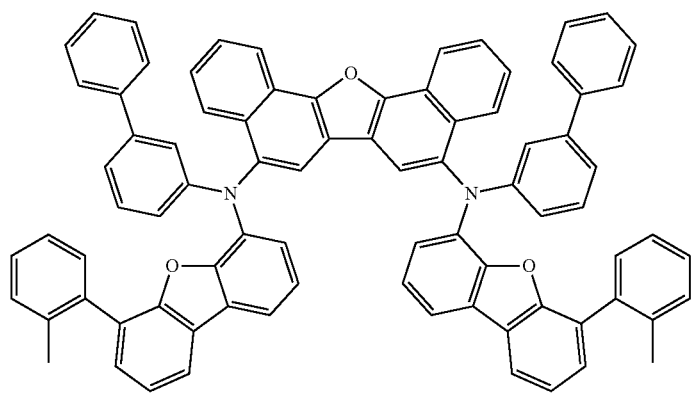
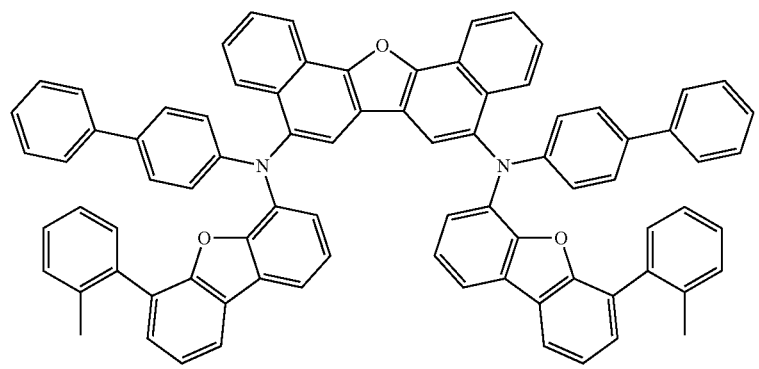

913 914
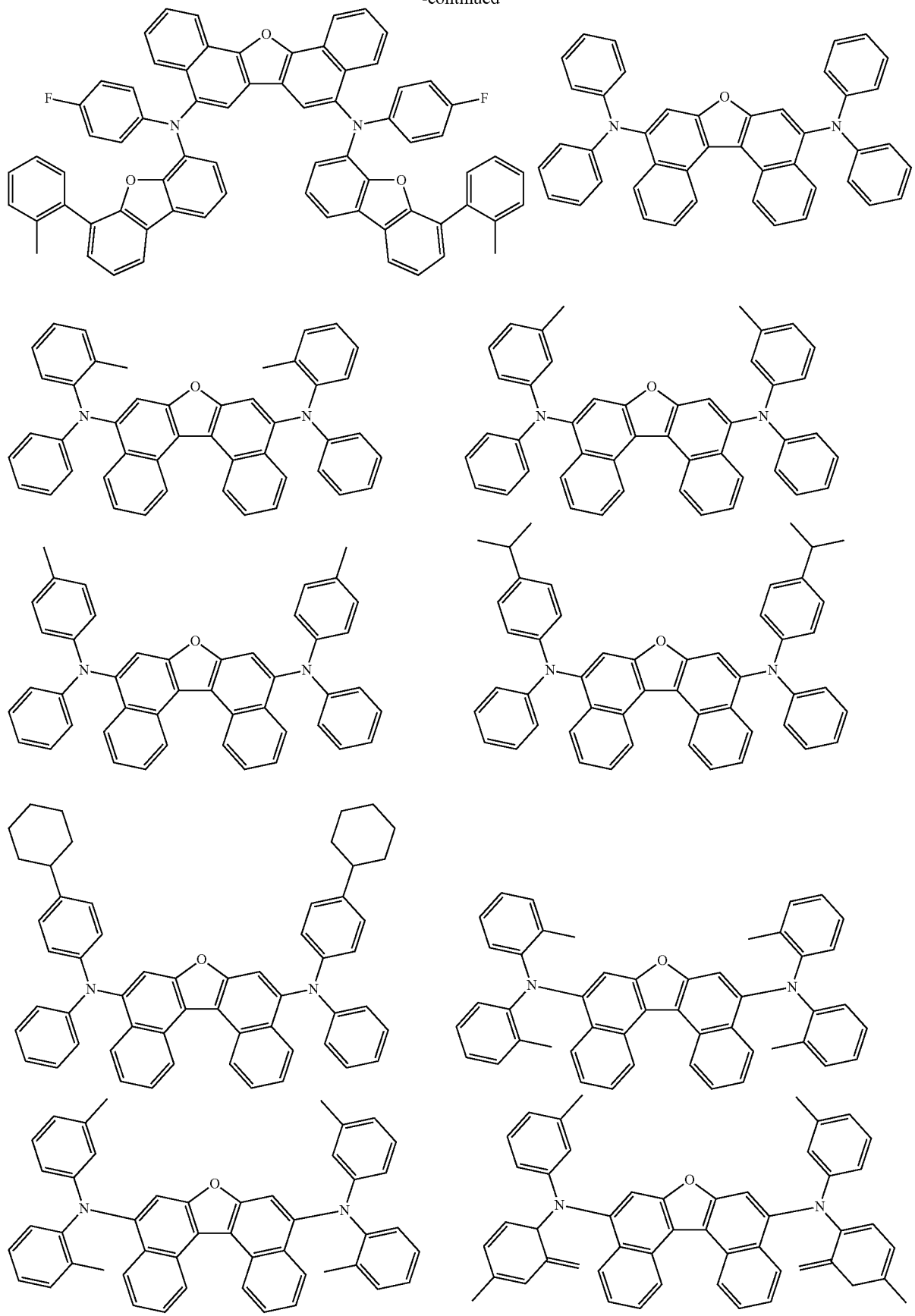

-continued
| 915 | 916 |
|---|---|
| 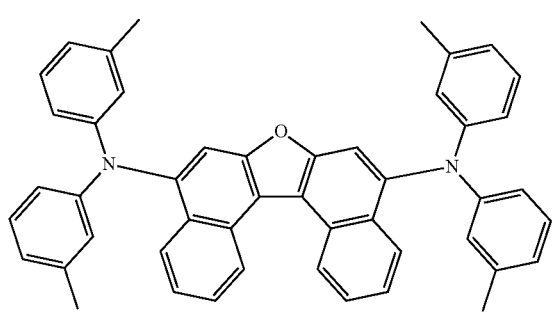 | 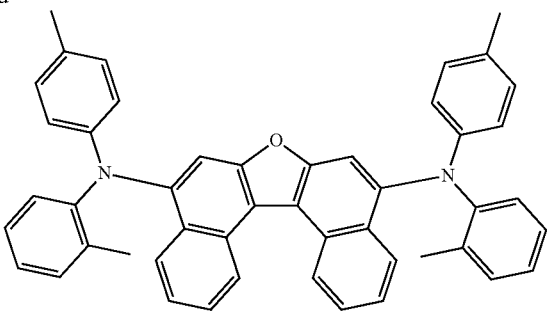 |
| 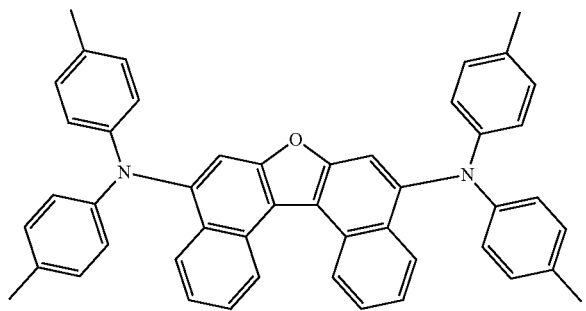 | 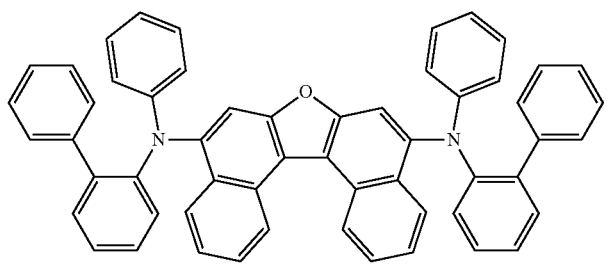 |
| 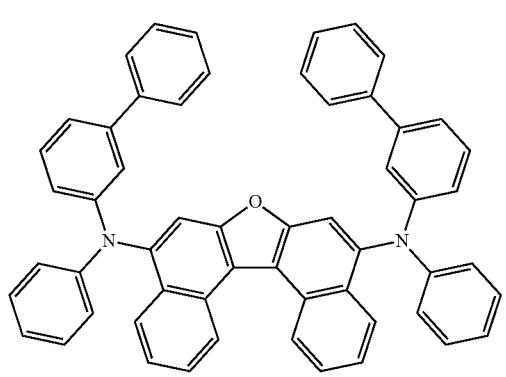 | 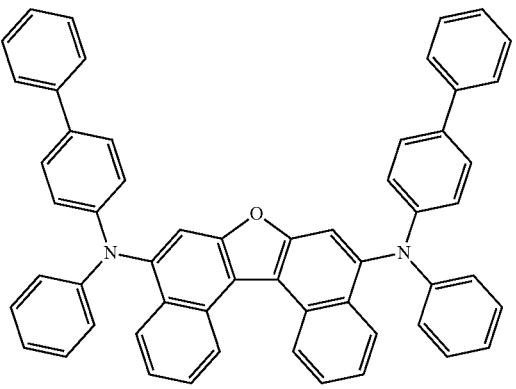 |
| 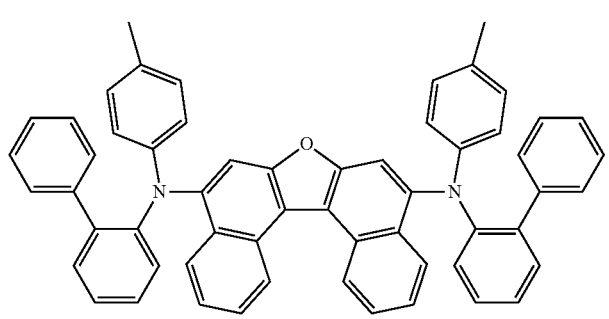 | 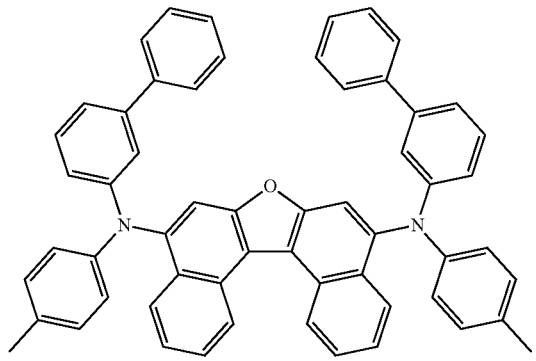 |

-continued
917
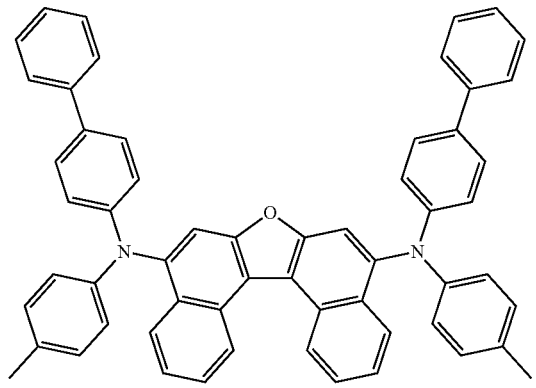
918
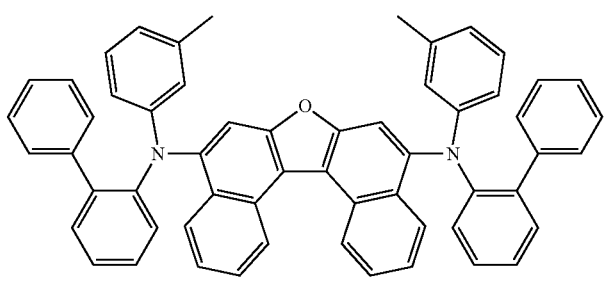
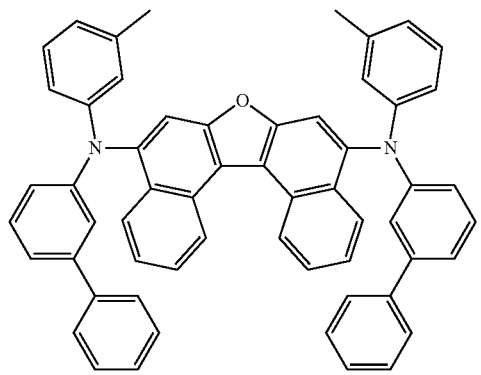
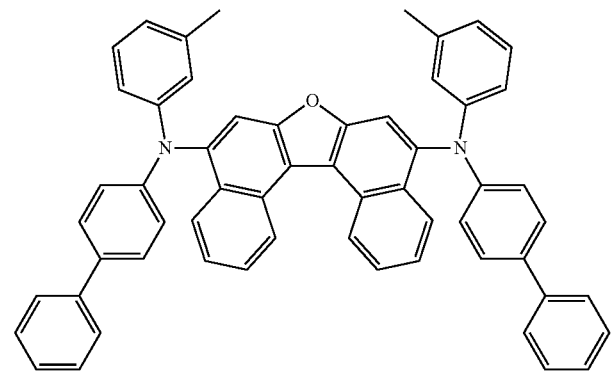
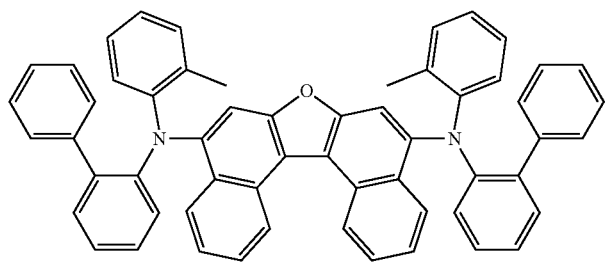
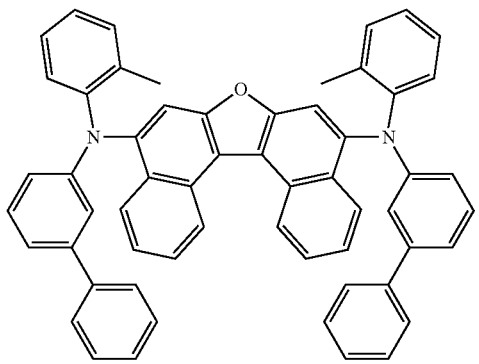
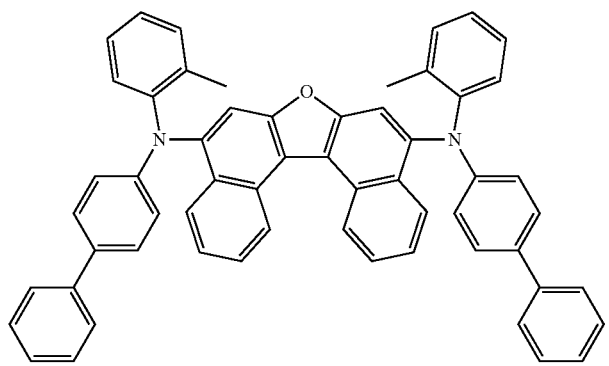

-continued
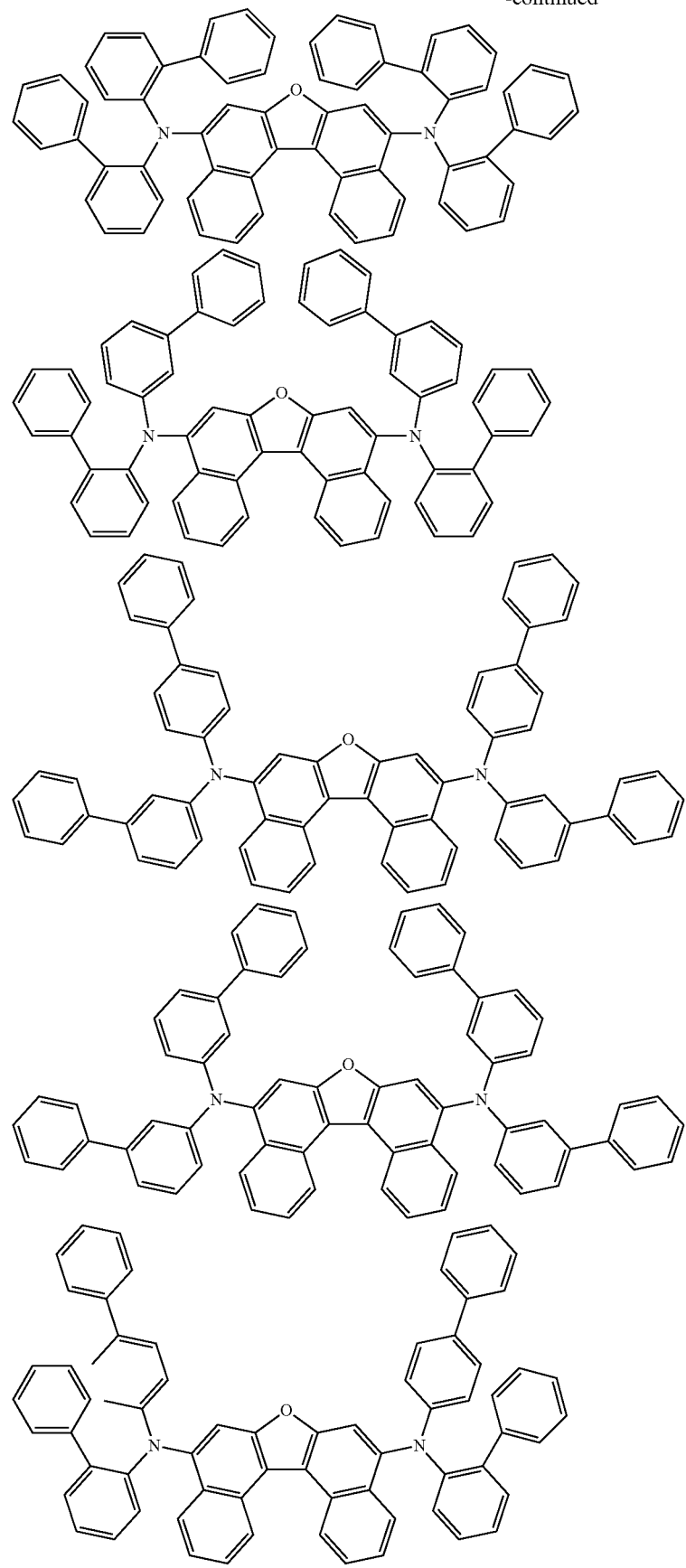

-continued
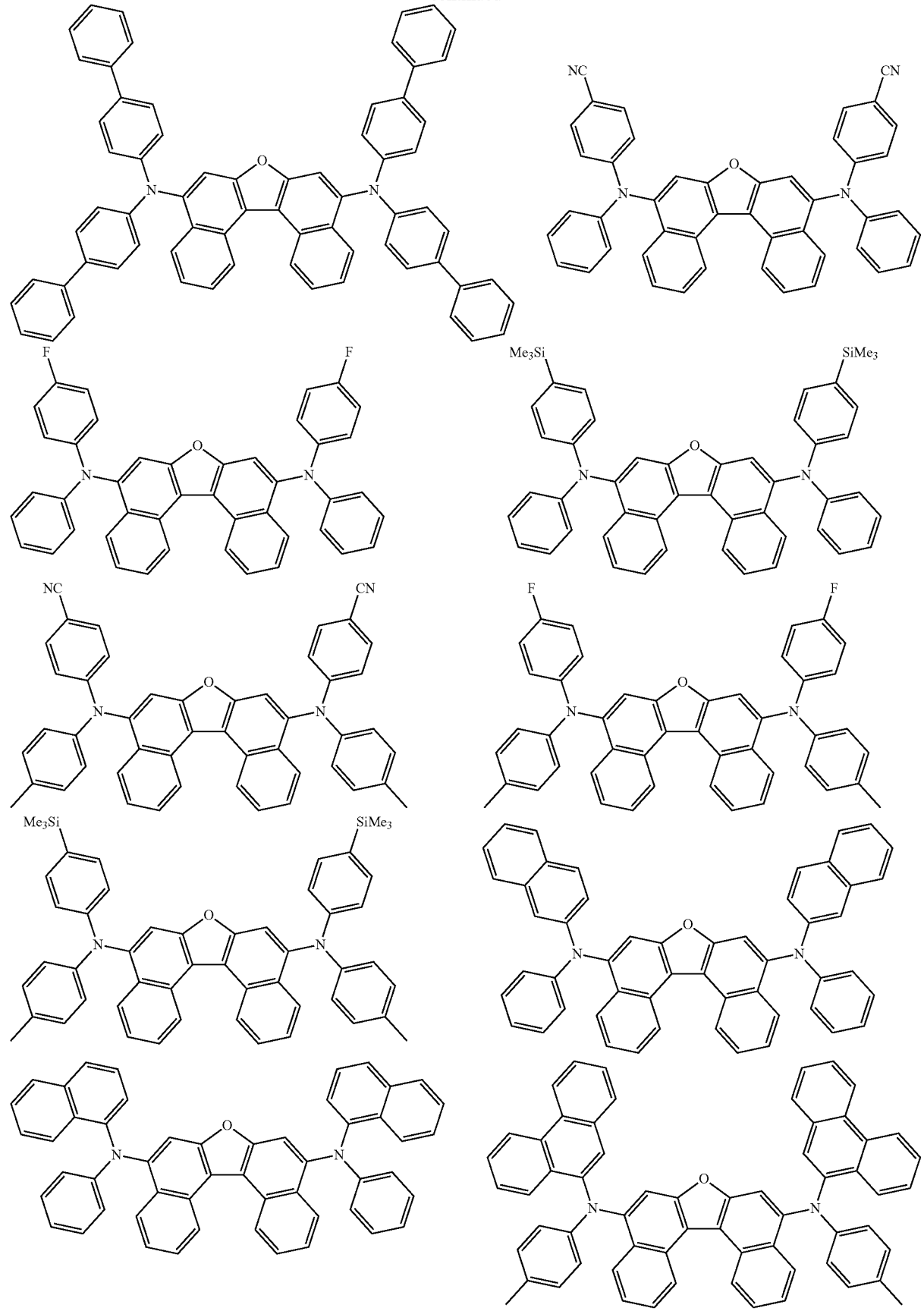

923
-continued
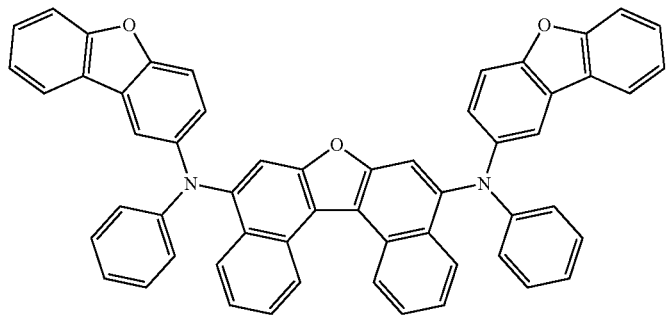
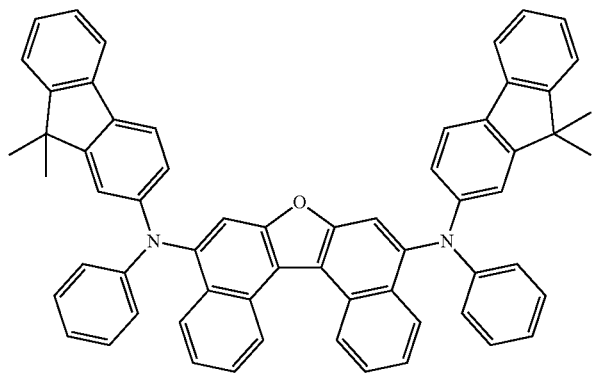
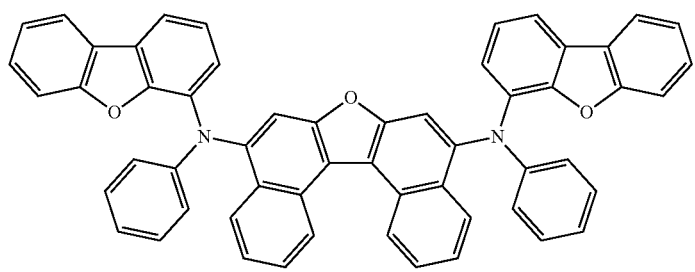
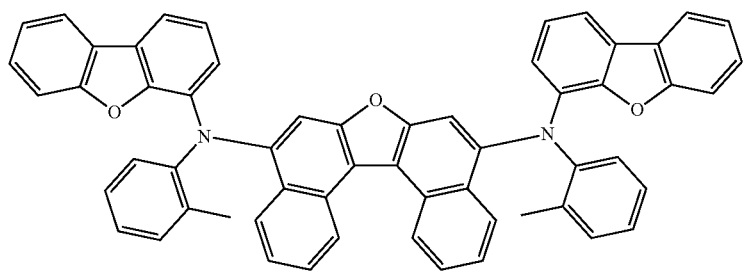
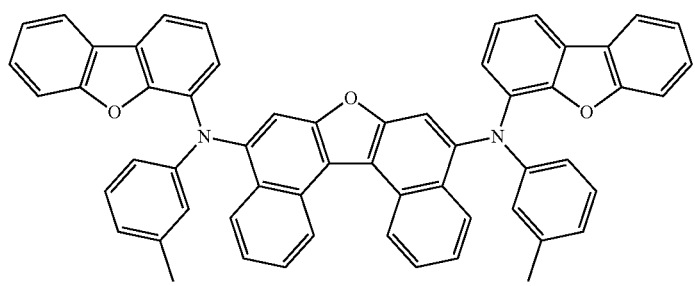
924

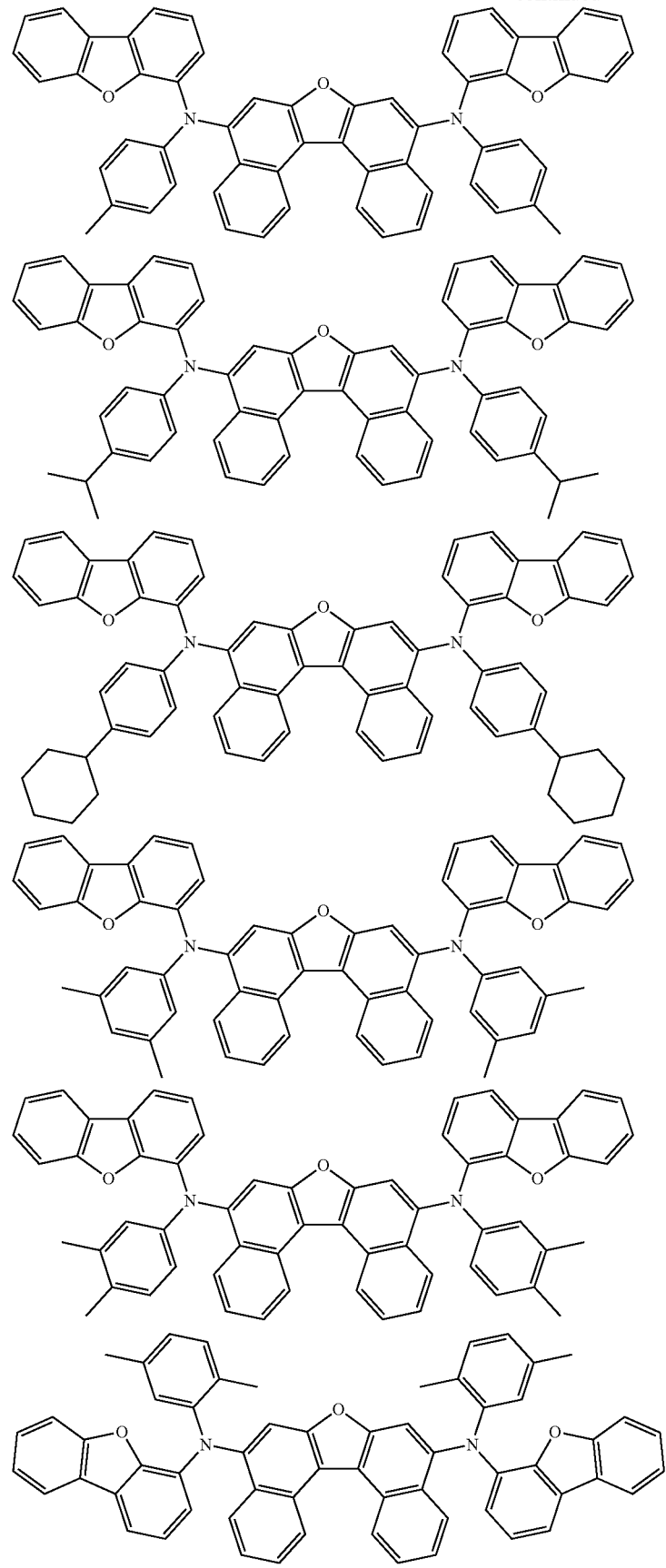

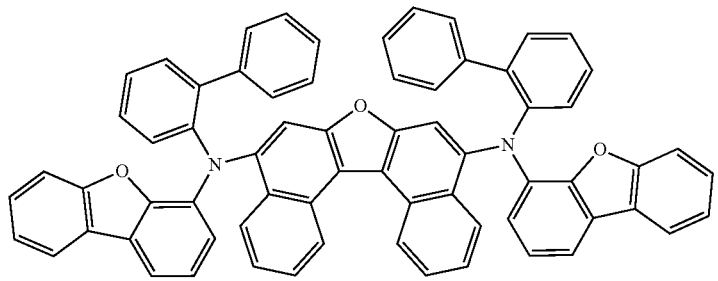
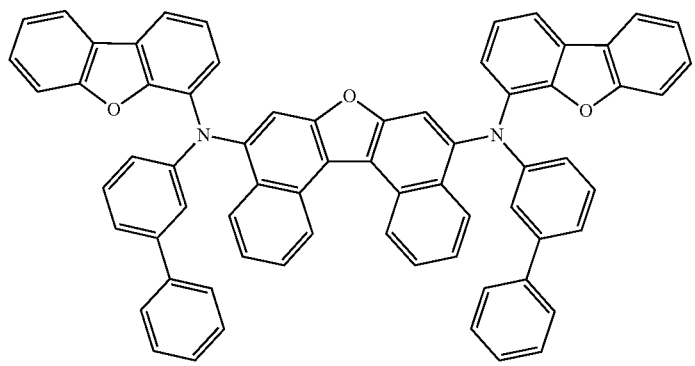
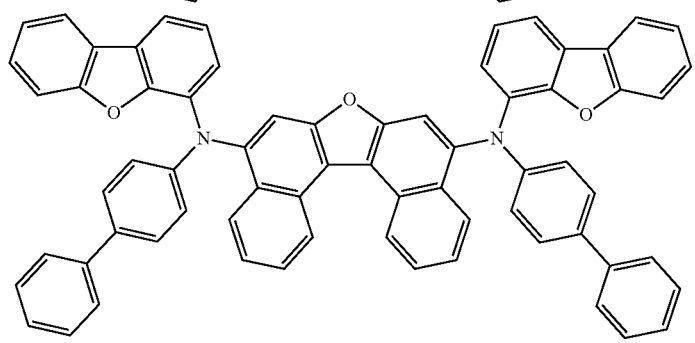
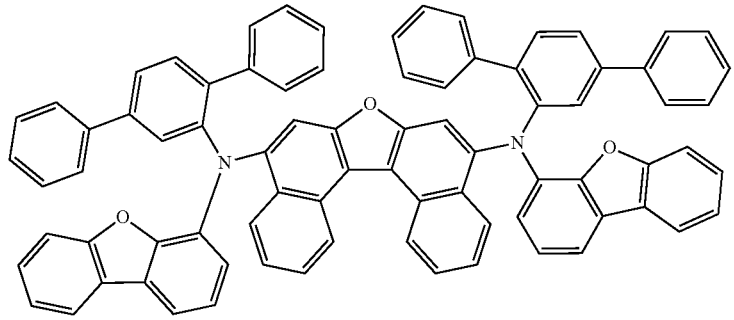
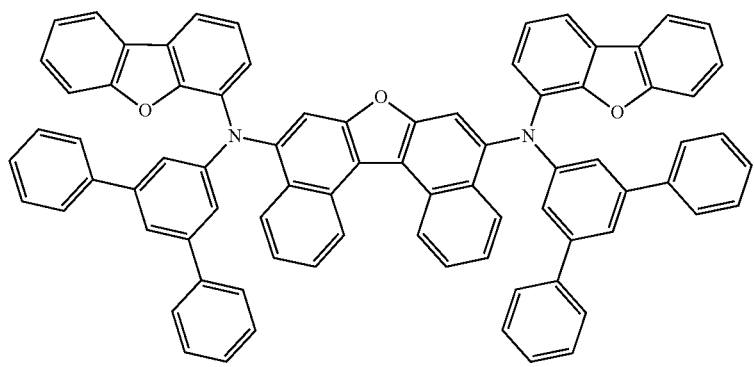

-continued
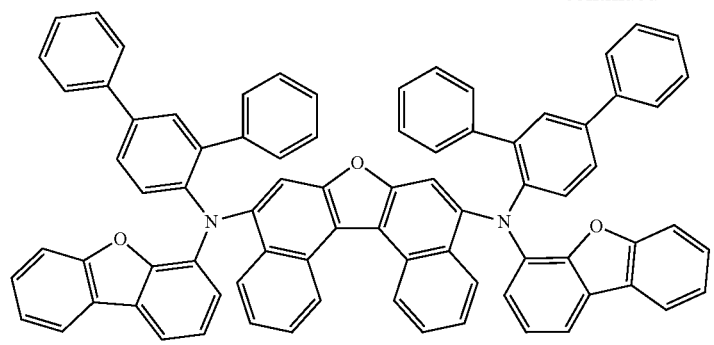
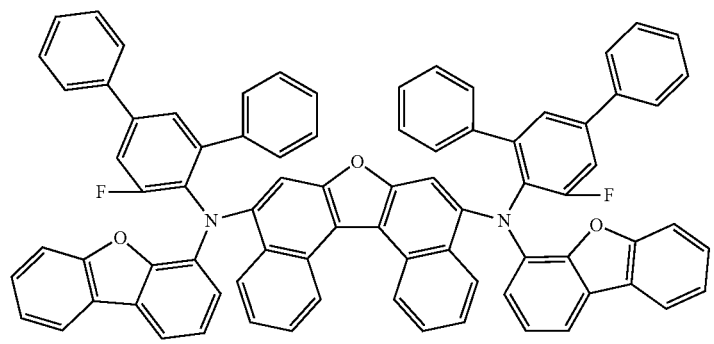
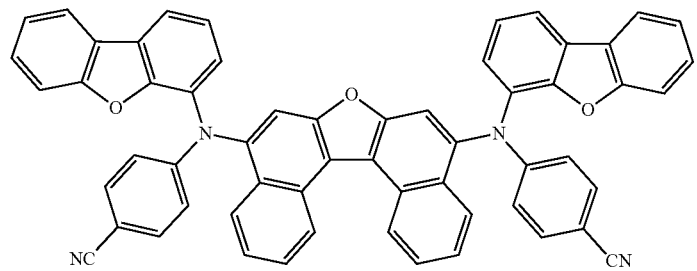
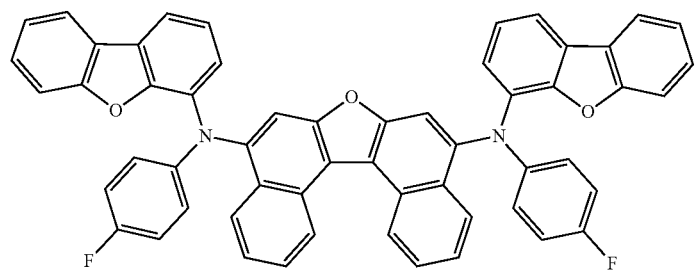
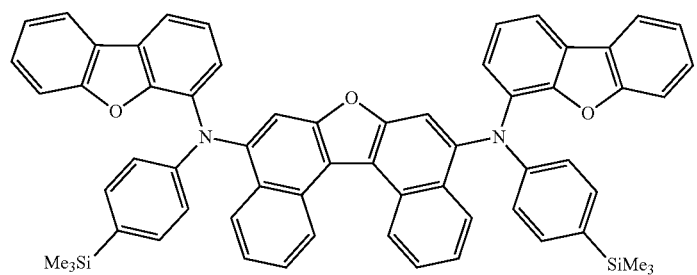

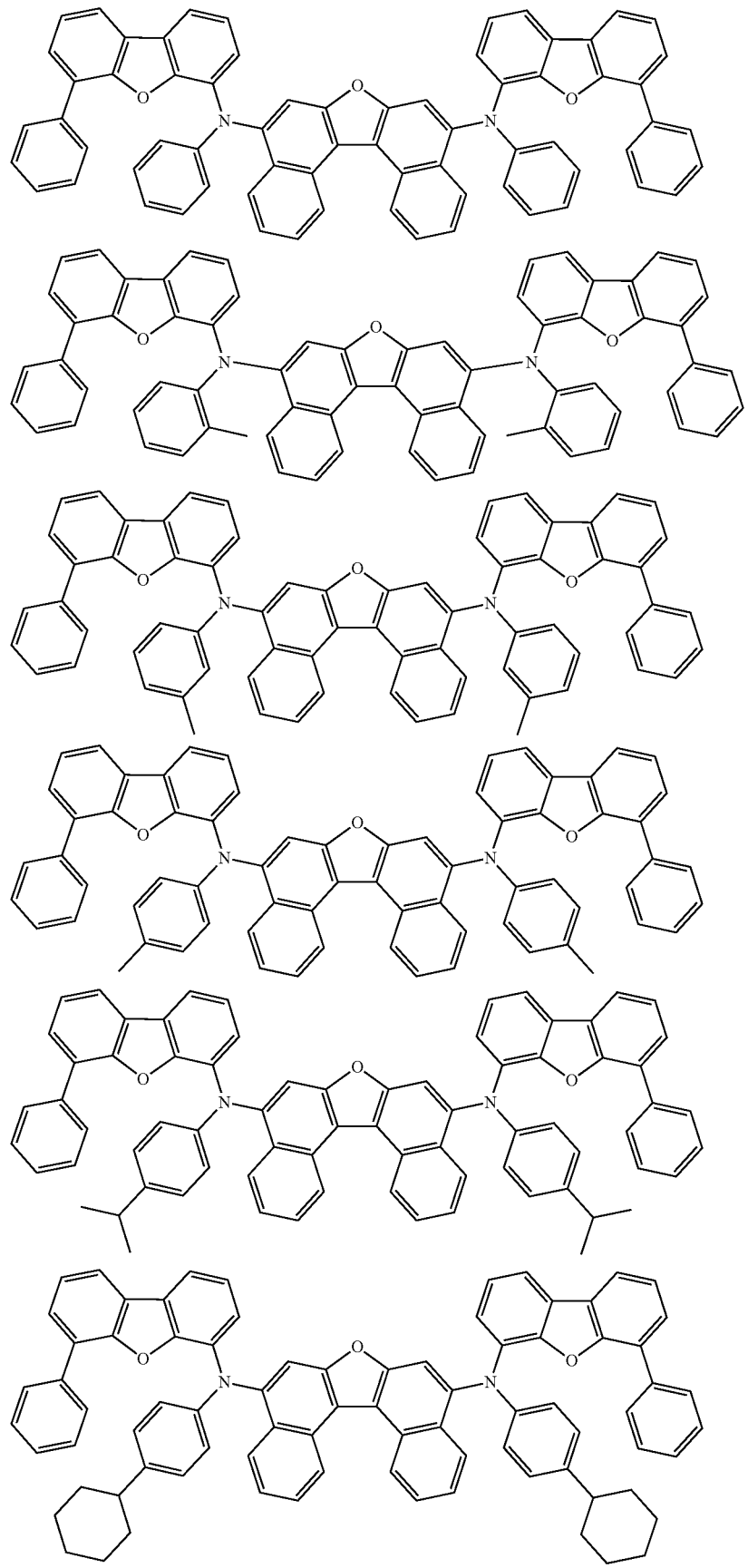

-continued
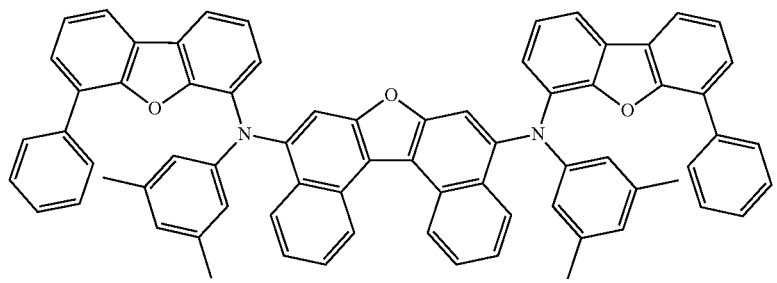
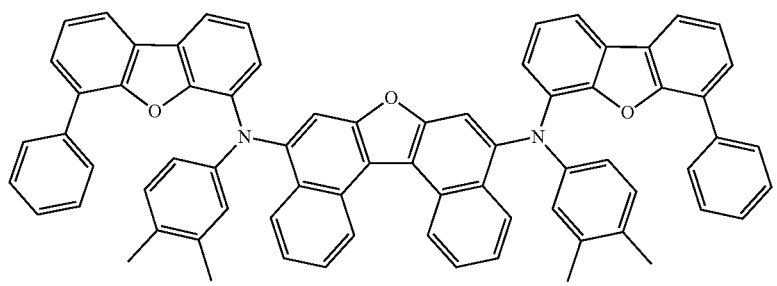
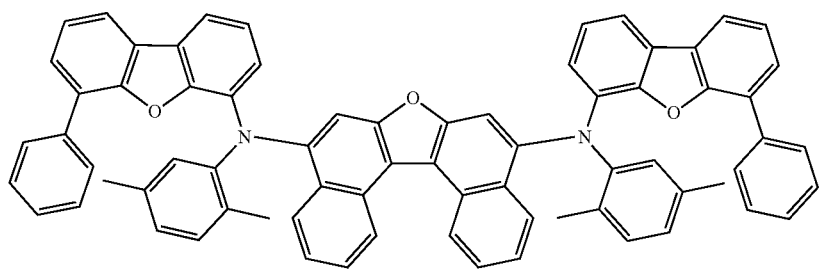
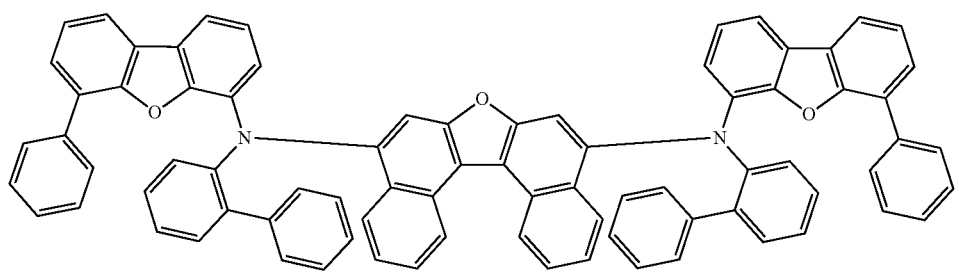
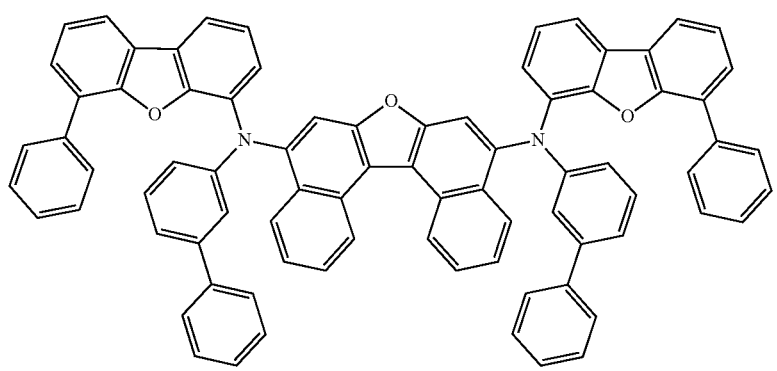

935 936
-continued
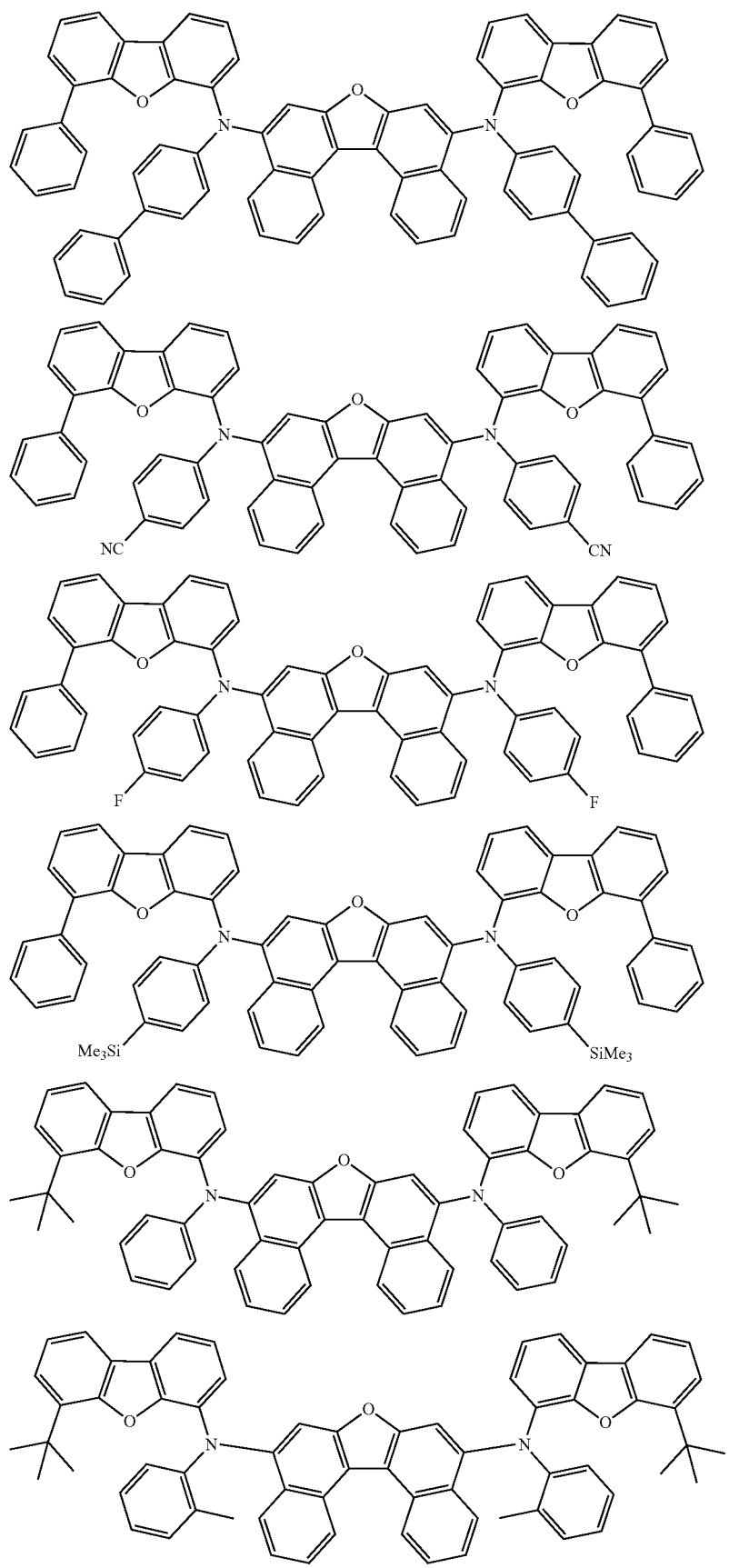

-continued
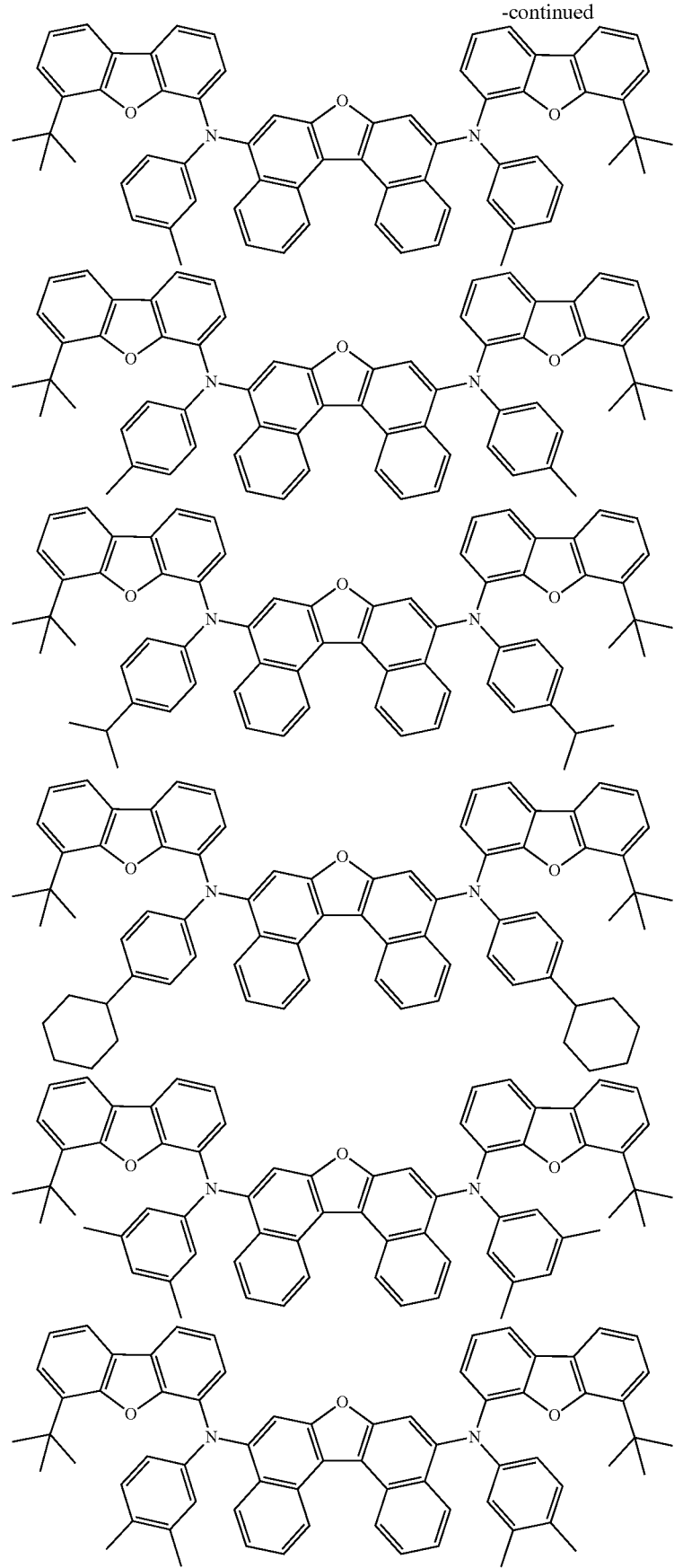

-continued
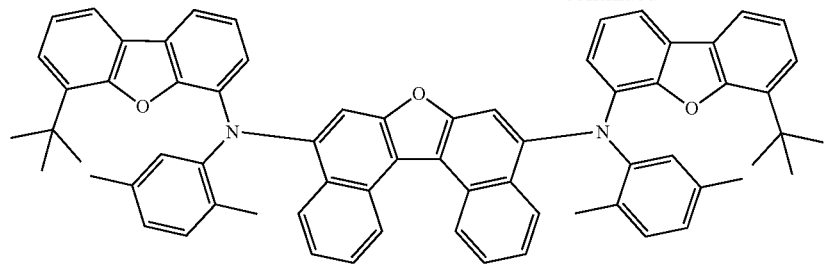
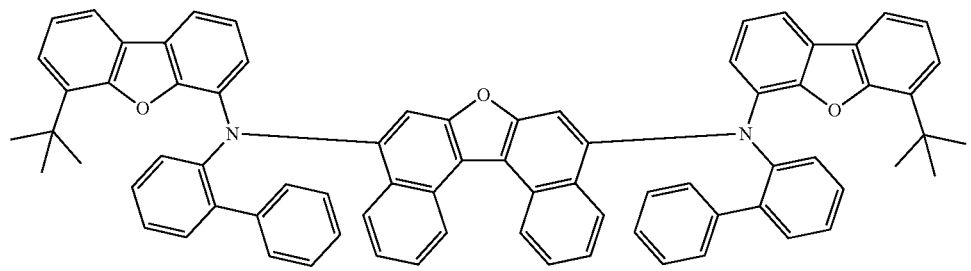
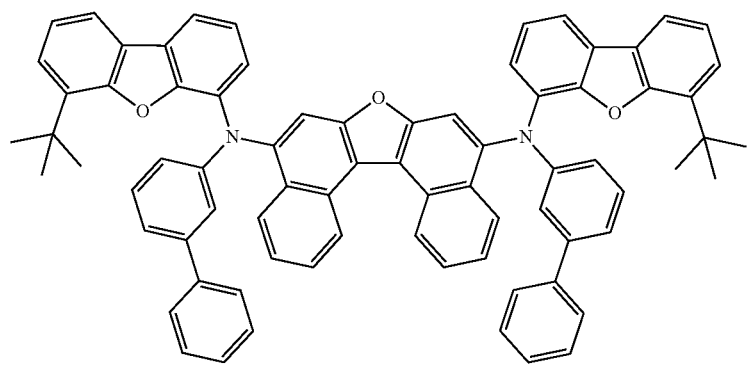
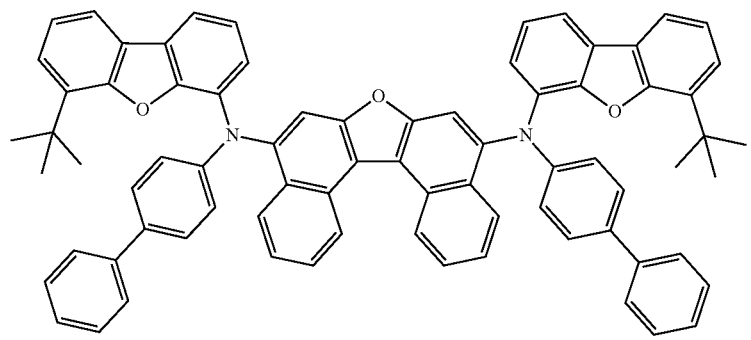
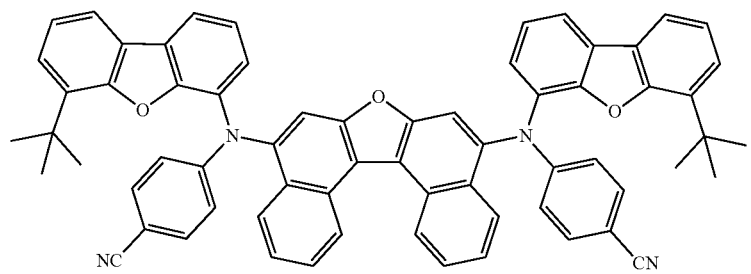

-continued
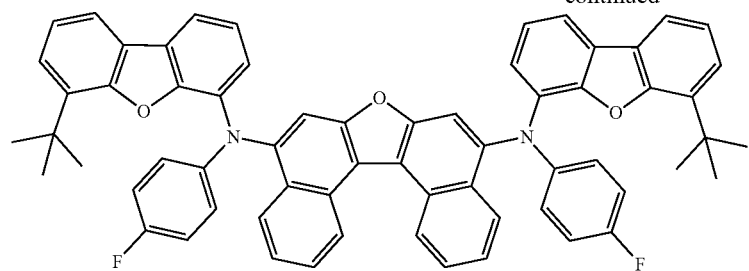
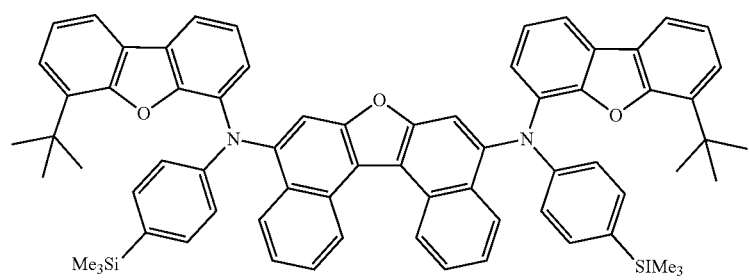
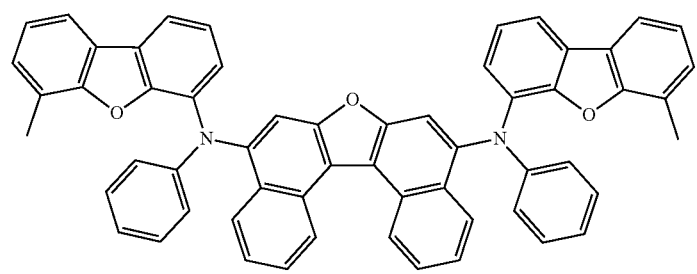
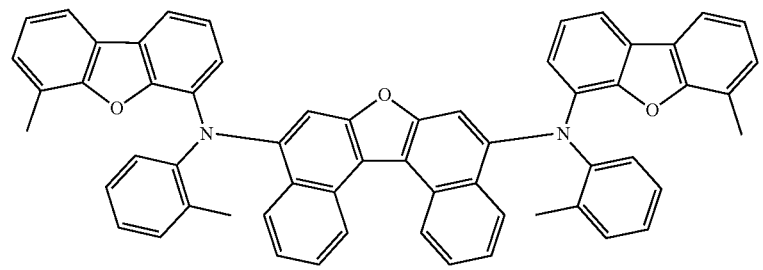
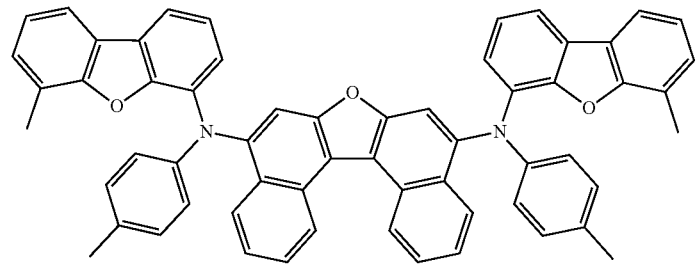
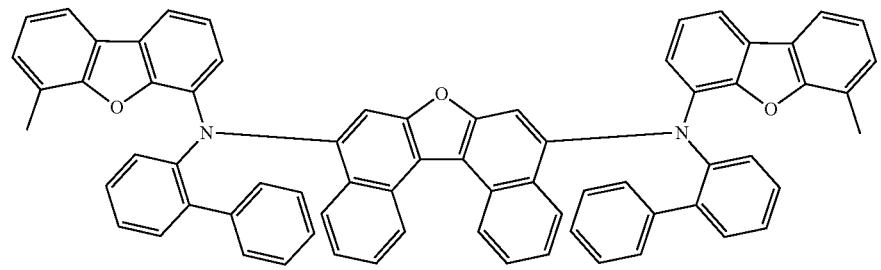

-continued
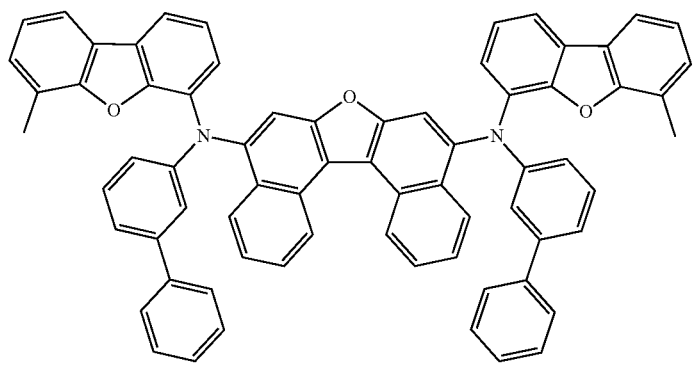
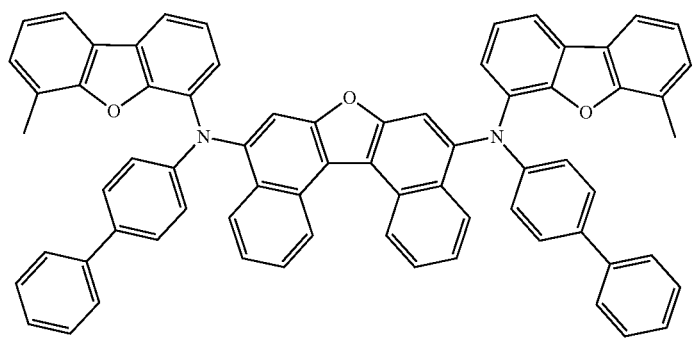
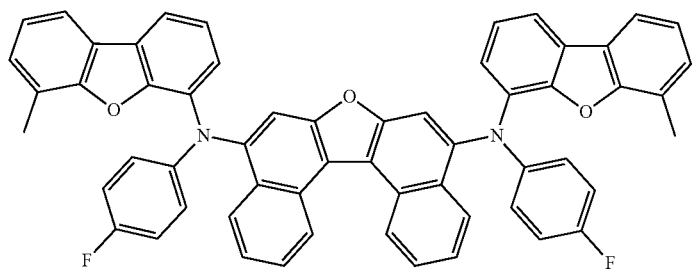
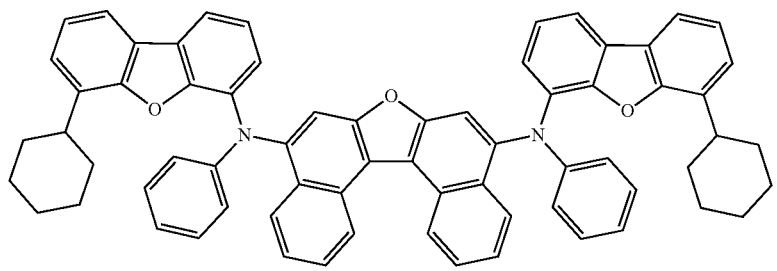
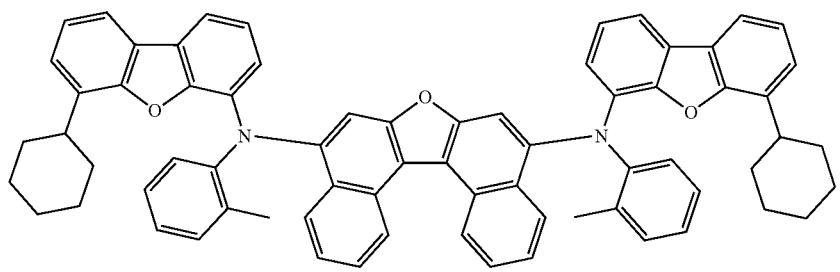

945
-continued
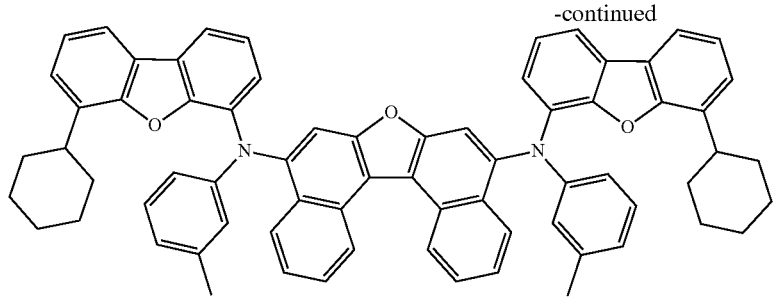
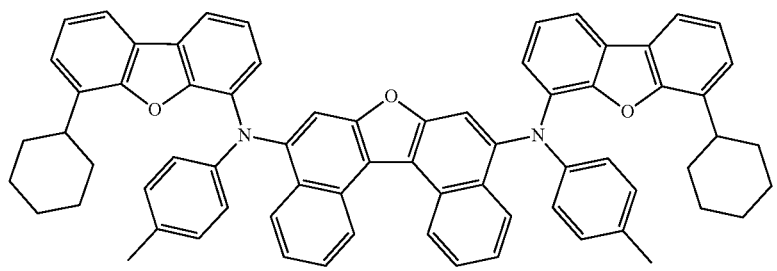
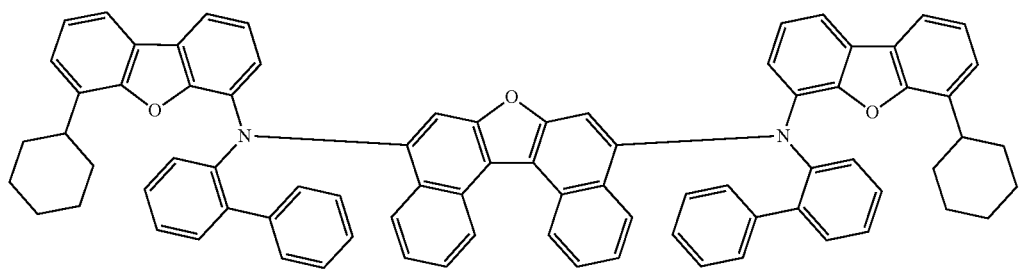
946
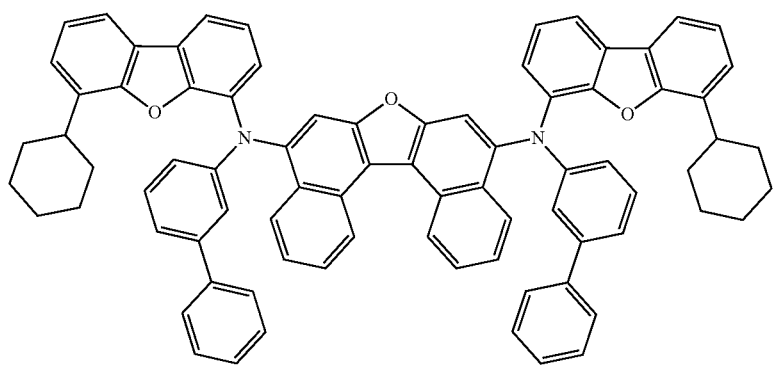
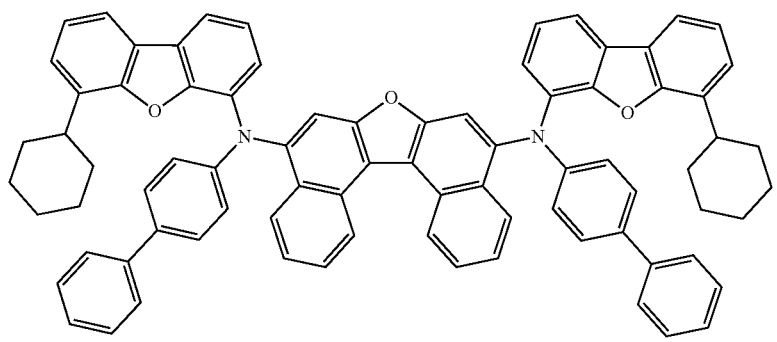

-continued
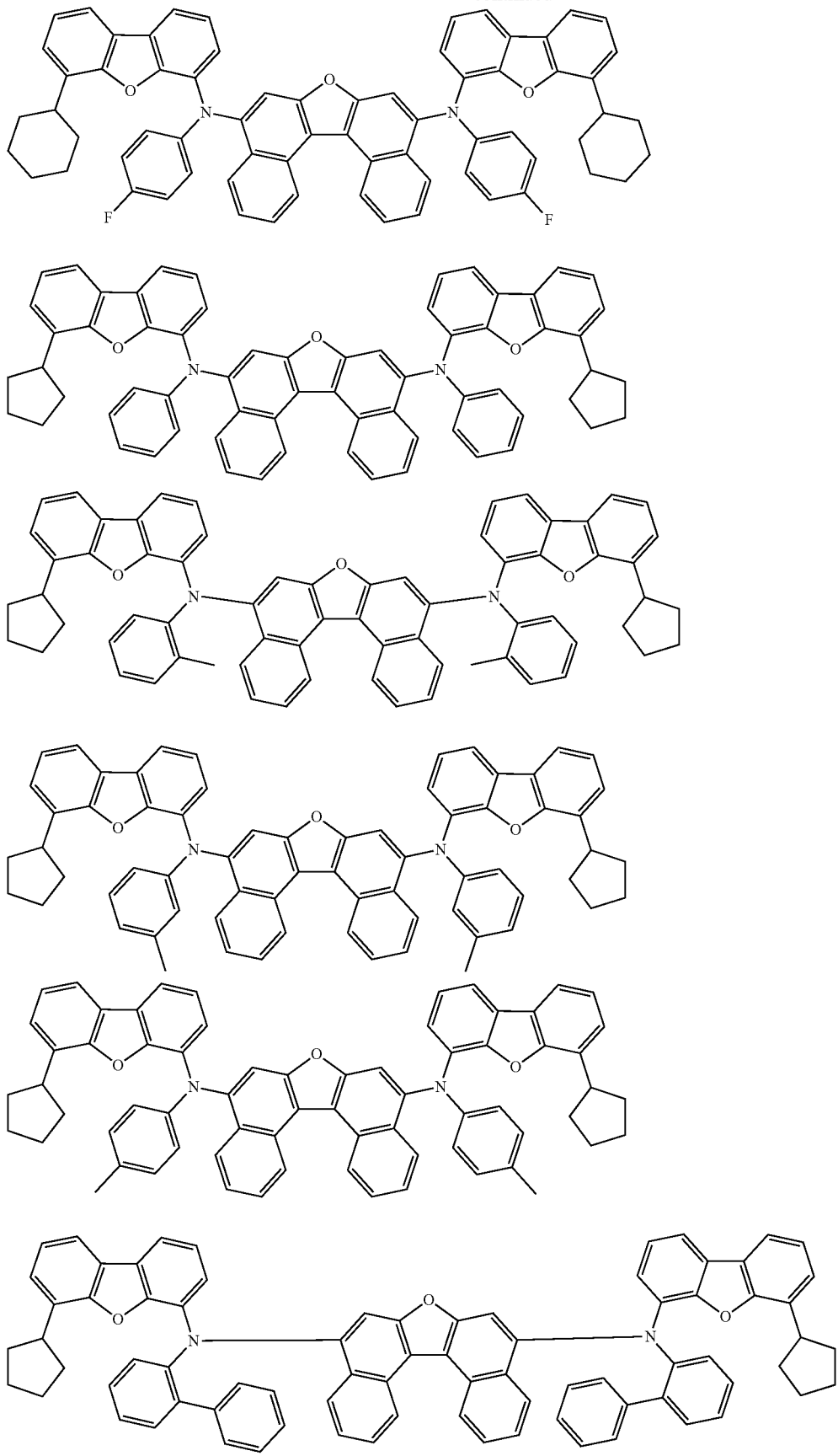

-continued
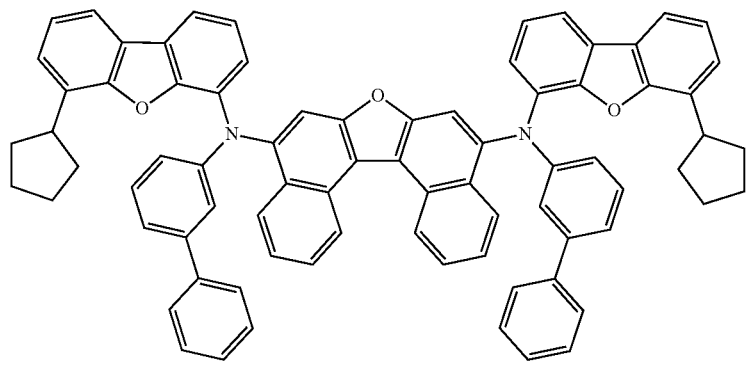
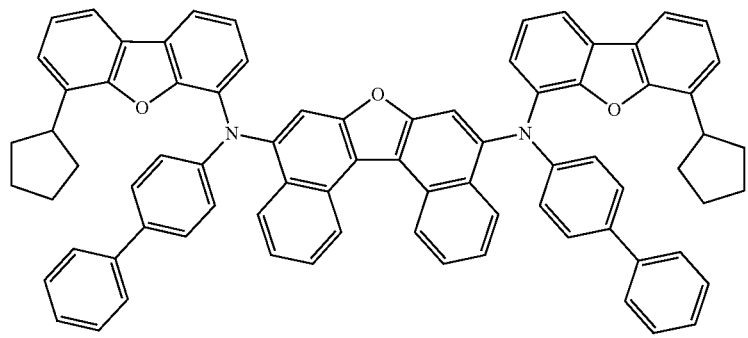
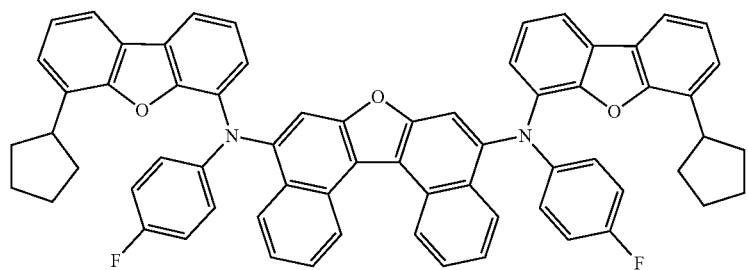
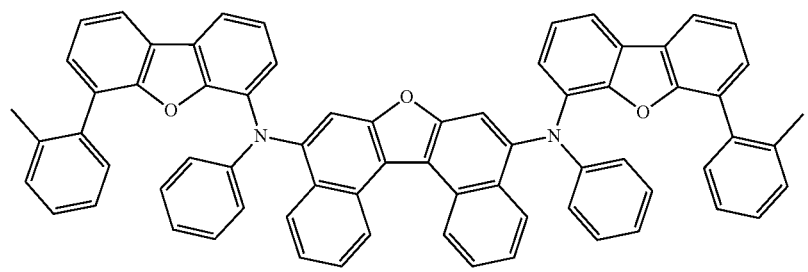
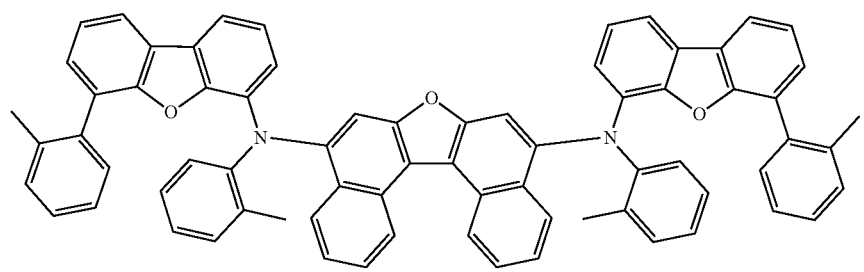

-continued
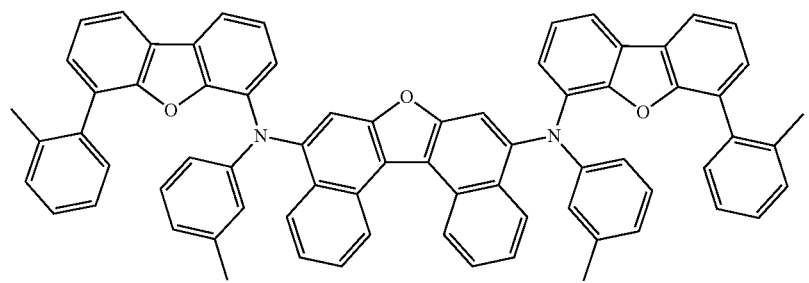
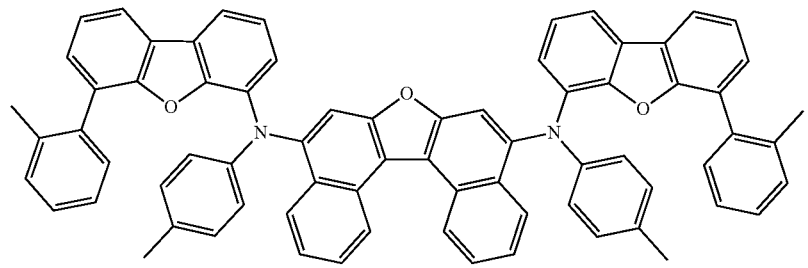
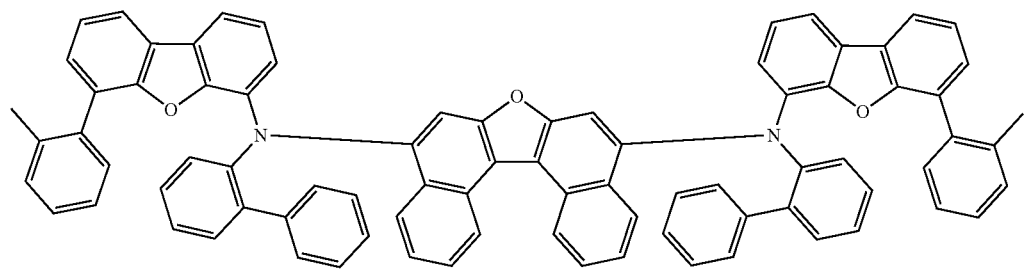
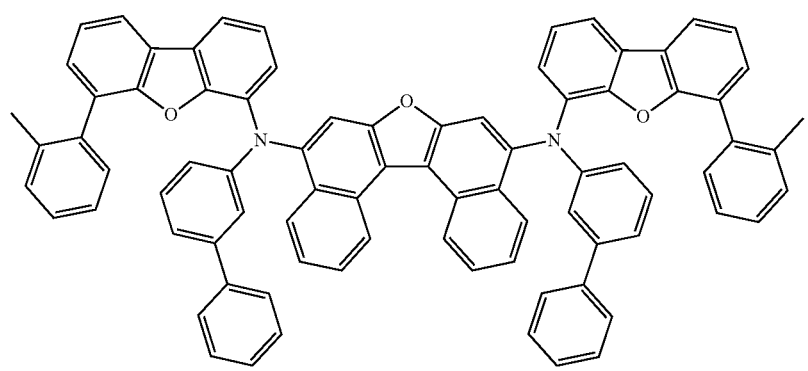
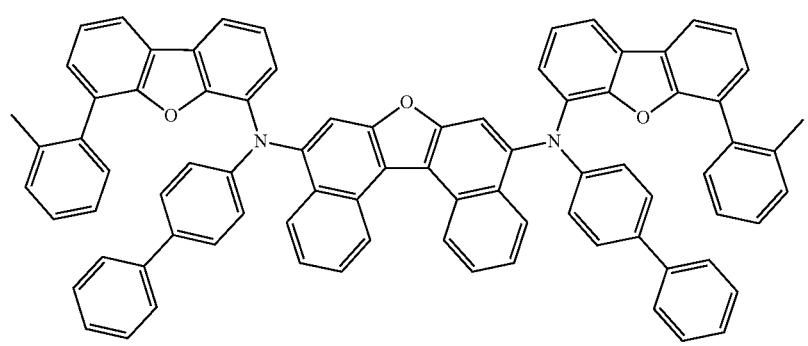

953                                            954
-continued
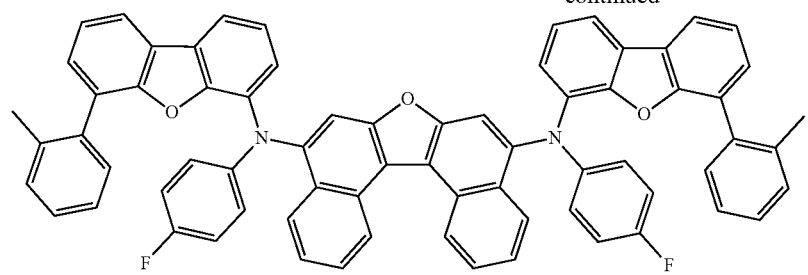
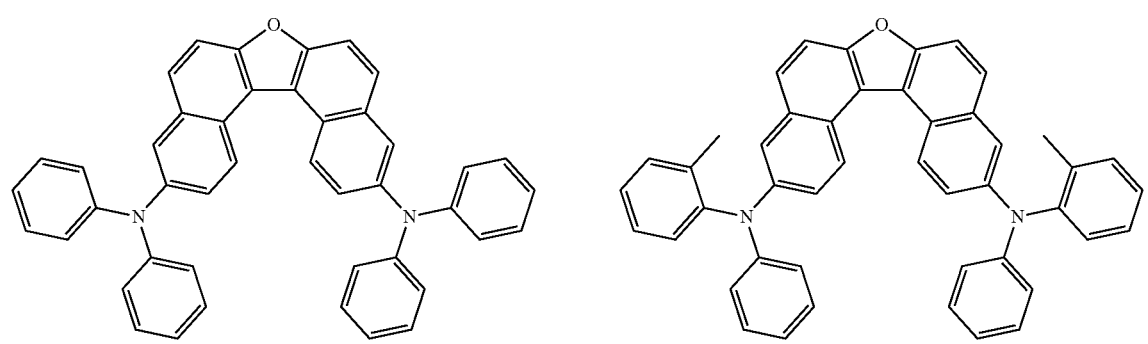
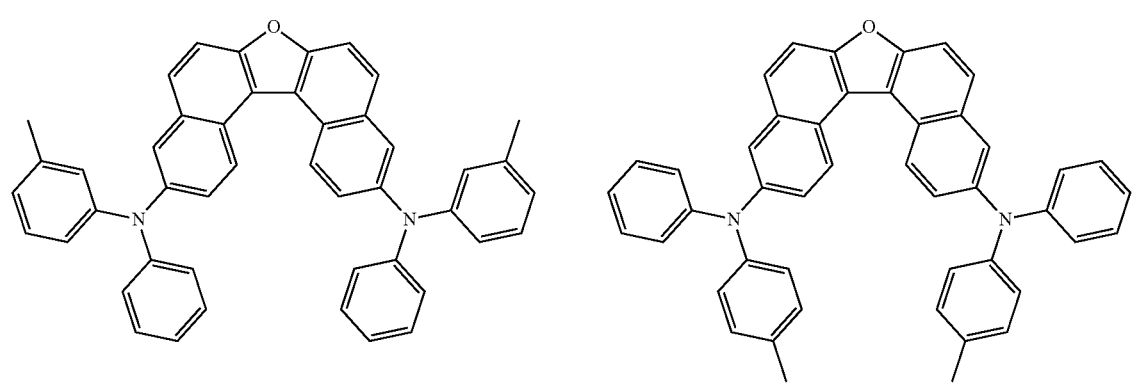
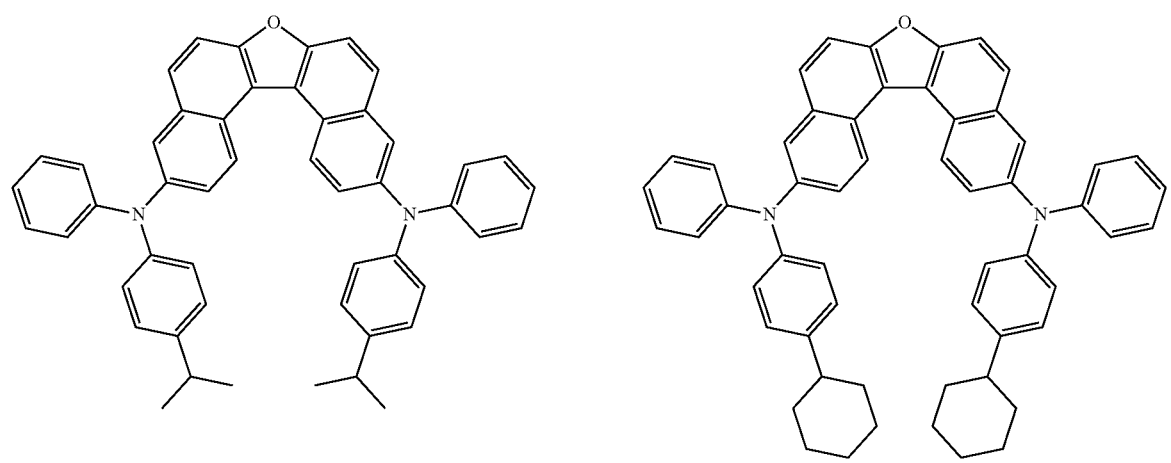

955
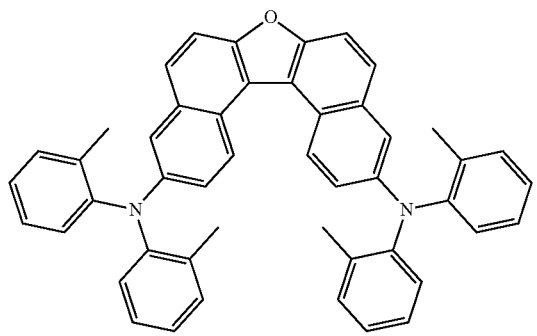
956
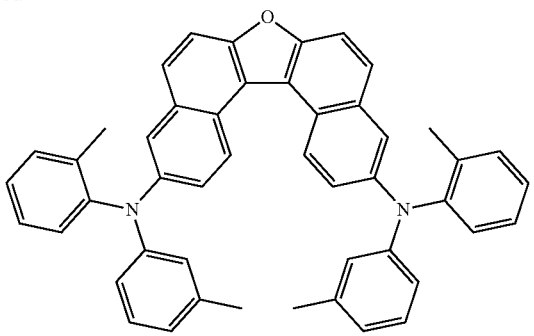
-continued
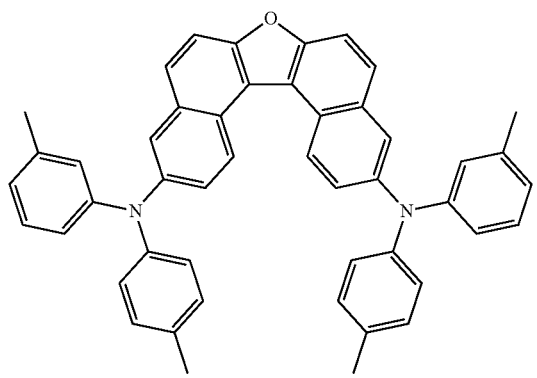
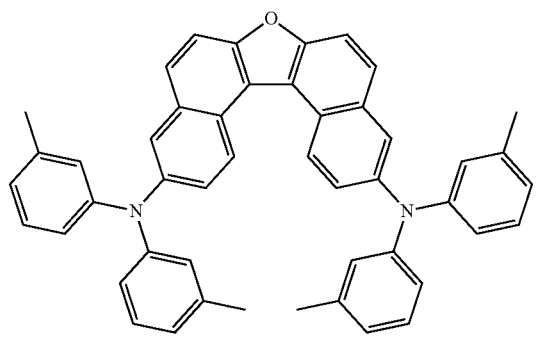
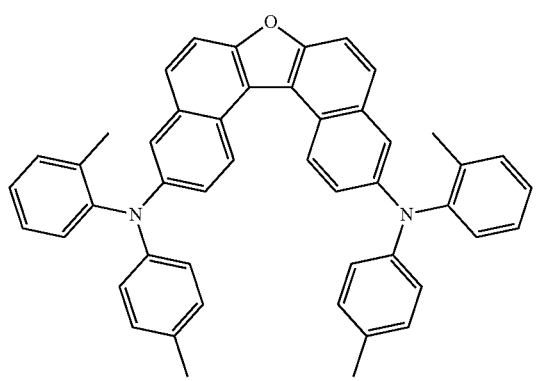
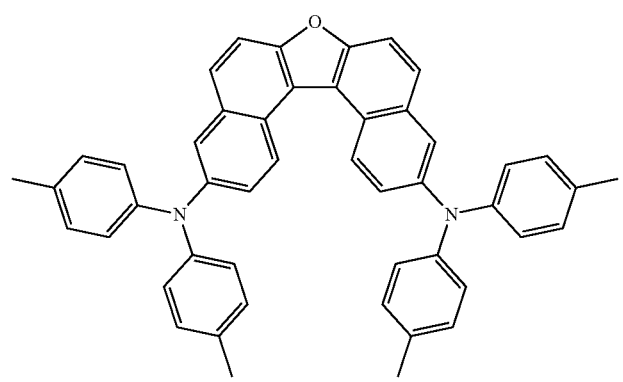
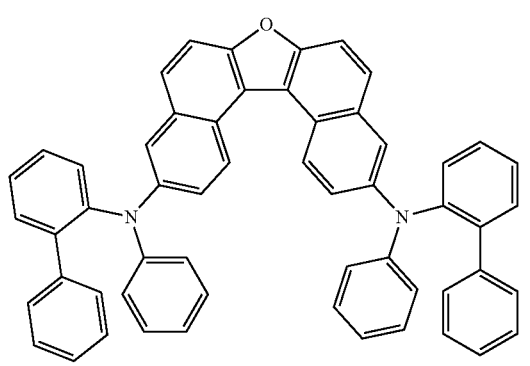
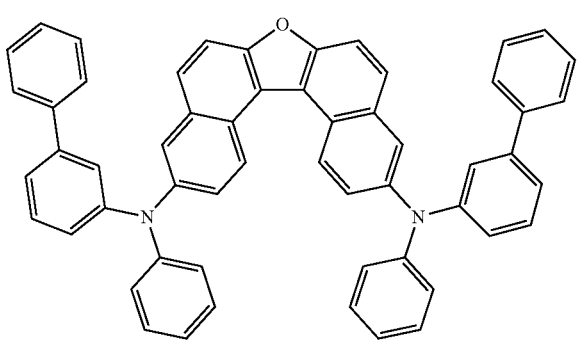

957                                                958
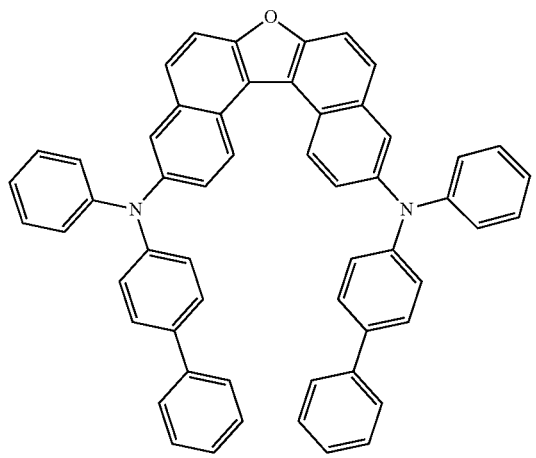 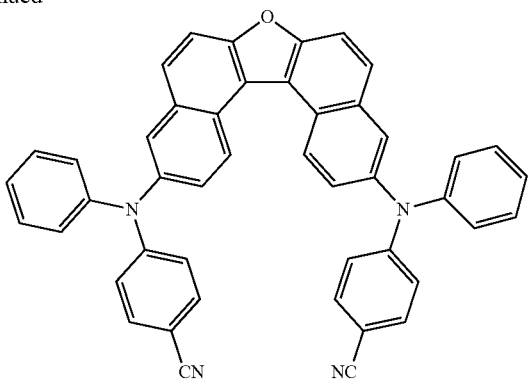
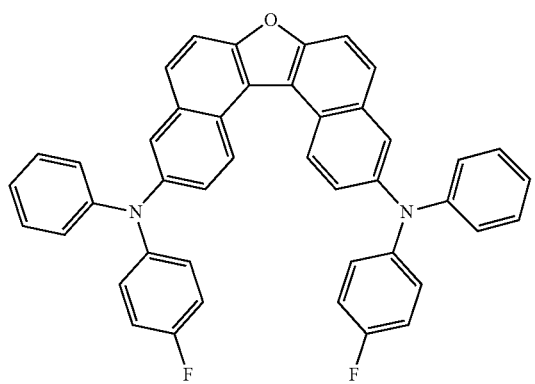 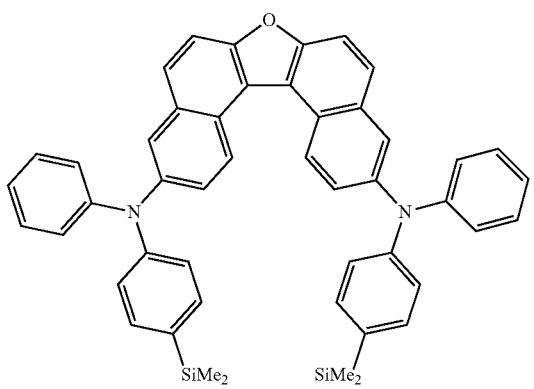
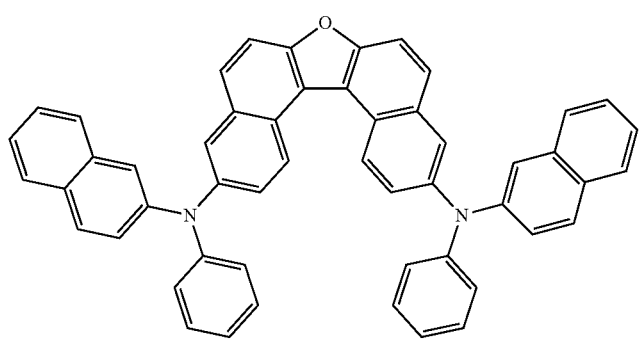 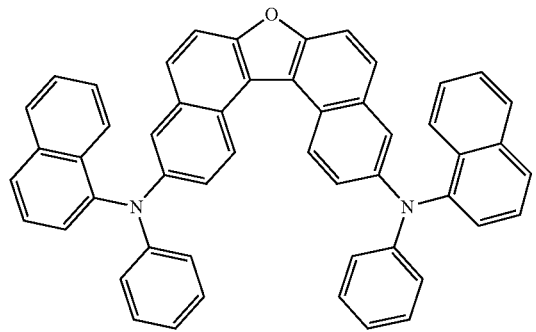
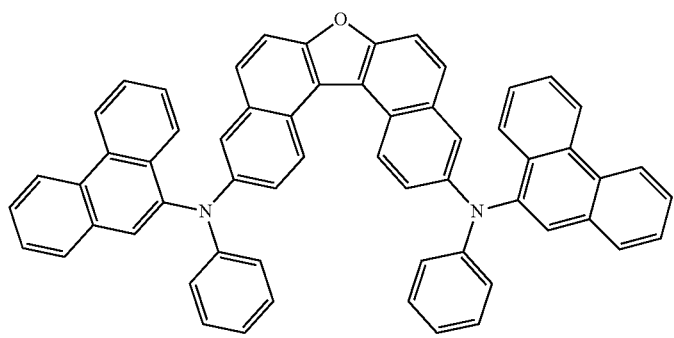

959
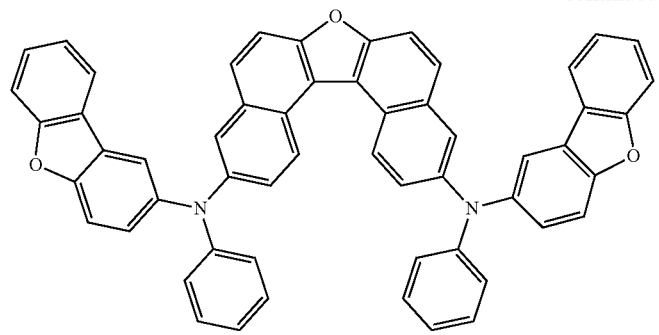
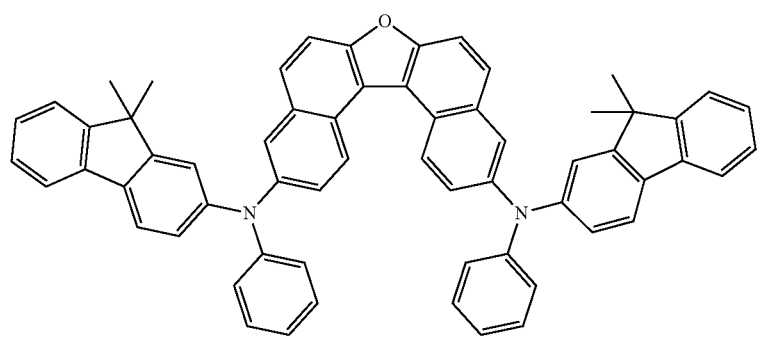
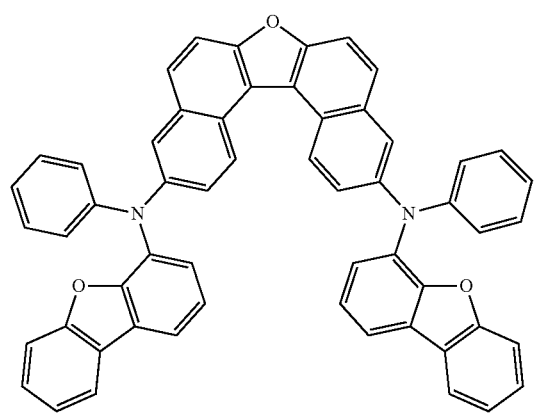
960
-continued
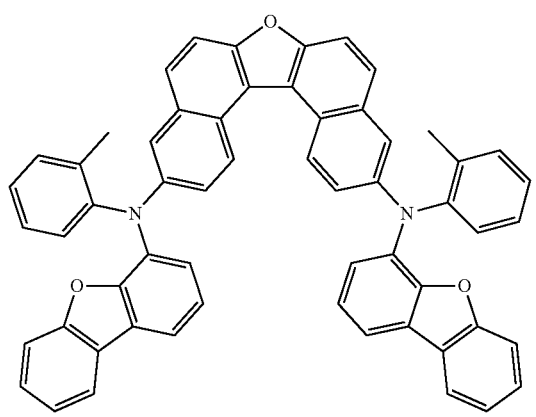
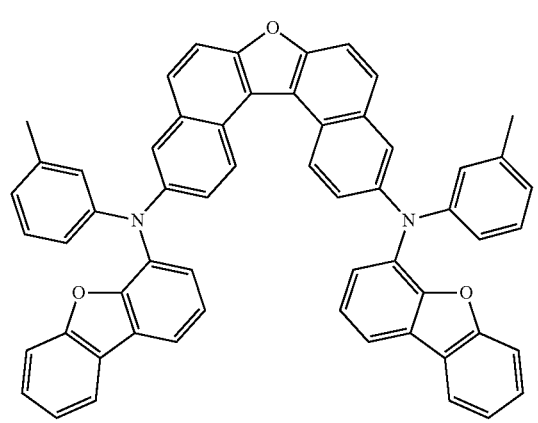
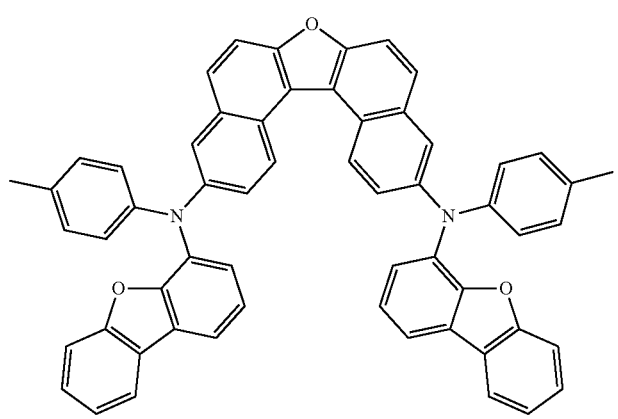

961 962
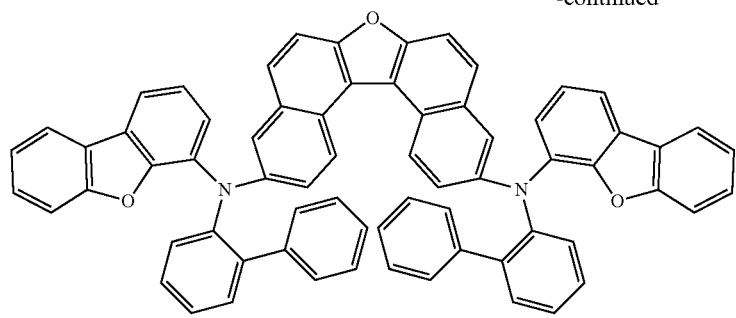
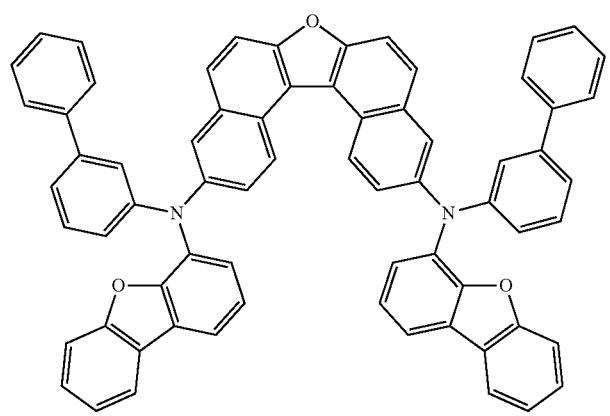
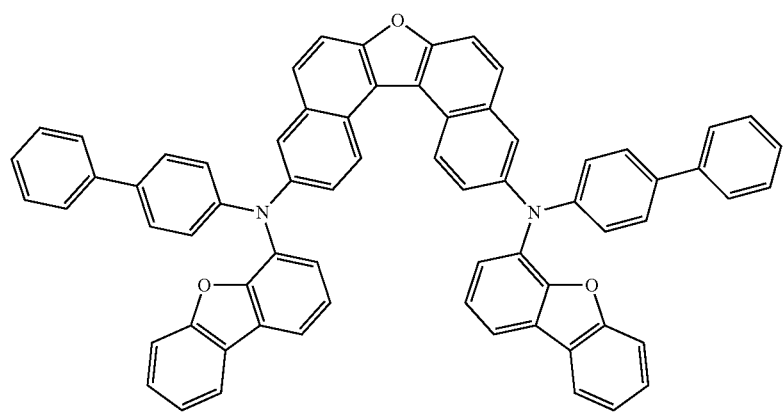
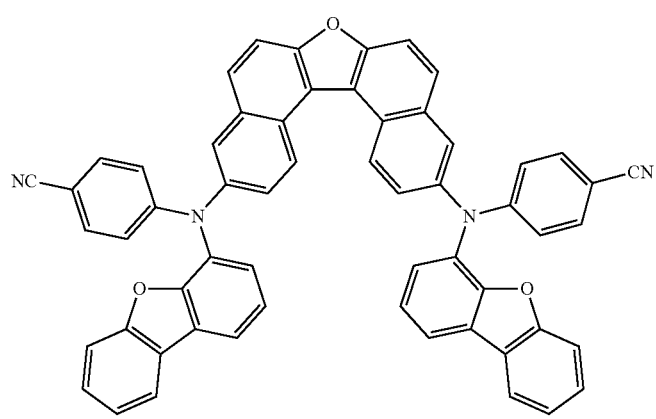

-continued
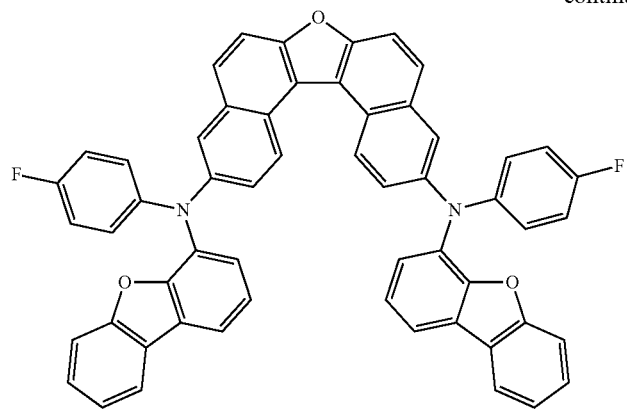
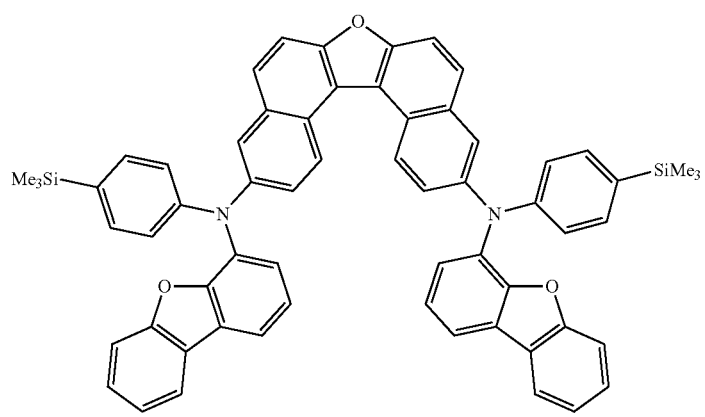
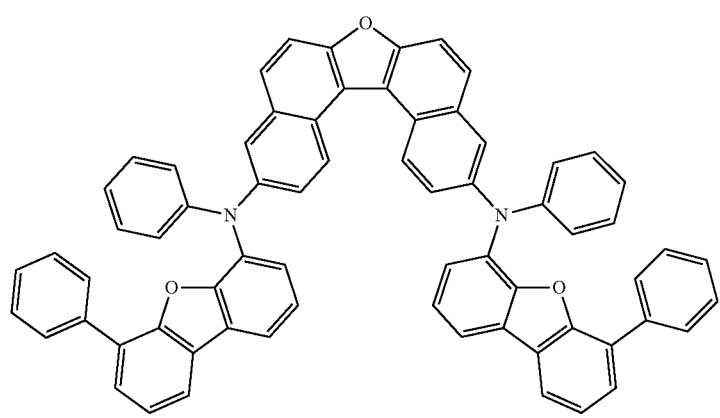
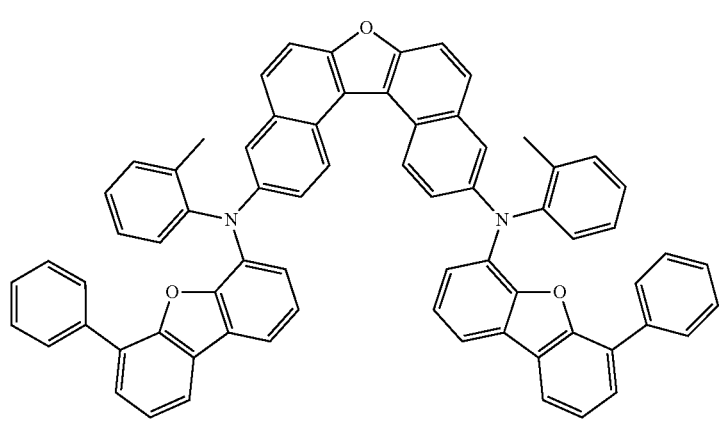

965
-continued
966
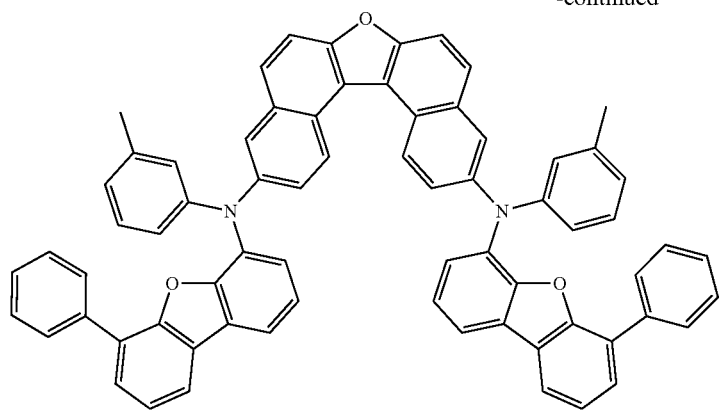
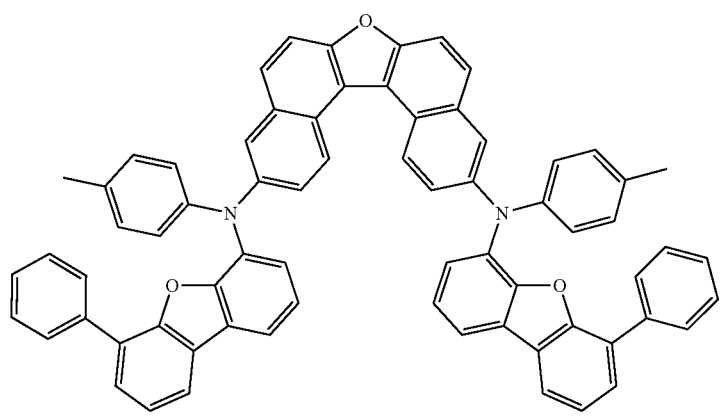
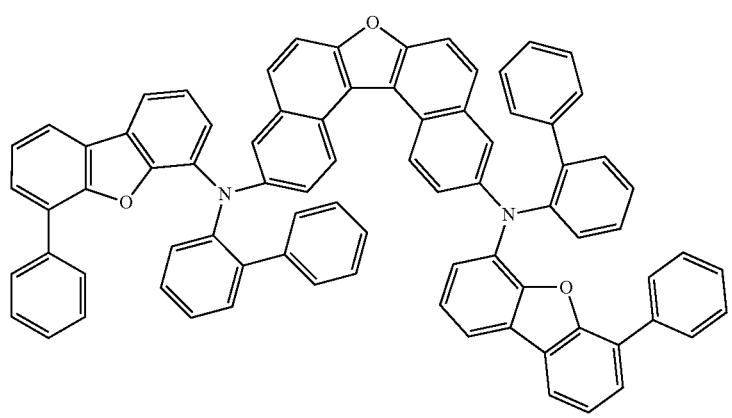
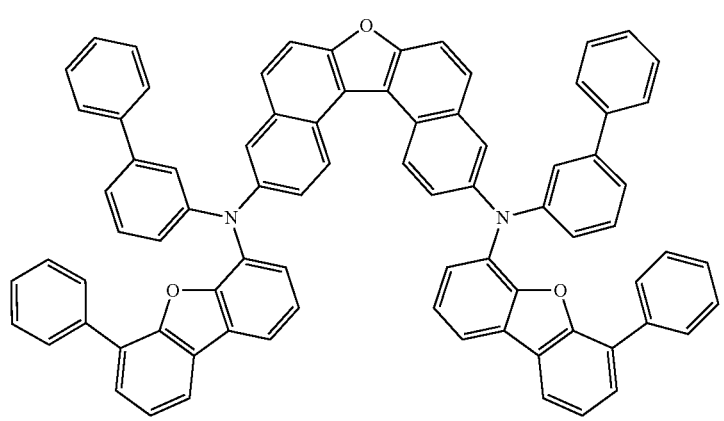

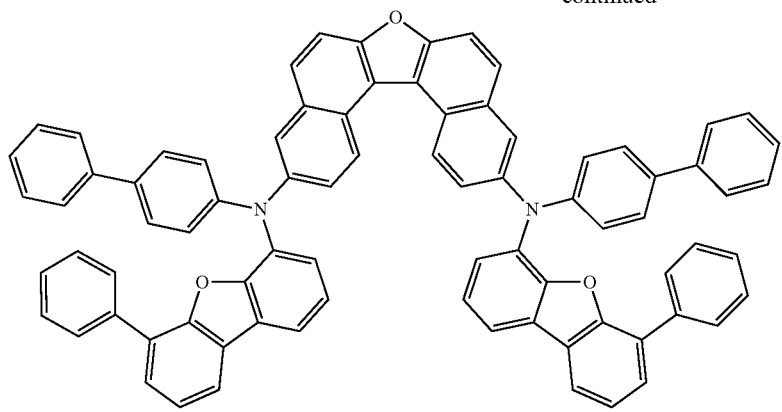
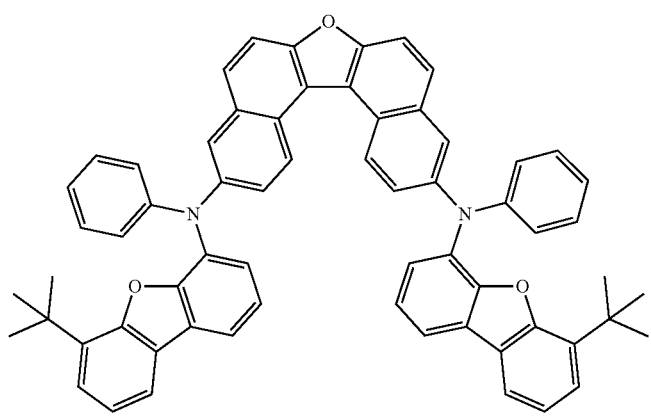
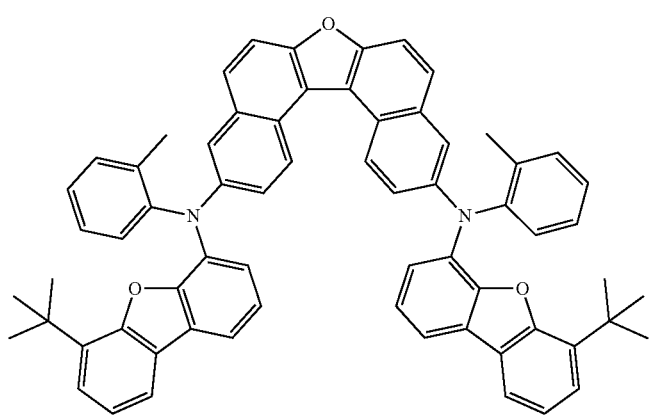
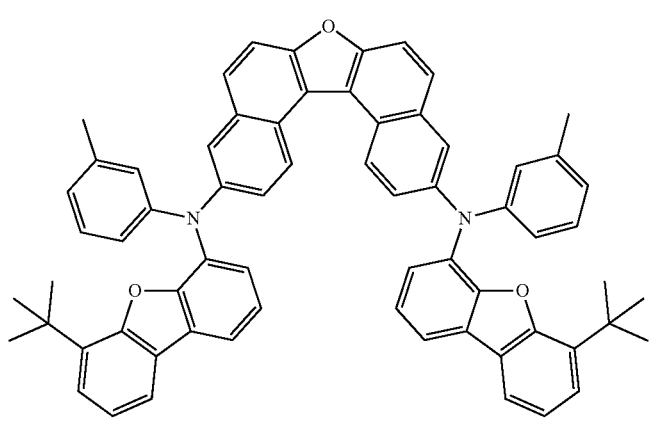

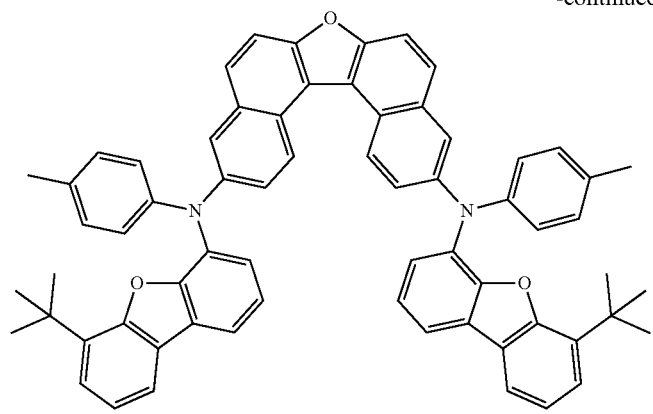
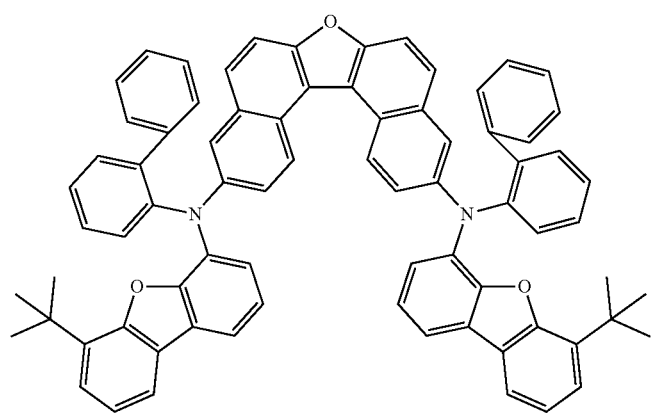
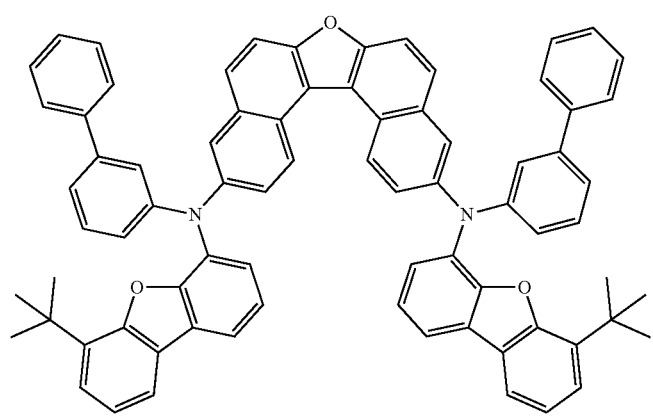
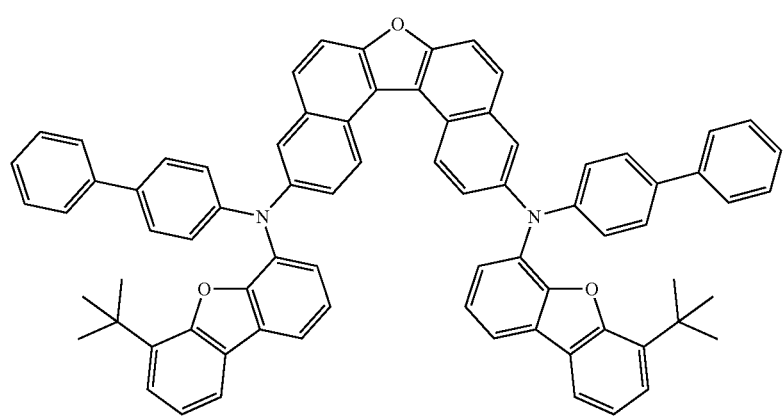

971
972
-continued
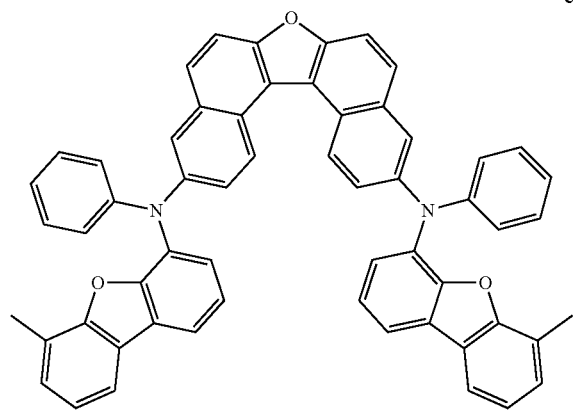

-continued
973
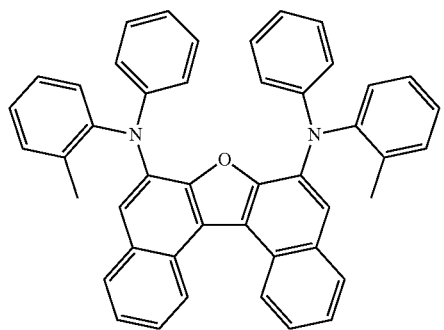
974
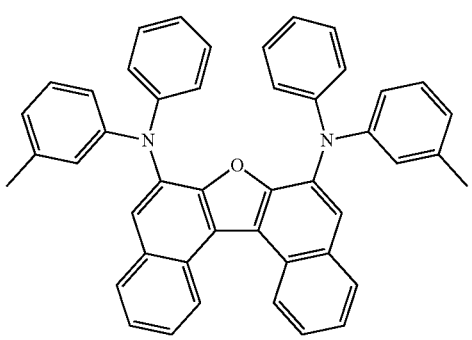
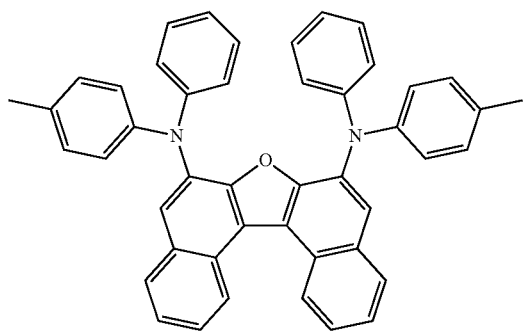
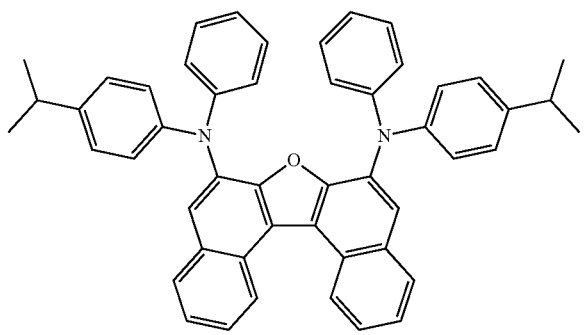
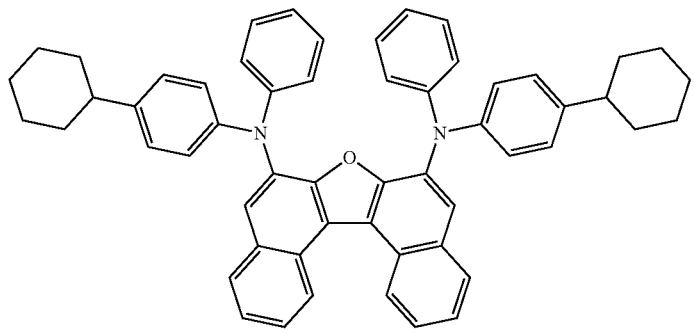
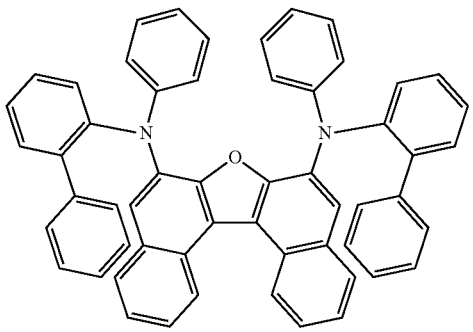
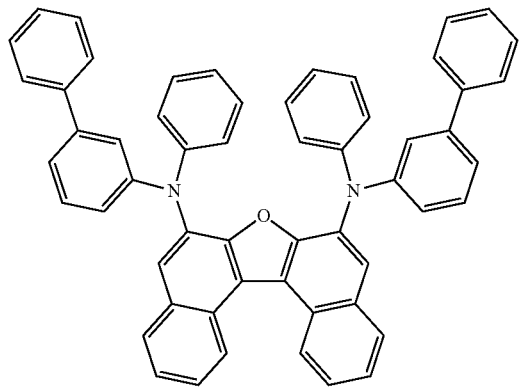

975
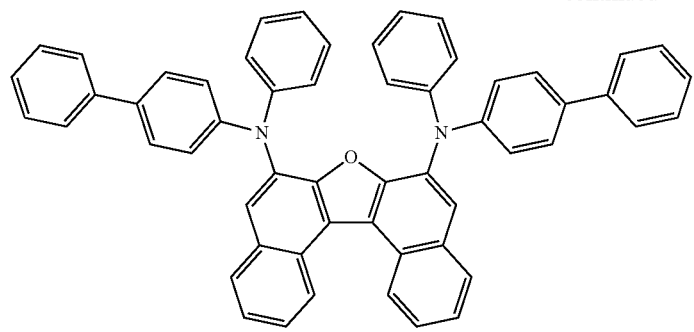
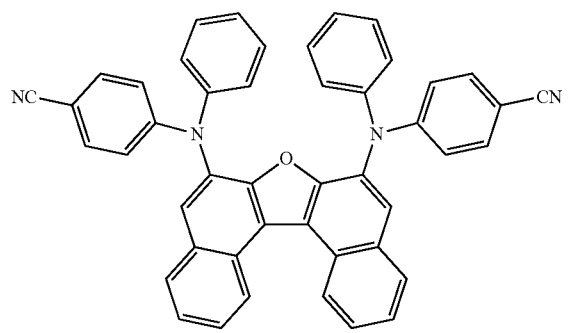
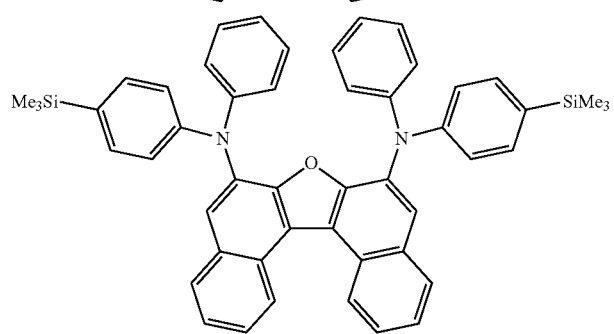
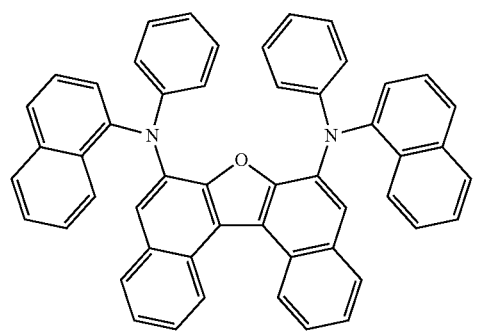
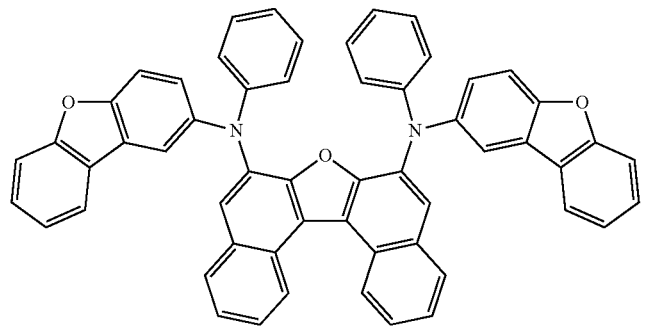
976
-continued
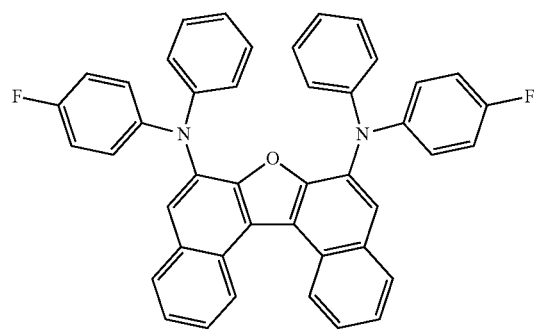
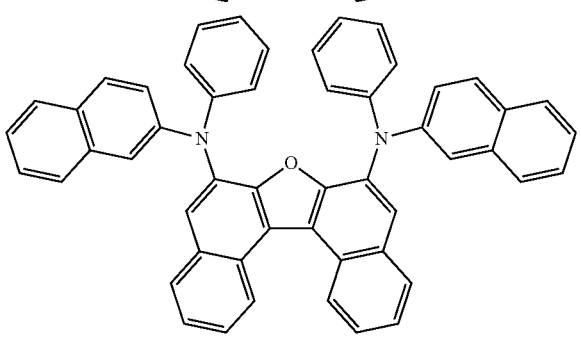
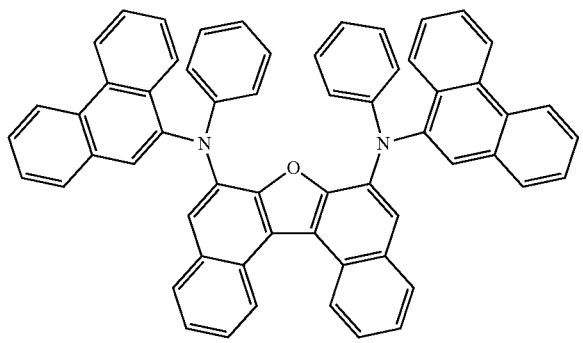

977 978
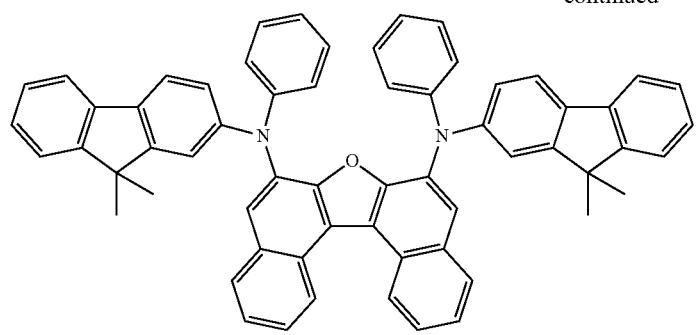
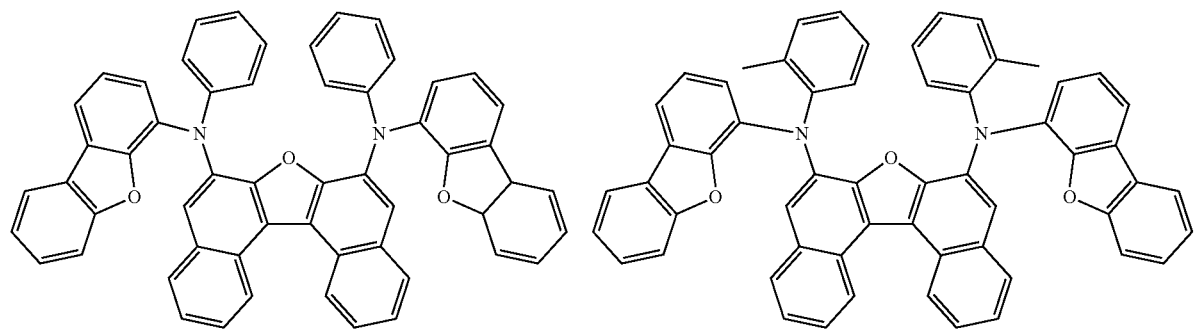
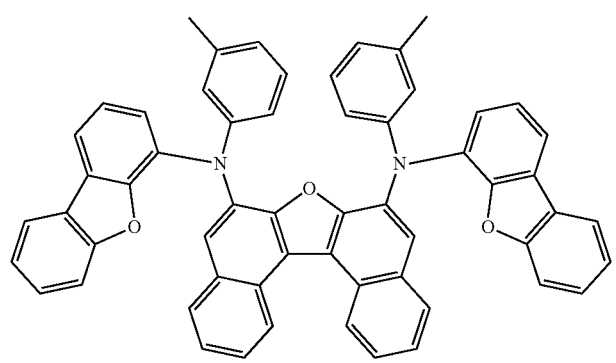
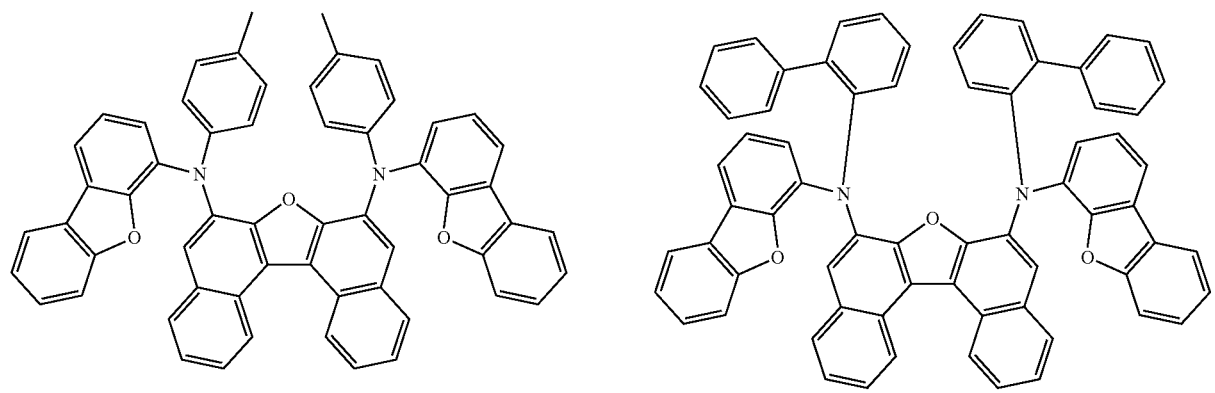

-continued
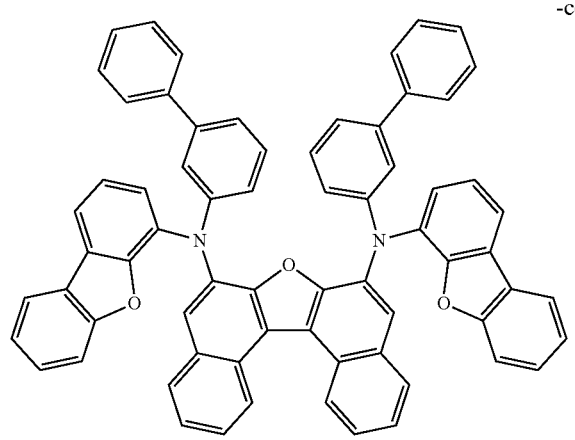
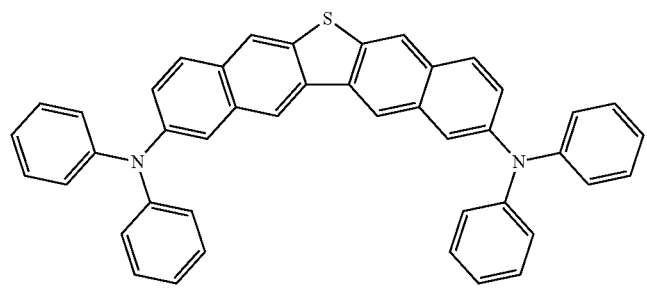
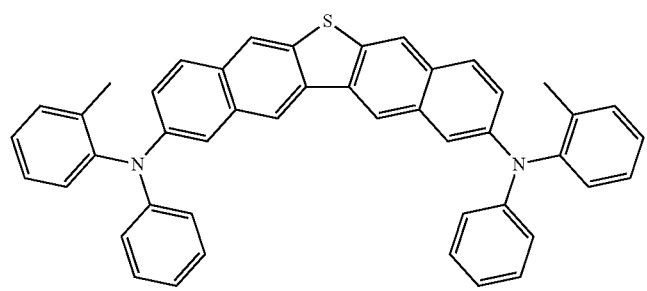
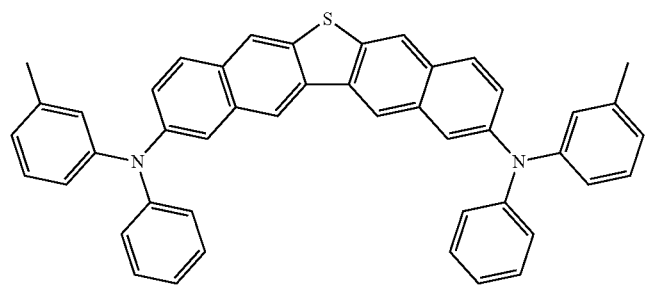
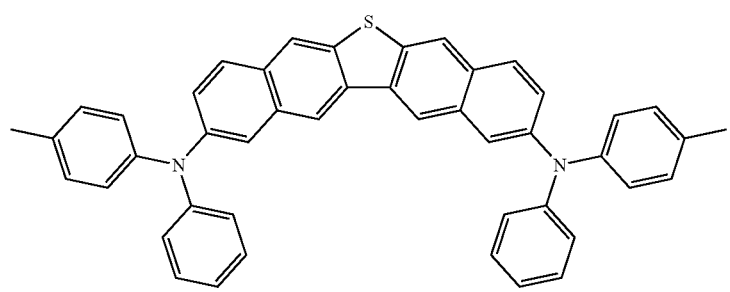

-continued
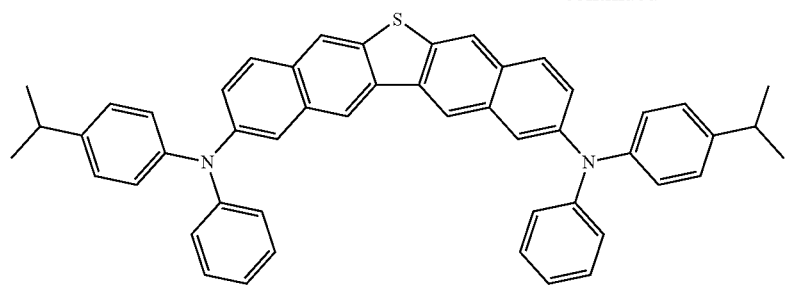
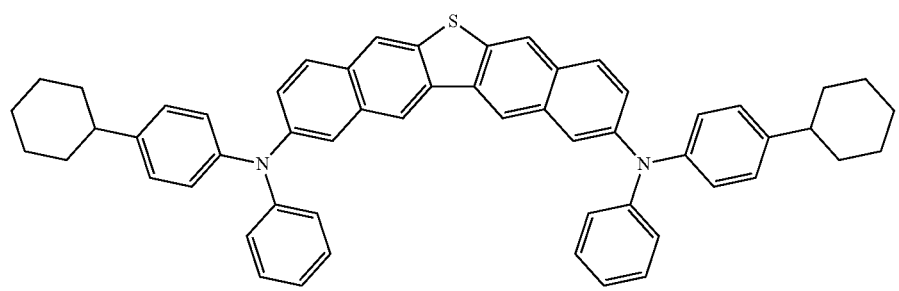
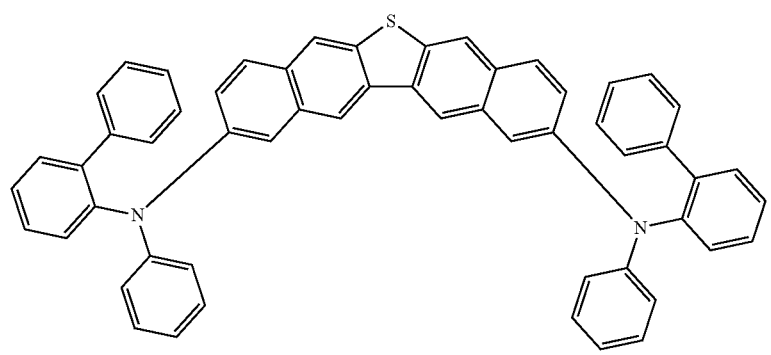
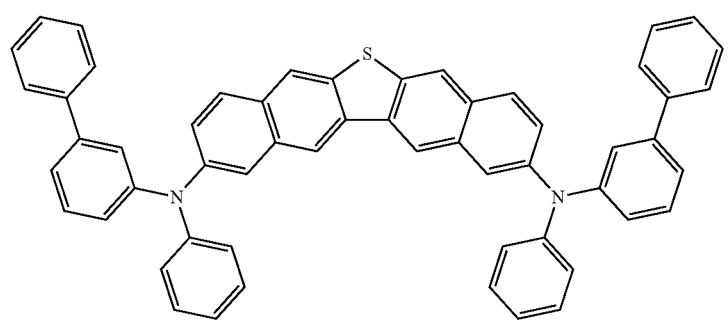
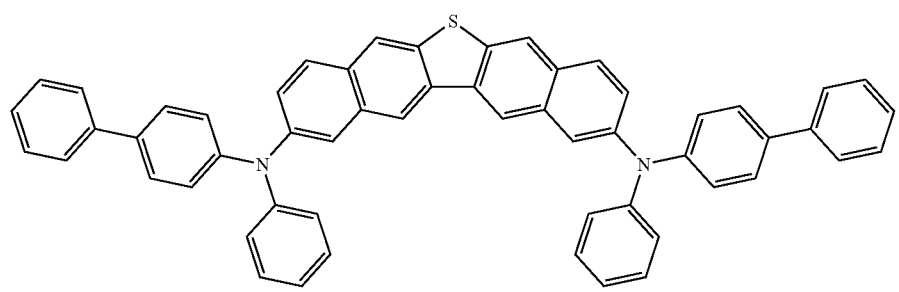

-continued
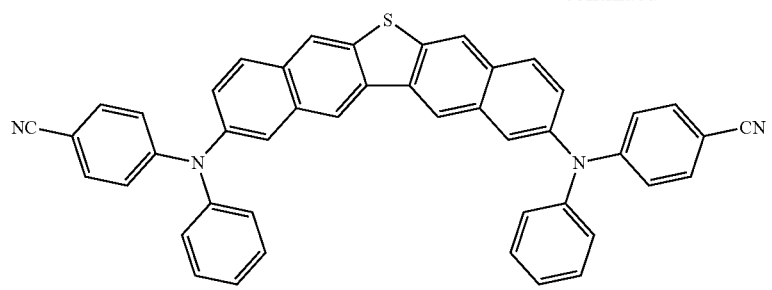
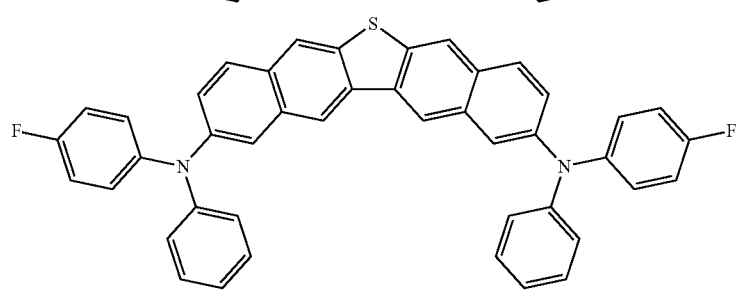
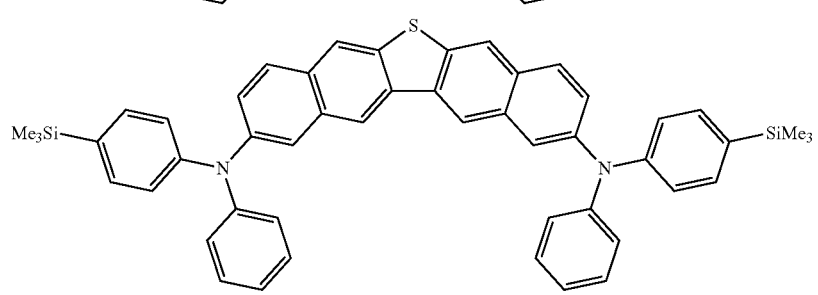
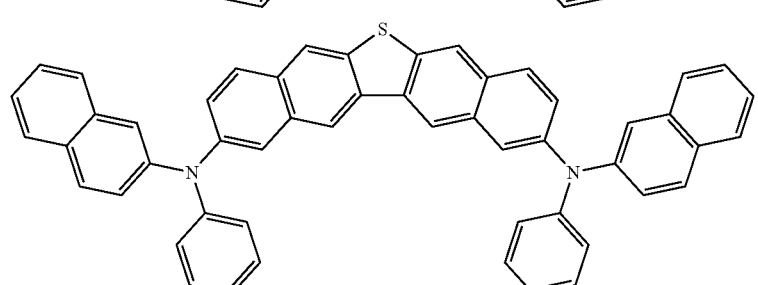
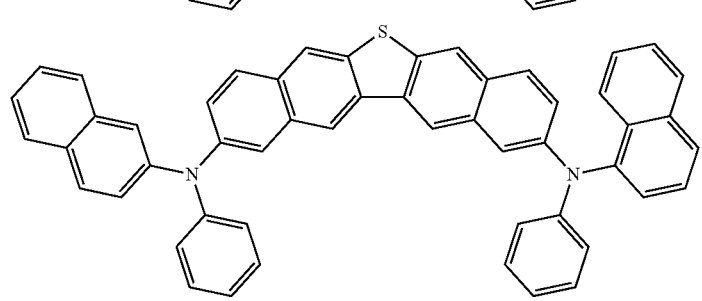
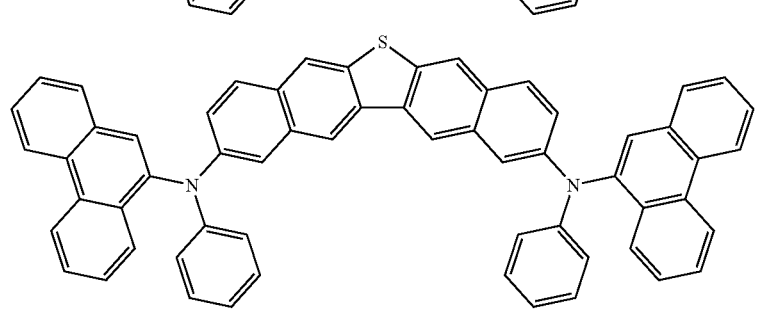

-continued
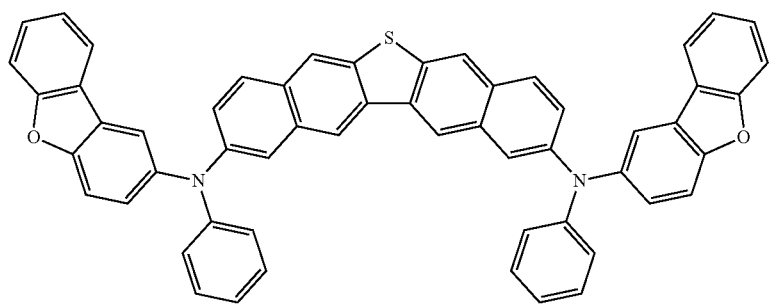
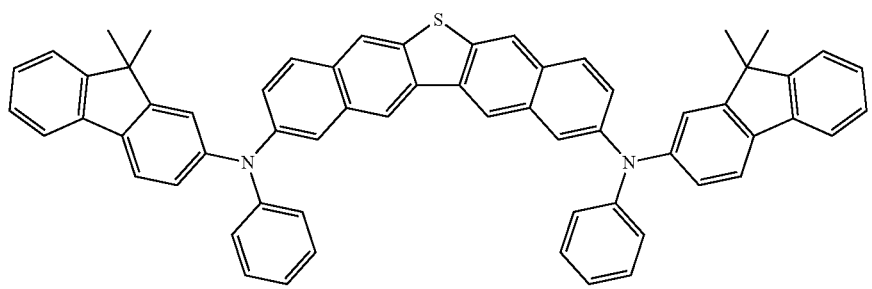
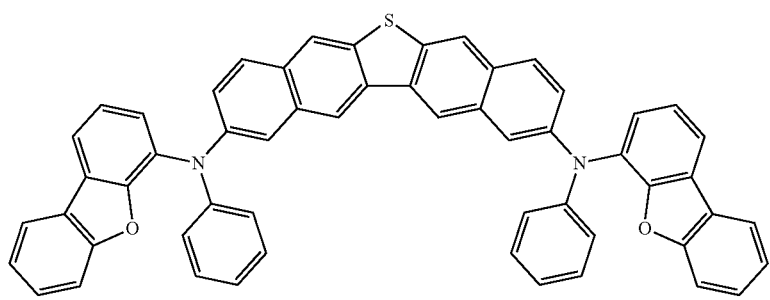
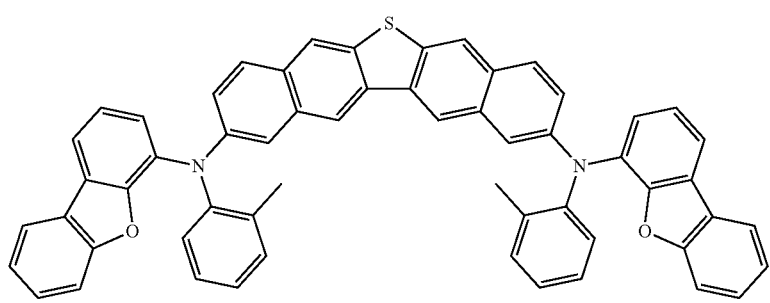
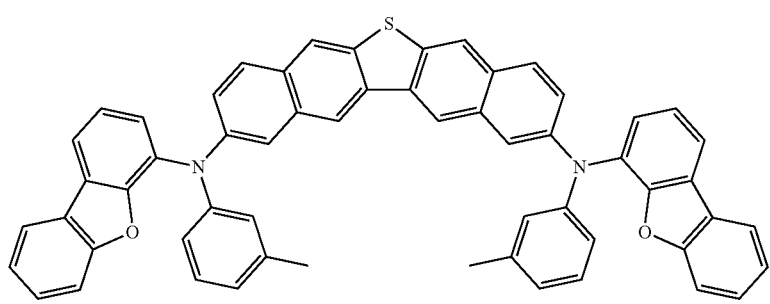

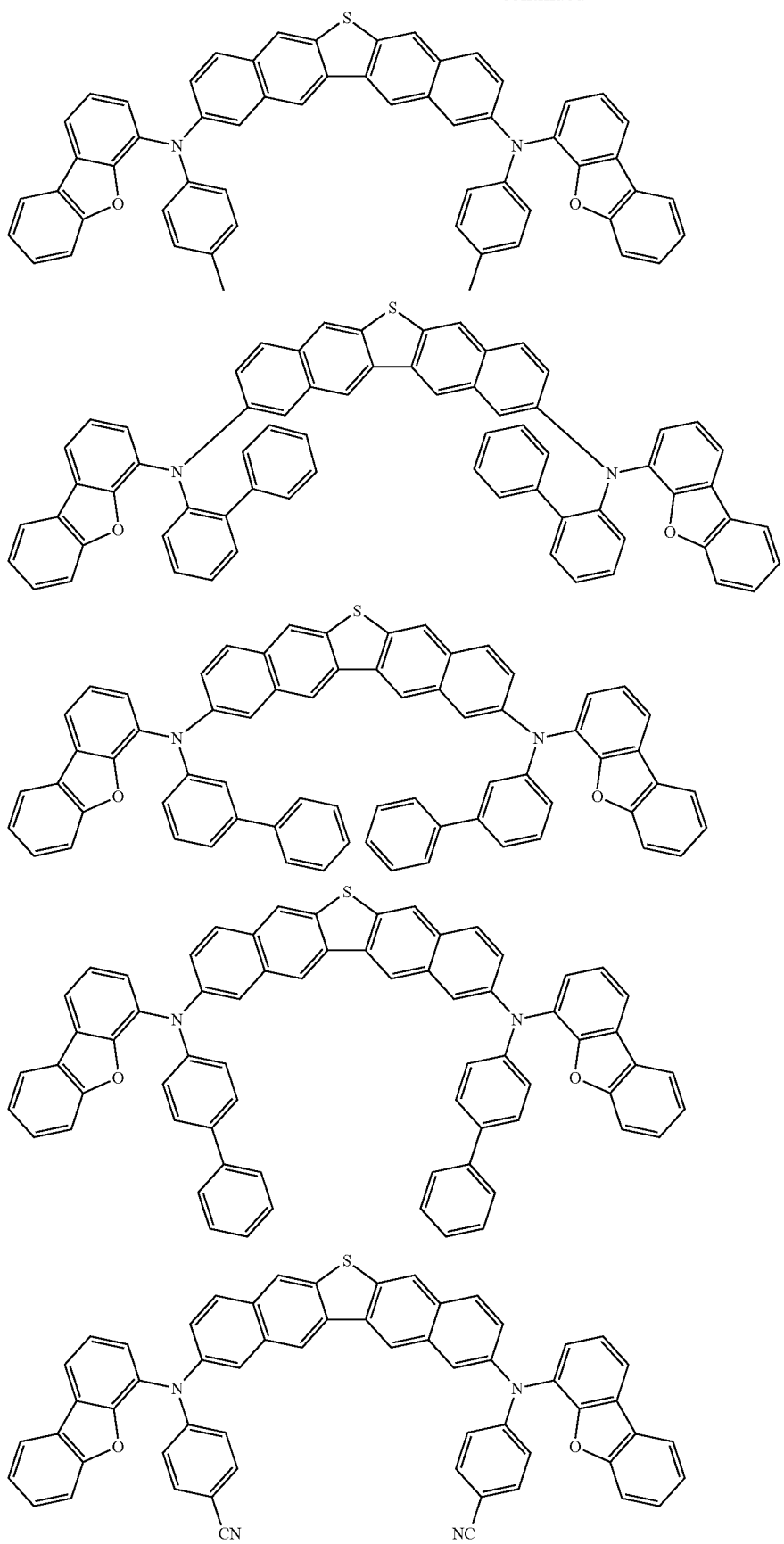

989
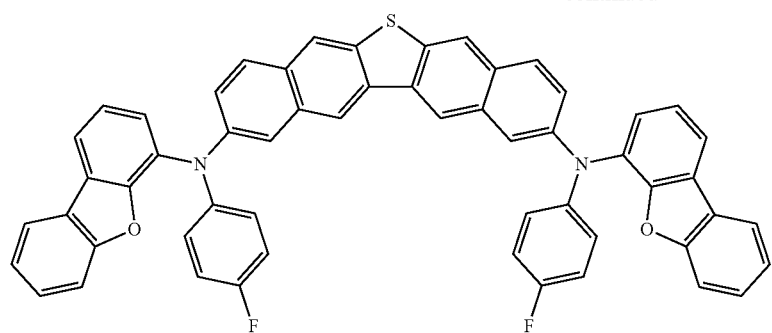
990
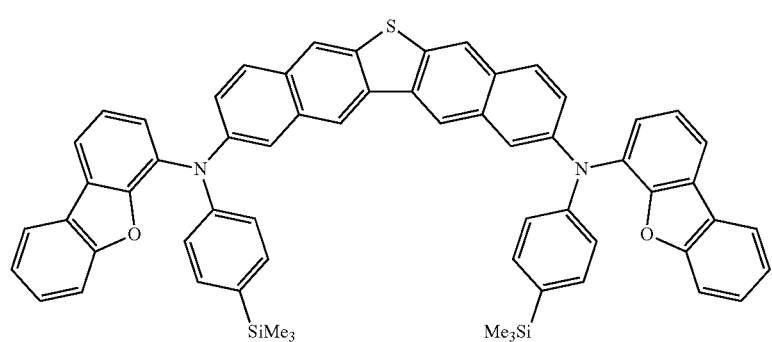
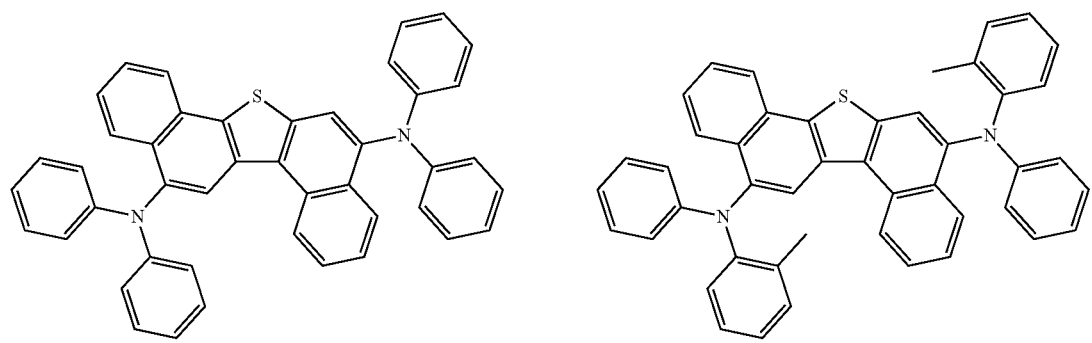
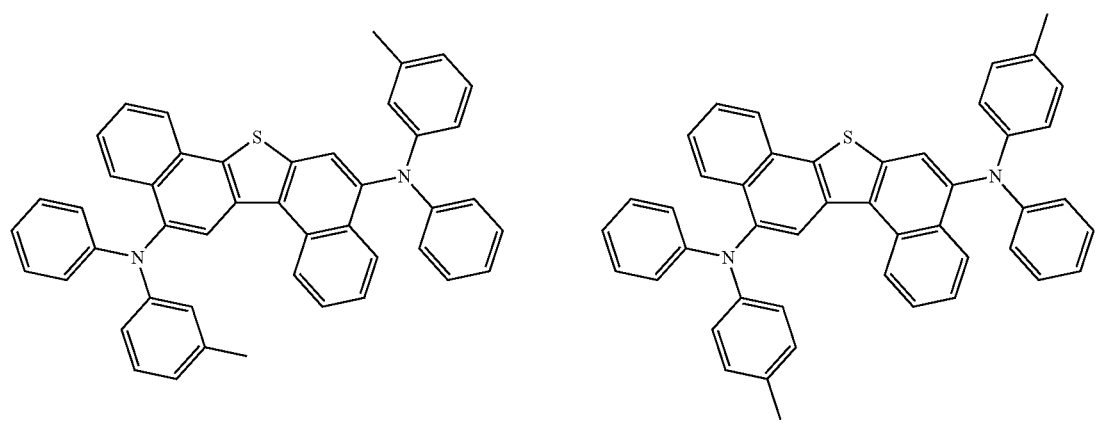

-continued
| 991 | 992 |
|---|---|
| 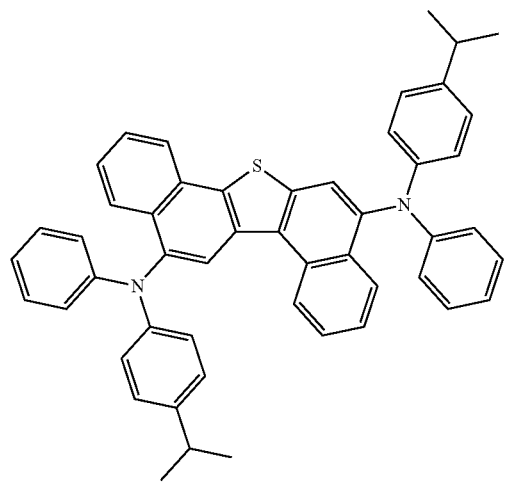 | 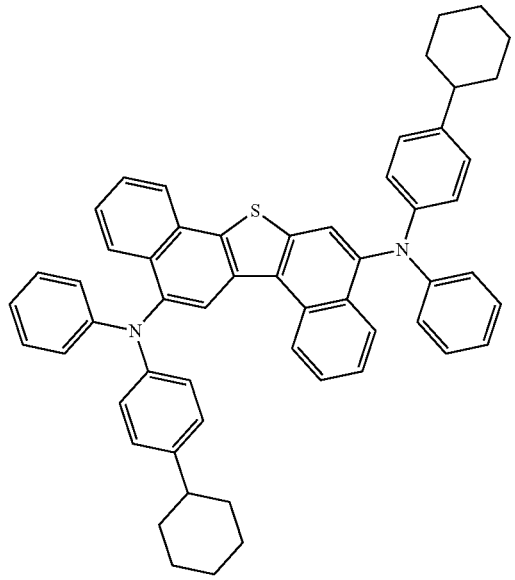 |
| 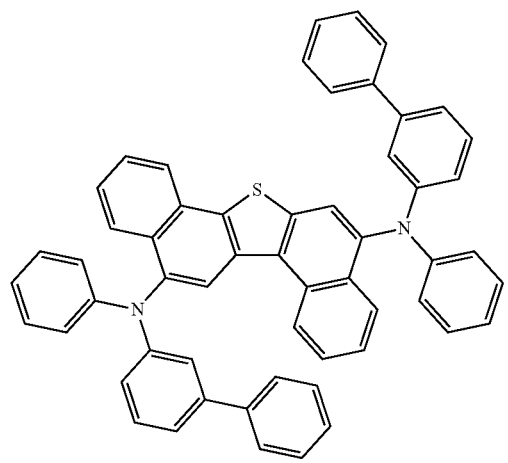 | 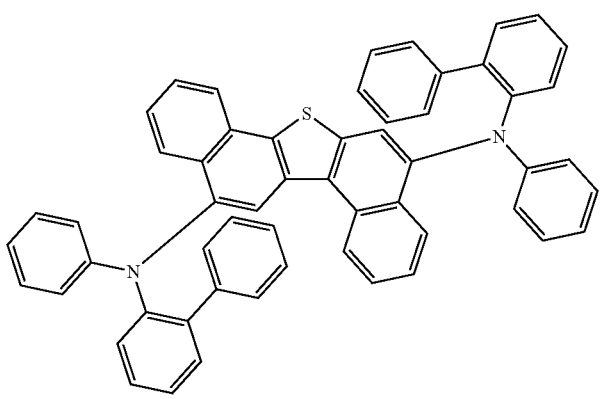 |
| 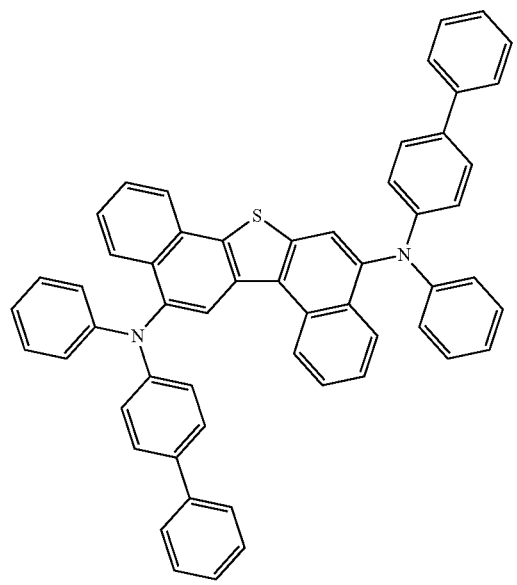 | 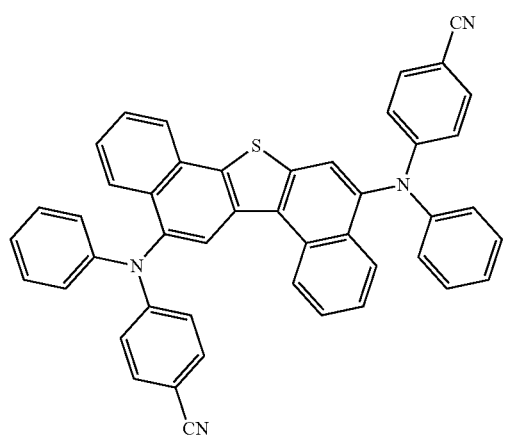 |

-continued
993 994
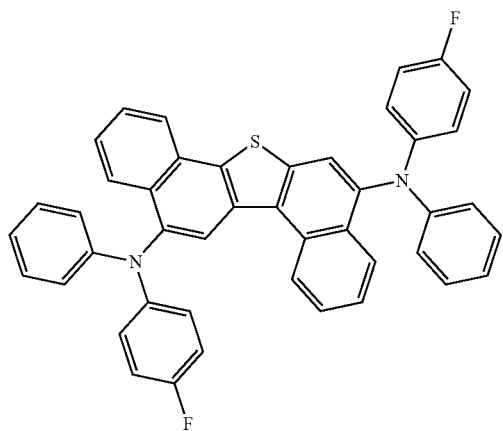
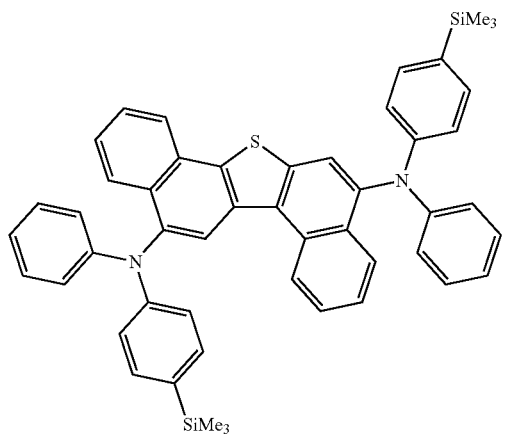
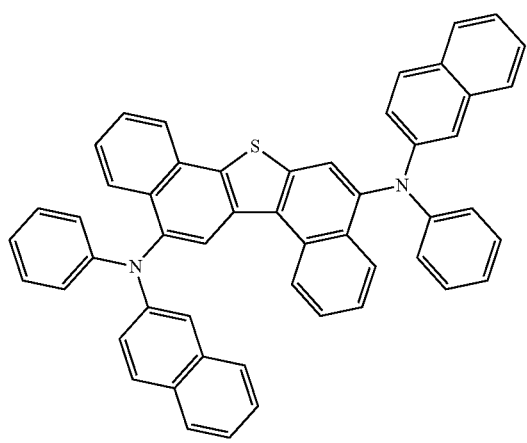
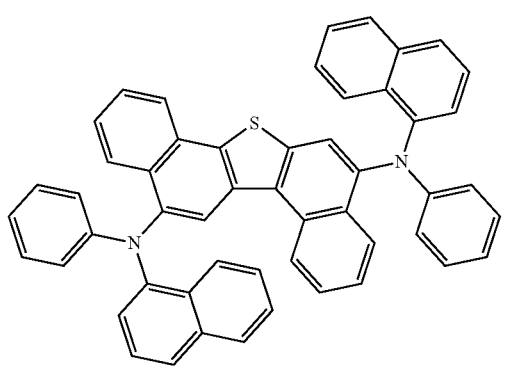
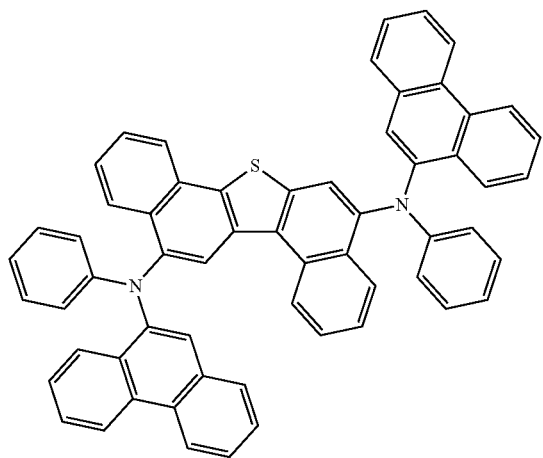

-continued
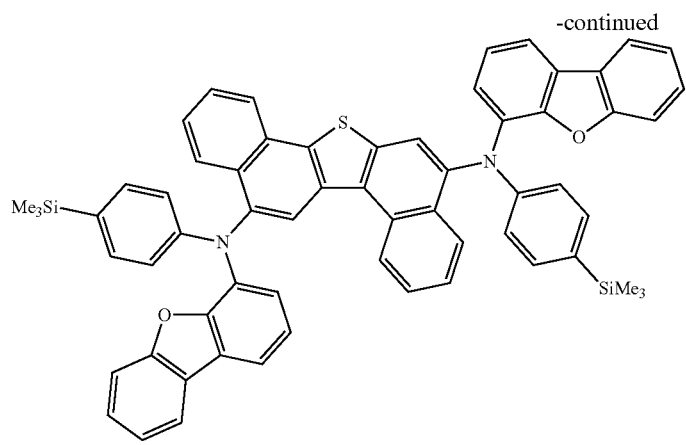
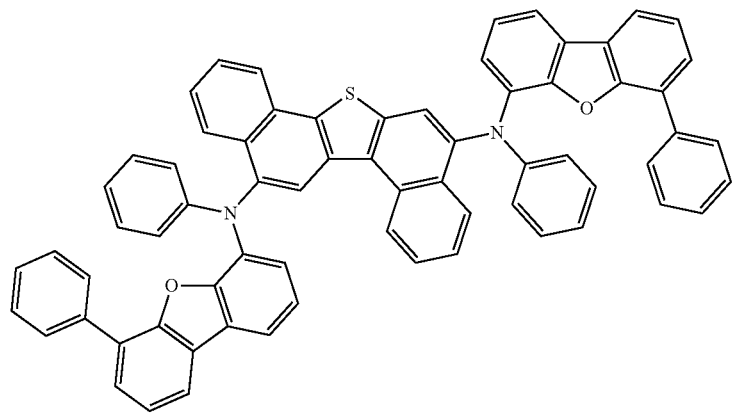
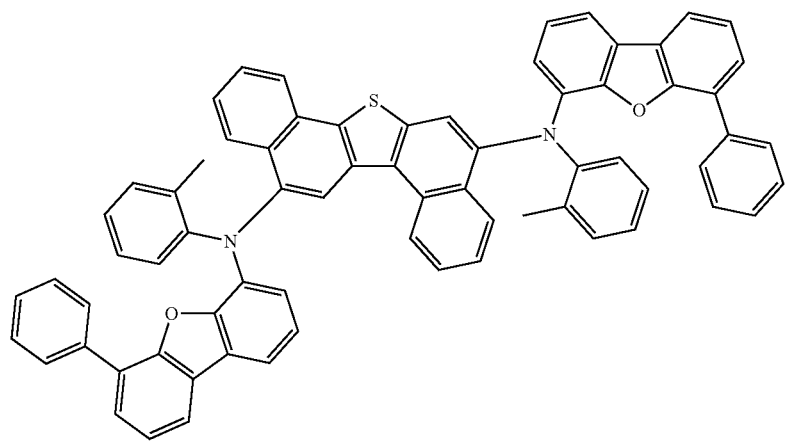
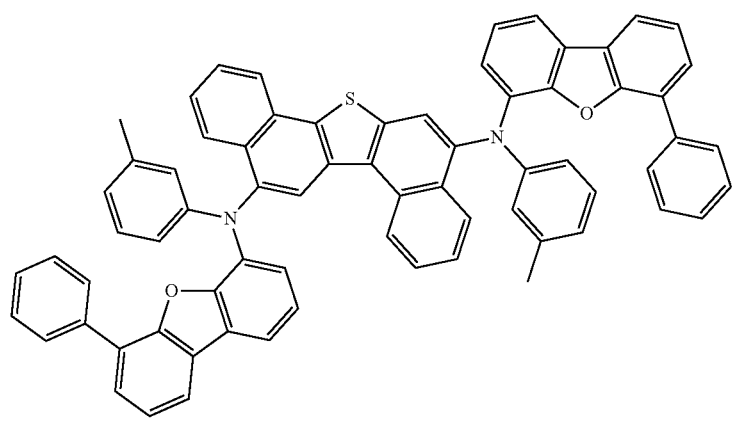

-continued
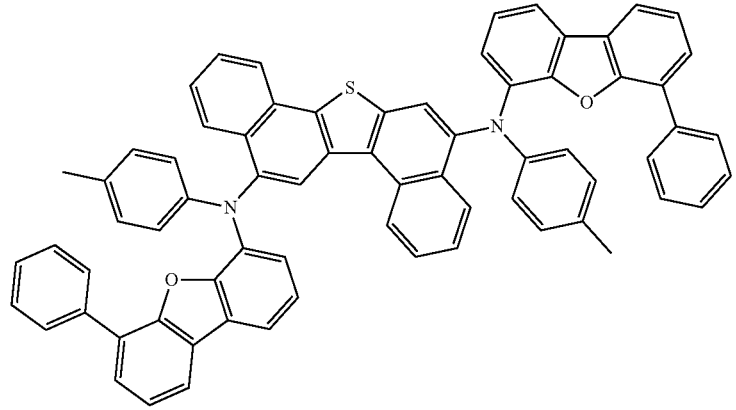
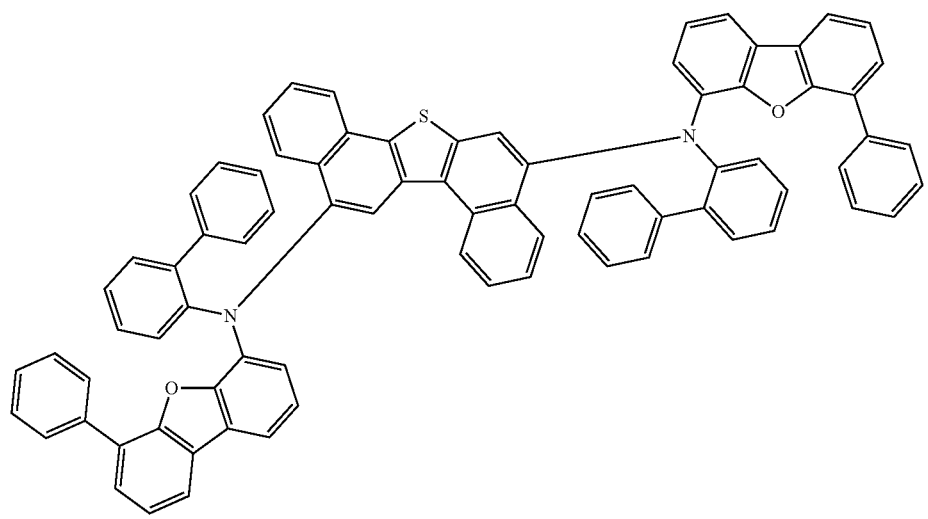
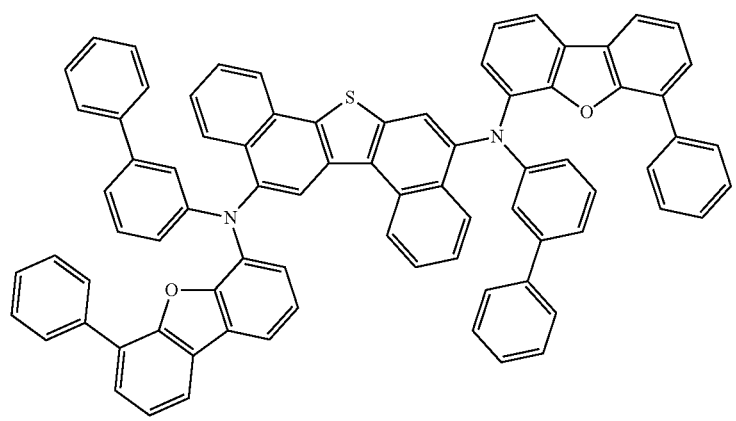

999                                                                                  1000
-continued
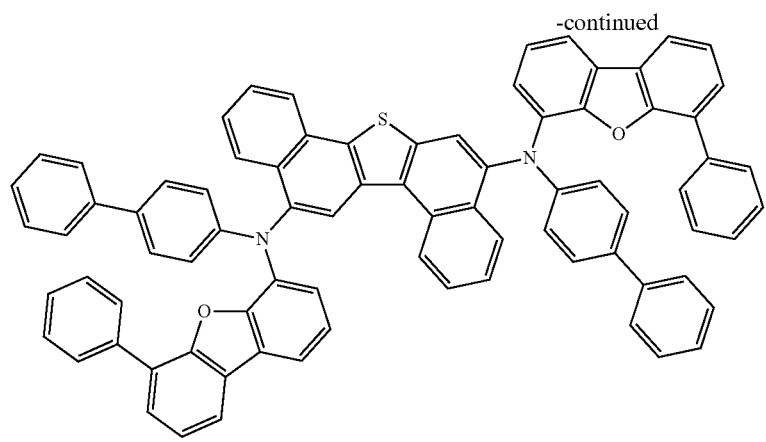
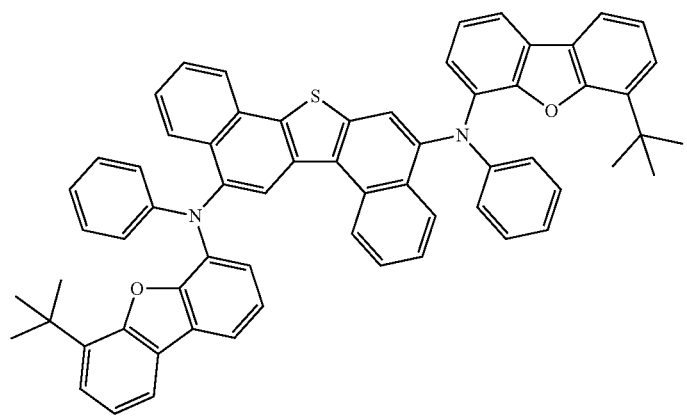
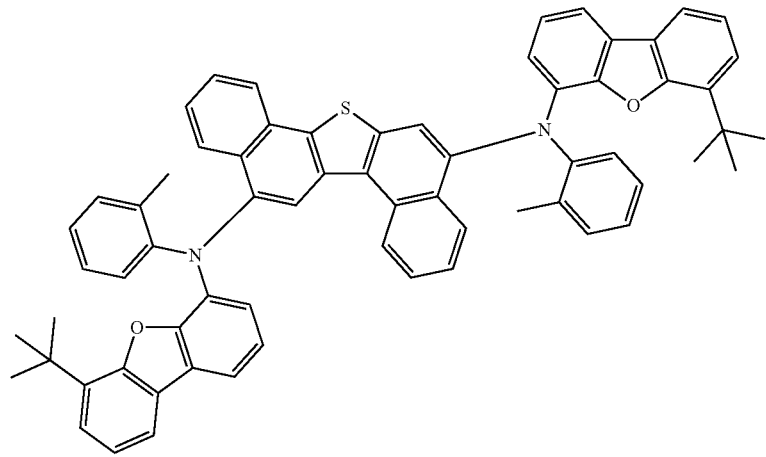
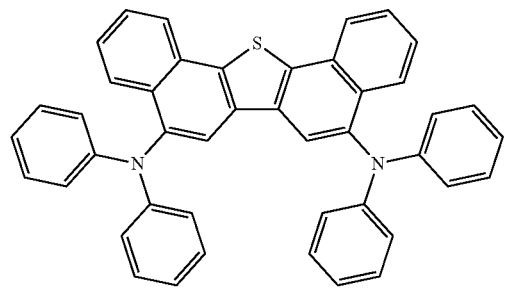
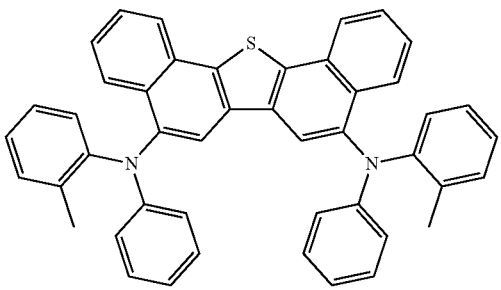

-continued
| 1001 | 1002 |
|---|---|
| 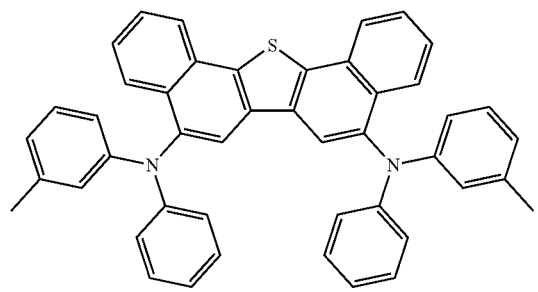 | 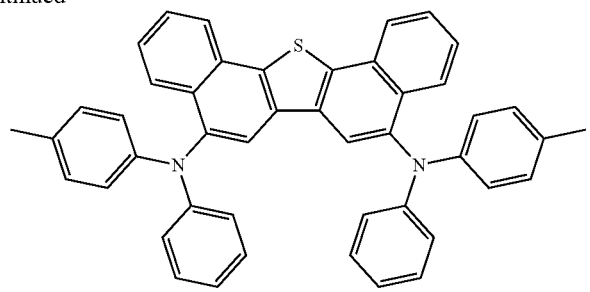 |
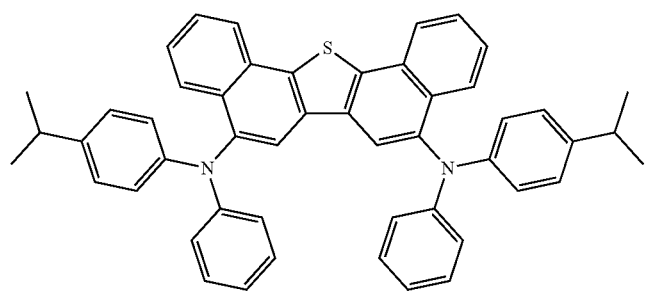
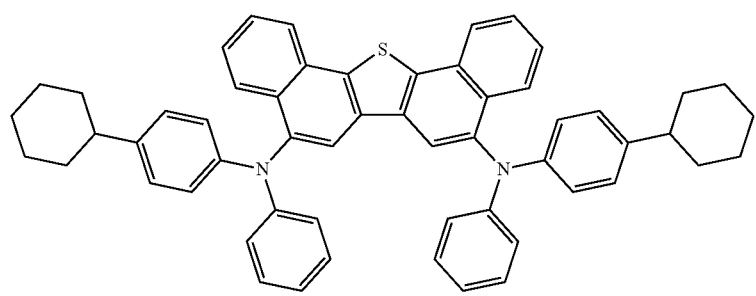
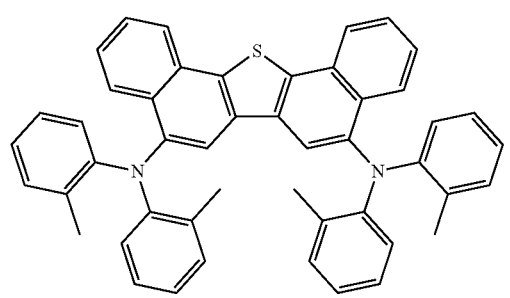
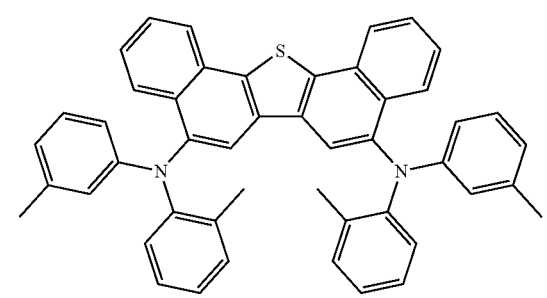
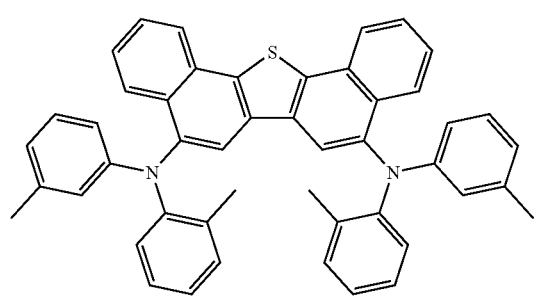
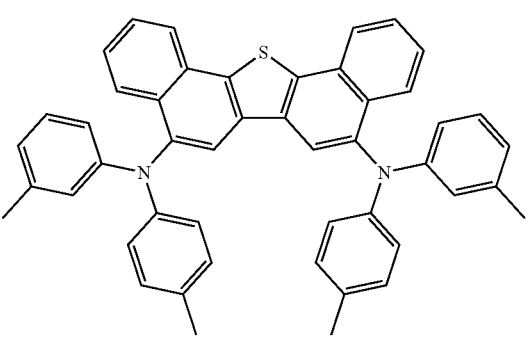

1003 1004
-continued
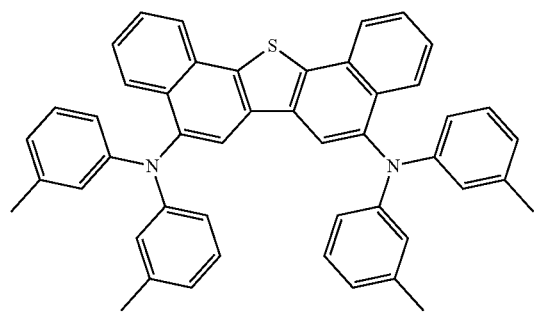
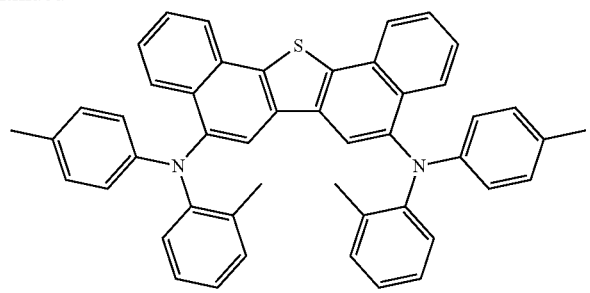
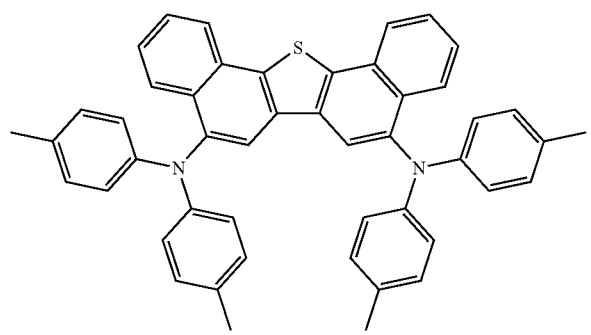
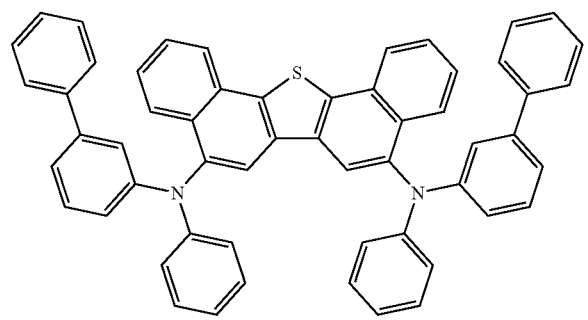
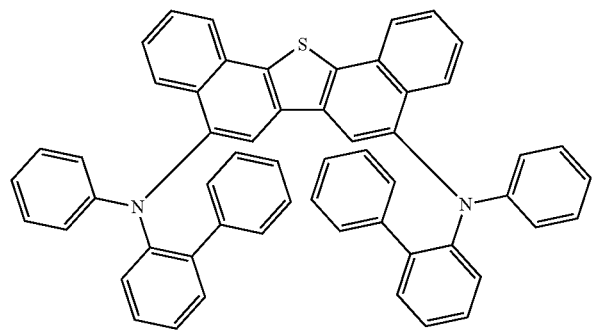
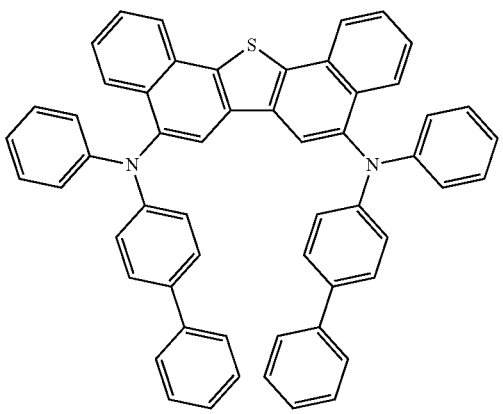
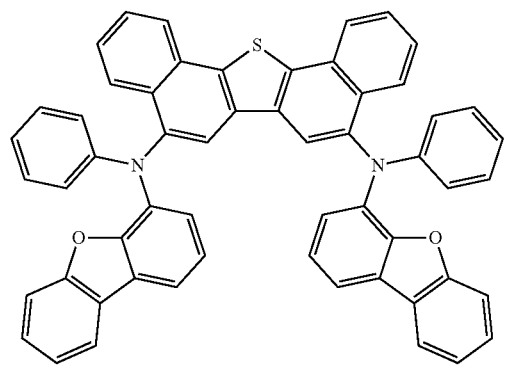
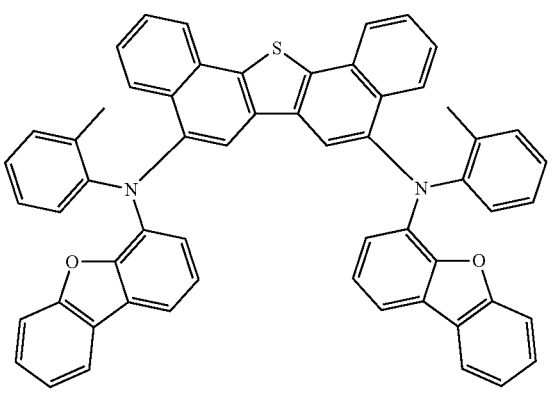

-continued
| 1005 | 1006 |
|---|---|
| 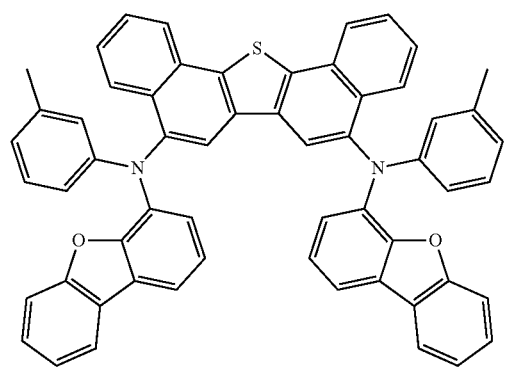 | 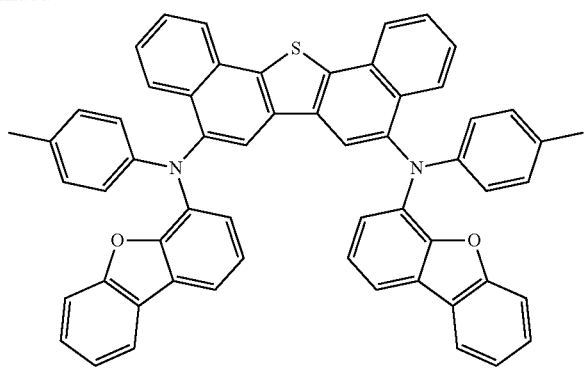 |
| 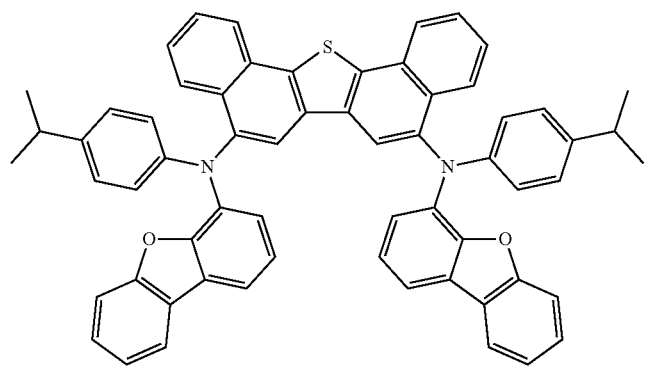 | |
| 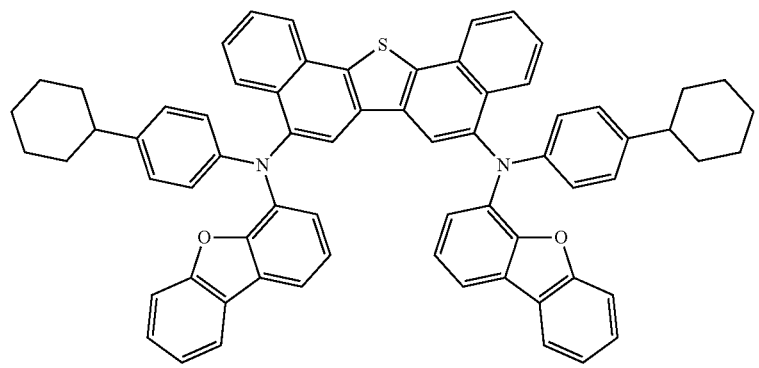 | |
| 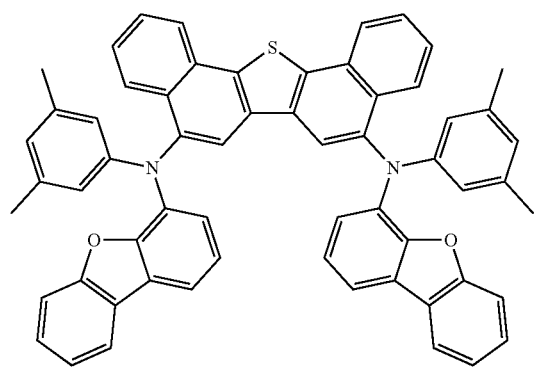 | 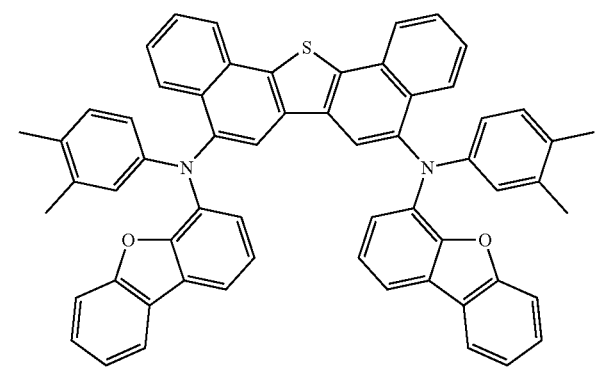 |

US 10,777,752 B2
1007                                                   1008
-continued
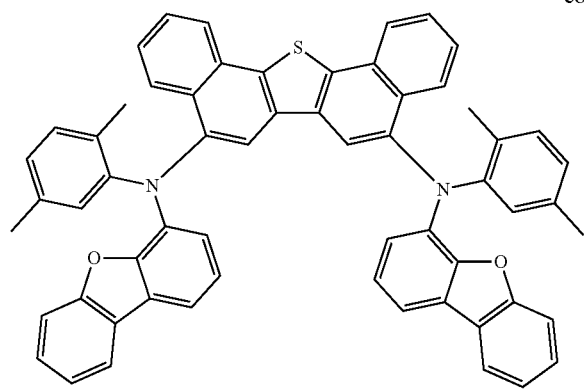

-continued
1009            1010
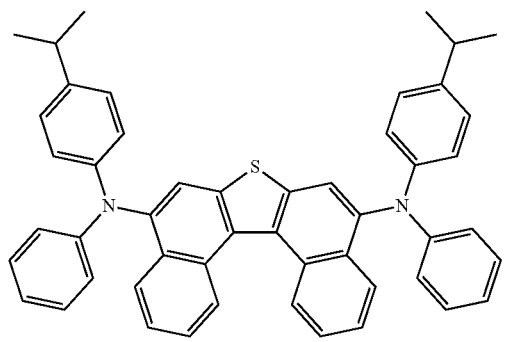 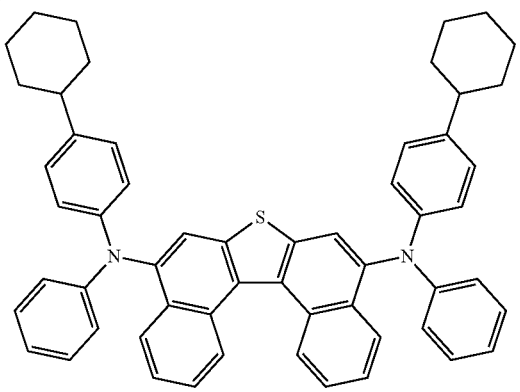
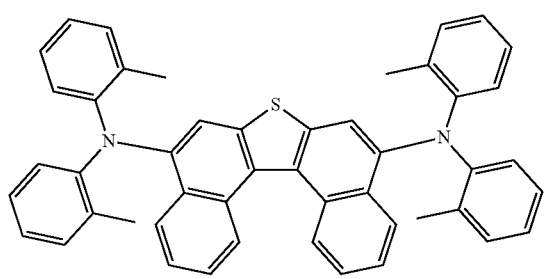 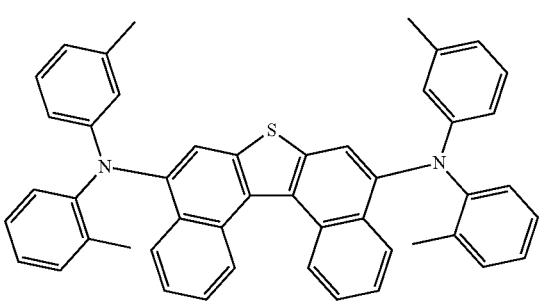
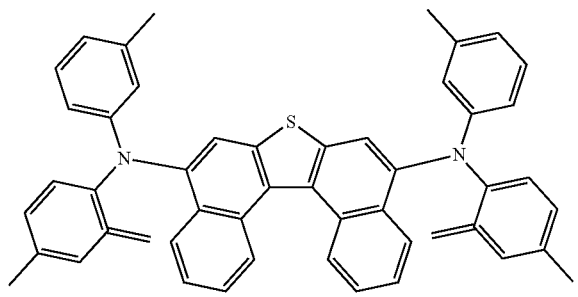 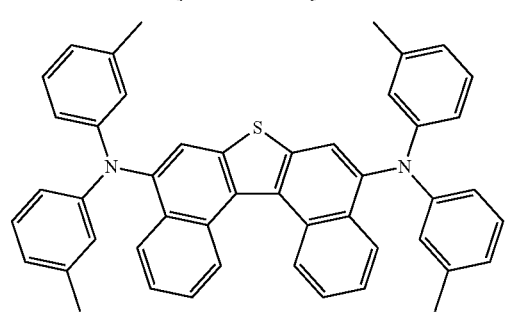
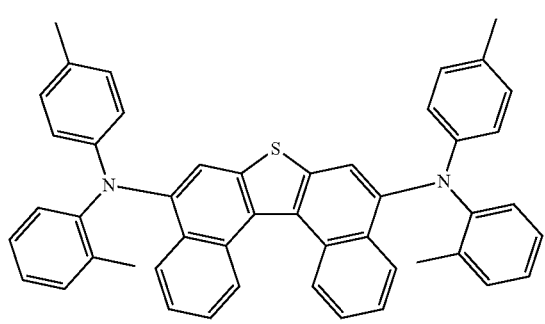 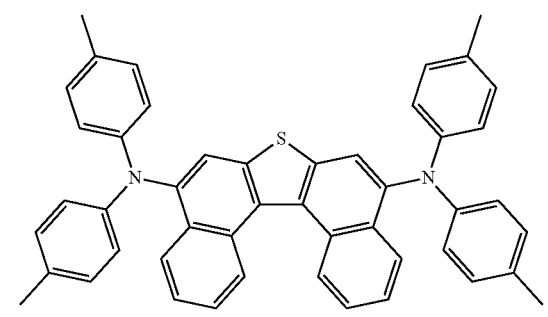
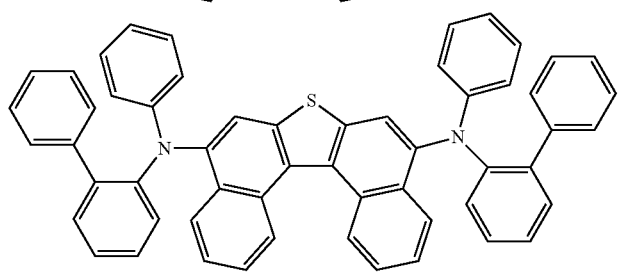 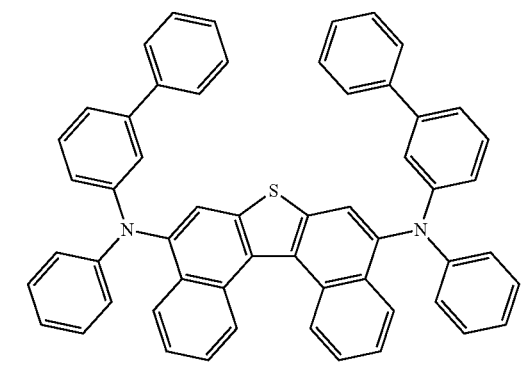

-continued
1011
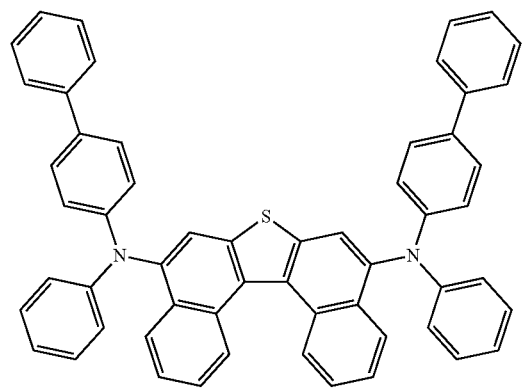
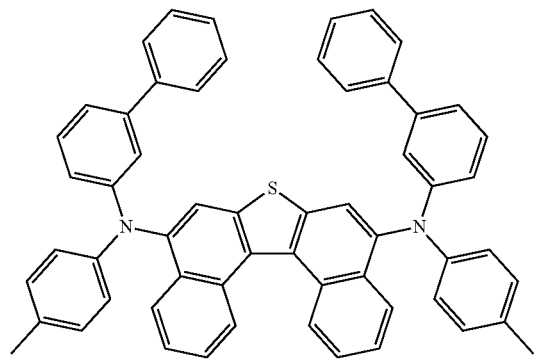
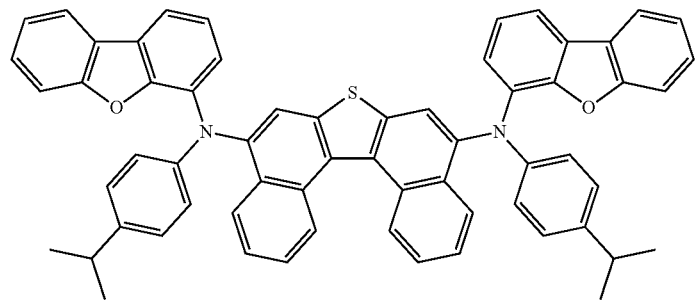
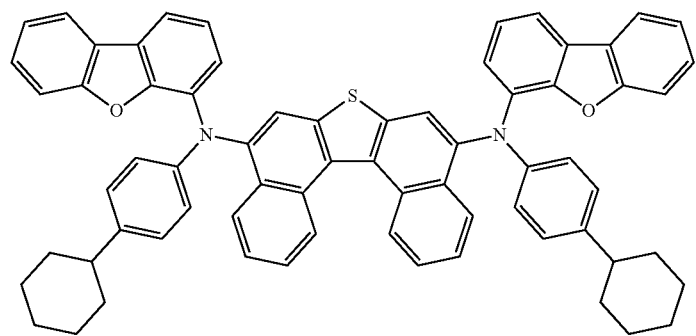
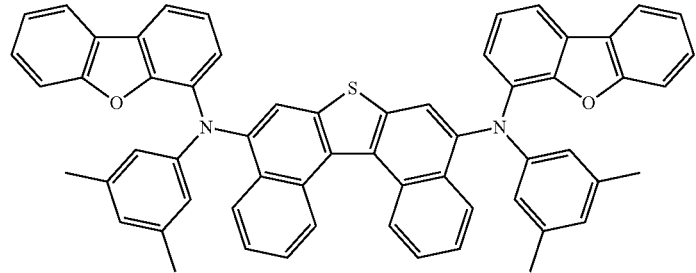
1012
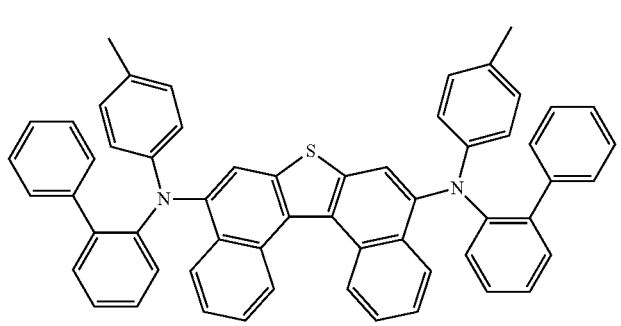
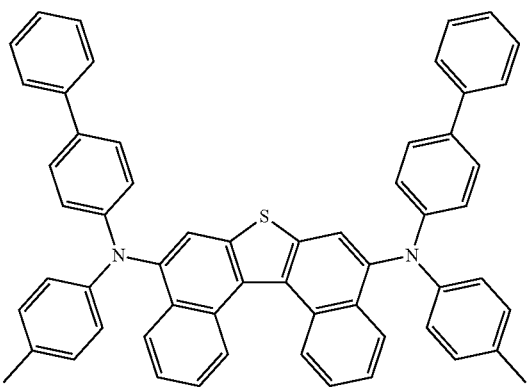

1013
-continued
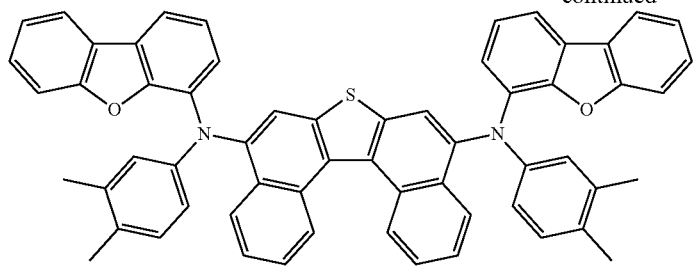
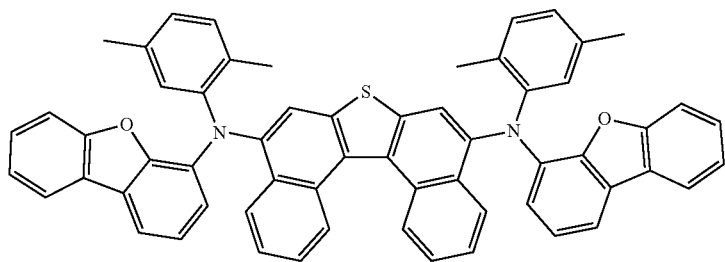
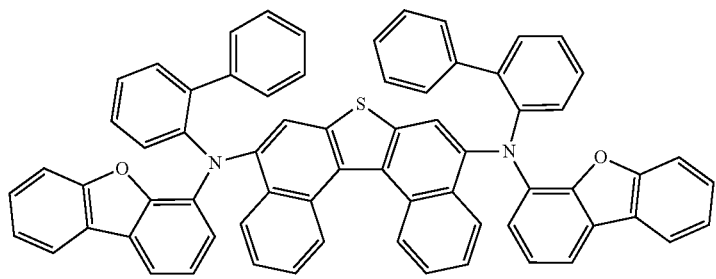
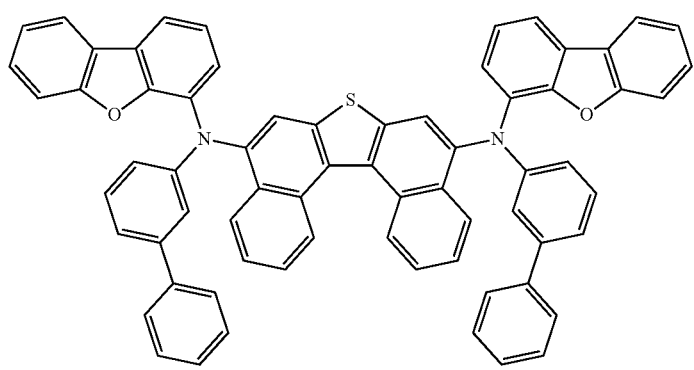
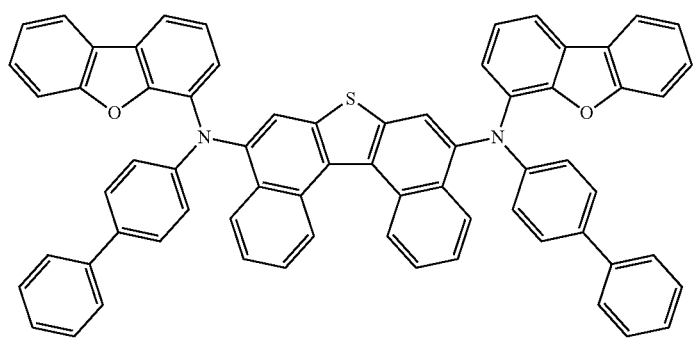
1014

1015
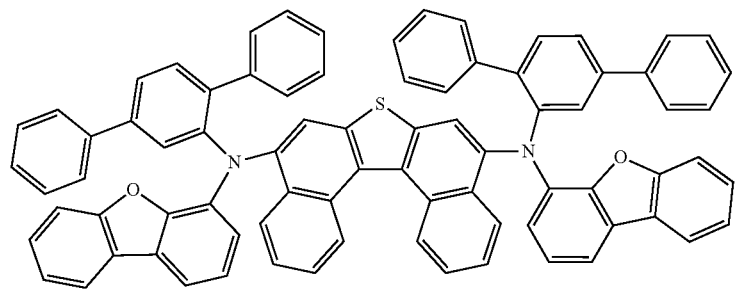
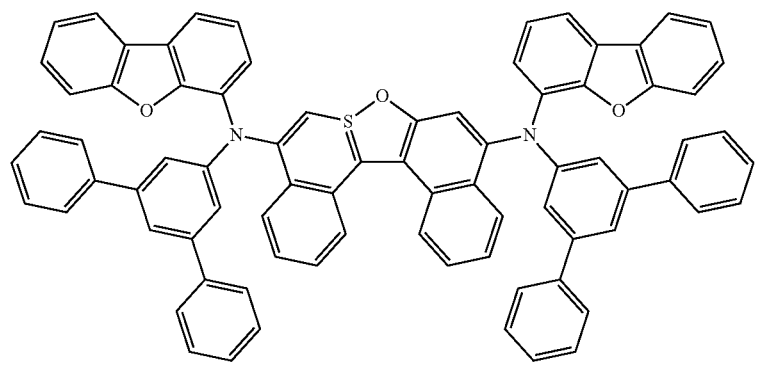
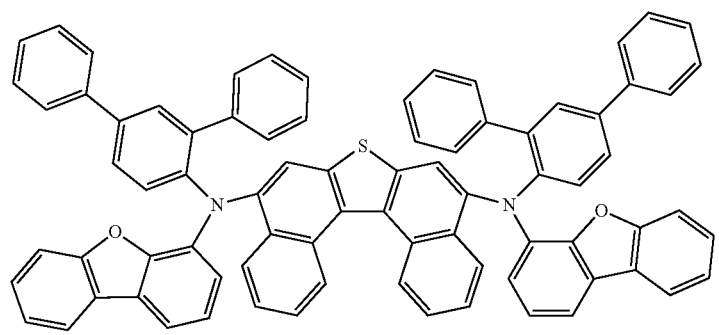
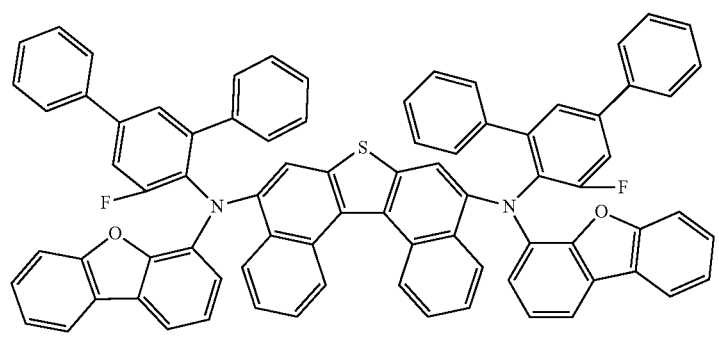
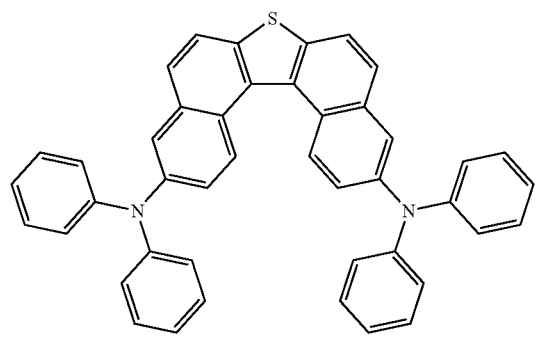
1016
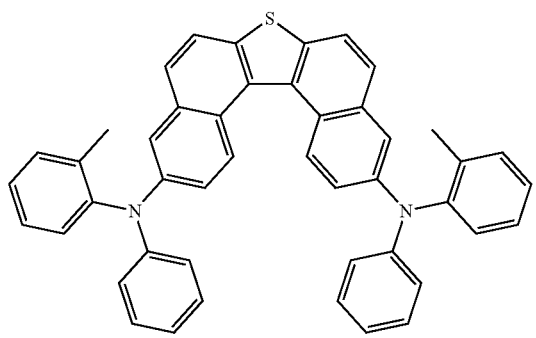

| 1017 | 1018 |
|---|---|
| 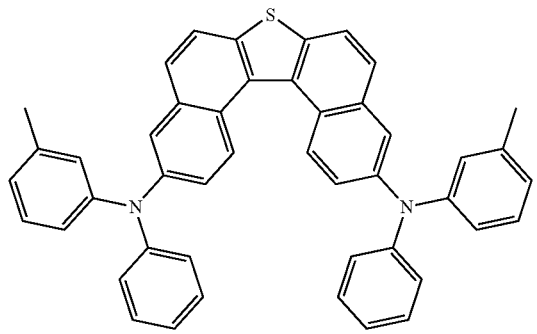 | 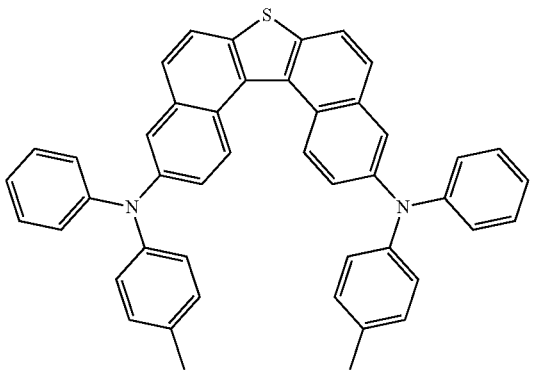 |
| 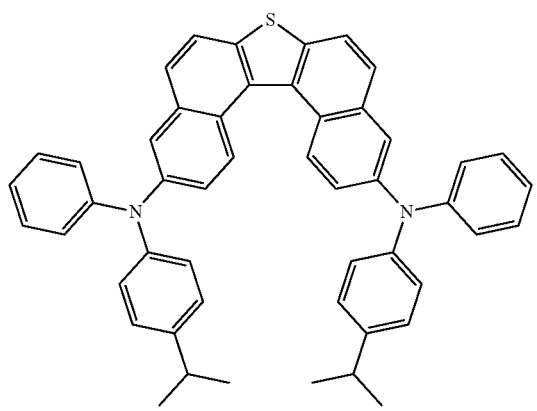 | 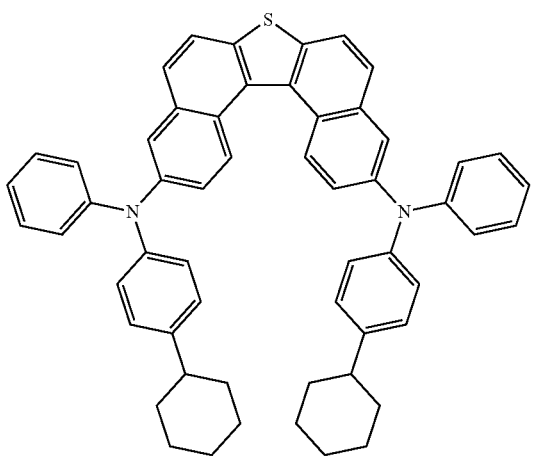 |
| 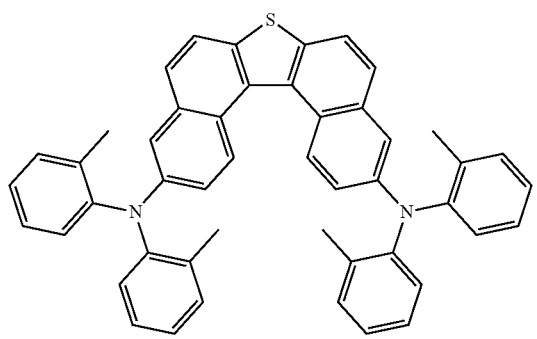 | 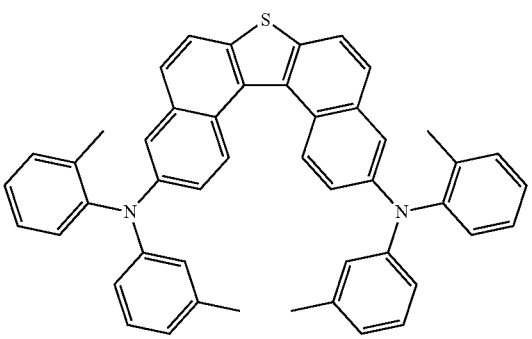 |
| 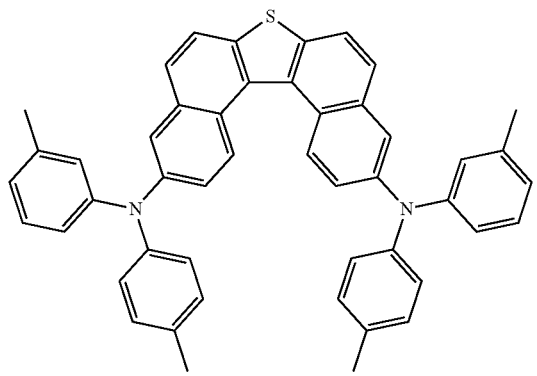 | 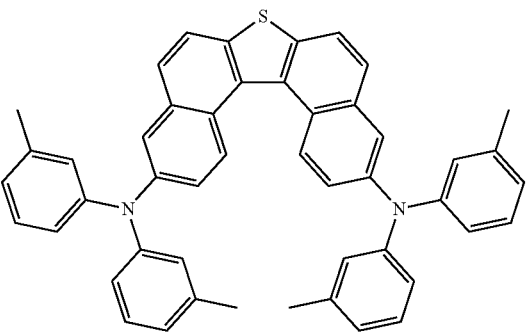 |

| 1019 | 1020 |
|---|---|
| 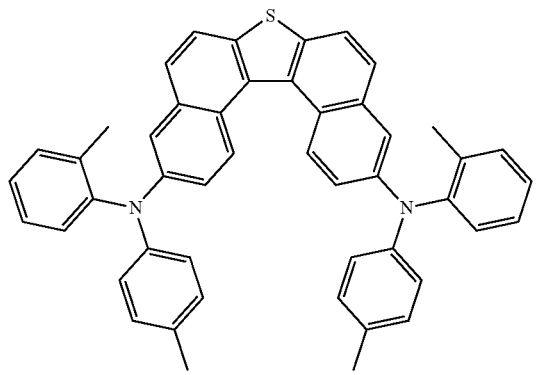 | 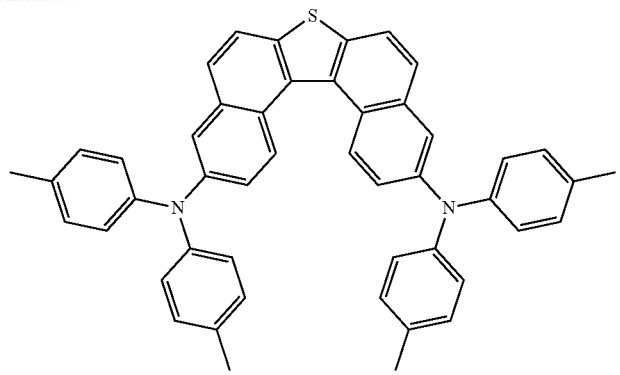 |
| 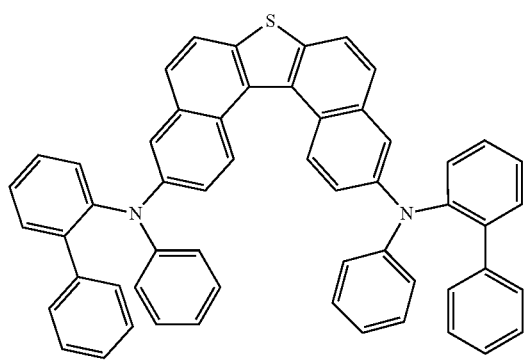 | 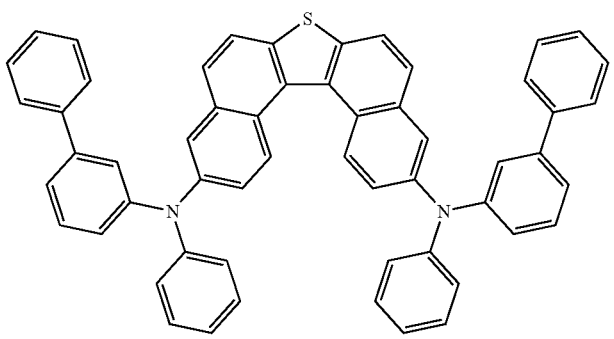 |
| 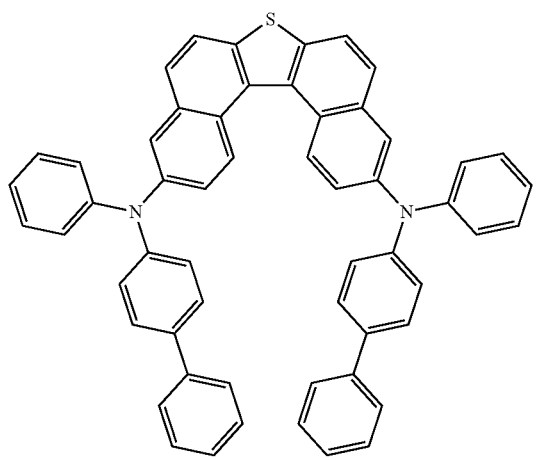 | 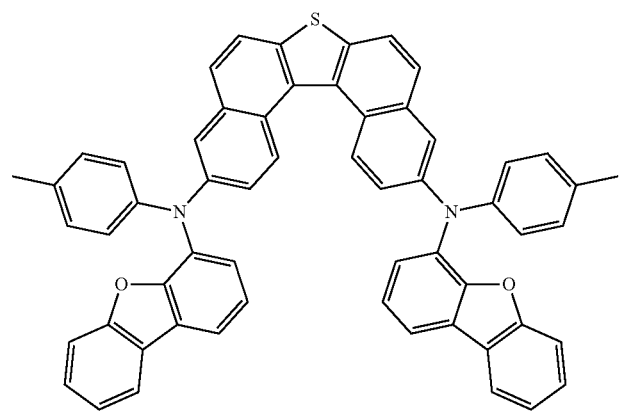 |
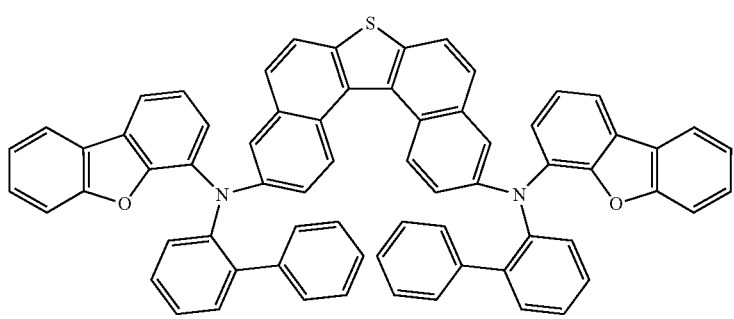

1021
-continued
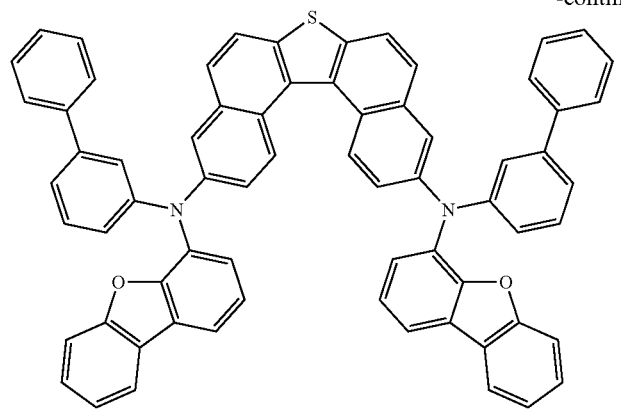
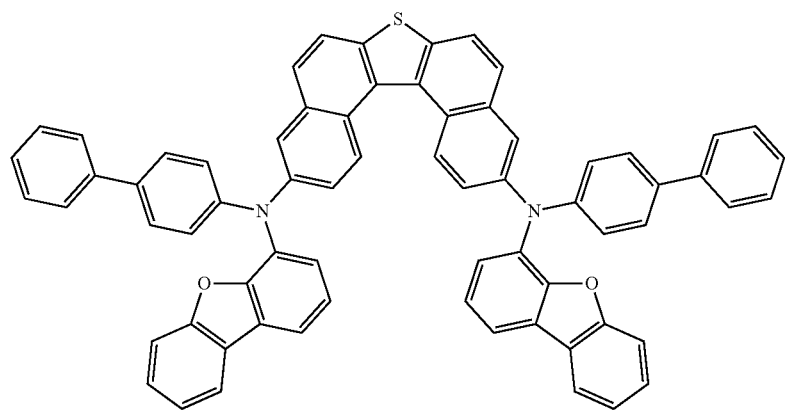
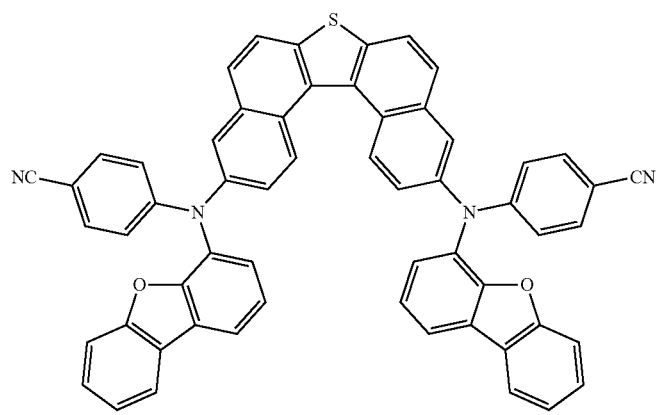
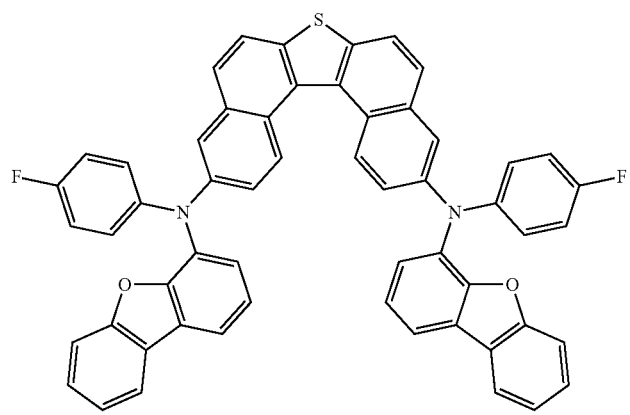
1022

1023　　　　　-continued　　　　　1024
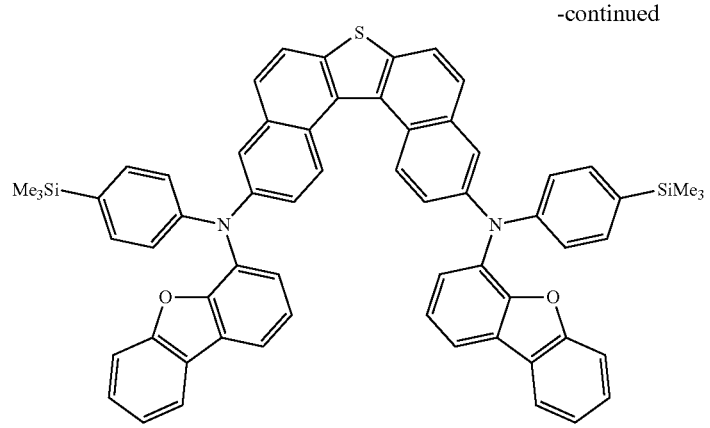
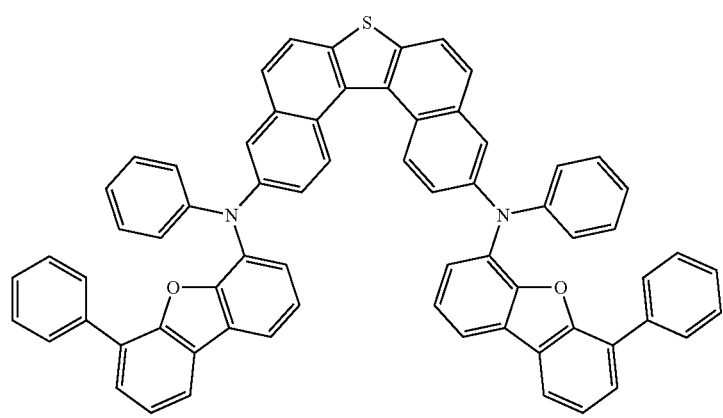
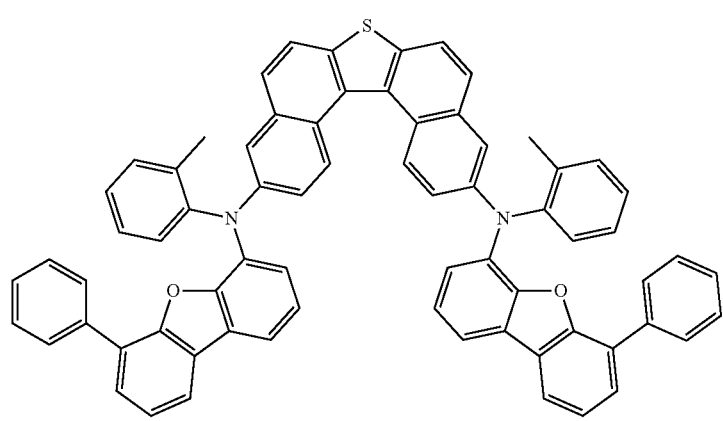
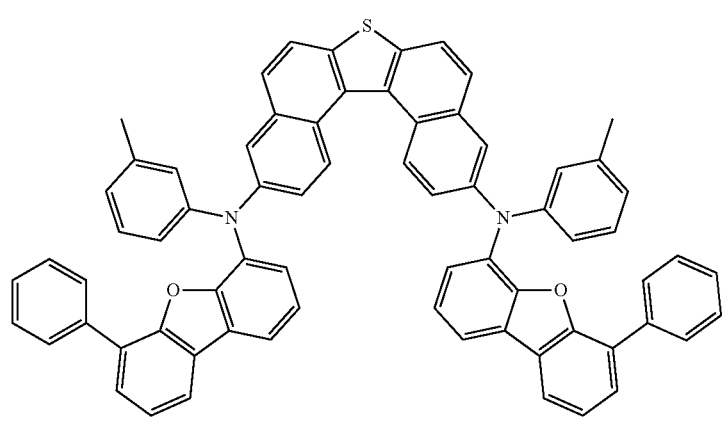
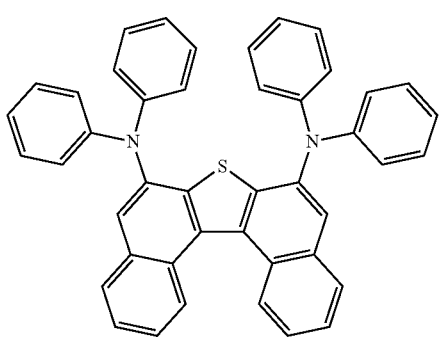

1025   1026
-continued
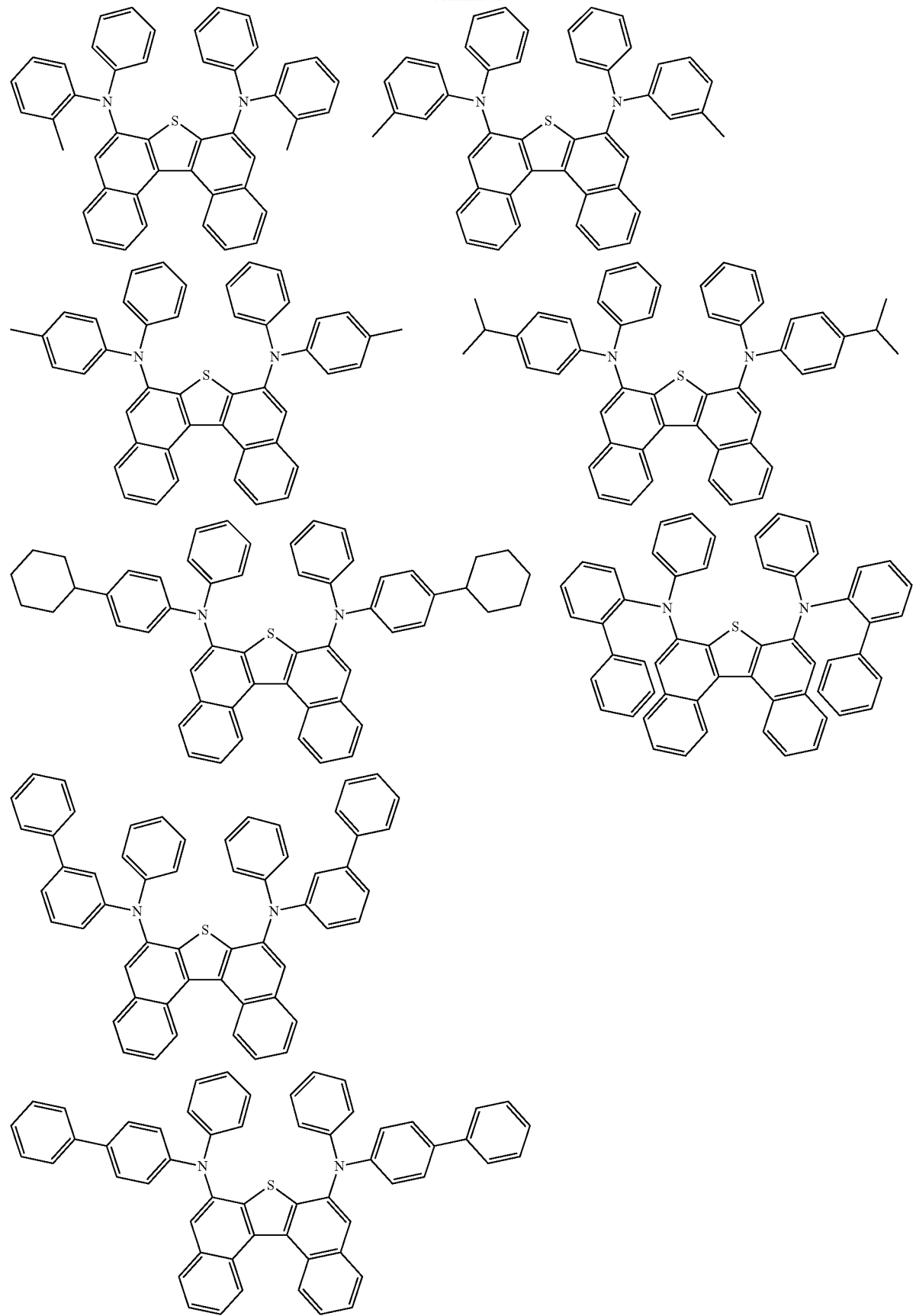

1027     1028
-continued
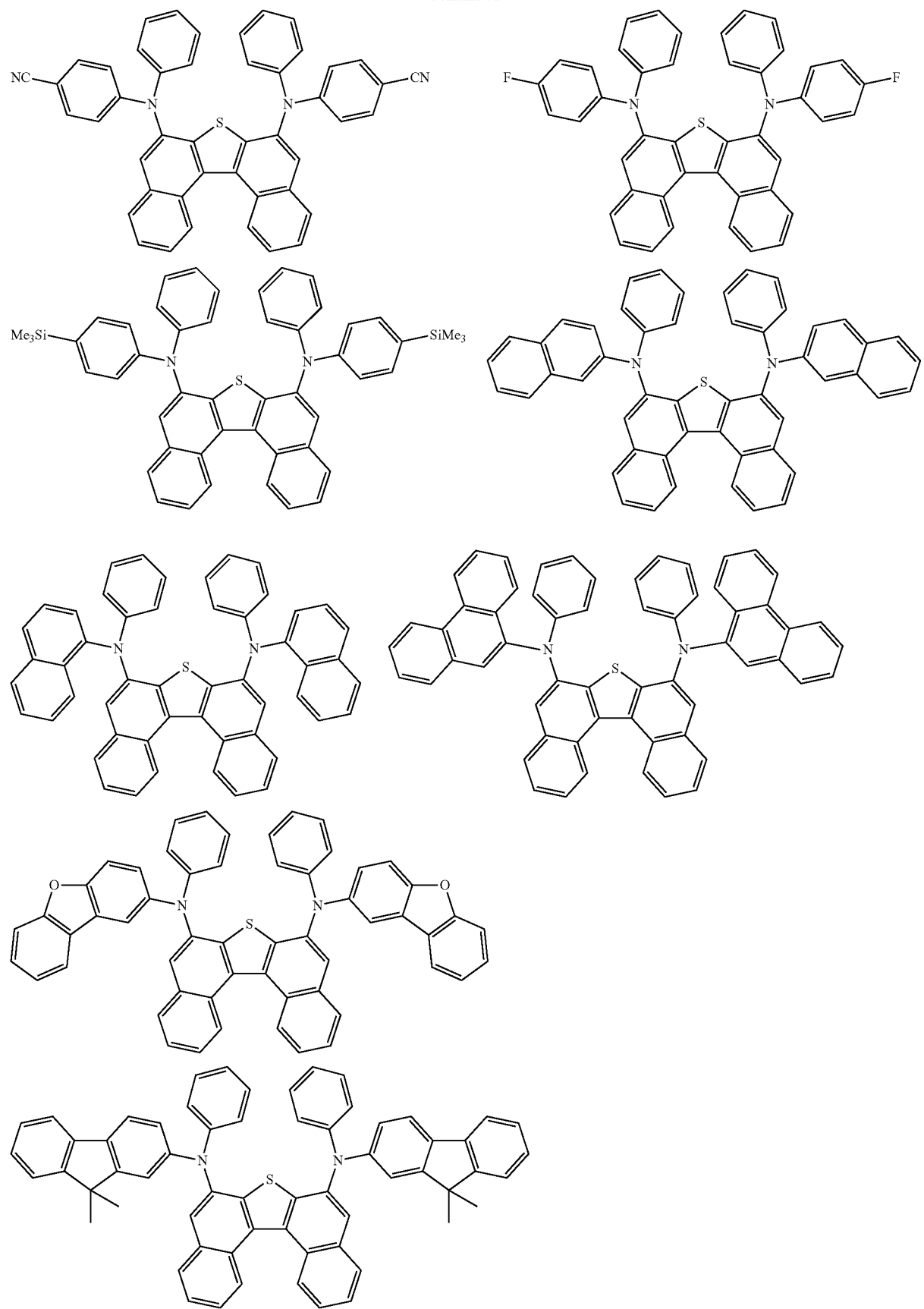

1029 1030

-continued

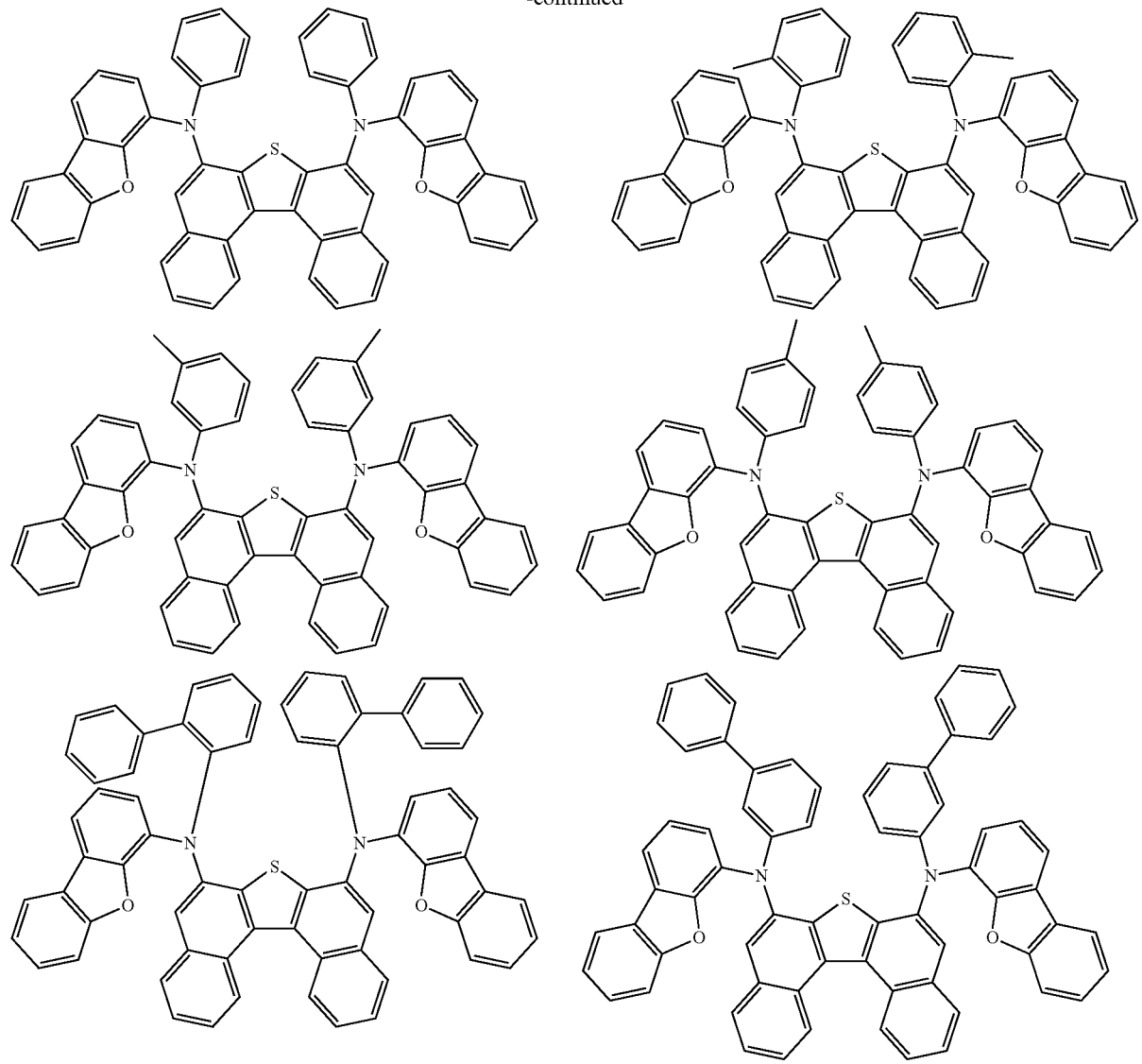

(Compound Represented by Formula (71))

The compound represented by the formula (71) is explained below.

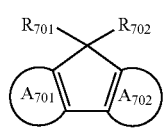
(71)

wherein, in the formula (71),

A$_{701}$ ring and A$_{702}$ ring are independently a substituted or unsubstituted aromatic hydrocarbon ring having 6 to 50 ring carbon atoms, or a substituted or unsubstituted heterocyclic ring having 5 to 50 ring atoms;

One or more rings selected from the group consisting of A$_{701}$ ring and A$_{702}$ ring are

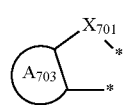
(72)

wherein, in the formula (72),

A$_{703}$ rings are independently a substituted or unsubstituted aromatic hydrocarbon ring having 6 to 50 ring carbon atoms, or a substituted or unsubstituted heterocyclic ring having 5 to 50 ring atoms;

X$_{701}$ is NR$_{703}$, C(R$_{704}$)(R$_{705}$), Si(R$_{706}$) (R$_{707}$), Ge(R$_{708}$) (R$_{709}$), O, S or Se;

R$_{701}$ and R$_{702}$ are bonded with each other to form a substituted or unsubstituted, saturated or unsaturated ring or do not form a substituted or unsubstituted saturated or unsaturated ring;

R$_{701}$ and R$_{702}$ that do not form the substituted or unsubstituted, saturated or unsaturated ring, and R$_{703}$ to R$_{709}$ are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
One or more selected from the group consisting of $A_{701}$ ring and $A_{702}$ ring is bonded to * in the structure represented by the formula (72). That is, in one embodiment, the ring carbon atom of the aromatic hydrocarbon ring or the ring atom of the heterocyclic ring of $A_{701}$ ring is bonded to * in the structure represented by the formula (72). In one embodiment, the ring carbon atom of the aromatic hydrocarbon ring or the ring atom of the heterocyclic ring of $A_{702}$ ring is bonded to * in the structure represented by the formula (72).

In one embodiment, the group represented by the formula (73) is bonded to one or both of $A_{701}$ ring and $A_{702}$ ring.

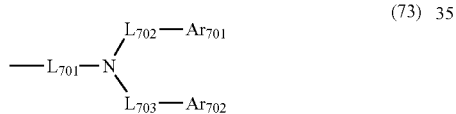
(73)

wherein in the formula (73), $Ar_{7001}$ and $Ar_{702}$ are independently
a substituted or unsubstituted aryl group having 6 to 50 ring carbon atoms, or
a substituted or unsubstituted monovalent heterocyclic group having 5 to 50 ring atoms; and
$L_{701}$ to $L_{703}$ are independently
a single bonded,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups.

In one embodiment, in addition to $A_{701}$ ring, the ring carbon atom of the aromatic hydrocarbon ring or the ring atom of the heterocyclic ring of $A_{702}$ ring is bonded to * in the structure represented by the formula (72). In this case, the structures represented by formula (72) may be the same or different.

In one embodiment, $R_{701}$ and $R_{702}$ are independently a substituted or unsubstituted aryl group having 6 to 50 ring carbon atoms.

In one embodiment, $R_{701}$ and $R_{702}$ are bonded with each other to form a fluorene structure.

In one embodiment, $Ar_{701}$ ring and $Ar_{702}$ ring are substituted or unsubstituted aromatic hydrocarbon rings having 6 to 50 ring carbon atoms, and they are substituted or unsubstituted benzene rings, for example.

In one embodiment, $Ar_{703}$ ring is a substituted or unsubstituted aromatic hydrocarbon ring having 6 to 50 ring carbon atoms, and it is a substituted or unsubstituted benzene ring, for example.

In one embodiment, $X_{701}$ is O or S.

As specific example of the compound represented by the formula (71), the following compounds can be given, for example.

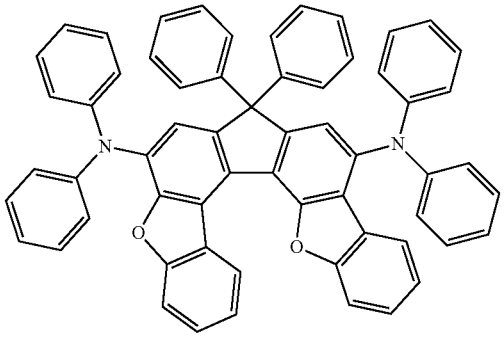

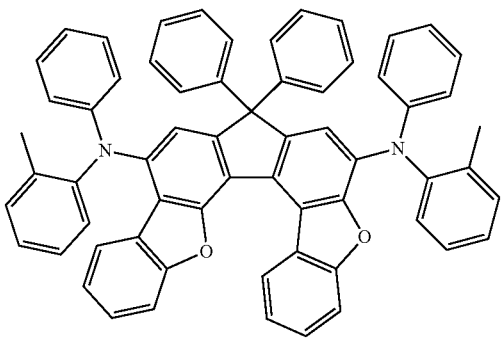

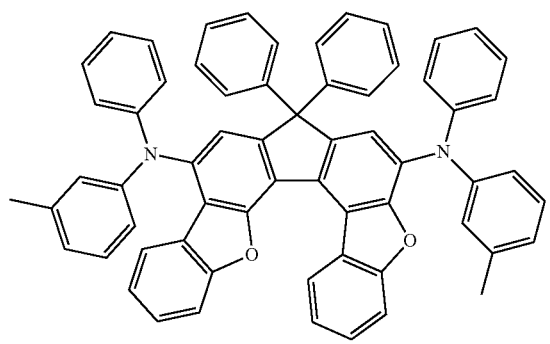

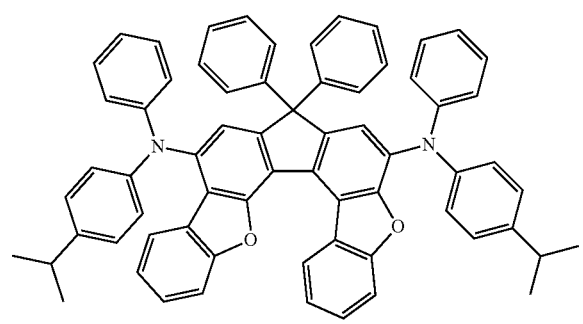

1033
-continued
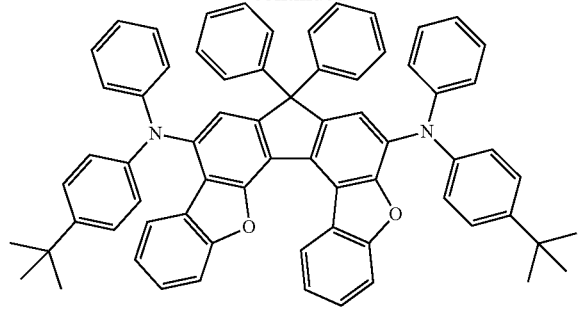
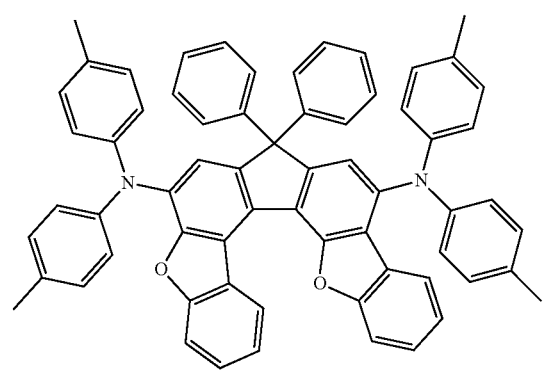
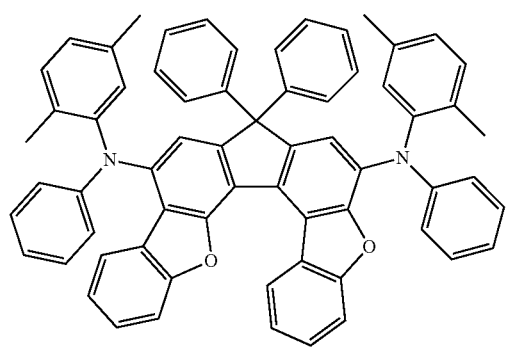
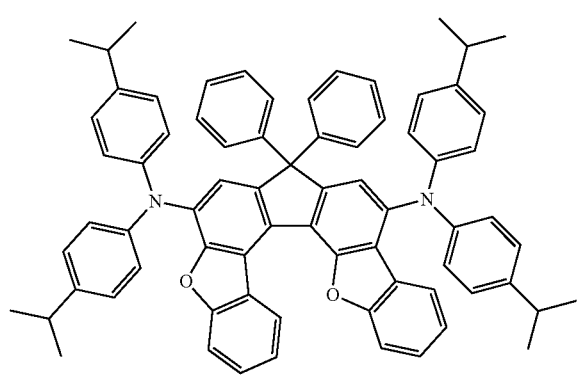
1034
-continued
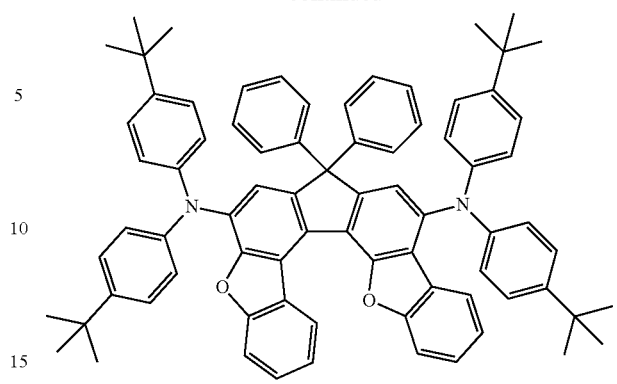
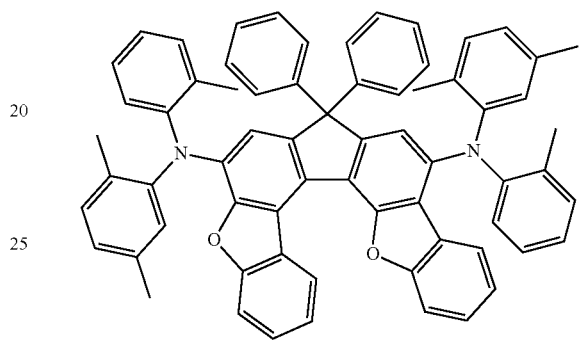
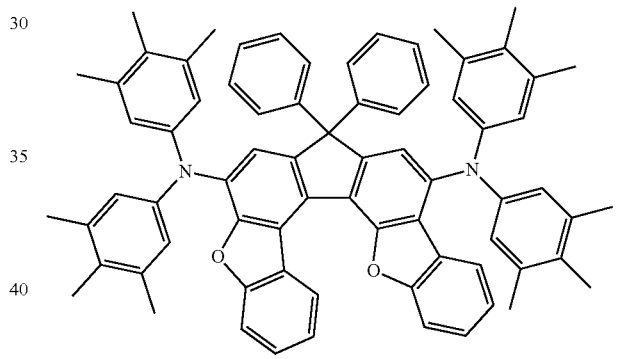
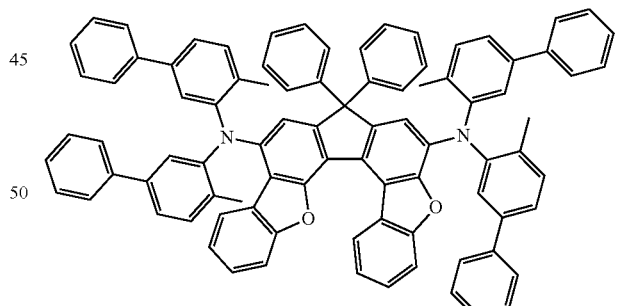
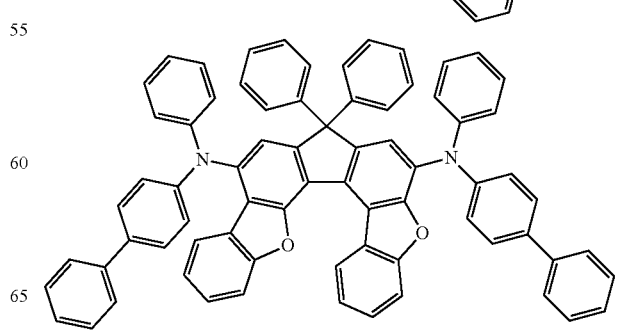

1035
-continued
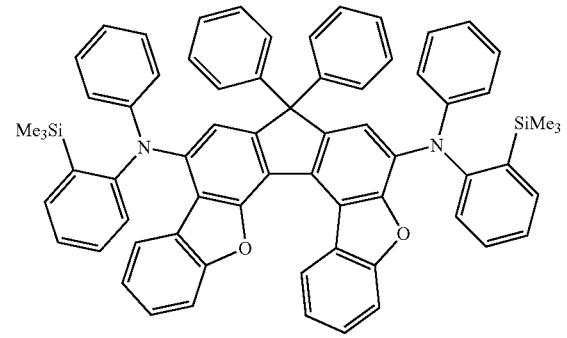
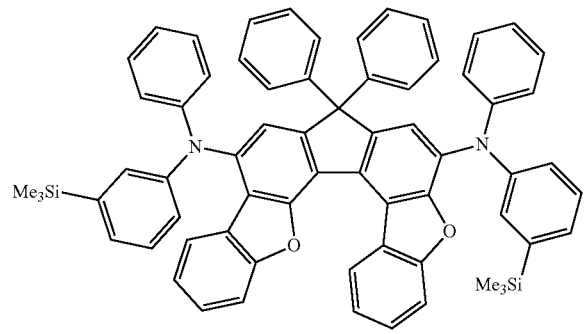
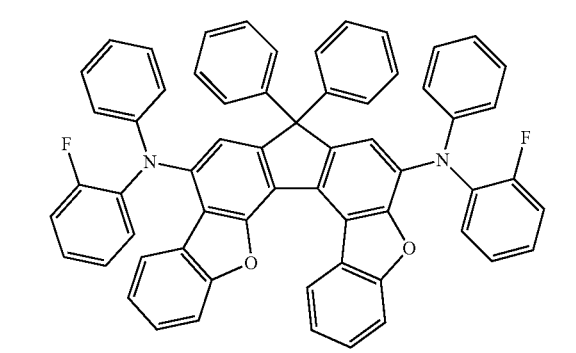
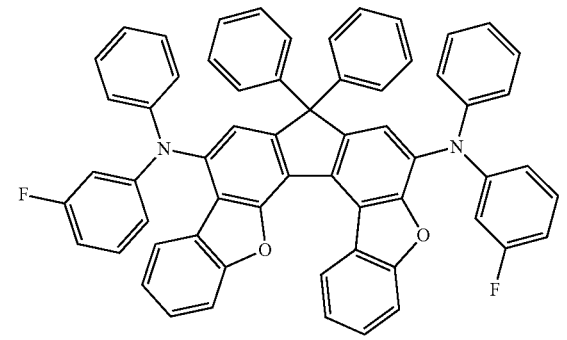
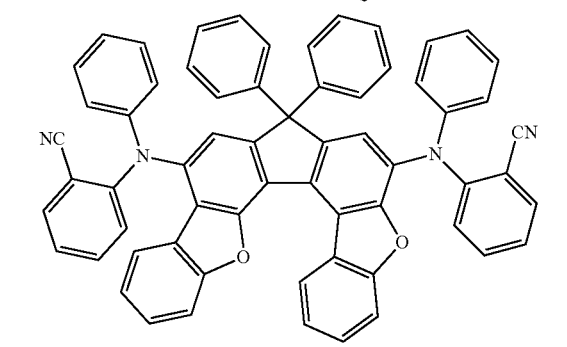
1036
-continued
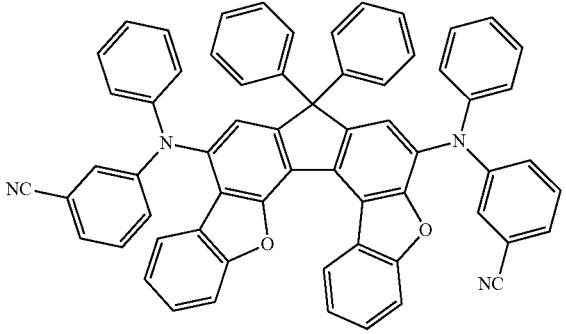
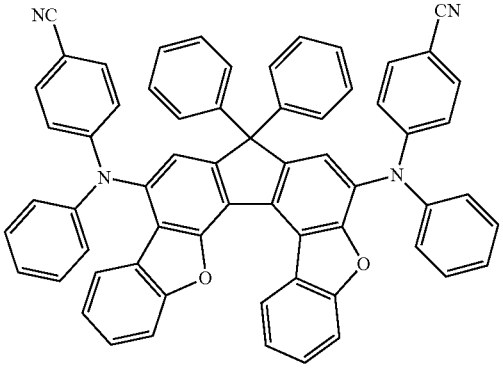
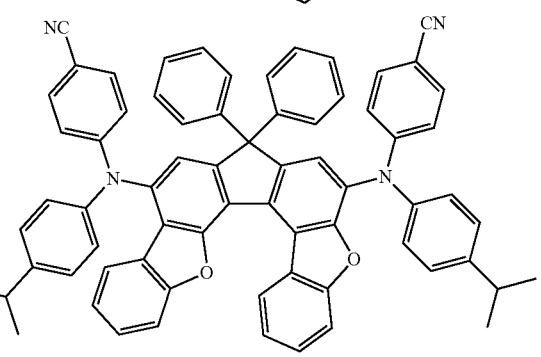
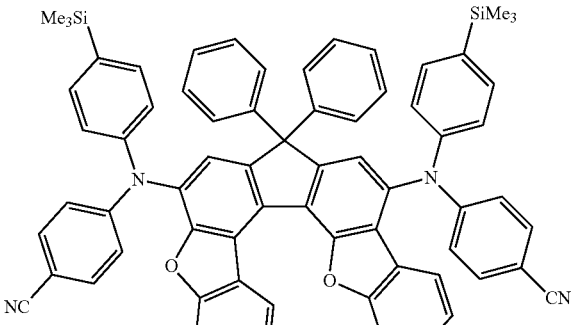
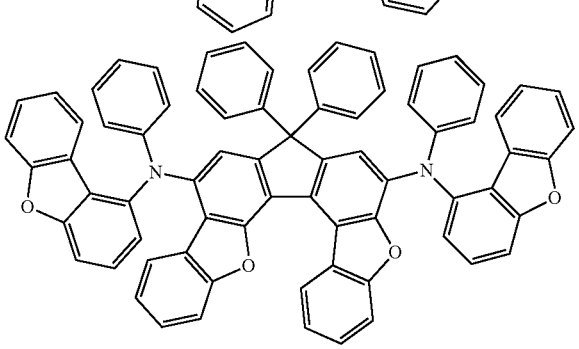

| 1037 -continued | 1038 -continued |
|---|---|
| 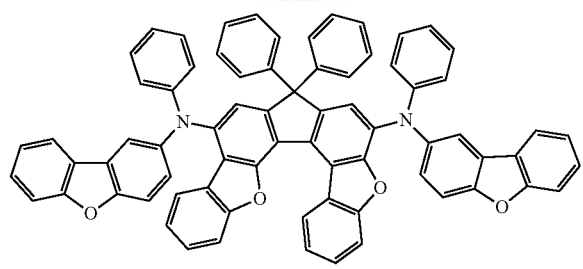 | 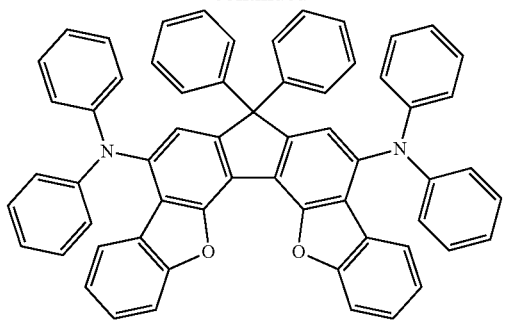 |
| 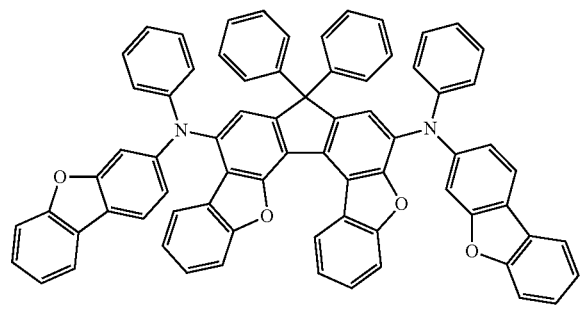 | 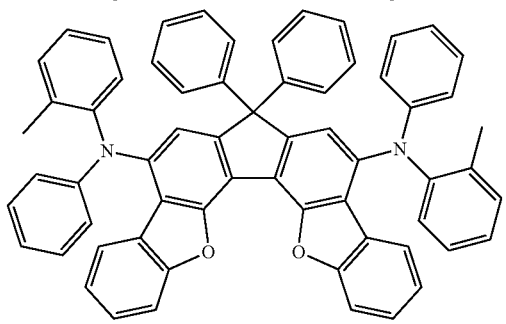 |
| 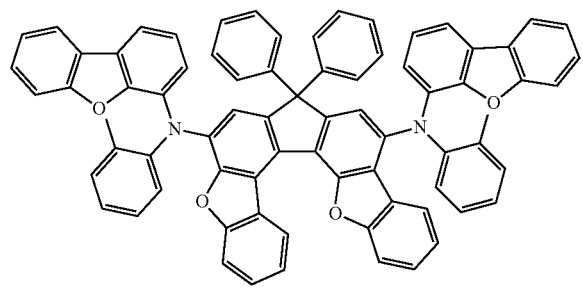 | 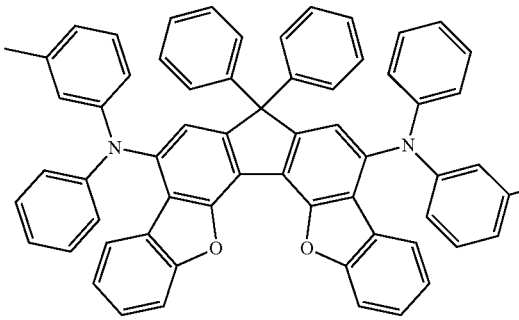 |
| 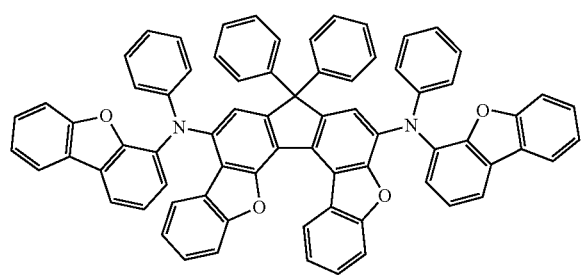 | 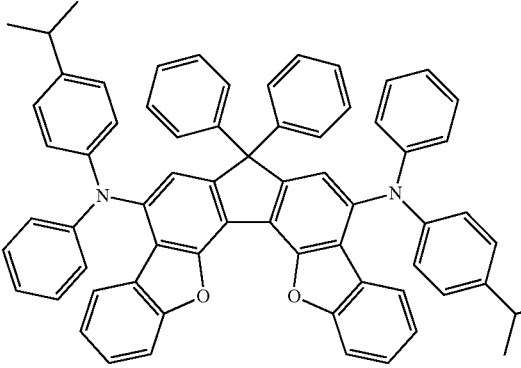 |
| 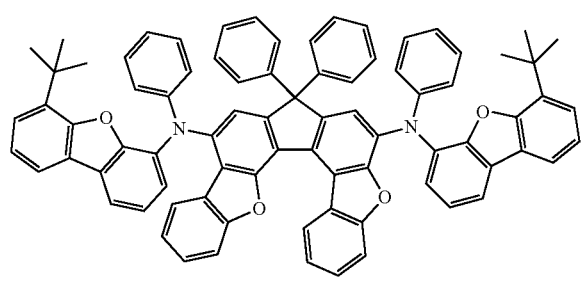 | 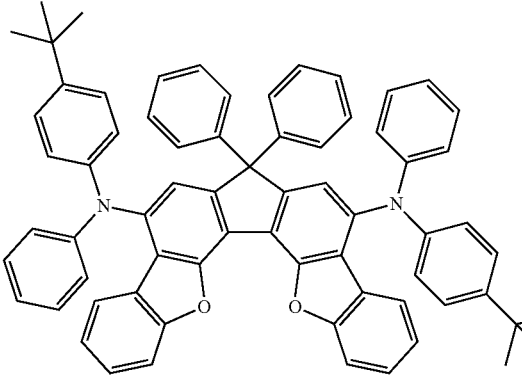 |
| 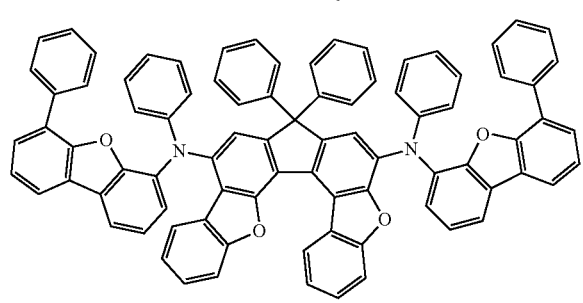 | |

1039
-continued
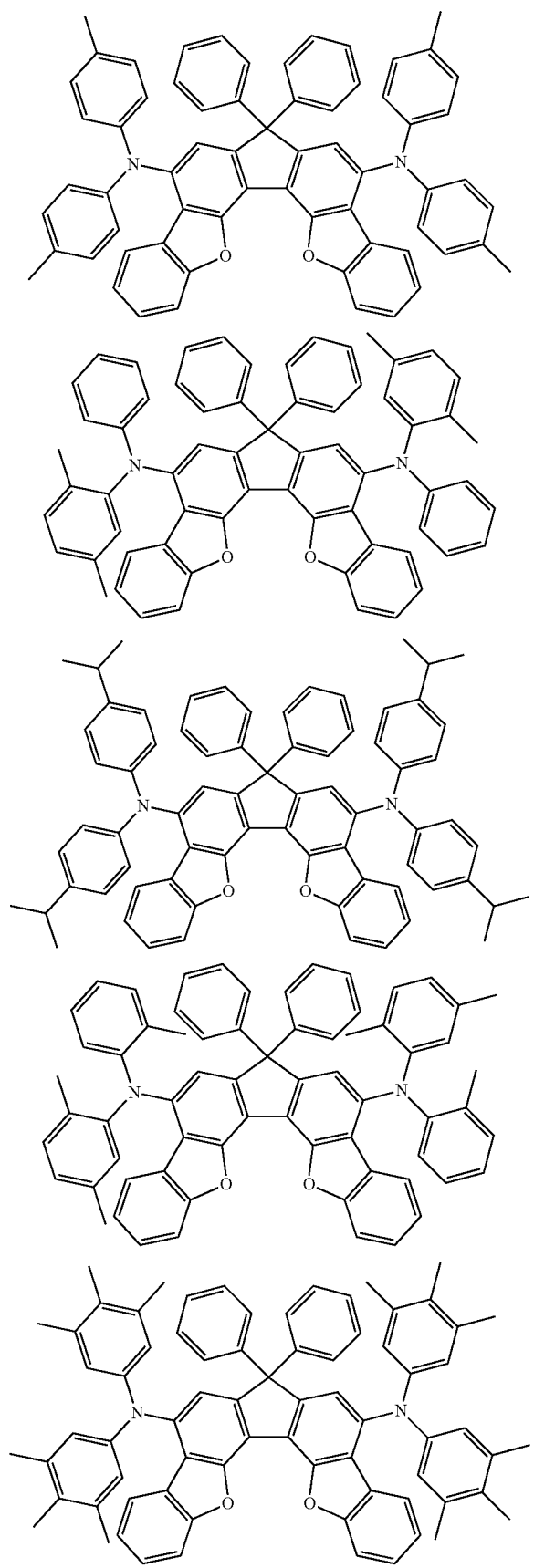
1040
-continued
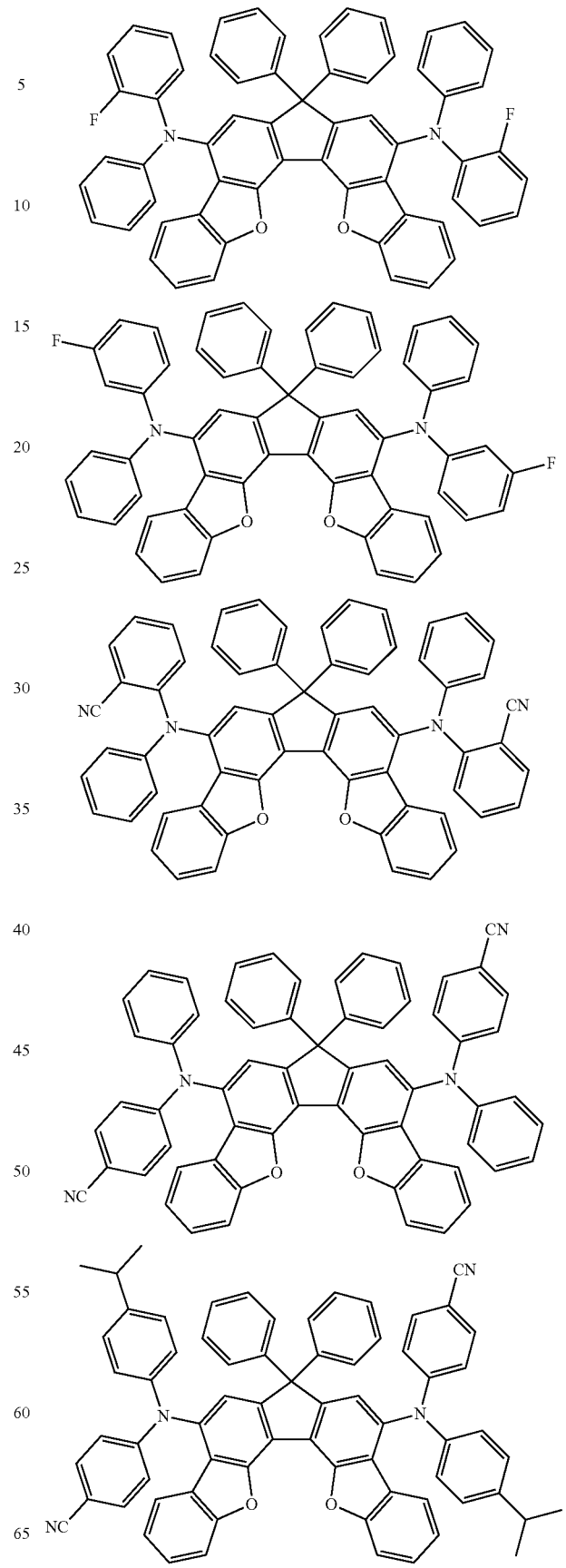

1041
-continued
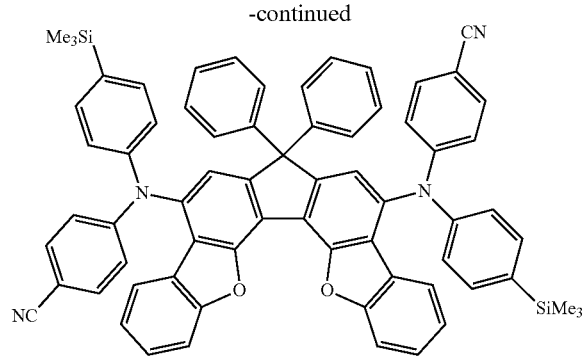
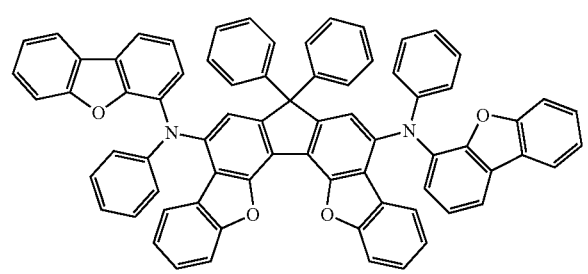
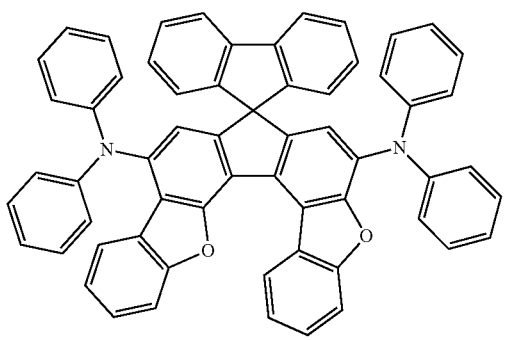
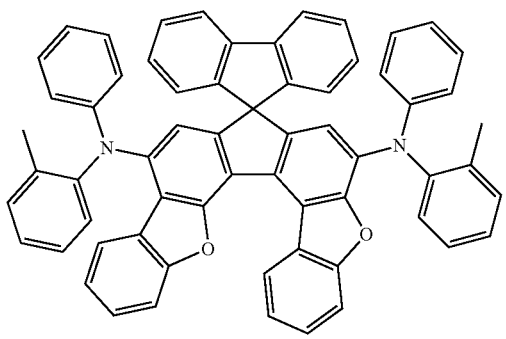
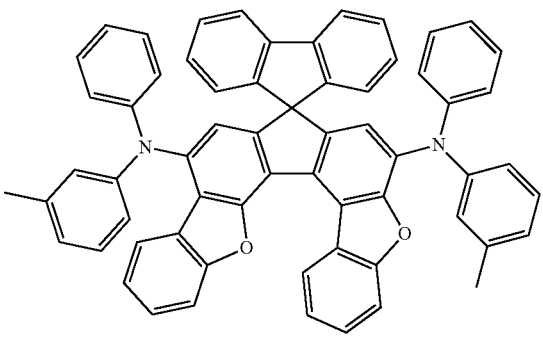
1042
-continued
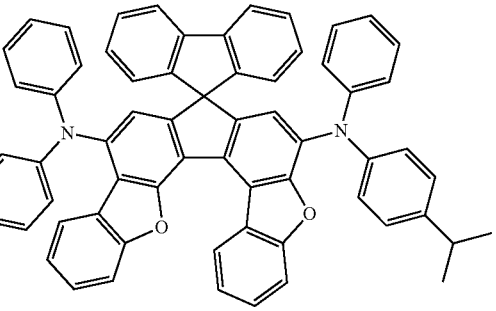
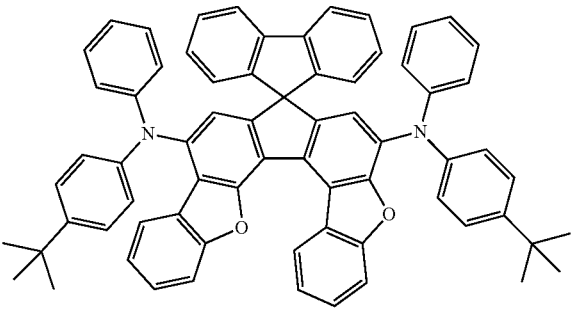
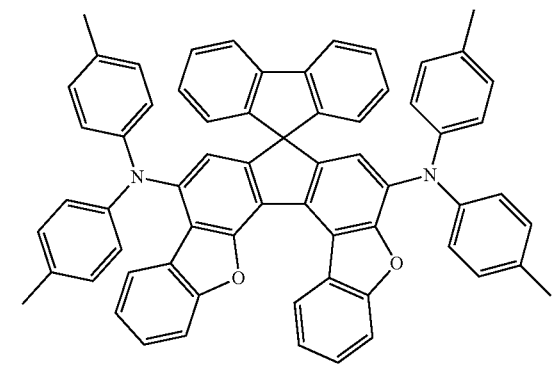
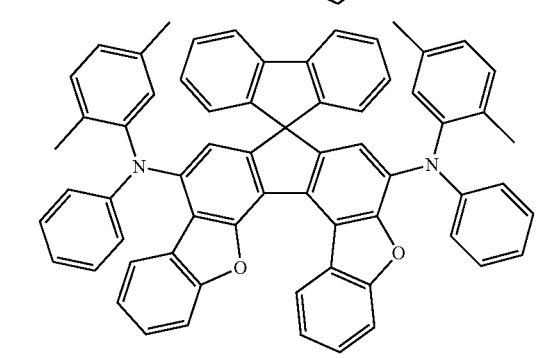
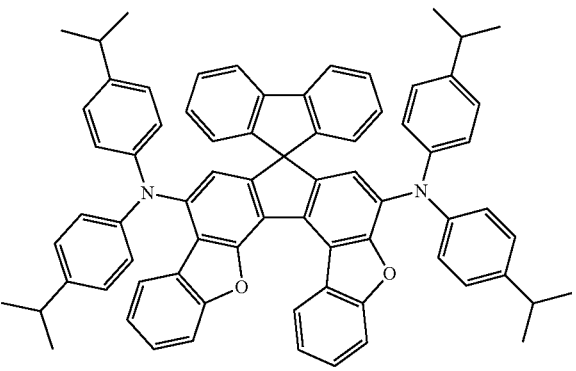

1043
-continued
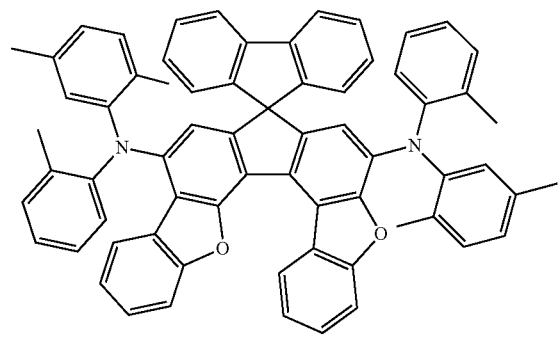
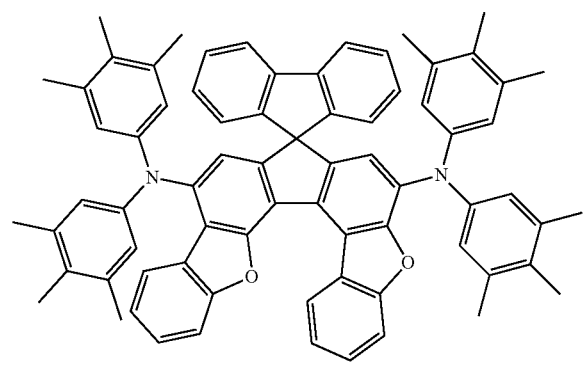
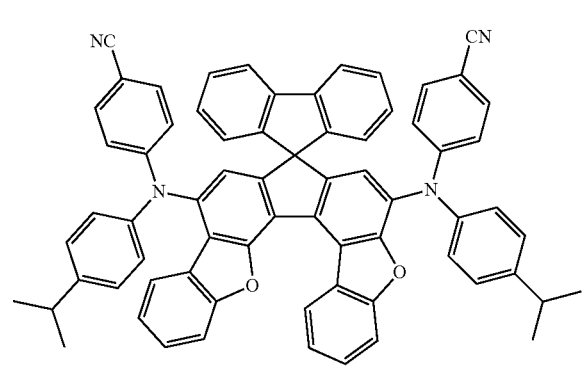
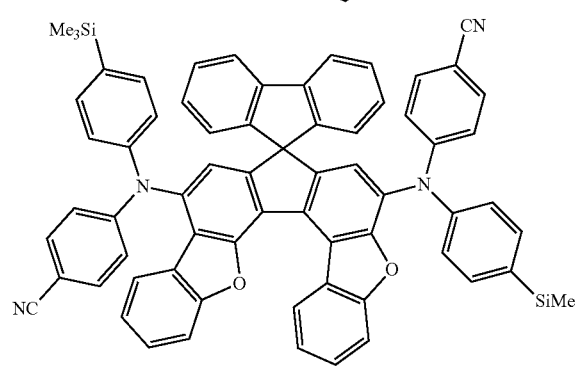
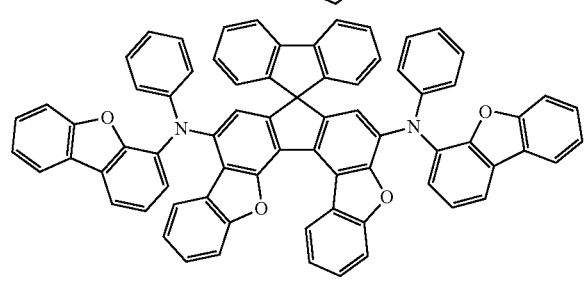
1044
-continued
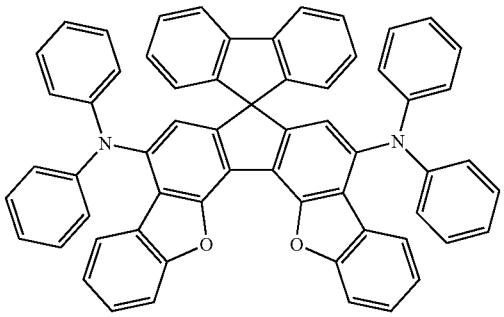
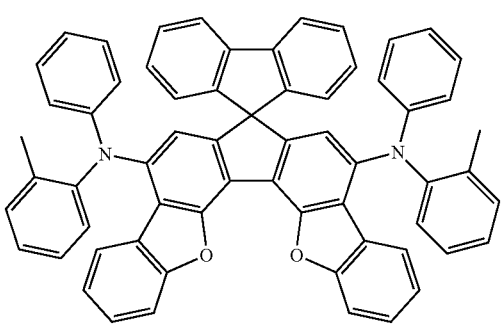
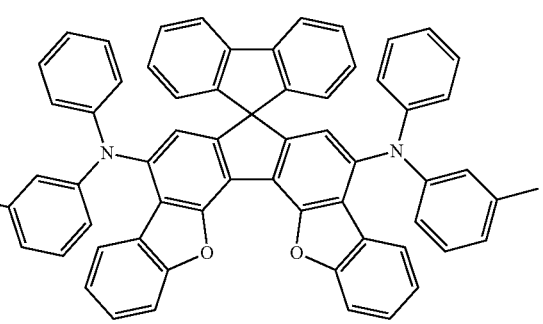
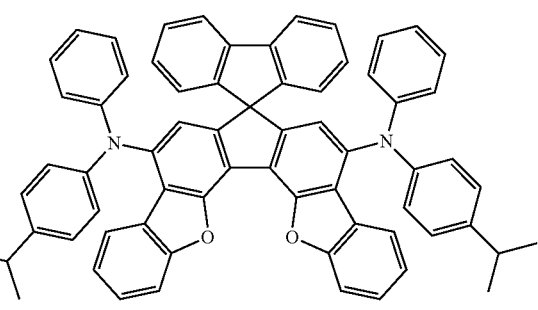
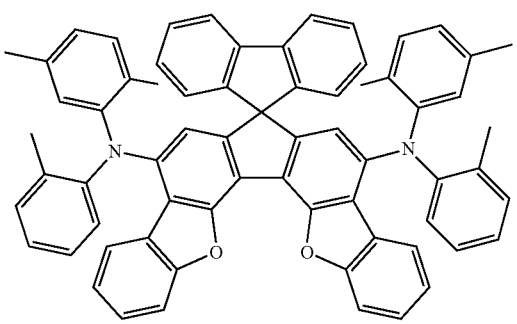

-continued

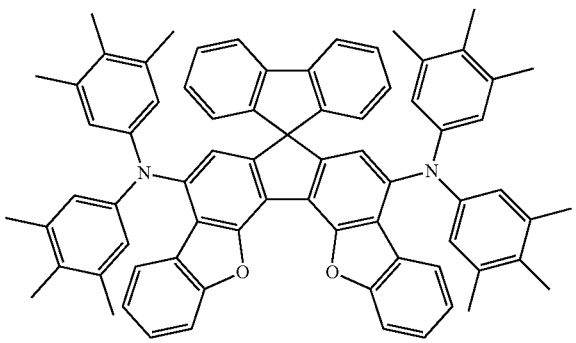

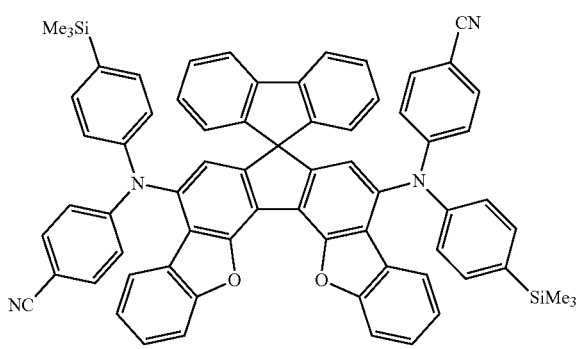

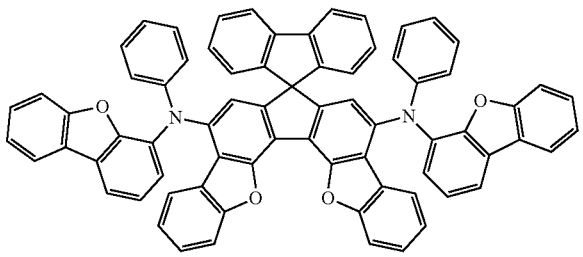

(Compound Represented by Formula (81))

The compound represented by the formula (81) is explained below.

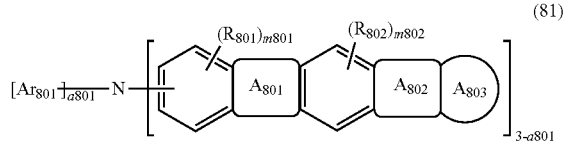 (81)

 (82)

 (83)

wherein, in the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when these are 2, plural $R_{801}$s or $R_{802}$s may be the same or different;

a801 is an integer of 0 to 2; when a801 is 0 or 1, the structure in the parenthese indicated by "3-a801" may be the same or different from each other; when a801 is 2, $Ar_{801}$s may be the same or different from each other.

In one embodiment, $Ar_{801}$ is a substituted or unsubstituted aryl group having 6 to 50 ring carbon atoms.

In one embodiment, $A_{803}$ ring is a substituted or unsubstituted aromatic hydrocarbon ring having 6 to 50 ring carbon atoms, and it is a substituted or unsubstituted benzene ring, a substituted or unsubstituted naphthalene ring, or a substituted or unsubstituted anthracene ring, for example.

In one embodiment, $R_{803}$ and $R_{804}$ are independently a substituted or unsubstituted alkyl group having 1 to 50 carbon atoms.

In one embodiment, a801 is 1.

As specific example of the compound represented by the formula (81), the following compounds can be given, for example.

1047
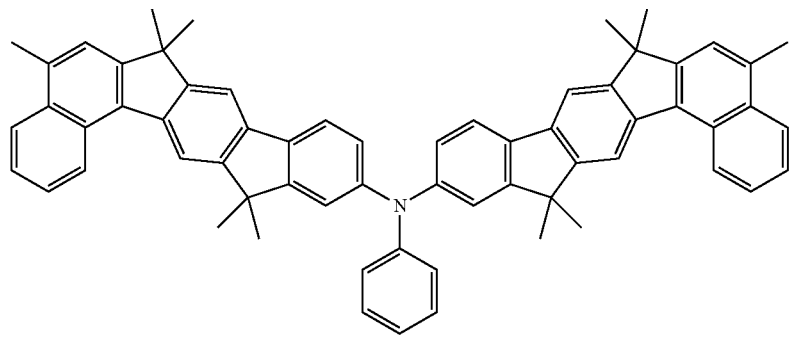
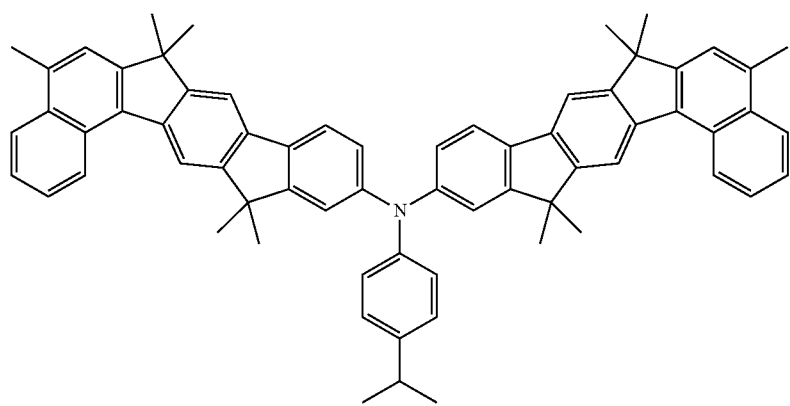
1048
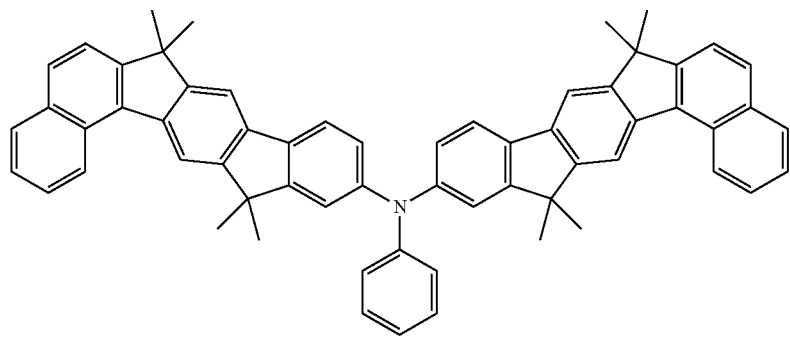
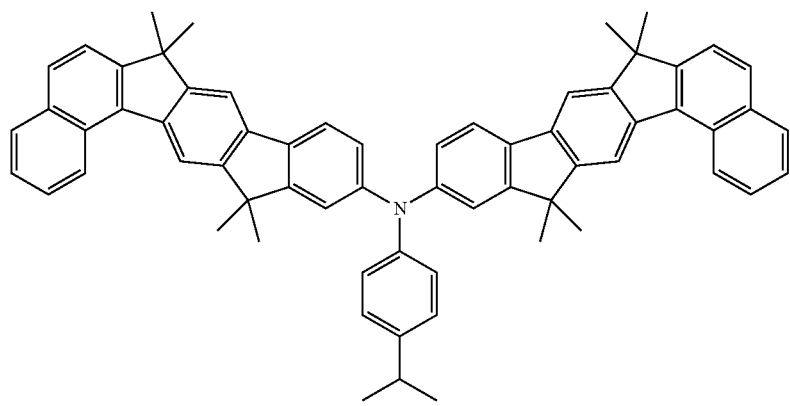

1049
-continued
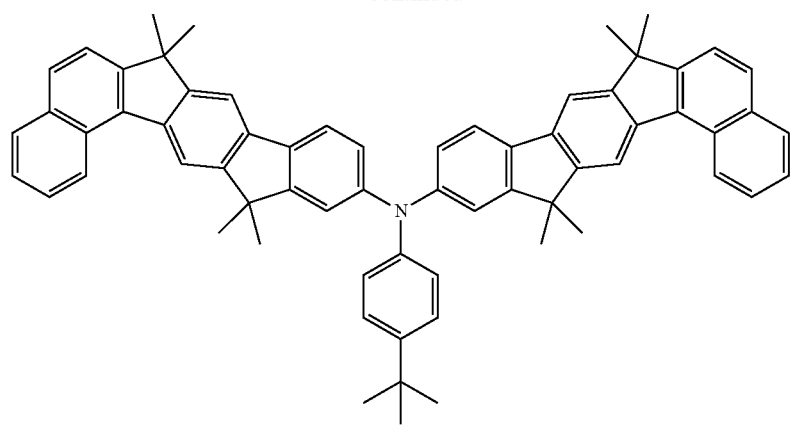
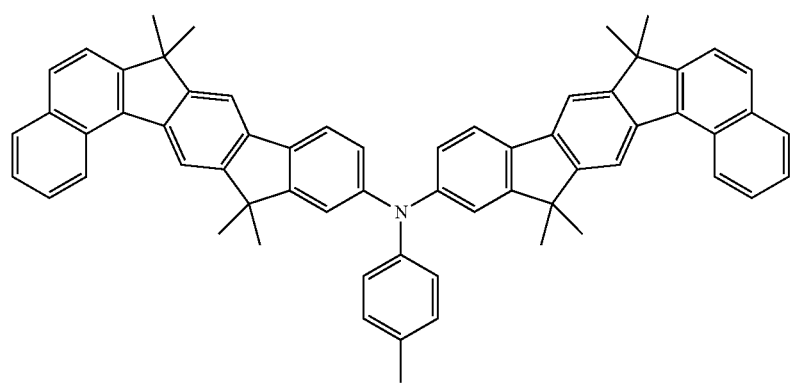
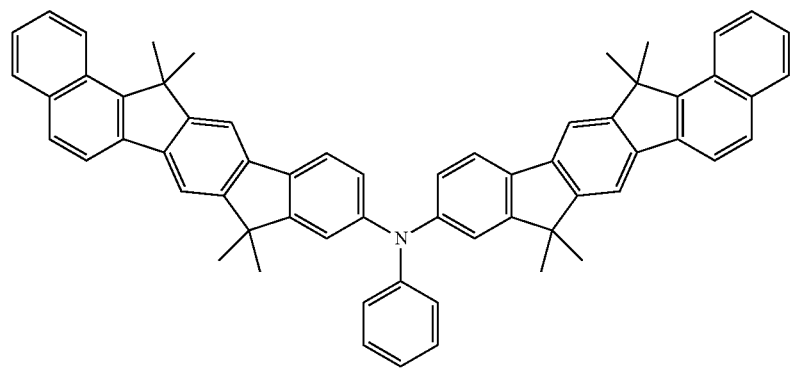
1050
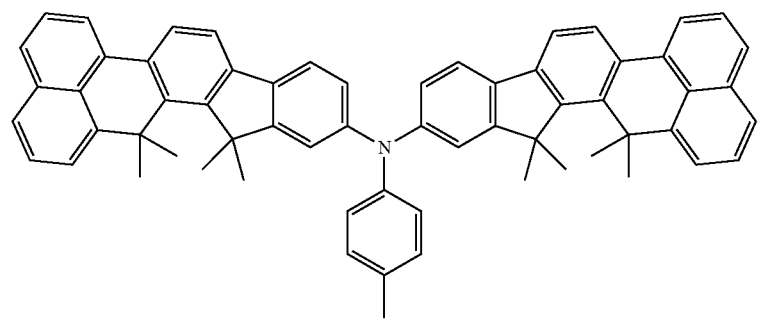

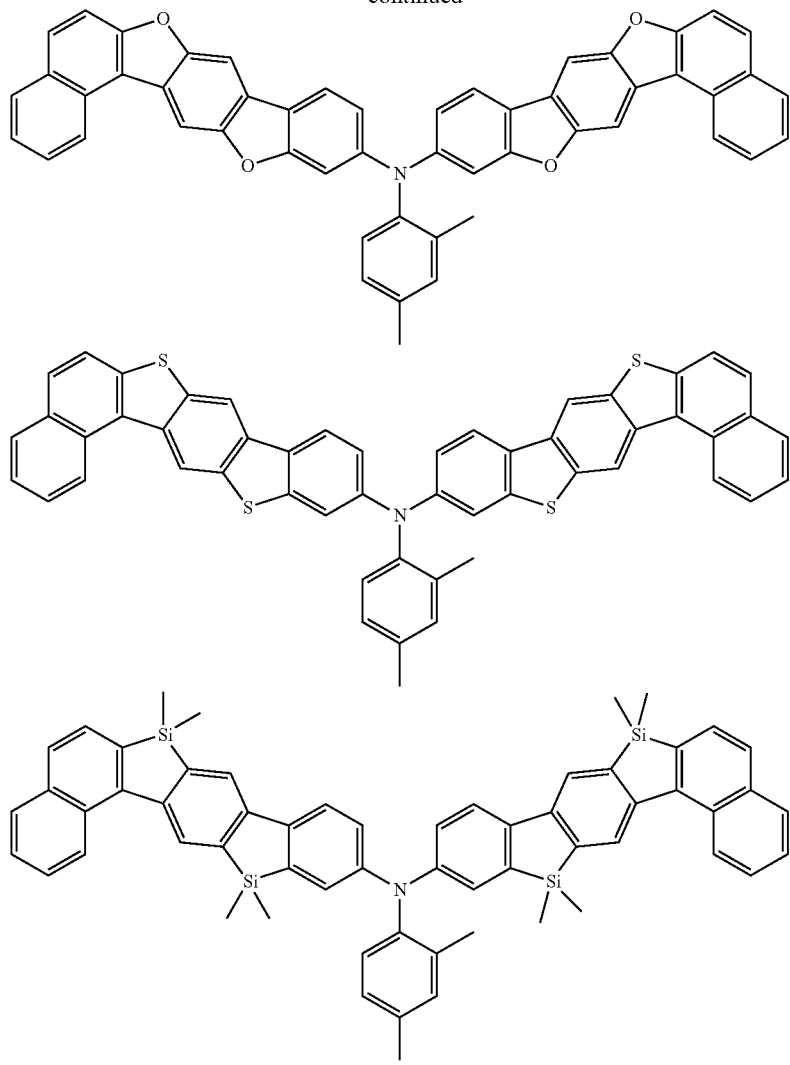

Specific examples of the above groups are as described in [Definition] of this specification.

In the organic EL device according to one aspect of the invention, known materials and device configurations may be applied as long as the device includes a cathode, an anode, and an emitting layer disposed between the cathode and the anode, and the emitting layer includes a compound represented by the following formula (1) and one or more compounds selected from the group consisting of compounds represented by formulas (11), (21), (31), (41), (51), (61), (71) and (81) as described above, and as long as the effect of the invention is not impaired.

A content of the compound represented by the formula (1) in the emitting layer is preferably 80 mass % or more and 99 mass % or less based on the total mass of the emitting layer.

A content of the one or more compounds selected from the group consisting of compounds represented by formulas (11), (21), (31), (41), (51), (61), (71) and (81) is preferably 1 mass % or more and 20 mass % or less based on a total mass of the emitting layer.

One embodiment of the organic EL device preferably has the hole-transporting layer between the anode and the emitting layer.

One embodiment of the organic EL device preferably has the electron-transporting layer between the cathode and the emitting layer.

Specific examples of a typified device configuration of the organic EL device of the invention include structures such as
(1) an anode/an emitting layer/a cathode,
(2) an anode/a hole-injecting layer/an emitting layer/a cathode,
(3) an anode/an emitting layer/an electron-injecting-transporting layer/a cathode,
(4) an anode/a hole-injecting layer/an emitting layer/an electron-injecting-transporting layer/a cathode,
(5) an anode/an organic semiconductor layer/an emitting layer/a cathode,
(6) an anode/an organic semiconductor layer/an electron barrier layer/an emitting layer/a cathode,
(7) an anode/an organic semiconductor layer/an emitting layer/an adhesion improving layer/a cathode,
(8) an anode/a hole-injecting-transporting layer/an emitting layer/an electron-injecting-transporting layer/a cathode,
(9) an anode/an insulating layer/an emitting layer/an insulating layer/a cathode,
(10) an anode/an inorganic semiconductor layer/an insulating layer/an emitting layer/an insulating layer/a cathode,

(11) an anode/an organic semiconductor layer/an insulating layer/an emitting layer/an insulating layer/a cathode,
(12) an anode/an insulating layer/a hole-injecting-transporting layer/an emitting layer/an insulating layer/a cathode, and
(13) an anode/an insulating layer/a hole-injecting-transporting layer/an emitting layer/an electron-injecting-transporting layer/a cathode.

Among the above-described structures, a configuration of (8) is preferably used, but the configuration is not limited thereto.

In this specification, the term "hole-injecting-transporting layer" herein means "at least one of the hole-injecting layer and the hole-transporting layer", and the term "electron-injecting-transporting layer" herein means "at least one of the electron-injecting layer and the electron-transporting layer".

Hereinbelow, an explanation will be made on elements and materials other than the above-mentioned compound constituting each layer that can be used in the organic EL device according to one aspect of the invention.

(Substrate)

The substrate is used as a supporting body of the emitting device. As the substrate, glass, quarts, plastic or the like can be used. Further, a flexible substrate may be used. The flexible substrate means a substrate that can be bent. For example, a plastic substrate made of polycarbonate or vinyl polychloride or the like can be given.

(Anode)

In an anode formed on a substrate, it is preferable to use a metal having a large work function (specifically, 4.0 eV or more), an alloy, an electric conductive compound, a mixture of these or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, or the like can be given. In addition, gold (Au), platinum (Pt) or a nitride of a metal material (e.g. titanium nitride) or the like can be given.

(Hole-Injecting Layer)

The hole-injecting layer is a layer containing a substance having a high hole-injecting property. As a substance having a high hole-injecting property, a substance selected from molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (oligomer, dendrimer, polymer, etc.) or the like can also be used (Hole-Transporting Layer)

The hole-transporting layer is a layer containing a substance having a high hole-transporting property. For the hole-transporting layer, aromatic amine compounds, carbazole derivatives, anthracene derivatives and the like can be used. Polymer compounds such as poly (N-vinylcarbazole) (abbreviation: PVK) and poly(4-vinyltriphenylamine) (abbreviation: PVTPA) can also be used. However, any substance other than these may be used as long as it is a substance having a higher transporting property for holes than electrons. Note that the layer containing a substance having a high hole-transporting property is not limited to a single layer, but may be a stacked body of two or more layers made of the above substances.

(Guest Material of the Emitting Layer)

The emitting layer is a layer that comprises a substance having high luminous property, and various materials can be used. For example, as the substance having high luminous property, a fluorescent compound that emits fluorescent light or a phosphorescent compound that emits phosphorescent light can be used. The fluorescent compound is a compound capable of emitting light from a singlet excited state and the phosphorescent compound is a compound capable of emitting light from a triplet excited state.

As a blue fluorescent material that can be used for the emitting layer, pyrene derivatives, styrylamine derivatives, chrysene derivatives, fluoranthene derivatives, fluorene derivatives, diamine derivatives, triarylamine derivatives and the like can be used. An aromatic amine derivative or the like can be used as a green fluorescent light-emitting material that can be used in the emitting layer. As a red fluorescent material which can be used in emitting layer, a tetracene derivative, a diamine derivative or the like can be used.

Metal complexes such as iridium complexes, osmium complexes, platinum complexes and the like are used as the blue phosphorescent material that can be used in the emitting layer. An iridium complex or the like is used as a green phosphorescent material that can be used in the emitting layer. Metal complexes such as iridium complexes, platinum complexes, terbium complexes, europium complexes and the like are used as red phosphorescent materials that can be used in the emitting layer.

(Host Material of Emitting Layer)

The emitting layer may have a structure in which the substance having high luminescent property (guest material) described above is dispersed in another substance (host material). Various materials can be used as substances for dispersing substances with high luminescent properties, and it is preferable to use a material having a high lowest unoccupied molecular orbital level (LUMO level) and a low highest occupied molecular orbital level (HOMO level), rather than a material having a high luminous property.

As a substance (host material) for dispersing a substance having a high luminous property, 1) a metal complex such as an aluminum complex, a beryllium complex or a zinc complex, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative or a chrysene derivative, and 4) an aromatic amine compound such as a triarylamine derivative or a fused polycyclic aromatic amine derivative are used.

(Electron-Transporting Layer)

The electron-transporting layer is a layer containing a substance having a high electron-transporting property. For the electron-transporting layer, 1) a metal complex such as an aluminum complex, a beryllium complex, or a zinc complex, 2) a heteroaromatic compound such as an imidazole derivative, a benzimidazole derivative, an azine derivative, a carbazole derivative or a phenanthroline derivative, and 3) a polymer compound can be used.

(Electron-Injecting Layer)

The electron-injection layer is a layer containing a substance having a high electron-injection property. For the electron-injection layer, alkali metals, alkaline earth metals or a compound thereof such as lithium (Li), ytterbium (Yb), lithium fluoride (LiF), cesium fluoride (CsF), calcium fluoride ($CaF_2$), metal complex compound such as 8-quinolinolato lithium (Liq), lithium oxide (LiOx) or the like can be used.

(Cathode)

It is preferable to use a metal, an alloy, an electrically conductive compound, a mixture thereof, or the like having a small work function (specifically, 3.8 eV or less) for the cathode. Specific examples of such cathode material include elements belonging to Group 1 or Group 2 of the periodic table of elements, that is, alkali metals such as lithium ($L_1$) and cesium (Cs), alkaline earth metals such as magnesium (Mg), calcium (Ca), and strontium (Sr), an alloy containing these metals (for example, MgAg and AlLi), a rare earth metal such as europium (Eu) and ytterbium (Yb), and an alloy containing a rare earth metal.

In the organic EL device according to one aspect of the invention, the method for forming each layer is not particularly restricted. A conventionally known forming method such as a vacuum deposition method, a spin coating method or the like can be used. Each layer such as the emitting layer or the like can be formed by a vacuum deposition method, a molecular beam evaporation method (MBE method), or a known coating method such as a dipping method, a solution spin coating method, a casting method, a bar coating method, or the like, that uses a solution of a material forming each layer dissolved in a solvent.

In the organic EL device according to one aspect of the invention, the thickness of each layer is not particularly restricted. In general, in order to suppress occurrence of defects such as pinholes and to suppress the applied voltage and to improve luminous efficiency, the thickness is normally preferably in a range of several nm to 1 µm.

[Electronic Device]

The electronic device according to one aspect of the invention is characterized in that it is provided with the organic EL device according to one aspect of the invention.

Specific examples of the electronic device includes a display element such as an organic EL panel module; a display such as a TV, a mobile phone or a PC; and emitting devices such as lightings and lights for automobiles or the like.

EXAMPLES

Now, the invention will be explained in detail with reference to Examples and Comparative Examples. However, it should be understood that the invention be not restricted at all by these Examples.

Synthesis Example 1 [Synthesis of Compound BH-1]

(Synthesis of Intermediate 1)

Under argon atmosphere, 75 mL of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 6.4 g (52.5 mmol) of phenylboronic acid, and 1.2 g (1.00 mmol) of $Pd[PPh_3]_4$, and the mixture was refluxed and stirred with heat for 10 hours.

After completion of the reaction, the reaction solution was cooled to room temperature. The sample of the reaction mixture was transferred to a separation funnel and extracted with dichloromethane. The organic phase was dried over $MgSO_4$, followed by filtration and concentration. The concentrated residue was purified by silica gel column chromatography to obtain 10.9 g of white solid. The obtained compound was subjected to FD-MS analysis, and it was identified as Intermediate 1 below (yield: 83%).

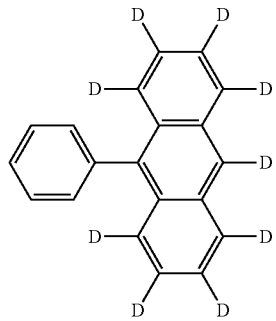

Intermediate 1

(Synthesis of Intermediate 2)

A solution of 5.3 g (20.0 mmol) of Intermediate 1 dissolved in 120 mL of dichloromethane was dropwise added at room temperature to a solution of 3.2 g (20.0 mmol) of bromine dissolved in 12 mL of dichloromethane, followed by stirring for one hour.

After completion of the reaction, the sample was transferred to a separation funnel, and washed with a 2M $Na_2S_2O_3$ aqueous solution. Subsequently, the organic phase was washed with 10% $Na_2CO_3$, and then with water, and the separated organic phase was dried over $MgSO_4$, followed by filtration and concentration.

The concentrated residue was suspended in 100 mL of methanol, and the precipitated crystals were collected to obtain 6.5 g of white solid. The obtained compound was subjected to FD-MS analysis, and was identified as Intermediate 2 below (yield: 95%).

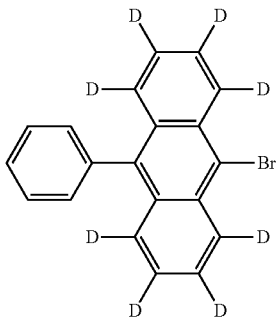

Intermediate 2

(Synthesis of Compound BH-1)

Under argon atmosphere, 7.5 mL of toluene, 7.5 mL of dimethoxyethane, and 7.5 mL (15.0 mmol) of a 2M $Na_2CO_3$ aqueous solution were added to 1.7 g (5.0 mmol) of Intermediate 2, 1.4 g (5.3 mmol) of benzo[b]naphtho[2,3-d]furan-2-boronic acid, and 0.1 g (0.1 mmol) of $Pd[PPh_3]_4$, and refluxed and stirred with heat for 10 hours.

After completion of the reaction, the reaction solution was cooled to room temperature, and the sample was transferred to a separation funnel and extracted with dichloromethane. The organic phase was dried over $MgSO_4$, followed by filtration and concentration. The concentrated residue was purified by silica gel column chromatography to obtain 1.7 g of white solid. The obtained compound was subjected to FD-MS analysis, and was identified as Compound BH-1 below (yield: 70%).

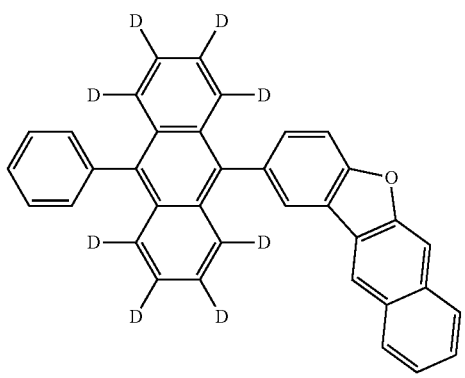

BH-1

Synthesis Example 2 [Synthesis of Compound BH-2]

(Synthesis of Intermediate 3)

Under argon atmosphere, 75 mL of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 9.0 g (52.5 mmol) of 1-naphthalene boronic acid, and 1.2 g (1.00 mmol) of $Pd[PPh_3]_4$, and the reaction mixture was refluxed and stirred with heat for 10 hours.

After completion of the reaction, the reaction solution was cooled to room temperature, and the sample was transferred to a separation funnel and extracted with dichloromethane. The organic phase was dried over $MgSO_4$, followed by filtration and concentration. The concentrated residue was purified by silica gel column chromatography to obtain 13.3 g of white solid. The obtained compound was subjected to FD-MS analysis, and identified as Intermediate 3 below (yield: 85%).

Intermediate 3

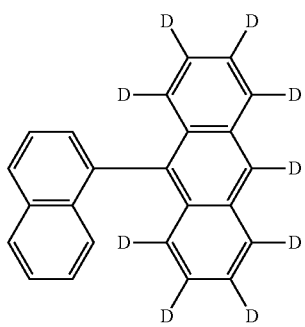

(Synthesis of Intermediate 4)

A solution of 6.3 g (20.0 mmol) of Intermediate 3 dissolved in 120 mL of dichloromethane was dropwise added at room temperature to a solution of 3.2 g (20.0 mmol) of bromine dissolved in 12 mL of dichloromethane, and stirred for one hour.

After completion of the reaction, the sample was transferred to a separation funnel, and washed with a 2M $Na_2S_2O_3$ aqueous solution. Subsequently, the organic phase was washed with 10% $Na_2CO_3$, and then, washed with water three times. The organic phase was dried over $MgSO_4$, followed by filtration and concentration.

The concentrated residue was suspended in 100 mL of methanol, and precipitated crystals were collected to obtain 7.5 g of white solid. The obtained compound was subjected to FD-MS analysis, and identified as Intermediate 4 below (yield: 96%).

Intermediate 4

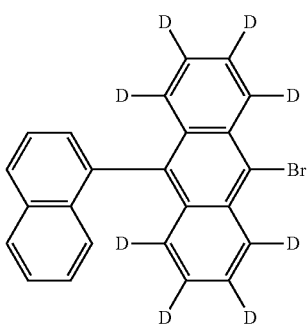

(Synthesis of Compound BH-2)

Under argon atmosphere, 7.5 mL of toluene, 7.5 mL of dimethoxyethane, and 7.5 mL (15.0 mmol) of a 2M $Na_2CO_3$ aqueous solution were added to 2.0 g (5.0 mmol) of Intermediate 4, 1.4 g (5.3 mmol) of benzo[b]naphtho[2,3-d]furan-2-boronic acid, and 0.1 g (0.1 mmol) of $Pd[PPh_3]_4$, and the reaction mixture was refluxed and stirred with heat for 10 hours.

After completion of the reaction, the reaction solution was cooled to room temperature, and the sample was transferred to a separation funnel and extracted with dichloromethane. The organic phase was dried over $MgSO_4$, followed by filtration and concentration. The concentrated residue was purified by silica gel column chromatography to obtain 1.9 g of white solid. The obtained compound was subjected to FD-MS analysis, and identified as Compound BH-2 below (yield: 73%).

BH-2

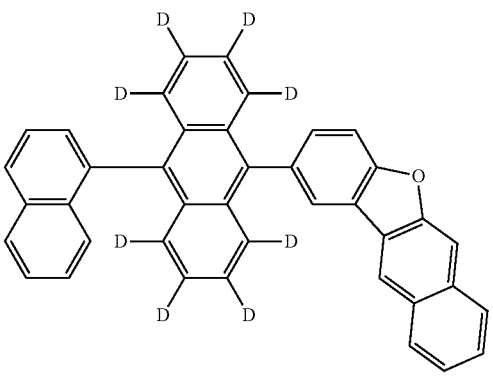

Synthesis Example 3

(Synthesis of Compound BH-3)

The same reaction was conducted in the same manner as in Synthesis Example 1 except that 1.4 g (5.3 mmol) of benzo[b]naphtho[2,3-d]furan-1-boronic acid was used in place of benzo[b]naphtho[2,3-d]furan-2-boronic acid, to obtain 1.4 g of white crystals. The obtained compound was subjected to FD-MS analysis, and identified as Compound BH-3 below (yield: 57%).

BH-3

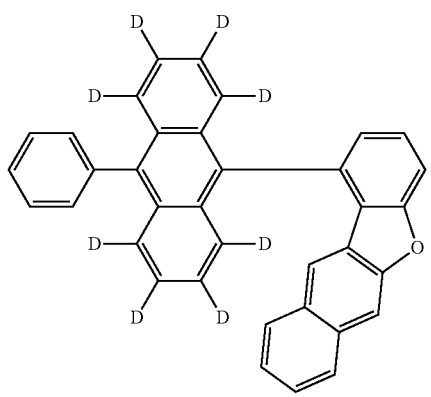

Synthesis Example 4

(Synthesis of Compound BH-4)

The same reaction was conducted in the same manner as in Synthesis Example 1 except that 1.4 g (5.3 mmol) of benzo[b]naphtho[2,3-d]furan-3-boronic acid was used in place of benzo[b]naphtho[2,3-d]furan-2-boronic acid, to obtain 1.8 g of white crystals. The obtained compound was subjected to FD-MS analysis, and identified as Compound BH-4 below (yield: 74%).

BH-4

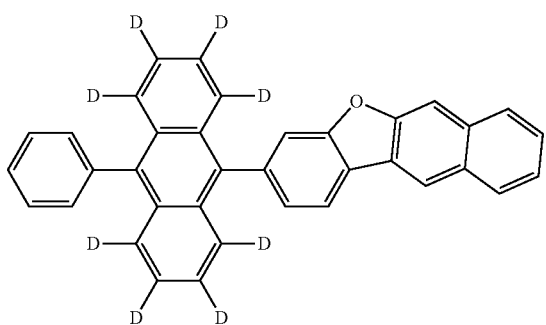

Synthesis Example 5

[Synthesis of Compound BH-5]
(Synthesis of Intermediate 5)

Under argon atmosphere, 75 mL of toluene, 75 mL of dimethoxyethane, and 75 mL (150.0 mmol) of a 2M $Na_2CO_3$ aqueous solution were added to 13.3 g (50.0 mmol) of 9-bromoanthracene-d9, 13.0 g (52.5 mmol) of 4-(1-naphthyl)phenylboronic acid, and 1.2 g (1.00 mmol) of Pd[PPh$_3$]$_4$, and the reaction mixture was refluxed and stirred with heat for 10 hours.

After completion of the reaction, the reaction solution was cooled to room temperature, and the sample was transferred to a separation funnel and extracted with dichloromethane. The organic phase was dried over MgSO$_4$, followed by filtration and concentration. The concentrated residue was purified by silica gel column chromatography to obtain 15.6 g of white solid. The obtained compound was subjected to FD-MS analysis, and identified as Intermediate 5 below (yield: 80%).

Intermediate 5

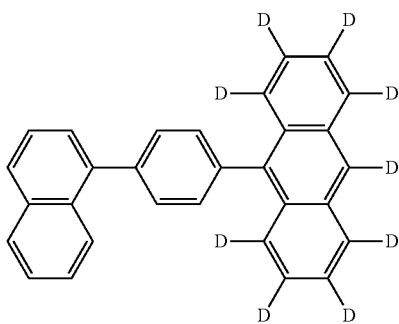

(Synthesis of Intermediate 6)

A solution of 7.8 g (20.0 mmol) of Intermediate 5 dissolved in 120 mL of dichloromethane was dropwise added at room temperature to a solution of 3.2 g (20.0 mmol) of bromine dissolved in 12 ml of dichloromethane, and the reaction mixture was stirred for one hour.

After completion of the reaction, the sample was transferred to a separation funnel, and washed with a 2M $Na_2S_2O_3$ aqueous solution. Subsequently, the organic phase was washed with 10% $Na_2CO_3$, and with water three times. The organic phase was dried over MgSO$_4$, followed by filtration and concentration.

The concentrated residue was suspended in 100 mL of methanol, and precipitated crystals were collected to obtain 8.6 g of white solid. The obtained compound was subjected to FD-MS analysis, and identified as Intermediate 6 below (yield: 92%).

Intermediate 6

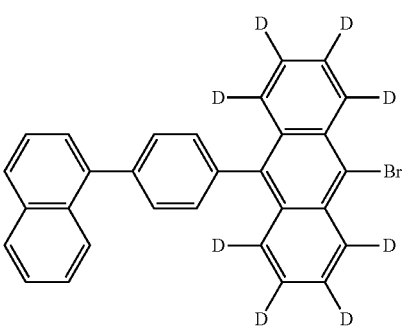

(Synthesis of Compound BH-5)

Under argon atmosphere, 7.5 mL of toluene, 7.5 mL of dimethoxyethane, and 7.5 mL (15.0 mmol) of a 2M $Na_2CO_3$ aqueous solution were added to 2.3 g (5.0 mmol) of Intermediate 6, 1.4 g (5.3 mmol) of benzo[b]naphtho[2,3-d]furan-2-boronic acid, and 0.1 g (0.1 mmol) of Pd[PPh$_3$]$_4$, and the reaction mixture was refluxed and stirred with heat for 10 hours.

After completion of the reaction, the reaction solution was cooled to room temperature, and the sample was transferred to a separation funnel, and extracted with dichloromethane.

The organic phase was dried over MgSO₄, followed by filtration and concentration. The concentrated residue was purified by silica gel column chromatography to obtain 2.1 g of white solid. The obtained compound was subjected to FD-MS analysis, and identified as Compound BH-5 below (yield: 68%).

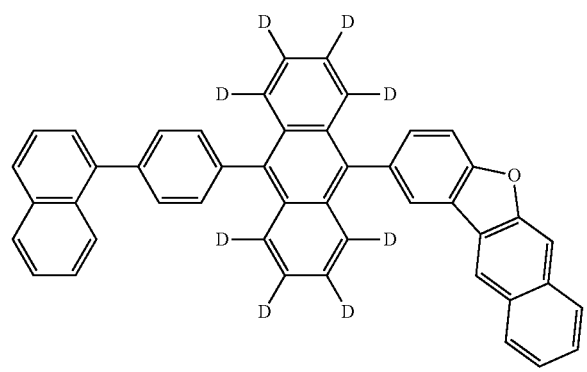

Synthesis Example 6

(Synthesis of Compound BH-6)

The reaction was conducted in the same manner as in Synthesis Example 1 except that 1.4 g (5.3 mmol) of benzo[b]naphtho[1,2-d]furan-10-boronic acid was used in place of benzo[b]naphtho[2,3-d]furan-2-boronic acid, to obtain 1.7 g of white crystals. The obtained compound was subjected to FD-MS analysis, and identified as Compound BH-6 below (yield: 71%).

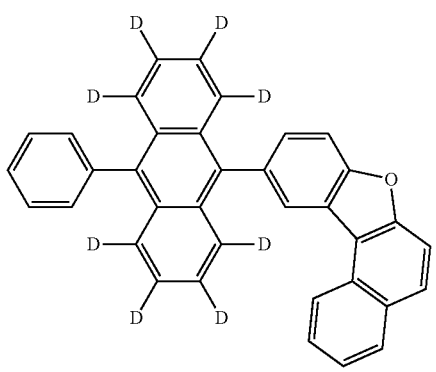

Synthesis Example 7

(Synthesis of Compound BH-7)

The reaction was conducted in the same manner as in Synthesis Example 1 except that 1.4 g (5.3 mmol) of benzo[b]naphtho[2,1-d]furan-8-boronic acid was used in place of benzo[b]naphtho[2,3-d]furan-2-boronic acid, to obtain 1.6 g of white crystals. The obtained compound was subjected to FD-MS analysis, and identified as Compound BH-7 below (yield: 65%).

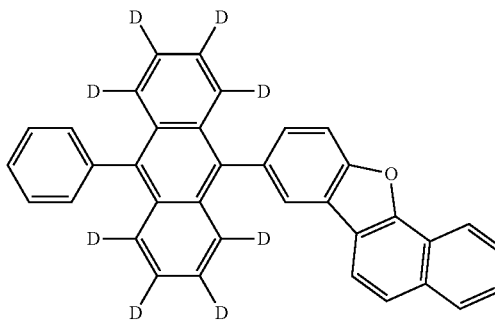

Synthesis Example 8

[Synthesis of Compound BH-8]
(Synthesis of Intermediate 7)

Under argon atmosphere, 75 ml of toluene, 75 mL of dimethoxyethane, and 75 mL (150.0 mmol) of a 2M Na₂CO₃ aqueous solution were added to 13.3 g (50.0 mmol) of 9-bromoanthracene-d9, 10.4 g (52.5 mmol) of 3-biphenyl-boronic acid, and 1.2 g (1.00 mmol) of Pd[PPh₃]₄, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over MgSO₄, followed by filtration and concentration. The concentrated residue was purified by silica gel column chromatography to obtain 13.6 g of white solid. The obtained compound was subjected to FD-MS analysis, and identified as Intermediate 7 below (yield: 80%).

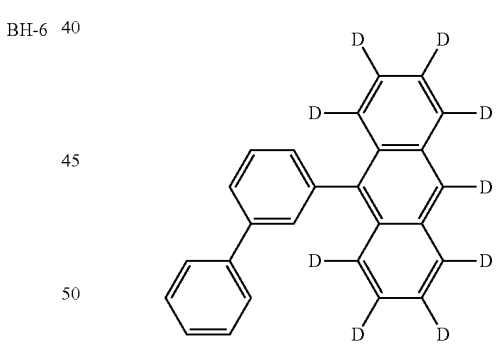

(Synthesis of Intermediate 8)

A solution of 6.8 g (20.0 mmol) of Intermediate 7 dissolved in 120 mL of dichloromethane was dropwise added to a solution of 3.2 g (20.0 mmol) of bromine dissolved in 12 mL of dichloromethane, and the reaction mixture was stirred for one hour.

After completion of the reaction, the sample was transferred to a separation funnel, and washed with a 2M Na₂S₂O₃ aqueous solution. Subsequently, the organic phase was washed with 10% Na₂CO₃, and then, with water three times. The organic phase was dried over MgSO₄, followed by filtration and concentration.

The concentrated residue was suspended in 100 mL of methanol, and precipitated crystals were collected to obtain 8.0 g of white solid. The obtained compound was subjected to FD-MS analysis, and identified as Intermediate 8 below (yield: 96%).

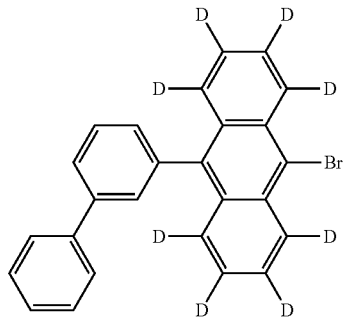

Intermediate 8

(Synthesis of Compound BH-8)

Under argon atmosphere, 7.5 mL of toluene, 7.5 mL of dimethoxyethane, and 7.5 mL (15.0 mmol) of a 2M $Na_2CO_3$ aqueous solution were added to 2.1 g (5.0 mmol) of Intermediate 8, 1.4 g (5.3 mmol) of benzo[b]naphtho[2,3-d]furan-1-boronic acid, and 0.1 g (0.1 mmol) of $Pd[PPh_3]_4$, and the reaction mixture was refluxed and stirred with heat for 10 hours.

After completion of the reaction, the reaction solution was cooled to room temperature, and the sample was transferred to a separation funnel, and extracted with dichloromethane. The organic phase was dried over $MgSO_4$, followed by filtration and concentration. The concentrated residue was purified by silica gel column chromatography to obtain 1.7 g of white solid. The obtained compound was subjected to FD-MS analysis, and identified as Compound BH-8 below (yield: 60%).

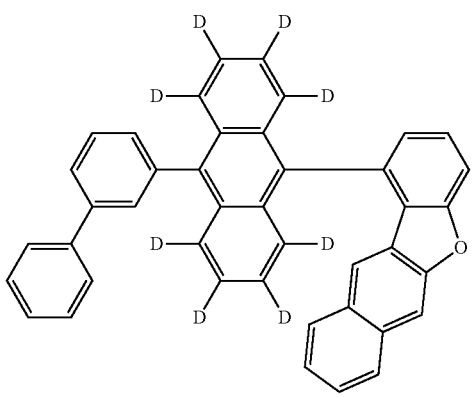

BH-8

Synthesis Example 9

(Synthesis of Compound BH-9)

The reaction was conducted in the same manner as in Synthesis Example 1 except that 1.4 g (5.3 mmol) of benzo[b]naphtho[2,1-d]furan-7-boronic acid was used in place of benzo[b]naphtho[2,3-d]furan-2-boronic acid, to obtain 1.6 g of white crystals. The obtained compound was subjected to FD-MS analysis, and identified as Compound BH-9 below (yield: 65%).

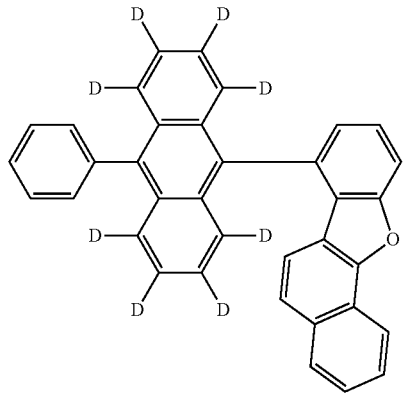

BH-9

Example 1

(Fabrication of Organic EL Device)

A glass substrate of 25 mm by 75 mm by 1.1 mm thick with an ITO transparent electrode (anode) (manufactured by GEOMATEC Co., Ltd.) was subjected to ultrasonic cleaning with isopropyl alcohol for 5 minutes, and then subjected to UV-ozone cleaning for 30 minutes. The thickness of the ITO was 130 nm.

The cleaned glass substrate with a transparent electrode was mounted in a substrate holder of a vacuum vapor deposition apparatus. First, the compound HI was deposited on the surface where the transparent electrode was formed so as to cover the transparent electrode, thereby to form a 5 nm-thick HI film was formed. This HI film serves as a hole-injecting layer.

Subsequent to the formation of the HI film, the compound HT-1 was deposited, whereby a 80 nm-thick HT-1 film was formed on the HI film. This HT-1 film serves as a hole-transporting layer (first hole-transporting layer).

Subsequent to the formation of the HT-1 film, the compound HT-2 was deposited, whereby a 10 nm-thick HT-2 film was formed on the HT-1 film. This HT-2 film serves as an electron blocking layer (second hole-transporting layer).

On the HT-2 film, compound BH-1 (host material) and compound BD-1 (dopant material) were co-deposited such that the amount ratio of BD-1 (mass ratio) became 4%, whereby a 25 nm-thick BH-1:BD-1 film was formed. The BH-1:BD-1 film serves as an emitting layer.

On the emitting layer, compound ET-1 was deposited, whereby a 10 nm-thick ET-1 film was formed. This ET-1 film serves as a hole barrier layer.

On the ET-1 film, compound ET-2 was deposited, whereby a 15 nm-thick ET-2 film was formed. This ET-2 film serves as an electron transporting layer. On this ET-2 film, LiF was deposited, whereby a 1 nm-thick LiF film. On this LiF film, metal Al was deposited, whereby a 80 nm-thick metal cathode was formed. By the above-mentioned procedures, an organic EL device was fabricated.

The resultant organic EL device has the following layer structure: ITO(130)/HI(5)/HT-1(80)/HT-2(10)/BH-1:BD-1 (25:4 mass %)/ET-1 (10)/ET-2(15)/LiF(1)/Al(80).

The numerical value in the parenthesis indicates the film thickness (unit: nm).

Materials used in Example 1 and the below-mentioned Examples and Comparative Examples are shown below.

1065
HI
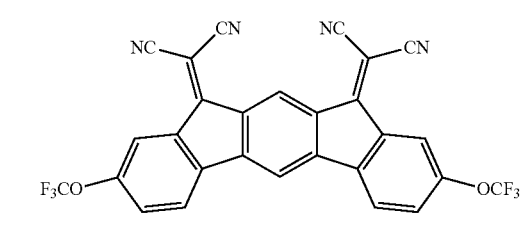
HT-1
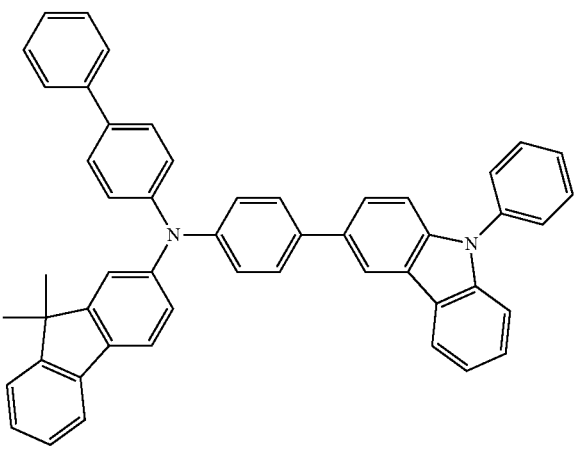
HT-2
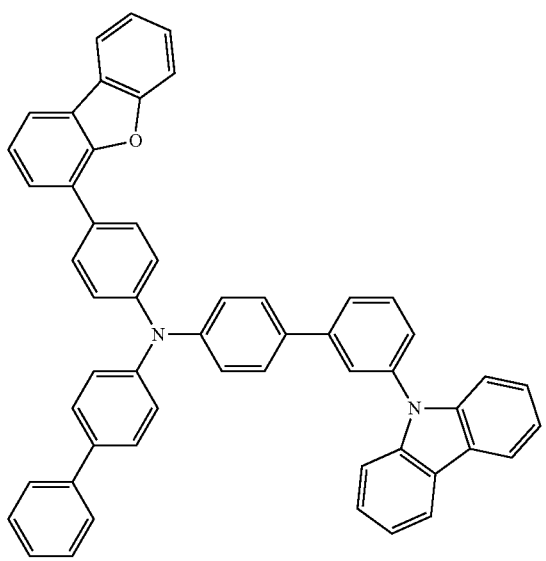
ET-1
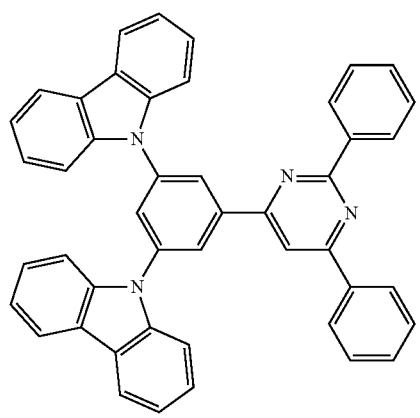
1066
-continued
ET-2
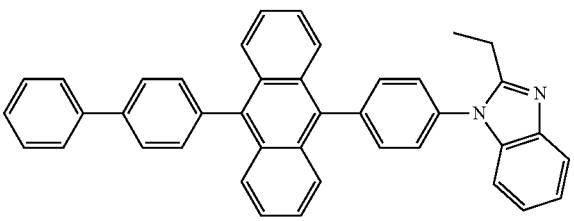
BH-1
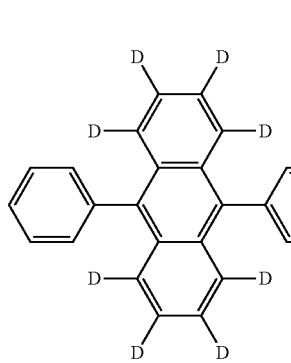
BH-1-a
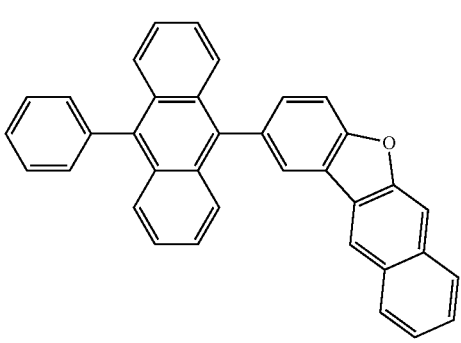
BH-2
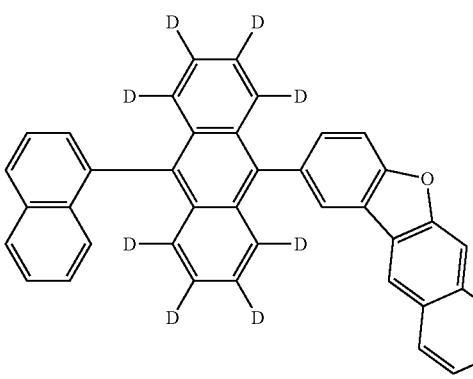

BH-2-a
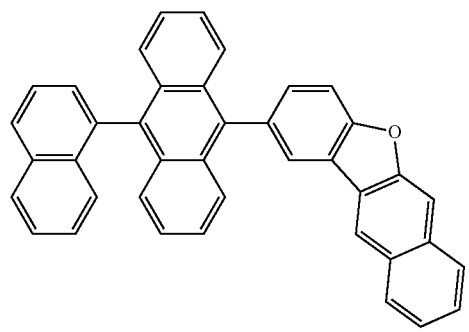
BH-4-a
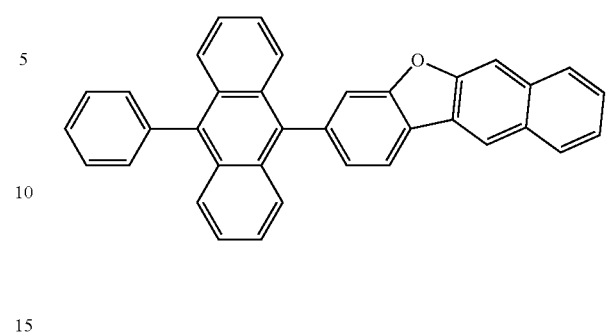
BH-3
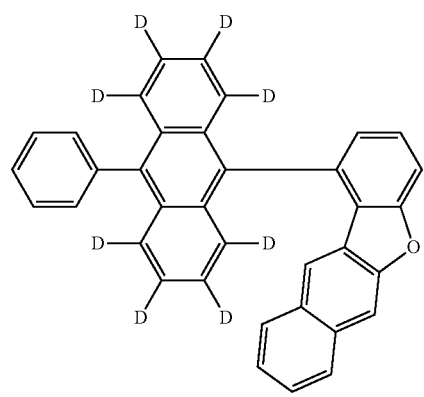
BH-5
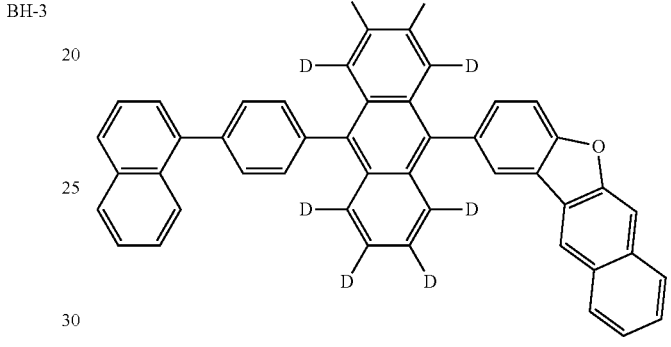
BH-3-a
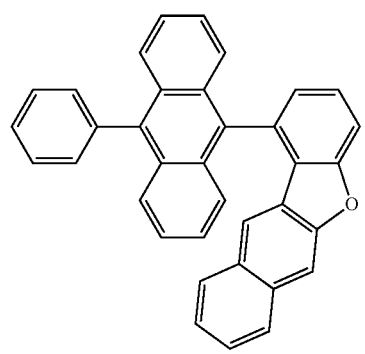
BH-5-a
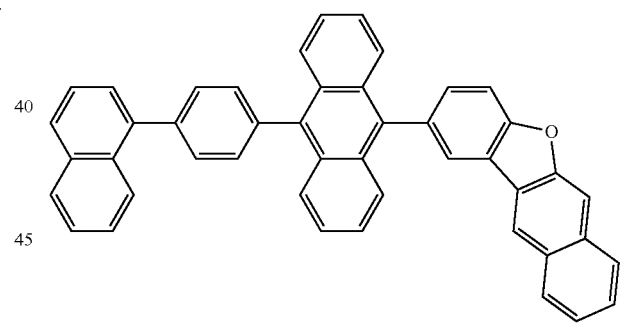
BH-4
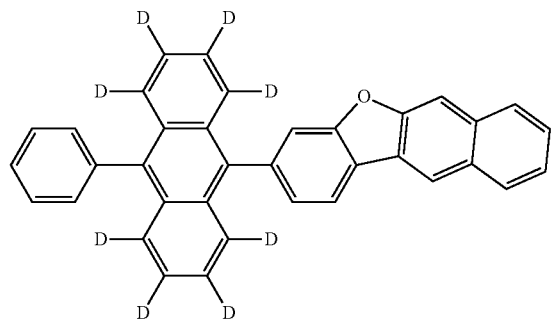
BH-6
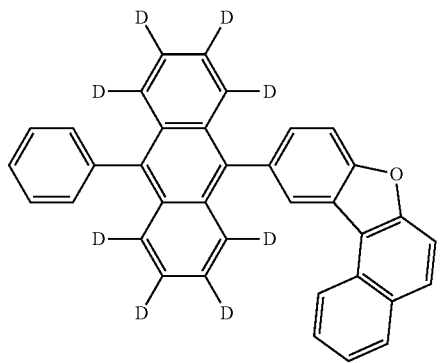

1069
-continued
BH-6-a
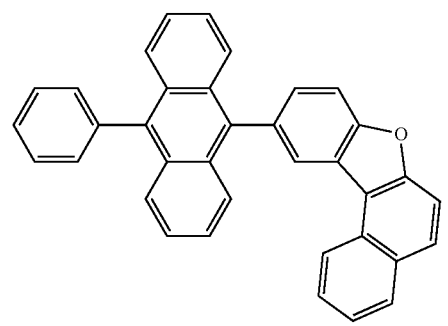
BH-7
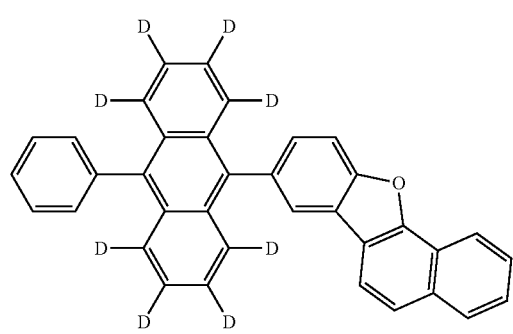
BH-7-a
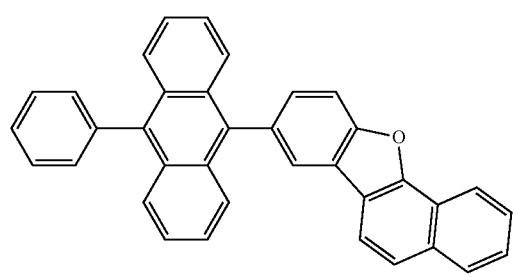
BH-8
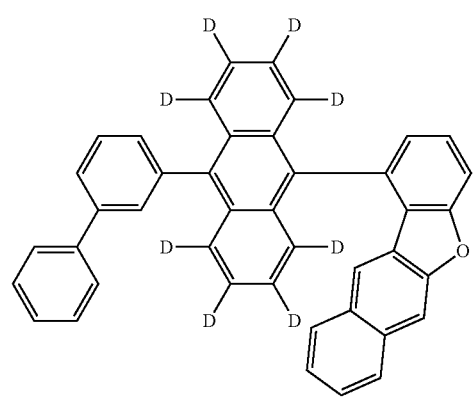
1070
-continued
BH-8-a
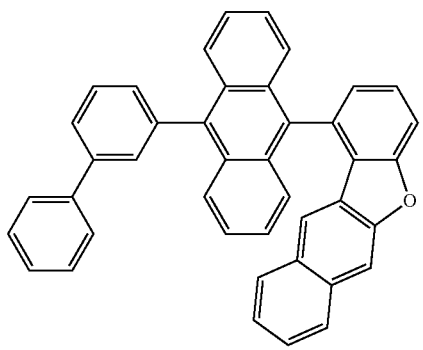
BH-9
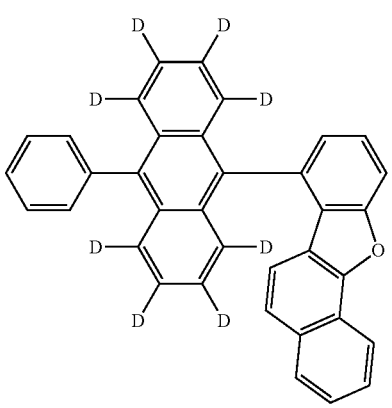
BH-9-a
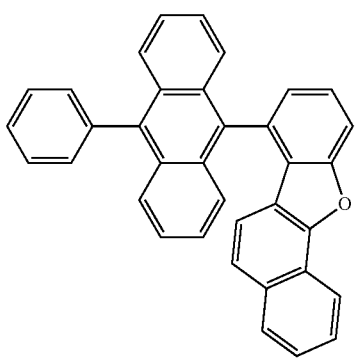
BD-1

BD-2
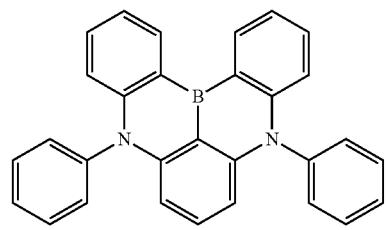
BD-3
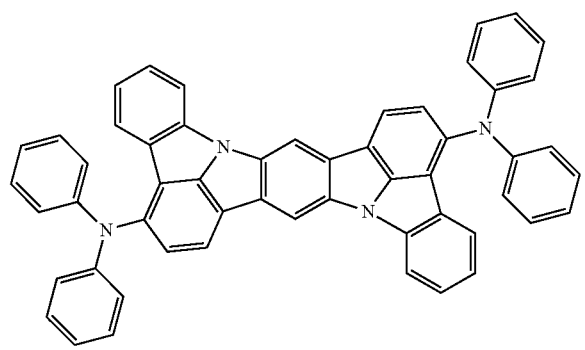
BD-4
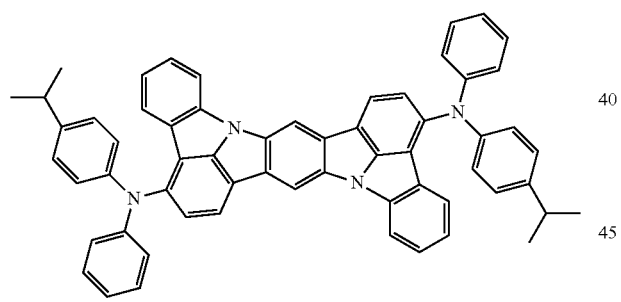
BD-5
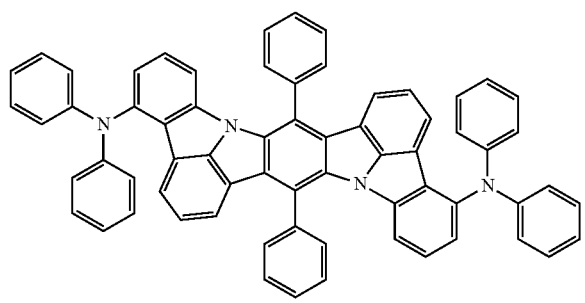
BD-6
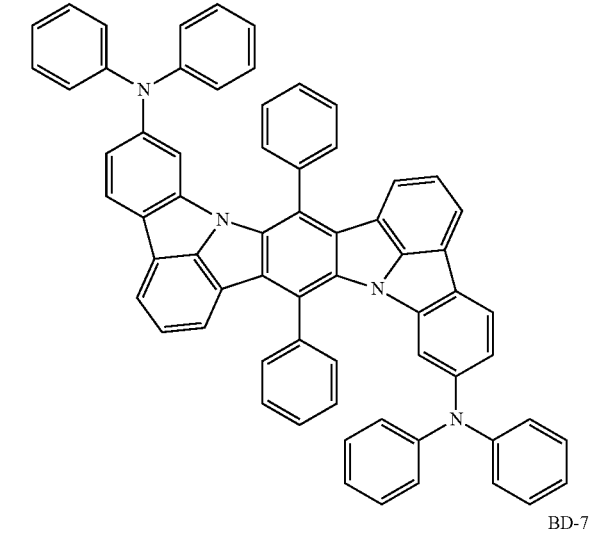
BD-7
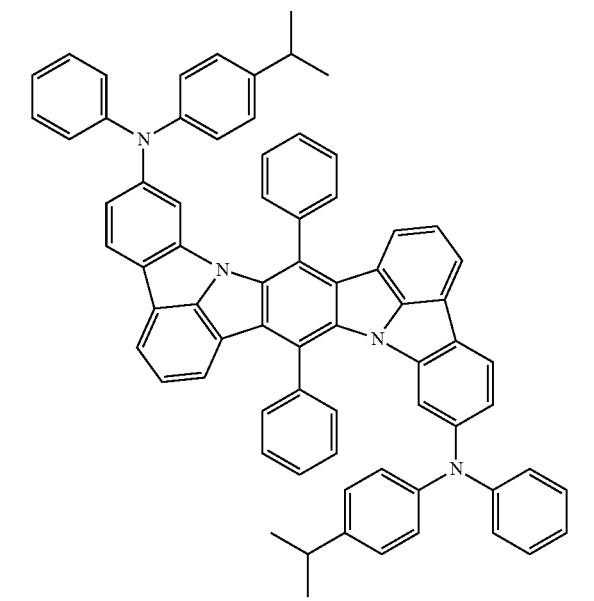
BD-8
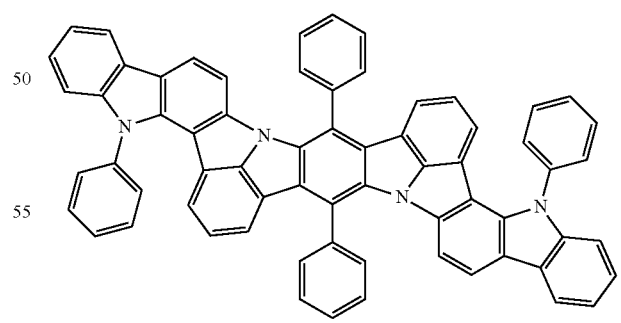
(Evaluation of Organic EL Device)
A voltage was applied to the resulting organic EL device such that the current density became 50 mA/cm², and the time taken until the luminance became 95% of the initial luminance (lifetime, LT95) were measured. The results are shown in Table 1.

Further, the CIE1931 chromaticity coordinates (CIEx and CIEy) of the resulting organic EL device at the time when a voltage was applied thereto such that the current density became 10 mA/cm$^2$, were determined from a spectral radiance spectrum measured by means of a spectral radiance meter CS-1000 (manufactured by Konica Minolta, Inc.). The results are shown in Table 1.

Comparative Example 1

The organic EL device was fabricated in the same manner as in Example 1 except that the compound indicated in the following table was used as the host material, and evaluated. The results are shown in Table 1.

TABLE 1

| | Emitting layer | | | | |
|---|---|---|---|---|---|
| | Host material | Dopant material | LT95(h) | Chromaticity CIEx | CIEy |
| Example 1 | BH-1 | BD-1 | 98 | 0.139 | 0.091 |
| Comparative Example 1 | BH-1-a | BD-1 | 60 | 0.139 | 0.091 |

Example 2 and Comparative Example 2

The organic EL device was fabricated in the same manner as in Example 1 except that the compound indicated in Table 2 was used as materials for the emitting layer, and evaluated. The results are shown in Table 2.

TABLE 2

| | Emitting layer | | | | |
|---|---|---|---|---|---|
| | Host material | Dopant material | LT95(h) | Chromaticity CIEx | CIEy |
| Example 2 | BH-1 | BD-2 | 33 | 0.137 | 0.068 |
| Comparative Example 2 | BH-1-a | BD-2 | 20 | 0.137 | 0.068 |

Example 3 and Comparative Example 3

The organic EL device was fabricated in the same manner as in Example 1 except that the compound indicated in Table 3 was used as materials for the emitting layer, and evaluated. The results are shown in Table 3.

TABLE 3

| | Emitting layer | | | | |
|---|---|---|---|---|---|
| | Host material | Dopant material | LT95(h) | Chromaticity CIEx | CIEy |
| Example 3 | BH-2 | BD-1 | 65 | 0.139 | 0.090 |
| Comparative Example 3 | BH-2-a | BD-1 | 40 | 0.139 | 0.090 |

Example 4 and Comparative Example 4

The organic EL device was fabricated in the same manner as in Example 1 except that the compound indicated in Table 4 was used as materials for the emitting layer, and evaluated. The results are shown in Table 4.

TABLE 4

| | Emitting layer | | | | |
|---|---|---|---|---|---|
| | Host material | Dopant material | LT95(h) | Chromaticity CIEx | CIEy |
| Example 4 | BH-2 | BD-2 | 23 | 0.137 | 0.067 |
| Comparative Example 4 | BH-2-a | BD-2 | 13 | 0.137 | 0.067 |

Example 5 and Comparative Example 5

The organic EL device was fabricated in the same manner as in Example 1 except that the compound indicated in Table 5 was used as materials for the emitting layer, and evaluated. The results are shown in Table 5.

TABLE 5

| | Emitting layer | | | | |
|---|---|---|---|---|---|
| | Host material | Dopant material | LT95(h) | Chromaticity CIEx | CIEy |
| Example 5 | BH-3 | BD-1 | 110 | 0.139 | 0.091 |
| Cornparative Example 5 | BH-3-a | BD-1 | 69 | 0.139 | 0.091 |

Example 6 and Comparative Example 6

The organic EL device was fabricated in the same manner as in Example 1 except that the compound indicated in Table 6 was used as materials for the emitting layer, and evaluated. The results are shown in Table 6.

TABLE 6

| | Emitting layer | | | | |
|---|---|---|---|---|---|
| | Host material | Dopant material | LT95(h) | Chromaticity CIEx | CIEy |
| Example 6 | BH-3 | BD-2 | 40 | 0.137 | 0.068 |
| Comparative Example 6 | BH-3-a | BD-2 | 25 | 0.137 | 0.068 |

Example 7 and Comparative Example 7

The organic EL device was fabricated in the same manner as in Example 1 except that the compound indicated in Table 7 was used as materials for the emitting layer, and evaluated. The results are shown in Table 7.

TABLE 7

| | Emitting layer | | | | |
|---|---|---|---|---|---|
| | Host material | Dopant material | LT95(h) | Chromaticity CIEx | CIEy |
| Example 7 | BH-4 | BD-1 | 60 | 0.139 | 0.090 |
| Comparative Example 7 | BH-4-a | BD-1 | 35 | 0.139 | 0.090 |

Example 8 and Comparative Example 8

The organic EL device was fabricated in the same manner as in Example 1 except that the compound indicated in Table 8 was used as materials for the emitting layer, and evaluated. The results are shown in Table 8.

TABLE 8

| | Emitting layer | | | | |
|---|---|---|---|---|---|
| | Host material | Dopant material | LT95(h) | Chromaticity CIEx | CIEy |
| Example 8 | BH-4 | BD-2 | 23 | 0.137 | 0.067 |
| Comparative Example 8 | BH-4-a | BD-2 | 13 | 0.137 | 0.067 |

Example 11 and Comparative Example 11

The organic EL device was fabricated in the same manner as in Example 1 except that the compound indicated in the following table was used as materials for the emitting layer (host material and dopant material), and evaluated. The results are shown in Table 9.

TABLE 9

| | Emitting layer | | | | |
|---|---|---|---|---|---|
| | Host material | Dopant material | LT95(h) | Chromaticity CIEx | CIEy |
| Example 11 | BH-1 | BD-3 | 117 | 0.140 | 0.080 |
| Comparative Example 11 | BH-1-a | BD-3 | 73 | 0.140 | 0.080 |

Example 12 and Comparative Example 12

The organic EL device was fabricated in the same manner as in Example 1 except that the compound indicated in the following table was used as materials for the emitting layer (host material and dopant material), and evaluated. The results are shown in Table 10.

TABLE 10

| | Emitting layer | | | | |
|---|---|---|---|---|---|
| | Host material | Dopant material | LT95(h) | Chromaticity CIEx | CIEy |
| Example 12 | BH-2 | BD-3 | 74 | 0.140 | 0.080 |
| Comparative Example 12 | BH-2-a | BD-3 | 46 | 0.140 | 0.080 |

Example 13 and Comparative Example 13

The organic EL device was fabricated in the same manner as in Example 1 except that the compound indicated in the following table was used as materials for the emitting layer (host material and dopant material), and evaluated. The results are shown in Table 11.

TABLE 11

| | Emitting layer | | | | |
|---|---|---|---|---|---|
| | Host material | Dopant material | LT95(h) | Chromaticity CIEx | CIEy |
| Example 13 | BH-3 | BD-3 | 130 | 0.140 | 0.080 |
| Comparative Example 13 | BH-3-a | BD-3 | 82 | 0.140 | 0.081 |

Example 14 and Comparative Example 14

The organic EL device was fabricated in the same manner as in Example 1 except that the compound indicated in the following table was used as materials for the emitting layer (host material and dopant material), and evaluated. The results are shown in Table 12.

TABLE 12

| | Emitting layer | | | | |
|---|---|---|---|---|---|
| | Host material | Dopant material | LT95(h) | Chromaticity CIEx | CIEy |
| Example 14 | BH-4 | BD-3 | 74 | 0.140 | 0.080 |
| Comparative Example 14 | BH-4-a | BD-3 | 42 | 0.140 | 0.080 |

Example 15 and Comparative Example 15

The organic EL device was fabricated in the same manner as in Example 1 except that the compound indicated in the following table was used as materials for the emitting layer (host material and dopant material), and evaluated. The results are shown in Table 13.

TABLE 13

| | Emitting layer | | | | |
|---|---|---|---|---|---|
| | Host material | Dopant material | LT95(h) | Chromaticity CIEx | CIEy |
| Example 15 | BH-5 | BD-3 | 68 | 0.140 | 0.080 |
| Comparative Example 15 | BH-5-a | BD-3 | 49 | 0.140 | 0.080 |

Example 16 and Comparative Example 16

The organic EL device was fabricated in the same manner as in Example 1 except that the compound indicated in the following table was used as materials for the emitting layer (host material and dopant material), and evaluated. The results are shown in Table 14.

TABLE 14

| | Emitting layer | | | | |
|---|---|---|---|---|---|
| | Host material | Dopant material | LT95(h) | Chromaticity CIEx | CIEy |
| Example 16 | BH-6 | BD-3 | 141 | 0.140 | 0.080 |
| Comparative Example 16 | BH-6-a | BD-3 | 90 | 0.140 | 0.080 |

Example 17 and Comparative Example 17

The organic EL device was fabricated in the same manner as in Example 1 except that the compound indicated in the following table was used as materials for the emitting layer (host material and dopant material), and evaluated. The results are shown in Table 15.

TABLE 15

| | Emitting layer | | | Chromaticity | |
|---|---|---|---|---|---|
| | Host material | Dopant material | LT95(h) | CIEx | CIEy |
| Example 17 | BH-7 | BD-3 | 127 | 0.140 | 0.080 |
| Comparative Example 17 | BH-7-a | BD-3 | 68 | 0.140 | 0.080 |

Example 18 and Comparative Example 18

The organic EL device was fabricated in the same manner as in Example 1 except that the compound indicated in the following table was used as materials for the emitting layer (host material and dopant material), and evaluated. The results are shown in Table 16.

TABLE 16

| | Emitting layer | | | Chromaticity | |
|---|---|---|---|---|---|
| | Host material | Dopant material | LT95(h) | CIEx | CIEy |
| Example 18 | BH-8 | BD-3 | 126 | 0.140 | 0.080 |
| Comparative Example 18 | BH-8-a | BD-3 | 73 | 0.140 | 0.080 |

Example 19 and Comparative Example 19

The organic EL device was fabricated in the same manner as in Example 1 except that the compound indicated in the following table was used as materials for the emitting layer (host material and dopant material), and evaluated. The results are shown in Table 17.

TABLE 17

| | Emitting layer | | | Chromaticity | |
|---|---|---|---|---|---|
| | Host material | Dopant material | LT95(h) | CIEx | CIEy |
| Example 19 | BH-9 | BD-3 | 128 | 0.140 | 0.080 |
| Comparative Example 19 | BH-9-a | BD-3 | 76 | 0.140 | 0.080 |

Example 21 and Comparative Example 21

The organic EL device was fabricated in the same manner as in Example 1 except that the compound indicated in the following table was used as materials for the emitting layer (host material and dopant material), and evaluated. The results are shown in Table 18.

TABLE 18

| | Emitting layer | | | Chromaticity | |
|---|---|---|---|---|---|
| | Host material | Dopant material | LT95(h) | CIEx | CIEy |
| Example 21 | BH-1 | BD-4 | 137 | 0.135 | 0.098 |
| Comparative Example 21 | BH-1-a | BD-4 | 86 | 0.135 | 0.098 |

Example 22 and Comparative Example 22

The organic EL device was fabricated in the same manner as in Example 1 except that the compound indicated in the following table was used as materials for the emitting layer (host material and dopant material), and evaluated. The results are shown in Table 19.

TABLE 19

| | Emitting layer | | | Chromaticity | |
|---|---|---|---|---|---|
| | Host material | Dopant material | LT95(h) | CIEx | CIEy |
| Example 22 | BH-2 | BD-4 | 94 | 0.135 | 0.098 |
| Comparative Example 22 | BH-2-a | BD-4 | 58 | 0.135 | 0.098 |

Example 23 and Comparative Example 23

The organic EL device was fabricated in the same manner as in Example 1 except that the compound indicated in the following table was used as materials for the emitting layer (host material and dopant material), and evaluated. The results are shown in Table 20.

TABLE 20

| | Emitting layer | | | Chromaticity | |
|---|---|---|---|---|---|
| | Host material | Dopant material | LT95(h) | CIEx | CIEy |
| Example 23 | BH-3 | BD-4 | 152 | 0.135 | 0.098 |
| Comparative Example 23 | BH-3-a | BD-4 | 100 | 0.135 | 0.098 |

Example 24 and Comparative Example 24

The organic EL device was fabricated in the same manner as in Example 1 except that the compound indicated in the following table was used as materials for the emitting layer (host material and dopant material), and evaluated. The results are shown in Table 21.

TABLE 21

| | Emitting layer | | | Chromaticity | |
|---|---|---|---|---|---|
| | Host material | Dopant material | LT95(h) | CIEx | CIEy |
| Example 24 | BH-4 | BD-4 | 82 | 0.135 | 0.098 |
| Comparative Example 24 | BH-4-a | BD-4 | 53 | 0.135 | 0.098 |

Example 25 and Comparative Example 25

The organic EL device was fabricated in the same manner as in Example 1 except that the compound indicated in the following table was used as materials for the emitting layer (host material and dopant material), and evaluated. The results are shown in Table 22.

TABLE 22

| | Emitting layer | | | | |
|---|---|---|---|---|---|
| | | Dopant | | Chromaticity | |
| | Host material | material | LT95(h) | CIEx | CIEy |
| Example 25 | BH-5 | BD-4 | 77 | 0.135 | 0.098 |
| Comparative Example 25 | BH-5-a | BD-4 | 57 | 0.135 | 0.098 |

Example 26 and Comparative Example 26

The organic EL device was fabricated in the same manner as in Example 1 except that the compound indicated in the following table was used as materials for the emitting layer (host material and dopant material), and evaluated. The results are shown in Table 23.

TABLE 23

| | Emitting layer | | | | |
|---|---|---|---|---|---|
| | | Dopant | | Chromaticity | |
| | Host material | material | LT95(h) | CIEx | CIEy |
| Example 26 | BH-6 | BD-4 | 172 | 0.135 | 0.098 |
| Comparative Example 26 | BH-6-a | BD-4 | 100 | 0.135 | 0.098 |

Example 27 and Comparative Example 27

The organic EL device was fabricated in the same manner as in Example 1 except that the compound indicated in the following table was used as materials for the emitting layer (host material and dopant material), and evaluated. The results are shown in Table 24.

TABLE 24

| | Emitting layer | | | | |
|---|---|---|---|---|---|
| | | Dopant | | Chromaticity | |
| | Host material | material | LT95(h) | CIEx | CIEy |
| Example 27 | BH-7 | BD-4 | 142 | 0.135 | 0.099 |
| Comparative Example 27 | BH-7-a | BD-4 | 84 | 0.135 | 0.098 |

Example 28 and Comparative Example 28

The organic EL device was fabricated in the same manner as in Example 1 except that the compound indicated in the following table was used as materials for the emitting layer (host material and dopant material), and evaluated. The results are shown in Table 25.

TABLE 25

| | Emitting layer | | | | |
|---|---|---|---|---|---|
| | | Dopant | | Chromaticity | |
| | Host material | material | LT95(h) | CIEx | CIEy |
| Example 28 | BH-8 | BD-4 | 147 | 0.135 | 0.098 |
| Comparative Example 28 | BH-8-a | BD-4 | 85 | 0.135 | 0.098 |

Example 29 and Comparative Example 29

The organic EL device was fabricated in the same manner as in Example 1 except that the compound indicated in the following table was used as materials for the emitting layer (host material and dopant material), and evaluated. The results are shown in Table 26.

TABLE 26

| | Emitting layer | | | | |
|---|---|---|---|---|---|
| | | Dopant | | Chromaticity | |
| | Host material | material | LT95(h) | CIEx | CIEy |
| Example 29 | BH-9 | BD-4 | 150 | 0.135 | 0.098 |
| Comparative Example 29 | BH-9-a | BD-4 | 90 | 0.135 | 0.098 |

Example 31 and Comparative Example 31

The organic EL device was fabricated in the same manner as in Example 1 except that the compound indicated in the following table was used as materials for the emitting layer (host material and dopant material), and evaluated. The results are shown in Table 27.

TABLE 27

| | Emitting layer | | | | |
|---|---|---|---|---|---|
| | | Dopant | | Chromaticity | |
| | Host material | material | LT95(h) | CIEx | CIEy |
| Example 31 | BH-1 | BD-5 | 142 | 0.135 | 0.086 |
| Comparative Example 31 | BH-1-a | BD-5 | 86 | 0.135 | 0.086 |

Example 32 and Comparative Example 32

The organic EL device was fabricated in the same manner as in Example 1 except that the compound indicated in the following table was used as materials for the emitting layer (host material and dopant material), and evaluated. The results are shown in Table 28.

TABLE 28

| | Emitting layer | | | | |
|---|---|---|---|---|---|
| | | Dopant | | Chromaticity | |
| | Host material | material | LT95(h) | CIEx | CIEy |
| Example 32 | BH-2 | BD-5 | 92 | 0.135 | 0.086 |
| Comparative Example 32 | BH-2-a | BD-5 | 59 | 0.135 | 0.086 |

Example 33 and Comparative Example 33

The organic EL device was fabricated in the same manner as in Example 1 except that the compound indicated in the following table was used as materials for the emitting layer (host material and dopant material), and evaluated. The results are shown in Table 29.

TABLE 29

| | Emitting layer | | | Chromaticity | |
|---|---|---|---|---|---|
| | Host material | Dopant material | LT95(h) | CIEx | CIEy |
| Example 33 | BH-3 | BD-5 | 163 | 0.135 | 0.086 |
| Comparative Example 33 | BH-3-a | BD-5 | 99 | 0.135 | 0.086 |

Example 34 and Comparative Example 34

The organic EL device was fabricated in the same manner as in Example 1 except that the compound indicated in the following table was used as materials for the emitting layer (host material and dopant material), and evaluated. The results are shown in Table 30.

TABLE 30

| | Emitting layer | | | Chromaticity | |
|---|---|---|---|---|---|
| | Host material | Dopant material | LT95(h) | CIEx | CIEy |
| Example 34 | BH-4 | BD-5 | 83 | 0.135 | 0.086 |
| Comparative Example 34 | BH-4-a | BD-5 | 51 | 0.135 | 0.086 |

Example 35 and Comparative Example 35

The organic EL device was fabricated in the same manner as in Example 1 except that the compound indicated in the following table was used as materials for the emitting layer (host material and dopant material), and evaluated. The results are shown in Table 31.

TABLE 31

| | Emitting layer | | | Chromaticity | |
|---|---|---|---|---|---|
| | Host material | Dopant material | LT95(h) | CIEx | CIEy |
| Example 35 | BH-5 | BD-5 | 81 | 0.135 | 0.086 |
| Comparative Example 35 | BH-5-a | BD-5 | 56 | 0.135 | 0.086 |

Example 36 and Comparative Example 36

The organic EL device was fabricated in the same manner as in Example 1 except that the compound indicated in the following table was used as materials for the emitting layer (host material and dopant material), and evaluated. The results are shown in Table 32.

TABLE 32

| | Emitting layer | | | Chromaticity | |
|---|---|---|---|---|---|
| | Host material | Dopant material | LT95(h) | CIEx | CIEy |
| Example 36 | BH-6 | BD-5 | 173 | 0.135 | 0.086 |
| Comparative Example 36 | BH-6-a | BD-5 | 97 | 0.135 | 0.086 |

Example 37 and Comparative Example 37

The organic EL device was fabricated in the same manner as in Example 1 except that the compound indicated in the following table was used as materials for the emitting layer (host material and dopant material), and evaluated. The results are shown in Table 33.

TABLE 33

| | Emitting layer | | | Chromaticity | |
|---|---|---|---|---|---|
| | Host material | Dopant material | LT95 (h) | CIEx | CIEy |
| Example 37 | BH-7 | BD-5 | 142 | 0.135 | 0.085 |
| Comparative Example 37 | BH-7-a | BD-5 | 84 | 0.135 | 0.086 |

Example 38 and Comparative Example 38

The organic EL device was fabricated in the same manner as in Example 1 except that the compound indicated in the following table was used as materials for the emitting layer (host material and dopant material), and evaluated. The results are shown in Table 34.

TABLE 34

| | Emitting layer | | | Chromaticity | |
|---|---|---|---|---|---|
| | Host material | Dopant material | LT95 (h) | CIEx | CIEy |
| Example 38 | BH-8 | BD-5 | 149 | 0.135 | 0.086 |
| Comparative Example 38 | BH-8-a | BD-5 | 94 | 0.135 | 0.086 |

Example 39 and Comparative Example 39

The organic EL device was fabricated in the same manner as in Example 1 except that the compound indicated in the following table was used as materials for the emitting layer (host material and dopant material), and evaluated. The results are shown in Table 35.

TABLE 35

| | Emitting layer | | | Chromaticity | |
|---|---|---|---|---|---|
| | Host material | Dopant material | LT95 (h) | CIEx | CIEy |
| Example 39 | BH-9 | BD-5 | 152 | 0.135 | 0.086 |
| Comparative Example 39 | BH-9-a | BD-5 | 90 | 0.135 | 0.086 |

Example 41 and Comparative Example 41

The organic EL device was fabricated in the same manner as in Example 1 except that the compound indicated in the following table was used as materials for the emitting layer (host material and dopant material), and evaluated. The results are shown in Table 36.

TABLE 36

| | Emitting layer | | | Chromaticity | |
|---|---|---|---|---|---|
| | Host material | Dopant material | LT95 (h) | CIEx | CIEy |
| Example 41 | BH-1 | BD-6 | 170 | 0.135 | 0.080 |
| Comparative Example 41 | BH-1-a | BD-6 | 101 | 0.135 | 0.080 |

Example 42 and Comparative Example 42

The organic EL device was fabricated in the same manner as in Example 1 except that the compound indicated in the following table was used as materials for the emitting layer (host material and dopant material), and evaluated. The results are shown in Table 37.

TABLE 37

| | Emitting layer | | | Chromaticity | |
|---|---|---|---|---|---|
| | Host material | Dopant material | LT95 (h) | CIEx | CIEy |
| Example 42 | BH-2 | BD-6 | 121 | 0.135 | 0.080 |
| Comparative Example 42 | BH-2-a | BD-6 | 70 | 0.135 | 0.080 |

Example 43 and Comparative Example 43

The organic EL device was fabricated in the same manner as in Example 1 except that the compound indicated in the following table was used as materials for the emitting layer (host material and dopant material), and evaluated. The results are shown in Table 38.

TABLE 38

| | Emitting layer | | | Chromaticity | |
|---|---|---|---|---|---|
| | Host material | Dopant material | LT95 (h) | CIEx | CIEy |
| Example 43 | BH-3 | BD-6 | 205 | 0.135 | 0.080 |
| Comparative Example 43 | BH-3-a | BD-6 | 123 | 0.135 | 0.080 |

Example 44 and Comparative Example 44

The organic EL device was fabricated in the same manner as in Example 1 except that the compound indicated in the following table was used as materials for the emitting layer (host material and dopant material), and evaluated. The results are shown in Table 39.

TABLE 39

| | Emitting layer | | | Chromaticity | |
|---|---|---|---|---|---|
| | Host material | Dopant material | LT95 (h) | CIEx | CIEy |
| Example 44 | BH-4 | BD-6 | 108 | 0.135 | 0.080 |
| Comparative Example 44 | BH-4-a | BD-6 | 62 | 0.135 | 0.080 |

Example 45 and Comparative Example 45

The organic EL device was fabricated in the same manner as in Example 1 except that the compound indicated in the following table was used as materials for the emitting layer (host material and dopant material), and evaluated. The results are shown in Table 40.

TABLE 40

| | Emitting layer | | | Chromaticity | |
|---|---|---|---|---|---|
| | Host material | Dopant material | LT95 (h) | CIEx | CIEy |
| Example 45 | BH-5 | BD-6 | 99 | 0.135 | 0.080 |
| Comparative Example 45 | BH-5-a | 6D-6 | 71 | 0.135 | 0.080 |

Example 46 and Comparative Example 46

The organic EL device was fabricated in the same manner as in Example 1 except that the compound indicated in the following table was used as materials for the emitting layer (host material and dopant material), and evaluated. The results are shown in Table 41.

TABLE 41

| | Emitting layer | | | Chromaticity | |
|---|---|---|---|---|---|
| | Host material | Dopant material | LT95 (h) | CIEx | CIEy |
| Example 46 | BH-6 | BD-6 | 214 | 0.135 | 0.081 |
| Comparative Example 46 | BH-6-a | 6D-6 | 125 | 0.135 | 0.080 |

Example 47 and Comparative Example 47

The organic EL device was fabricated in the same manner as in Example 1 except that the compound indicated in the following table was used as materials for the emitting layer (host material and dopant material), and evaluated. The results are shown in Table 42.

TABLE 42

| | Emitting layer | | | Chromaticity | |
|---|---|---|---|---|---|
| | Host material | Dopant material | LT95 (h) | CIEx | CIEy |
| Example 47 | BH-7 | BD-6 | 175 | 0.135 | 0.080 |
| Comparative Example 47 | BH-7-a | BD-6 | 106 | 0.135 | 0.080 |

Example 48 and Comparative Example 48

The organic EL device was fabricated in the same manner as in Example 1 except that the compound indicated in the following table was used as materials for the emitting layer (host material and dopant material), and evaluated. The results are shown in Table 43.

TABLE 43

| | Emitting layer | | | | |
| --- | --- | --- | --- | --- | --- |
| | Host material | Dopant material | LT95 (h) | Chromaticity | |
| | | | | CIEx | CIEy |
| Example 48 | BH-8 | BD-6 | 183 | 0.135 | 0.081 |
| Comparative Example 48 | BH-8-a | BD-6 | 111 | 0.135 | 0.080 |

Example 49 and Comparative Example 49

The organic EL device was fabricated in the same manner as in Example 1 except that the compound indicated in the following table was used as materials for the emitting layer (host material and dopant material), and evaluated. The results are shown in Table 44.

TABLE 44

| | Emitting layer | | | | |
| --- | --- | --- | --- | --- | --- |
| | Host material | Dopant material | LT95 (h) | Chromaticity | |
| | | | | CIEx | CIEy |
| Example 49 | BH-9 | BD-6 | 192 | 0.135 | 0.080 |
| Comparative Example 49 | BH-9-a | BD-6 | 115 | 0.135 | 0.080 |

Example 51 and Comparative Example 51

The organic EL device was fabricated in the same manner as in Example 1 except that the compound indicated in the following table was used as materials for the emitting layer (host material and dopant material), and evaluated. The results are shown in Table 45.

TABLE 45

| | Emitting layer | | | | |
| --- | --- | --- | --- | --- | --- |
| | Host material | Dopant material | LT95 (h) | Chromaticity | |
| | | | | CIEx | CIEy |
| Example 51 | BH-1 | BD-7 | 210 | 0.136 | 0.090 |
| Cornparative Example 51 | BH-1-a | BD-7 | 127 | 0.136 | 0.090 |

Example 52 and Comparative Example 52

The organic EL device was fabricated in the same manner as in Example 1 except that the compound indicated in the following table was used as materials for the emitting layer (host material and dopant material), and evaluated. The results are shown in Table 46.

TABLE 46

| | Emitting layer | | | | |
| --- | --- | --- | --- | --- | --- |
| | Host material | Dopant material | LT95 (h) | Chromaticity | |
| | | | | CIEx | CIEy |
| Example 52 | BH-2 | BD-7 | 143 | 0.136 | 0.090 |
| Comparative Example 52 | BH-2-a | BD-7 | 80 | 0.136 | 0.090 |

Example 53 and Comparative Example 53

The organic EL device was fabricated in the same manner as in Example 1 except that the compound indicated in the following table was used as materials for the emitting layer (host material and dopant material), and evaluated. The results are shown in Table 47.

TABLE 47

| | Emitting layer | | | | |
| --- | --- | --- | --- | --- | --- |
| | Host material | Dopant material | LT95 (h) | Chromaticity | |
| | | | | CIEx | CIEy |
| Example 53 | BH-3 | BD-7 | 236 | 0.136 | 0.090 |
| Comparative Example 53 | BH-3-a | BD-7 | 150 | 0.136 | 0.090 |

Example 54 and Comparative Example 54

The organic EL device was fabricated in the same manner as in Example 1 except that the compound indicated in the following table was used as materials for the emitting layer (host material and dopant material), and evaluated. The results are shown in Table 48.

TABLE 48

| | Emitting layer | | | | |
| --- | --- | --- | --- | --- | --- |
| | Host material | Dopant material | LT95 (h) | Chromaticity | |
| | | | | CIEx | CIEy |
| Example 54 | BH-4 | BD-7 | 119 | 0.136 | 0.090 |
| Comparative Example 54 | BH-4-a | BD-7 | 74 | 0.136 | 0.090 |

Example 55 and Comparative Example 55

The organic EL device was fabricated in the same manner as in Example 1 except that the compound indicated in the following table was used as materials for the emitting layer (host material and dopant material), and evaluated. The results are shown in Table 49.

TABLE 49

| | Emitting layer | | | | |
| --- | --- | --- | --- | --- | --- |
| | Host material | Dopant material | LT95 (h) | Chromaticity | |
| | | | | CIEx | CIEy |
| Example 55 | BH-5 | BD-7 | 121 | 0.136 | 0.090 |
| Comparative Example 55 | BH-5-a | BD-7 | 85 | 0.136 | 0.090 |

Example 56 and Comparative Example 56

The organic EL device was fabricated in the same manner as in Example 1 except that the compound indicated in the following table was used as materials for the emitting layer (host material and dopant material), and evaluated. The results are shown in Table 50.

TABLE 50

| | Emitting layer | | | | |
|---|---|---|---|---|---|
| | Host material | Dopant material | LT95 (h) | Chromaticity | |
| | | | | CIEx | CIEy |
| Example 56 | BH-6 | BD-7 | 251 | 0.136 | 0.090 |
| Comparative Example 56 | BH-6-a | BD-7 | 137 | 0.136 | 0.090 |

Example 57 and Comparative Example 57

The organic EL device was fabricated in the same manner as in Example 1 except that the compound indicated in the following table was used as materials for the emitting layer (host material and dopant material), and evaluated. The results are shown in Table 51.

TABLE 51

| | Emitting layer | | | | |
|---|---|---|---|---|---|
| | Host material | Dopant material | LT95 (h) | Chromaticity | |
| | | | | CIEx | CIEy |
| Example 57 | BH-7 | BD-7 | 210 | 0.136 | 0.090 |
| Comparative Example 57 | BH-7-a | BD-7 | 130 | 0.136 | 0.091 |

Example 58 and Comparative Example 58

The organic EL device was fabricated in the same manner as in Example 1 except that the compound indicated in the following table was used as materials for the emitting layer (host material and dopant material), and evaluated. The results are shown in Table 52.

TABLE 52

| | Emitting layer | | | | |
|---|---|---|---|---|---|
| | Host material | Dopant material | LT95 (h) | Chromaticity | |
| | | | | CIEx | CIEy |
| Example 58 | BH-8 | BD-7 | 221 | 0.136 | 0.090 |
| Comparative Example 58 | BH-8-a | BD-7 | 135 | 0.136 | 0.090 |

Example 59 and Comparative Example 59

The organic EL device was fabricated in the same manner as in Example 1 except that the compound indicated in the following table was used as materials for the emitting layer (host material and dopant material), and evaluated. The results are shown in Table 53.

TABLE 53

| | Emitting layer | | | | |
|---|---|---|---|---|---|
| | Host material | Dopant material | LT95 (h) | Chromaticity | |
| | | | | CIEx | CIEy |
| Example 59 | BH-9 | BD-7 | 225 | 0.136 | 0.090 |
| Comparative Example 59 | BH-9-a | BD-7 | 140 | 0.136 | 0.090 |

Example 61 and Comparative Example 61

The organic EL device was fabricated in the same manner as in Example 1 except that the compound indicated in the following table was used as materials for the emitting layer (host material and dopant material), and evaluated. The results are shown in Table 54.

TABLE 54

| | Emitting layer | | | | |
|---|---|---|---|---|---|
| | Host material | Dopant material | LT95 (h) | Chromaticity | |
| | | | | CIEx | CIEy |
| Example 61 | BH-1 | BD-8 | 107 | 0.144 | 0.060 |
| Comparative Example 61 | BH-1-a | BD-8 | 66 | 0.144 | 0.061 |

Example 62 and Comparative Example 62

The organic EL device was fabricated in the same manner as in Example 1 except that the compound indicated in the following table was used as materials for the emitting layer (host material and dopant material), and evaluated. The results are shown in Table 55.

TABLE 55

| | Emitting layer | | | | |
|---|---|---|---|---|---|
| | Host material | Dopant material | LT95 (h) | Chromaticity | |
| | | | | CIEx | CIEy |
| Example 62 | BH-2 | BD-8 | 68 | 0.144 | 0.061 |
| Comparative Example 62 | BH-2-a | BD-8 | 46 | 0.144 | 0.061 |

Example 63 and Comparative Example 63

The organic EL device was fabricated in the same manner as in Example 1 except that the compound indicated in the following table was used as materials for the emitting layer (host material and dopant material), and evaluated. The results are shown in Table 56.

TABLE 56

| | Emitting layer | | | | |
|---|---|---|---|---|---|
| | Host material | Dopant material | LT95 (h) | Chromaticity | |
| | | | | CIEx | CIEy |
| Example 63 | BH-3 | BD-8 | 120 | 0.144 | 0.061 |
| Comparative Example 63 | BH-3-a | BD-8 | 76 | 0.144 | 0.061 |

Example 64 and Comparative Example 64

The organic EL device was fabricated in the same manner as in Example 1 except that the compound indicated in the following table was used as materials for the emitting layer (host material and dopant material), and evaluated. The results are shown in Table 57.

TABLE 57

| | Emitting layer | | | | |
|---|---|---|---|---|---|
| | Host material | Dopant material | LT95 (h) | Chromaticity CIEx | CIEy |
| Example 64 | BH-4 | BD-8 | 69 | 0.144 | 0.061 |
| Comparative Example 64 | BH-4-a | BD-8 | 40 | 0.144 | 0.061 |

Example 65 and Comparative Example 65

The organic EL device was fabricated in the same manner as in Example 1 except that the compound indicated in the following table was used as materials for the emitting layer (host material and dopant material), and evaluated. The results are shown in Table 58.

TABLE 58

| | Emitting layer | | | | |
|---|---|---|---|---|---|
| | Host material | Dopant material | LT95 (h) | Chromaticity CIEx | CIEy |
| Example 65 | BH-5 | BD-8 | 64 | 0.144 | 0.061 |
| Comparative Example 65 | BH-5-a | BD-8 | 49 | 0.144 | 0.061 |

Example 66 and Comparative Example 66

The organic EL device was fabricated in the same manner as in Example 1 except that the compound indicated in the following table was used as materials for the emitting layer (host material and dopant material), and evaluated. The results are shown in Table 59.

TABLE 59

| | Emitting layer | | | | |
|---|---|---|---|---|---|
| | Host material | Dopant material | LT95 (h) | Chromaticity CIEx | CIEy |
| Example 66 | BH-6 | BD-8 | 137 | 0.144 | 0.061 |
| Comparative Example 66 | BH-6-a | BD-8 | 83 | 0.144 | 0.061 |

Example 67 and Comparative Example 67

The organic EL device was fabricated in the same manner as in Example 1 except that the compound indicated in the following table was used as materials for the emitting layer (host material and dopant material), and evaluated. The results are shown in Table 60.

TABLE 60

| | Emitting layer | | | | |
|---|---|---|---|---|---|
| | Host material | Dopant material | LT95 (h) | Chromaticity CIEx | CIEy |
| Example 67 | BH-7 | BD-8 | 118 | 0.144 | 0.061 |
| Comparative Example 67 | BH-7-a | BD-8 | 66 | 0.144 | 0.061 |

Example 68 and Comparative Example 68

The organic EL device was fabricated in the same manner as in Example 1 except that the compound indicated in the following table was used as materials for the emitting layer (host material and dopant material), and evaluated. The results are shown in Table 61.

TABLE 61

| | Emitting layer | | | | |
|---|---|---|---|---|---|
| | Host material | Dopant material | LT95 (h) | Chromaticity CIEx | CIEy |
| Example 68 | BH-8 | BD-8 | 119 | 0.144 | 0.061 |
| Comparative Example 68 | BH-8-a | BD-8 | 70 | 0.144 | 0.061 |

Example 69 and Comparative Example 69

The organic EL device was fabricated in the same manner as in Example 1 except that the compound indicated in the following table was used as materials for the emitting layer (host material and dopant material), and evaluated. The results are shown in Table 62.

TABLE 62

| | Emitting layer | | | | |
|---|---|---|---|---|---|
| | Host material | Dopant material | LT95 (h) | Chromaticity CIEx | CIEy |
| Example 69 | BH-9 | BD-8 | 120 | 0.144 | 0.061 |
| Comparative Example 69 | BH-9-a | BD-8 | 75 | 0.144 | 0.061 |

From the results shown in Tables 1 to 62, when the compound (host material) represented by the formula (1) which has a deuterium atom at a particular position is used for the emitting layer in combination of a particular dopant material, it is understood that the lifetime of the organic EL device becomes longer than that of one which uses a compound (host material) which has no deuterium atom at the particular position in combination with the corresponding dopant material.

Several embodiments and/or examples of the present invention have been described in detail above. However, without substantially departing from novel teachings and effects of the present invention, the person skilled in the art can readily make a number of modifications to the embodiments and/or examples which are exemplifications of these teachings and effects. Thus, these modifications are included in the scope of the present invention.

The documents described in this specification and the contents of the application that serves as the basis of priority claim under Paris convention are incorporated herein by reference in its entirety.

The invention claimed is:
1. An organic electroluminescence device comprising:
a cathode,
an anode, and
an emitting layer disposed between the cathode and the anode, wherein
the emitting layer comprises a compound represented by the following formula (1) and a compound represented by the following formula (31):

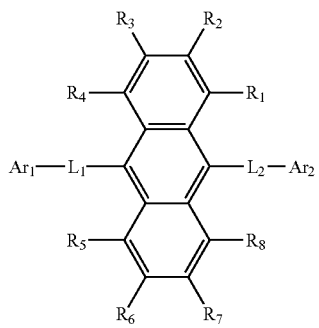
(1)

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or unsubstituted, saturated or unsaturated ring;
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$ and two or more adjacent groups of $R_5$ to $R_8$ do not form a ring;

$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;
$Ar_1$ is
a substituted or unsubstituted aryl group having 6 to 50 ring carbon atoms, or
a substituted or unsubstituted monovalent heterocyclic group having 5 to 50 ring atoms;
$Ar_2$ is a monovalent group represented by the following formula (2), (3) or (4);

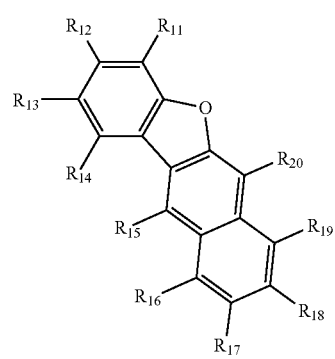
(2)

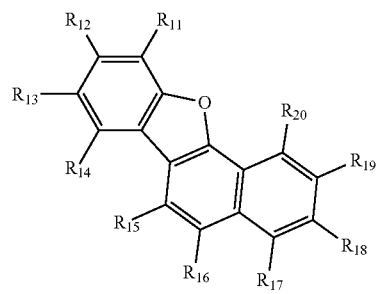
(3)

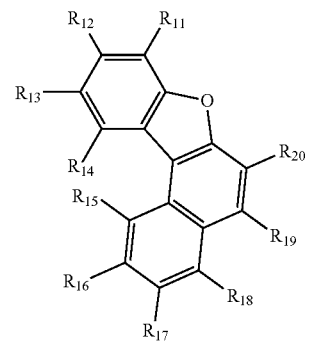
(4)

wherein in the formulas (2) to (4),
one or more pairs of two adjacent groups of $R_{15}$ to $R_{20}$ are bonded with each other to form a substituted or unsubstituted, saturated or unsaturated ring, or do not form a substituted or unsubstituted, saturated or unsaturated ring;
when one or more pairs of two adjacent groups of $R_{15}$ to $R_{20}$ are not bonded with each other and do not form a substituted or unsubstituted, saturated or unsaturated ring, one of $R_{11}$ to $R_{20}$ is a single bond bonding to $L_2$;
when one or more pairs of two adjacent groups of $R_{15}$ to $R_{20}$ are bonded with each other to form a substituted or unsubstituted, saturated or unsaturated ring, one of $R_{15}$ to $R_{20}$ which does not form a substituted or unsubstituted, saturated or unsaturated ring and $R_{11}$ to $R_{14}$ is a single bond bonding to $L_2$;

$R_{11}$ to $R_{20}$ that do not form the substituted or unsubstituted, saturated or unsaturated ring and that are not a single bond bonding to $L_2$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1);

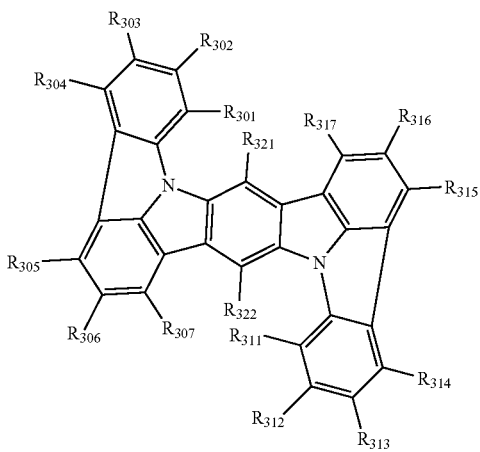

(31)

wherein in the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

2. The organic electroluminescence device according to claim 1, wherein in the formula (1), at least two of $R_1$ to $R_8$ are deuterium atoms.

3. The organic electroluminescence device according to claim 1, wherein in the formula (1), $R_1$ to $R_8$ are all deuterium atoms.

4. The organic electroluminescence device according to claim 1, wherein in the formula (1), one or more groups selected from the group consisting of $L_1$ and $L_2$ are an unsubstituted arylene group having 6 to 30 ring carbon atoms in which at least one hydrogen atom is a deuterium atom, or an unsubstituted divalent heterocyclic group having 5 to 30 ring atoms in which at least one hydrogen atom is a deuterium atom.

5. The organic electroluminescence device according to claim 1, wherein in the formula (1), $L_1$ and $L_2$ are independently a single bond, or a substituted or unsubstituted arylene group having 6 to 14 ring carbon atoms.

6. The organic electroluminescence device according to claim 1, wherein any one of $R_{11}$ to $R_{14}$ in the formulas (2) to (4) is a single bond bonding to $L_2$.

7. The organic electroluminescence device according to claim 1, wherein one or more pairs of two or more adjacent groups of $R_{15}$ to $R_{20}$ in the formulas (2) to (4) are not bonded with each other and do not form a substituted to unsubstituted, saturated or unsaturated ring.

8. The organic electroluminescence device according to claim 1, wherein in the formula (1), $Ar_1$ is an unsubstituted aryl group having 6 to 50 ring carbon atoms in which at least one hydrogen atom is a deuterium atom, or an unsubstituted monovalent heterocyclic group having 5 to 50 ring atoms in which at least one hydrogen atom is a deuterium atom.

9. The organic electroluminescence device according to claim 1, wherein in the formula (1), $Ar_1$ is a substituted or unsubstituted aryl group having 6 to 50 ring carbon atoms.

10. The organic electroluminescence device according to claim 9, wherein in the formula (1), $Ar_1$ is selected from groups represented by the following formulas (a1) to (a4):

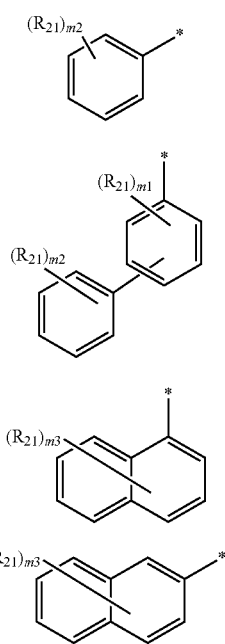

wherein in the formulas (a1) to (a4),
* is a single bond bonding to $L_1$;
$R_{21}$ is
  a halogen atom, a cyano group, a nitro group,
  a substituted or unsubstituted alkyl group having 1 to 50 carbon atoms,
  a substituted or unsubstituted alkenyl group having 2 to 50 carbon atoms,
  a substituted or unsubstituted alkynyl group having 2 to 50 carbon atoms,
  a substituted or unsubstituted cycloalkyl group having 3 to 50 ring carbon atoms,
  $Si(R_{901})(R_{902})(R_{903})$,
  —O—$(R_{904})$,
  —S—$(R_{905})$,
  —N$(R_{906})(R_{907})$,
  a substituted or unsubstituted aryl group having 6 to 50 ring carbon atoms, or
  a substituted or unsubstituted monovalent heterocyclic group having 5 to 50 ring atoms;
$R_{901}$ to $R_{907}$ are as defined in the formula (1);
m1 is an integer of 0 to 4;
m2 is an integer of 0 to 5;
m3 is an integer of 0 to 7;
when each of m1 to m3 is 2 or more, the plural $R_{21}$s may be the same or different; and
when each of m1 to m3 is 2 or more, adjacent plural $R_{21}$s are bonded with each other to form a substituted or unsubstituted, saturated or unsaturated ring, or do not form a substituted or unsubstituted, saturated or unsaturated ring.

11. The organic electroluminescence device according to claim 1, wherein at least one of $R_{11}$ to $R_{20}$ that do not form the substituted or unsubstituted, saturated or unsaturated ring and that are not a single bond bonding to $L_2$ and that are not a single bond bonding to $L_2$ is a deuterium atom.

12. The organic electroluminescence device according to claim 1, wherein the compound represented by the formula (1) is the compound represented by any one of following formulas (1-1) to (1-3):

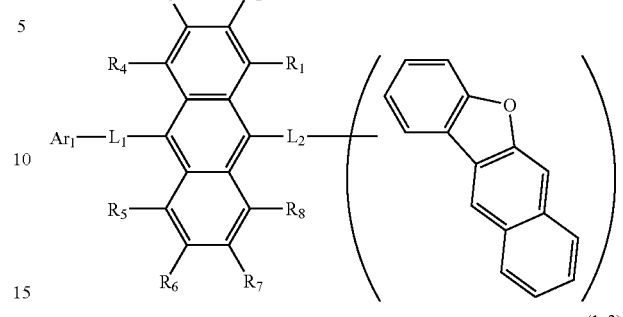

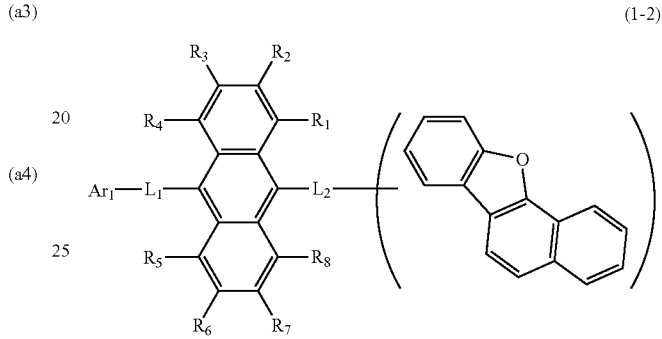

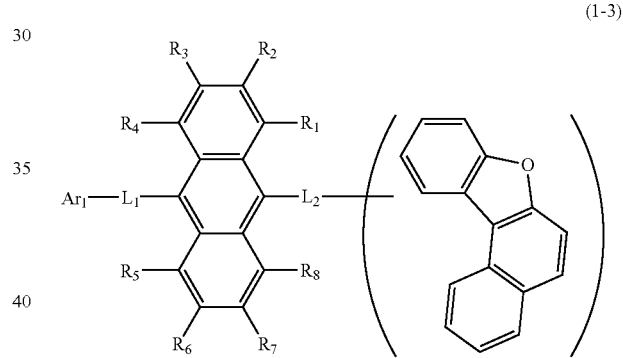

wherein in the formulas (1-1) to (1-3), $R_1$ to $R_8$, $Ar_1$, $L_1$ and $L_2$ are as defined in the formula (1).

13. The organic electroluminescence device according to claim 1, wherein the compound represented by the formula (1) is a compound represented by any one of following formulas (1-11) to (1-13):

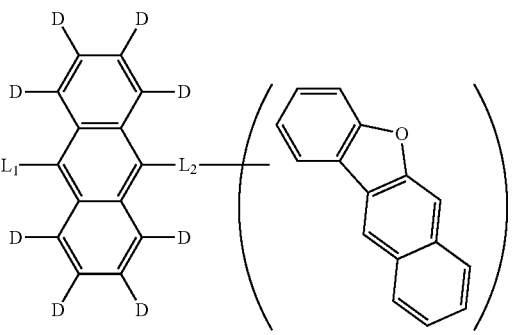

1097

-continued (1-12)

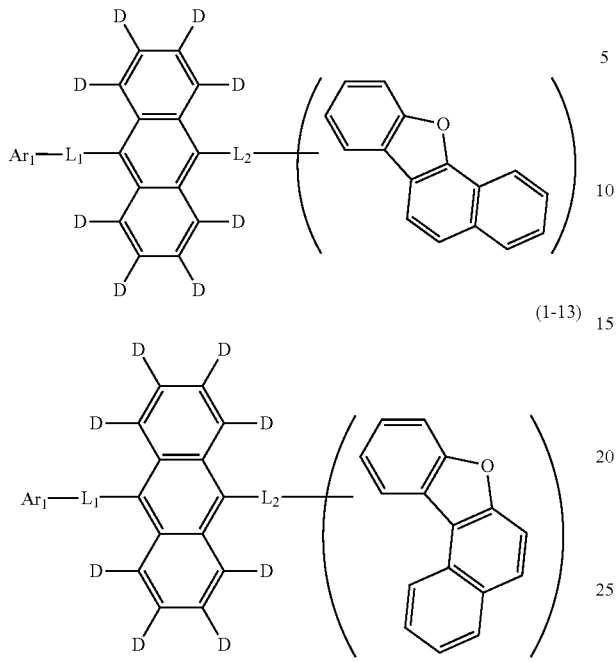

(1-13)

wherein in the formulas (1-11) to (1-13), $Ar_1$, $L_1$ and $L_2$ are as defined in the formula (1).

14. The organic electroluminescence device according to claim 1, wherein the emitting layer contains a protium compound, the protium compound is a compound defined by formula 1 wherein only protium atoms are contained as hydrogen atoms, and the emitting layer is represented by the following equation:

$$\frac{\text{Protium Compound}}{\text{Compound of Formula(1)} + \text{Protium Compound}} = 99 \text{ mol \% or less.}$$

15. The organic electroluminescence device according to claim 1, wherein in the formula (31), at least two of $R_{301}$ to $R_{307}$ and $R_{311}$ to $R_{317}$ are groups represented by —N($R_{906}$)($R_{907}$).

16. The organic electroluminescence device according to claim 1, wherein the compound represented by the formula (31) is one or more compounds selected from a group consisting of the following formulas (32), (34-2) and (35-2):

(32)

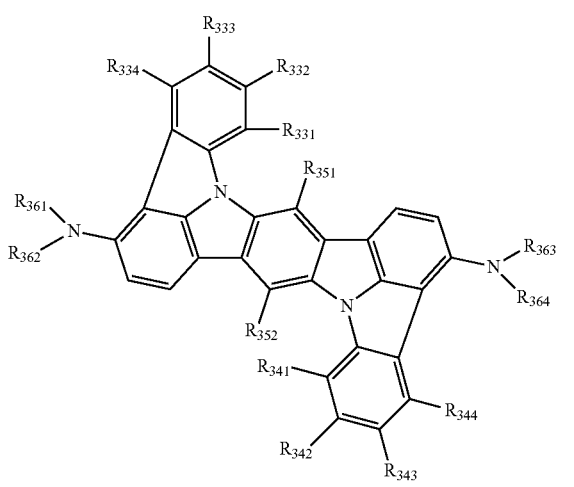

1098

-continued (34-2)

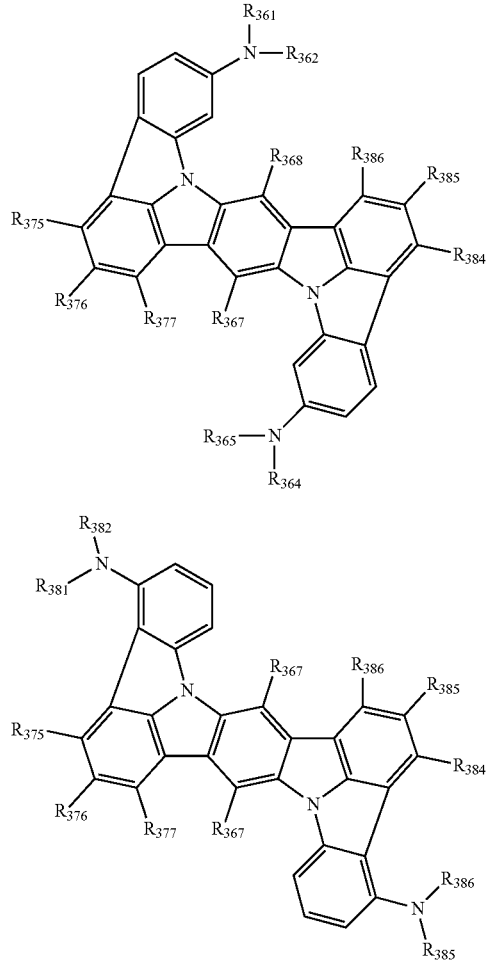

(35-2)

wherein in the formula (32),
one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted, saturated or unsaturated ring;
$R_{331}$ to $R_{334}$ and $R_{341}$ to $R_{344}$ that do not form the substituted or unsubstituted, saturated or unsaturated ring, and $R_{351}$ and $R_{352}$ are independently
a hydrogen atom,
a substituted or unsubstituted aryl group having 6 to 50 ring carbon atoms, or
a substituted or unsubstituted monovalent heterocyclic group having 5 to 50 ring atoms;
$R_{361}$ to $R_{364}$ are independently
a substituted or unsubstituted aryl group having 6 to 50 ring carbon atoms, or
a substituted or unsubstituted monovalent heterocyclic group having 5 to 50 ring atoms;
wherein in the formulas (34-2) and (35-2), $R_{361}$ to $R_{364}$ are as defined in the formula (32);
one or more pairs of two or more adjacent groups of $R_{375}$ to $R_{377}$ and $R_{384}$ to $R_{386}$ form a substituted or unsubstituted, saturated or unsaturated ring, or do not form a substituted or unsubstituted, saturated or unsaturated ring;
$R_{375}$ to $R_{377}$ and $R_{384}$ to $R_{386}$ that do not form the substituted or unsubstituted, saturated or unsaturated ring, and $R_{387}$ are independently a hydrogen atom,
a substituted or unsubstituted aryl group having 6 to 50 ring carbon atoms, or
a substituted or unsubstituted monovalent heterocyclic group having 5 to 50 ring atoms.

17. The organic electroluminescence device according to claim 1, wherein the compound represented by the formula (31) is one or more compounds selected from a group consisting of the following formulas (32-11), (34-11) and (35-11):

(32-11)

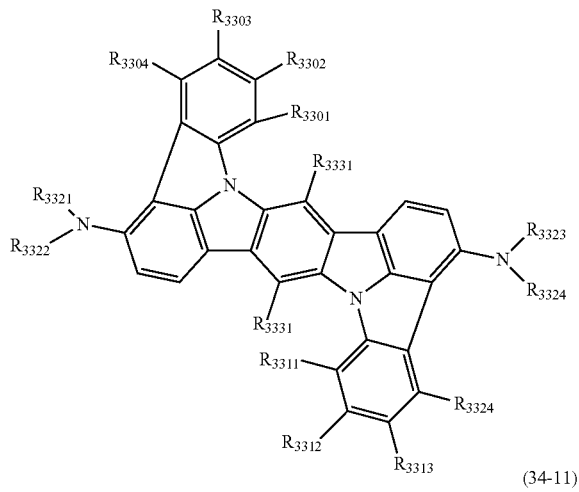

(34-11)

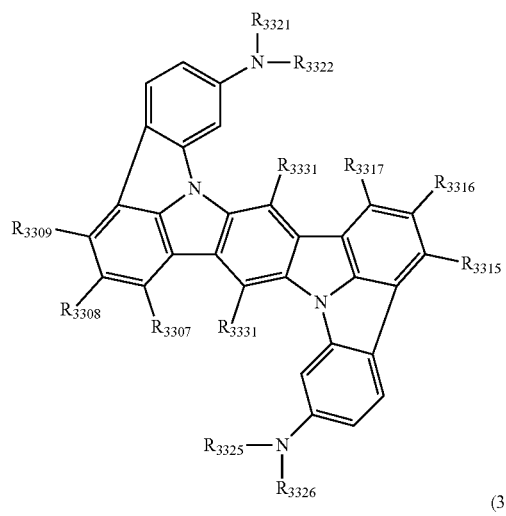

(35-11)

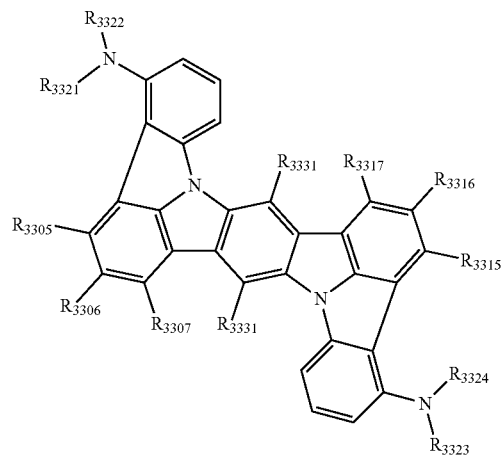

wherein in the formulas (32-11), (34-11) and (35-11),
one or more pairs of two or more adjacent groups of $R_{3301}$ to $R_{3307}$ and $R_{3311}$ to $R_{3317}$ form a substituted or unsubstituted, saturated or unsaturated ring, or do not form a substituted or unsubstituted, saturated or unsaturated ring;

$R_{3301}$ to $R_{3307}$ and $R_{3311}$ to $R_{3317}$ that do not form the substituted or unsubstituted, saturated or unsaturated ring, and $R_{3331}$ are independently
a hydrogen atom,
a substituted or unsubstituted aryl group having 6 to 20 ring carbon atoms, or
a substituted or unsubstituted monovalent heterocyclic group having 5 to 20 ring atoms two $R_{3331}$s may be the same with or different from each other;

$R_{3321}$ to $R_{3324}$ are independently
a substituted or unsubstituted aryl group having 6 to 20 ring carbon atoms, or
a substituted or unsubstituted monovalent heterocyclic group having 5 to 20 ring atoms.

18. The organic electroluminescence device according to claim 17, wherein the one or more compounds selected from the group consisting of the formulas (32-11), (34-11) and (35-11) is one or more compounds selected from a group consisting of the following formulas (32-12), (34-12) and (35-12);

(32-12)

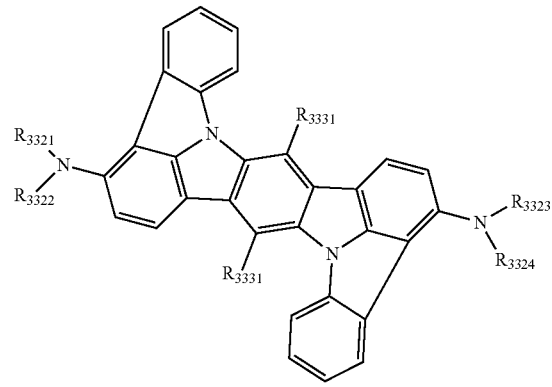

(34-12)

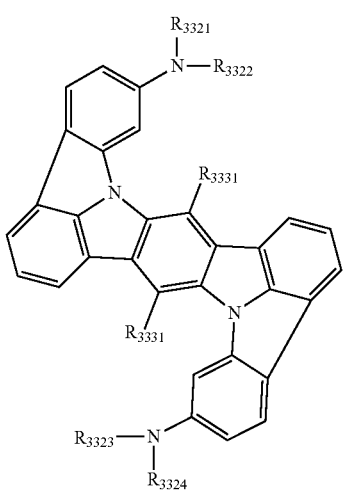

(35-12)

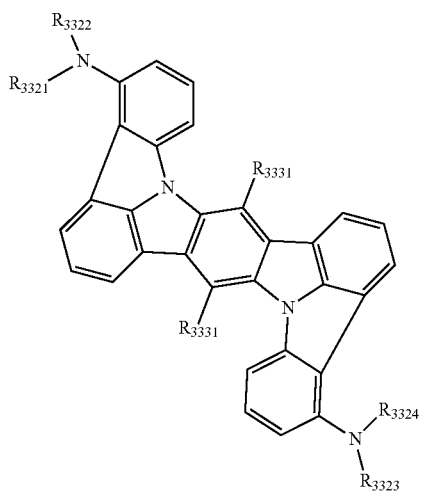

wherein the formulas (32-12), (34-12) and (35-12), $R_{3321}$ to $R_{3324}$ and $R_{3331}$ are as defined in the formulas (32-11), (34-11) and (35-11).

19. The organic electroluminescence device according to claim 17, wherein $R_{3321}$ to $R_{3324}$ are independently a substituted or unsubstituted phenyl group.

20. The organic electroluminescence device according to claim 17, wherein two $R_{3331}$s are independently a hydrogen atom.

21. The organic electroluminescence device according to claim 17, wherein the substituent in the case of "substituted or unsubstituted" is an alkyl group having 1 to 5 carbon atoms.

22. The organic electroluminescence device according to claim 17, wherein $R_{3321}$ to $R_{3324}$ are independently a substituted or unsubstituted phenyl group, two $R_{3331}$s are independently a hydrogen atom, and the substituent in the case of "substituted or unsubstituted" is an alkyl group having 1 to 5 carbon atoms.

23. The organic electroluminescence device according to claim 1, wherein the compound represented by the formula (31) is one or more compounds selected from the group consisting of the following formulas (36-1) to (36-6):

(36-1)

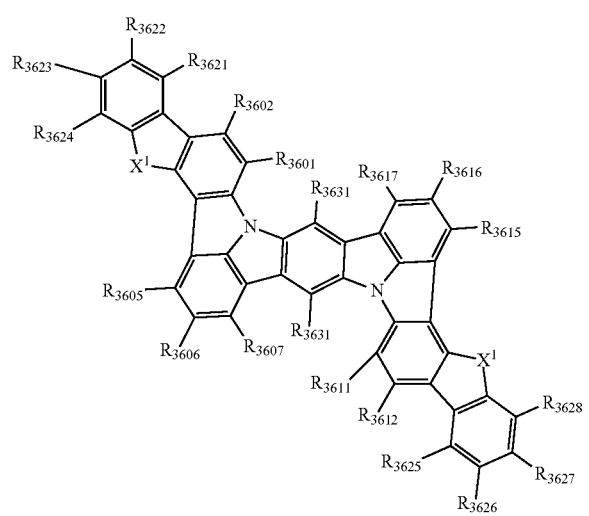

(36-2)

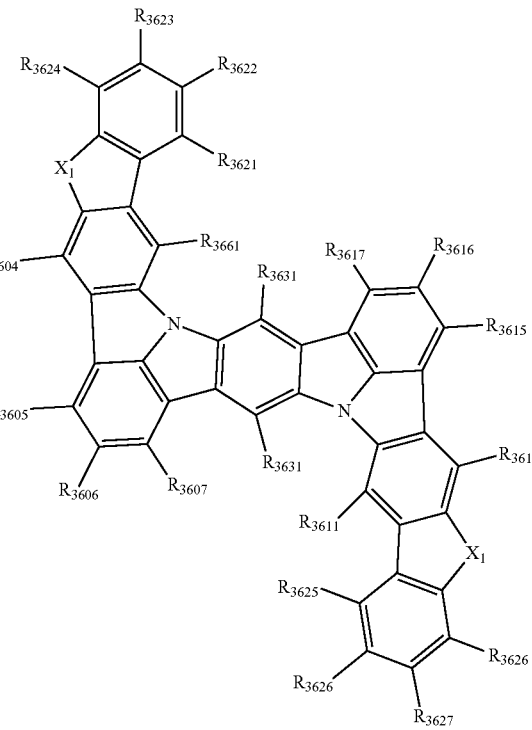

(36-3)

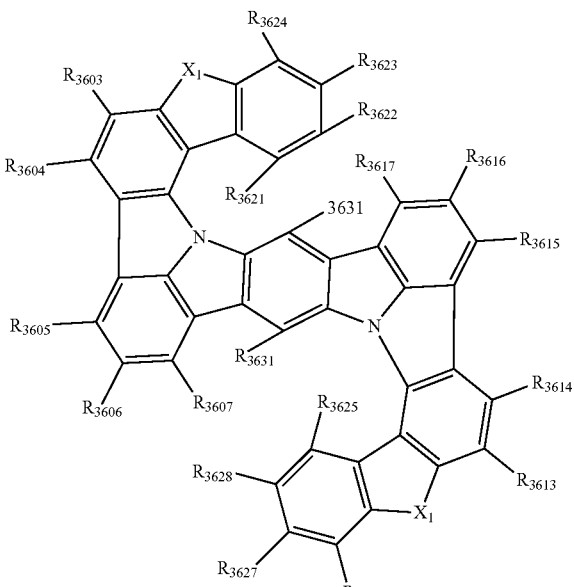

(36-4)

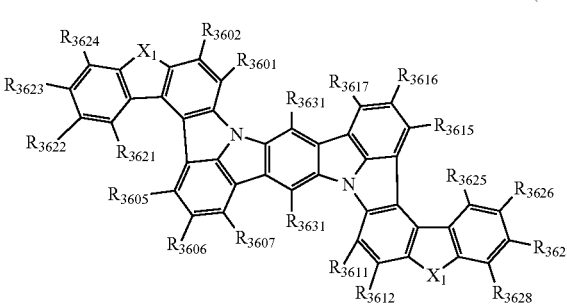

wherein in the formulas (36-1) to (36-6), one or more pairs of two or more adjacent groups of $R_{3605}$ to $R_{3607}$, $R_{3615}$ to $R_{3617}$ and $R_{3631}$ bond with each other to form a substituted or unsubstituted, saturated or unsaturated ring or do not form the ring;

one or more pairs of two or more adjacent groups of $R_{3601}$ to $R_{3604}$, $R_{3611}$ to $R_{3614}$ and $R_{3621}$ to $R_{3628}$ bond with each other to form a substituted or unsubstituted, saturated or unsaturated ring or do not form the ring;

$R_{3601}$ to $R_{3607}$, $R_{3611}$ to $R_{3617}$, $R_{3621}$ to $R_{3628}$ and $R_{3631}$ that do not form the ring are independently
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

when two or more of $R_{901}$ to $R_{907}$ exist, two or more of $R_{901}$ to $R_{907}$ may be the same with or different from each other;

$X_1$ is selected from O, S and N($R_{3641}$), and two $X_1$s may be the same with or different from each other;

$R_{3641}$ and one or more selected from $R_{3601}$ to $R_{3604}$, $R_{3611}$ to $R_{3614}$, $R_{3624}$ and $R_{3628}$ bond with each other to form a substituted or unsubstituted, saturated or unsaturated ring or do not form the ring;

$R_{3641}$ that do not form the ring is a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

24. The organic electroluminescence device according to claim 23, wherein the compound represented by the formula (31) is a compound represented by the formula (36-1).

25. The organic electroluminescence device according to claim 23, wherein two $R_{3631}$s are a phenyl group.

26. The organic electroluminescence device according to claim 23, wherein $X_1$ is N($R_{3641}$).

27. The organic electroluminescence device according to claim 26, wherein $R_{3641}$ is a substituted or unsubstituted aryl group having 6 to 50 ring carbon atoms.

28. The organic electroluminescence device according to claim 1, which further comprises a hole-transporting layer between the anode and the emitting layer.

29. The organic electroluminescence device according to claim 1, which further comprises an electron-transporting layer between the cathode and the emitting layer.

30. An electronic apparatus wherein the organic electroluminescence device according to claim 1 is provided.

* * * * *